(12) United States Patent
Altman et al.

(10) Patent No.: US 10,759,825 B2
(45) Date of Patent: Sep. 1, 2020

(54) CYCLIC DI-NUCLEOTIDE COMPOUNDS AS STING AGONISTS

(71) Applicant: Merck Sharp & Dohme Corp., Rahway, NJ (US)

(72) Inventors: Michael D. Altman, Needham, MA (US); Brian Andresen, Sharon, MA (US); Wonsuk Chang, Princeton, NJ (US); Matthew Lloyd Childers, Medfield, MA (US); Jared N. Cumming, Winchester, MA (US); James P. Jewell, Newton, MA (US); Jongwon Lim, Lexington, MA (US); Alan B. Northrup, Belmont, CA (US); Ryan D. Otte, Natick, MA (US); Benjamin Wesley Trotter, Medfield, MA (US); Quang T. Truong, Morganville, NJ (US); Shawn P. Walsh, Bridgewater, NJ (US); Kake Zhao, Westfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/886,568

(22) Filed: Feb. 1, 2018

(65) Prior Publication Data
US 2018/0244712 A1   Aug. 30, 2018

Related U.S. Application Data

(63) Continuation of application No. 15/234,182, filed on Aug. 11, 2016, now Pat. No. 10,106,574.
(Continued)

(51) Int. Cl.
*A01N 43/04* (2006.01)
*A61K 31/70* (2006.01)
(Continued)

(52) U.S. Cl.
CPC ............. *C07H 21/04* (2013.01); *A61K 39/39* (2013.01); *A61P 35/00* (2018.01); *C07H 19/20* (2013.01);
(Continued)

(58) Field of Classification Search
None
See application file for complete search history.

(56) References Cited

U.S. PATENT DOCUMENTS

| 7,488,802 B2 | 2/2009 | Collins et al. |
| 7,521,051 B2 | 4/2009 | Collins et al. |

(Continued)

FOREIGN PATENT DOCUMENTS

| EP | 3135290 A1 | 1/2018 |
| WO | 2001002369 A2 | 1/2001 |

(Continued)

OTHER PUBLICATIONS

Fagundes et al., Building unique bonds to tight misplaced DNA, Cell Research, 2013, 1065-1066, 2-9.
(Continued)

*Primary Examiner* — Patrick T Lewis
(74) *Attorney, Agent, or Firm* — Julie M. Lake; Catherine D. Fitch

(57) ABSTRACT

A class of polycyclic compounds of general formula (I), of general formula (I'), or of general formula (I''), wherein $Base^1$, $Base^2$, Y, $Y^a$, $X^a$, $X^{a1}$, $X^b$, $X^{b1}$, $X^c$, $X^{c1}$, $X^d$, $X^{d1}$, $R^1$, $R^{1a}$, $R^2$, $R^{2a}$, $R^3$, $R^4$, $R^{4a}$, $R^5$, $R^6$, $R^{6a}$, $R^7$, $R^{7a}$, $R^8$, and $R^{8a}$ are defined herein, that may be useful as inductors of type I interferon production, specifically as STING active agents, are provided. Also provided are processes for the synthesis and use of compounds.

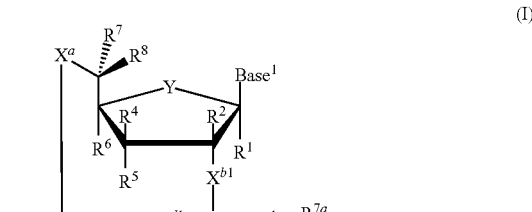

(I)

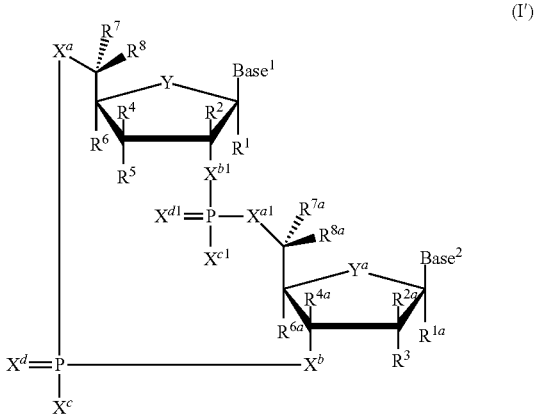

(I')

(Continued)

-continued

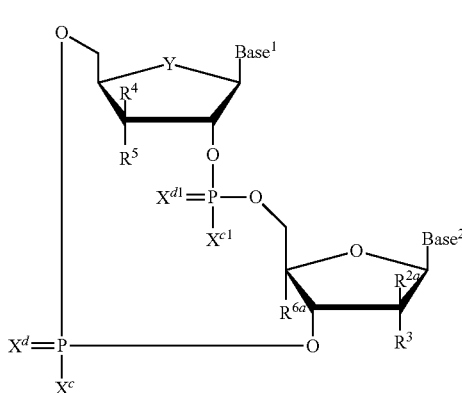

(I'')

22 Claims, No Drawings

Specification includes a Sequence Listing.

Related U.S. Application Data

(60) Provisional application No. 62/356,125, filed on Jun. 29, 2016, provisional application No. 62/268,723, filed on Dec. 17, 2015, provisional application No. 62/204,677, filed on Aug. 13, 2015.

(51) Int. Cl.

| | | |
|---|---|---|
| C07H 21/04 | (2006.01) | |
| C07H 21/02 | (2006.01) | |
| A61K 39/39 | (2006.01) | |
| C07H 19/20 | (2006.01) | |
| C07H 19/23 | (2006.01) | |
| C07H 21/00 | (2006.01) | |
| A61P 35/00 | (2006.01) | |
| A61K 31/7064 | (2006.01) | |
| A61K 31/7084 | (2006.01) | |
| A61K 31/708 | (2006.01) | |
| A61K 31/706 | (2006.01) | |
| A61K 31/7076 | (2006.01) | |

(52) U.S. Cl.
CPC ............ *C07H 19/23* (2013.01); *C07H 21/00* (2013.01); *C07H 21/02* (2013.01); *A61K 31/706* (2013.01); *A61K 31/708* (2013.01); *A61K 31/7064* (2013.01); *A61K 31/7076* (2013.01); *A61K 31/7084* (2013.01)

(56) References Cited

U.S. PATENT DOCUMENTS

| | | | |
|---|---|---|---|
| 7,595,048 | B2 | 9/2009 | Honjo et al. |
| 8,008,449 | B2 | 8/2011 | Korman et al. |
| 8,168,757 | B2 | 5/2012 | Finnefroch et al. |
| 8,354,509 | B2 | 1/2013 | Carven et al. |
| 8,383,796 | B2 | 2/2013 | Korman et al. |
| 9,724,408 | B2 | 8/2017 | Dubensky, Jr. et al. |
| 2006/0040887 | A1 | 3/2006 | Karaolis |
| 2006/0167241 | A1* | 7/2006 | Hayakawa ............ C07H 19/10 536/26.2 |
| 2008/0025979 | A1 | 1/2008 | Honjo et al. |
| 2008/0286296 | A1 | 11/2008 | Ebensen et al. |
| 2011/0271358 | A1 | 11/2011 | Gordon et al. |
| 2014/0206640 | A1 | 7/2014 | Girijavallabhan et al. |
| 2014/0329889 | A1 | 11/2014 | Vance et al. |
| 2014/0341976 | A1* | 11/2014 | Dubensky, Jr. ........ C07H 21/02 424/450 |
| 2015/0056224 | A1 | 2/2015 | Dubensky, Jr. et al. |
| 2015/0158886 | A1 | 6/2015 | Jones et al. |
| 2016/0074507 | A1 | 3/2016 | Manel et al. |
| 2016/0287698 | A1 | 10/2016 | Yan et al. |
| 2016/0362441 | A1 | 12/2016 | Vernejoul et al. |
| 2017/0050967 | A1 | 2/2017 | Burai et al. |
| 2017/0158724 | A1 | 6/2017 | Adams et al. |

FOREIGN PATENT DOCUMENTS

| | | |
|---|---|---|
| WO | WO0210192 | 2/2002 |
| WO | WO02057245 | 7/2002 |
| WO | WO02068470 | 9/2002 |
| WO | 2004004771 | 2/2004 |
| WO | 2004056875 | 7/2004 |
| WO | 2004072286 | 8/2004 |
| WO | 2010027827 | 3/2010 |
| WO | 2010047774 | 4/2010 |
| WO | 2010077634 | 7/2010 |
| WO | 2011066342 | 6/2011 |
| WO | 2013019906 | 2/2013 |
| WO | 2013185052 A1 | 12/2013 |
| WO | 2014093936 | 6/2014 |
| WO | WO201409941 | 6/2014 |
| WO | WO2014099824 | 6/2014 |
| WO | WO2014099941 | 6/2014 |
| WO | 2014189805 A1 | 11/2014 |
| WO | WO201479335 | 11/2014 |
| WO | WO2014179335 | 11/2014 |
| WO | WO2014179760 | 11/2014 |
| WO | WO2014189805 | 11/2014 |
| WO | WO2014189806 | 11/2014 |
| WO | WO2015017652 | 2/2015 |
| WO | 2015074145 | 5/2015 |
| WO | WO2015077354 | 5/2015 |
| WO | 2015148746 A1 | 10/2015 |
| WO | WO2015161137 | 10/2015 |
| WO | 2015189117 | 12/2015 |
| WO | WO2015185565 | 12/2015 |
| WO | 2016100261 | 6/2016 |
| WO | WO2016096174 | 6/2016 |
| WO | WO2016096577 | 6/2016 |
| WO | 2016120605 | 8/2016 |
| WO | WO2016120305 | 8/2016 |
| WO | WO2016145102 | 9/2016 |
| WO | 2017011522 | 1/2017 |
| WO | 2017011622 | 1/2017 |
| WO | 2017011920 | 1/2017 |
| WO | 2017027645 | 2/2017 |
| WO | 2017027646 | 2/2017 |
| WO | 2017075477 | 5/2017 |
| WO | 2017093933 | 6/2017 |
| WO | 2017100305 | 6/2017 |
| WO | 2017123657 | 7/2017 |
| WO | 2017123669 | 7/2017 |
| WO | 2017161349 | 9/2017 |
| WO | 2017175147 | 10/2017 |
| WO | 2017175156 | 10/2017 |
| WO | 2017216726 | 12/2017 |
| WO | 2018009466 | 1/2018 |

OTHER PUBLICATIONS

Gadthula et al., Synthesis and Anti-HIV Activity of β-D-3'-Azido-2',3'-unsaturated Nucleosides and β-D-3'-Azido-3'deoxyribofuranosylnucleosides, Nucleoside, Nucleotides, Nucleic Acids, 2005, 1707-1727, 24.

Gosselin et al., Systematic Synthesis and Biological Evaluation of α- and β-D-lyxofuranosyl Nucleosides of the Five Naturally Occurring Nucleic Acid Bases, J. Med. Chem, 1987, 982-991, 30.

Li et al., Cyclic GMP-AMP Synthase is Activated by Double-Stranded DNA-Induced Oligomerization, Immunity, 2013, 1019-1031, 39.

Ramesh et al., A convenient synthesis of 1-(β-D-ribofuranosyl)imidazo[4,5-d]pyridazin-4(5H)-one (2-aza-3-

(56) References Cited

OTHER PUBLICATIONS deazainosine) and its 2'-deoxy counterpart by ring closure of imidazole nucleosides, Journal of the Chemical Society, Perkin Transaction 1, 1989, 1769-1774, 10.
Urata et al., Regio- and Diastereo-Selectivity of Montmorillonite-Catalyzed Oligomerization of Racemic Adenosine 5'-Phosphorimidazolide, Nucleosides, Nucleotides and Nucleic Acids, Nucleosides, Nucleotides and Nucleic Acids, 2008, 421-430, 27.
Berge, S.M., et al.,, "Pharmaceutical Salts", J. Pharm. Sci, 1977, pp. 1-19, vol. 66, No. 1.
Bruno et al., N-Substituted 2-aminobiphenylpalladium Methanesulfonate Precatalysts and Their Use in C-C and C-N Cross Couplings, The Journal of Organic Chamistry, 2014, 4161-4166, 79.
Goerlitzer, et al., 1,3-Dicarbonyl Compounds. XIV: 4-Oxo-4H-[1]benzofuro[3,2-b]pyrans, Archiv der Pharmazie, 1980, 385-398, vol. 313; Issue 5.
Gould, Salt Selections for Basic Drugs, Intl. J. Pharmaceutics, 1986, pp. 201-217, vol. 33.
Stahl et al., Aminoquinazoline Compounds as A2A Antagonist, Handbook of Pharmaceutical Salts Properties, Selection, and Use, 2002, 330-331.
Heping Shi, et al., Molecular basis for the specific recognition of the metazoan cyclic GMP-AMP by the innate immune adaptor protein STING, PNAS, 2015, 8947-8952, vol. 112/No. 29.
Tezuka, T. et al, Synthesis of 2'-Modified Cyclic Bis(3'-5')diadenylic Acids (c-di-AMPs) and Their Promotion of Cell Division in a Freshwater Green Alga, Chem. Lett., 2012, 1723-1725, 41.
Burdette, Dana L., STING is a direct innate immune sensor of cyclic di-GMP, Nature, Oct. 27, 2011, 515-519, 478.
Burdette, Dara L., STING and the innate immune response to nucleic acids in the cytosol, Nature Immunology, Jan. 2013, 19-26, 14(1).
Dubensky, et al., Rationale, progress and development of vaccines utilizing STING-activating cyclic dinucleotide adjuvants, Therapeutic Advances in Vaccines, 2013, 131-143, 1(4).
Fu, Juan, et al., STING agonist formulated cancer vaccines can cure established tumors resistant to PD-1 blockade, Science Translational Medicine, 2015, 1-13, 7.
Sheridan, Cormac, Drug Developers Switch Gears to Inhibit STING, Nature Biotechnology, Mar. 4, 2019, 199-208, 37.
U.S. Appl. No. 15/234,182, filed Aug. 11, 2016.
Ablasser et al., Cell intrinsic immunity spreads to bystander cells via the intercellular transfer of cGAMP, Nature, Nov. 28, 2013, 530-546, 503.
Ablasser et al., cGAS produces a 2'-5'-linked cyclic dinucleotide second messenger that activates STING, Nature, Jun. 20, 2013, 380-385, 498.
Ausmees et al., Genetic Data Indicate that Proteins Containing the GGDEF Domain Possess Diguanylate Cyclase Activity, FEMS Microbiology, 2001, 163-167, Letters 204.
Bhattacharya et al., Total Synthesis of 2'-deoxy-2'-arafluoro-tubericidin, -toyocamycin, -sangivamycin and certain related molecules, J. Chem. Soc., Perkin Trans. 1; Organic and Bio-Organic Chemistry, 1995, 1543-1550, 12).
Boehr et al., Establishing the Principles of Recognition in the Adenine-Binding Region of an Aminoglycoside Antibiotic Kinase [APH(3')-IIIa], Biochemistry, 2005, 12445-12453, 44(37).
Bookser et al., High-Throughput Five Minute Microwave Accelerated Glycosylation Approach to the Synthesis of Nucleoside Libraries, JOC Article, 2007, 173-179, 72.
Dande et al., Improving RNA Interference in Mammalian Cells by 4'-Thio-Modified Small interfering RNA (siRNA): Effect on siRNA Activity and Nuclease Stability When Used in Combination with 2'-O-Alkyl Modifications, Journal of Medicinal Chemistry, 2006, 1624-1634, 49(5).
Diner et al., The Innate Immune DNA Sensor cGAS Produces a Noncanonical Cyclic Dinucleotide that Activates Human STING, 3 Cell Reports, Cell Reports, 2013, 1355-1361, 3.
Downey et al., DMXAA Causes Tumor Site-Specific Vascular Disruption in Murine Non-Small Molecule Lung Cancer, and Like the Endogenous Non-Canonical Cyclic Dinucleotide STING Agonist, 2'3'-cGAMP, Induces M2 Macrophage Repolarization, Plos One, 2014, 1-14, 9-6-e99988.
Ertem et al., Synthesis of RNA oligomers on heterogeneous templates, Nature, 1996, 238-240, 379-18.
Fagundes et al., Building unique bonds to fight misplaced DNA, Cell Research, 2013, 1065-1066, 2-9.
Gadthula et al., Synthesis and Anti-HIV Activity of β-D-3'-Azido-3',3'-unsaturated Nucleosides and β-D-3'-Azido-3'deoxyribofuranosylnucleosides, Nucleoside, Nucleotides, Nucleic Acids, 2005, 1707-1727, 24.
Gaffney et al., One-Flask Syntheses of c-di-GMP and the [Rp,Rp] and [Rp,Sp] Thiophosphate Analogues, Organic Letters, 2010, 3269-3271, 12-14.
Gao et al., Cyclic [G(2',5')pA(3',5")p] Is the Metazoan Second Messenger Produced by DNA-Activated Cyclic GMP-AMP Synthase, Cell, 2013, 1094-1107, 153.
Gao et al., Structure-Function Ananlysis of STING Activation by c[G(2',5')pA(3',5')p] and Targeting by Antiviral DMXAA, Cell, 2013, 748-762, 154.
Gosselin et al., Systematic Synthesis and Biological Evaluation of α- and β-D-Iyxofuranosyl Nucleosides of the Five Naturally Occurring Nucleic Acid Bases, J. Med. Chem, 1987, 982-991, 30.
Ikeuchi et al., Practical synthesis of natural plant-growth regulator 2-azahypoxanthine, its derivatives, and biotin-labeled probes, Organic & Biomolecular Chemistry, 2014, 3813, 12(23).
Joshi et al., Selectivity of montmorillonite catalyzed prebiotic reactions of D, L-nucleotides, Orig Life Evol Biosph, 2007, 3-26, 37-3.
Kim et al., A Convenient and Versatile Syntheses of 2' (and 3') amino (and azido)-2'(and 3') deoxyadenosine as Diverse Synthetic Precursors of Cyclic Adenosine Diphosphate Ribose (cADPR), Bull. Korean Chem. Soc., 2004, 243, 25-2.
Kobayashi et al., Bacterial c-di-GMP Affects Hematopoietic Stem/Progenitors and their Niches through STING, Cell Reports, 2015, 71-84, 11.
Kranzusch et al., Structure-Guided Reprogramming of Human cGAS Dinucleotide Linkage Specificity, Cell Inc., Elsevier Inc., 2014, 1011-1021, 158.
Li et al., Cyclic GMP-AMP Synthase is Activated by Double-Stranded DNA-Induced Oligornerization, Immunity, 2013, 1019-1031, 39.
Li et al., Hydrolysis of 2'3'-cGAMP by ENPP1 and Design of Nonhydrolyzable Analogs, 10 Nature Chemical Biology 1043 (Dec. 2014); Li et al., Hydrolysis of 2'3'-cGAMP by ENPP1 and Design of Nonhydrolyzable Analogs: Erratum, Nature Chemical Biology, 2014, 1043, 10.
Li et al., Synthesis of 2'-Deoxy-2'- C-a-methylpurine Nucleosides, Synthesis, 2005, 2865-2870, 2005(17).
Liu et al,, Activated STING in a Vascular and Pulmonary Syndrome, The New England Journal of Medicine, 2015, 507, 371-6.
Liu et al, Hepatitis B Virus Polymerase Disrupts K63-Linked Ubiquitination of STING to Block Inate Cytosolic DNA-Sensing Pathways, Journal of Virology, 2015, 2287, 89-4.
Lolicato et al., Cyclic Dinucleotides Bind the C-Linker of HCN4 to Control Channel cGAMP Responsiveness, 10 Nature Chemical Biology 457 (Jun. 2014); Lolicato et al., Cyclic Dinucleotides Bind the C-Linker of HCN4 to Control Channel cGAMP Responsiveness, Nature Chemical Biology, 2014, 457, 10.
Mikhailov et al., Conformational Peculiarities of 5'-C-methylnucleosides, Bioorganicheskaya Khimiya, 1989, 969-975, 15(7).
Minakawa et al., Nucleosides and nucleotides. 116. Convenient syntheses of 3-deazaadenosine, 3-deazaguanosine, and 3-deazainosine via ring closure of 5-ethynyl-1-B-D-ribofuranosylimidazole-4-carboxamide or -carbonitrile, Tetrahedron, 1993, 557-570, 49(3).
Minakawa et al., Nucleosides and Nucleotides. 143. Synthesis of 5-Amino-4-imidazolecarboxamide (AICA) Deoxyribosides from Deoxyinosines and Their Conversion into 3-Deazapurine Derivatives, Chemical & Pharmaceutical Bulletin, 1996, 288-295, 44(2).
O'Neill et al., Sensing the Dark Side of DNA, Sceince, 2013, 763, 339.

(56) References Cited

OTHER PUBLICATIONS

Ora et al., Hydrolytic reactions of cyclic bis(3'-5') diadenylic acid (c-di-AMP), J. Phys. Org. Chem, 2013, 218-225, 26.
Panne et al., Cytosolic DNA sensing unraveled, Nature Chemical Biology, 2013, 533, 9.
Patil et al., 4-aza-7,9-dideazaadenosine, a new cytotoxic synthetic C-nucleoside analogue of adenosine, Tetrahedron Letters, 1994, 5339-5342, 35(30).
Puech et al., Synthesis of 9-(3-deoxy- and 2,3-dideoxy-3-fluoro-β-D-xylofuranosyl)guanines as potential antiviral agents, Tetrahedron Letters, 1989, 3171-3174, 30-24.
Ramesh et al., A convenient synthesis of 1-(β-D-ribofuranosyl)imidazo[4,5-d]pyridazin-4(5H)-one (2-aza-3-deazainosine) and its 2'-deoxy counterpart by ring closure of imidazole nucleosides, Journal of the Chemical Society, Perkin Transaction 1, 1969, 1769-1774, 10.
Ren et al., Structural Basis for Molecular Discrimination by a 3',3'-cGAMP Sensing Riboswitch, Cell Reports, 2015, 1-12. 11.
Robins et al., Nucleic acid related compounds. 74. Synthesis and biological activity of 2'(and 3')-deoxy-2'(and 3')- methylenenucleoside analogs that function as mechanism-based inhibitors of S-adenosyl-L-homocysteine hydrolase and/or ribonucleotide reductase, Journal of Medicinal Chemistry, 1992, 2283-2293, 35(12).
Robins et al., Nucleic Acid-Related Compounds. 91. Biomimetic Reactions Are in Harmony with Loss of 2'- Substituents as Free Radicals (Not Anions) during Mechanism-Based Inactivation of Ribonucleotide Reductases. Differential Interactions of Azide, Halogen, and Alkylthio, J. Am. Chem. Soc., 1996, pp. 11341-11348, 118(46).
Roembke et al., A cyclic dinucleotide contianing 2-aminopurine is a general fluorescent sensor for c-di-GMP and 3'-3'-cGAMP, Molecular BioSystems, 2014, 1568-1575, 10.
Sawai et al., Preparation and Properties of Oligocytidylates with 2'-5' Internucleotide Linkage, Chem. Pharm. Bull. Jpn, 1985, 361-366, 58.
Sawai et al., Synthesis of 2'-5' Linked Oligouridylates in Awueous Medium using the Pd2+ Ion, Chem. Pharm. Bull, 1981, 2237-2245, 29(8).
Seela et al., Fluorinated Pyrrolo[2,3-d]pyrimidine Nucleosides: 7-Fluoro-7-deazapurine 2'-Deoxyribofuranosides and 2'-Deoxy-2'-fluoroarabinofuranosyl Derivatives, Synthesis, 2006, 2005-2012, (12).
Simm et al., Phenotypic Convergence Mediated by GGDEF-Domain-Containing Proteins, 187(19) J Bacteriology 6816 (Oct. 2005);
Simm et al., Phenotypic Convergence Mediated by GGDEF-Domain-Containing Proteins, Journal of Bacteriology, 2005, 6816-6823, 187-19.
Sun et al., Cyclic GMP-AMP Synthase is a Cytosolic DNA Sensor That Activates the Type I Interferon Pathway, Science, 2013, 786, 339.
Tosolini et al., Human Monocyte Recognition of Adenosine-Based Cyclic Dinucleotides Unveils the A2a G∞s Protein-Coupled Receptor Tonic Inhibition of Mitochondrially Induced Cell Death, Molecular and Cellular Biology, 2015, 479-495, 35-2.
Urata et al., Regio- and Diastereo-Selectivity of Montmorillonite-Catalyzed Oligornerization of Racemic Adenosine 5'-Phosphorimidazolide, Nucleosides, Nucleotides and Nucleic Acids, Nucleosides, Nucleotides and Nucleic Acids, 2008, 421-430, 27.
Wang et al., Synthesis and Biological Activity of 5-Fluorotubercidin, Nucleosides, Nucleotides and Nucleic Acids, 2004, 161-170, 23(1).
Wu et al., Cyclic GMP-AMP Is an Endogenous Second Messenger in Innate Immune Signaling by Cytosolic DNA, Science 826, 2013, 826-830, 339.
Yi et al., Single Nucleotide Polymorphisms of Human STING Can Affect Innate Immune Response to Cyclic Dinucleotides, Plos One, 2013, 1-16, 8-10-e77846.
Zeng et al., MAVS, cGAS, and Endogenous Retroviruses in T-Independent B Cell Responses, Science, 2014, 1486-1492, 346-6216.
Zhang et al., Cyclic GMP-AMP Containing Mixed Phosphodiester Linkages Is An Endogenous High-Affinity Ligand for STING, Molecular Cell, 2013, 226-235, 51.
Zhou et al., The ER-Associated Protein ZDHHC1 Is a Positive Regulator of DNA Virus-Triggered, MITA/STING-Dependent Innate Immune Signaling, Cell Host & Microbe, 2014, 450-461, 16.

\* cited by examiner

CYCLIC DI-NUCLEOTIDE COMPOUNDS AS STING AGONISTS

CROSS-REFERENCE TO RELATED APPLICATIONS

This application claims the benefit of U.S. Provisional Patent Application No. 62/204,677, filed Aug. 13, 2015, U.S. Provisional Patent Application No. 62/268,723, filed Dec. 17, 2015, and U.S. Provisional Patent Application No. 62/356,125, filed Jun. 29, 2016.

FIELD OF THE INVENTION

The present disclosure relates to cyclic di-nucleotide compounds and derivatives thereof that may be useful as STING (Stimulator of Interferon Genes) agonists that activate the STING pathway. The present disclosure also relates to processes for the synthesis and to uses of such cyclic di-nucleotide compounds.

BACKGROUND OF THE INVENTION

The immune system has evolved to recognize and neutralize different types of threats in order to maintain the homeostasis of the host, and it is generally broken down into two arms: adaptive and innate. The adaptive immune system is specialized to recognize antigens not naturally expressed in the host as foreign and to mount an anti-antigen response through the coordinated actions of many leukocyte subsets. The hallmark of adaptive immune responses is their ability to provide "memory" or long-lasting immunity against the encountered antigen. While this specific and long-lasting effect is critical to host health and survival, the adaptive immune response requires time to generate a full-blown response.

The innate immune system compensates for this time delay and is specialized to act quickly against different insults or danger signals. It provides the first line of defense against bacteria, viruses, parasites and other infectious threats, but it also responds strongly to certain danger signals associated with cellular or tissue damage. The innate immune system has no antigen specificity but does respond to a variety of effector mechanisms. Opsonization, phagocytosis, activation of the complement system, and production of soluble bioactive molecules such as cytokines or chemokines are all mechanisms by which the innate immune system mediates its response. By responding to these damage-associated molecular patterns (DAMPs) or pathogen-associated molecular patterns (PAMPs) described above, the innate immune system is able to provide broad protection against a wide range of threats to the host.

Free cytosolic DNA and RNA are among these PAMPs and DAMPs. It has recently been demonstrated that the main sensor for cytosolic DNA is cGAS (cyclic GMP-AMP synthase). Upon recognition of cytosolic DNA, cGAS catalyzes the generation of the cyclic-dinucleotide 2'-3' cGAMP, an atypical second messenger that strongly binds to the ER-transmembrane adaptor protein STING. A conformational change is undergone by cGAMP-bound STING, which translocates to a perinuclear compartment and induces the activation of critical transcription factors IRF-3 and NF-κB. This leads to a strong induction of type I interferons and production of pro-inflammatory cytokines such as IL-6, TNF-α and IFN-γ.

The importance of type I interferons and pro-inflammatory cytokines on various cells of the immune system has been very well established. In particular, these molecules strongly potentiate T cell activation by enhancing the ability of dendritic cells and macrophages to uptake, process, present and cross-present antigens to T cells. The T cell stimulatory capacity of these antigen-presenting cells is augmented by the up-regulation of critical co-stimulatory molecules, such as CD80 or CD86. Finally, type I interferons can rapidly engage their cognate receptors and trigger the activation of interferon-responsive genes that can significantly contribute to adaptive immune cell activation.

From a therapeutic perspective, type I interferons are shown to have antiviral activities by directly inhibiting human hepatitis B virus and hepatitis C virus replication, and by stimulating immune responses to virally infected cells. Compounds that can induce type I interferon production are used in vaccines, where they act as adjuvants, enhancing specific immune responses to antigens and minimizing side effects by reducing dosage and broadening the immune response.

In addition, interferons, and compounds that can induce interferon production, have potential use in the treatment of human cancers. Such molecules are potentially useful as anti-cancer agents with multiple pathways of activity. Interferons can inhibit human tumor cell proliferation directly and may be synergistic with various approved chemotherapeutic agents.

Type I interferons can significantly enhance anti-tumor immune responses by inducing activation of both the adaptive and innate immune cells. Finally, tumor invasiveness may be inhibited by interferons by modulating enzyme expression related to tissue remodeling.

In view of the potential of type I interferons and type I interferon-inducing compounds as anti-viral and anti-cancer agents, there remains a need for new agents that can induce potent type I interferon production. With the growing body of data demonstrating that the cGAS-STING cytosolic DNA sensory pathway has a significant capacity to induce type I interferons, the development of STING activating agents is rapidly taking an important place in today's anti-tumor therapy landscape.

SUMMARY OF THE INVENTION

The present disclosure relates to novel cyclic di-nucleotide compounds of general formula (I), general formula (I'), and/or general formula (I"). In particular, the present disclosure relates to compounds having the general structural formula (I):

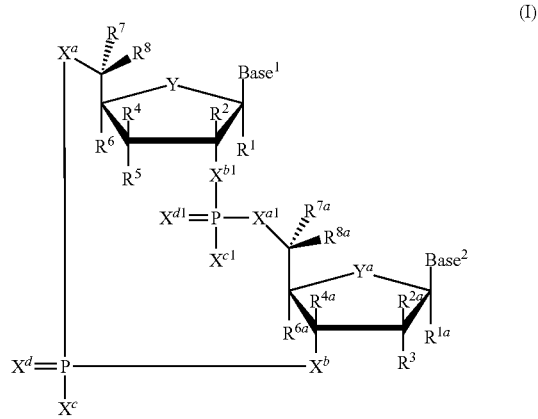

or pharmaceutically acceptable salts, hydrates, solvates, or prodrugs thereof, as described herein. The present disclosure also relates to compounds having general structural formula (I'):

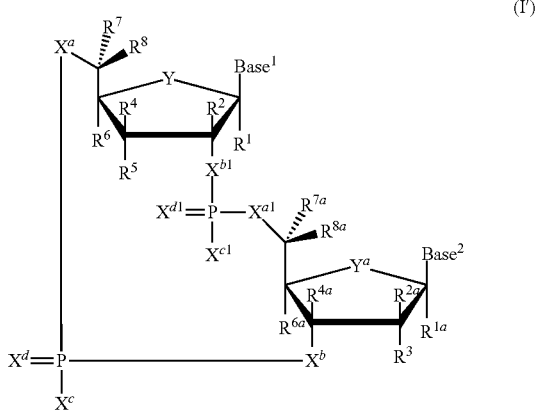

(I')

or pharmaceutically acceptable salts, hydrates, solvates, or prodrugs thereof, as described herein. The present disclosure also relates to compounds having general structural formula (I''):

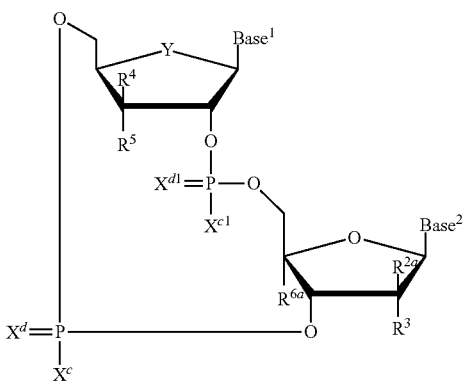

(I'')

or pharmaceutically acceptable salts, hydrates, solvates, or prodrugs thereof, as described herein.

Embodiments of the disclosure include compounds of general formula (I), compounds of general formula (I'), and/or compounds of general formula (I''), and pharmaceutically acceptable salts, hydrates, solvates, or prodrugs thereof, as well as synthesis and isolation of compounds of general formula (I), compounds of general formula (I'), and/or compounds of general formula (I''), and pharmaceutically acceptable salts, hydrates, solvates, or prodrugs thereof. Uses of compounds of general formula (I), compounds of general formula (I'), and/or compounds of general formula (I'') are also disclosed.

Other embodiments, aspects and features of the present disclosure are either further described in or will be apparent from the ensuing description, examples and appended claims.

BRIEF DESCRIPTION OF THE DRAWINGS

Not Applicable

DETAILED DESCRIPTION OF THE INVENTION

The present disclosure includes compounds of general formula (I), compounds of general formula (I'), and/or compounds of general formula (I'') above, and pharmaceutically acceptable salts, hydrates, solvates, or prodrugs thereof. These compounds and their pharmaceutically acceptable salts, hydrates, solvates, and/or prodrugs are useful as agents to induce interferon production.

A first embodiment of the disclosure relates to cyclic di-nucleotide compounds of general formula (I):

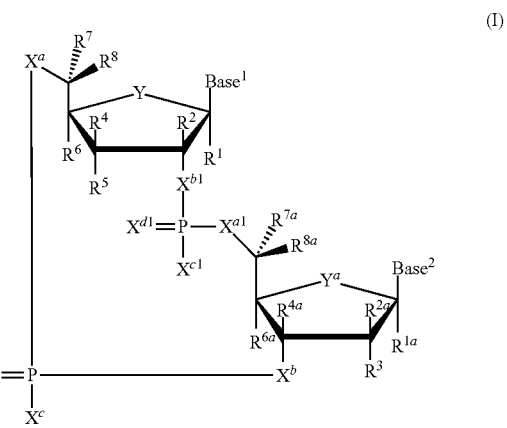

(I)

or a pharmaceutically acceptable salt, hydrate, solvate, or prodrug thereof, wherein $Base^1$ and $Base^2$ are each independently selected from the group consisting of,

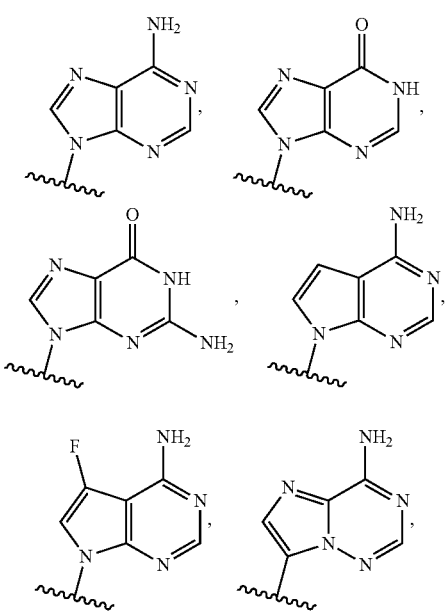

-continued
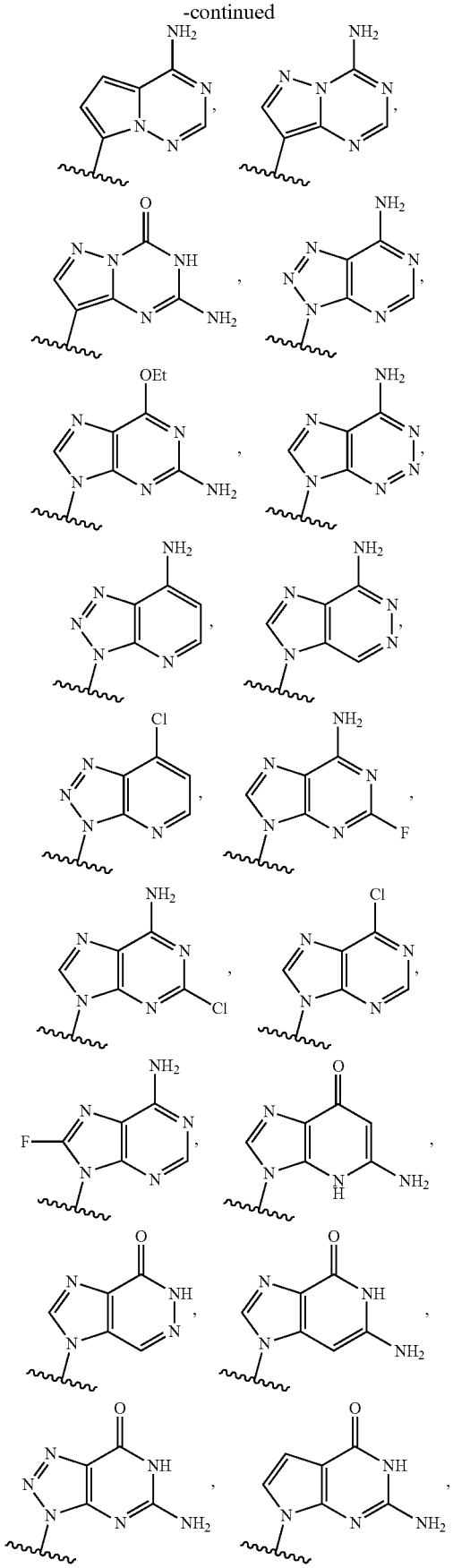
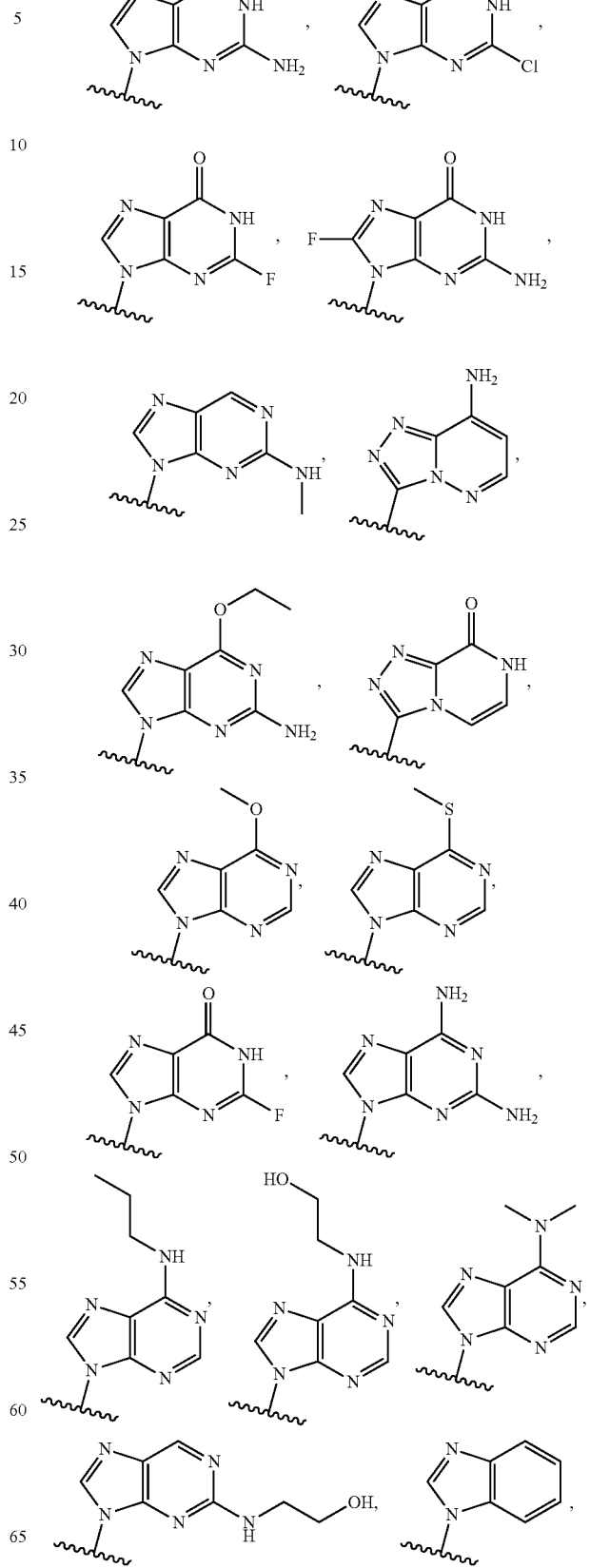

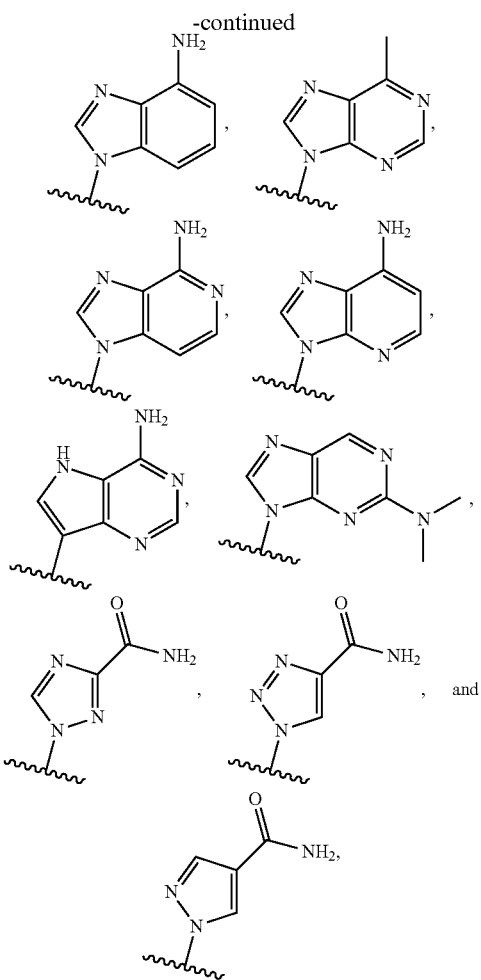

where Base[1] and Base[2] each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$; Y and $Y^a$ are each independently selected from the group consisting of —O—, —S—, —SO$_2$—, —CH$_2$—, and —CF$_2$—; $X^a$ and $X^{a1}$ are each independently selected from the group consisting of O, C, and S; $X^b$ and $X^{b1}$ are each independently selected from the group consisting of O, C, and S; $X^c$ and $X^{c1}$ are each independently selected from the group consisting of O$^-$, S$^-$, OR$^9$, and NR$^9$R$^9$; $X^d$ and $X^{d1}$ are each independently selected from the group consisting of O and S; $R^1$ and $R^{1a}$ are each independently selected from the group consisting of H, F, Cl, Br, I, OH, CN, N$_3$, C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl, where said $R^1$ and $R^{1a}$ C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl are substituted by 0 to 3 substituents selected from the group consisting of F, Cl, Br, I, OH, CN, and N$_3$; $R^2$ and $R^{2a}$ are each independently selected from the group consisting of H, F, Cl, Br, I, OH, CN, N$_3$, C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl, where said $R^2$ and $R^{2a}$ C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl are substituted by 0 to 3 substituents selected from the group consisting of F, Cl, Br, I, OH, CN, and N$_3$; $R^3$ is selected from the group consisting of H, F, Cl, Br, I, OH, CN, N$_3$, C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl, where said $R^3$ C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl are substituted by 0 to 3 substituents selected from the group consisting of F, Cl, Br, I, OH, CN, and N$_3$; $R^4$ and $R^{4a}$ are each independently selected from the group consisting of H, F, Cl, Br, I, OH, CN, N$_3$, C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl, where said $R^4$ and $R^{4a}$ C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl are substituted by 0 to 3 substituents selected from the group consisting of F, Cl, Br, I, OH, CN, and N$_3$; $R^5$ is selected from the group consisting of H, F, Cl, Br, I, OH, CN, N$_3$, C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl, where said $R^5$ C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl are substituted by 0 to 3 substituents selected from the group consisting of F, Cl, Br, I, OH, CN, and N$_3$; $R^6$ and $R^{6a}$ are each independently selected from the group consisting of H, F, Cl, Br, I, OH, CN, N$_3$, C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl, where said $R^6$ and $R^{6a}$ C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl are substituted by 0 to 3 substituents selected from the group consisting of F, Cl, Br, I, OH, CN, and N$_3$; $R^7$ and $R^{7a}$ are each independently selected from the group consisting of H, F, Cl, Br, I, OH, CN, N$_3$, C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl, where said $R^7$ and $R^{7a}$ C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl are substituted by 0 to 3 substituents selected from the group consisting of F, Cl, Br, I, OH, CN, and N$_3$; $R^8$ and $R^{8a}$ are each independently selected from the group consisting of H, F, Cl, Br, I, OH, CN, N$_3$, C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl, where said $R^8$ and $R^{8a}$ C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl are substituted by 0 to 3 substituents selected from the group consisting of F, Cl, Br, I, OH, CN, and N$_3$; each $R^9$ is independently selected from the group consisting of H, C$_1$-C$_{20}$ alkyl,

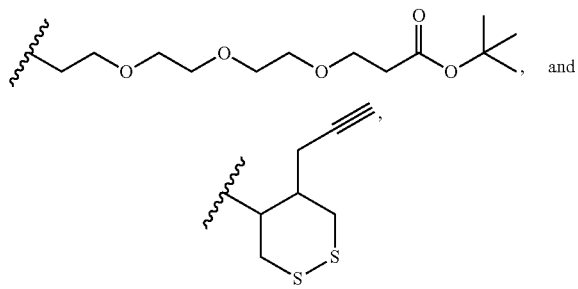

where each $R^9C_1$-$C_{20}$ alkyl is optionally substituted by 0 to 3 substituents independently selected from the group consisting of OH, —O—$C_1$-$C_{20}$ alkyl, —S—$C(O)C_1$-$C_6$ alkyl, and $C(O)OC_1$-$C_6$ alkyl; optionally $R^{1a}$ and $R^3$ are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^{1a}$ and $R^3$ are connected to form —O—$C_1$-$C_6$ alkylene, —O—$C_2$-$C_6$ alkenylene, or —O—$C_2$-$C_6$ alkynylene, said O is bound at the $R^3$ position; optionally $R^{2a}$ and $R^3$ are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^{2a}$ and $R^3$ are connected to form —O—$C_1$-$C_6$ alkylene, —O—$C_2$-$C_6$ alkenylene, or —O—$C_2$-$C_6$ alkynylene, said O is bound at the $R^3$ position; optionally $R^3$ and $R^{6a}$ are connected to form —O—$C_1$-$C_6$ alkylene, —O—$C_2$-$C_6$ alkenylene, or —O—$C_2$-$C_6$ alkynylene, such that where $R^3$ and $R^{6a}$ are connected to form —O—$C_1$-$C_6$ alkylene, —O—$C_2$-$C_6$ alkenylene, or —O—$C_2$-$C_6$ alkynylene, said O is bound at the $R^3$ position; optionally $R^4$ and $R^5$ are connected to form are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^4$ and $R^5$ are connected to form —O—$C_1$-$C_6$ alkylene, —O—$C_2$-$C_6$ alkenylene, or —O—$C_2$-$C_6$ alkynylene, said O is bound at the $R^5$ position; optionally $R^5$ and $R^6$ are connected to form —O—$C_1$-$C_6$ alkylene, —O—$C_2$-$C_6$ alkenylene, or —O—$C_2$-$C_6$ alkynylene, such that where $R^5$ and $R^6$ are connected to form —O—$C_1$-$C_6$ alkylene, —O—$C_2$-$C_6$ alkenylene, or —O—$C_2$-$C_6$ alkynylene, said O is bound at the $R^5$ position; optionally $R^7$ and $R^8$ are connected to form $C_1$-$C_6$ alkylene, $C_2$-$C_6$ alkenylene, or $C_2$-$C_6$ alkynylene; and optionally $R^{7a}$ and $R^{8a}$ are connected to form $C_1$-$C_6$ alkylene, $C_2$-$C_6$ alkenylene, or $C_2$-$C_6$ alkynylene.

In specific aspects of this embodiment, when Y and $Y^a$ are each O, $X^a$ and $X^{a1}$ are each O, $X^b$ and $X^{b1}$ are each O, and $X^c$ and $X^{c1}$ are each OH or SH, $X^d$ and $X^{d1}$ are each O, $R^1$ and $R^{1a}$ are each H, $R^2$ is H, $R^6$ and $R^{6a}$ are each H, $R^7$ and $R^{7a}$ are each H, $R^8$ and $R^{8a}$ are each H, and Base$^1$ and Base$^2$ are each selected from the group consisting of

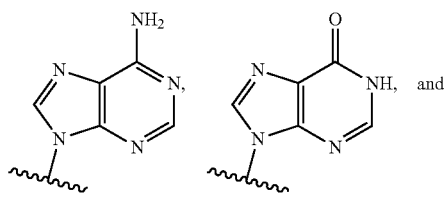

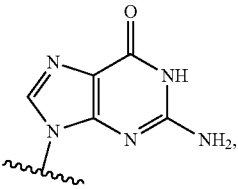

$R^5$ and $R^3$ are not both selected from the group consisting of H, F and OH. That is, when Y and $Y^a$ are each O, $X^a$ and $X^{a1}$ are each O, $X^b$ and $X^{b1}$ are each O, and $X^c$ and $X^{c1}$ are each OH or SH, $X^d$ and $X^{d1}$ are each O, $R^1$ and $R^{1a}$ are each H, $R^2$ is H, $R^6$ and $R^{6a}$ are each H, $R^7$ and $R^{7a}$ are each H, $R^8$ and $R^{8a}$ are each H, and Base$^1$ and Base$^2$ are each selected from the group consisting of

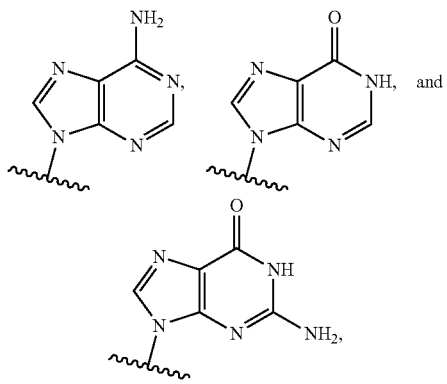

either only one of $R^5$ and $R^3$ is selected from the group consisting of H, F, and OH, or neither $R^5$ and $R^3$ is selected from the group consisting of H, F, and OH. In further specific instances of this aspect, when Y and $Y^a$ are each O, $X^a$ and $X^{a1}$ are each O, $X^b$ and $X^{b1}$ are each O, and $X^c$ and $X^{c1}$ are each OH, $X^d$ and $X^{d1}$ are each O or S, $R^1$ and $R^{1a}$ are each H, $R^2$ is H, $R^6$ and $R^{6a}$ are each H, $R^7$ and $R^{7a}$ are each H, $R^8$ and $R^{8a}$ are each H, and Base$^1$ and Base$^2$ are each selected from the group consisting of

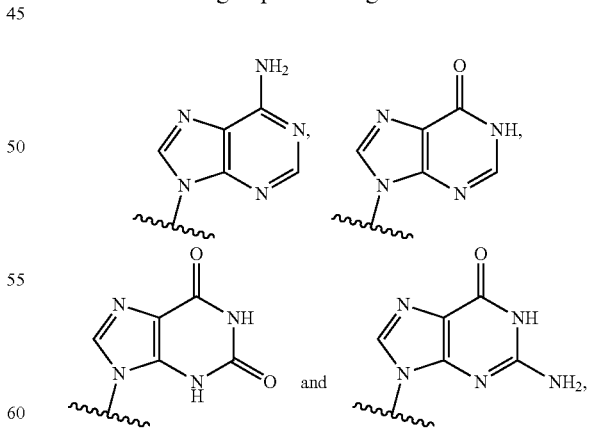

$R^5$ and $R^3$ are not both selected from the group consisting of H, $C_1$-$C_6$ alkyl, $C_2$-$C_6$ alkenyl, $C_2$-$C_6$ alkynyl, where said $C_1$-$C_6$ alkyl, $C_2$-$C_6$ alkenyl and $C_2$-$C_6$ alkynyl are substituted by 0 to 3 substituents selected from the group consisting of F, Cl, Br, I and OH.

In further specific aspects of this embodiment, when Base¹ and Base² are each selected from the group consisting of

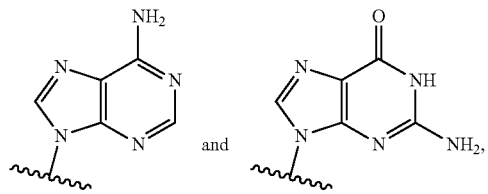 [SMILES: *n1cnc2c(N)ncnc21 ; *n1cnc2c(=O)[nH]c(N)nc21]

and R is F and $R^5$ is F, at least one of $X^c$ and $X^{c1}$ is $SR^9$.

In a first aspect of the first embodiment, Base¹ and Base² are each independently selected from the group consisting of,

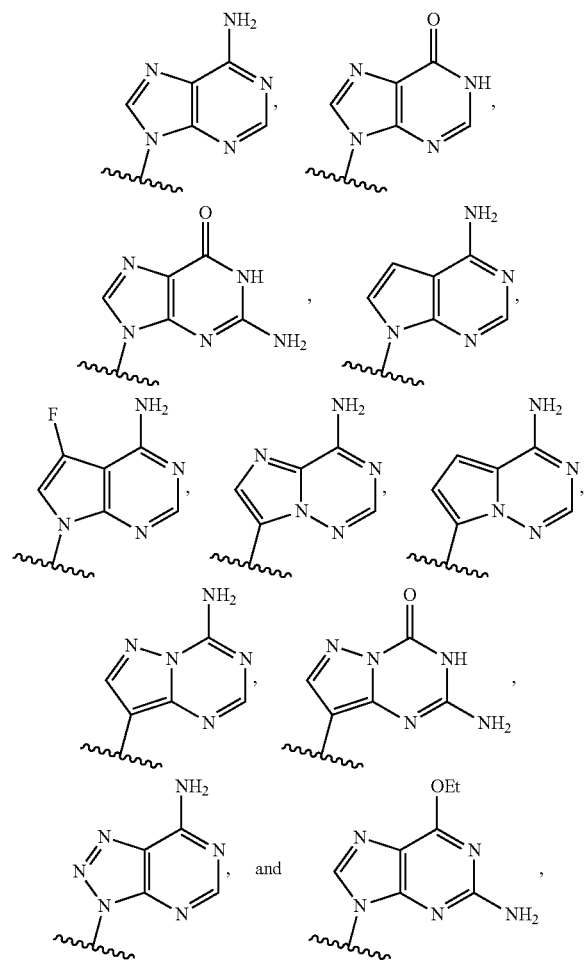

where Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$. In particular instances, Base¹ and Base² are each independently selected from the group consisting of

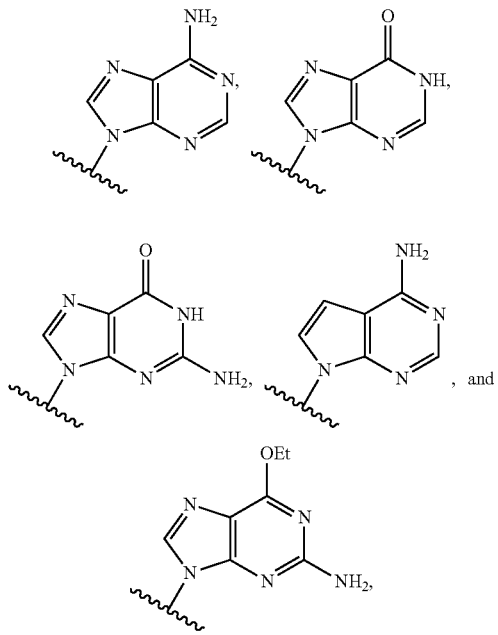

where Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$. In even more particular instances, Base¹ and Base² are each independently selected from the group consisting of

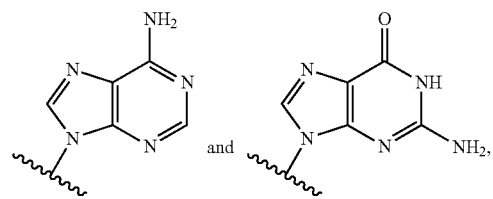 [SMILES: *n1cnc2c(N)ncnc21 ; *n1cnc2c(=O)[nH]c(N)nc21]

where Base¹ and Base² each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$. In this aspect, all other groups are as provided in the general formula (I) of the first embodiment above.

In a second aspect of the first embodiment, Y and $Y^a$ are each independently selected from the group consisting of —O— and —S—. In this aspect, all other groups are as provided in the general formula (I) of the first embodiment above or in the first aspect described above.

In a third aspect of the first embodiment, $X^a$ and $X^{a1}$ are each independently selected from the group consisting of O and S. In this aspect, all other groups are as provided in the general formula (I) of the first embodiment above or in the first through second aspects described above.

In a fourth aspect of the first embodiment, $X^b$ and $X^{b1}$ are each independently selected from the group consisting of O and S. In this aspect, all other groups are as provided in the general formula (I) of the first embodiment above or in the first through third aspects described above.

In a fifth aspect of the first embodiment, $X^c$ and $X^{c1}$ are each independently selected from the group consisting of $O^-$, $S^-$, $OR^9$, and $NR^9R^9$, where each $R^9$ is independently selected from the group consisting of H, $C_1$-$C_{20}$ alkyl,

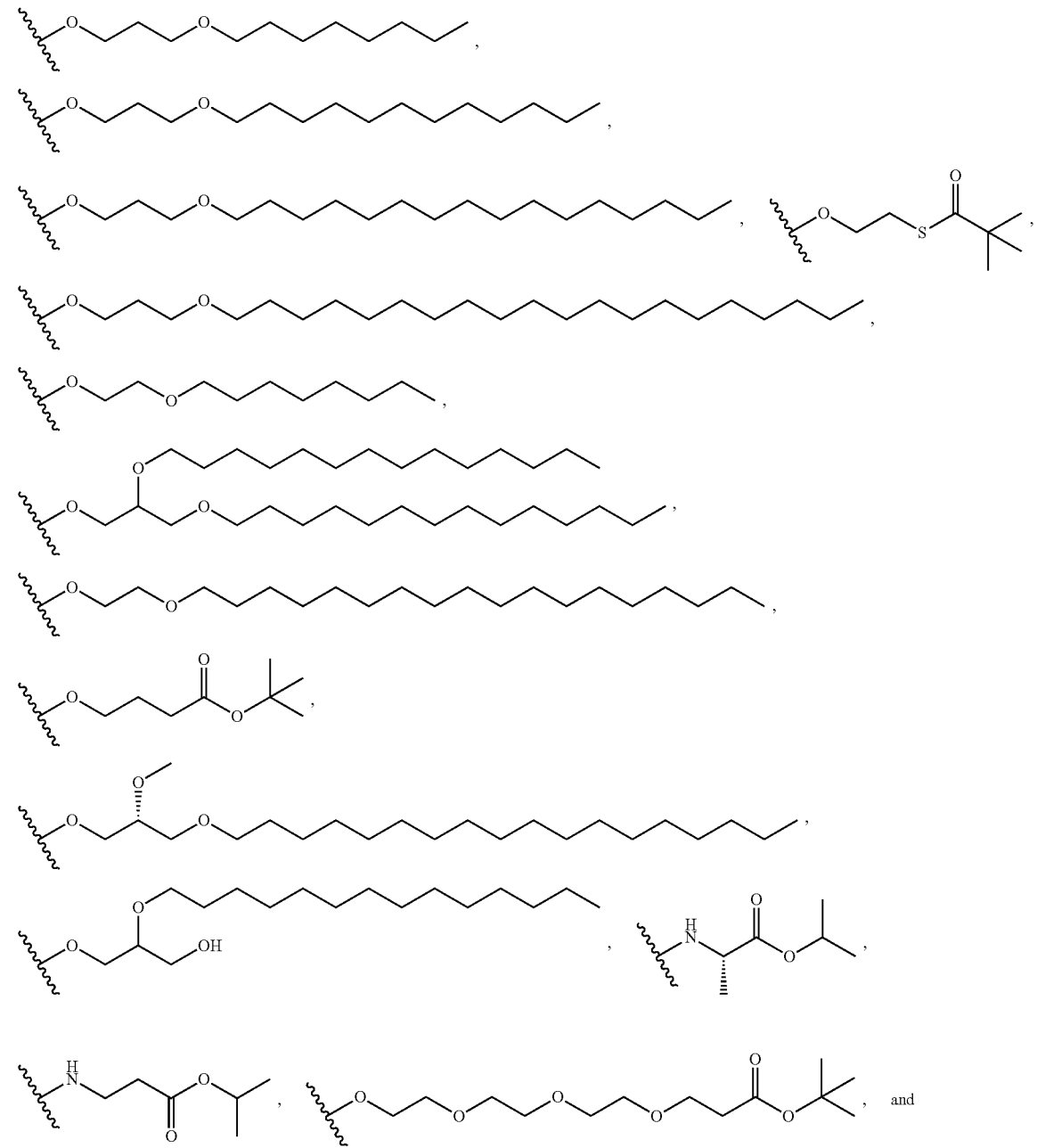

where each $R^9 C_1$-$C_{20}$ alkyl is optionally substituted by 0 to 3 substituents independently selected from the group consisting of OH, —O—$C_1$-$C_{20}$ alkyl, —S—C(O)$C_1$-$C_6$ alkyl, and C(O)O$C_1$-$C_6$ alkyl. In particular instances, $X^c$ and $X^{c1}$ are each independently selected from the group consisting of $O^-$, $S^-$,

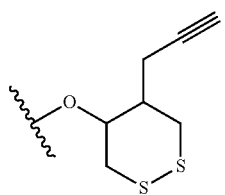

In all instances of this aspect, all other groups are as provided in the general formula (I) of the first embodiment above or in the first through fourth aspects described above.

In a sixth aspect of the first embodiment, $X^d$ and $X^{d1}$ are each independently selected from the group consisting of O and S. In this aspect, all other groups are as provided in the general formula (I) of the first embodiment above or in the first through fifth aspects described above.

In a seventh aspect of the first embodiment, $R^1$ and $R^{1a}$ are each H. In this aspect, all other groups are as provided in the general formula (I) of the first embodiment above or in the first through sixth aspects described above.

In an eighth aspect of the first embodiment, $R^2$ and $R^{2a}$ are each independently selected from the group consisting of H, F, Cl, I, Br, OH, $N_3$, $C_1$-$C_6$ alkyl, and $C_1$-$C_6$ haloalkyl, where said $R^2$ and $R^{2a}$ $C_1$-$C_6$ alkyl or $C_1$-$C_6$ haloalkyl are substituted by 0 to 3 substituents selected from the group consisting of F, Cl, Br, I, OH, CN, and $N_3$. In particular instances, $R^2$ and $R^{2a}$ are each independently selected from the group consisting of H, F, Cl, I, Br, OH, CN, $N_3$, $CF_3$, $CH_3$, $CH_2OH$, and $CH_2CH_3$. In this aspect, all other groups are as provided in the general formula (I) of the first embodiment above or in the first through seventh aspects described above.

In a ninth aspect of the first embodiment, $R^3$ is selected from the group consisting H, F, Cl, I, Br, OH, $N_3$, $C_1$-$C_6$ alkyl, and $C_1$-$C_6$ haloalkyl, where said $R^3$ $C_1$-$C_6$ alkyl or $C_1$-$C_6$ haloalkyl are substituted by 0 to 3 substituents selected from the group consisting of F, Cl, Br, I, OH, CN, and $N_3$. In particular instances, $R^3$ are each independently selected from the group consisting of H, F, Cl, I, Br, OH, CN, $N_3$, $CF_3$, $CH_3$, $CH_2OH$, and $CH_2CH_3$. In this aspect, all other groups are as provided in the general formula (I) of the first embodiment above or in the first through eighth aspects described above.

In a tenth aspect of the first embodiment, $R^4$ and $R^{4a}$ are each independently selected from the group consisting of H, F, Cl, I, Br, OH, $N_3$, $C_1$-$C_6$ alkyl, and $C_1$-$C_6$ haloalkyl, where said $R^4$ and $R^{4a}$ $C_1$-$C_6$ alkyl or $C_1$-$C_6$ haloalkyl are substituted by 0 to 3 substituents selected from the group consisting of F, Cl, Br, I, OH, CN, and $N_3$. In particular instances, $R^4$ and $R^{4a}$ are each independently selected from the group consisting of H, F, Cl, I, Br, OH, CN, $N_3$, $CF_3$, $CH_3$, $CH_2OH$, and $CH_2CH_3$. In this aspect, all other groups are as provided in the general formula (I) of the first embodiment above or in the first through ninth aspects described above.

In an eleventh aspect of the first embodiment, $R^5$ is selected from the group consisting of H, F, Cl, I, Br, OH, $N_3$, $C_1$-$C_6$ alkyl, and $C_1$-$C_6$ haloalkyl, where said $R^5$ $C_1$-$C_6$ alkyl or $C_1$-$C_6$ haloalkyl are substituted by 0 to 3 substituents selected from the group consisting of F, Cl, Br, I, OH, CN, and $N_3$. In particular instances, $R^5$ are each independently selected from the group consisting of H, F, Cl, I, Br, OH, CN, $N_3$, $CF_3$, $CH_3$, $CH_2OH$, and $CH_2CH_3$. In this aspect, all other groups are as provided in the general formula (I) of the first embodiment above or in the first through tenth aspects described above.

In a twelfth aspect of the first embodiment, $R^6$ and $R^{6a}$ are each independently selected from the group consisting of H, F, Cl, I, Br, OH, $C_1$-$C_6$ alkyl, $C_2$-$C_6$ alkenyl, and $C_2$-$C_6$ alkynyl. In this aspect, all other groups are as provided in the general formula (I) of the first embodiment above or in the first through eleventh aspects described above.

In a thirteenth aspect of the first embodiment, $R^7$ and $R^{7a}$ are each H. In this aspect, all other groups are as provided in the general formula (I) of the first embodiment above or in the first through twelfth aspects described above.

In a fourteenth aspect of the first embodiment, $R^8$ and $R^{8a}$ are each H. In this aspect, all other groups are as provided in the general formula (I) of the first embodiment above or in the first through thirteenth aspects described above.

In a fifteenth aspect of the first embodiment, $R^{1a}$ and $R^3$ are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^{1a}$ and $R^3$ are connected to form —O—$C_1$-$C_6$ alkylene, —O—$C_2$-$C_6$ alkenylene, or —O—$C_2$-$C_6$ alkynylene, said O is bound at the $R^3$ position. In this aspect, all other groups are as provided in the general formula (I) of the first embodiment above or in the first through fourteenth aspects described above.

In a sixteenth aspect of the first embodiment, $R^{2a}$ and $R^3$ are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^{2a}$ and $R^3$ are connected to form —O—$C_1$-$C_6$ alkylene, —O—$C_2$-$C_6$ alkenylene, or —O—$C_2$-$C_6$ alkynylene, said O is bound at the $R^3$ position. In this aspect, all other groups are as provided in the general formula (I) of the first embodiment above or in the first through fourteenth aspects described above.

In a seventeenth aspect of the first embodiment, $R^3$ and $R^{6a}$ are connected to form —O—$C_1$-$C_6$ alkylene, —O—$C_2$-$C_6$ alkenylene, and —O—$C_2$-$C_6$ alkynylene, such that where $R^3$ and $R^{6a}$ are connected to form —O—$C_1$-$C_6$ alkylene, —O—$C_2$-$C_6$ alkenylene, or —O—$C_2$-$C_6$ alkynylene, said O is bound at the $R^3$ position. In this aspect, all other groups are as provided in the general formula (I) of the first embodiment above or in the first through fourteenth aspects described above.

In an eighteenth aspect of the first embodiment, $R^4$ and $R^5$ are connected by $C_1$-$C_6$ alkylene, —O—$C_1$-$C_6$ alkylene, —O—$C_2$-$C_6$ alkenylene, or —O—$C_2$-$C_6$ alkynylene, such that where $R^4$ and $R^5$ are connected to form —O—$C_1$-$C_6$ alkylene, —O—$C_2$-$C_6$ alkenylene, or —O—$C_2$-$C_6$ alkynylene, said O is bound at the $R^5$ position. In this aspect, all other groups are as provided in the general formula (I) of the first embodiment above or in the first through fourteenth aspects described above.

In a nineteenth aspect of the first embodiment, $R^5$ and $R^6$ are connected to form —O—$C_1$-$C_6$ alkylene, —O—$C_2$-$C_6$ alkenylene, or —O—$C_2$-$C_6$ alkynylene, such that where $R^5$ and $R^6$ are connected to form —O—$C_1$-$C_6$ alkylene, —O—$C_2$-$C_6$ alkenylene, or —O—$C_2$-$C_6$ alkynylene, said O is bound at the $R^5$ position. In this aspect, all other groups are as provided in the general formula (I) of the first embodiment above or in the first through fourteenth aspects described above.

In a twentieth aspect of the first embodiment, $R^7$ and $R^8$ are connected to form $C_1$-$C_6$ alkylene, $C_2$-$C_6$ alkenylene, or $C_2$-$C_6$ alkynylene. In this aspect, all other groups are as provided in the general formula (I) of the first embodiment above or in the first through fourteenth aspects described above.

In a twenty-first aspect of the first embodiment, $R^{7a}$ and $R^{8a}$ are connected to form $C_1$-$C_6$ alkylene, $C_2$-$C_6$ alkenylene, or $C_2$-$C_6$ alkynylene. In this aspect, all other groups are as provided in the general formula (I) of the first embodiment above or in the first through fourteenth aspects described above.

In a twenty-second aspect of the first embodiment, Base$^1$ and Base$^2$ are each independently selected from the group consisting of

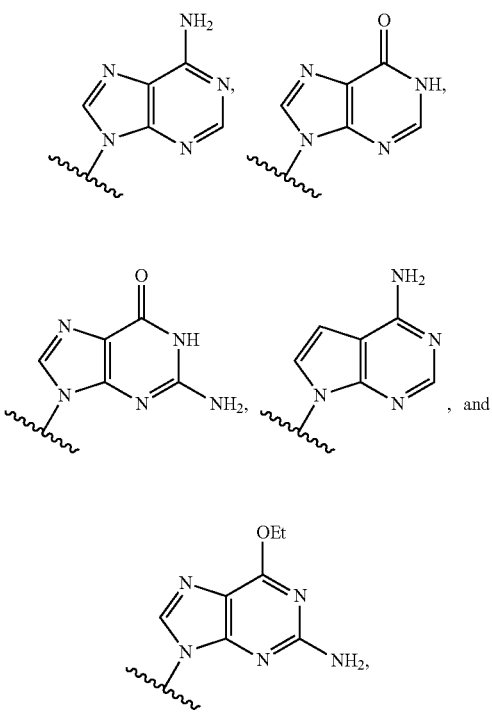

where Base$^1$ and Base$^2$ each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, O($C_{1-3}$ alkyl), O($C_{3-6}$ cycloalkyl), S($C_{1-3}$ alkyl), S($C_{3-6}$ cycloalkyl), NH($C_{1-3}$ alkyl), NH($C_{3-6}$ cycloalkyl), N($C_{1-3}$ alkyl)$_2$, and N($C_{3-6}$ cycloalkyl)$_2$; Y and Y$^a$ are each independently selected from the group consisting of —O—, —S—, —SO$_2$—, —CH$_2$—, and —CF$_2$—; X$^a$ and X$^{a1}$ are each independently selected from the group consisting of O and S; X$^b$ and X$^{b1}$ are each independently selected from the group consisting of O and S; X$^c$ and X$^{c1}$ are each independently selected from the group consisting of O$^-$, S$^-$, OR$^9$, and NR$^9$R$^9$; X$^d$ and X$^{d1}$ are each independently selected from the group consisting of O and S; $R^1$ and $R^{1a}$ are each H; $R^2$ and $R^{2a}$ are each independently selected from the group consisting of H, F, Cl, I, Br, OH, $N_3$, $C_1$-$C_6$ alkyl, and $C_1$-$C_6$ haloalkyl, where said $R^2$ and $R^{2a}$ $C_1$-$C_6$ alkyl or $C_1$-$C_6$ haloalkyl are substituted by 0 to 3 substituents selected from the group consisting of F, Cl, Br, I, OH, CN, and $N_3$; $R^3$ is selected from the group consisting of H, F, Cl, I, Br, OH, CN, $N_3$, $C_1$-$C_6$ alkyl, and $C_1$-$C_6$ haloalkyl, where said $R^3$ $C_1$-$C_6$ alkyl or $C_1$-$C_6$ haloalkyl are substituted by 0 to 3 substituents selected from the group consisting of F, Cl, Br, I, OH, CN, and $N_3$; $R^4$ and $R^{4a}$ are each independently selected from the group consisting of H, $C_1$-$C_6$ alkyl, and $C_1$-$C_6$ haloalkyl, where said $R^4$ and $R^{4a}$ $C_1$-$C_6$ alkyl or $C_1$-$C_6$ haloalkyl are substituted by 0 to 3 substituents selected from the group consisting of F, Cl, Br, I, OH, CN, and $N_3$; $R^5$ is selected from the group consisting of H, F, Cl, I, Br, OH, $N_3$, $C_1$-$C_6$ alkyl, and $C_1$-$C_6$ haloalkyl, where said $R^5$ $C_1$-$C_6$ alkyl or $C_1$-$C_6$ haloalkyl are substituted by 0 to 3 substituents selected from the group consisting of F, Cl, Br, I, OH, CN, and $N_3$; $R^6$ and $R^{6a}$ are each independently selected from the group consisting of H, F, Cl, I, Br, OH, $C_1$-$C_6$ alkyl, $C_2$-$C_6$ alkenyl, $C_2$-$C_6$ alkynyl, and $C_1$-$C_6$ haloalkyl, where said $R^6$ and $R^{6a}$ $C_1$-$C_6$ alkyl or $C_1$-$C_6$ haloalkyl are substituted by 0 to 3 substituents selected from the group consisting of F, Cl, Br, I, OH, CN, and $N_3$; $R^7$ and $R^{7a}$ are each H; $R^8$ and $R^{8a}$ are each H; each $R^9$ is independently selected from the group consisting of H, $C_2$-$C_3$ alkyl,

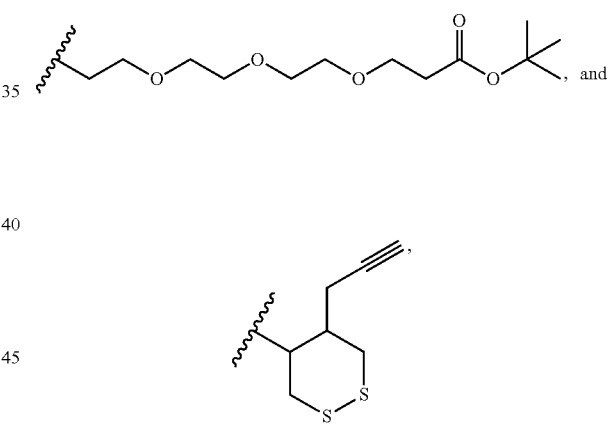

where each $R^9$ $C_2$-$C_3$ alkyl is optionally substituted by 1 to 2 substituents independently selected from the group consisting of OH, —O—$C_1$-$C_{20}$ alkyl, —S—C(O)$C_1$-$C_6$ alkyl, and C(O)O$C_1$-$C_6$ alkyl; optionally $R^3$ and $R^{6a}$ are connected to form —O—$C_1$-$C_6$ alkylene, —O—$C_2$-$C_6$ alkenylene, and —O—$C_2$-$C_6$ alkynylene, such that where $R^3$ and $R^{6a}$ are connected to form —O—$C_1$-$C_6$ alkylene, —O—$C_2$-$C_6$ alkenylene, or —O—$C_2$-$C_6$ alkynylene, said O is bound at the $R^3$ position or optionally $R^4$ and $R^5$ are connected by $C_1$-$C_6$ alkylene, —O—$C_1$-$C_6$ alkylene, —O—$C_2$-$C_6$ alkenylene, or —O—$C_2$-$C_6$ alkynylene, such that where $R^4$ and $R^5$ are connected to form —O—$C_1$-$C_6$ alkylene, —O—$C_2$-$C_6$ alkenylene, or —O—$C_2$-$C_6$ alkynylene, said O is bound at the $R^5$ position. In this aspect, all other groups are as provided in the general formula (I) of the first embodiment above.

In a twenty-third aspect of the first embodiment, the compound of formula (I) is a compound of formula (Ia):

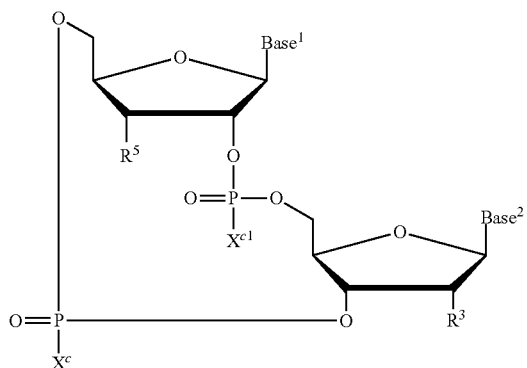
(Ia)
or a pharmaceutically acceptable salt, hydrate, solvate, or prodrug thereof, wherein Base¹ and Base² are each independently selected from the group consisting of
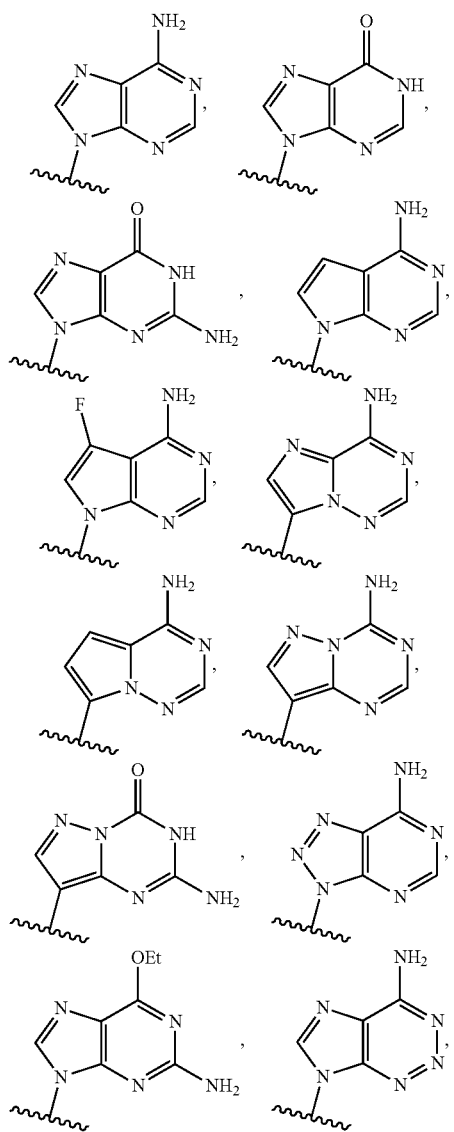
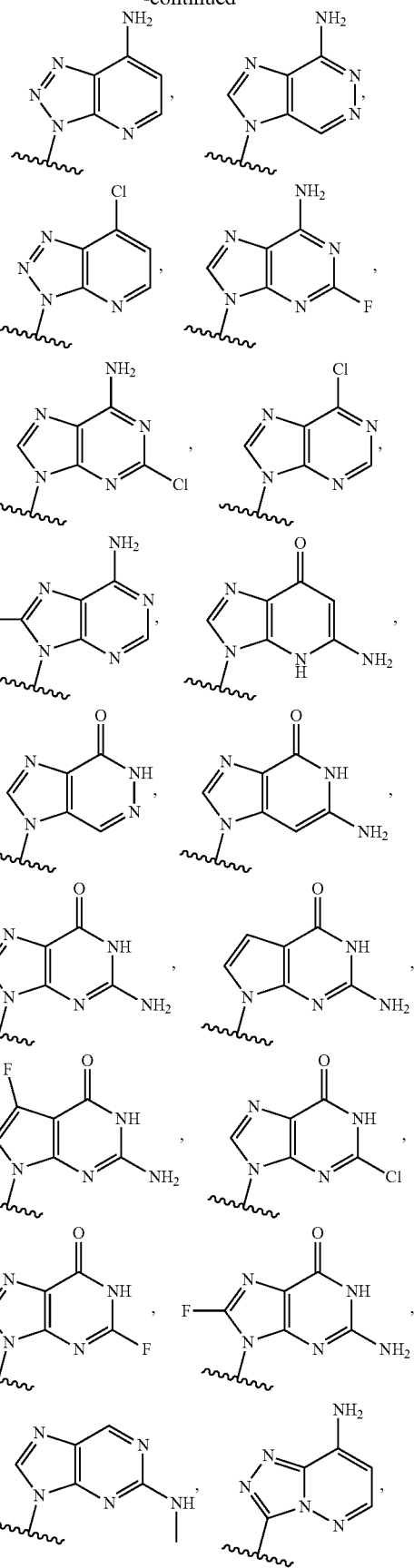

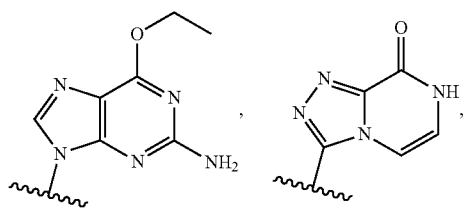
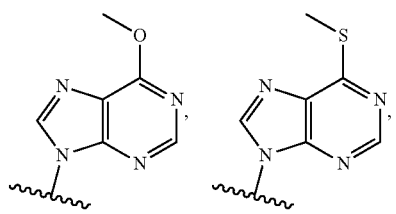
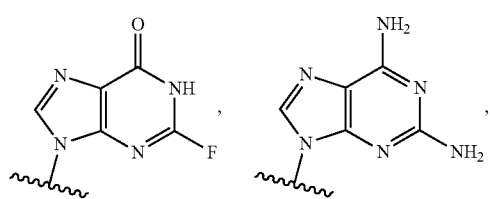
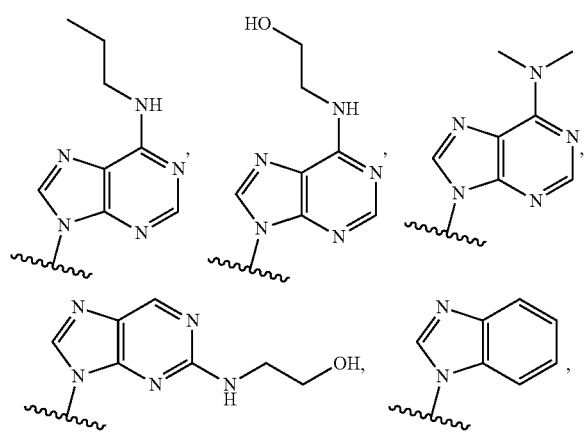
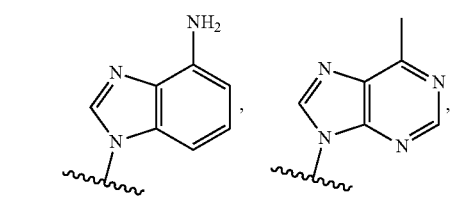
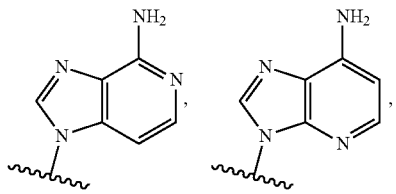
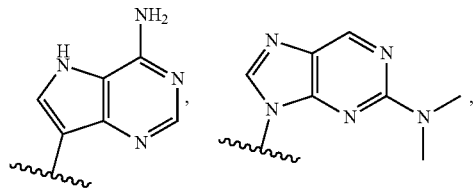

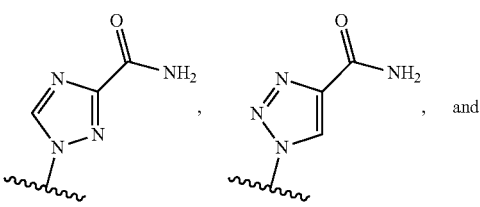
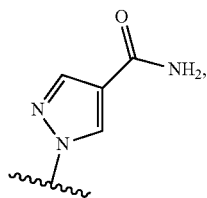

where Base$^1$ and Base$^2$ each may be independently substituted by 0-3 substituents R$^{10}$, where each R$^{10}$ is independently selected from the group consisting of F, Cl, I, Br, OH, SH, NH$_2$, C$_{1-3}$ alkyl, C$_{3-6}$ cycloalkyl, O(C$_{1-3}$ alkyl), O(C$_{3-6}$ cycloalkyl), S(C$_{1-3}$ alkyl), S(C$_{3-6}$ cycloalkyl), NH(C$_{1-3}$ alkyl), NH(C$_{3-6}$ cycloalkyl), N(C$_{1-3}$ alkyl)$_2$, and N(C$_{3-6}$ cycloalkyl)$_2$; X$^c$ and X$^{c1}$ are each independently selected from the group consisting of O$^-$, S$^-$, OR$^9$, and NR$^9$R$^9$; R$^3$ is selected from the group consisting of H, F, Cl, I, Br, OH, CN, N$_3$, C$_1$-C$_6$ alkyl, and C$_1$-C$_6$ haloalkyl, where said R$^3$C$_1$-C$_6$ alkyl or C$_1$-C$_6$ haloalkyl are substituted by 0 to 3 substituents selected from the group consisting of F, Cl, I, Br, and OH; R$^5$ is selected from the group consisting of H, F, Cl, I, Br, OH, CN, N$_3$, C$_1$-C$_6$ alkyl, and C$_1$-C$_6$ haloalkyl, where said R$^5$C$_1$-C$_6$ alkyl or C$_1$-C$_6$ haloalkyl are substituted by 0 to 3 substituents selected from the group consisting of F, Cl, I, Br, and OH; R$^3$ and R$^5$ are not both selected from the group consisting of OH, C$_1$-C$_6$ alkyl substituted with OH, and C$_1$-C$_6$ haloalkyl substituted with OH; and each R$^9$ is independently selected from the group consisting of H, C$_2$-C$_3$ alkyl,

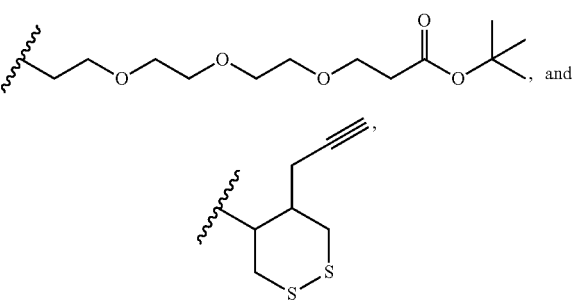

where each R$^9$C$_2$-C$_3$ alkyl is optionally substituted by 1 to 2 substituents independently selected from the group consisting of OH, —O—C$_1$-C$_{20}$ alkyl, —S—C(O)C$_1$-C$_6$ alkyl, and C(O)OC$_1$-C$_6$ alkyl. In this aspect, all other groups are as provided in the general formula (I) of the first embodiment above.

In a twenty-fourth aspect of the first embodiment, the compound of formula (I) is a compound of formula (Ib):

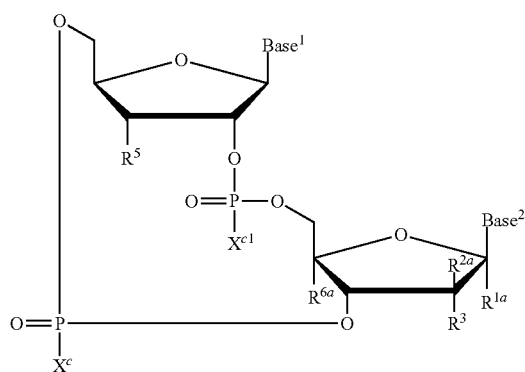
(Ib)
or a pharmaceutically acceptable salt, hydrate, solvate, or prodrug thereof, wherein Base¹ and Base² are each independently selected from the group consisting of
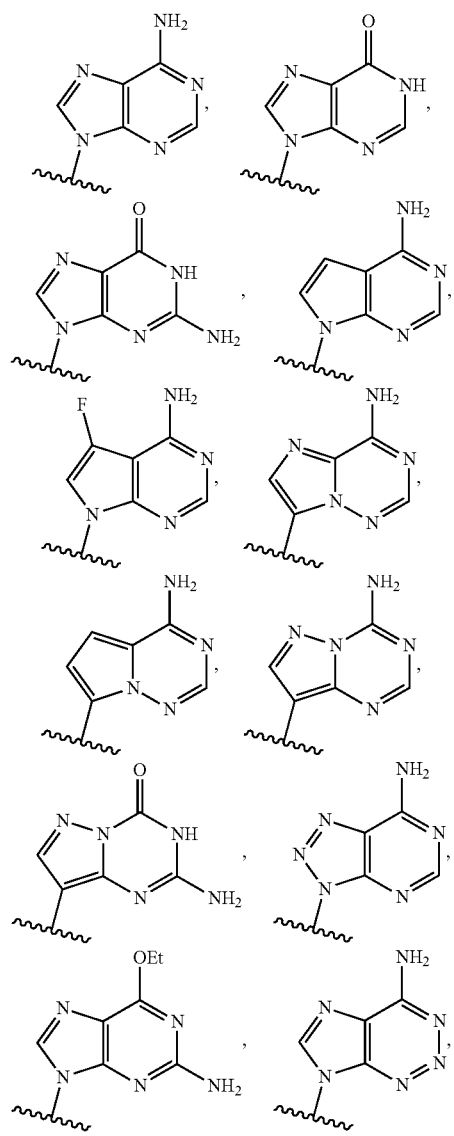
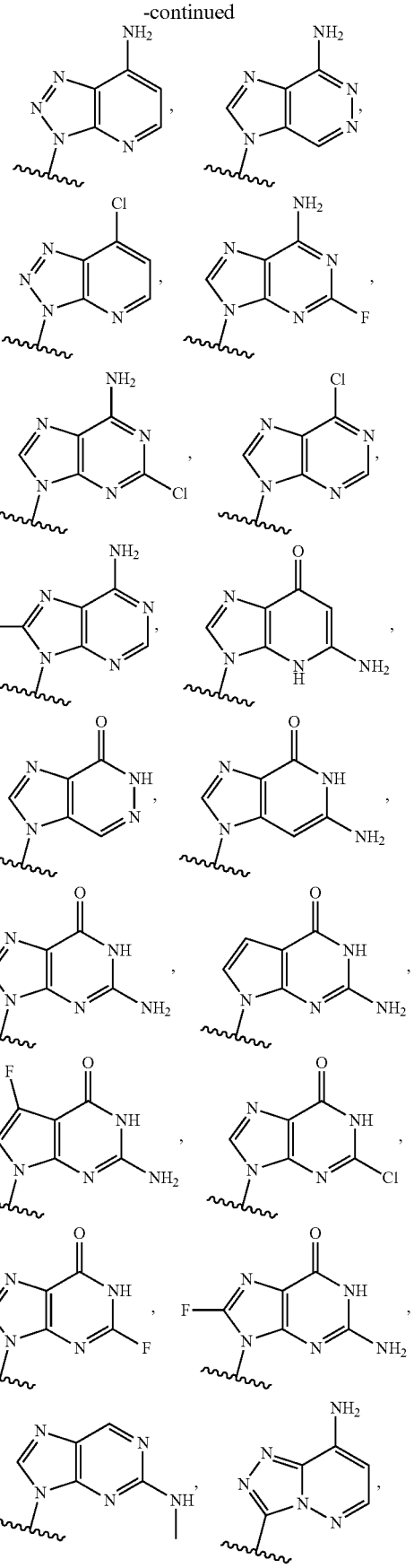

25
-continued

26
-continued

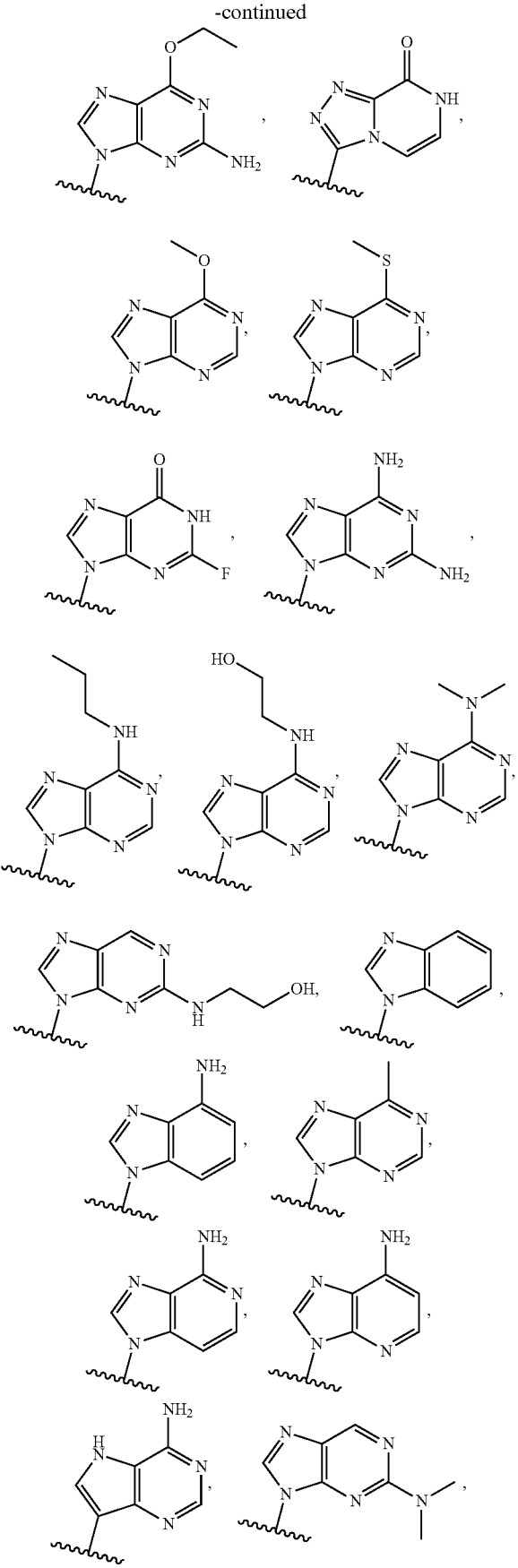

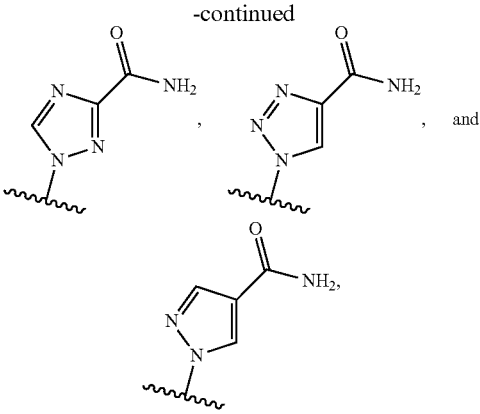

where Base$^1$ and Base$^2$ each may be independently substituted by 0-3 substituents R$^{10}$, where each R$^{10}$ is independently selected from the group consisting of F, Cl, I, Br, OH, SH, NH$_2$, C$_{1-3}$ alkyl, C$_{3-6}$ cycloalkyl, O(C$_{1-3}$ alkyl), O(C$_{3-6}$ cycloalkyl), S(C$_{1-3}$ alkyl), S(C$_{3-6}$ cycloalkyl), NH(C$_{1-3}$ alkyl), NH(C$_{3-6}$ cycloalkyl), N(C$_{1-3}$ alkyl)$_2$, and N(C$_{3-6}$ cycloalkyl)$_2$; X$^c$ and X$^{c1}$ are each independently selected from the group consisting of O$^-$, S$^-$, OR$^9$, and NR$^9$R$^9$; R$^{1a}$ is selected from the group consisting of H, F, Cl, Br, I, OH, CN, N$_3$, C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl, where said R$^{1a}$ C$_1$-C$_6$ alkyl, C$_2$-C$_6$ alkenyl, C$_2$-C$_6$ alkynyl, C$_1$-C$_6$ haloalkyl, C$_2$-C$_6$ haloalkenyl, C$_2$-C$_6$ haloalkynyl, —O—C$_1$-C$_6$ alkyl, —O—C$_2$-C$_6$ alkenyl, and —O—C$_2$-C$_6$ alkynyl are substituted by 0 to 3 substituents selected from the group consisting of F, Cl, Br, I, OH, CN, and N$_3$; R$^{2a}$ is selected from the group consisting of H, F, Cl, I, Br, OH, CN, N$_3$, C$_1$-C$_6$ alkyl, and C$_1$-C$_6$ haloalkyl, where said R$^{2a}$ C$_1$-C$_6$ alkyl or C$_1$-C$_6$ haloalkyl are substituted by 0 to 3 substituents selected from the group consisting of F, Cl, I, Br, and OH; R$^3$ is selected from the group consisting of H, F, Cl, I, Br, OH, CN, N$_3$, C$_1$-C$_6$ alkyl, and C$_1$-C$_6$ haloalkyl, where said R$^3$C$_1$-C$_6$ alkyl or C$_1$-C$_6$ haloalkyl are substituted by 0 to 3 substituents selected from the group consisting of F, Cl, I, Br, and OH; R$^5$ is selected from the group consisting of H, F, Cl, I, Br, OH, CN, N$_3$, C$_1$-C$_6$ alkyl, and C$_1$-C$_6$ haloalkyl, where said R$^5$C$_1$-C$_6$ alkyl or C$_1$-C$_6$ haloalkyl are substituted by 0 to 3 substituents selected from the group consisting of F, Cl, I, Br, and OH; R$^3$ and R$^5$ are not both selected from the group consisting of OH, C$_1$-C$_6$ alkyl substituted with OH, and C$_1$-C$_6$ haloalkyl substituted with OH; R$^{6a}$ is selected from the group consisting of H, F, Cl, I, Br, OH, C$_1$-C$_6$ alkyl, C$_2$-C$_6$ alkenyl, and C$_2$-C$_6$ alkynyl; each R$^9$ is independently selected from the group consisting of H, C$_2$-C$_3$ alkyl,

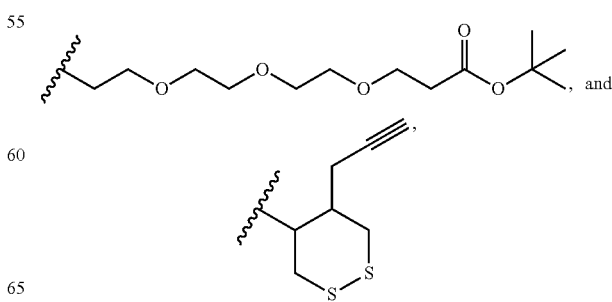

where each $R^9C_2$-$C_3$ alkyl is optionally substituted by 1 to 2 substituents independently selected from the group consisting of OH, —O—$C_1$-$C_{20}$ alkyl, —S—C(O)$C_1$-$C_6$ alkyl, and C(O)O$C_1$-$C_6$ alkyl; and optionally $R^3$ and $R^{6a}$ are connected to form —O—$C_1$-$C_6$ alkylene, —O—$C_2$-$C_6$ alkenylene, and —O—$C_2$-$C_6$ alkynylene, such that where $R^3$ and $R^{6a}$ are connected to form —O—$C_1$-$C_6$ alkylene, —O—$C_2$-$C_6$ alkenylene, or —O—$C_2$-$C_6$ alkynylene, said O is bound at the $R^3$ position. In this aspect, all other groups are as provided in the general formula (I) of the first embodiment above.

In a twenty-fifth aspect of the first embodiment, the compound of formula (I) is a compound of formula (Ic):

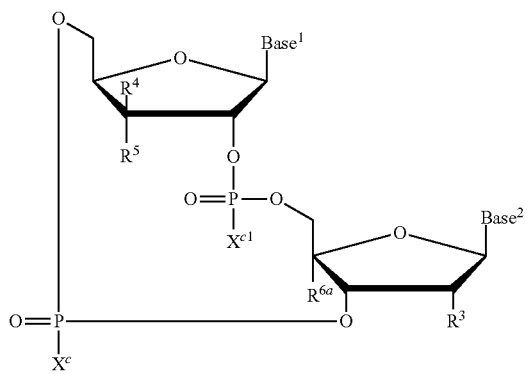

(Ic)

or a pharmaceutically acceptable salt, hydrate, solvate, or prodrug thereof, wherein Base$^1$ and Base$^2$ are each independently selected from the group consisting of

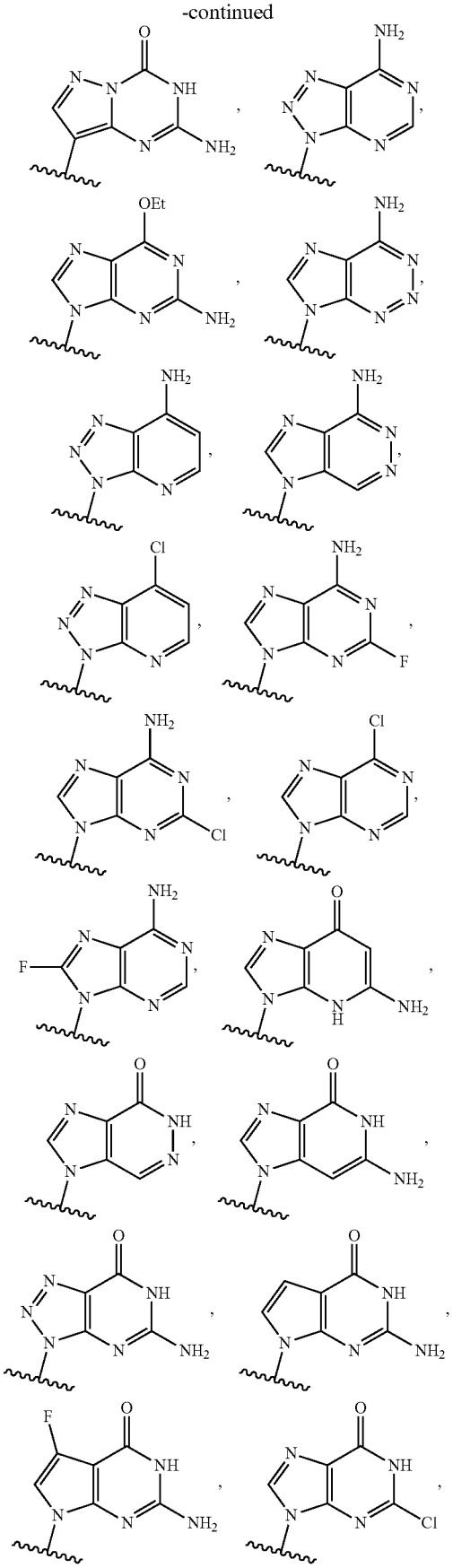

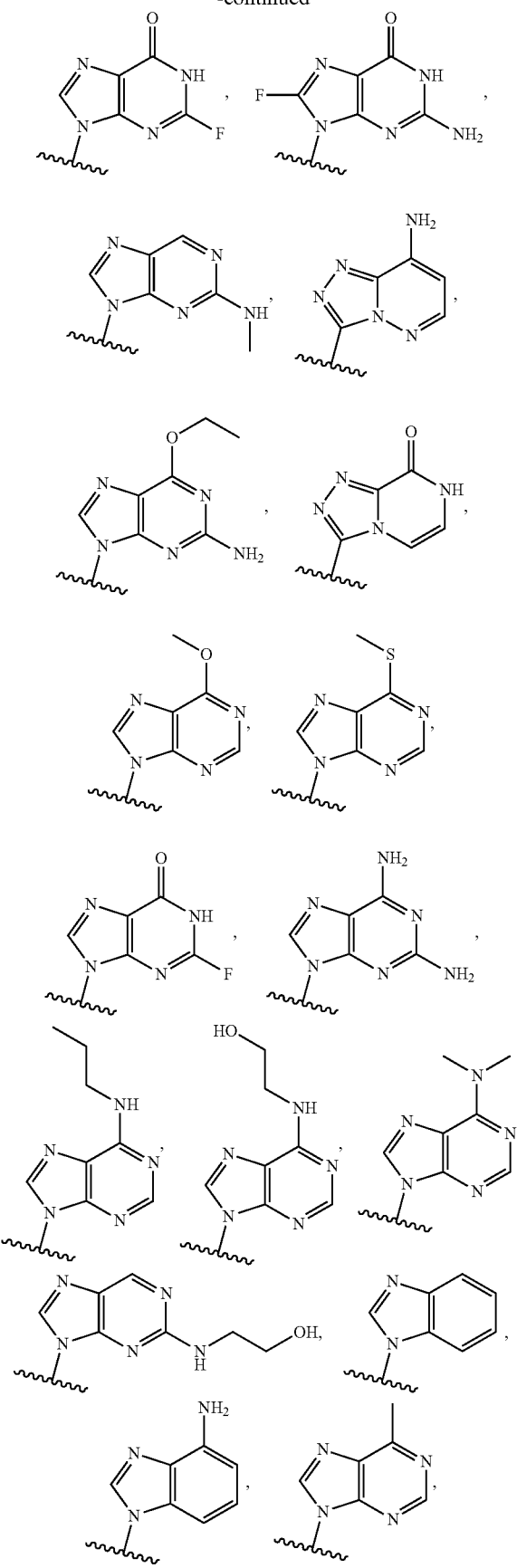

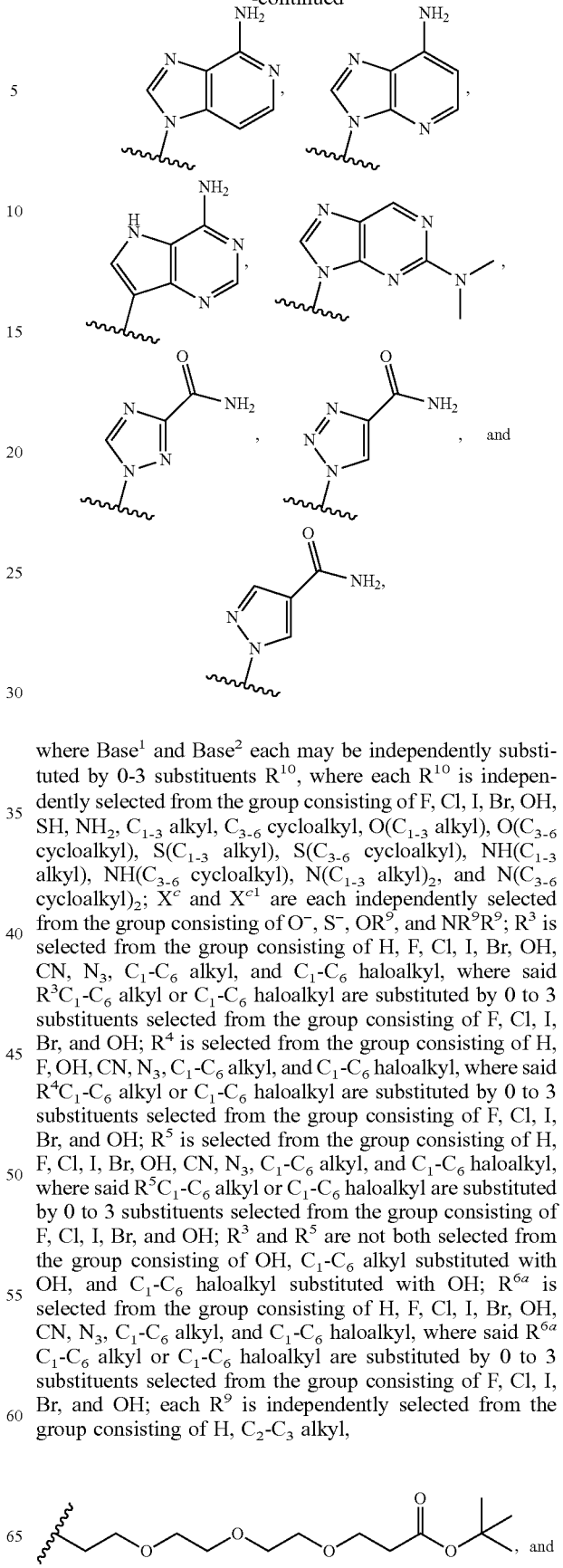

where Base[1] and Base[2] each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$; $X^c$ and $X^{c1}$ are each independently selected from the group consisting of $O^-$, $S^-$, $OR^9$, and $NR^9R^9$; $R^3$ is selected from the group consisting of H, F, Cl, I, Br, OH, CN, $N_3$, $C_1$-$C_6$ alkyl, and $C_1$-$C_6$ haloalkyl, where said $R^3C_1$-$C_6$ alkyl or $C_1$-$C_6$ haloalkyl are substituted by 0 to 3 substituents selected from the group consisting of F, Cl, I, Br, and OH; $R^4$ is selected from the group consisting of H, F, OH, CN, $N_3$, $C_1$-$C_6$ alkyl, and $C_1$-$C_6$ haloalkyl, where said $R^4C_1$-$C_6$ alkyl or $C_1$-$C_6$ haloalkyl are substituted by 0 to 3 substituents selected from the group consisting of F, Cl, I, Br, and OH; $R^5$ is selected from the group consisting of H, F, Cl, I, Br, OH, CN, $N_3$, $C_1$-$C_6$ alkyl, and $C_1$-$C_6$ haloalkyl, where said $R^5C_1$-$C_6$ alkyl or $C_1$-$C_6$ haloalkyl are substituted by 0 to 3 substituents selected from the group consisting of F, Cl, I, Br, and OH; $R^3$ and $R^5$ are not both selected from the group consisting of OH, $C_1$-$C_6$ alkyl substituted with OH, and $C_1$-$C_6$ haloalkyl substituted with OH; $R^{6a}$ is selected from the group consisting of H, F, Cl, I, Br, OH, CN, $N_3$, $C_1$-$C_6$ alkyl, and $C_1$-$C_6$ haloalkyl, where said $R^{6a}$ $C_1$-$C_6$ alkyl or $C_1$-$C_6$ haloalkyl are substituted by 0 to 3 substituents selected from the group consisting of F, Cl, I, Br, and OH; each $R^9$ is independently selected from the group consisting of H, $C_2$-$C_3$ alkyl, -continued

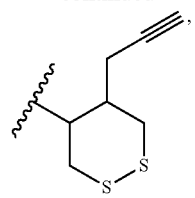

where each $R^9C_2$-$C_3$ alkyl is optionally substituted by 1 to 2 substituents independently selected from the group consisting of OH, —O—$C_1$-$C_{20}$ alkyl, —S—C(O)$C_1$-$C_6$ alkyl, and C(O)O$C_1$-$C_6$ alkyl; and optionally $R^4$ and $R^5$ are connected by $C_1$-$C_6$ alkylene, —O—$C_1$-$C_6$ alkylene, —O—$C_2$-$C_6$ alkenylene, or —O—$C_2$-$C_6$ alkynylene, such that where $R^4$ and $R^5$ are connected to form —O—$C_1$-$C_6$ alkylene, —O—$C_2$-$C_6$ alkenylene, or —O—$C_2$-$C_6$ alkynylene, said O is bound at the $R^5$ position. In this aspect, all other groups are as provided in the general formula (I) of the first embodiment above.

A twenty-sixth aspect of the first embodiment relates to a pharmaceutical composition, said pharmaceutical composition comprising (a) a compound according to any one of general formula (I) of the first embodiment above or in the first through twenty-fifth aspects described above or a pharmaceutically acceptable salt, hydrate, solvate, or prodrug thereof, and (b) a pharmaceutically acceptable carrier.

A twenty-seventh aspect of the first embodiment relates to methods of inducing an immune response in a subject, comprising administering a therapeutically effective amount of a compound according to any one of general formula (I) of the first embodiment above or in the first through twenty-fifth aspects described above or a pharmaceutically acceptable salt, hydrate, solvate, or prodrug thereof to the subject.

A twenty-eighth aspect of the first embodiment relates to methods of inducing an immune response in a subject, comprising administering a therapeutically effective amount of a composition according to the twenty-sixth aspect described above to the subject.

A twenty-ninth aspect of the first embodiment relates to methods of inducing a STING-dependent type I interferon production in a subject, comprising administering a therapeutically effective amount of a compound according to any one of general formula (I) of the first embodiment above or in the first through twenty-fifth aspects described above or a pharmaceutically acceptable salt, hydrate, solvate, or prodrug thereof to the subject.

A thirtieth aspect of the first embodiment relates to methods of inducing a STING-dependent type I interferon production in a subject, comprising administering a therapeutically effective amount of a composition according to the twenty-sixth aspect described above to the subject.

A thirty-first aspect of the first embodiment relates to methods of inducing a STING-dependent cytokine production in a subject, comprising administering a therapeutically effective amount of a compound according to any one of general formula (I) of the first embodiment above or in the first through twenty-fifth aspects described above or a pharmaceutically acceptable salt, hydrate, solvate, or prodrug thereof to the subject.

A thirty-second aspect of the first embodiment relates to methods of inducing a STING-dependent cytokine production in a subject, comprising administering a therapeutically effective amount of a composition according to the twenty-sixth aspect described above to the subject.

A second embodiment of the disclosure relates to cyclic di-nucleotide compounds of general formula (I'):

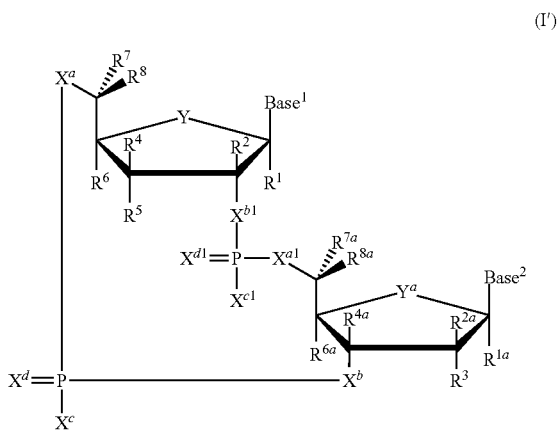

(I')

or a pharmaceutically acceptable salt, hydrate, solvate, or prodrug thereof, wherein Base[1] and $NH_2NH$ Base[2] are each independently selected from the group consisting of

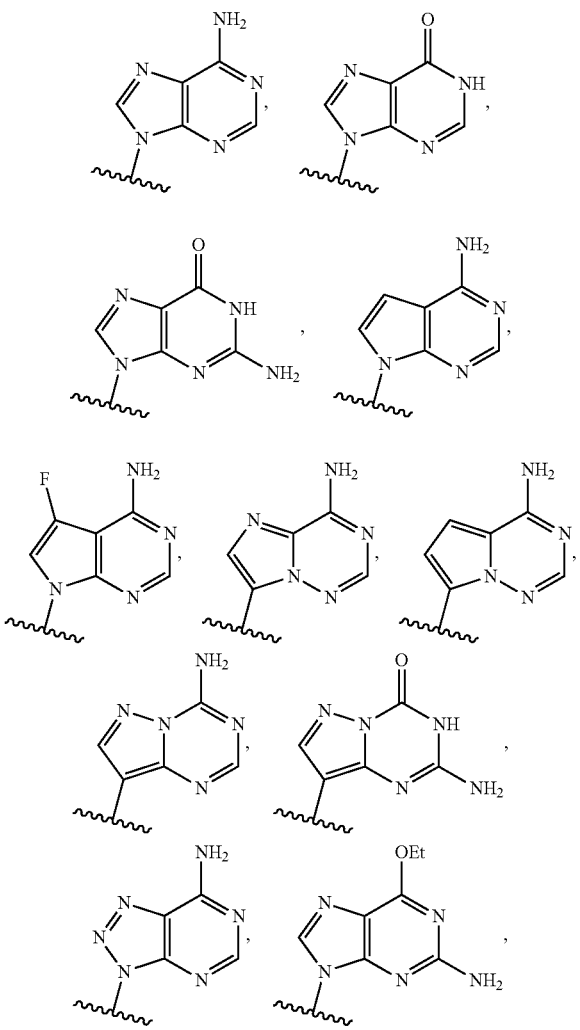

-continued
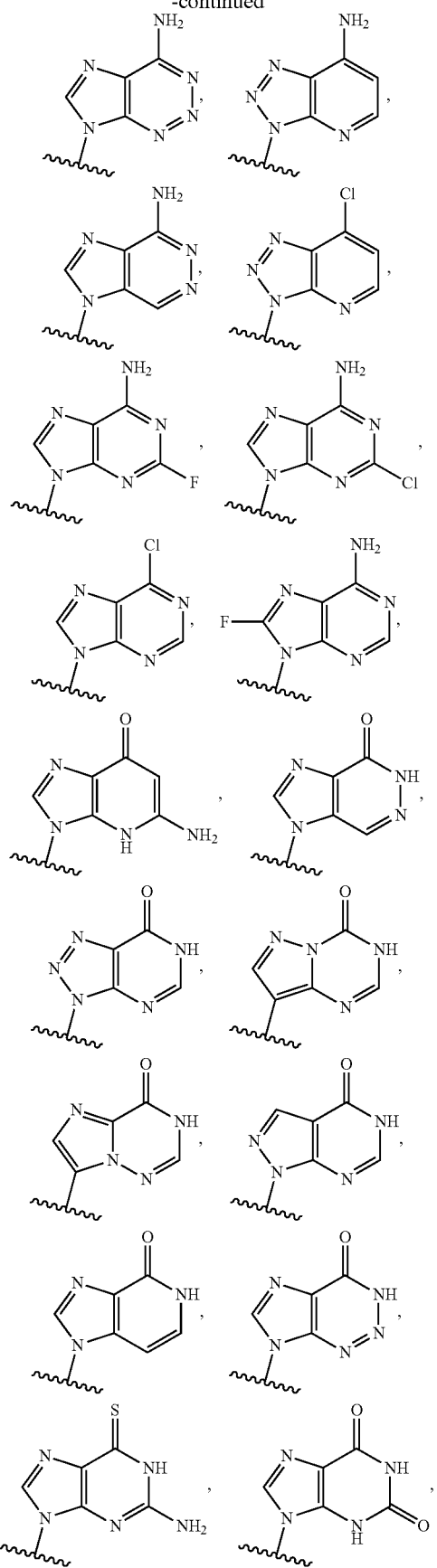
-continued
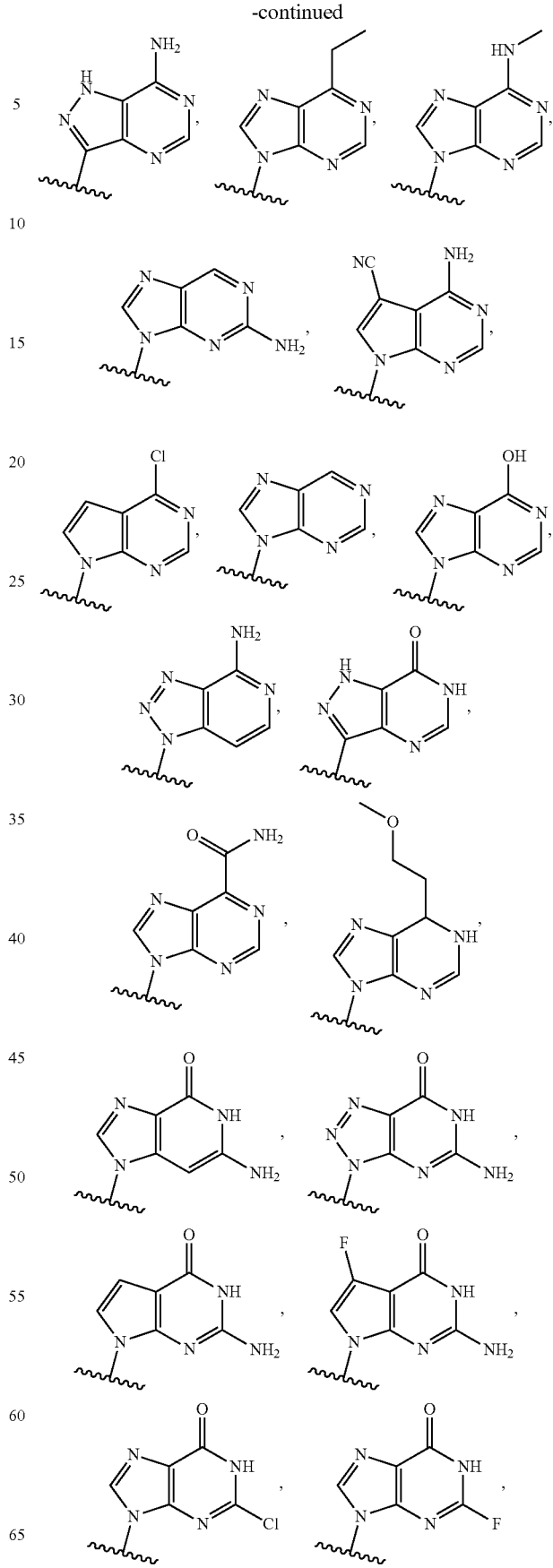

-continued

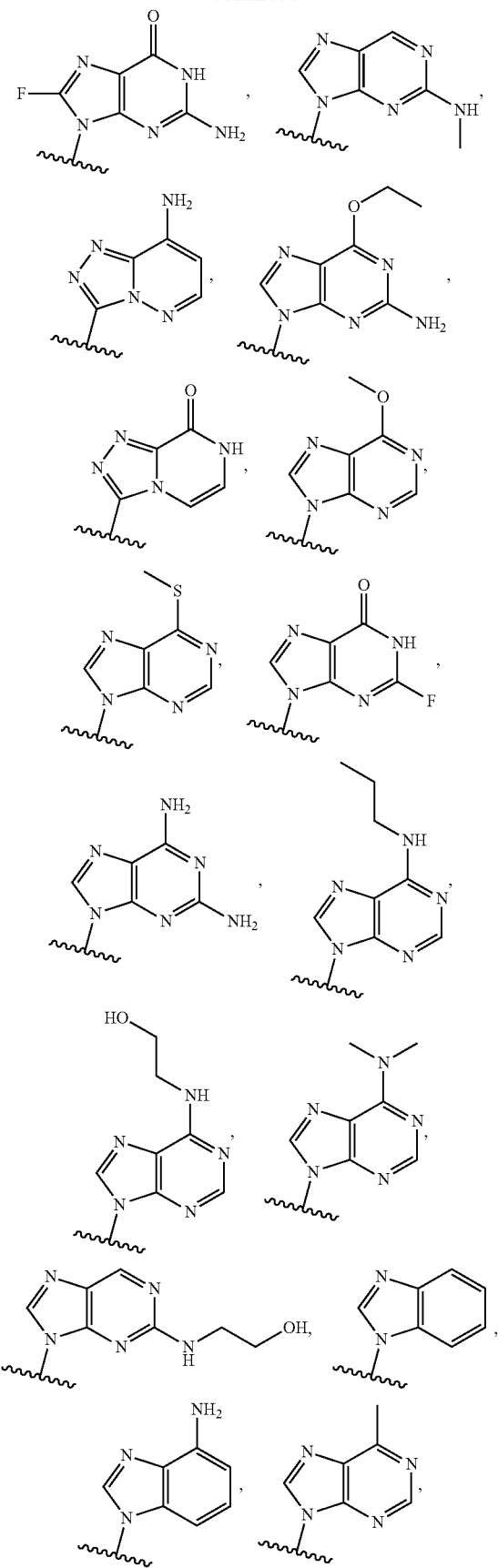

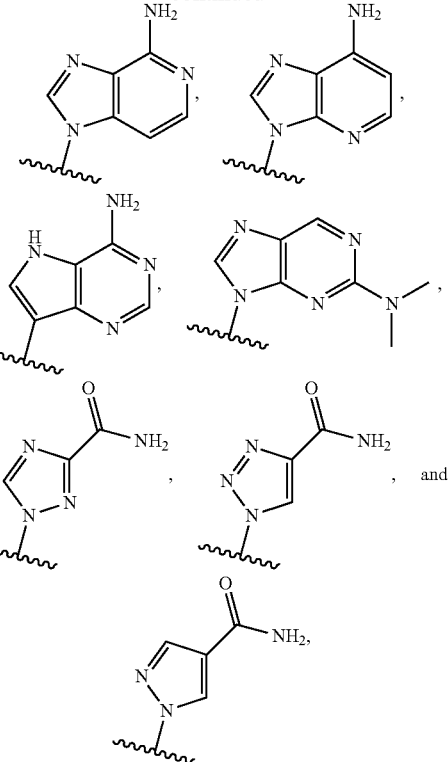

where Base[1] and Base[2] each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$; Y and $Y^a$ are each independently selected from the group consisting of —O— and —S—; $X^a$ and $X^{a1}$ are each independently selected from the group consisting of O, and S; $X^b$ and $X^{b1}$ are each independently selected from the group consisting of O, and S; $X^c$ and $X^{c1}$ are each independently selected from the group consisting of $OR^9$, $SR^9$, and $NR^9R^9$; $X^d$ and $X^{d1}$ are each independently selected from the group consisting of O and S; $R^1$ and $R^{1a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^1$ and $R^{1a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^2$ and $R^{2a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^2$ and $R^{2a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^3$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^3C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^4$ and $R^{4a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^4$ and $R^{4a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^5$ is selected from the group consisting of H, F, Cl, Br, I, OH, CN, $NH_2$, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^5C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, $NR^9R^9$, and $N_3$; $R^6$ and $R^{6a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^6$ and $R^{6a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^7$ and $R^{7a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^7$ and $R^{7a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^8$ and $R^{8a}$ are each independently selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^8$ and $R^{8a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; each $R^9$ is independently selected from the group consisting of H, $C_1$-$C_{20}$ alkyl,

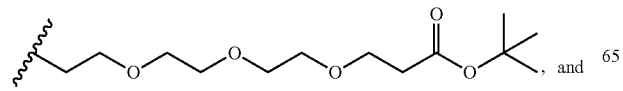, and

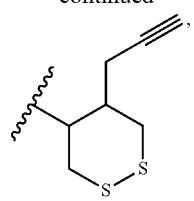, where each $R^9C_1$-$C_{20}$ alkyl is optionally substituted by 0 to 3 substituents independently selected from the group consisting of OH, —O—$C_1$-$C_{20}$ alkyl, —S—C(O)$C_1$-$C_6$ alkyl, and C(O)O$C_1$-$C_6$ alkyl; optionally $R^{1a}$ and $R^3$ are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^{1a}$ and $R^3$ are connected to form —O—$C_1$-$C_6$ alkylene, —O—$C_2$-$C_6$ alkenylene, or —O—$C_2$-$C_6$ alkynylene, said O is bound at the $R^3$ position; optionally $R^{2a}$ and $R^3$ are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^{2a}$ and $R^3$ are connected to form —O—$C_1$-$C_6$ alkylene, —O—$C_2$-$C_6$ alkenylene, or —O—$C_2$-$C_6$ alkynylene, said O is bound at the $R^3$ position; optionally $R^3$ and $R^{6a}$ are connected to form —O—$C_1$-$C_6$ alkylene, —O—$C_2$-$C_6$ alkenylene, or —O—$C_2$-$C_6$ alkynylene, such that where $R^3$ and $R^{6a}$ are connected to form —O—$C_1$-$C_6$ alkylene, —O—$C_2$-$C_6$ alkenylene, or —O—$C_2$-$C_6$ alkynylene, said O is bound at the $R^3$ position; optionally $R^4$ and $R^5$ are connected to form are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^4$ and $R^5$ are connected to form —O—$C_1$-$C_6$ alkylene, —O—$C_2$-$C_6$ alkenylene, or —O—$C_2$-$C_6$ alkynylene, said O is bound at the $R^5$ position; optionally $R^5$ and $R^6$ are connected to form —O—$C_1$-$C_6$ alkylene, —O—$C_2$-$C_6$ alkenylene, or —O—$C_2$-$C_6$ alkynylene, such that where $R^5$ and $R^6$ are connected to form —O—$C_1$-$C_6$ alkylene, —O—$C_2$-$C_6$ alkenylene, or —O—$C_2$-$C_6$ alkynylene, said O is bound at the $R^5$ position; optionally $R^7$ and $R^8$ are connected to form $C_1$-$C_6$ alkylene, $C_2$-$C_6$ alkenylene, or $C_2$-$C_6$ alkynylene; and optionally $R^{7a}$ and $R^{8a}$ are connected to form $C_1$-$C_6$ alkylene, $C_2$-$C_6$ alkenylene, or $C_2$-$C_6$ alkynylene.

In specific aspects of this embodiment, when Y and $Y^a$ are each O, $X^a$ and $X^{a1}$ are each O, $X^b$ and $X^{b1}$ are each O, and $X^c$ and $X^{c1}$ are each OH or SH, $X^d$ and $X^{d1}$ are each O, $R^1$ and $R^{1a}$ are each H, $R^2$ is H, $R^6$ and $R^{6a}$ are each H, $R^7$ and $R^{7a}$ are each H, $R^8$ and $R^{8a}$ are each H, and Base$^1$ and Base$^2$ are each selected from the group consisting of

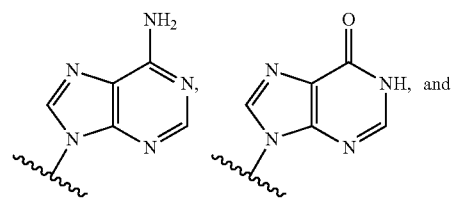

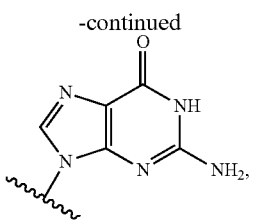

$R^5$ and $R^3$ are not both selected from the group consisting of H, F and OH. That is, when Y and $Y^a$ are each O, $X^a$ and $X^{a1}$ are each O, $X^b$ and $X^{b1}$ are each O, and $X^c$ and $X^{c1}$ are each OH or SH, $X^d$ and $X^{d1}$ are each O, $R^1$ and $R^{1a}$ are each H, $R^2$ is H, $R^6$ and $R^{6a}$ are each H, $R^7$ and $R^{7a}$ are each H, $R^8$ and $R^{8a}$ are each H, and Base$^1$ and Base$^2$ are each selected from the group consisting of

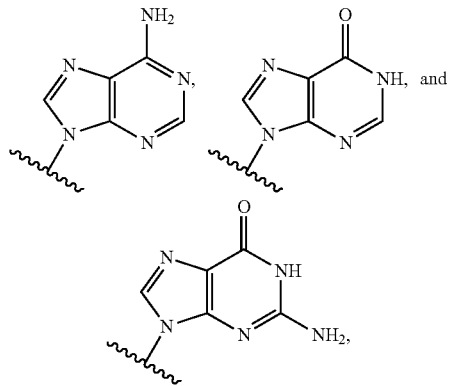

either only one of $R^5$ and $R^3$ is selected from the group consisting of H, F, and OH, or neither $R^5$ and $R^3$ is selected from the group consisting of H, F, and OH. In further specific instances of this aspect, when Y and $Y^a$ are each O, $X^a$ and $X^{a1}$ are each O, $X^b$ and $X^{b1}$ are each O, and $X^c$ and $X^{c1}$ are each OH, $X^d$ and $X^{d1}$ are each O or S, $R^1$ and $R^{1a}$ are each H, $R^2$ is H, $R^6$ and $R^{6a}$ are each H, $R^7$ and $R^{7a}$ are each H, $R^8$ and $R^{8a}$ are each H, and Base$^1$ and Base$^2$ are each selected from the group consisting of

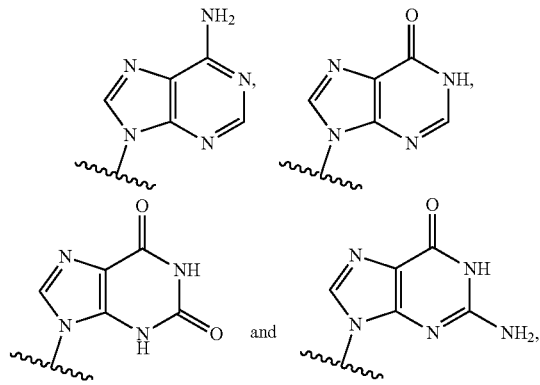

$R^5$ and $R^3$ are not both selected from the group consisting of H, $C_1$-$C_6$ alkyl, $C_2$-$C_6$ alkenyl, $C_2$-$C_6$ alkynyl, where said $C_1$-$C_6$ alkyl, $C_2$-$C_6$ alkenyl and $C_2$-$C_6$ alkynyl are substituted by 0 to 3 substituents selected from the group consisting of F, Cl, Br, I and OH.

In further specific aspects of this embodiment, when Base$^1$ and Base$^2$ are each selected from the group consisting of

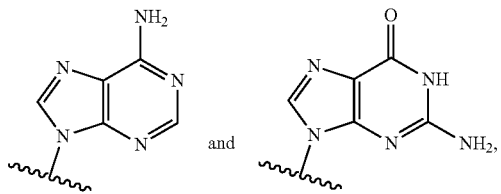 [SMILES: *n1cnc2c(N)ncnc21 ; *n1cnc2c(=O)[nH]c(N)nc21]

and $R^{2a}$ is F and $R^5$ is F, at least one of $X^c$ and $X^{c1}$ is $SR^9$.

In a first aspect of the second embodiment, Base$^1$ and Base$^2$ are each independently selected from the group consisting of

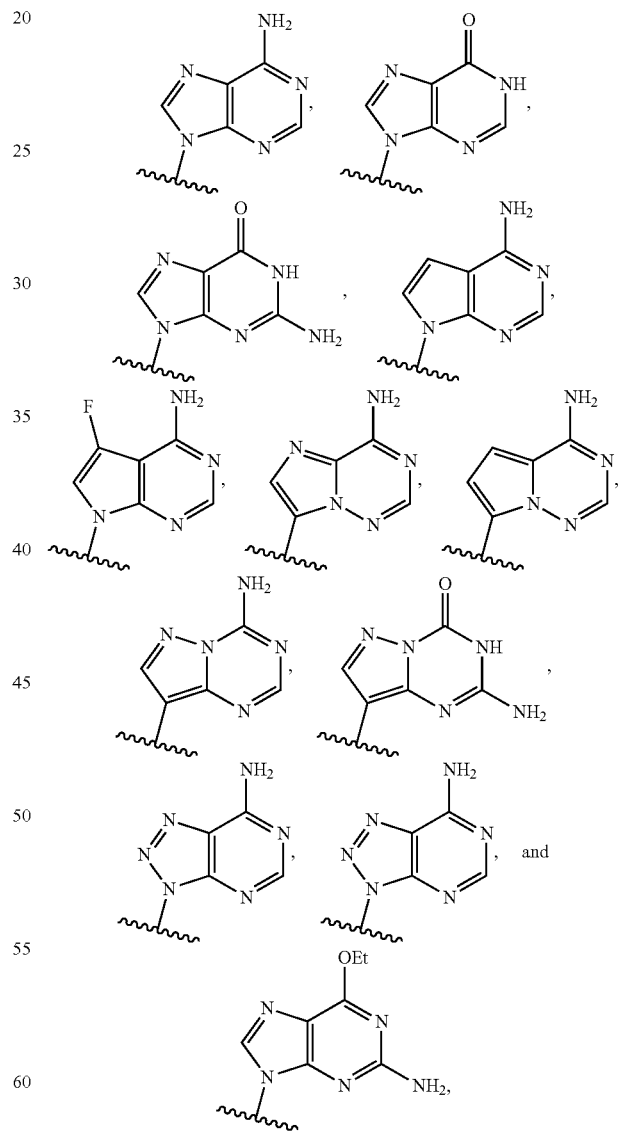

where Base$^1$ and Base$^2$ each may be independently substituted by 0-3 substituents $R^{10}$, where each $R^{10}$ is independently selected from the group consisting of F, Cl, I, Br, OH, SH, NH$_2$, $C_{1-3}$ alkyl, $C_{3-6}$ cycloalkyl, O($C_{1-3}$ alkyl), O($C_{3-6}$ cycloalkyl), S(C$_{1-3}$ alkyl), S(C$_{3-6}$ cycloalkyl), NH(C$_{1-3}$ alkyl), NH(C$_{3-6}$ cycloalkyl), N(C$_{1-3}$ alkyl)$_2$, and N(C$_{3-6}$ cycloalkyl)$_2$. In particular instances, Base$^1$ and Base$^2$ are each independently selected from the group consisting of

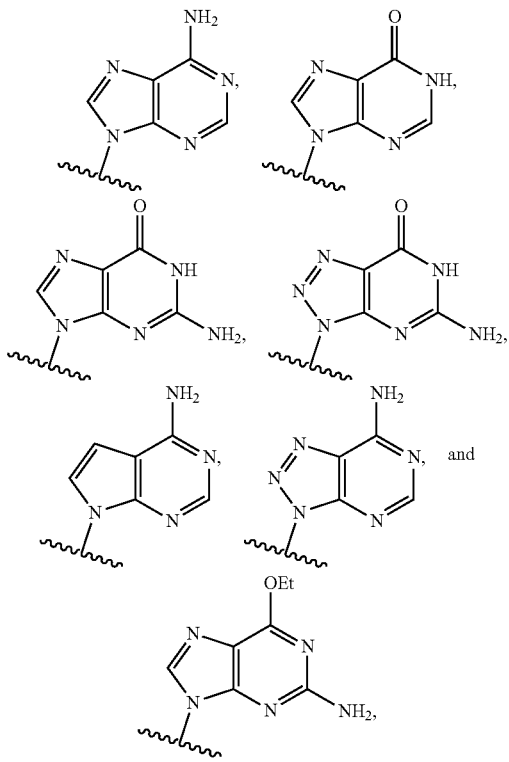

where Base$^1$ and Base$^2$ each may be independently substituted by 0-3 substituents R$^{10}$, where each R$^{10}$ is independently selected from the group consisting of F, Cl, I, Br, OH, SH, NH$_2$, C$_{1-3}$ alkyl, C$_{3-6}$ cycloalkyl, O(C$_{1-3}$ alkyl), O(C$_{3-6}$ cycloalkyl), S(C$_{1-3}$ alkyl), S(C$_{3-6}$ cycloalkyl), NH(C$_{1-3}$ alkyl), NH(C$_{3-6}$ cycloalkyl), N(C$_{1-3}$ alkyl)$_2$, and N(C$_{3-6}$ cycloalkyl)$_2$. In even more particular instances, Base$^1$ and Base$^2$ are each independently selected from the group consisting of

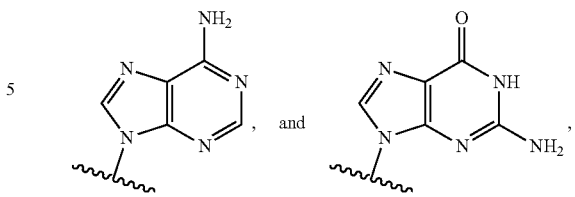

where Base$^1$ and Base$^2$ each may be independently substituted by 0-3 substituents R$^{10}$, where each R$^{10}$ is independently selected from the group consisting of F, Cl, I, Br, OH, SH, NH$_2$, C$_{1-3}$ alkyl, C$_{3-6}$ cycloalkyl, O(C$_{1-3}$ alkyl), O(C$_{3-6}$ cycloalkyl), S(C$_{1-3}$ alkyl), S(C$_{3-6}$ cycloalkyl), NH(C$_{1-3}$ alkyl), NH(C$_{3-6}$ cycloalkyl), N(C$_{1-3}$ alkyl)$_2$, and N(C$_{3-6}$ cycloalkyl)$_2$. In this aspect, all other groups are as provided in the general formula (I') of the second embodiment above.

In a second aspect of the second embodiment, X$^c$ and X$^{c1}$ are each independently selected from the group consisting of OR$^9$, SR$^9$, and NR$^9$R$^9$, where each R$^9$ is independently selected from the group consisting of H, C$_1$-C$_{20}$ alkyl,

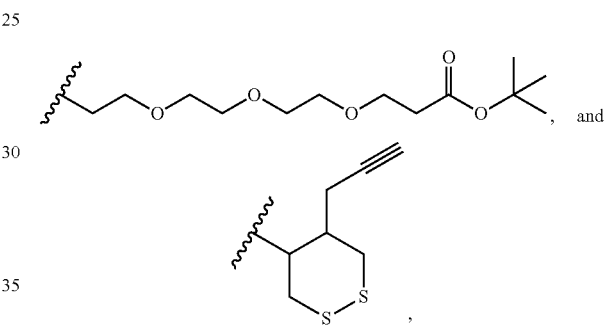

where each R$^9$C$_1$-C$_{20}$ alkyl is optionally substituted by 0 to 3 substituents independently selected from the group consisting of OH, —O—C$_1$-C$_{20}$ alkyl, —S—C(O)C$_1$-C$_6$ alkyl, and C(O)OC$_1$-C$_6$ alkyl. In particular instances, X$^c$ and X$^{c1}$ are each independently selected from the group consisting of O$^-$, S$^-$,

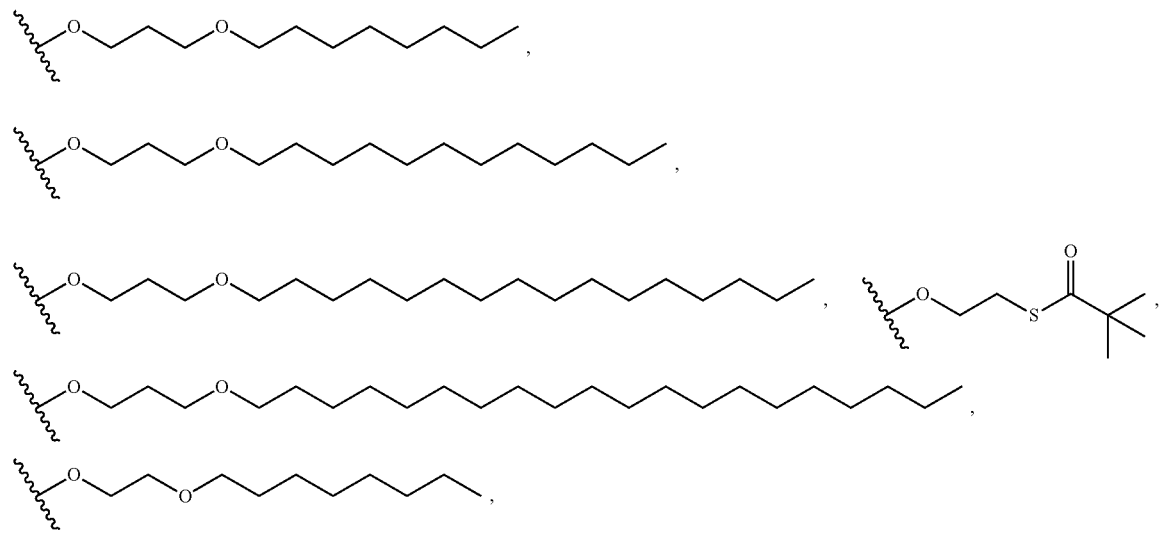

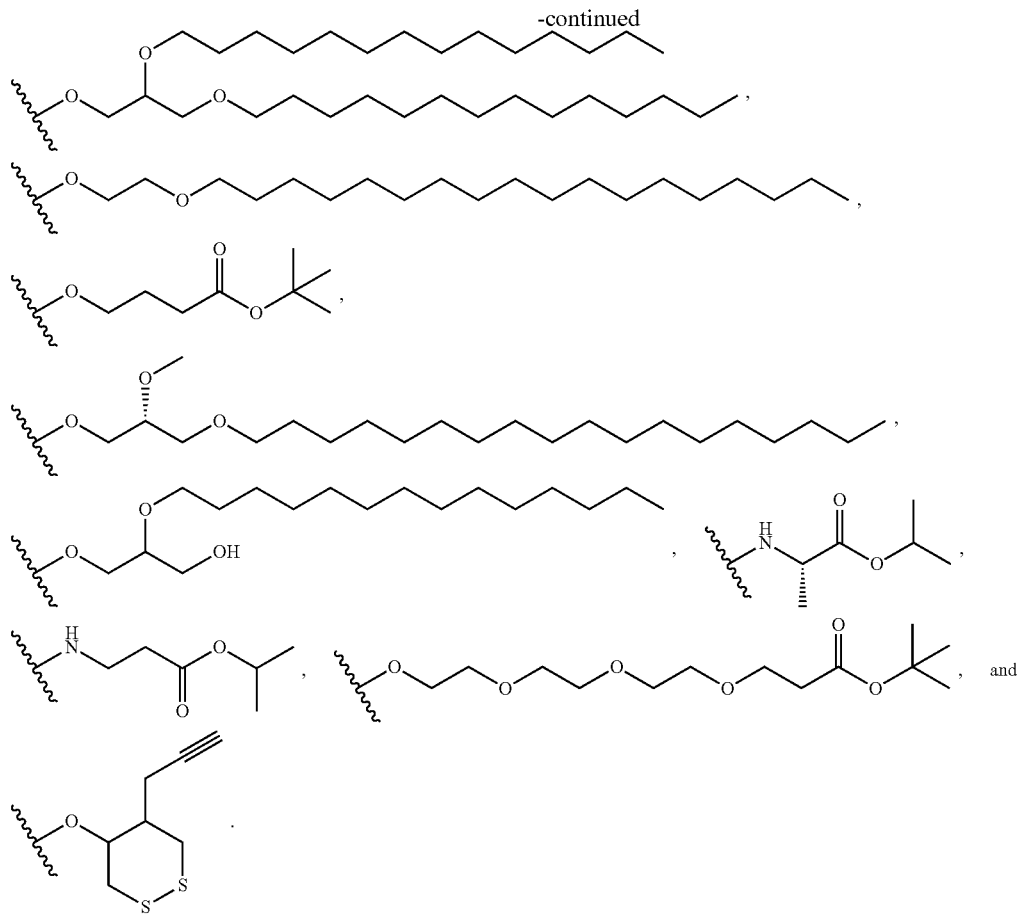

In all instances of this aspect, all other groups are as provided in the general formula (I') of the second embodiment above or in the first aspect described above.

In a third aspect of the second embodiment, $R^1$ and $R^{1a}$ are each H. In this aspect, all other groups are as provided in the general formula (I') of the second embodiment above or in the first through second aspects described above.

In a fourth aspect of the second embodiment, $R^2$ and $R^{2a}$ are each independently selected from the group consisting of H, F, Cl, I, Br, OH, $N_3$, $C_1$-$C_6$ alkyl, and $C_1$-$C_6$ haloalkyl, where said $R^2$ and $R^{2a}$ $C_1$-$C_6$ alkyl or $C_1$-$C_6$ haloalkyl are substituted by 0 to 3 substituents selected from the group consisting of F, Cl, Br, I, OH, CN, and $N_3$. In particular instances, $R^2$ and $R^{2a}$ are each independently selected from the group consisting of H, F, Cl, I, Br, OH, CN, $N_3$, $CF_3$, $CH_3$, $CH_2OH$, and $CH_2CH_3$. In this aspect, all other groups are as provided in the general formula (I') of the second embodiment above or in the first through third aspects described above.

In a fifth aspect of the second embodiment, $R^3$ is selected from the group consisting H, F, Cl, I, Br, OH, $N_3$, $C_1$-$C_6$ alkyl, and $C_1$-$C_6$ haloalkyl, where said $R^3C_1$-$C_6$ alkyl or $C_1$-$C_6$ haloalkyl are substituted by 0 to 3 substituents selected from the group consisting of F, Cl, Br, I, OH, CN, and $N_3$. In particular instances, $R^3$ are each independently selected from the group consisting of H, F, Cl, I, Br, OH, CN, $N_3$, $CF_3$, $CH_3$, $CH_2OH$, and $CH_2CH_3$. In even more particular instances, $R^3$ is selected from $NH_2$ and $N_3$. In this aspect, all other groups are as provided in the general formula (I') of the second embodiment above or in the first through fourth aspects described above.

In a sixth aspect of the second embodiment, $R^4$ and $R^{4a}$ are each independently selected from the group consisting of H, F, Cl, I, Br, OH, $N_3$, $C_1$-$C_6$ alkyl, and $C_1$-$C_6$ haloalkyl, where said $R^4$ and $R^{4a}$ $C_1$-$C_6$ alkyl or $C_1$-$C_6$ haloalkyl are substituted by 0 to 3 substituents selected from the group consisting of F, Cl, Br, I, OH, CN, and $N_3$. In particular instances, $R^4$ and $R^{4a}$ are each independently selected from the group consisting of H, F, Cl, I, Br, OH, CN, $N_3$, $CF_3$, $CH_3$, $CH_2OH$, and $CH_2CH_3$. In even more particular instances, $R^4$ and $R^{4a}$ are each F. In this aspect, all other groups are as provided in the general formula (I') of the second embodiment above or in the first through fifth aspects described above.

In a seventh aspect of the second embodiment, $R^5$ is selected from the group consisting of H, F, Cl, Br, I, OH, $NH_2$, $N_3$, $C_1$-$C_6$ alkyl, and $C_1$-$C_6$ haloalkyl, where said $R^5C_1$-$C_6$ alkyl or $C_1$-$C_6$ haloalkyl are substituted by 0 to 3 substituents selected from the group consisting of F, Cl, Br, I, OH, CN, $NR^9R^9$, and $N_3$. In particular instances, $R^5$ are each independently selected from the group consisting of H, F, Cl, I, Br, OH, CN, $N_3$, $CF_3$, $CH_3$, $CH_2OH$, and $CH_2CH_3$. In even more particular instances, $R^5$ is selected from $NH_2$ and $N_3$. In this aspect, all other groups are as provided in the general formula (I') of the second embodiment above or in the first through sixth aspects described above.

In an eighth aspect of the second embodiment, $R^6$ and $R^{6a}$ are each independently selected from the group consisting of H, F, Cl, I, Br, OH, $C_1$-$C_6$ alkyl, $C_2$-$C_6$ alkenyl, and $C_2$-$C_6$ alkynyl. In this aspect, all other groups are as provided in the general formula (I') of the second embodiment above or in the first through seventh aspects described above.

In a ninth aspect of the second embodiment, $R^7$ and $R^{7a}$ are each independently selected from the group consisting of H and $C_1$-$C_6$ alkyl. In particular instances, $R^7$ and $R^{7a}$ are each independently selected from the group consisting of H and $CH_3$. In more particular instances, $R^{7a}$ is $CH_3$. In additional instances, $R^7$ and $R^{7a}$ are each H. In this aspect, all other groups are as provided in the general formula (I') of the second embodiment above or in the first through eighth aspects described above.

In a tenth aspect of the second embodiment, $R^8$ and $R^{8a}$ are each independently selected from the group consisting of H and $C_1$-$C_6$ alkyl. In particular instances, $R^8$ and $R^{8a}$ are each independently selected from the group consisting of H and $CH_3$. In more particular instances, $R^{8a}$ is $CH_3$. In additional instances, $R^8$ and $R^{8a}$ are each H. In this aspect, all other groups are as provided in the general formula (I') of the second embodiment above or in the first through ninth aspects described above.

In an eleventh aspect of the second embodiment, $R^{1a}$ and $R^3$ are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^{1a}$ and $R^3$ are connected to form —O—$C_1$-$C_6$ alkylene, —O—$C_2$-$C_6$ alkenylene, or —O—$C_2$-$C_6$ alkynylene, said O is bound at the $R^3$ position. In this aspect, all other groups are as provided in the general formula (I') of the second embodiment above or in the first through tenth aspects described above.

In a twelfth aspect of the second embodiment, $R^{2a}$ and $R^3$ are connected to form $C_1$-$C_6$ alkylene, $C_2$-$C_6$ alkenylene, $C_2$-$C_6$ alkynylene, —O—$C_1$-$C_6$ alkylene, —O—$C_2$-$C_6$ alkenylene, or —O—$C_2$-$C_6$ alkynylene, such that where $R^{2a}$ and $R^3$ are connected to form —O—$C_1$-$C_6$ alkylene, —O—$C_2$-$C_6$ alkenylene, or —O—$C_2$-$C_6$ alkynylene, said O is bound at the $R^3$ position. In this aspect, all other groups are as provided in the general formula (I') of the second embodiment above or in the first through eleventh aspects described above.

In a thirteenth aspect of the second embodiment, $R^3$ and $R^{6a}$ are connected to form —O—$C_1$-$C_6$ alkylene, —O—$C_2$-$C_6$ alkenylene, and —O—$C_2$-$C_6$ alkynylene, such that where $R^3$ and $R^{6a}$ are connected to form —O—$C_1$-$C_6$ alkylene, —O—$C_2$-$C_6$ alkenylene, or —O—$C_2$-$C_6$ alkynylene, said O is bound at the $R^3$ position. In this aspect, all other groups are as provided in the general formula (I') of the second embodiment above or in the first through eleventh aspects described above.

In a fourteenth aspect of the second embodiment, $R^4$ and $R^5$ are connected by $C_1$-$C_6$ alkylene, —O—$C_1$-$C_6$ alkylene, —O—$C_2$-$C_6$ alkenylene, or —O—$C_2$-$C_6$ alkynylene, such that where $R^4$ and $R^5$ are connected to form —O—$C_1$-$C_6$ alkylene, —O—$C_2$-$C_6$ alkenylene, or —O—$C_2$-$C_6$ alkynylene, said O is bound at the $R^5$ position. In this aspect, all other groups are as provided in the general formula (I') of the second embodiment above or in the first through eleventh aspects described above.

In a fifteenth aspect of the second embodiment, $R^5$ and $R^6$ are connected to form —O—$C_1$-$C_6$ alkylene, —O—$C_2$-$C_6$ alkenylene, or —O—$C_2$-$C_6$ alkynylene, such that where $R^5$ and $R^6$ are connected to form —O—$C_1$-$C_6$ alkylene, —O—$C_2$-$C_6$ alkenylene, or —O—$C_2$-$C_6$ alkynylene, said O is bound at the $R^5$ position. In this aspect, all other groups are as provided in the general formula (I') of the second embodiment above or in the first through eleventh aspects described above.

In a sixteenth aspect of the second embodiment, $R^7$ and $R^8$ are connected to form $C_1$-$C_6$ alkylene, $C_2$-$C_6$ alkenylene, or $C_2$-$C_6$ alkynylene. In this aspect, all other groups are as provided in the general formula (I') of the second embodiment above or in the first through eleventh aspects described above.

In a seventeenth aspect of the second embodiment, $R^{7a}$ and $R^{8a}$ are connected to form $C_1$-$C_6$ alkylene, $C_2$-$C_6$ alkenylene, or $C_2$-$C_6$ alkynylene. In this aspect, all other groups are as provided in the general formula (I') of the second embodiment above or in the first through eleventh aspects described above.

In an eighteenth aspect of the second embodiment, $Base^1$ and $Base^2$ are each independently selected from the group consisting of

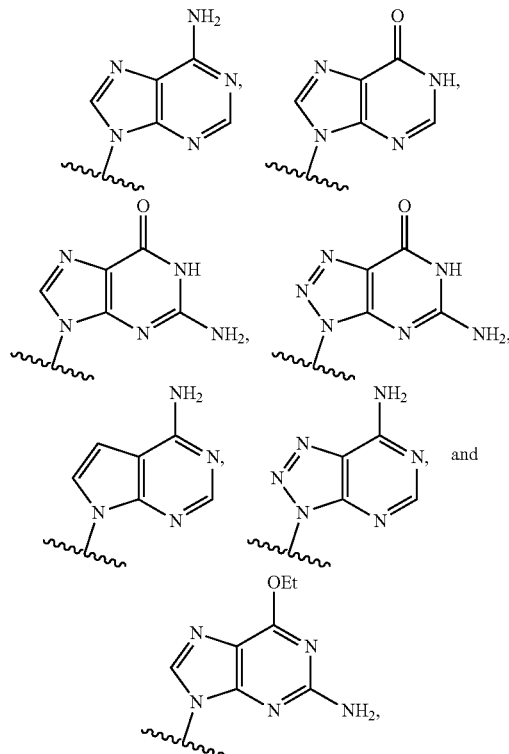

where $Base^1$ and $Base^2$ each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl$)_2$, and $N(C_{3-6}$ cycloalkyl$)_2$; Y and $Y^a$ are each independently selected from the group consisting of —O— and —S—; $X^a$ and $X^{a1}$ are each independently selected from the group consisting of O and S; $X^b$ and $X^{b1}$ are each independently selected from the group consisting of O and S; $X^c$ and $X^{c1}$ are each independently selected from the group consisting of $OR^9$, $SR^9$, and $NR^9R^9$; $X^d$ and $X^{d1}$ are each independently selected from the group consisting of O and S; $R^1$ and $R^{1a}$ are each H; $R^2$ and $R^{2a}$ are each independently selected from the group consisting of H, F, Cl, Br, I, OH, $N_3$, $C_1$-$C_6$ alkyl, and $C_1$-$C_6$ haloalkyl, where said $R^2$ and $R^{2a}$ $C_1$-$C_6$ alkyl or $C_1$-$C_6$ haloalkyl are substituted by 0 to 3 substituents selected from the group consisting of F, Cl, Br, I, OH, CN, and $N_3$; $R^3$ is selected from the group consisting of H, F, Cl, Br, I, OH, CN, $N_3$, $C_1$-$C_6$ alkyl, and $C_1$-$C_6$ haloalkyl, where said $R^3 C_1$-$C_6$ alkyl or $C_1$-$C_6$ haloalkyl are substituted by 0 to 3 substituents selected from the group consisting of F, Cl, Br, I, OH, CN, and $N_3$; $R^4$ and $R^{4a}$ are each independently selected from the group consisting of H, $C_1$-$C_6$ alkyl, and $C_1$-$C_6$ haloalkyl, where said $R^4$ and $R^{4a}$ $C_1$-$C_6$ alkyl or $C_1$-$C_6$ haloalkyl are substituted by 0 to 3 substituents selected from the group consisting of F, Cl, Br, I, OH, CN, and $N_3$; $R^5$ is selected from the group consisting of H, F, Cl, Br, I, OH, $NH_2$, $N_3$, $C_1$-$C_6$ alkyl, and $C_1$-$C_6$ haloalkyl, where said $R^5 C_1$-$C_6$ alkyl or $C_1$-$C_6$ haloalkyl are substituted by 0 to 3 substituents selected from the group consisting of F, Cl, Br, I, OH, CN, $NR^9R^9$, and $N_3$; $R^6$ and $R^{6a}$ are each independently selected from the group consisting of H, F, Cl, Br, I, OH, $C_1$-$C_6$ alkyl, $C_2$-$C_6$ alkenyl, $C_2$-$C_6$ alkynyl, and $C_1$-$C_6$ haloalkyl, where said $R^6$ and $R^{6a}$ $C_1$-$C_6$ alkyl or $C_1$-$C_6$ haloalkyl are substituted by 0 to 3 substituents selected from the group consisting of F, Cl, Br, I, OH, CN, and $N_3$; $R^7$ and $R^{7a}$ are each H; $R^8$ and $R^{8a}$ are each H; each $R^9$ is independently selected from the group consisting of H, $C_2$-$C_3$ alkyl,

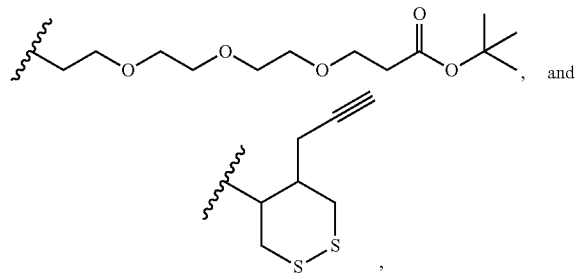

, and where each $R^9 C_2$-$C_3$ alkyl is optionally substituted by 1 to 2 substituents independently selected from the group consisting of OH, —O—$C_1$-$C_{20}$ alkyl, —S—C(O)$C_1$-$C_6$ alkyl, and C(O)O$C_1$-$C_6$ alkyl; optionally $R^3$ and $R^{6a}$ are connected to form —O—$C_1$-$C_6$ alkylene, —O—$C_2$-$C_6$ alkenylene, and —O—$C_2$-$C_6$ alkynylene, such that where $R^3$ and $R^{6a}$ are connected to form —O—$C_1$-$C_6$ alkylene, —O—$C_2$-$C_6$ alkenylene, or —O—$C_2$-$C_6$ alkynylene, said O is bound at the $R^3$ position or optionally $R^4$ and $R^5$ are connected by $C_1$-$C_6$ alkylene, —O—$C_1$-$C_6$ alkylene, —O—$C_2$-$C_6$ alkenylene, or —O—$C_2$-$C_6$ alkynylene, such that where $R^4$ and $R^5$ are connected to form —O—$C_1$-$C_6$ alkylene, —O—$C_2$-$C_6$ alkenylene, or —O—$C_2$-$C_6$ alkynylene, said O is bound at the $R^5$ position. In all instances of this aspect, all other groups are as provided in the general formula (I') of the second embodiment above.

In a nineteenth aspect of the second embodiment, the compound of formula (I') is a compound of formula (I'a):

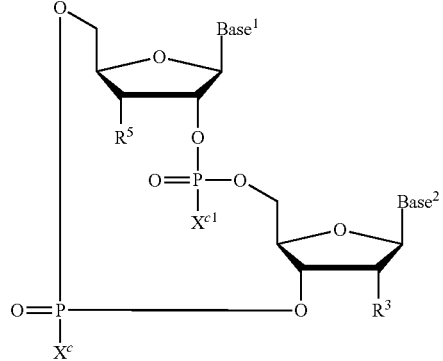

or a pharmaceutically acceptable salt, hydrate, solvate, or prodrug thereof, wherein Base$^1$ and Base$^2$ are each independently selected from the group consisting of

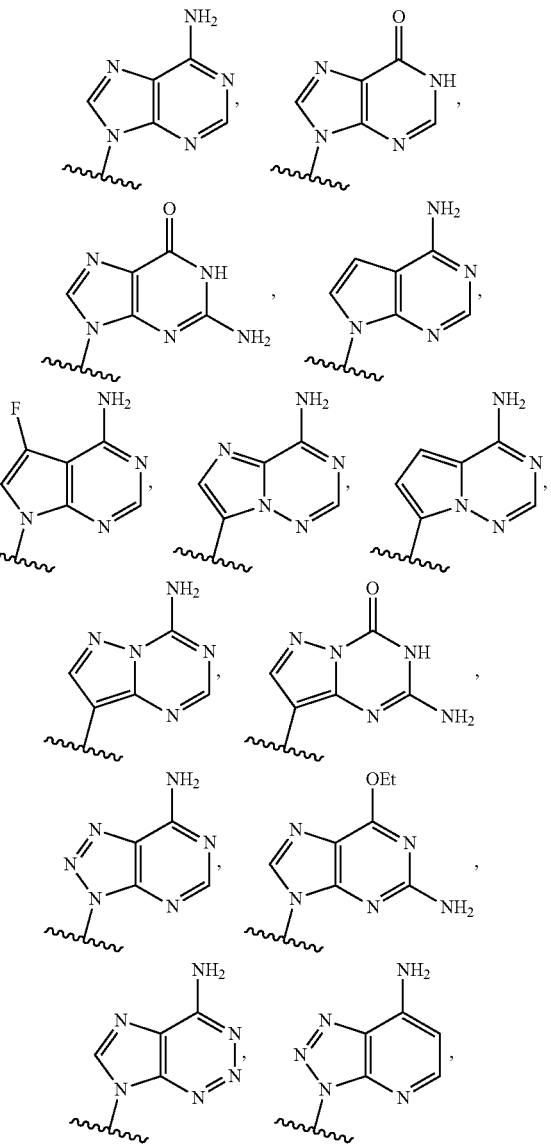

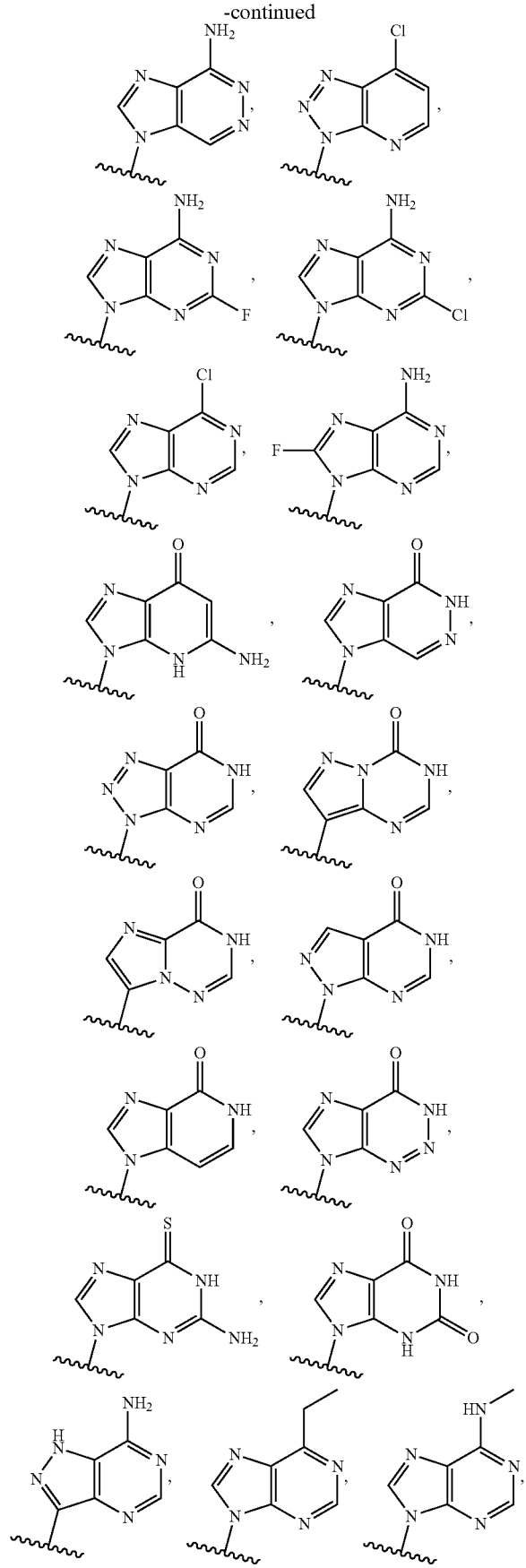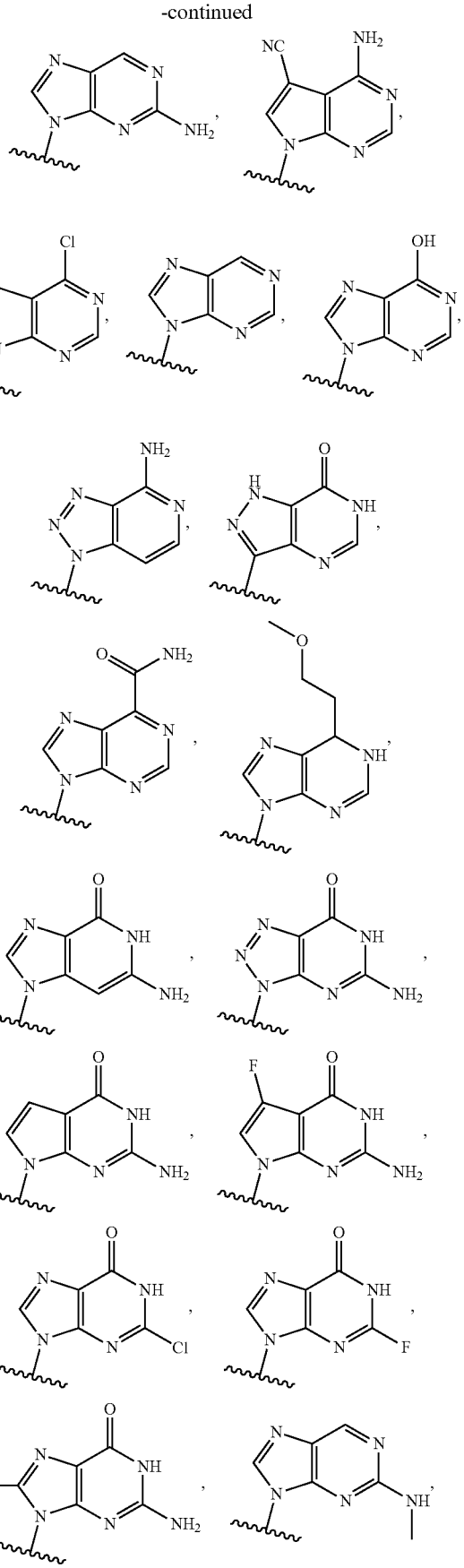

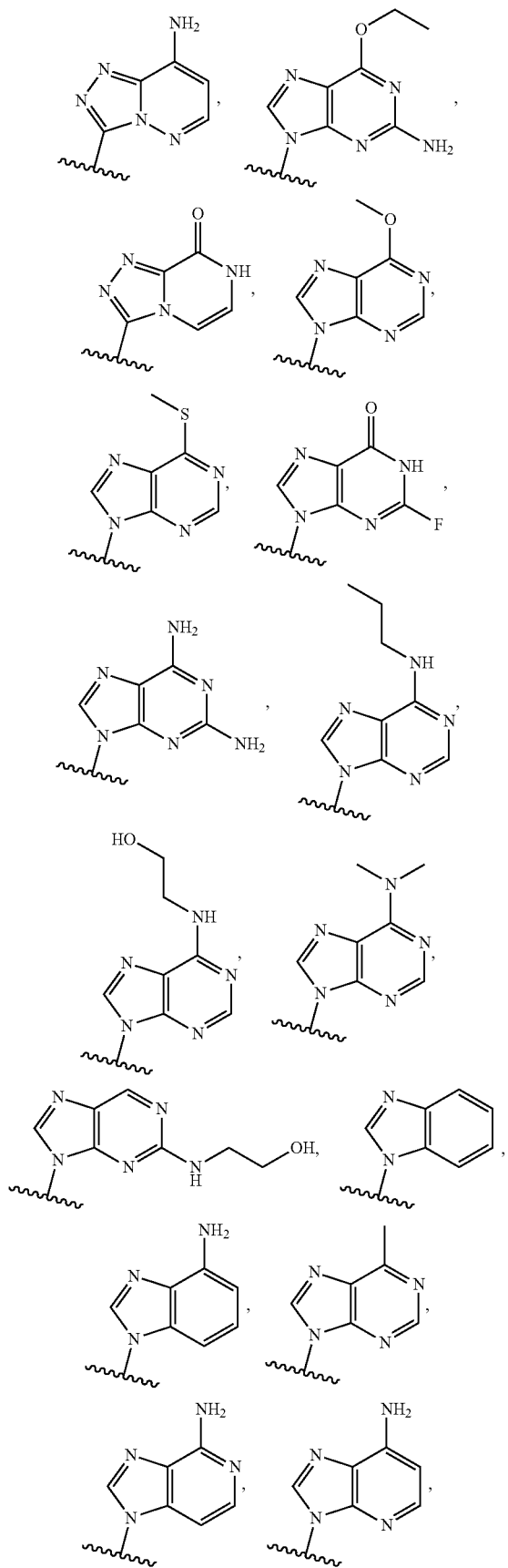

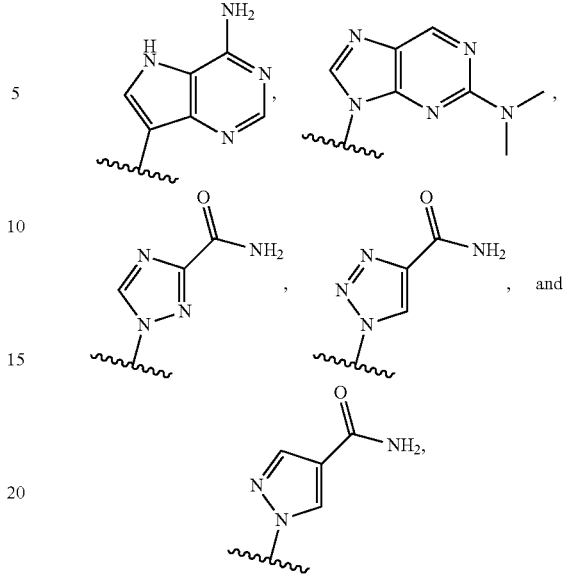

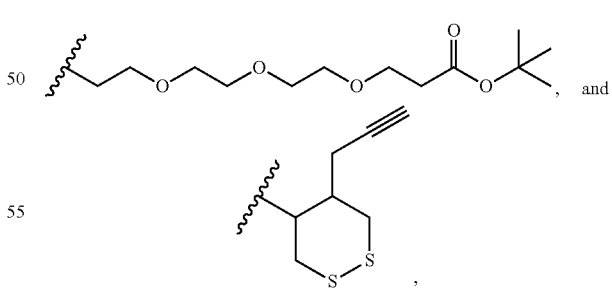

where Base$^1$ and Base$^2$ each may be independently substituted by 0-3 substituents R$^{10}$, where each R$^{10}$ is independently selected from the group consisting of F, Cl, I, Br, OH, SH, NH$_2$, C$_{1-3}$ alkyl, C$_{3-6}$ cycloalkyl, O(C$_{1-3}$ alkyl), O(C$_{3-6}$ cycloalkyl), S(C$_{1-3}$ alkyl), S(C$_{3-6}$ cycloalkyl), NH(C$_{1-3}$ alkyl), NH(C$_{3-6}$ cycloalkyl), N(C$_{1-3}$ alkyl)$_2$, and N(C$_{3-6}$ cycloalkyl)$_2$; X$^c$ and X$^{c1}$ are each independently selected from the group consisting of OR$^9$, SR$^9$, and NR$^9$R$^9$; R$^3$ is selected from the group consisting of H, F, Cl, Br, I, OH, CN, N$_3$, C$_1$-C$_6$ alkyl, and C$_1$-C$_6$ haloalkyl, where said R$^3$C$_1$-C$_6$ alkyl or C$_1$-C$_6$ haloalkyl are substituted by 0 to 3 substituents selected from the group consisting of F, Cl, Br, I, and OH; R$^5$ is selected from the group consisting of H, F, Cl, Br, I, OH, CN, NH$_2$, N$_3$, C$_1$-C$_6$ alkyl, and C$_1$-C$_6$ haloalkyl, where said R$^5$C$_1$-C$_6$ alkyl or C$_1$-C$_6$ haloalkyl are substituted by 0 to 3 substituents selected from the group consisting of F, Cl, Br, I, and OH; R$^3$ and R$^5$ are not both selected from the group consisting of: OH, R$^5$C$_1$-C$_6$ alkyl substituted with OH, or C$_1$-C$_6$ haloalkyl substituted with OH; and each R$^9$ is independently selected from the group consisting of H, C$_2$-C$_3$ alkyl, where each R$^9$C$_2$-C$_3$ alkyl is optionally substituted by 1 to 2 substituents independently selected from the group consisting of OH, —O—C$_1$-C$_{20}$ alkyl, —S—C(O)C$_1$-C$_6$ alkyl, and C(O)OC$_1$-C$_6$ alkyl. In all instances of this aspect, all other groups are as provided in the general formula (I') of the second embodiment above.

In a twentieth aspect of the second embodiment, the compound of formula (I') is a compound of formula (I'b):

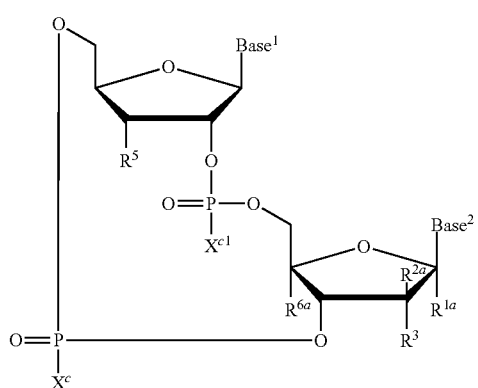
(I′b)
or a pharmaceutically acceptable salt, hydrate, solvate, or prodrug thereof, wherein Base¹ and Base² are each independently selected from the group consisting of
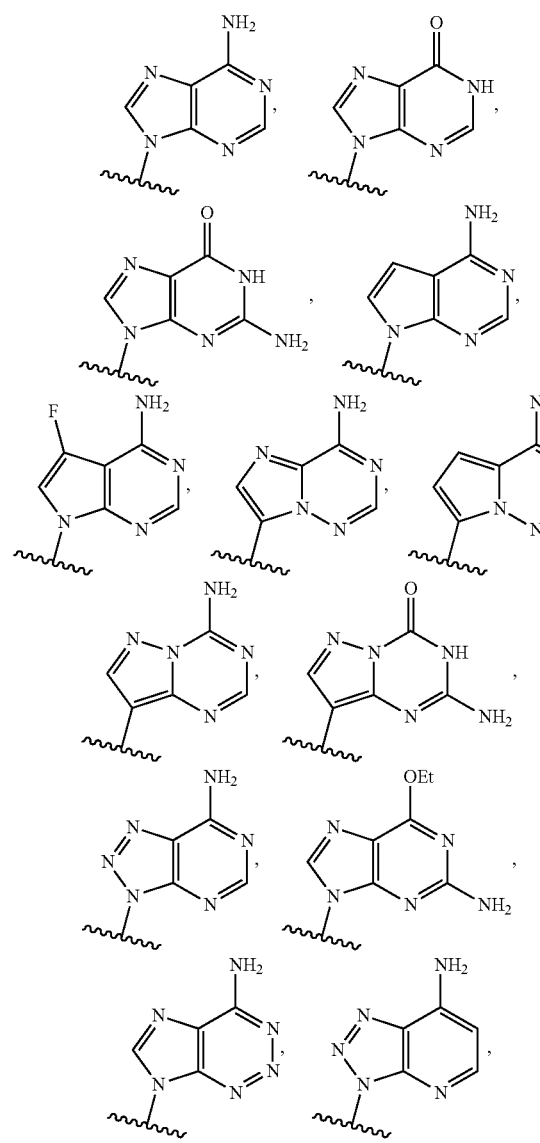
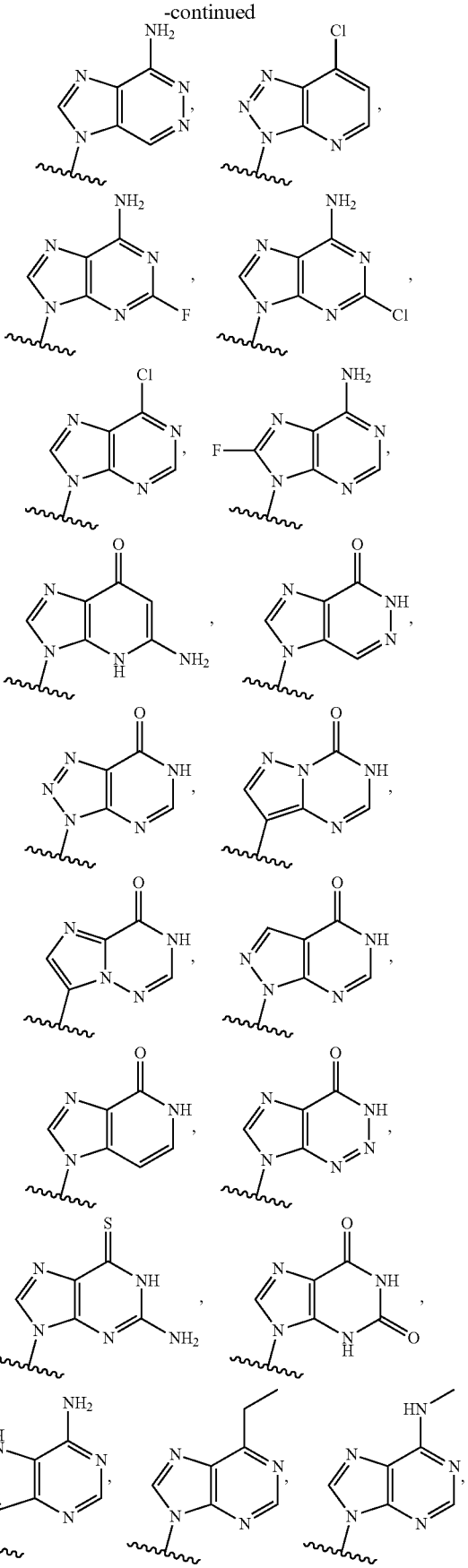

-continued
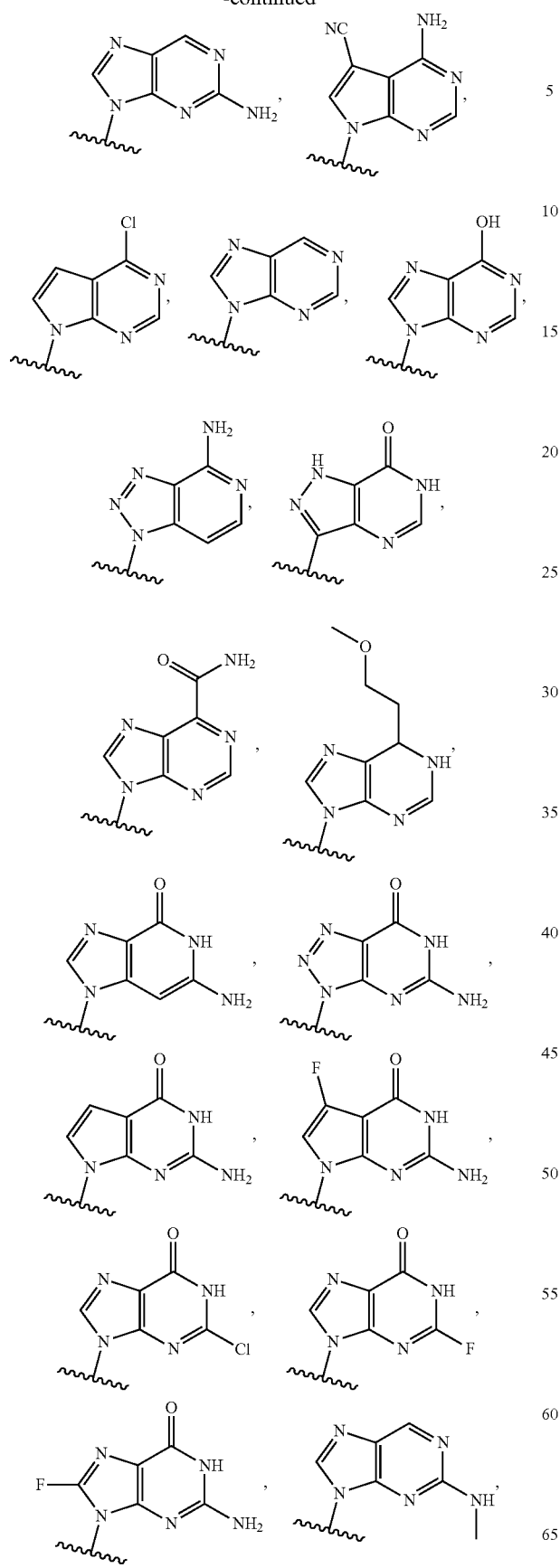
-continued
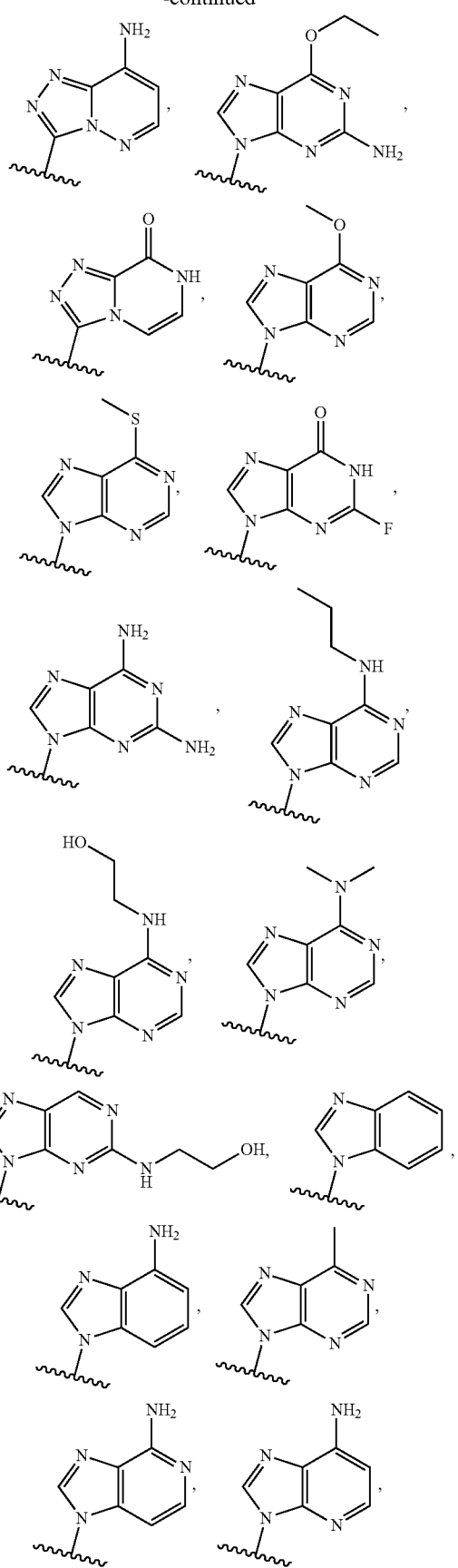

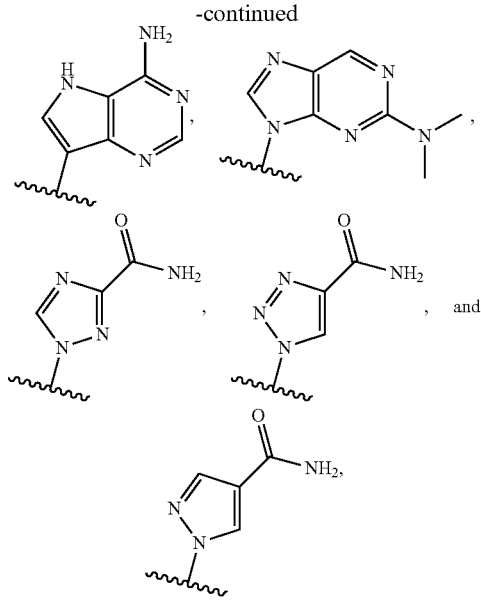

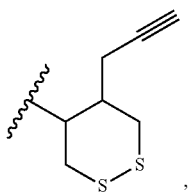

where Base[1] and Base[2] each may be independently substituted by 0-3 substituents $R^{10}$, where each $R^{10}$ is independently selected from the group consisting of F, Cl, I, Br, OH, SH, $NH_2$, $C_{1-3}$ alkyl, $C_{3-6}$ cycloalkyl, $O(C_{1-3}$ alkyl), $O(C_{3-6}$ cycloalkyl), $S(C_{1-3}$ alkyl), $S(C_{3-6}$ cycloalkyl), $NH(C_{1-3}$ alkyl), $NH(C_{3-6}$ cycloalkyl), $N(C_{1-3}$ alkyl)$_2$, and $N(C_{3-6}$ cycloalkyl)$_2$; $X^c$ and $X^{c1}$ are each independently selected from the group consisting of $OR^9$, $SR^9$, and $NR^9R^9$; $R^{1a}$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl, where said $R^{1a}$ $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl are substituted by 0 to 3 substituents selected from the group consisting of F, Cl, Br, I, OH, CN, and $N_3$; $R^{2a}$ is selected from the group consisting of H, F, Cl, Br, I, OH, CN, $N_3$, $C_1$-$C_6$ alkyl, and $C_1$-$C_6$ haloalkyl, where said $R^{2a}$ $C_1$-$C_6$ alkyl or $C_1$-$C_6$ haloalkyl are substituted by 0 to 3 substituents selected from the group consisting of F, Cl, Br, I, and OH; $R^3$ is selected from the group consisting of H, F, Cl, Br, I, OH, CN, $N_3$, $C_1$-$C_6$ alkyl, and $C_1$-$C_6$ haloalkyl, where said $R^3 C_1$-$C_6$ alkyl or $C_1$-$C_6$ haloalkyl are substituted by 0 to 3 substituents selected from the group consisting of F, Cl, Br, I, and OH; $R^5$ is selected from the group consisting of H, F, Cl, Br, I, OH, CN, $NH_2$, $N_3$, $C_1$-$C_6$ alkyl, and $C_1$-$C_6$ haloalkyl, where said $R^5 C_1$-$C_6$ alkyl or $C_1$-$C_6$ haloalkyl are substituted by 0 to 3 substituents selected from the group consisting of F, Cl, Br, I, and OH; $R^3$ and $R^5$ are not both selected from the group consisting of OH, $C_1$-$C_6$ alkyl substituted with OH, and $C_1$-$C_6$ haloalkyl substituted with OH; $R^{6a}$ is selected from the group consisting of H, F, Cl, Br, I, OH, $C_1$-$C_6$ alkyl, $C_2$-$C_6$ alkenyl, and $C_2$-$C_6$ alkynyl; each $R^9$ is independently selected from the group consisting of H, $C_2$-$C_3$ alkyl,

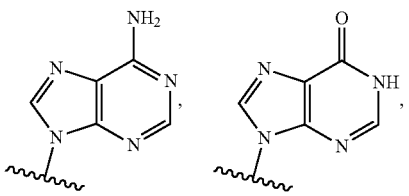, and

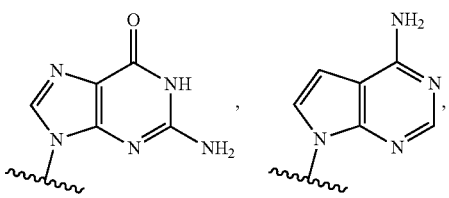

where each $R^9 C_2$-$C_3$ alkyl is optionally substituted by 1 to 2 substituents independently selected from the group consisting of OH, —O—$C_1$-$C_{20}$ alkyl, —S—$C(O)C_1$-$C_6$ alkyl, and $C(O)OC_1$-$C_6$ alkyl; and optionally $R^3$ and $R^{6a}$ are connected to form —O—$C_1$-$C_6$ alkylene, —O—$C_2$-$C_6$ alkenylene, and —O—$C_2$-$C_6$ alkynylene, such that where $R^3$ and $R^{6a}$ are connected to form —O—$C_1$-$C_6$ alkylene, —O—$C_2$-$C_6$ alkenylene, or —O—$C_2$-$C_6$ alkynylene, said O is bound at the $R^3$ position. In this aspect, all other groups are as provided in the general formula (I') of the second embodiment above.

In a twenty-first aspect of the second embodiment, the compound of formula (I') is a compound of formula (I'c):

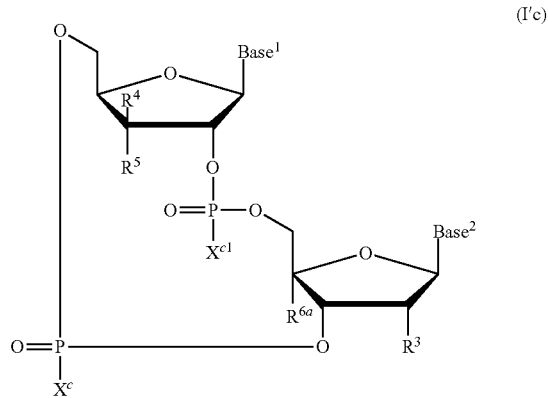

(I'c)

or a pharmaceutically acceptable salt, hydrate, solvate, or prodrug thereof, wherein Base[1] and Base[2] are each independently selected from the group consisting of -continued
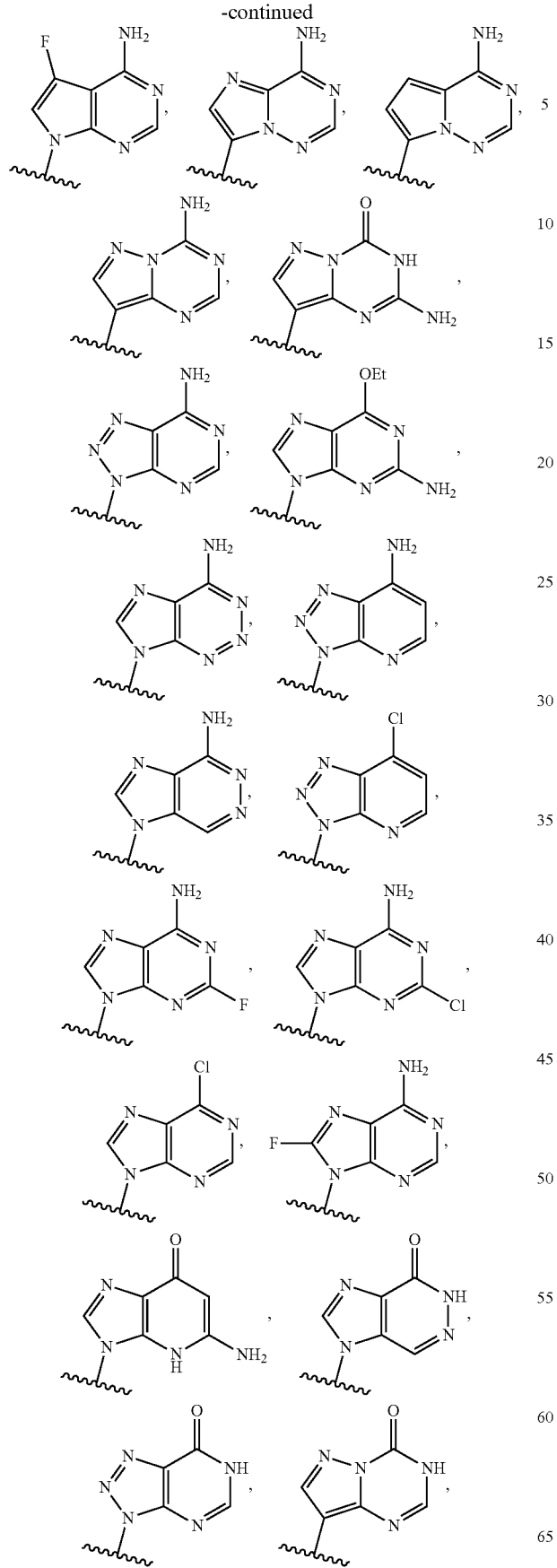
-continued
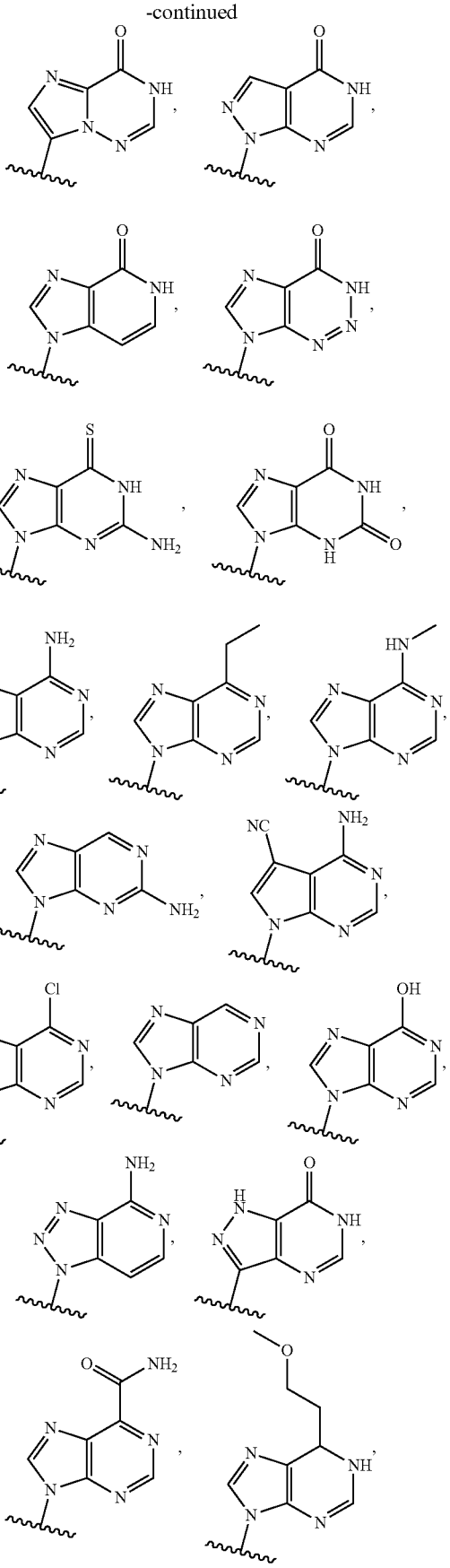

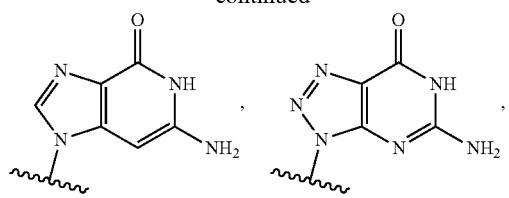
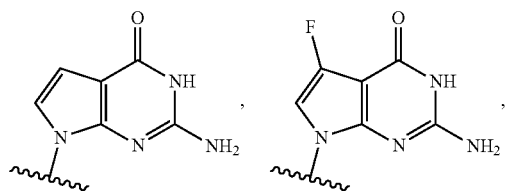
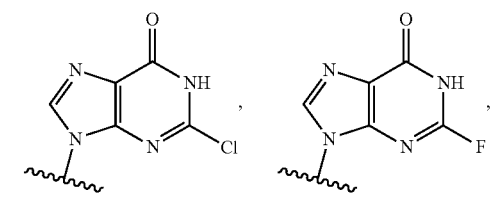
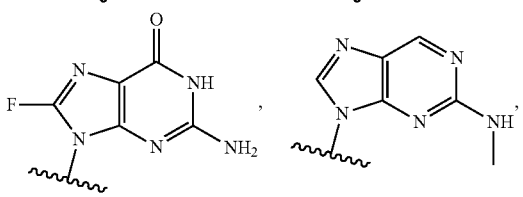
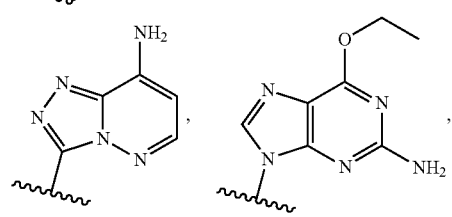
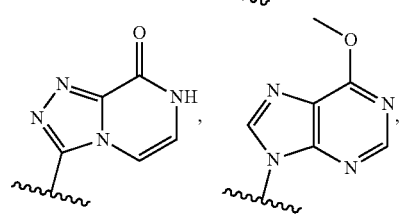
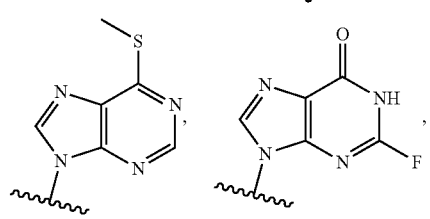
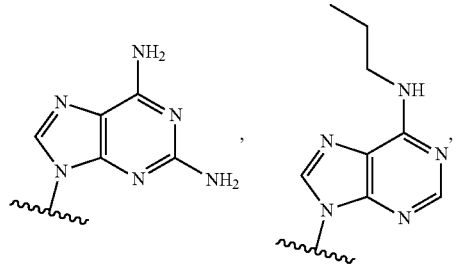

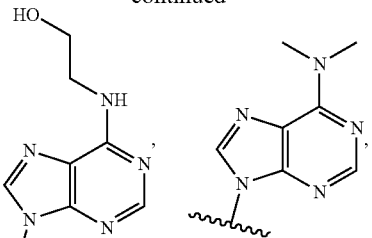
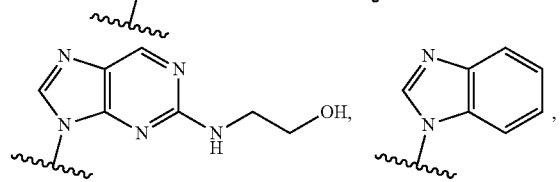
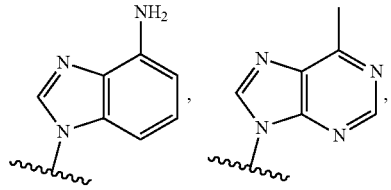
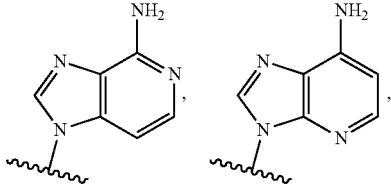
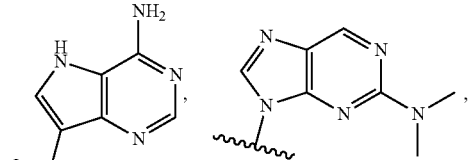
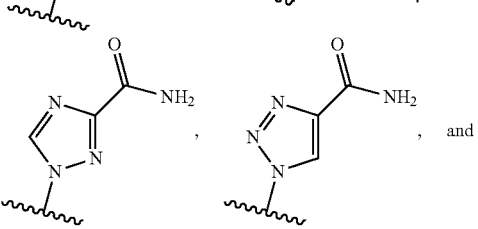
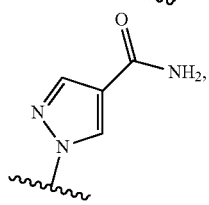, and where Base$^1$ and Base$^2$ each may be independently substituted by 0-3 substituents R$^{10}$, where each R$^{10}$ is independently selected from the group consisting of F, Cl, I, Br, OH, SH, NH$_2$, C$_{1-3}$ alkyl, C$_{3-6}$ cycloalkyl, O(C$_{1-3}$ alkyl), O(C$_{3-6}$ cycloalkyl), S(C$_{1-3}$ alkyl), S(C$_{3-6}$ cycloalkyl), NH(C$_{1-3}$ alkyl), NH(C$_{3-6}$ cycloalkyl), N(C$_{1-3}$ alkyl)$_2$, and N(C$_{3-6}$ cycloalkyl)$_2$; X$^c$ and X$^{c1}$ are each independently selected from the group consisting of OR$^9$, SR$^9$, and NR$^9$R$^9$; R$^3$ is selected from the group consisting of H, F, Cl, Br, I, OH, CN, N$_3$, C$_1$-C$_6$ alkyl, and C$_1$-C$_6$ haloalkyl, where said R$^3$C$_1$-C$_6$ alkyl or C$_1$-C$_6$ haloalkyl are substituted by 0 to 3 substituents selected from the group consisting of F, Cl, Br, I, and OH; R$^4$ is selected from the group consisting of H, F, Cl, Br, I, OH, CN, $N_3$, $C_1$-$C_6$ alkyl, and $C_1$-$C_6$ haloalkyl, where said $R^4 C_1$-$C_6$ alkyl or $C_1$-$C_6$ haloalkyl are substituted by 0 to 3 substituents selected from the group consisting of F, Cl, Br, I, and OH; $R^5$ is selected from the group consisting of H, F, Cl, Br, I, OH, CN, $NH_2$, $N_3$, $C_1$-$C_6$ alkyl, and $C_1$-$C_6$ haloalkyl, where said $R^5 C_1$-$C_6$ alkyl or $C_1$-$C_6$ haloalkyl are substituted by 0 to 3 substituents selected from the group consisting of F, Cl, Br, I, and OH; $R^{6a}$ is selected from the group consisting of H, F, Cl, Br, I, OH, CN, $N_3$, $C_1$-$C_6$ alkyl, and $C_1$-$C_6$ haloalkyl, where said $R^{6a}$ $C_1$-$C_6$ alkyl or $C_1$-$C_6$ haloalkyl are substituted by 0 to 3 substituents selected from the group consisting of F, Cl, Br, I, and OH; each $R^9$ is independently selected from the group consisting of H, $C_2$-$C_3$ alkyl,

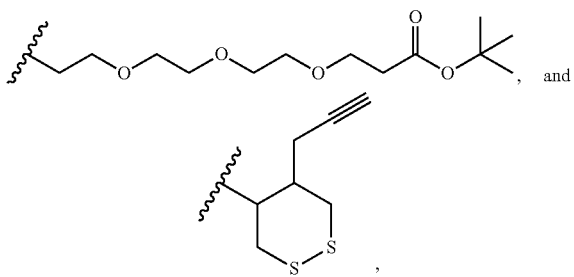

, and where each $R^9 C_2$-$C_3$ alkyl is optionally substituted by 1 to 2 substituents independently selected from the group consisting of OH, —O—$C_1$-$C_{20}$ alkyl, —S—C(O)$C_1$-$C_6$ alkyl, and C(O)O$C_1$-$C_6$ alkyl; and optionally $R^4$ and $R^5$ are connected by $C_1$-$C_6$ alkylene, —O—$C_1$-$C_6$ alkylene, —O—$C_2$-$C_6$ alkenylene, or —O—$C_2$-$C_6$ alkynylene, such that where $R^4$ and $R^5$ are connected to form —O—$C_1$-$C_6$ alkylene, —O—$C_2$-$C_6$ alkenylene, or —O—$C_2$-$C_6$ alkynylene, said O is bound at the $R^5$ position. In this aspect, all other groups are as provided in the general formula (I') of the second embodiment above.

A twenty-second aspect of the second embodiment relates to a pharmaceutical composition, said pharmaceutically acceptable composition comprising (a) a compound according to any one of general formula (I') of the second embodiment above or in the first through twenty-first aspects described above or a pharmaceutically acceptable salt, hydrate, solvate or prodrug thereof, and (b) a pharmaceutically acceptable carrier.

A twenty-third aspect of the second embodiment relates to methods of inducing an immune response in a subject, comprising administering a therapeutically effective amount of a compound according to any one of general formula (I') of the second embodiment above or in the first through twenty-first aspects described above or a pharmaceutically acceptable salt, hydrate, solvate or prodrug thereof to the subject.

A twenty-fourth aspect of the second embodiment relates to methods of inducing an immune response in a subject, comprising administering a therapeutically effective amount of a composition according to the twenty-second aspect described above or a pharmaceutically acceptable salt, hydrate, solvate or prodrug thereof to the subject.

A twenty-fifth aspect of the second embodiment relates to methods of inducing a STING-dependent type I interferon production in a subject, comprising administering a therapeutically effective amount of a compound according to any one of general (I') of the second embodiment above or in the first through twenty-first aspects described above or a pharmaceutically acceptable salt, hydrate, solvate or prodrug thereof to the subject.

A twenty-sixth aspect of the second embodiment relates to methods of inducing a STING-dependent type I interferon production in a subject, comprising administering a therapeutically effective amount of a composition according to the twenty-second aspect described above to the subject.

A twenty-seventh aspect of the second embodiment relates to methods of inducing a STING-dependent cytokine production in a subject, comprising administering a therapeutically effective amount of a compound according to any one of general (I') of the second embodiment above or in the first through twenty-first aspects described above or a pharmaceutically acceptable salt, hydrate, solvate or prodrug thereof to the subject.

A thirty-third aspect of the second embodiment relates to methods of inducing a STING-dependent cytokine production in a subject, comprising administering a therapeutically effective amount of a composition according to the twenty-second aspect described above to the subject.

A third embodiment of the disclosure relates to cyclic di-nucleotide compounds of general formula (I''):

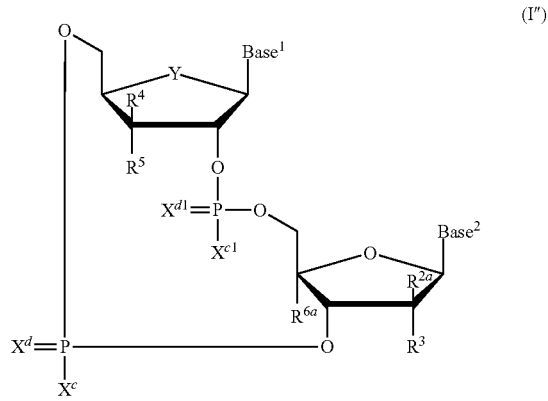

(I'')

or a pharmaceutically acceptable salt, hydrate, solvate, or prodrug thereof, wherein Base$^1$ and Base$^2$ are each independently selected from the group consisting of

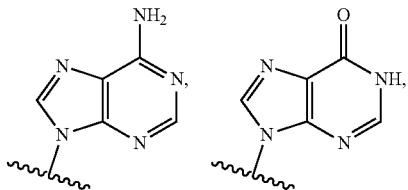

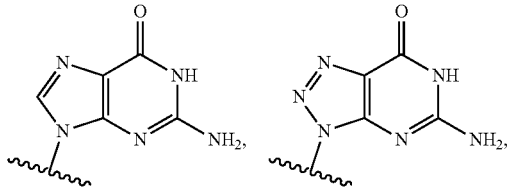

-continued

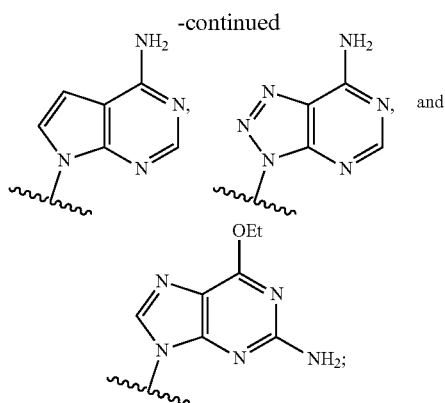

Y is selected from the group consisting of —O— and —S—; $X^c$ and $X^{c1}$ are each independently selected from the group consisting of $OR^9$ and $SR^9$; $X^d$ and $X^{d1}$ are each independently selected from the group consisting of O and S; $R^{2a}$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl; $R^3$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl; $R^4$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl; $R^5$ is selected from the group consisting of H, F, Cl, Br, I, OH, CN, $NH_2$, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl; $R^{6a}$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl; each $R^9$ is independently selected from the group consisting of H, $C_1$-$C_{20}$ alkyl,

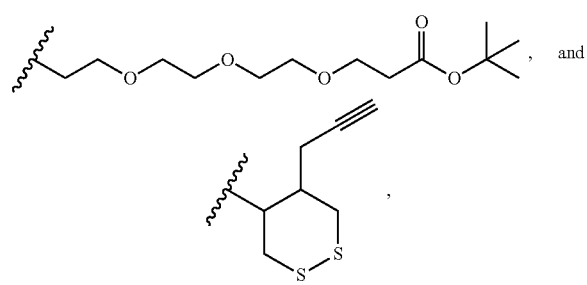

where each $R^9 C_1$-$C_{20}$ alkyl is optionally substituted by 0 to 3 substituents independently selected from the group consisting of OH, —O—$C_1$-$C_{20}$ alkyl, —S—$C(O)C_1$-$C_6$ alkyl, and $C(O)OC_1$-$C_6$ alkyl; and optionally $R^3$ and $R^{6a}$ are connected to form —O—$C_1$-$C_6$ alkylene, —O—$C_2$-$C_6$ alkenylene, or —O—$C_2$-$C_6$ alkynylene, such that where $R^3$ and $R^{6a}$ are connected to form —O—$C_1$-$C_6$ alkylene, —O—$C_2$-$C_6$ alkenylene, or —O—$C_2$-$C_6$ alkynylene, said O is bound at the $R^3$ position.

In specific aspects of this embodiment, when Y and $Y^a$ are each O, $X^a$ and $X^{a1}$ are each O, $X^b$ and $X^{b1}$ are each O, and $X^c$ and $X^{c1}$ are each OH or SH, $X^d$ and $X^{d1}$ are each O, $R^1$ and $R^{1a}$ are each H, $R^2$ is H, $R^6$ and $R^{6a}$ are each H, $R^7$ and $R^{7a}$ are each H, $R^8$ and $R^{8a}$ are each H, and Base$^1$ and Base$^2$ are each selected from the group consisting of

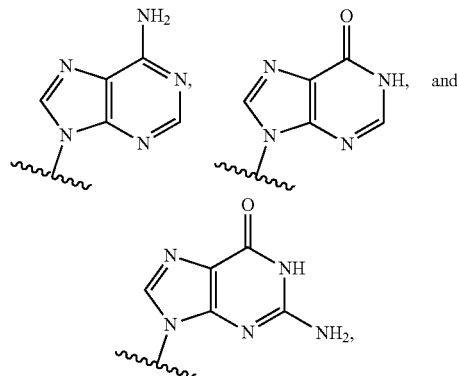

$R^5$ and $R^3$ are not both selected from the group consisting of H, F and OH. That is, when Y and $Y^a$ are each O, $X^a$ and $X^{a1}$ are each O, $X^b$ and $X^{b1}$ are each O, and $X^c$ and $X^{c1}$ are each OH or SH, $X^d$ and $X^{d1}$ are each O, $R^1$ and $R^{1a}$ are each H, $R^2$ is H, $R^6$ and $R^{6a}$ are each H, $R^7$ and $R^{7a}$ are each H, $R^8$ and $R^{8a}$ are each H, and Base$^1$ and Base$^2$ are each selected from the group consisting of

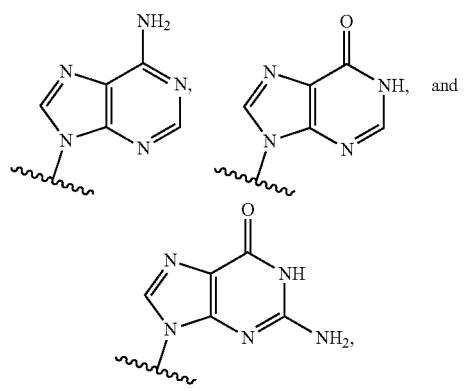

either only one of $R^5$ and $R^3$ is selected from the group consisting of H, F, and OH, or neither $R^5$ and $R^3$ is selected from the group consisting of H, F, and OH. In further specific instances of this aspect, when Y and $Y^a$ are each O, $X^a$ and $X^{a1}$ are each O, $X^b$ and $X^{b1}$ are each O, and $X^c$ and $X^{c1}$ are each OH, $X^d$ and $X^{d1}$ are each O or S, $R^1$ and $R^{1a}$ are each H, $R^2$ is H, $R^6$ and $R^{6a}$ are each H, $R^7$ and $R^{7a}$ are each H, $R^8$ and $R^{8a}$ are each H, and Base$^1$ and Base$^2$ are each selected from the group consisting of

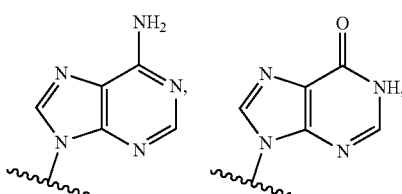

-continued

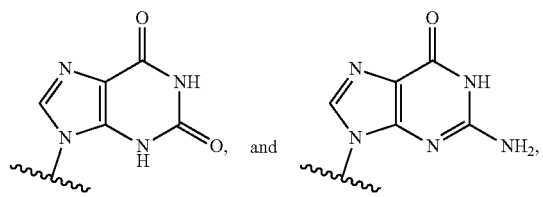

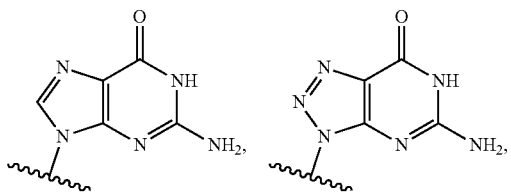

$R^5$ and $R^3$ are not both selected from the group consisting of H, $C_1$-$C_6$ alkyl, $C_2$-$C_6$ alkenyl, $C_2$-$C_6$ alkynyl, where said $C_1$-$C_6$ alkyl, $C_2$-$C_6$ alkenyl and $C_2$-$C_6$ alkynyl are substituted by 0 to 3 substituents selected from the group consisting of F, Cl, Br, I and OH.

In further specific aspects of this embodiment, when Base$^1$ and Base$^2$ are each selected from the group consisting of

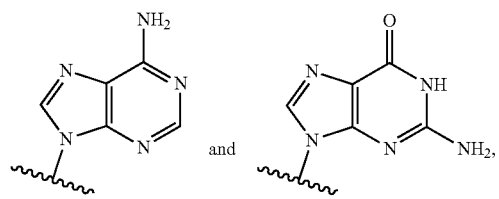 [SMILES: *n1cnc2c(N)ncnc21 ; *n1cnc2c(=O)[nH]c(N)nc21]

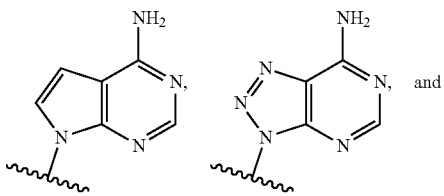

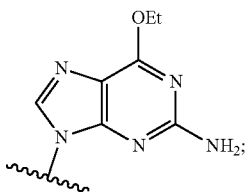

and $R^{2a}$ is F and $R^5$ is F, at least one of $X^c$ and $X^{c1}$ is $SR^9$.

In a first aspect of the third embodiment, the compound of formula (I″) is a compound of formula (I″a):

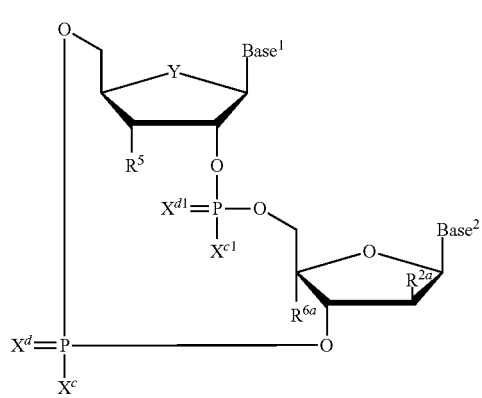

(I″a)

or a pharmaceutically acceptable salt, hydrate, solvate, or prodrug thereof, wherein Base$^1$ and Base$^2$ are each independently selected from the group consisting of

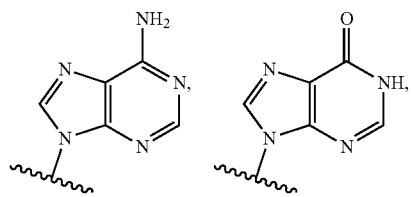

Y is selected from the group consisting of —O— and —S—; $X^c$ and $X^{c1}$ are each independently selected from the group consisting of $OR^9$ and $SR^9$; $X^d$ and $X^{d1}$ are each independently selected from the group consisting of O and S; $R^{2a}$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl; $R^5$ is selected from the group consisting of H, F, Cl, Br, I, OH, CN, $NH_2$, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl; $R^{6a}$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl; and each $R^9$ is independently selected from the group consisting of H, $C_1$-$C_{20}$ alkyl,

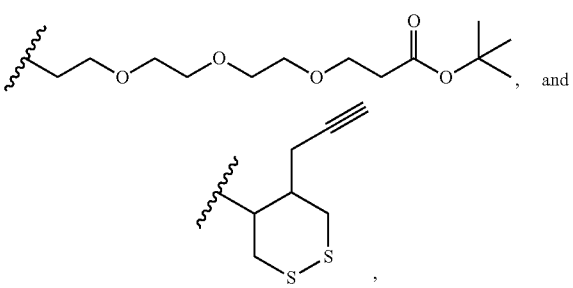

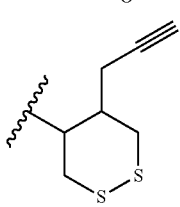

where each $R^9C_1$-$C_{20}$ alkyl is optionally substituted by 0 to 3 substituents independently selected from the group consisting of OH, —O—$C_1$-$C_{20}$ alkyl, —S—C(O)$C_1$-$C_6$ alkyl, and C(O)O$C_1$-$C_6$ alkyl. In instances of this aspect, Base$^1$ and Base$^2$ are each independently selected from the group consisting of

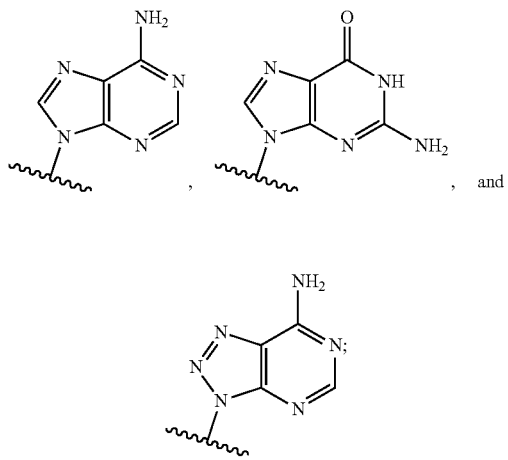

Y is selected from the group consisting of —O— and —S—; $X^c$ and $X^{c1}$ are each independently selected from the group consisting of $OR^9$ and $SR^9$; $X^d$ and $X^{d1}$ are each independently selected from the group consisting of O and S; $R^{2a}$ is F; $R^5$ is selected from the group consisting of H, F, Cl, Br, I, OH, CN, $NH_2$, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl; $R^{6a}$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl; and each $R^9$ is independently H.

In a second aspect of the third embodiment, the compound of formula (I″) is a compound wherein $R^3$ and $R^{6a}$ are connected to form —O—$C_1$-$C_6$ alkylene, —O—$C_2$-$C_6$ alkenylene, or —O—$C_2$-$C_6$ alkynylene, such that where $R^3$ and $R^{6a}$ are connected to form —O—$C_1$-$C_6$ alkylene, —O—$C_2$-$C_6$ alkenylene, or —O—$C_2$-$C_6$ alkynylene, said O is bound at the $R^3$ position.

In a third aspect of the third embodiment, the compound of formula (I″) is a compound of formula (I″b):

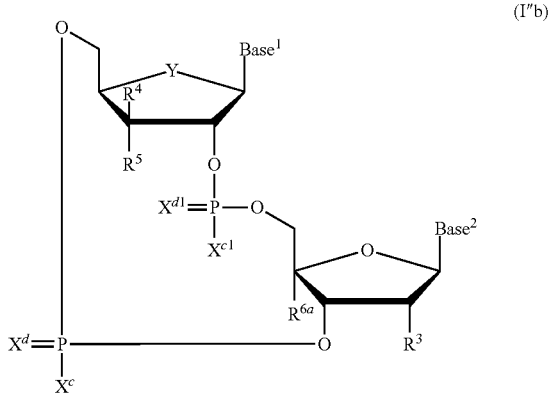

(I″b)

or a pharmaceutically acceptable salt, hydrate, solvate, or prodrug thereof, wherein Base$^1$ and Base$^2$ are each independently selected from the group consisting of

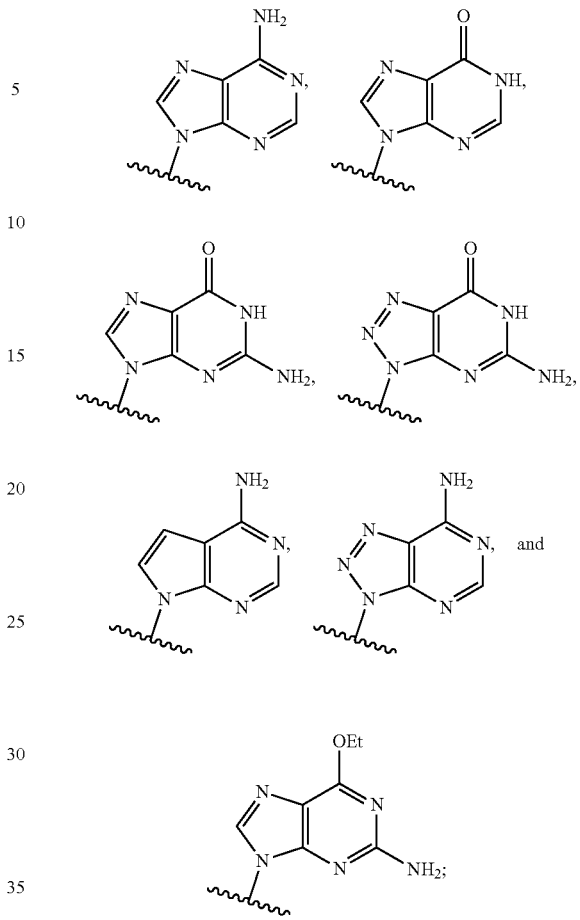

Y is selected from the group consisting of —O— and —S—; $X^c$ and $X^{c1}$ are each independently selected from the group consisting of $OR^9$ and $SR^9$; $X^d$ and $X^{d1}$ are each independently selected from the group consisting of O and S; $R^3$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl; $R^4$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl; $R^5$ is selected from the group consisting of H, F, Cl, Br, I, OH, CN, $NH_2$, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl; $R^{6a}$ is selected from the group consisting of H, F, Cl, Br, I, OH, CN, $N_3$, $C_1$-$C_6$ alkyl, $C_2$-$C_6$ alkenyl, $C_2$-$C_6$ alkynyl, $C_1$-$C_6$ haloalkyl, $C_2$-$C_6$ haloalkenyl, $C_2$-$C_6$ haloalkynyl, —O—$C_1$-$C_6$ alkyl, —O—$C_2$-$C_6$ alkenyl, and —O—$C_2$-$C_6$ alkynyl; each $R^9$ is independently H; and $R^3$ and $R^{6a}$ are connected to form —O—$C_1$-$C_6$ alkylene, —O—$C_2$-$C_6$ alkenylene, or —O—$C_2$-$C_6$ alkynylene, such that where $R^3$ and $R^{6a}$ are connected to form —O—$C_1$-$C_6$ alkylene, —O—$C_2$-$C_6$ alkenylene, or —O—$C_2$-$C_6$ alkynylene, said O is bound at the $R^3$ position. In instances of this aspect, Base$^1$ and Base$^2$ are each independently selected from the group consisting of

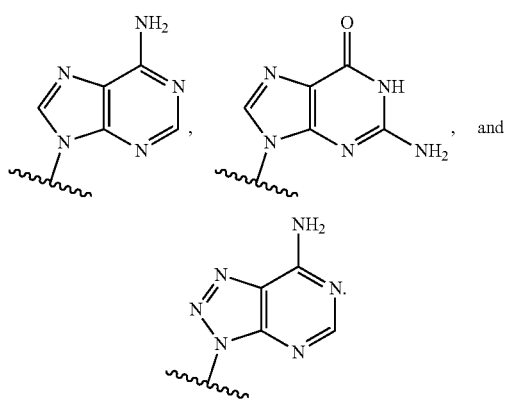

In a fourth aspect of the third embodiment, the compound of formula (I″) is a compound wherein at least one of Base¹ and Base² are each independently selected from the group consisting of

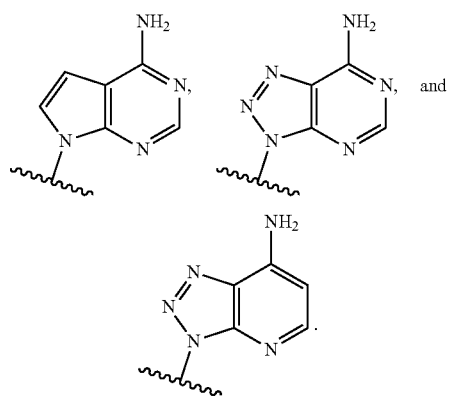

A fifth aspect of the third embodiment relates to a pharmaceutical composition, said pharmaceutical composition comprising (a) a compound according to any one of general formula (I″) of the third embodiment or a pharmaceutically acceptable salt, hydrate, solvate or prodrug thereof; and (b) a pharmaceutically acceptable carrier.

A sixth aspect of the third embodiment relates to methods of inducing an immune response in a subject, comprising administering a therapeutically effective amount of a compound according to general formula (I″) of the third embodiment above or a pharmaceutically acceptable salt, hydrate, solvate, or prodrug thereof to the subject.

A seventh aspect of the third embodiment relates to methods of inducing an immune response in a subject, comprising administering a therapeutically effective amount of a composition according to the fifth aspect described above to the subject.

An eighth aspect of the third embodiment relates to methods of inducing a STING-dependent type I interferon production in a subject, comprising administering a therapeutically effective amount of a compound according general formula (I″) of the third embodiment above or a pharmaceutically acceptable salt, hydrate, solvate, or prodrug thereof to the subject.

A ninth aspect of the third embodiment relates to methods of inducing a STING-dependent type I interferon production in a subject, comprising administering a therapeutically effective amount of a composition according to the fifth aspect described above to the subject.

A tenth aspect of the third embodiment relates to methods of inducing a STING-dependent cytokine production in a subject, comprising administering a therapeutically effective amount of a compound according to general formula (I″) of the third embodiment above or a pharmaceutically acceptable salt, hydrate, solvate, or prodrug thereof to the subject.

An eleventh aspect of the third embodiment relates to methods of inducing a STING-dependent cytokine production in a subject, comprising administering a therapeutically effective amount of a composition according to the fifth aspect described above to the subject.

In an additional embodiment, the compound is selected from the group consisting of

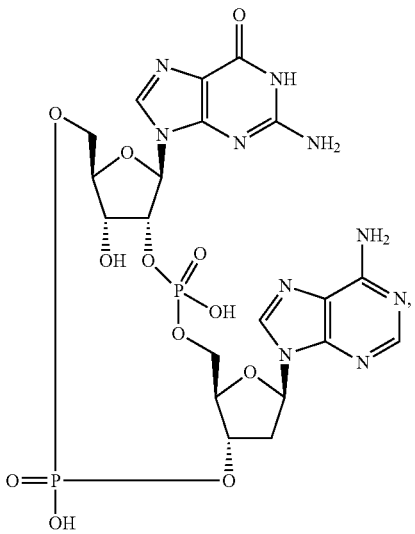

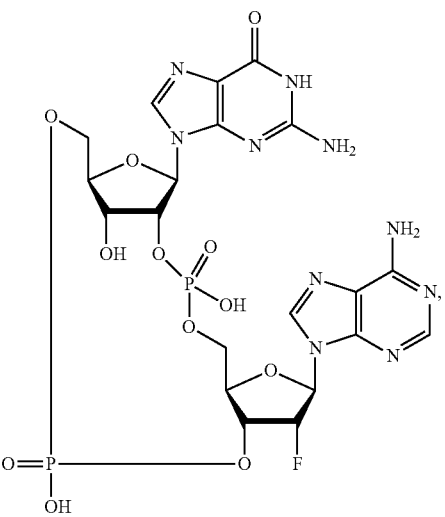

73
-continued
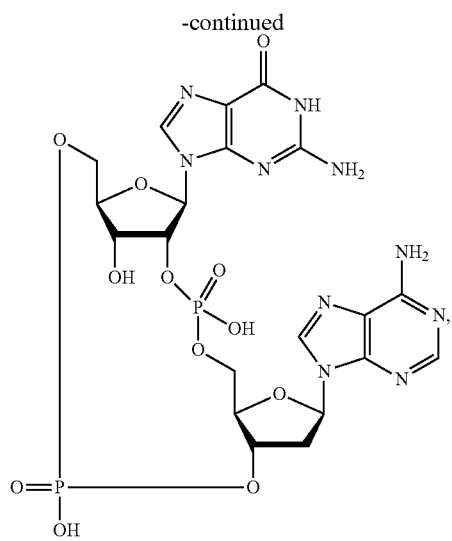
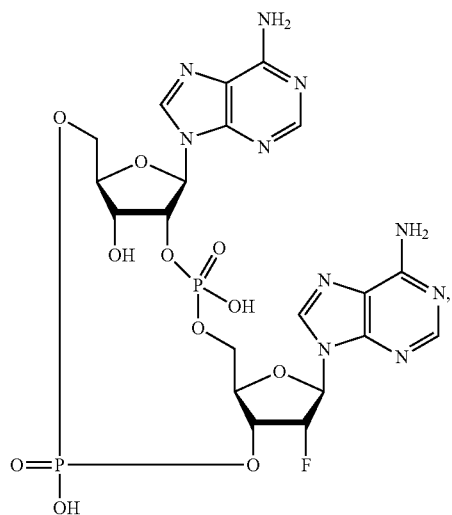
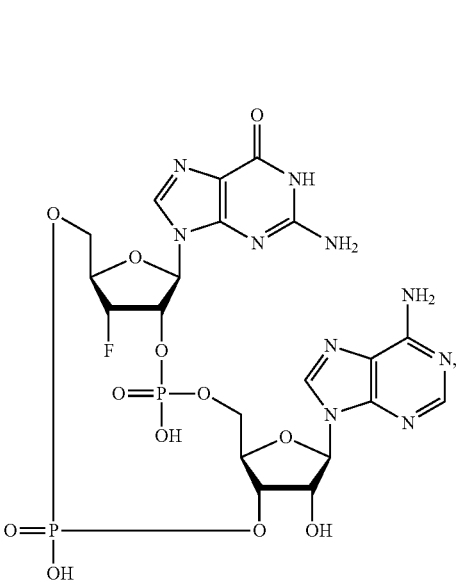
74
-continued
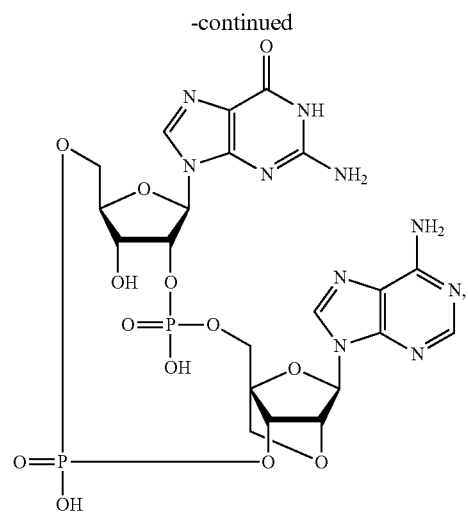
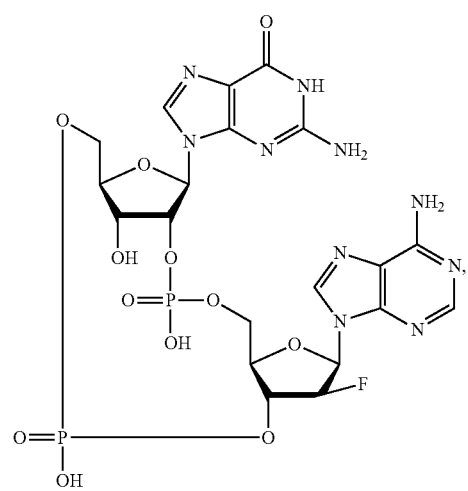
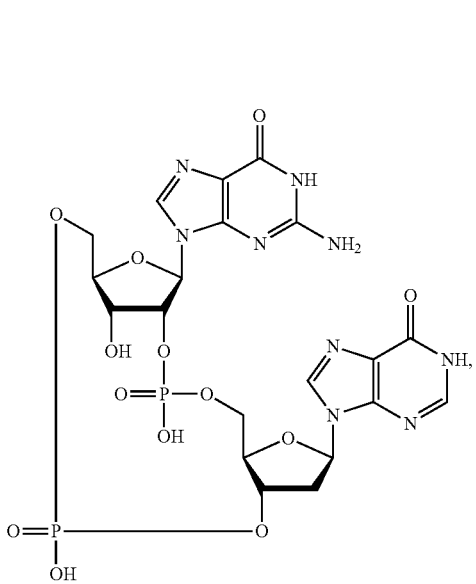

75
-continued
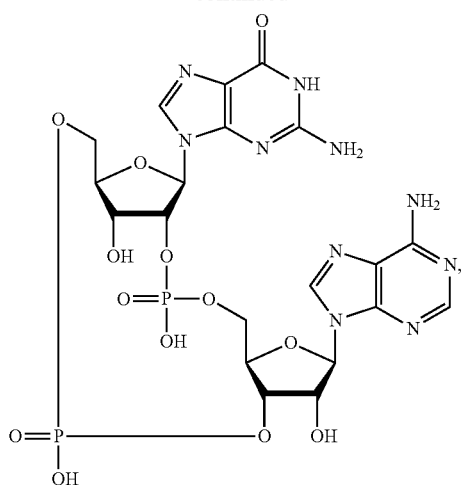
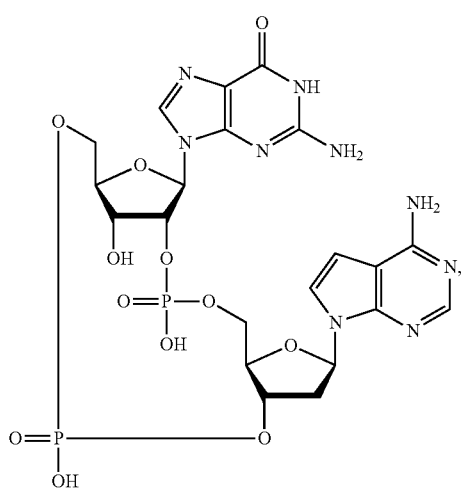
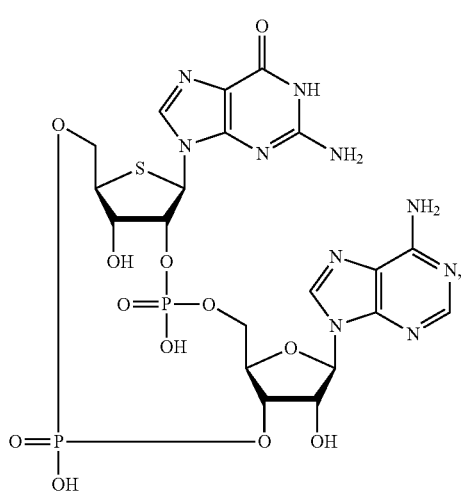
76
-continued
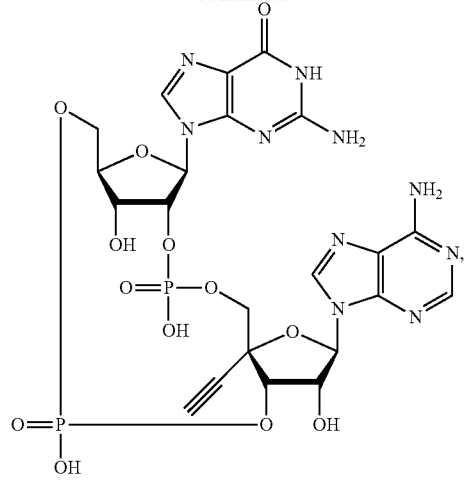
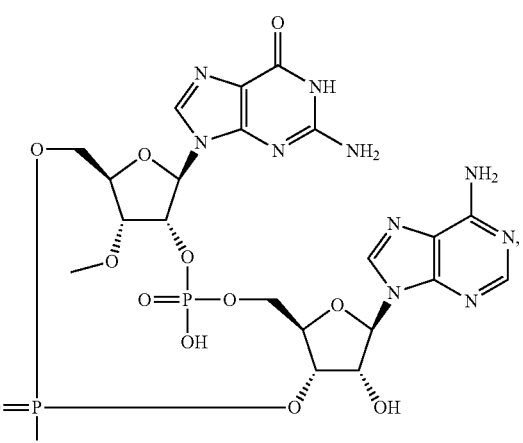
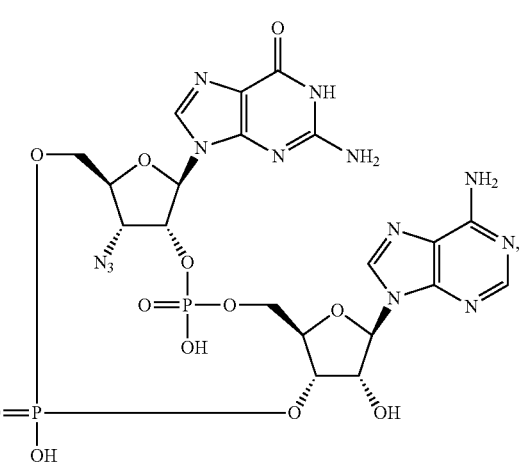

77
-continued
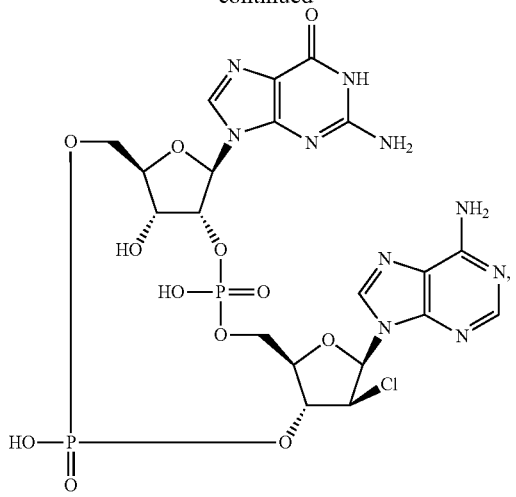
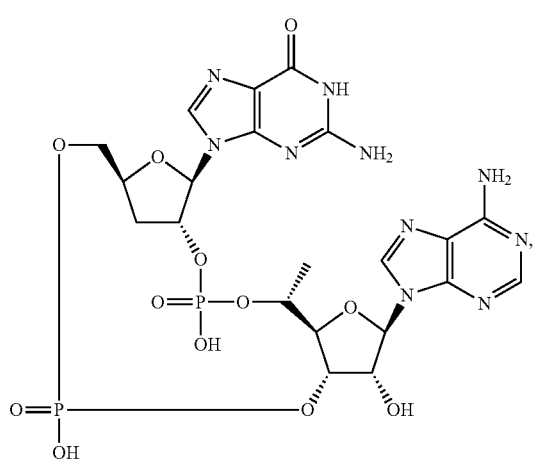
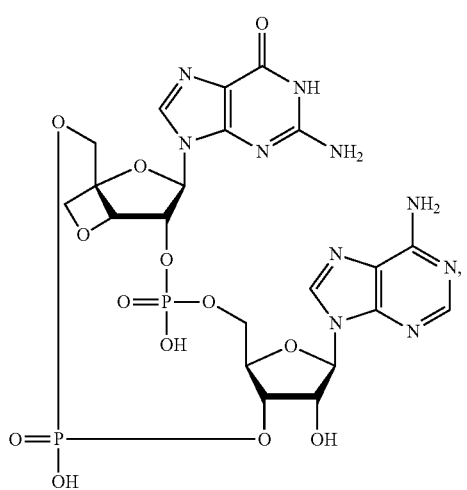
78
-continued
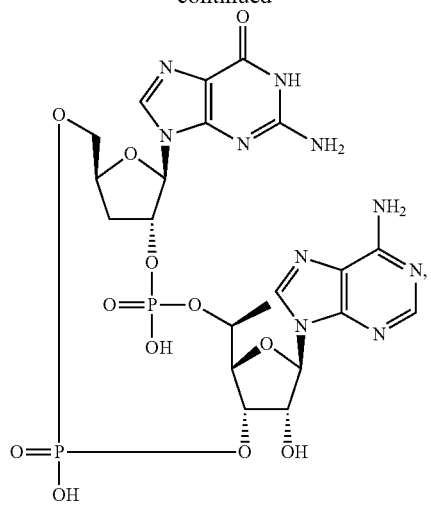
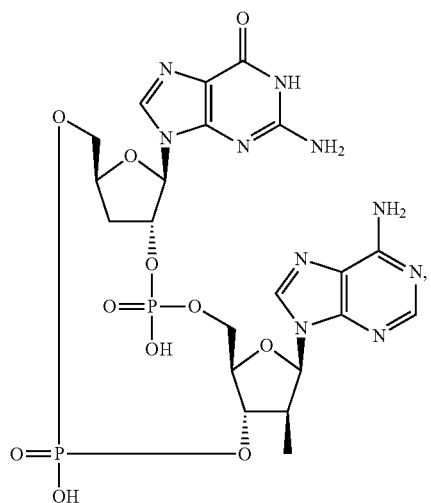
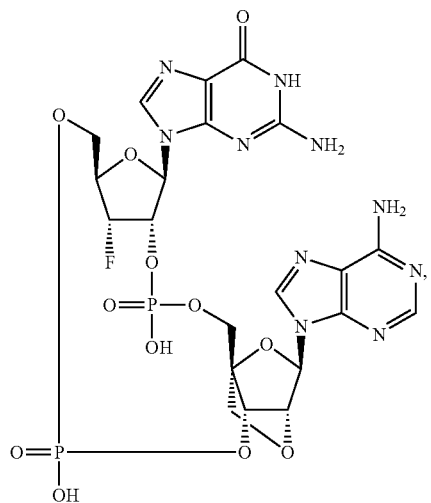

-continued
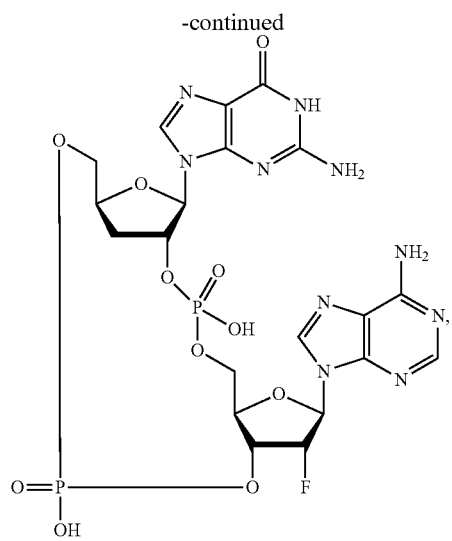
79
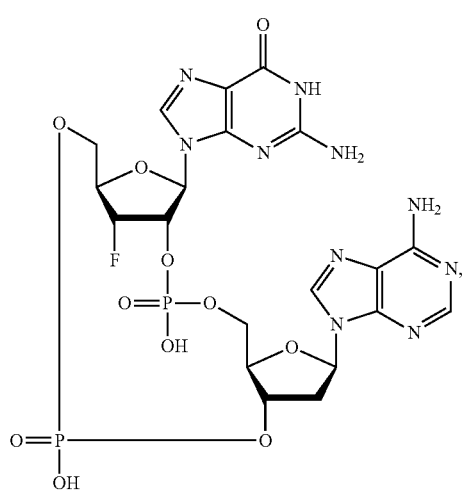
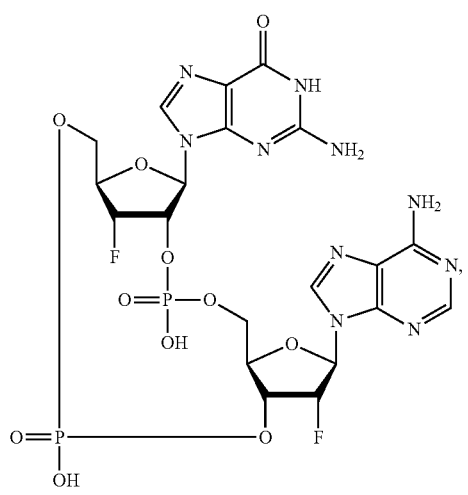
-continued
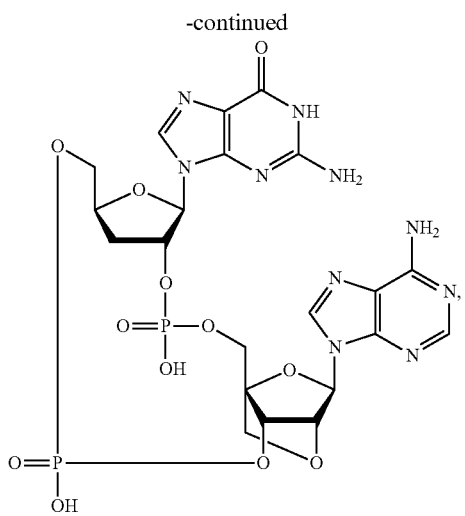
80
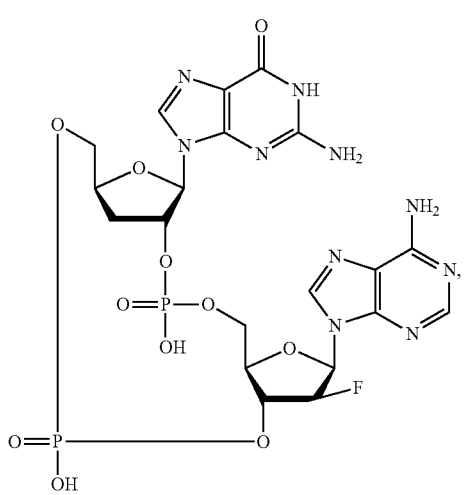
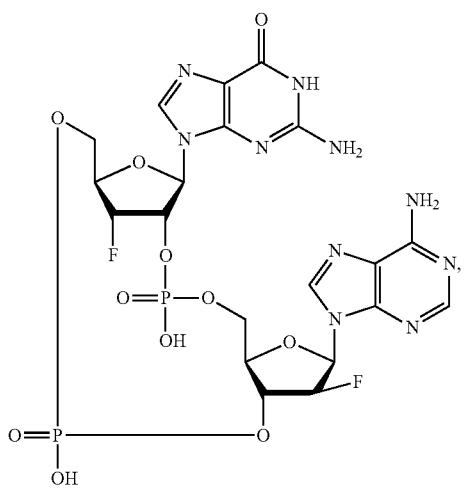

| 81 | 82 |
|---|---|
| -continued | -continued |
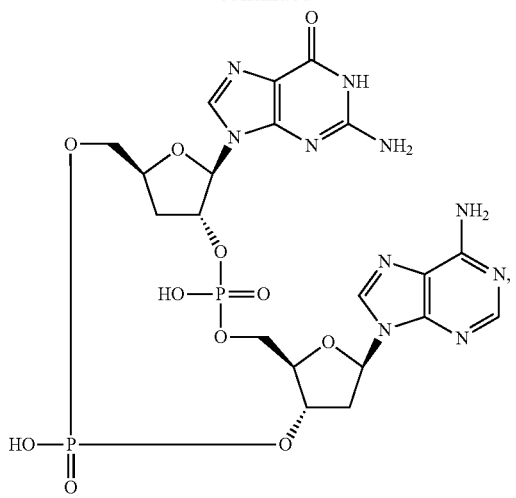
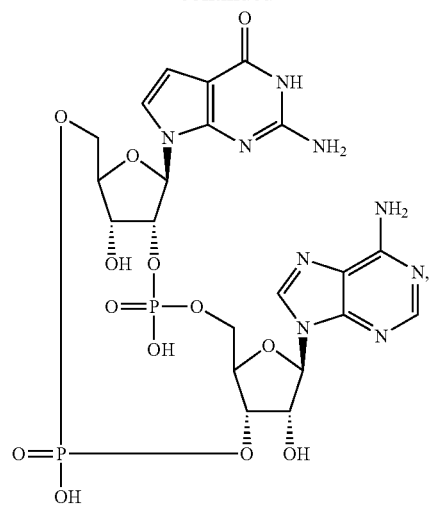
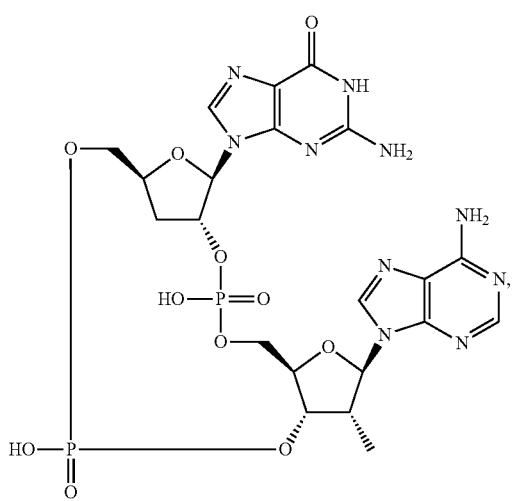
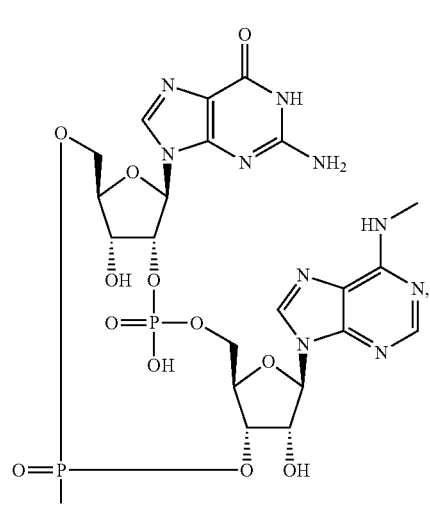
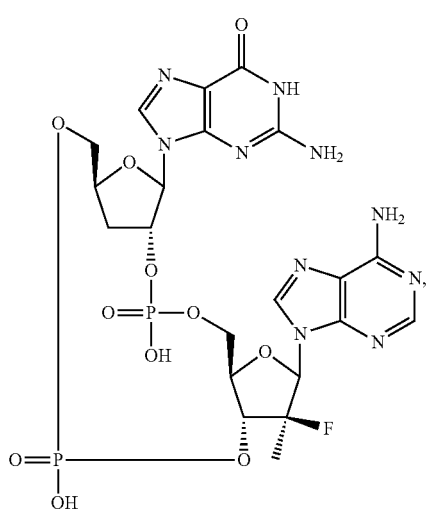
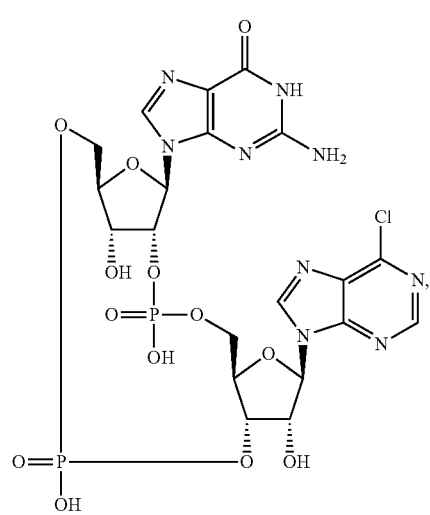

-continued
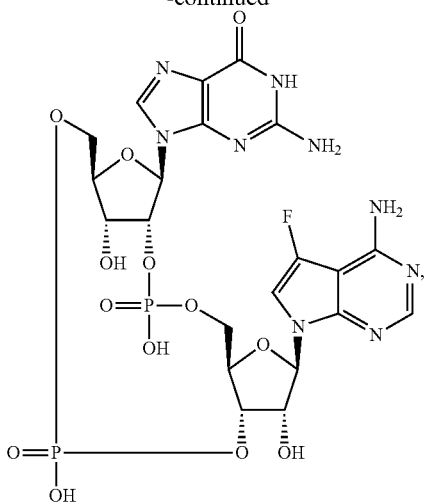
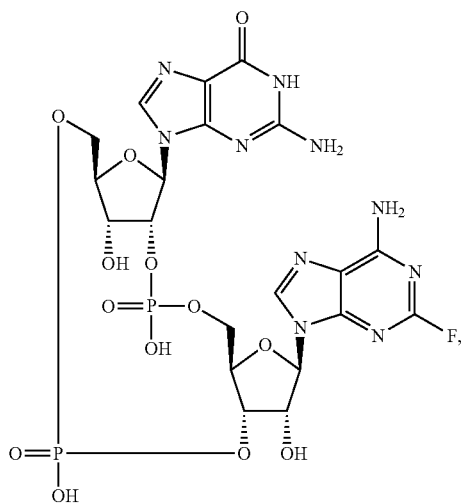
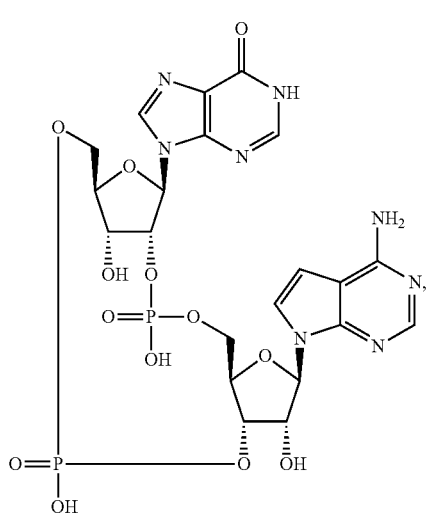
-continued
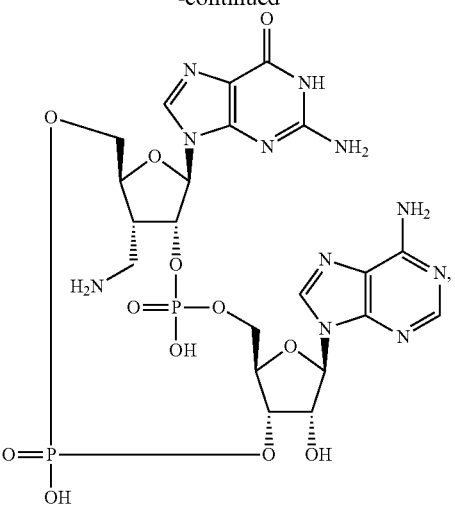
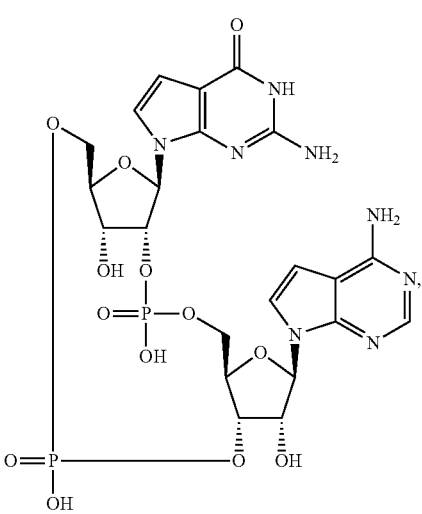
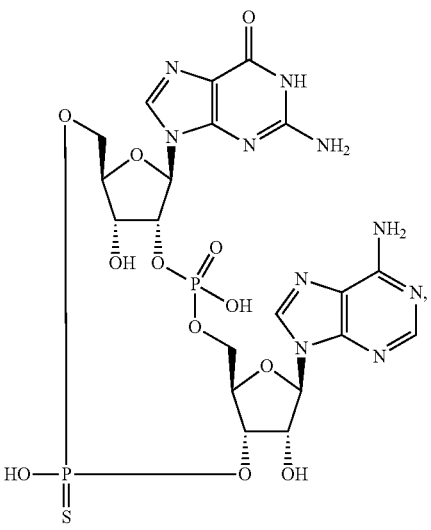

85
-continued
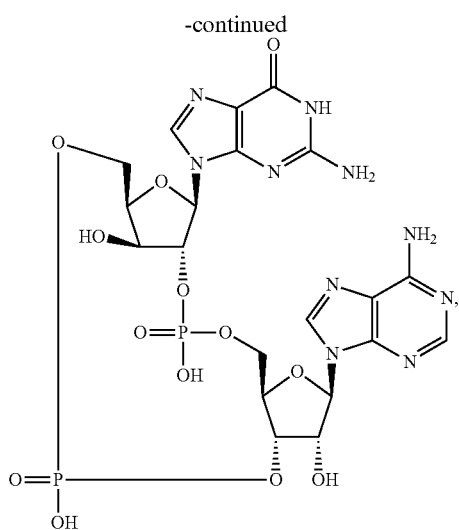
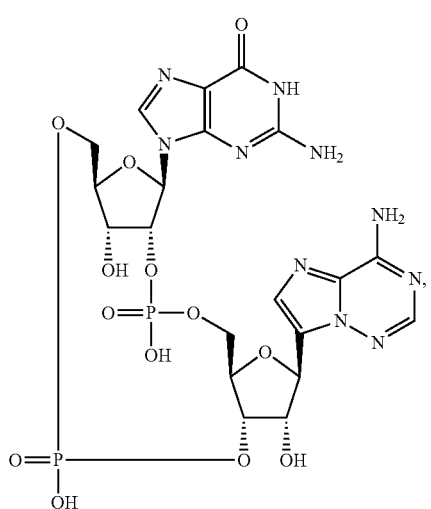
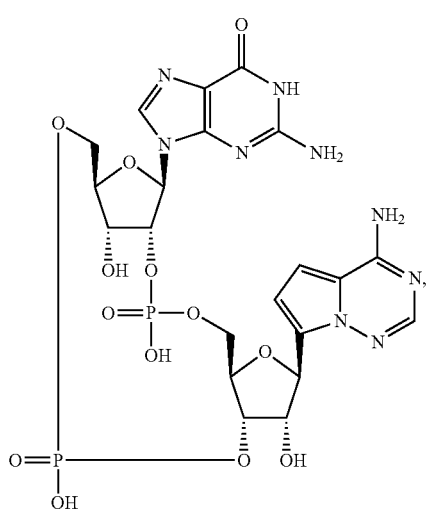
86
-continued
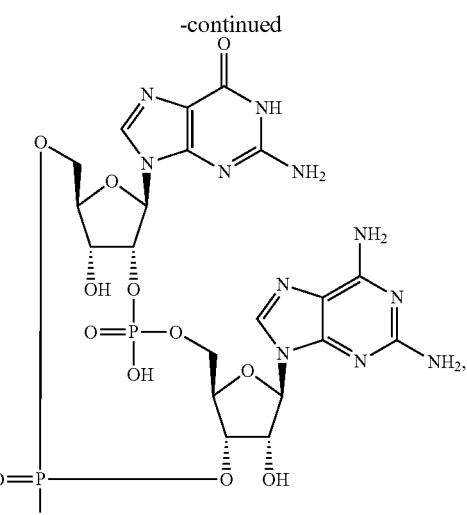
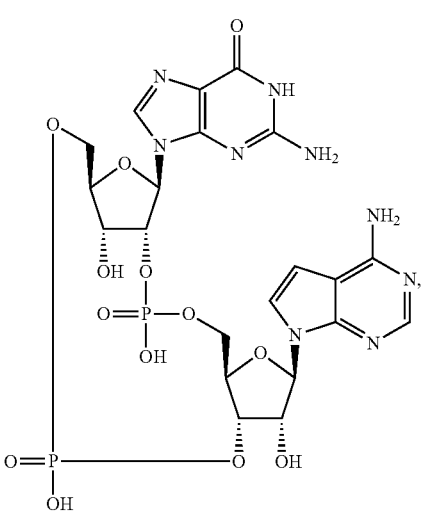
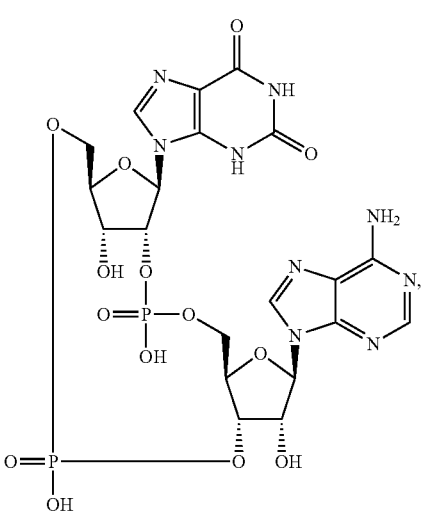

87
-continued
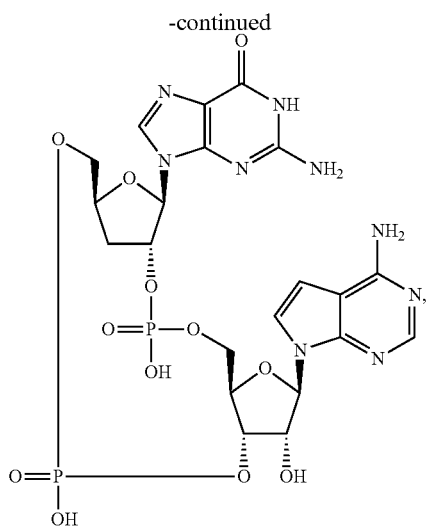
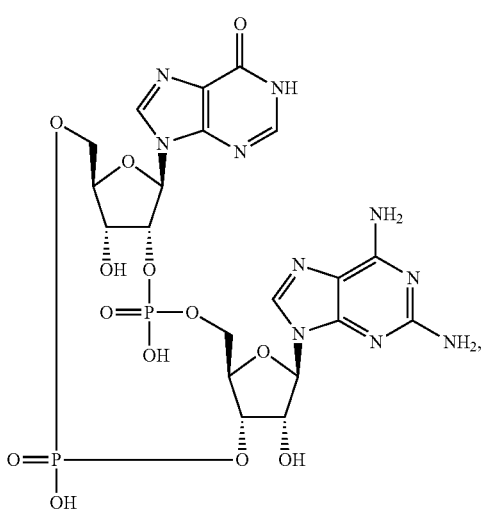
88
-continued
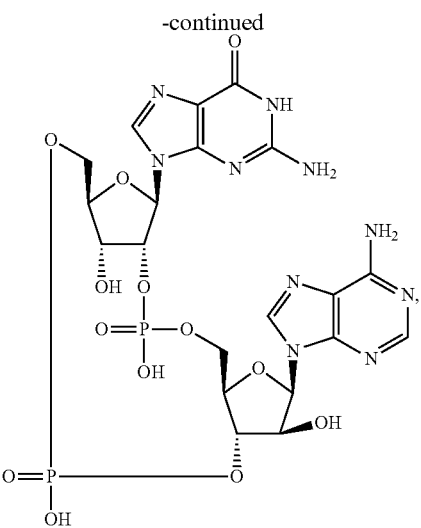
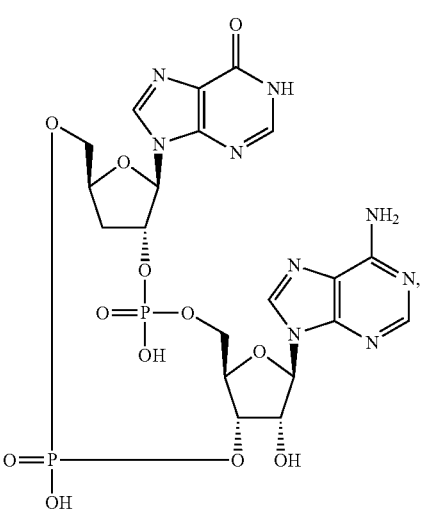

89
-continued
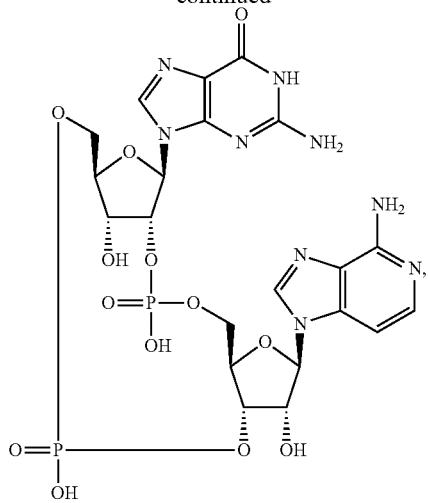
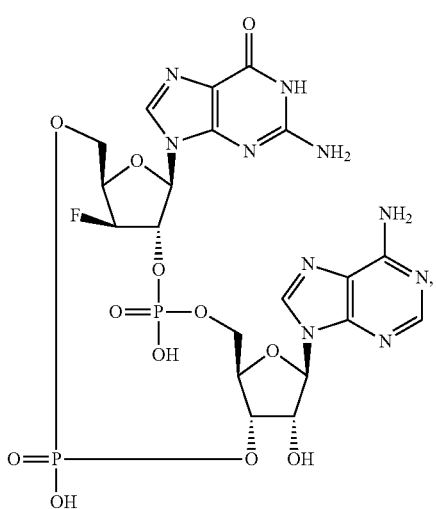
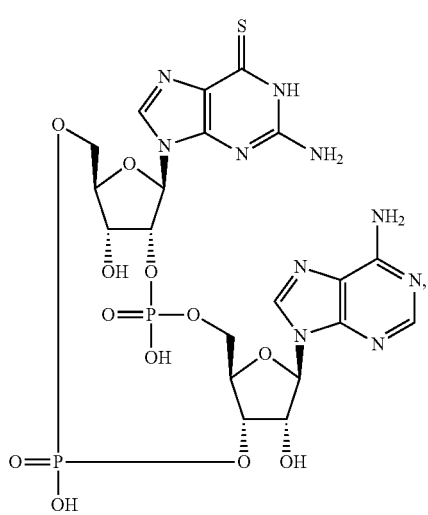
90
-continued
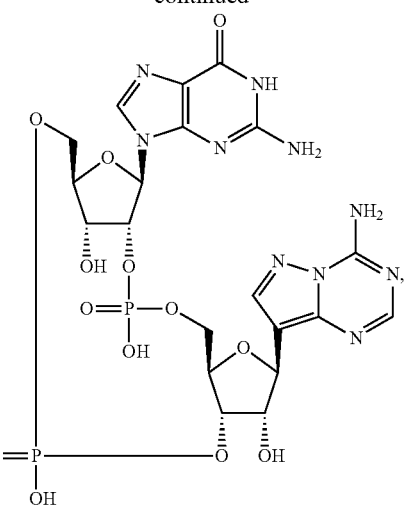
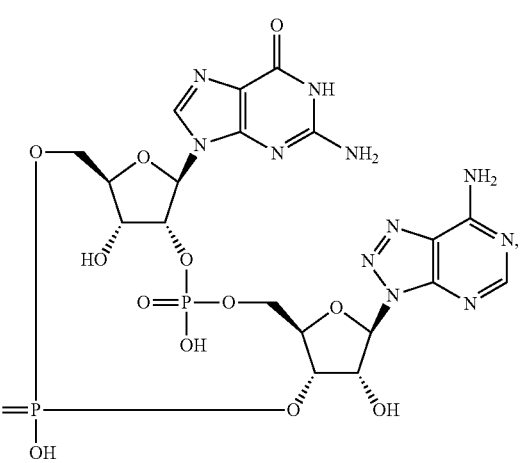
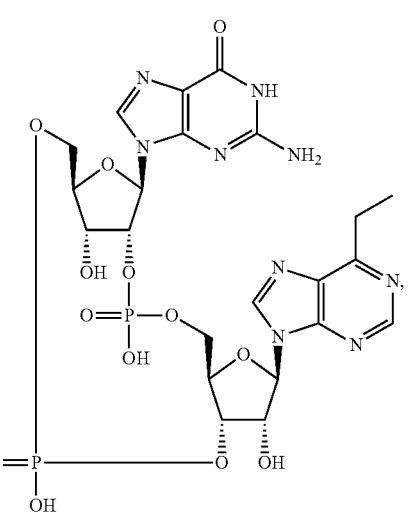

91
-continued
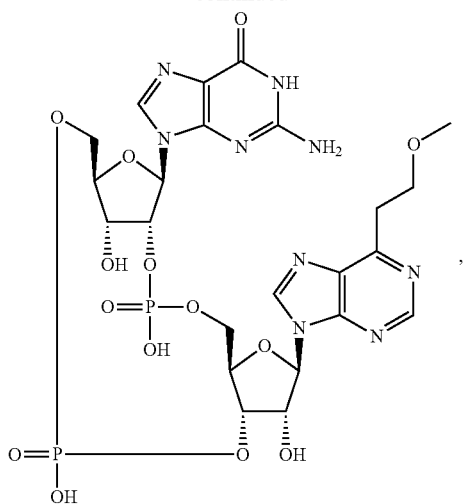
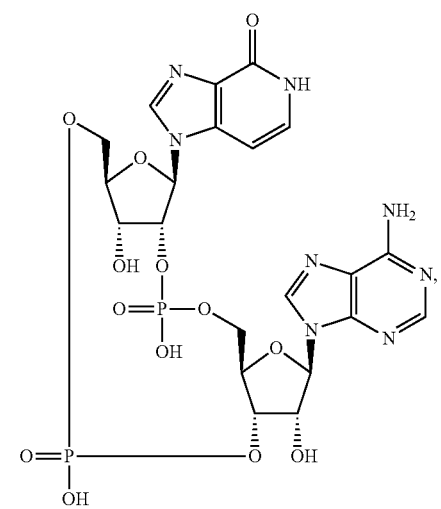
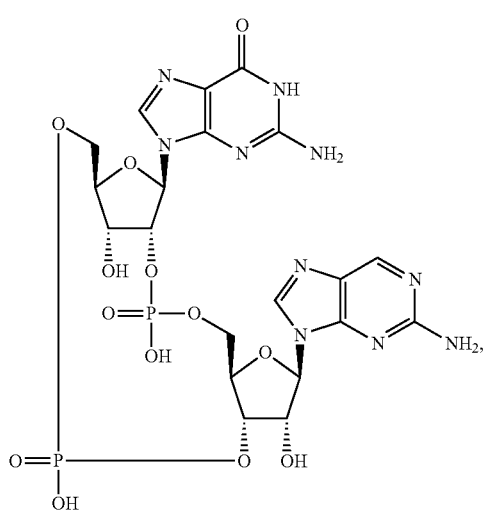
92
-continued
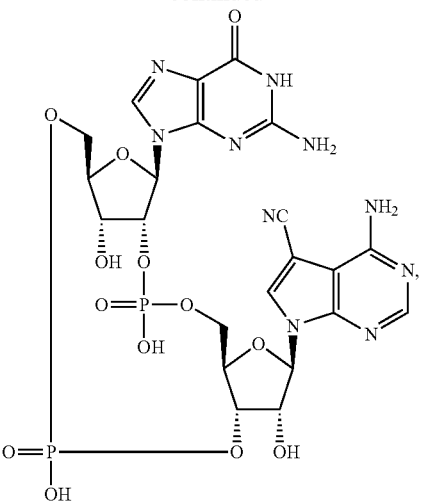
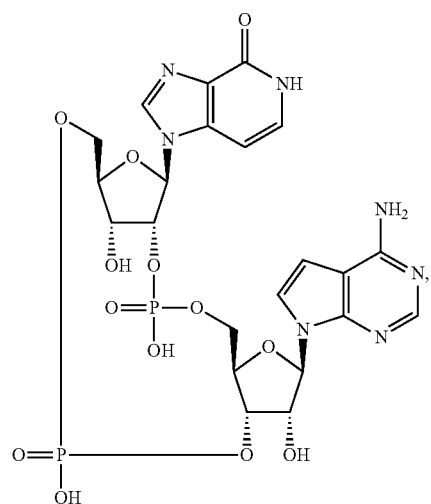
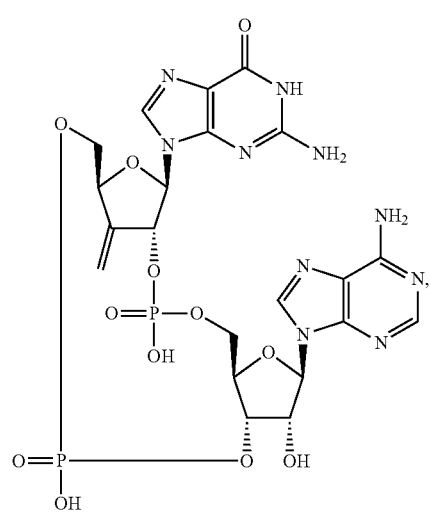

-continued
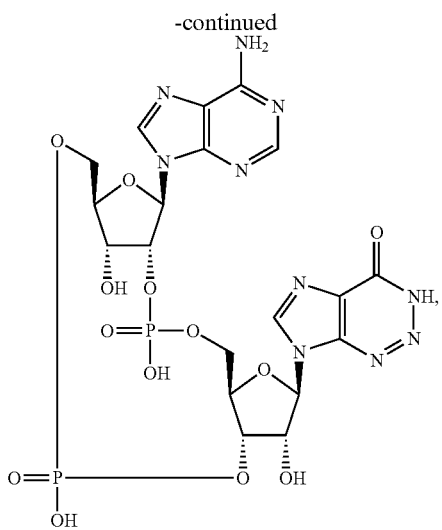
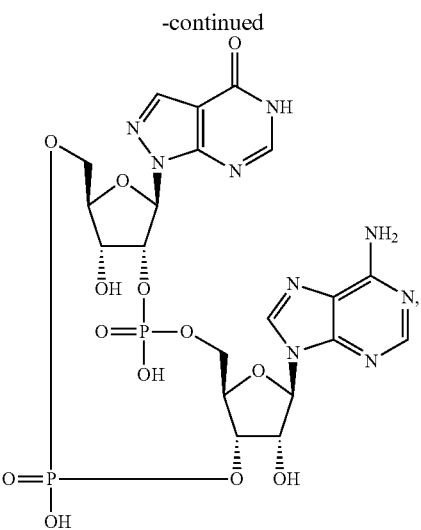
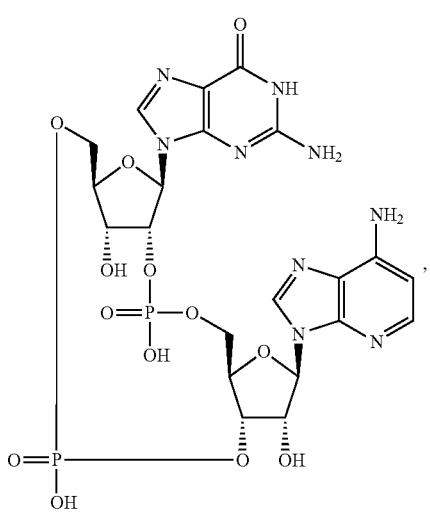
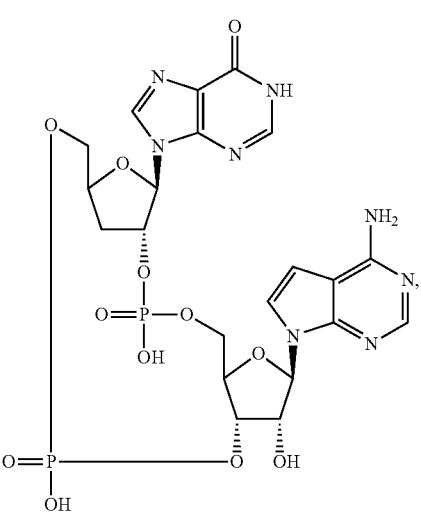
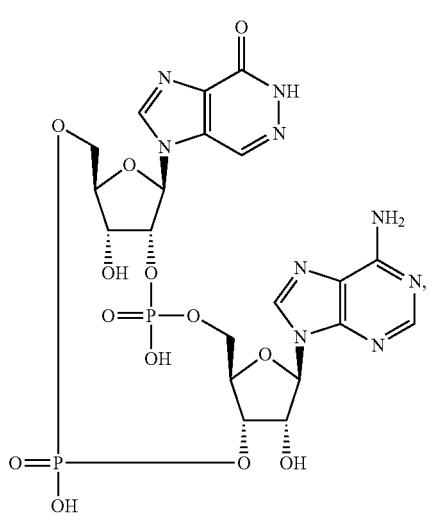
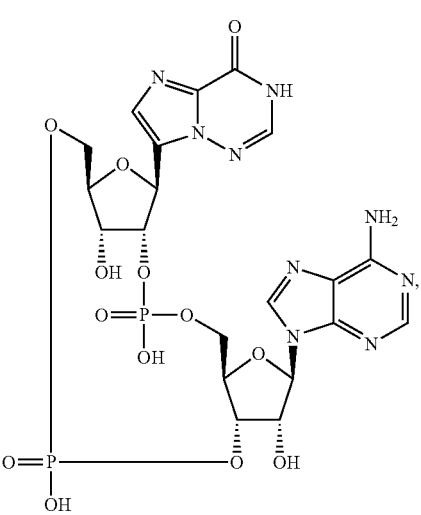

-continued
95
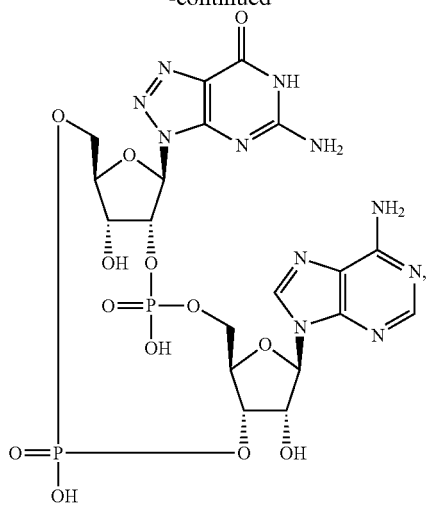
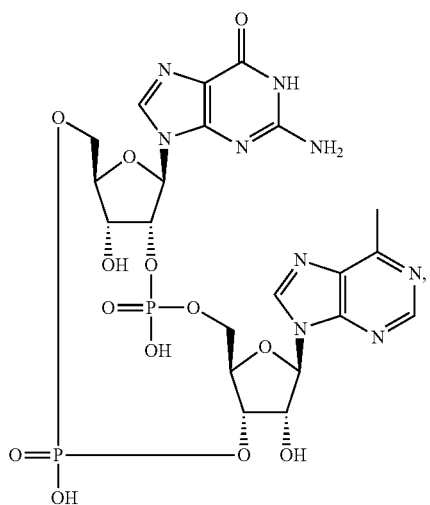
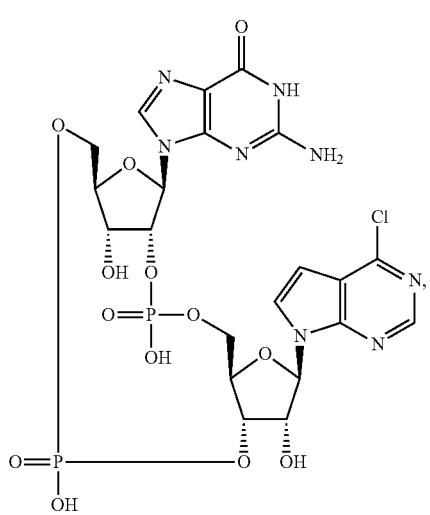
96
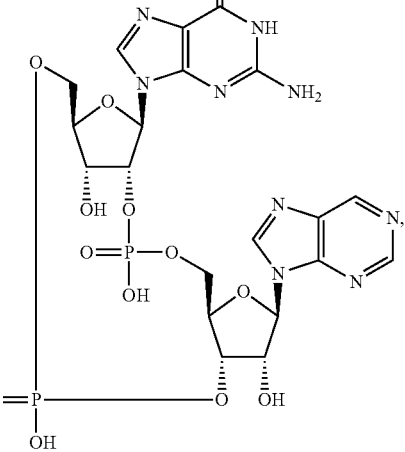
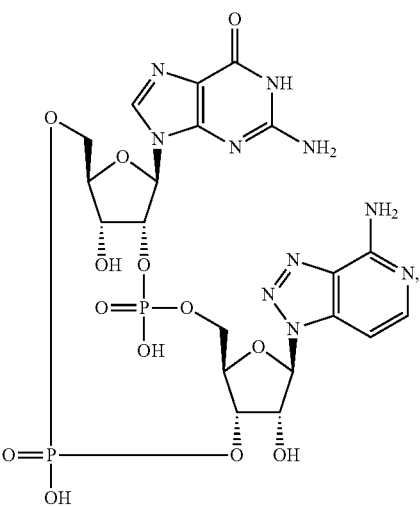
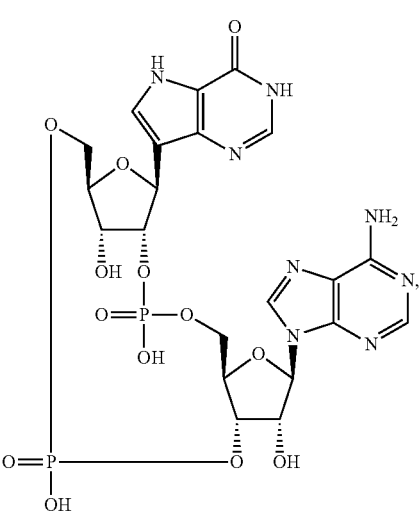

97
-continued
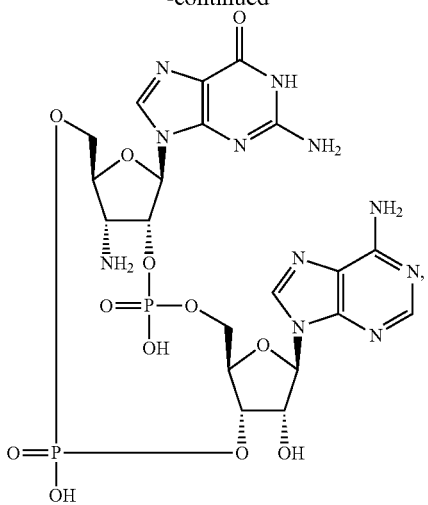
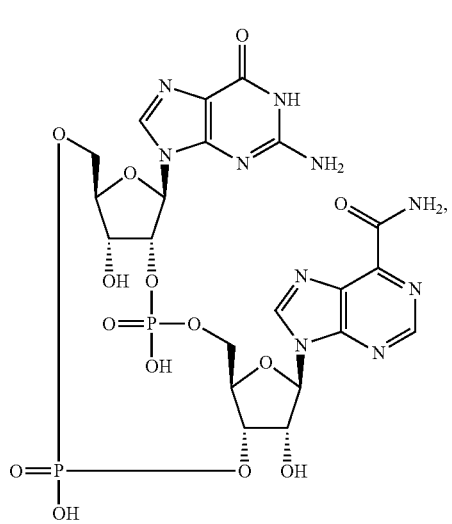
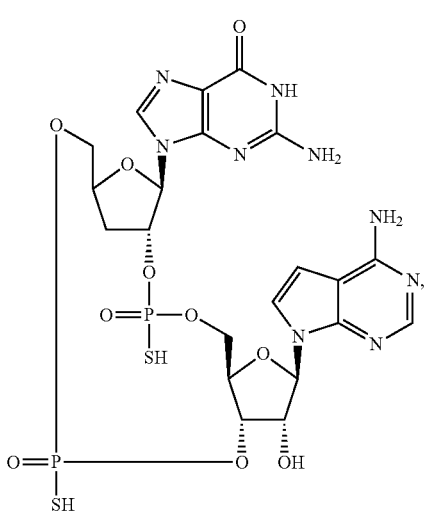
98
-continued
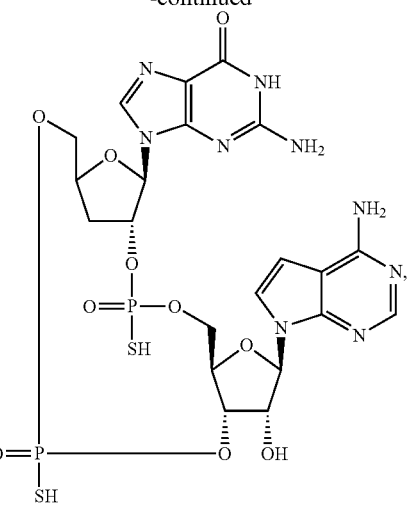
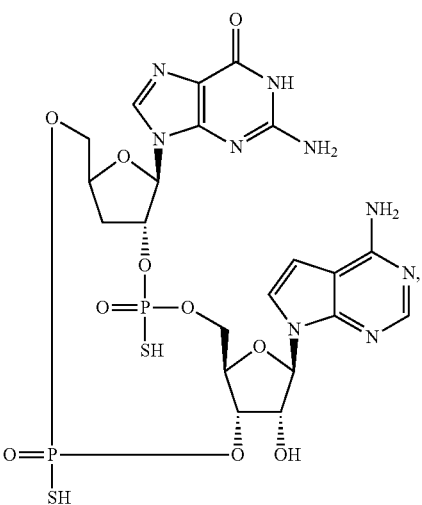
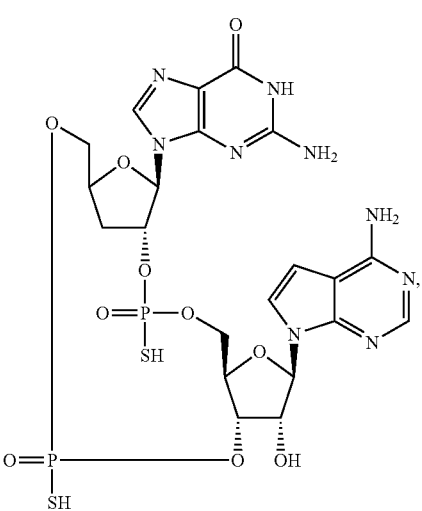

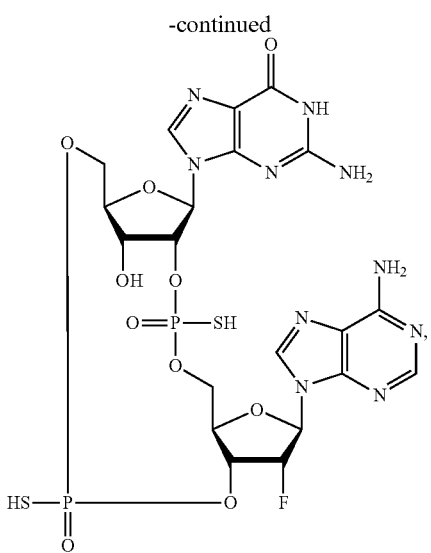
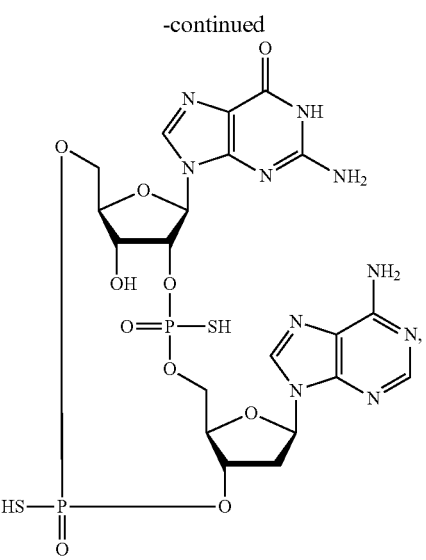
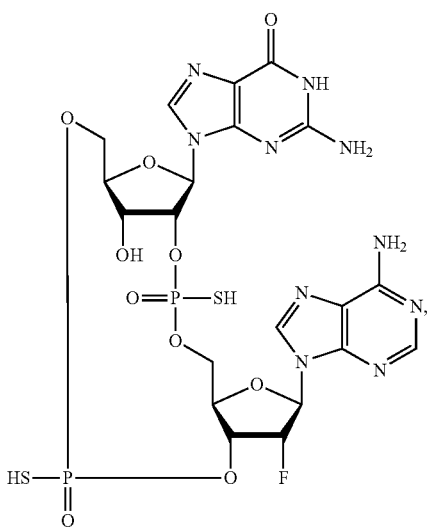
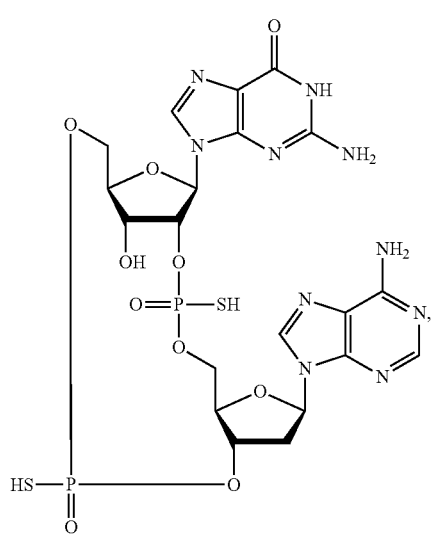
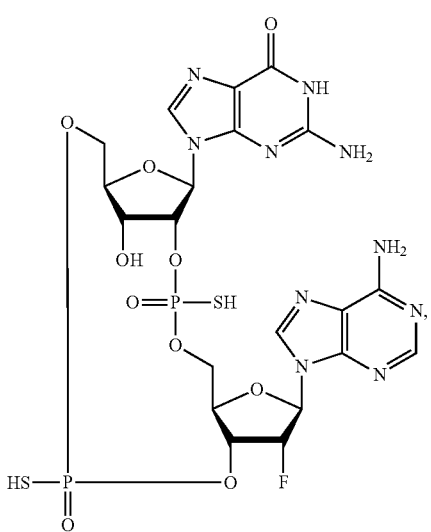
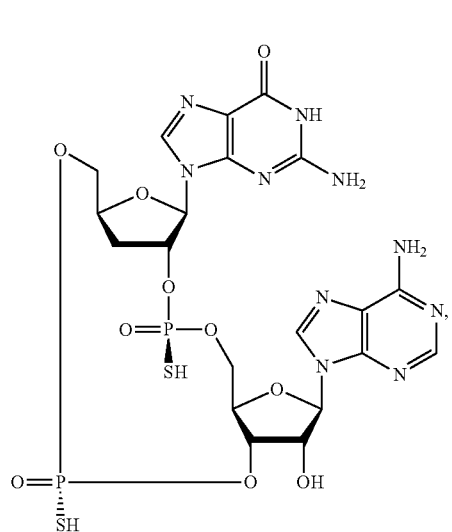

101
-continued
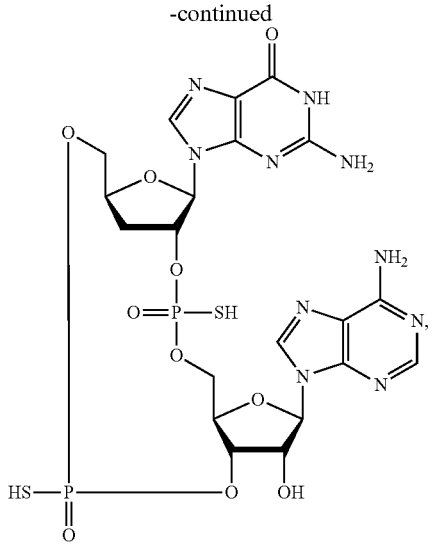
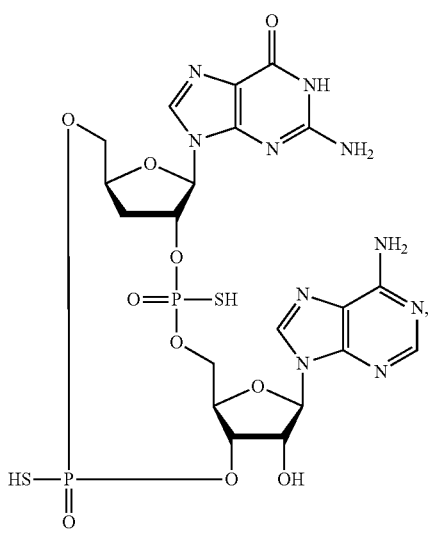
102
-continued
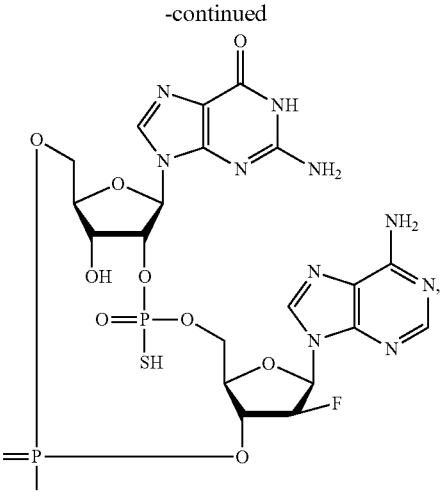
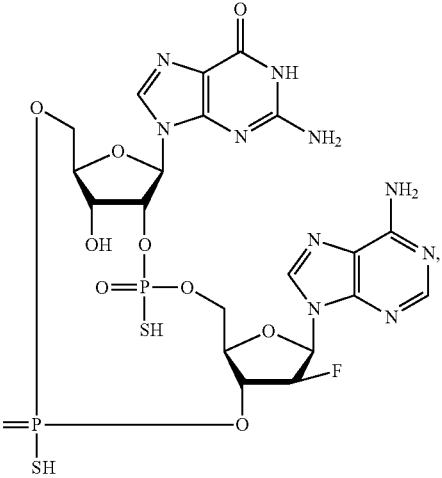
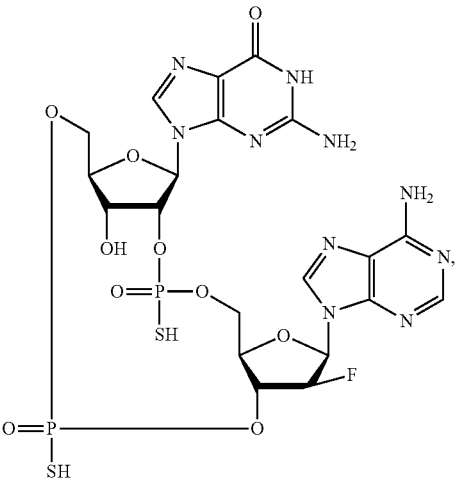

103
-continued
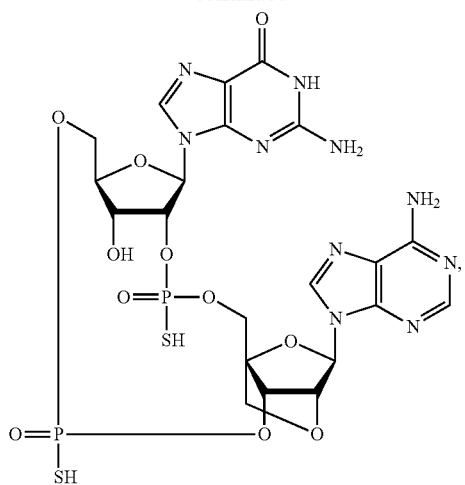
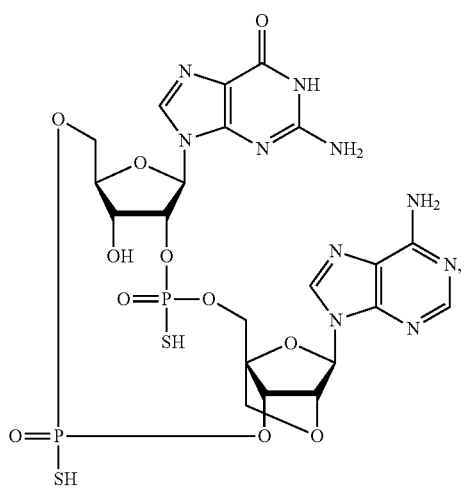
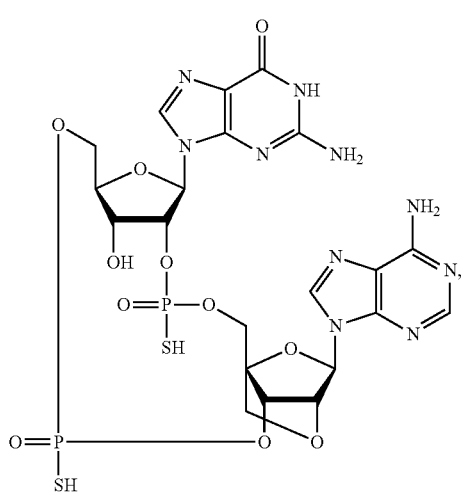
104
-continued
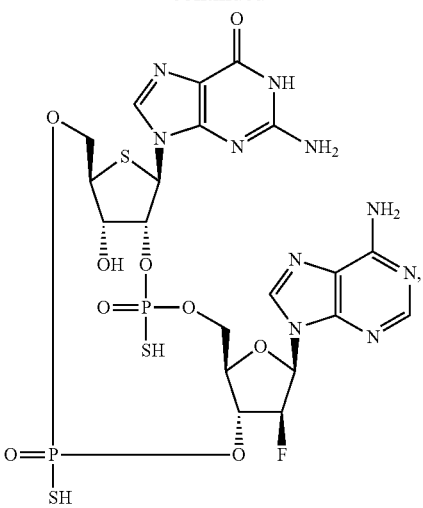
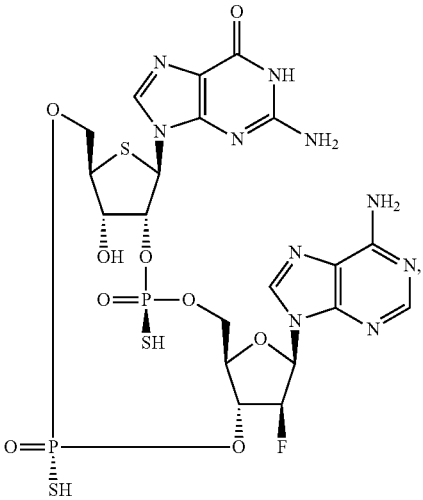
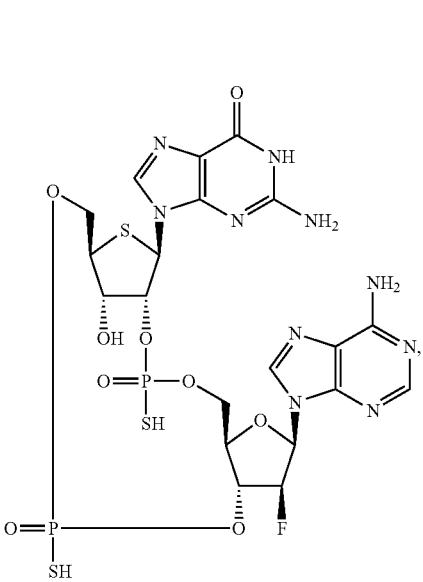

105
-continued
106
-continued
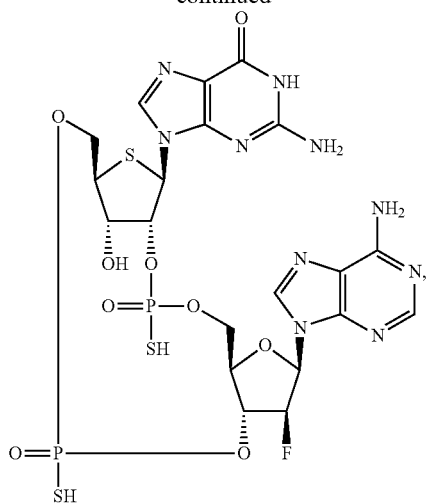
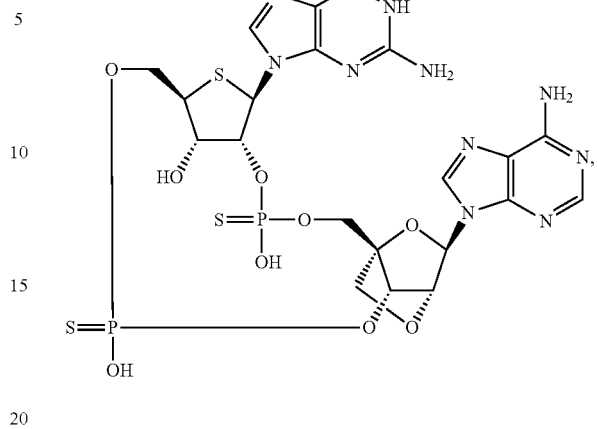
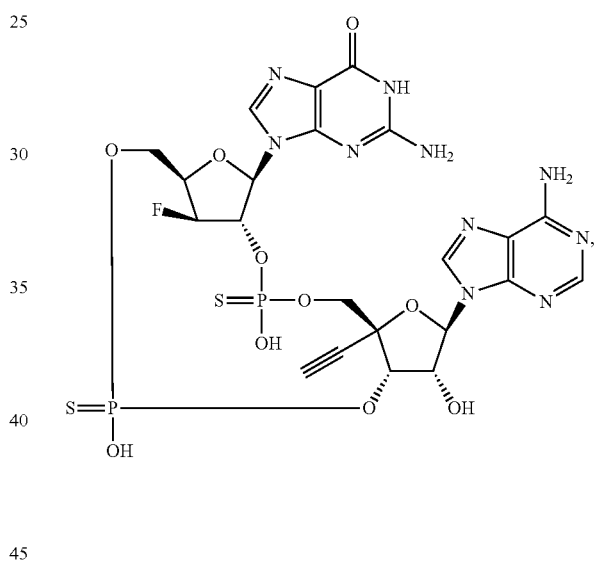
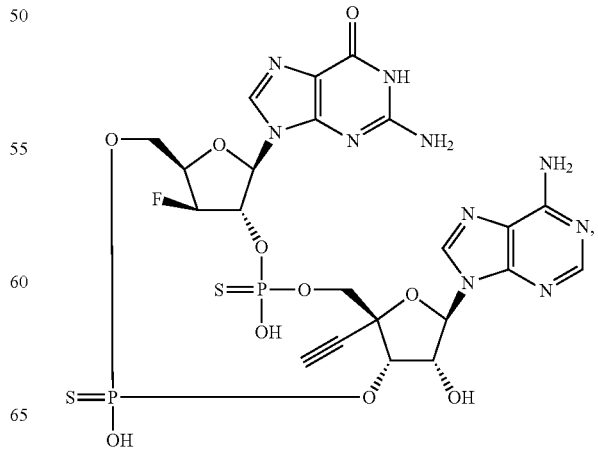

107
-continued
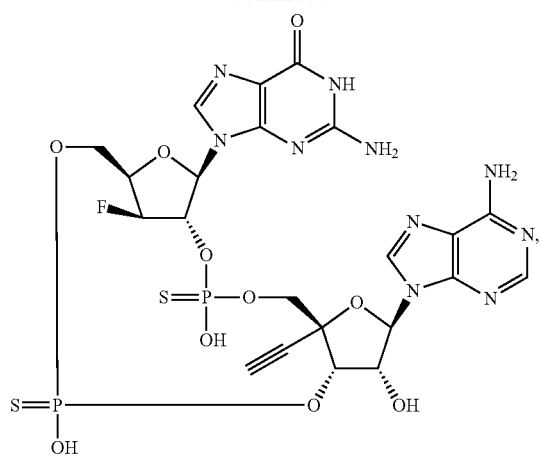 [SMILES: C#C[C@@]12COP(O)(=S)O[C@@H]3[C@@H](F)[C@@H](COP(O)(=S)O[C@H]1[C@@H](O)[C@H](n1cnc4c(N)ncnc41)O2)O[C@H]3n1cnc2c(=O)[nH]c(N)nc21]
108
-continued
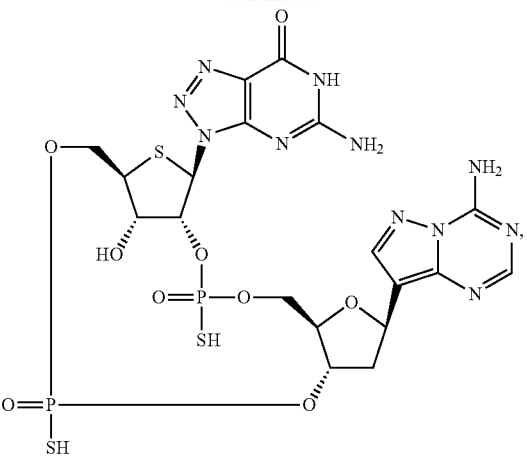
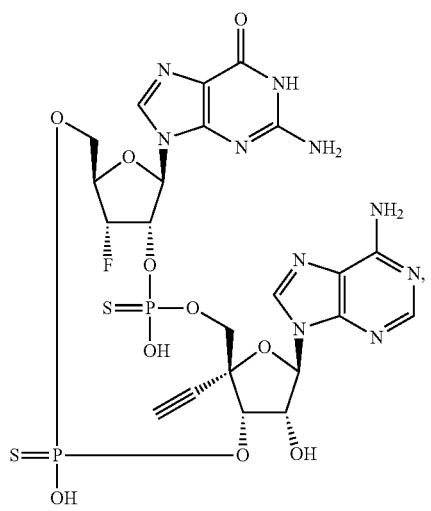
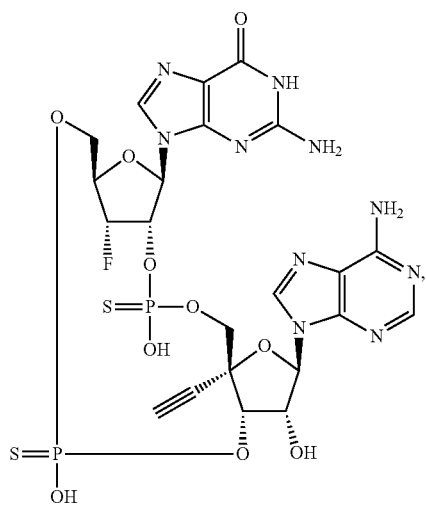
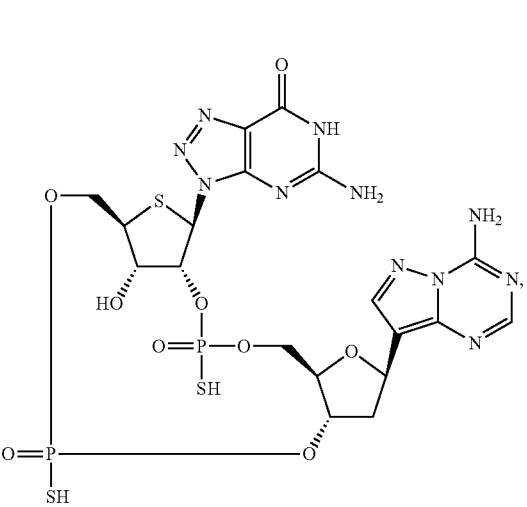

-continued
109
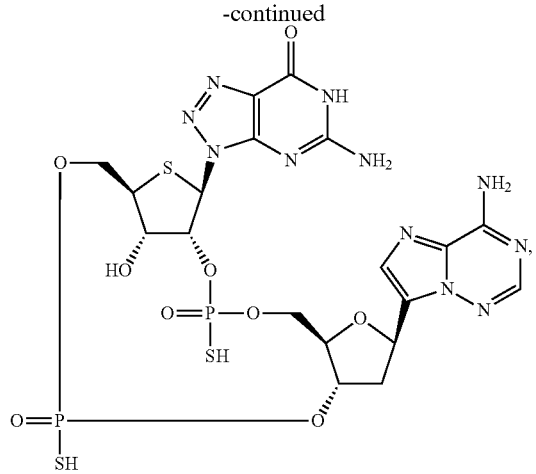
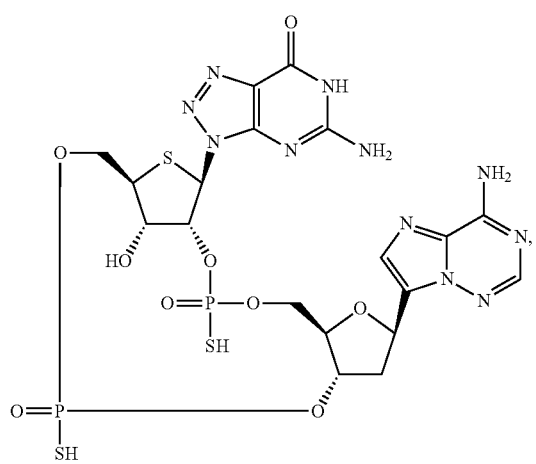
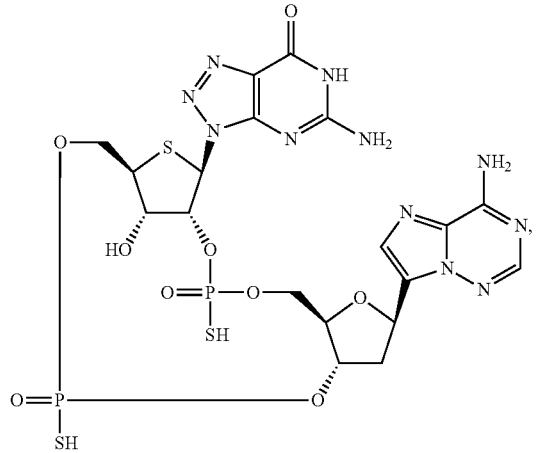
-continued
110
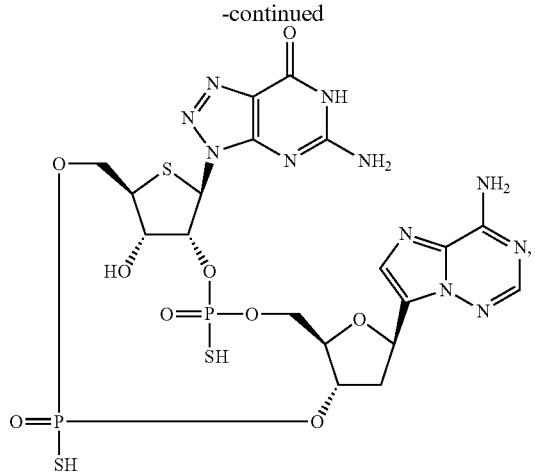
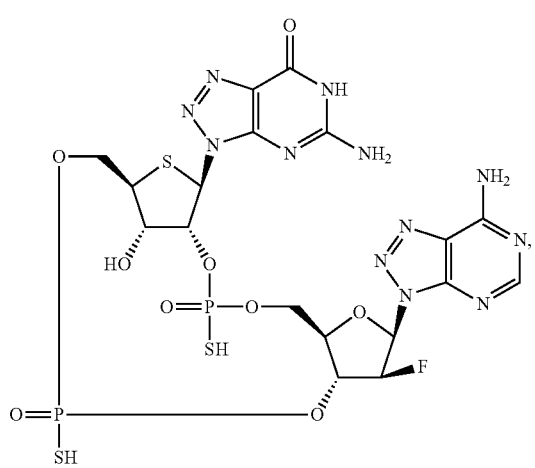
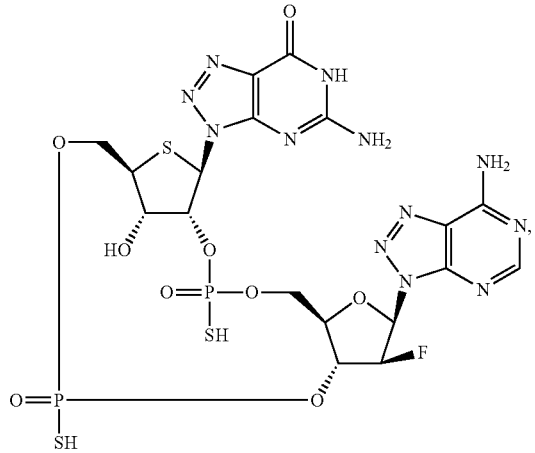

111
-continued
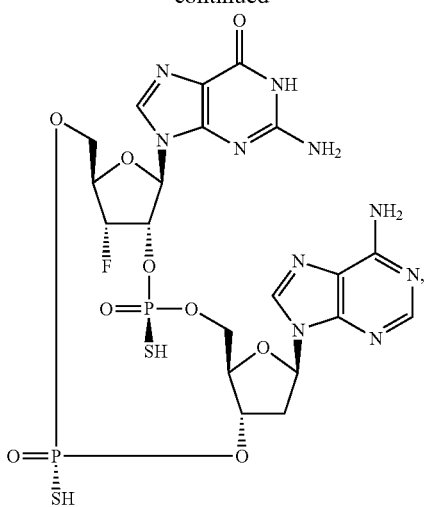
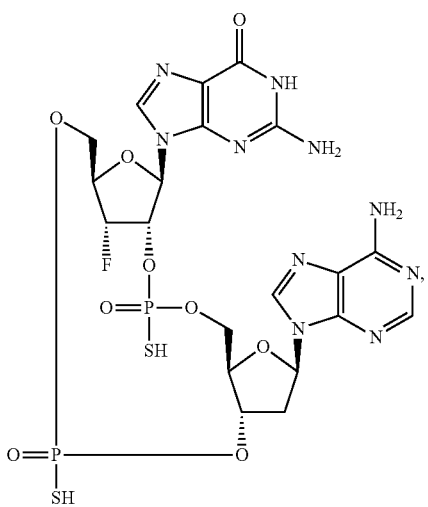
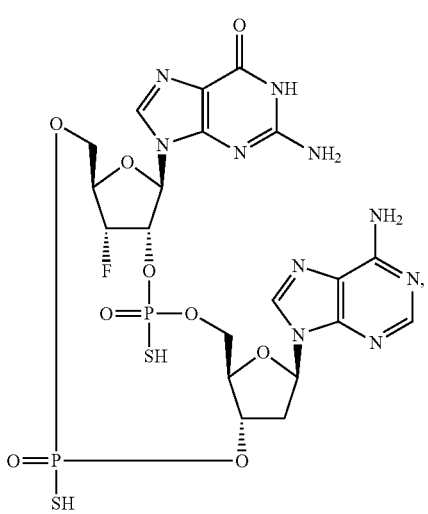
112
-continued
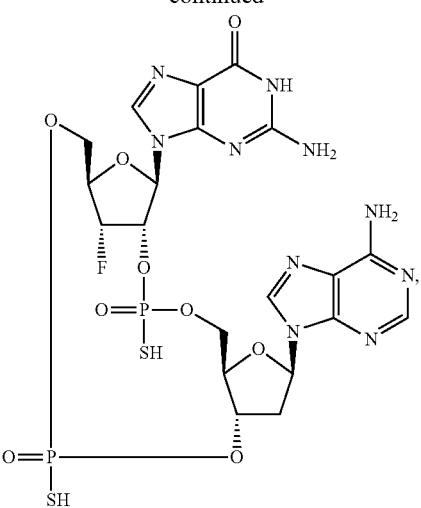
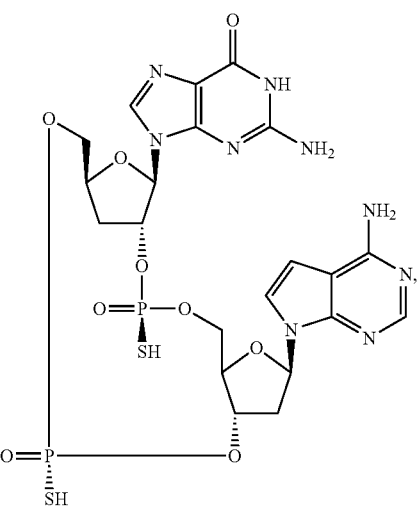 [SMILES: Nc1nc2c(ncn2[C@@H]2O[C@@H]3CO[P@@](=O)(S)O[C@H]4C[C@H](n5ccc6c(N)ncnc65)OC4CO[P@@](=O)(S)O[C@@H]2C3)c(=O)[nH]1]
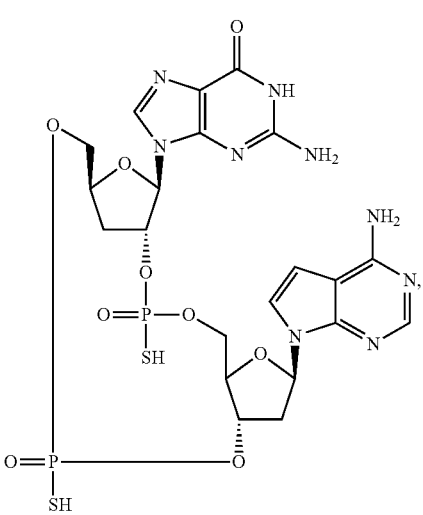

113 -continued
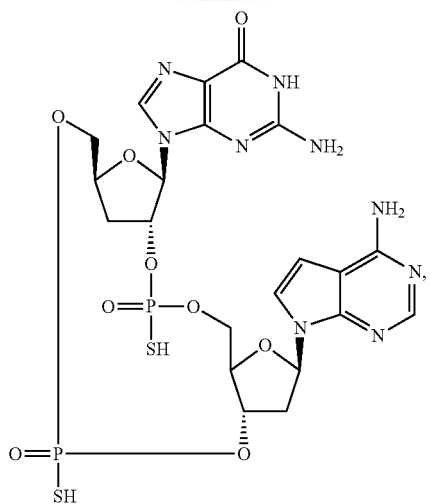
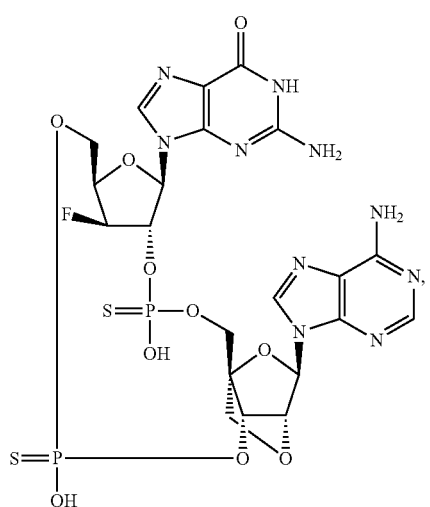
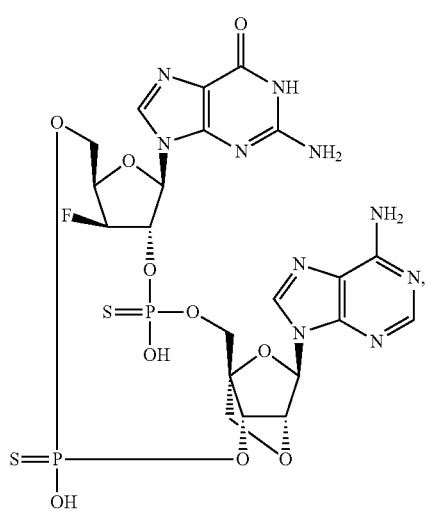
114 -continued
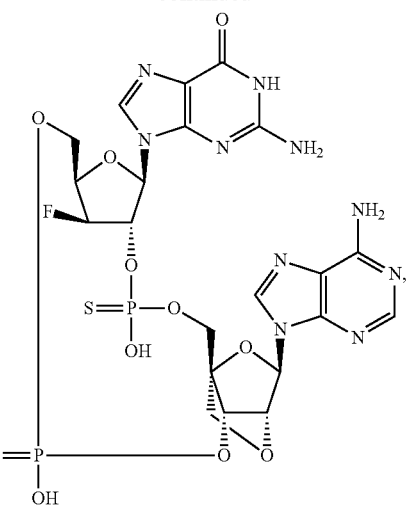
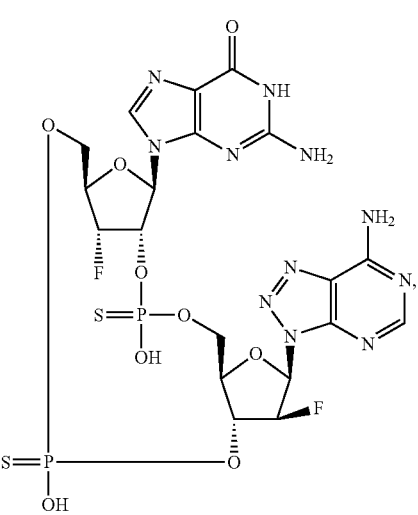
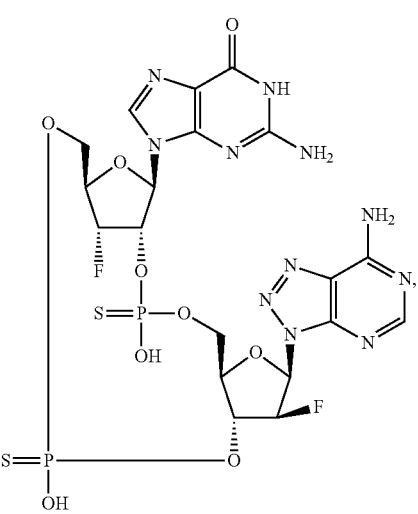

115
-continued
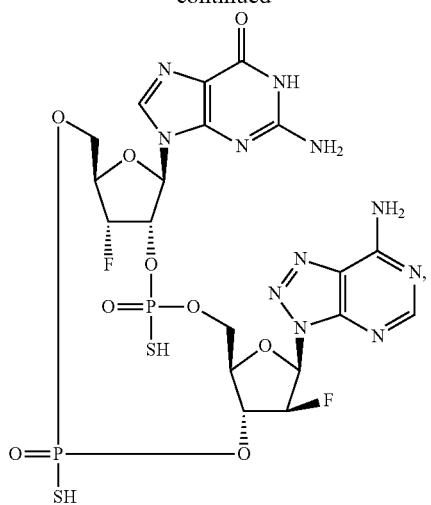
116
-continued
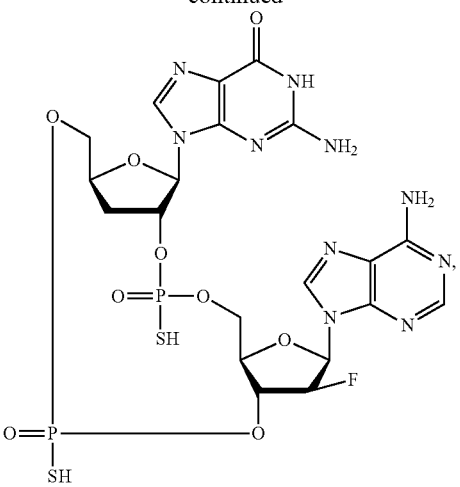
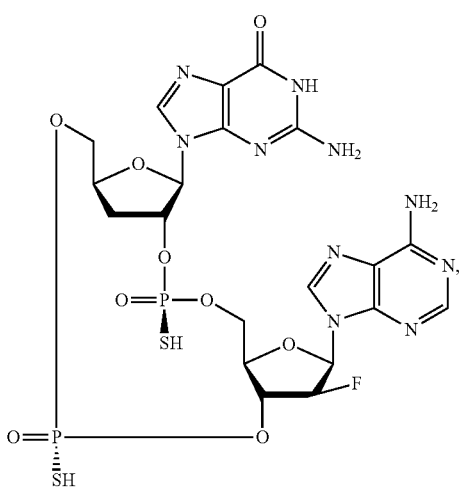
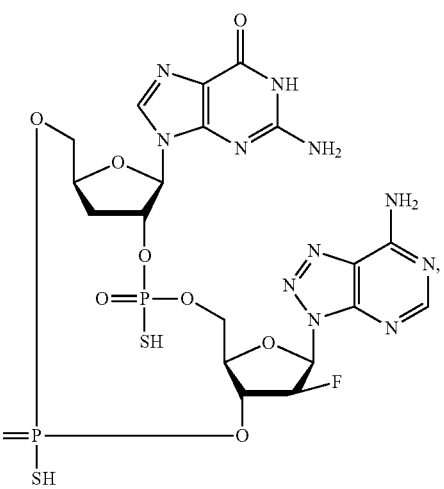
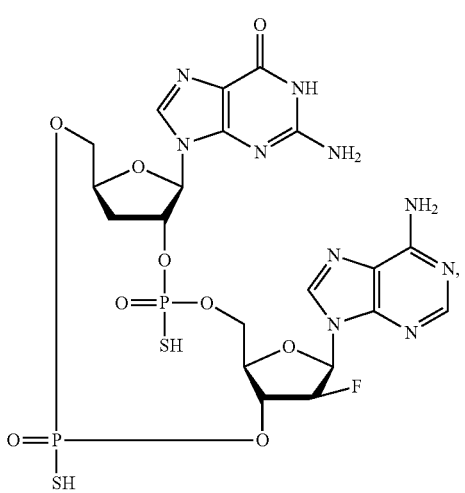
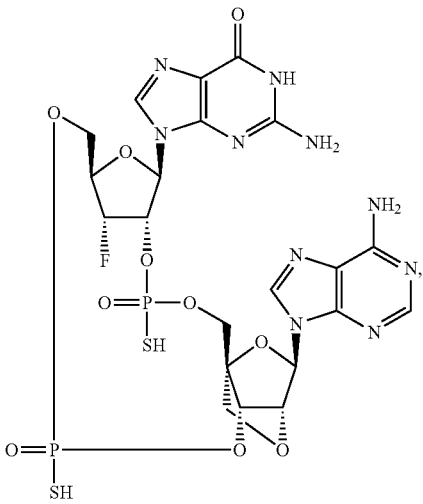

117
-continued
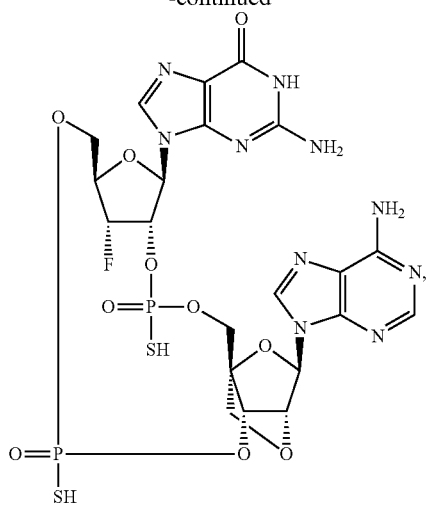
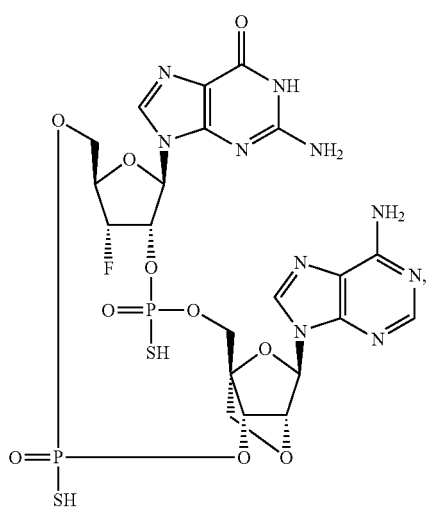 [SMILES: Nc1nc2c(ncn2[C@@H]2O[C@@H]3COP(=O)(S)O[C@H]4[C@H]5OC[C@]4(COP(=O)(S)O[C@@H]2[C@@H]3F)O[C@H]5n2cnc3c(N)ncnc32)c(=O)[nH]1]
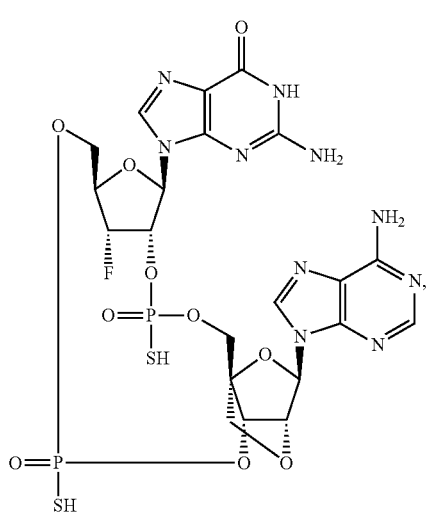
118
-continued
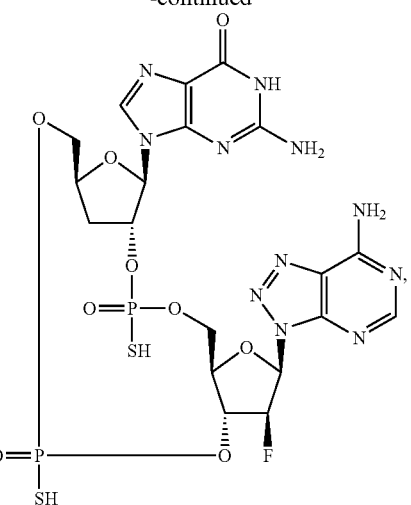
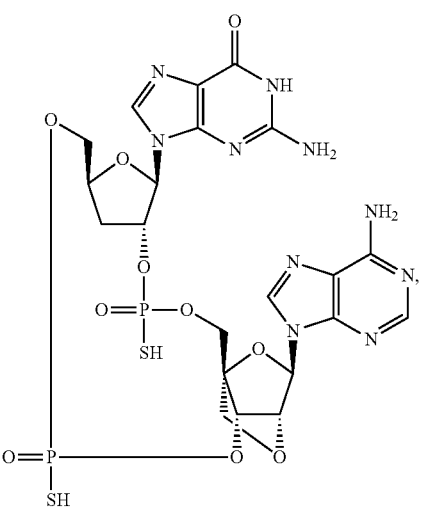
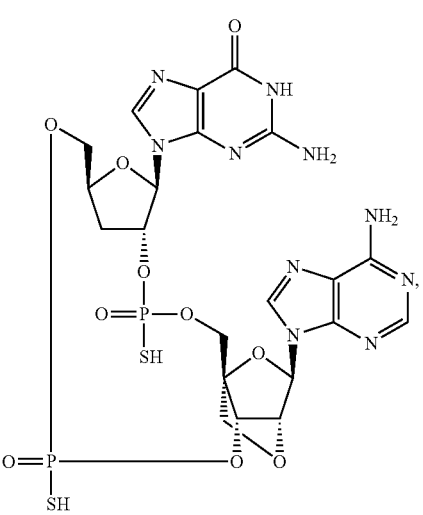

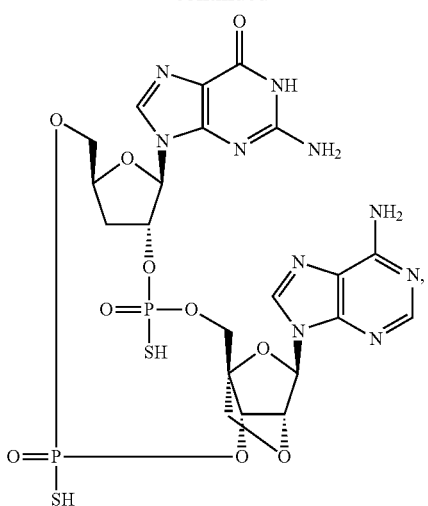
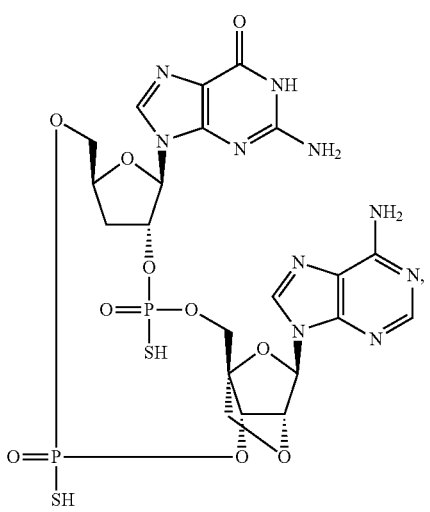
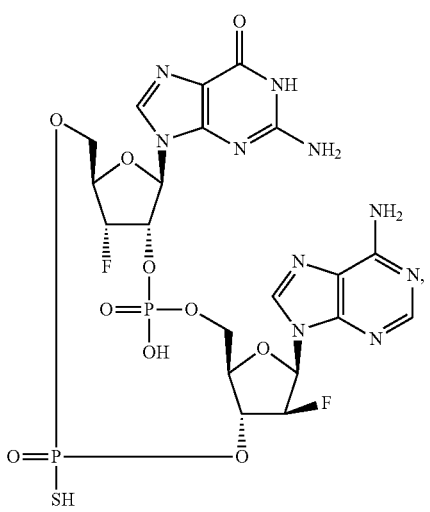
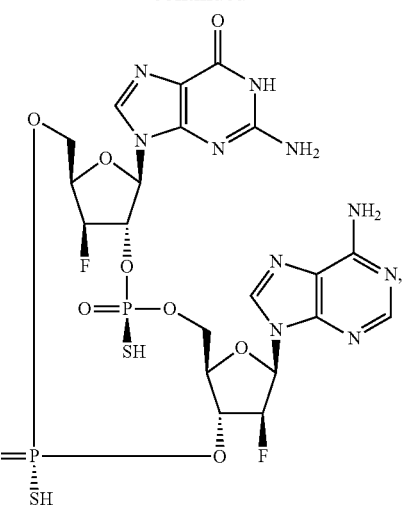
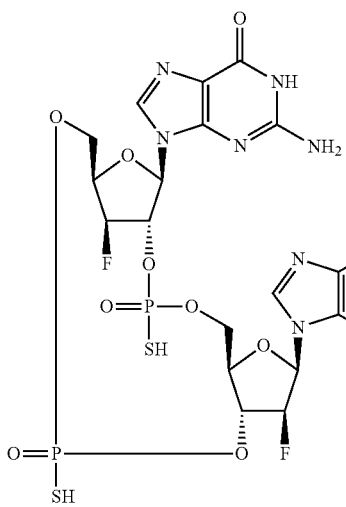

121
-continued
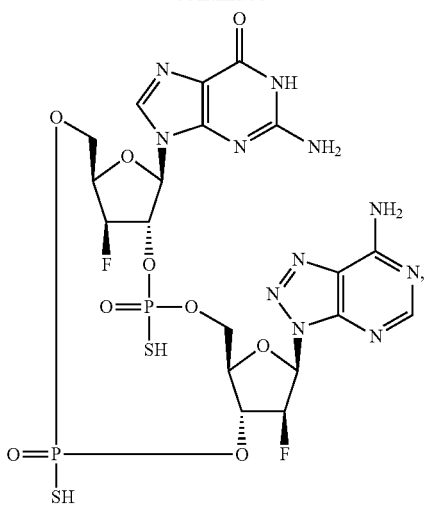
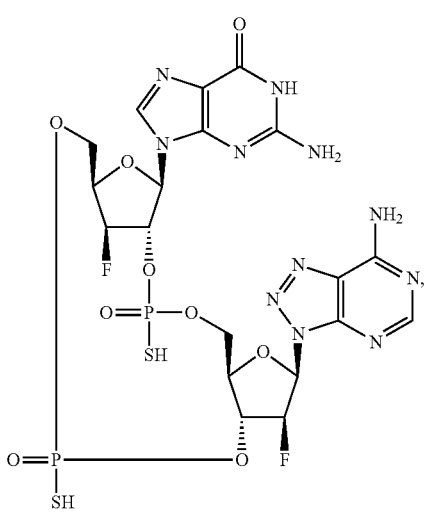
122
-continued
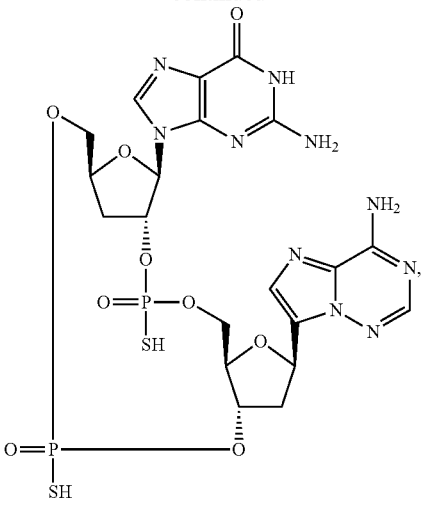
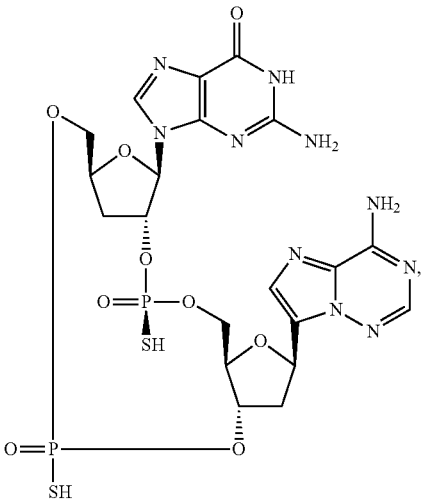
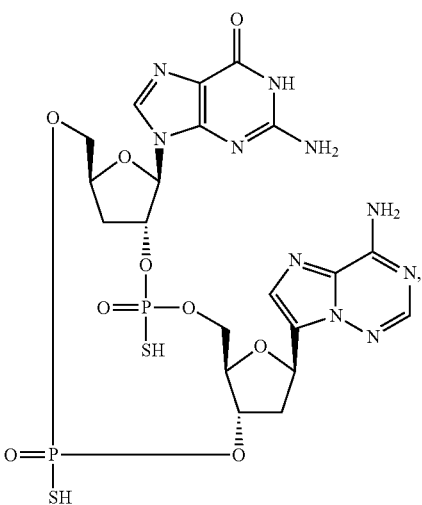

123
-continued
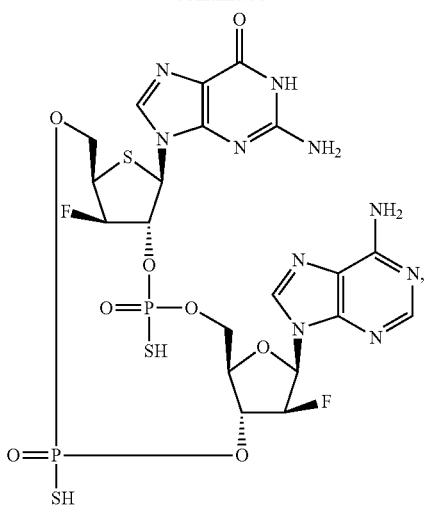 [SMILES: Nc1nc2c(ncn2[C@@H]2S[C@@H]3COP(=O)(S)O[C@H]4[C@H](F)[C@H](n5cnc6c(N)ncnc65)O[C@@H]4COP(=O)(S)O[C@@H]2[C@H]3F)c(=O)[nH]1]
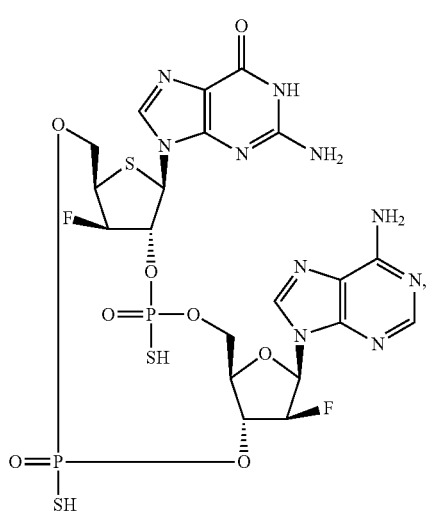
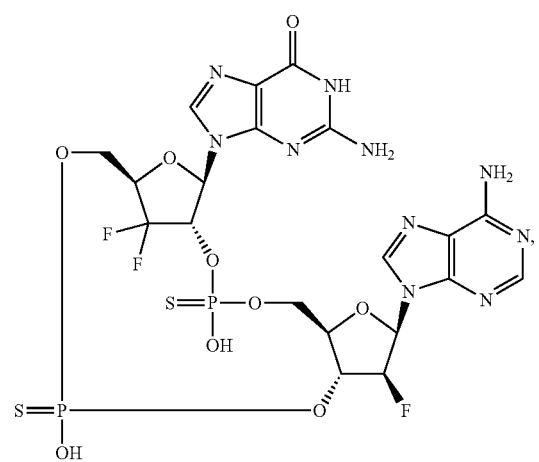
124
-continued
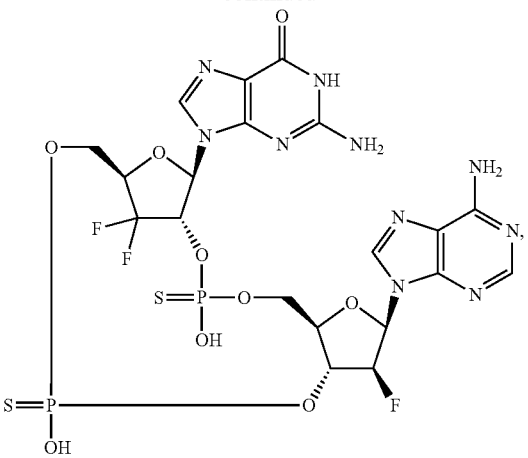
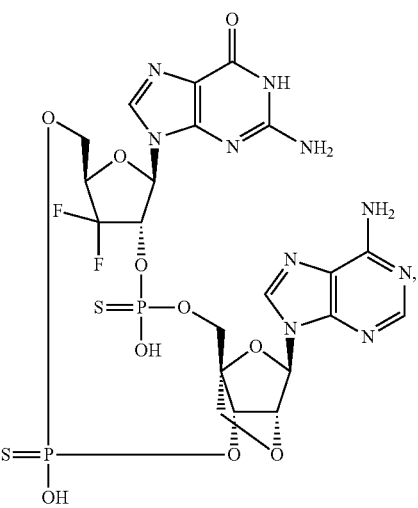
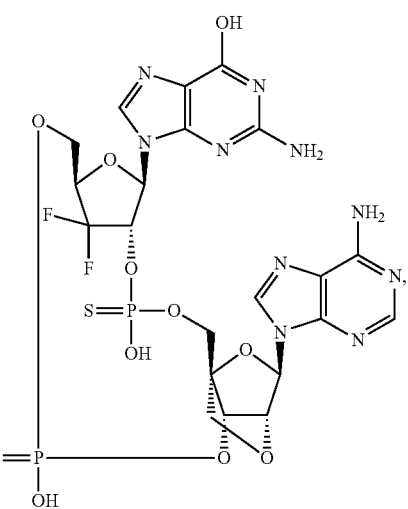

125
-continued
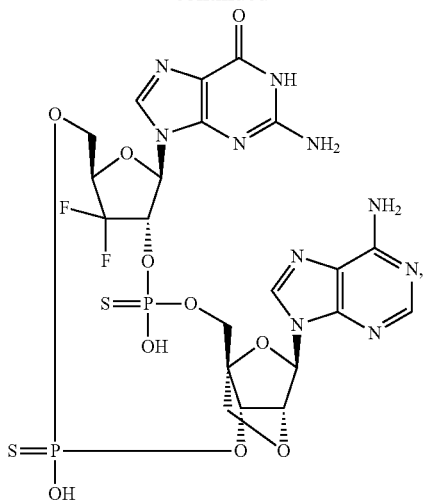
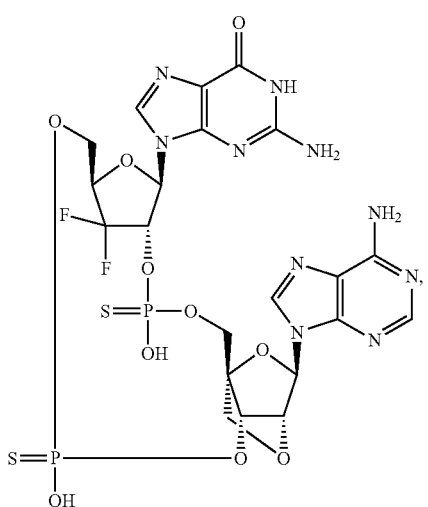
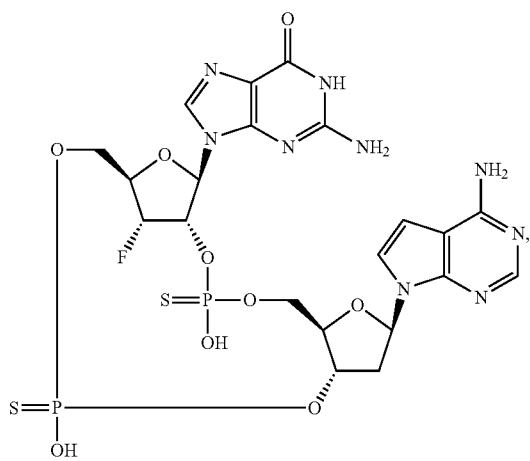
126
-continued
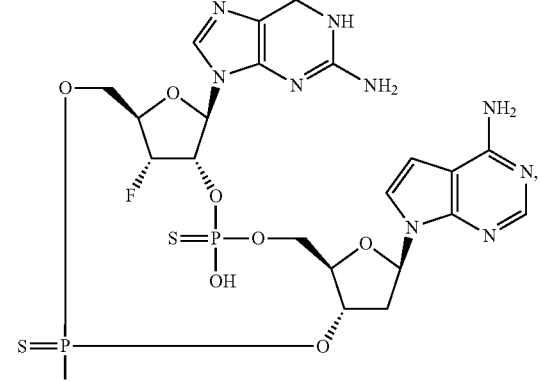
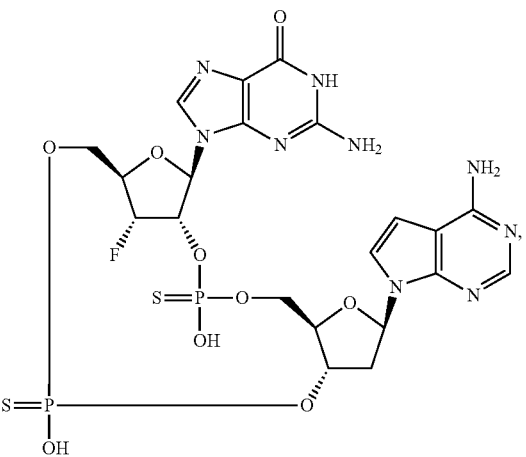
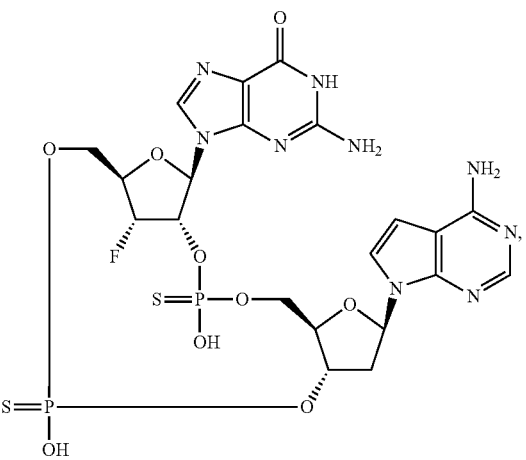

127
-continued
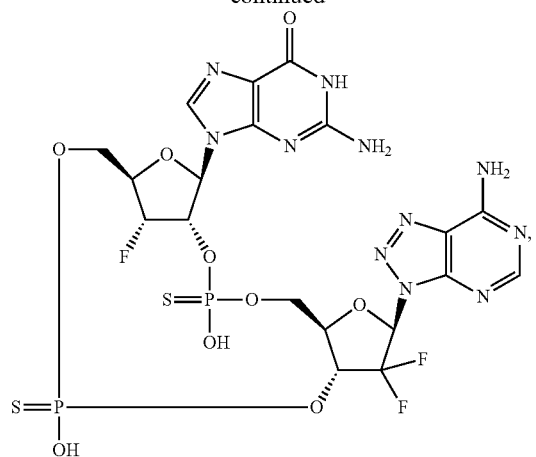
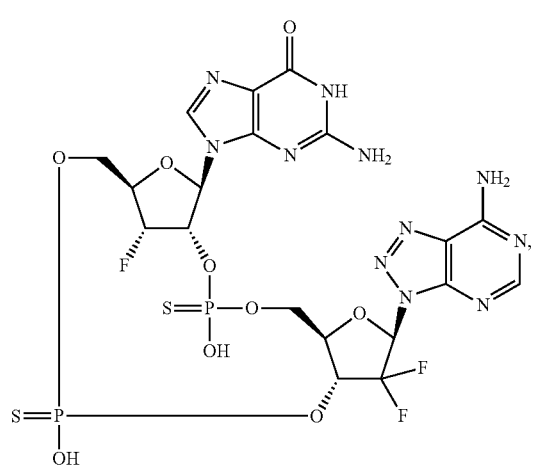
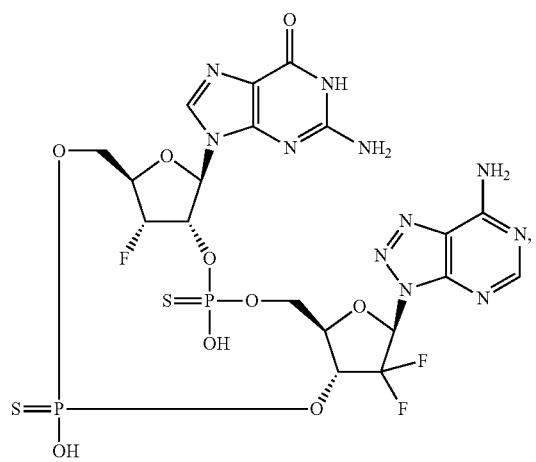
128
-continued
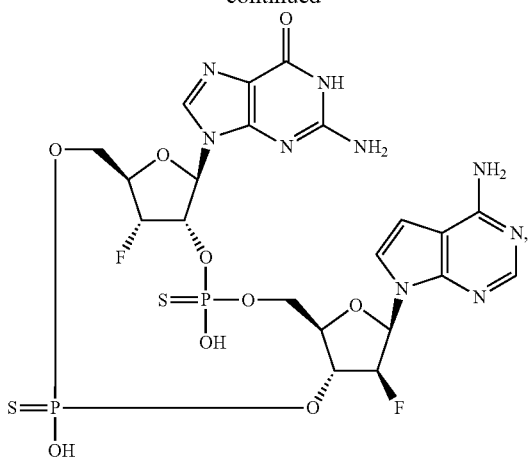
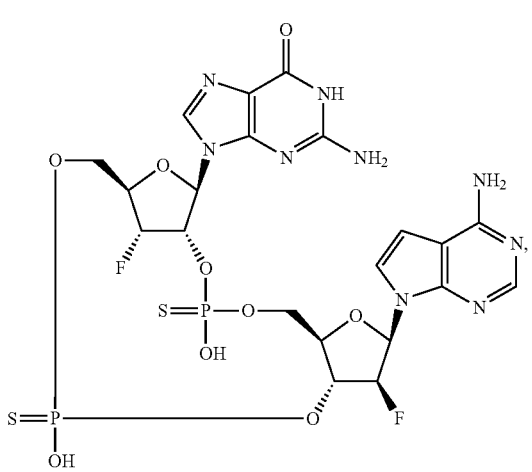
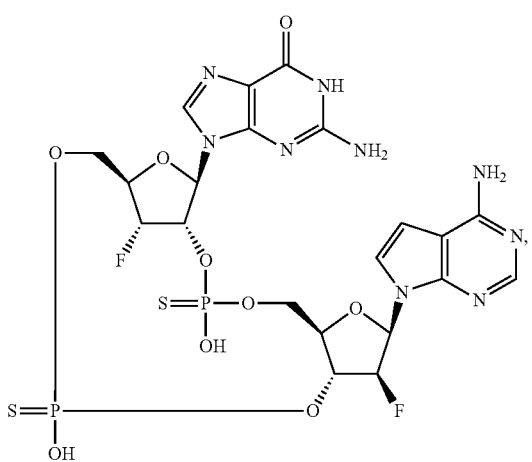

129
-continued
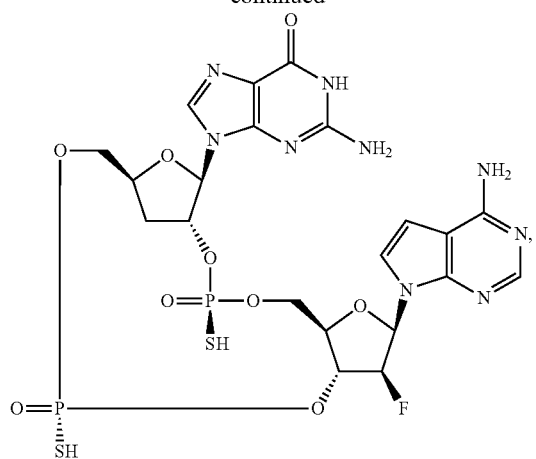
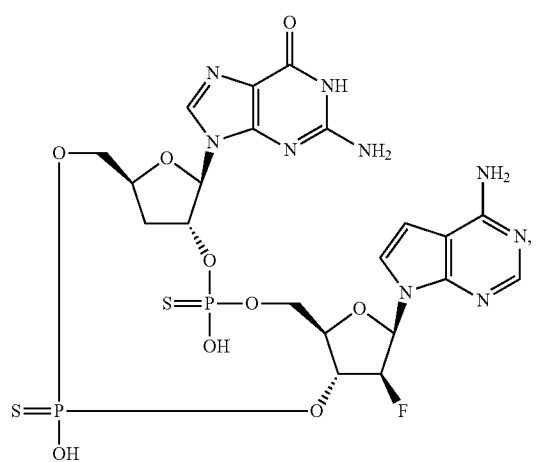
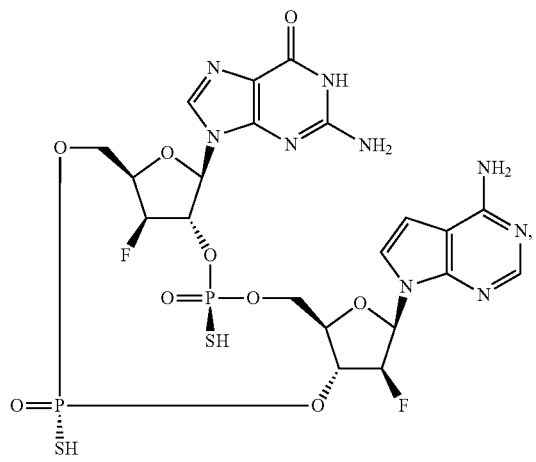
130
-continued
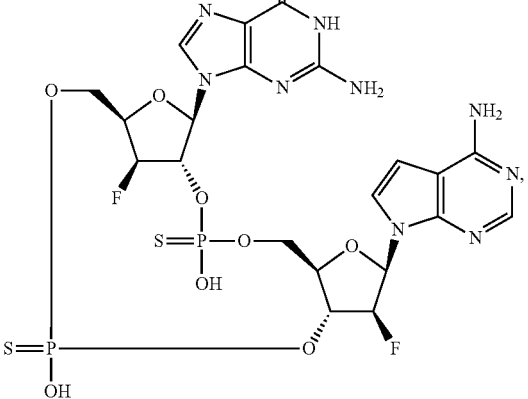
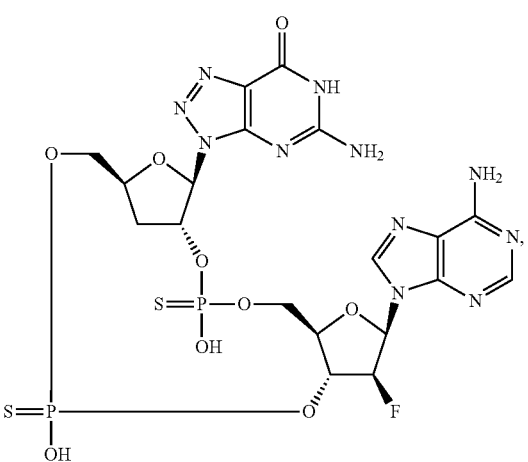
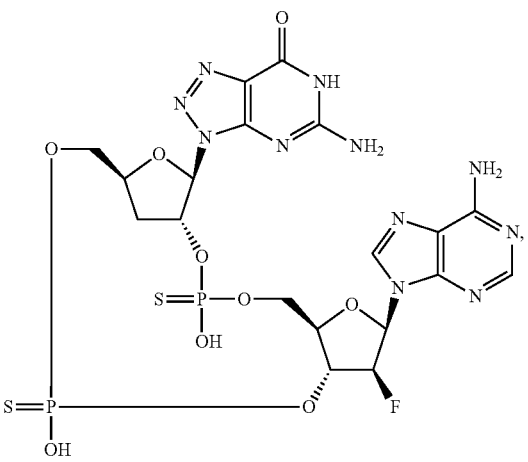

131
-continued
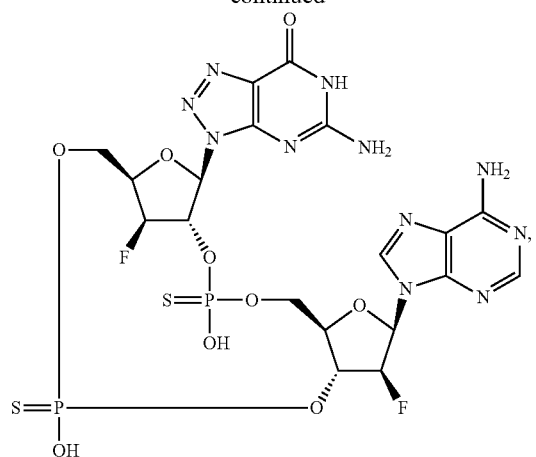
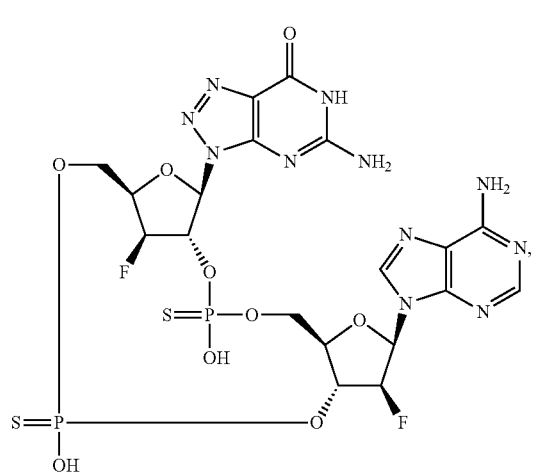
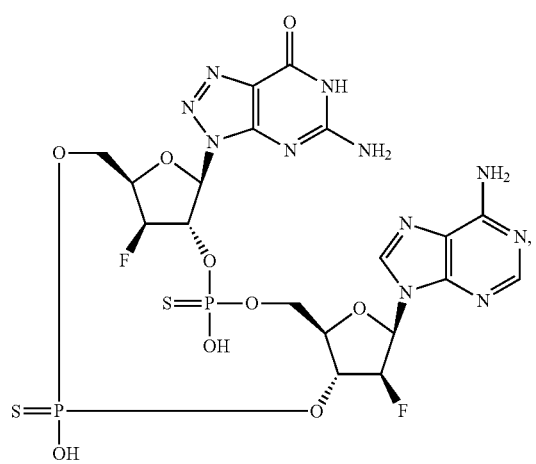
132
-continued
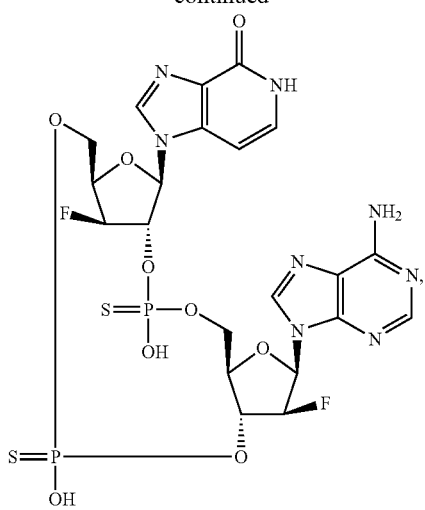
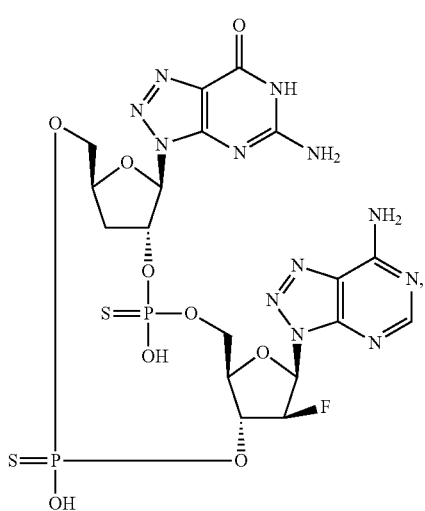
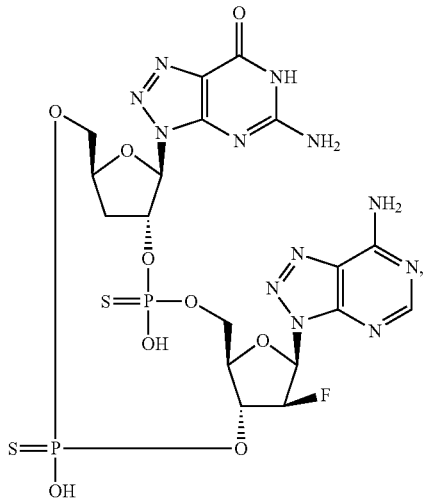

133
-continued
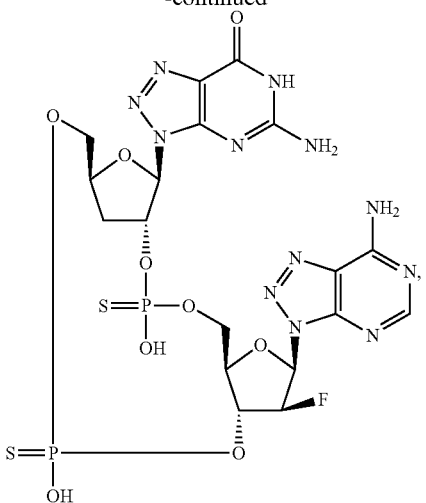
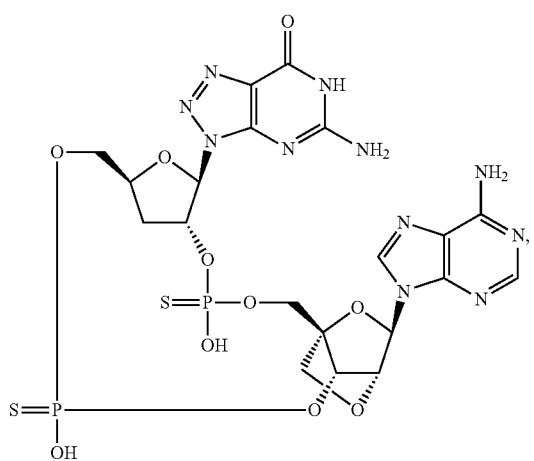
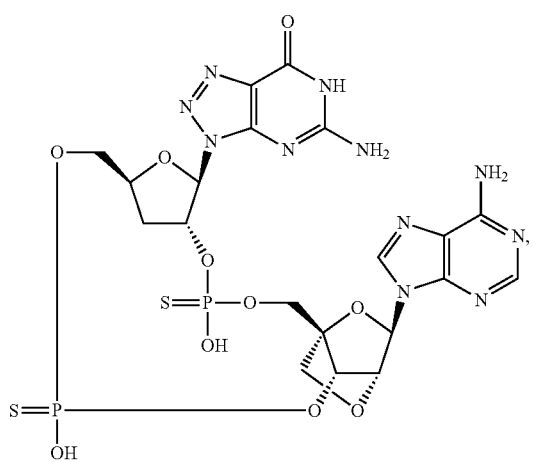
134
-continued
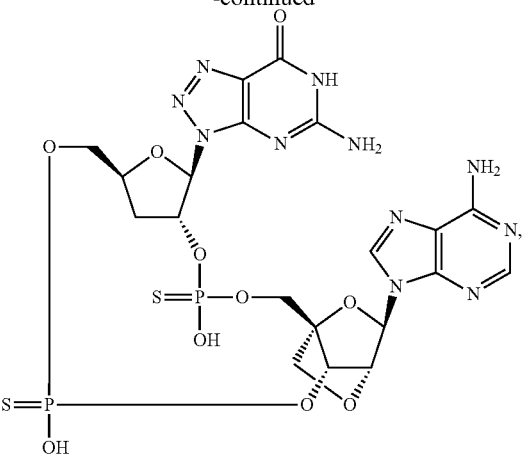
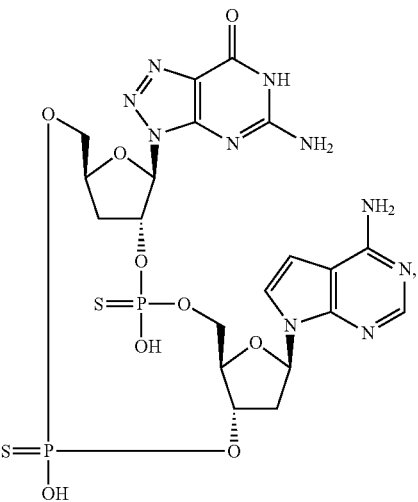

135
-continued
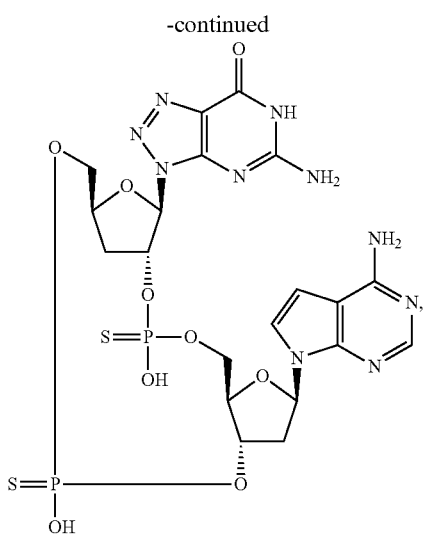
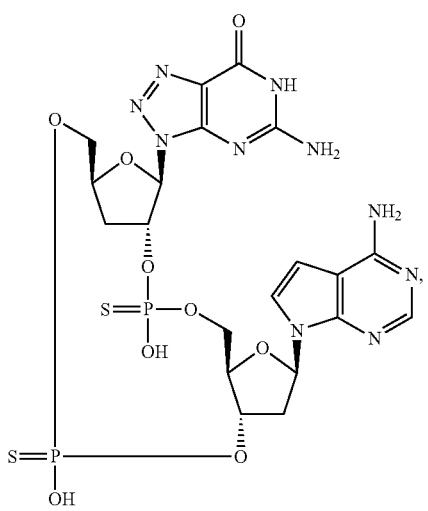
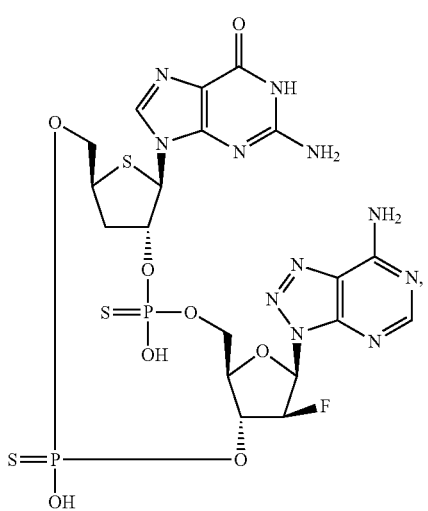
136
-continued
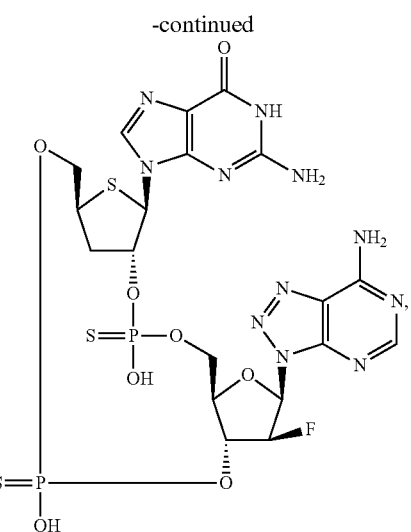
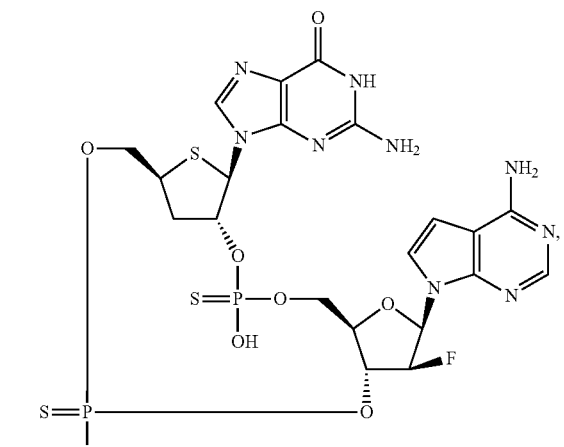
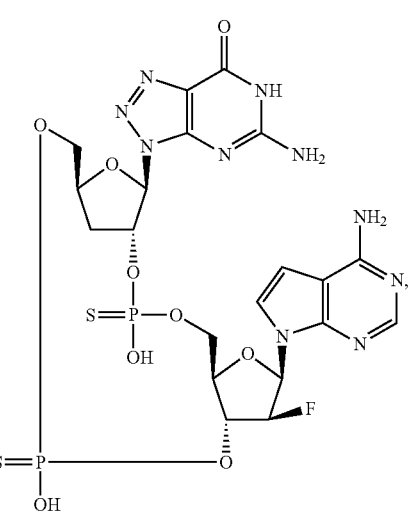

137
-continued
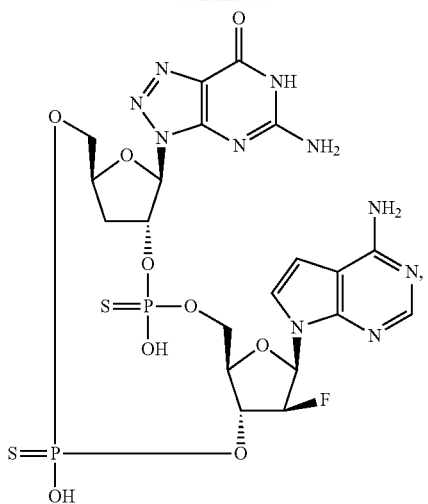
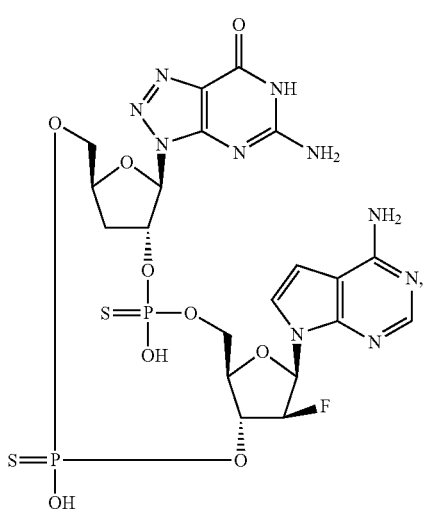
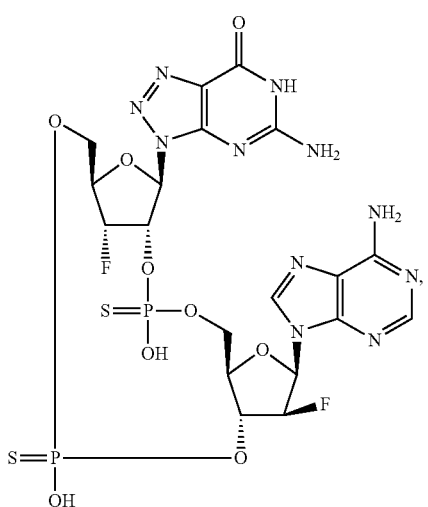
138
-continued
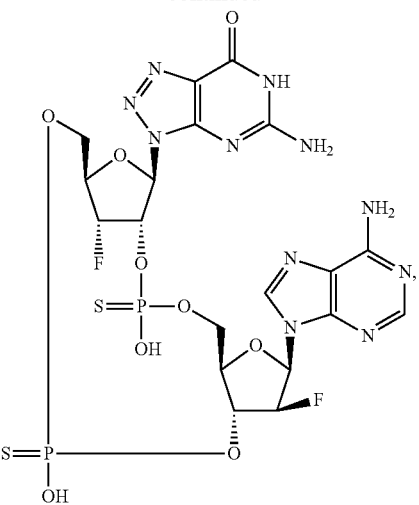
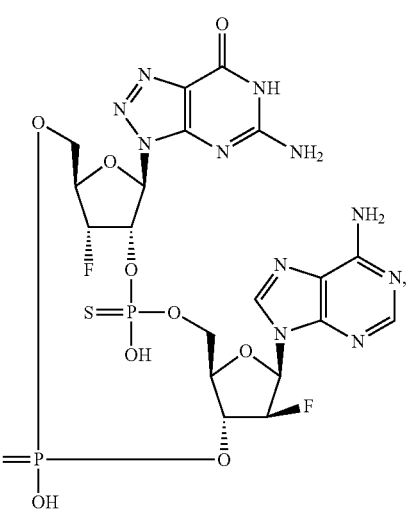
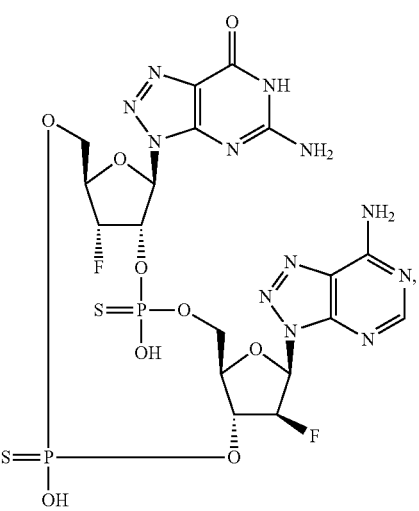

139
-continued
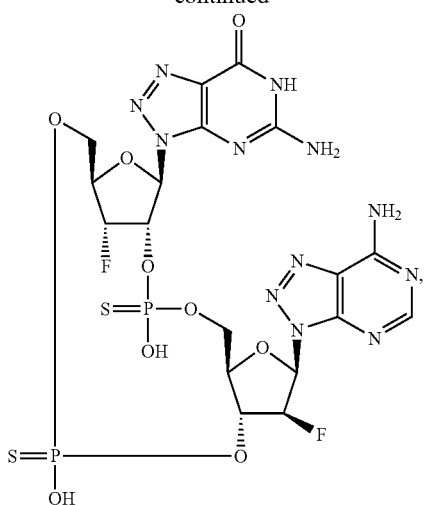
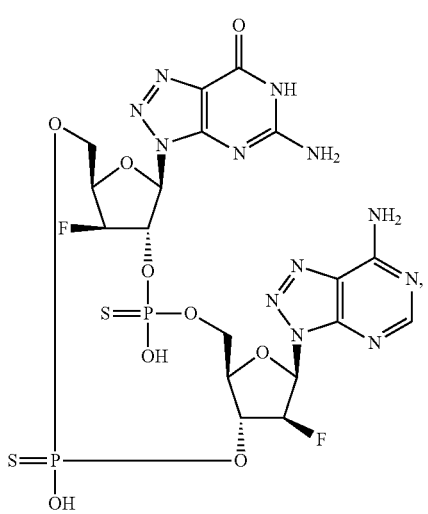
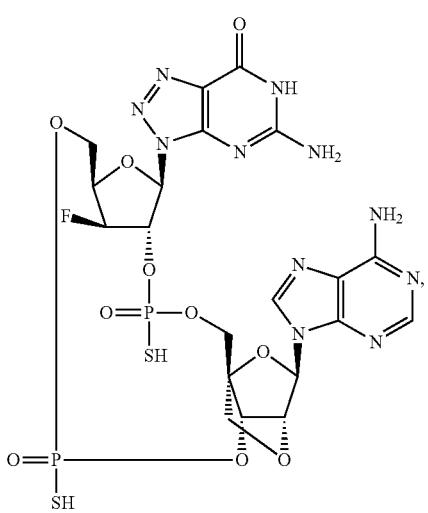
140
-continued
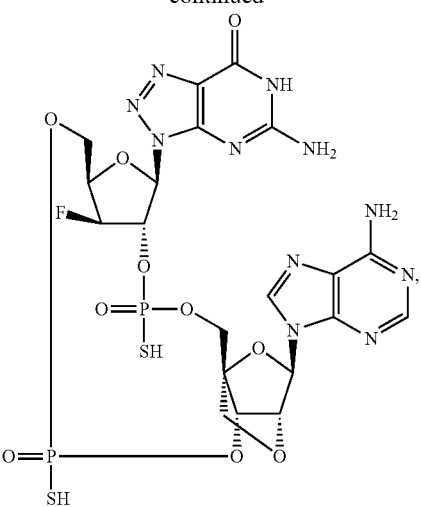
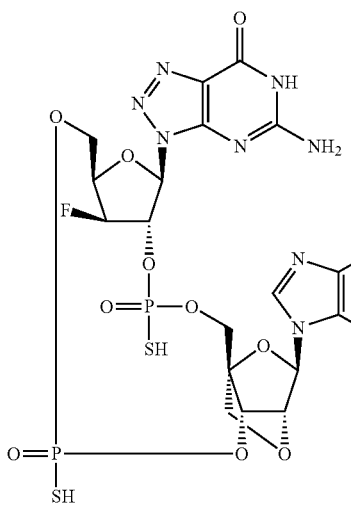
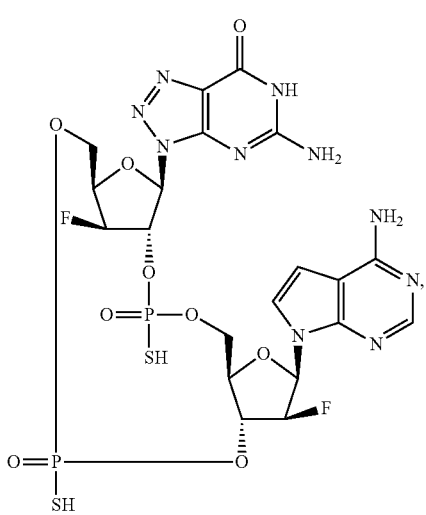

141
-continued
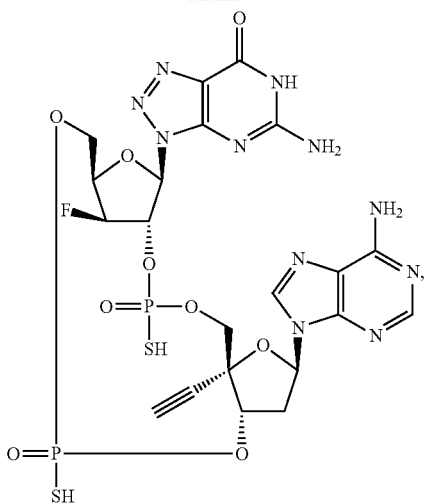
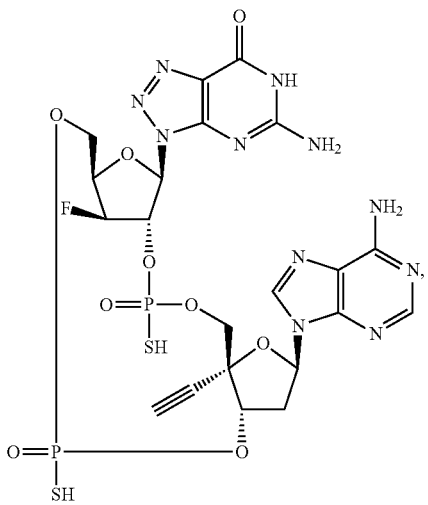
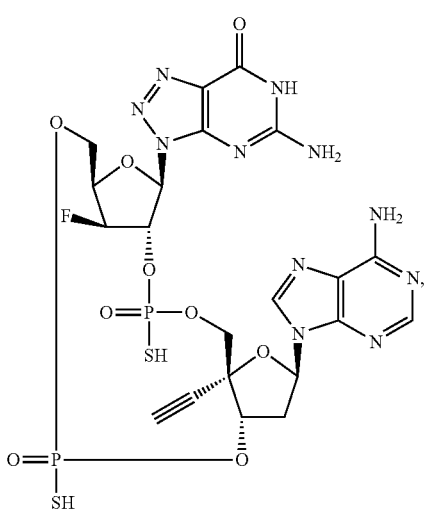
142
-continued
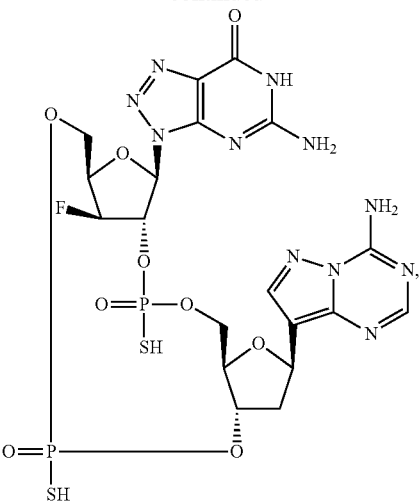
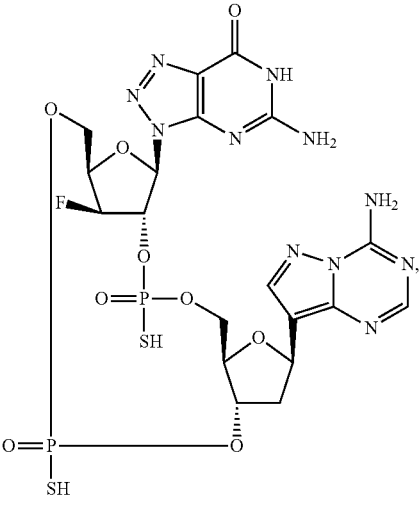
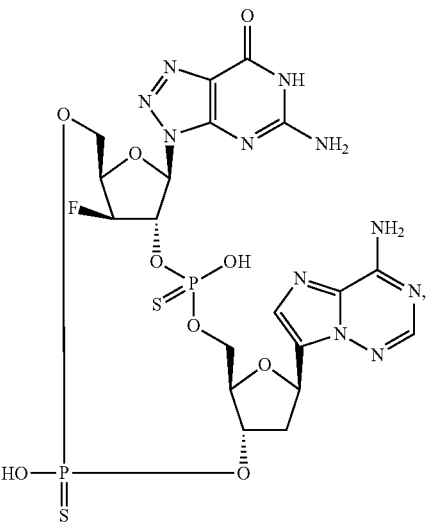

143
-continued
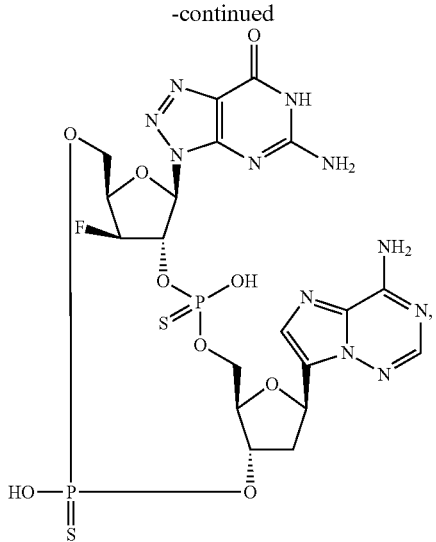
144
-continued
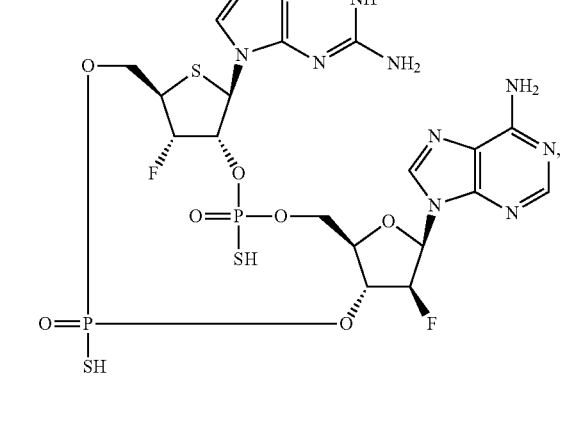
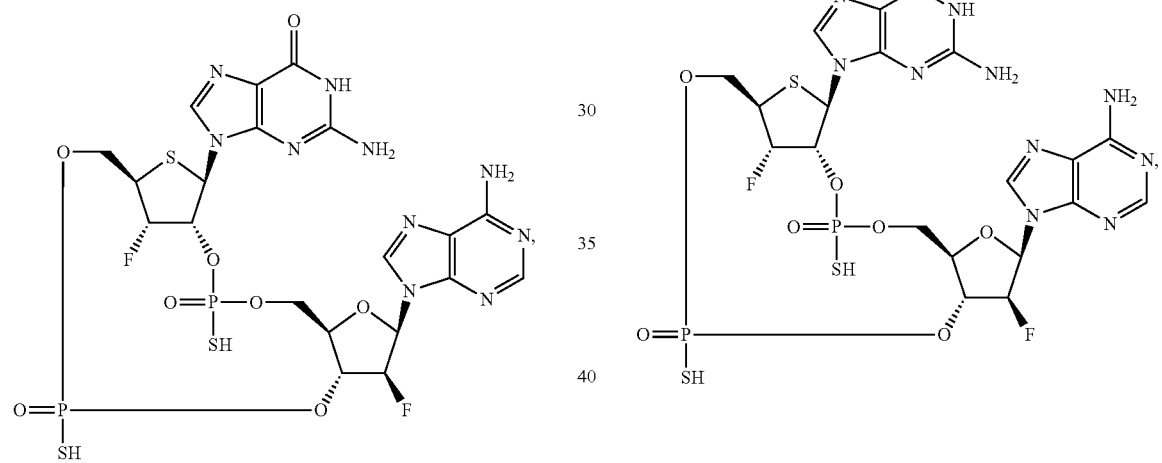
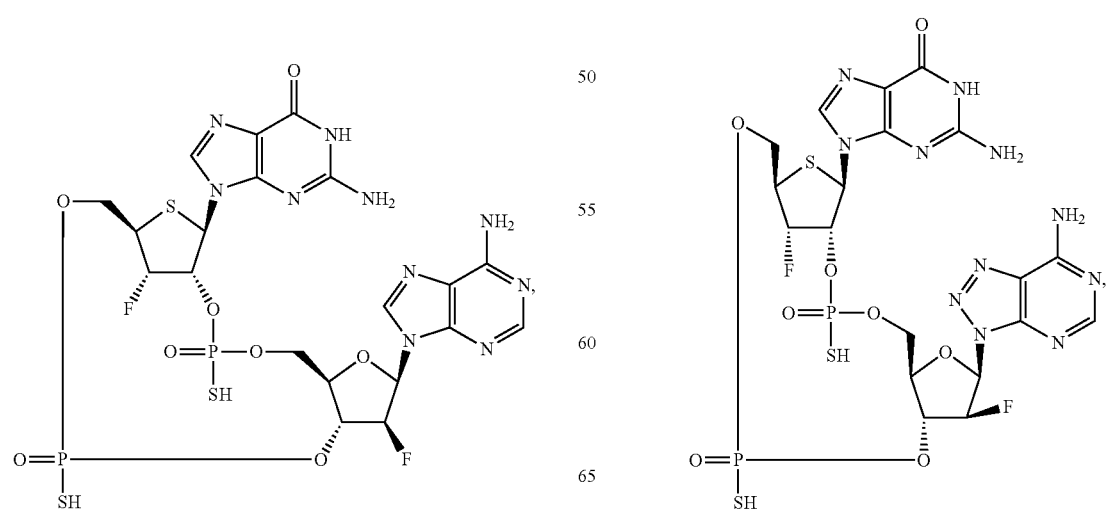

145
-continued
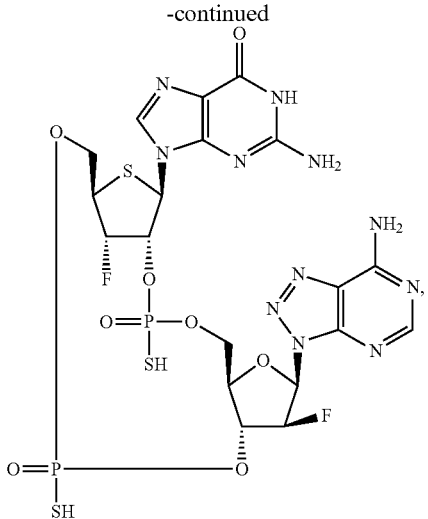
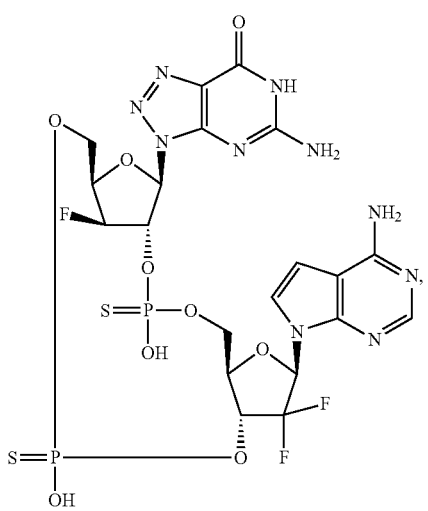
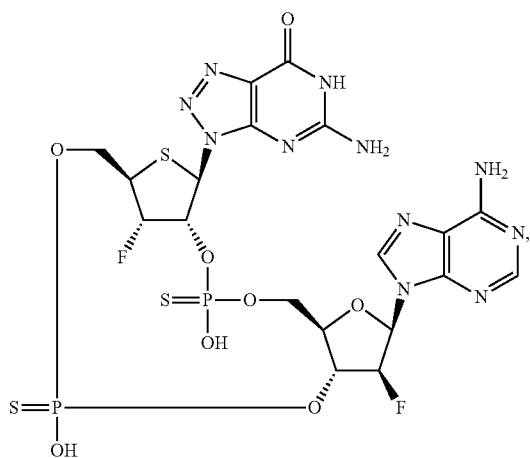
146
-continued
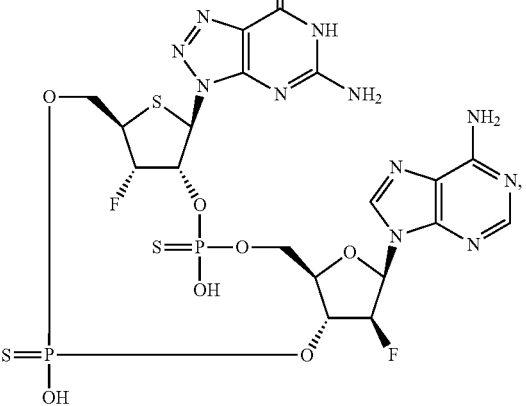
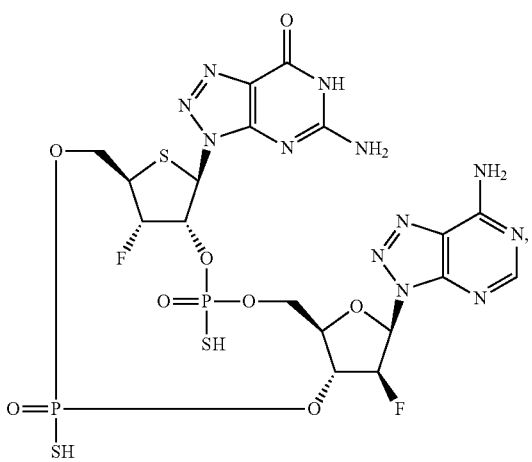

147
-continued
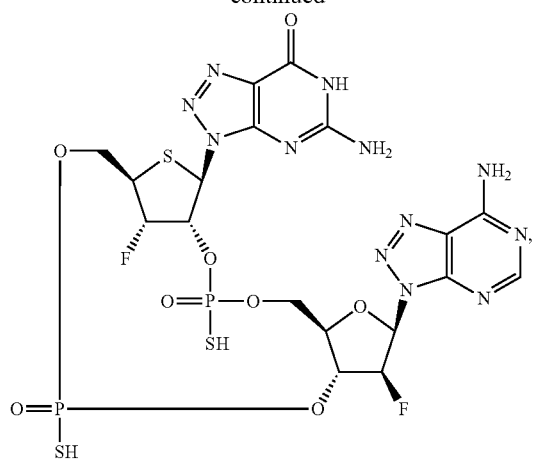
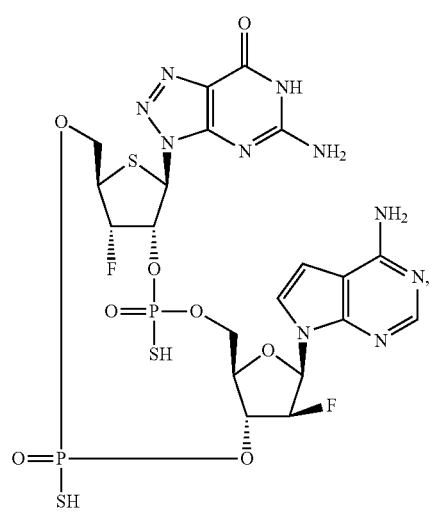
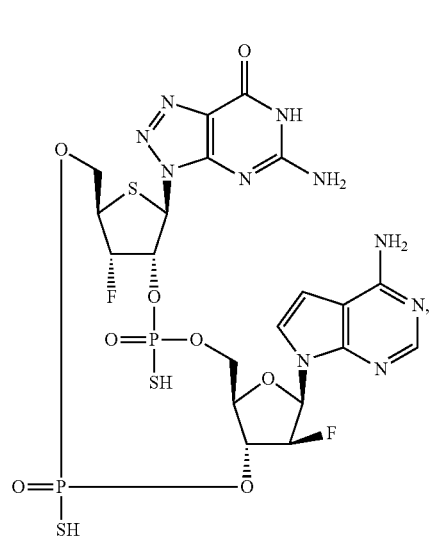
148
-continued
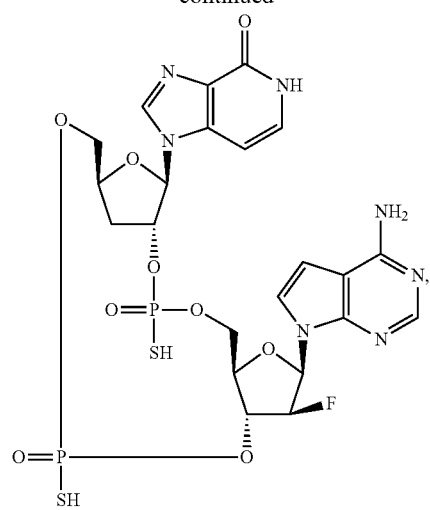
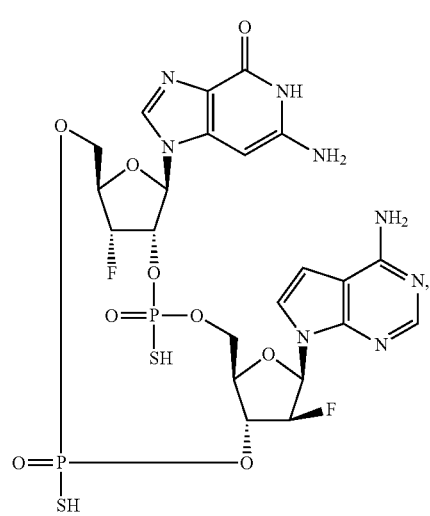
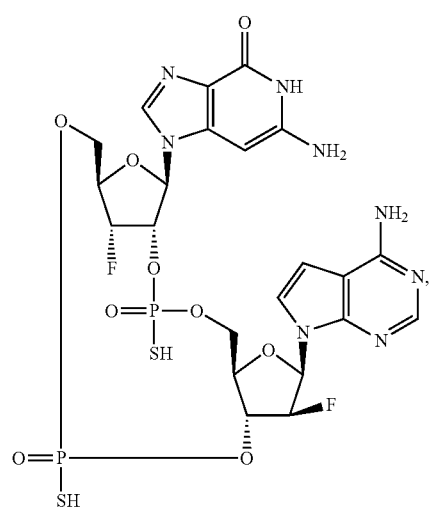

149
-continued
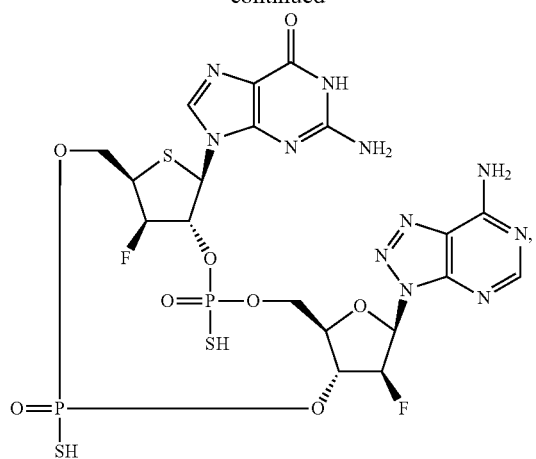
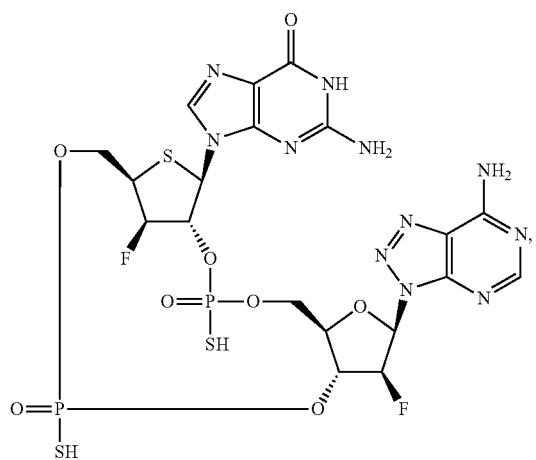
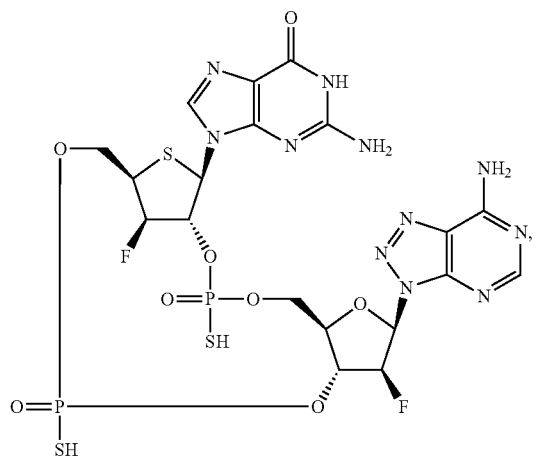
150
-continued
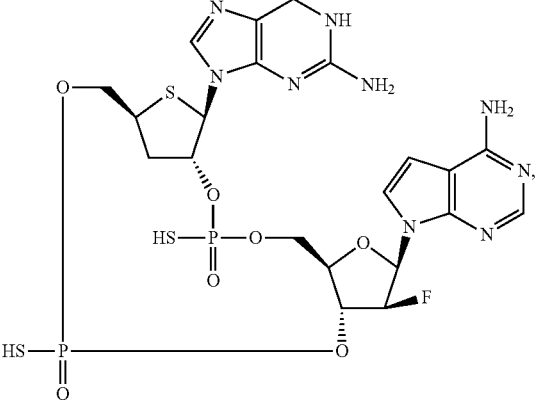
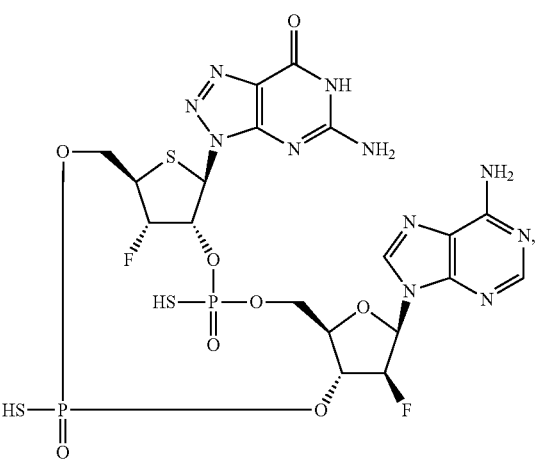
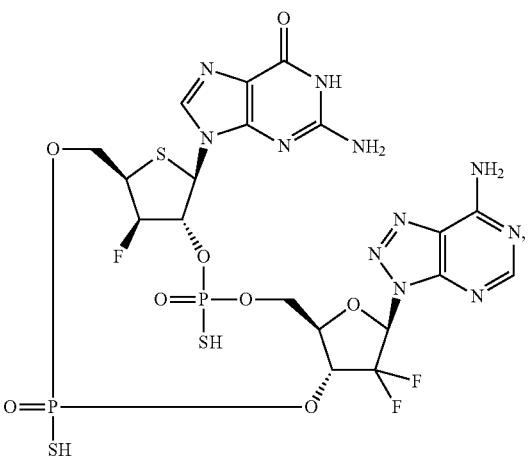

151
-continued
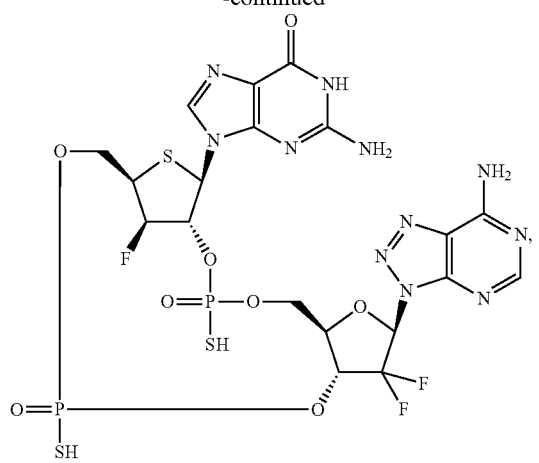
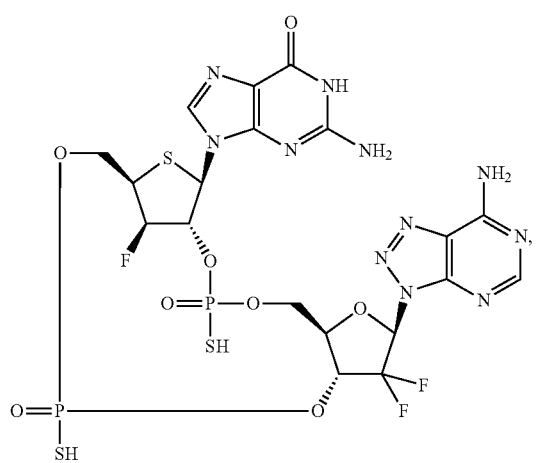
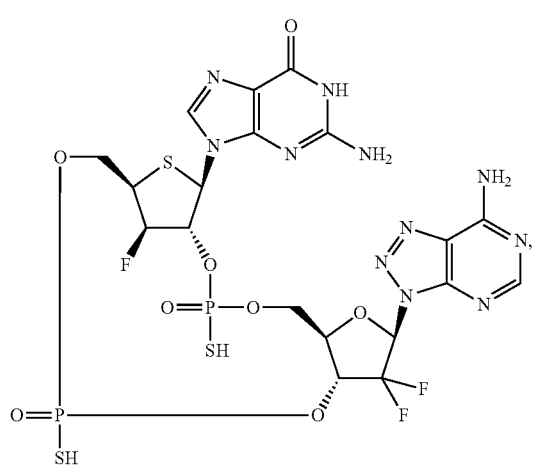
152
-continued
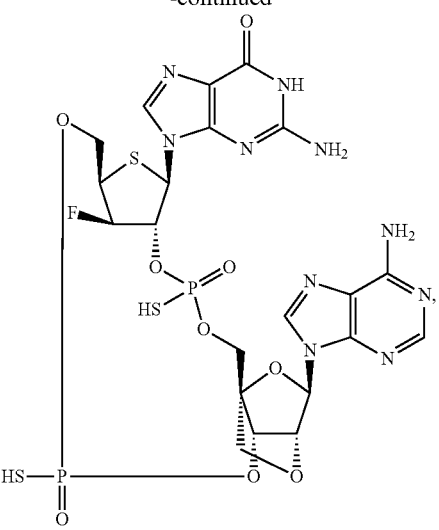
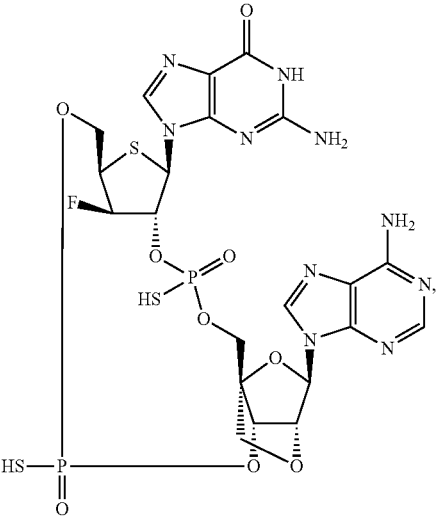
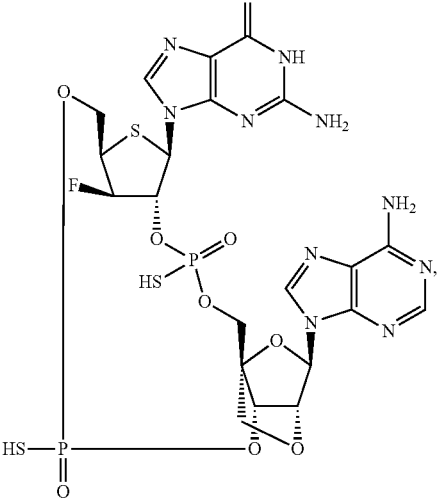

153
-continued
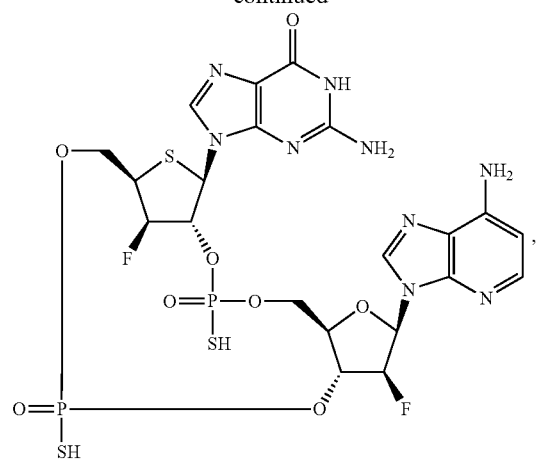
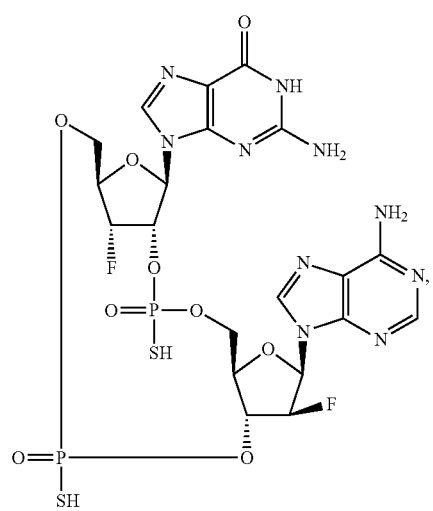
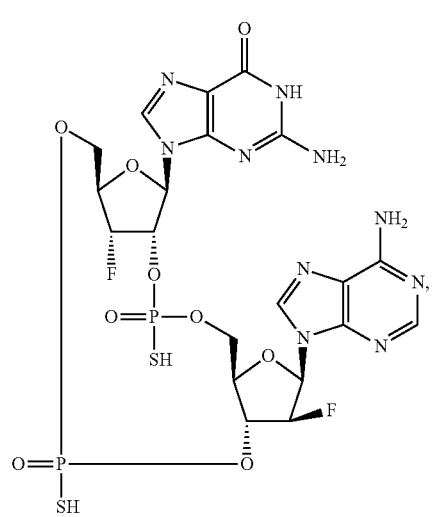
154
-continued
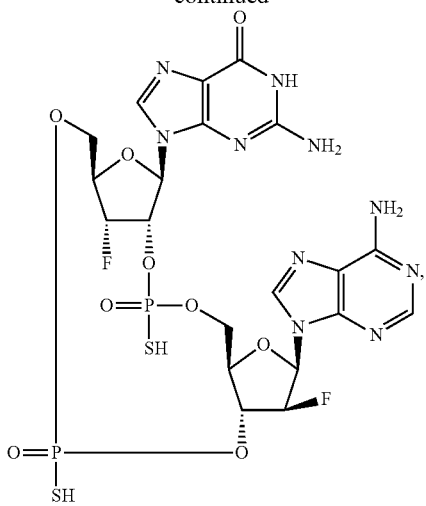
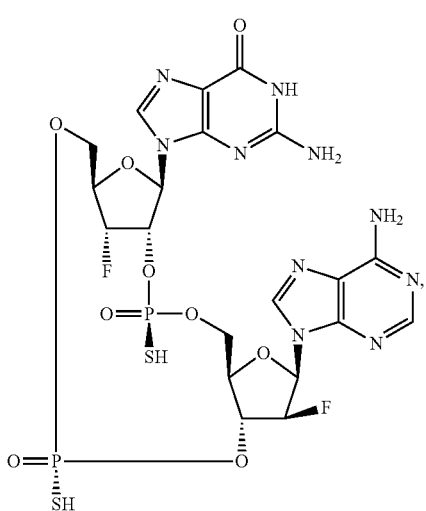
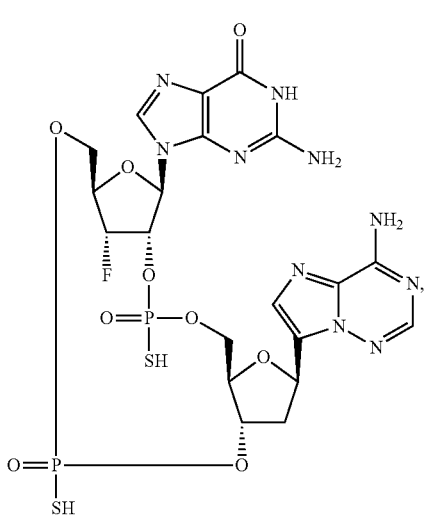

155
-continued
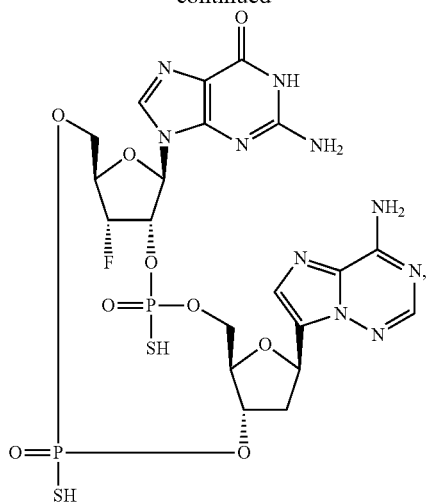
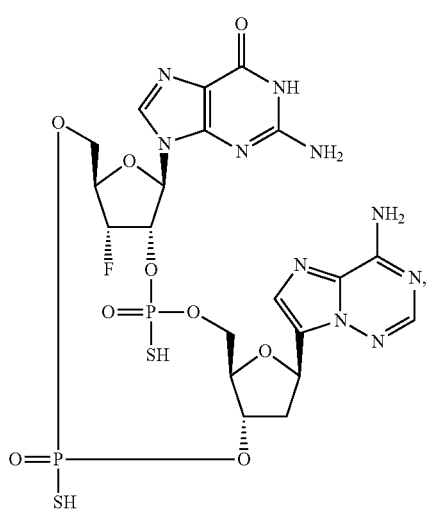
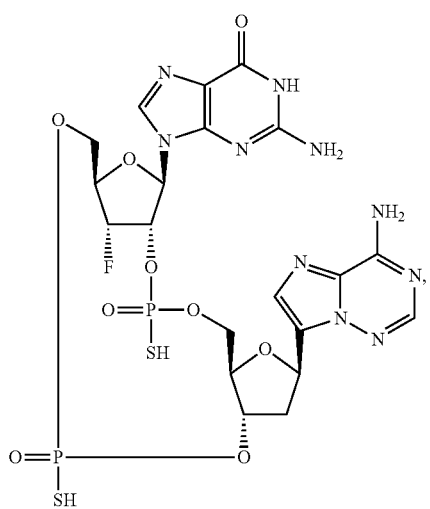
156
-continued
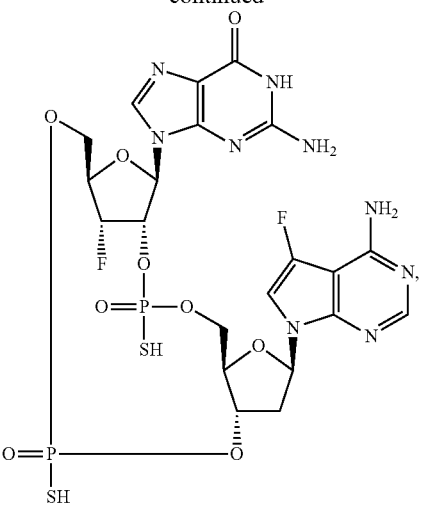
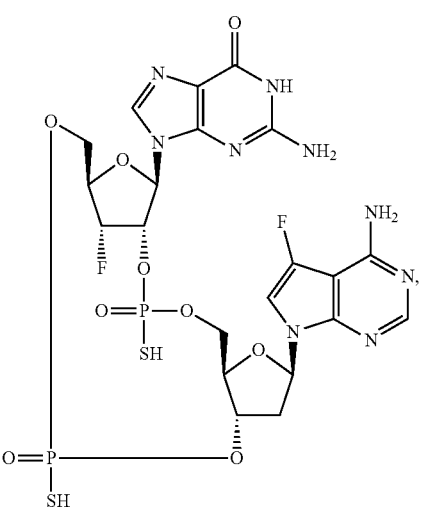
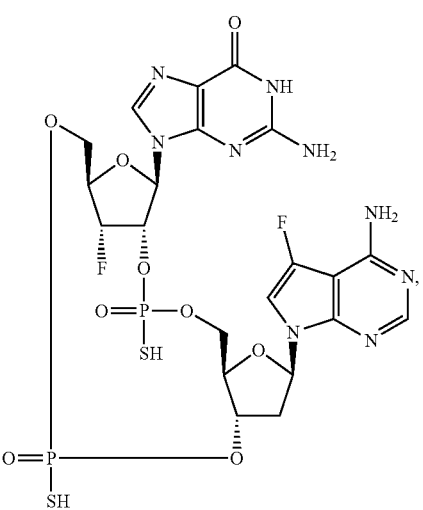

157
-continued
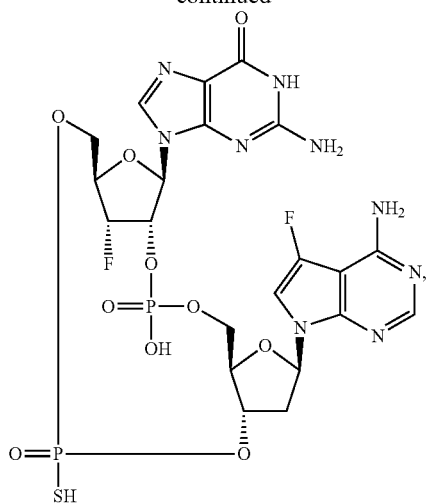
158
-continued
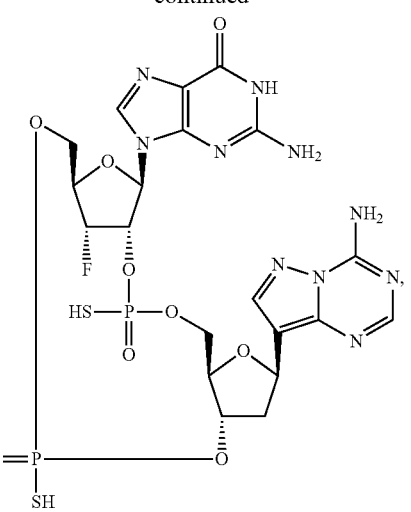
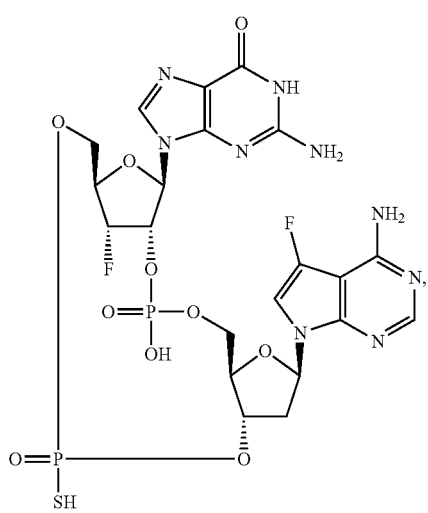
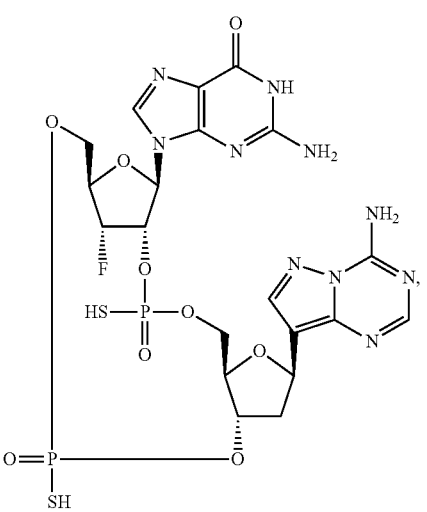
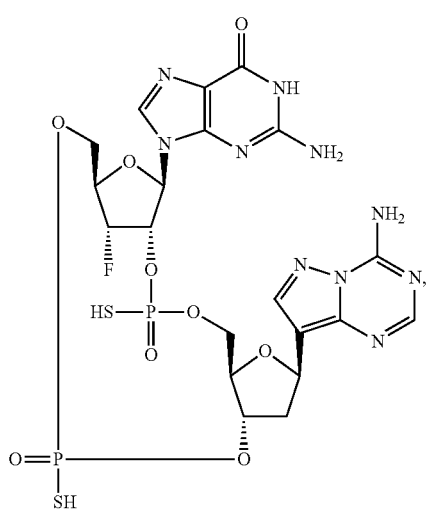
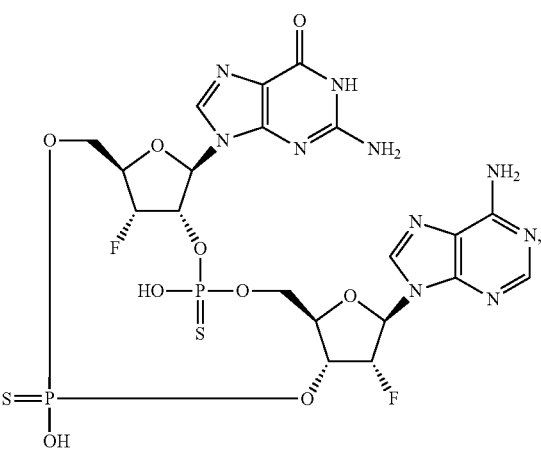

159
-continued
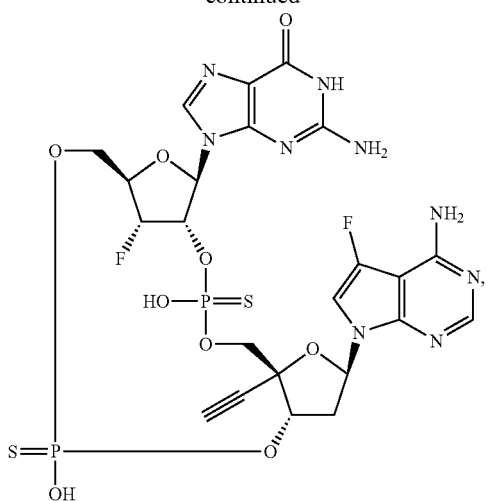
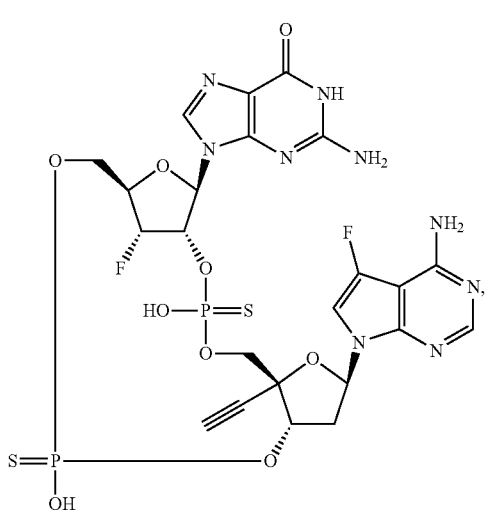
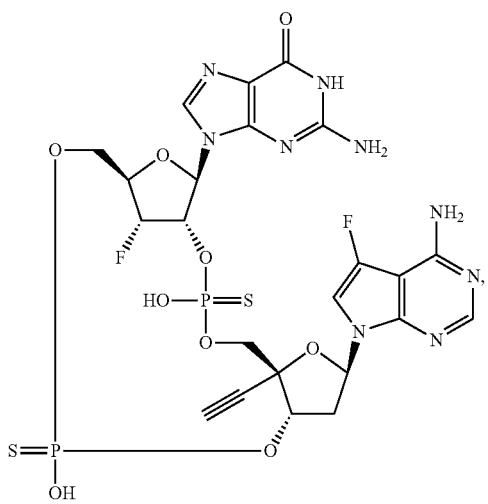
160
-continued
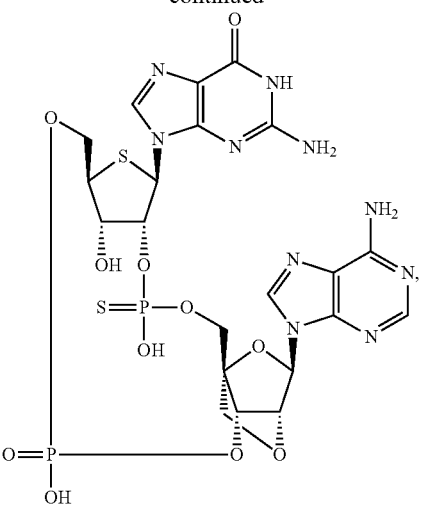
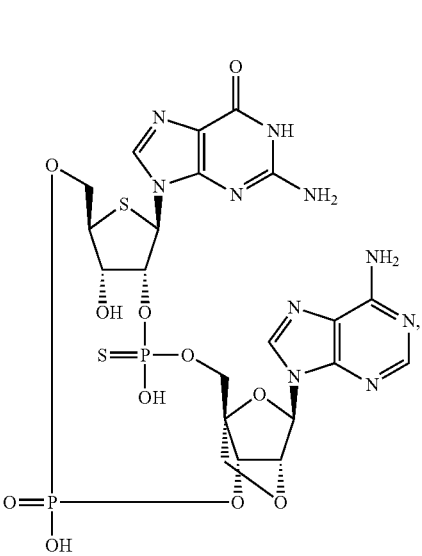 [SMILES: Nc1nc2c(ncn2[C@@H]2S[C@@H]3COP(=O)(O)O[C@H]4[C@H]5OC[C@]4(COP(O)(=S)O[C@@H]2[C@@H]3O)O[C@H]5n2cnc3c(N)ncnc32)c(=O)[nH]1]
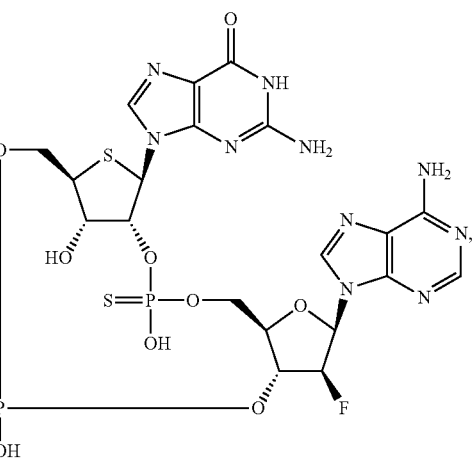

161
-continued
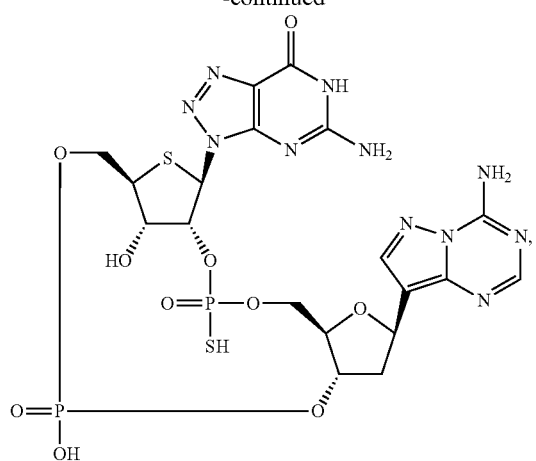
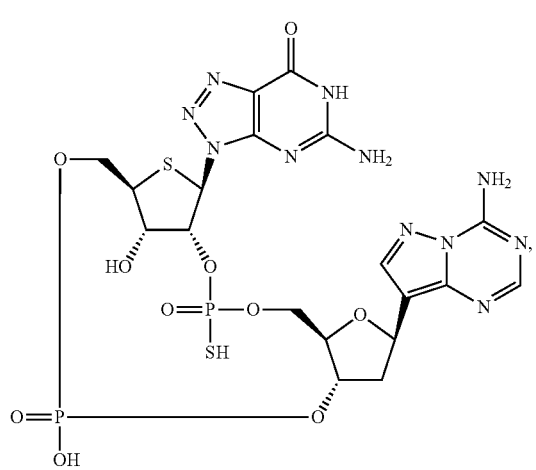
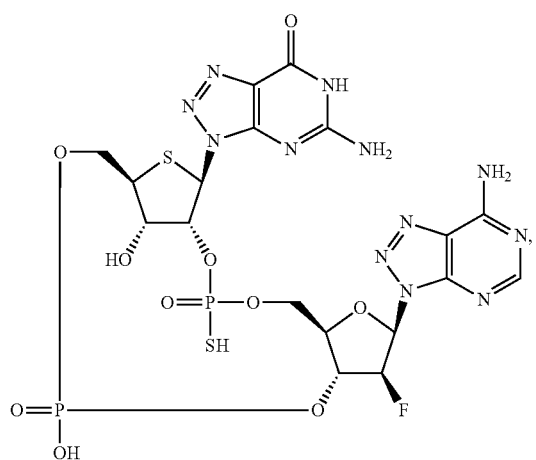
162
-continued
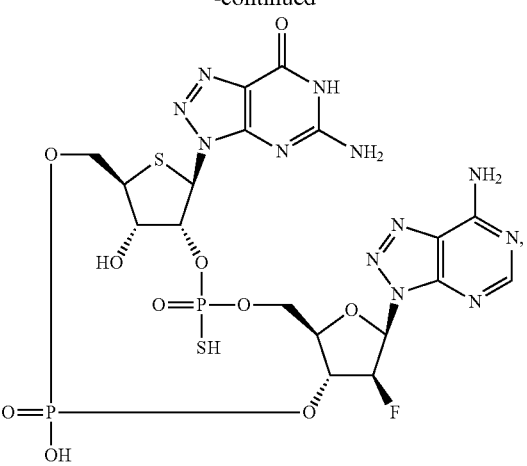
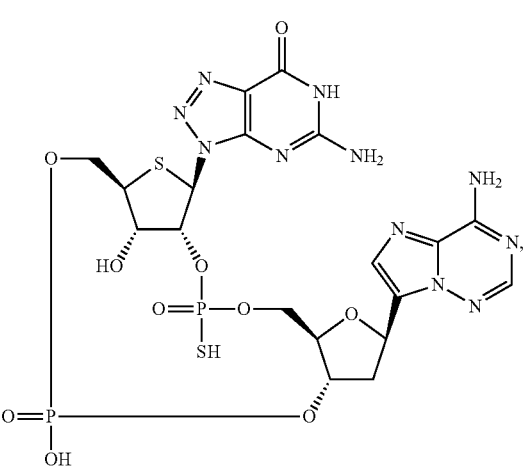
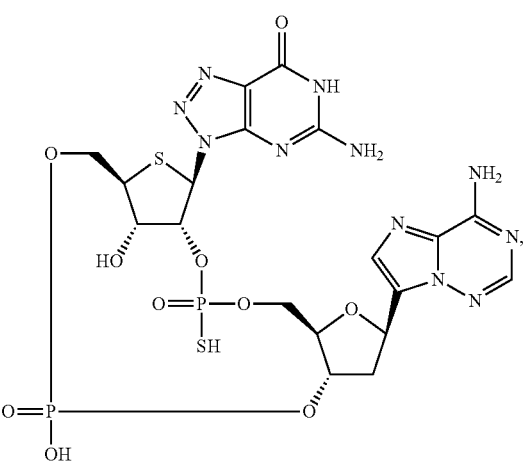

163
-continued
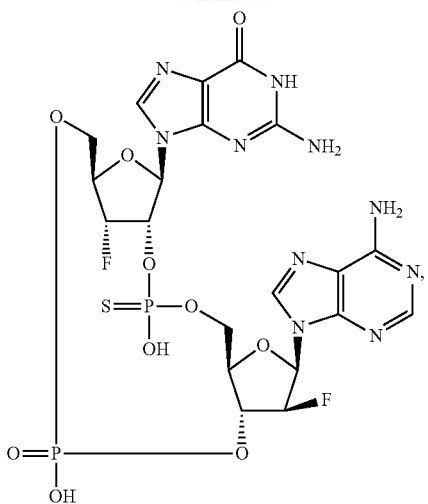
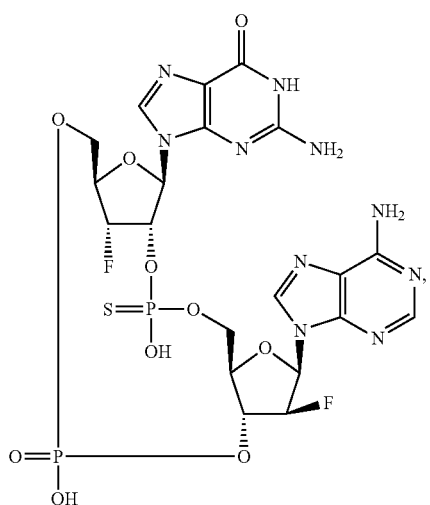
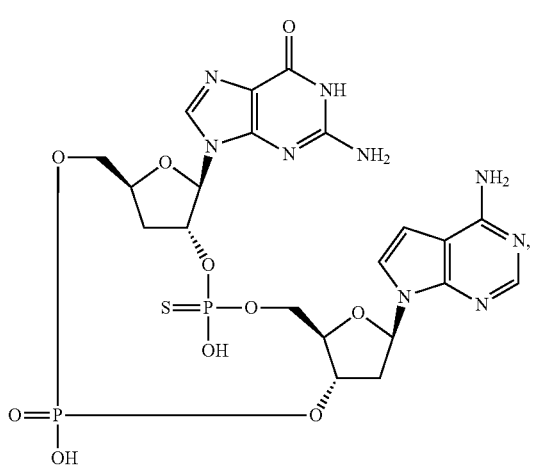
164
-continued
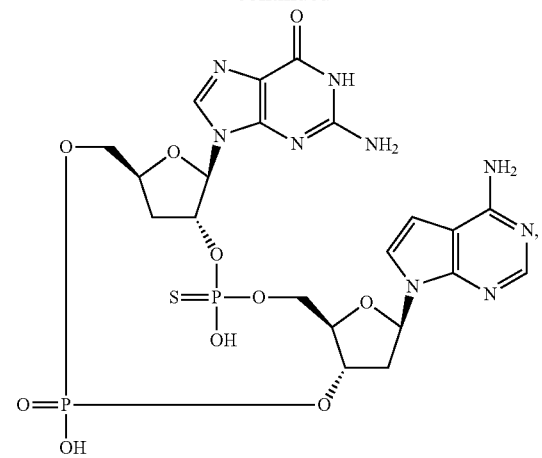
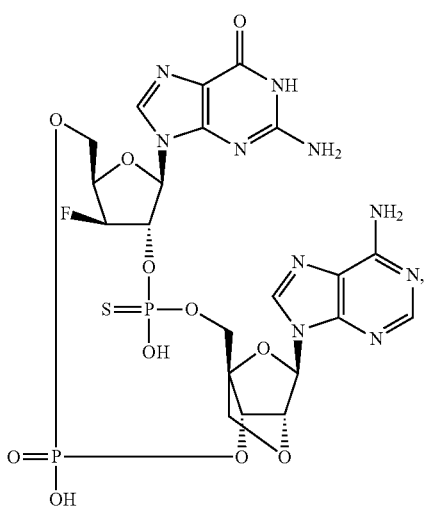

165
-continued
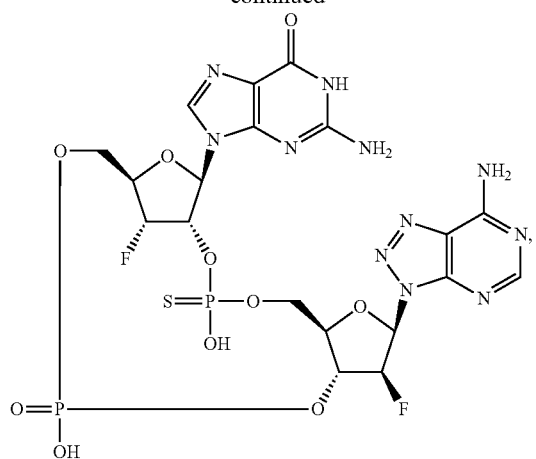
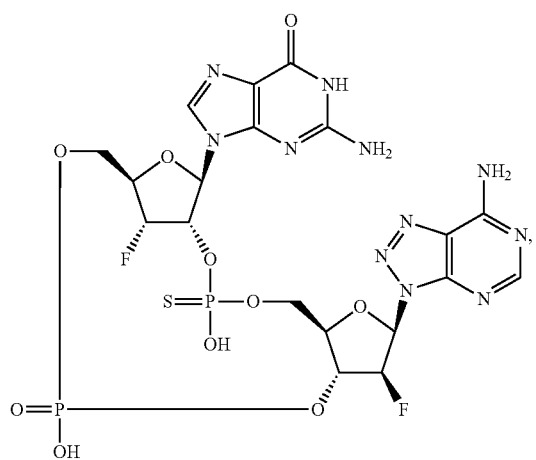
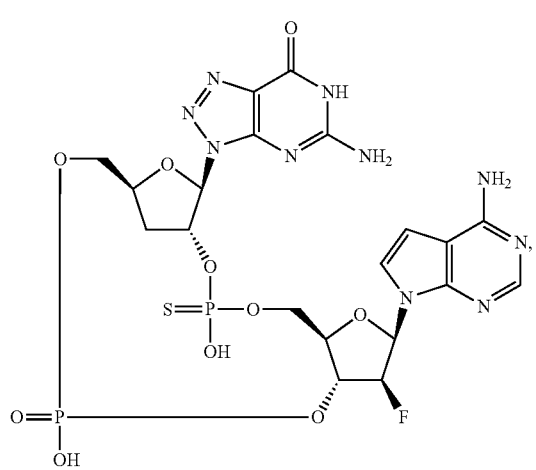
166
-continued
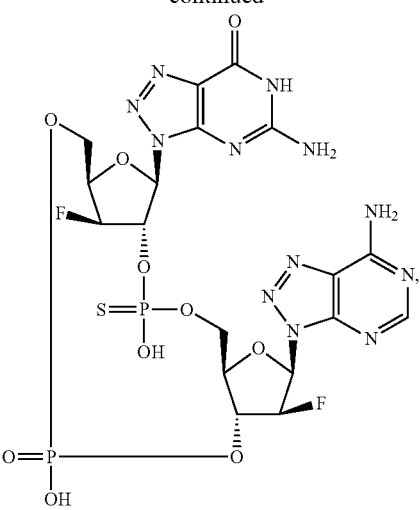
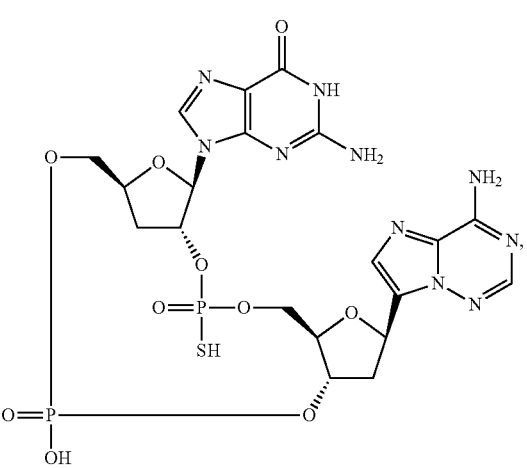
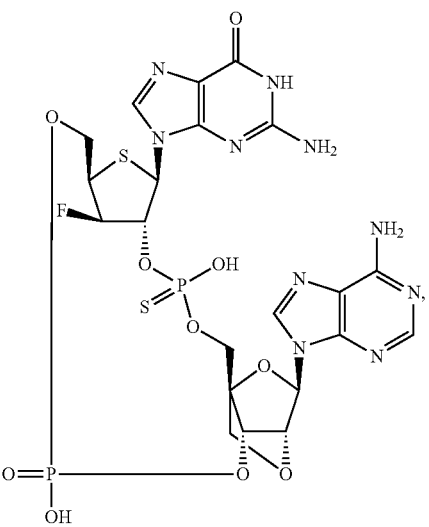

167
-continued
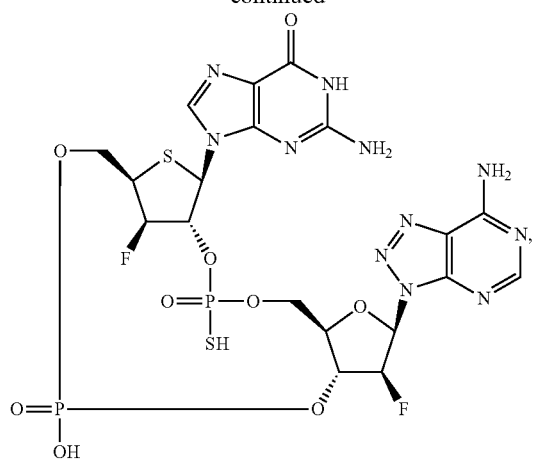
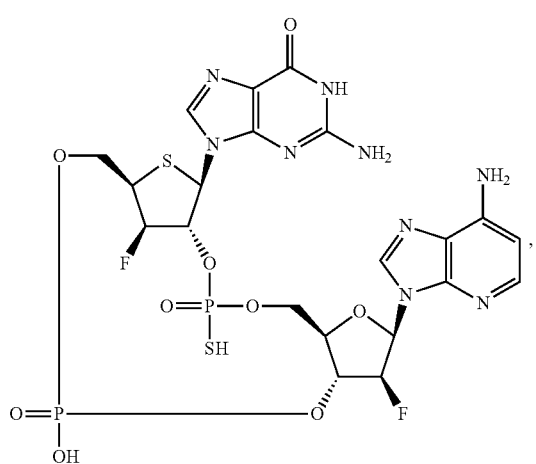
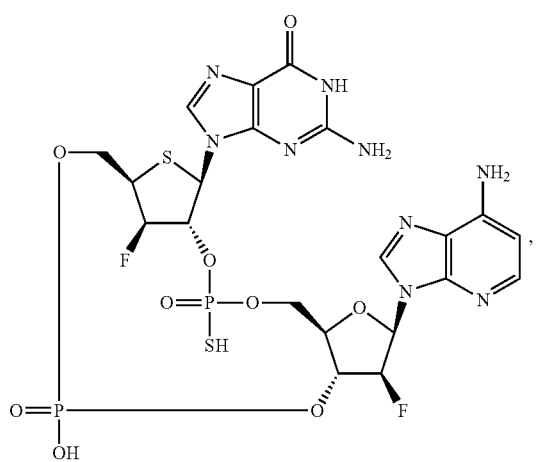
168
-continued
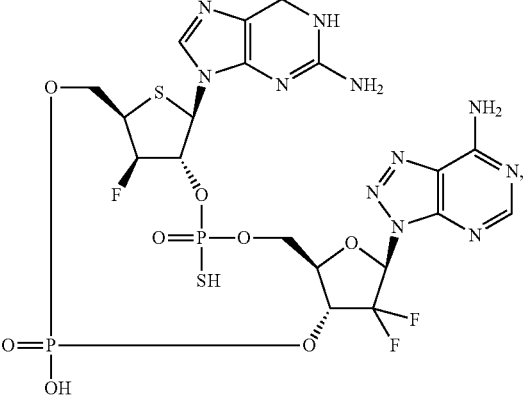
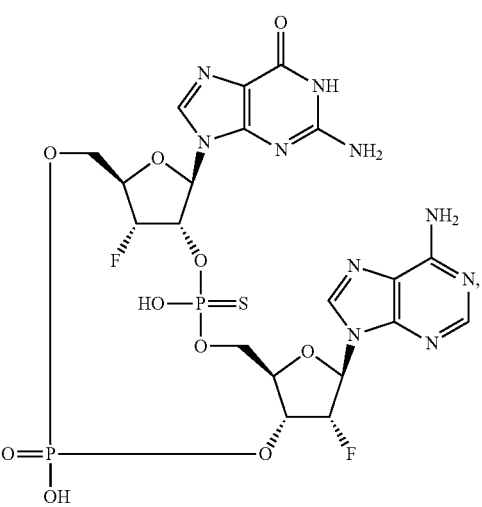
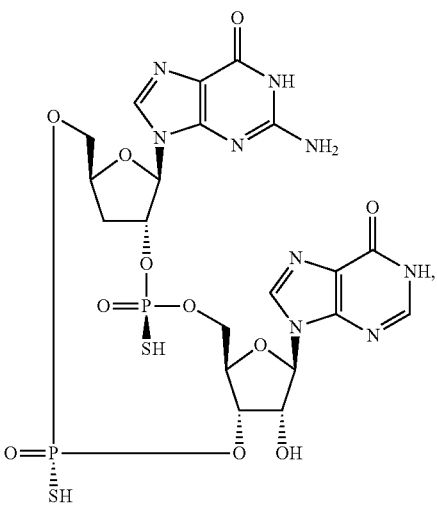

169
-continued
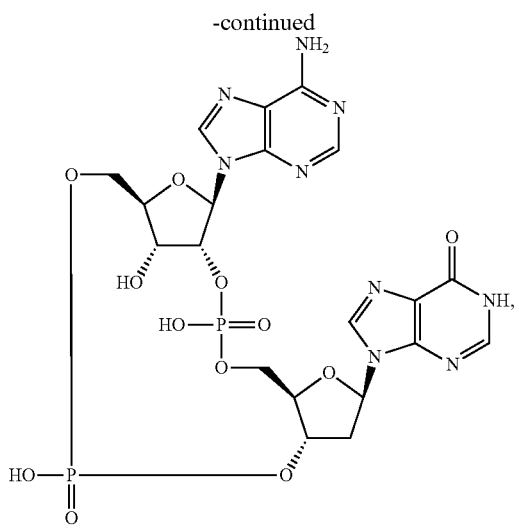
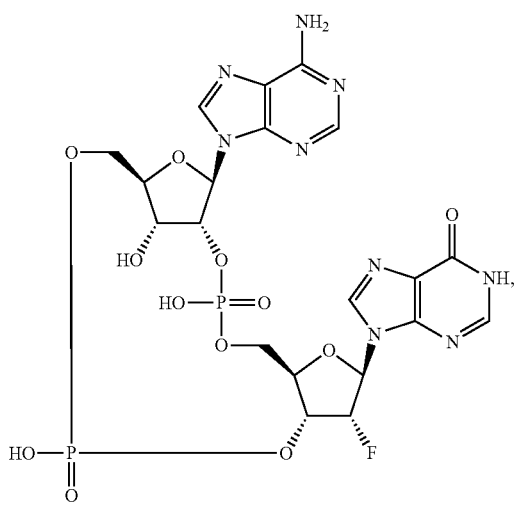
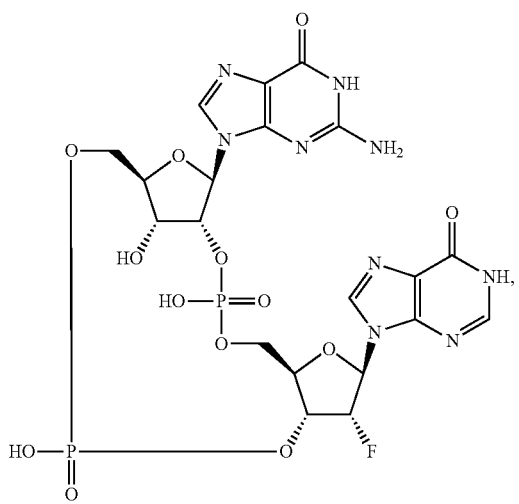
170
-continued
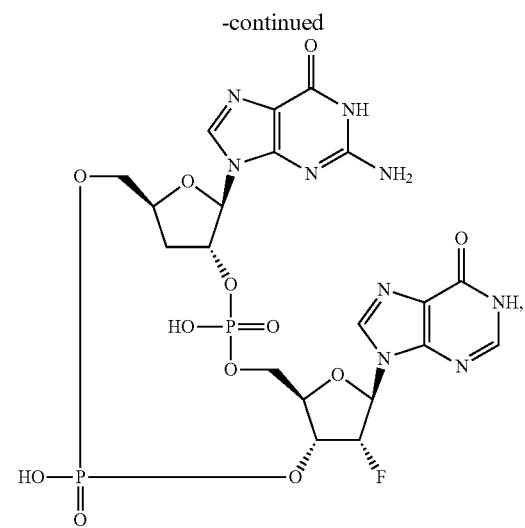
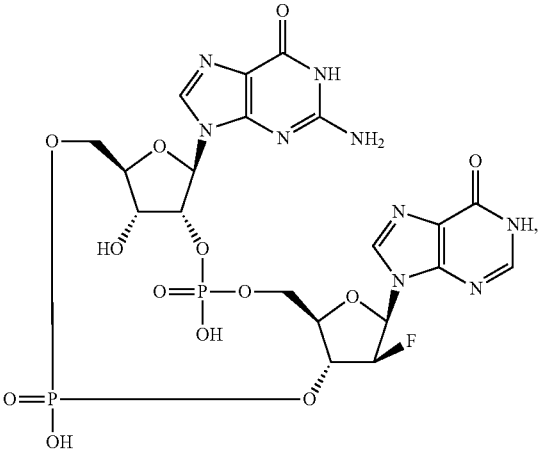
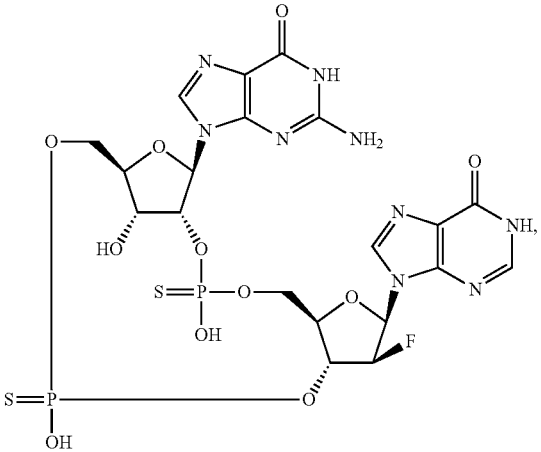

171
-continued
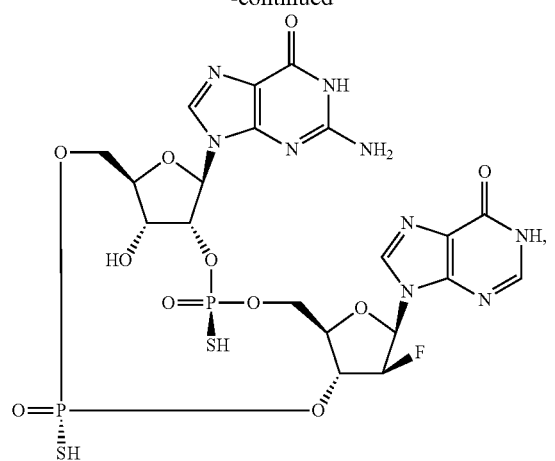
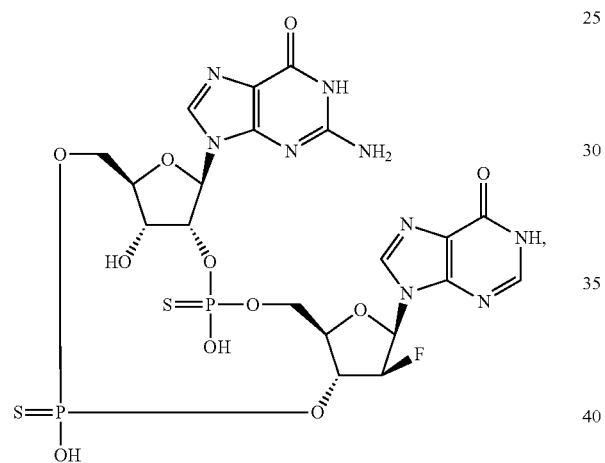
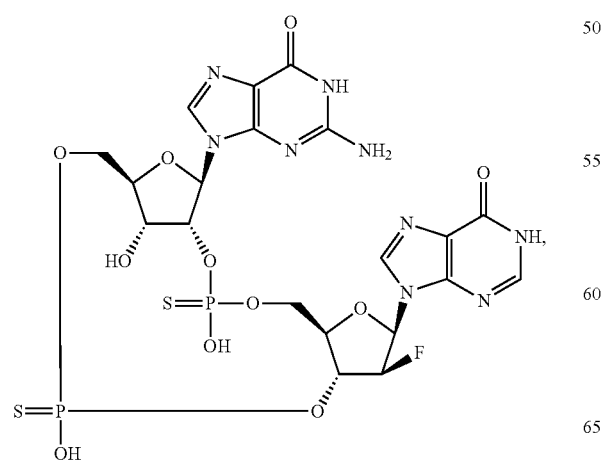
172
-continued
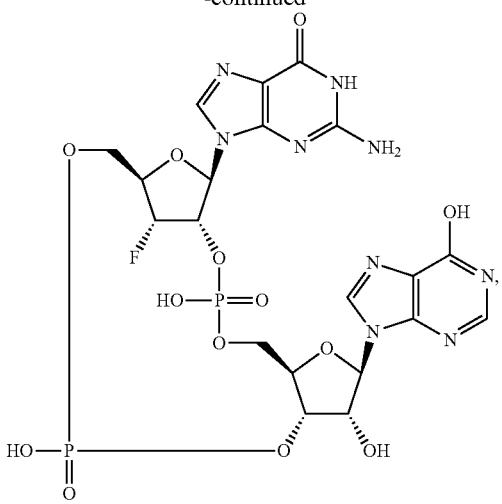
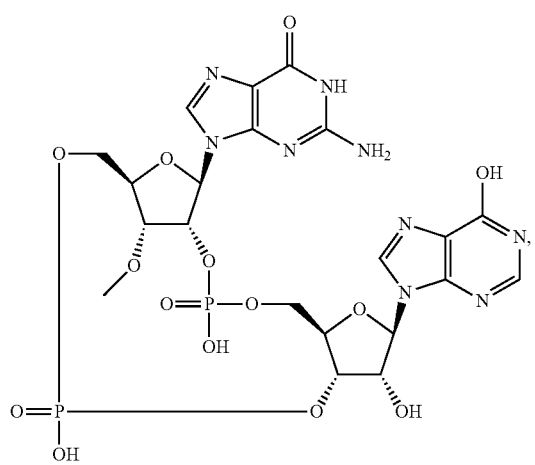
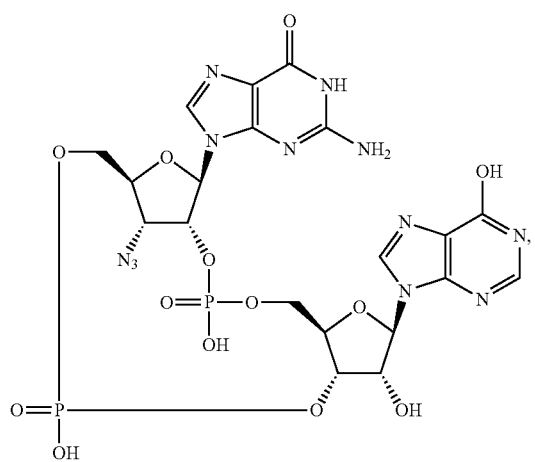

173
-continued
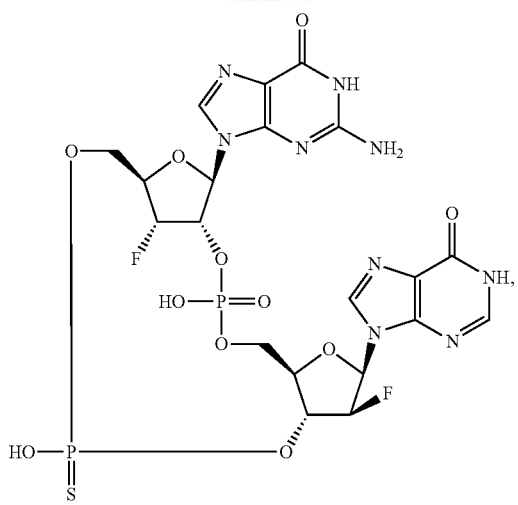
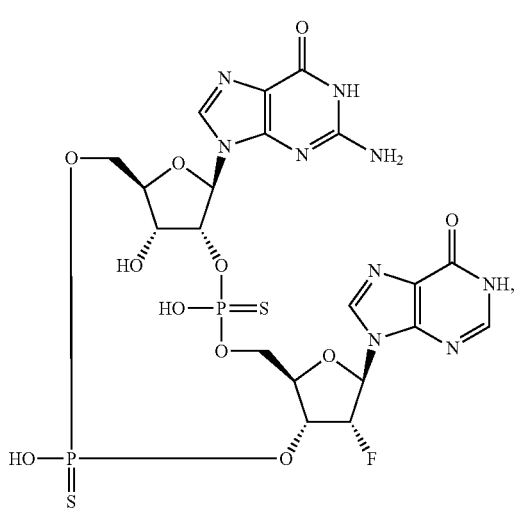
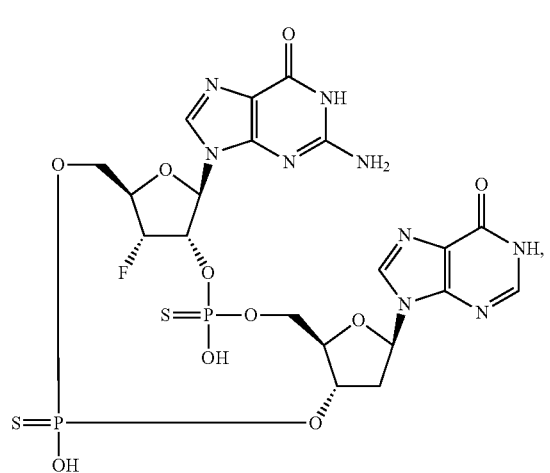
174
-continued
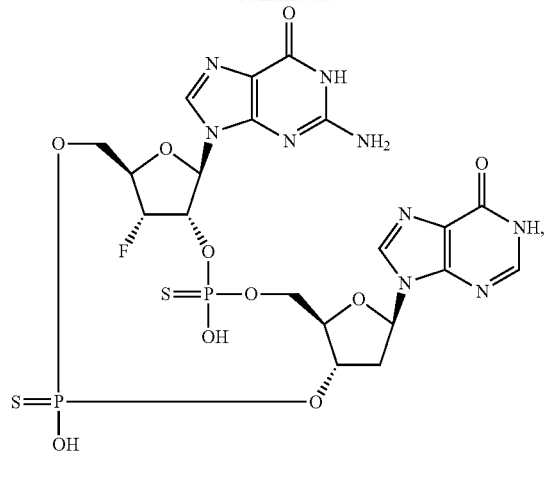
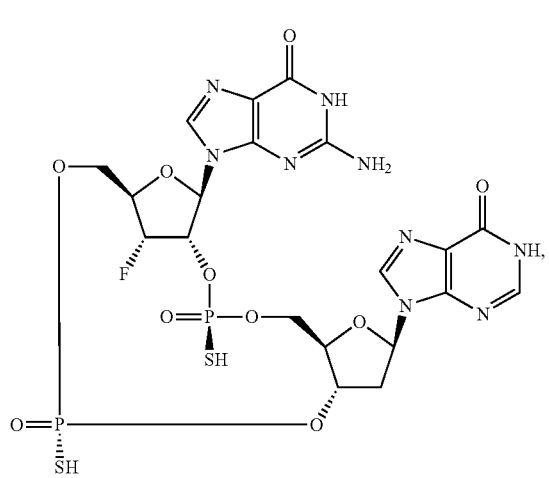
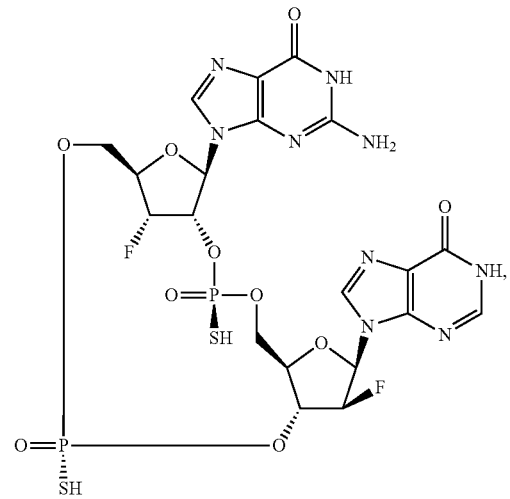

175
-continued
176
-continued
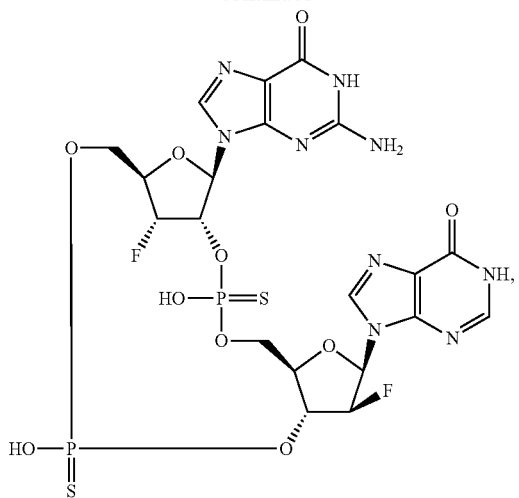
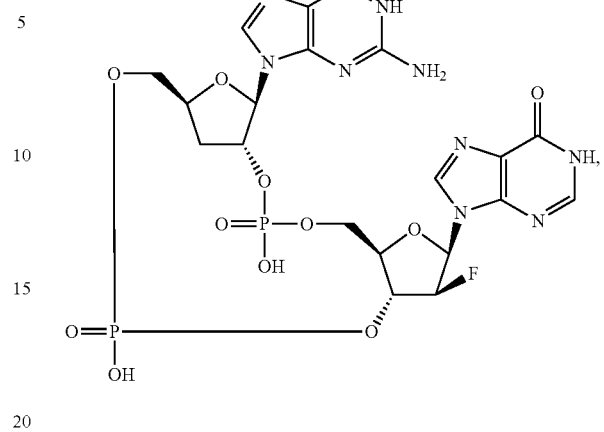
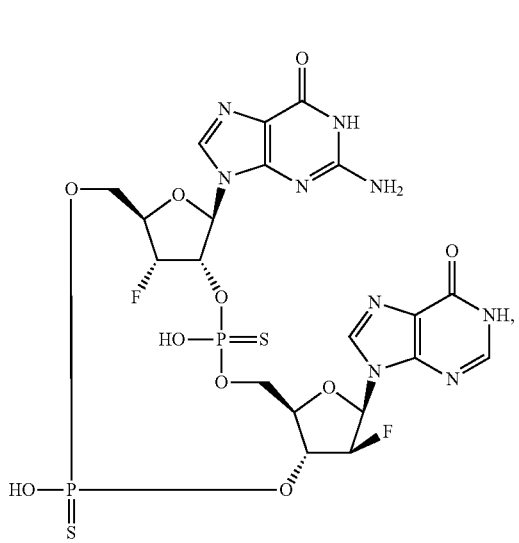
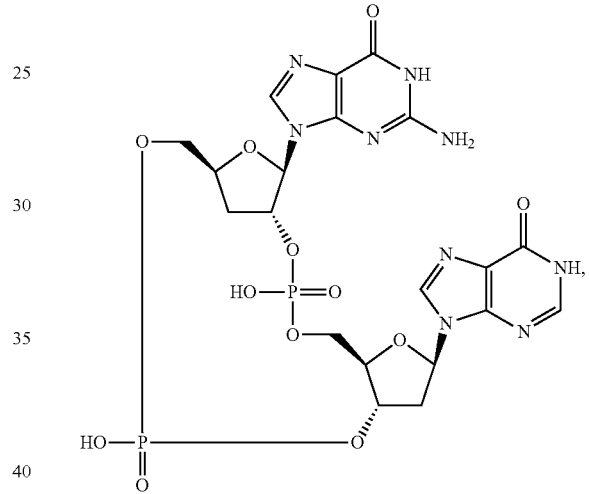
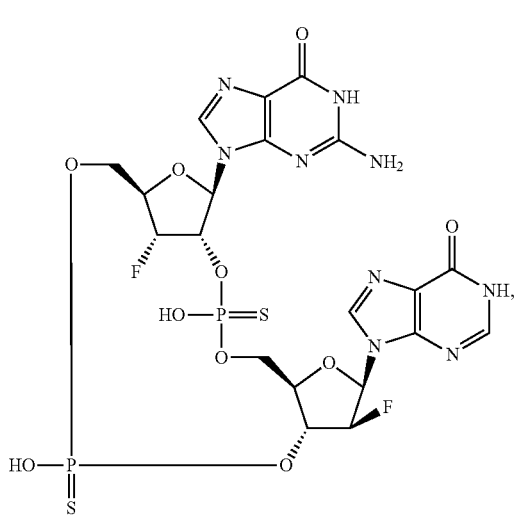 [SMILES: Nc1nc2c(ncn2[C@@H]2O[C@@H]3COP(O)(=S)O[C@H]4[C@H](F)[C@H](n5cnc6c(=O)[nH]cnc65)O[C@@H]4COP(O)(=S)O[C@@H]2[C@@H]3F)c(=O)[nH]1]
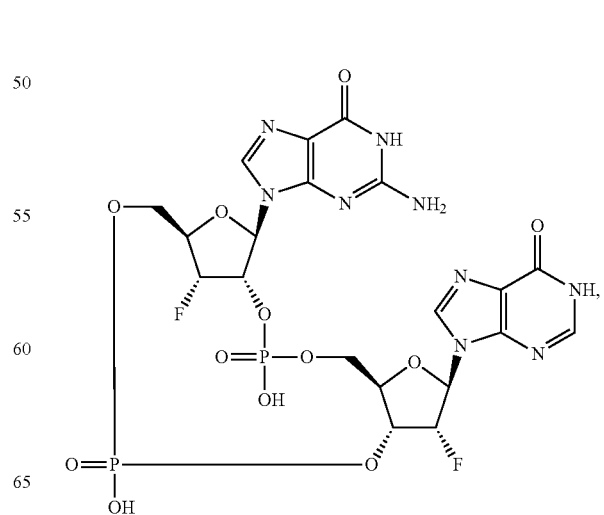

177
-continued
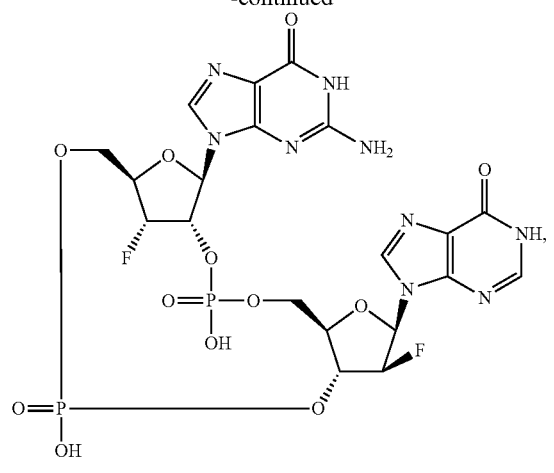
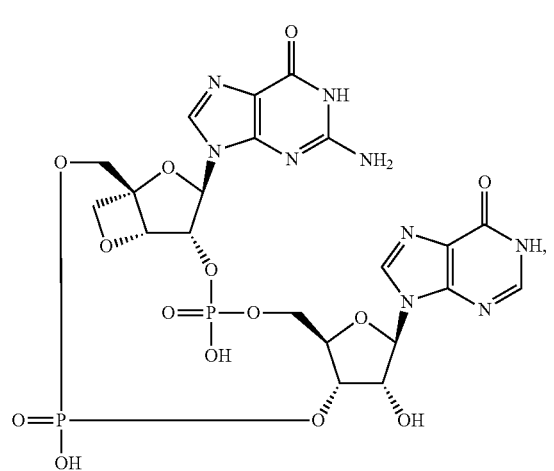
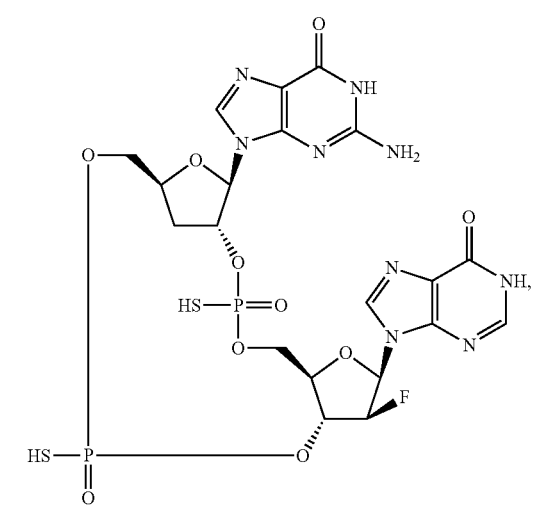
178
-continued
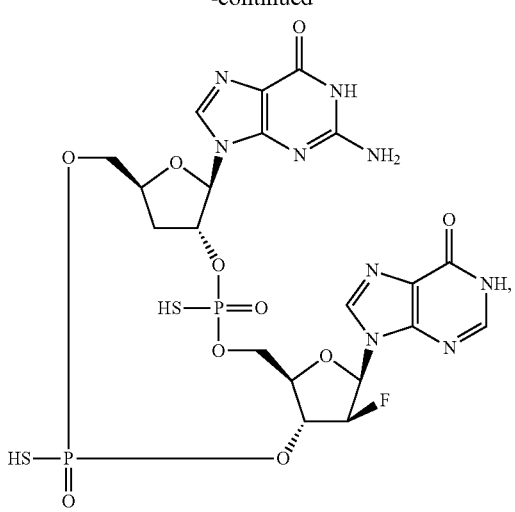
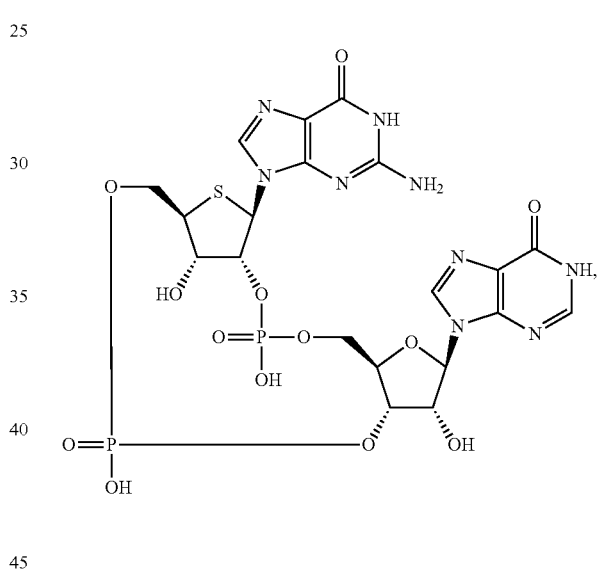
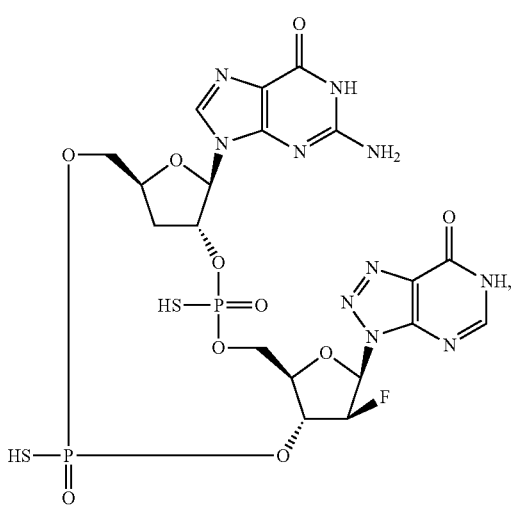

179
-continued
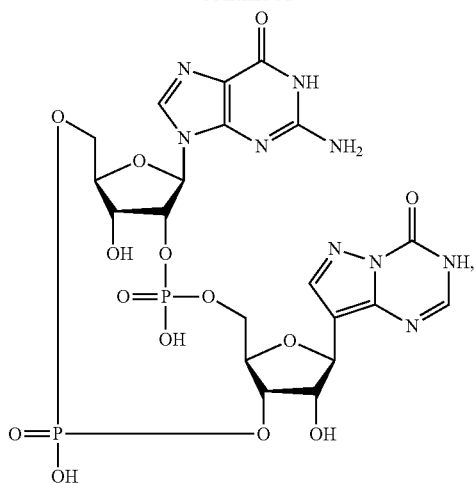
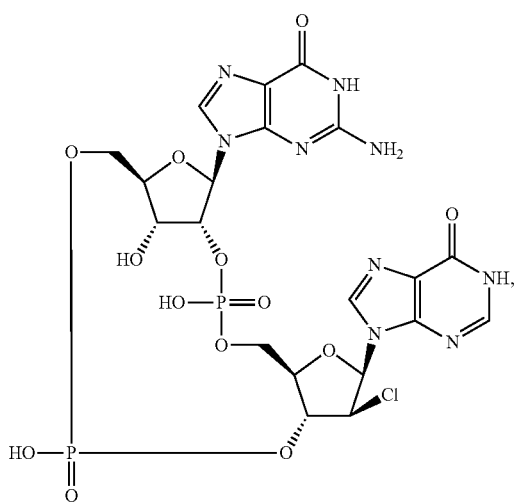
180
-continued
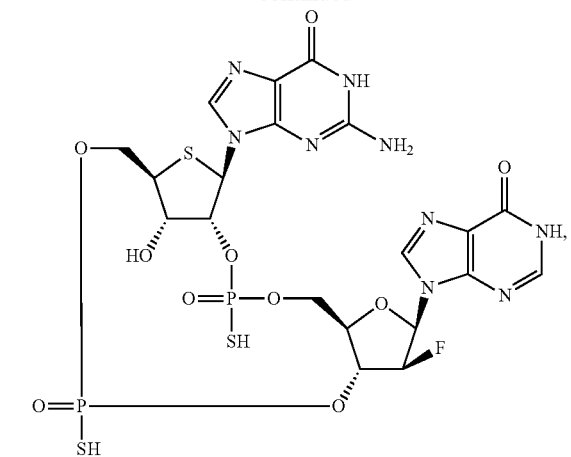
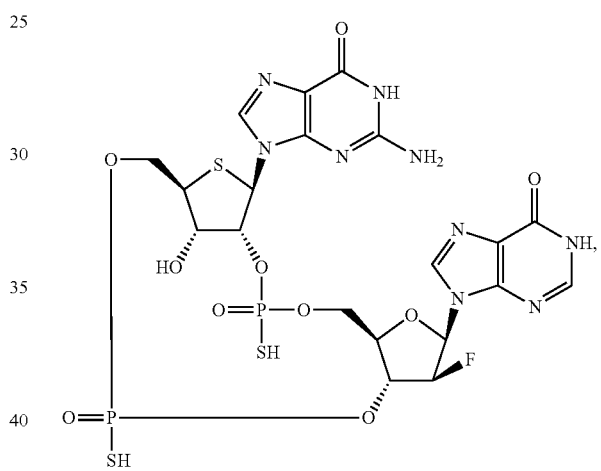
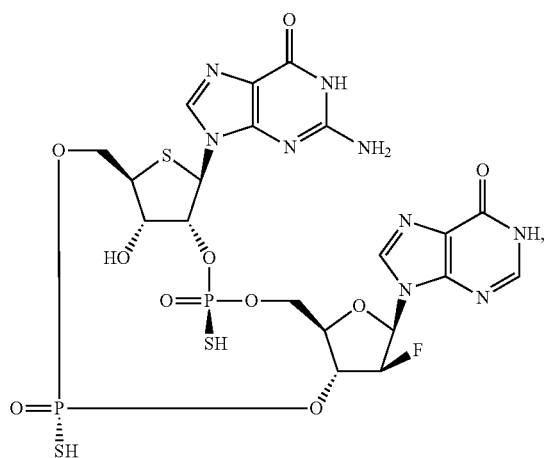
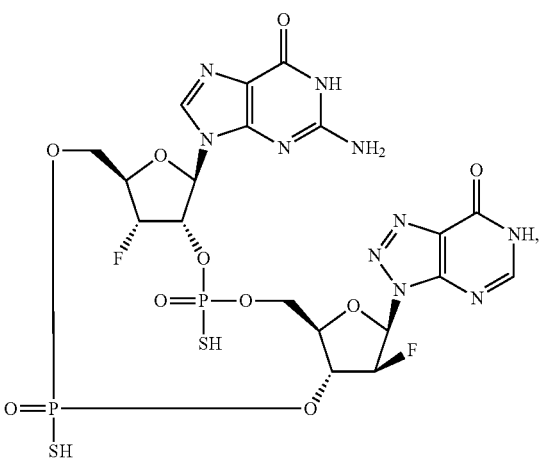

181
-continued
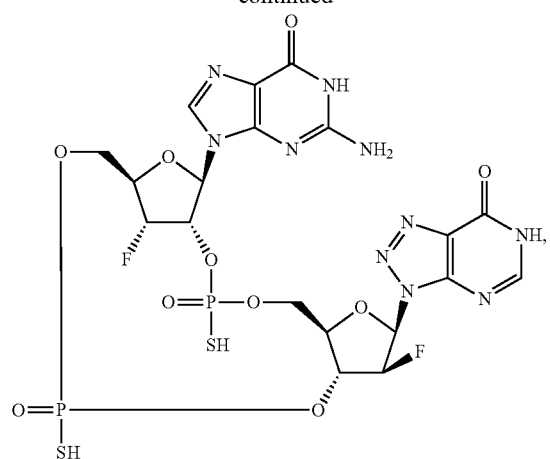
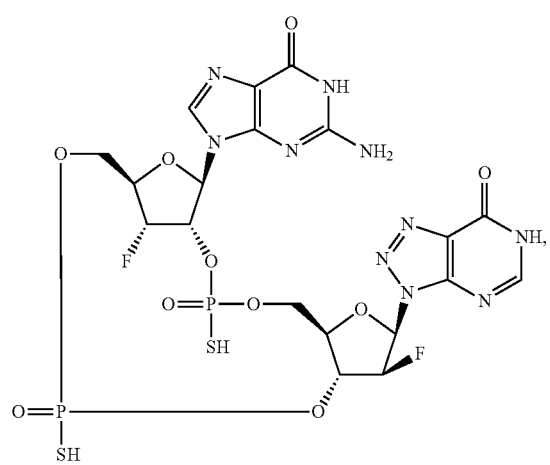
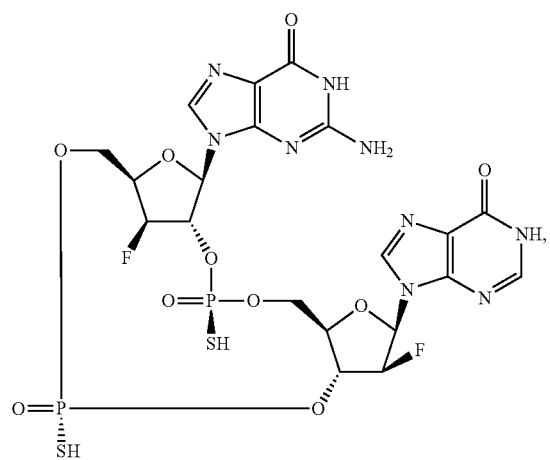
182
-continued
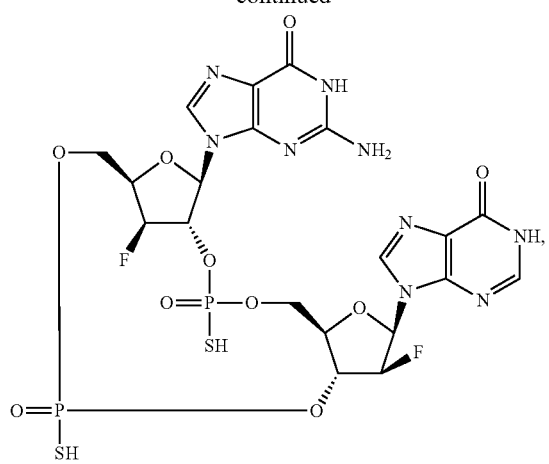
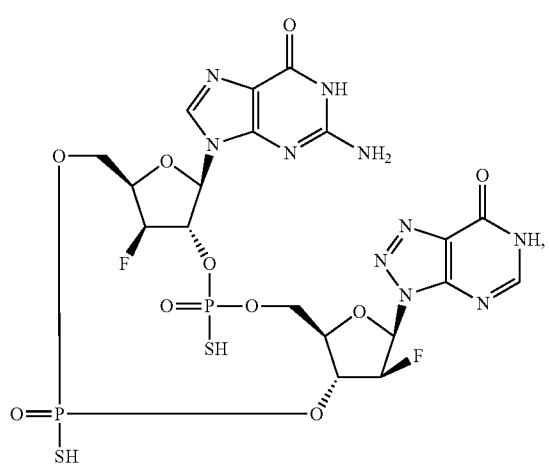
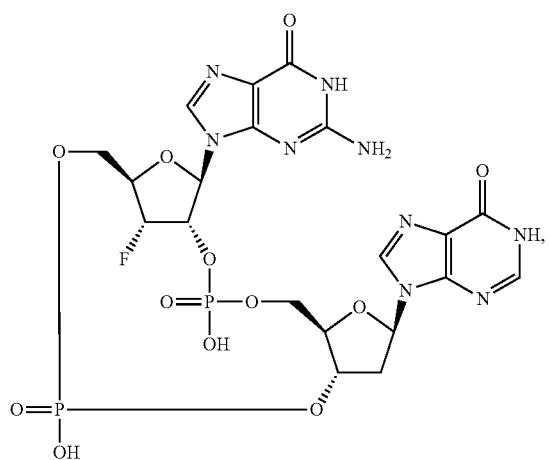

-continued
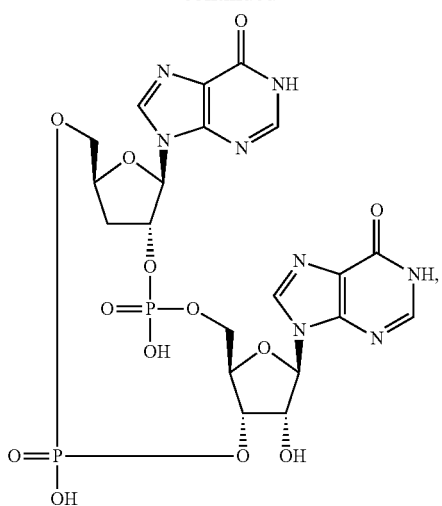
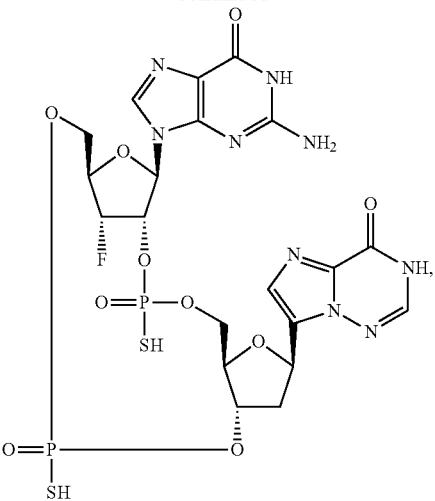
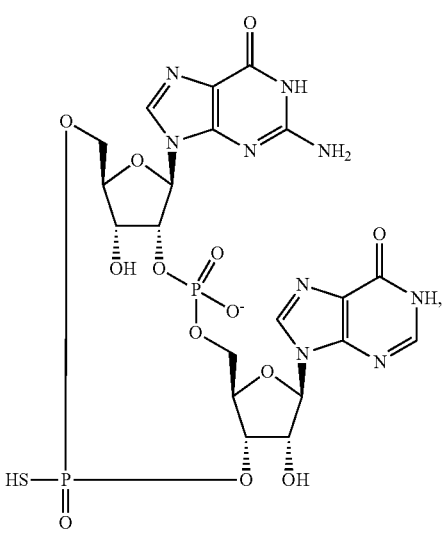
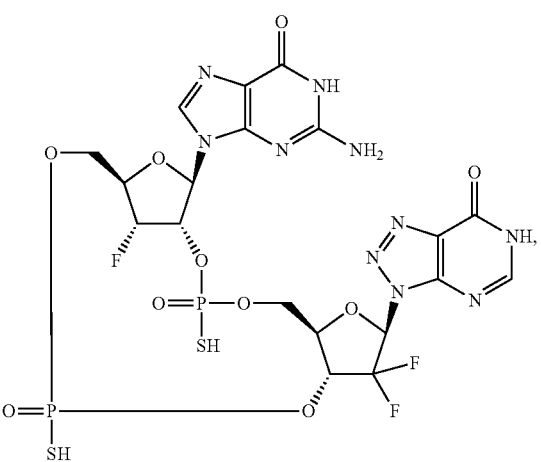
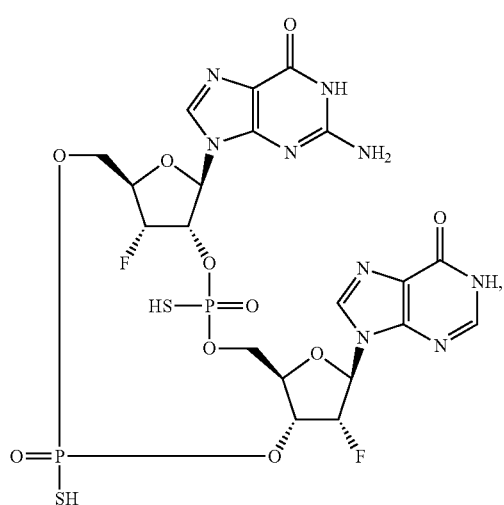
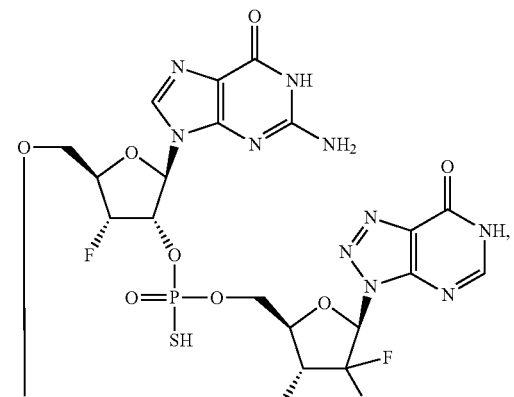

185
-continued
186
-continued
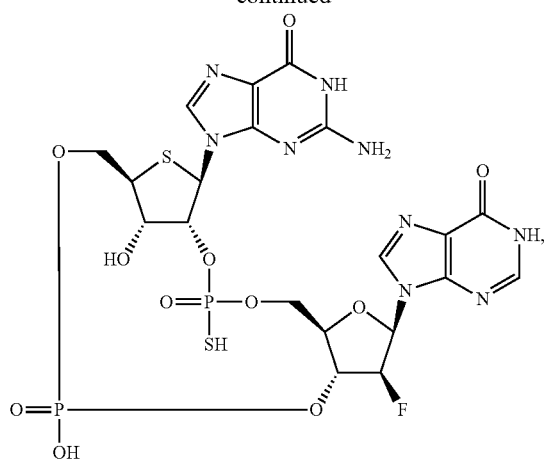
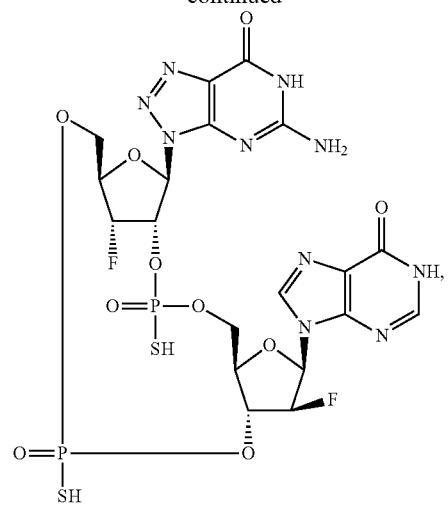
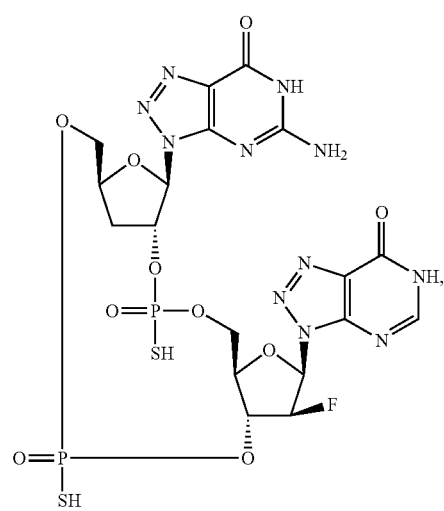
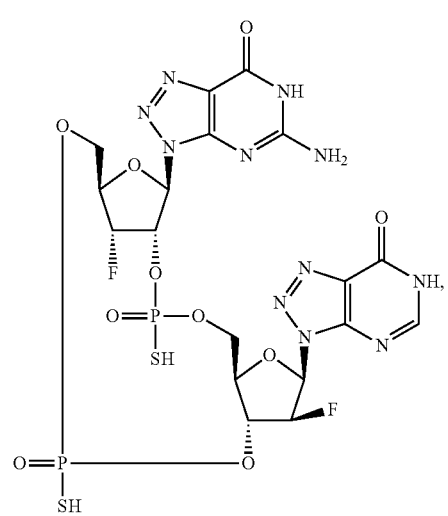
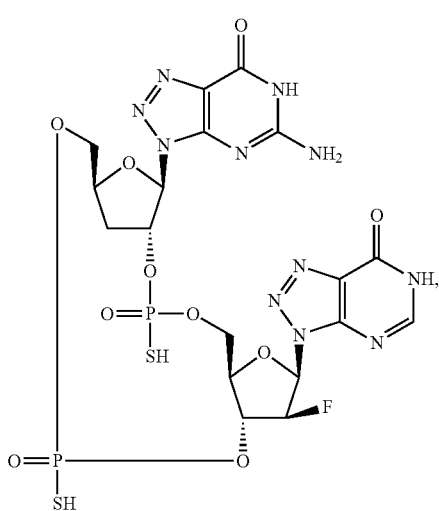

187
-continued
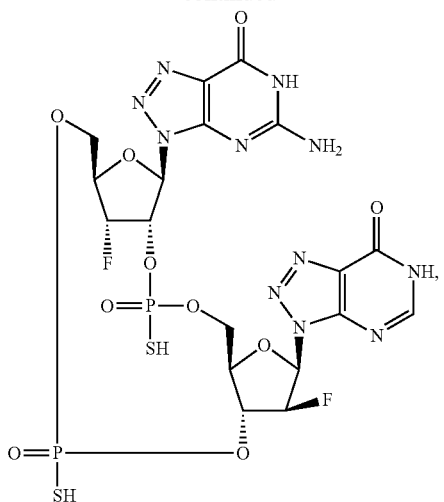
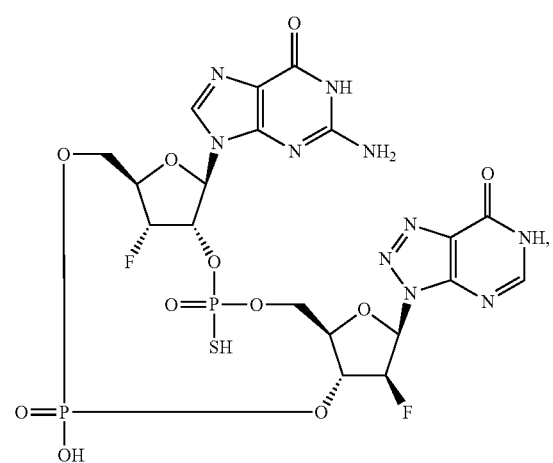 [SMILES: Nc1nc2c(nnn2[C@@H]2O[C@@H]3COP(=O)(S)O[C@H]4[C@H](F)[C@H](n5cnc6c(=O)[nH]cnc65)O[C@@H]4COP(=O)(S)O[C@@H]2[C@H]3F)c(=O)[nH]1]
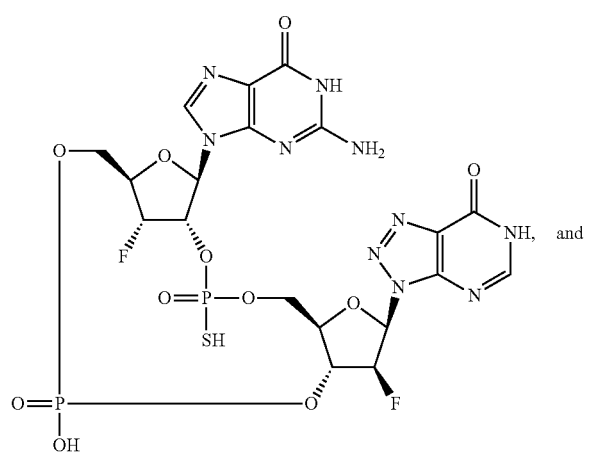
188
-continued
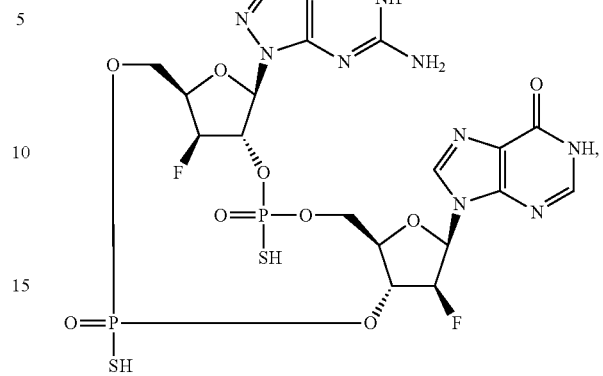
and pharmaceutically acceptable salts, hydrates, solvates, or prodrugs thereof. In aspects of this embodiment, the compound is selected from the group consisting of
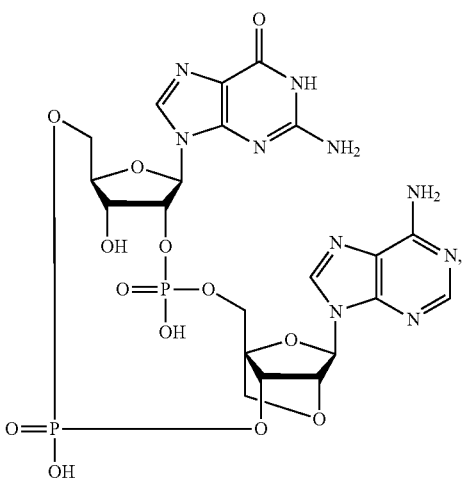
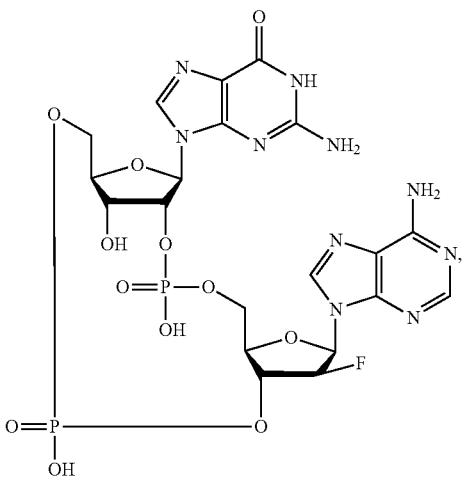

189
-continued

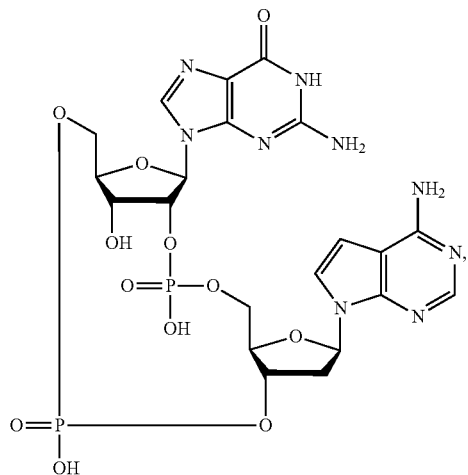
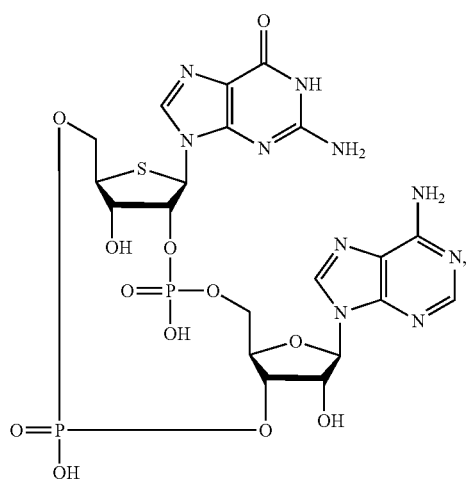
190
-continued
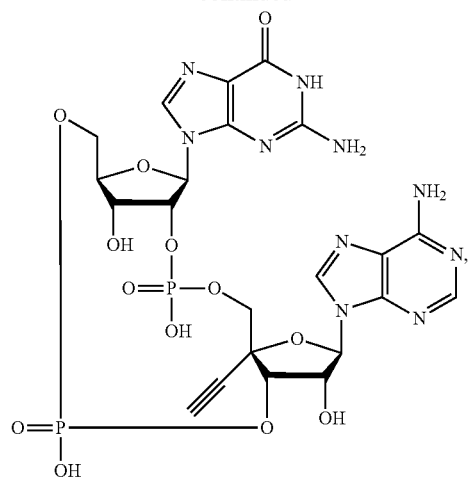
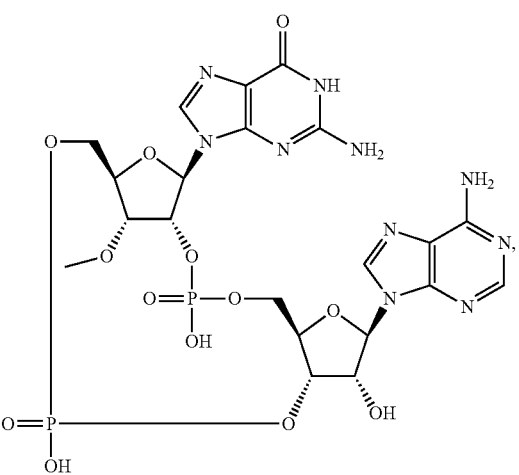
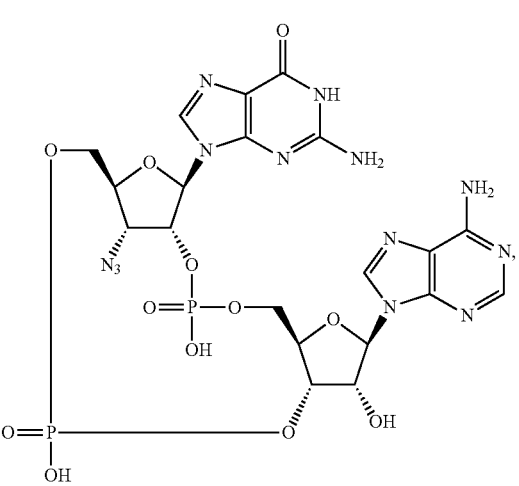

191
-continued
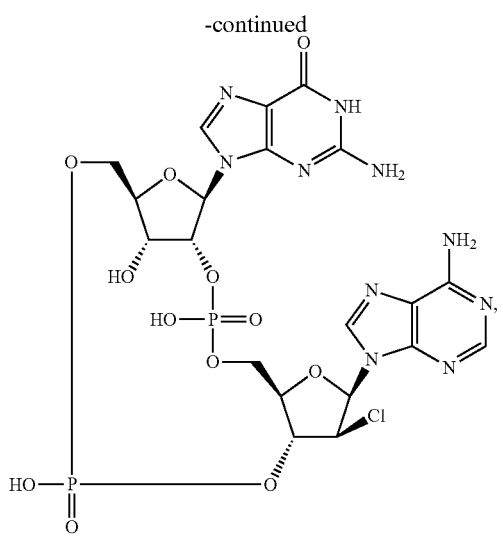
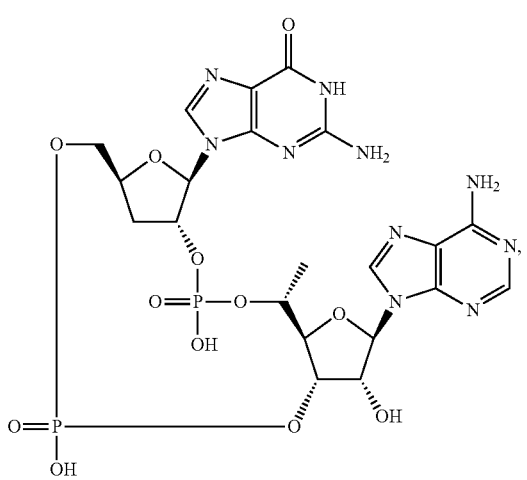
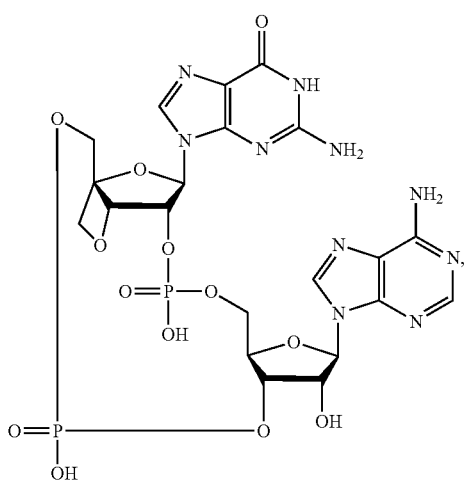
192
-continued
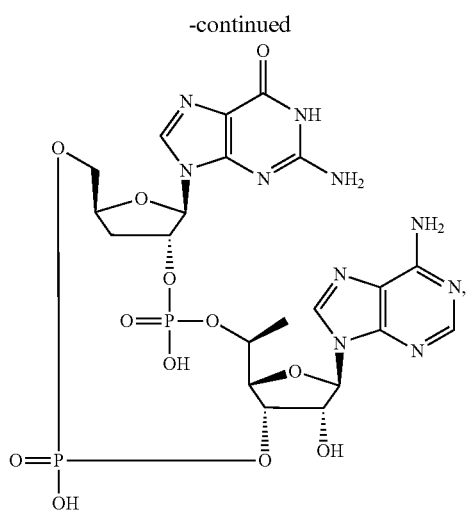
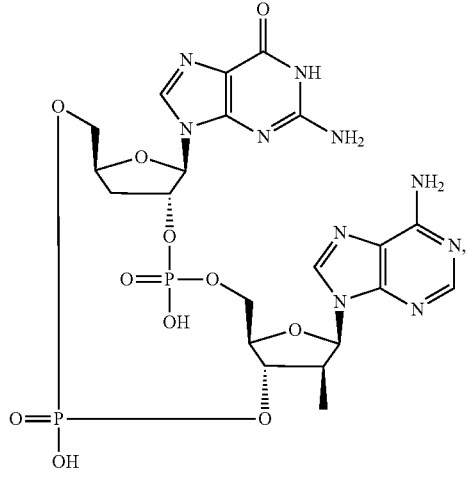
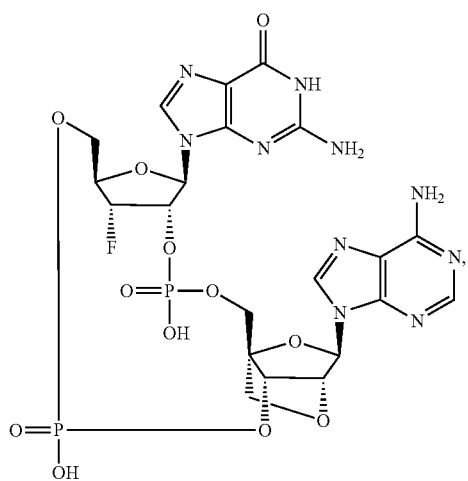

193
-continued
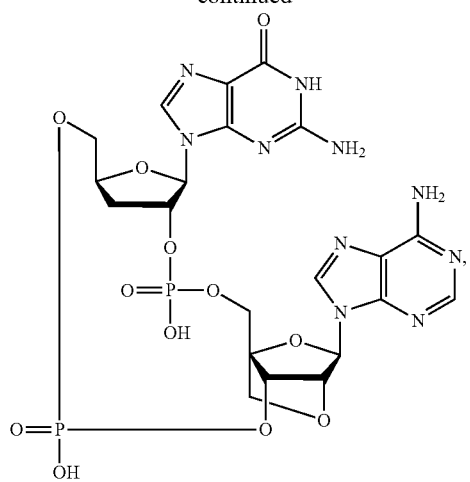
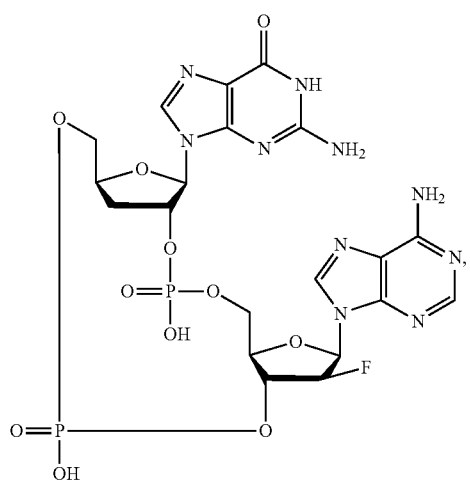
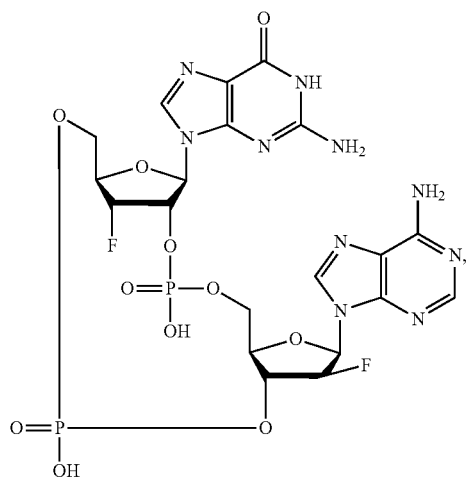
194
-continued
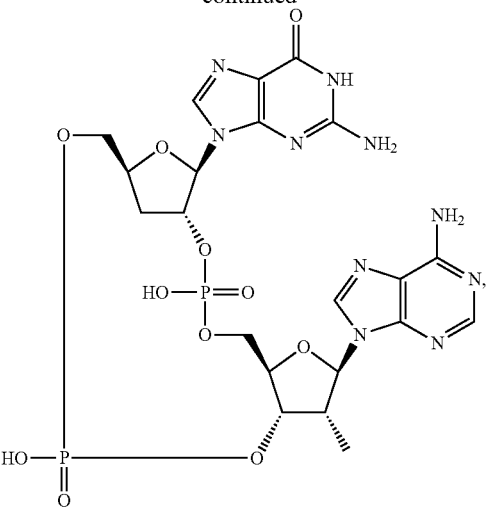
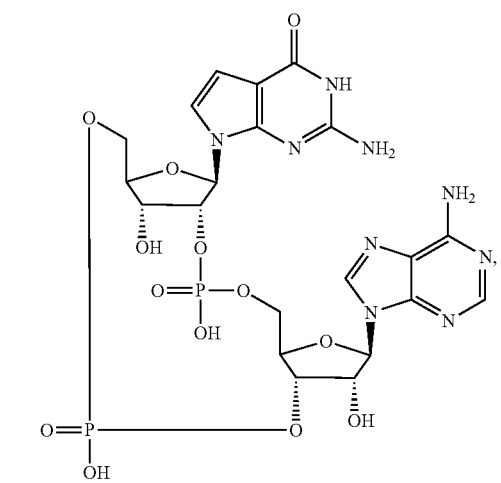

195
-continued
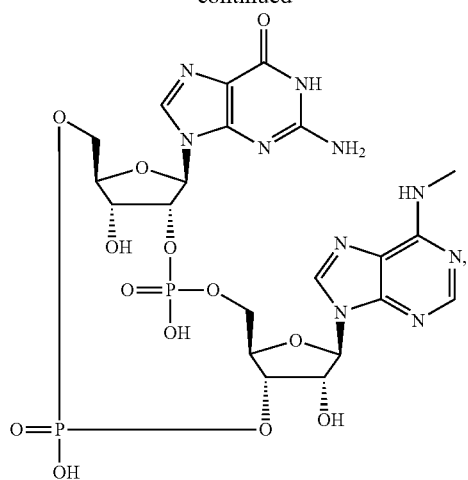
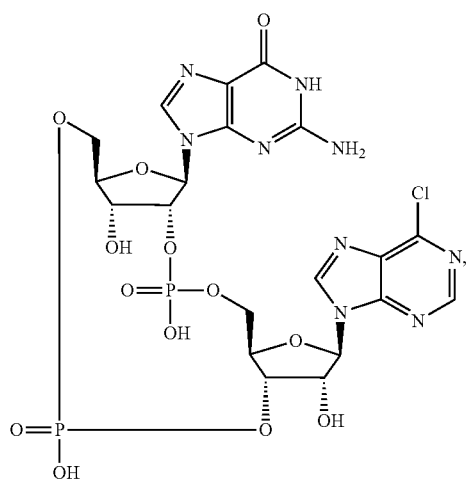
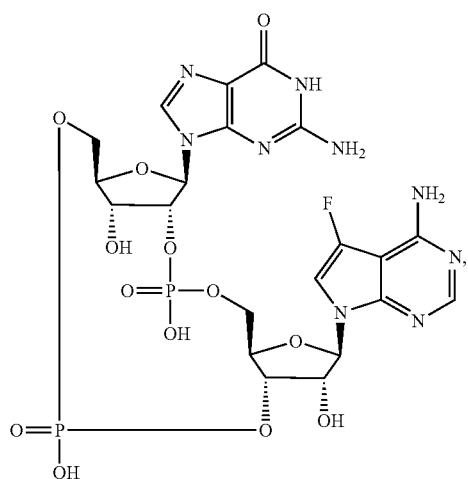
196
-continued
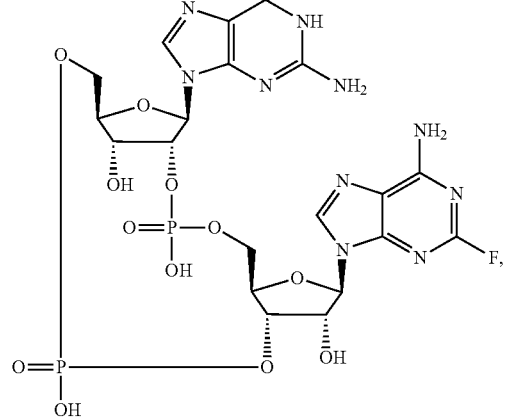
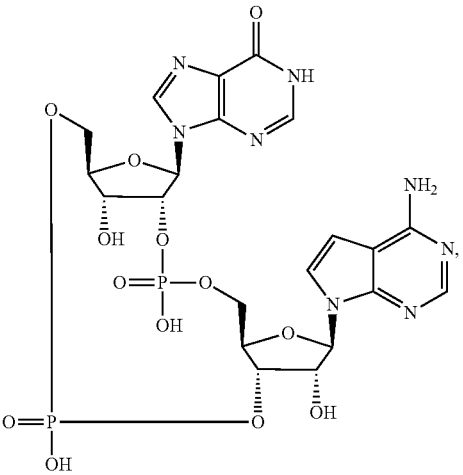
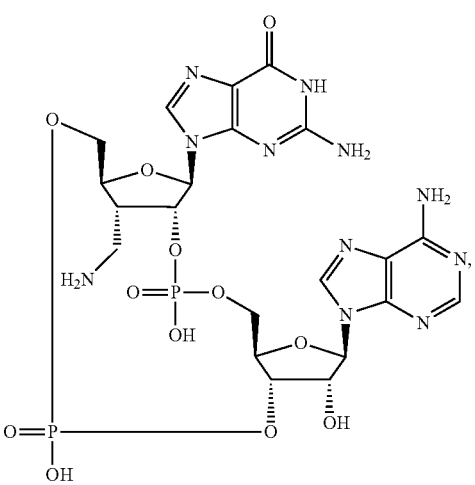

197
-continued
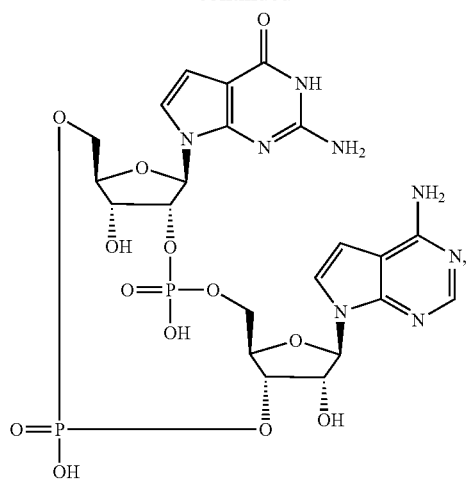
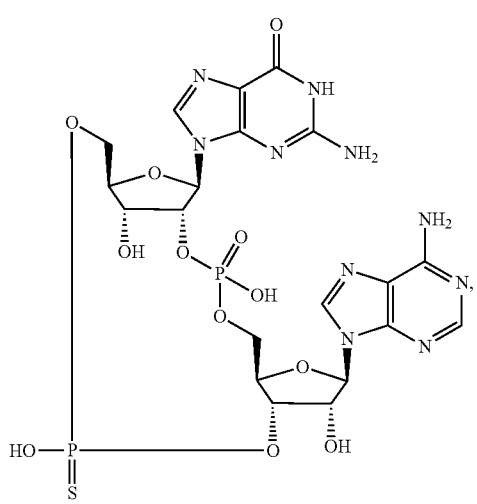
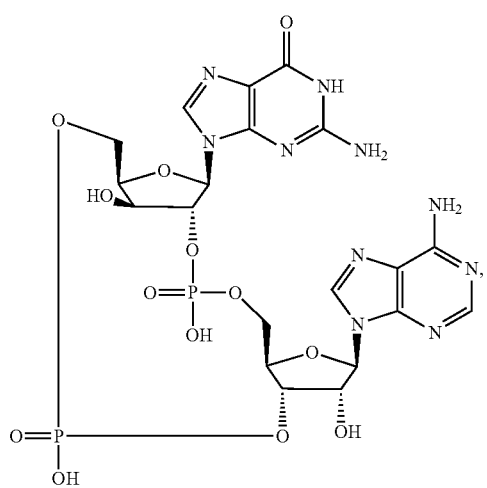
198
-continued

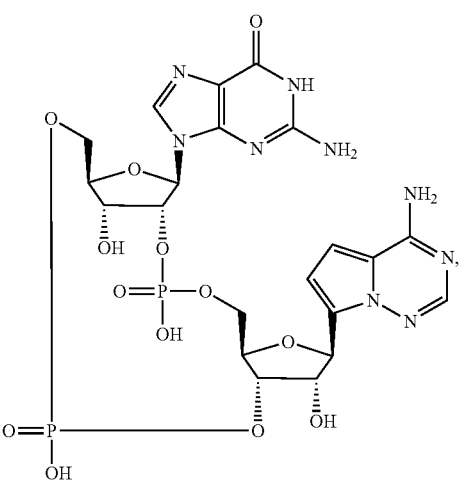
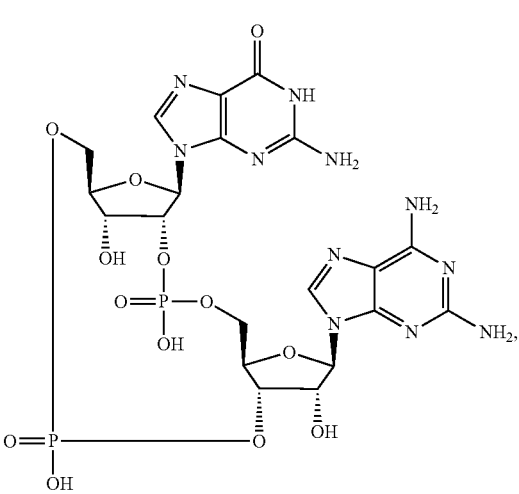

199
-continued
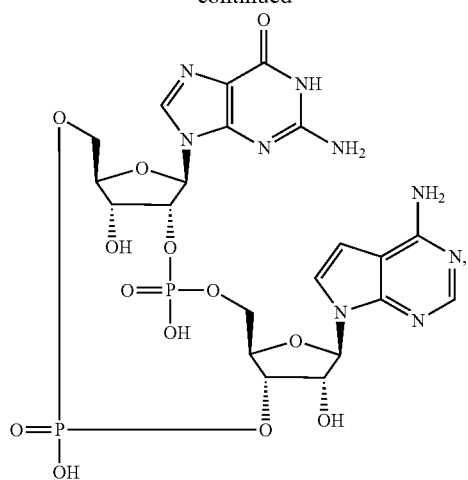
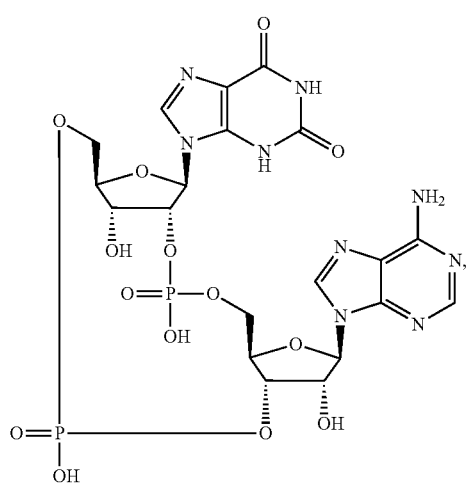
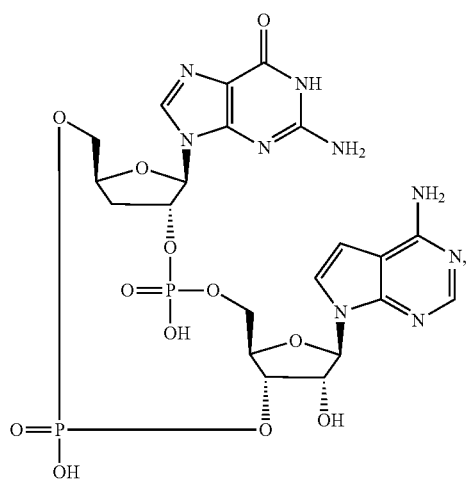
200
-continued
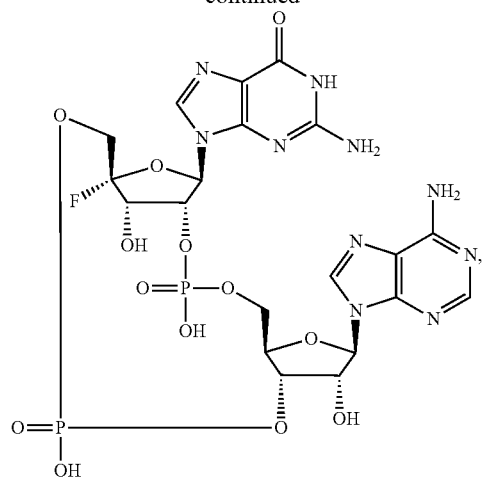
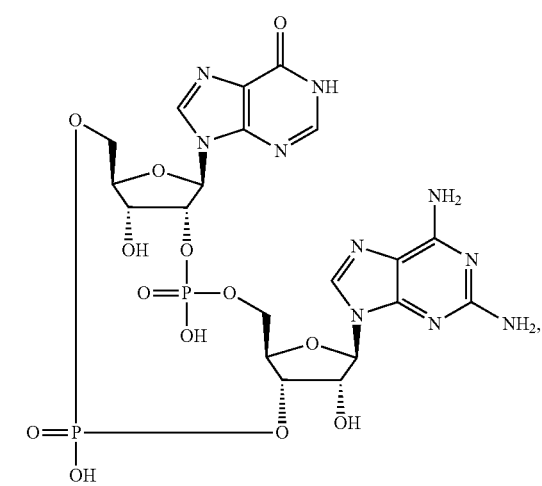
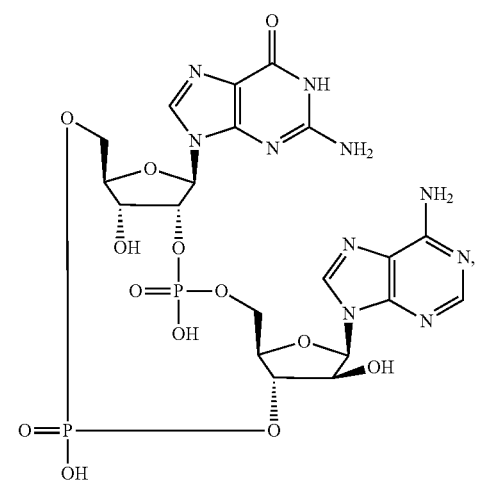

201
-continued
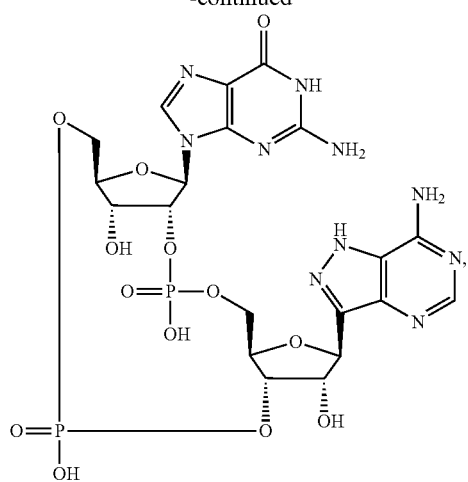
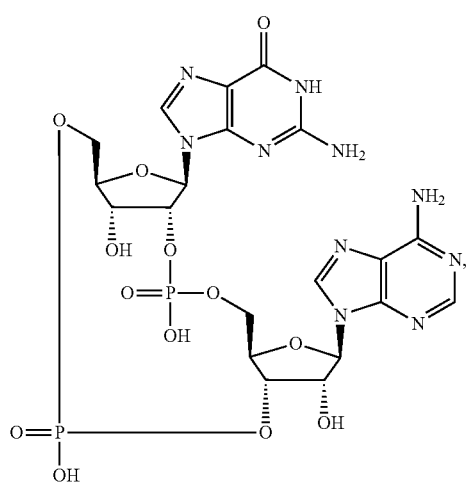
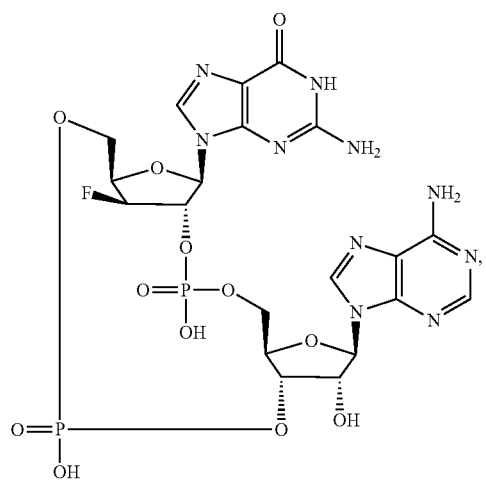
202
-continued
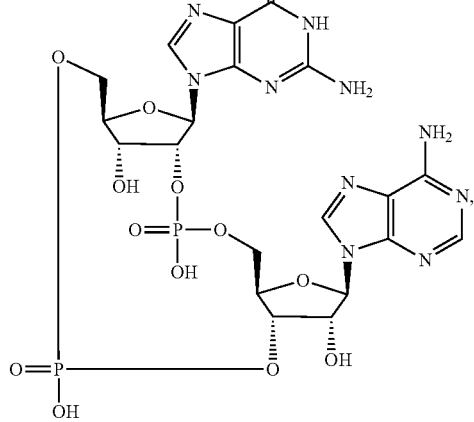
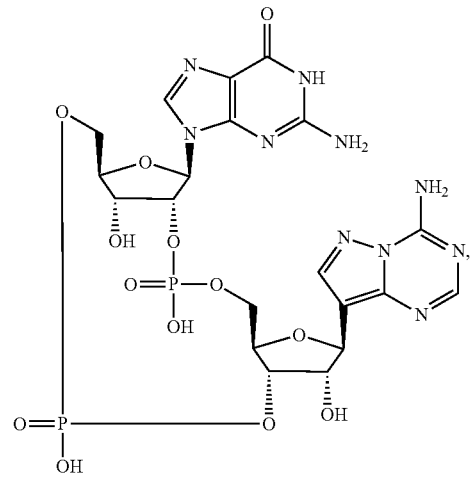
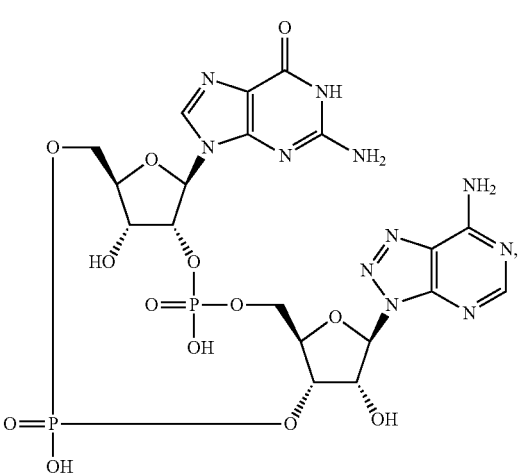

203 -continued
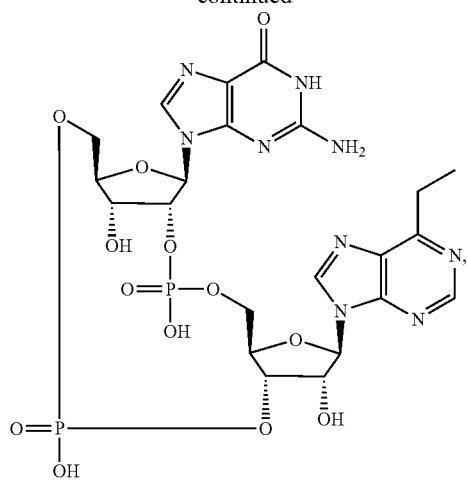
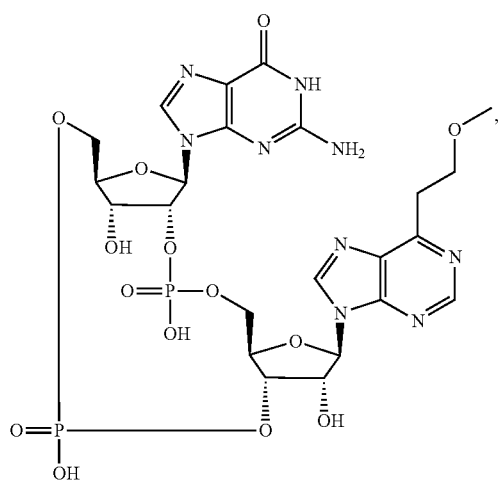
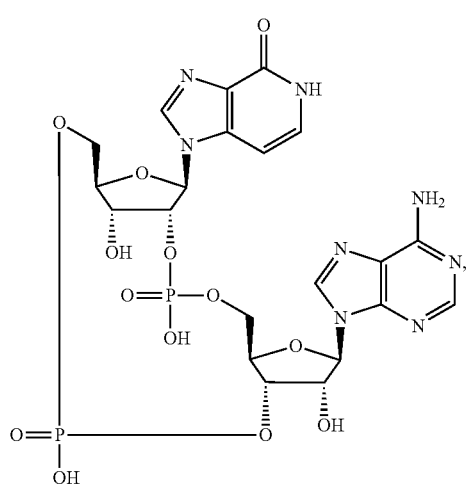
204 -continued
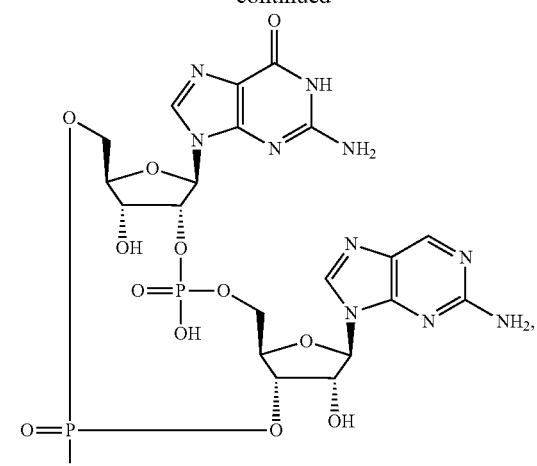
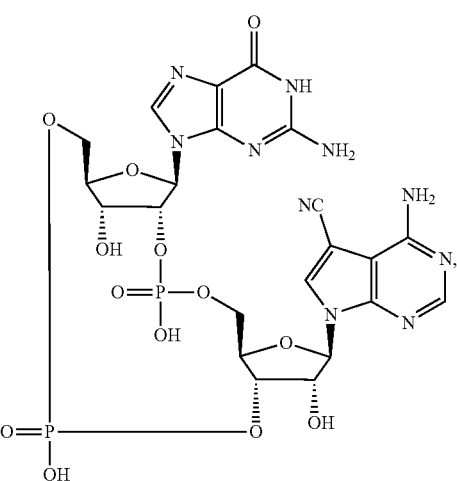
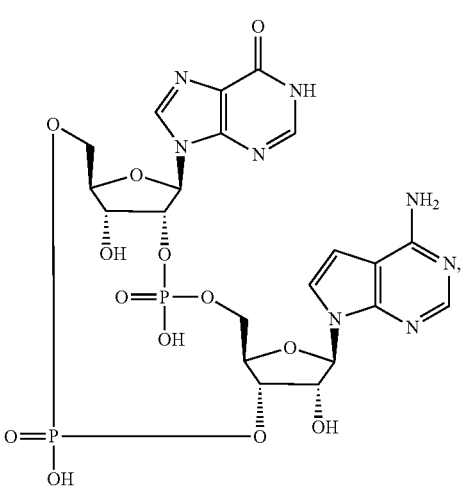

205
-continued

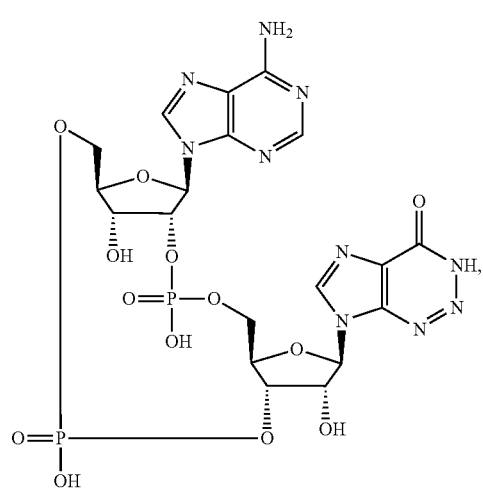
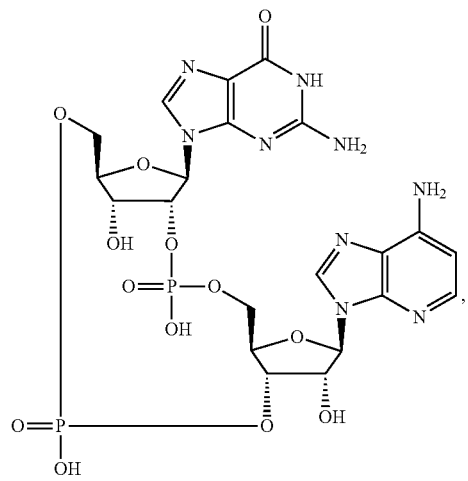
206
-continued
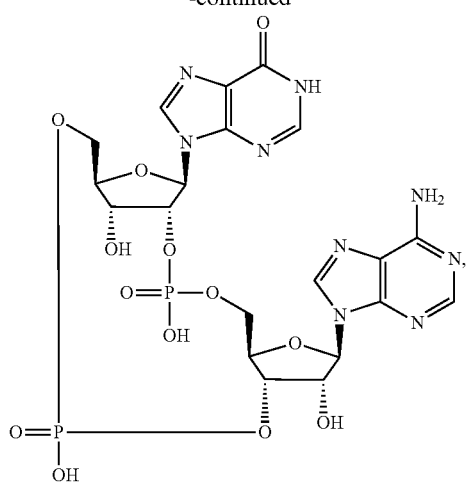
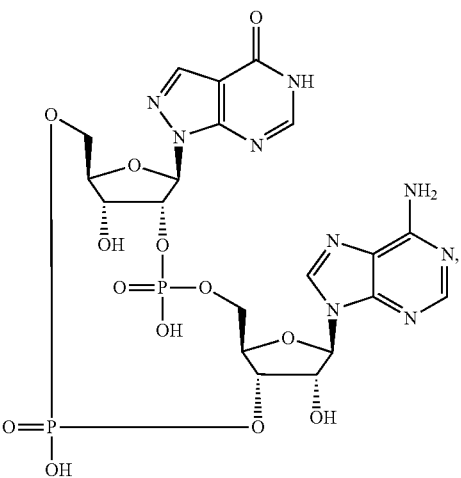
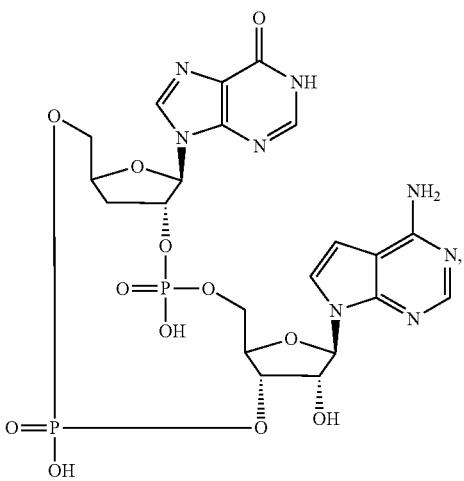

207
-continued
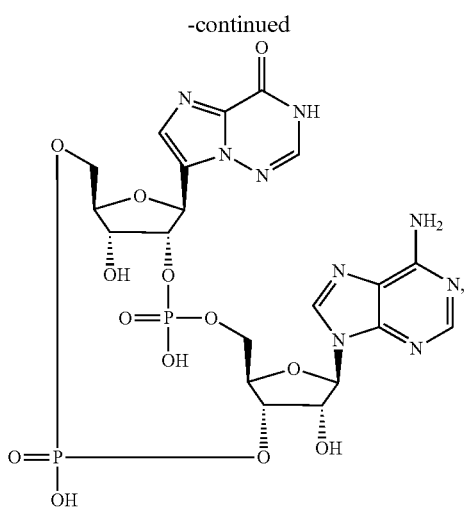
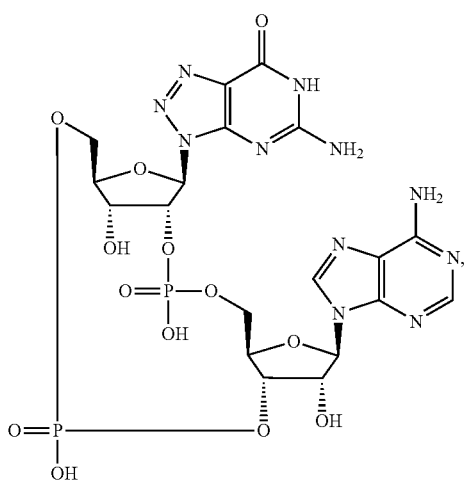
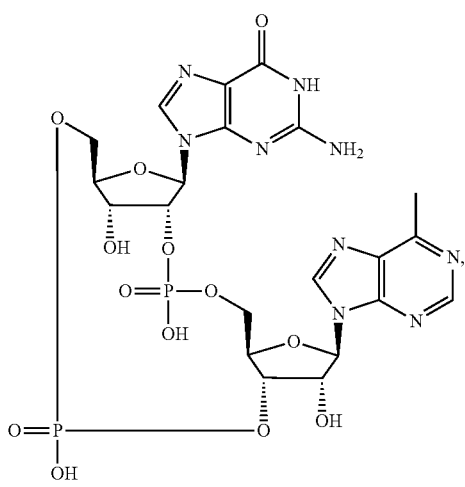
208
-continued
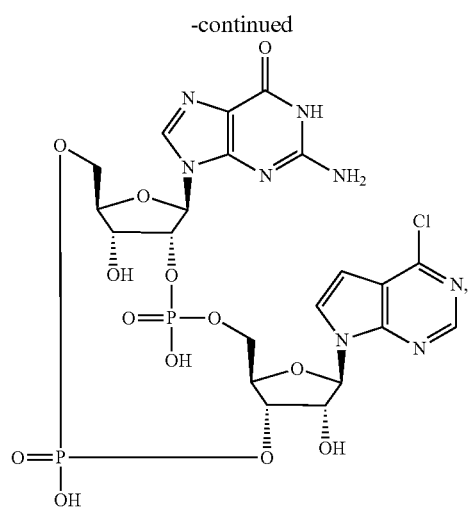
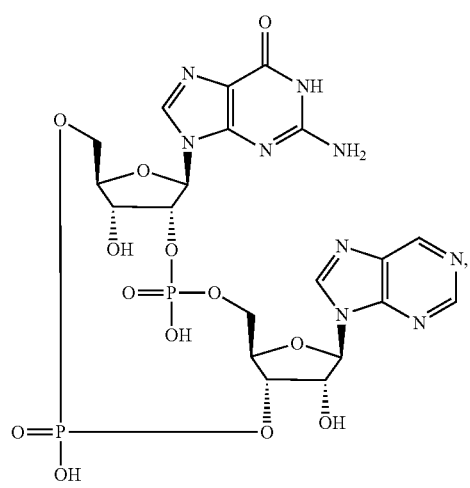
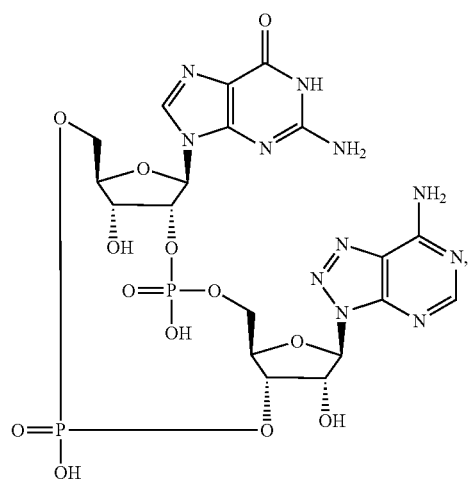

209
-continued
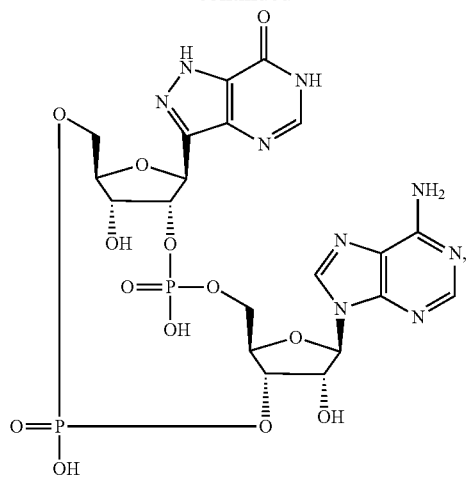
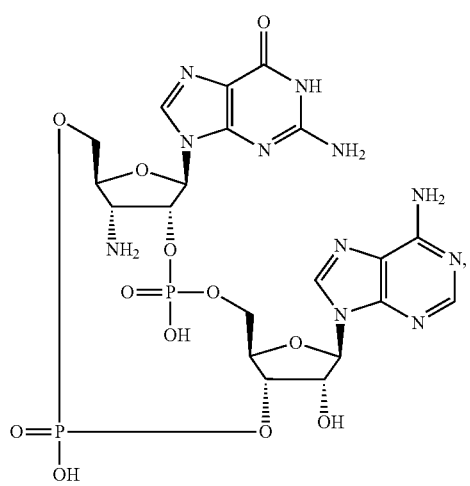
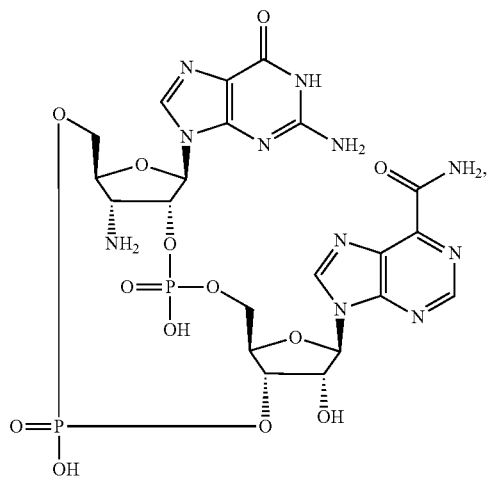
210
-continued
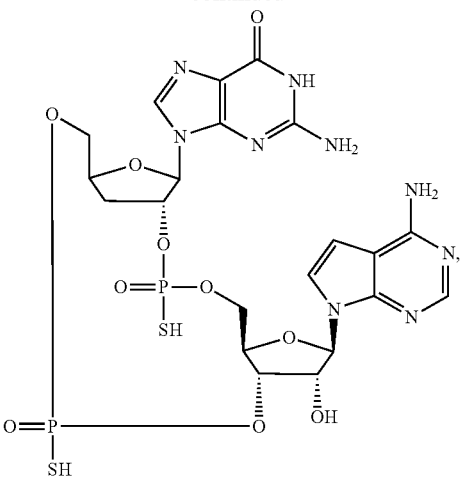
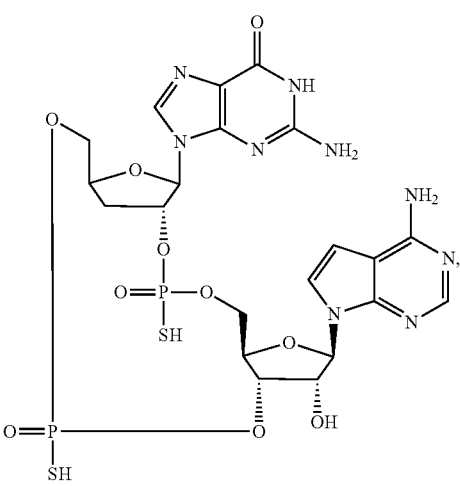
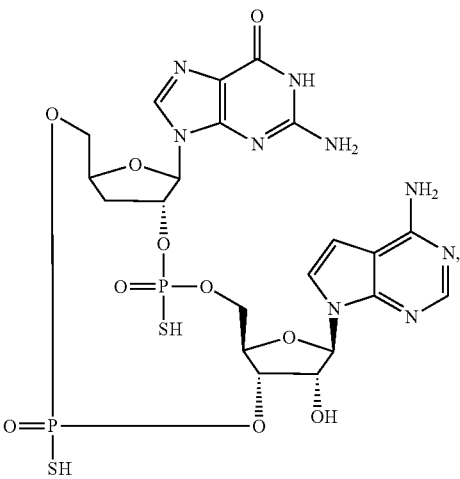

211
-continued

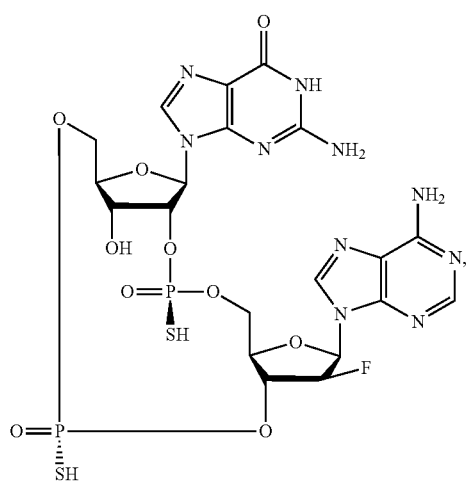
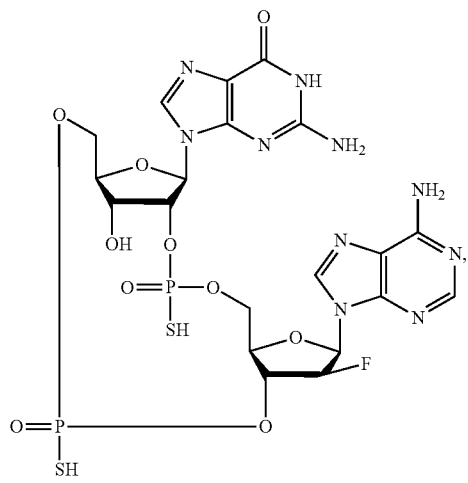
212
-continued
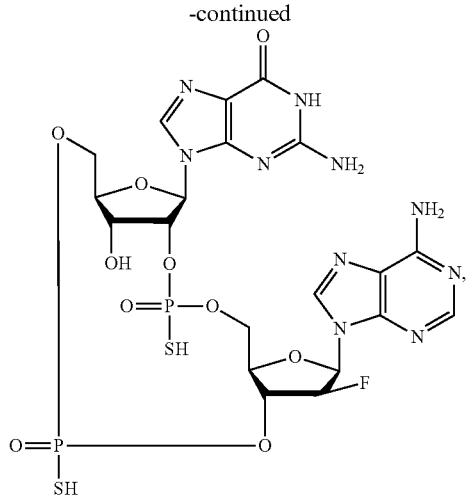
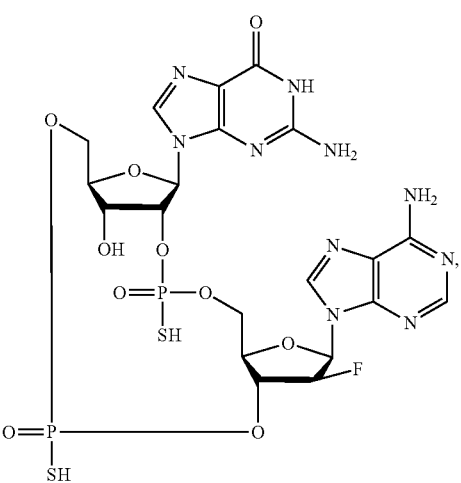
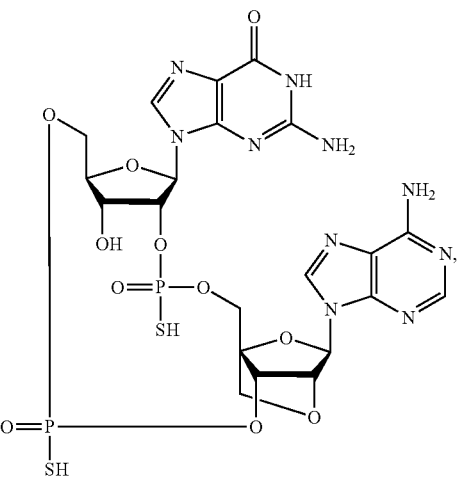

213
-continued
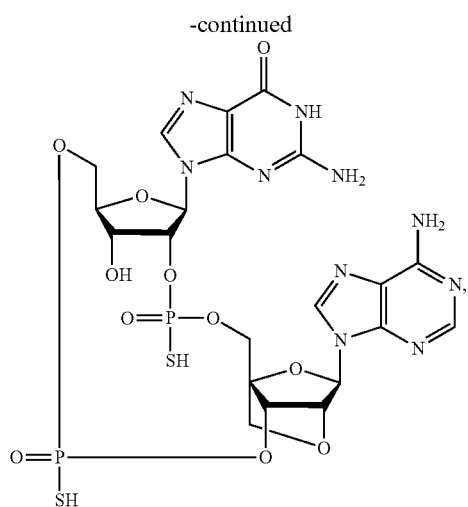
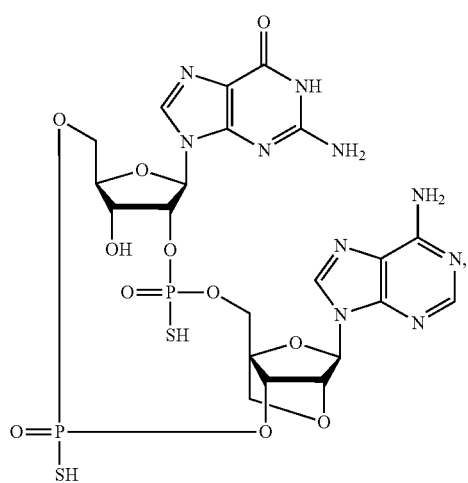
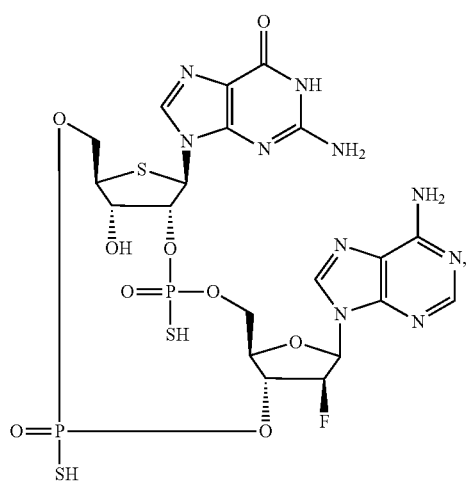
214
-continued
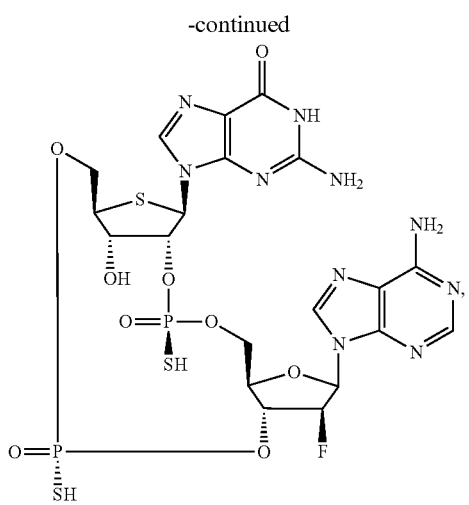
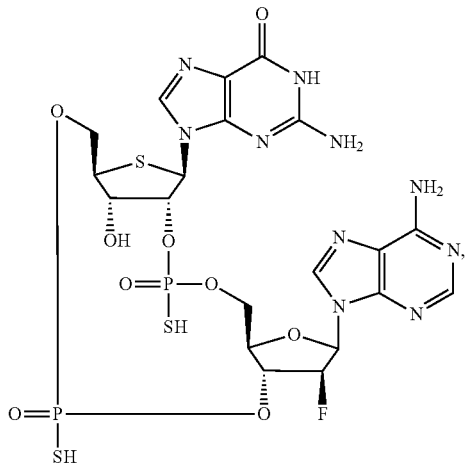
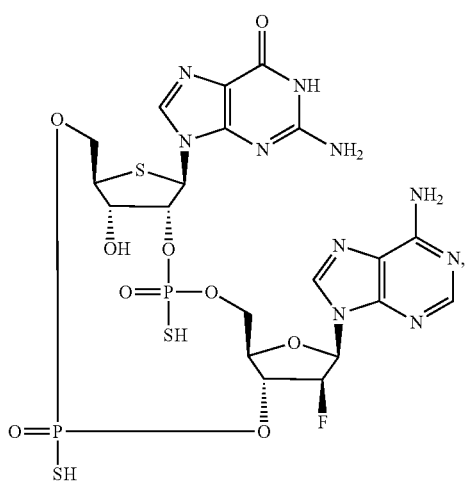

215
-continued
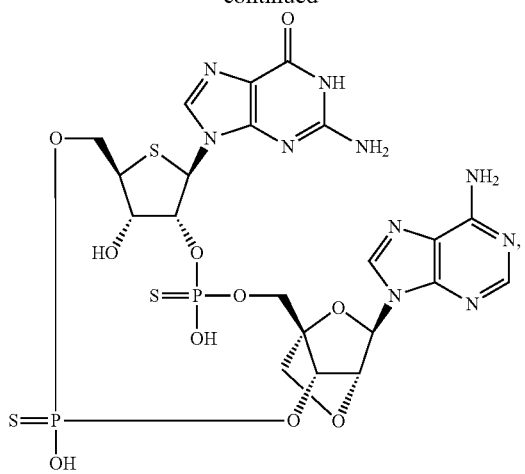
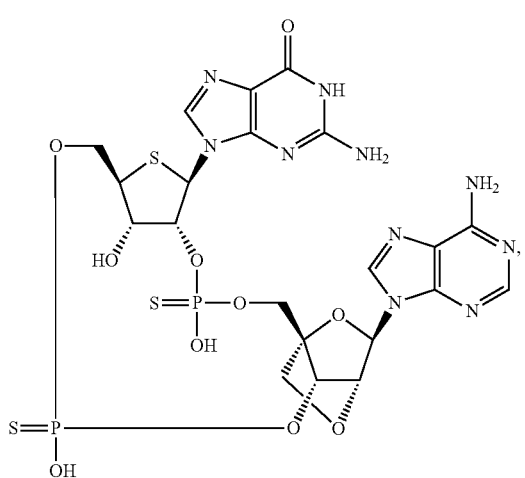
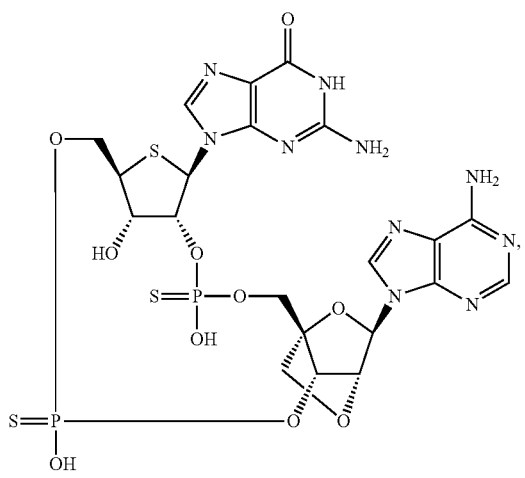
216
-continued
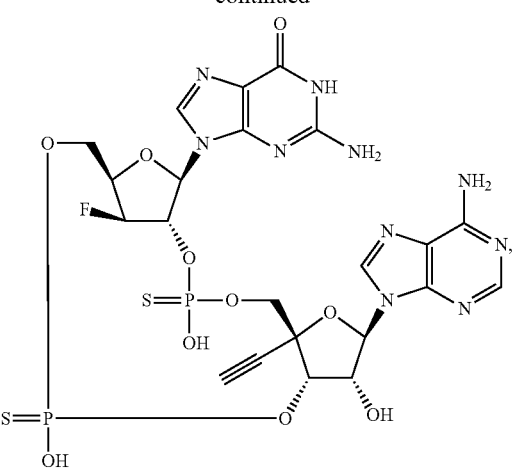
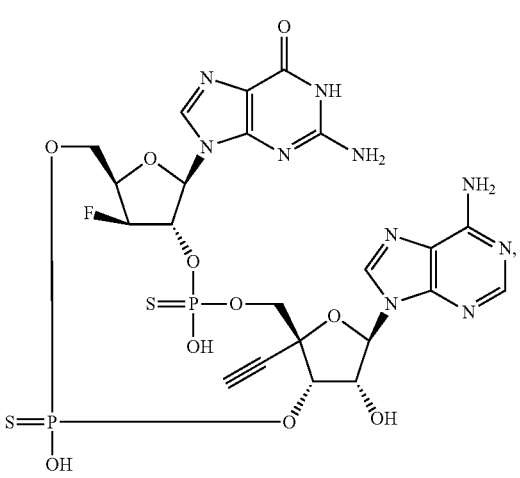
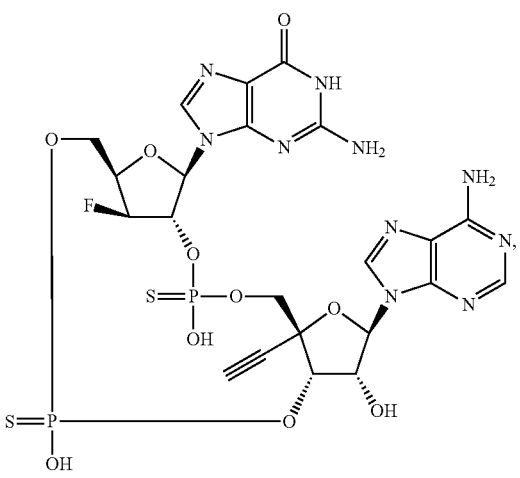

217
-continued
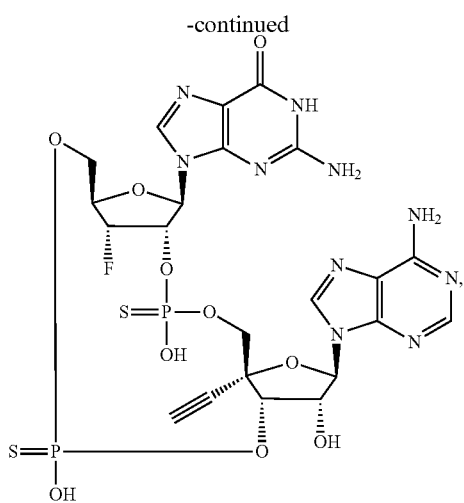
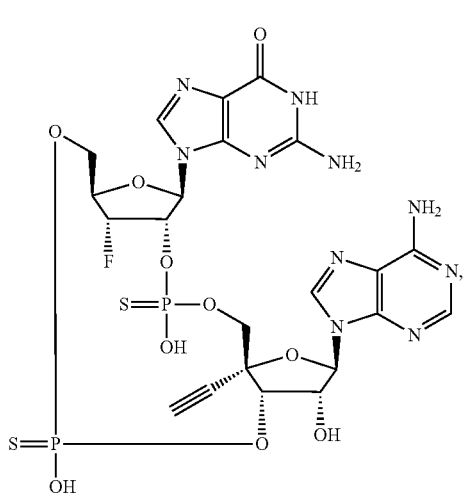
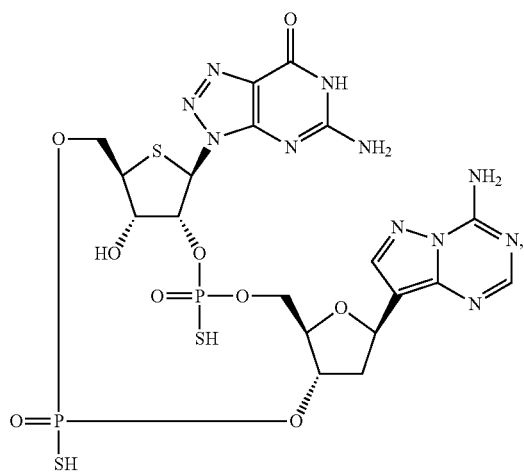
218
-continued
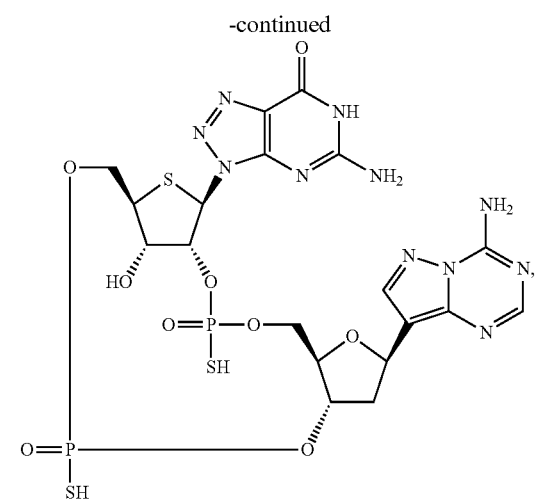
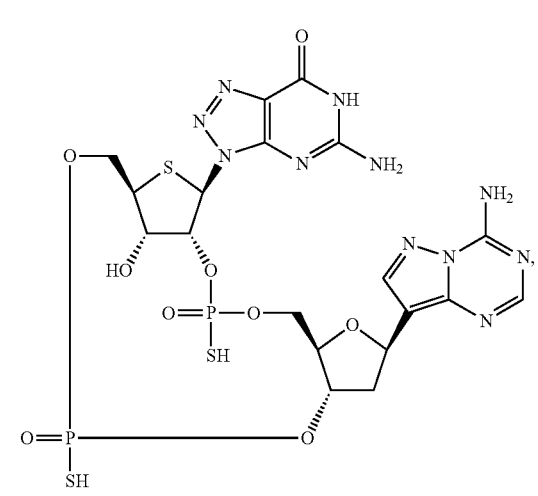
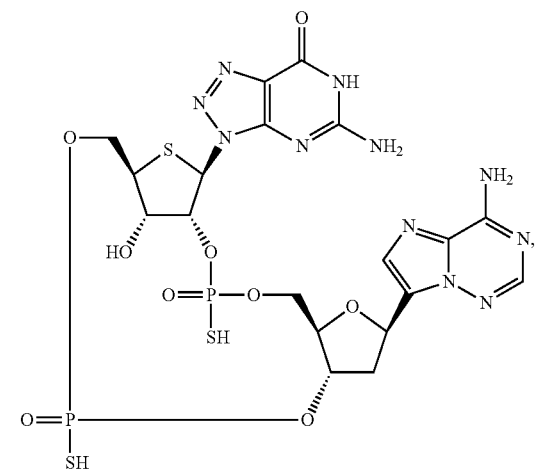

219
-continued
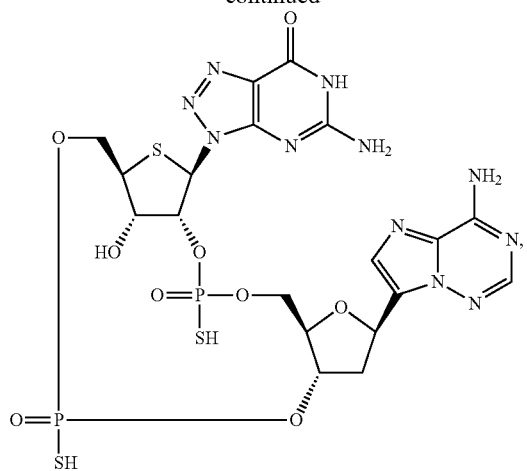
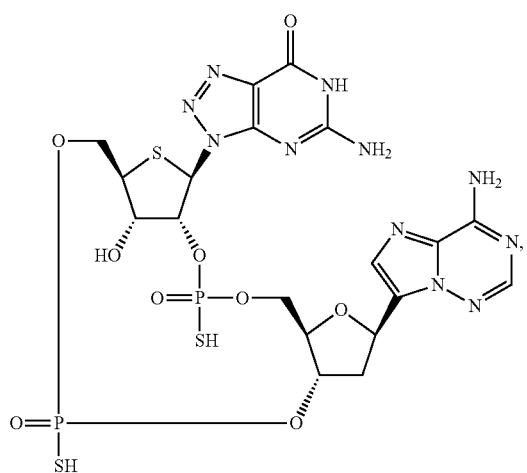
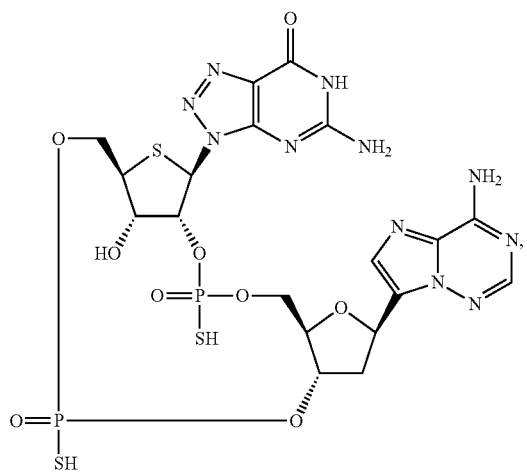
220
-continued
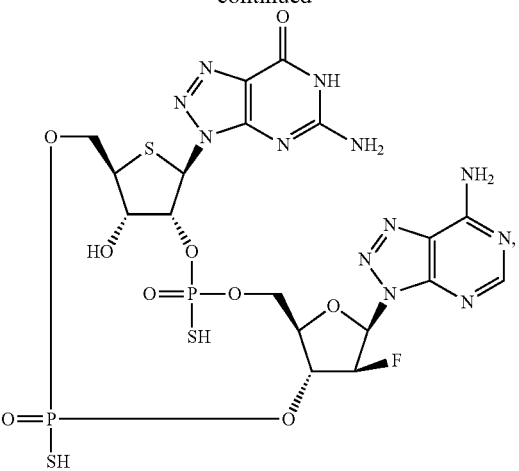
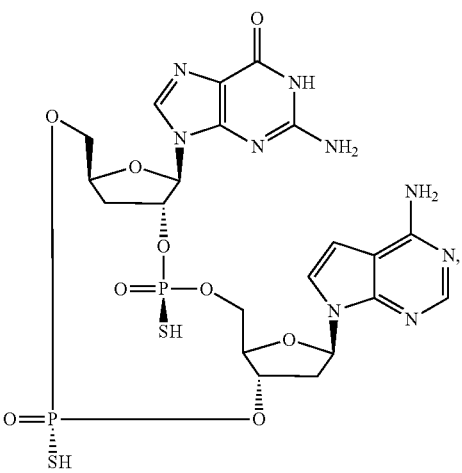

221
-continued
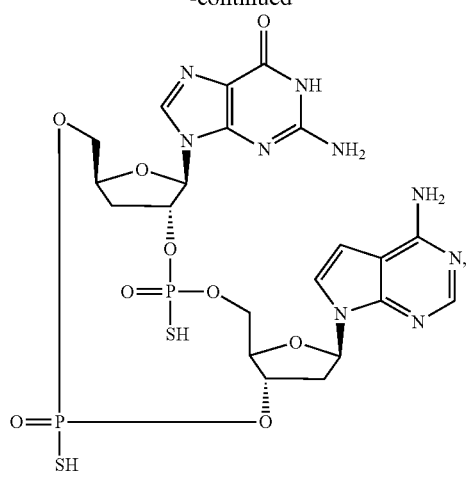
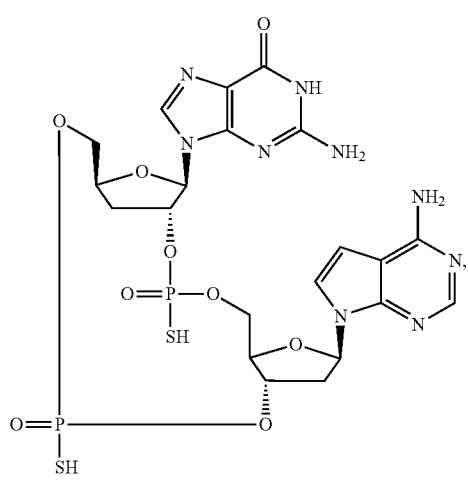
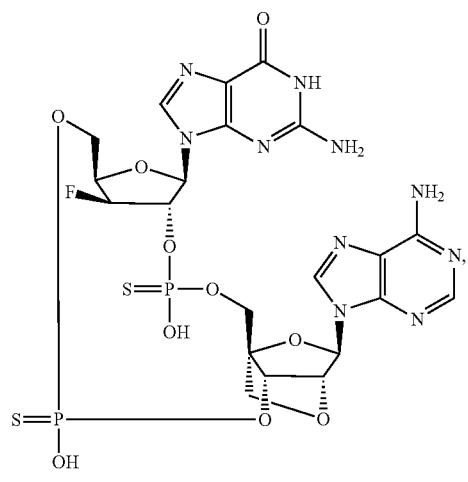
222
-continued
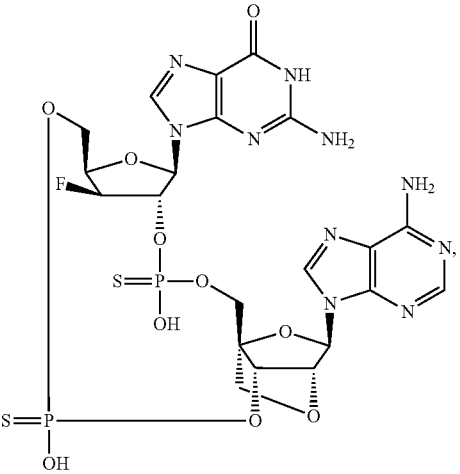
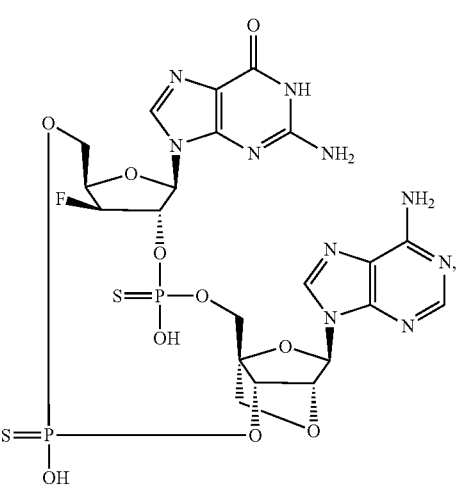
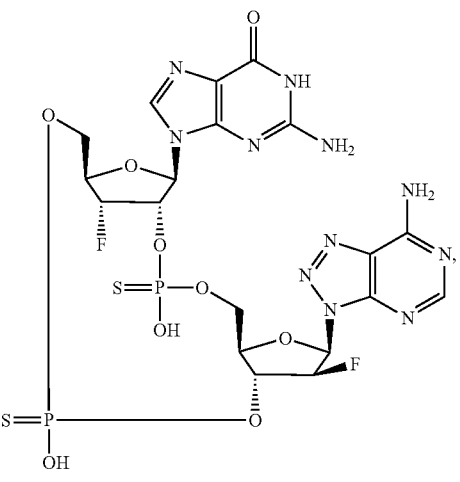

223
-continued
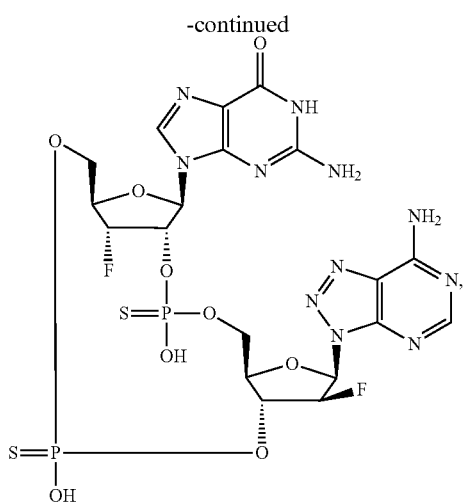
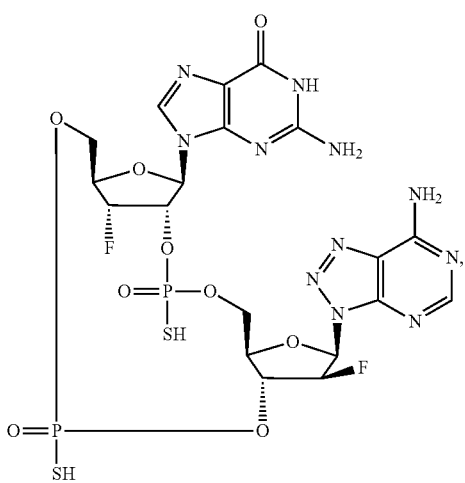
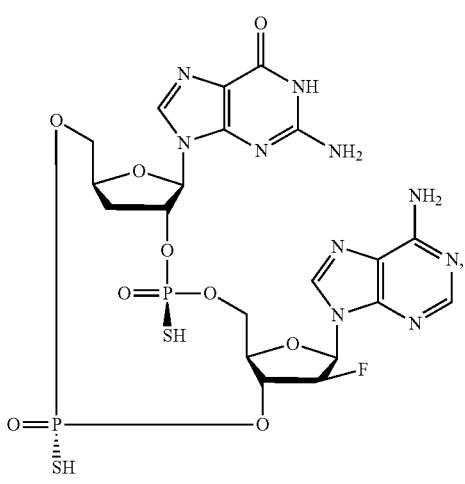
224
-continued
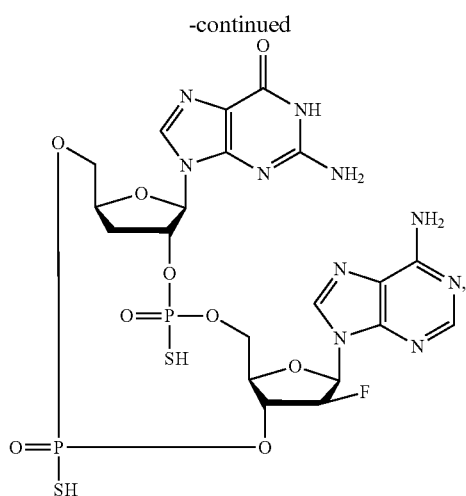
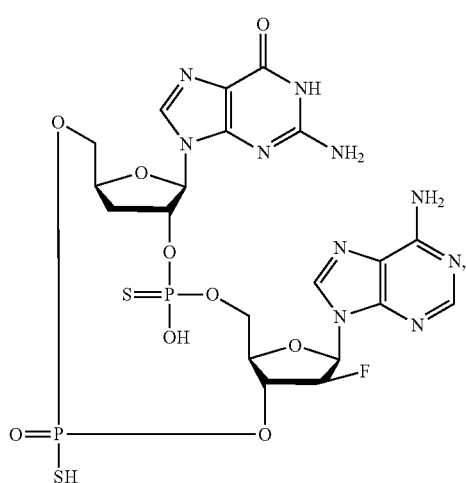
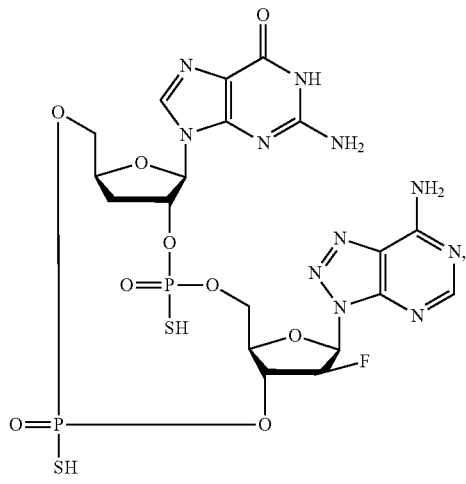

225
-continued
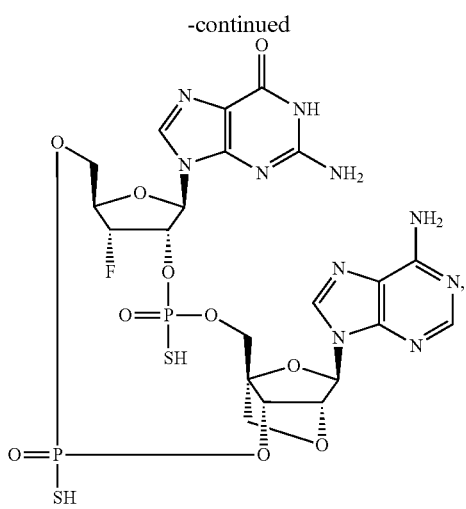
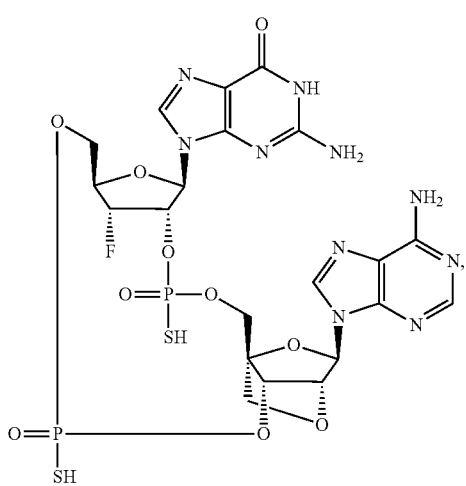
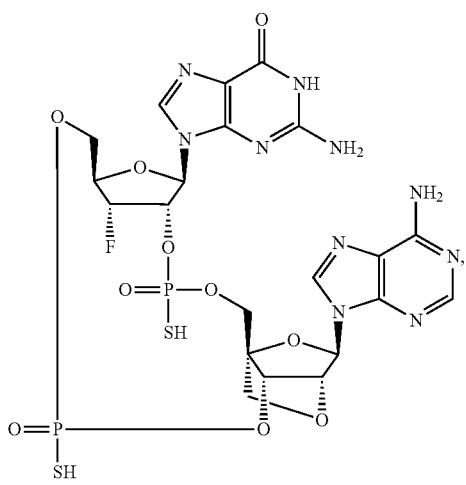
226
-continued
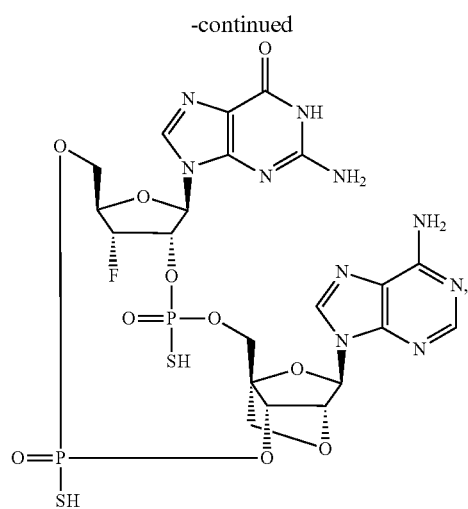
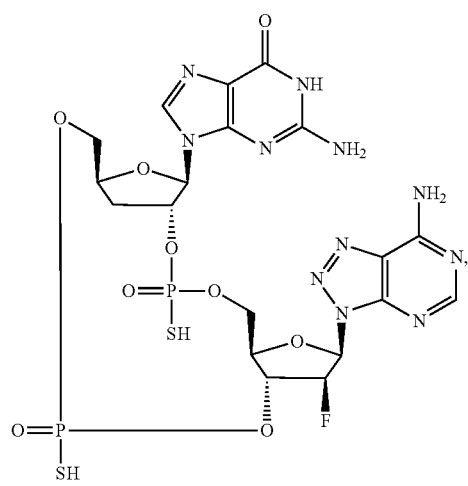
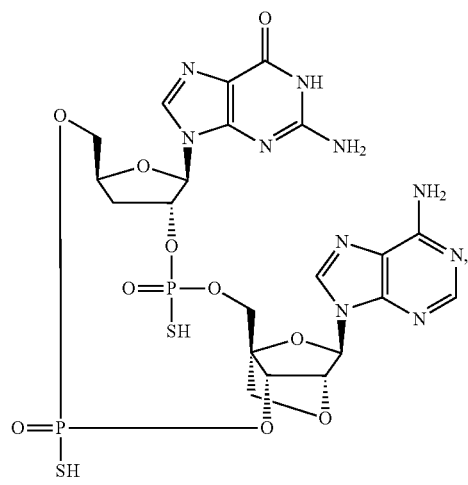

227                                    228
-continued                         -continued
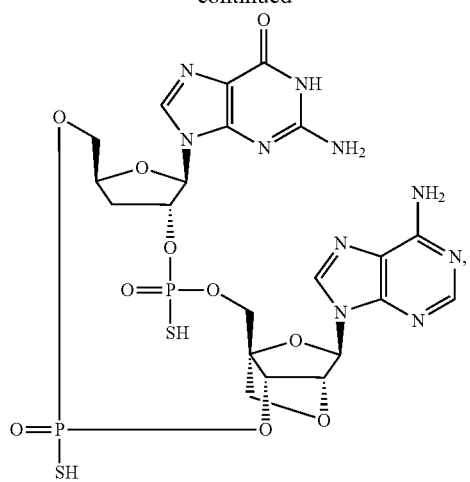
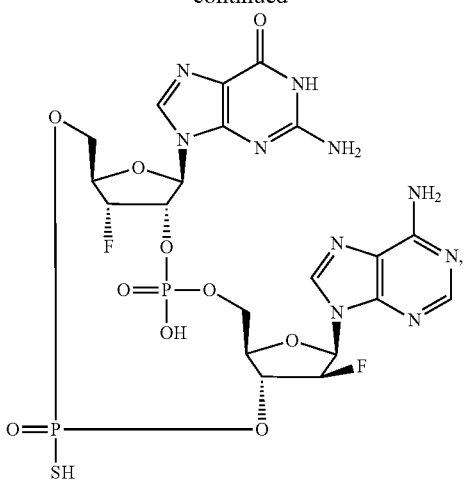
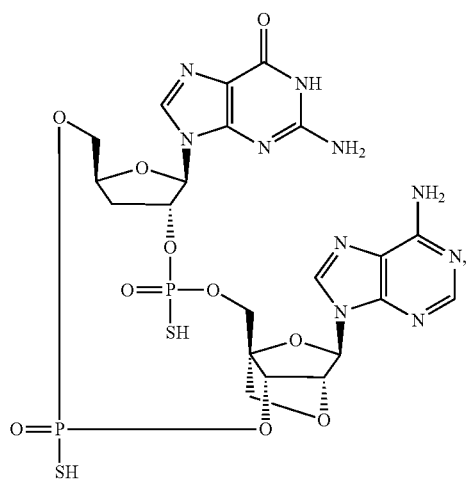
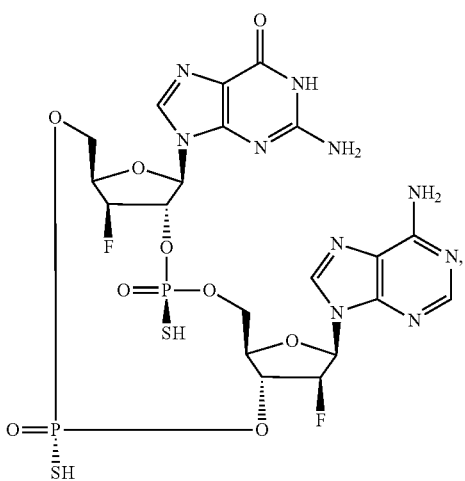
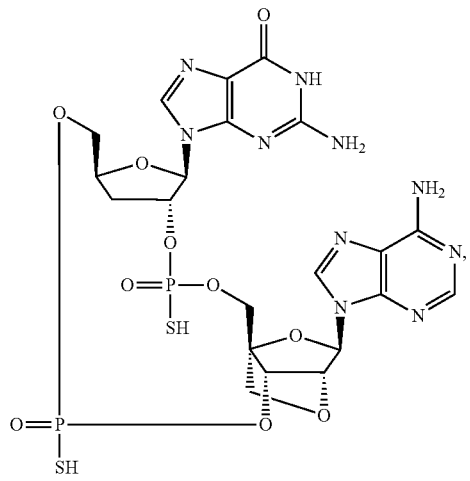
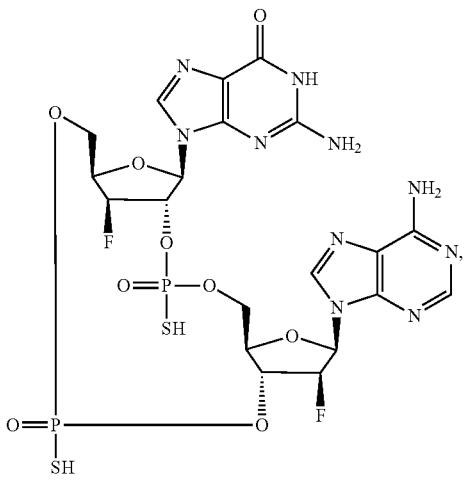

229
-continued
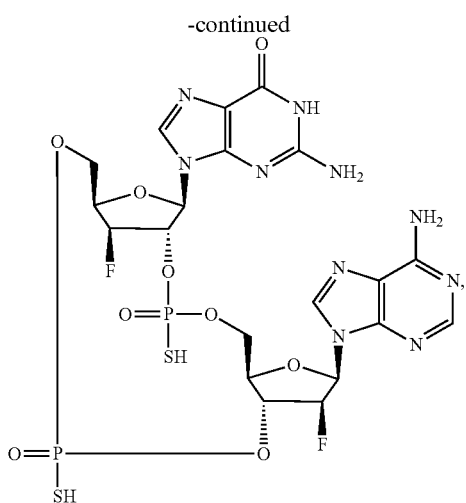
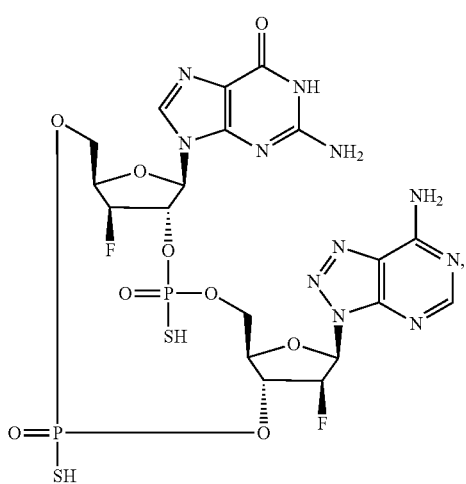
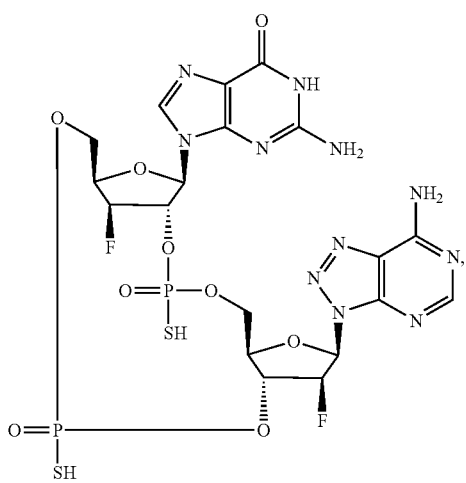
230
-continued
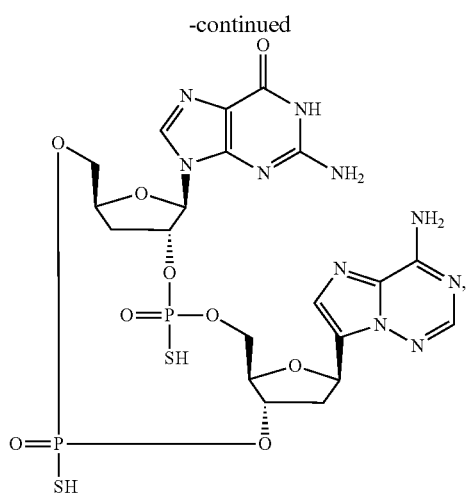
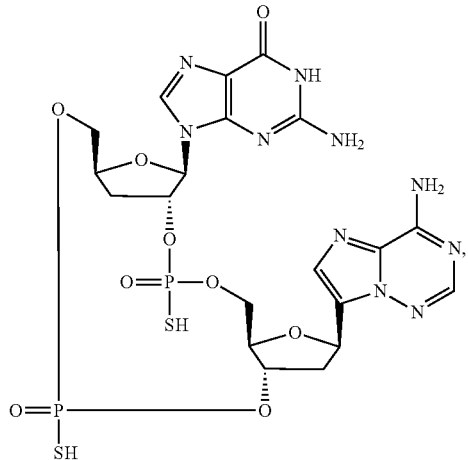
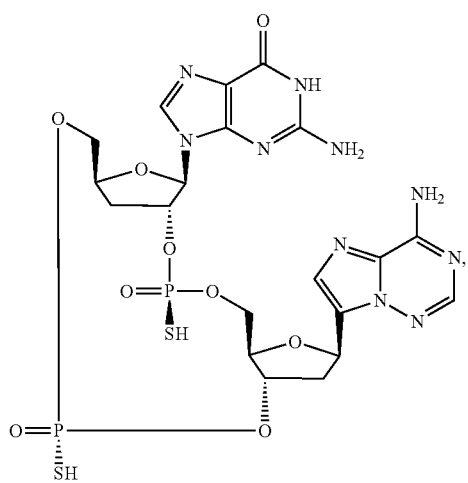

231
-continued
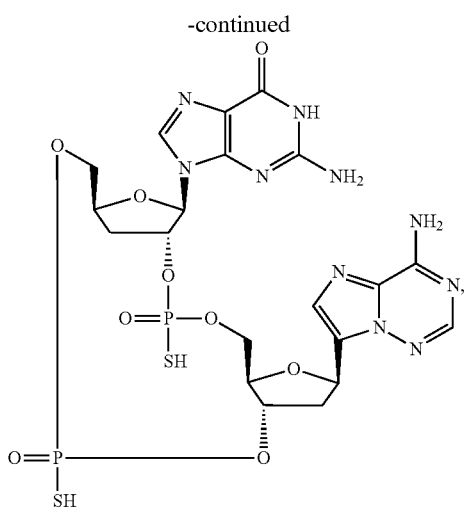
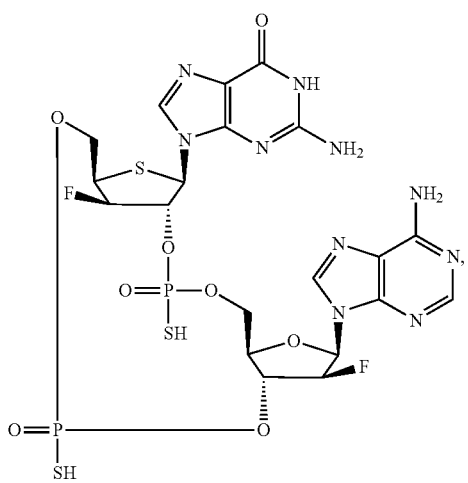
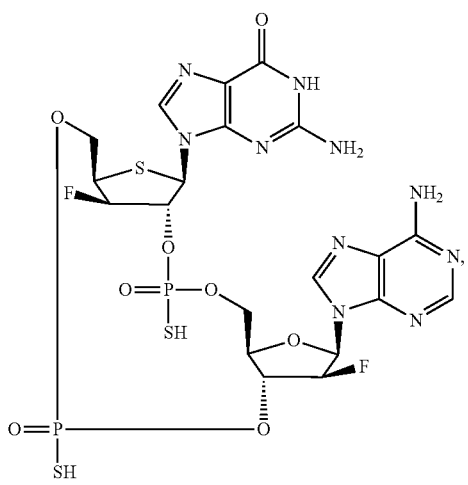
232
-continued
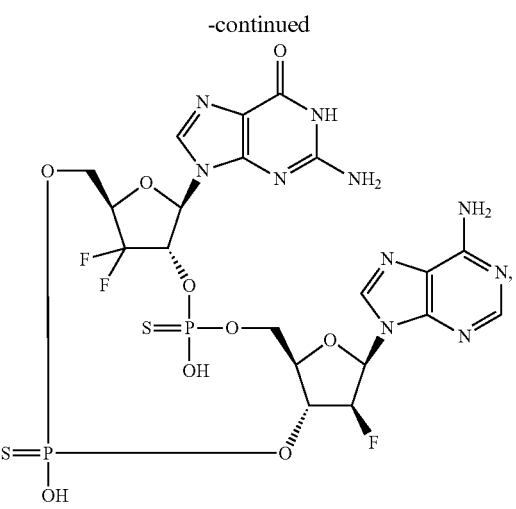
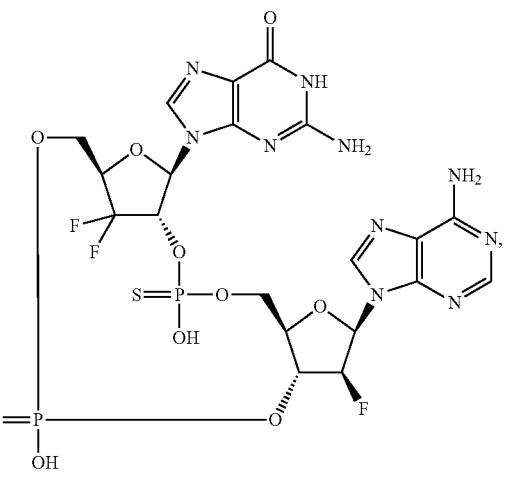
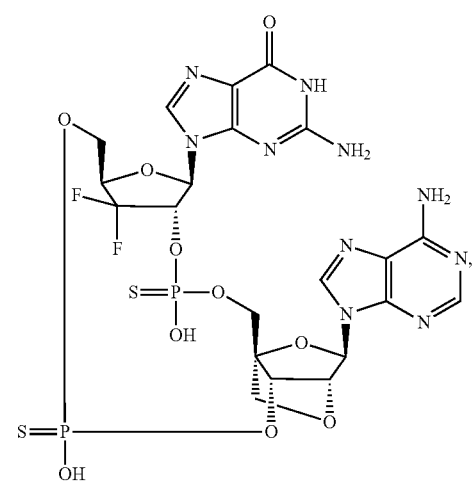

233
-continued
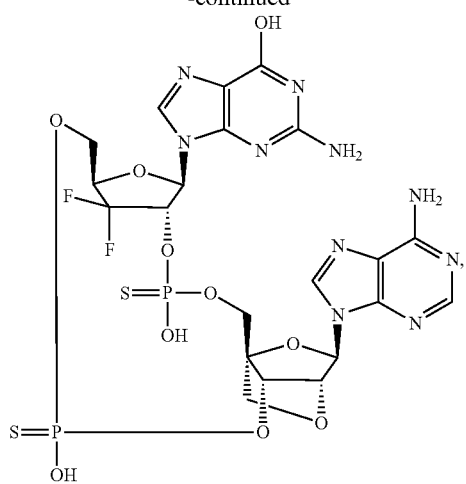
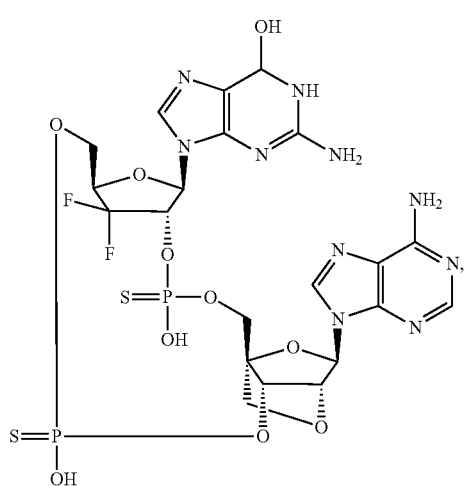
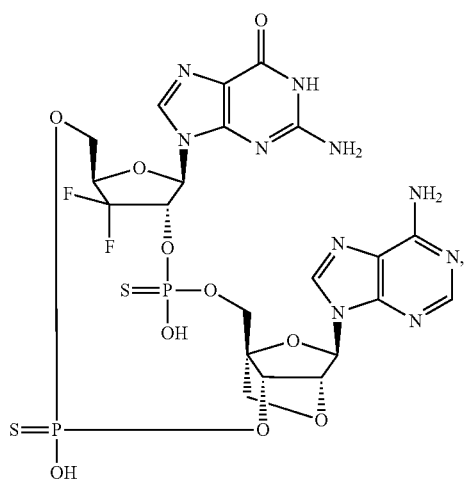
234
-continued
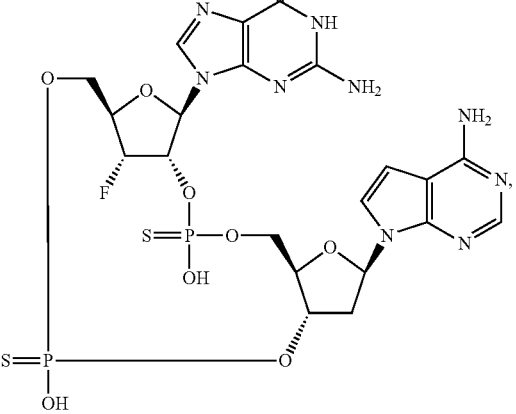
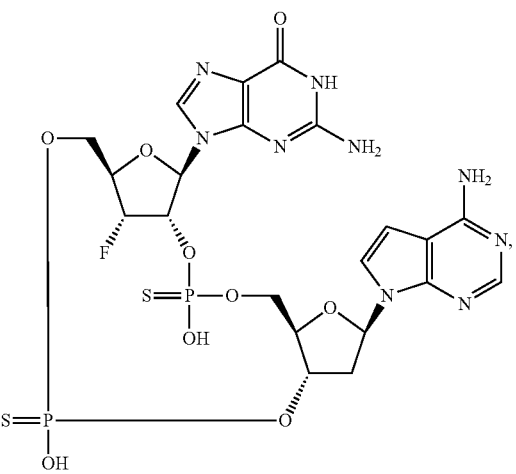
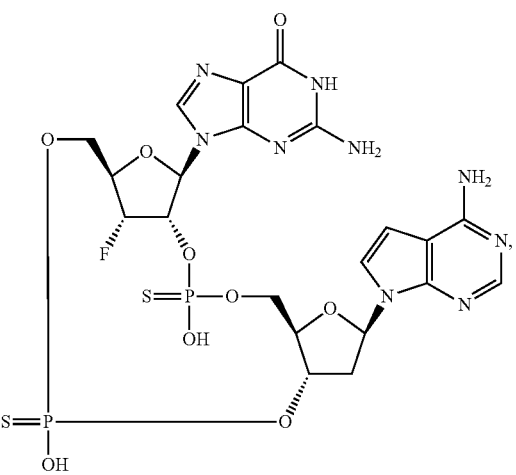

235
-continued
236
-continued
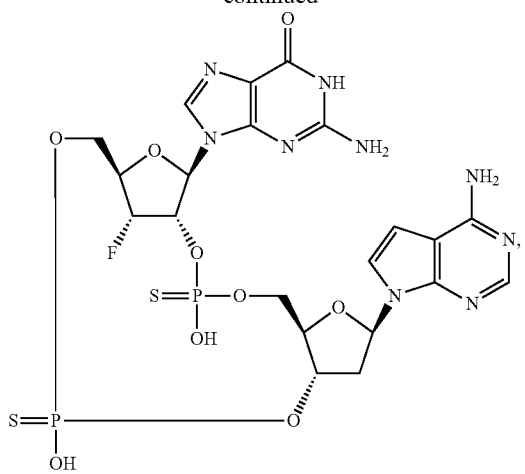
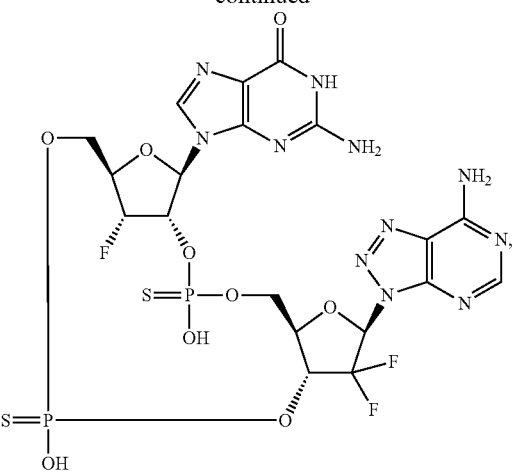
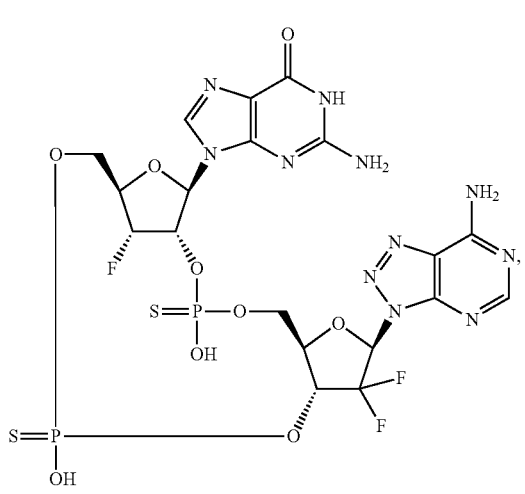
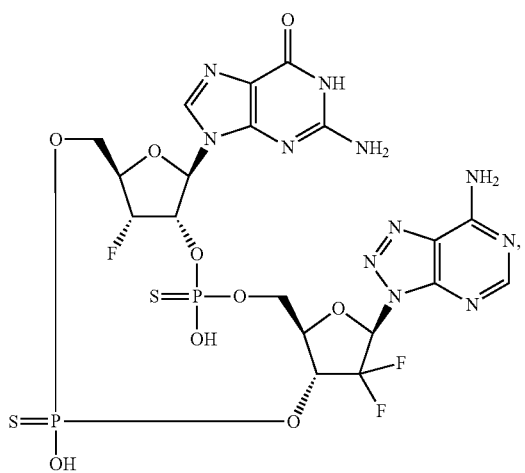
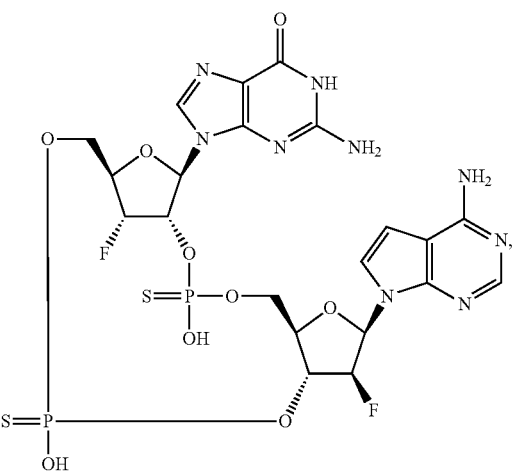

237
-continued
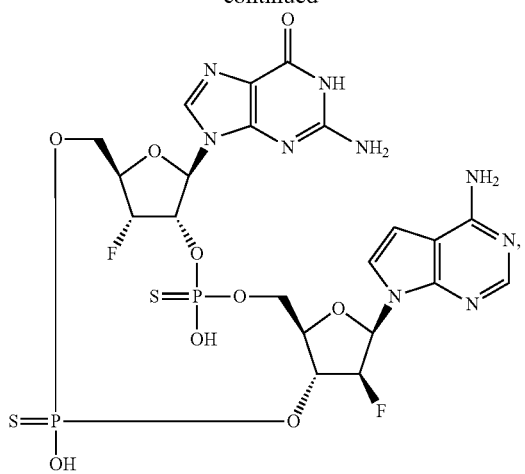
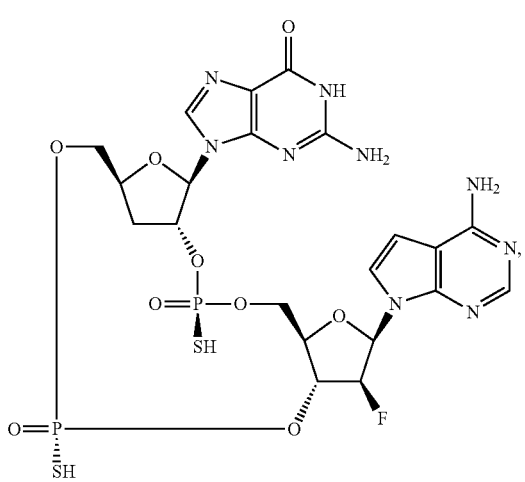
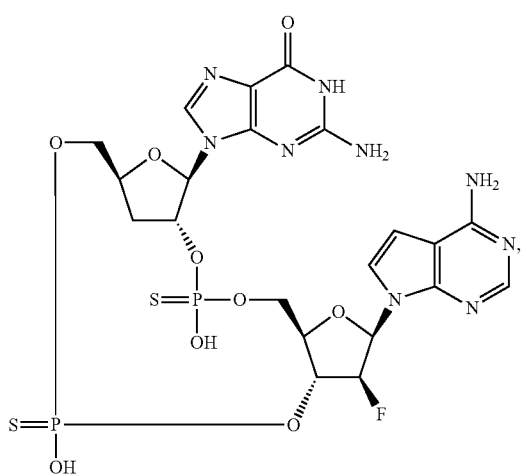
238
-continued
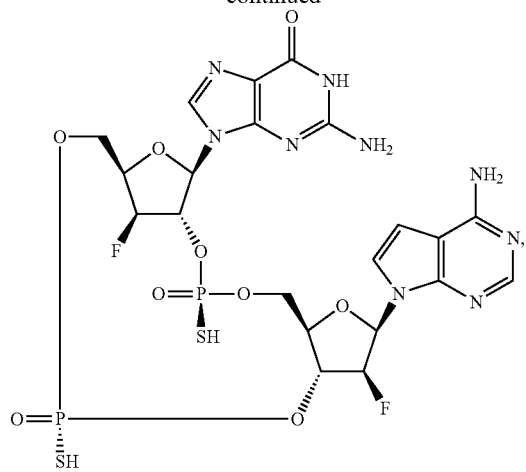
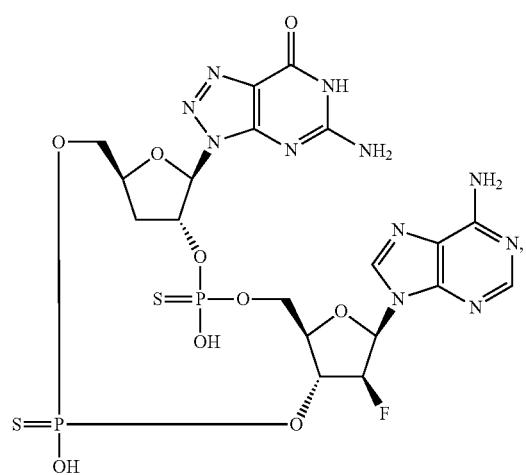

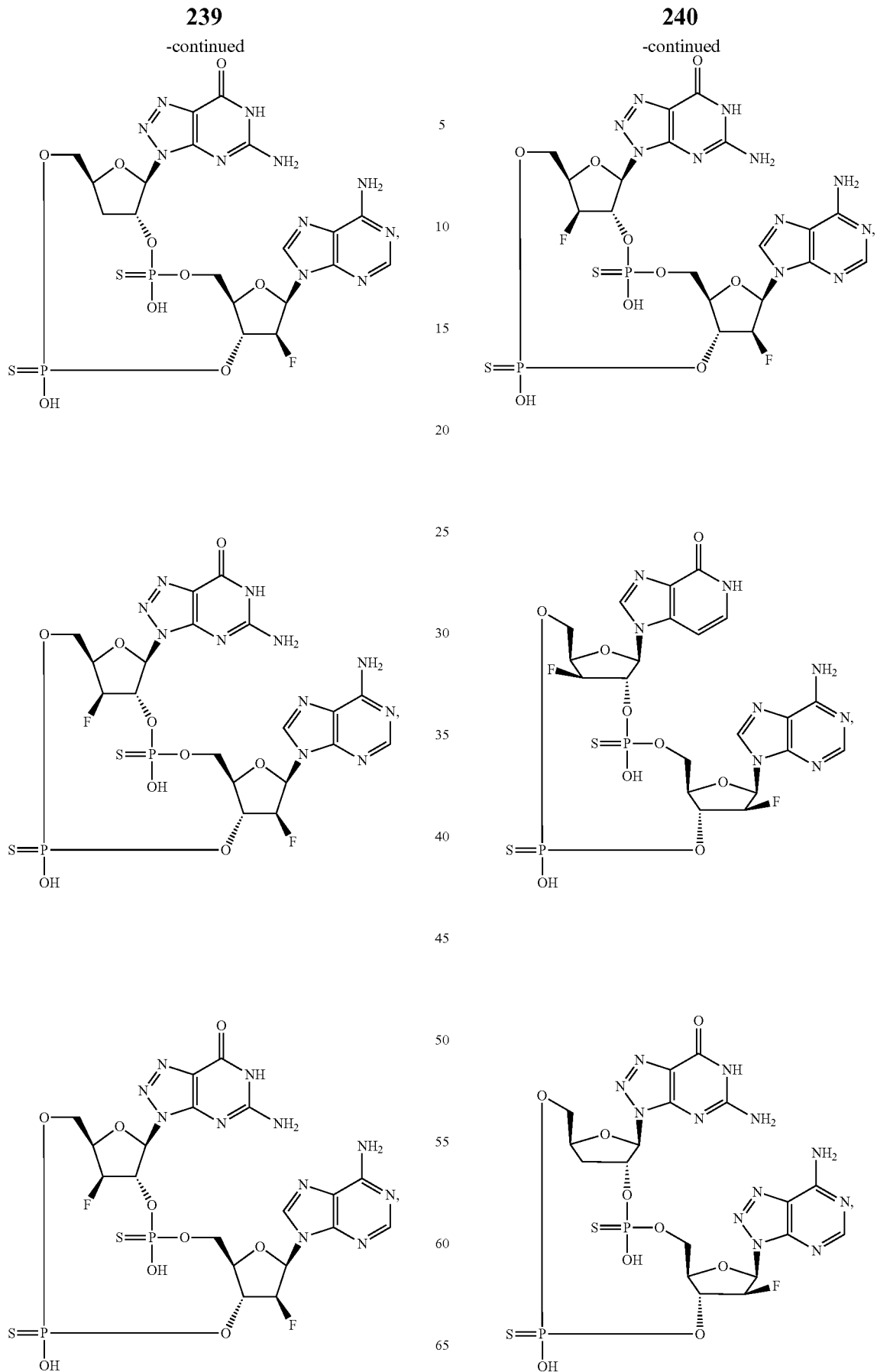

241
-continued
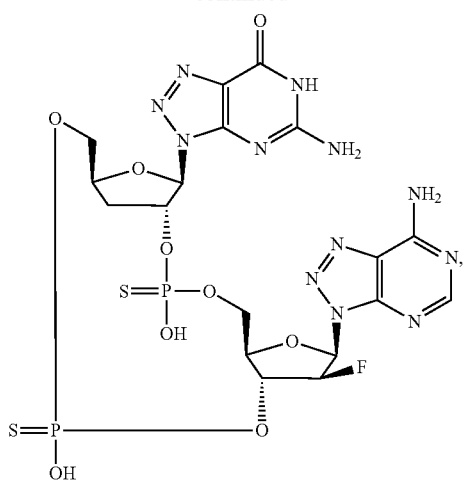
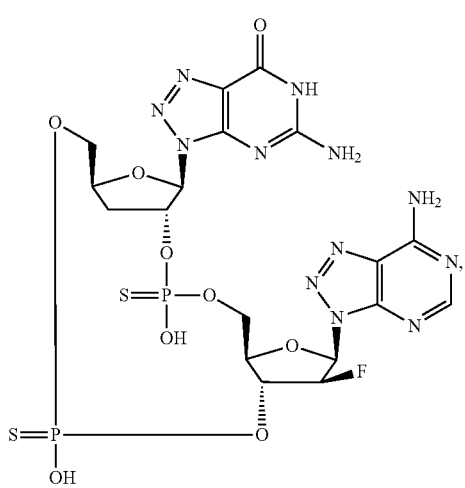
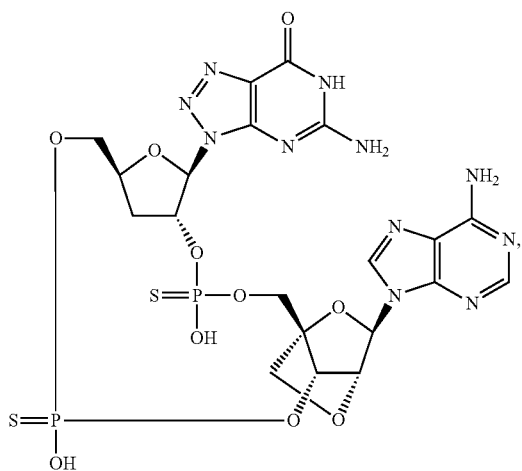
242
-continued
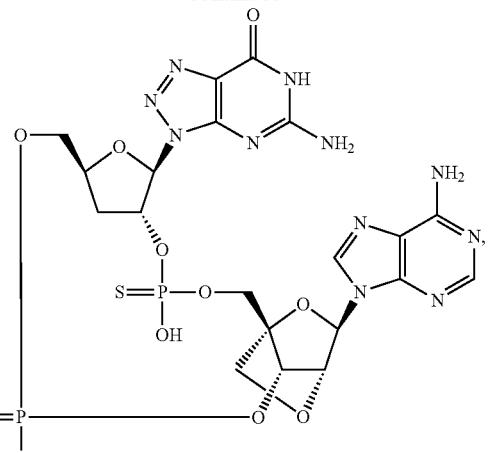
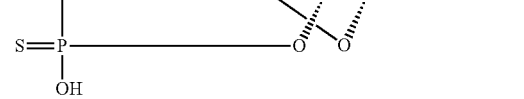
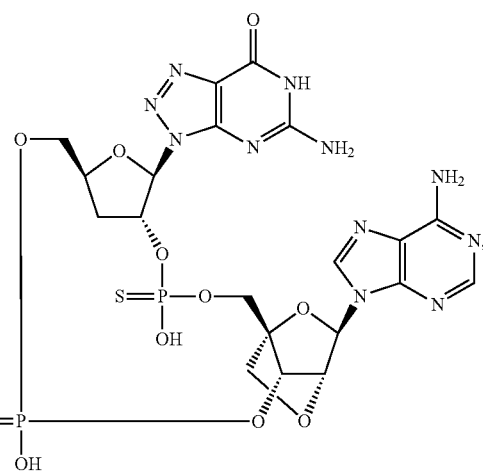

243
-continued
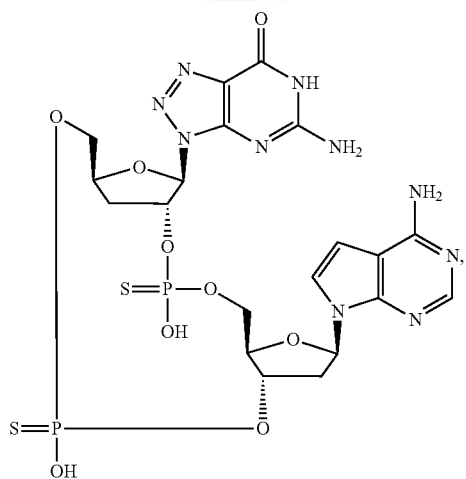
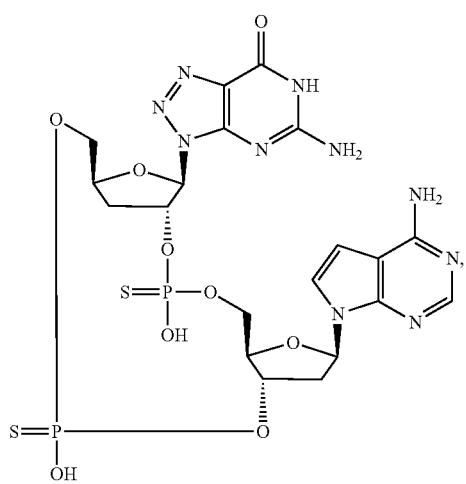
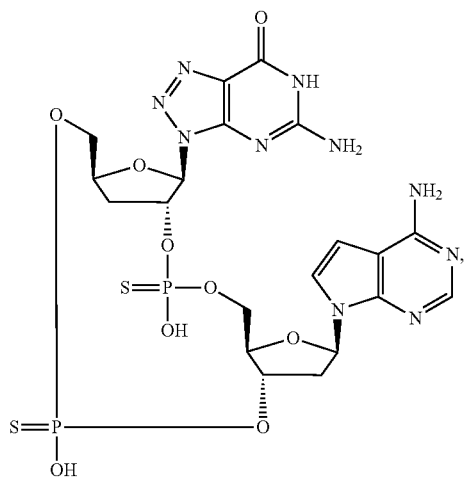
244
-continued
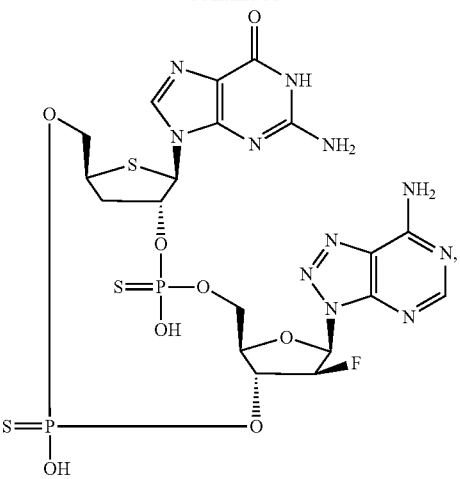
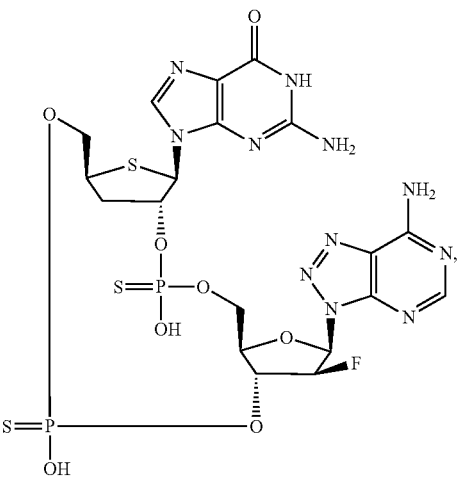
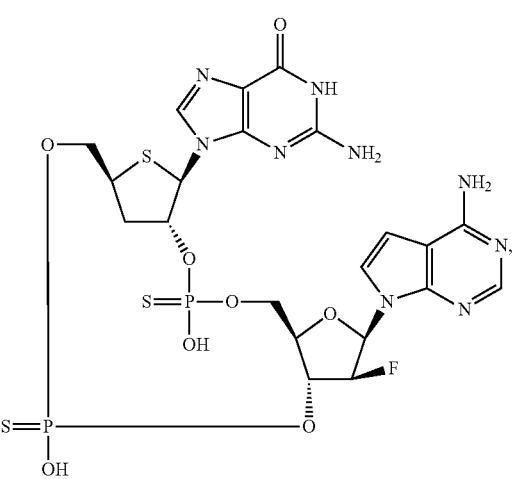

245
-continued
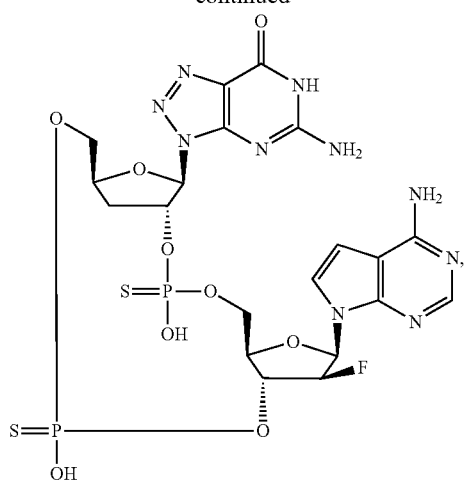
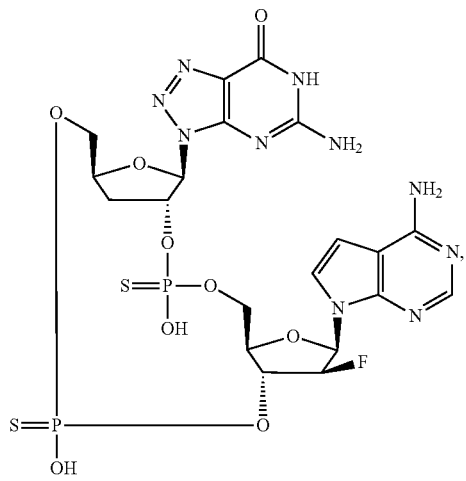
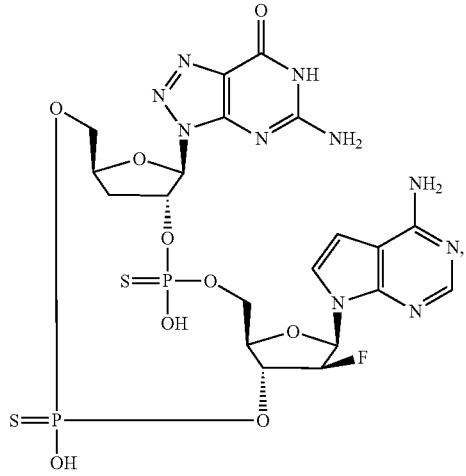
246
-continued
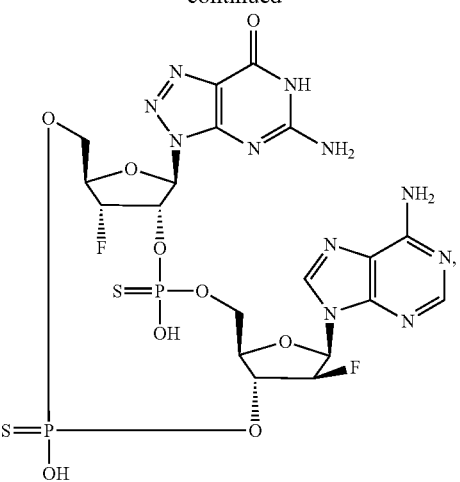
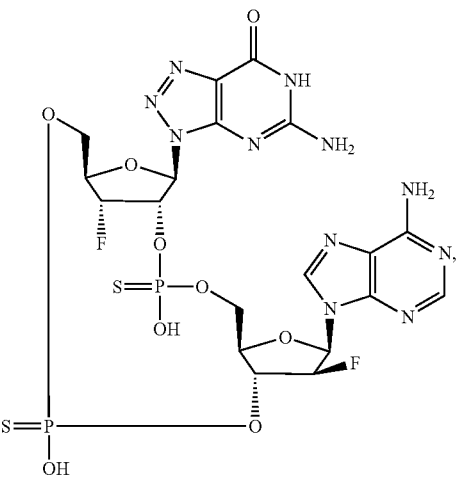
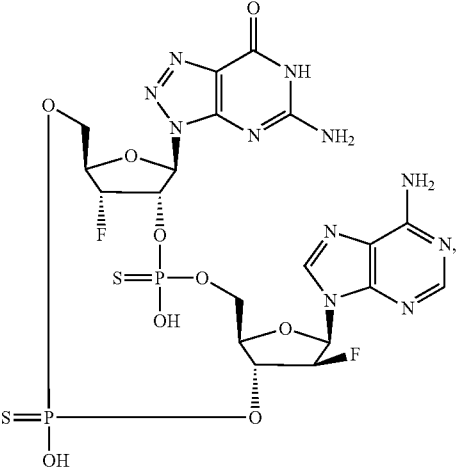

247
-continued
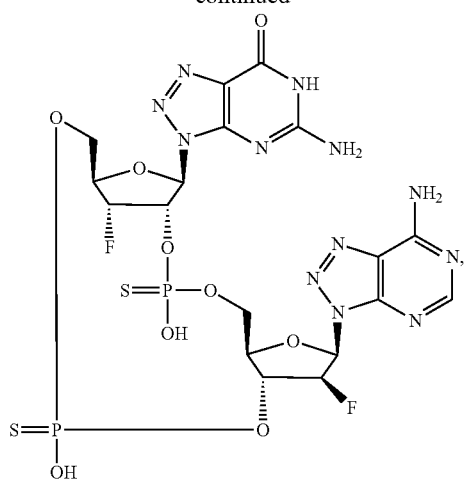
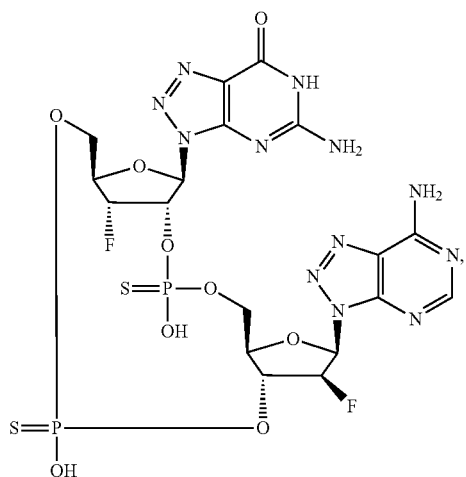
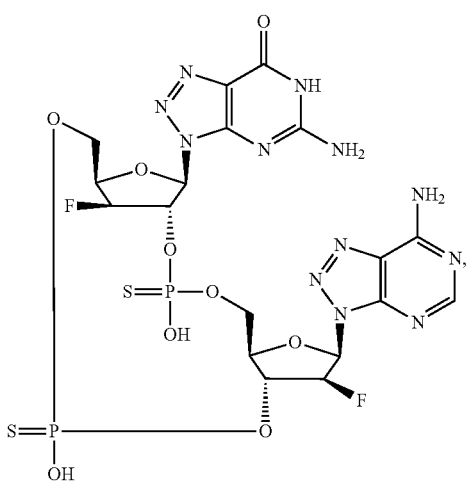
248
-continued
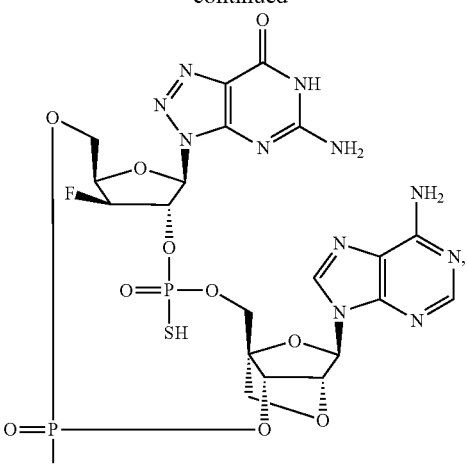
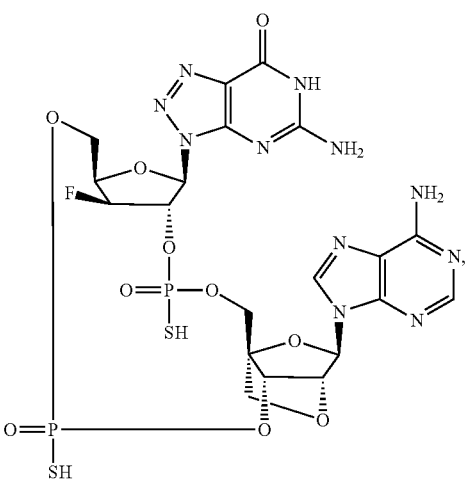
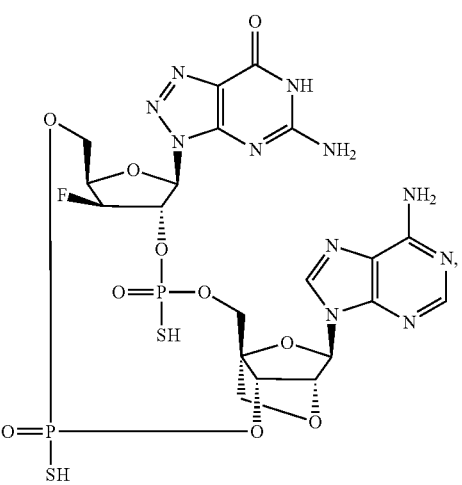

249
-continued
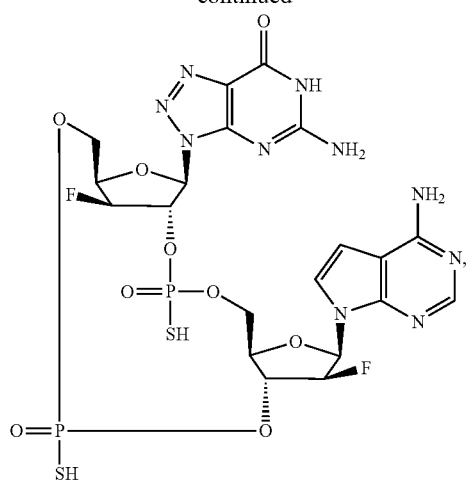
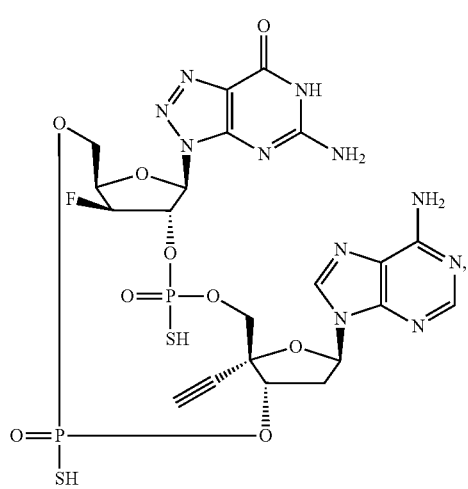
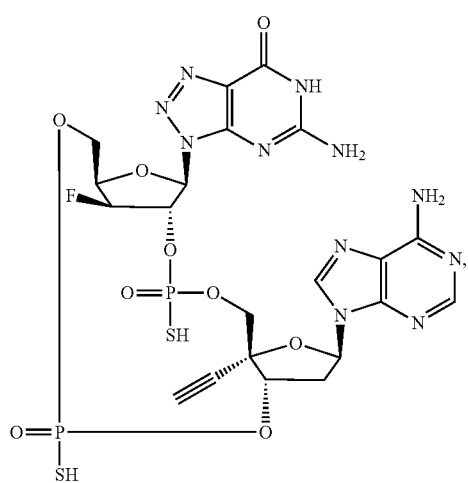
250
-continued
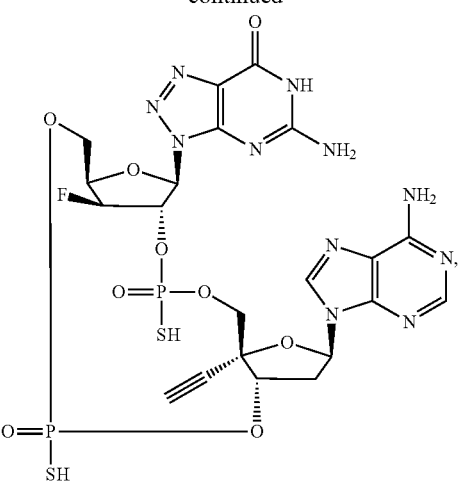
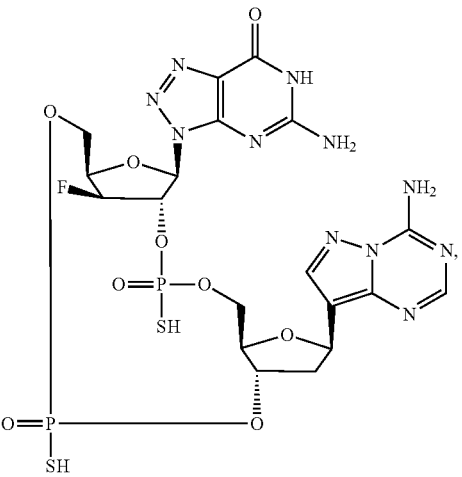
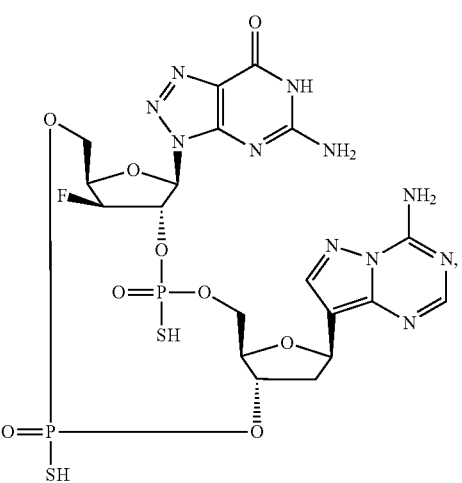

251
-continued
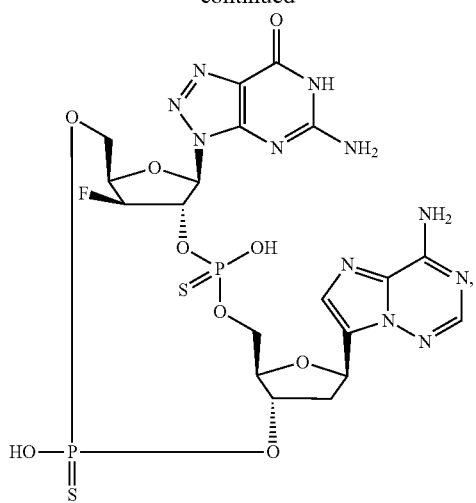
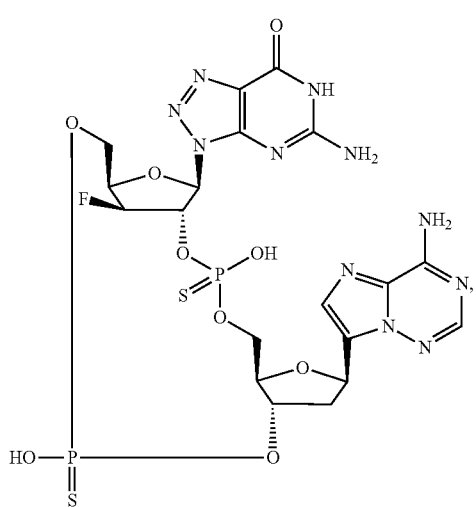
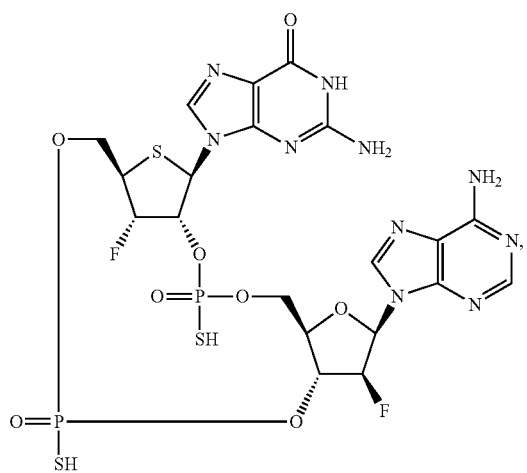
252
-continued
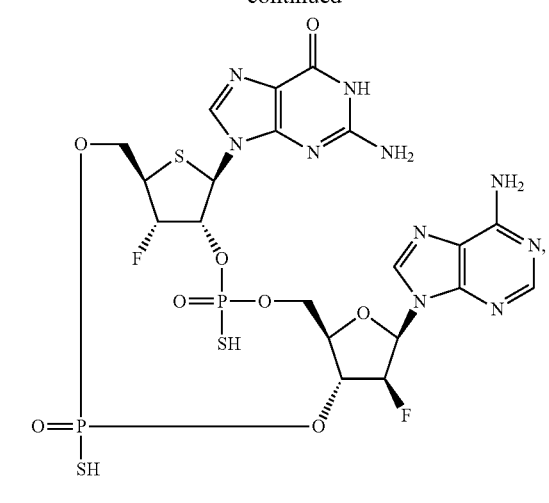
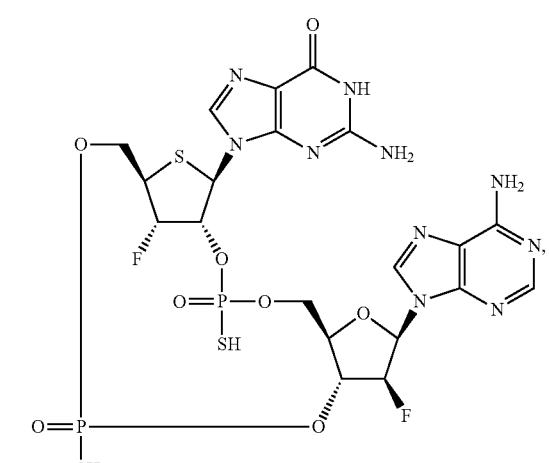
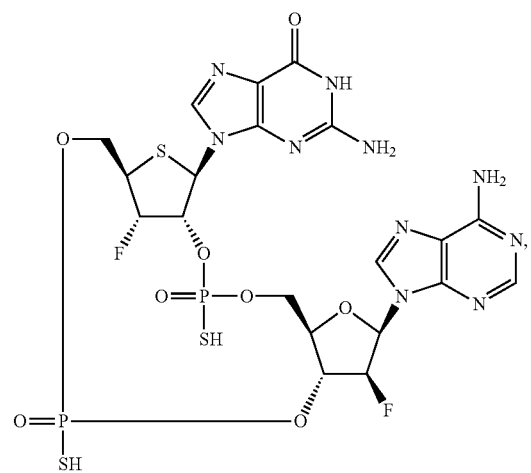

253
-continued
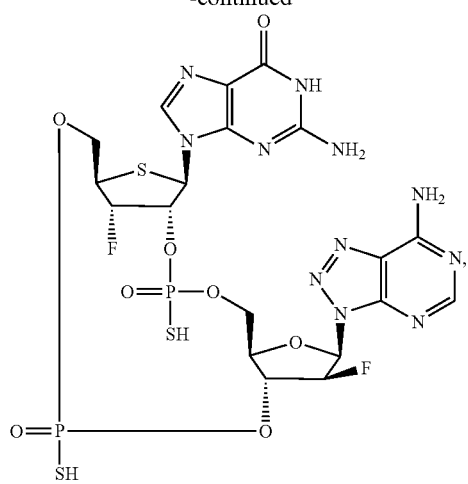
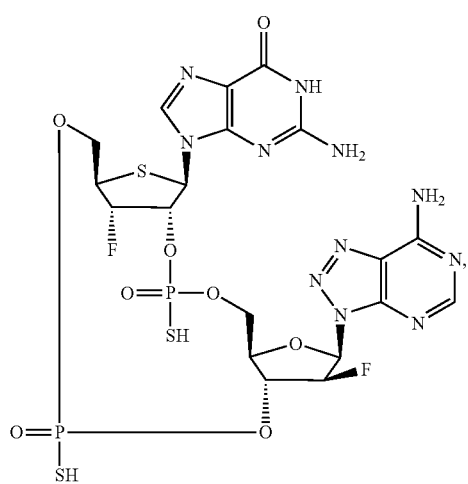
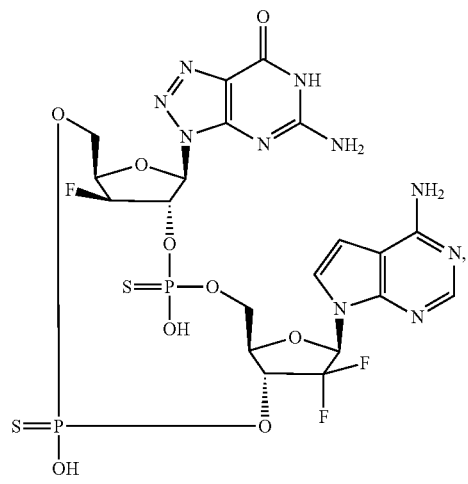
254
-continued
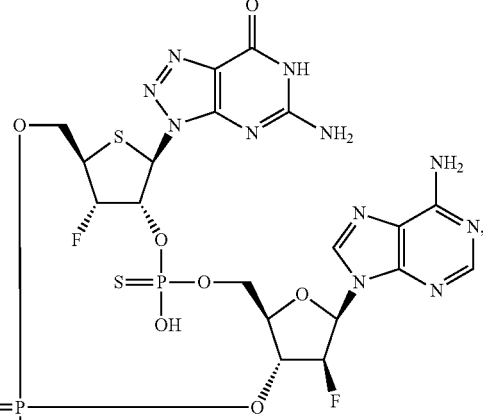
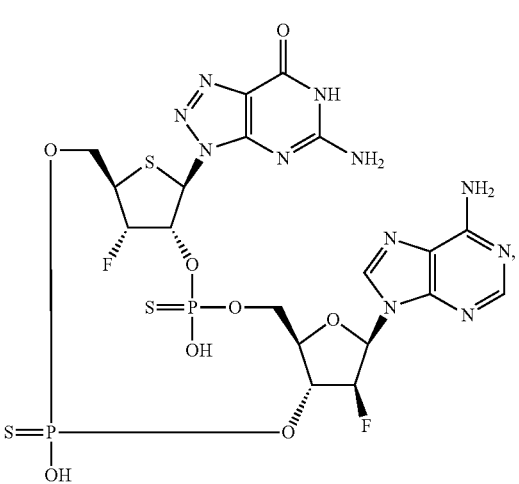
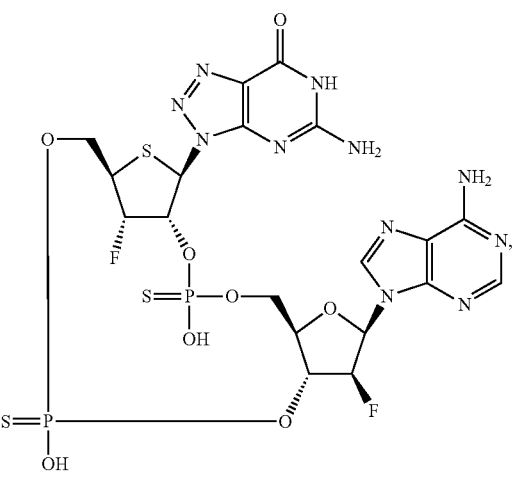

255
-continued
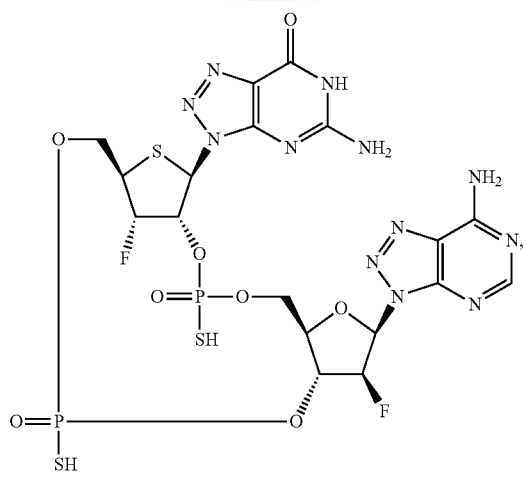
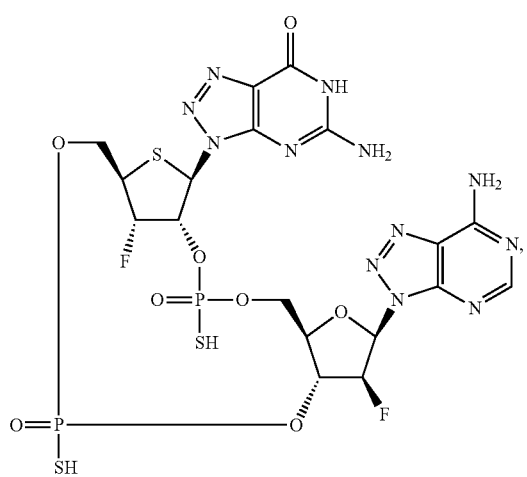
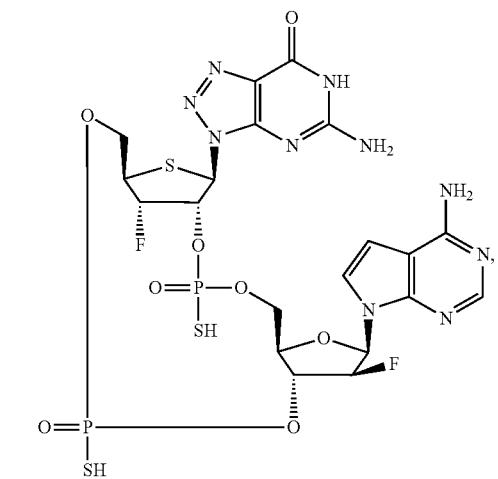
256
-continued
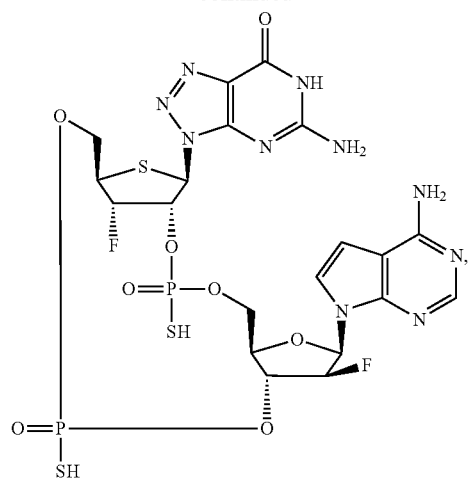
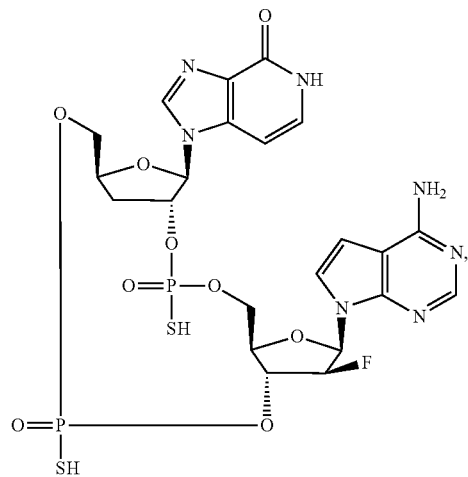
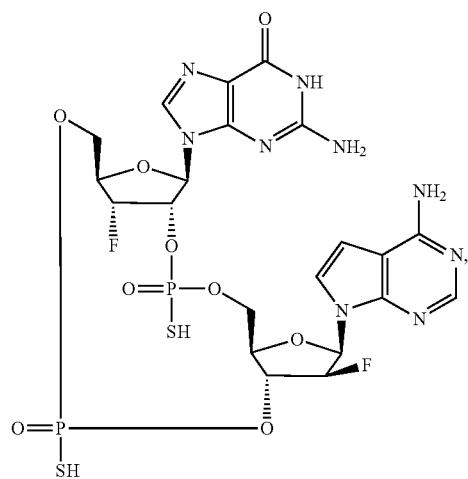

257
-continued
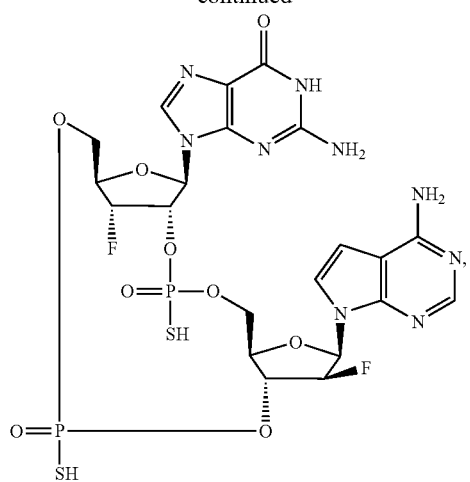
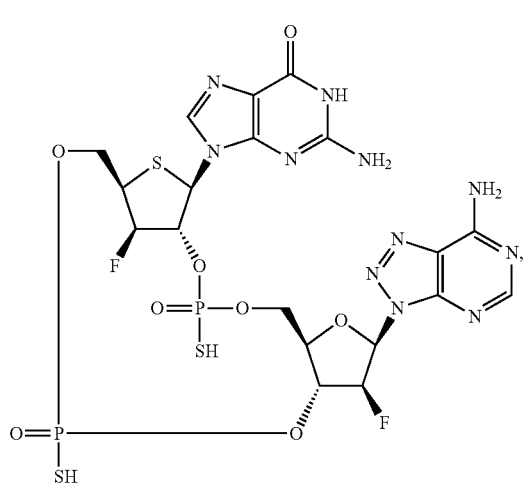
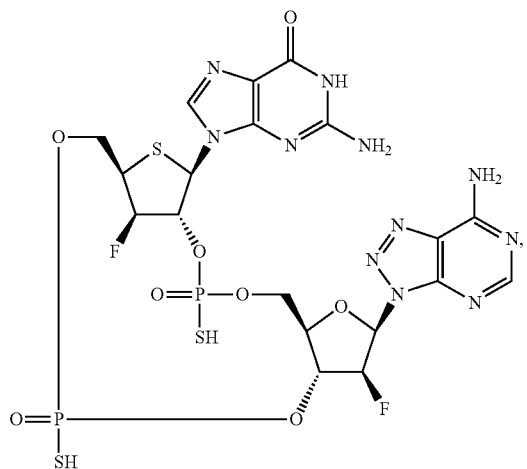
258
-continued
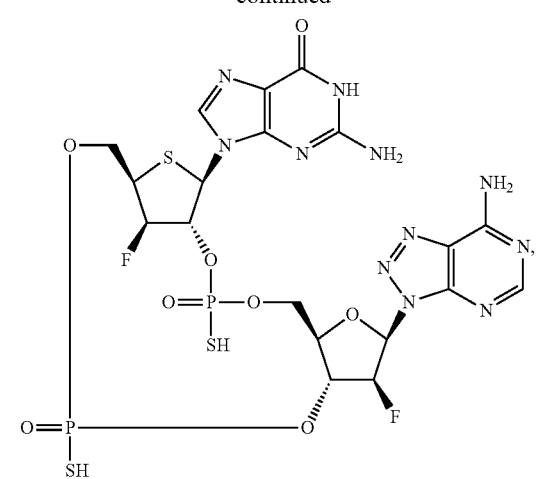
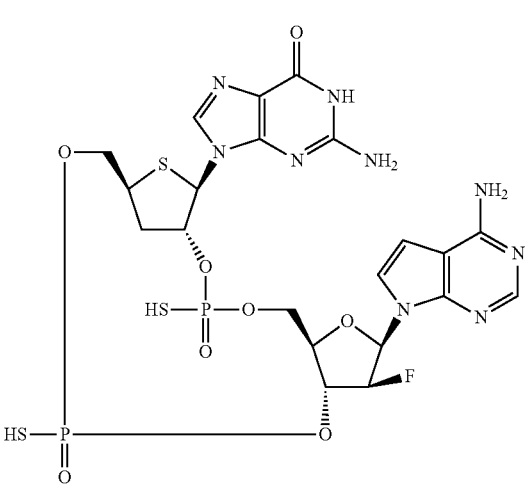
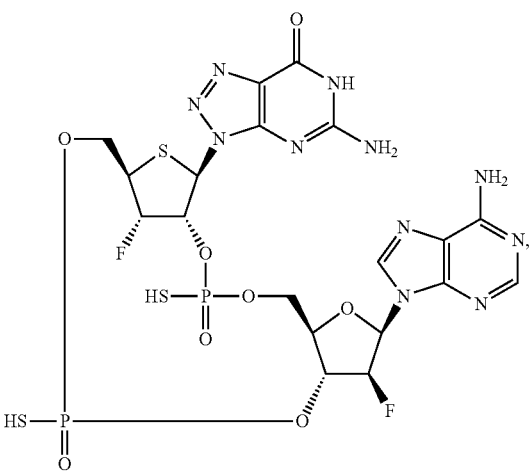

259
-continued
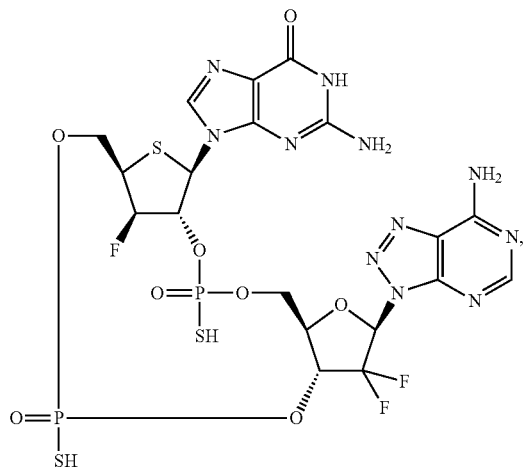
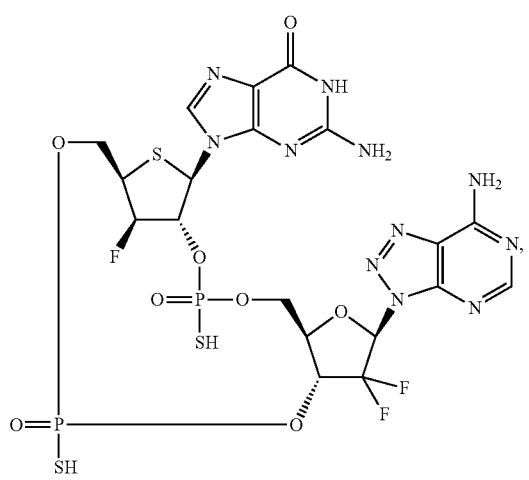
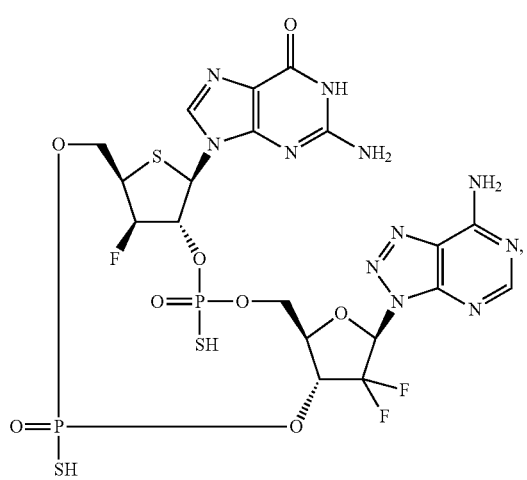
260
-continued
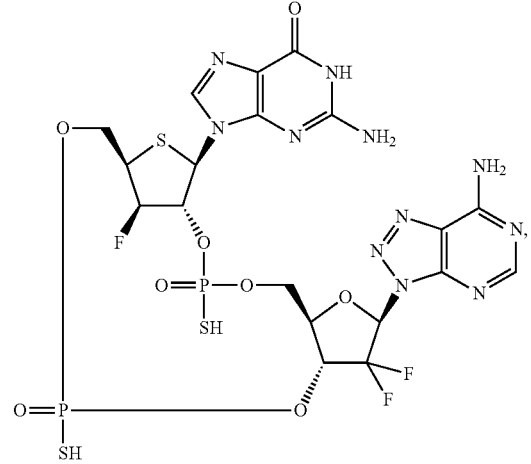
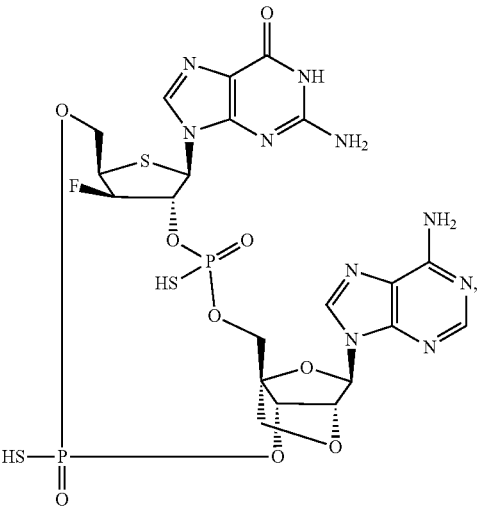
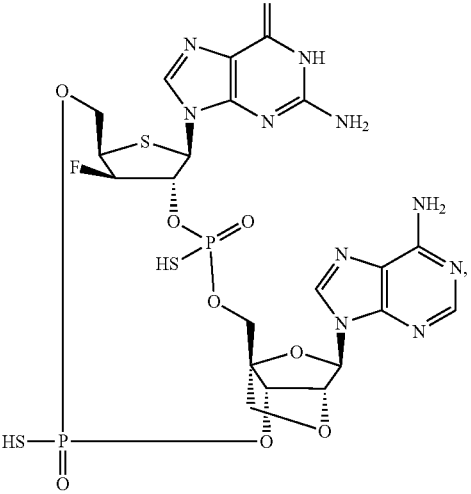

261
-continued
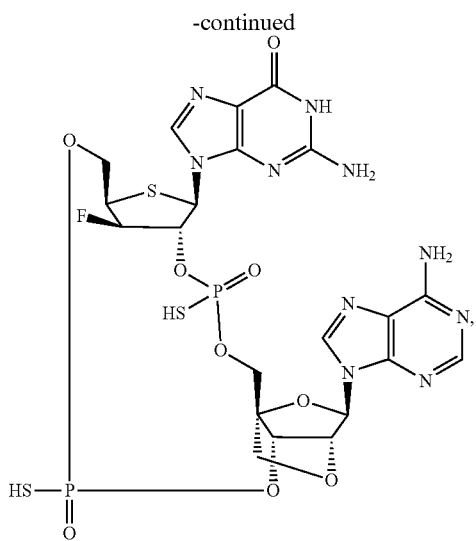
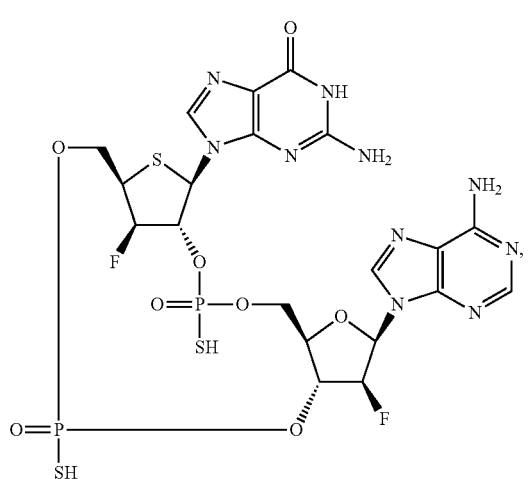
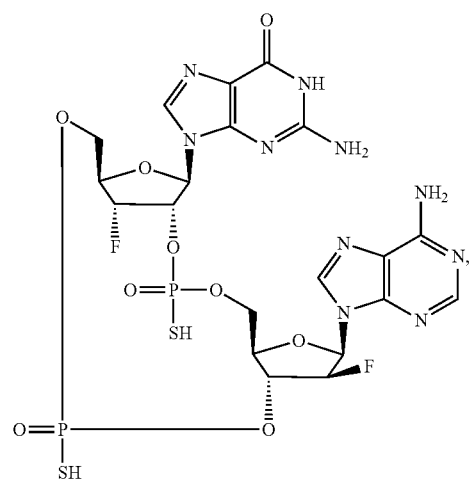
262
-continued
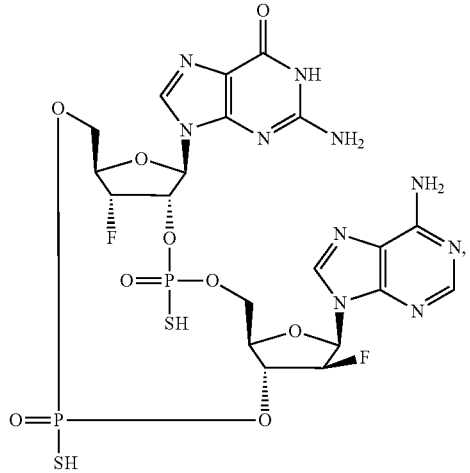
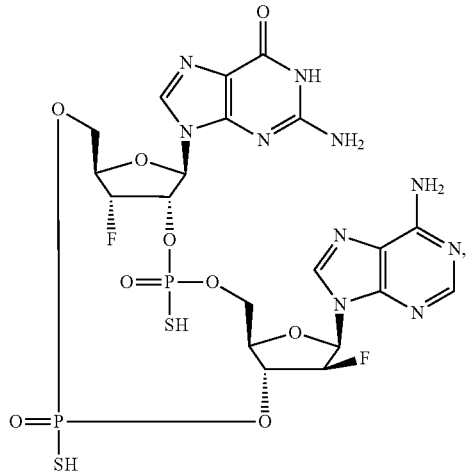
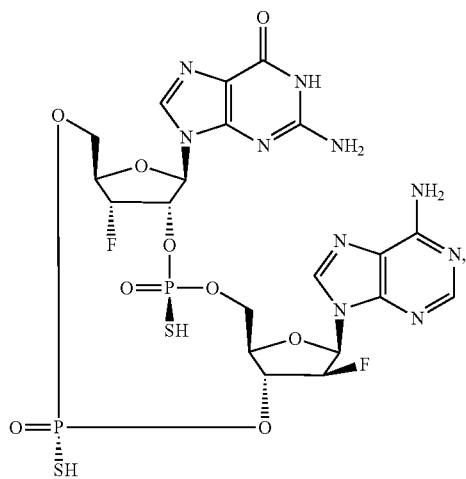

263
-continued
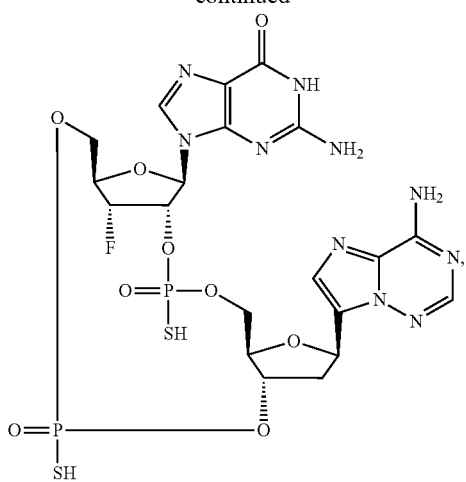
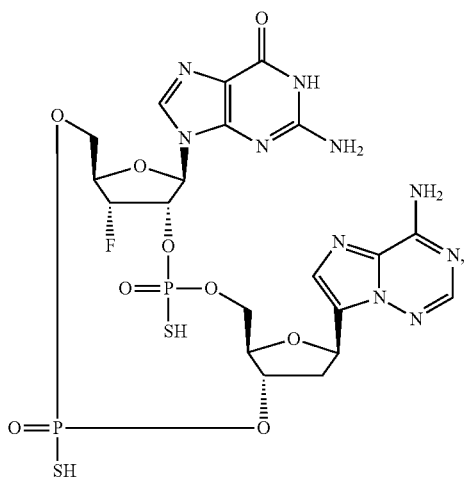
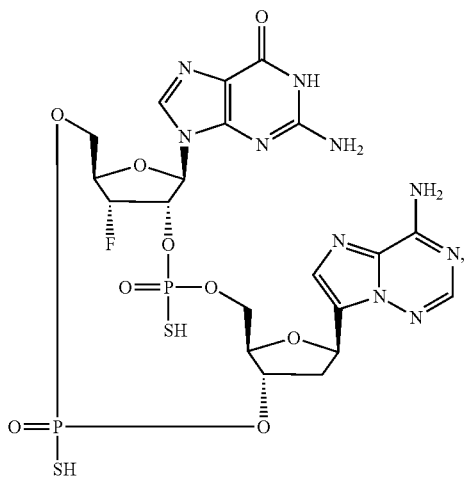
264
-continued
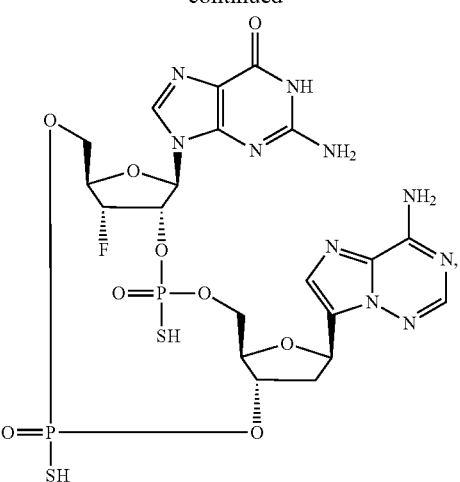
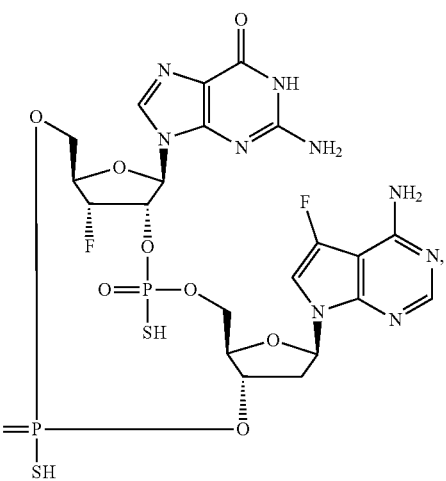
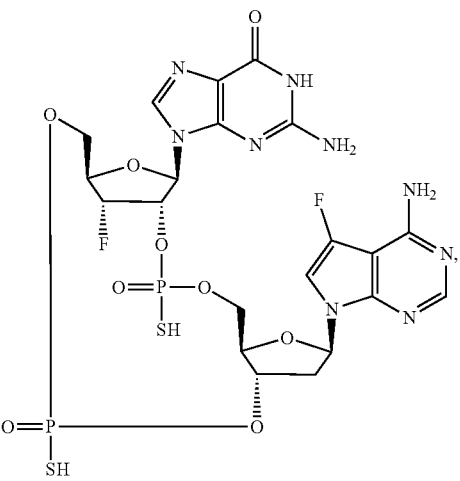

265
-continued
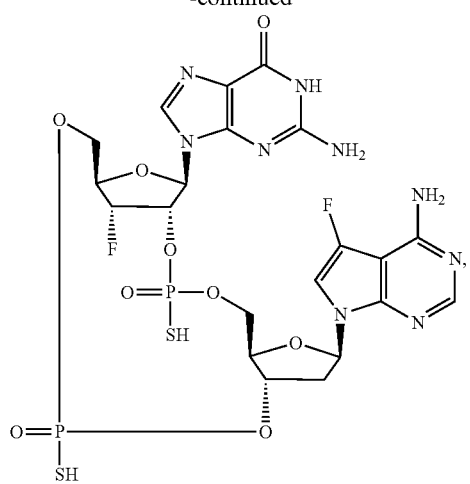
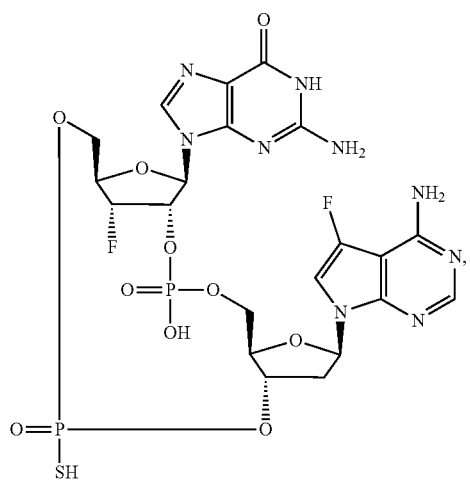
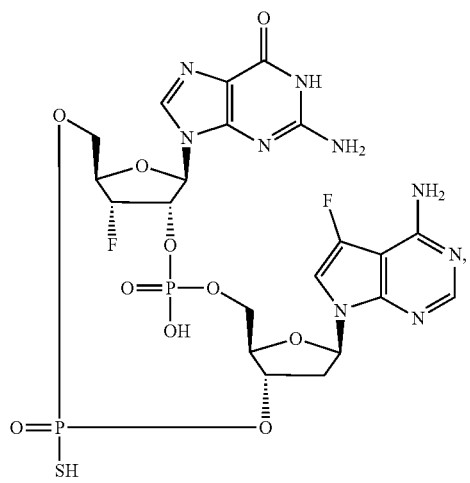
266
-continued
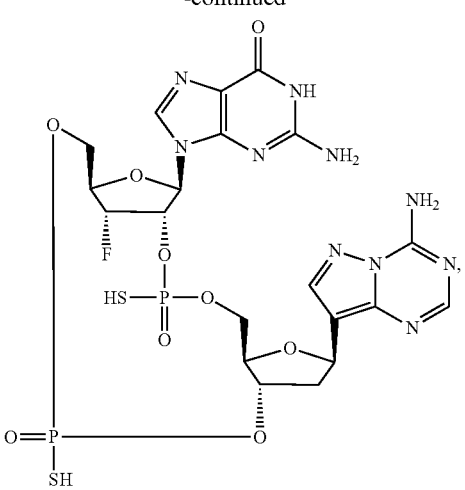
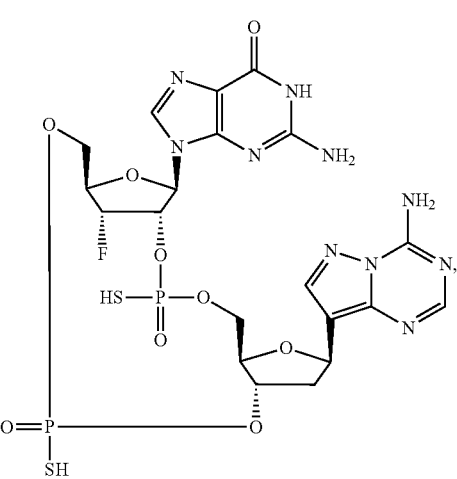
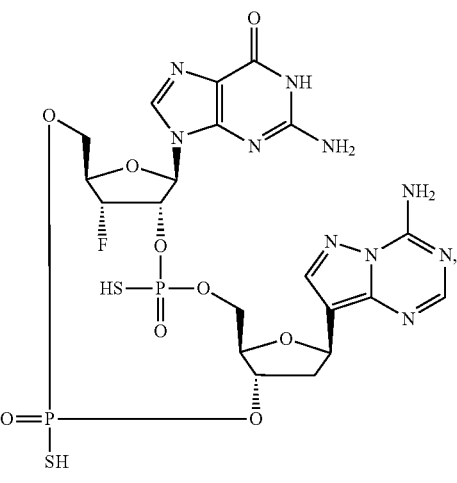

267
-continued
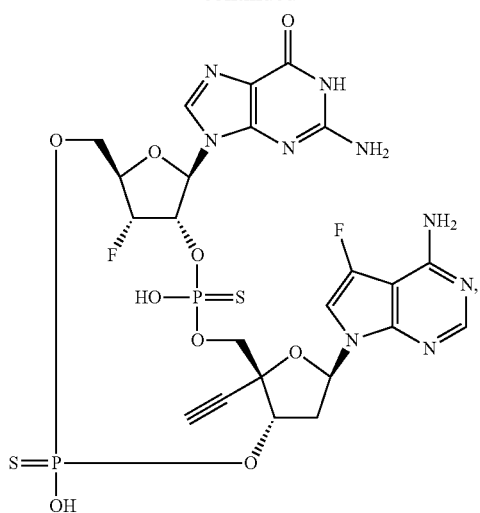
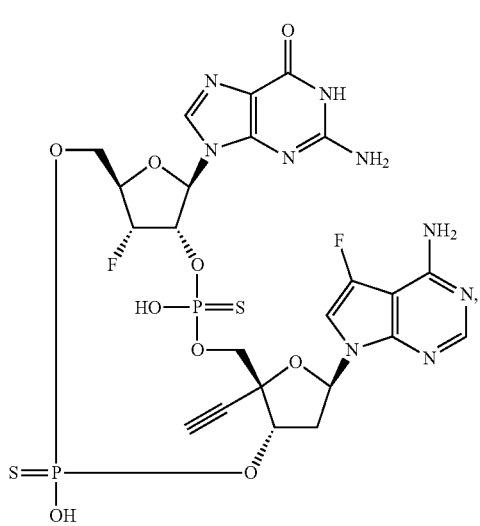
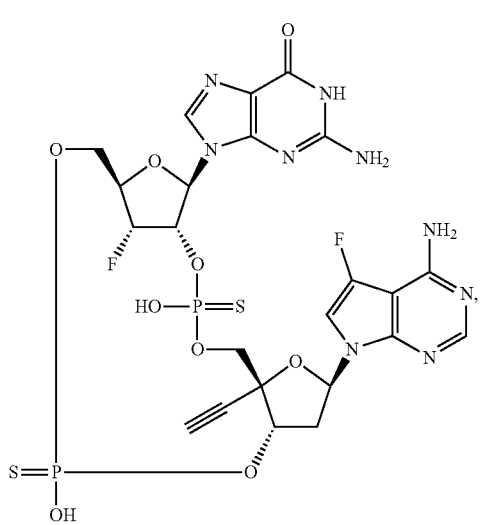
268
-continued
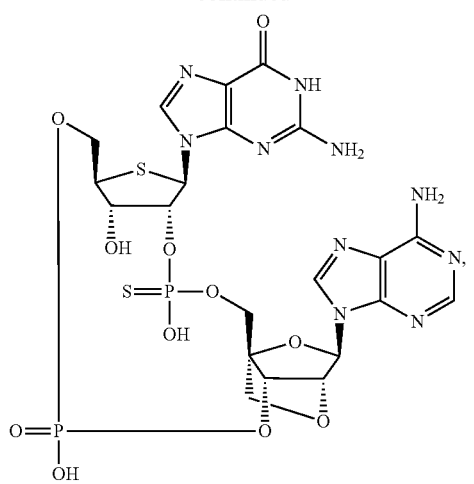
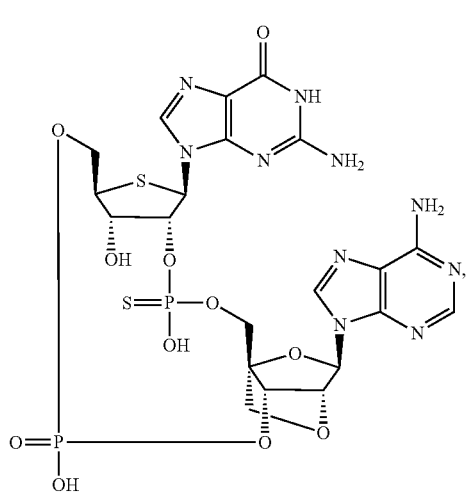

269
-continued
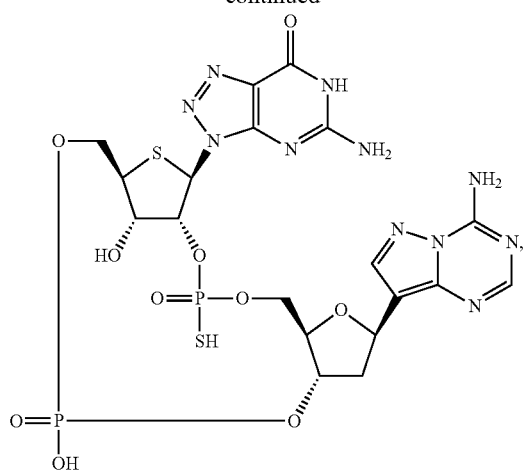
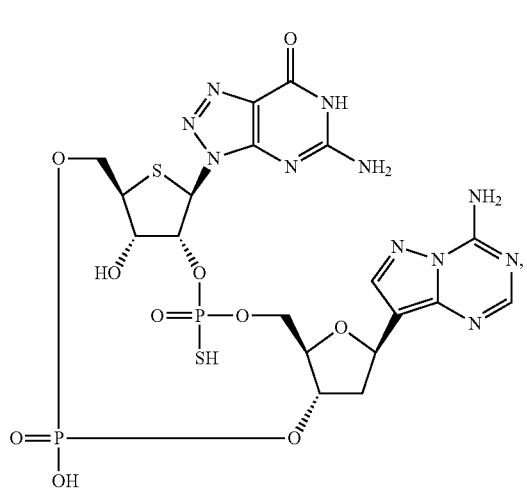
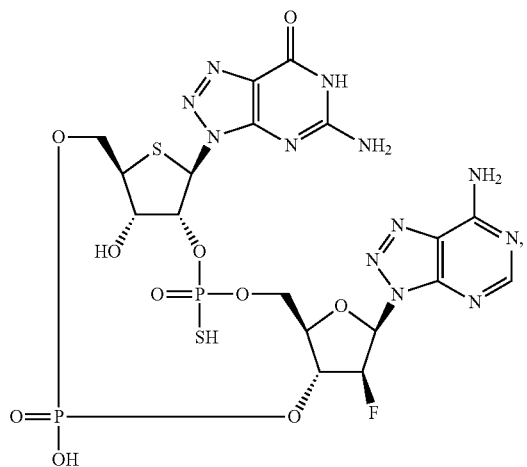
270
-continued
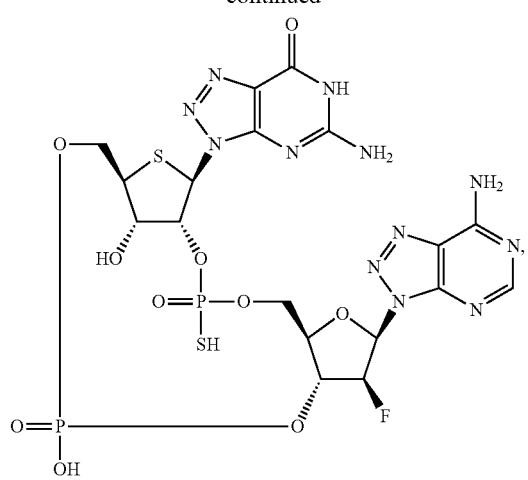
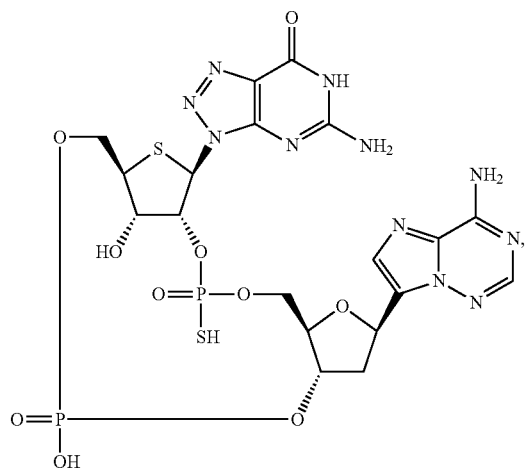
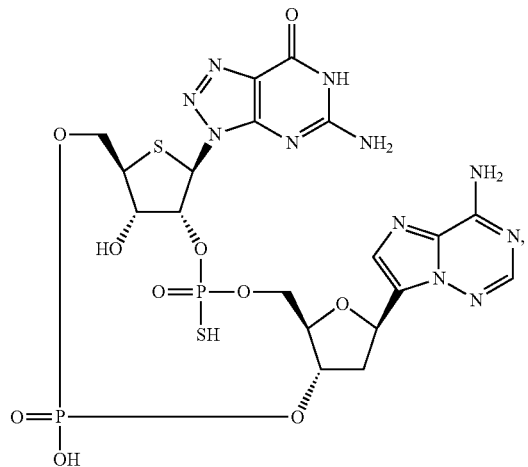

271
-continued
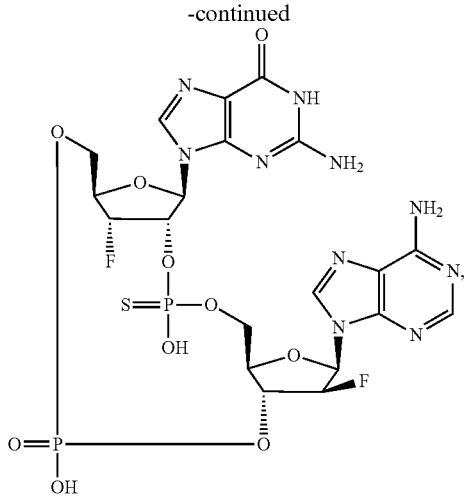
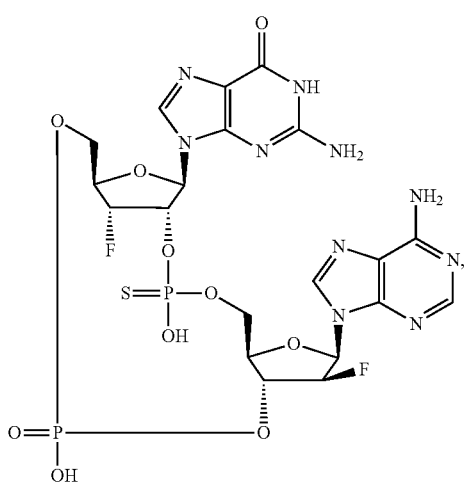
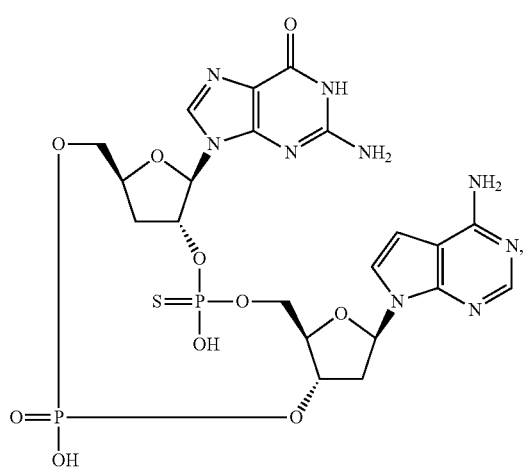
272
-continued
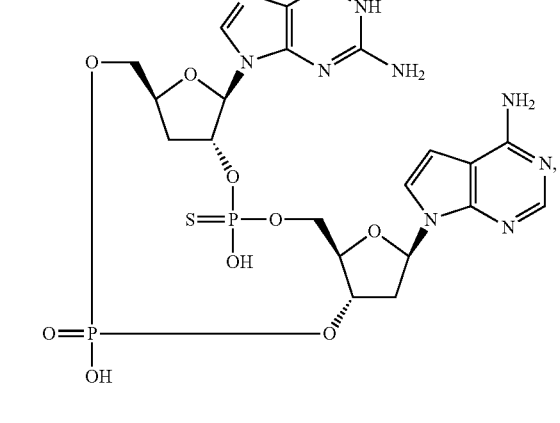
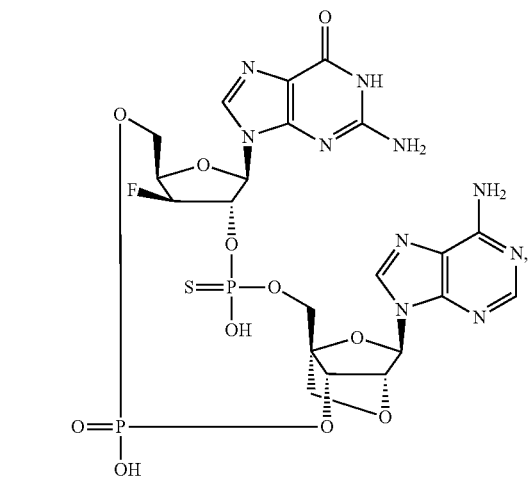
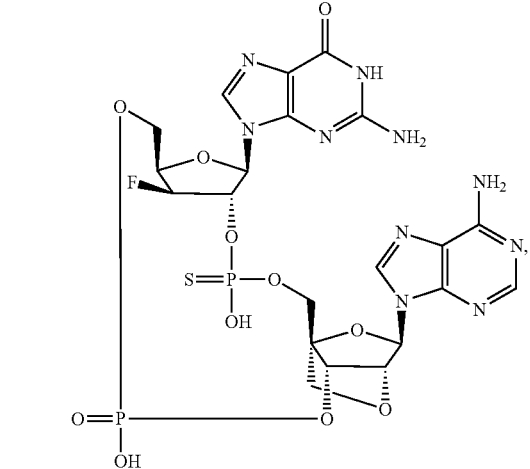

273
-continued
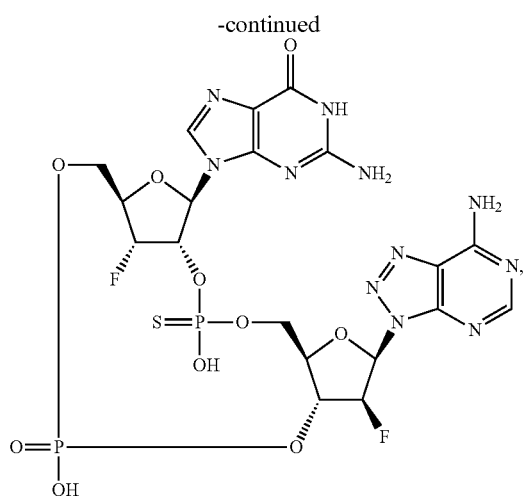
274
-continued
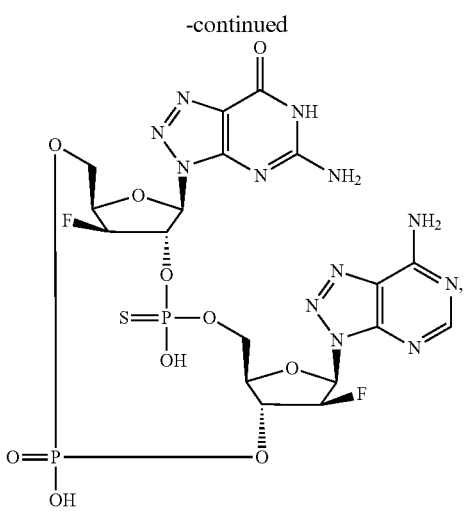
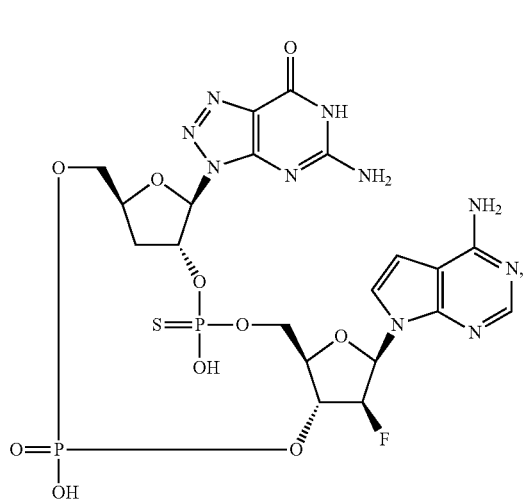

275
-continued
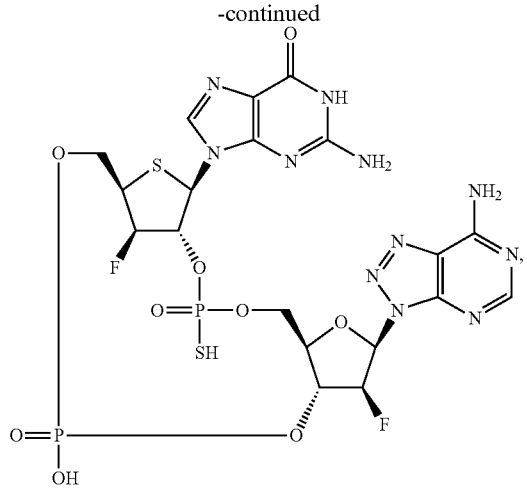
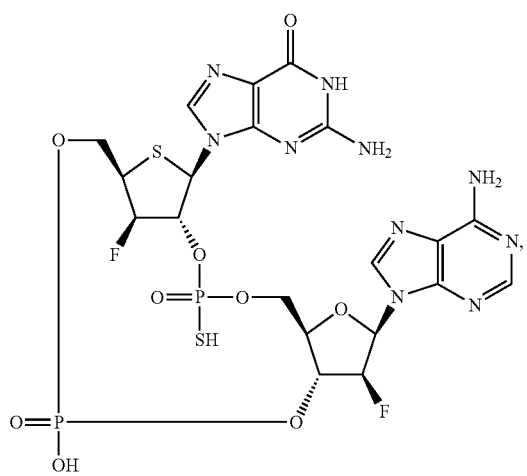
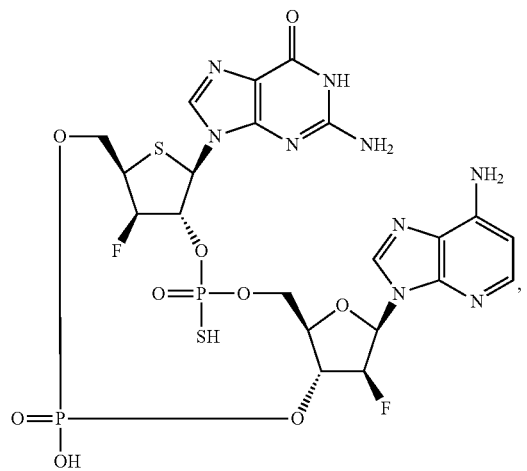
276
-continued
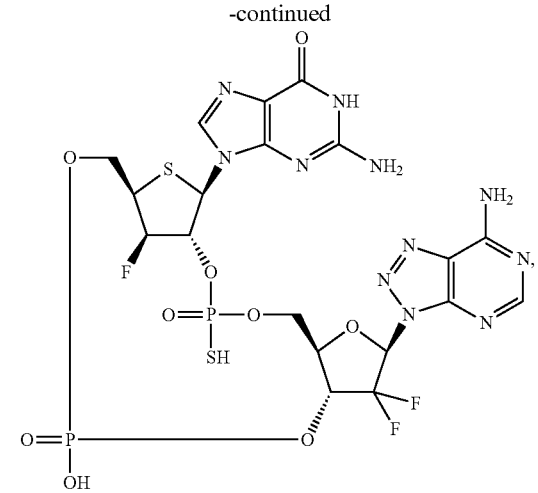
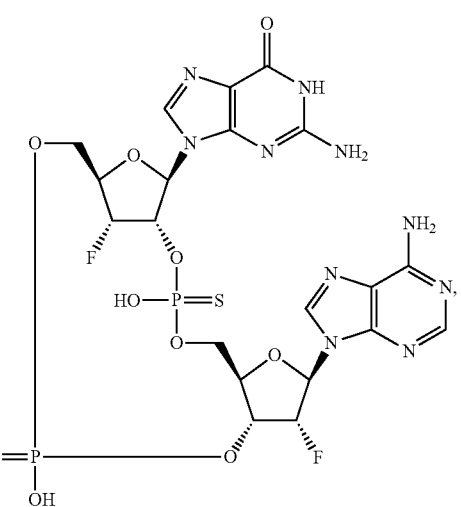
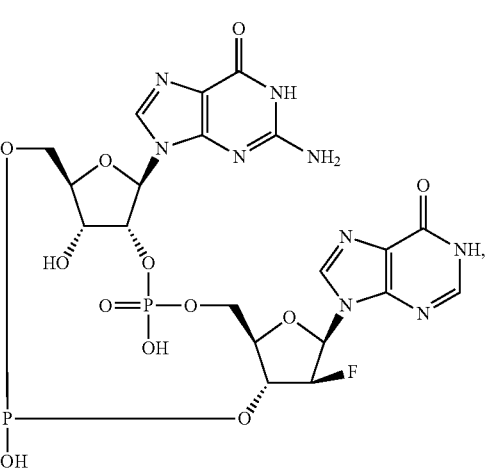

277
-continued
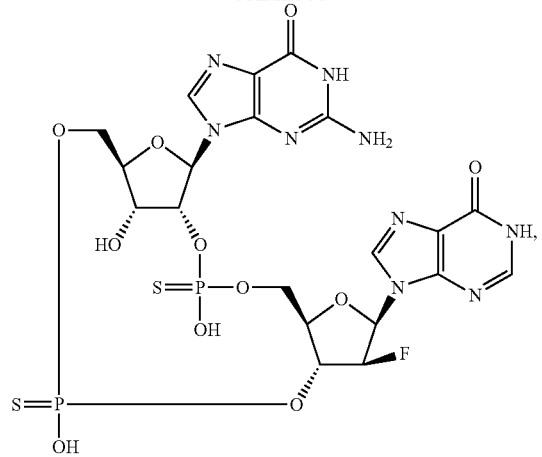
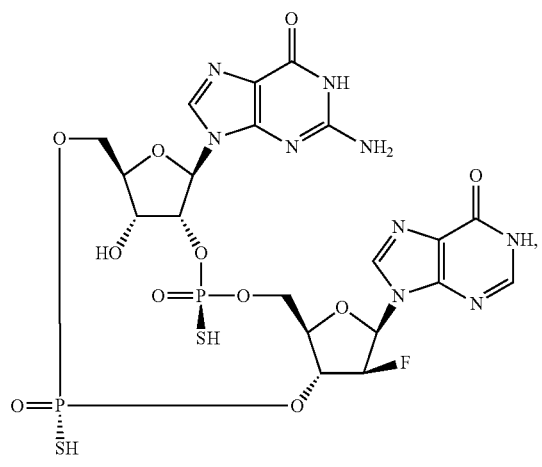
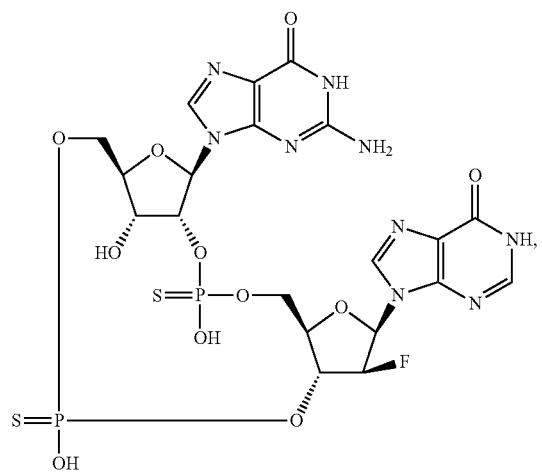
278
-continued
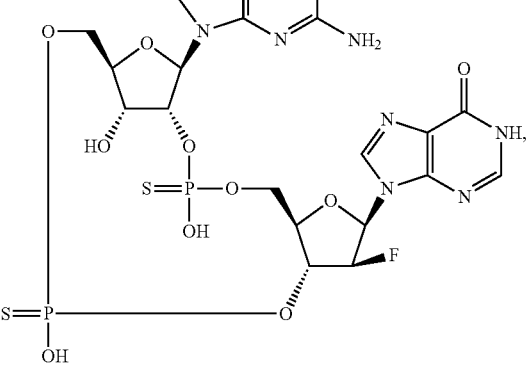
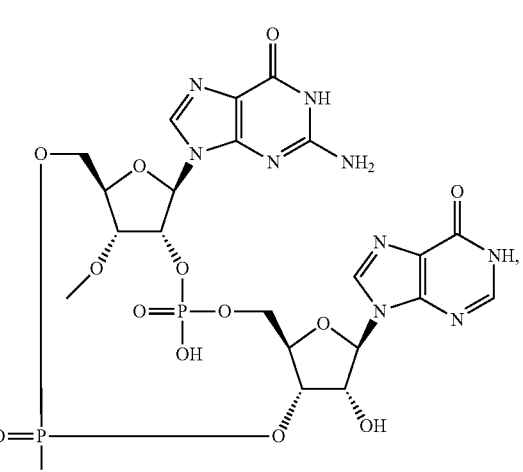
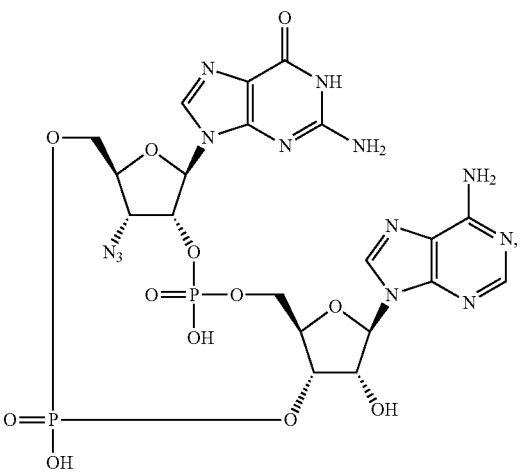

279
-continued
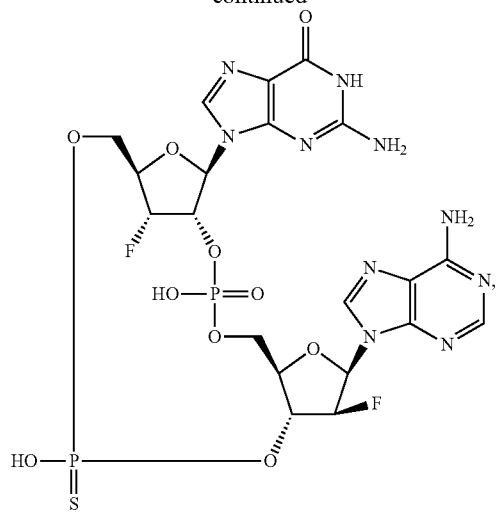
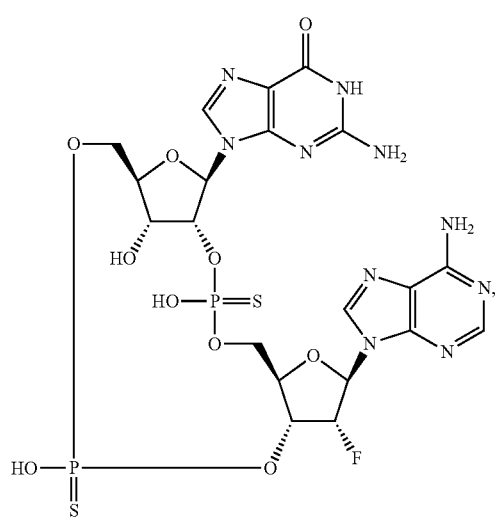
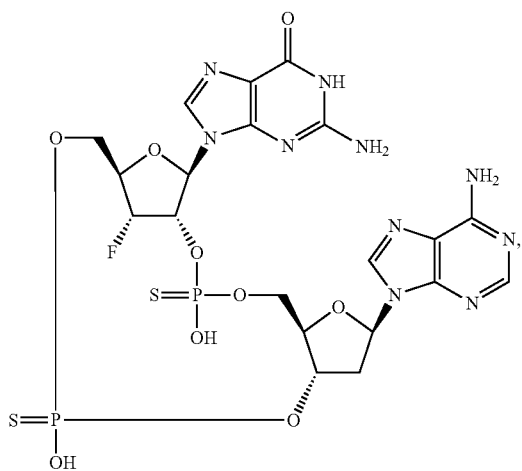
280
-continued
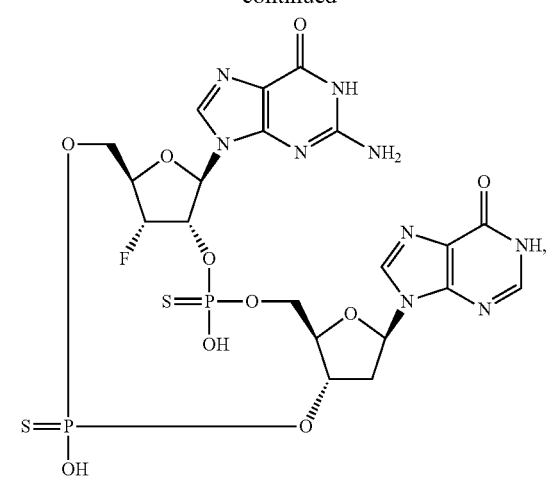
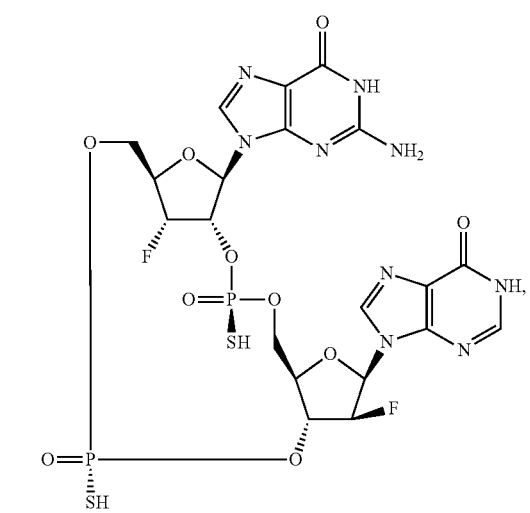
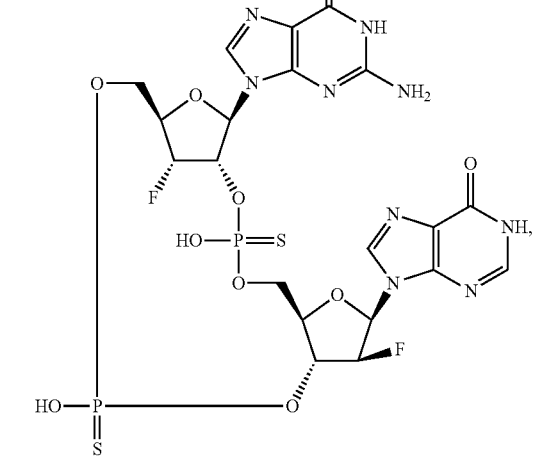

281
-continued
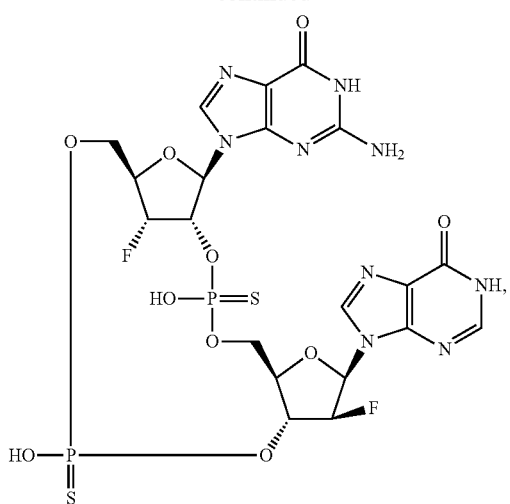
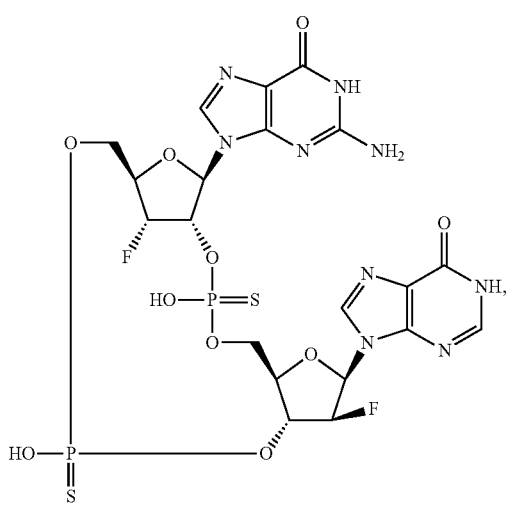
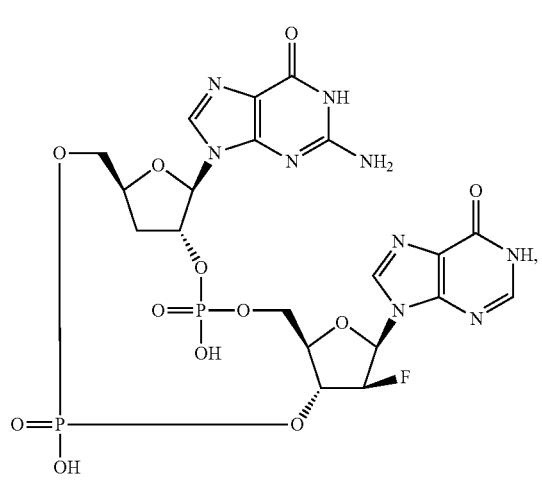
282
-continued
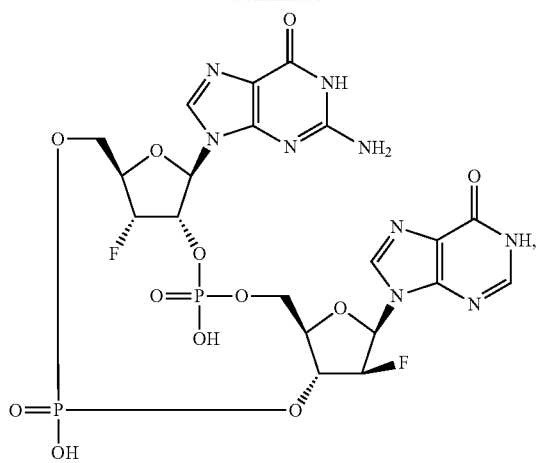
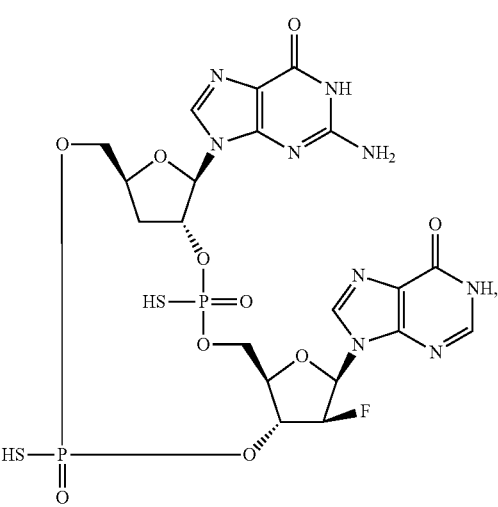

283
-continued
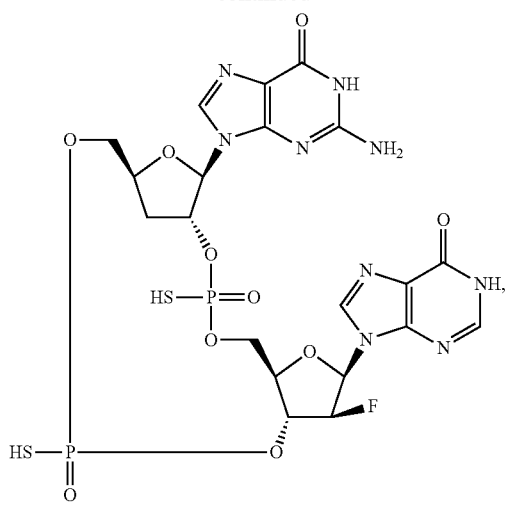
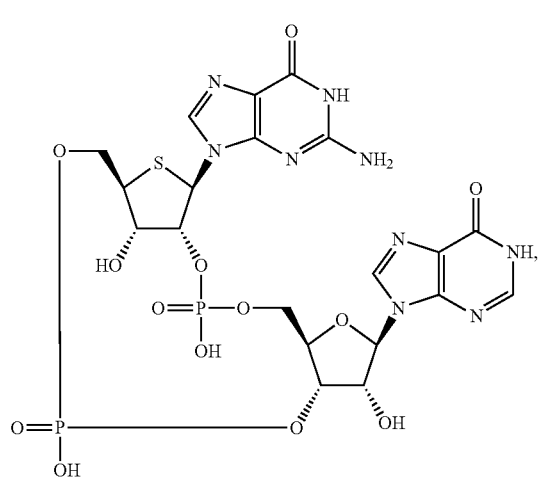
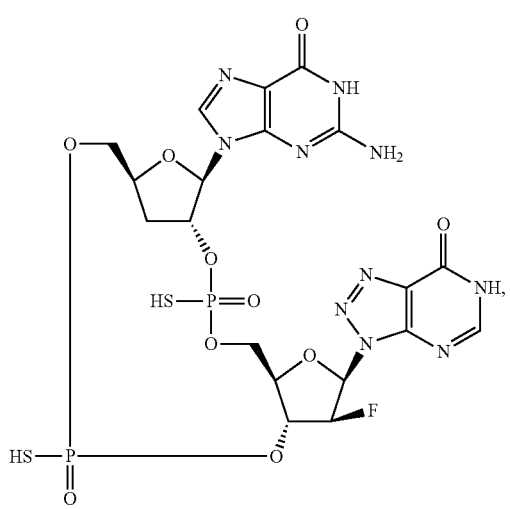
284
-continued
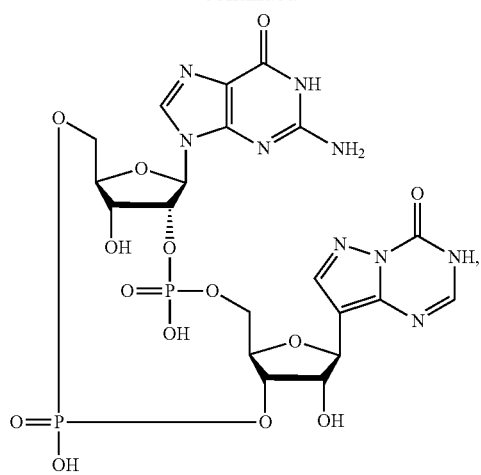
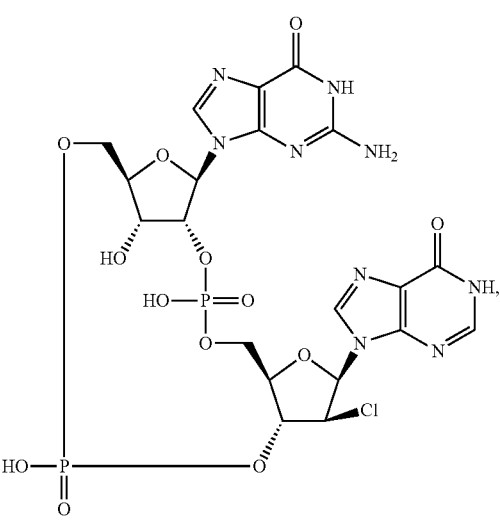
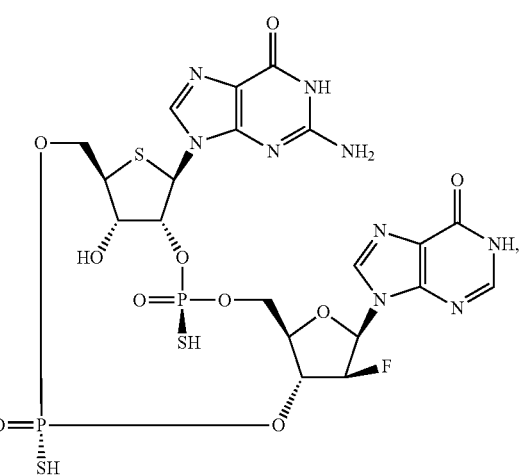

285
-continued
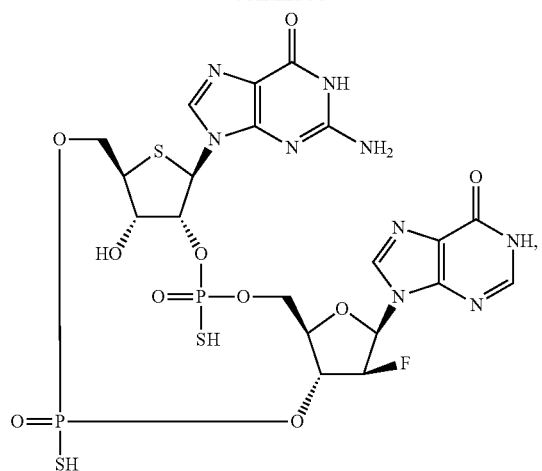
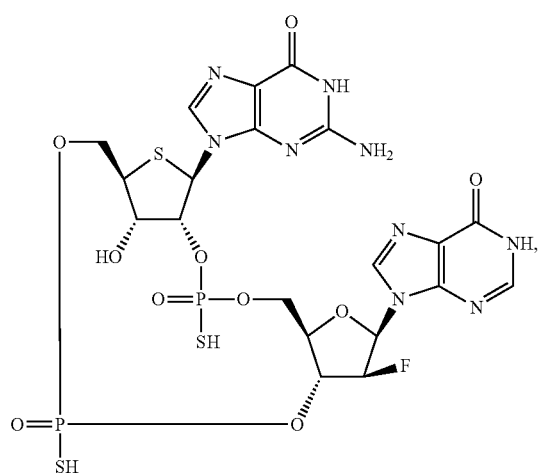
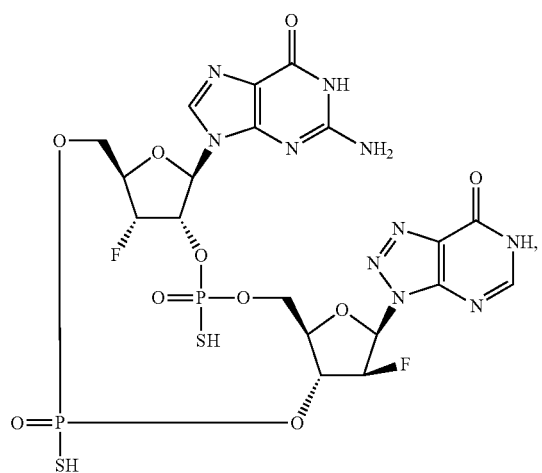
286
-continued
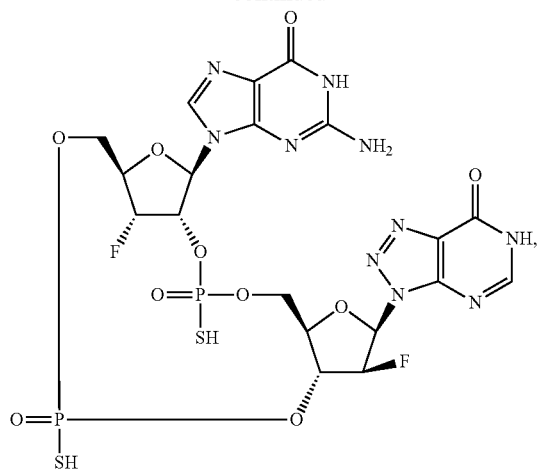
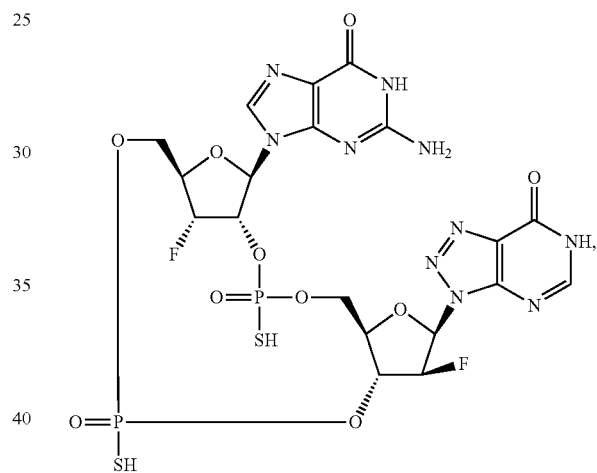
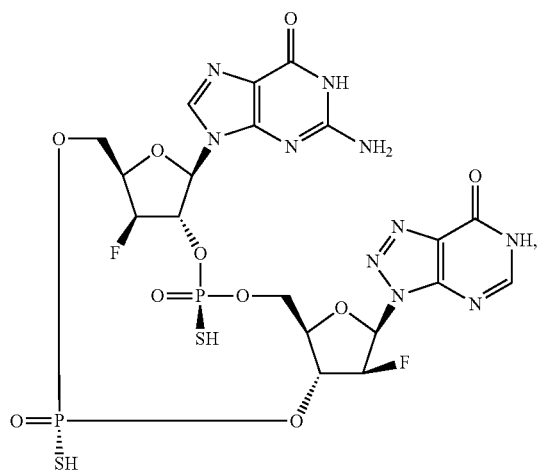

287
-continued
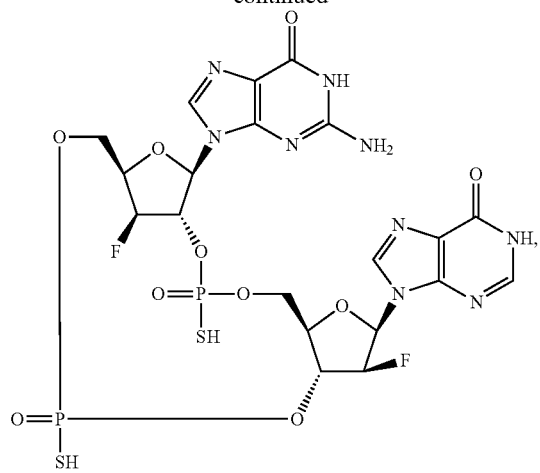
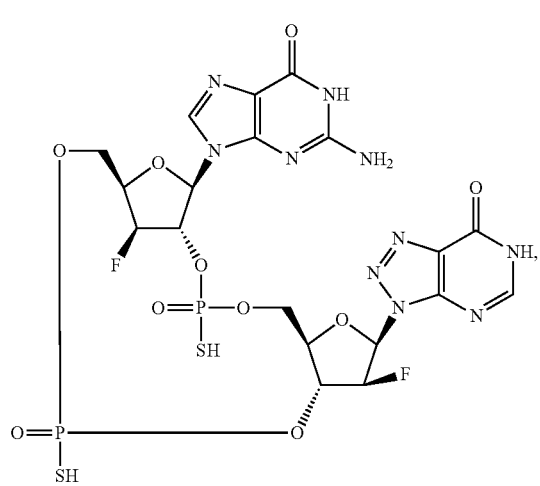
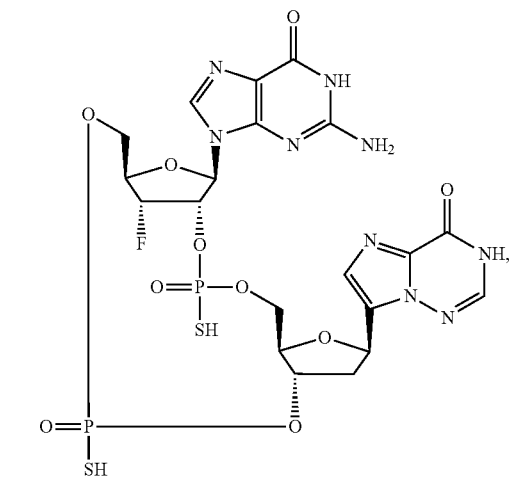
288
-continued
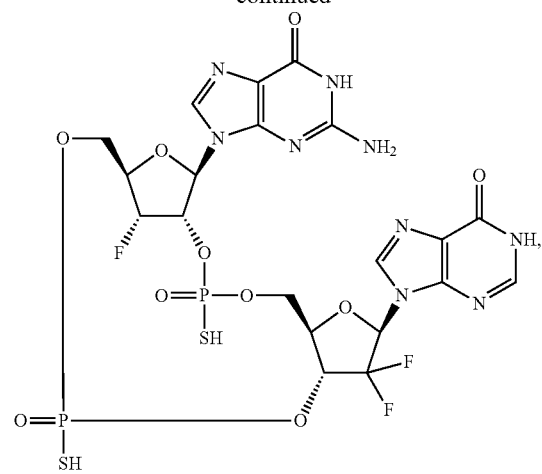
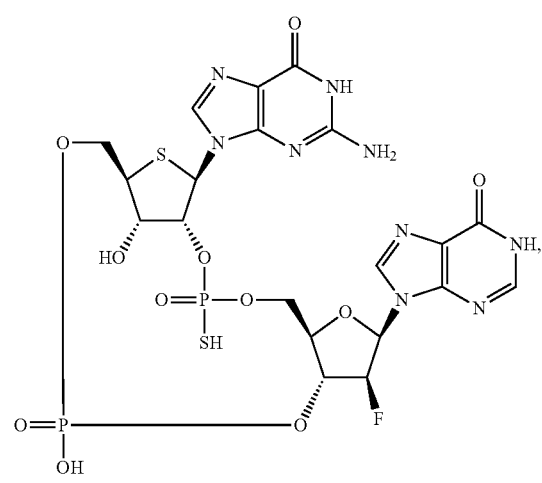

289
-continued
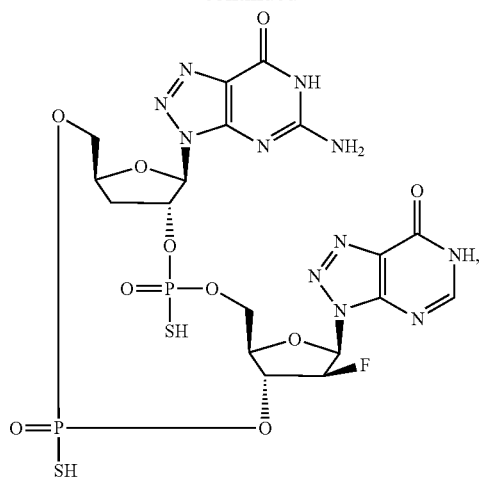
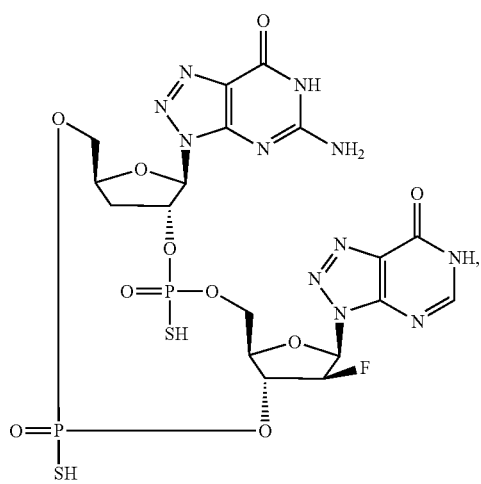
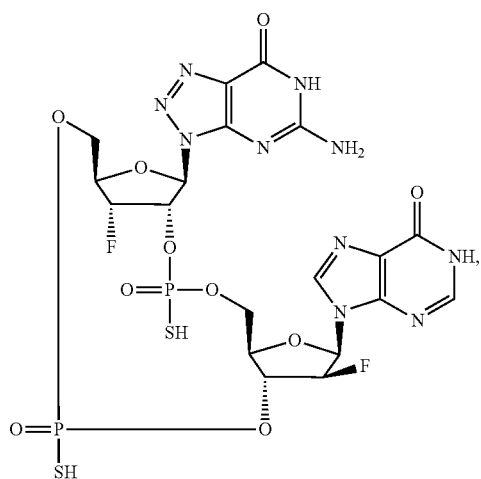
290
-continued
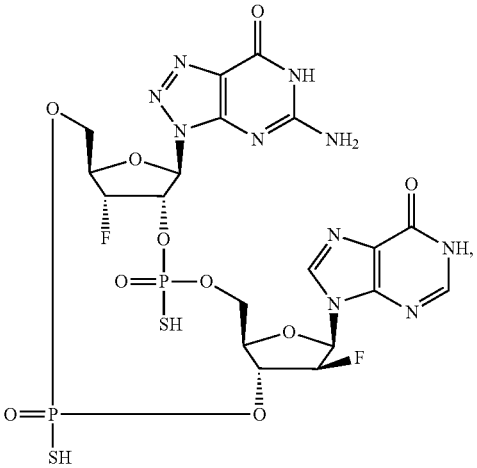
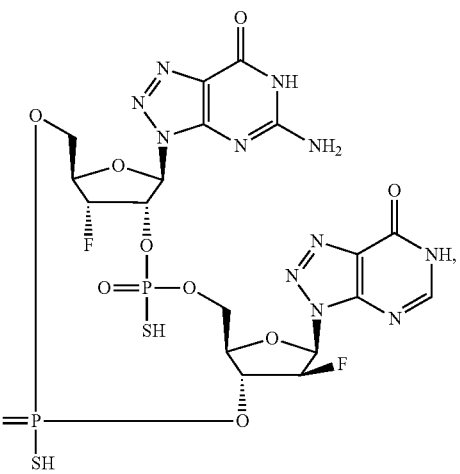
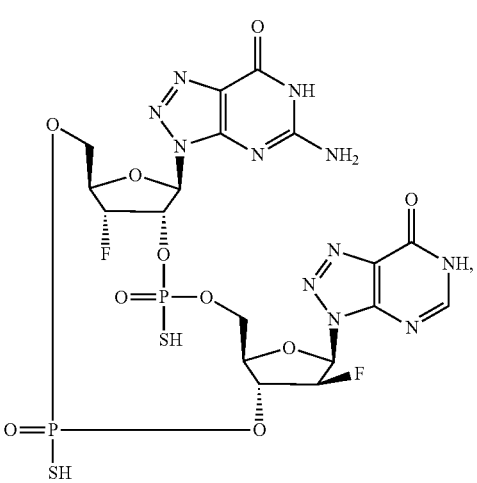

291
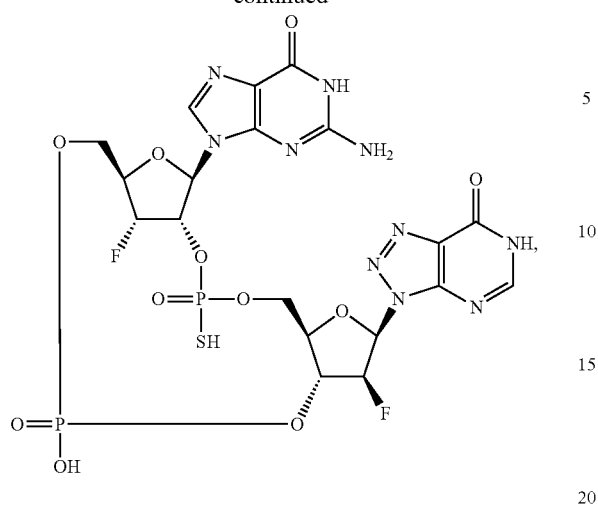
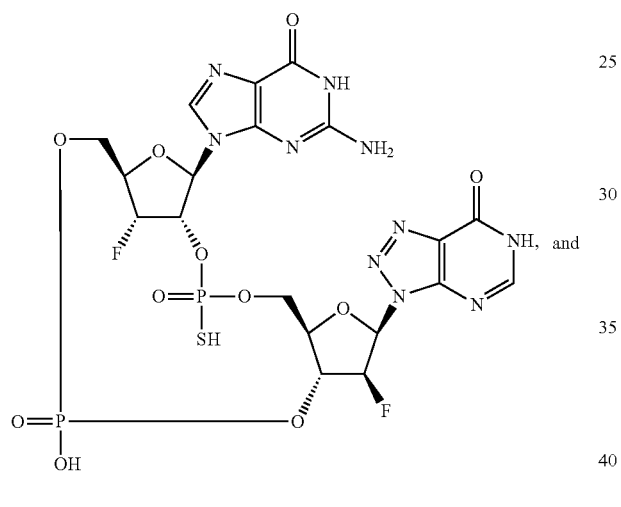
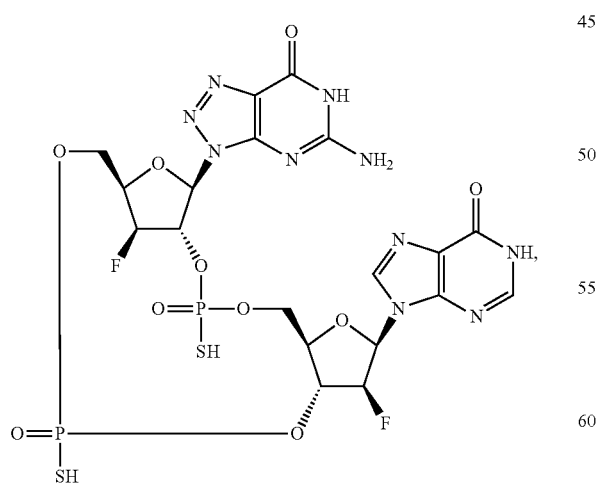
292
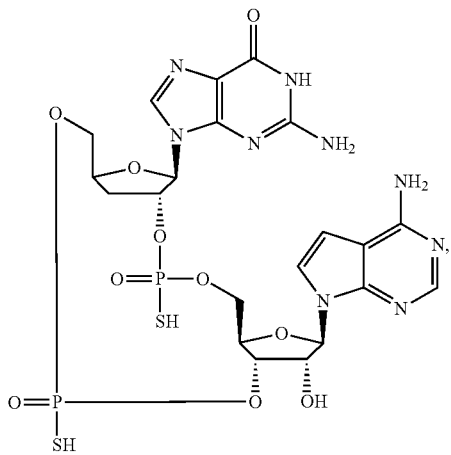
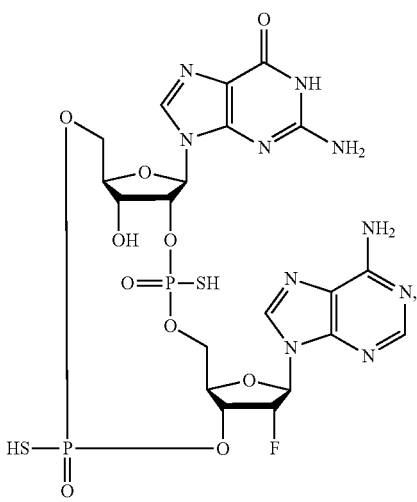
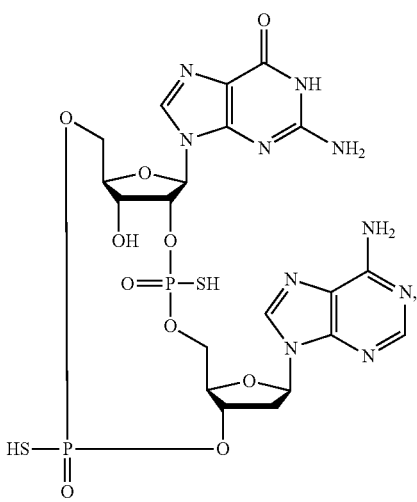
and pharmaceutically acceptable salts, hydrates, solvates, or prodrugs thereof. In particular aspects, the compound is selected from the group consisting of

293
-continued
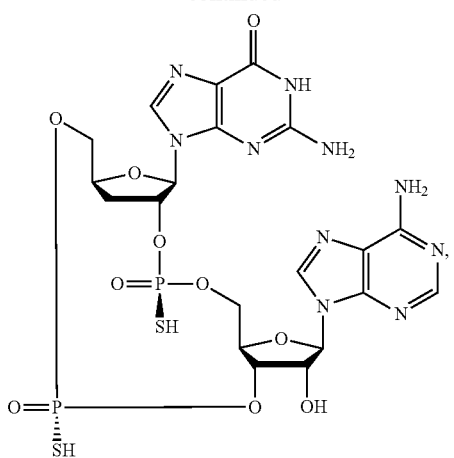
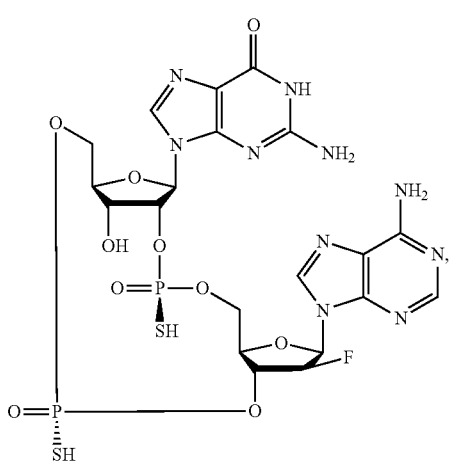
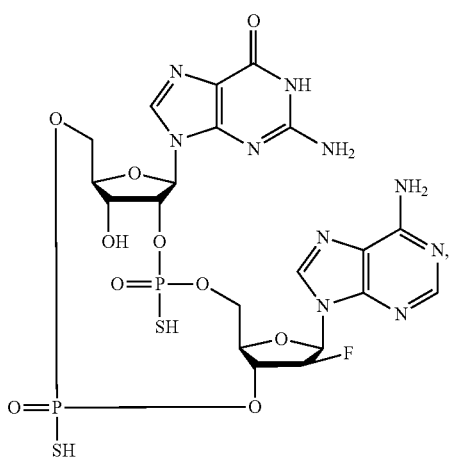
294
-continued
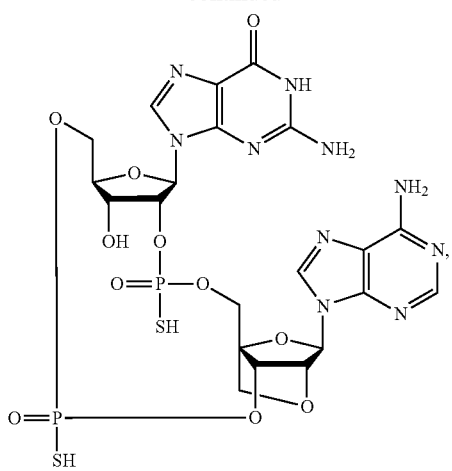
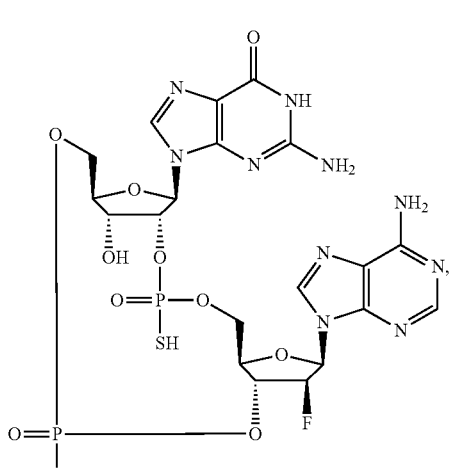
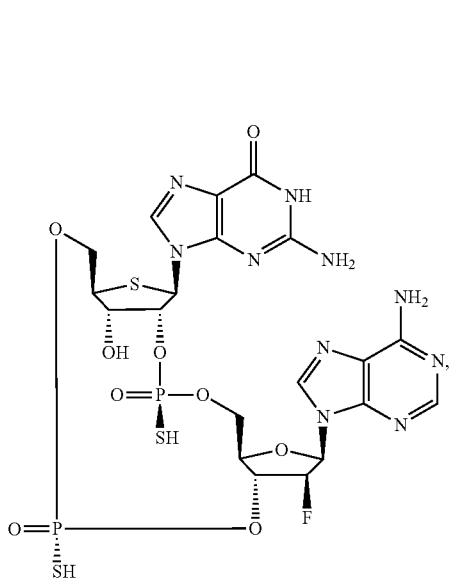

295
-continued
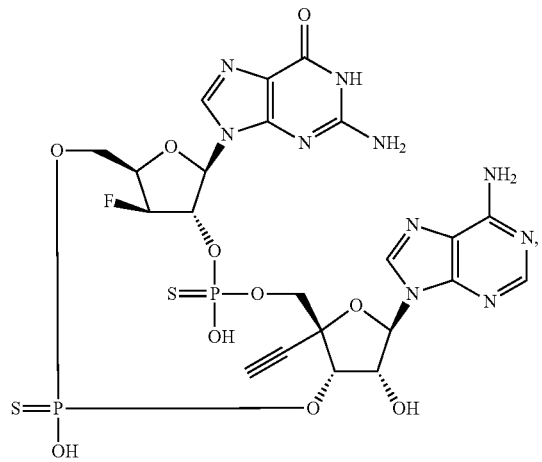
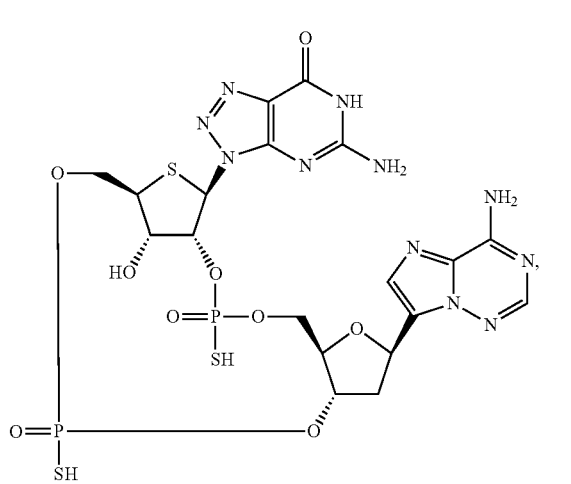
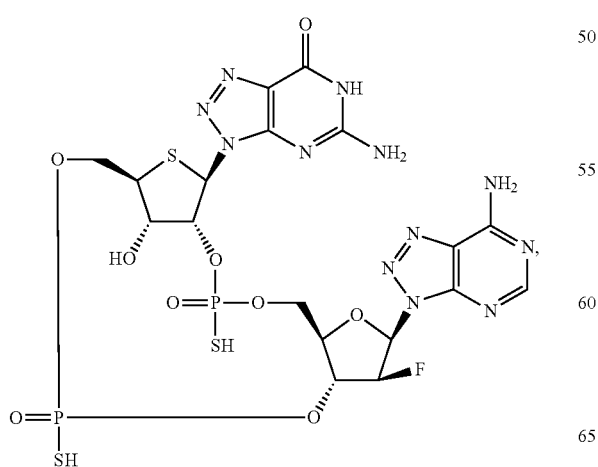
296
-continued
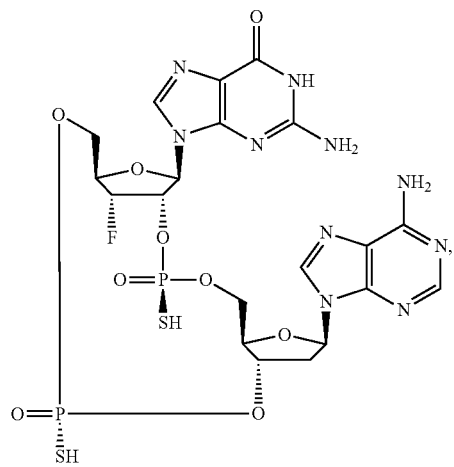
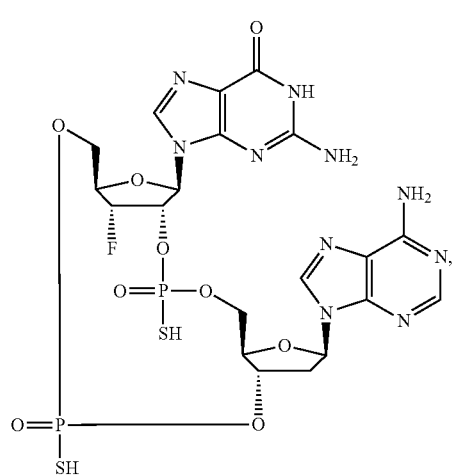
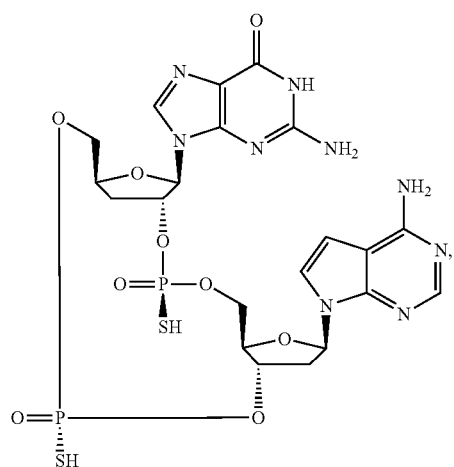

297
-continued
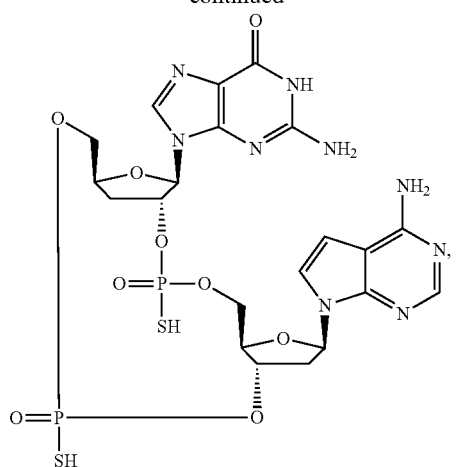
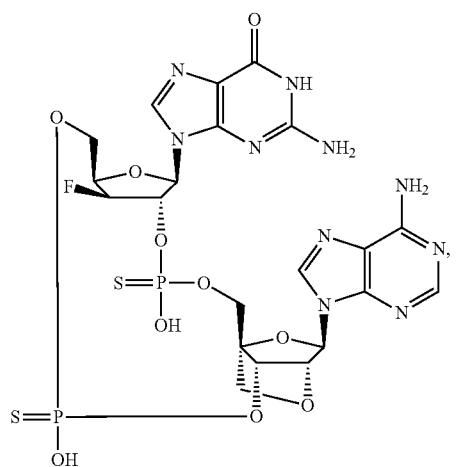
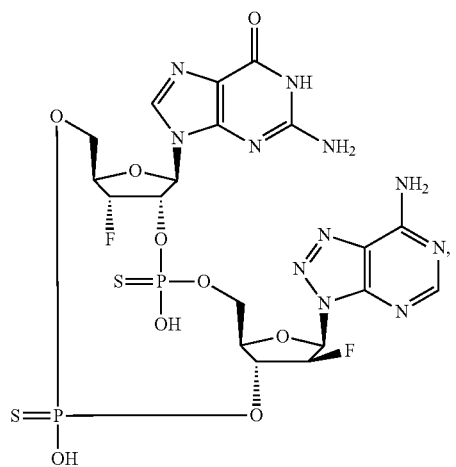
298
-continued
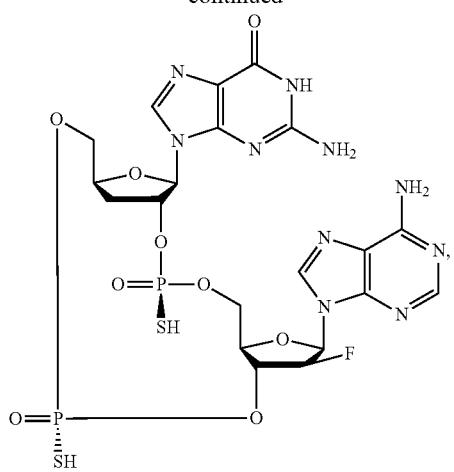
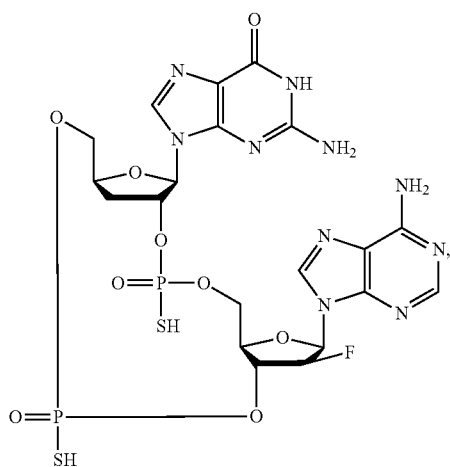
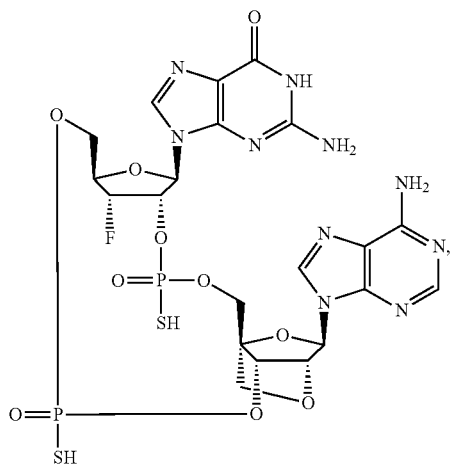

299
-continued
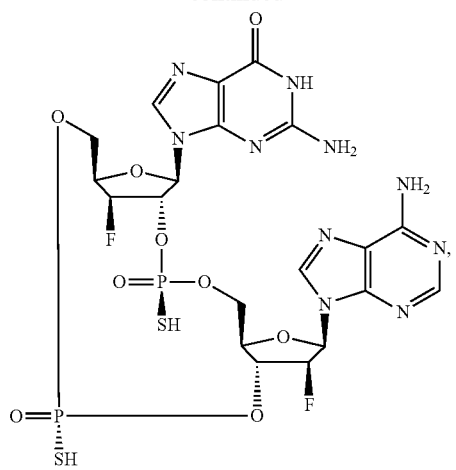
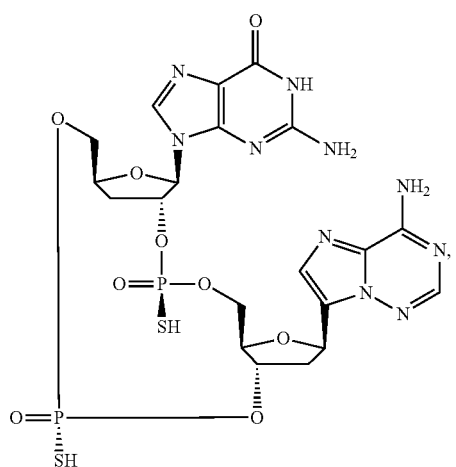
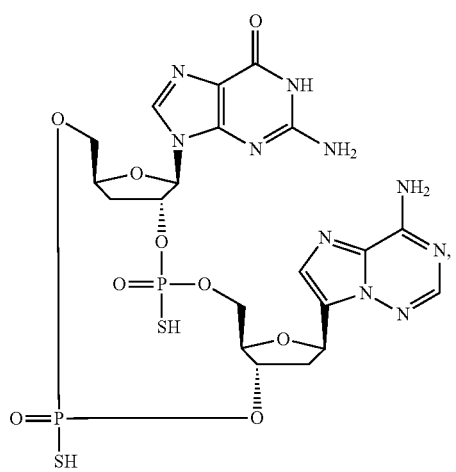
300
-continued
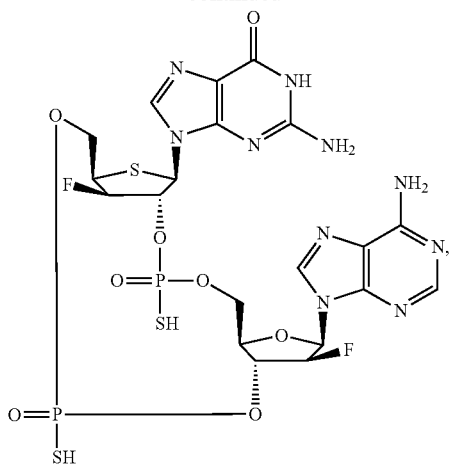
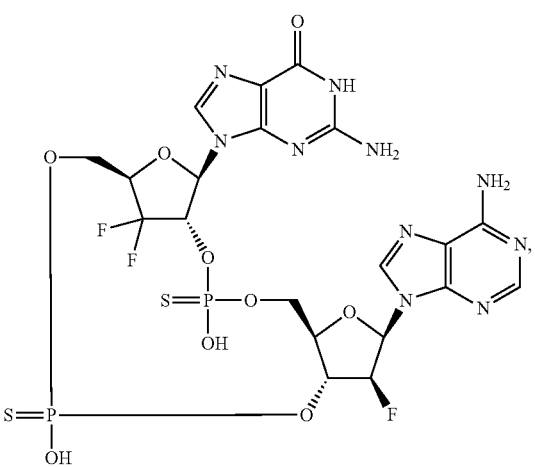
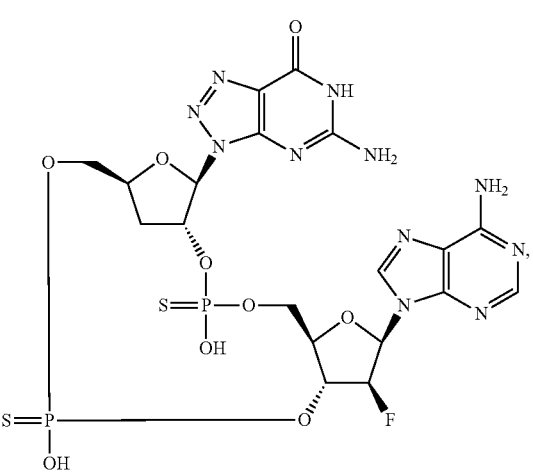

301
-continued
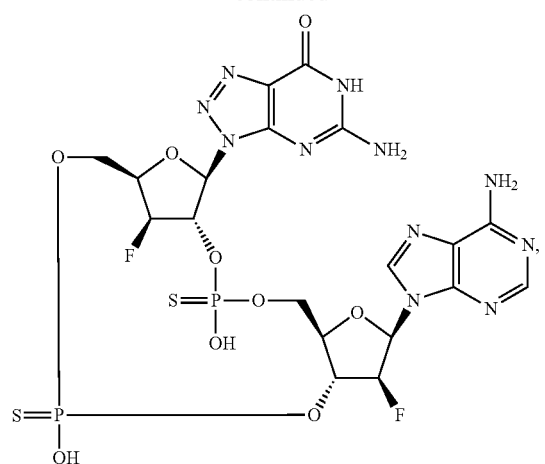
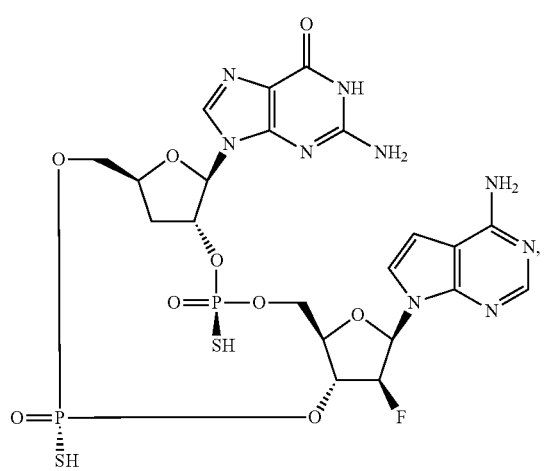
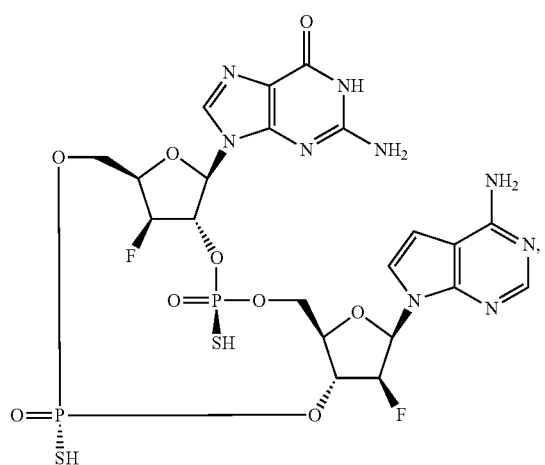
302
-continued
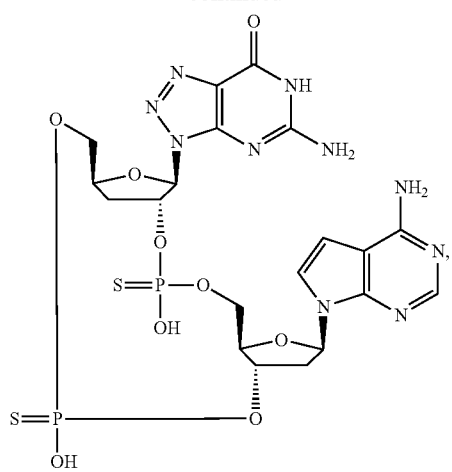
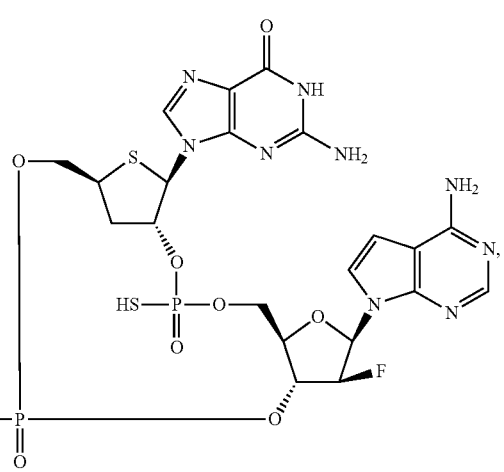
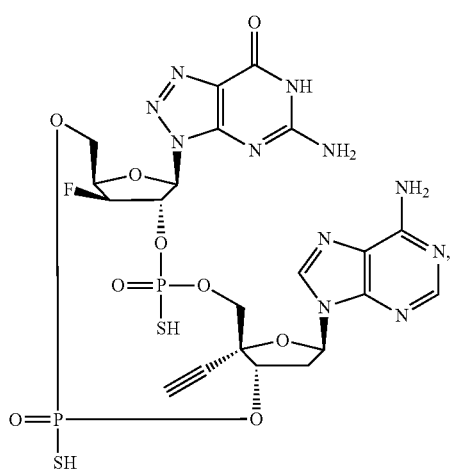

303
-continued
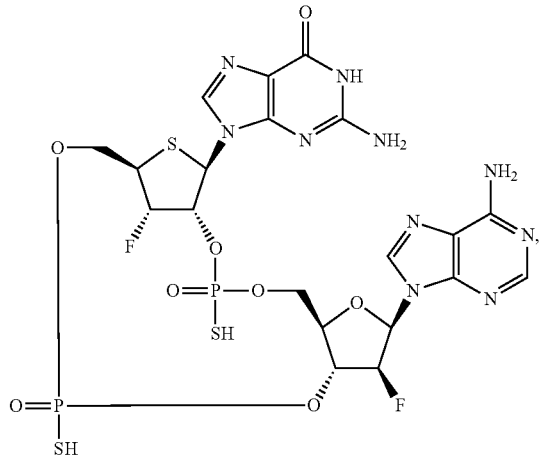
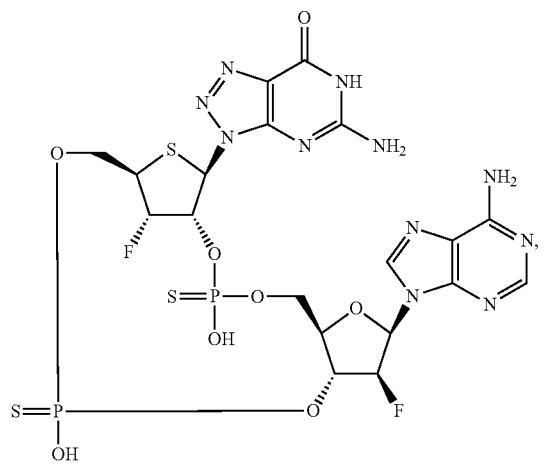
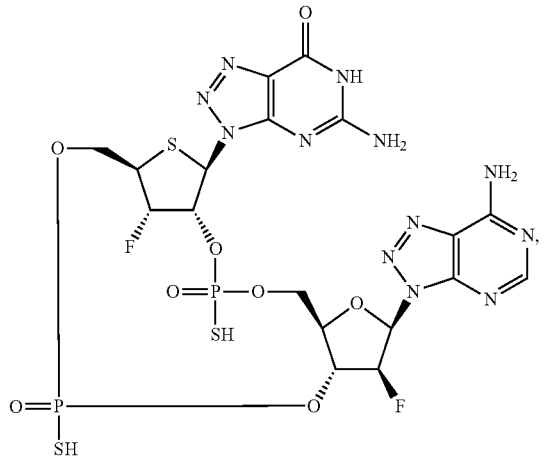
304
-continued
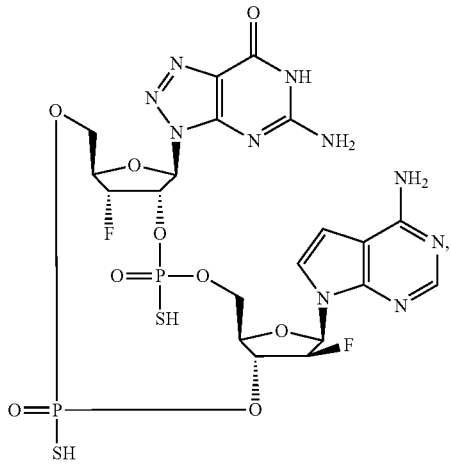
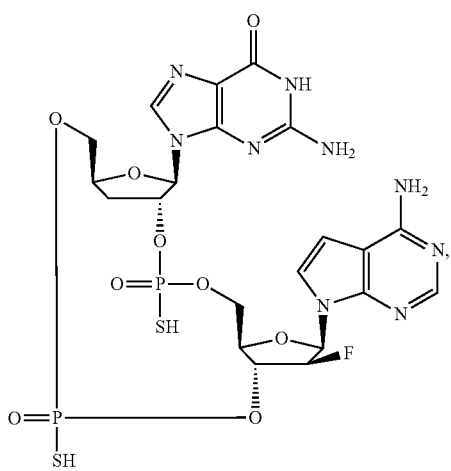
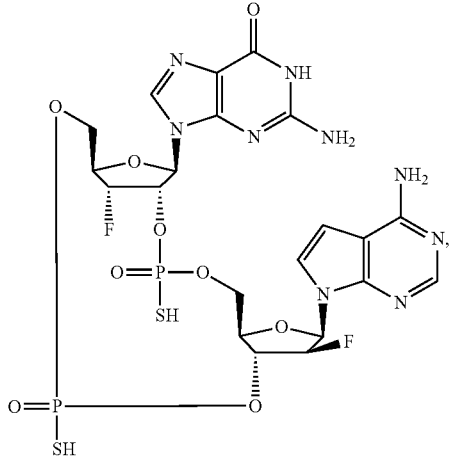

305
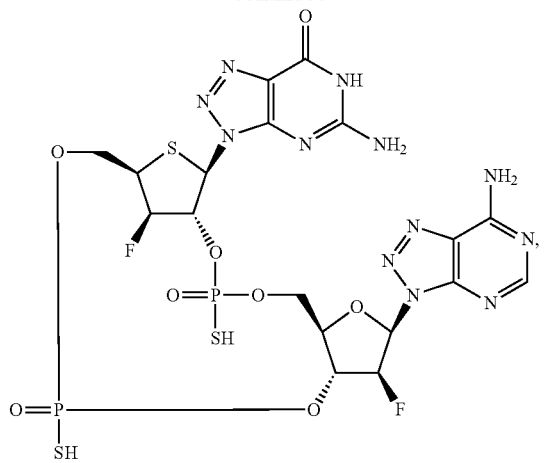
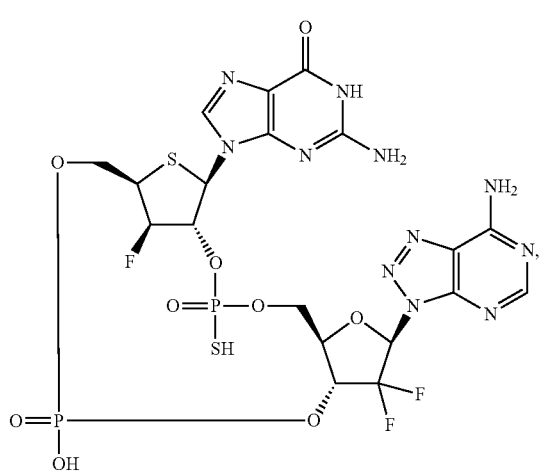
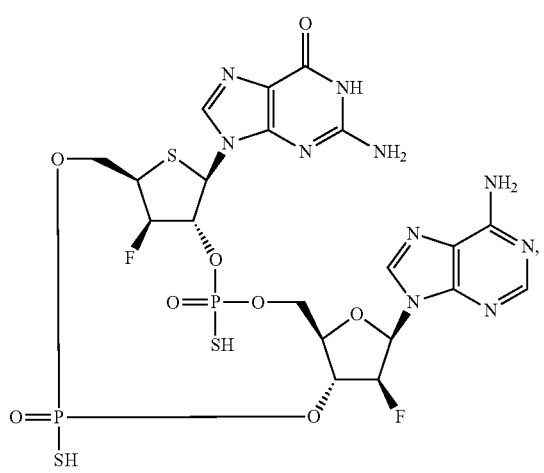
306
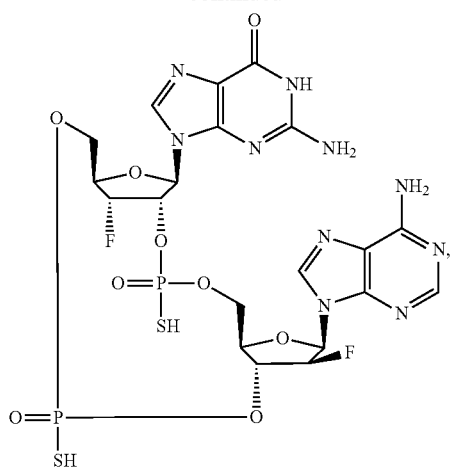
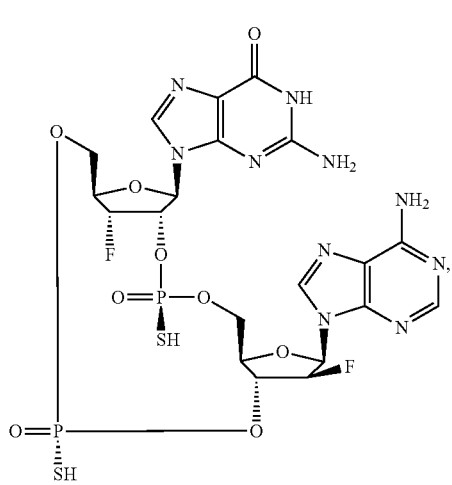
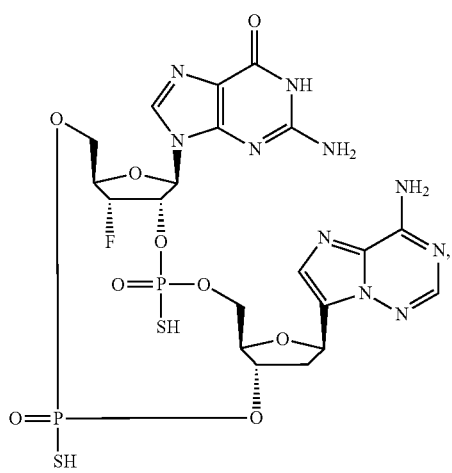

307
-continued
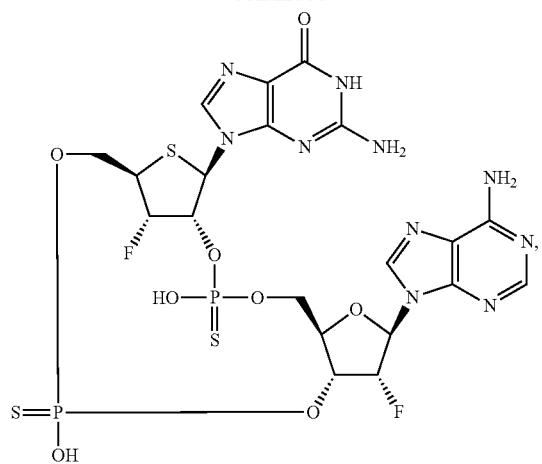
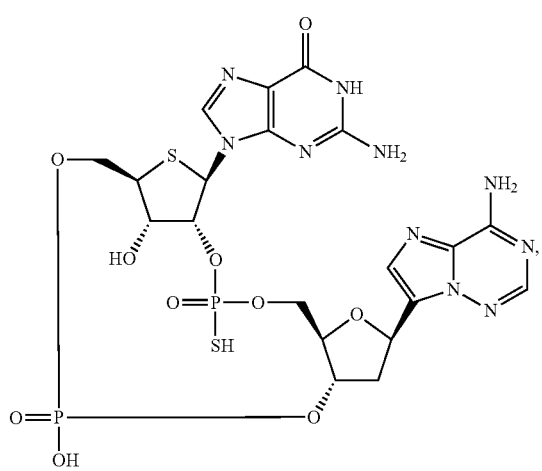
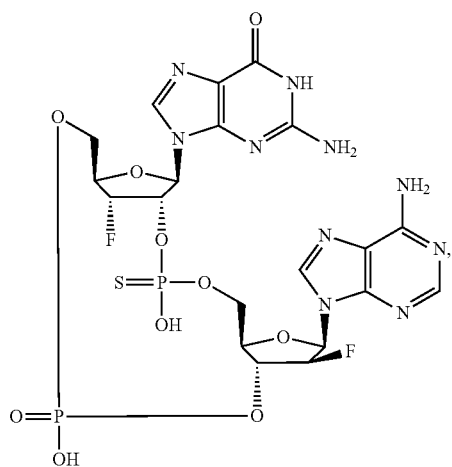
308
-continued
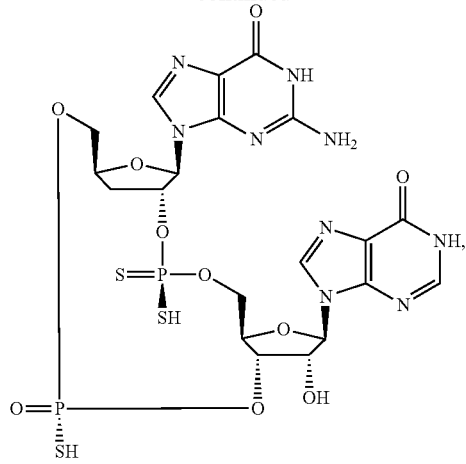
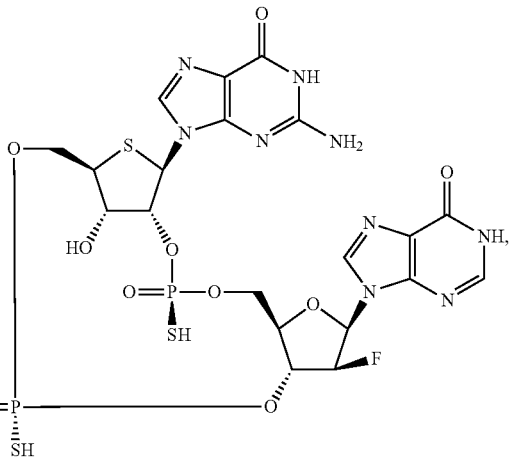
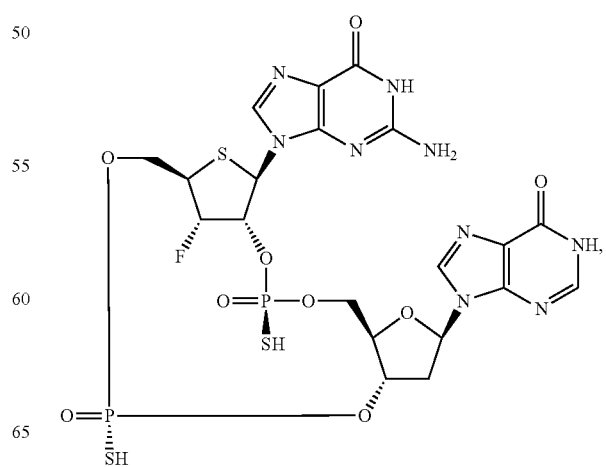

309
-continued
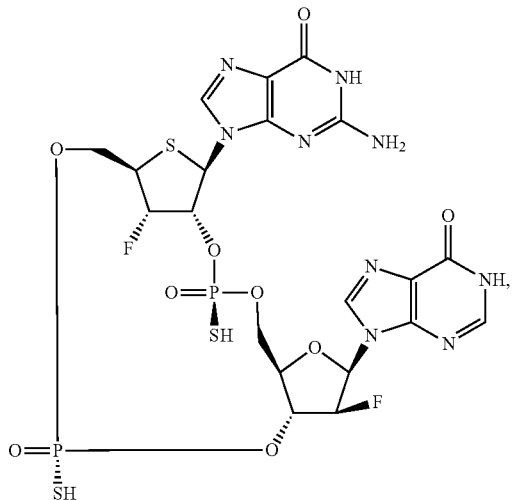
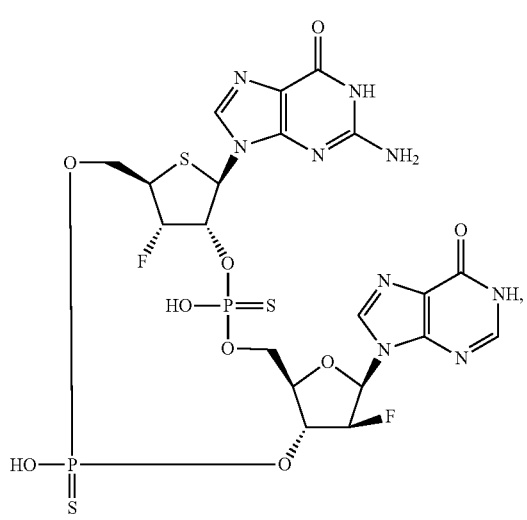
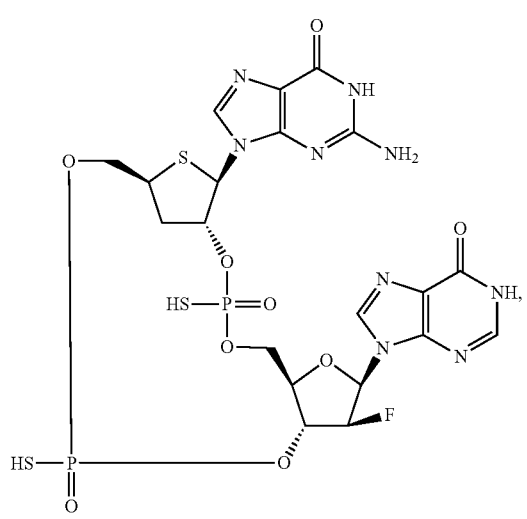
310
-continued
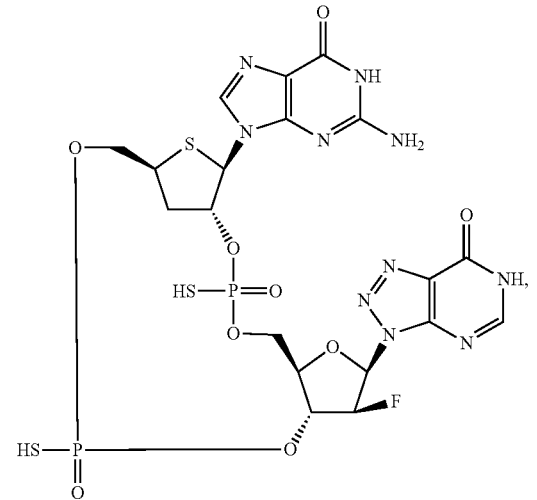
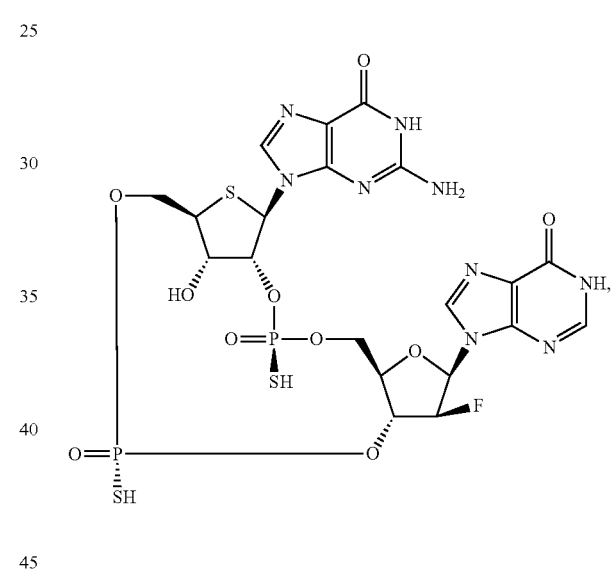
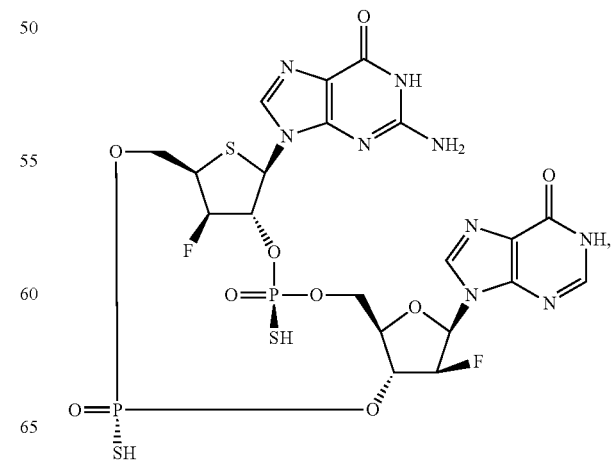

311
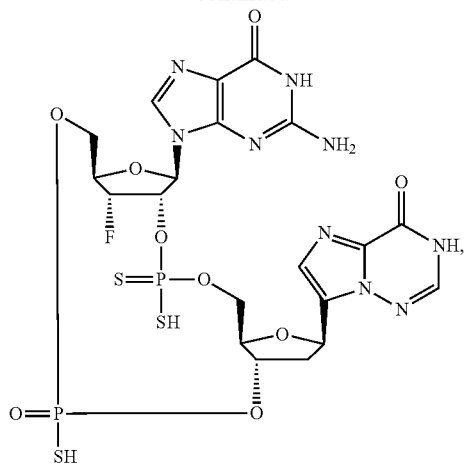
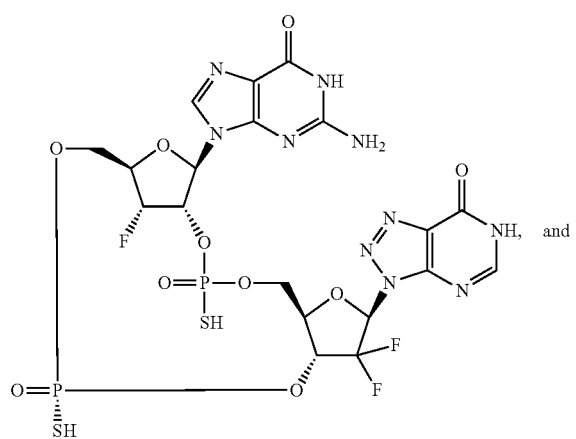
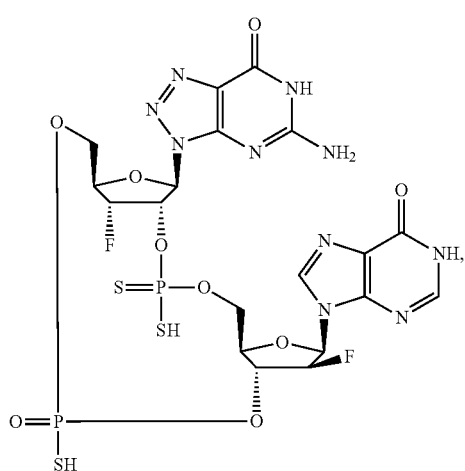
and pharmaceutically acceptable salts, hydrates, solvates, or prodrugs thereof. In more particular aspects of this embodiment, the compound is selected from the group consisting of
312
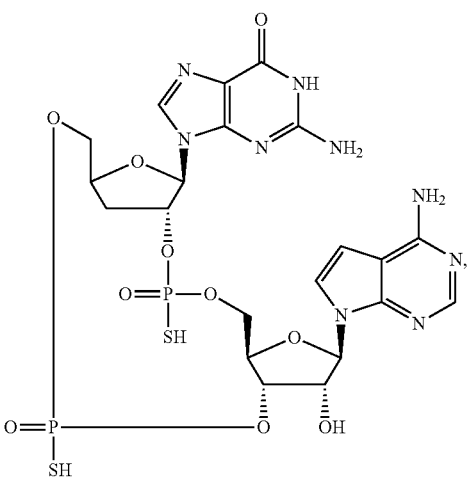
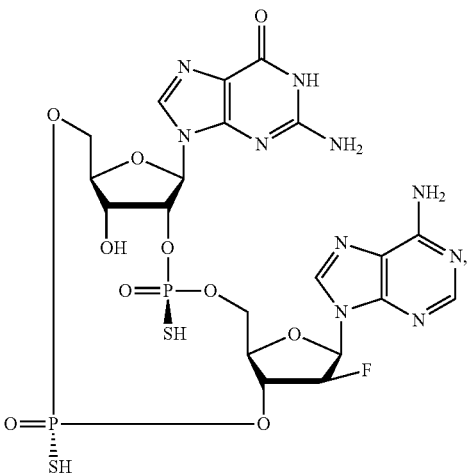
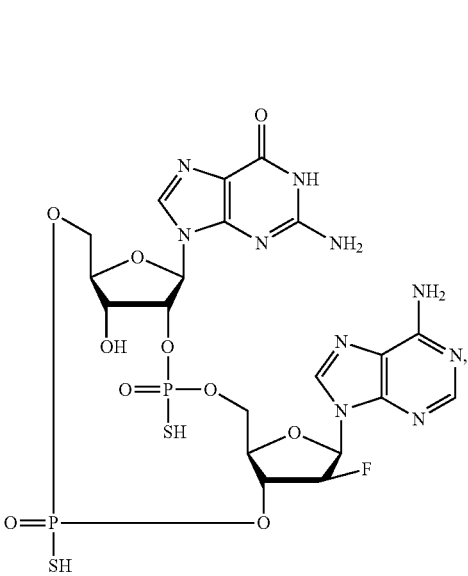

313
-continued
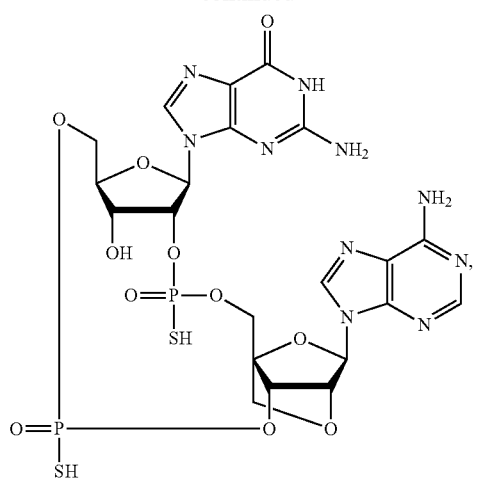
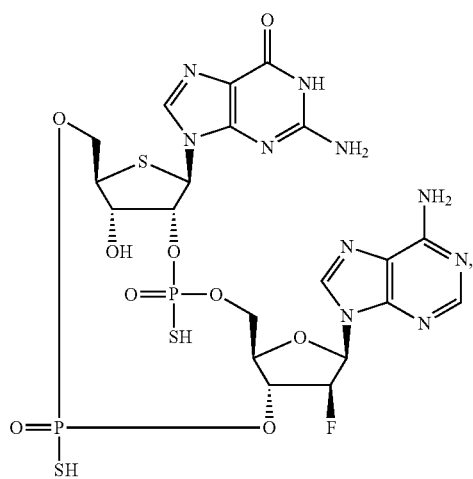
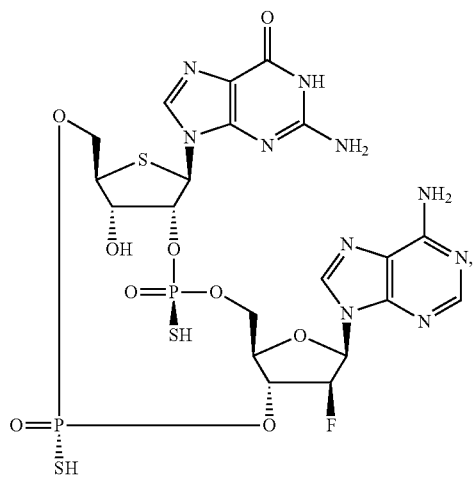
314
-continued
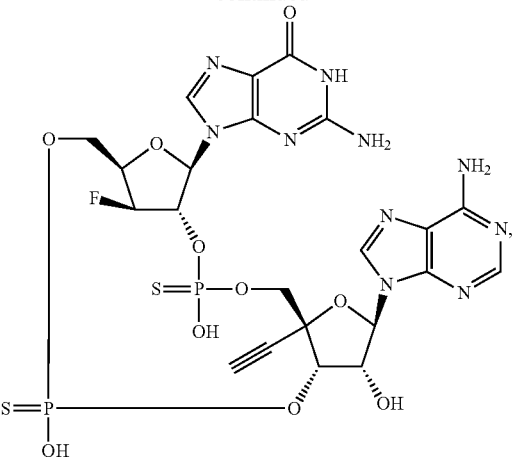
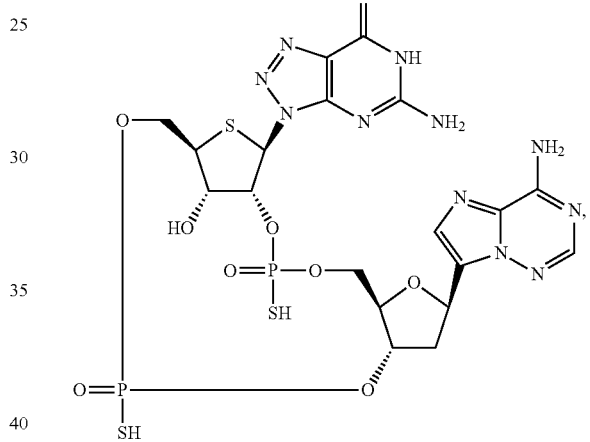
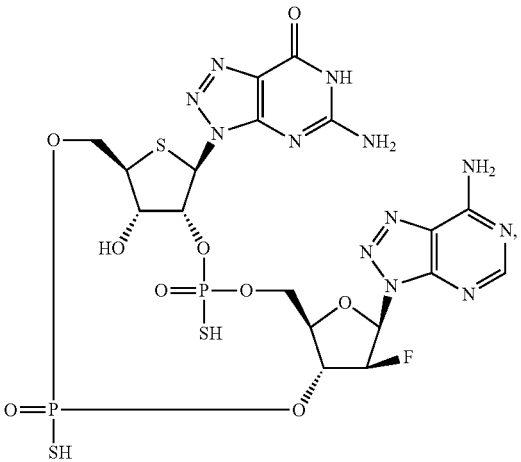

315
-continued
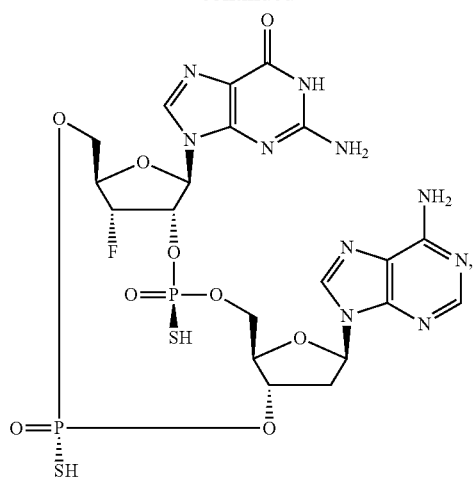
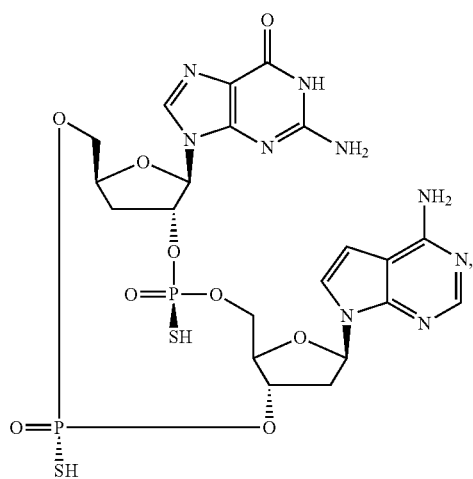
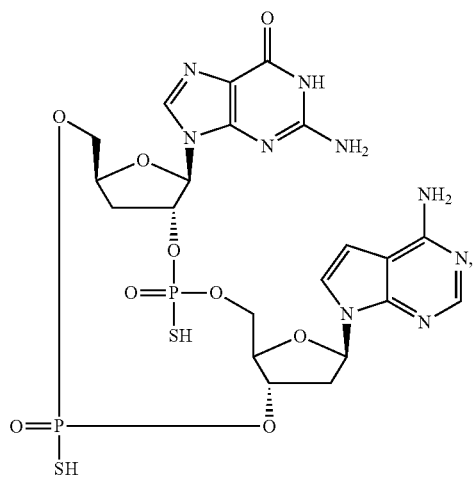
316
-continued
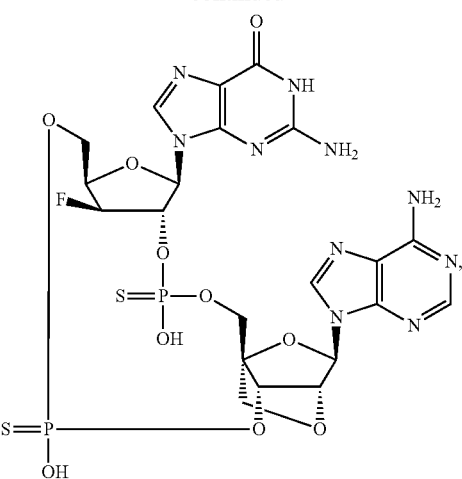
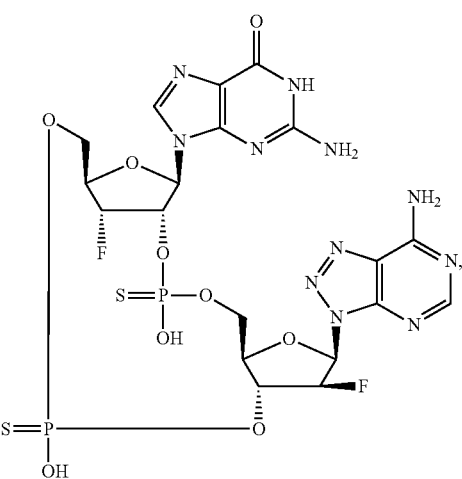
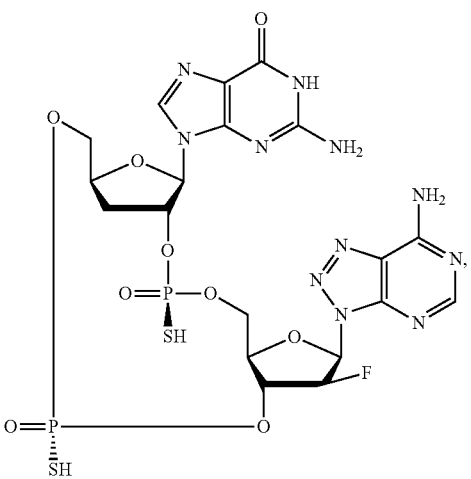

317
-continued
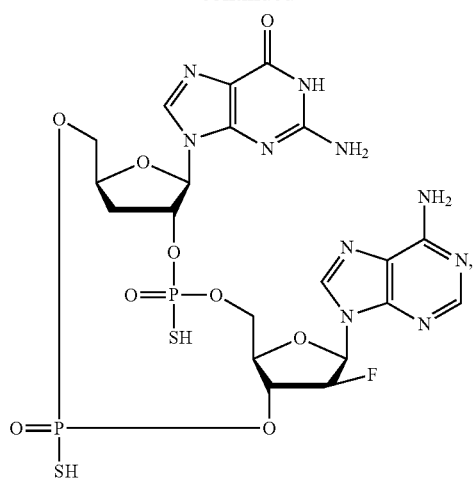
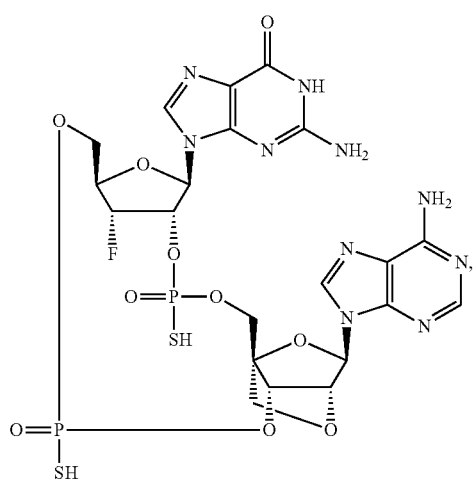
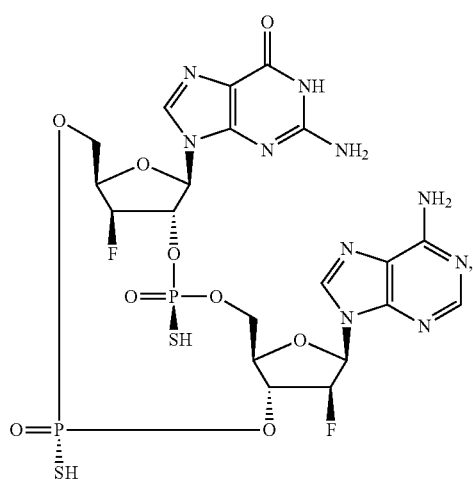
318
-continued
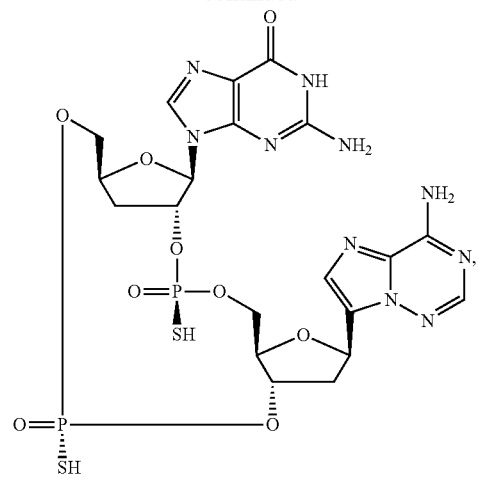
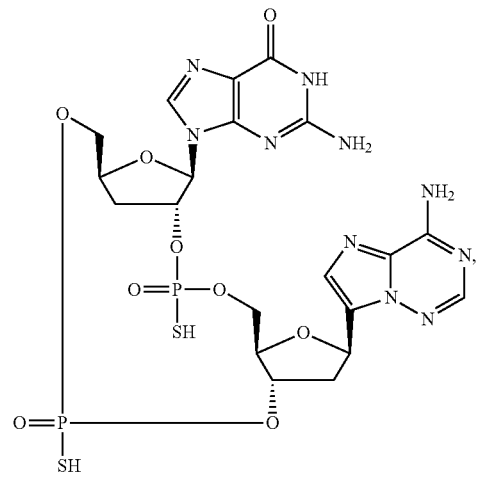
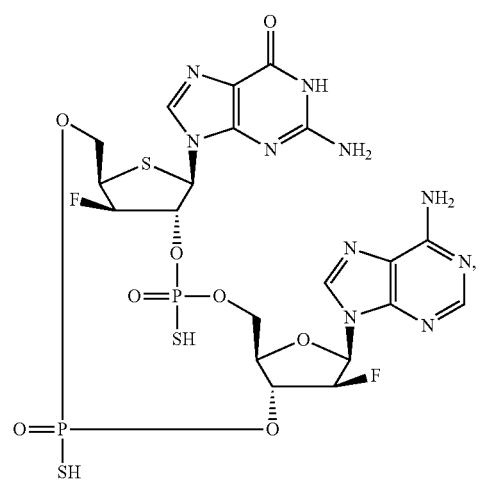

319
-continued
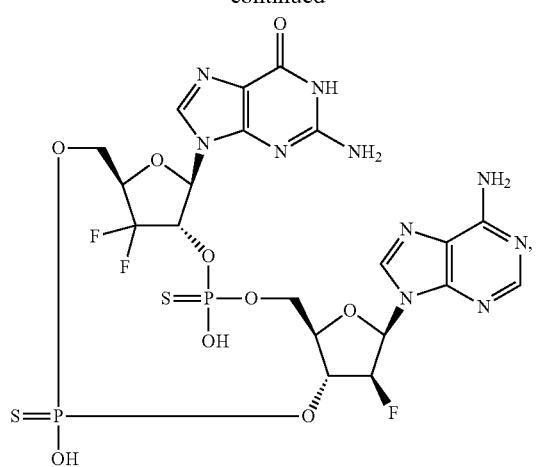
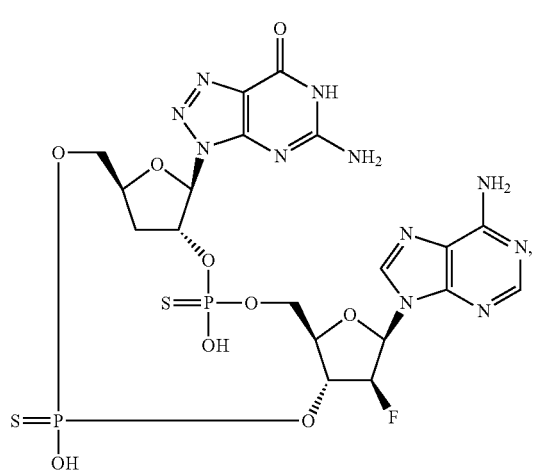
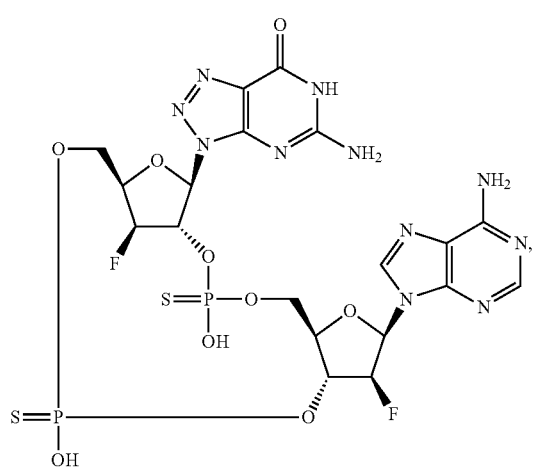
320
-continued
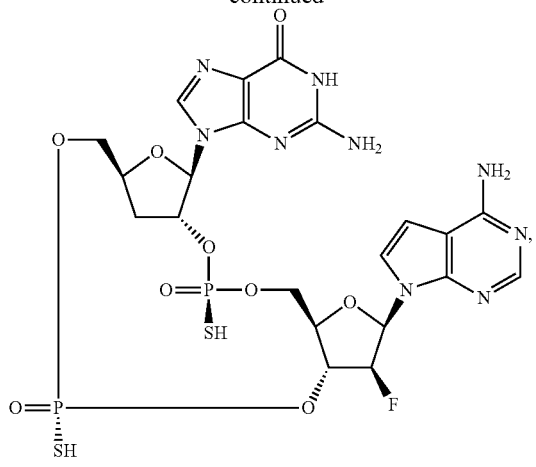
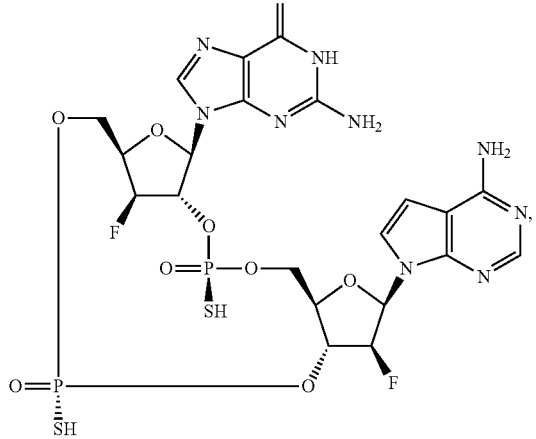
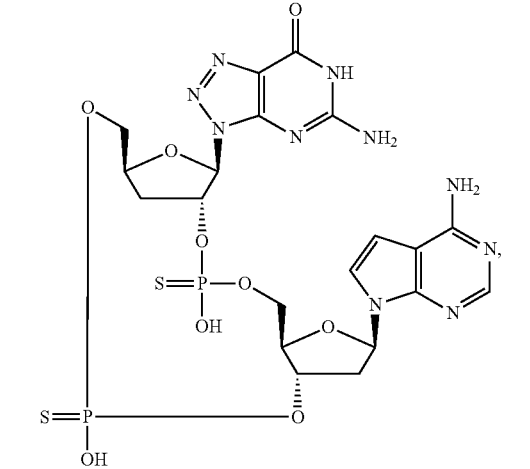

321
-continued
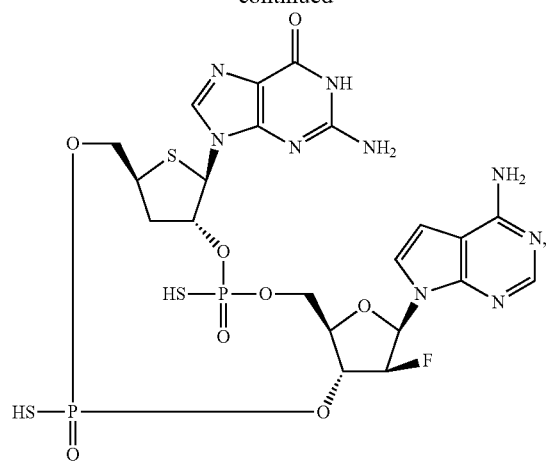
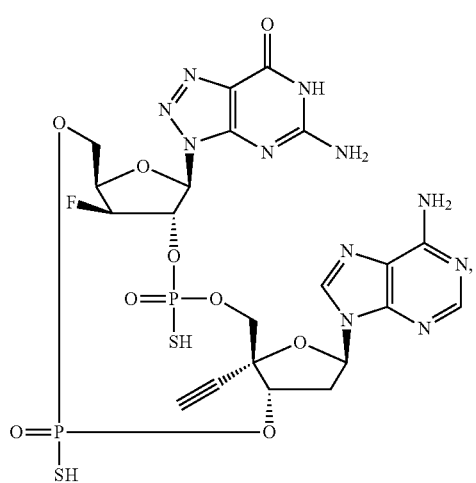
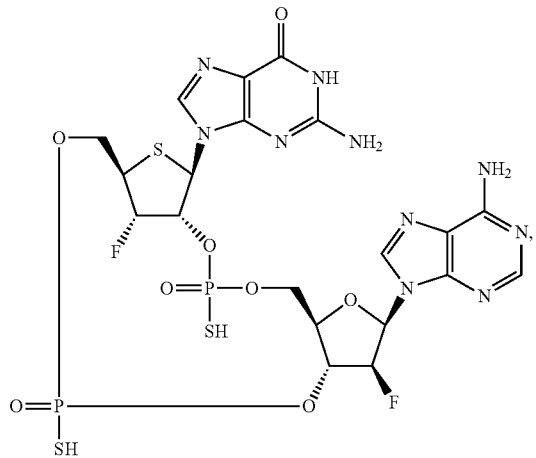
322
-continued
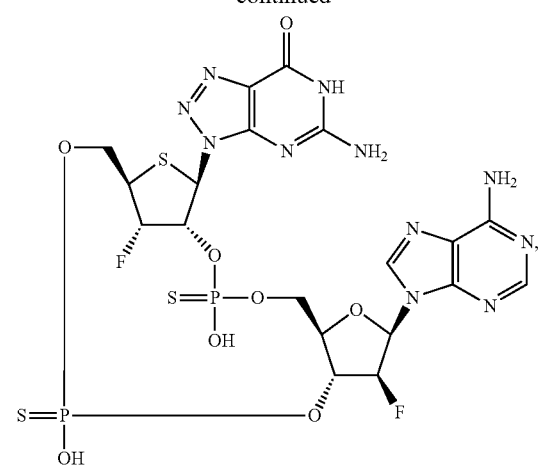
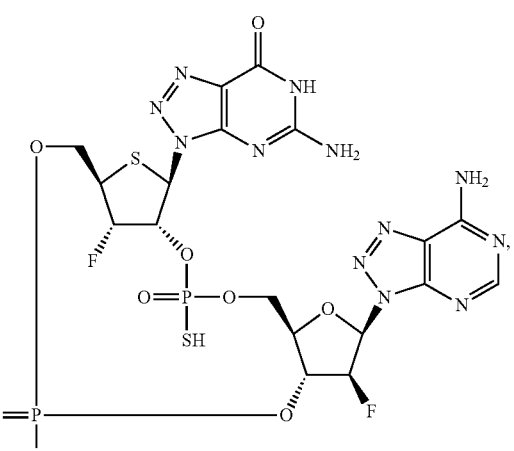
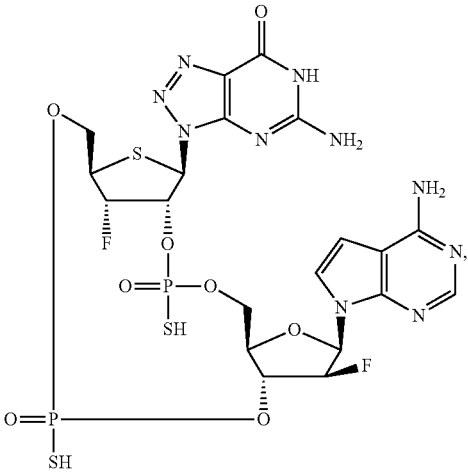

323
-continued
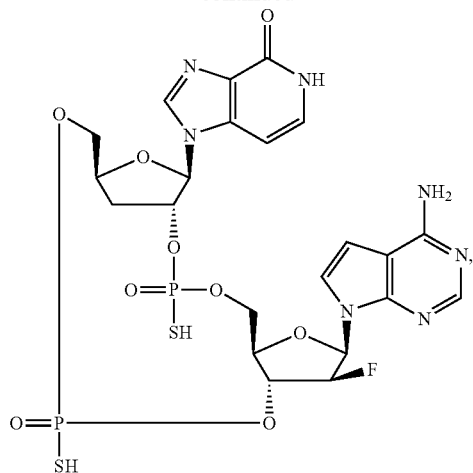
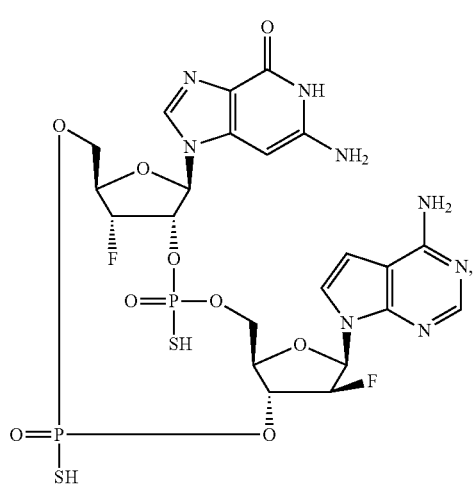
324
-continued
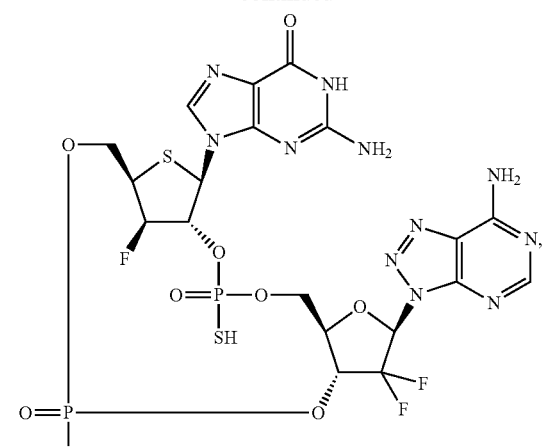
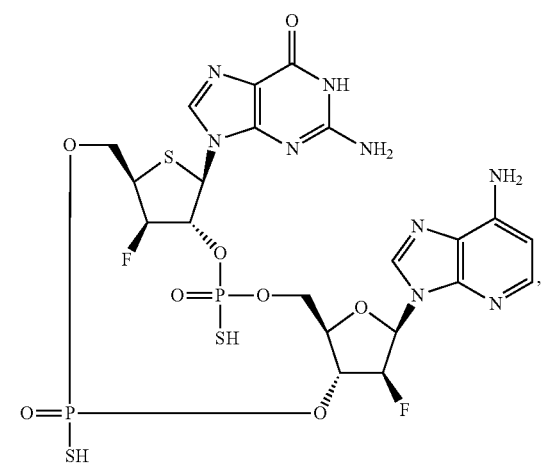
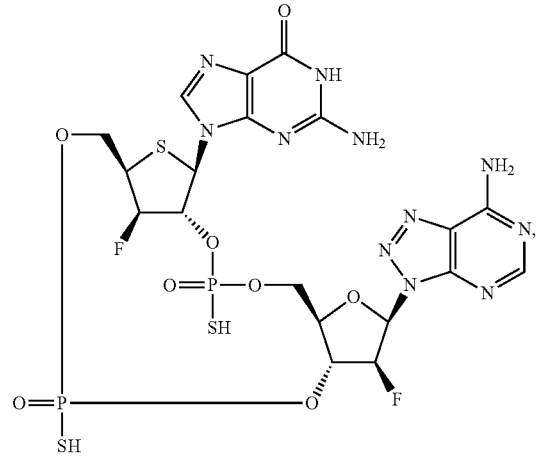
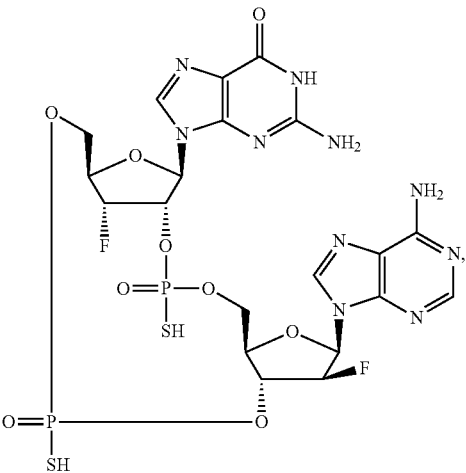

325
-continued
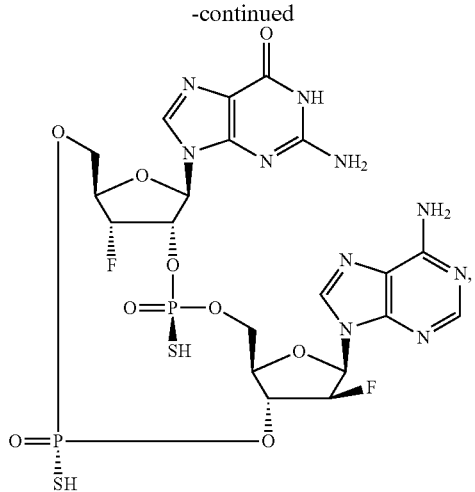
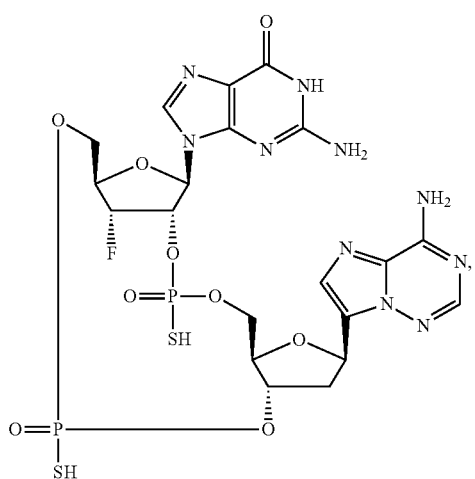
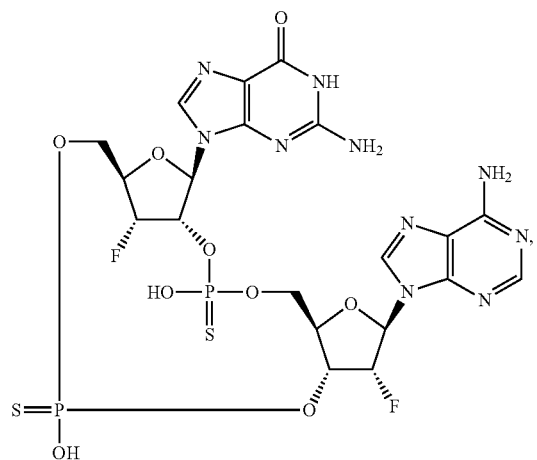
326
-continued
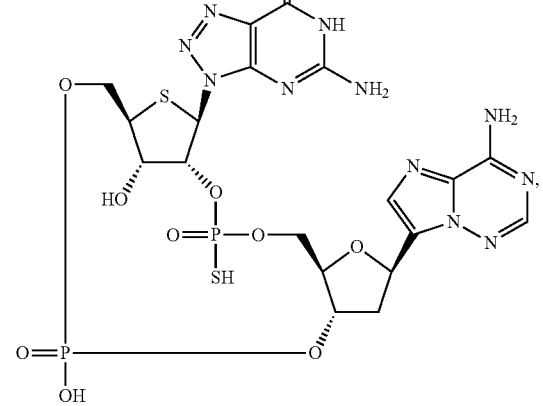
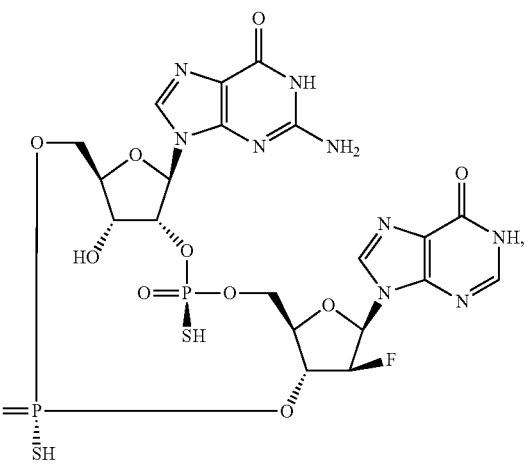

327
-continued
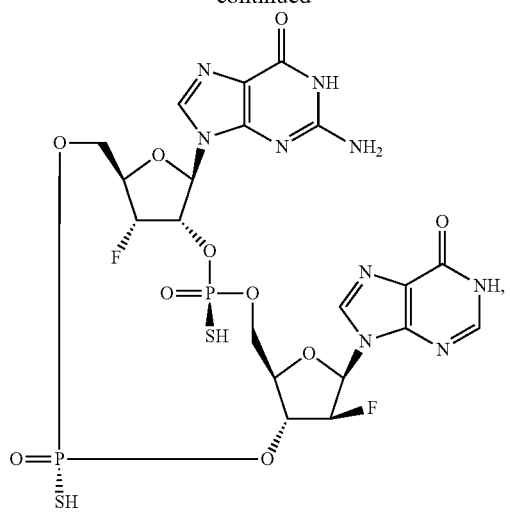
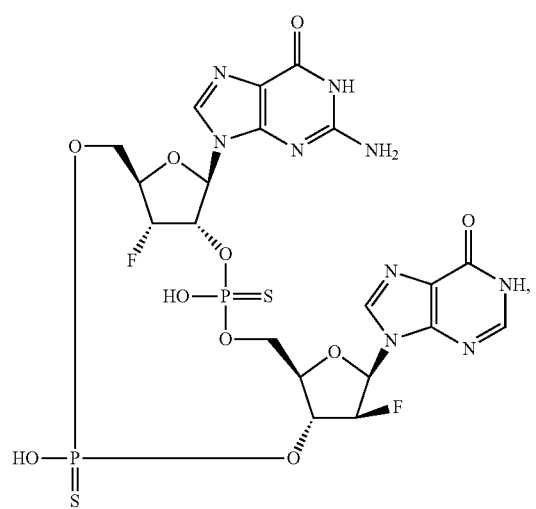
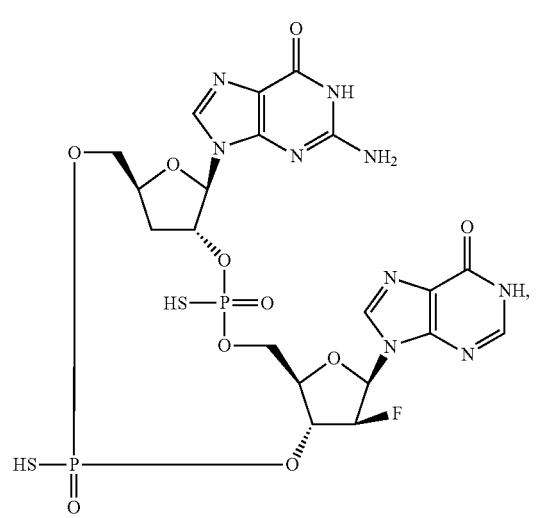
328
-continued
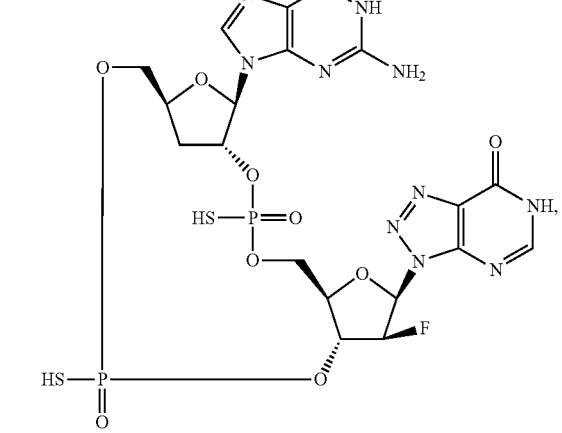
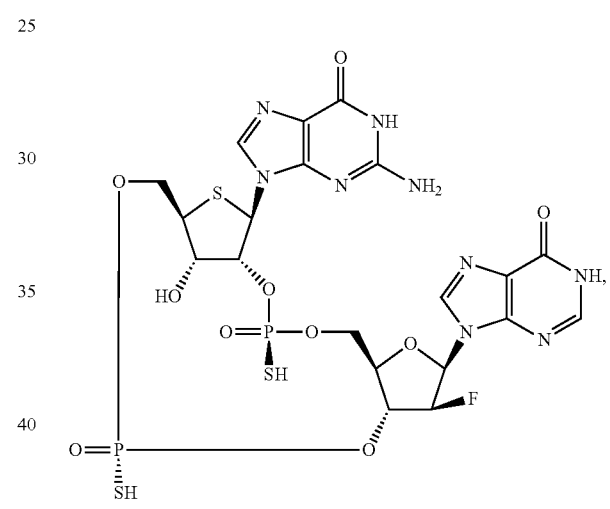
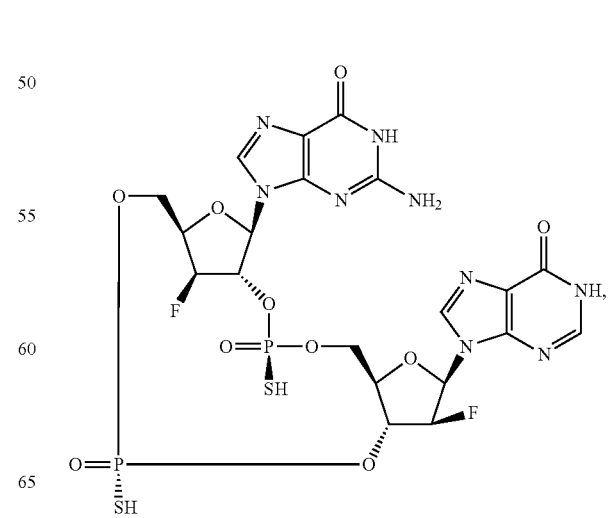

329
-continued
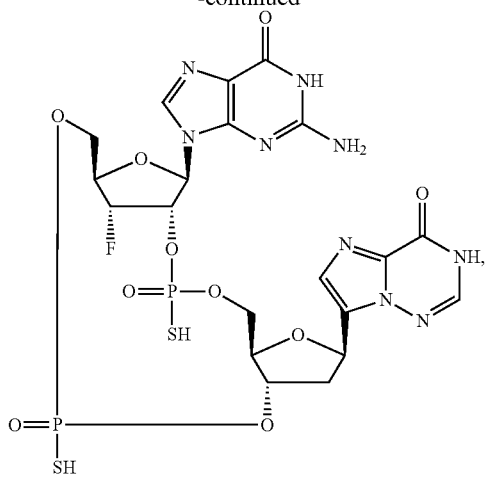
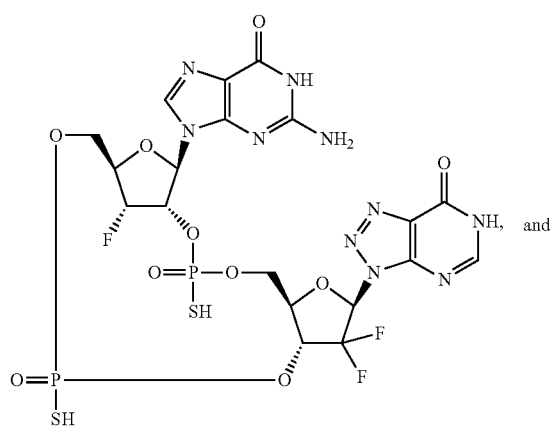
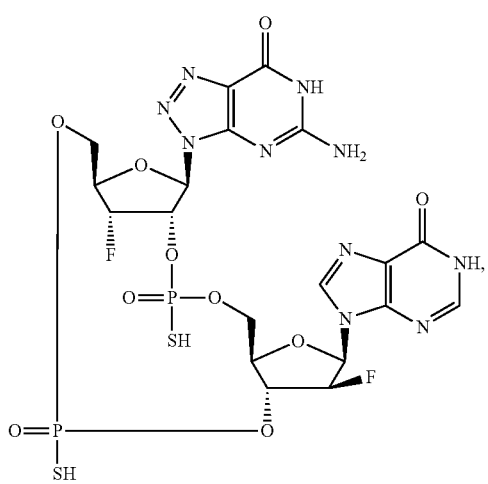
and pharmaceutically acceptable salts, hydrates, solvates, or prodrugs thereof. In still more particular aspects, the compound is selected from the group consisting of
330
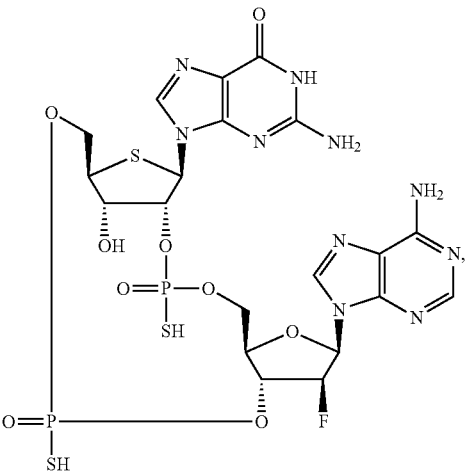
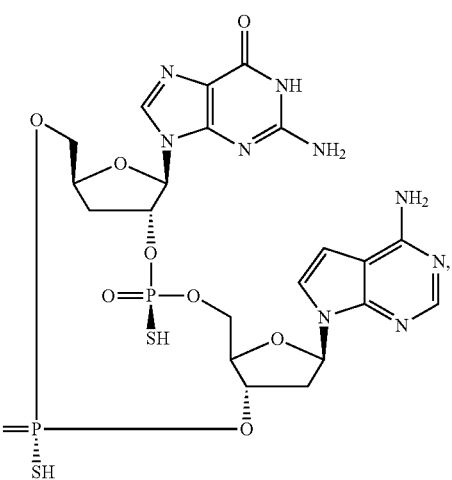
and
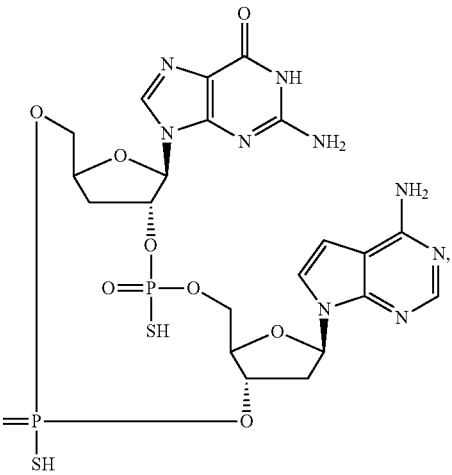

331
-continued
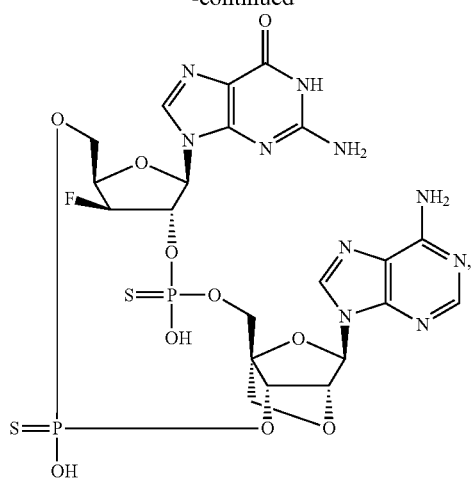
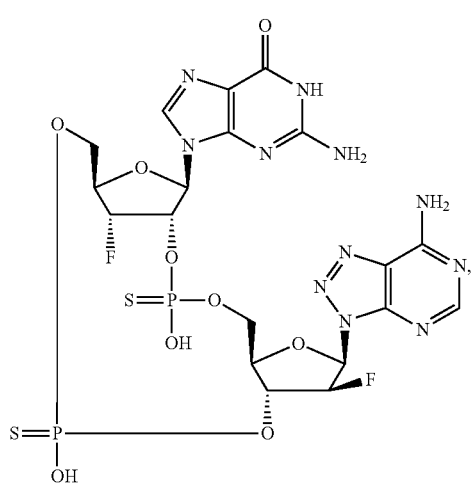
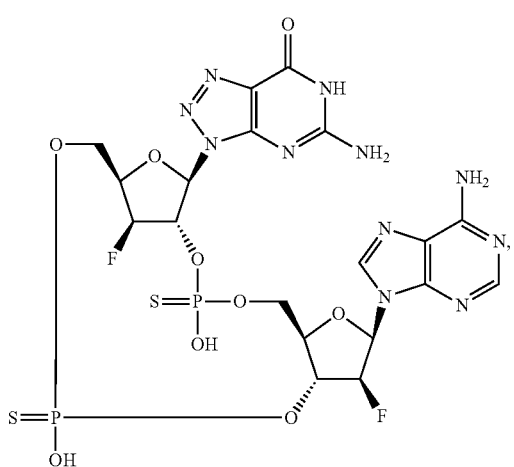
332
-continued
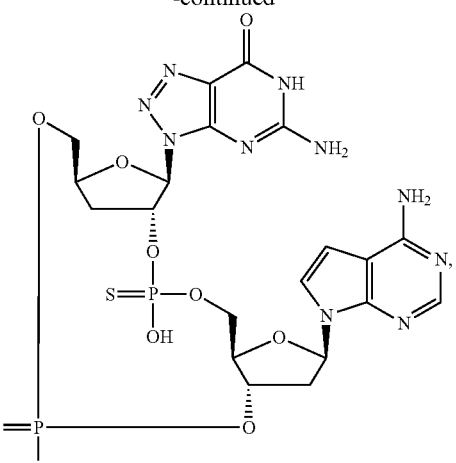
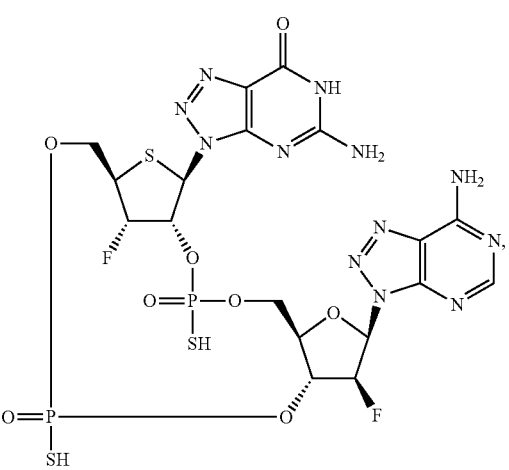
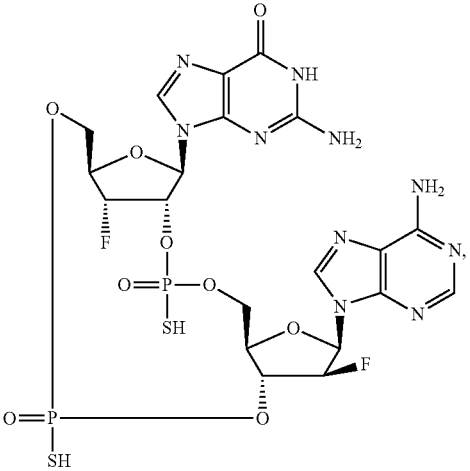

333

-continued

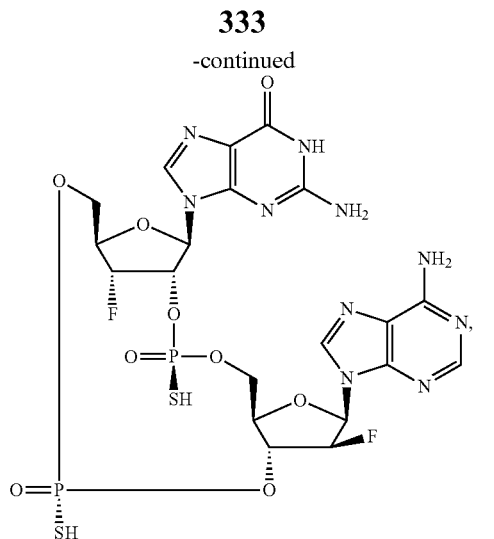

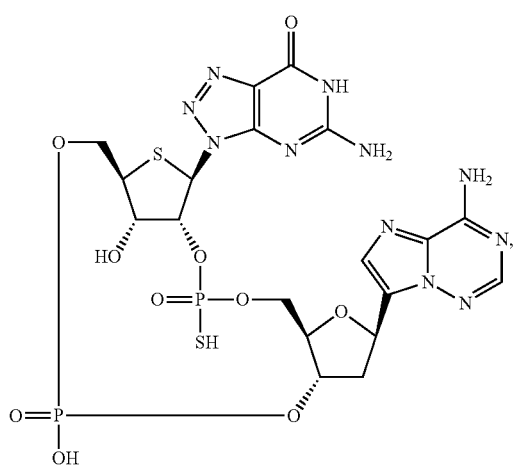

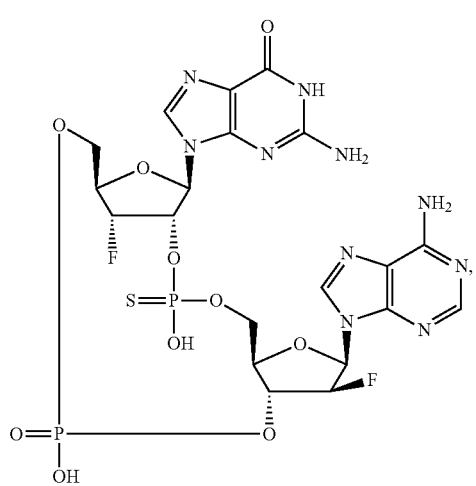

334

-continued

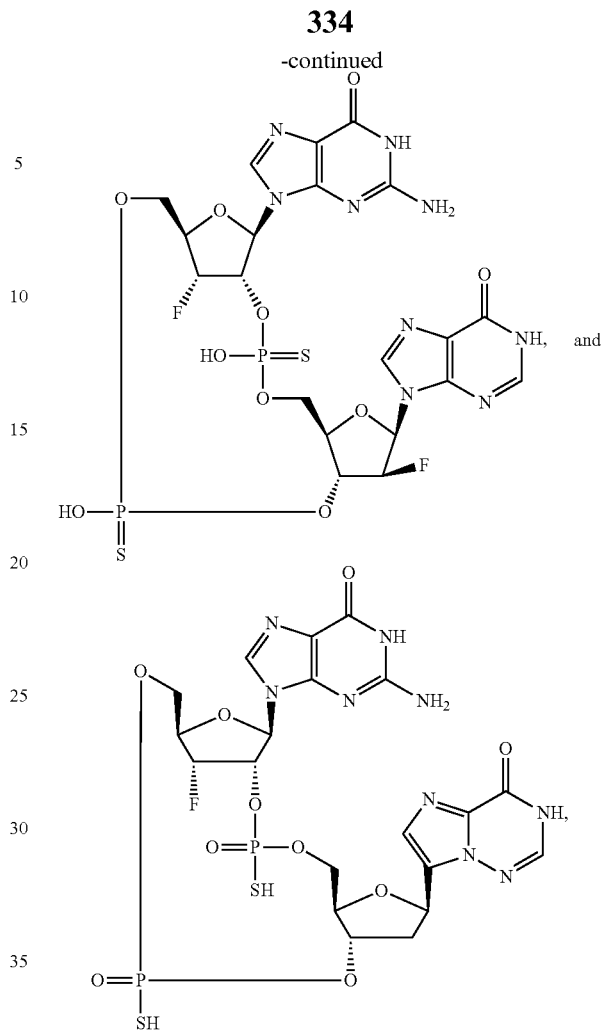

and pharmaceutically acceptable salts, hydrates, solvates, or prodrugs thereof.

In another embodiment, for the compounds of general formula (I), compounds of general formula (I') and compounds of general formula (I''), variables Base$^1$, Base$^2$, Y, Y$^a$, X$^a$, X$^{a1}$, X$^b$, X$^{b1}$, X$^c$, X$^{c1}$, X$^d$, X$^{d1}$, R$^1$, R$^{1a}$, R$^2$, R$^{2a}$, R$^3$, R$^4$, R$^{4a}$, R$^5$, R$^6$, R$^{6a}$, R$^7$, R$^{7a}$, R$^8$, R$^{8a}$, R$^9$, and R$^{10}$ are each selected independently from each other.

In another embodiment of the disclosure, the compound of the disclosure is selected from the exemplary species depicted in Examples 1 through 348 shown below.

Other embodiments of the present disclosure include the following:

(a) A pharmaceutical composition comprising an effective amount of a compound of general formula (I) or a compound of general formula (I'), or a compound of general formula (I''), or a pharmaceutically acceptable salt, hydrate, solvate, or prodrug thereof, and a pharmaceutically acceptable carrier.

(b) The pharmaceutical composition of (a), further comprising a second therapeutic agent selected from the group consisting of STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents.

(c) A pharmaceutical combination that is (i) a compound of general formula (I) or a compound of general formula (I'), or a compound of general formula (I"), or a pharmaceutically acceptable salt, hydrate, solvate, or prodrug thereof, and (ii) a second therapeutic agent selected from the group consisting of STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents; wherein the a compound of general formula (I) or compound of general formula (I'), or compound of general formula (I"), or a pharmaceutically acceptable salt, hydrate, solvate, or prodrug thereof, and the second therapeutic agent are each employed in an amount that renders the combination effective for inducing an immune response in a patient.

(e) A method of inducing an immune response in a patient, which comprises administering to the subject an effective amount of a compound of general formula (I) or a compound of general formula (I'), or a compound of general formula (I"), or a pharmaceutically acceptable salt, hydrate, solvate, or prodrug thereof.

(f) A method of inducing an immune response in a patient, which comprises administering to the subject an effective amount of a composition of (a), a composition of (b) or a combination of (c).

(g) A method of inducing STING-dependent type I interferon production in a patient, which comprises administering to the subject an effective amount of a compound of general formula (I) or a compound of general formula (I'), or a compound of general formula (I").

(h) A method of inducing STING-dependent type I interferon production in a patient, which comprises administering to the subject an effective amount of a composition of (a), a composition of (b) or a combination of (c).

(i) A method of inducing STING-dependent cytokine production in a patient, which comprises administering to the subject an effective amount of a compound of general formula (I) or a compound of general formula (I'), or a compound of general formula (I"), or a pharmaceutically acceptable salt, hydrate, solvate, or prodrug thereof.

(j) A method of inducing STING-dependent cytokine production in a patient, which comprises administering to the subject an effective amount of a composition of (a), a composition of (b) or a combination of (c).

(k) A method of treating a cell proliferation disorder in a subject, said method comprising administering a therapeutically effective amount of a compound of general formula (I) or a compound of general formula (I'), or a compound of general formula (I"), or a pharmaceutically acceptable salt, hydrate, solvate, or prodrug thereof to the subject;

(l) The method of (k), wherein the cell proliferation disorder is cancer.

(m). A method of treating a cell proliferation disorder in a subject, said method comprising administering a therapeutically effective amount of a pharmaceutical composition of (a), a composition of (b) or a combination of (c) to the subject.

(n) The method of (m), wherein the cell proliferation disorder is cancer.

The present disclosure also includes a compound of the present disclosure for use (i) in, (ii) as a medicament for, or (iii) in the preparation of a medicament for: (a) inducing an immune response in a patient, or (b) inducing a STING-dependent cytokine production in a patient. In these uses, the compounds of the present disclosure can optionally be employed in combination with one or more second therapeutic agents selected from STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents.

Additional embodiments of the disclosure include the pharmaceutical compositions, combinations and methods set forth in (a)-(n) above and the uses set forth in the preceding paragraph, wherein the compound of the present disclosure employed therein is a compound of one of the embodiments, aspects, classes, sub-classes, or features of the compounds described above. In all of these embodiments, the compound may optionally be used in the form of a pharmaceutically acceptable salt, hydrate, solvate or prodrug as appropriate.

In the embodiments of the compound provided above, it is to be understood that each embodiment may be combined with one or more other embodiments, to the extent that such a combination provides a stable compound and is consistent with the description of the embodiments. It is further to be understood that the embodiments of compositions and methods provided as (a) through (n) above are understood to include all embodiments of the compounds, including such embodiments as result from combinations of embodiments.

The term "subject" (alternatively referred to herein as "patient") as used herein refers to an animal, preferably a mammal, such as a human being, male or female, that has been the object of treatment, observation, or experiment. A subject also refers to one or more of cows, sheep, goats, horses, dogs, cats, rabbits, rats, mice, fish, and birds. In embodiments, the subject is human.

As used herein, the term "immune response" relates to any one or more of the following: specific immune response, non-specific immune response, both specific and non-specific response, innate response, primary immune response, adaptive immunity, secondary immune response, memory immune response, immune cell activation, immune cell proliferation, immune cell differentiation, and cytokine expression. In certain embodiments, the compound of general formula (I), compound of general formula (I'), or compound of general formula (I"), or pharmaceutically acceptable salt, hydrate, solvate, or prodrug thereof, is administered in conjunction with one or more additional therapeutic agents including vaccines intended to stimulate an immune response to one or more predetermined anti-viral compounds, antigens, adjuvants, CTLA-4 and PD-1 pathway antagonists and other immunomodulatory agents, lipids, liposomes, peptides, anti-cancer and chemotherapeutic agents, etc. In certain embodiments, the compound of general formula (I), compound of general formula (I'), or compound of general formula (I"), or a pharmaceutically acceptable salt, hydrate, solvate, or prodrug thereof, is administered in conjunction with one or more additional compositions including vaccines intended to stimulate an immune response to one or more predetermined anti-viral compounds, antigens, adjuvants, CTLA-4 and PD-1 pathway antagonists and other immunomodulatory agents, lipids, liposomes, peptides, anti-cancer and chemotherapeutic agents, etc.

Compounds

The term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and tert-butyl, n- and iso-propyl, ethyl, and methyl. As another example, "$C_{1-4}$ alkyl" refers to n-, iso-, sec- and tert-butyl, n- and isopropyl, ethyl, and methyl.

As used herein, the term "alkylene" refers to a bivalent straight chain, saturated aliphatic hydrocarbon radical having a number of carbon atoms in the specified range.

As used herein, the term "alkenyl" refers to a monovalent straight or branched chain, unsaturated aliphatic hydrocarbon radical having a number of carbon atoms in the specified range and including one or more double bond.

As used herein, the term "alkenylene" refers to a bivalent straight chain, unsaturated aliphatic hydrocarbon radical having a number of carbon atoms in the specified range and including one or more double bond.

As used herein, the term "alkynyl" refers to a monovalent straight or branched chain, unsaturated aliphatic hydrocarbon radical having a number of carbon atoms in the specified range and including one or more triple bond.

As used herein, the term "alkynylene" refers to a bivalent straight chain, unsaturated aliphatic hydrocarbon radical having a number of carbon atoms in the specified range and including one or more triple bond.

The term "halogen" (or "halo") refers to fluorine, chlorine, bromine, and iodine (alternatively referred to as fluoro, chloro, bromo, and iodo or F, Cl, Br, and I).

The term "haloalkyl" refers to an alkyl group as defined above in which one or more of the hydrogen atoms have been replaced with a halogen. Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

As used herein, the term "haloalkenyl" refers to an alkenyl group as defined above in which one or more of the hydrogen atoms have been replaced with a halogen.

As used herein, the term "haloalkynyl" refers to an alkynyl group as defined above in which one or more of the hydrogen atoms have been replaced with a halogen.

As used herein, the term "spirocycle" or "spirocyclic ring" refers to a pendant cyclic group formed by substituents on a single atom. For example, in general formula (I), a spirocycle may be formed by $R^{2a}$ and $R^3$.

Unless expressly stated to the contrary, all ranges cited herein are inclusive; i.e., the range includes the values for the upper and lower limits of the range as well as all values in between.

As an example, temperature ranges, percentages, ranges of equivalents, and the like described herein include the upper and lower limits of the range and any value in the continuum there between. Numerical values provided herein, and the use of the term "about", may include variations of ±1%, ±2%, ±3%, ±4%, ±5%, ±10%, ±15%, and ±20% and their numerical equivalents.

As used herein, the term "one or more" item includes a single item selected from the list as well as mixtures of two or more items selected from the list.

In the compounds of general formula (I), compounds of general formula (I'), and compounds of general formula (I"), the atoms may exhibit their natural isotopic abundances, or one or more of the atoms may be artificially enriched in a particular isotope having the same atomic number, but an atomic mass or mass number different from the atomic mass or mass number predominantly found in nature. The present disclosure is meant to include all suitable isotopic variations of the compounds of general formula (I), compounds of general formula (I'), and compounds of general formula (I"). For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within general formula (I) can be prepared without undue experimentation by conventional techniques well known to those skilled in the art or by processes analogous to those described in the Schemes and Examples herein using appropriate isotopically-enriched reagents and/or intermediates.

In particular embodiments of the compounds of general formula (I), compounds of general formula (I'), and compounds of general formula (I"), the compounds are isotopically enriched with deuterium. In aspects of these embodiments, one or more of $R^1$, $R^{1a}$, $R^2$, $R^{2a}$, $R^3$, $R^4$, $R^{4a}$, $R^5$, $R^6$, $R^{6a}$, $R^7$, $R^{7a}$, $R^8$, $R^{8a}$, $R^9$, and $R^{10}$ may be deuterium.

As shown in the general structural formulas and the structures of specific compounds as provided herein, a straight line at a chiral center includes both (R) and (S) stereoisomers and mixtures thereof. Also, unless otherwise specified (e.g., 100% purified compound), reference to a particular stereochemistry at a position provides a compound having the indicated stereochemistry, but does not exclude the presence of stereoisomers having different stereochemistry at the indicated position.

Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. The separation of a mixture of stereoisomers can be carried out at an intermediate step during the synthesis of a compound of general formula (I), a compound of general formula (I'), and/or a compound of general formula (I"), or it can be done on a final racemic product. Absolute stereochemistry may be determined by X-ray crystallography of crystalline products or crystalline intermediates, which are derivatized, if necessary, with a reagent containing a stereogenic center of known configuration. Alternatively, absolute stereochemistry may be determined by Vibrational Circular Dichroism (VCD) spectroscopy analysis. The present invention includes all such isomers, as well as salts, solvates (which includes hydrates) and solvated salts of such racemates, enantiomers, diastereomers and tautomers and mixtures thereof.

Those skilled in the art will recognize that chiral compounds, and in particular sugars, can be drawn in a number of different ways that are equivalent. Those skilled in the art will further recognize that the identity and regiochemical position of the substituents on ribose can vary widely and that the same principles of stereochemical equivalence apply regardless of substituent. Non-limiting examples of such equivalence include those exemplified below.

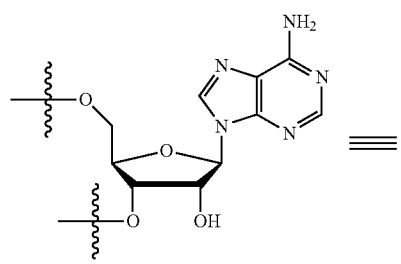
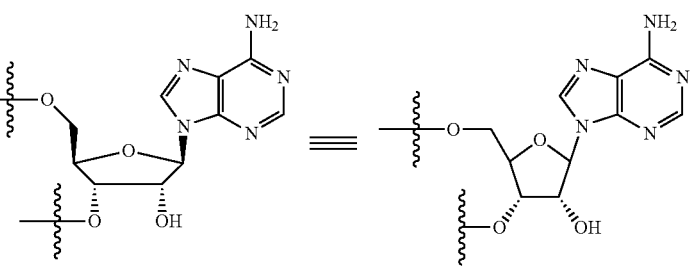
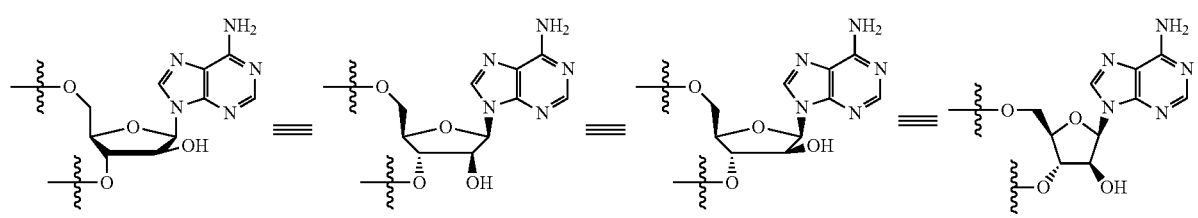

Salts

Compounds described herein having appropriate functional groups can be provided as salts. Examples of such compounds are described herein by reference to possible salts. Such reference is for illustration only. Additional embodiments include salts of any compounds described herein having suitable groups.

Pharmaceutically acceptable salts can be used with compounds for treating patients. Non-pharmaceutical salts may, however, be useful in the preparation of intermediate compounds.

Pharmaceutically acceptable salts are suitable for administration to a patient, preferably, a human. Suitable salts include acid addition salts that may, for example, be formed by mixing a solution of a compound with a solution of a pharmaceutically acceptable acid such as hydrochloric acid, sulfuric acid, acetic acid, trifluoroacetic acid, or benzoic acid. Compounds carrying an acidic moiety can be mixed with suitable pharmaceutically acceptable salts to provide, for example, alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

Methods of Preparing Compounds

Several methods for preparing the compounds of general formula (I), compounds of general formula (I'), and compounds of general formula (I"), or pharmaceutically acceptable salts, hydrates, solvates, or prodrugs thereof, are described in the following Schemes and Examples. Starting materials and intermediates are purchased from commercial sources, made from known procedures, or are otherwise illustrated. In some cases the order of carrying out the steps of the reaction schemes may be varied to facilitate the reaction or to avoid unwanted reaction products.

Method 1

One method for the preparation of examples of the disclosure is detailed in Scheme 1. This procedure was adequately modified from the previously reported procedure for cyclic dinucleotide synthesis (Barbara L. Gaffney et al., *One-Flask Syntheses of c-di-GMP and the [Rp,Rp] and [Rp,Sp] Thiophosphate Analogues*, 12 ORG. LETT. 3269-3271 (2010)). The sequence starts with modified ribo-nucleoside with a nucleobase of which amino group was appropriately protected with an alkyl or phenyl carbonyl group, a phosphoramidite functionality at 2'-O position, and DMTr ether at 5'-O position. It was treated with aqueous TFA/pyridine condition and subsequently t-butylamine to convert the 2'-phosphoramidite moiety to an H-phosphonate. Then, DMTr ether was removed under acidic condition. The resulting 5'-hydroxyl group was reacted with 3'-phosphoramidites of fully protected second modified ribo-nucleoside to give a cyclized compound. It was immediately oxidized with t-butyl hydroperoxide. Then, the 5'-hydroxyl group of the second ribo-nucleoside was deprotected with dichloroacetic acid. Using 2-chloro-5,5-dimethyl-1,3,2-dioxaphosphinane 2-oxide as a coupling reagent, the H-phosphonate at 2'-O of the first ribo-nucleoside was reacted with 5'-OH of the second ribo-nucleoside to give a cyclic product. It was immediately oxidized with aqueous iodine. Treatment with t-butylamine and methylamine plus fluoride anion in case silyl protection was used provided the desired cyclic dinucleotide 1G.

SCHEME 1

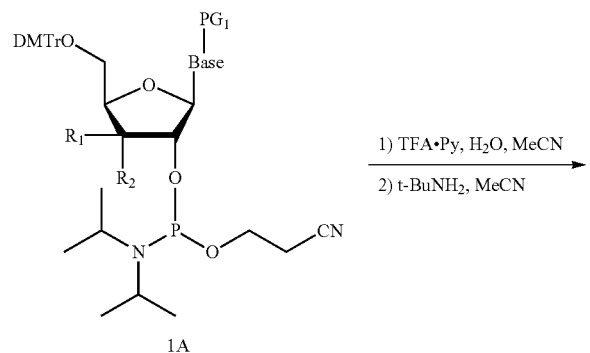

1A

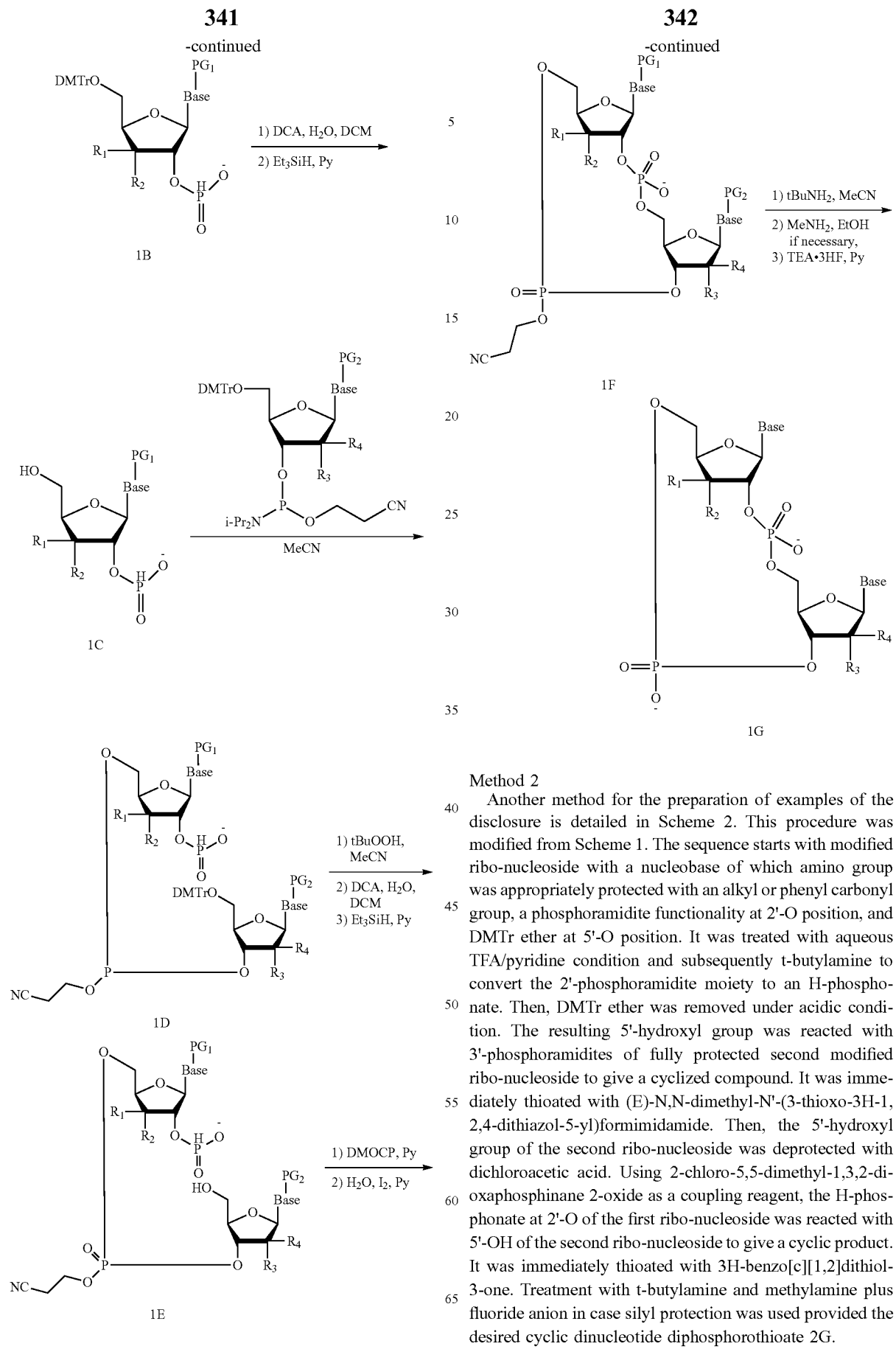

Method 2

Another method for the preparation of examples of the disclosure is detailed in Scheme 2. This procedure was modified from Scheme 1. The sequence starts with modified ribo-nucleoside with a nucleobase of which amino group was appropriately protected with an alkyl or phenyl carbonyl group, a phosphoramidite functionality at 2'-O position, and DMTr ether at 5'-O position. It was treated with aqueous TFA/pyridine condition and subsequently t-butylamine to convert the 2'-phosphoramidite moiety to an H-phosphonate. Then, DMTr ether was removed under acidic condition. The resulting 5'-hydroxyl group was reacted with 3'-phosphoramidites of fully protected second modified ribo-nucleoside to give a cyclized compound. It was immediately thioated with (E)-N,N-dimethyl-N'-(3-thioxo-3H-1,2,4-dithiazol-5-yl)formimidamide. Then, the 5'-hydroxyl group of the second ribo-nucleoside was deprotected with dichloroacetic acid. Using 2-chloro-5,5-dimethyl-1,3,2-dioxaphosphinane 2-oxide as a coupling reagent, the H-phosphonate at 2'-O of the first ribo-nucleoside was reacted with 5'-OH of the second ribo-nucleoside to give a cyclic product. It was immediately thioated with 3H-benzo[c][1,2]dithiol-3-one. Treatment with t-butylamine and methylamine plus fluoride anion in case silyl protection was used provided the desired cyclic dinucleotide diphosphorothioate 2G.

SCHEME 2

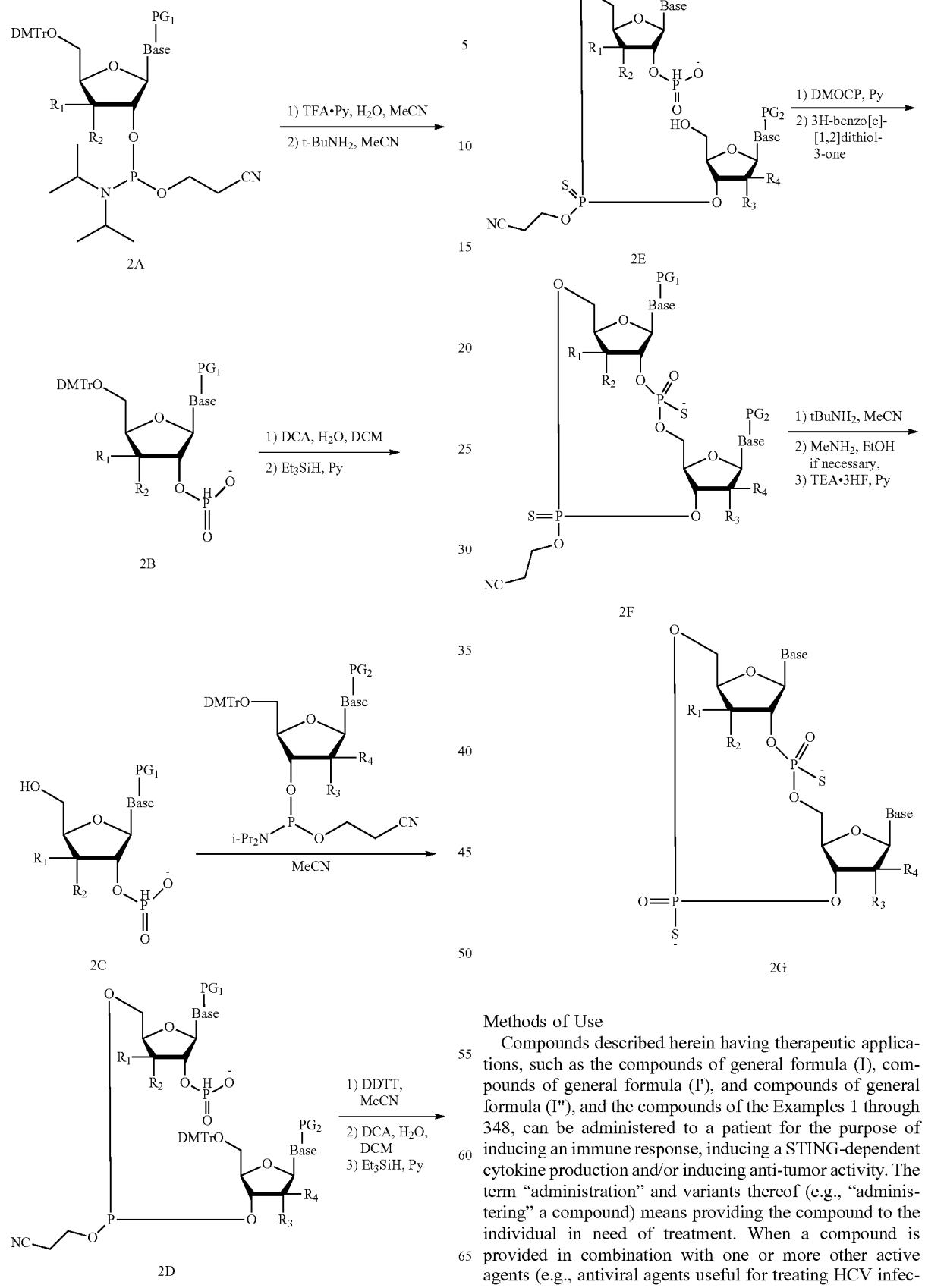

Methods of Use

Compounds described herein having therapeutic applications, such as the compounds of general formula (I), compounds of general formula (I'), and compounds of general formula (I"), and the compounds of the Examples 1 through 348, can be administered to a patient for the purpose of inducing an immune response, inducing a STING-dependent cytokine production and/or inducing anti-tumor activity. The term "administration" and variants thereof (e.g., "administering" a compound) means providing the compound to the individual in need of treatment. When a compound is provided in combination with one or more other active agents (e.g., antiviral agents useful for treating HCV infection or anti-tumor agents for treating cancers), "administration" and its variants are each understood to include concurrent and sequential provision of the compound or salt and other agents.

The compounds disclosed herein are STING agonists and inhibitors of viral replication. These compounds are potentially useful in treating diseases or disorders including, but not limited to, cell proliferation disorders, such as cancer.

Cell-proliferation disorders include, but are not limited to, cancer. Examples of such cancers include, but are not limited to, Acute Lymphoblastic Leukemia; Acute Myeloid Leukemia; Adrenocortical Carcinoma; AIDS-Related Lymphoma; AIDS-Related Malignancies; Anal Cancer; Astrocytoma; Bile Duct Cancer; Bladder Cancer; Bone Cancer, Osteosarcoma/Malignant Fibrous Histiocytoma; Brain Stem Glioma; Brain Tumor, Cerebellar Astrocytoma; Brain Tumor, Cerebral Astrocytoma/Malignant Glioma; Brain Tumor, Ependymoma; Brain Tumor, Medulloblastoma; Brain Tumor, Supratentorial Primitive Neuroectodermal Tumors; Brain Tumor, Visual Pathway and Hypothalamic Glioma; Breast Cancer; Bronchial Adenomas/Carcinoids; Carcinoid Tumor; Carcinoid Tumor, Gastrointestinal; Carcinoma, Adrenocortical; Carcinoma, Islet Cell; Central Nervous System Lymphoma, Primary; Cerebral Astrocytoma/ Malignant Glioma; Cervical Cancer; Chronic Lymphocytic Leukemia; Chronic Myelogenous Leukemia; Chronic Myeloproliferative Disorders; Clear Cell Sarcoma of Tendon Sheaths; Colon Cancer; Colorectal Cancer; Cutaneous T-Cell Lymphoma; Endometrial Cancer; Ependymoma; Epithelial Cancer, Ovarian; Esophageal Cancer; Esophageal Cancer; Ewing's Family of Tumors; Extracranial Germ Cell Tumor; Extrahepatic Bile Duct Cancer; Eye Cancer, Intraocular Melanoma; Eye Cancer, Retinoblastoma; Gallbladder Cancer; Gastric (Stomach) Cancer; Gastrointestinal Carcinoid Tumor; Germ Cell Tumor, Extracranial, Childhood; Germ Cell Tumor, Extragonadal; Germ Cell Tumor, Ovarian; Gestational Trophoblastic Tumor; Glioma, Childhood Brain Stem; Glioma, Childhood Visual Pathway and Hypothalamic; Hairy Cell Leukemia; Head and Neck Cancer; Hepatocellular (Liver) Cancer; Hodgkin's Lymphoma; Hypopharyngeal Cancer; Hypothalamic and Visual Pathway Glioma; Intraocular Melanoma; Islet Cell Carcinoma (Endocrine Pancreas); Kaposi's Sarcoma; Kidney Cancer; Laryngeal Cancer; Leukemia, Acute Lymphoblastic; Leukemia, Acute Myeloid; Leukemia, Chronic Lymphocytic; Leukemia, Chronic Myelogenous; Leukemia, Hairy Cell; Lip and Oral Cavity Cancer; Liver Cancer; Lung Cancer, Non-Small Cell; Lung Cancer, Small Cell; Lymphoblastic Leukemia; Lymphoma, AIDS-Related; Lymphoma, Central Nervous System (Primary); Lymphoma, Cutaneous T-Cell; Lymphoma, Hodgkin's; Lymphoma, Hodgkin's During Pregnancy; Lymphoma, Non-Hodgkin's; Lymphoma, Primary Central Nervous System; Macroglobulinemia, Waldenstrom's; Male Breast Cancer; Malignant Mesothelioma; Malignant Thymoma; Medulloblastoma, Childhood; Melanoma; Melanoma, Intraocular; Merkel Cell Carcinoma; Mesothelioma, Malignant; Metastatic Squamous Neck Cancer with Occult Primary; Multiple Endocrine Neoplasia Syndrome, Childhood; Multiple Myeloma/Plasma Cell Neoplasm; Mycosis Fungoides; Myelodysplastic Syndromes; Myelogenous Leukemia, Chronic; Myeloid Leukemia; Myeloma, Multiple; Myeloproliferative Disorders, Chronic; Nasal Cavity and Paranasal Sinus Cancer; Nasopharyngeal Cancer; Neuroblastoma; Non-Hodgkin's Lymphoma; Non-Small Cell Lung Cancer; Oral Cancer; Oral Cavity and Lip Cancer; Oropharyngeal Cancer; steosarcoma/Malignant Fibrous Histiocytoma of Bone; Ovarian Epithelial Cancer; Ovarian Germ Cell Tumor; Ovarian Low Malignant Potential Tumor; Pancreatic Cancer; Paranasal Sinus and Nasal Cavity Cancer; Parathyroid Cancer; Penile Cancer; Pheochromocytoma; Pineal and Supratentorial Primitive Neuroectodermal Tumors; Pituitary Tumor; Plasma Cell Neoplasm/Multiple Myeloma; Pleuropulmonary Blastoma; Pregnancy and Breast Cancer; Pregnancy and Hodgkin's Lymphoma; Pregnancy and Non-Hodgkin's Lymphoma; Primary Central Nervous System Lymphoma; Primary Liver Cancer; Prostate Cancer; Rectal Cancer; Renal Cell (Kidney) Cancer; Renal Pelvis and Ureter, Transitional Cell Cancer; Retinoblastoma; Rhabdomyosarcoma; Salivary Gland Cancer; Sarcoma, Ewing's Family of Tumors; Sarcoma, Kaposi's; Sarcoma (Osteosarcoma)/Malignant Fibrous Histiocytoma of Bone; Sarcoma, Soft Tissue; Sezary Syndrome; Skin Cancer; Skin Cancer (Melanoma); Skin Carcinoma, Merkel Cell; Small Cell Lung Cancer; Small Intestine Cancer; Soft Tissue Sarcoma; Squamous Neck Cancer with Occult Primary, Metastatic; Stomach (Gastric) Cancer; Supratentorial Primitive Neuroectodermal Tumors; T-Cell Lymphoma, Cutaneous; Testicular Cancer; Thymoma, Malignant; Thyroid Cancer; Transitional Cell Cancer of the Renal Pelvis and Ureter; Trophoblastic Tumor, Gestational; Ureter and Renal Pelvis, Transitional Cell Cancer; Urethral Cancer; Uterine Sarcoma; Vaginal Cancer; Visual Pathway and Hypothalamic Glioma; Vulvar Cancer; Waldenstrom's Macro globulinemia; and Wilms' Tumor.

In one embodiment, the cancer is brain cancer, such as an astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma); oligodendroglial tumor (e.g., oligodendroglioma, and anaplastic oligodendroglioma); oligoastrocytic tumor (e.g., oligoastrocytoma, and anaplastic oligoastrocytoma); ependymoma (e.g., myxopapillary ependymoma, and anaplastic ependymoma); medulloblastoma; primitive neuroectodermal tumor, schwannoma, meningioma, atypical meningioma, anaplastic meningioma; and pituitary adenoma. In another embodiment, the brain cancer is glioma, glioblastoma multiforme, paraganglioma, or supratentorial primordial neuroectodermal tumors (sPNET).

In another embodiment, the cancer is leukemia, such as acute myeloid leukemia (AML), myelodysplastic syndrome (MDS), chronic myelogenous leukemia (CML), myeloproliferative neoplasm (MPN), post-MPN AML, post-MDS AML, del(5q)-associated high risk MDS or AML, blast-phase chronic myelogenous leukemia, angioimmunoblastic lymphoma, and acute lymphoblastic leukemia.

In one embodiment, the cancer is skin cancer, including melanoma. In another embodiment, the cancer is prostate cancer, breast cancer, thyroid cancer, colon cancer, or lung cancer. In another embodiment, the cancer is sarcoma, including central chondrosarcoma, central and periosteal chondroma, and fibrosarcoma. In another embodiment, the cancer is cholangiocarcinoma.

As used herein, the terms "treatment" and "treating" refer to all processes wherein there may be a slowing, interrupting, arresting, controlling, or stopping of the progression of a disease or disorder described herein. The terms do not necessarily indicate a total elimination of all disease or disorder symptoms.

The terms "administration of" and or "administering" a compound should be understood to include providing a compound described herein, or a pharmaceutically acceptable salt, hydrate, solvate or prodrug thereof, and compositions of the foregoing to a subject.

The amount of a compound administered to a subject is an amount sufficient to induce an immune response and/or to induce STING-dependent type I interferon production in the subject.

In an embodiment, the amount of a compound can be an "effective amount" or "therapeutically effective amount," wherein the subject compound is administered in an amount that will elicit, respectively, a biological or medical (i.e., intended to treat) response of a tissue, system, animal or human that is being sought by a researcher, veterinarian, medical doctor or other clinician. An effective amount does not necessarily include considerations of toxicity and safety related to the administration of a compound.

An effective amount of a compound will vary with the particular compound chosen (e.g., considering the potency, efficacy, and/or half-life of the compound); the route of administration chosen; the condition being treated; the severity of the condition being treated; the age, size, weight, and physical condition of the subject being treated; the medical history of the subject being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life which can be determined by a skilled artisan. In addition, suitable dosing regimens, including the duration such regimens are administered, for a compound disclosed herein depend on the disease or condition being treated, the severity of the disease or condition, the age and physical condition of the subject being treated, the medical history of the subject being treated, the nature of concurrent therapy, the desired therapeutic effect, and like factors within the knowledge and expertise of the skilled artisan. It will be further understood by such skilled artisans that suitable dosing regimens may require adjustment given an individual subject's response to the dosing regimen or over time as the individual subject needs change. Typical daily dosages may vary depending upon the particular route of administration chosen.

One embodiment of the present disclosure provides for a method of treating a cell proliferation disorder comprising administration of a therapeutically effective amount of a compound of general formula (I), a compound of general formula (I'), or a compound of general formula (I") to a subject in need of treatment thereof. In one embodiment, the cell proliferation disorder is cancer.

In one embodiment, the cancer is brain cancer, leukemia, skin cancer, prostate cancer, thyroid cancer, colon cancer, lung cancer or sarcoma. In another embodiment the cancer is selected from the group consisting of glioma, glioblastoma multiforme, paraganglioma, suprantentorial primordial neuroectodermal tumors, acute myeloid leukemia, myelodysplastic syndrome, chronic myelogenous leukemia, melanoma, breast, prostate, thyroid, colon, lung, central chondrosarcoma, central and periosteal chondroma tumors, fibrosarcoma, and cholangiocarcinoma.

In one embodiment, disclosed herein is the use of a compound of general formula (I), compound of general formula (I'), and/or compound of general formula (I"), or a pharmaceutically acceptable salt, hydrate, solvate or prodrug thereof, in a therapy. The compound may be useful in a method of inducing an immune response and/or inducing STING-dependent type I interferon production in a subject, such as a mammal in need of such inhibition, comprising administering an effective amount of the compound to the subject.

In one embodiment, disclosed herein is a pharmaceutical composition comprising at least one compound of general formula (I), compound of general formula (I'), and/or compound of general formula (I"), or a pharmaceutically acceptable salt, hydrate, solvate or prodrug thereof, for use in potential treatment to induce an immune response and/or to induce STING-dependent type I interferon production.

In one embodiment, disclosed herein is the use of a compound of general formula (I), compound of general formula (I'), and/or compound of general formula (I"), or a pharmaceutically acceptable salt, hydrate, solvate or prodrug thereof, in the manufacture of a medicament for the treatment to induce an immune response and/or to induce STING-dependent type I interferon production. In one embodiment, the disease or disorder to be treated is a cell proliferation disorder. In another embodiment, the cell proliferation disorder is cancer. In another embodiment, the cancer is brain cancer, leukemia, skin cancer, breast, prostate cancer, thyroid cancer, colon cancer, lung cancer, or sarcoma. In another embodiment, the cancer is glioma, glioblastoma multiforme, paraganglioma, suprantentorial primordial neuroectodermal tumors, acute myeloid leukemia, myelodysplastic syndrome, chronic myelogenous leukemia, melanoma, breast, prostate, thyroid, colon, lung, central chondrosarcoma, central and periosteal chondroma tumors, fibrosarcoma, and/or cholangiocarcinoma.

Compositions

The term "composition" as used herein is intended to encompass a dosage form comprising a specified compound in a specified amount, as well as any dosage form which results, directly or indirectly, from combination of a specified compound in a specified amount. Such term is intended to encompass a dosage form comprising a compound of general formula (I), a compound of general formula (I'), and/or a compound of general formula (I"), or a pharmaceutically acceptable salt, hydrate, solvate, or prodrug thereof, and one or more pharmaceutically acceptable carriers or excipients. Accordingly, the compositions of the present disclosure encompass any composition made by admixing a compound of the present disclosure and one or more pharmaceutically acceptable carrier or excipients. By "pharmaceutically acceptable", it is meant the carriers or excipients are compatible with the compound disclosed herein and with other ingredients of the composition.

For the purpose of inducing an immune response and/or inducing a STING-dependent type I interferon production, the compounds, optionally in the form of a salt, hydrate, solvate or prodrug, can be administered by means that produces contact of the active agent with the agent's site of action. They can be administered by conventional means available for use in conjunction with pharmaceuticals, either as individual therapeutic agents or in a combination of therapeutic agents. They can be administered alone, but typically are administered with a pharmaceutical carrier selected on the basis of the chosen route of administration and standard pharmaceutical practice.

In one embodiment, disclosed herein is a composition comprising a compound of general formula (I), a compound of general formula (I'), and/or a compound of general formula (I"), or a pharmaceutically acceptable salt thereof, and one or more pharmaceutically acceptable carriers or excipients. The composition may be prepared and packaged in bulk form wherein an effective amount of a compound of the disclosure can be extracted and then given to a subject, such as with powders or syrups. Alternatively, the composition may be prepared and packaged in unit dosage form wherein each physically discrete unit contains an effective amount of a compound of general formula (I), a compound of general formula (I'), and/or a compound of general formula (I").

The compounds disclosed herein and a pharmaceutically acceptable carrier or excipient(s) will typically be formulated into a dosage form adapted for administration to a subject by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the subject, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the disclosure. In addition, there are a number of resources available to the skilled artisan, which describe pharmaceutically acceptable carriers and excipients and may be useful in selecting suitable pharmaceutically acceptable carriers and excipients. Examples include Remington's Pharmaceutical Sciences (Mack Publishing Company), The Handbook of Pharmaceutical Additives (Gower Publishing Limited), and The Handbook of Pharmaceutical Excipients (the American Pharmaceutical Association and the Pharmaceutical Press).

The compositions of the disclosure are prepared using techniques and methods known to those skilled in the art. Some methods commonly used in the art are described in Remington's Pharmaceutical Sciences (Mack Publishing Company).

In one embodiment, the disclosure is directed to a solid oral dosage form such as a tablet or capsule comprising an effective amount of a compound of the disclosure and a diluent or filler. Suitable diluents and fillers include lactose, sucrose, dextrose, mannitol, sorbitol, starch (e.g., corn starch, potato starch, and pre-gelatinized starch), cellulose and its derivatives, (e.g., microcrystalline cellulose), calcium sulfate, and dibasic calcium phosphate. The oral solid dosage form may further comprise a binder. Suitable binders include starch (e.g., corn starch, potato starch, and pre-gelatinized starch) gelatin, acacia, sodium alginate, alginic acid, tragacanth, guar gum, povidone, and cellulose and its derivatives (e.g., microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the disclosure may be coupled to a class of biodegradable polymers useful in achieving controlled release of a drug, for example polylactic acid, polepsilon caprolactone, polyhydroxy butyric acid, polyorthoesters, polyacetals, polydihydropyrans, polycyanacrylates and cross-linked or amphipathic block copolymers of hydrogels.

In one embodiment, the disclosure is directed to a liquid oral dosage form. Oral liquids such as solution, syrups and elixirs can be prepared in dosage unit form so that a given quantity contains a predetermined amount of a compound disclosed herein. Syrups can be prepared by dissolving the compound of the disclosure in a suitably flavored aqueous solution; while elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil or other natural sweeteners or saccharin or other artificial sweeteners and the like can also be added.

In one embodiment, the disclosure is directed to compositions for parenteral administration. Compositions adapted for parenteral administration include aqueous and non-aqueous sterile injection solutions which may contain antioxidants, buffers, bacteriostats, and solutes that render the formulation isotonic with the blood of the intended recipient; and aqueous and non-aqueous sterile suspensions that may include suspending agents and thickening agents. The compositions may be presented in unit-dose or multi-dose containers, for example sealed ampoules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules and tablets.

Combinations

The compounds of general formula (I), compounds of general formula (I'), and/or compounds of general formula (I"), or pharmaceutically acceptable salt, hydrate, solvate, or prodrug thereof, may be administered in combination with one or more additional therapeutic agents. In embodiments, one or more a compound of general formula (I), compound of general formula (I'), or compound of general formula (I"), or pharmaceutically acceptable salt, hydrate, solvate, or prodrug thereof, and the one or more additional therapeutic agents may be co-adminstered. The additional therapeutic agent(s) may be administered in a single dosage form with the compound of general formula (I), compound of general formula (I'), or compound of general formula (I"), or pharmaceutically acceptable salt, hydrate, solvate, or prodrug thereof, or the additional therapeutic agent(s) may be administered in separate dosage form(s) from the dosage form containing the compound of general formula (I), compound of general formula (I'), or compound of general formula (I"), or pharmaceutically acceptable salt, hydrate, solvate, or prodrug thereof. The additional therapeutic agent(s) may be one or more agents selected from the group consisting of STING agonist compounds, anti-viral compounds, antigens, adjuvants, anti-cancer agents, CTLA-4, LAG-3 and PD-1 pathway antagonists, lipids, peptides, cytotoxic agents, chemotherapeutic agents, immunomodulatory cell lines, checkpoint inhibitors, vascular endothelial growth factor (VEGF) receptor inhibitors, topoisomerase II inhibitors, smoothen inhibitors, alkylating agents, anti-tumor antibiotics, antimetabolites, retinoids, and immunomodulatory agents including but not limited to anti-cancer vaccines. It will be understood the descriptions of the above additional therapeutic agents may be overlapping. It will also be understood that the treatment combinations are subject to optimization, and it is understood that the best combination to use of the compounds of general formula (I), compounds of general formula (I'), or compounds of general formula (I") and one or more additional therapeutic agents will be determined based on the individual patient needs.

A compound disclosed herein may be used in combination with one or more other active agents, including but not limited to, other anti-cancer agents that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present disclosure.

When a compound disclosed herein is used contemporaneously with one or more other active agents, a composition containing such other active agents in addition to the compound disclosed herein is contemplated. Accordingly, the compositions of the present disclosure include those that also contain one or more other active ingredients, in addition to a compound disclosed herein. A compound disclosed herein may be administered either simultaneously with, or before or after, one or more other therapeutic agent(s). A compound disclosed herein may be administered separately, by the same or different route of administration, or together in the same pharmaceutical composition as the other agent(s).

Products provided as combinations may include a composition comprising a compound of general formula (I), compound of general formula (I'), or compound of general formula (I"), or pharmaceutically acceptable salt, hydrate, solvate, or prodrug thereof, and one or more other active agent(s) together in the same pharmaceutical composition, or may include a composition comprising a compound of general formula (I), compound of general formula (I'), or compound of general formula (I"), or pharmaceutically acceptable salt, hydrate, solvate, or prodrug thereof, and a composition comprising one or more other therapeutic agent(s) in separate form, e.g. in the form of a kit or in any form designed to enable separate administration either concurrently or on separate dosing schedules.

The weight ratio of a compound disclosed herein to a second active agent may be varied and will depend upon the effective dose of each agent. Generally, an effective dose of each will be used. Combinations of a compound disclosed herein and other active agents will generally also be within the aforementioned range, but in each case, an effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, this disclosure provides a composition comprising a compound of general formula (I), compound of general formula (I'), or compound of general formula (I"), or pharmaceutically acceptable salt, hydrate, solvate, or prodrug thereof, and at least one other therapeutic agent as a combined preparation for simultaneous, separate or sequential use in therapy. In one embodiment, the therapy is the treatment of a cell proliferation disorder, such as cancer.

In one embodiment, the disclosure provides a kit comprising two or more separate pharmaceutical compositions, at least one of which contains a compound of general formula (I), compound of general formula (I'), or compound of general formula (I"), or pharmaceutically acceptable salt, hydrate, solvate, or prodrug thereof. In one embodiment, the kit comprises means for separately retaining said compositions, such as a container, divided bottle, or divided foil packet. An example of such a kit is a blister pack, as typically used for the packaging of tablets, capsules, and the like.

A kit of this disclosure may be used for administration of different dosage forms, for example, oral and parenteral, for administration of the separate compositions at different dosage intervals, or for titration of the separate compositions against one another. To assist with compliance, a kit of the disclosure typically comprises directions for administration.

Disclosed herein is a use of a compound of general formula (I), compound of general formula (I'), or compound of general formula (I"), or pharmaceutically acceptable salt, hydrate, solvate, or prodrug thereof, for treating a cell proliferation disorder, wherein the medicament is prepared for administration with another active agent. The disclosure also provides the use of another active agent for treating a cell proliferation disorder, wherein the medicament is administered with a compound of general formula (I).

The disclosure also provides the use of a compound of general formula (I), compound of general formula (I'), or compound of general formula (I"), or pharmaceutically acceptable salt, hydrate, solvate, or prodrug thereof, for treating a cell proliferation disorder, wherein the patient has previously (e.g., within 24 hours) been treated with another active agent. The disclosure also provides the use of another therapeutic agent for treating a cell proliferation disorder, wherein the patient has previously (e.g., within 24 hours) been treated with a compound of general formula (I), compound of general formula (I'), or compound of general formula (I"), or pharmaceutically acceptable salt, hydrate, solvate, or prodrug thereof. The second agent may be applied a week, several weeks, a month, or several months after the administration of a compound disclosed herein.

STING agonist compounds that may be used in combination with the compounds of general formula (I), compounds of general formula (I'), and compounds of general formula (I") disclosed herein include but are not limited to cyclic di-nucleotide compounds.

Anti-viral compounds that may be used in combination with the compounds of general formula (I), compounds of general formula (I'), and compounds of general formula (I") disclosed herein include hepatitis B virus (HBV) inhibitors, hepatitis C virus (HCV) protease inhibitors, HCV polymerase inhibitors, HCV NS4 Å inhibitors, HCV NS5A inhibitors, HCV NS5b inhibitors, and human immunodeficiency virus (HIV) inhibitors.

Antigens and adjuvants that may be used in combination with the compounds of general formula (I), compounds of general formula (I'), and compounds of general formula (I") disclosed herein include B7 costimulatory molecule, interleukin-2, interferon-γ, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryllipid A, lipoteichoic acid, imiquimod, resiquimod, and in addition retinoic acid-inducible gene I (RIG-I) agonists such as poly I:C, used separately or in combination with the described compositions are also potential adjuvants.

CLTA-4 and PD-1 pathways are important negative regulators of immune response. Activated T-cells upregulate CTLA-4, which binds on antigen-presenting cells and inhibits T-cell stimulation, IL-2 gene expression, and T-cell proliferation; these anti-tumor effects have been observed in mouse models of colon carcinoma, metastatic prostate cancer, and metastatic melanoma. PD-1 binds to active T-cells and suppresses T-cell activation; PD-1 antagonists have demonstrated anti-tumor effects as well. CTLA-4 and PD-1 pathway antagonists that may be used in combination with the compounds of general formula (I) disclosed herein include ipilimumab, tremelimumab, nivolumab, pembrolizumab, CT-011, AMP-224, and MDX-1106.

"PD-1 antagonist" or "PD-1 pathway antagonist" means any chemical compound or biological molecule that blocks binding of PD-L1 expressed on a cancer cell to PD-1 expressed on an immune cell (T-cell, B-cell, or NKT-cell) and preferably also blocks binding of PD-L2 expressed on a cancer cell to the immune-cell expressed PD-1. Alternative names or synonyms for PD-1 and its ligands include: PDCD1, PD1, CD279, and SLEB2 for PD-1; PDCD1L1, PDL1, B7H1, B7-4, CD274, and B7-H for PD-L1; and PDCD1L2, PDL2, B7-DC, Btdc, and CD273 for PD-L2. In any of the treatment method, medicaments and uses of the present disclosure in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present disclosure include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody, or a chimeric antibody and may include a human constant region. In some embodiments, the human constant region is selected from the group consisting of IgG1, IgG2, IgG3, and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv, and Fv fragments.

Examples of mAbs that bind to human PD-1, and useful in the treatment method, medicaments and uses of the present disclosure, are described in U.S. Pat. Nos. 7,488, 802, 7,521,051, 8,008,449, 8,354,509, and 8,168,757, PCT International Patent Application Publication Nos. WO2004/004771, WO2004/072286, and WO2004/056875, and U.S. Patent Application Publication No. US2011/0271358.

Examples of mAbs that bind to human PD-L1, and useful in the treatment method, medicaments and uses of the present disclosure, are described in PCT International Patent Application Nos. WO2013/019906 and WO2010/077634 A1 and in U.S. Pat. No. 8,383,796. Specific anti-human PD-L1 mAbs useful as the PD-1 antagonist in the treatment method, medicaments and uses of the present disclosure include MPDL3280A, BMS-936559, MEDI4736, MSB0010718C, and an antibody that comprises the heavy chain and light chain variable regions of SEQ ID NO:24 and SEQ ID NO:21, respectively, of WO2013/019906.

Other PD-1 antagonists useful in any of the treatment method, medicaments, and uses of the present disclosure include an immune-adhesion that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immune-adhesion molecules that specifically bind to PD-1 are described in PCT International Patent Application Publication Nos. WO2010/027827 and WO2011/066342. Specific fusion proteins useful as the PD-1 antagonist in the treatment method, medicaments, and uses of the present disclosure include AMP-224 (also known as B7-DCIg), which is a PD-L2-FC fusion protein and binds to human PD-1.

Examples of cytotoxic agents that may be used in combination with the compounds of general formula (I), compounds of general formula (I'), and compounds of general formula (I"), or pharmaceutically acceptable salts, hydrates, solvates, or prodrugs thereof, disclosed herein include, but are not limited to, arsenic trioxide (sold under the tradename TRISENOX®), asparaginase (also known as L-asparaginase, and Erwinia L-asparaginase, sold under the tradenames ELSPAR® and KIDROLASE®).

Chemotherapeutic agents that may be used in combination with the compounds of general formula (I), compounds of general formula (I'), and compounds of general formula (I"), or pharmaceutically acceptable salts, hydrates, solvates, or prodrugs thereof, disclosed herein include abiraterone acetate, altretamine, anhydrovinblastine, auristatin, bexarotene, bicalutamide, BMS 184476, 2,3,4,5,6-pentafluoro-N-(3-fluoro-4-methoxyphenyl)benzene sulfonamide, bleomycin, N,N-dimethyl-L-valyl-L-valyl-N-methyl-L-valyl-L-proly-1-Lproline-tbutylamide, cachectin, cemadotin, chlorambucil, cyclophosphamide, 3',4'-didehydro-4'deoxy-8'-norvin-caleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyureataxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, nivolumab, onapristone, paclitaxel, pembrolizumab, prednimustine, procarbazine, RPR109881, stramustine phosphate, tamoxifen, tasonermin, taxol, tretinoin, vinblastine, vincristine, vindesine sulfate, and vinflunine.

Examples of vascular endothelial growth factor (VEGF) receptor inhibitors include, but are not limited to, bevacizumab (sold under the trademark AVASTIN by Genentech/Roche), axitinib (described in PCT International Patent Publication No. WO01/002369), Brivanib Alaninate ((S)-((R)-1-(4-(4-Fluoro-2-methyl-1H-indol-5-yloxy)-5-methyl-pyrrolo[2,1-f][1,2,4]triazin-6-yloxy)propan-2-yl)2-amino-propanoate, also known as BMS-582664), motesanib (N-(2,3-dihydro-3,3-dimethyl-1H-indol-6-yl)-2-[(4-pyridinylmethyl)amino]-3-pyridinecarboxamide. and described in PCT International Patent Application Publication No. WO02/068470), pasireotide (also known as SO 230, and described in PCT International Patent Publication No. WO02/010192), and sorafenib (sold under the tradename NEXAVAR).

Examples of topoisomerase II inhibitors, include but are not limited to, etoposide (also known as VP-16 and Etoposide phosphate, sold under the tradenames TOPOSAR, VEPESID, and ETOPOPHOS), and teniposide (also known as VM-26, sold under the tradename VUMON).

Examples of alkylating agents, include but are not limited to, 5-azacytidine (sold under the trade name VIDAZA), decitabine (sold under the trade name of DECOGEN), temozolomide (sold under the trade names TEMODAR and TEMODAL by Schering-Plough/Merck), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX® and MYLERAN®), carboplatin (sold under the tradename PARAPLATIN®), lomustine (also known as CCNU, sold under the tradename CEENU®), cisplatin (also known as CDDP, sold under the tradenames PLATINOL® and PLATINOL®-AQ), chlorambucil (sold under the tradename LEUKERAN®), cyclophosphamide (sold under the tradenames CYTOXAN® and NEOSAR®), dacarbazine (also known as DTIC, DIC and imidazole carboxamide, sold under the tradename DTIC-DOME®), altretamine (also known as hexamethylmelamine (HMM) sold under the tradename HEXALEN®), ifosfamide (sold under the tradename IFEX®), procarbazine (sold under the tradename MATULANE®), mechlorethamine (also known as nitrogen mustard, mustine and mechloroethamine hydrochloride, sold under the tradename MUSTARGEN®), streptozocin (sold under the tradename ZANOSAR®), thiotepa (also known as thiophosphoamide, TESPA and TSPA, and sold under the tradename THIOPLEX®.

Examples of anti-tumor antibiotics include, but are not limited to, doxorubicin (sold under the tradenames ADRIAMYCIN® and RUBEX®), bleomycin (sold under the tradename LENOXANE®), daunorubicin (also known as dauorubicin hydrochloride, daunomycin, and rubidomycin hydrochloride, sold under the tradename CERUBIDINE®), daunorubicin liposomal (daunorubicin citrate liposome, sold under the tradename DAUNOXOME®), mitoxantrone (also known as DHAD, sold under the tradename NOVANTRONE®), epirubicin (sold under the tradename ELLENCE™), idarubicin (sold under the tradenames IDAMYCIN®, IDAMYCIN PFS®), and mitomycin C (sold under the tradename MUTAMYCIN®).

Examples of anti-metabolites include, but are not limited to, claribine (2-chlorodeoxyadenosine, sold under the tradename LEUSTATIN®), 5-fluorouracil (sold under the tradename ADRUCIL®), 6-thioguanine (sold under the tradename PURINETHOL®), pemetrexed (sold under the tradename ALIMTA®), cytarabine (also known as arabinosylcytosine (Ara-C), sold under the tradename CYTOSAR-U®), cytarabine liposomal (also known as Liposomal Ara-C, sold under the tradename DEPOCYT™), decitabine (sold under the tradename DACOGEN®), hydroxyurea (sold under the tradenames HYDREA®, DROXIA™ and MYLOCEL™), fludarabine (sold under the tradename FLUDARA®), floxuridine (sold under the tradename FUDR®), cladribine (also known as 2-chlorodeoxyadenosine (2-CdA) sold under the tradename LEUSTATIN™), methotrexate (also known as amethopterin, methotrexate sodium (MTX), sold under the tradenames RHEUMATREX® and TREXALL™), and pentostatin (sold under the tradename NIPENT®).

Examples of retinoids include, but are not limited to, alitretinoin (sold under the tradename PANRETIN®), tretinoin (all-trans retinoic acid, also known as ATRA, sold under the tradename VESANOID®), Isotretinoin (13-c/s-retinoic acid, sold under the tradenames ACCUTANE®, AMNESTEEM®, CLARAVIS®, CLARUS®, DECUTAN®, ISOTANE®, IZOTECH®, ORATANE®, ISOTRET®, and SOTRET®), and bexarotene (sold under the tradename TARGRETIN®).

Activity: STING Biochemical [3H]cGAMP Competition Assay

The individual compounds described in the Examples herein are defined as STING agonists by demonstrating binding to the STING protein with an $EC_{50}$ of 20 uM or less in the STING Biochemical [3H]cGAMP Competition Assay and demonstrating interferon production with a 20% or greater luminescence induction at 30 uM in the IFN-β secretion in the THP1 cell assay.

The ability of compounds to bind STING is quantified by the ability to compete with tritiated cGAMP ligand for human STING receptor membrane using a radioactive filter-binding assay. The binding assay employs STING receptor obtained from Hi-Five cell membranes overexpressing full-length HAQ STING prepared in-house and tritiated cGAMP ligand also purified in-house.

Abbreviations

1H-NMR Proton nuclear magnetic resonance spectroscopy
19F-NMR 19F nuclear magnetic resonance spectroscopy
31P-NMR 31P nuclear magnetic resonance spectroscopy
Å Angstrom
$A^{Bz}$ 6-N-benzoyladenine
aq Aqueous
Ar Argon
ATP Adenosine 5'-triphosphate
Bz Benzoyl
$CD_3OD$ Deuterium-enriched methyl alcohol, deuterium-enriched methanol
$CHCl_3$ Trichloromethane
Ci Curie, a non-standard unit of radioactivity; 1 Ci=3.7× $10^{10}$Bq, where Bq is Becquerel, the SI unit of radioactivity, equivalent to 1 disintegration per second (dps)
$CO_2$ Carbon dioxide
d Doublet
d Day(s)
$D_2O$ Deuterium-enriched water
DCA Dichloroacetic acid
DCM, $CH_2Cl_2$ Dichloromethane
ddd Doublet of doublet of doublet
ddt Doublet of doublet of triplet
DDTT (E)-N,N-dimethyl-N'-(3-thioxo-3H-1,2,4-dithiazol-5-yl)formimidamide
DMF N,N-dimethylformamide
DMOCP 2-chloro-5,5-dimethyl-1,3,2-dioxaphosphineane 2-oxide
DMSO Dimethyl sulfoxide
DMTr 4,4'-dimethoxytrityl
DMTrCl 4,4'-dimethoxytrityl chloride
dq Doublet of quartet
$EC_{50}$ half maximal effective concentration, concentration of a drug, antibody or toxicant that induces a response halfway between the baseline and maximum after a specified exposure time
eq Equivalents
ES Electron spray
Et Ethyl
$Et_2O$ Diethyl ether
$Et_3$ SiH Triethylsilane
EtOAc Ethyl acetate
EtOH Ethyl alcohol, ethanol
g Gram
GTP Guanosine 5'-triphosphate
h Hour
$H_2O$ Water
HEPES 2-[4-(2-hydroxyethyl)piperazin 1-yl]ethanesulfonic acid, a zwitterionic organic chemical buffering agent
hept Heptet
Hex Hexanes
HF-Pyr Hydrogen fluoride-pyridine complex
HPLC High performance liquid chromatography
Hz Hertz
ITP Inosine 5'-triphosphate
J NMR Coupling constant
LCMS Liquid chromatography-mass spectroscopy
m Multiplet
M Molar, moles per liter
mCi Millicurie
Me Methyl
MeCN Acetonitrile
$MeNH_2$ Methylamine
mg Milligram
$MgCl_2$ Magnesium chloride
MHz Megahertz
min Minute(s)
mL, ml Milliliter
mM Millimole per liter
mmol Millimole
MOI Multiplicity of infection
MPLC Medium pressure liquid chromatography
MTBE Methyl t-butyl ether, methyl tertiary butyl ether
$Na_2SO_4$ Sodium sulfate
NaCl Sodium chloride
$NaHCO_3$ Sodium bicarbonate
$NaHSO_3$ Sodium bisulfite
NaOH Sodium hydroxide
ng Nanogram(s)
$NH_4HCO_3$ Ammonium bicarbonate
$NH_4OH$ Ammonium hydroxide
nL Nanoliter
nm Nanometer
nM Nanomolar
$P_2O_5$ Phosphorus pentoxide
Py Pyridine
q Quartet
RPM, rpm Revolutions per minute
RT, rt Room temperature, approximately 25° C.
s Singlet
sat Saturated
t Triplet
TB S t-Butyldimethylsilyl
TMA Trimethylamine
TEA, $Et_3N$ Triethylamine
TFA Trifluoroacetic acid
TLC Thin layer chromatography
TMSCl Trimethylsilyl chloride
$T_R$ Retention time
TrisCl Tris(hydroxymethyl)aminomethane hydrochloride
v/v Volume/volume
$\lambda_{em}$ Emission wavelength
$\lambda_{ex}$ Excitation wavelength
μg Microgram
μL, uL Microliter
μM, uM Micromolar Preparation 1: N-(3-((2R,3S,4R,5R)-5-((bis(4-methoxyphenyl)(phenyl)methoxy)-methyl)-3-fluoro-4-hydroxytetrahydrofuran-2-yl)-3H-[1,2,3]triazolo[4,5-d]pyrimidin-7-yl)benzamide

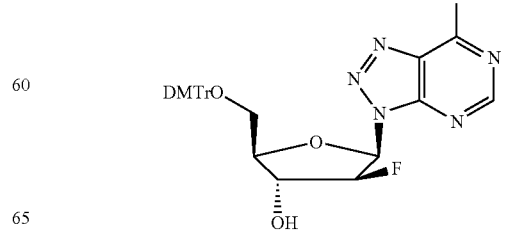

Step 1: (2R,3R,4S,5R)-5-(7-amino-3H-[1,2,3]triazolo[4,5-d]pyrimidin-3-yl)-2-((benzoyloxy)methyl)-4-fluorotetrahydrofuran-3-yl benzoate

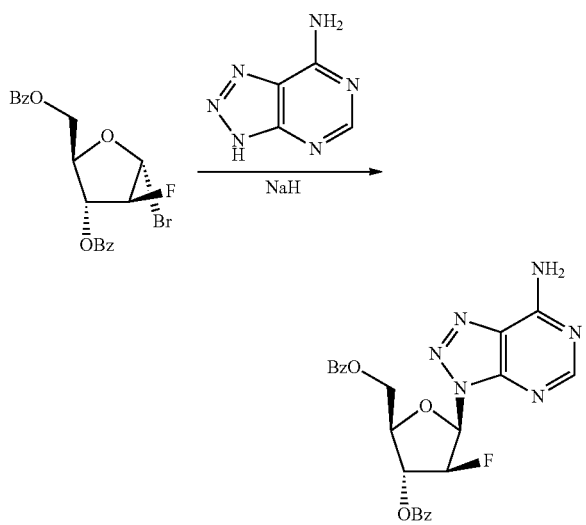

To a mixture of 3H-[1,2,3]triazolo[4,5-d]pyrimidin-7-amine (2.36 g, 17.4 mmol) in NMP (50 ml) was added NaH (60%, 0.744 g, 18.6 mmol). The mixture was vigorously stirred and after 1 h, generation of bubbles had completely ceased. The mixture was added to ((2R,3R,4S,5R)-3-(benzoyloxy)-5-bromo-4-fluorotetrahydrofuran-2-yl)methyl benzoate (neat, 5.25 g, 12.4 mmol) in one portion. The reaction was stirred for 18 h. LCMS showed several peaks with the desired mass (m/e=479). EtOAc (70 mL) and water (70 mL) were added to the reaction. Layers were separated, and the organic layer was washed with half saturated brine (3×10 mL) and brine (1×10 mL), dried (MgSO₄), and concentrated. The crude was purified via silica column eluting with 0 to 50% EtOAc in Hex to give the product. LCMS (ES, m/z): 479.3 [M+H]⁺. ¹H-NMR (500 MHz, DMSO-d₆): δ 8.62 (s, 1H), 8.34 (s, 1H), 8.28 (s, 1H), 8.10-8.04 (m, 2H), 7.97-7.90 (m, 2H), 7.77-7.69 (m, 1H), 7.67-7.55 (m, 3H), 7.49-7.42 (m, 2H), 6.97 (dd, J=6.5, 3.1 Hz, 1H), 6.49 (dt, J=17.6, 6.9 Hz, 1H), 6.16 (dt, J=56, 6.6 Hz, 1H), 4.76-4.62 (m, 3H).

Step 2. (2R,3R,4S,5R)-5-(7-amino-3H-[1,2,3]triazolo[4,5-d]pyrimidin-3-yl)-4-fluoro-2-(hydroxymethyl)tetrahydrofuran-3-ol

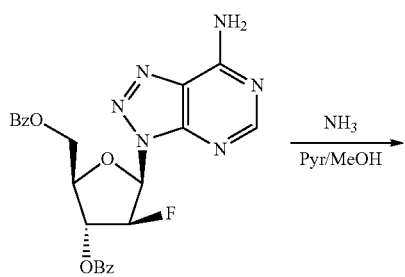

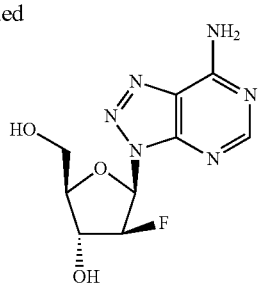

To a solution of (2R,3R,4S,5R)-5-(7-amino-3H-[1,2,3]triazolo[4,5-d]pyrimidin-3-yl)-2-((benzoyloxy)methyl)-4-fluorotetrahydrofuran-3-yl benzoate (2.00 g, 4.18 mmol) in pyridine (10 mL) at was added NH₃ in MeOH (7N, 20 mL, 140 mmol). It was stirred for 48 h. LCMS showed completion of the reaction (m/e=271). It was concentrated and purified by silica column chromatography eluting with 10% MeOH in CH₂Cl₂ to give the desired product. LCMS (ES, m/z): 271.1 [M+H]⁻. ¹H-NMR (500 MHz, DMSO-d6): δ 8.54 (s, 1H), 8.33 (s, 1H), 8.22 (s, 1H), 6.73 (dd, J=6.5, 2.6 Hz, 1H), 6.00 (d, J=5.4 Hz, 1H), 5.51 (ddd, J=53, 7.2, 6.5 Hz, 1H), 4.93 (t, J=5.8 Hz, 1H), 4.86-4.74 (m, 1H), 3.91-3.83 (m, 1H), 3.77-3.61 (m, 2H).

Step 3: N-(3-((2R,3S,4R,5R)-3-fluoro-4-hydroxy-5-(hydroxymethyl)tetrahydrofuran-2-yl)-3H-[1,2,3]triazolo[4,5-d]pyrimidin-7-yl)benzamide

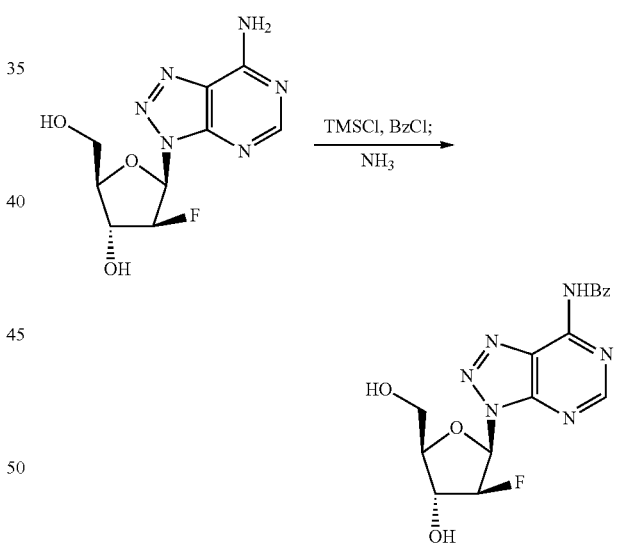

To a solution of (2R,3R,4S,5R)-5-(7-amino-3H-[1,2,3]triazolo[4,5-d]pyrimidin-3-yl)-4-fluoro-2-(hydroxymethyl)tetrahydrofuran-3-ol (1.34 g, 4.96 mmol) in pyridine (30 mL) at 0° C. was added TMSCl (1.46 mL, 11.4 mmol). It was warmed to rt and stirred for 1 h. Then, it was recooled to 0° C. and BzCl (0.921 mL, 7.93 mmol) was added dropwise. The reaction was slowly warmed to rt over 2 h. LCMS showed completion of reaction (m/e=375, 479). Water (3 mL) was added. It was cooled to 0° C. and NH₃ in MeOH (7N, 2.8 mL, 20 mmol) was added. After 1 h, the reaction mixture was concentrated. It was purified by silica column chromatography eluting with 0 to 10% MeOH in CH₂Cl₂ to give the product. LCMS (ES, m/z): 375.2

[M+H]+. 1H-NMR (500 MHz, DMSO-d6): δ 11.95 (s, 1H), 8.98 (s, 1H), 8.10 (d, J=7.6 Hz, 2H), 7.73-7.66 (m, 1H), 7.59 (t, J=7.7 Hz, 2H), 6.91 (d, J=6.2 Hz, 1H), 6.06 (d, J=5.6 Hz, 1H), 5.59 (t, J=53, 6.8 Hz, 1H), 4.90 (t, J=5.8 Hz, 1H), 4.82 (dq, J=19.8, 7.0 Hz, 1H), 3.92 (td, J=7.6, 2.9 Hz, 1H), 3.75 (ddd, J=12.1, 5.6, 3.0 Hz, 1H), 3.66 (dt, J=12.0, 6.6 Hz, 1H).

Step 4: N-(3-((2R,3S,4R,5R)-5-((bis(4-methoxyphenyl)(phenyl)methoxy)methyl)-3-fluoro-4-hydroxytetrahydrofuran-2-yl)-3H-[1,2,3]triazolo[4,5-d]pyrimidin-7-yl)benzamide

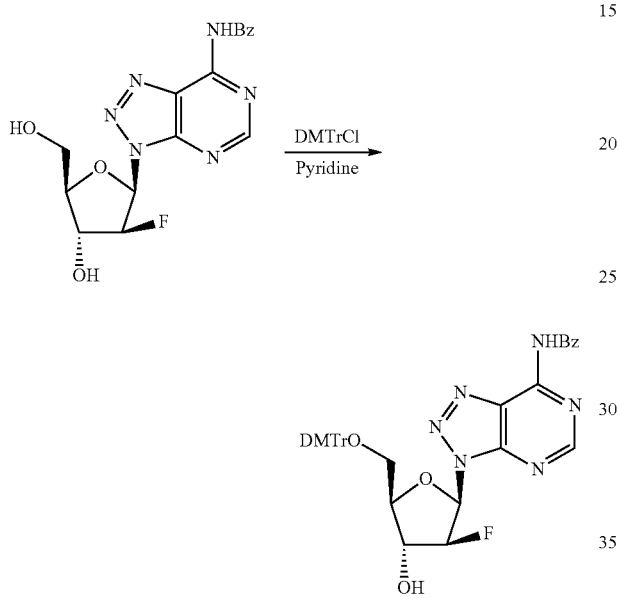

To a solution of N-(3-((2R,3S,4R,5R)-3-fluoro-4-hydroxy-5-(hydroxymethyl)-tetrahydrofuran-2-yl)-3H-[1,2,3]triazolo[4,5-d]pyrimidin-7-yl)benzamide (1.25 g, 3.34 mmol) in pyridine (15 mL) at 0° C. was added DMTrCl (1.58 g, 4.68 mmol). It was stirred at rt for 1 h. LCMS showed a peak with the desired mass (m/e=677). It was partly concentrated (to 5 mL), and EtOAc (20 mL) and water (10 mL) were added. Layers were separated, and the aq layer was extracted with EtOAc (2×10 mL). The combined organics were washed with brine (5 mL), dried (MgSO4), concentrated and purified by silica column chromatography eluting with 0 to 60% EtOAc in Hex to give the product. LCMS (ES, m/z): 675.5 [M–H]−. 1H-NMR (500 MHz, DMSO-d6): δ 8.13-8.07 (m, 2H), 7.69 (t, J=7.4 Hz, 1H), 7.59 (t, J=7.6 Hz, 2H), 7.35-7.29 (m, 2H), 7.23-7.10 (m, 6H), 6.97 (d, J=6.5 Hz, 1H), 6.81-6.74 (m, 2H), 6.74-6.67 (m, 2H), 6.07 (d, J=5.7 Hz, 1H), 5.62 (dt, J=53, 7.0 Hz, 1H), 4.91-4.79 (m, 1H), 4.15-4.07 (m, 1H), 3.69 (s, 3H), 3.67 (s, 3H), 3.44 (dd, J=10.4, 8.0 Hz, 1H), 3.21 (dd, J=10.3, 2.4 Hz, 1H).

Preparation 2: (2R,3R,4S,5R)-5-(7-benzamido-3H-[1,2,3]triazolo[4,5-d]pyrimidin-3-yl)-2-((bis(4-methoxyphenyl)(phenyl)methoxy)methyl)-4-fluorotetrahydrofuran-3-yl (2-cyanoethyl) diisopropylphosphoramidite Step 1: (2R,3R,4S,5R)-5-(7-benzamido-3H-[1,2,3]triazolo[4,5-d]pyrimidin-3-yl)-2-((bis(4-methoxyphenyl)(phenyl)methoxy)methyl)-4-fluorotetrahydrofuran-3-yl (2-cyanoethyl) diisopropylphosphoramidite

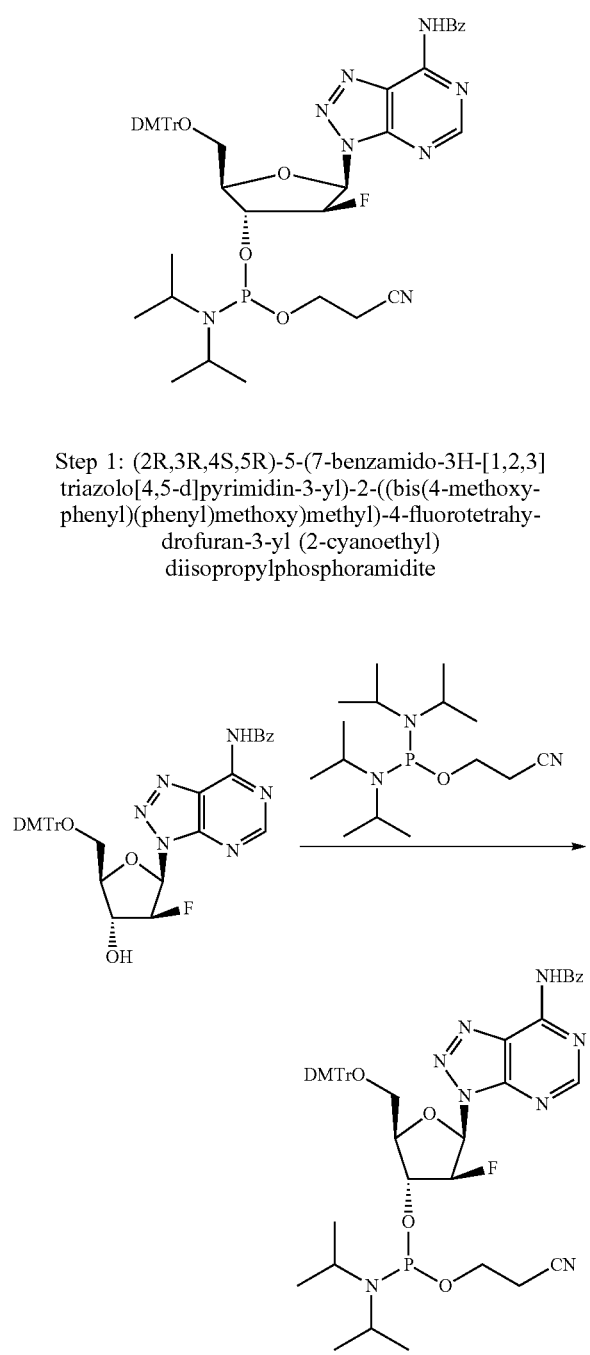

To a solution of 3-((bis(diisopropylamino)phosphino)oxy)propanenitrile (8.02 g, 26.6 mmol) in ACN (90 mL) at rt was added pyridin-1-ium 2,2,2-trifluoroacetate (3.85 g, 19.95 mmol) and a solution of N-(3-((2R,3 S,4R,5R)-5-((bis (4-methoxyphenyl)(phenyl)methoxy) methyl)-3-fluoro-4-hydroxytetrahydrofuran-2-yl)-3H-[1,2,3]triazolo[4,5-d]pyrimidin-7-yl)benzamide (9 g, 13.30 mmol) in ACN (90 mL).

The resulting mixture was stirred for 1 h. Then, it was concentrated and the residue was dissolved in CH$_2$Cl$_2$ (1000 mL). It was washed with aq NaHCO$_3$ (1%, 2×300 mL), water (300 mL) and brine (300 mL), dried (Na$_2$SO$_4$), concentrated, and purified by reverse phase (C18) chromatography eluting with 0 to 95% ACN in water to give the product. LCMS (ES, m/z): 877.5 [M+H]$^+$. $^1$H-NMR: (400 MHz, DMSO-d$_6$): δ 12.01 (s, 1H), 8.92 (s, 1H), 8.11 (d, J=7.6 Hz, 2H), 7.66 (dt, J=42.3, 7.5 Hz, 3H), 7.32 (td J=7.2, 6.6, 2.9 Hz, 2H), 7.22-7.00 (m, 9H), 6.83-6.63 (m, 4H), 5.86 (ddt, J=52.8, 17.6, 6.9 Hz, 1H), 5.16 (td, J=17.7, 17.2, 8.8 Hz, 1H), 3.78-3.63 (m, 7H), 3.59-3.35 (m, 5H), 2.74 (t, J=5.9 Hz, 1H), 2.63 (t, J=5.9 Hz, 1H), 1.23-0.99 (m, 10H), 0.91 (d, J=6.7 Hz, 2H). $^{31}$P-NMR: (162 MHz, DMSO-d$_6$): δ 150.26, 149.60 (2 s, 1P).

Preparation 3. N-(9-((2R,3S,4S,5R)-5-((bis(4-methoxyphenyl)(phenyl)methoxy)methyl)-4-fluoro-3-hydroxytetrahydrofuran-2-yl)-6-oxo-6,9-dihydro-1H-purin-2-yl)isobutyramide

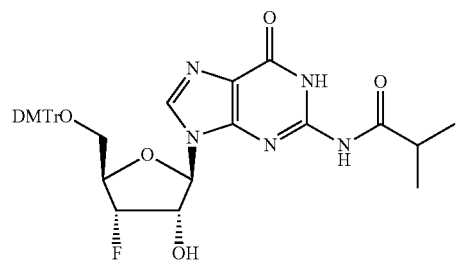

Step 1: N-(9-((2R,3S,4S,5R)-4-fluoro-3-hydroxy-5-(hydroxymethyl)tetrahydrofuran-2-yl)-6-oxo-6,9-dihydro-1H-purin-2-yl)isobutyramide

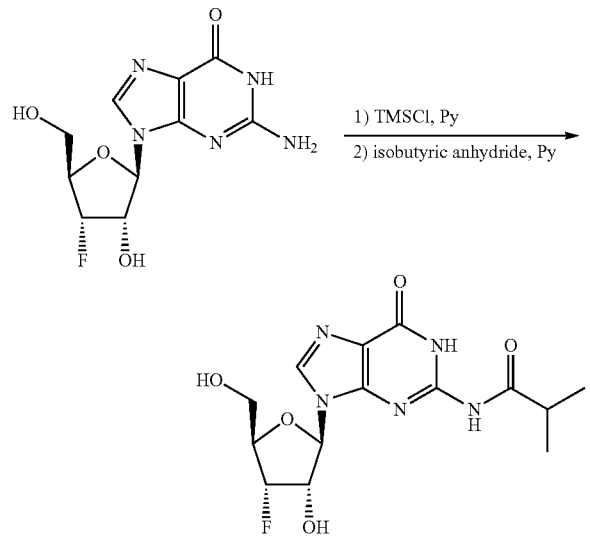

To a suspension of 2-amino-9-((2R,3S,4S,5R)-4-fluoro-3-hydroxy-5-(hydroxymethyl)tetrahydrofuran-2-yl)-1,9-dihydro-6H-purin-6-one (Carbosynth catalog # ND10826, 1.50 g, 5.26 mmol) in pyridine (30 mL) at 0-5° C. was added TMSCl (2.86 g, 26.3 mmol), and the mixture was stirred at rt for 30 min. Then, isobutyric anhydride (2.50 g, 15.8 mmol) was added dropwise, and it was stirred for an additional for 2 h. Then, MeOH (5.3 mL) was added. After 5 min, NH$_4$OH (10.5 mL) was added dropwise and stirring was continued for 30 min. The reaction mixture was concentrated under reduced pressure, and MeOH (2 mL) in CH$_2$Cl$_2$ (18 mL) was added to the residue. Insolubles were filtered off, and the filtrate was concentrated and purified by flash column chromatography with 2-10% MeOH in CH$_2$Cl$_2$ to give the product. LCMS (ES, m/z): 356.1 [M+H]$^+$. $^1$H-NMR: (400 MHz, DMSO-d$_6$): δ 12.11 (s, 1H), 11.68 (s, 1H), 8.28 (s, 1H), 5.98 (d, J=6.1 Hz, 1H), 5.85 (d, J=8.0 Hz, 1H), 5.24 (t, J=5.4 Hz, 1H), 5.14 (d, J=4.1 Hz, 0.5H), 5.01 (d, J=4.2 Hz, 0.5H), 4.87-4.69 (m, 1H), 4.26 (t, J=4.4 Hz, 0.5H), 4.19 (t, J=4.4 Hz, 0.5H), 3.61 (t, J=4.9 Hz, 2H), 2.77 (hept, J=6.8 Hz, 1H), 1.13 (d, J=6.7 Hz, 6H). $^{19}$F-NMR: (376 MHz, DMSO-d$_6$): δ −197.5 (s).

Step 2: N-(9-((2R,3S,4S,5R)-5-((bis(4-methoxyphenyl)(phenyl)methoxy)methyl)-4-fluoro-3-hydroxytetrahydrofuran-2-yl)-6-oxo-6,9-dihydro-1H-purin-2-yl)isobutyramide

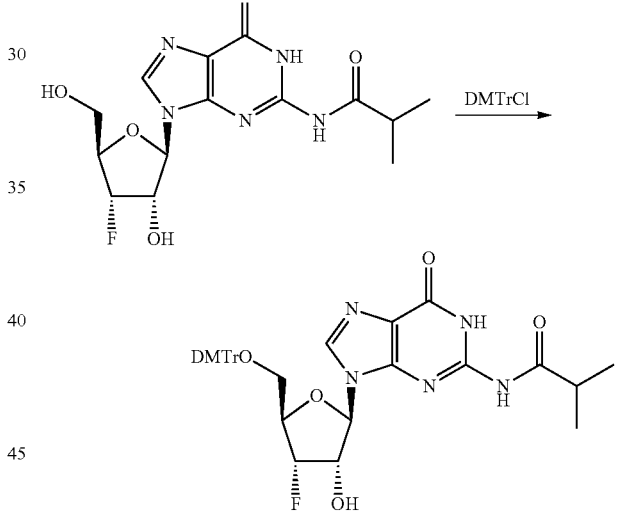

N-(9-((2R,3S,4S,5R)-4-fluoro-3-hydroxy-5-(hydroxymethyl)tetrahydrofuran-2-yl)-6-oxo-6,9-dihydro-1H-purin-2-yl)isobutyramide (1.30 g, 3.66 mmol) was co-evaporated with pyridine (3×10 mL) and re-dissolved in pyridine (26 mL). To the solution at 0-5° C. was added DMTrCl (1.36 g, 4.02 mmol). It was stirred at rt for 3 h and then, concentrated. CH$_2$Cl$_2$ (40 mL, with 1% Et$_3$N) was added, and it was washed with sat aq NaHCO$_3$ (15 mL), water (10 mL) and brine (10 mL). The organic solution was dried (Na$_2$SO$_4$), concentrated and purified by silica gel column chromatography using 0-10% MeOH in CH$_2$Cl$_2$ (1% Et$_3$N) to give the product. LCMS (ES, m/z): 656.2 [M−H]$^−$. $^1$H-NMR: (400 MHz, DMSO-d$_6$): δ 12.10 (s, 1H), 11.61 (s, 1H), 8.14 (s, 1H), 7.40-7.31 (m, 2H), 7.31-7.19 (m, 7H), 6.89-6.78 (m, 4H), 6.08 (d, J=6.1 Hz, 1H), 5.87 (d, J=7.3 Hz, 1H), 5.23 (dd, J=4.1, 1.8 Hz, 0H), 5.10 (d, J=4.4 Hz, 0H), 4.96 (dq, J=22.4, 5.9 Hz, 1H), 4.30 (dt, J=26.1, 4.6 Hz, 1H), 3.74 (d, J=1.1 Hz, 6H), 3.39 (dd, J=10.6, 5.7 Hz, 1H), 3.22 (dd, J=10.6, 3.8 Hz, 1H), 2.76 (p, J=6.8 Hz, 1H), 1.13 (d, J=6.8 Hz, 6H). $^{19}$F-NMR: (376 MHz, DMSO-d$_6$): δ −198.1 (s, 1F).

The product of Preparation 3 may optionally be treated according to the procedures of Preparation 22, Steps 4 and 5 (below), to afford (2R,3S,4R,5R)-5-((bis(4-methoxyphenyl)(phenyl)-methoxy)methyl)-4-fluoro-2-(2-isobutyramido-6-oxo-1,6-dihydro-9H-purin-9-yl)tetrahydrofuran-3-yl hydrogen phosphonate. LCMS (ES, m/z): 720 [M−H]$^−$.

Preparation 4: N-(3-((2R,3S,4S,5R)-5-((bis(4-methoxyphenyl)(phenyl)methoxy)methyl)-4-fluoro-3-hydroxytetrahydrofuran-2-yl)-7-oxo-6,7-dihydro-3H-[1,2,3]triazolo[4,5-d]pyrimidin-5-yl)isobutyramide

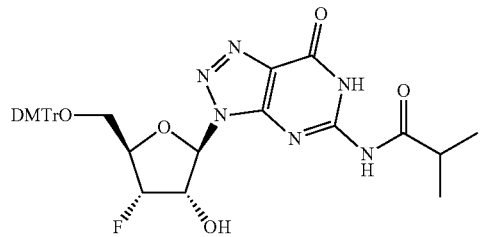

Step 1: ((2R,3R,4S,5R)-5-(5-amino-7-oxo-6,7-dihydro-3H-[1,2,3]triazolo[4,5-d]pyrimidin-3-yl)-4-(benzoyloxy)-3-fluorotetrahydrofuran-2-yl)methyl benzoate

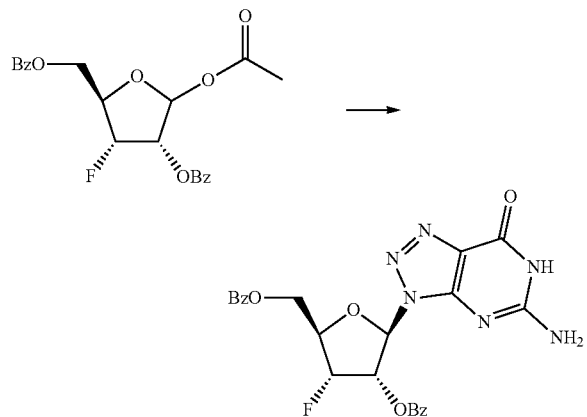

To a suspension of 8-azaguanine (5.14 g, 33.8 mmol) in anhydrous CH$_3$CN (100 mL) at rt was added dropwise (E)-trimethylsilyl N-(trimethylsilyl)acetimidate (16.53 mL, 67.6 mmol), then the mixture was stirred at 70° C. for 2 h. The reaction was cooled to rt, and a solution of ((2R,3R,4S)-5-acetoxy-4-(benzoyloxy)-3-fluorotetrahydrofuran-2-yl)methyl benzoate (6.8 g, 16.90 mmol) in anhydrous CH$_3$CN (20 mL) was added followed by dropwise addition of tin(IV) chloride (67.6 mL, 67.6 mmol). The homogeneous solution was stirred at 70° C. for 2 h. The reaction was cooled to rt and concentrated. The residue was dissolved in EtOAc (1000 mL) and neutralized by pouring into sat aq NaHCO$_3$ (500 mL). The organic layer was separated, and the aq layer was extracted with EtOAc (4×500 mL). The organic layers were combined and washed with water (3×700 mL), brine, dried over anhydrous sodium sulfate, filtered, and concentrated to afford title compound without further purification. LCMS (ES, m/z): 495.3 [M+H]$^+$.

Step 2: ((2R,3R,4S,5R)-4-(benzoyloxy)-3-fluoro-5-(5-isobutyramido-7-oxo-6,7-dihydro-3H-[1,2,3]triazolo[4,5-d]pyrimidin-3-yl)tetrahydrofuran-2-yl)methyl benzoate

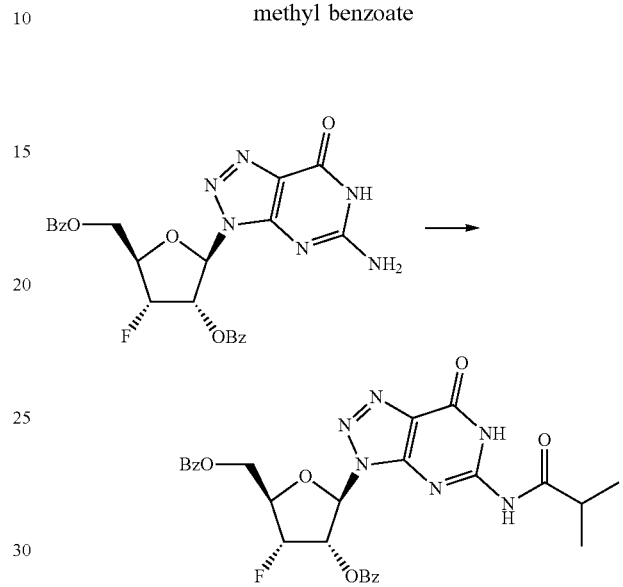

To a solution of ((2R,3R,4S,5R)-5-(5-amino-7-oxo-6,7-dihydro-3H-[1,2,3]triazolo[4,5-d]pyrimidin-3-yl)-4-(benzoyloxy)-3-fluorotetrahydrofuran-2-yl)methyl benzoate (8 g, 16.18 mmol) from Step 1 in anhydrous DMA (40 mL) at rt was added dropwise isobutyric anhydride (4.02 mL, 24.27 mmol). The mixture was stirred at 140° C. for 4 h. The reaction was cooled and diluted with EtOAc (600 mL), washed with sat aq NH$_4$Cl (4×500 mL), brine, dried over anhydrous sodium sulfate, filtered and concentrated. The crude product was purified by MPLC (220 g silica gel, eluting with a gradient of 100% hexanes to 100% ethyl acetate) to afford ((2R,3R,4S,5R)-4-(benzoyloxy)-3-fluoro-5-(5-isobutyramido-7-oxo-6,7-dihydro-3H-[1,2,3]triazolo[4,5-d]pyrimidin-3-yl)tetrahydrofuran-2-yl)methyl benzoate. LCMS (ES, m/z): 565.3 [M+H]$^+$.

Step 3: N-(3-((2R,3S,4S,5R)-4-fluoro-3-hydroxy-5-(hydroxymethyl)tetrahydrofuran-2-yl)-7-oxo-6,7-dihydro-3H-[1,2,3]triazolo[4,5-d]pyrimidin-5-yl)isobutyramide

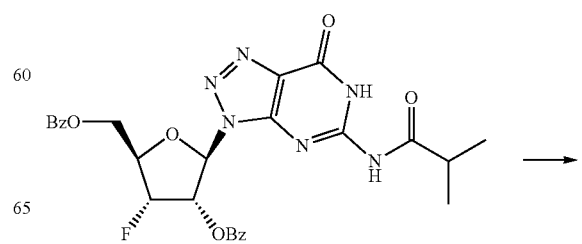

-continued

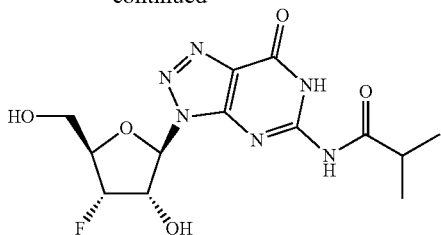

To a solution of ((2R,3R,4S,5R)-4-(benzoyloxy)-3-fluoro-5-(5-isobutyramido-7-oxo-6,7-dihydro-3H-[1,2,3]triazolo[4,5-d]pyrimidin-3-yl)tetrahydrofuran-2-yl)methyl benzoate (6 g, 10.63 mmol) in THF (20 mL), CH₃OH (16 mL), and water (4 mL) at 0° C. was added 5N aqueous NaOH (4.89 mL, 24.45 mmol) and stirred for 1 h. The reaction was neutralized with formic acid (1.223 mL, 31.9 mmol). The solvent was removed, and the residue was purified by MPLC (120 g, silica gel, eluting with a gradient of 100% CH₂Cl₂ to 20% CH₃OH/CH₂Cl₂) to afford N-(3-((2R,3 S,4S,5R)-4-fluoro-3-hydroxy-5-(hydroxymethyl)tetrahydrofuran-2-yl)-7-oxo-6,7-dihydro-3H-[1,2,3]triazolo[4,5-d]pyrimidin-5-yl)isobutyramide. LCMS (ES, m/z): 357.2 [M+H]⁺.

Step 4: N-(3-((2R,3S,4S,5R)-5-((bis(4-methoxyphenyl)(phenyl)methoxy)methyl)-4-fluoro-3-hydroxytetrahydrofuran-2-yl)-7-oxo-6,7-dihydro-3H-[1,2,3]triazolo[4,5-d]pyrimidin-5-yl)isobutyramide

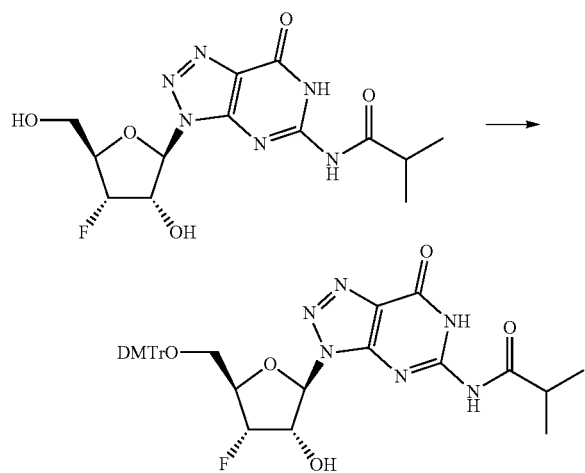

To a solution of N-(3-((2R,3S,4S,5R)-4-fluoro-3-hydroxy-5-(hydroxymethyl)tetrahydrofuran-2-yl)-7-oxo-6,7-dihydro-3H-[1,2,3]triazolo[4,5-d]pyrimidin-5-yl)isobutyramide (3 g, 8.42 mmol) in anhydrous pyridine (40 mL) at 0° C. was added 4,4'-dimethoxytrityl chloride (3.42 g, 10.10 mmol). The ice bath was removed, and the reaction mixture was allowed to reach RT and was stirred for 2 h. The mixture was diluted with EtOAc (400 mL), washed with sat aq NaHCO₃ (100 mL), water (3×100 mL), brine, and dried over anhydrous sodium sulfate, filtered and concentrated. The crude product was purified by MPLC (120 g silica gel, eluting with a gradient of 100% CH₂Cl₂ to 15% CH₃OH/CH₂CH₂ to afford N-(3-((2R,3S,4S,5R)-5-((bis(4-methoxyphenyl)(phenyl)methoxy)methyl)-4-fluoro-3-hydroxytetrahydrofuran-2-yl)-7-oxo-6,7-dihydro-3H-[1,2,3]triazolo[4,5-d]pyrimidin-5-yl)isobutyramide. LCMS (ES, m/z): 659.3 [M+H]⁺.

Preparation 5: N-(3-((2R,3S,4R,5R)-5-((bis(4-methoxyphenyl)(phenyl)methoxy)methyl)-4-fluoro-3-hydroxytetrahydrofuran-2-yl)-7-oxo-6,7-dihydro-3H-[1,2,3]triazolo[4,5-d]pyrimidin-5-yl) isobutyramide

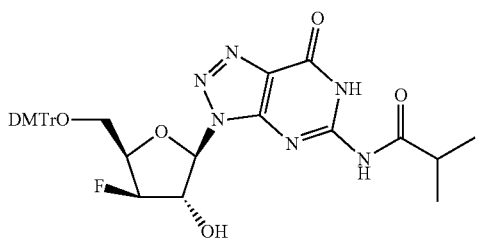

N-(3-((2R,3 S,4R,5R)-5-((bis(4-methoxyphenyl)(phenyl)methoxy)methyl)-4-fluoro-3-hydroxytetrahydrofuran-2-yl)-7-oxo-6,7-dihydro-3H-[1,2,3]triazolo[4,5-d]pyrimidin-5-yl)isobutyramide was prepared according to procedures analogous to those described for Preparation 4 using the appropriately substituted ribose in Step 1. LCMS (ES, m/z): 659.4 [M+H]+.

Preparation 6: N-(3-((2R,3R,5S)-5-((bis(4-methoxyphenyl)(phenyl)methoxy)methyl)-3-hydroxytetrahydrofuran-2-yl)-7-oxo-6,7-dihydro-3H-[1,2,3]triazolo[4,5-d]pyrimidin-5-yl) isobutyramide N-(3-((2R,3R,5 S)-5-((bis(4-methoxyphenyl)(phenyl)methoxy)methyl)-3-hydroxytetrahydrofuran-2-yl)-7-oxo-6,7-dihydro-3H-[1,2,3]triazolo[4,5-d]pyrimidin-5-yl)isobutyramide was prepared according to procedures analogous to those described for Preparation 4 using the appropriately substituted ribose in Step 1. LCMS (ES, m/z): 641.2 [M+H]+.

Preparation 7: 3-{5-O-[bis(4-methoxyphenyl)(phenyl)methyl]-2-deoxy-2-fluoro-3-D-arabinofuranosyl}-N-(phenylcarbonyl)-3H-imidazo[4,5-b]pyridin-7-amine

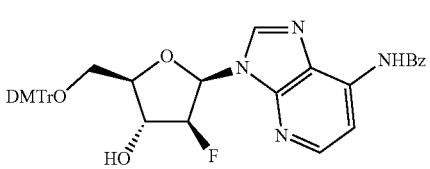

Step 1: 3-[2-deoxy-2-fluoro-3,5-bis-O-(phenylcarbonyl)-β-D-arabinofuranosyl]-7-nitro-3H-imidazo[4,5-b]pyridine

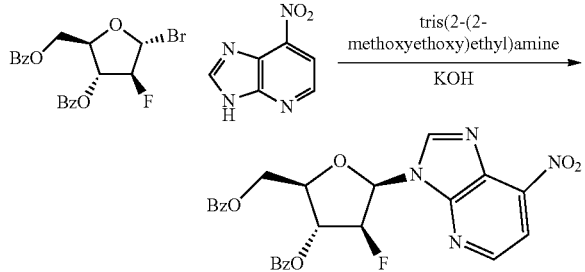

To a stirred mixture of freshly ground KOH (308 mg, 5.48 mmol) in acetonitrile (50 mL) was added tris(2-(2-methoxyethoxy)ethyl)amine (0.070 mL, 0.219 mmol). The reaction mixture was aged for 15 min at ambient temperature followed by addition of 7-nitro-3H-imidazo[4,5-b]pyridine (600 mg, 3.66 mmol) in a single portion. The resulting mixture was stirred at ambient temperature for 15 min. A solution of 2-deoxy-2-fluoro-3,5-bis-O-(phenylcarbonyl)-α-D-arabinofuranosyl bromide (1700 mg, 4.02 mmol) in acetonitrile (10 mL) was added dropwise and the resulting mixture was vigorously stirred at RT for 17 h. The reaction mixture was diluted with sat aq ammonium chloride (80 mL) and extracted with DCM (3×150 mL). The organic extracts were combined, dried over sodium sulphate and concentrated under reduced pressure. The resulting residue was purified by column chromatography on silica gel; 120 g prepacked, (0-70% ethyl acetate/hexanes) to afford 3-[2-deoxy-2-fluoro-3,5-bis-O-(phenylcarbonyl)-3-D-arabinofuranosyl]-7-nitro-3H-imidazo[4,5-b]pyridine. MS: 507 (M+H)+.

Step 2: 3-[2-deoxy-2-fluoro-3,5-bis-O-(phenylcarbonyl)-β-D-arabinofuranosyl]-3H-imidazo[4,5-b]pyridin-7-amine

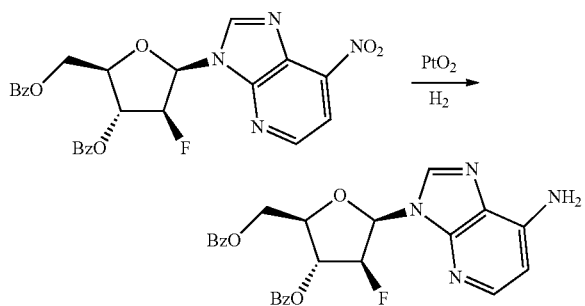

To a stirred solution of 3-[2-deoxy-2-fluoro-3,5-bis-O-(phenylcarbonyl)-3-D-arabinofuranosyl]-7-nitro-3H-imidazo[4,5-b]pyridine (1380 mg, 2.72 mmol) in methanol (55 mL) at RT was added platinum(IV) oxide (61.9 mg, 0.272 mmol). The reaction mixture was placed under an atmosphere of hydrogen and stirred at RT for 72 h. The catalyst was removed by filtration through a plug of CELITE. The filtrate was concentrated under reduced pressure, and the resulting residue was purified by column chromatography on silica gel; 80 g prepacked, ((0-40% (3:1, ethyl acetate:ethanol)/hexanes) to afford 3-[2-deoxy-2-fluoro-3,5-bis-O-(phenylcarbonyl)-3-D-arabinofuranosyl]-3H-imidazo[4,5-b]pyridin-7-amine. MS: 477 (M+H)+.

Step 3: 3-(2-deoxy-2-fluoro-β-D-arabinofuranosyl)-3H-imidazo[4,5-b]pyridin-7-amine

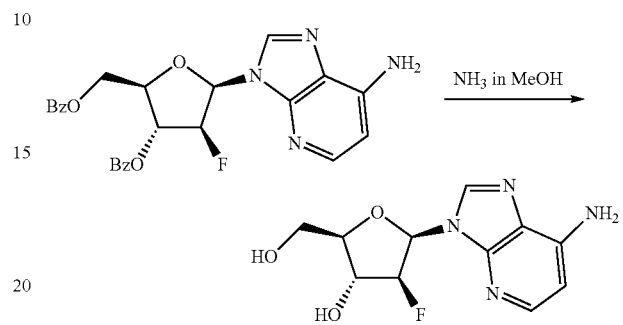

To a stirred solution of 3-[2-deoxy-2-fluoro-3,5-bis-O-(phenylcarbonyl)-3-D-arabinofuranosyl]-3H-imidazo[4,5-b]pyridin-7-amine (995 mg, 2.09 mmol) in methanol (36 mL) at ambient temperature was added ammonia (7N in methanol, 12 mL, 84.0 mmol). The resulting solution was brought to 80° C. and stirred for 5 h. The reaction mixture was cooled to RT and concentrated under reduced pressure. The resulting residue was suspended in methanol/dichloromethane and sonicated until a solid precipitated out of solution. Solid was collected by filtering through a glass frit affording 3-(2-deoxy-2-fluoro-β-D-arabinofuranosyl)-3H-imidazo[4,5-b]pyridin-7-amine. MS: 269 (M+H)+.

Step 4: 3-(2-deoxy-2-fluoro-β-D-arabinofuranosyl)-N-(phenylcarbonyl)-3H-imidazo[4,5-b]pyridin-7-amine

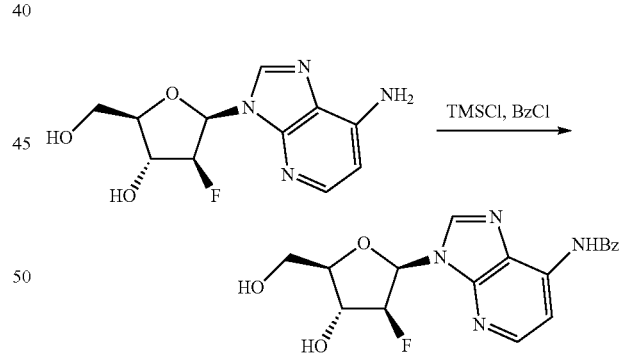

To a stirred solution of 3-(2-deoxy-2-fluoro-β-D-arabinofuranosyl)-3H-imidazo[4,5-b]pyridin-7-amine (550 mg, 2.05 mmol) in pyridine (6.5 mL) at RT was added TMSCl (2.62 mL, 20.5 mmol). The resulting solution was stirred for 1.5 h followed by addition of benzoyl chloride (0.357 mL, 3.08 mmol). After stirring for an additional hour, water (2.15 mL) was added to the reaction mixture, which was then stirred for 45 min. The reaction mixture was cooled to 0° C. and aqueous ammonia (28% w/w) (0.370 mL, 4.79 mmol) was added. The reaction mixture was returned to RT and stirred for 45 min and then concentrated under reduced pressure. The resulting residue was taken up in water (20 mL) and extracted with ethyl acetate (3×40 mL). The organic extracts were combined washed with brine, dried over sodium sulphate and concentrated under reduced pressure. The resulting residue was purified by column chromatography on silica gel; 120 g prepacked, (0-7% methanol/dichloromethane) to afford 3-(2-deoxy-2-fluoro-β-D-arabinofuranosyl)-N-(phenylcarbonyl)-3H-imidazo[4,5-b]pyridin-7-amine. MS: 373 (M+H)+.

Step 5: 3-{5-O-[bis(4-methoxyphenyl)(phenyl)methyl]-2-deoxy-2-fluoro-β-D-arabinofuranosyl}-N-(phenylcarbonyl)-3H-imidazo[4,5-b]pyridin-7-amine

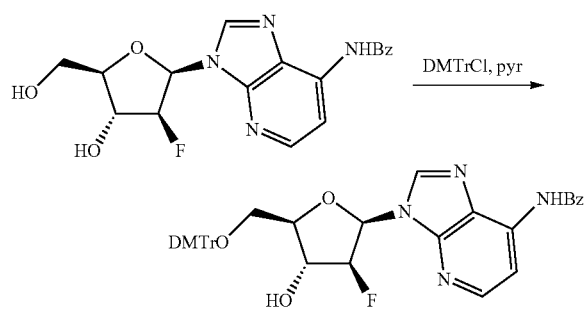

To a stirred mixture of 3-(2-deoxy-2-fluoro-β-D-arabinofuranosyl)-N-(phenylcarbonyl)-3H-imidazo[4,5-b]pyridin-7-amine (185 mg, 0.497 mmol) and 4 Å molecular sieves in pyridine (3 mL) at 0° C. was added 4,4'-dimethoxytrityl chloride (253 mg, 0.745 mmol) in a single portion. The reaction mixture was allowed to warm to RT and was stirred for 18 h. Sieves were removed by filtration and the filtrate was concentrated under reduced pressure. The resulting residue was taken up in a mixture of methanol/ether and added to water. The phases were separated, and the aqueous layer was extracted with ether (3 times). The organic extracts were combined, washed with brine, dried over sodium sulphate and concentrated under reduced pressure. The resulting residue was purified by column chromatography on silica gel; 40 g prepacked, ((0-40% (3:1, ethyl acetate:ethanol)/hexanes) to afford 3-{5-O-[bis(4-methoxyphenyl)(phenyl)methyl]-2-deoxy-2-fluoro-β-D-arabinofuranosyl}-N-(phenylcarbonyl)-3H-imidazo[4,5-b]pyridin-7-amine. MS: 675 (M+H)+.

Preparation 8: 1-((2R,3S,4R,5R)-5-((bis(4-methoxyphenyl)(phenyl)methoxy)methyl)-4-fluoro-3-hydroxytetrahydrofuran-2-yl)-1,5-dihydro-4H-imidazo[4,5-c]pyridin-4-one

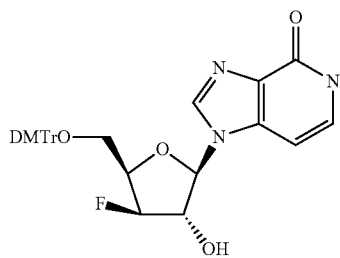

Step 1: ((2R,3S,4S)-4-acetoxy-3-fluoro-5-(4-oxo-4,5-dihydro-1H-imidazo[4,5-c]pyridin-1-yl)tetrahydrofuran-2-yl)methyl benzoate

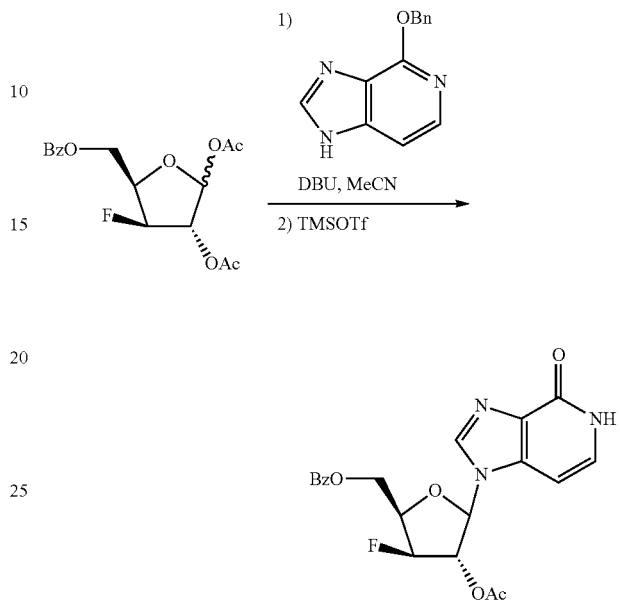

To a suspension of 4-(benzyloxy)-1H-imidazo[4,5-c]pyridine (0.795 g, 3.53 mmol) and (3S,4S,5R)-5-((benzoyloxy)methyl)-4-fluorotetrahydrofuran-2,3-diyl diacetate (1 g, 2.94 mmol) in ACN (20 mL) and CH$_2$Cl$_2$ (10 mL) at 0° C. under Ar was added 2,3,4,6,7,8,9,10-octahydropyrimido[1,2-a]azepine (1.34 g, 8.815 mmol). The resulting mixture was stirred at 0° C. for 30 min. Then, trimethylsilyl trifluoromethanesulfonate (3.92 g, 17.65 mmol) was added to the solution, and it was stirred at 0° C. for 30 min. Then, it was heated to 80° C. for 16 h. The reaction was cooled to rt and sat aq NaHCO$_3$ (10 mL) and water (30 mL) were added. It was extracted with EtOAc (3×50 mL). The combined organic layers was washed with brine, dried over (Na$_2$SO$_4$), concentrated, and the residue was purified by silica gel column chromatography, eluted with 1 to 10% MeOH in CH$_2$Cl$_2$ to give the product. LCMS (ES, m/z): 416.3 [M+H]+.

Step 2: 1-((2R,3S,4R,5R)-4-fluoro-3-hydroxy-5-(hydroxymethyl)tetrahydrofuran-2-yl)-1,5-dihydro-4H-imidazo[4,5-c]pyridin-4-one

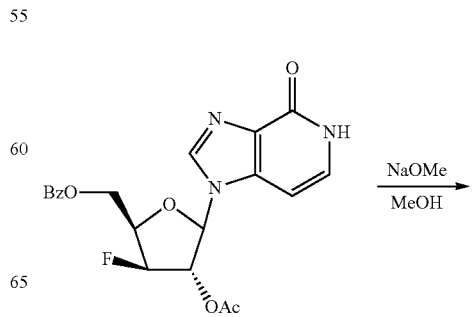

-continued

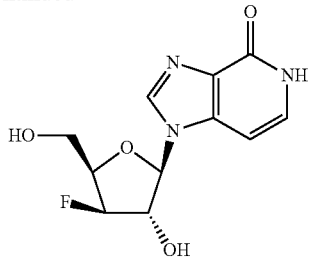

To a solution of ((2R,3S,4S)-4-acetoxy-3-fluoro-5-(4-oxo-4,5-dihydro-1H-imidazo[4,5-c]pyridin-1-yl)tetrahydrofuran-2-yl)methyl benzoate (2.5 g, 5.3 mmol) in MeOH (10 mL) was added sodium methanolate (3.47 g, 21.2 mmol). The solution was stirred at rt for 1 h. It was neutralized with AcOH, and the solution was concentrated. The residue was purified by reverse phase (AQ C18) chromatography eluted with 0 to 30% ACN in aq $NH_4HCO_3$ (5 mM) to give the product. LCMS (ES, m/z): 270.0 [M+H]$^+$. $^1$H NMR (400 MHz, DMSO-$d_6$) δ 11.31 (s, 1H), 8.06 (s, 1H), 7.23 (d, J=7.1 Hz, 1H), 6.62 (d, J=7.1 Hz, 1H), 6.37 (d, J=2.9 Hz, 1H), 5.85 (d, J=2.8 Hz, 1H), 5.22-4.98 (m, 2H), 4.54 (d, J=17.7 Hz, 1H), 4.28 (dtd, J=29.6, 6.0, 3.1 Hz, 1H), 3.93-3.62 (m, 2H).

Step 3: 1-((2R,3S,4R,5R)-5-((bis(4-methoxyphenyl)(phenyl)methoxy)methyl)-4-fluoro-3-hydroxytetrahydrofuran-2-yl)-1,5-dihydro-4H-imidazo[4,5-c]pyridin-4-one

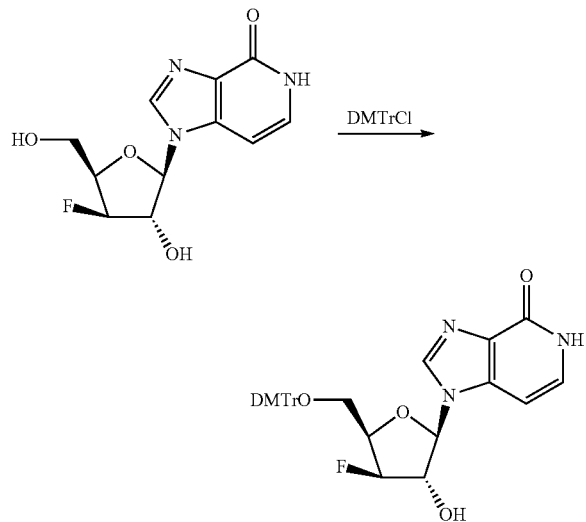

To a stirred solution of 1-((2R,3S,4R,5R)-4-fluoro-3-hydroxy-5-(hydroxymethyl)tetrahydrofuran-2-yl)-1H-imidazo[4,5-c]pyridin-4(5H)-one (340 mg, 1.26 mmol) in pyridine (3 mL) at rt was added 4,4'-(chloro(phenyl)methylene)bis(methoxybenzene) (426 mg, 1.1 mmol).

It was stirred for 4 h. The mixture was concentrated under reduced pressure, and the residue was purified by silica gel column chromatography eluted with 1 to 10% MeOH in $CH_2Cl_2$ (0.5% $Et_3N$) to give the product. LCMS (ES, m/z): 572.3 [M+H]$^+$. $^1$H NMR (400 MHz, DMSO-$d_6$) δ 11.32 (d, J=5.9 Hz, 1H), 7.95 (s, 1H), 7.41 (d, J=7.8 Hz, 2H), 7.37-7.15 (m, 8H), 6.86 (dd, J=10.5, 8.6 Hz, 4H), 6.60 (d, J=7.1 Hz, 1H), 6.50-6.36 (m, 1H), 5.92 (d, J=2.6 Hz, 1H), 5.77 (s, 1H), 5.27-5.06 (m, 1H), 4.65-4.42 (m, 2H), 3.73 (d, J=2.6 Hz, 6H), 3.30-3.24 (m, 1H).

Preparation 9: N-(7-((2R,4S,5R)-5-((bis(4-methoxyphenyl)(phenyl)methoxy)methyl)-4-hydroxytetrahydrofuran-2-yl)imidazo[2,1-f][1,2,4]triazin-4-yl)benzamide

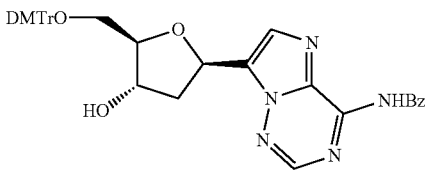

Step 1: (3R,4R,5R)-2-(4-aminoimidazo[2,1-f][1,2,4]triazin-7-yl)-3,4-bis(benzyloxy)-5-((benzyloxy)methyl)tetrahydrofuran-2-ol

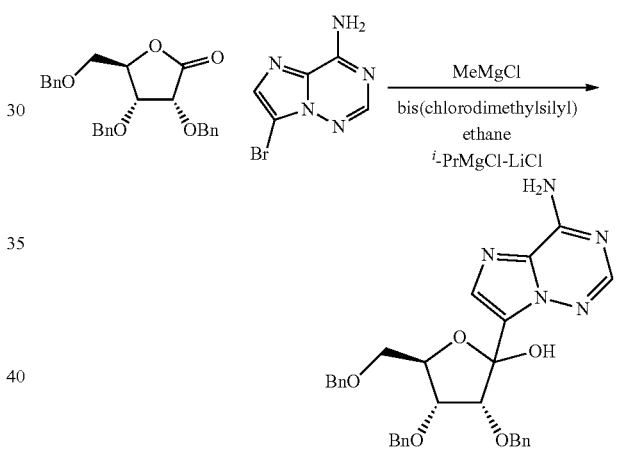

To a stirring mixture of 7-bromoimidazo[2,1-f][1,2,4]triazin-4-amine (41 g, 0.19 mol) in THF (0.50 L) at 0° C. was added MeMgBr (3.0M in THF, 66 mL, 0.19 mol) dropwise to maintain the internal temperature below 10° C. Bis(chlorodimethylsilyl)ethane (41 g, 190 mmol) was added in one portion. MeMgBr (3.0M in diethyl ether, 66 mL, 0.19 mol) was then added dropwise to maintain the internal temperature below 10° C. i-PrMgCl—LiCl (1.3 M in THF, 0.16 L, 0.21 mol) was added while maintaining the internal temperature below 10° C. A mixture of (3R,4R,5R)-3,4-bis(benzyloxy)-5-((benzyloxy)methyl)dihydrofuran-2(3H)-one (160 g, 0.38 mol) in THF was added dropwise at 0° C., and the mixture was then allowed to warm to rt and was stirred for 12 h. The mixture was diluted with saturated aqueous ammonium chloride (100 mL) and extracted with ethyl acetate (3×1000 mL). The combined organic layers were dried over sodium sulfate and concentrated under reduced pressure. The resulting residue was purified by column chromatography (column height: 2500 mm, diameter: 1000 mm, 25% to 75% ethyl acetate gradient in hexanes) to afford (3R,4R,5R)-2-(4-aminoimidazo[2,1-f][1,2,4]triazin-7-yl)-3,4-bis(benzyloxy)-5-((benzyloxy)methyl)-tetrahydrofuran-2-ol.

Step 2: 7-((3S,4R,5R)-3,4-bis(benzyloxy)-5-((benzyloxy)methyl)tetrahydrofuran-2-yl)imidazo[2,1-f][1,2,4]triazin-4-amine

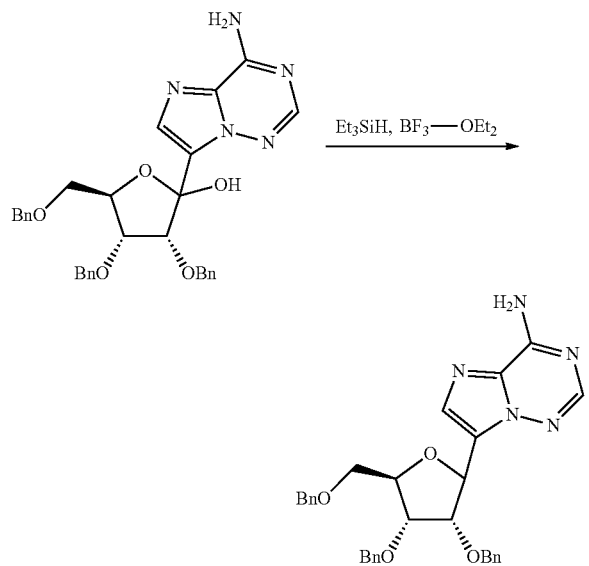

To a stirring mixture of (3R,4R,5R)-2-(4-aminoimidazo[2,1-f][1,2,4]triazin-7-yl)-3,4-bis(benzyloxy)-5-((benzyloxy)methyl)tetrahydrofuran-2-ol (64 g, 0.12 mmol) in DCM (1.3 L) at 0° C. was added triethylsilane (81 g, 0.69 mol), and then boron trifluoride diethyl etherate (21 g, 0.15 mol). The mixture was then allowed to warm to 25° C., and the mixture was stirred for 1 h. More boron trifluoride diethyl etherate (57 g, 0.40 mol) was added, and the mixture was then heated to 35° C. for 4 h. Upon cooling to rt, the mixture was quenched with saturated aqueous sodium bicarbonate (200 mL) and then extracted with ethyl acetate (3×300 mL). The combined organic layers were dried over sodium sulfate and concentrated under reduced pressure. The resulting residue was purified by column chromatography (15-75% ethyl acetate gradient in hexanes) to afford 7-((3S,4R,5R)-3,4-bis(benzyloxy)-5-((benzyloxy)methyl)tetrahydrofuran-2-yl)imidazo[2,1-f][1,2,4]triazin-4-amine. MS (ES, m/z) =538 [M+H]+.

Step 3: (3R,4S,5R)-2-(4-aminoimidazo[2,1-f][1,2,4]triazin-7-yl)-5-(hydroxymethyl)-tetrahydrofuran-3,4-diol

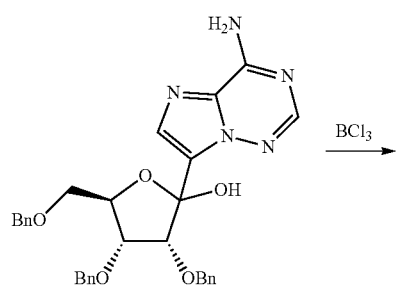

To a stirring mixture of 7-((3S,4R,5R)-3,4-bis(benzyloxy)-5-((benzyloxy)methyl)-tetrahydrofuran-2-yl)imidazo[2,1-f][1,2,4]triazin-4-amine (12 g, 22 mmol) in DCM (850 mL) at −78° C. was added boron trichloride (18 g, 0.16 mol) dropwise. Upon completion, the mixture was stirred at −78° C. for 3 h. After 3 h, the mixture was quenched with methanol (50 mL) at −78° C., and the mixture was allowed to warm to 25° C. The mixture was concentrated under reduced pressure. The residue was purified by column chromatography (9-25% methanol gradient in dichloromethane) to afford (3R,4S,5R)-2-(4-aminoimidazo[2,1-f][1,2,4]triazin-7-yl)-5-(hydroxymethyl)tetrahydrofuran-3,4-diol.

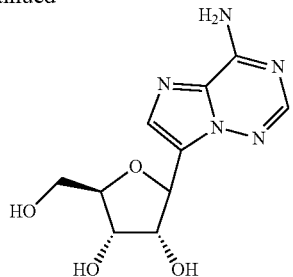

Step 4: (6aR,8S,9S,9aS)-8-(4-aminoimidazo[2,1-f][1,2,4]triazin-7-yl)-2,2,4,4-tetraisopropyltetrahydro-6H-furo[3,2-f][1,3,5,2,4]trioxadisilocin-9-ol

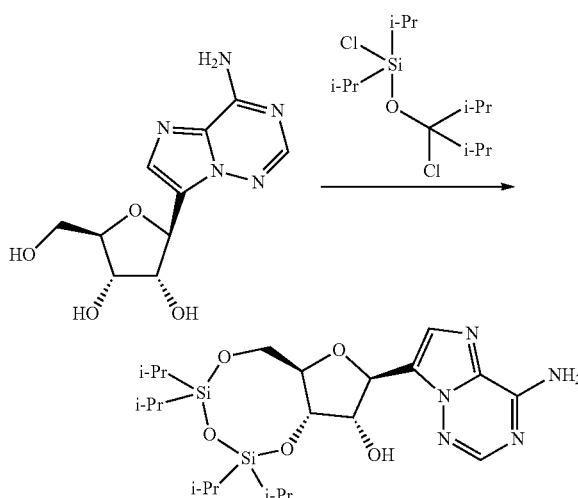

To a stirred mixture of (2S,3R,4S,5R)-2-(4-aminoimidazo[2,1-f][1,2,4]triazin-7-yl)-5-(hydroxymethyl)tetrahydrofuran-3,4-diol (4.0 g, 15 mmol) in pyridine (0.10 L) was added 1,3-dichloro-1,1,3,3-tetraisopropyldisiloxane (5.8 mL, 18 mmol). After 3 h, the mixture was diluted with toluene (50 mL) and then concentrated. The resulting mixture was taken up in DCM and methanol and then silica gel (40 g) was added. The mixture was concentrated, placed under vacuum for 1 h and then purified by column chromatography (0-80% ethyl acetate gradient in hexanes) to afford (6aR,8S,9S,9aS)-8-(4-aminoimidazo[2,1-f][1,2,4]triazin-7-yl)-2,2,4,4-tetraisopropyltetrahydro-6H-furo[3,2-f][1,3,5,2,4]trioxadisilocin-9-ol. MS (ES, m/z)=510 [M+H]+.

Step 5: O-((6aR,8S,9S,9aR)-8-(4-aminoimidazo[2,1-f][1,2,4]triazin-7-yl)-2,2,4,4-tetraisopropyltetrahydro-6H-furo[3,2-f][1,3,5,2,4]trioxadisilocin-9-yl) 1H-imidazole-1-carbothioate

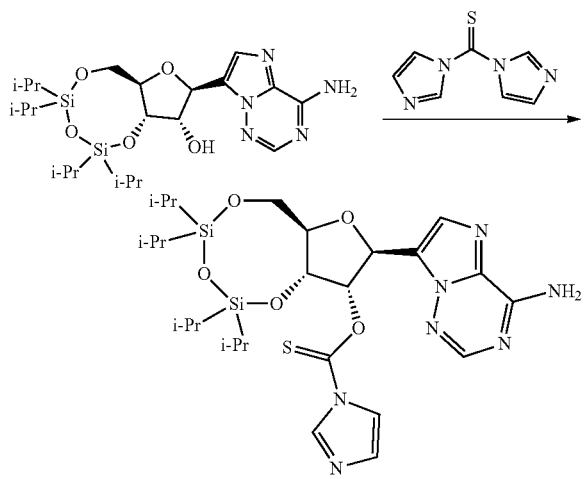

To a mixture of (6aR,8S,9S,9aS)-8-(4-aminoimidazo[2,1-f][1,2,4]triazin-7-yl)-2,2,4,4-tetraisopropyltetrahydro-6H-furo[3,2-f][1,3,5,2,4]trioxadisilocin-9-ol (6.45 g, 12.7 mmol) in acetonitrile (63.0 mL) and pyridine (63.0 mL) was added 1,1'-thiocarbonyldiimidazole (2.71 g, 15.2 mmol). After 90 min, more 1,1'-thiocarbonyldiimidazole (2.71 g, 15.2 mmol) was added, and the mixture was stirred overnight. After stirring overnight, the mixture was concentrated and purified by column chromatography (0-100% ethyl acetate gradient in hexanes) to afford O-((6aR,8S,9S,9aR)-8-(4-aminoimidazo[2,1-f][1,2,4]triazin-7-yl)-2,2,4,4-tetraisopropyltetrahydro-6H-furo[3,2-][1,3,5,2,4]trioxadisilocin-9-yl) 1H-imidazole-1-carbothioate. MS (ES, m/z)=620 [M+H]+.

Step 6: 7-((6aR,8R,9aS)-2,2,4,4-tetraisopropyltetrahydro-6H-furo[3,2-f][1,3,5,2,4]trioxadisilocin-8-yl)imidazo[2,1-f][1,2,4]triazin-4-amine

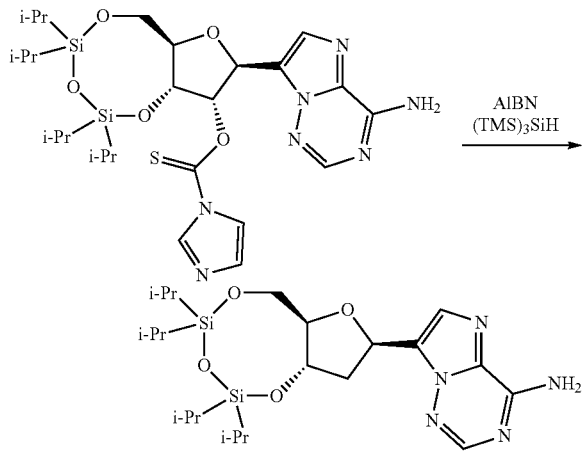

To a mixture of O-((6aR,8S,9S,9aR)-8-(4-aminoimidazo[2,1-f][1,2,4]triazin-7-yl)-2,2,4,4-tetraisopropyltetrahydro-6H-furo[3,2-][1,3,5,2,4]trioxadisilocin-9-yl) (5.65 g, 9.11 mmol) in toluene (91.0 mL) was added 2,2'-azobis(2-methylpropionitrile) (0.300 g, 1.82 mmol) and tris(trimethylsilyl)silane (4.22 mL, 13.7 mmol). The mixture was heated to 85° C. for 30 min. After 30 min, the mixture was allowed to cool to rt and placed directly on the column and purified (0-80% ethyl acetate gradient in hexanes) to afford 7-((6aR,8R,9aS)-2,2,4,4-tetraisopropyltetrahydro-6H-furo[3,2-f][1,3,5,2,4]trioxadisilocin-8-yl)imidazo[2,1-f][1,2,4]triazin-4-amine. MS (ES, m/z)=494 [M+H]+ 494.

Step 7: N-benzoyl-N-(7-((6aR,8R,9aS)-2,2,4,4-tetraisopropyltetrahydro-6H-furo[3,2-f][1,3,5,2,4]trioxadisilocin-8-yl)imidazo[2,1-f][1,2,4]triazin-4-yl)benzamide

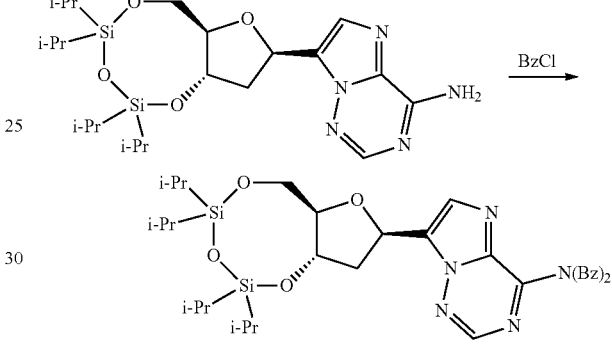

To a mixture of 7-((6aR,8R,9aS)-2,2,4,4-tetraisopropyltetrahydro-6H-furo[3,2-f][1,3,5,2,4]trioxadisilocin-8-yl)imidazo[2,1-f][1,2,4]triazin-4-amine (15.7 g, 31.8 mmol) in pyridine (64.0 mL) was added benzoyl chloride (11.0 mL, 95.0 mmol), and the mixture was heated to 50° C. for 45 min. After 45 min, the mixture was allowed to cool to rt. After cooling, a precipitate formed and was filtered off. The filtrate was diluted with DCM (50 mL) and toluene (50 mL). The mixture was concentrated to about 50 mL. The mixture was filtered, and the solids washed with DCM. The filtrate and washes were combined, loaded onto a column, and purified (0-50% ethyl acetate gradient in hexanes) to afford N-benzoyl-N-(7-((6aR,8R,9aS)-2,2,4,4-tetraisopropyltetrahydro-6H-furo[3,2-f][1,3,5,2,4]trioxadisilocin-8-yl)imidazo[2,1-f][1,2,4]triazin-4-yl)benzamide. MS (ES, m/z)=702 [M+H]+.

Step 8: N-(7-((2R,4S,5R)-4-hydroxy-5-(hydroxymethyl)tetrahydrofuran-2-yl)imidazo[2,1-f][1,2,4]triazin-4-yl)benzamide

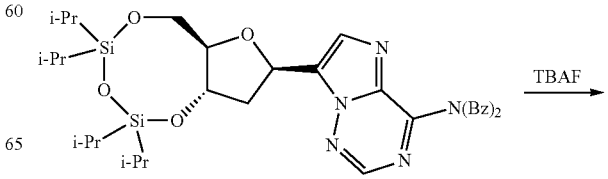

379

-continued

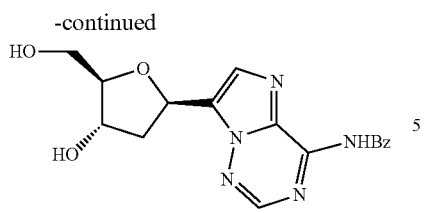

To a mixture of N-benzoyl-N-(7-((6aR,8R,9aS)-2,2,4,4-tetraisopropyltetrahydro-6H-furo[3,2-f][1,3,5,2,4]trioxadisilocin-8-yl)imidazo[2,1-f][1,2,4]triazin-4-yl)benzamide (10 g, 14 mmol) in tetrahydrofuran (0.14 L) was added TBAF ((1.0M in THF, 29 mL, 29 mmol), and the mixture was stirred for 1 h. After 1 h, the mixture was concentrated and purified by column chromatography to afford N-(7-((2R,4S,5R)-4-hydroxy-5-(hydroxymethyl)tetrahydro-furan-2-yl)imidazo[2,1-f][1,2,4]triazin-4-yl)benzamide. MS (ES, m/z)=356 [M+H]+.

Step 9: N-(7-((2R,4S,5R)-5-((bis(4-methoxyphenyl)(phenyl)methoxy)methyl)-4-hydroxytetrahydro-furan-2-yl) imidazo[2,1-f][1,2,4]triazin-4-yl)benz-amide

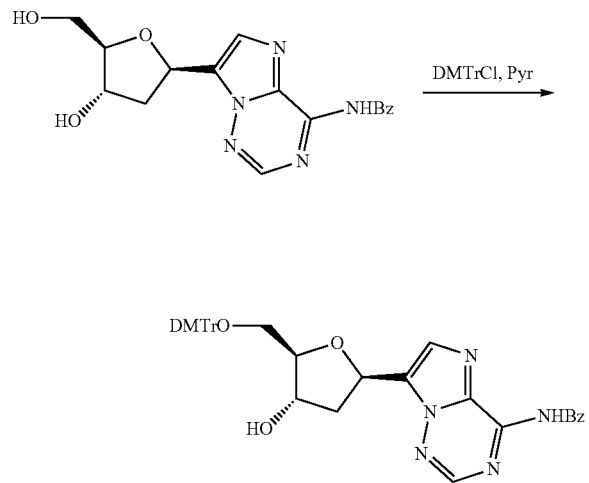

To a mixture of N-(7-((2R,4S,5R)-4-hydroxy-5-(hydroxymethyl)tetrahydrofuran-2-yl)imidazo[2,1-f][1,2,4]triazin-4-yl)benzamide (6.1 g, 17 mmol) in pyridine (86 mL) at 0° C. was added 4,4'-(chloro(phenyl)methylene)bis(methoxybenzene) (5.8 g, 17 mmol), and the mixture was allowed to warm to RT overnight. After stirring overnight, the mixture was diluted with toluene and then concentrated under reduced pressure to afford the crude product. The crude product was purified by silica gel chromatography (0-100% ethyl acetate gradient in hexanes) to afford N-(7-((2R,4S,5R)-5-((bis(4-methoxyphenyl)(phenyl)-methoxy)methyl)-4-hydroxytetrahydrofuran-2-yl)imidazo[2,1-f][1,2,4]triazin-4-yl)benzamide. MS (ES, m/z)=658 [M+H]+.

380

Preparation 10: (2R,3R,4S,5R)-2-(4-amino-1H-[1,2,3]triazolo[4,5-c]pyridin-1-yl)-5-(hydroxymethyl)tetrahydrofuran-3,4-diol

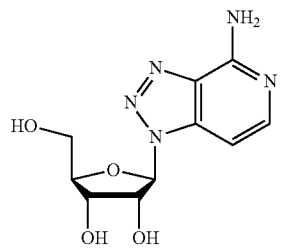

Step 1: (2R,3R,4R,5R)-2-(acetoxymethyl)-5-(4-chloro-1H-[1,2,3]triazolo[4,5-c]pyridin-1-yl)tetrahydrofuran-3,4-diyl diacetate

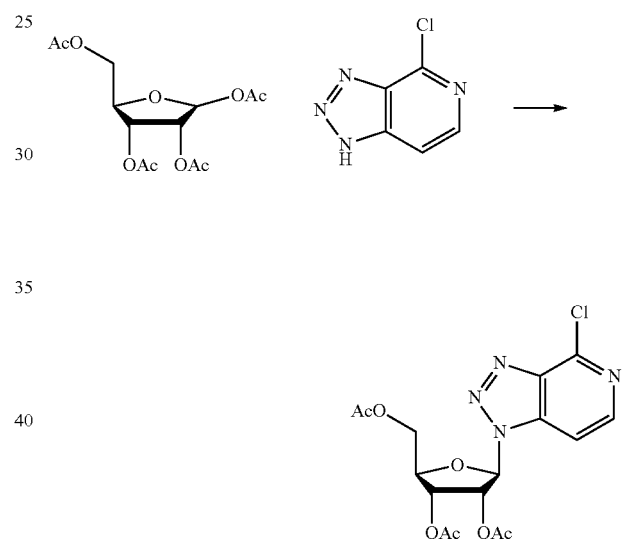

To a suspension of 4-chloro-1H-[1,2,3]triazolo[4,5-c]pyridine (1.0 g, 6.5 mmol) and (3R,4R,5R)-5-(acetoxymethyl)tetrahydrofuran-2,3,4-triyl triacetate (3.1 g, 9.7 mmol) in nitromethane (50 mL) was added BF$_3$.Et$_2$O (1.23 mL, 9.7 mmol), and the resulting mixture was heated at 50° C. for 2 h. The reaction mixture was cooled to rt, diluted with 100 mL of DCM and washed with sat aq. NaHCO$_3$ (100 mL) and brine (100 mL). The separated organic layer was dried over Na$_2$SO$_4$ and concentrated in vacuo. The residue was purified by a silica gel column, eluting with 0-100% EtOAc:EtOH (3:1)/Hexane. LCMS (ES, m/z): 413.07 [M+H]+. $^1$H NMR (500 MHz, Chloroform-d) δ 8.40 (d, J=5.8 Hz, 1H), 7.56 (d, J=5.8 Hz, 1H), 6.43 (d, J=4.1 Hz, 1H), 6.17 (dd, J=5.3, 4.1 Hz, 1H), 5.74 (t, J=5.3 Hz, 1H), 5.32 (s, 1H), 4.58 (ddd, J=5.3, 3.9, 2.9 Hz, 1H), 4.42 (dd, J=12.5, 3.0 Hz, 1H), 4.25 (dd, J=12.5, 3.9 Hz, 1H), 2.17 (d, J=18.8 Hz, 6H), 2.03 (s, 3H).

Step 2: (2R,3R,4S,5R)-2-(4-amino-1H-[1,2,3]triazolo[4,5-c]pyridin-1-yl)-5-(hydroxymethyl)tetrahydrofuran-3,4-diol

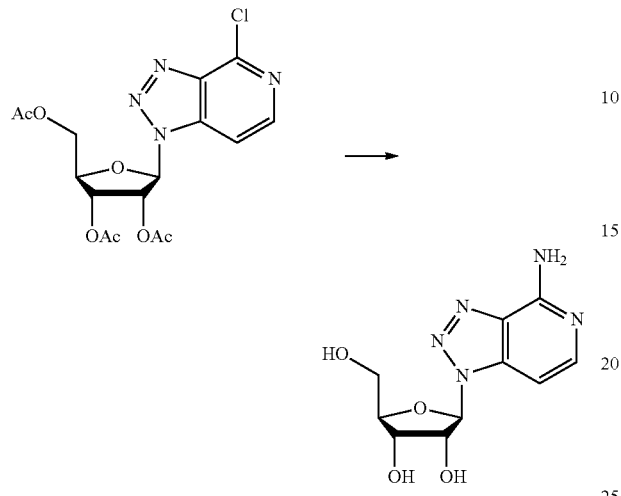

To a solution of (2R,3R,4R,5R)-2-(acetoxymethyl)-5-(4-chloro-1H-[1,2,3]triazolo[4,5-c]pyridin-1-yl)tetrahydrofuran-3,4-diyl diacetate (1.2 g, 2.9 mmol) in MeOH (8.3 mL) was added a 7N solution of ammonia in MeOH (8.3 mmol, 58.1 mmol). The reaction mixture was stirred at 150° C. in a sealed Q-Tube™ Pressure Tube Reactor for 18 h. Excess solvent was removed under reduced pressure, and the residue was purified by a reverse phase silica gel column, eluting with 0-10% Acetonitrile/H$_2$O containing 0.05% TFA. LCMS (ES, m/z): 268.17 [M+H]$^+$. $^1$H NMR (500 MHz, DMSO-d$_6$) δ 13.87 (s, 2H), 9.34 (s, 4H), 7.89 (d, J=7.1 Hz, 2H), 7.51 (d, J=7.0 Hz, 2H), 7.42 (s, 4H), 7.32 (s, 6H), 7.22 (s, 5H), 6.69 (s, 2H), 6.30 (d, J=4.9 Hz, 2H), 5.72 (s, 2H), 5.41 (s, 2H), 4.75-4.67 (m, 0H), 4.65 (t, J=5.0 Hz, 2H), 4.27 (t, J=4.6 Hz, 2H), 4.07 (q, J=4.2 Hz, 2H), 3.86-3.67 (m, 2H), 3.69-3.58 (m, 2H), 3.54 (dd, J=12.0, 4.7 Hz, 2H), 3.48-3.38 (m, 1H), 3.28 (s, 1H), 3.23 (s, 0H), 1.76 (d, J=0.5 Hz, 5H), 1.11 (dt, J=26.0, 7.1 Hz, 1H).

Preparation 11: 9-{3-azido-5-O-[bis(4-methoxyphenyl)(phenyl)methyl]-3-deoxy-β-D-ribofuranosyl}-2-[(2-methylpropanoyl)amino]-1,9-dihydro-6H-purin-6-one

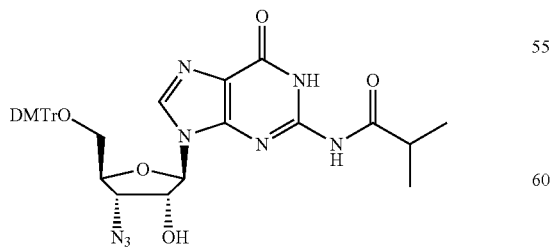

The title compound was prepared according to published procedures (*Nucleosides, Nucleotides & Nucleic Acids* 2005, 24(10-12), 1707-1727).

Preparation 12: 9-{5-O-[bis(4-methoxyphenyl)(phenyl)methyl]-3-deoxy-3-fluoro-β-D-xylofuranosyl}-2-[(2-methylpropanoyl)amino]-1,9-dihydro-6H-purin-6-one

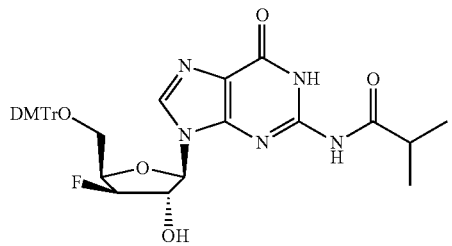

The title compound was prepared according to published procedures (*Tetrahedron Letters*, 1989, 30(24), 3171-3174).

Preparation 13: 1-{5-O-[bis(4-methoxyphenyl)(phenyl)methyl]-3-deoxy-3-fluoro-β-D-ribofuranosyl}-6-[(2-methylpropanoyl)amino]-1,5-dihydro-4H-imidazo[4,5-c]pyridin-4-one

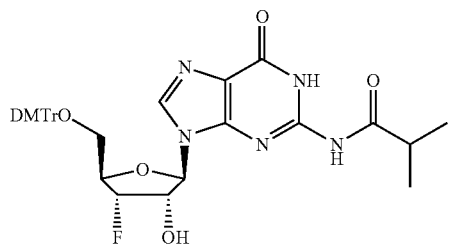

The title compound was prepared according to published procedures (WO2002057425).

Preparation 14: N-(3-((2R,4R,5R)-5-((bis(4-methoxyphenyl)(phenyl)methoxy)methyl)-3,3-difluoro-4-hydroxytetrahydrofuran-2-yl)-3H-[1,2,3]triazolo[4,5-d]pyrimidin-7-yl)benzamide

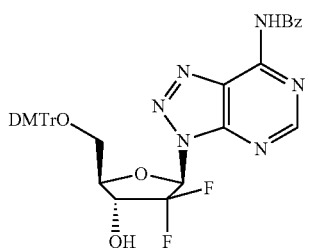

Step 1: (((2R,3R)-3-(benzoyloxy)-5-((diphenoxy-phosphoryl)oxy)-4,4-difluorotetrahydrofuran-2-yl) methyl benzoate

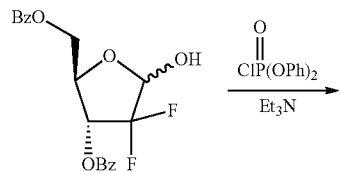

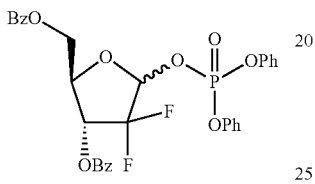

To ((2R,3R)-3-(benzoyloxy)-4,4-difluoro-5-hydroxytetrahydrofuran-2-yl)methyl benzoate (20.0 g, 52.9 mmol) in toluene (150 mL) at 0° C. were added Et$_3$N (7.74 mL, 55.5 mmol) and diphenyl phosphoryl chloride (12.1 mL, 58.2 mmol) in toluene (20 mL) dropwise. The reaction was warmed to rt and stirred for 3 h. LCMS showed completion of the reaction (m/e=611). Water (30 mL) and aq HCl (1 M, 5 mL) were added. Layers were separated, and the aq layer was extracted with CH$_2$Cl$_2$ (2×30 mL). The combined organic solution was washed with sat aq NaHCO$_3$ (20 mL), and Brine (20 mL), dried (MgSO$_4$), and concentrated. It was purified by silica column chromatography eluting with 0 to 30% EtOAc in Hex to give the product. LCMS (ES, m/z): 611.3 [M+H]$^+$.

Step 2: ((2R,3R,5R)-3-(benzoyloxy)-5-bromo-4,4-difluorotetrahydrofuran-2-yl)methyl benzoate

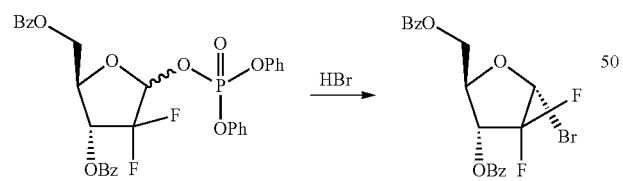

To ((2R,3R)-3-(benzoyloxy)-5-((diphenoxyphosphoryl)oxy)-4,4-difluorotetrahydrofuran-2-yl)methyl benzoate (23.8 g, 39.0 mmol) at 0° C. was added HBr in acetic acid (33%, 51.2 mL, 292 mmol). It was stirred as it warmed to rt. After 6 h, LCMS showed completion of the reaction (m/e=441 and 443). CH$_2$Cl$_2$ (200 mL) was added, and the organic layer was washed with water (2×50 mL), sat aq NaHCO$_3$ (2×50 mL) and brine (50 mL). It was dried (MgSO$_4$) and concentrated to give the crude product. It was used in the next step without purification. LCMS (ES, m/z): 441.1, 443.1 [M+H]$^+$.

Step 3: (2R,3R,5R)-5-(7-amino-3H-[1,2,3]triazolo[4,5-d]pyrimidin-3-yl)-2-((benzoyloxy)methyl)-4,4-difluorotetrahydrofuran-3-yl benzoate

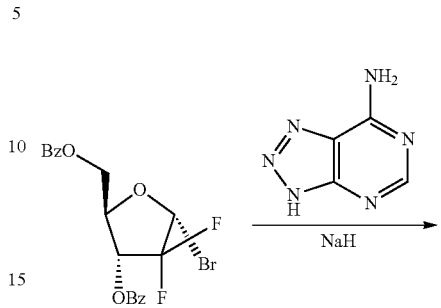

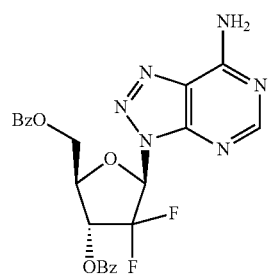

To a mixture of 3H-[1,2,3]triazolo[4,5-d]pyrimidin-7-amine (3.21 g, 23.6 mmol) in NMP (60 mL) was added NaH (60%, 0.979 g, 24.5 mmol). The mixture was vigorously stirred, and after 1 h, generation of bubbles had completely ceased. To the mixture was added to ((2R,3R,5R)-3-(benzoyloxy)-5-bromo-4,4-difluorotetrahydrofuran-2-yl)methyl benzoate (neat, 8.00 g, 18.1 mmol). The mixture was stirred vigorously for 30 min. Then, it was heated to 90° C. for 5 h. It was cooled to rt, and CH$_2$Cl$_2$ (300 mL) and water (150 mL) were added. The phases were separated, and the organic layer was washed with water (8×150 mL) and brine (50 mL), dried (MgSO$_4$) and concentrated. The residue was purified by silica column chromatography eluting with 0% to 30% EtOAc to give the desired product. LCMS (ES, m/z): 497.1 [M+H]$^+$. $^1$H NMR (500 MHz, Chloroform-d) δ 8.44 (s, 1H), 8.15-8.08 (m, 2H), 8.08-7.99 (m, 2H), 7.63 (ddt, J=8.7, 7.1, 1.3 Hz, 1H), 7.56-7.44 (m, 3H), 7.40-7.32 (m, 2H), 6.79-6.68 (m, 2H), 6.04 (bs, 2H), 4.92-4.84 (m, 1H), 4.80-4.72 (m, 2H).

Step 4. (2R,3R,5R)-5-(7-amino-3H-[1,2,3]triazolo[4,5-d]pyrimidin-3-yl)-4,4-difluoro-2-(hydroxymethyl)tetrahydrofuran-3-ol

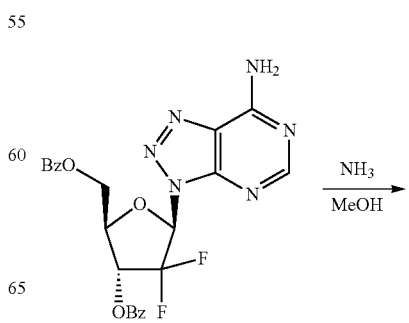

-continued

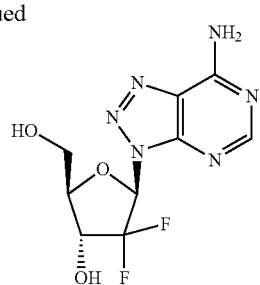

To (2R,3R,5R)-5-(7-amino-3H-[1,2,3]triazolo[4,5-d]pyrimidin-3-yl)-2-((benzoyloxy) methyl)-4,4-difluorotetrahydrofuran-3-yl benzoate (1.05 g, 2.11 mmol) was added ammonia in MeOH (7N, 9.0 mL, 63 mmol), and the mixture was stirred for 24 h. LCMS showed completion of reaction (m/e=289). It was concentrated and purified by silica column chromatography eluting with 0 to 15% MeOH in CH$_2$Cl$_2$ to give the desired product. LCMS (ES, m/z): 289.1 [M+H]$^+$. $^1$H-NMR (500 MHz, DMSO-d$_6$): δ 8.65 (s, 1H), 8.36 (s, 1H), 8.32 (s, 1H), 6.65 (d, J=12.4 Hz, 1H), 6.40 (d, J=6.7 Hz, 1H), 5.03 (dd, J=6.4, 5.3 Hz, 1H), 4.83 (dq, J=16.5, 8.9 Hz, 1H), 4.00 (t, J=6.7 Hz, 1H), 3.77 (ddd, J=12.3, 5.2, 2.5 Hz, 1H), 3.68 (dt, J=12.5, 6.3 Hz, 1H).

Step 5: N-(3-((2R,4R,5R)-3,3-difluoro-4-hydroxy-5-(hydroxymethyl)tetrahydrofuran-2-yl)-3H-[1,2,3]triazolo[4,5-d]pyrimidin-7-yl)benzamide

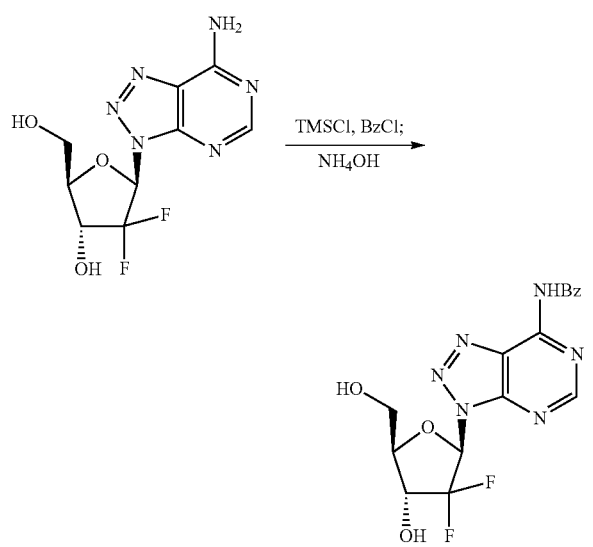

To a solution of (2R,3R,5R)-5-(7-amino-3H-[1,2,3]triazolo[4,5-d]pyrimidin-3-yl)-4,4-difluoro-2-(hydroxymethyl)tetrahydrofuran-3-ol (0.57 g, 2.0 mmol) in pyridine (15 mL) at 0° C. was added TMSCl (0.55 mL, 4.3 mmol). It was warmed to rt and stirred for 1 h. Then, it was recooled to 0° C. and BzCl (0.34 mL, 2.9 mmol) was added dropwise. The reaction was slowly warmed rt over 2 h. LCMS showed completion of reaction (m/e=393,497). It was cooled to 0° C., and ammonium hydroxide (28%, 1.1 mL, 7.9 mmol) was added. After 30 min, it was concentrated and purified by silica column chromatography eluting with 0 to 10% MeOH in CH$_2$Cl$_2$ to give the product. LCMS (ES, m/z): 393.3 [M+H]$^+$. $^1$H-NMR (500 MHz, DMSO-d$_6$): δ 12.02 (s, 1H), 9.01 (s, 1H), 8.13-8.07 (m, 2H), 7.73-7.66 (m, 1H), 7.64-7.55 (m, 2H), 6.86 (d, J=11.6 Hz, 1H), 6.46 (d, J=6.7 Hz, 1H), 5.01 (dd, J=6.3, 5.4 Hz, 1H), 4.86 (dt, J=16.7, 8.3 Hz, 1H), 4.04 (ddd, J=8.8, 6.2, 2.6 Hz, 1H), 3.78 (ddd, J=12.3, 5.4, 2.7 Hz, 1H), 3.68 (dt, J=12.4, 6.2 Hz, 1H).

Step 6: N-(3-((2R,4R,5R)-5-((bis(4-methoxyphenyl)(phenyl)methoxy)methyl)-3,3-difluoro-4-hydroxytetrahydrofuran-2-yl)-3H-[1,2,3]triazolo[4,5-d]pyrimidin-7-yl)benzamide

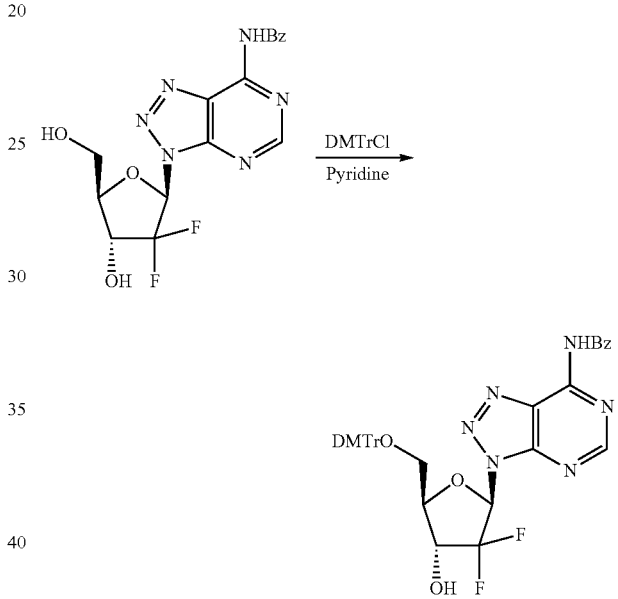

To a solution of N-(3-((2R,4R,5R)-3,3-difluoro-4-hydroxy-5-(hydroxymethyl)-tetrahydrofuran-2-yl)-3H-[1,2,3]triazolo[4,5-d]pyrimidin-7-yl)benzamide (0.68 g, 1.7 mmol) in pyridine (15 mL) at 0° C. was added DMTrCl (0.65 g, 1.9 mmol). It was stirred at rt for 1 h. LCMS showed a peak with the desired mass (m/e=695). It was partly concentrated (to 5 mL), and EtOAc (20 mL) and water (10 mL) were added. The phases were separated, and the aqueous layer was extracted with EtOAc (2×10 mL). The combined organic portions were washed with brine, dried (MgSO$_4$), concentrated and purified by silica column chromatography eluting with 0% to 60% EtOAc in Hex to give the product. LCMS (ES, m/z): 695.2 [M+H]$^+$. $^1$H-NMR (500 MHz, DMSO-d$_6$): δ 12.05 (s, 1H), 8.93 (s, 1H), 8.11 (d, J=7.6 Hz, 2H), 7.70 (m, 1H), 7.60 (t, J=7.7 Hz, 2H), 7.38-7.32 (m, 2H), 7.25-7.13 (m, 7H), 6.96 (d, J=11.9 Hz, 1H), 6.84-6.73 (m, 4H), 6.48 (d, J=6.9 Hz, 1H), 4.97 (dq, J=16.7, 8.3 Hz, 1H), 4.23 (m, 1H), 3.70 (s, 3H), 3.69 (s, 3H), 3.42-3.36 (m, 1H), 3.32-3.28 (m, 1H).

Preparation 15: N-(7-((2R,4R,5R)-5-((bis(4-methoxyphenyl)(phenyl)methoxy)methyl)-3,3-difluoro-4-hydroxytetrahydrofuran-2-yl)-7H-pyrrolo[2,3-d]pyrimidin-4-yl)benzamide

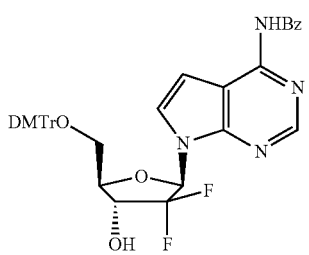

Step 1: ((2R,3R,5R)-3-(benzoyloxy)-5-(4-chloro-7H-pyrrolo[2,3-d]pyrimidin-7-yl)-4,4-difluorotetrahydrofuran-2-yl)methyl benzoate

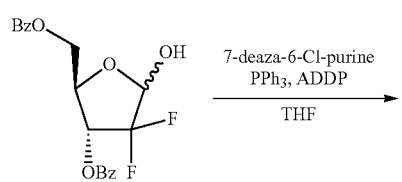

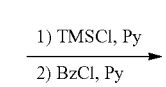

To a solution of 4-chloro-7H-pyrrolo[2,3-d]pyrimidine (4.06 g, 26.4 mmol) and ((2R,3R)-3-(benzoyloxy)-4,4-difluoro-5-hydroxytetrahydrofuran-2-yl)methyl benzoate (10.0 g, 26.4 mmol) and triphenylphosphine (20.80 g, 79 mmol) in THF (100 mL) was added (E)-diazene-1,2-diylbis(piperidin-1-ylmethanone) (20.01 g, 79 mmol) dropwise. It was slowly warmed to rt. After stirring for 2 h, the mixture was concentrated. The residue was purified by silica gel column chromatography using 0-20% EtOAc in Petroleum Ether to give the product. LCMS (ES, m/z): 514.3 [M+H]$^+$. $^1$H-NMR (300 MHz, DMSO-d$_6$): δ 8.71 (s, 1H), 8.08-7.87 (m, 5H), 7.76-7.42 (m, 6H), 6.98 (dd, J=10.3, 7.9 Hz, 1H), 6.84 (d, J=3.8 Hz, 1H), 6.29 (ddd, J=10.0, 6.0, 3.8 Hz, 1H), 5.44 (q, J=5.5 Hz, 1H), 4.79-4.60 (m, 2H).

Step 2. (2R,3R,5R)-5-(4-amino-7H-pyrrolo[2,3-d]pyrimidin-7-yl)-4,4-difluoro-2-(hydroxymethyl)tetrahydrofuran-3-ol

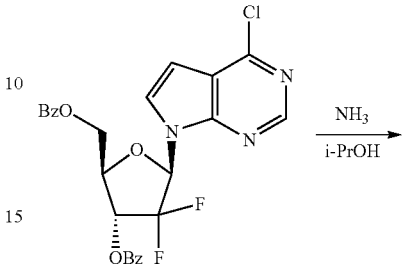

A solution of ((2R,3R,5R)-3-(benzoyloxy)-5-(4-chloro-7H-pyrrolo[2,3-d]pyrimidin-7-yl)-4,4-difluorotetrahydrofuran-2-yl)methyl benzoate (1.9 g, 3.70 mmol) in NH$_3$/2-propanol (saturated at −78° C., 100 mL) was stirred at 90° C. for 16 h. It was cooled to rt, concentrated, and purified by silica gel column chromatography using 0-10% MeOH in CH$_2$Cl$_2$ to give the product. LCMS (ES, m/z): 287.1 [M+H]$^+$. $^1$H-NMR (300 MHz, DMSO-d$_6$): δ 8.06 (s, 1H), 7.40-7.25 (m, 1H), 7.14 (s, 2H), 6.82 (d, J=5.9 Hz, 1H), 6.60 (d, J=3.7 Hz, 1H), 6.34 (dd, J=16.2, 2.1 Hz, 1H), 4.88 (t, J=5.7 Hz, 1H), 4.27 (ddd, J=9.9, 6.2, 3.6 Hz, 1H), 4.08 (dq, J=6.8, 4.1, 3.5 Hz, 1H), 3.78 (dt, J=11.1, 5.4 Hz, 1H), 3.62 (dt, J=11.4, 5.8 Hz, 1H).

Step 3: N-(7-((2R,4R,5R)-3,3-difluoro-4-hydroxy-5-hydroxymethyl)tetrahydrofuran-2-yl)-7H-pyrrolo[2,3-d]pyrimidin-4-yl)benzamide

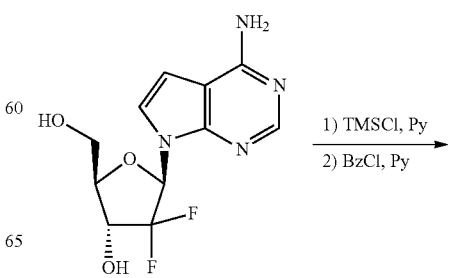

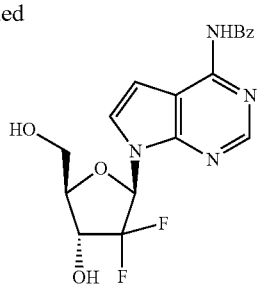

To a solution of (2R,3R,5R)-5-(4-amino-7H-pyrrolo[2,3-d]pyrimidin-7-yl)-4,4-difluoro-2-(hydroxymethyl)tetrahydrofuran-3-ol (900 mg, 3.14 mmol) in pyridine (15 mL) at 0° C. was added chlorotrimethylsilane (3.42 g, 31.4 mmol). It was warmed to rt over 1 h and benzoyl chloride (663 mg, 4.72 mmol) was added dropwise. After 2 h, NH$_4$OH (28%, 15.00 mL) was added, and it was stirred for 0.5 h. The resulting mixture was concentrated, and the residue was purified by silica gel column chromatography using 0-10% MeOH in CH$_2$Cl$_2$ to give the product. LCMS (ES, m/z): 391.1 [M+H]$^+$. $^1$H-NMR (300 MHz, DMSO-d$_6$): δ 8.61 (s, 1H), 8.08-7.98 (m, 2H), 7.97-7.91 (m, 1H), 7.67-7.51 (m, 2H), 7.50-7.47 (m, 1H), 6.70 (d, J=3.9 Hz, 1H), 6.56 (dd, J=15.6, 1.5 Hz, 1H), 4.32 (dd, J=9.4, 3.6 Hz, 1H), 4.16 (d, J=5.6 Hz, 1H), 3.80 (dd, J=11.5, 5.2 Hz, 1H), 3.66 (dd, J=11.5, 6.5 Hz, 1H), 3.12 (s, 2H).

Step 4: N-(7-((2R,4R,5R)-5-((bis(4-methoxyphenyl)(phenyl)methoxy)methyl)-3,3-difluoro-4-hydroxytetrahydrofuran-2-yl)-7H-pyrrolo[2,3-d]pyrimidin-4-yl)benzamide

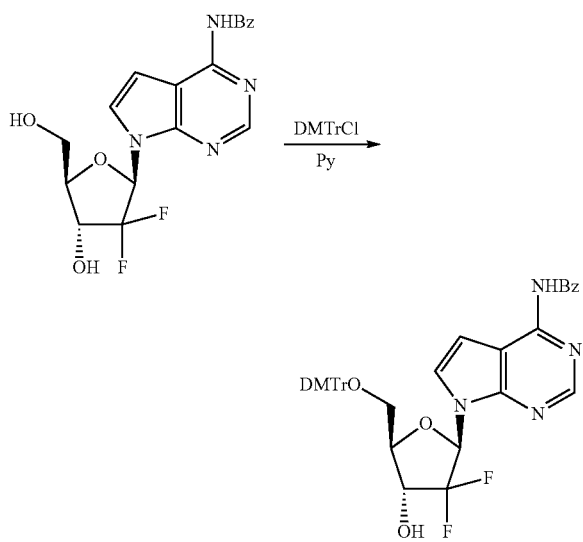

To a solution of N-(7-((2S,4R,5R)-3,3-difluoro-4-hydroxy-5-(hydroxymethyl)-tetrahydrofuran-2-yl)-7H-pyrrolo[2,3-d]pyrimidin-4-yl)benzamide (1.1 g, 2.82 mmol) in pyridine (12 mL) at 0° C. was added 4,4'-(chloro(phenyl)methylene)-bis(methoxybenzene) (0.955 g, 2.82 mmol). It was warmed to RT and stirred for 3 h. The mixture was concentrated. The product was purified by silica gel column chromatography using 0-10% MeOH in CH$_2$Cl$_2$ to give the product. LCMS (ES, m/z): 693.3 [M+H]$^+$. $^1$H-NMR (300 MHz, DMSO-d$_6$): δ 11.25 (s, 1H), 8.67 (s, 1H), 8.09-8.01 (m, 2H), 7.60-7.48 (m, 2H), 7.47-7.36 (m, 3H), 7.33-7.18 (m, 7H), 6.91-6.78 (m, 4H), 6.75-6.57 (m, 3H), 5.76 (s, 1H), 4.55-4.33 (m, 2H), 3.74 (s, 6H), 3.44 (t, J=8.7 Hz, 1H), 3.35 (s, 1H).

Preparation 16: N-(9-((2R,3S,5R)-5-((bis(4-methoxyphenyl)(phenyl)methoxy)methyl)-4,4-difluoro-3-hydroxytetrahydrofuran-2-yl)-6-oxo-6,9-dihydro-1H-purin-2-yl)isobutyramide

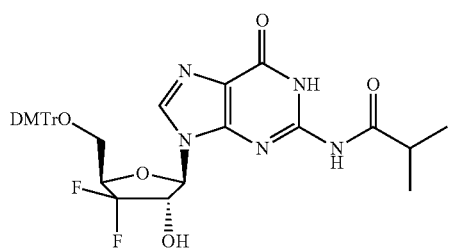

Step 1: (2R,4S)-4-(benzyloxy)-4-((R)-2,2-dimethyl-1,3-dioxolan-4-yl)-3,3-difluoro-2-hydroxybutyl benzoate

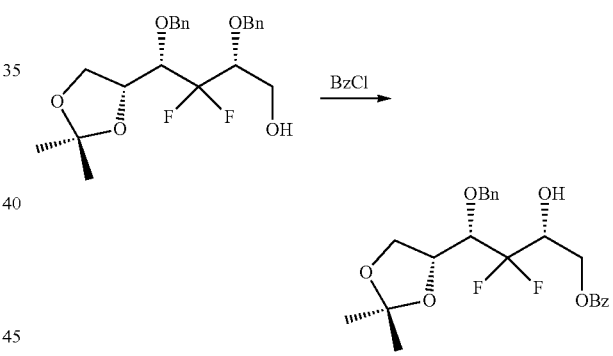

To a solution of (2R,4S)-4-(benzyloxy)-4-((R)-2,2-dimethyl-1,3-dioxolan-4-yl)-3,3-difluorobutane-1,2-diol (3.50 g, 10.5 mmol) in CH$_2$Cl$_2$ (52 mL) and pyridine (26 mL) at −70° C. was added benzoyl chloride (1.48 g, 10.5 mmol) in CH$_2$Cl$_2$ (11 mL) dropwise over 50 min. After 2 h, methanol (150 mL) was added. The mixture was stirred at RT for 0.5 h. Water (200 mL) was added. Layers were separated, and the aq layer was extracted with ether (4×150 mL). The combined organic layers were washed with aq HCl (1 N, 2×150 mL), sat aq NaHCO$_3$ (2×150 mL) and brine (2×150 mL). It was dried (Na$_2$SO$_4$), concentrated and purified by silica gel column chromatography (EtOAc/petroleum ether=1/10) to give the product. $^1$H-NMR (400 MHz, CDCl$_3$): δ 8.11-8.01 (m, 2H), 7.61-7.55 (m, 1H), 7.48-7.31 (m, 7H), 4.89-4.53 (m, 4H), 4.46-4.41 (m, 1H), 4.40-4.29 (m, 1H), 4.17-4.02 (m, 2H), 3.98-3.84 (m, 0.5H), 3.74-3.66 (m, 0.5H), 1.46 (s, 3H), 1.28 (s, 3H). $^{19}$F-NMR: (376 MHz, CDCl$_3$): δ −106.8 (d, J=270.7 Hz, 1F), −119.2 (d, J=270.7 Hz, 1F).

Step 2: ((2R,4S)-4-(benzyloxy)-3,3-difluoro-5-hydroxytetrahydrofuran-2-yl)methyl benzoate

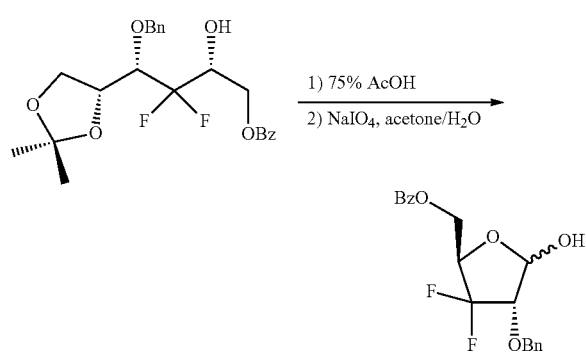

(2R,4 S)-4-(benzyloxy)-4-((R)-2,2-dimethyl-1,3-dioxolan-4-yl)-3,3-difluoro-2-hydroxybutyl benzoate (3.00 g, 6.87 mmol) was dissolved in aq AcOH (75%, 66 mL). It was stirred at 50° C. for 3 h. It was partly concentrated. The residue was redissolved in acetone (33 mL). To the solution at rt was added sodium periodate (1.20 g, 5.61 mmol) in water (33 mL). After 1.5 h, the solid formed was filtered off and washed with acetone. The filtrate was concentrated. Water and $CH_2Cl_2$ were added, and layers were separated. The aq layer was extracted with $CH_2Cl_2$ (4×150 mL). The combined organic layers were dried ($Na_2SO_4$), concentrated, and purified by silica gel column chromatography (ethyl acetate/petroleum ether=1/5) to give the product. $^1$H-NMR (400 MHz, $CDCl_3$): δ 8.05-8.01 (m, 2H), 7.59-7.52 (m, 1H), 7.46-7.35 (m, 7H), 5.49-5.42 (m, 1H), 4.99-4.72 (m, 1H), 4.67-4.47 (m, 4H), 4.11-3.80 (m, 1H). $^{19}$F-NMR: (376 MHz, $CDCl_3$): δ −117.1 (d, J=240.6 Hz, 1F), −117.9 (d, J=251.9 Hz, 1F).

Step 3: ((2R,4S)-5-acetoxy-4-(benzyloxy)-3,3-difluorotetrahydrofuran-2-yl)methyl benzoate

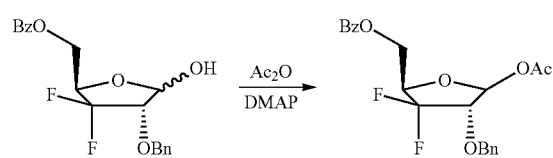

To a solution of ((2R,4S)-4-(benzyloxy)-3,3-difluoro-5-hydroxytetrahydrofuran-2-yl)methyl benzoate (2.40 g, 6.59 mmol) in $CH_2Cl_2$ (66 mL) at rt was added N,N-dimethylpyridin-4-amine (0.080 g, 0.659 mmol) and acetic anhydride (4.03 g, 39.5 mmol) dropwise. After 6 h, it was quenched by addition of sat aq $NaHCO_3$ (30 mL). Layers were separated, and the aq layer was extracted with $CH_2Cl_2$ (3×150 mL). The combined organic layers were washed with water (2×150 mL) and brine (2×100 mL), dried ($Na_2SO_4$), concentrated and purified by silica gel column chromatography (ethyl acetate/petroleum ether=1/7) to give the product. $^1$H-NMR (300 MHz, $CDCl_3$): δ 8.08-7.89 (m, 2H), 7.61-7.48 (m, 1H), 7.47-7.25 (m, 7H), 6.15 (d, J=6.0 Hz, 1H), 4.89-4.75 (m, 1H), 4.73-4.40 (m, 4H), 4.18-4.02 (m, 1H), 1.98 (s, 3H). $^{19}$F-NMR: (282 MHz, $CDCl_3$): δ −116.5 (d, J=248.2 Hz, 1F), −120.9 (d, J=248.2 Hz, 1F).

Step 4. ((2R,4S)-5-acetoxy-3,3-difluoro-4-hydroxytetrahydrofuran-2-yl)methyl benzoate

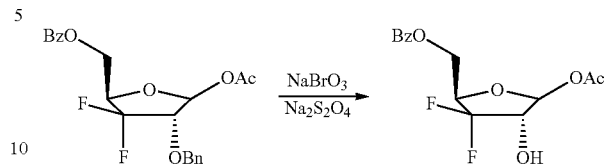

To a solution of ((2R,4S)-5-acetoxy-4-(benzyloxy)-3,3-difluorotetrahydrofuran-2-yl)methyl benzoate (2.50 g, 6.15 mmol) in EtOAc (60 mL) was added sodium bromate (5.57 g, 36.9 mmol) in water (46 mL). The mixture was stirred vigorously, and to it was added sodium dithionite (6.43 g, 36.9 mmol) in water (92 mL) dropwise over 1 h. After 5 h, layers were separated, and the aq layer was extracted with EtOAc (5×150 mL). The combined organic layers were washed with sat aq $Na_2S_2O_3$ (2×150 mL) and brine (2×150 mL), dried ($Na_2SO_4$), concentrated, and purified by silica gel column chromatography (ethyl acetate/petroleum ether=1/5) to give the product. $^1$H-NMR (300 MHz, $CDCl_3$): δ 8.10-7.89 (m, 2H), 7.63-7.50 (m, 1H), 7.48-7.30 (m, 2H), 6.09 (d, J=6.0 Hz, 1H), 4.71-4.42 (m, 3H), 4.36-4.26 (m, 1H), 2.04 (s, 3H). $^{19}$F-NMR: (282 MHz, $CDCl_3$): δ −119.5 (d, J=248.2 Hz, 1F), −122.0 (d, J=248.2 Hz, 1F).

Step 5: (3S,5R)-5-((benzoyloxy)methyl)-4,4-difluorotetrahydrofuran-2,3-diyl diacetate

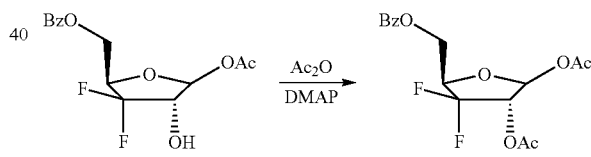

To a solution of ((2R,4S)-5-acetoxy-3,3-difluoro-4-hydroxytetrahydrofuran-2-yl)methyl benzoate (2.00 g, 6.32 mmol) in $CH_2Cl_2$ (84 mL) at rt was added DMAP (0.08 g, 0.632 mmol) and acetic anhydride (3.87 g, 37.9 mmol) dropwise. After 6 h, it was quenched by addition of sat aq $NaHCO_3$ (30 mL). Layers were separated, and the aq layer was extracted with $CH_2Cl_2$ (3×140 mL). The combined organic layers were washed with water (2×140 mL) and brine (2×140 mL), dried ($Na_2SO_4$), concentrated and purified by silica gel column chromatography (ethyl acetate/petroleum ether=1/6) to give the product. $^1$H-NMR (400 MHz, $CDCl_3$): δ 8.11-8.01 (m, 2H), 7.63-7.54 (m, 1H), 7.50-7.41 (m, 2H), 6.20 (d, J=4.0 Hz, 1H), 5.39 (d, J=8.0 Hz, 1H), 4.69-4.48 (m, 3H), 2.23 (s, 3H), 2.08 (s, 3H). $^{19}$F-NMR: (376 MHz, $CDCl_3$): δ −117.6 (d, J=251.9 Hz, 1F), −119.5 (d, J=251.9 Hz, 1F).

Step 6. ((2R,4S,5R)-4-acetoxy-5-(6-chloro-2-isobutyramido-9H-purin-9-yl)-3,3-difluorotetrahydrofuran-2-yl)methyl benzoate

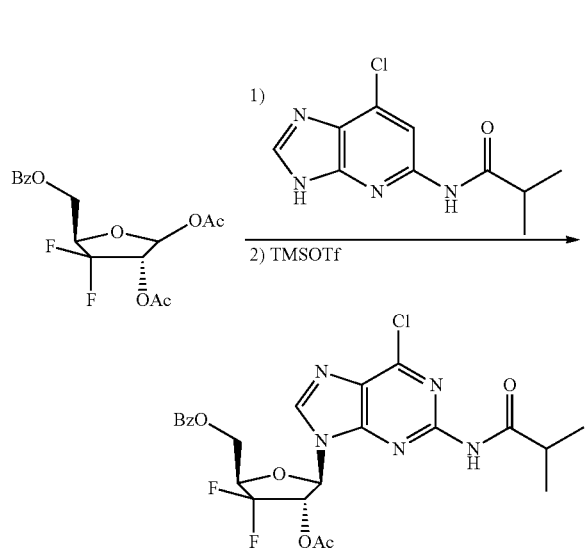

To a solution of (3 S,5R)-5-((benzoyloxy)methyl)-4,4-difluorotetrahydrofuran-2,3-diyl diacetate (2.20 g, 6.14 mmol) and N-(6-chloro-9H-purin-2-yl)isobutyramide (1.77 g, 7.37 mmol) in ACN (80 mL) at 0° C. was added 2,3,4,6,7,8,9,10-octahydropyrimido[1,2-a]azepine (2.80 mL, 18.4 mmol). After 0.5 h, trimethylsilyl trifluoromethanesulfonate (6.82 mL, 36.8 mmol) was added dropwise to the reaction at 0° C. After 0.5 h, it was heated at 80° C. for 16 h. The reaction was then quenched by the addition of water (150 mL). Layers were separated, and the aq layer was extracted with EtOAc (3×150 mL). The combined organic layers were washed with sat aq NaHCO₃ (2×150 mL) and brine (2×150 mL), dried (Na₂SO₄), concentrated and purified by silica gel column chromatography (ethyl acetate/petroleum ether=1/1) to give the product. $^1$H-NMR (400 MHz, CDCl₃): δ 8.10 (s, 1H), 8.08-7.98 (m, 2H), 7.64-7.53 (m, 1H), 7.51-7.40 (m, 2H), 6.25 (d, J=4.0 Hz, 1H), 5.98-5.93 (m, 1H), 4.85-4.53 (m, 3H), 2.92-2.80 (m, 1H), 2.22 (s, 3H) 1.28 (d, J=4.0 Hz, 6H). $^{19}$F-NMR: (376 MHz, CDCl₃): δ −116.7 (d, J=248.2 Hz, 1F), −118.1 (d, J=248.2 Hz, 1F).

Step 7: ((2R,4S,5R)-5-(2-acetamido-6-oxo-1,6-dihydro-9H-purin-9-yl)-4-acetoxy-3,3-difluorotetrahydrofuran-2-yl)methyl benzoate

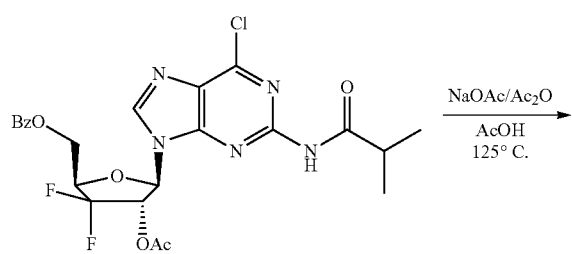

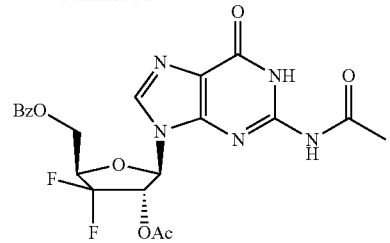

To a solution of ((2R,4S,5R)-4-acetoxy-5-(6-chloro-2-isobutyramido-9H-purin-9-yl)-3,3-difluorotetrahydrofuran-2-yl)methyl benzoate (1.80 g, 3.35 mmol) in AcOH (29 mL) was added Sodium acetate (1.37 g, 16.7 mmol) and acetic anhydride (29 mL). The reaction was stirred at 125° C. for 2.5 h. It was cooled to rt, and MeOH (50 mL) was added. The mixture was concentrated under reduced pressure, and the residue was coevaporated with ethanol (2×50 mL). DCM (150 mL) and water (150 mL) were added, and layers were separated. The organic phase was washed with sat aq NaHCO₃ (2×150 mL), dried (Na₂SO₄), and concentrated to give the product. LCMS (ES, m/z): 492.1 [M+H]⁺.

Step 8: 2-amino-9-((2R,3S,5R)-4,4-difluoro-3-hydroxy-5-(hydroxymethyl)tetrahydrofuran-2-yl)-1,9-dihydro-6H-purin-6-one

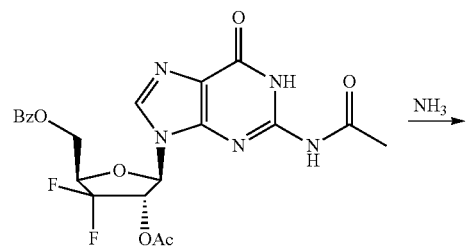

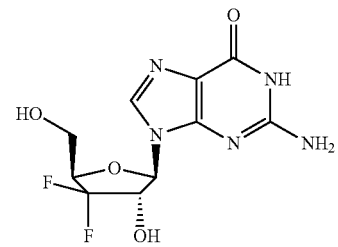

To ((2R,4S,5R)-5-(2-acetamido-6-oxo-1,6-dihydro-9H-purin-9-yl)-4-acetoxy-3,3-difluorotetrahydrofuran-2-yl)methyl benzoate (neat, 1.80 g, 3.66 mmol) was added NH₃ in MeOH (7 M, 90 mL, MeOH). It was stirred at rt for 60 h. It was concentrated and purified by reverse phase (C18) chromatography eluting with 5-20% MeCN in aq NH₄HCO₃ (5 mM) to give the product. $^1$H-NMR (300 MHz, DMSO-d₆): δ 10.7 (s, 1H), 7.95 (s, 1H), 6.56-6.44 (m, 3H), 5.62 (d, J=6.0 Hz, 1H), 5.32 (t, J=5.4 Hz, 1H), 4.90-4.77 (m, 1H), 4.23-4.08 (m, 1H), 3.68-3.52 (m, 2H). $^{19}$F-NMR: (282 MHz, DMSO-d₆): δ −113.1 (d, J=234.1 Hz, 1F), −121.8 (d, J=234.1 Hz, 1F).

Step 9: N-(9-((2R,3S,5R)-4,4-difluoro-3-hydroxy-5-(hydroxymethyl)tetrahydrofuran-2-yl)-6-oxo-6,9-dihydro-1H-purin-2-yl)isobutyramide

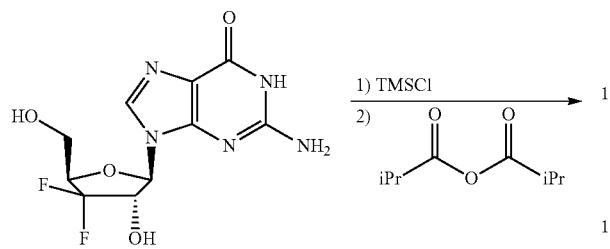

2-amino-9-((2R,3 S,5R)-4,4-difluoro-3-hydroxy-5-(hydroxymethyl)tetrahydrofuran-2-yl)-1,9-dihydro-6H-purin-6-one (800 mg, 2.64 mmol) was co-evaporated with pyridine (3×3 mL). It was re-suspended in pyridine (13 mL). To the mixture at 0° C. was added chlorotrimethylsilane (1.686 mL, 13.19 mmol) dropwise. It was warmed to rt and stirred for 2 h. The reaction was cooled to 0° C., and isobutyric anhydride (0.656 mL, 3.96 mmol) was added dropwise. It was warmed to rt, stirred for 2 h, and then water (4 mL) and NH$_4$OH (8 mL) were added to the reaction. After 30 min, it was concentrated. The residue was purified by flash column chromatography with 0-10% MeOH in CH$_2$Cl$_2$ to give the product. LCMS (ES, m/z): 374.1 [M+H]$^+$. $^1$H-NMR: (300 MHz, DMSO-d$_6$) δ 12.11 (s, 1H), 11.69 (s, 1H), 8.30 (s, 1H), 6.58 (d, J=6.0 Hz, 1H), 5.74 (dd, J=9.0, 3.0 Hz, 1H), 5.33 (t, J=6.0 Hz, 1H), 4.96-4.83 (m, 1H), 4.26-4.17 (m, 1H), 3.72-3.62 (m, 2H), 2.80-2.71 (m, 1H), 1.11 (d, J=9.0 Hz, 6H).

Step 10: N-(9-((2R,3S,5R)-5-((bis(4-methoxyphenyl)(phenyl)methoxy)methyl)-4,4-difluoro-3-hydroxytetrahydrofuran-2-yl)-6-oxo-6,9-dihydro-1H-purin-2-yl)isobutyramide

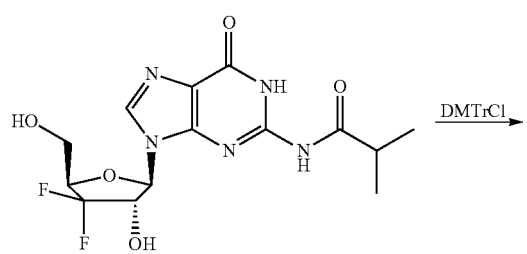

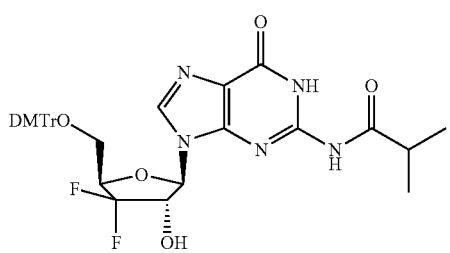

N-(9-((2R,3 S,5R)-4,4-difluoro-3-hydroxy-5-(hydroxymethyl)tetrahydrofuran-2-yl)-6-oxo-6,9-dihydro-1H-purin-2-yl)isobutyramide (640 mg, 1.714 mmol) was co-evaporated with pyridine (3×3 mL) and then re-suspended in pyridine (5.7 mL). To the suspension was added 4,4'-(chloro(phenyl)methylene)bis(methoxybenzene) (639 mg, 1.886 mmol), and it was stirred for 16 h. Then, it was concentrated and then, co-evaporated with toluene (3×20 mL). The crude was purified by silica column chromatography eluting with 1 to 30% MeOH in CH$_2$Cl$_2$ (containing 1% Et$_3$N) to give the product. LCMS (ES, m/z): 676.3 [M+H]$^+$. $^1$H-NMR: (300 MHz, DMSO-d$_6$) δ 12.11 (s, 1H), 11.61 (s, 1H), 8.15 (s, 1H), 7.34 (J=6.0, 3.0 Hz, 2H), 7.28-7.19 (m, 7H), 6.85-6.80 (m, 4H), 6.71 (d, J=6.0 Hz, 1H), 5.78 (d, J=6.0 Hz, 1H), 5.13-5.05 (m, 1H), 4.46-4.39 (m, 1H), 3.71 (s, 6H), 3.46-3.40 (m, 1H), 3.22-3.18 (m, 1H), 2.78-2.70 (m, 1H), 1.11 (d, J=9.0 Hz, 6H).

Preparation 17: N-(9-((2R,3R,4R,5R)-5-((bis(4-methoxyphenyl)(phenyl)-methoxy)methyl)-4-fluoro-3-hydroxytetrahydrothiophen-2-yl)-6-oxo-6,9-dihydro-1H-purin-2-yl)isobutyramide

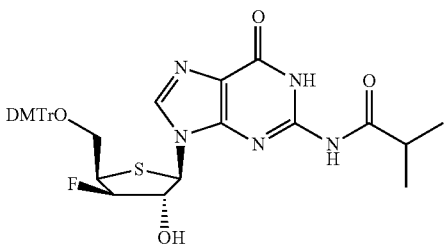

Step 1: 2-amino-9-((4aR,6R,7R,7aR)-2,2-di-tert-butyl-7-hydroxytetrahydro-4H-thieno[3,2-d][1,3,2]dioxasilin-6-yl)-1,9-dihydro-6H-purin-6-one

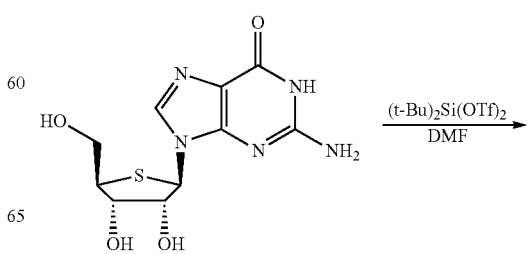

-continued

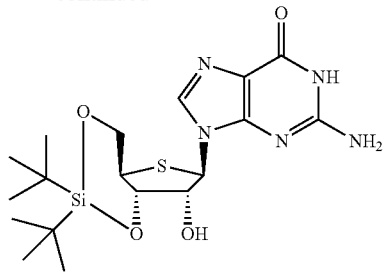

To a stirred suspension of 2-amino-9-((2R,3R,4S,5R)-3,4-dihydroxy-5-(hydroxymethyl)tetrahydrothiophen-2-yl)-1H-purin-6(9H)-one (15 g, 50.1 mmol) in DMF (150 mL) at 0° C. under Ar was injected di-tert-butylsilanediyl bis(trifluoromethanesulfonate) (26.5 g, 60.1 mmol). The resulting solution was stirred at rt for 1 h. It was used for the next reaction step directly without purification. LCMS (ES, m/z): 440.2 [M+H]+.

Step 2: 2-amino-9-((4aR,6R,7R,7aR)-2,2-di-tert-butyl-7-((tert-butyldimethylsilyl)oxy) tetrahydro-4H-thieno[3,2-d][1,3,2]dioxasilin-6-yl)-1,9-dihydro-6H-purin-6-one

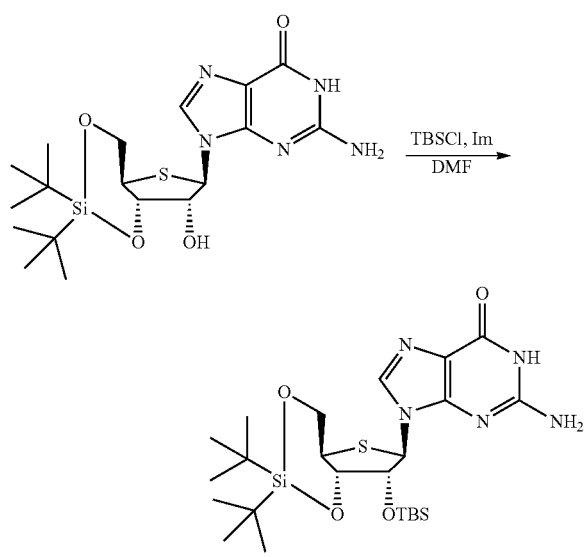

To the reaction mixture from the previous step at 0° C. was added 1H-imidazole (17.05 g, 251 mmol) in one portion. The mixture was stirred rt for 0.5 h. tert-butylchlorodimethylsilane (15.10 g, 100 mmol) was added to the mixture, and it was stirred at 60° C. for 16 h. Then, the volatile components were removed under reduced pressure. The solid was suspended in cold methanol (75 mL), filtered, and washed with cold methanol (2×30 mL). The solid was kept under reduced pressure to give the product. LCMS (ES, m/z): 554.4 [M+H]+. 1H-NMR (400 MHz, DMSO-$d_6$): δ 10.80 (s, 1H), 7.98 (s, 1H), 6.49 (s, 2H), 5.53 (s, 1H), 4.46 (d, J=3.2 Hz, 1H), 4.42 (d, J=9.9 Hz, 1H), 4.34 (dd, J=9.9, 4.7 Hz, 1H), 4.21 (t, J=10.5 Hz, 1H), 3.70-3.64 (m, 1H), 1.04 (s, 9H), 1.00 (s, 9H), 0.92 (s, 9H), 0.19 (s, 3H), 0.11 (s, 3H).

Step 3: N-(9-((4aR,6R,7R,7aR)-2,2-di-tert-butyl-7-((tert-butyldimethylsilyl)oxy)tetrahydro-4H-thieno[3,2-d][1,3,2]dioxasilin-6-yl)-6-oxo-6,9-dihydro-1H-purin-2-yl)isobutyramide

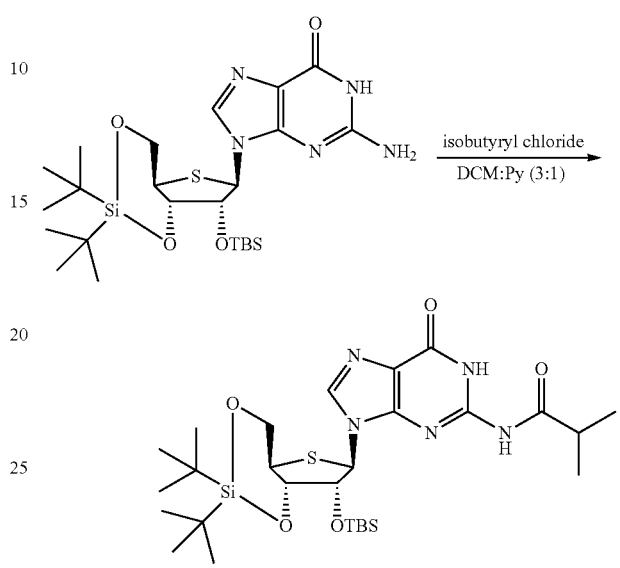

2-amino-9-((4aR,6R,7R,7aS)-2,2-di-tert-butyl-7-((tert-butyldimethylsilyl)oxy)tetrahydro-4H-thieno[3,2-d][1,3,2]dioxasilin-6-yl)-1H-purin-6(9H)-one (29.1 g, 52.5 mmol) was co-evaporated with dry pyridine (3×50 mL) and re-dissolved in pyridine (70 mL) and dichloromethane (210 mL). The mixture was charged with Ar and cooled to 0° C. To the mixture was added isobutyryl chloride (11.20 g, 105 mmol). It was stirred at rt for 4 h. It was concentrated under reduced pressure. The solid was suspended in cold methanol (100 mL), filtered, and washed with cold methanol (3×50 mL). The solid was kept under reduced pressure to give the product. LCMS (ES, m/z): 624.1 [M+H]+. 1H-NMR (400 MHz, DMSO-$d_6$): δ 12.13 (s, 1H), 11.39 (s, 1H), 8.32 (s, 1H), 5.61 (s, 1H), 4.66 (d, J=3.4 Hz, 1H), 4.48 (d, J=9.9 Hz, 1H), 4.38-4.33 (m, 1H), 4.21 (t, J=9.9 Hz, 1H), 3.76-3.70 (m, 1H), 2.84-2.80 (m, 1H), 1.13 (d, J=6.7 Hz, 6H), 1.06 (s, 9H), 1.01 (s, 9H), 0.91 (s, 9H), 0.16 (s, 3H), 0.11 (s, 3H).

Step 4. N-(9-((2R,3R,4S,5R)-3-((tert-butyldimethylsilyl)oxy)-4-hydroxy-5-(hydroxymethyl)tetrahydrothiophen-2-yl)-6-oxo-6,9-dihydro-1H-purin-2-yl)isobutyramide

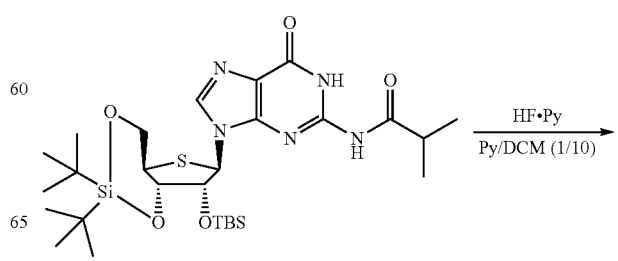

-continued

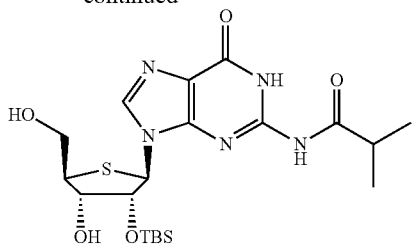

HF-Pyridine (26.6 g, 188 mmol) at 0° C. was diluted with pyridine (29 mL). The resulting solution was added slowly to a stirred suspension of N-(9-((4aR,6R,7R,7aS)-2,2-di-tert-butyl-7-((tert-butyldimethylsilyl)oxy)tetrahydro-4H-thieno[3,2-d][1,3,2]dioxasilin-6-yl)-6-oxo-6,9-dihydro-1H-purin-2-yl)isobutyramide (29.3 g, 47.0 mmol) in CH$_2$Cl$_2$ (290 mL) at 0° C. It was stirred at 0° C. for 2 h. The reaction mixture was diluted with CH$_2$Cl$_2$ (500 mL). It was washed with water (500 mL) and sat aq NaHCO$_3$ (500 mL). The organic layer was dried (Na$_2$SO$_4$) and concentrated to give the product. LCMS (ES, m/z): 484.4 [M+H]$^+$. $^1$H-NMR (400 MHz, DMSO-d$_6$): δ 12.05 (s, 1H), 11.73 (s, 1H), 8.43 (s, 1H), 5.89 (d, J=7.9 Hz, 1H), 5.34 (d, J=3.9 Hz, 1H), 5.27 (t, J=5.6 Hz, 1H), 4.60 (dd, J=8.1, 3.2 Hz, 1H), 4.19-4.17 (m, 1H), 3.80-3.74 (m, 1H), 3.66-3.60 (m, 1H), 3.30 (t, J=8.0 Hz, 1H), 2.80-2.73 (m, 1H), 1.12 (d, J=6.7 Hz, 6H), 0.68 (s, 9H), −0.06 (s, 3H), −0.29 (s, 3H).

Step 5. N-(9-((2R,3R,4S,5R)-5-((bis(4-methoxyphenyl)(phenyl)methoxy)methyl)-3-((tert-butyldimethylsilyl)oxy)-4-hydroxytetrahydrothiophen-2-yl)-6-oxo-6,9-dihydro-1H-purin-2-yl)isobutyramide

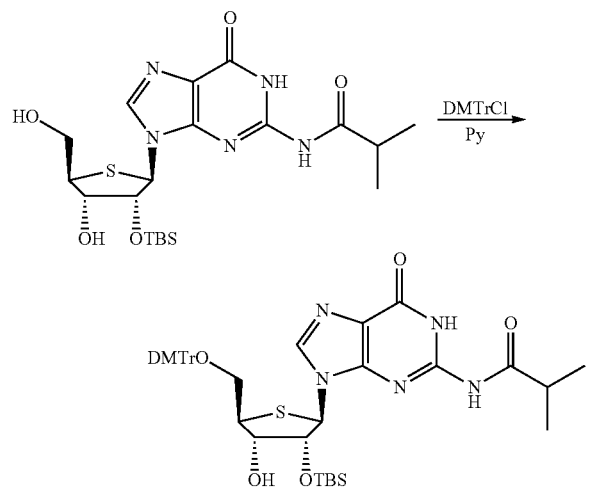

N-(9-((2R,3R,4S,5R)-3-((tert-butyldimethylsilyl)oxy)-4-hydroxy-5-(hydroxymethyl)tetrahydrothiophen-2-yl)-6-oxo-6,9-dihydro-1H-purin-2-yl)isobutyramide (21 g, 43.4 mmol) was co-evaporated with pyridine (3×50 mL) and dissolved in pyridine (210 mL). 4,4'-(chloro(phenyl)methylene)bis(methoxybenzene) (16.2 g, 47.8 mmol) was added, and it was stirred at rt for 3 h and then concentrated under reduced pressure and co-evaporated with toluene (3×50 mL). The crude was purified by silica gel chromatography eluting with 0-40% EtOAc in CH$_2$Cl$_2$ (containing 0.1% Et$_3$N) to give the product. LCMS (ES, m/z): 786.4 [M+H]$^+$. $^1$H-NMR (300 MHz, DMSO-d$_6$): δ 12.06 (s, 1H), 11.71 (s, 1H), 8.19 (s, 1H), 7.44-7.42 (m, 2H), 7.37-7.22 (m, 7H), 6.92 (d, J=8.5 Hz, 4H), 5.87 (d, J=7.2 Hz, 1H), 5.44 (d, J=4.4 Hz, 1H), 4.40 (dd, J=7.3, 3.3 Hz, 1H), 4.19 (d, J=5.9 Hz, 1H), 3.75 (s, 6H), 3.54-3.35 (m, 2H), 3.34-3.28 (m, 1H), 2.83-2.71 (m, 1H), 1.11 (d, J=6.7 Hz, 6H), 0.70 (s, 9H), −0.08 (s, 3H), −0.29 (s, 3H).

Step 6: N-(9-((2R,3R,4R,5R)-5-((bis(4-methoxyphenyl)(phenyl)methoxy)methyl)-3-((tert-butyldimethylsilyl)oxy)-4-fluorotetrahydrothiophen-2-yl)-6-oxo-6,9-dihydro-1H-purin-2-yl)isobutyramide

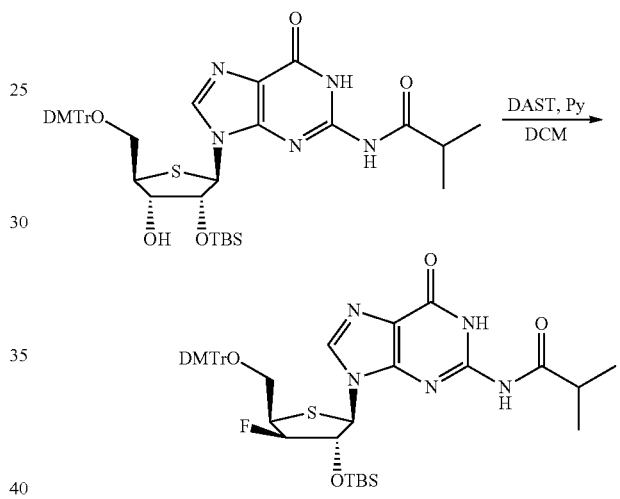

To a solution of N-(9-((2R,3R,4S,5R)-5-((bis(4-methoxyphenyl)(phenyl)methoxy)-methyl)-3-((tert-butyldimethylsilyl)oxy)-4-hydroxytetrahydrothiophen-2-yl)-6-oxo-6,9-dihydro-1H-purin-2-yl)isobutyramide (22 g, 28.0 mmol) in CH$_2$Cl$_2$ (220 mL) at 0° C. was added pyridine (18.11 mL, 224 mmol) and DAST (14.79 mL, 112 mmol) dropwise. The reaction was allowed to warm to rt and stirred for 7 h. It was then cooled to 0° C. and quenched by slow addition of sat aq NaHCO$_3$ (500 mL). More CH$_2$Cl$_2$ (500 mL) was added, and the phases were separated. The organic phase was washed with sat aq NaHCO$_3$ (3×200 mL) and brine (300 mL), dried (Na$_2$SO$_4$), concentrated, and purified by reverse phase (C18) chromatography eluting with 45-95% of ACN in aq NH$_4$HCO$_3$ (5 mM) to give the product. LCMS (ES, m/z): 788.2 [M+H]$^+$. $^1$H-NMR (400 MHz, DMSO-d$_6$): δ 12.06 (s, 1H), 11.56 (s, 1H), 8.02 (s, 1H), 7.44-7.42 (m, 2H), 7.34-7.23 (m, 7H), 6.92-6.89 (m, 4H), 5.71 (d, J=4.9 Hz, 1H), 5.14 (dt, J=51.0, 5.6 Hz, 1H), 5.01-4.96 (m, 1H), 3.88-3.85 (m, 1H), 3.75 (s, 6H), 3.57 (t, J=8.8 Hz, 1H), 3.50 (dd, J=10.0, 5.3 Hz, 1H), 2.81-2.74 (m, 1H), 1.12 (d, J=6.8 Hz, 6H), 0.77 (s, 9H), 0.00 (s, 3H), −0.16 (s, 3H). F-NMR: (376 MHz, DMSO-d$_6$, ppm) δ −193.99 (s, 1F).

Step 7: N-(9-((2R,3R,4R,5R)-5-((bis(4-methoxyphenyl)(phenyl)methoxy)methyl)-4-fluoro-3-hydroxytetrahydrothiophen-2-yl)-6-oxo-6,9-dihydro-1H-purin-2-yl)isobutyramide

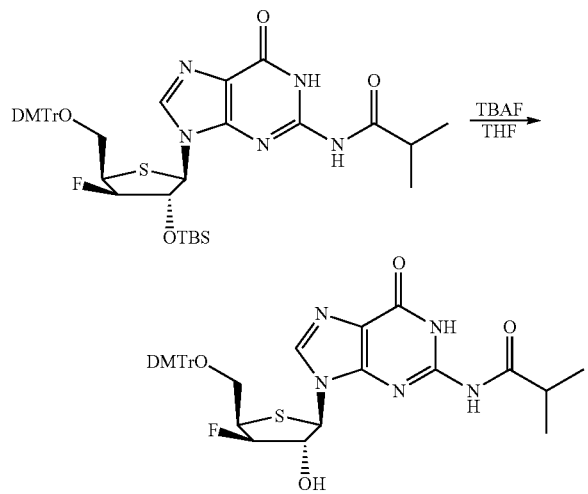

To a solution of N-(9-((2R,3R,4R,5R)-5-((bis(4-methoxyphenyl)(phenyl)-methoxy) methyl)-3-((tert-butyldimethylsilyl)oxy)-4-fluorotetrahydrothiophen-2-yl)-6-oxo-6,9-dihydro-1H-purin-2-yl)isobutyramide (7.2 g, 6.85 mmol) in THF (70 mL) at rt was added TBAF (1.0M in THF, 8.22 mL, 8.22 mmol) dropwise. It was stirred at rt for 30 min, the solution was concentrated, and CH$_2$Cl$_2$ (300 mL) was added. The mixture was washed with NaHCO$_3$ (3×200 mL) and brine (200 mL), and the organic phase was separated, dried (Na$_2$SO$_4$), concentrated and purified by reverse phase (C18) chromatography eluting with 0-95% of ACN in aq NH$_4$HCO$_3$ (5 mM) to give the product. LCMS (ES, m/z): 674.3 [M+H]$^+$. $^1$H-NMR (400 MHz, DMSO-d$_6$): δ 12.02 (br, 1H), 7.85 (s, 1H), 7.44-7.41 (m, 2H), 7.36-7.24 (m, 7H), 6.94-6.90 (m, 4H), 6.33 (bs, 1H), 5.78 (d, J=2.7 Hz, 1H), 5.19 (dt, J=50.2, 4.0 Hz, 1H), 4.80-4.75 (m, 1H), 4.10-4.02 (m, 1H), 3.76 (s, 6H), 3.55 (dd, J=9.3, 5.6 Hz, 1H), 3.44 (t, J=8.9 Hz, 1H), 2.79-2.71 (m, 1H), 1.12 (d, J=6.8 Hz, 6H). F-NMR: (376 MHz, DMSO-d$_6$) δ −194.75 (s).

Preparation 18: N-(9-((2R,3R,5S)-5-((bis(4-methoxyphenyl)(phenyl)methoxy)methyl)-3-hydroxytetrahydrothiophen-2-yl)-6-oxo-6,9-dihydro-1H-purin-2-yl)isobutyramide

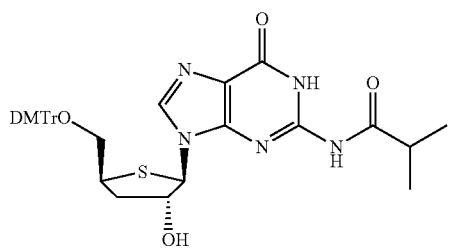

Step 1: (3R,4S,5R)-4-hydroxy-5-(hydroxymethyl)tetrahydrothiophen-3-yl 2,4-dimethoxybenzoate

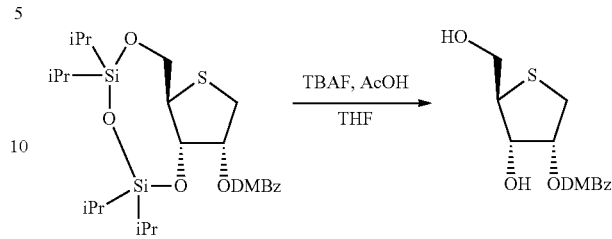

To a solution of (6aR,9R,9aS)-2,2,4,4-tetraisopropyltetrahydro-6H-thieno[3,2-f][1,3,5,2,4]trioxadisilocin-9-yl 2,4-dimethoxybenzoate (60 g, 108 mmol) in THF (500 mL) were added AcOH (13.59 g, 226 mmol) and TBAF in THF (1 M, 226 mL, 226 mmol). After 1 h, it was concentrated under reduced pressure and purified by silica gel column chromatography eluting with 0-20% EtOAc in CH$_2$Cl$_2$ to give the product. LCMS (ES, m/z): 315.1 [M+H]$^+$. 1H-NMR (400 MHz, CDCl$_3$) δ 7.87 (d, J=8.7 Hz, 1H), 6.58-6.46 (m, 2H), 5.51 (dt, J=5.0, 3.7 Hz, 1H), 4.31 (td, J=6.9, 3.7 Hz, 1H), 3.88 (d, J=12.0 Hz, 8H), 3.58 (dt, J=7.1, 4.7 Hz, 1H), 3.26 (dd, J=12.2, 5.0 Hz, 1H), 3.15-3.01 (m, 2H), 2.31 (s, 1H).

Step 2: (3R,4S,5R)-5-(((tert-butyldiphenylsilyl)oxy)methyl)-4-hydroxytetrahydrothiophen-3-yl 2,4-dimethoxybenzoate

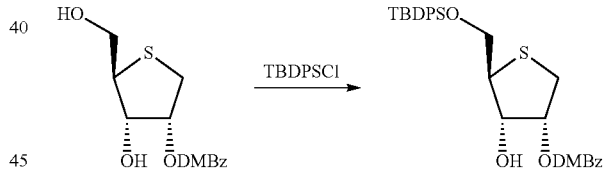

To a solution of (3R,4S,5R)-4-hydroxy-5-(hydroxymethyl)tetrahydrothiophen-3-yl 2,4-dimethoxybenzoate (33 g, 105 mmol) in pyridine (300 mL) was added tert-butylchlorodiphenylsilane (43.3 g, 157 mmol). It was stirred at rt for 4 h. Then, water (300 mL) was added. Layers were separated, and the aq layer was extracted with CH$_2$Cl$_2$ (3×300 mL). The combined organic layer was washed with brine (300 mL), dried (Na$_2$SO$_4$), concentrated, and purified by silica gel column chromatography eluting with 1 to 10% EtOAc in petroleum ether to give the product. LCMS (ES, m/z): 575.3 [M+Na]$^+$. $^1$H-NMR (400 MHz, DMSO-d$_6$) δ 7.83 (d, J=8.7 Hz, 1H), 7.68 (t, J=5.5 Hz, 5H), 7.54-7.38 (m, 6H), 6.69-6.60 (m, 2H), 5.40 (d, J=5.6 Hz, 1H), 5.35-5.29 (m, 1H), 4.12 (s, 1H), 4.05 (d, J=7.3 Hz, 1H), 3.85 (d, J=7.2 Hz, 6H), 3.78-3.66 (m, 1H), 3.55 (d, J=7.2 Hz, 1H), 3.14 (dd, J=11.0, 5.0 Hz, 1H), 2.86-2.77 (m, 1H), 1.03 (s, 9H).

Step 3: (3R,4S,5R)-4-(((1H-imidazole-1-carbonothioyl)oxy)-5-(((tert-butyldiphenylsilyl)oxy)methyl)tetrahydrothiophen-3-yl 2,4-dimethoxybenzoate

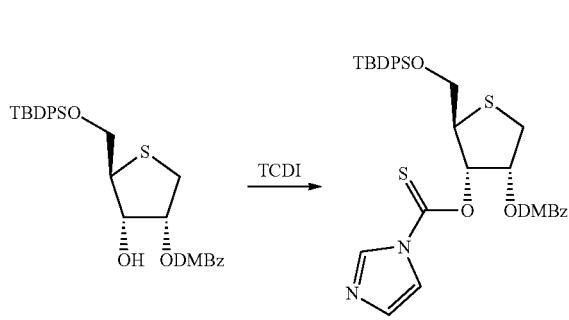

To a solution of (3R,4S,5R)-5-(((tert-butyldiphenylsilyl)oxy)methyl)-4-hydroxytetrahydrothiophen-3-yl 2,4-dimethoxybenzoate (48 g, 87 mmol) in dichloroethane (500 mL) was added di(1H-imidazol-1-yl)methanethione (20.12 g, 113 mmol). It was heated at 85° C. under Ar for 1 h. Then, it was concentrated and used in the next step without purification. LCMS (ES, m/z): 663.2 [M+H]+.

Step 4: (3R,5S)-5-(((tert-butyldiphenylsilyl)oxy)methyl)tetrahydrothiophen-3-yl 2,4-dimethoxybenzoate

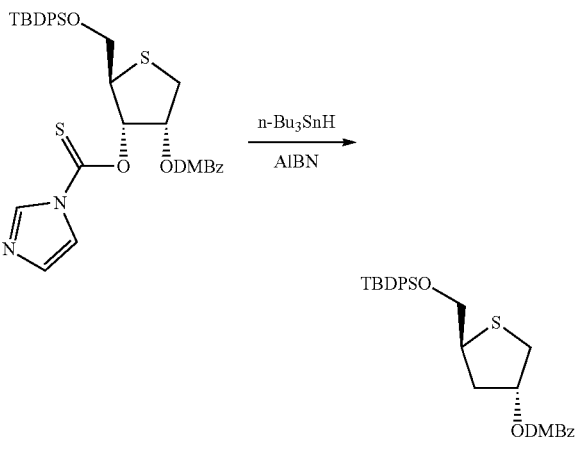

To a solution of (3R,4S,5R)-4-((1H-imidazole-1-carbonothioyl)oxy)-5-(((tert-butyldiphenylsilyl)oxy)methyl)tetrahydrothiophen-3-yl 2,4-dimethoxybenzoate (crude, 57.6 g, 87 mmol) in THF (40 mL) and toluene (200 mL) was added tributylstannane (139 g, 478 mmol). It was heated at 95° C., and 2,2'-(diazene-1,2-diyl)bis(2-methylpropanenitrile) (1.427 g, 8.69 mmol) in toluene (200 mL) was added over 30 min. After 1 h, the resulting mixture was concentrated and purified by silica gel column chromatography eluting with 0 to 10% EtOAc in petroleum ether to give the product. LCMS (ES, m/z): 537.3 [M+H]+. 1H-NMR (400 MHz, CDCl3) δ 7.88 (d, J=8.6 Hz, 1H), 7.77-7.67 (m, 4H), 7.50-7.36 (m, 6H), 6.58-6.48 (m, 2H), 5.70 (p, J=3.8 Hz, 1H), 3.95-3.74 (m, 10H), 3.28 (dd, J=12.0, 4.6 Hz, 1H), 3.10-3.02 (m, 1H), 2.49-2.39 (m, 1H), 1.92 (ddd, J=13.3, 8.6, 4.1 Hz, 1H), 1.09 (s, 9H).

Step 5: (JR,3R,5S)-5-(((tert-butyldiphenylsilyl)oxy)methyl)-1-oxidotetrahydrothiophen-3-yl 2,4-dimethoxybenzoate

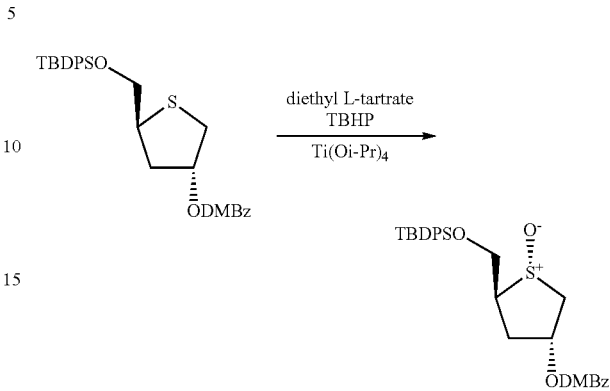

To a solution of Ti(OiPr)4 (23.29 mL, 78 mmol) in CH2Cl2 (130 mL) under Ar was added diethyl (L)-tartrate (38.3 mL, 224 mmol) dropwise. After 10 min, the mixture was cooled to −20° C., and then TBHP in decane (~5.5M, 27.1 mL, 149 mmol) was added dropwise. After 5 min, a solution of (3R,5S)-5-(((tert-butyldiphenylsilyl)oxy)methyl)tetrahydrothiophen-3-yl 2,4-dimethoxybenzoate (40 g, 74.5 mmol) in CH2Cl2 (130 mL) was added to the reaction at −20° C. The resulting mixture was stirred at −20° C. for 16 h. It was quenched by the addition of ice water (300 mL) and allowed to warm up to rt. The precipitate was filtered off and washed with EtOAc (3×300 mL). The filtrate was washed with water (3×200 mL). The aq layer was extracted with EtOAc (400 mL). The combined organic layer was dried (Na2SO4), concentrated and purified by flash chromatography eluting with 0 to 70% EtOAc in petroleum ether to give the product (mixture of two isomers). LCMS (ES, m/z): 553.2 [M+H]+. 1H-NMR (400 MHz, DMSO-d6) δ 7.81 (d, J=8.7 Hz, 1H), 7.75-7.61 (m, 4H), 7.54-7.39 (m, 6H), 6.67-6.56 (m, 2H), 5.66 (q, J=3.8 Hz, 1H), 4.12 (dt, J=10.5, 4.4 Hz, 1H), 3.92-3.79 (m, 8H), 3.58-3.42 (m, 1H), 3.20-3.09 (m, 1H), 2.97 (d, J=15.0 Hz, 1H), 2.05 (ddd, J=14.5, 10.5, 4.3 Hz, 1H), 1.02 (s, 9H).

Step 6: (3R,5S)-2-acetoxy-5-(((tert-butyldiphenylsilyl)oxy)methyl)tetrahydrothiophen-3-yl 2,4-dimethoxybenzoate

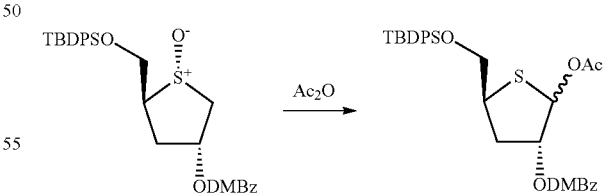

A solution of (3R,5S)-2-acetoxy-5-(((tert-butyldiphenylsilyl)oxy)methyl)-tetrahydrothiophen-3-yl 2,4-dimethoxybenzoate (21 g, 34.2 mmol) in acetic anhydride (210 mL) was heated at 110° C. After stirring of 3.5 h, the reaction mixture was cooled to rt and concentrated. The residue was purified by silica gel column chromatography eluting with 0% to 20% EtOAc in petroleum ether to give the product. LCMS (ES, m/z): 535.3 [M−OAc]+. 1H-NMR (400 MHz, DMSO-d6) δ 7.76-7.61 (m, 5H), 7.46 (dq, J=7.6, 4.5, 3.7 Hz, 6H), 6.68-6.58 (m, 2H), 6.22 (d, J=4.3 Hz, 0.65H), 5.94 (s, 0.28H), 5.51-5.46 (m, 0.33H), 5.38 (ddd, J=11.1, 7.2, 4.3 Hz, 0.65H), 3.96-3.61 (m, 9H), 2.40-2.21 (m, 2H), 2.03 (d, J=1.6 Hz, 3H), 1.01 (s, 9H).

Step 7: (3R,5S)-5-(((tert-butyldiphenylsilyl)oxy)methyl)-2-(6-chloro-2-isobutyramido-9H-purin-9-yl)tetrahydrothiophen-3-yl 2,4-dimethoxybenzoate

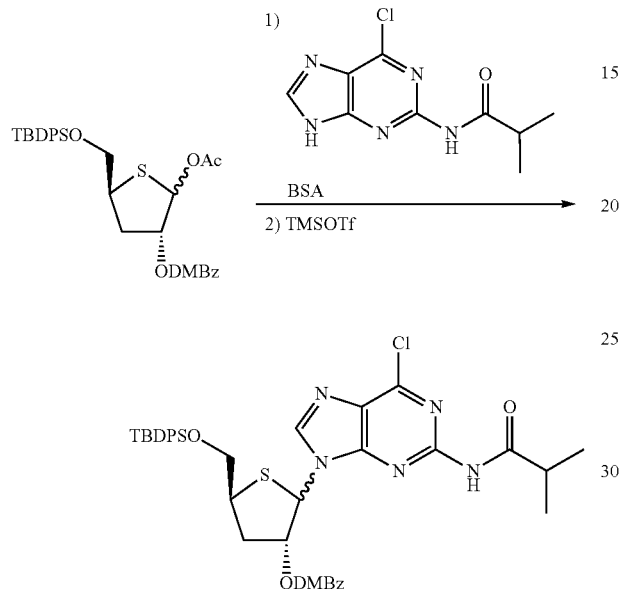

To a solution of N-(6-chloro-9H-purin-2-yl)isobutyramide (10.27 g, 42.9 mmol) in toluene (600 mL) at 0° C. was added trimethylsilyl N-(trimethylsilyl)acetimidate (23.26 g, 114 mmol). It was heated at 80° C. for 1 h and was cooled to 0° C. again. To the reaction was then added a solution of (3R,5S)-2-acetoxy-5-(((tert-butyldiphenylsilyl)oxy)methyl)-tetrahydrothiophen-3-yl 2,4-dimethoxybenzoate (17 g, 28.6 mmol) in toluene (600 mL) and trimethylsilyl trifluoromethanesulfonate (19.06 g, 86 mmol). It was heated to 80° C. and stirred under Ar for 12 h. At that time, the reaction was cooled to rt, and sat aq NaHCO₃ (400 mL) was added. Layers were separated, and the aq layer was extracted with EtOAc (4×1000 mL). The combined organic phase was dried (Na₂SO₄), concentrated and purified by silica gel column chromatography eluting with 10% to 40% EtOAc in petroleum ether to give the product (mixture of α and β isomers). LCMS (ES, m/z): 774.3 [M+H]⁺. ¹H-NMR (400 MHz, CDCl₃) δ 8.48 (s, 0.32H), 8.35 (s, 0.69H), 7.97-7.83 (m, 1.67H), 7.70 (dq, J=8.4, 1.5 Hz, 4H), 7.54 (d, J=8.7 Hz, 0.33H), 7.49-7.36 (m, 6H), 6.57-6.36 (m, 2.5H), 6.18 (d, J=2.4 Hz, 0.7H), 5.87-5.80 (m, 0.35H), 5.73 (q, J=3.3 Hz, 0.75H), 4.23-4.01 (m, 1.2H), 3.98-3.74 (m, 7.8H), 3.11 (s, 0.73H), 2.95 (s, 0.37H), 2.57-2.36 (m, 1.75H), 2.30-2.20 (m, 0.34H), 1.23 (d, J=6.8 Hz, 2.19H), 1.19 (dd, J=6.8, 3.5 Hz, 4.38H), 1.09 (d, J=1.7 Hz, 9H).

Step 8. (2R,3R,5S)-2-(6-chloro-2-isobutyramido-9H-purin-9-yl)-5-(hydroxymethyl)-tetrahydrothiophen-3-yl 2,4-dimethoxybenzoate

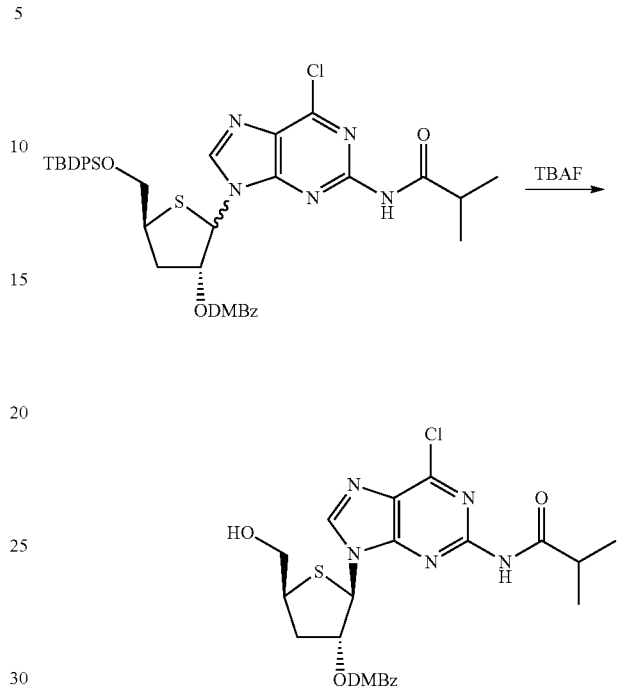

To a solution of (3R,5S)-5-(((tert-butyldiphenylsilyl)oxy)methyl)-2-(6-chloro-2-isobutyramido-9H-purin-9-yl)tetrahydrothiophen-3-yl 2,4-dimethoxybenzoate (20 g, 25.8 mmol) in THF (135 mL) was added TBAF in THF (1 M, 31 mL, 31 mmol) dropwise. After 1 h, the reaction mixture was concentrated and purified by column chromatography using 1% to 10% MeOH in CH₂Cl₂ as the eluent to give a mixture of two isomers. It was re-purified by reverse phase (C18) chromatography eluting with 10 to 45% ACN in aq NH₄CO₃ (5 mM) to give the product. LCMS (ES, m/z): 536.2 [M+H]⁺. ¹H-NMR (400 MHz, DMSO-d₆) δ 10.80 (s, 1H), 8.83 (s, 1H), 7.72 (d, J=8.7 Hz, 1H), 6.65-6.55 (m, 2H), 6.18 (d, J=2.5 Hz, 1H), 5.80 (q, J=3.5 Hz, 1H), 5.22 (t, J=5.1 Hz, 1H), 3.93-3.67 (m, 9H), 2.85 (p, J=6.9 Hz, 1H), 2.70 (ddd, J=13.4, 8.5, 4.5 Hz, 1H), 2.36 (dt, J=14.1, 5.0 Hz, 1H), 1.06 (dd, J=6.8, 3.3 Hz, 6H).

Step 9: 2-amino-9-((2R,3R,5S)-3-hydroxy-5-(hydroxymethyl)tetrahydrothiophen-2-yl)-1,9-dihydro-6H-purin-6-one

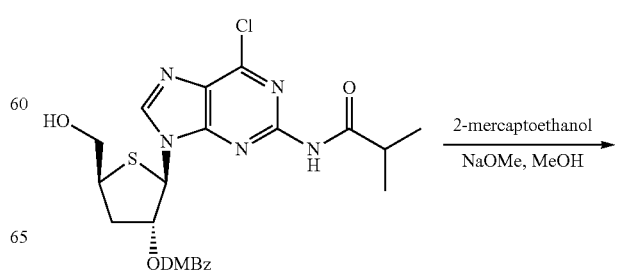

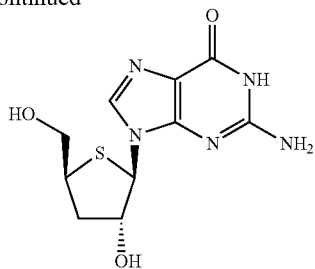

To a solution of (2R,3R,5 S)-2-(6-chloro-2-isobutyramido-9H-purin-9-yl)-5-(hydroxymethyl)tetrahydrothiophen-3-yl 2,4-dimethoxybenzoate (6.0 g, 11.19 mmol) in MeOH (300 mL) were added 2-mercaptoethanol (3.50 g, 44.8 mmol) and NaOMe (10.08 g, 56 mmol, 30% in MeOH). It was heated at 60° C. for 16 h, cooled to rt, and conc. HCl (4 mL) was added. The resulting mixture was concentrated, and water (100 mL) and EtOAc (100 mL) were added. Layers were separated, and the aq layer was extracted with EtOAc (3×100 mL). The aq layer was basified with NaHCO$_3$ (solid) to ~pH 8 and stirred at rt for 1 h. The precipitate was filtered and kept under reduced pressure to give the product. LCMS (ES, m/z): 284.1 [M+H]$^+$. $^1$H-NMR (400 MHz, DMSO-d$_6$) δ 10.57 (s, 1H), 7.98 (s, 1H), 6.46 (s, 2H), 5.57 (dd, J=10.9, 3.9 Hz, 2H), 5.12 (t, J=5.4 Hz, 1H), 4.48 (p, J=4.1 Hz, 1H), 3.78-3.53 (m, 3H), 2.11-1.99 (m, 2H).

Step 10: N-(9-((2R,3R,5S)-3-hydroxy-5-(hydroxymethyl)tetrahydrothiophen-2-yl)-6-oxo-6,9-dihydro-1H-purin-2-yl)isobutyramide

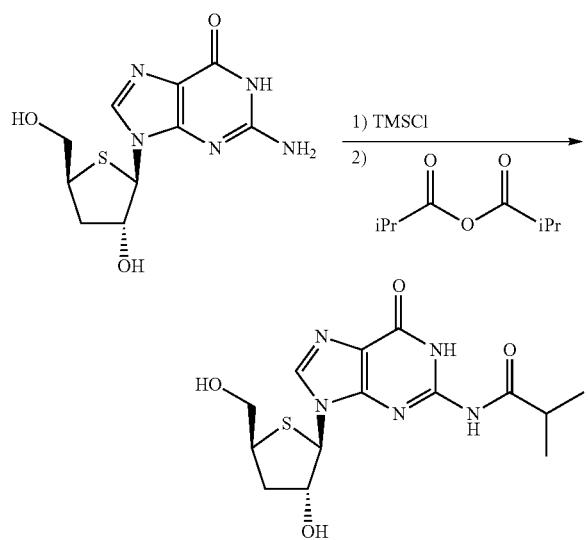

2-amino-9-((2R,3R,5S)-3-hydroxy-5-(hydroxymethyl)tetrahydrothiophen-2-yl)-1,9-dihydro-6H-purin-6-one (580 mg, 2.047 mmol) was co-evaporated with pyridine (3×20 mL) and then re-dissolved in pyridine (20 mL). The mixture was cooled to 0° C. and then treated with chlorotrimethylsilane (1557 mg, 14.33 mmol). It was warmed to rt and stirred for 2 h. Then, the reaction was cooled to 0° C. again, and isobutyric anhydride (486 mg, 3.07 mmol) was added dropwise. It was warmed to rt and stirred for 2 h. The reaction was quenched by the addition of methanol (5 mL). After 5 min, NH$_4$OH (ca 29%, 10 mL) was added. The mixture was stirred at rt for 30 min. Then, it was concentrated and purified by column chromatography on silica gel eluting with 10% to 20% MeOH in CH$_2$Cl$_2$ to give the product. LCMS (ES, m/z): 354.1 [M+H]$^+$. $^1$H-NMR (300 MHz, CD$_3$OD) δ: 8.40 (s, 1H), 5.83-5.82 (m, 1H), 4.62-4.59 (m, 1H), 3.89-3.80 (m, 2H), 3.79-3.74 (m, 1H), 2.73-2.64 (m, 1H), 2.19-2.11 (m, 2H), 1.20 (d, J=6.8 Hz, 6H).

Step 11: N-(9-((2R,3R,5S)-5-((bis(4-methoxyphenyl)(phenyl)methoxy)methyl)-3-hydroxytetrahydrothiophen-2-yl)-6-oxo-6,9-dihydro-1H-purin-2-yl)isobutyramide

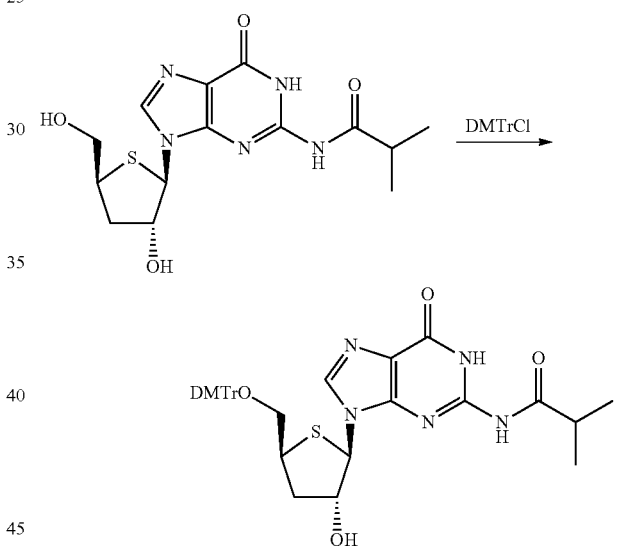

N-(9-((2R,3R,5 S)-3-hydroxy-5-(hydroxymethyl)tetrahydrothiophen-2-yl)-6-oxo-6,9-dihydro-1H-purin-2-yl)isobutyramide (510 mg, 1.443 mmol) was co-evaporated with pyridine (3×5 mL) and then re-suspended in pyridine (7 mL). To the suspension was added 4,4'-(chloro(phenyl)methylene)bis(methoxybenzene) (538 mg, 1.587 mmol), and the mixture was stirred at rt for 2 h. At that time the mixture was concentrated under reduced pressure, and the residue was purified by column chromatography on silica gel eluting with 1% to 4% MeOH in CH$_2$Cl$_2$ (containing 1% Et$_3$N) to give the product. LCMS (ES, m/z): 656.0 [M+H]$^+$. $^1$H-NMR (400 MHz, CD$_3$OD) δ: 8.02 (s, 1H), 7.51-7.43 (m, 2H), 7.40-7.17 (m, 7H), 6.91-6.82 (m, 4H), 5.85-5.84 (d, J=2.3 Hz, 1H), 4.59-4.57 (m, 1H), 4.02-3.95 (m, 1H), 3.78 (s, 6H), 3.52-3.34 (m, 3H), 2.72-2.68 (m, 1H), 1.95-191 (m, 1H), 1.38 (d, J=6.8 Hz, 6H).

Preparation 19: N-(9-((2R,3R,4S,5R)-5-((bis(4-methoxyphenyl)(phenyl)-methoxy)methyl)-4-fluoro-3-hydroxytetrahydrothiophen-2-yl)-6-oxo-6,9-dihydro-1H-purin-2-yl)isobutyramide

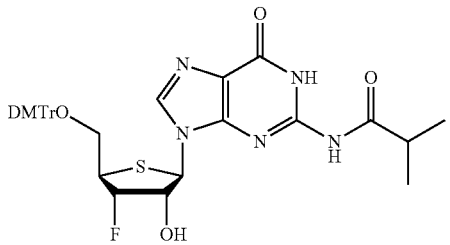

Step 1: ((2R,3R,4S)-4-(benzoyloxy)-3-fluoro-5-hydroxytetrahydrofuran-2-yl)methyl benzoate

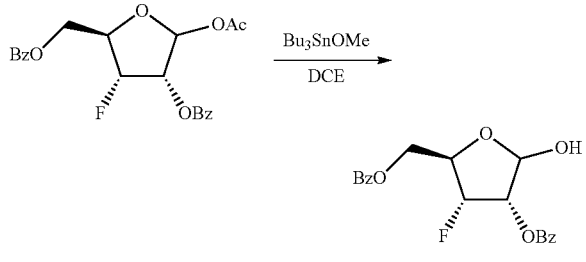

To a stirred solution of ((2R,3R,4S)-5-acetoxy-4-(benzoyloxy)-3-fluorotetrahydrofuran-2-yl)methyl benzoate (20.0 g, 49.7 mmol) in dry 1,2-dichloroethane (200 mL) was added tri-N-butyltin methoxide (28.8 mL, 99 mmol). The resulting mixture was stirred at 80° C. for 3 h and then concentrated in vacuo. The residue was diluted in 500 mL of ethyl acetate and washed with sat aq. NH$_4$Cl (500 mL) and brine (500 mL). The separated organic layer was dried over anhydrous Na$_2$SO$_4$, filtered, and concentrated in vacuo. The residue was purified by a silica gel column, eluting with 0-40% EtOAc/Hexane. LCMS (ES, m/z): 343.2 [M+H−H$_2$O]$^+$. $^1$H NMR (500 MHz, Chloroform-d) δ 8.18-8.00 (m, 7H), 7.68-7.57 (m, 3H), 7.61-7.35 (m, 7H), 5.73 (dd, J=8.3, 4.6 Hz, 1H), 5.65 (dt, J=3.9, 2.0 Hz, 1H), 5.54 (t, J=4.7 Hz, 0H), 5.50-5.40 (m, 2H), 5.36-5.24 (m, 1H), 4.87 (dtd, J=25.5, 4.0, 1.5 Hz, 1H), 4.74-4.46 (m, 4H), 4.15 (q, J=7.2 Hz, 1H), 3.39 (d, J=4.1 Hz, 1H), 3.30 (dd, J=8.6, 3.4 Hz, 1H), 2.07 (s, 2H), 1.41-1.23 (m, 3H).

Step 2. (2R,3R,4S)-3-fluoro-2-hydroxy-5-(methoxyimino)pentane-1,4-diyl dibenzoate

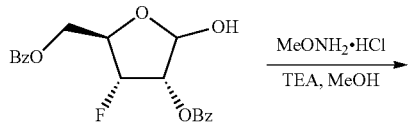

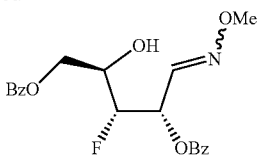

To a stirred solution of ((2R,3R,4S)-4-(benzoyloxy)-3-fluoro-5-hydroxytetrahydrofuran-2-yl)methyl benzoate (17.9 g, 49.7 mmol) in dry MeOH (100 mL) was added O-methylhydroxylamine hydrochloride (6.23 g, 74.6 mmol), followed by triethylamine (10.39 mL, 74.6 mmol). The reaction mixture was stirred at rt for 2 h and then concentrated in vacuo. The residue was diluted in 500 mL of ethyl acetate and washed with sat aq. NH$_4$Cl (500 mL) and brine (500 mL). The organic layer was dried over anhydrous Na$_2$SO$_4$, filtered, and concentrated in vacuo. The residue was used for the next step directly without further purification. LCMS (ES, m/z): 390.2 [M+H]$^+$.

Step 3: (2R,3S,4S)-3-fluoro-5-(methoxyimino)-2-(((4-nitrophenyl)sulfonyl)oxy)pentane-1,4-diyl dibenzoate

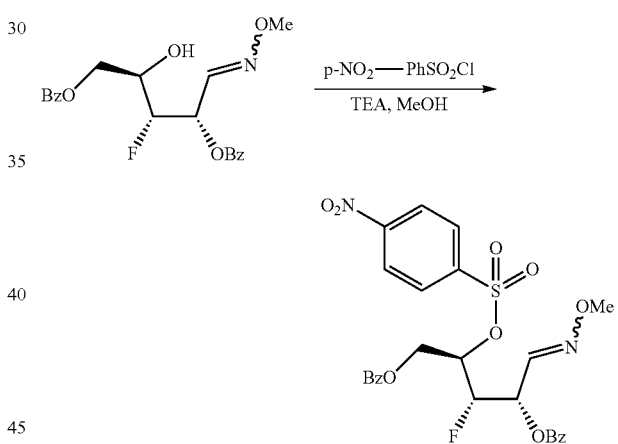

To a stirred solution of (2R,3R,4S)-3-fluoro-2-hydroxy-5-(methoxyimino)pentane-1,4-diyl dibenzoate (19.4 g, 49.7 mmol) in dry EtOAc (100 mL) was added 4-nitrobenzenesulfonyl chloride (16.5 g, 74.6 mmol), followed by triethylamine (10.4 mL, 74.6 mmol). The reaction mixture was stirred at rt for 18 h and was then diluted with 200 mL of ethyl acetate, washed with water (300 mL) and brine (300 mL). The separated organic layer was dried over anhydrous Na$_2$SO$_4$, filtered, and concentrated in vacuo. The residue was purified by a silica gel column, eluting with 0-30% EtOAc/Hexane. LCMS (ES, m/z): 575.3 [M+H]$^+$. $^1$H NMR (500 MHz, Chloroform-d) δ 8.25-7.99 (m, 7H), 7.94-7.80 (m, 2H), 7.68-7.55 (m, 2H), 7.57-7.46 (m, 3H), 7.50-7.38 (m, 3H), 6.55 (ddd, J=17.2, 5.3, 2.8 Hz, 0H), 5.89 (ddd, J=17.7, 6.2, 4.1 Hz, 1H), 5.46-5.37 (m, 1H), 5.40-5.28 (m, 1H), 5.21 (t, J=4.3 Hz, 0H), 4.84 (tdd, J=12.8, 2.6, 1.5 Hz, 1H), 4.53 (dddd, J=23.1, 13.0, 7.0, 1.8 Hz, 1H), 4.14 (q, J=7.2 Hz, 1H), 3.99 (d, J=36.3 Hz, 4H), 2.06 (s, 2H), 1.44-1.23 (m, 2H).

Step 4: (2S,3S,4S)-2-bromo-3-fluoro-5-(methoxy-imino)pentane-1,4-diyl dibenzoate

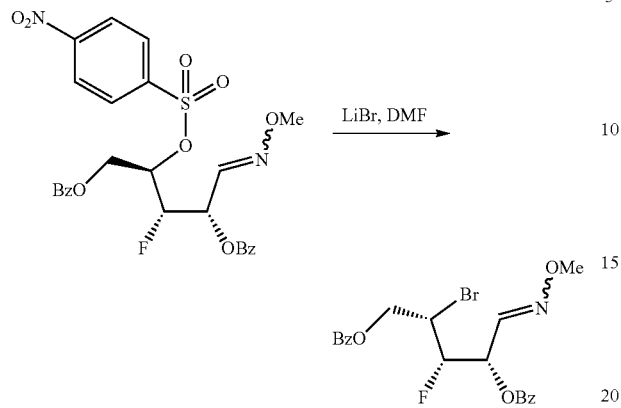

To a stirred solution of (2R,3S,4S)-3-fluoro-5-(methoxy-imino)-2-(((4-nitrophenyl)sulfonyl)oxy)pentane-1,4-diyl dibenzoate (21.3 g, 37.1 mmol) in dry DMF (100 mL) was added freshly opened lithium bromide powder (16.1 g, 185 mmol). The resulting mixture was stirred at 60° C. for 18 h. The reaction mixture was diluted in 300 mL of ethyl acetate and washed with water (500 mL) and brine (500 mL). The separated organic layer was dried over anhydrous $Na_2SO_4$, filtered, and concentrated in vacuo. The residue was purified by a silica gel column, eluting with 0-25% EtOAc/Hexane to give product. LCMS (ES, m/z): 452.1 [M+H]$^+$. $^1$H NMR (500 MHz, Chloroform-d) δ 8.15-8.03 (m, 1H), 7.69-7.56 (m, 8H), 7.56-7.41 (m, 12H), 6.93-6.86 (m, 1H), 6.45 (ddd, J=14.7, 5.9, 4.7 Hz, 0H), 5.93 (ddd, J=11.8, 6.7, 5.9 Hz, 2H), 5.32 (s, 1H), 5.29-5.10 (m, 3H), 4.89-4.77 (m, 3H), 4.80-4.67 (m, 3H), 4.60-4.40 (m, 3H), 3.95 (d, J=16.9 Hz, 2H), 3.89 (s, 6H), 1.32-1.22 (m, 1H).

Step 5: (2S,3S,4S)-2-bromo-3-fluoro-5-oxopentane-1,4-diyl dibenzoate

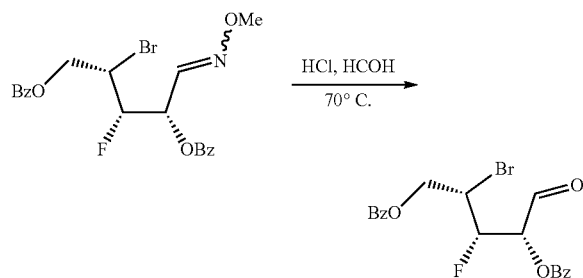

To a stirred solution of (2S,3S,4S)-2-bromo-3-fluoro-5-(methoxyimino)pentane-1,4-diyl dibenzoate (20.0 g, 44.2 mmol) in THF (200 mL) was added 37% aqueous solution of formaldehyde (32.9 mL, 442 mmol) and 1N HCl (44.2 mL, 44.2 mmol). The resulting mixture was stirred at 55° C. for 5 h. The reaction mixture was concentrated in vacuo to remove most of the THF. The residue was diluted in 300 mL of ethyl acetate and washed with water (300 mL) and brine (300 mL). The separated organic layer was dried over anhydrous $Na_2SO_4$, filtered, and concentrated in vacuo. The residue was used for the next step without further purification. LCMS (ES, m/z): 423.2 [M+H]$^+$.

Step 6: ((2R,3S,4R)-4-(benzoyloxy)-3-fluoro-5-hydroxytetrahydrothiophen-2-yl)methyl benzoate

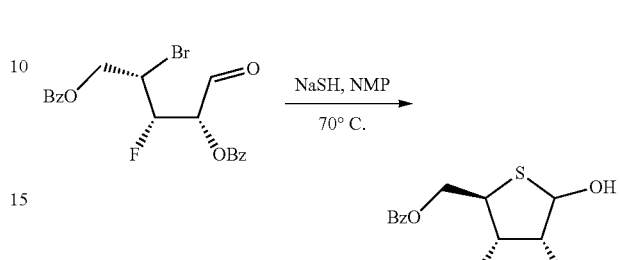

To a stirred solution of (2S,3S,4S)-2-bromo-3-fluoro-5-oxopentane-1,4-diyl dibenzoate (18.7 g, 44.2 mmol) in NMP (150 mL) at 0° C. was added sodium hydrosulfide (5.0 g, 89.0 mmol). The resulting mixture was stirred at 0° C. for 30 min and then at rt for 30 min. The reaction mixture was diluted in 300 mL of ethyl acetate and washed with water (300 mL) and brine (300 mL). The organic layer was dried over anhydrous $Na_2SO_4$, filtered, and concentrated in vacuo. The residue was used for the next step without further purification. LCMS (ES, m/z): 359.2 [M+H–$H_2O$]$^+$.

Step 6: ((2R,3S,4R)-5-acetoxy-4-(benzoyloxy)-3-fluorotetrahydrothiophen-2-yl)methyl benzoate

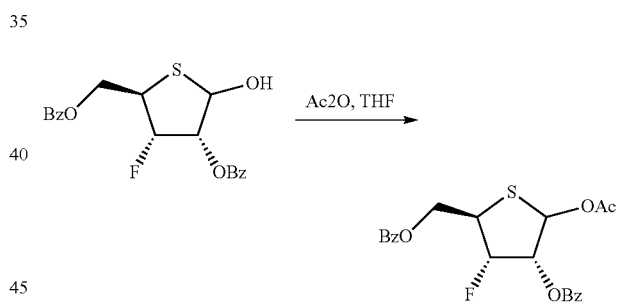

To a stirred solution of ((2R,3S,4R)-4-(benzoyloxy)-3-fluoro-5-hydroxytetrahydrothiophen-2-yl)methyl benzoate (16.6 g, 44.2 mmol) in dry THF (150 mL) at 0° C. was added acetic anhydride (8.3 mL, 133 mmol) and trimethylamine (18.5 mL, 133 mmol). The resulting mixture was stirred at 0° C. for 30 min and then at rt for 2 h. The reaction was quenched by addition of MeOH, and the reaction mixture was concentrated in vacuo to remove most of the THF. The residue was diluted in 300 mL of ethyl acetate and washed with water (300 mL) and brine (300 mL). The separated organic layer was dried over anhydrous $Na_2SO_4$, filtered, and concentrated in vacuo. The residue was purified by a silica gel column, eluting with 0-25% EtOAc/Hexane to give product. LCMS (ES, m/z): 441.2 [M+Na]$^+$. $^1$H NMR (500 MHz, Chloroform-d) δ 8.15-8.02 (m, 4H), 7.68-7.57 (m, 2H), 7.55-7.42 (m, 4H), 6.02 (t, J=2.4 Hz, 1H), 5.88 (ddd, J=6.1, 3.6, 2.4 Hz, 1H), 5.50-5.42 (m, 0H), 5.35 (dd, J=7.3, 3.6 Hz, 0H), 5.32 (s, 0H), 4.80-4.69 (m, 1H), 4.56 (dd, J=11.6, 5.9 Hz, 1H), 4.26-4.10 (m, 2H), 2.25-2.11 (m, 1H), 2.08 (d, J=10.0 Hz, 3H), 1.29 (t, J=7.1 Hz, 1H).

Step 7: ((2R,3S,4R,5R)-4-(benzoyloxy)-3-fluoro-5-(2-isobutyramido-6-oxo-1,6-dihydro-9H-purin-9-yl)tetrahydrothiophen-2-yl)methyl benzoate

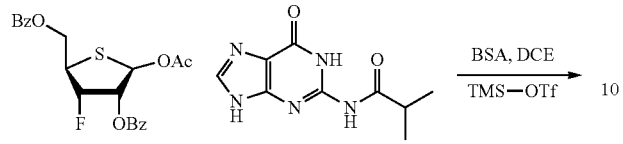

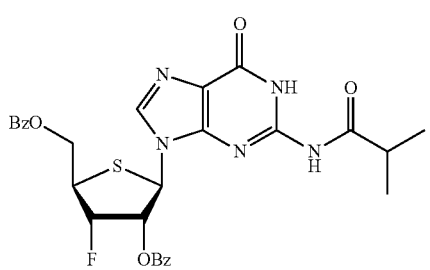

To a suspension of N-(6-oxo-6,9-dihydro-1H-purin-2-yl)isobutyramide (15.86 g, 71.7 mmol) in ClCH$_2$CH$_2$C$_1$ (300 mL) was added (Z)-trimethylsilyl N-(trimethylsilyl)acetimidate (35.1 mL, 143 mmol). The suspension was stirred at 70° C. overnight and was then cooled to −15° C. To this mixture was added ((2R,3S,4R)-5-acetoxy-4-(benzoyloxy)-3-fluoro-tetrahydrothiophen-2-yl)methyl benzoate (10 g, 23.90 mmol), followed by TMS-OTf (8.64 mL, 47.8 mmol). The reaction mixture was stirred at −15° C. for 2 h, then at rt for 5 h and finally at 70° C. for 5 d. The reaction mixture was allowed to cool to RT and was then filtered. The filtrate was washed with sat. aq. NaHCO$_3$, brine and then dried over Na$_2$SO$_4$ and concentrated in vacuo. The residue was purified by silica gel column, eluting with 0-60% EtOAc/Hexane. Subsequent recrystallization from EtOAc gave product. LCMS (ES, m/z): 580.5 [M+H]$^+$. $^1$H NMR (500 MHz, Chloroform-d) δ 12.19 (s, 0H), 9.56 (s, 1H), 8.12-8.06 (m, 1H), 8.02-7.96 (m, 1H), 7.66 (s, 0H), 7.71-7.58 (m, 1H), 7.57-7.50 (m, 1H), 7.54-7.42 (m, 1H), 6.59 (ddd, J=25.3, 7.4, 3.1 Hz, 1H), 6.20 (d, J=7.4 Hz, 0H), 5.68-5.59 (m, 1H), 4.87 (ddd, J=11.7, 7.7, 1.5 Hz, 1H), 4.26-4.11 (m, 1H), 2.96 (hept, J=6.8 Hz, 1H), 1.38 (dd, J=19.0, 6.9 Hz, 3H).

Step 8: N-(9-((2R,3R,4S,5R)-4-fluoro-3-hydroxy-5-(hydroxymethyl)tetrahydrothiophen-2-yl)-6-oxo-6,9-dihydro-1H-purin-2-yl)isobutyramide

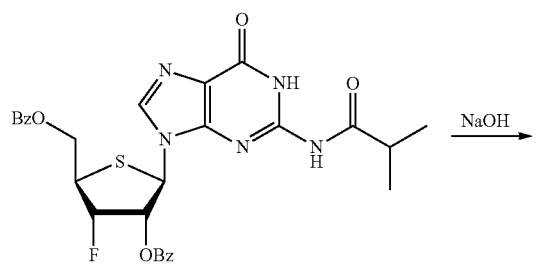

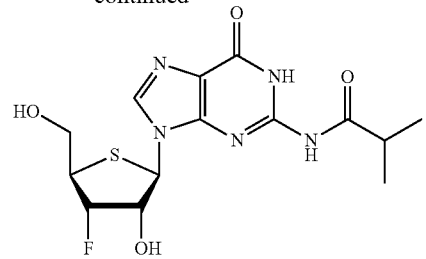

To a solution of ((2R,3S,4R,5R)-4-(benzoyloxy)-3-fluoro-5-(2-isobutyramido-6-oxo-1,6-dihydro-9H-purin-9-yl)tetrahydrothiophen-2-yl)methyl benzoate (0.96 g, 1.66 mmol) in THF (5 mL)/MeOH (4 mL)/H$_2$O (1 mL) at 0° C. was added 2N sodium hydroxide (1.8 mL, 3.6 mmol). The reaction mixture was stirred at 0° C. for 30 min and then neutralized with acetic acid (0.38 mL, 6.6 mmol). The product was collected by filtration and carried on to the next step without further purification. LCMS (ES, m/z): 372.3 [M+H]$^+$.

Step 9: N-(9-((2R,3R,4S,5R)-5-((bis(4-methoxyphenyl)(phenyl)methoxy)methyl)-4-fluoro-3-hydroxytetrahydrothiophen-2-yl)-6-oxo-6,9-dihydro-1H-purin-2-yl)isobutyramide

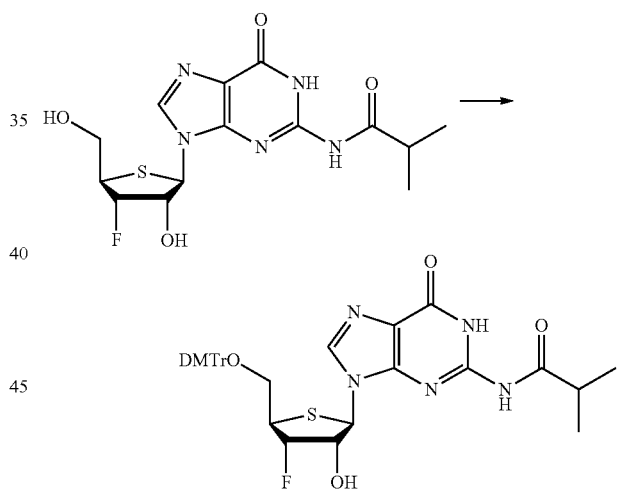

To a solution of N-(9-((2R,3R,4S,5R)-4-fluoro-3-hydroxy-5-(hydroxymethyl)-tetrahydrothiophen-2-yl)-6-oxo-6,9-dihydro-1H-purin-2-yl)isobutyramide (0.62 g, 1.66 mmol) in pyridine (25 mL) at 0° C. was added 4,4'-dimethoxytrityl chloride (0.84 g, 2.48 mmol). The reaction mixture was stirred at 0° C. for 3 h. The reaction was quenched with H$_2$O (1 mL), and the mixture was concentrated. The residue was diluted in 100 mL of ethyl acetate and washed with saturated aq. NaHCO$_3$ (100 mL) and brine (100 mL). The separated organic layer was dried over anhydrous Na$_2$SO$_4$, filtered, and concentrated in vacuo. The residue was purified by a silica gel column, eluting with 0-100% EtOAc/Hexane containing 0.1% Et$_3$N to give product. LCMS (ES, m/z): 674.6 [M+H]$^-$. $^1$H NMR (500 MHz, Chloroform-d) δ 11.96 (s, 0H), 8.35 (s, 0H), 7.70 (s, 0H), 7.63-7.56 (m, 1H), 7.50-7.43 (m, 2H), 7.38-7.24 (m, 1H), 6.93-6.85 (m, 2H), 5.92 (d, J=8.3 Hz, 0H), 5.35-5.23 (m, 1H), 4.15 (q, J=7.1 Hz, 1H), 3.85-3.69 (m, 3H), 3.46 (dd, J=10.2, 5.4 Hz, 0H), 3.35 (dd, J=10.2, 5.2 Hz, 0H), 2.09 (d, J=19.4 Hz, 2H), 1.34-1.22 (m, 2H), 1.01 (d, J=6.8 Hz, 1H), 0.91 (d, J=6.9 Hz, 1H).

Preparation 20: N-(3-((2R,3R,4S,5R)-5-((bis(4-methoxyphenyl)(phenyl)-methoxy)methyl)-4-fluoro-3-hydroxytetrahydrothiophen-2-yl)-7-oxo-6,7-dihydro-3H-[1,2,3]triazolo[4,5-d]pyrimidin-5-yl)isobutyramide

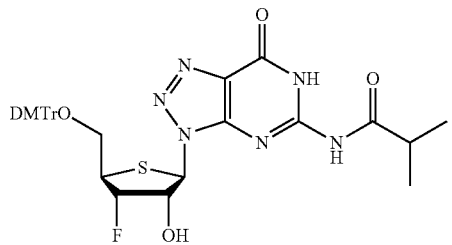

Step 1: N-(7-oxo-6,7-dihydro-3H-[1,2,3]triazolo[4,5-d]pyrimidin-5-yl)isobutyramide

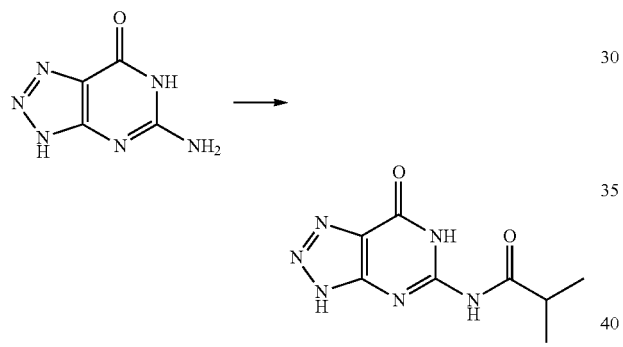

To a suspension of 5-amino-3,6-dihydro-7H-[1,2,3]triazolo[4,5-d]pyrimidin-7-one (5.0 g, 32.9 mmol) in anhydrous DMF (60 mL) was added isobutyric anhydride (12.5 mL, 76.0 mmol) dropwise. The reaction mixture was refluxed at 150° C. for 1 h. The reaction was quenched with MeOH (6.6 mL, 164 mmol) and concentrated in vacuo. The residue was taken up in DCM (50 mL)/Hexane (100 mL) and was stirred at vigorously at rt for 15 min. The product was collected by filtration. LCMS (ES, m/z): 223.2 [M+H]+. 1H NMR (500 MHz, DMSO-d6) δ 16.04 (s, 1H), 12.19 (s, 1H), 11.78 (s, 1H), 2.78 (hept, J=6.7 Hz, 1H), 1.13 (d, J=6.8 Hz, 6H).

Step 2: ((2R,3S,4R,5R)-4-(benzoyloxy)-3-fluoro-5-(5-isobutyramido-7-oxo-6,7-dihydro-3H-[1,2,3]triazolo[4,5-d]pyrimidin-3-yl)tetrahydrothiophen-2-yl)methyl benzoate

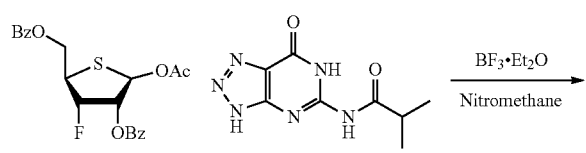

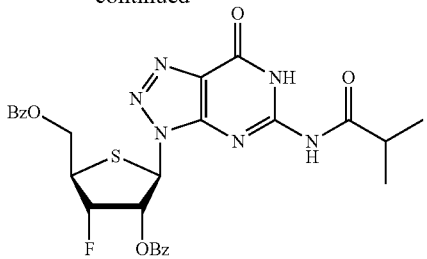

To a mixture of ((2R,3 S,4R)-5-acetoxy-4-(benzoyloxy)-3-fluorotetrahydrothiophen-2-yl)methyl benzoate (1.5 g, 3.6 mmol) and N-(7-oxo-6,7-dihydro-3H-[1,2,3]triazolo[4,5-d]pyrimidin-5-yl)isobutyramide (0.96 g, 4.3 mmol) in nitromethane (20 mL) was added BF3.Et2O (0.54 mL, 4.3 mmol) and the resulting mixture was heated at 100° C. under microwave irradiation for 1 h. The reaction mixture was cooled, diluted in 100 mL of ethyl acetate and washed with saturated aq. NaHCO3 (100 mL) and brine (100 mL). The organic portion was dried over Na2SO4 and concentrated in vacuo. The residue was purified by a silica gel column, eluting with 0-35% EtOAc/Hexane. LCMS (ES, m/z): 581.4 [M+H]+. 1H NMR (500 MHz, Chloroform-d) δ 12.27 (s, 2H), 9.73 (s, 2H), 8.19-7.93 (m, 8H), 7.86-7.80 (m, 0H), 7.71-7.55 (m, 4H), 7.57-7.39 (m, 8H), 7.40-7.33 (m, 0H), 6.76 (d, J=6.7 Hz, 2H), 6.62-6.48 (m, 2H), 5.79 (t, J=2.9 Hz, 1H), 5.69 (t, J=2.9 Hz, 1H), 5.62-5.54 (m, 2H), 4.89 (ddd, J=11.6, 7.8, 1.3 Hz, 2H), 4.78-4.65 (m, 1H), 4.31-4.18 (m, 2H), 4.15 (q, J=7.1 Hz, 3H), 2.95 (hept, J=6.9 Hz, 2H), 2.81-2.68 (m, 1H), 2.07 (s, 4H), 1.39 (dd, J=17.5, 6.9 Hz, 10H), 1.34-1.24 (m, 8H).

Step 3: N-(3-((2R,3R,4S,5R)-4-fluoro-3-hydroxy-5-(hydroxymethyl)tetrahydrothiophen-2-yl)-7-oxo-6,7-dihydro-3H-[1,2,3]triazolo[4,5-d]pyrimidin-5-yl)isobutyramide

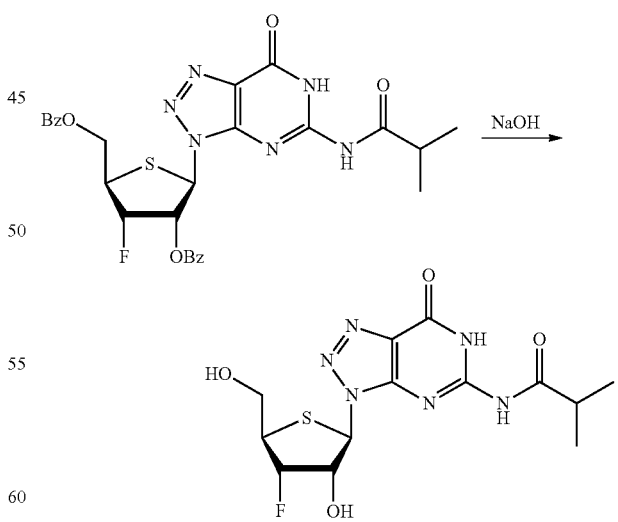

To a solution of ((2R,3 S,4R,5R)-4-(benzoyloxy)-3-fluoro-5-(5-isobutyramido-7-oxo-6,7-dihydro-3H-[1,2,3]triazolo[4,5-d]pyrimidin-3-yl)tetrahydrothiophen-2-yl)methyl benzoate (4.5 g, 7.8 mmol) in THF (35 mL)/MeOH (28 mL)/H (7 mL) at 0° C. was added 2N sodium hydroxide (8.6 mL, 17.2 mmol). The reaction mixture was stirred at 0° C. for 1 h and then neutralized with acetic acid (2.3 mL, 39.0 mmol). Product was collected by filtration and carried on to the next step without further purification. LCMS (ES, m/z): 373.3 [M+H]$^+$.

Step 4. N-(3-((2R,3R,4S,5R)-5-((bis(4-methoxyphenyl)(phenyl)methoxy)methyl)-4-fluoro-3-hydroxytetrahydrothiophen-2-yl)-7-oxo-6,7-dihydro-3H-[1,2,3]triazolo[4,5-d]pyrimidin-5-yl)isobutyramide

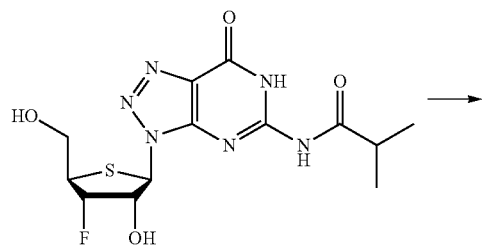

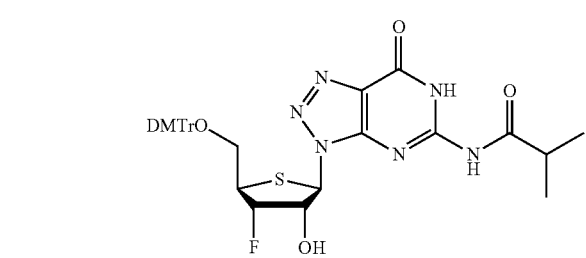

To a solution of N-(3-((2R,3R,4S,5R)-4-fluoro-3-hydroxy-5-(hydroxymethyl)-tetrahydrothiophen-2-yl)-7-oxo-6,7-dihydro-3H-[1,2,3]triazolo[4,5-d]pyrimidin-5-yl)isobutyramide (1.8 g, 4.8 mmol) in pyridine (30 mL) at 0° C. was added 4,4'-dimethoxytrityl chloride (1.8 g, 5.3 mmol). The reaction mixture was stirred at 0° C. for 1 h. The reaction was quenched with H$_2$O (1 mL), and the mixture was concentrated. The residue was diluted in 100 mL of ethyl acetate and washed with saturated aq. NaHCO$_3$ (100 mL) and brine (100 mL). The separated organic layer was dried over anhydrous Na$_2$SO$_4$, filtered, and concentrated in vacuo. The residue was purified by a silica gel column, eluting with 0-100% EtOAc/Hexane containing 0.1% Et$_3$N to give product. LCMS (ES, m/z): 675.5 [M+H]$^+$. $^1$H NMR (500 MHz, Chloroform-d) δ 12.16 (s, 1H), 8.48 (s, 0H), 7.57-7.50 (m, 1H), 7.49-7.37 (m, 2H), 7.39-7.29 (m, 0H), 7.31 (s, 1H), 7.32-7.14 (m, 1H), 6.91-6.81 (m, 2H), 6.22-6.16 (m, 0H), 5.42-5.31 (m, 1H), 3.77 (d, J=36.0 Hz, 7H), 3.46 (dd, J=10.2, 5.6 Hz, 0H), 3.36 (dd, J=10.2, 5.4 Hz, 0H), 2.17 (p, J=6.9 Hz, 0H), 1.06 (dd, J=26.1, 6.9 Hz, 3H).

Preparation 21: N-(3-((2R,3R,4S,5R)-5-((bis(4-methoxyphenyl)(phenyl)-methoxy)methyl)-3,4-dihydroxytetrahydrothiophen-2-yl)-7-oxo-6,7-dihydro-3H-[1,2,3]triazolo[4,5-d]pyrimidin-5-yl)isobutyramide

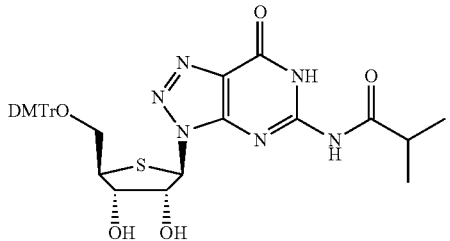

Step 1: (2R,3S,4R,5R)-2-((benzoyloxy)methyl)-5-(5-isobutyramido-7-oxo-6,7-dihydro-3H-1,2,3 triazolo[4,5-d]pyrimidin-3-yl)tetrahydrothiophene-3,4-diyl dibenzoate

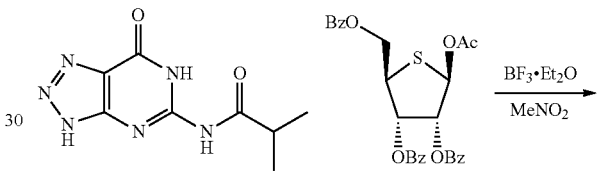

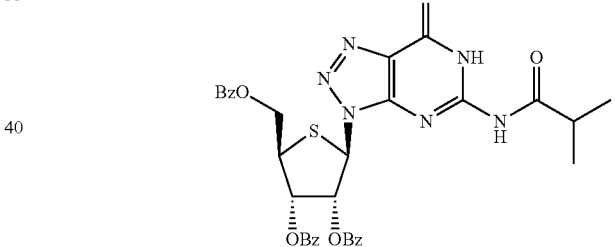

BF$_3$·OEt$_2$ (3.65 mL, 28.8 mmol) was added dropwise to a mixture of (2R,3R,4S,5R)-2-acetoxy-5-((benzoyloxy) methyl)tetrahydrothiophene-3,4-diyl dibenzoate (10.0 g, 19.2 mmol) and N-(7-oxo-6,7-dihydro-3H-[1,2,3]triazolo[4,5-d]pyrimidin-5 yl)isobutyramide (5.98 g, 26.9 mmol) in MeNO$_2$ (180 mL) at ambient temperature. Upon completion of addition, the mixture was heated at 120° C. in a microwave reactor for 45 min. The sample was cooled to rt and concentrated in vacuo. The residue was purified by flash column chromatography eluting with EtOAc/isohexane (10-90%) to give desired product. LCMS (ES, m/z): 683.5 [M+H]$^+$.H NMR (500 MHz, Chloroform-d) δ 12.24 (s, 1H), 9.77 (s, 1H), 8.08-7.95 (m, 4H), 7.94-7.87 (m, 2H), 7.70-7.35 (m, 9H), 6.84 (d, J=5.9 Hz, 1H), 6.67 (dd, J=5.9, 3.9 Hz, 1H), 6.49 (t, J=3.7 Hz, 1H), 5.52 (dd, J=11.4, 7.8 Hz, 1H), 5.04 (dd, J=11.4, 7.8 Hz, 1H), 4.28 (m, 1H), 2.97 (hept, J=6.9 Hz, 1H), 1.42 (dd, 6.9 Hz, 6H).

Step 2. N-(3-((2R,3R,4S,5R)-3,4-dihydroxy-5-(hydroxymethyl)tetrahydrothiophen-2-yl)-7-oxo-6,7-dihydro-3H-[1,2,3]triazolo[4,5-d]pyrimidin-5-yl)isobutyramide

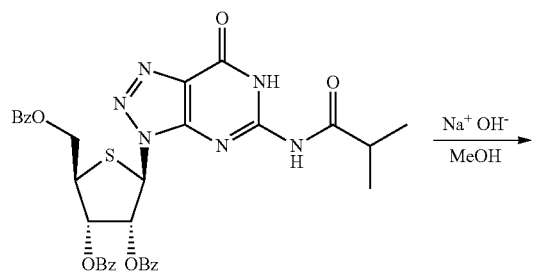

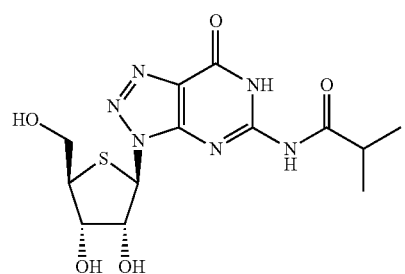

To a stirred solution of the product from Step 1 (5.3 g, 7.8 mmol) dissolved in Pyridine (8 mL) and MeOH (32 mL) at 25° C. was added sodium hydroxide (1.24 g, 31.1 mmol) in one portion. The mixture was stirred at 25° C. for 15 min before the addition of acetic acid (1.8 mL, 31.1 mmol). The mixture was concentrated in vacuo, and the residue was purified by flash column chromatography eluting with EtOAc/isohexane (70-100%) to give the desired product. LCMS (ES, m/z): 371.3 [M+H]$^+$. $^1$H NMR (500 MHz, DMSO-d$_6$) δ 12.24 (s, 1H), 11.96 (s, 1H), 5.91 (d, J=5.6 Hz, 1H), 5.73 (d, J=5.5 Hz, 1H), 5.43 (d, J=5.0 Hz, 1H), 5.12 (m, 1H), 4.81 (m, br, 1H), 4.40 (m, 1H), 3.89-3.77 (m, 1H), 3.53 (m, 1H), 3.46-3.36 (m, 1H), 2.79 (m, 1H), 1.14 (dd, J=6.7, 1.2 Hz, 6H).

Step 3. N-(3-((2R,3R,4S,5R)-5-((bis(4-methoxyphenyl)(phenyl)methoxy)methyl)-3,4-dihydroxytetrahydrothiophen-2-yl)-7-oxo-6,7-dihydro-3H-[1,2,3]triazolo[4,5-d]pyrimidin-5-yl)isobutyramide

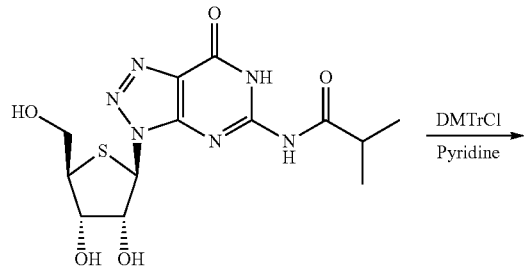

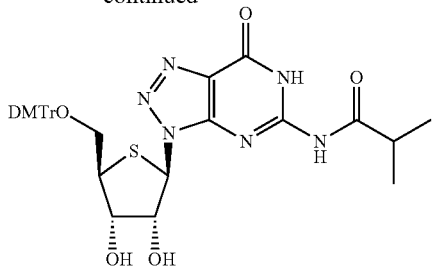

To the product from step 2 (2.3 g, 6.2 mmol) was added pyridine (62 mL) at ambient temperature. To this mixture was added DMTrCl (2.3 g, 6.8 mmol). After 1 h, water (2 mL) was added, and it was concentrated in vacuo. Ethyl acetate (15 mL), water (5 mL) and brine (1 mL) were added. Layers were separated, and the aqueous layer was extracted with ethyl acetate twice (20 mL×2). The combined organics were dried over MgSO$_4$, concentrated in vacuo and purified by flash column chromatography, eluting with 0 to 80% EtOAc in Hexane to give the desired product. LCMS (ES, m/z): 673.4 [M+H]$^+$ 0.1H NMR (500 MHz, DMSO-d$_6$) δ 12.24 (s, 1H), 11.96 (s, 1H), 7.50-7.36 (m, 2H), 7.35-7.10 (m, 9H), 6.96-6.82 (m, 4H), 5.88 (d, J=4.1 Hz, 1H), 5.83 (d, J=5.1 Hz, 1H), 5.42 (d, J=5.7 Hz, 1H), 4.66 (q, J=4.1 Hz, 1H), 4.45 (td, J=5.9, 3.5 Hz, 1H), 3.81-3.69 (6H), 3.65 (ddd, J=8.4, 6.0, 4.3 Hz, 1H), 3.46-3.35 (m, 1H), 3.19 (dd, J=9.4, 7.9 Hz, 1H), 2.78 (h, J=6.8 Hz, 1H), 1.22-1.05 (m, 6H).

Preparation 22: ammonium (2R,3R,4S,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrothiophen-3-yl phosphonate

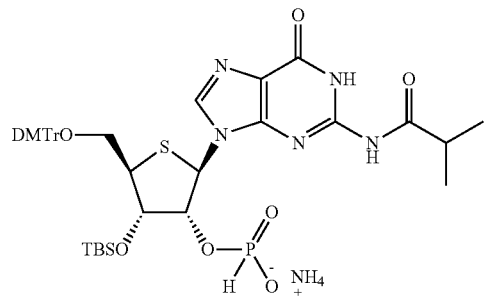

Step 1: N-(9-((2R,3R,4S,5R)-3,4-dihydroxy-5-(hydroxymethyl)tetrahydrothiophen-2-yl)-6-oxo-6,9-dihydro-1H-purin-2-yl)isobutyramide

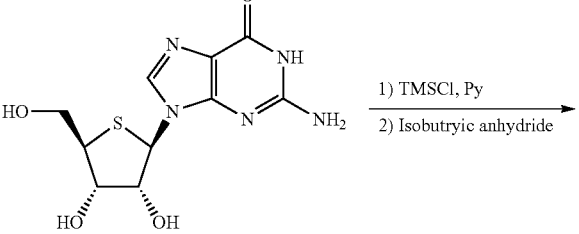

-continued

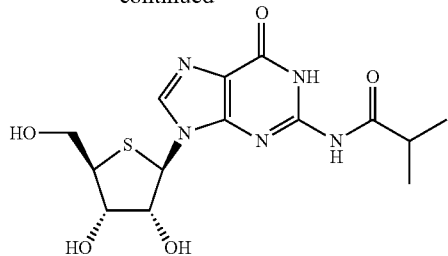

2-amino-9-((2R,3R,4S,5R)-3,4-dihydroxy-5-(hydroxymethyl)tetrahydrothiophen-2-yl)-1,9-dihydro-6H-purin-6-one (1.7 g, 5.7 mmol) was co-evaporated with pyridine (3×5 mL) and then, re-dissolved in pyridine (34 mL). To the mixture at 0° C. was added chlorotrimethylsilane (4.32 g, 39.8 mmol) dropwise. It was stirred at rt for 1 h and then, cooled to 0° C. again. Isobutyric anhydride (1.348 g, 8.52 mmol) was added dropwise, and it was stirred at rt for 3 h. It was quenched by the addition of water (8.5 mL). After 5 min, NH$_4$OH (ca. 29%, 17 mL) was added, and the mixture was stirred for 30 min. It was concentrated and purified by column chromatography eluted with 1 to 30% MeOH in CH$_2$Cl$_2$ to give the product. LCMS (ES, m/z): 396.9 [M+H]$^+$. $^1$H-NMR (400 MHz, DMSO-d$_6$): δ 9.52 (br s, 2H), 8.39 (s, 1H), 5.79 (d, J=7.1 Hz, 1H), 5.59 (s, 1H), 5.40 (s, 1H), 5.22 (s, 1H), 4.55 (d, J=6.7 Hz, 1H), 4.21 (s, 1H), 3.77 (t, J=9.3 Hz, 1H), 3.61 (s, 1H), 3.30 (dt, J=6.4, 3.3 Hz, 1H), 2.78 (p, J=6.9 Hz, 1H), 1.13 (d, J=6.8 Hz, 6H).

Step 2: N-(9-((2R,3R,4S,5R)-5-((bis(4-methoxyphenyl)(phenyl)methoxy)methyl)-3,4-dihydroxytetrahydrothiophen-2-yl)-6-oxo-6,9-dihydro-1H-purin-2-yl)isobutyramide

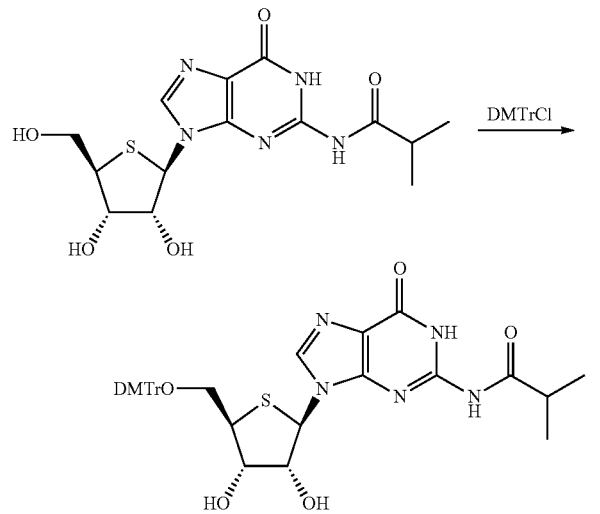

To a mixture of N-(9-((2R,3R,4S,5R)-3,4-dihydroxy-5-(hydroxymethyl)-tetrahydrothiophen-2-yl)-6-oxo-6,9-dihydro-1H-purin-2-yl)isobutyramide (480 mg, 1.299 mmol) in pyridine (10 mL) was added 4,4'-(chloro(phenyl)methylene)-bis(methoxybenzene) (484 mg, 1.43 mmol). It was stirred at rt for 16 h and then, concentrated. The crude was purified by column chromatography on silica gel eluted with 1 to 30% MeOH in CH$_2$Cl$_2$ (containing 1% Et$_3$N) to give the product. LCMS (ES, m/z): 672.2 [M+H]$^+$. $^1$H-NMR (400 MHz, DMSO-d$_6$+D$_2$O): δ 8.08 (s, 1H), 7.39 (d, J=7.2 Hz, 2H), 7.32 (t, J=7.6 Hz, 2H), 7.26 (dt, J=9.1, 3.3 Hz, 5H), 6.94-6.87 (m, 4H), 5.75 (d, J=5.9 Hz, 1H), 4.39 (dd, J=5.9, 3.5 Hz, 1H), 4.14 (t, J=3.9 Hz, 1H), 3.74 (s, 6H), 3.49-3.37 (m, 2H), 3.33 (dd, J=14.5, 7.3 Hz, 1H), 2.87-2.67 (m, 1H), 1.11 (dd, J=6.8, 1.6 Hz, 6H).

Step 3: N-(9-((2R,3R,4S,5R)-5-((bis(4-methoxyphenyl)(phenyl)methoxy)methyl)-4-((tert-butyldimethylsilyl)oxy)-3-hydroxytetrahydrothiophen-2-yl)-6-oxo-6,9-dihydro-1H-purin-2-yl)isobutyramide and N-(9-((2R,3R,4S,5R)-5-((bis(4-methoxyphenyl)(phenyl)methoxy)methyl)-3-((tert-butyldimethylsilyl)oxy)-4-hydroxytetrahydrothiophen-2-yl)-6-oxo-6,9-dihydro-1H-purin-2-yl)isobutyramide

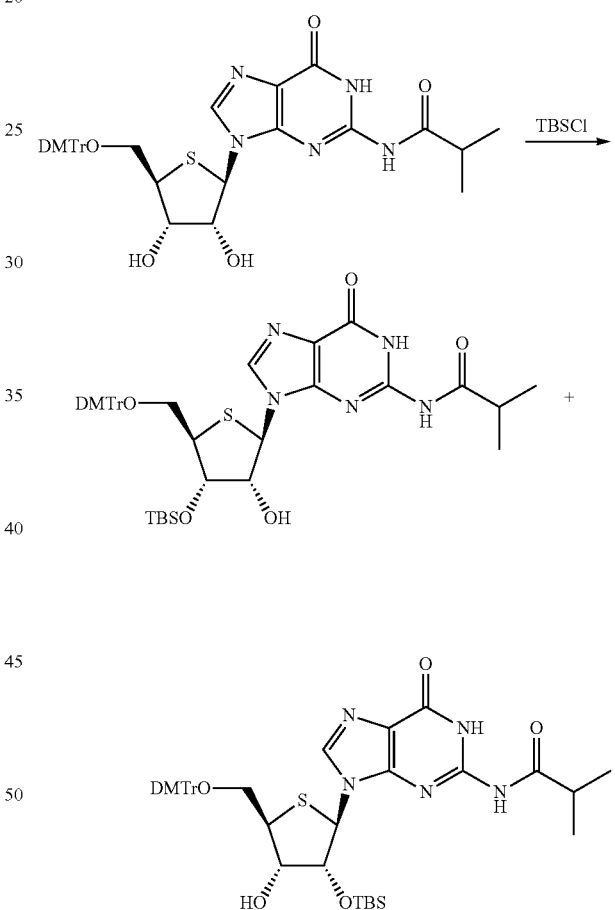

To a solution of N-(9-((2R,3R,4S,5R)-5-((bis(4-methoxyphenyl)(phenyl)-methoxy)methyl)-3,4-dihydroxytetrahydrothiophen-2-yl)-6-oxo-6,9-dihydro-1H-purin-2-yl)isobutyramide (580 mg, 0.863 mmol) in DMF (5 mL) at rt was added 1H-imidazole (147 mg, 2.16 mmol) and tert-butylchlorodimethylsilane (156 mg, 1.04 mmol). After 6 h, the mixture was diluted with EtOAc (50 mL) and washed with sat aq NaHCO$_3$ (2×20 mL) and brine (20 mL). It was dried (Na$_2$SO$_4$), concentrated, and purified by reverse phase (C18) chromatography eluted with 0 to 95% ACN in water to give the products. LCMS (ES, m/z): 786.3 [M+H]$^+$.

Step 4. (2R,3R,4S,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrothiophen-3-yl phenyl phosphonate and (2R,3S,4R,5R)-2-((bis(4-methoxyphenyl)(phenyl)methoxy)methyl)-4-((tert-butyldimethylsilyl)oxy)-5-(2-isobutyramido-6-oxo-1,6-dihydro-9H-purin-9-yl)tetrahydrothiophen-3-yl phenyl phosphonate

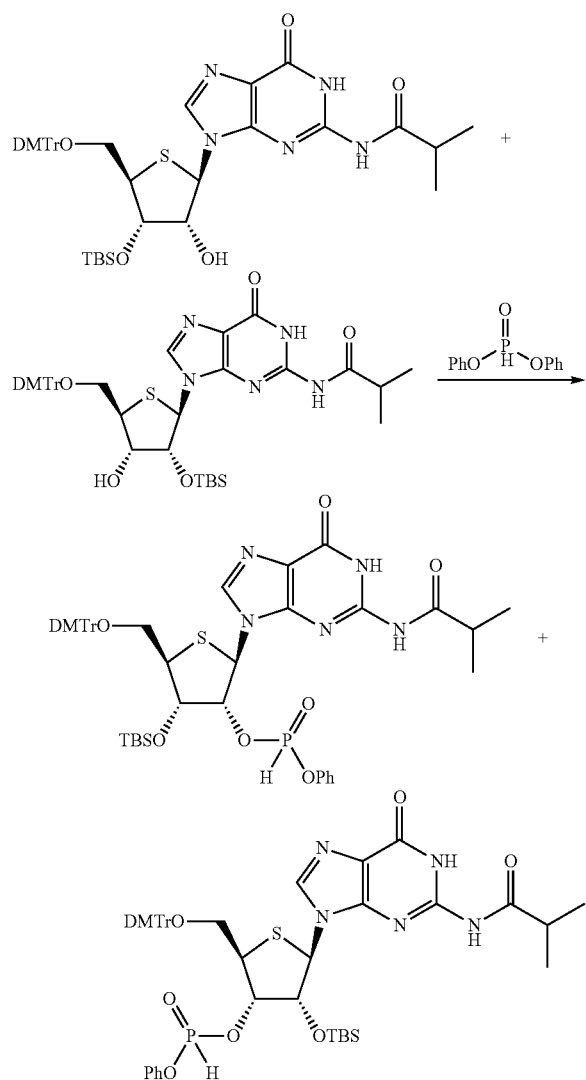

To a solution of a mixture of N-(9-((2R,3R,4S,5R)-5-((bis(4-methoxyphenyl)(phenyl)-methoxy)methyl)-4-((tert-butyldimethylsilyl)oxy)-3-hydroxytetrahydrothiophen-2-yl)-6-oxo-6,9-dihydro-1H-purin-2-yl)isobutyramide and N-(9-((2R,3R,4S,5R)-5-((bis(4-methoxyphenyl) (phenyl)methoxy)methyl)-3-((tert-butyldimethylsilyl)oxy)-4-hydroxytetrahydrothiophen-2-yl)-6-oxo-6,9-dihydro-1H-purin-2-yl) isobutyramide (220 mg, 0.280 mmol) in pyridine (2 mL) at 0° C. was added diphenyl phosphonate (98 mg, 0.420 mmol). The resulting mixture was stirred at rt for 20 min. It was used in the next reaction step without purification. LCMS (ES, m/z): 926.2 [M+H]$^+$.

Step 5: ammonium (2R,3R,4S,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrothiophen-3-yl phosphonate

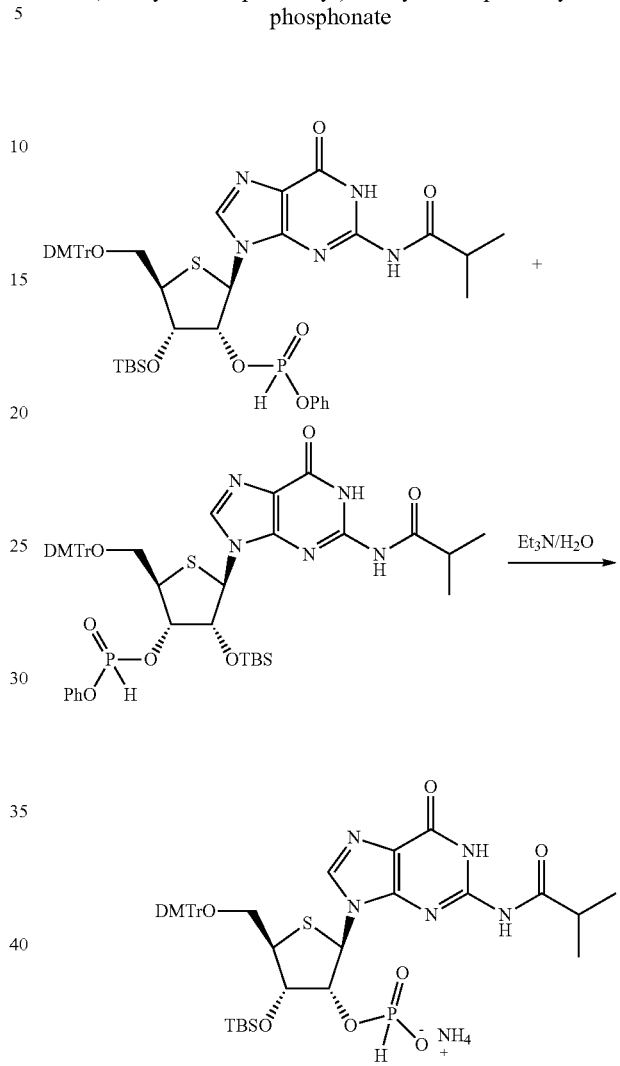

To the reaction mixture from Step 4 at 0° C. was added Et$_3$N (0.28 mL, 2.0 mmol) and water (0.28 mL). It was stirred at rt for 30 min. It was concentrated, and the residue was partitioned between CH$_2$Cl$_2$ (40 mL) and aq NaHCO$_3$ (5%, 30 mL). The organic layer was washed with aq NaHCO$_3$ (5%, 2×30 mL), dried (Na$_2$SO$_4$), concentrated and purified by silica gel column chromatography using 0-10% MeOH in CHCl$_3$ containing 1% Et$_3$N to give a mixture. The mixture was further purified by prep-HPLC Prep-HPLC (XBridge Shield RP18 OBD Column, 19×150 mm) eluted with 46 to 79% ACN in aq NH$_4$HCO$_3$ (10 mM) over 7 min to give the product. LCMS (ES, m/z): 850.2 [M+H]$^+$. $^1$H-NMR (400 MHz, CD$_3$OD): δ 8.18 (s, 1H), 7.68 (s, 0.5H), 7.59-7.49 (m, 2H), 7.45-7.36 (m, 4H), 7.37-7.30 (m, 2H), 7.28-7.22 (m, 1H), 6.95-6.87 (m, 4H), 6.16-6.07 (m, 2H), 4.88-4.87 (m, 1H), 4.69 (dd, J=7.3, 3.3 Hz, 1H), 3.81 (s, 6H), 3.51 (dd, J=4.9, 1.9 Hz, 2H), 3.37 (s, 1H), 2.67 (p, J=6.9 Hz, 1H), 1.21 (dd, J=6.9, 0.9 Hz, 6H), 0.77 (s, 9H), 0.01 (s, 3H), −0.28 (s, 3H). $^{31}$P-NMR (162 MHz, DMSO-d$_6$): δ −0.74 (s, 1P).

Preparation 23: 2-amino-9-[5-O-(hydroxy{[hydroxy(phosphonooxy)phosphoryl]oxy]-phosphoryl)-β-D-xylofuranosyl}-1,9-dihydro-6H-purin-6-one

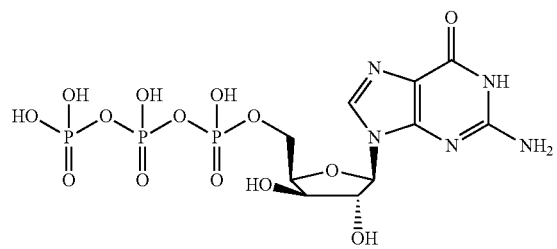 [SMILES: Nc1nc2c(ncn2[C@@H]2O[C@H](COP(=O)(O)OP(=O)(O)OP(=O)(O)O)[C@H](O)[C@H]2O)c(=O)[nH]1]

Step 1: 2-amino-9-[5-O-(hydroxy{[hydroxy(phosphonooxy)phosphoryl]oxy}-phosphoryl)-β-D-xylofuranosyl]-1,9-dihydro-6H-purin-6-one

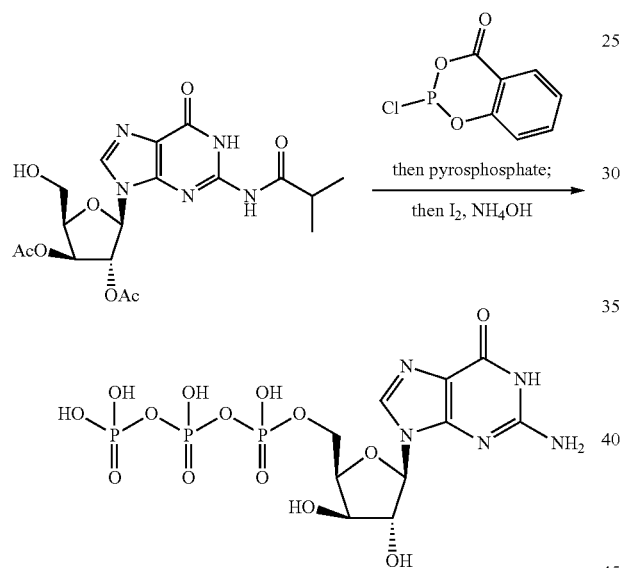

To a stirred solution of 9-(2,3-di-O-acetyl-β-D-xylofuranosyl)-2-[(2-methylpropanoyl)-amino]-1,9-dihydro-6H-purin-6-one (100 mg, 0.229 mmol) in pyridine (0.25 mL) and 1,4-dioxane (0.75 mL) was added a freshly prepared solution of 2-chloro-4H-1,3,2-benzodioxaphosphorin-4-one (50 mg, 0.247 mmol) in 1,4-dioxane (0.25 mL). The reaction mixture was stirred at ambient temperature for 10 min, and then a solution of tributylammonium pyrophosphate (189 mg, 0.344 mmol) in DMF (0.69 mL) was added, followed by addition of tributylamine (0.23 mL, 0.968 mmol) in one portion at ambient temperature. The reaction mixture was stirred for 10 min at ambient temperature, and then a solution of iodine (29.0 mg, 0.114 mmol) in pyridine (0.50 mL) and water (0.05 mL) was added. The reaction mixture was stirred for 15 min, excess iodine was quenched with 5% aq NaHSO$_3$ (3 mL), and the reaction mixture was evaporated to dryness. The residue was dissolved in 10 mL H$_2$O, and after standing at rt for 30 min, 28% aq ammonium hydroxide (5 mL) was added. The reaction mixture was stirred at 50° C. for 5 h. LCMS indicated full conversion to desired product, and the mixture was filtered and lyophilyzed. The product was purified using mass-directed reverse phase HPLC with a Waters SunFire C18 OBD Prep Column, 100 Å, 5 μm, 19 mm×150 mm, [Waters Part #186002568] using a gradient solvent system with MeCN and 100 mM aq triethylammonium acetate. Lyophilization of the product fractions furnished 2-amino-9-[5-O-(hydroxy{[hydroxy(phosphonooxy)phosphoryl]oxy}phosphoryl)-3-D-xylofuranosyl]-1,9-dihydro-6H-purin-6-one as the tetra-triethylamine salt. LCMS (ES, m/z): 522 [M−H]$^-$.

Preparation 24: ((2R,3S,4R,5S)-5-(7-amino-1H-pyrazolo[4,3-d]pyrimidin-3-yl)-3,4-dihydroxytetrahydrofuran-2-yl)methyl tetrahydrogen triphosphate

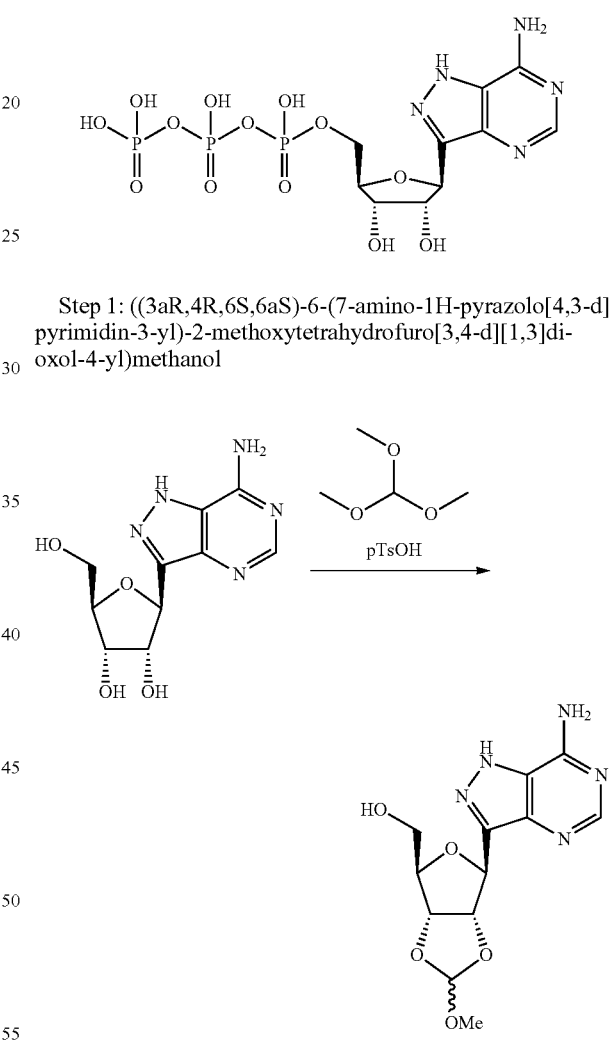

Step 1: ((3aR,4R,6S,6aS)-6-(7-amino-1H-pyrazolo[4,3-d]pyrimidin-3-yl)-2-methoxytetrahydrofuro[3,4-d][1,3]dioxol-4-yl)methanol To the stirred suspension of (2S,3R,4S,5R)-2-(7-amino-1H-pyrazolo[4,3-d]pyrimidin-3-yl)-5-(hydroxymethyl)tetrahydrofuran-3,4-diol (30 mg, 0.105 mmol) in 1,4-dioxane (0.3 mL) was added trimethyl orthoformate (0.22 mL, 2.011 mmol) in one portion at ambient temperature, followed by p-toluenesulfonic acid monohydrate (22 mg, 0.116 mmol). The reaction mixture was stirred at ambient temperature for 16 h. LCMS indicated significant conversion to desired product, and the crude mixture was carefully quenched by adding triethylamine (0.05 mL) at 0° C. Following concentration, the residue was purified by flash column chromatography on 12 gram silica gel using a gradient solvent system with MeOH and CH$_2$Cl$_2$. Concentration of the product fractions furnished ((3aR,4R,6S,6aS)-6-(7-amino-1H-pyrazolo[4,3-d]pyrimidin-3-yl)-2-methoxytetrahydrofuro[3,4-d][1,3]dioxol-4-yl)methanol. LCMS (ES, m/z): 310 [M+H]$^+$.

Step 2: ((3aR,4R,6S,6aS)-6-(7-amino-1H-pyrazolo[4,3-d]pyrimidin-3-yl)-2-methoxytetrahydrofuro[3,4-d][1,3]dioxol-4-yl)methyl tetrahydrogen triphosphate

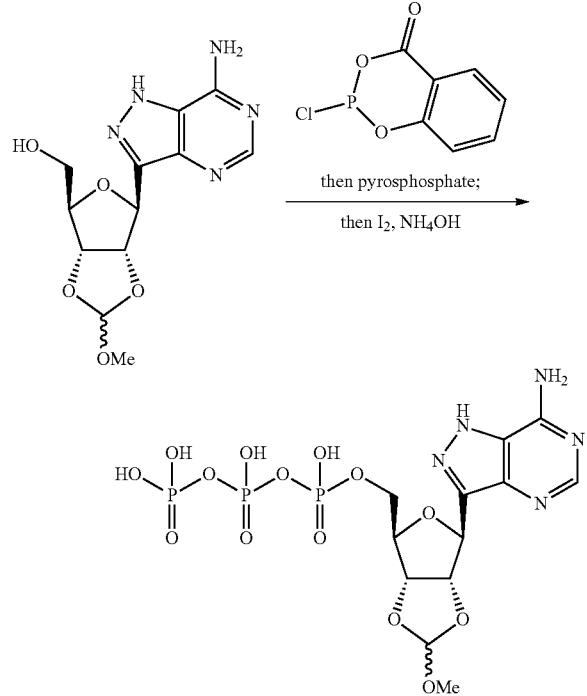

To the stirred suspension of ((3aR,4R,6S,6aS)-6-(7-amino-1H-pyrazolo[4,3-d]pyrimidin-3-yl)-2-methoxytetrahydrofuro[3,4-d][1,3]dioxol-4-yl)methanol (16 mg, 0.052 mmol) in pyridine (0.05 mL) and 1,4-dioxane (0.15 mL) was added DMF (0.05 mL) to form a homogeneous solution. To this solution was added a freshly prepared solution of 2-chloro-4H-1,3,2-benzodioxaphosphorin-4-one (12 mg, 0.059 mmol) in 1,4-dioxane (0.05 mL) at ambient temperature. The reaction mixture was stirred at ambient temperature for 15 min, and then a solution of tributylammonium pyrophosphate (43 mg, 0.078 mmol) in DMF (0.10 mL) was added, followed by tributylamine (0.052 mL, 0.219 mmol). The reaction mixture was stirred at ambient temperature for 15 min, and then a solution of iodine (6.58 mg, 0.026 mmol) in pyridine (0.10 mL) and water (0.01 mL) was added. The reaction mixture was stirred at ambient temperature for 15 min and excess iodine was quenched with 5% aqueous NaHSO$_3$ (0.5 mL). LCMS indicated significant conversion to desired product, and the reaction mixture was concentrated to yield ((3 aR,4R,6S,6aS)-6-(7-amino-1H-pyrazolo[4,3-d]pyrimidin-3-yl)-2-methoxytetrahydrofuro[3,4-d][1,3]dioxol-4-yl)methyl tetrahydrogen triphosphate, which was used directly in the next reaction step without additional purification. LCMS (ES, m/z): 548 [M−H]$^-$.

Step 3. ((2R,3S,4R,5S)-5-(7-amino-H-pyrazolo[4,3-d]pyrimidin-3-yl)-3,4-dihydroxytetrahydrofuran-2-yl)methyl tetrahydrogen triphosphate

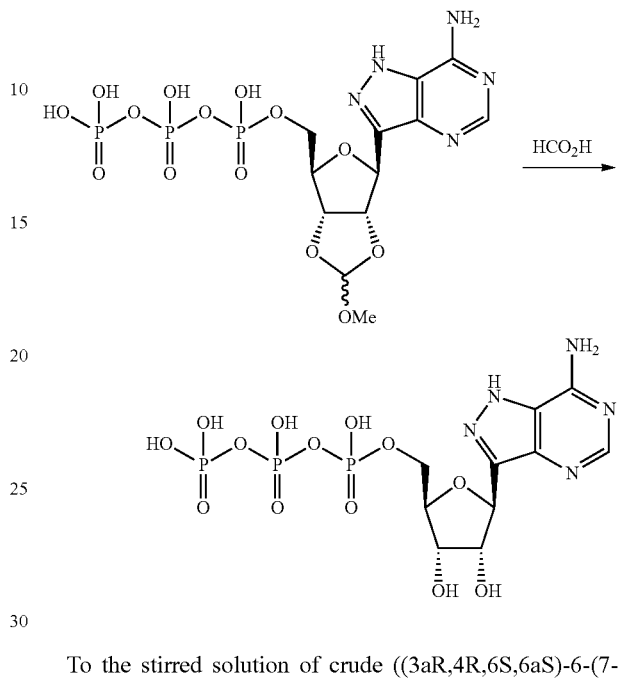

To the stirred solution of crude ((3aR,4R,6S,6aS)-6-(7-amino-1H-pyrazolo[4,3-d]pyrimidin-3-yl)-2-methoxytetrahydrofuro[3,4-d][1,3]dioxol-4-yl)methyl tetrahydrogen triphosphate (49.4 mg, 0.090 mmol) in water (0.15 mL) and DMF (0.15 mL) was added formic acid (0.4 mL, 10.60 mmol) in one portion. The reaction mixture was stirred at ambient temperature for 18 h. LCMS indicated significant conversion to desired product, and the mixture was filtered and lyophilyzed. The product was purified using mass-directed reverse phase HPLC with a Waters SunFire C18 OBD Prep Column, 100 Å, 5 μm, 19 mm×150 mm, [Waters Part #186002568] using a gradient solvent system with MeCN and 100 mM aqueous triethylammonium acetate. Lyophilization of the product fractions furnished ((2R,3 S,4R,5 S)-5-(7-amino-1H-pyrazolo[4,3-d]pyrimidin-3-yl)-3,4-dihydroxytetrahydrofuran-2-yl)methyl tetrahydrogen triphosphate. LCMS (ES, m/z): 506 [M−H]$^-$.

Preparation 25: ((2R,3S,4R,5R)-5-(6-amino-2-fluoro-9H-purin-9-yl)-3,4-dihydroxytetrahydrofuran-2-yl)methyl tetrahydrogen triphosphate

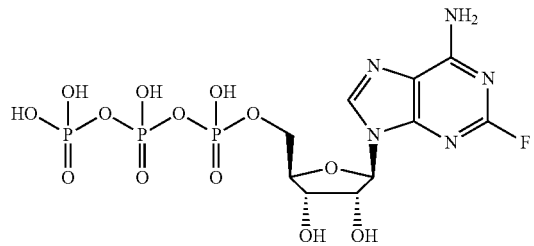 [SMILES: Nc1nc(F)nc2c1ncn2[C@@H]1O[C@H](COP(=O)(O)OP(=O)(O)OP(=O)(O)O)[C@@H](O)[C@H]1O]

Step 1: ((2R,3S,4R,5R)-5-(6-amino-2-fluoro-9H-purin-9-yl)-3,4-dihydroxytetrahydrofuran-2-yl)methyl tetrahydrogen triphosphate

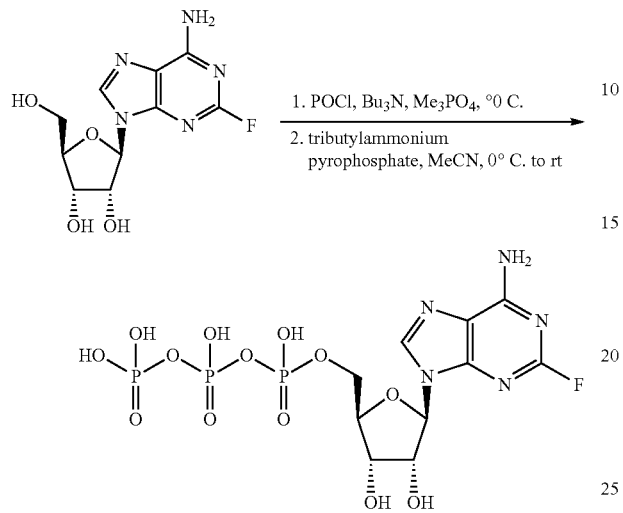

To a mixture of 2-fluoroadenosine (200 mg, 0.701 mmol) in trimethylphosphate (1.948 mL, 16.83 mmol) was added tributylamine (0.500 mL, 2.104 mmol), and the mixture was stirred 15 min at rt and then cooled in an ice/brine bath. Then POCl$_3$ (0.137 mL, 1.472 mmol) was added dropwise with bath temperature maintained at −5 to 0° C. After 1.25 h, a 0° C. mixture of tributylammonium pyrophosphate (327 mg, 0.596 mmol), MeCN (2.8 mL) and tributylamine (1.000 mL, 4.21 mmol) were added, and the mixture was allowed to warm to rt, followed by 16 h stirring at rt. The mixture was purified directly by reverse phase HPLC using a gradient of 1-20% MeCN with 100 mM aqueous triethylammonium acetate to furnish ((2R,3 S,4R,5R)-5-(6-amino-2-fluoro-9H-purin-9-yl)-3,4-dihydroxytetrahydrofuran-2-yl)methyl tetrahydrogen triphosphatemg. LCMS (ES, m/z): 524 [M−H]⁻.

Preparation 26: 3'-(aminomethyl)-3'-deoxyguanosine 5'-(tetrahydrogen triphosphate)

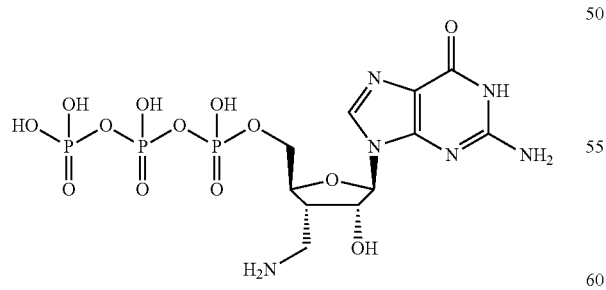

The title compound was prepared according to published procedures (WO2015161137).

The Preparations below were used as shown or were further modified through additional synthetic manipulations analogous to those described in Preparations 1-26.

Preparation 27: 2-amino-9-((β-D-xylofuranosyl)-1,9-dihydro-6H-purin-6-one

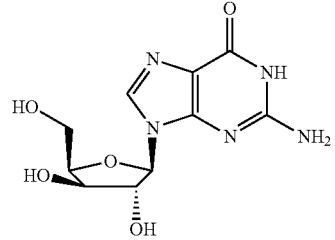 [SMILES: Nc1nc2c(ncn2[C@@H]2O[C@H](CO)[C@H](O)[C@H]2O)c(=O)[nH]1]

The title compound was prepared according to published procedures (*Journal of Medicinal Chemistry* 1987, 30(6), 982-991).

Preparation 28: 5-amino-3-(β-D-ribofuranosyl)-3,6-dihydro-7H-[1,2,3]triazolo[4,5-d]pyrimidin-7-one

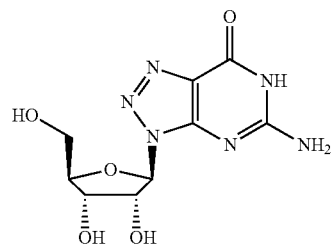 [SMILES: Nc1nc2c(nnn2[C@@H]2O[C@H](CO)[C@@H](O)[C@H]2O)c(=O)[nH]1]

The title compound was prepared according to published procedures (*Journal of Organic Chemistry* 2007, 72(1), 173-179).

Preparation 29: 9-{3-azido-5-O-[bis(4-methoxyphenyl)(phenyl)methyl]-3-deoxy-β-D-ribofuranosyl}-N-(phenylcarbonyl)-9H-purin-6-amine

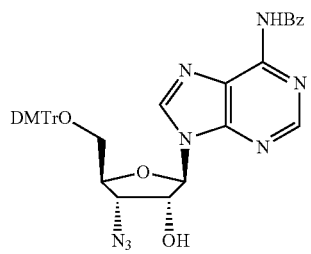

The title compound was prepared according to published procedures (*Bulletin of the Korean Chemical Society* 2004, 25(2), 243-248 and *Nucleosides, Nucleotides & Nucleic Acids* 2005 24(10-12), 1707-1727).

Preparation 30: 1-(β-D-ribofuranosyl)-1H-imidazo[4,5-c]pyridin-4-amine

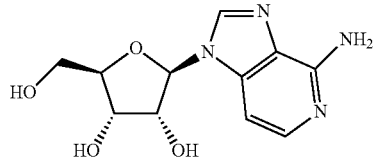 [SMILES: Nc1nccc2c1ncn2[C@@H]1O[C@H](CO)[C@@H](O)[C@H]1O]

The title compound was prepared according to published procedures (*Tetrahedron* 1993, 49(3), 557-570).

Preparation 31: 1-(β-D-ribofuranosyl)-1,5-dihydro-4H-imidazo[4,5-c]pyridin-4-one

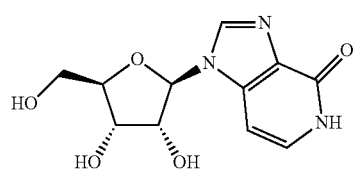 [SMILES: O=c1[nH]ccc2c1ncn2[C@@H]1O[C@H](CO)[C@@H](O)[C@H]1O]

The title compound was prepared according to published procedures (*Tetrahedron* 1993, 49(3), 557-570)

Preparation 32: 4'-thioadenosine

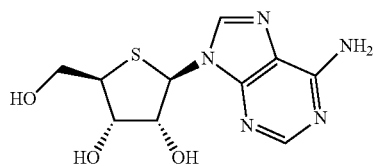 [SMILES: Nc1ncnc2c1ncn2[C@@H]1S[C@H](CO)[C@@H](O)[C@H]1O]

The title compound was prepared according to published procedures (*Journal of Medicinal Chemistry* 2006, 49(5), 1624-1634).

Preparation 33: 7-(β-D-ribofuranosyl)-3,7-dihydro-4H-imidazo[4,5-d][1,2,3]triazin-4-one

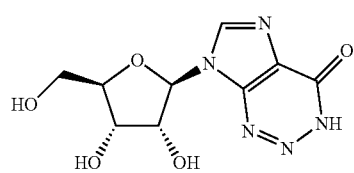 [SMILES: O=c1[nH]nnc2c1ncn2[C@@H]1O[C@H](CO)[C@@H](O)[C@H]1O]

The title compound was prepared according to published procedures (*Organic & Biomolecular Chemistry* 2014, 12(23), 3813-3815).

Preparation 34: 3-(β-D-ribofuranosyl)-3H-imidazo[4,5-b]pyridin-7-amine

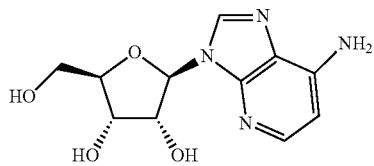 [SMILES: Nc1ccnc2c1ncn2[C@@H]1O[C@H](CO)[C@@H](O)[C@H]1O]

The title compound was prepared according to published procedures (*Biochemistry* 2005, 44(37), 12445-12453).

Preparation 35: 7-(2-deoxy-2-fluoro-β-D-arabino-furanosyl)-7H-pyrrolo[2,3-d]pyrimidin-4-amine

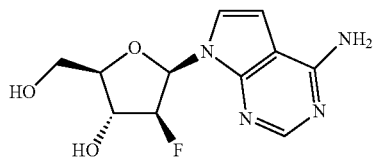 [SMILES: Nc1ncnc2c1ccn2[C@@H]1O[C@H](CO)[C@@H](O)[C@@H]1F]

The title compound was prepared according to published procedures (*Journal of the Chemical Society, Perkin Transactions 1: Organic and Bio-Organic Chemistry* 1995 (12), 1543-50).

Preparation 36: 1-(3-deoxy-β-D-erythro-pentofuranosyl)-1,5-dihydro-4H-imidazo[4,5-c]pyridin-4-one

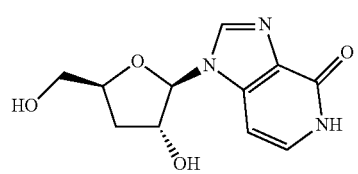 [SMILES: O=c1[nH]ccc2c1ncn2[C@@H]1O[C@H](CO)C[C@H]1O]

The title compound was prepared according to published procedures (*Chemical & Pharmaceutical Bulletin* 1996, 44(2), 288-295).

Preparation 37: 7-(2-deoxy-β-D-erythro-pentofuranosyl)-5-fluoro-7H-pyrrolo[2,3-d]pyrimidin-4-amine

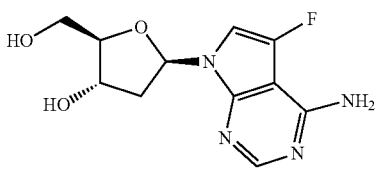 [SMILES: Nc1ncnc2c1c(F)cn2[C@H]1C[C@H](O)[C@@H](CO)O1]

The title compound was prepared according to published procedures (*Synthesis* 2006 (12), 2005-2012).

Preparation 38: (2S,3R,4S,5R)-2-(4-aminopyrazolo[1,5-a][1,3,5]triazin-8-yl)-5-(hydroxymethyl)tetrahydrofuran-3,4-diol

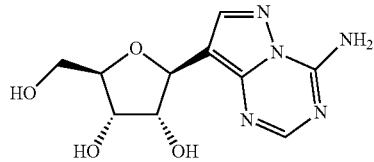 [SMILES: Nc1ncnc2c([C@@H]3O[C@H](CO)[C@@H](O)[C@H]3O)cnn12]

The title compound was prepared according to published procedures (WO2015148746).

Preparation 39: N-(8-((2R,4S,5R)-5-((bis(4-methoxyphenyl)(phenyl)methoxy)methyl)-4-hydroxytetrahydrofuran-2-yl)pyrazolo[1,5-a][1,3,5]triazin-4-yl)benzamide

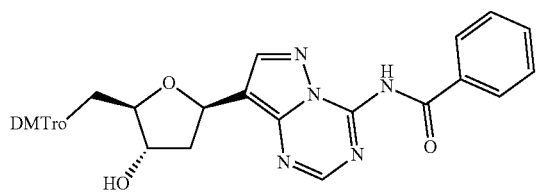

The title compound was prepared according to published procedures (WO2015148746).

Preparation 40: 7-(2-deoxy-4-ethynyl-β-D-erythropentofuranosyl)-5-fluoro-7H-pyrrolo[2,3-d]pyrimidin-4-amine

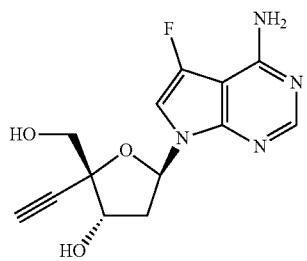 [SMILES: C#C[C@]1(CO)O[C@@H](n2cc(F)c3c(N)ncnc32)C[C@@H]1O]

The title compound was prepared according to published procedures (WO2015148746).

Preparation 41: 9-(2-chloro-2-deoxy-(β-D-arabinofuranosyl)-9H-purin-6-amine

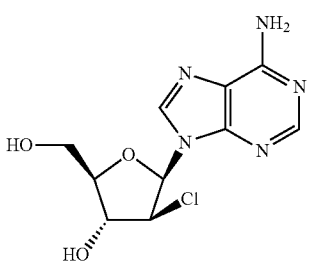 [SMILES: Nc1ncnc2c1ncn2[C@@H]1O[C@H](CO)[C@@H](O)[C@@H]1Cl]

The title compound was prepared according to published procedures (Journal of the American Chemical Society 1996, 118(46), 11341-11348).

Preparation 42: 2'-deoxy-2'-methyladenosine

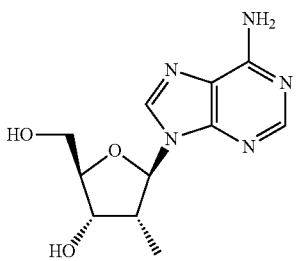 [SMILES: C[C@@H]1[C@H](O)[C@@H](CO)O[C@H]1n1cnc2c(N)ncnc21]

The title compound was prepared according to published procedures (Synthesis 2005 (17), 2865-2870).

Preparation 43: (2R,3R,4S,5R)-2-(6-amino-9H-purin-9-yl)-5-((R)-1-hydroxyethyl)tetrahydrofuran-3,4-diol

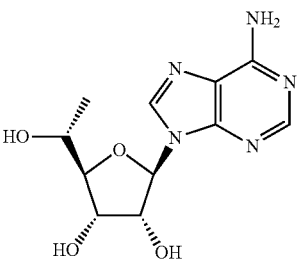 [SMILES: C[C@@H](O)[C@H]1O[C@@H](n2cnc3c(N)ncnc32)[C@H](O)[C@@H]1O]

The title compound was prepared according to published procedures (Bioorganicheskaya Khimiya 1989, 15(7), 969-975).

Preparation 44: 5-fluoro-7-(β3-D-ribofuranosyl)-7H-pyrrolo[2,3-d]pyrimidin-4-amine

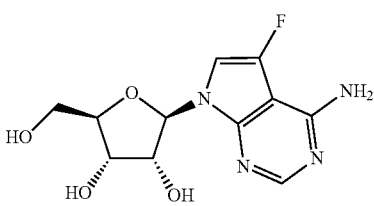 [SMILES: Nc1ncnc2c1c(F)cn2[C@@H]1O[C@H](CO)[C@@H](O)[C@H]1O]

The title compound was prepared according to published procedures (Nucleosides, Nucleotides, & Nucleic Acids 2004, 23(1-2), 161-170).

Preparation 45: 1-(β-D-ribofuranosyl)-1,5-dihydro-4H-imidazo[4,5-d]pyridazin-4-one

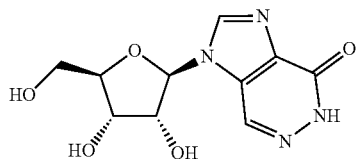 [SMILES: O=c1[nH]ncc2c1ncn2[C@@H]1O[C@H](CO)[C@@H](O)[C@H]1O]

The title compound was prepared according to published procedures (*Journal of the Chemical Society, Perkin Transactions 1: Organic and Bio-Organic Chemistry* (1972-1999), 1989 (10), 1769-1774).

Preparation 46: 2-amino-9-1(2R,3R,4S,5S)-5-fluoro-3,4-dihydroxy-5-(hydroxymethyl)tetrahydrofuran-2-yl)-1,9-dihydro-6H-purin-6-one

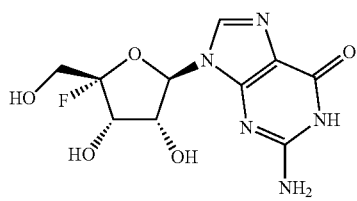 [SMILES: Nc1nc2c(ncn2[C@@H]2O[C@](F)(CO)[C@@H](O)[C@H]2O)c(=O)[nH]1]

The title compound was prepared according to published procedures (WO2014099941)

Preparation 47: 2-amino-9-((2R,3R,5S)-3-hydroxy-5-(hydroxymethyl)-4-methylenetetrahydrofuran-2-yl)-1,9-dihydro-6H-purin-6-one

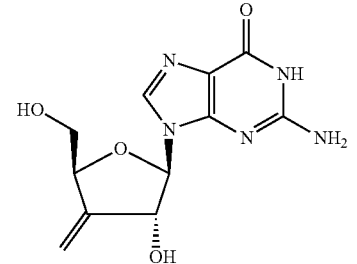 [SMILES: C=C1[C@@H](O)[C@H](n2cnc3c(=O)[nH]c(N)nc32)O[C@@H]1CO]

The title compound was prepared according to published procedures (*Journal of Medicinal Chemistry* 1992, 35, 2283-2293).

Preparation 48: (2S,3R,4S,5R)-2-(4-aminopyrrolo[2,1-f][1,2,4]triazin-7-yl)-5-(hydroxymethyl)tetrahydrofuran-3,4-diol

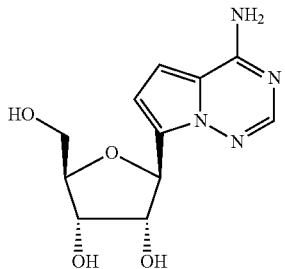 [SMILES: Nc1ncnn2c([C@@H]3O[C@H](CO)[C@@H](O)[C@H]3O)ccc12]

The title compound was prepared according to published procedures (*Tetrahedron Letters* 1994, 35(30), 5339).

The following experimental procedures detail the preparation of specific examples of the instant disclosure. The compounds of the examples are drawn in their neutral forms in the procedures and tables below. In some cases, the compounds were isolated as salts depending on the method used for their final purification and/or intrinsic molecular properties. The examples are for illustrative purposes only and are not intended to limit the scope of the instant disclosure in any way.

EXAMPLES

Example 1: (5R,7R,8R,12aR,14R,15aS,16R)-7-(2-amino-6-oxo-1,6-dihydro-9H-purin-9-yl)-14-(6-amino-9H-purin-9-yl)-16-hydroxyoctahydro-12H-5,8-methanofuro[3,2-l][1,3,6,9,11,2,10]pentaoxadiphosphacyclotetradecine-2,10-diolate 2,10-dioxide

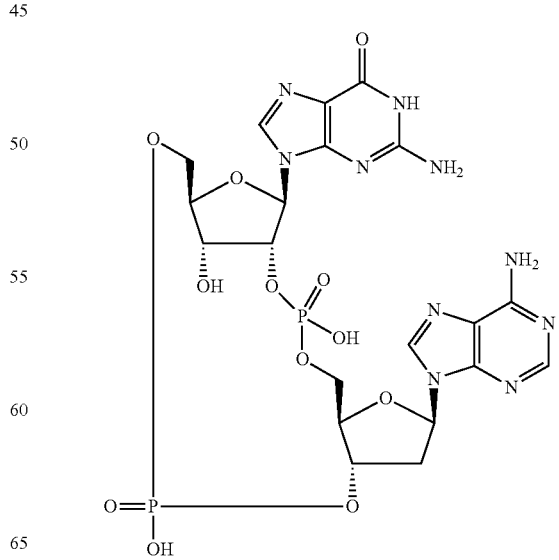

437

Step 1: (2R,3R,4R,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrofuran-3-yl (2-cyanoethyl) phosphonate

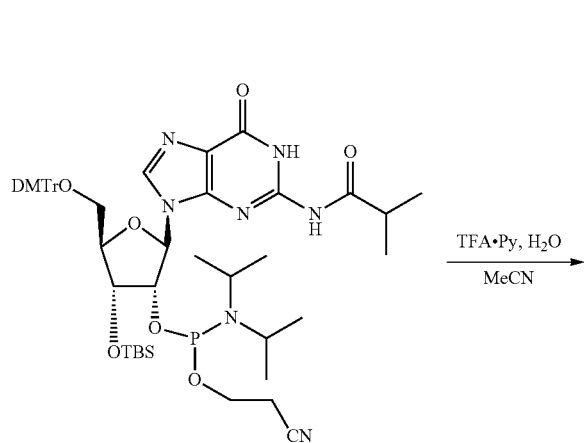

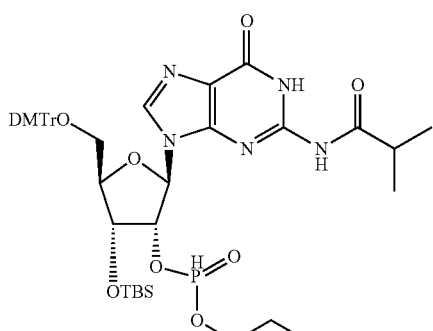

To a solution of (2R,3R,4R,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrofuran-3-yl (2-cyanoethyl) diisopropylphosphoramidite (3 g, 3.09 mmol) in ACN (15 mL) was added water (0.111 mL, 6.18 mmol) and pyridin-1-ium 2,2,2-trifluoroacetate (0.717, 3.71 mmol). The resulting mixture was stirred at RT, and the reaction progress was monitored by LCMS/TLC. After the phosphoramidite was consumed, the reaction mixture containing the product was used in the next step without purification. LCMS (ES, m/z): 887.4 [M+H]+.

438

Step 2: 2-methylpropan-2-aminium (2R,3R,4R,5R)-5-((bis(4-methoxyphenyl)(phenyl) methoxy)methyl)-4-((tert-butyldimethylsilyl)oxy)-2-(2-isobutyramido-6-oxo-1,6-dihydro-9H-purin-9-yl) tetrahydrofuran-3-yl phosphonate

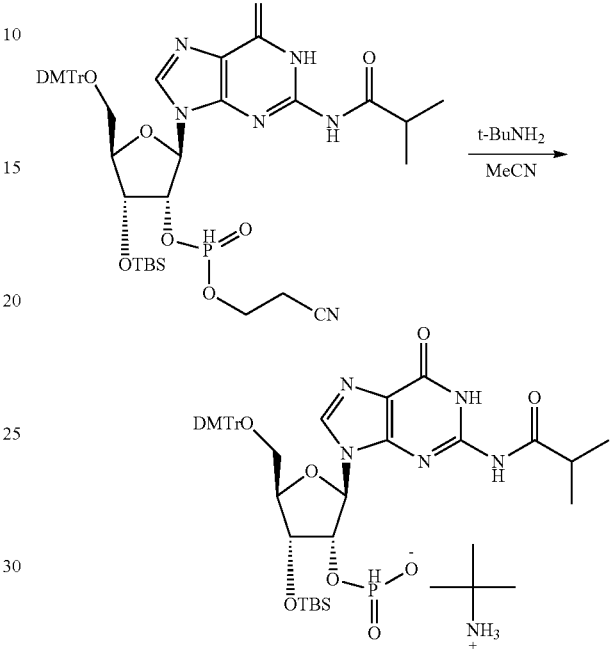

To the reaction mixture from Step 1 (assumed to contain 3.09 mmol of (2R,3S,4S,5R)-5-((bis(4-methoxyphenyl)(phenyl)methoxy)methyl)-4-(tert-butyldimethylsilyloxy)-2-(2-isobutyramido-6-oxo-1,6-dihydropurin-9-yl)-tetrahydrofuran-3-yl 2-cyanoethyl phosphonate) was added tert-butylamine (15.0 mL, 142 mmol) in one portion, and the resulting solution was stirred at rt for 40 min. It was concentrated, and the residue was co-evaporated with ACN (2×15 mL) to give the product, which was used for the next step without further purification. LCMS (ES, m/z): 832.3 [M−H]−.

Step 3: pyridin-1-ium (2R,3R,4R,5R)-4-((tert-butyldimethylsilyl)oxy)-5-(hydroxymethyl)-2-(2-isobutyramido-6-oxo-1,6-dihydro-9H-purin-9-yl)tetrahydrofuran-3-yl phosphonate

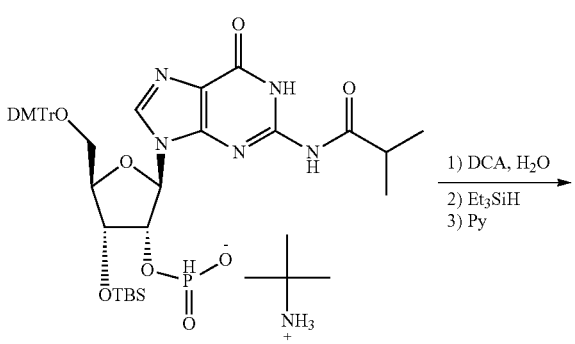

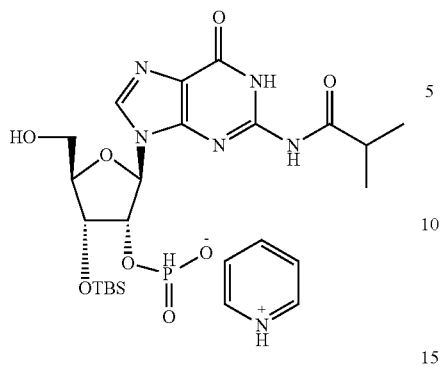

To a stirred solution of crude 2-methylpropan-2-aminium (2R,3R,4R,5R)-5-((bis(4-methoxyphenyl)(phenyl)methoxy)methyl)-4-((tert-butyldimethyl silyl)oxy)-2-(2-isobutyramido-6-oxo-1,6-dihydro-9H-purin-9-yl)tetrahydrofuran-3-yl phosphonate (~4.2 g, ~3.09 mmol, from step 2) in CH$_2$Cl$_2$ (37 mL) were added water (0.558 mL, 31.0 mmol) and dichloroacetic acid in CH$_2$Cl$_2$ (6%, 37 mL, 31.5 mmol). It was stirred for 40 min. Then, triethylsilane (60 mL) was added, and the solution was stirred for 1.5 h. Pyridine (4.5 mL) was added to the reaction. It was concentrated. The residue was triturated with MTBE (50 ml) and Hexane (50 mL), and the supernatant was decanted. This process was repeated twice. The crude mixture was kept over P$_2$O$_5$ under reduced pressure for 20 h to give a crude mixture containing the product. LCMS (ES, m/z): 532.2 [M+H]$^+$.

Step 4. (2R,3R,4R,5R)-5-((((((2R,3S,5R)-5-(6-benzamido-9H-purin-9-yl)-2-((bis(4-methoxyphenyl)(phenyl)methoxy)methyl)tetrahydrofuran-3-yl)oxy)(2-cyanoethoxy)phosphanyl)oxy)methyl)-4-((tert-butyldimethylsilyl)oxy)-2-(2-isobutyramido-6-oxo-1,6-dihydro-9H-purin-9-yl)tetrahydrofuran-3-yl phosphonate

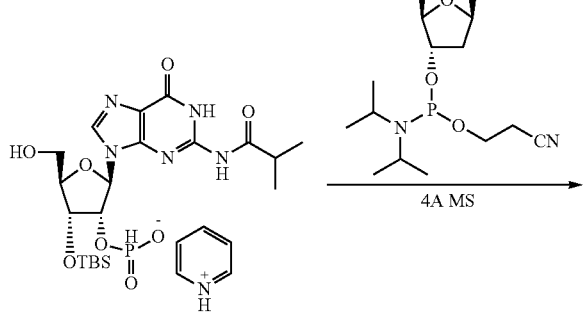

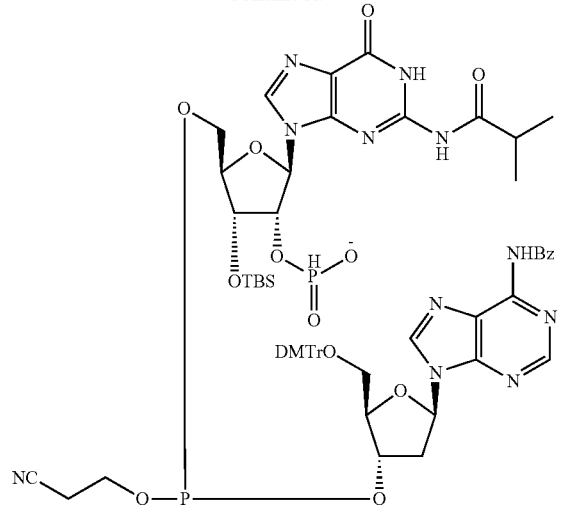

To a stirred solution of pyridin-1-ium (2R,3R,4R,5R)-4-((tert-butyldimethylsilyl)oxy)-5-(hydroxymethyl)-2-(2-isobutyramido-6-oxo-1,6-dihydro-9H-purin-9-yl)tetrahydrofuran-3-yl phosphonate (680 mg, crude, ~0.722 mmol) in ACN (5 mL) under Ar was added activated 4 Å molecular sieves (100 mg). The resulting mixture was stirred at rt over 30 min. (2R,3S,5R)-5-(6-benzamido-9H-purin-9-yl)-2-((bis(4-methoxyphenyl)(phenyl)methoxy)methyl)tetrahydrofuran-3-yl (2-cyanoethyl) diisopropylphosphoramidite (0.805 g, 0.939 mmol) was co-evaporated with ACN (3×1 mL), re-dissolved in ACN (5 mL), and dried by adding activated 4 Å molecular sieve (100 mg). After 30 min, it was added to the previously prepared mixture containing pyridin-1-ium (2R,3R,4R,5R)-4-((tert-butyldimethylsilyl)oxy)-5-(hydroxymethyl)-2-(2-isobutyramido-6-oxo-1,6-dihydro-9H-purin-9-yl)tetrahydrofuran-3-yl phosphonate. The mixture was stirred at rt for 1 h. The reaction mixture containing the product was used in the next reaction step immediately without purification. LCMS (ES, m/z): 1288.4 [M+H]$^+$.

Step 5. (2R,3R,4R,5R)-5-((((((2R,3S,5R)-5-(6-benzamido-9H-purin-9-yl)-2-((bis(4-methoxyphenyl)(phenyl)methoxy)methyl)tetrahydrofuran-3-yl)oxy)(2-cyanoethoxy)phosphoryl) oxy)methyl)-4-((tert-butyldimethylsilyl)oxy)-2-(2-isobutyramido-6-oxo-1,6-dihydro-9H-purin-9-yl)tetrahydrofuran-3-yl phosphonate

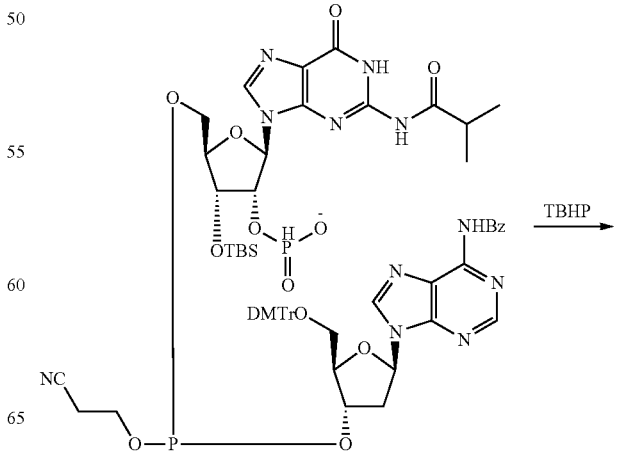

441

-continued

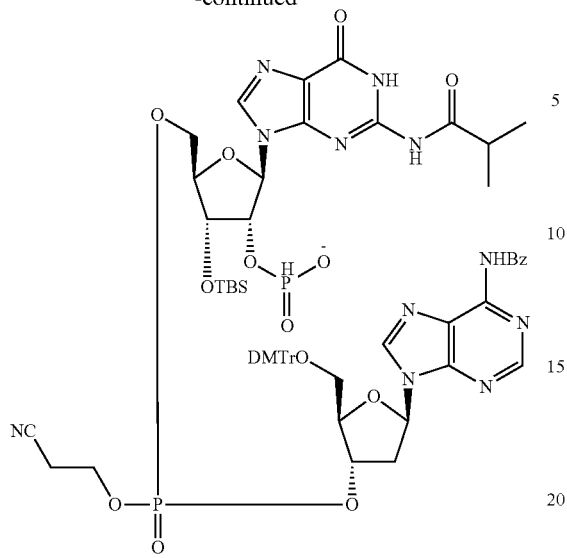

To the reaction mixture containing the crude (2R,3R,4R,5R)-5-((((((2R,3S,5R)-5-(6-benzamido-9H-purin-9-yl)-2-((bis(4-methoxyphenyl)(phenyl)methoxy)methyl)tetrahydrofuran-3-yl)oxy)(2-cyanoethoxy)phosphanyl)oxy)methyl)-4-((tert-butyldimethylsilyl)oxy)-2-(2-isobutyramido-6-oxo-1,6-dihydro-9H-purin-9-yl)tetrahydrofuran-3-yl phosphonate (~1 mmol, with excess pyridinium 2,2-dichloroacetate) was added tert-butyl hydroperoxide in decane (5.5M, 0.64 mL, 3.5 mmol) dropwise. It was stirred at rt for 1 h. Then, the solution was cooled to 0° C., and NaHSO₃ (250 mg) in water (5 mL) was added slowly. After 5 min, the mixture was concentrated, and the residue was purified by reverse phase (C18) chromatography eluted with 5 to 45% ACN in aq NH₄HCO₃ (0.04%) to give the product. LCMS (ES, m/z): 1305.6 [M+H]⁺.

Step 6. (2R,3R,4R,5R)-5-((((((2R,3S,5R)-5-(6-benzamido-9H-purin-9-yl)-2-(hydroxymethyl)tetrahydrofuran-3-yl)oxy)(2-cyanoethoxy)phosphoryl)oxy)methyl)-4-((tert-butyldimethylsilyl)oxy)-2-(2-isobutyramido-6-oxo-1,6-dihydro-9H-purin-9-yl)tetrahydrofuran-3-yl phosphonate

442

-continued

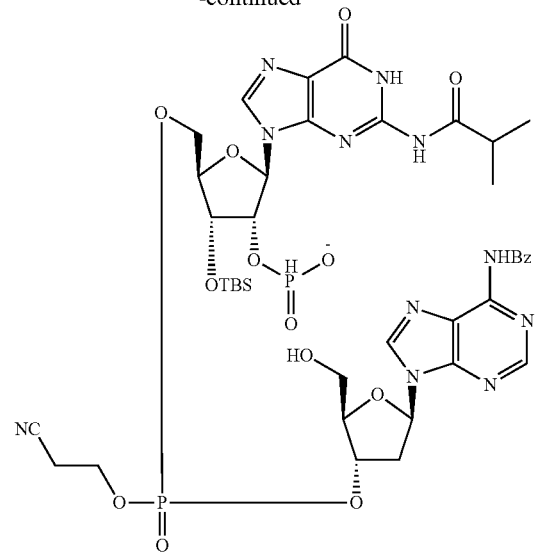

To a stirred solution of (2R,3R,4R,5R)-5-((((((2R,3S,5R)-5-(6-benzamido-9H-purin-9-yl)-2-((bis(4-methoxyphenyl)(phenyl)methoxy)methyl)tetrahydrofuran-3-yl)oxy)(2-cyanoethoxy)phosphoryl)oxy)methyl)-4-((tert-butyldimethylsilyl)oxy)-2-(2-isobutyramido-6-oxo-1,6-dihydro-9H-purin-9-yl)tetrahydrofuran-3-yl phosphonate (340 mg, 0.239 mmol) in CH₂Cl₂ (4 mL) were added water (44.5 mg, 2.468 mmol) and dichloroacetic acid (0.280 g, 2.17 mmol) in CH₂Cl₁ (5 ml). It was stirred at rt for 30 min. Et₃SiH (4 mL) was then added, and the mixture was stirred for 1.5 h. Pyridine (3 mL) was added to the reaction, and it was concentrated to give a crude product, which was used for the next step without purification. LCMS (ES, m/z): 1002.4 [M+H]⁺.

Step 7: (5R,7R,8R,12aR,14R,15aS,16R)-16-{[tert-butyl(dimethyl)silyl]oxy}-2-(2-cyanoethoxy)-7-{2-[(2-methylpropanoyl)amino]-6-oxo-1,6-dihydro-9H-purin-9-yl}-14-{6-[(phenylcarbonyl) amino]-9H-purin-9-yl}octahydro-12H-5,8-methanofuro[3,2-l][1,3,6,9,11,2,10]pentaoxadiphosphacyclotetradecin-10-olate 2-oxide

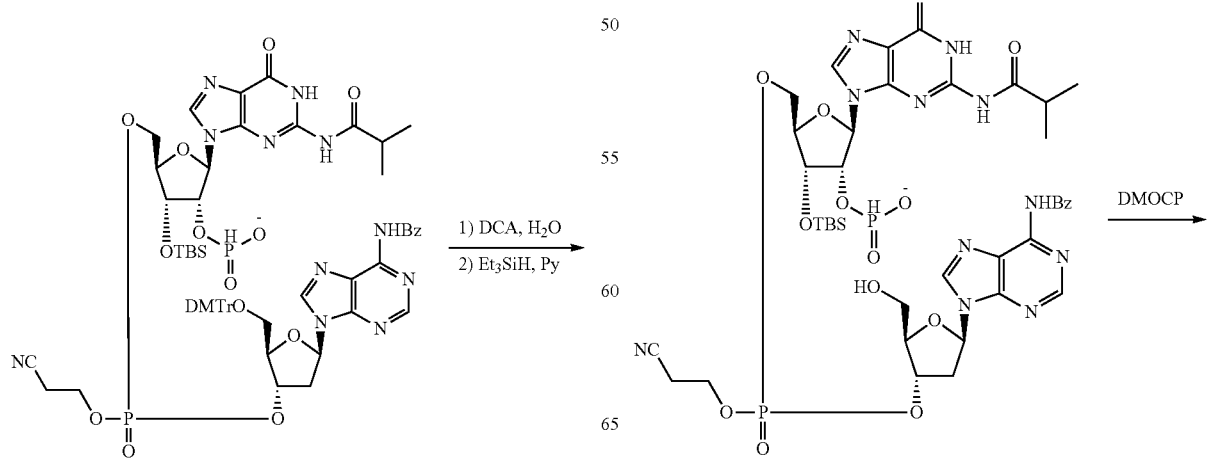

443

-continued

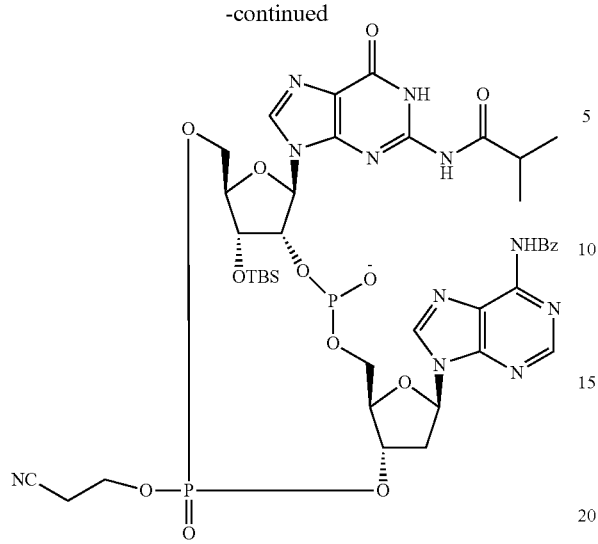

Crude (2R,3R,4R,5R)-5-((((((2R,3S,5R)-5-(6-benzamido-9H-purin-9-yl)-2-(hydroxymethyl)tetrahydrofuran-3-yl)oxy)(2-cyanoethoxy)phosphoryl)oxy)methyl)-4-((tert-butyldimethylsilyl)oxy)-2-(2-isobutyramido-6-oxo-1,6-dihydro-9H-purin-9-yl)tetrahydrofuran-3-yl phosphonate (1.5 g, ~0.24 mmol) was co-evaporated with pyridine (3×5 mL) and then re-dissolved in pyridine (4 mL). To the reaction was added 2-chloro-5,5-dimethyl-1,3,2-dioxaphosphinane 2-oxide (160 mg, 0.865 mmol) in one portion. The resulting mixture was stirred at rt for 1 h. It was used for the next reaction step directly without purification. LCMS (ES, m/z): 984.3 [M+H]⁺.

Step 8. (5R,7R,8R,12aR,14R,15aS,16R)-16-{[tert-butyl(dimethyl)silyl]oxy}-2-(2-cyanoethoxy)-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10]pentaoxadiphosphacyclotetradecin-10-olate 2,10-dioxide

444

-continued

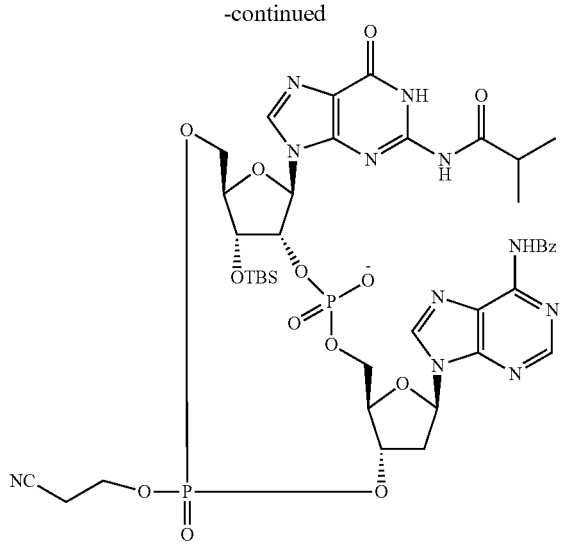

To the stirred mixture containing (5R,8R,12aR,14R,15aS,16R)-16-{[tert-butyl(dimethyl)silyl]oxy}-2-(2-cyanoethoxy)-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10]pentaoxadiphosphacyclotetradecin-10-olate 2-oxide was added water (156 mg, 8.65 mmol) and iodine (81 mg, 0.321 mmol). After 10 min, the mixture was poured into a solution of NaHSO₃ (52 mg) in water (36 ml), and it was stirred for 5 min. It was cooled to 0° C., and NaHCO₃ (1.04 g) was slowly added. After 5 min, EtOAc (50 mL) and Et₂O (50 ml) were added. Layers were separated, and the aq layer was extracted with EtOAc (1×30 ml). The organic layers were combined, concentrated, and purified by silica gel column chromatography eluted with 0-20% MeOH in CH₂Cl₂ to give the product. LCMS (ES, m/z): 998.3 [M+H]⁺.

Step 9. (5R,7R,8R,12aR,14R,15aS,16R)-16-{[tert-butyl(dimethyl)silyl]oxy}-7-{2-[(2-methylpropanoyl)amino]-6-oxo-1,6-dihydro-9H-purin-9-yl}-14-{6-[(phenylcarbonyl)amino-9H-purin-9-yl}octahydro-12H-5,8-methanofuro 3,2-l][1,3,6,9,11,2,10]pentaoxadiphosphacyclotetradecine-2,10-diolate 2,10-dioxide

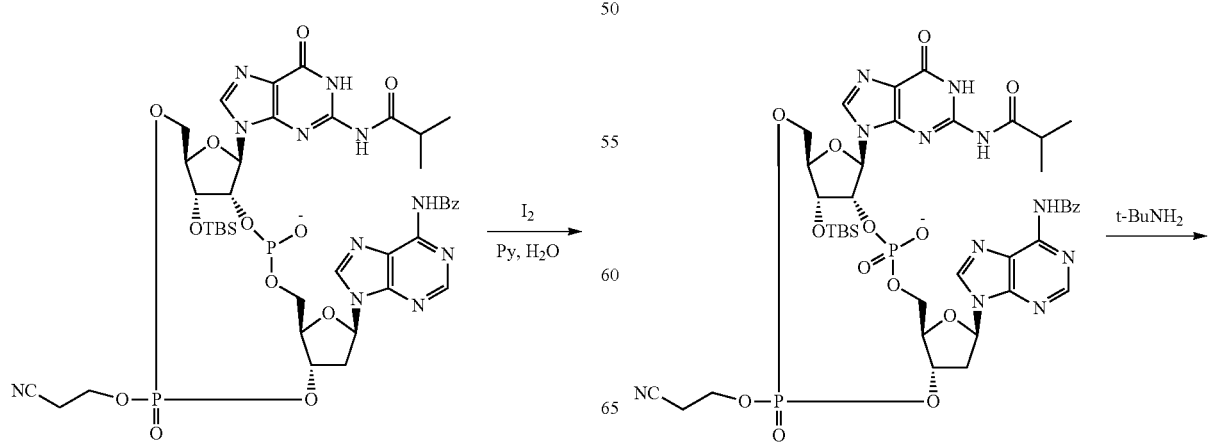

445

-continued

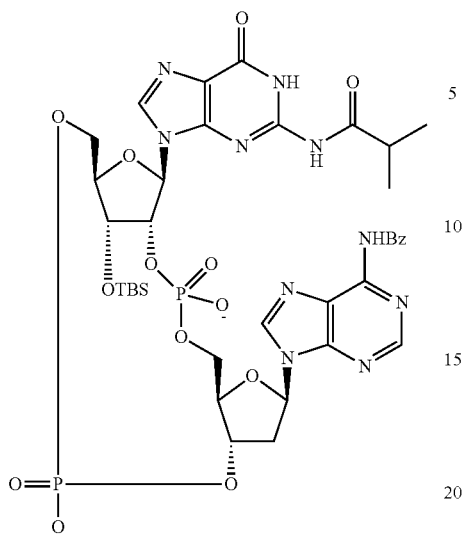

To a stirred solution of (5R,7R,8R,12aR,14R,15aS,16R)-16-{[tert-butyl(dimethyl)silyl]oxy}-2-(2-cyanoethoxy)-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10]pentaoxadiphosphacyclotetradecin-10-olate 2,10-dioxide (160 mg) in ACN (2 mL) was added tert-butylamine (2 mL) at rt. After 30 min, it was concentrated to give the crude product, which was used for the next step without purification. LCMS (ES, m/z): 945.2 [M+H]$^+$.

Step 10: (5R,7R,8R,12aR,14R,15aS,16R)-7-(2-amino-6-oxo-1,6-dihydro-9H-purin-9-yl)-14-(6-amino-9H-purin-9-yl)-16-{[tert-butyl(dimethyl)silyl]oxy}octahydro-12H-5,8-methanofuro[3,2-l][1,3,6,9,11,2,10]pentaoxadiphosphacyclotetradecine-2,10-diolate 2,10-dioxide

446

-continued

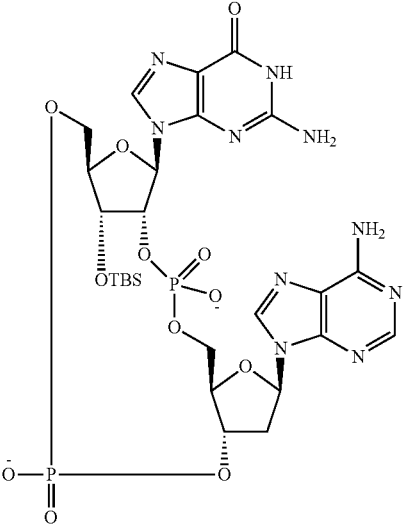

Crude (5R,7R,8R,12aR,14R,15aS,16R)-16-{[tert-butyl(dimethyl)silyl]oxy}-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10]pentaoxadiphosphacyclotetradecine-2,10-diolate 2,10-dioxide (220 mg) was dissolved in a solution of MeNH$_2$ in EtOH (30%, 4 mL), and it was stirred at rt for 5 h. Then, the volatile component was removed under reduced pressure to give a crude product, which was used for the next reaction step without purification. LCMS (ES, m/z): 773.2 [M+H]$^+$ and 771.3 [M−H]$^−$.

Step 11: (5R,7R,8R,12aR,14R,15aS,16R)-7-(2-amino-6-oxo-1,6-dihydro-9H-purin-9-yl)-14-(6-amino-9H-purin-9-yl)-16-hydroxyoctahydro-12H-5,8-methanofuro[3,2-l][1,3,6,9,11,2,10]pentaoxadiphosphacyclotetradecine-2,10-diolate 2,10-dioxide

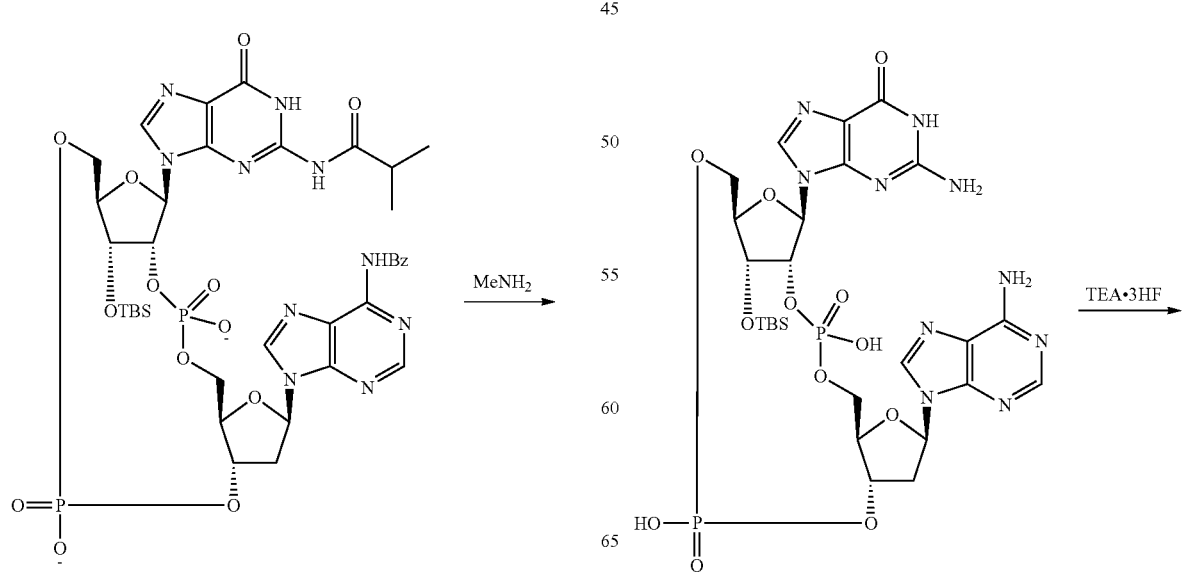

-continued

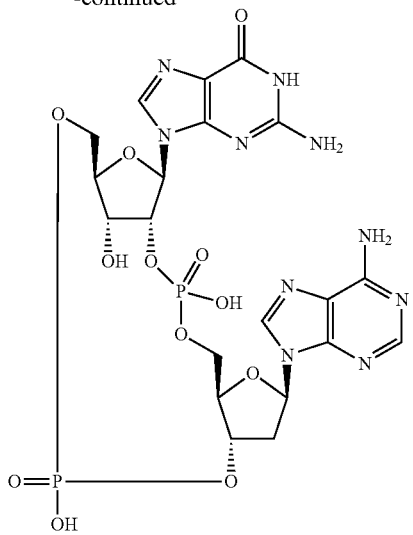

The crude from Step 10 was co-evaporated with pyridine (2.5 ml) and Et$_3$N (2.5 mL) three times. It was dissolved in pyridine (2 mL). To the solution was added Et$_3$N (1.51 g, 14.9 mmol) and triethylamine trihydrofluoride (1.2 g, 7.45 mmol) dropwise. The mixture was heated at 50° C. for 5 h. Then, it was concentrated and purified by preparative-HPLC (T3 Prep Column, 100 Å, 5 μm, 19 mm×250 mm) eluted with 0 to 10% ACN in aq NH$_4$HCO$_3$ (50 mM) to give the product. LCMS (ES, m/z): 657.1 [M−H]$^-$. $^1$H-NMR: (300 MHz, DMSO-d$_6$+D$_2$O): δ 8.35 (s, 1H), 8.16 (s, 1H), 8.03 (s, 1H), 6.34 (dd, J=8.8, 5.9 Hz, 1H), 5.85 (d, J=8.3 Hz, 1H), 5.12-4.98 (m, 2H), 4.36 (d, J=3.9 Hz, 1H), 4.22 (t, J=7.2 Hz, 1H), 4.09 (s, 1H), 3.96-3.79 (m, 4H), 3.09-2.99 (m, 1H), 2.64-2.51 (m, 1H). $^{31}$P-NMR: (121 MHz, DMSO-d$_6$+D$_2$O): δ −1.65 (s), −2.36 (s).

Examples 2 through 19, shown in Table 1 below, were prepared according to procedures analogous to those outlined in Example 1 above using the appropriate nucleoside monomers, described as Preparations or as obtained from commercial sources.

TABLE 1

| Ex. | Structure | Name | Mass [M − H]$^-$ |
|---|---|---|---|
| 2 | 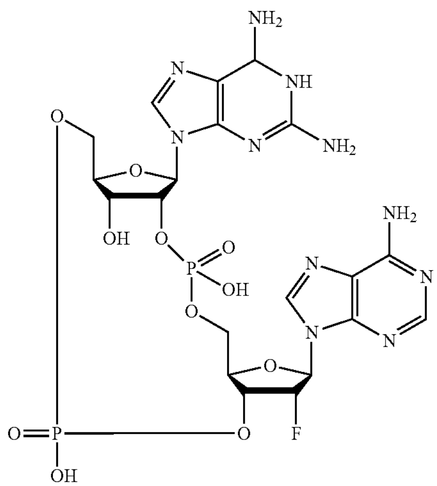 | (5R,7R,8R,12aR,14R,15R,15aR,16R)-7-(2-amino-6-oxo-1,6-dihydro-9H-purin-9-yl)-14-(6-amino-9H-purin-9-yl)-15-fluoro-16-hydroxyoctahydro-12H-5,8-methanofuro[3,2-l][1,3,6,9,11,2,10]pentaoxadiphosphacyclotetradecine-2,10-diolate 2,10-dioxide | 675 |
| 3 | 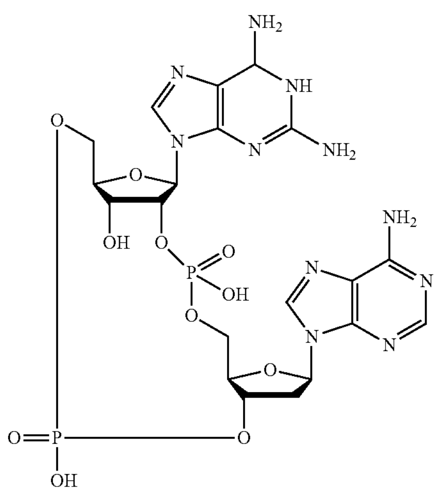 | (5R,7R,8R,12aR,14R,15aS,16R)-7,14-bis(6-amino-9H-purin-9-yl)-16-hydroxyoctahydro-12H-5,8-methanofuro[3,2-l][1,3,6,9,11,2,10]pentaoxadiphosphacyclotetradecine-2,10-diolate 2,10-dioxide | 657 |

TABLE 1-continued

| Ex. | Structure | Name | Mass [M − H]⁻ |
|---|---|---|---|
| 4 | 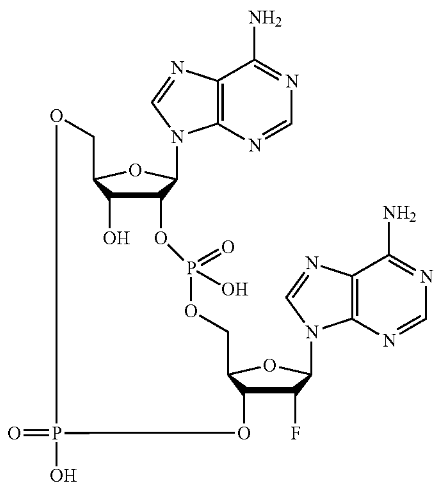 | (5R,7R,8R,12aR,14R,15R,15aR,16R)-7,14-bis(6-amino-9H-purin-9-yl)-15-fluoro-16-hydroxyoctahydro-12H-5,8-methanofuro[3,2-l][1,3,6,9,11,2,10]pentaoxadiphosphacyclotetradecine-2,10-diolate 2,10-dioxide | 659 |
| 5 | 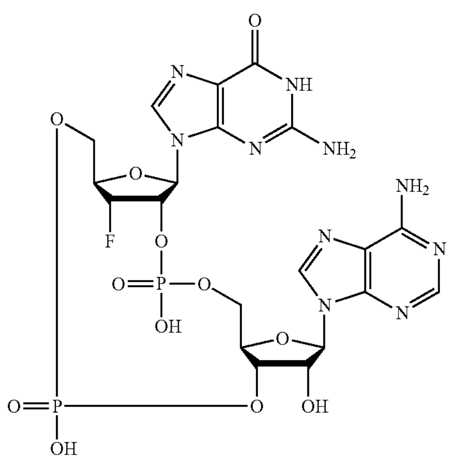 | (5R,7R,8S,12aR,14R,15R,15aS,16R)-7-(2-amino-6-oxo-1,6-dihydro-9H-purin-9-yl)-14-(6-amino-9H-purin-9-yl)-16-fluoro-15-hydroxyoctahydro-12H-5,8-methanofuro[3,2-l][1,3,6,9,11,2,10]pentaoxadiphosphacyclotetradecine-2,10-diolate 2,10-dioxide | 675 |
| 6 | 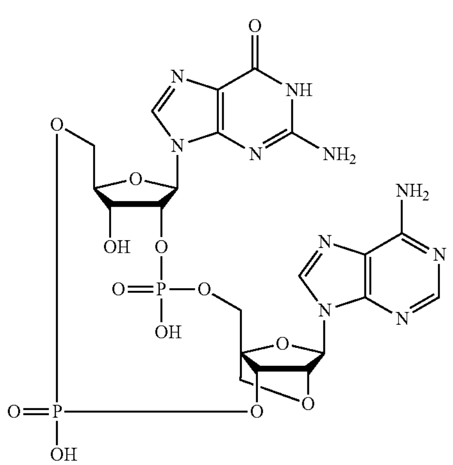 | (5R,7R,8R,12aR,14R,15R,15aS,18R)-7-(2-amino-6-oxo-1,6-dihydro-9H-purin-9-yl)-14-(6-amino-9H-purin-9-yl)-18-hydroxyhexahydro-14H-15,12a-(epoxymethano)-5,8-methanofuro[3,2-l][1,3,6,9,11,2,10]pentaoxadiphosphacyclotetradecine-2,10(12H)-diolate 2,10-dioxide | 685 |

TABLE 1-continued

| Ex. | Structure | Name | Mass [M − H]⁻ |
|---|---|---|---|
| 7 | 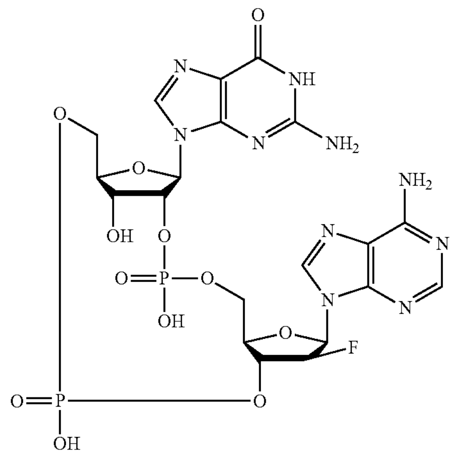 | (5R,7R,8R,12aR,14R,15S,15aR,16R)-7-(2-amino-6-oxo-1,6-dihydro-9H-purin-9-yl)-14-(6-amino-9H-purin-9-yl)-15-fluoro-16-hydroxyoctahydro-12H-5,8-methanofuro[3,2-l][1,3,6,9,11,2,10]pentaoxadiphosphacyclotetradecine-2,10-diolate 2,10-dioxide | 675 |
| 8 | 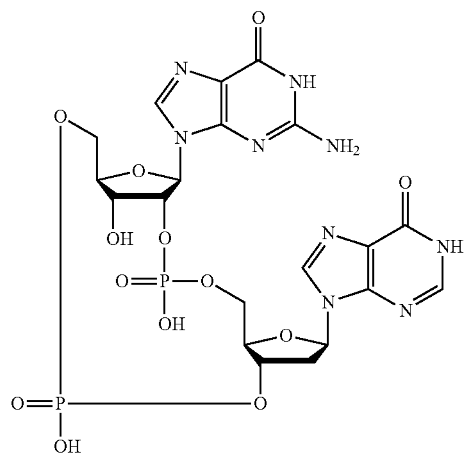 | (5R,7R,8R,12aR,14R,15aS,16R)-7-(2-amino-6-oxo-1,6-dihydro-9H-purin-9-yl)-16-hydroxy-14-(6-oxo-1,6-dihydro-9H-purin-9-yl)octahydro-12H-5,8-methanofuro[3,2-l][1,3,6,9,11,2,10]pentaoxadiphosphacyclotetradecine-2,10-diolate 2,10-dioxide | 660 [M + H]⁺ |
| 9 | 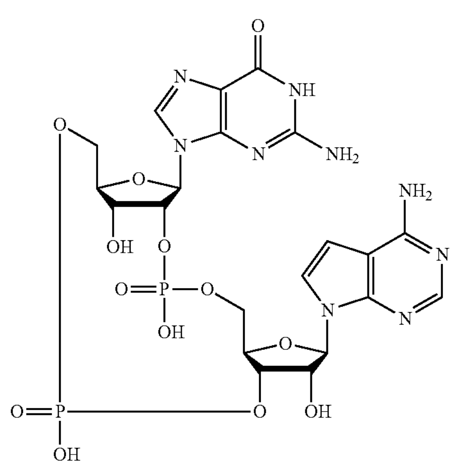 | (5R,7R,8R,12aR,14R,15R,15aS,16R)-7-(2-amino-6-oxo-1,6-dihydro-9H-purin-9-yl)-14-(4-amino-7H-pyrrolo[2,3-d]pyrimidin-7-yl)-15,16-dihydroxyoctahydro-12H-5,8-methanofuro[3,2-l][1,3,6,9,11,2,10]pentaoxadiphosphacyclotetradecine-2,10-diolate 2,10-dioxide | 672 |

TABLE 1-continued

| Ex. | Structure | Name | Mass [M − H]⁻ |
|---|---|---|---|
| 10 | 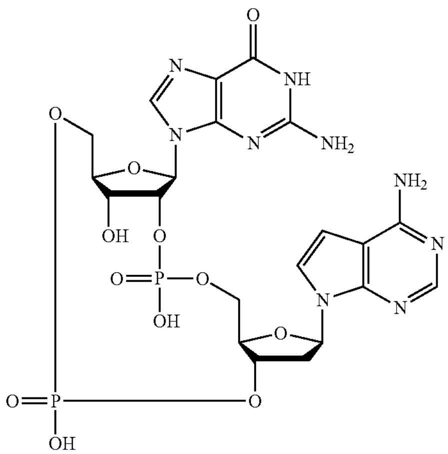 | (5R,7R,8R,12aR,14R,15R,15aS,16R)-7-(2-amino-6-oxo-1,6-dihydro-9H-purin-9-yl)-14-(4-amino-7H-pyrrolo[2,3-d]pyrimidin-7-yl)-16-hydroxyoctahydro-12H-5,8-methanofuro[3,2-l][1,3,6,9,11,2,10]pentaoxadiphosphacyclotetradecine-2,10-diolate 2,10-dioxide | 656 |
| 11 | 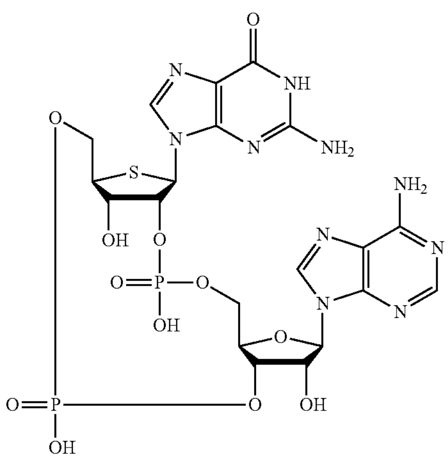 | (5R,7R,8R,12aR,14R,15R,15aS,16S)-7-(2-amino-6-oxo-1,6-dihydro-9H-purin-9-yl)-14-(6-amino-9H-purin-9-yl)-15,16-dihydroxyoctahydro-12H-5,8-methanofuro[3,2-l][1,3,9,11,6,2,10]tetraoxathiadiphosphacyclotetradecine-2,10-diolate 2,10-dioxide | 689 |
| 12 | 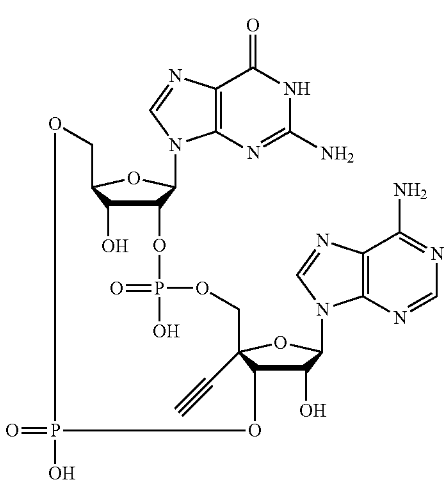 | (5R,7R,8R,12aR,14R,15R,15aS,16R)-7-(2-amino-6-oxo-1,6-dihydro-9H-purin-9-yl)-14-(6-amino-9H-purin-9-yl)-12a-ethynyl-15,16-dihydroxyoctahydro-12H-5,8-methanofuro[3,2-l][1,3,6,9,11,2,10]pentaoxadiphosphacyclotetradecine-2,10-diolate 2,10-dioxide | 699 [M + H]⁺ |

TABLE 1-continued

| Ex. | Structure | Name | Mass [M − H]⁻ |
|---|---|---|---|
| 13 | 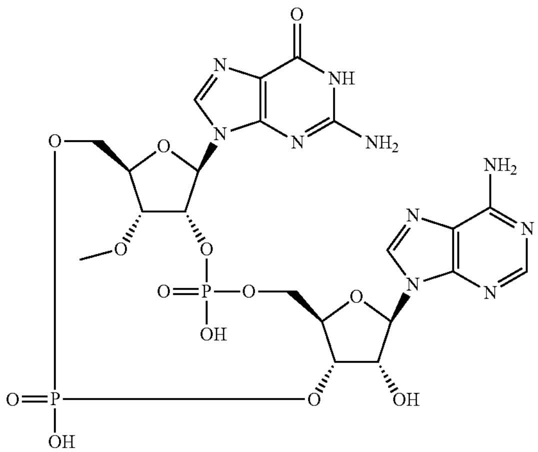 [SMILES: CO[C@H]1[C@H]2OP(=O)(O)OC[C@H]3O[C@@H](n4cnc5c(N)ncnc54)[C@H](O)[C@@H]3OP(=O)(O)OC[C@H]1O[C@H]2n1cnc2c(=O)[nH]c(N)nc21] | 2-amino-9-[(5R,7R,8R,12aR,14R,15R,15aS,16R)-14-(6-amino-9H-purin-9-yl)-2,10,15-trihydroxy-16-methoxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 687 |
| 14 | 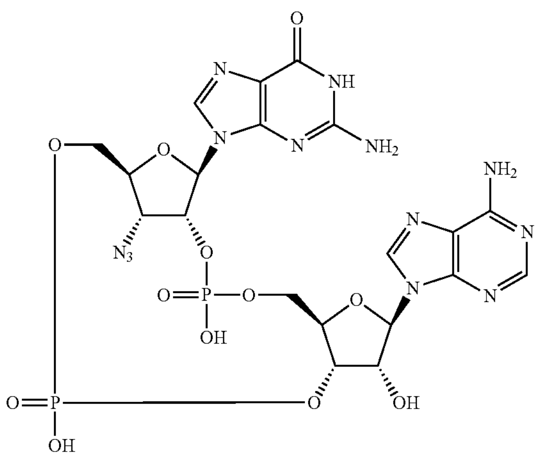 [SMILES: [N-]=[N+]=N[C@H]1[C@H]2OP(=O)(O)OC[C@H]3O[C@@H](n4cnc5c(N)ncnc54)[C@H](O)[C@@H]3OP(=O)(O)OC[C@H]1O[C@H]2n1cnc2c(=O)[nH]c(N)nc21] | 2-amino-9-[(5S,7R,8R,12aR,14R,15R,15aS,16R)-14-(6-amino-9H-purin-9-yl)-16-azido-2,10,15-trihydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 698 |
| 15 | 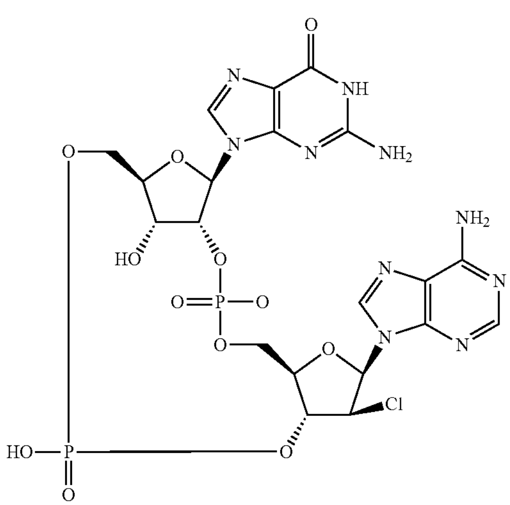 [SMILES: Nc1nc2c(ncn2[C@@H]2O[C@@H]3COP(=O)(O)O[C@H]4[C@H](Cl)[C@H](n5cnc6c(N)ncnc65)O[C@@H]4COP(=O)(O)O[C@@H]2[C@@H]3O)c(=O)[nH]1] | 2-amino-9-[(5R,7R,8R,12aR,14R,15S,15aR,16R)-14-(6-amino-9H-purin-9-yl)-15-chloro-2,10,16-trihydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 691 |

TABLE 1-continued

| Ex. | Structure | Name | Mass [M − H]⁻ |
|---|---|---|---|
| 16 | 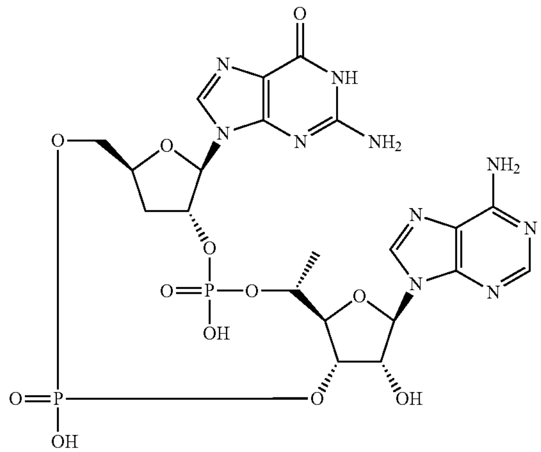 [SMILES: C[C@H]1OP(=O)(O)O[C@@H]2C[C@@H](COP(=O)(O)O[C@H]3[C@@H](O)[C@H](n4cnc5c(N)ncnc54)O[C@@H]31)O[C@H]2n1cnc2c(=O)[nH]c(N)nc21] | 2-amino-9-[(5S,7R,8R,12R,12aR,14R,15R,15aS)-14-(6-amino-9H-purin-9-yl)-2,10,15-trihydroxy-12-methyl-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 671 |
| 17 | 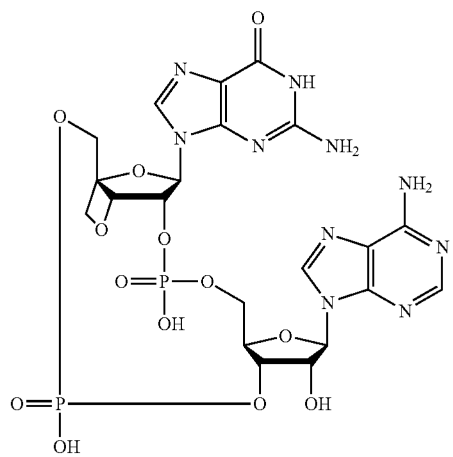 | 2-amino-9-[(2aR,5S,6aS,7R,8R,9aR,12S,14R,14aS,15R)-8-(6-amino-9H-purin-9-yl)-5,7,12-trihydroxy-5,12-dioxidohexahydro-6aH-2a,14-(epoxymethano)furo[3,2-d]oxeto[2,3-k][1,3,7,9,2,8]tetraoxadiphosphacyclotridecin-15(2H,3H)-yl]-1,9-dihydro-6H-purin-6-one | 685 |
| 18 | 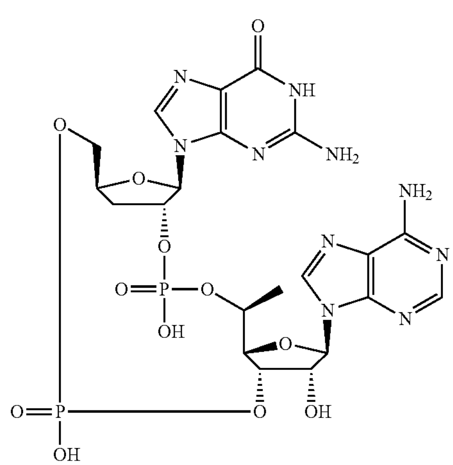 [SMILES: C[C@@H]1OP(=O)(O)O[C@@H]2C[C@@H](COP(=O)(O)O[C@H]3[C@@H](O)[C@H](n4cnc5c(N)ncnc54)O[C@H]31)O[C@H]2n1cnc2c(=O)[nH]c(N)nc21] | 2-amino-9-[(5S,7R,8R,12S,12aS,14R,15R,15aS)-14-(6-amino-9H-purin-9-yl)-2,10,15-trihydroxy-12-methyl-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 671 |

| Ex. | Structure | Name | Mass [M − H]⁻ |
|---|---|---|---|
| 19 | 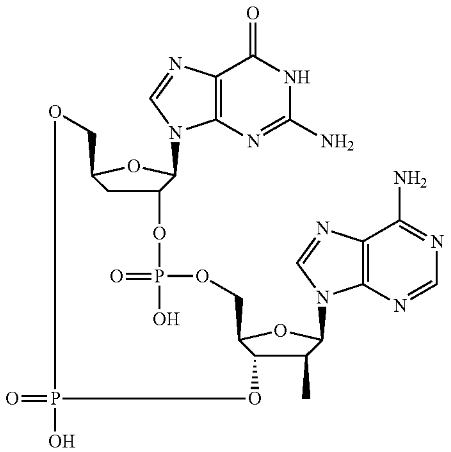 [SMILES: C[C@H]1[C@@H]2OP(=O)(O)OC[C@@H]3CC(OP(=O)(O)OC[C@H]2O[C@H]1n1cnc2c(N)ncnc21)[C@H](n1cnc2c(=O)[nH]c(N)nc21)O3] | 2-amino-9-[(5S,7R,8R,12aR,14R,15S,15aS)-14-(6-amino-9H-purin-9-yl)-2,10-dihydroxy-15-methyl-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 655 |

Example 20: (5R,7R,8S,12aR,14R,15R,15aS,18R)-7-(2-amino-6-oxo-1,6-dihydro-9H-purin-9-yl)-14-(6-amino-9H-purin-9-yl)-18-fluorohexahydro-14H-15,12a-(enoxymethano)-5,8-methanofuro[3,2-l][1,3,6,9,11,2,10]pentaoxadiphosphacyclotetradecine-2,10 (12H)-diolate

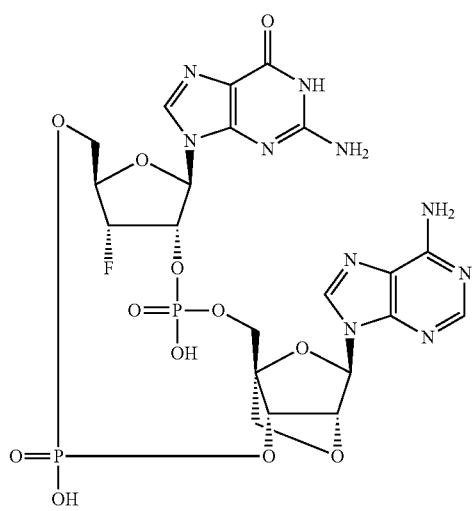 [SMILES: Nc1nc2c(ncn2[C@@H]2O[C@@H]3COP(=O)(O)O[C@H]4[C@H]5OC[C@]4(COP(=O)(O)O[C@@H]2[C@@H]3F)O[C@H]5n2cnc3c(N)ncnc32)c(=O)[nH]1]

Step 1. (2R,3S,4R,5R)-5-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl phenyl phosphonate

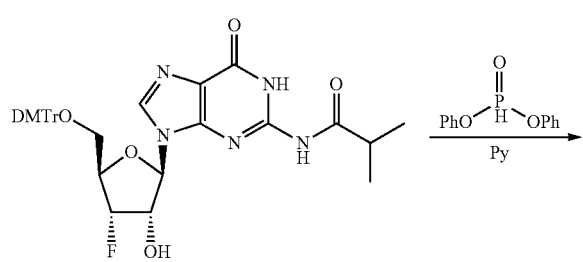

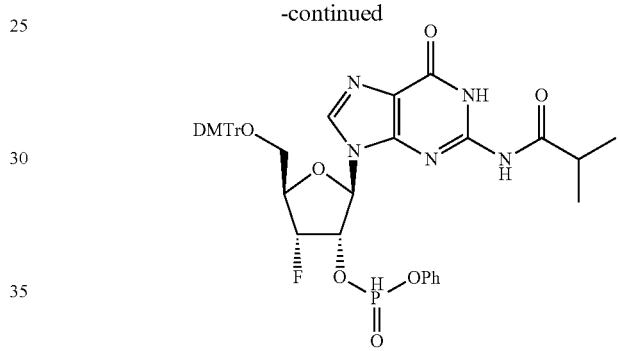

To a stirred solution of N-(9-((2R,3S,4S,5R)-5-((bis(4-methoxyphenyl)(phenyl)methoxy) methyl)-4-fluoro-3-hydroxytetrahydrofuran-2-yl)-6-oxo-6,9-dihydro-1H-purin-2-yl)isobutyramide (1 g, 1.520 mmol) in pyridine (7.6 mL) under Ar was added diphenyl phosphonate (1.068 g, 4.56 mmol), and it was stirred at rt for 20 min. The reaction mixture containing the product was used for the next reaction step without purification.

Step 2. (2R,3,4R,5R)-5-((bis(4-m ethoxyphenyl)(phenyl)methoxy)methyl)-4-fluoro-2-(2-isobutyramido-6-oxo-1,6-dihydro-9H-purin-9-yl)tetrahydrofuran-3-yl phosphonate

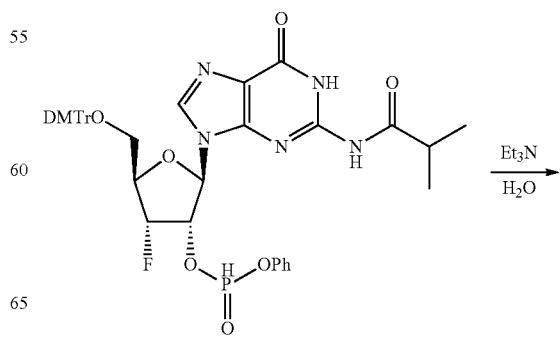

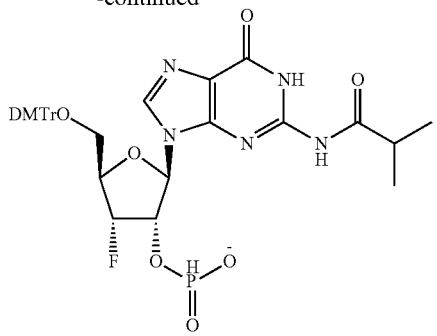

To the reaction mixture from Step 1 was added water (1.5 ml) and Et₃N (1.5 mL). The mixture was stirred at rt for 20 min. Then, it was concentrated, and the residue was partitioned between CH₂Cl₂ (50 mL) and aq NaHCO₃ (5%, 20 mL). Layers were separated. The organic layer was washed with aq NaHCO₃ (5%, 2×20 mL), dried (Na₂SO₄), concentrated and purified by silica gel column chromatography using 0 to 7% MeOH in CH₂Cl₂ (1% Et₃N) to give the product. LCMS (ES, m/z): 722 [M+H]⁺. ³¹P-NMR: (162 MHz, CD₃OD): δ 2.73 (s, 1P).

Step 3. (2R,3S,4R,5R)-4-fluoro-5-(hydroxymethyl)-2-(2-isobutyramido-6-oxo-1,6-dihydro-9H-purin-9-yl)tetrahydrofuran-3-yl phosphonate

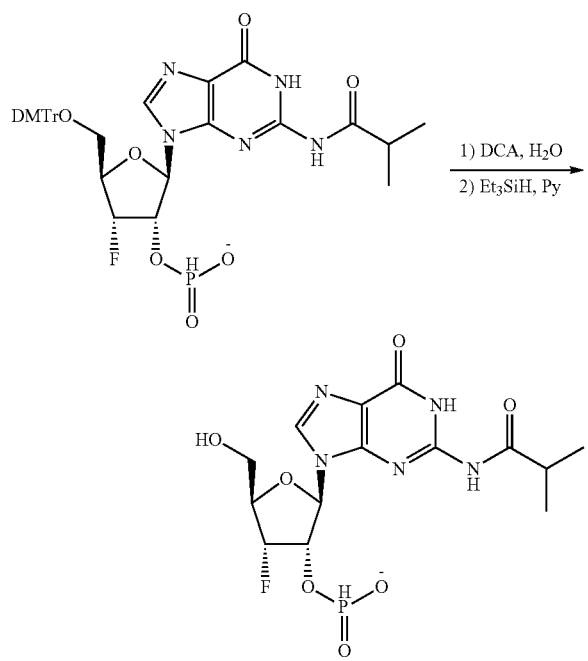

To a stirred solution of the product of Step 2 (0.9 g, 0.999 mmol) in CH₂Cl₂ (6 mL) were added water (0.180 g, 9.99 mmol) and 2,2-dichloroacetic acid (1.16 g, 8.99 mmol) in CH₂Cl₂ (10 ml). The mixture was stirred at rt for 15 min. Et₃SiH (10 mL) was added, and it was stirred for 1 h. Then, pyridine (2 mL) was added, and it was concentrated. The residue was purified by reverse phase (C18) chromatography eluted with 0 to 30% ACN in aq NH₄HCO₃ (0.04%) to give the product. LCMS (ES, m/z): 722 [M−H]⁻. 417.9.

¹H-NMR: (400 MHz, CD₃OD): δ 8.31 (s, 1H), 7.49 (d, J=1.6 Hz, 0.5H), 6.15 (d, J=6.8 Hz, 1H), 5.91 (d, J=1.6 Hz, 0.5H), 5.42-5.32 (m, 1.5H), 5.21 (dd, J=4.5, 1.9 Hz, 0.5H), 4.45-4.32 (m, 1H), 3.81 (d, J=3.5 Hz, 2H), 3.20 (q, J=7.4 Hz, 1H), 2.73 (p, J=6.9 Hz, 1H), 1.30 (t, J=7.3 Hz, 1.5H), 1.23 (d, J=6.9 Hz, 6H). ¹⁹F-NMR: (376 MHz, CD₃OD): δ −200.96 (s, 1F). ³¹P-NMR: (162 MHz, CD₃OD): δ 2.41 (s, 1P).

Step 4: (2R,3S,4R,5R)-5-((((((1R,3R,4R,7S)-3-(6-benzamido-9H-purin-9-yl)-1-((bis(4-methoxyphenyl)(phenyl)methoxy)methyl)-2,5-dioxabicyclo[2.2.1]heptan-7-yl)oxy)(2-cyanoethoxy)phosphanyl)oxy)methyl)-4-fluoro-2-(2-isobutyramido-6-oxo-1,6-dihydro-9H-purin-9-yl)tetrahydrofuran-3-yl phosphonate

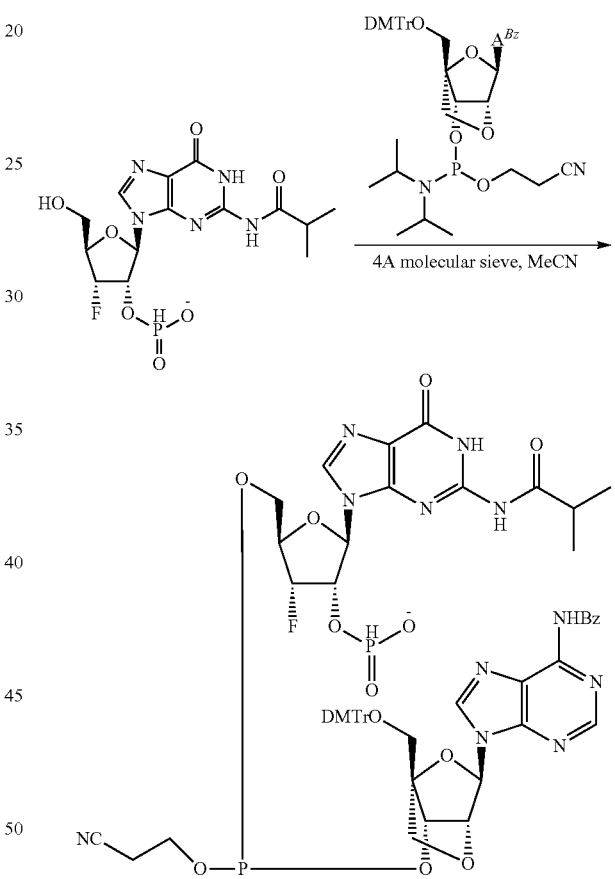

(2R,3S,4R,5R)-4-fluoro-5-(hydroxymethyl)-2-(2-isobutyramido-6-oxo-1,6-dihydro-9H-purin-9-yl)tetrahydrofuran-3-yl phosphonate (600 mg, 0.676 mmol) was co-evaporated with ACN (3×5 mL), re-dissolved in ACN (3 mL), dried by addition of activated 4 Å molecular sieves (150 mg) and kept under Ar. (1R,3R,4R,7S)-3-(6-benzamido-9H-purin-9-yl)-1-((bis(4-methoxyphenyl)(phenyl)methoxy)methyl)-2,5-dioxabicyclo[2.2.1]heptan-7-yl (2-cyanoethyl) diisopropylphosphoramidite (available from Exiqon (EQ-0063-1000), 235.5 mg, 0.56 mmol) and pyridinium 2,2,2-trifluoroacetate (162 mg, 0.84 mmol) were co-evaporated with ACN (3×5 mL), re-dissolved in ACN (5 mL), and dried by addition activated 4 Å molecular sieve (150 mg). After 30 min, it was added to the previously prepared mixture containing (2R,3S,4R,5R)-4-fluoro-5-(hydroxymethyl)-2-(2-isobutyramido-6-oxo-1,6-dihydro-9H-purin-9-yl)tetrahydrofuran-3-yl phosphonate. The mixture was stirred at rt for 1 h. The reaction mixture containing the product was used in the next reaction step immediately without purification. LCMS (ES, m/z): 1202.3 [M−H]⁻.

Step 5. (2R,3S,4R,5R)-5-((((((R,3R,4R,7S)-3-(6-benzamido-9H-purin-9-yl)-1-((bis(4-methoxyphenyl)(phenyl)methoxy)methyl)-2,5-dioxabicyclo[2.2.1]heptan-7-yl)oxy)(2-cyanoethoxy)phosphoryl)oxy)methyl)-4-fluoro-2-(2-isobutyramido-6-oxo-1,6-dihydro-9H-purin-9-yl)tetrahydrofuran-3-yl phosphonate

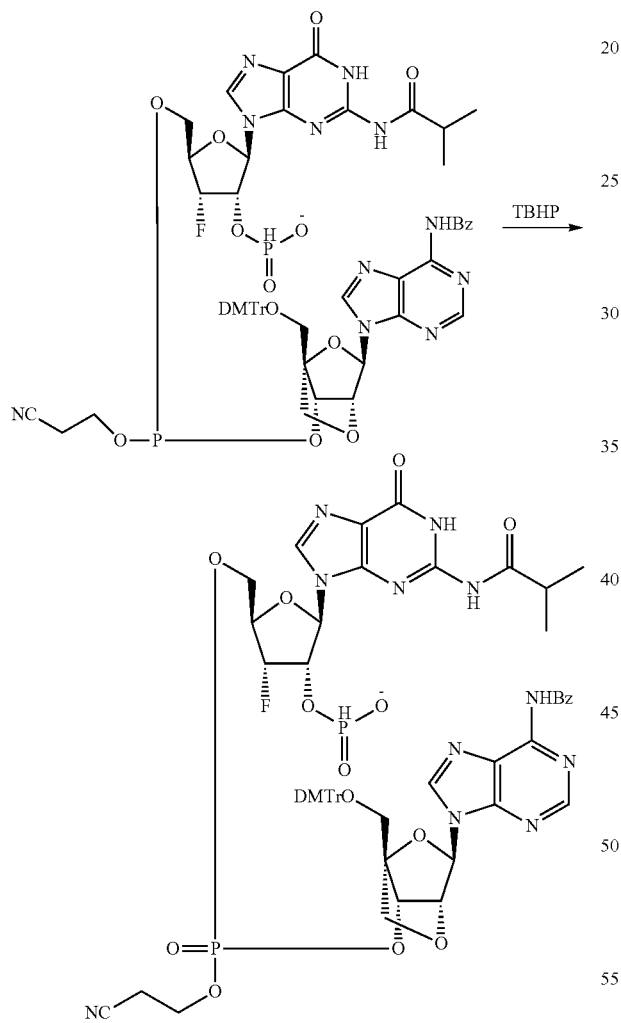

To the stirred reaction mixture from Step 4 was added tert-butyl hydroperoxide in decane (5.5M, 0.31 mL, 1.71 mmol) dropwise. The resulting mixture was stirred at rt for 1 h. After 30 min, the solution was cooled to 0° C., and NaHSO₃ (150 mg) in water (5 mL) was added slowly. After 5 min, the mixture was concentrated, and the residue was purified by reverse phase (C18) chromatography eluted with 0 to 75% ACN in aq NH₄HCO₃ (5 mM) to give the product. LCMS (ES, m/z): 1220.1 [M+H]⁺. ¹⁹F-NMR (376 MHz, CD₃OD): δ −200.38, −202.45 (2s, 1F). ³¹P-NMR: (162 MHz, CD₃OD): δ 2.57, 2.49 (2s, 1P); −3.52, −4.21 (2s, 1P).

Step 6. (2R,3S,4R,5R)-5-((((((S,3R,4R,7S)-3-(6-benzamido-9H-purin-9-yl)-1-(hydroxymethyl)-2,5-dioxabicyclo[2.2.1]heptan-7-yl)oxy)(2-cyanoethoxy)phosphoryl)oxy)methyl)-4-fluoro-2-(2-isobutyramido-6-oxo-1,6-dihydro-9H-purin-9-yl)tetrahydrofuran-3-yl phosphonate

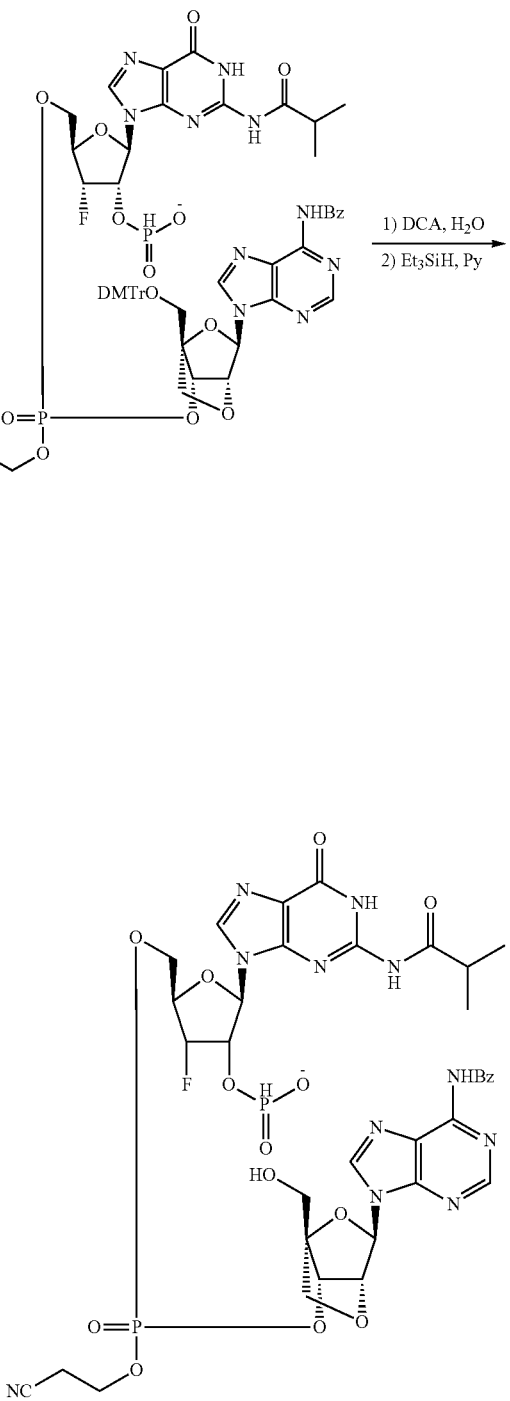

To a solution of (2R,3S,4R,5R)-5-((((((1R,3R,4R,7S)-3-(6-benzamido-9H-purin-9-yl)-1-((bis(4-methoxyphenyl)(phenyl)methoxy)methyl)-2,5-dioxabicyclo[2.2.1]heptan-7-yl)oxy)(2-cyanoethoxy)phosphoryl)oxy)methyl)-4-fluoro-2-(2-isobutyramido-6-oxo-1,6-dihydro-9H-purin-9-yl)tetrahydrofuran-3-yl phosphonate (190 mg, 0.16 mmol) in CH$_2$Cl$_2$ (2.5 mL) was added water (28.8 mg, 1.6 mmol) and dichloroacetic acid in CH$_2$Cl$_2$ (0.6M, 2.5 mL). The mixture was stirred at rt for 10 min, and then Et$_3$SiH (4.5 mL) was added. After 1 h, pyridine (0.5 mL) was added. After 10 min, the resulting mixture was concentrated to give the product, which was used for the next reaction step without purification. LCMS (ES, m/z): 917.9 [M+H]$^+$. $^{31}$P-NMR: (162 MHz, CD$_3$OD): δ 2.51, 2.34 (2s, 1P); −3.46, −3.82 (2s, 1P).

Step 7: (5R,7R,8S,12aR,14R,15R,15aS,18R)-2-(2-cyanoethoxy)-18-fluoro-7-{2-[(2-methylpropanoyl)amino]-6-oxo-1,6-dihydro-9H-purin-9-yl}-14-{6-[(phenylcarbonyl)amino]-9H-purin-9-yl}hexahydro-14H-15,12a-(epoxymethano)-5,8-methanofuro[3,2-l][1,3,6,9,11,2,10]pentaoxadiphosphacyclotetradecin-10 (12H)-olate 2,10-dioxide To pyridine (16 mL) under Ar was added diphenyl chlorophosphate (0.66 mL, 3.2 mmol). It was cooled at −40° C. and then, a solution of crude from Step 6 in CH$_2$Cl$_2$ (16 mL) was added dropwise over 20 min. The resulting mixture was stirred at −40° C. for 40 min. The reaction mixture was used in the next step without purification. LCMS (ES, m/z): 898.2 [M−H]$^−$.

Step 8. (5R,7R,8S,12aR,14R,15R,15aS,18R)-2-(2-cyanoethoxy)-18-fluoro-7-{2-[(2-methylpropanoyl)amino]-6-oxo-1,6-dihydro-9H-purin-9-yl}-14-{6-[(phenylcarbonyl)amino]-9H-purin-9-yl}hexahydro-14H-15,12a-(epoxymethano)-5,8-methanofuro[3,2-l][1,3,6,9,11,2,10]pentaoxadiphosphacyclotetradecin-10(12H)-olate 2,10-dioxide [3,2-l][1,3,6,9,11,2,10]pentaoxadiphosphacyclotetradecine-2,10 (12H)-diolate 2,10-dioxide

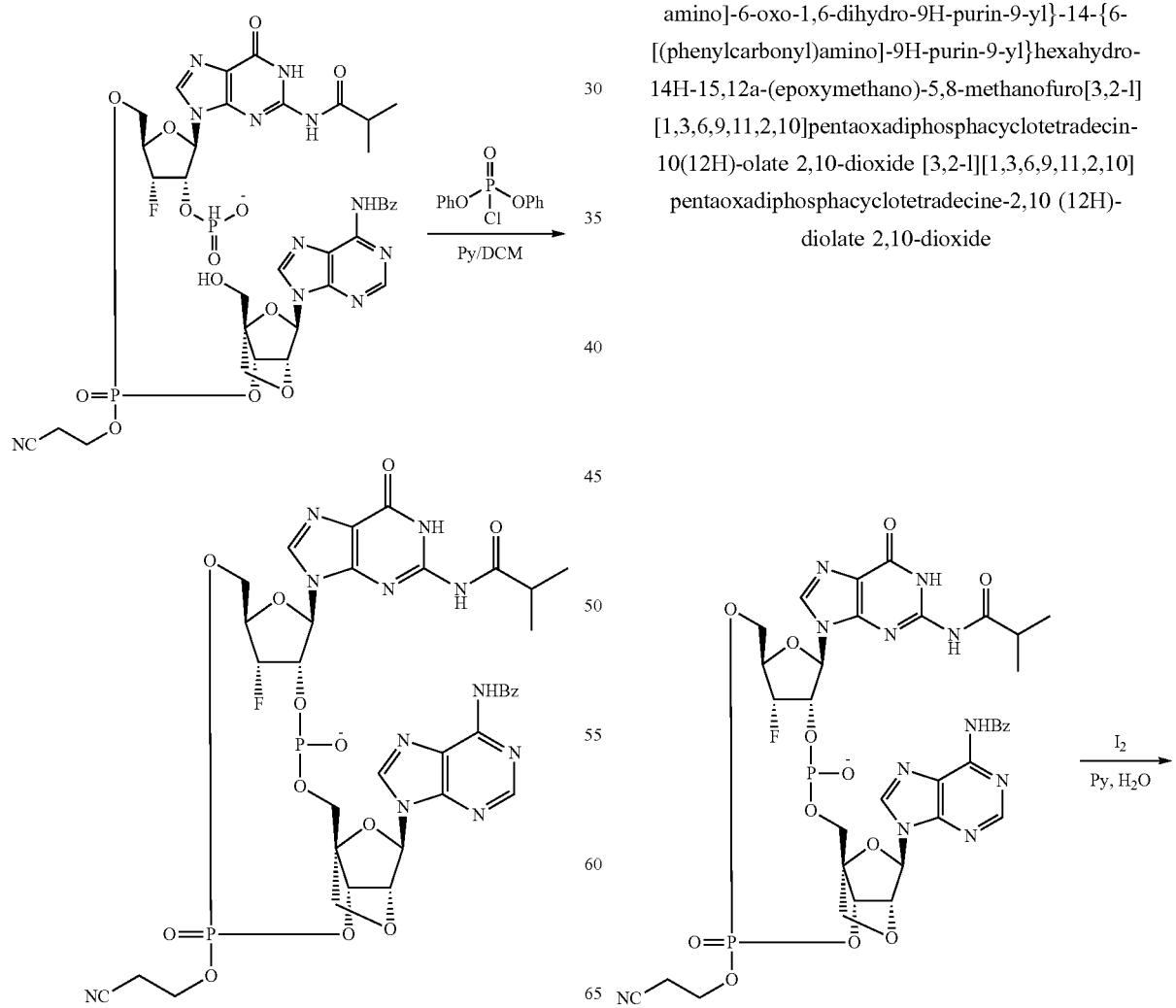

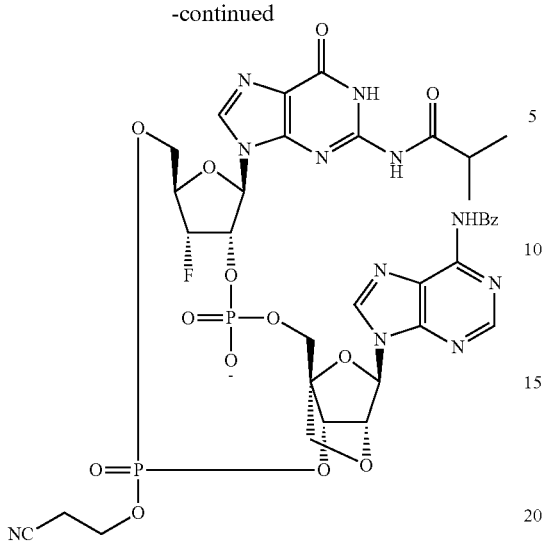

To the solution from Step 7 at 0° C. was added I$_2$ in pyridine/water (9/1) (3%, 1.76 mL) over 5 min. The mixture was stirred at rt for 40 min. Then, it was treated with a solution of Na$_2$S$_2$O$_3$.5H$_2$O (150 mg) in water (2 mL). After 5 min, the mixture was concentrated under reduced pressure. The residue was purified by reverse phase (C18) chromatography eluted with 0 to 45% ACN in aq NH$_4$HCO$_3$ (0.04%) to give the product. LCMS (ES, m/z): 915.8 [M+H]$^+$. $^{19}$F-NMR (376 MHz, CD$_3$OD): δ −198.70, −203.36 (2s, 1F). $^{31}$P-NMR (162 MHz, CD$_3$OD): δ −0.96, −1.75 (2s, 1P); −3.64, −4.71 (2s, 1P).

Step 9: (5R,7R,8S,12aR,14R,15R,15aS,18R)-7-(2-amino-6-oxo-1,6-dihydro-9H-purin-9-yl)-14-(6-amino-9H-purin-9-yl)-18-fluorohexahydro-14H-15,12a-(epoxymethano)-5,8-methanofuro [3,2-l][1,3,6,9,11,2,10]pentaoxadiphosphacyclotetradecine-2,10 (12H)-diolate 2,10-dioxide

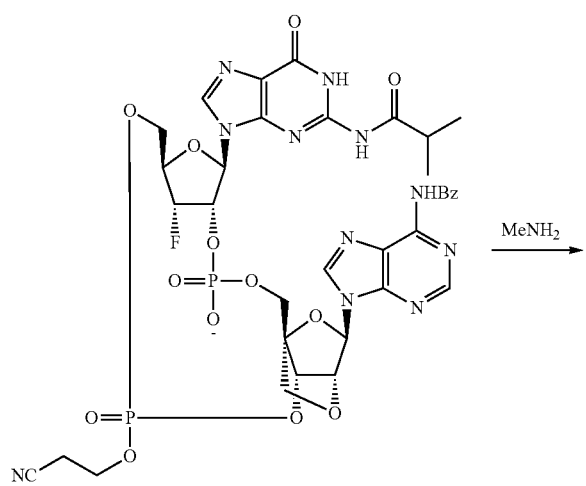

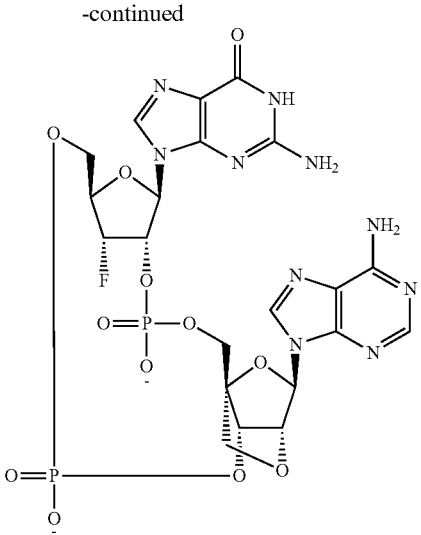

(5R,7R,8S,12aR,14R,15R,15aS,18R)-2-(2-cyanoethoxy)-18-fluoro-7-{2-[(2-methylpropanoyl)amino]-6-oxo-1,6-dihydro-9H-purin-9-yl}-14-{6-[(phenylcarbonyl)amino]-9H-purin-9-yl}hexahydro-14H-15,12a-(epoxymethano)-5,8-methanofuro[3,2-l][1,3,6,9,11,2,10]pentaoxadiphosphacyclotetradecin-10(12H)-olate 2,10-dioxide (110 mg, 0.12 mmol) was dissolved in a solution of MeNH$_2$ in EtOH (30%, 15 mL), and the resulting solution was stirred at rt for 3 h. Then, it was concentrated, and the residue was purified by preparative-HPLC (Atlantis Prep T3 Column, 19×250 mm) eluted with 0 to 9% ACN in aq NH$_4$HCO$_3$ (50 mM) to give the product. LCMS (ES, m/z): 686.9 [M−H]$^-$. $^1$H-NMR (400 MHz, D$_2$O): δ 8.14 (s, 1H), 7.85 (s, 1H), 7.80 (s, 1H), 6.01 (s, 1H), 5.99 (d, J=8.5 Hz, 1H), 5.84-5.66 (m, 1H), 5.44 (d, J=3.6 Hz, 0.5H), 5.31 (d, J=3.6 Hz, 0.5H), 4.96 (d, J=3.9 Hz, 1H), 4.84 (s, 1H), 4.65-4.53 (m, 1H), 4.33-4.15 (m, 4H), 4.10 (d, J=8.2 Hz, 1H), 3.96 (d, J=8.2 Hz, 1H). $^{19}$F-NMR (376 MHz, D$_2$O): δ −199.02 (s, 1F). $^{31}$P-NMR (162 MHz, D$_2$O): δ −1.89 (s, 1P), −2.49 (s, 1P).

Examples 21 through 29, as shown in Table 2 below, were prepared according to procedures analogous to those outlined in Example 20 above using the appropriate monomers, described as Preparations or as obtained from commercial sources, in the coupling step.

TABLE 2

| Ex. | Structure | Name | Mass [M − H] |
|---|---|---|---|
| 21 | 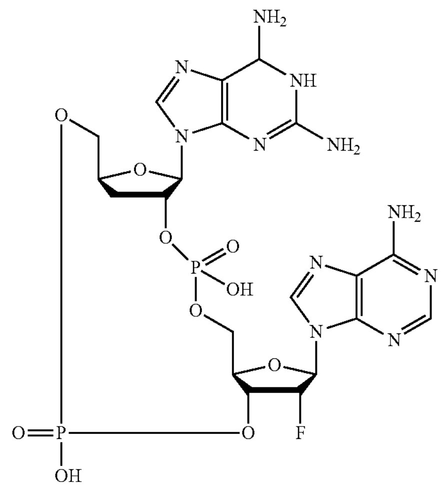 | 2-amino-9-[(5S,7R,8R,12aR,14R,15R,15aR)-14-(6-amino-9H-purin-9-yl)-15-fluoro-2,10-dihydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 659 |
| 22 | 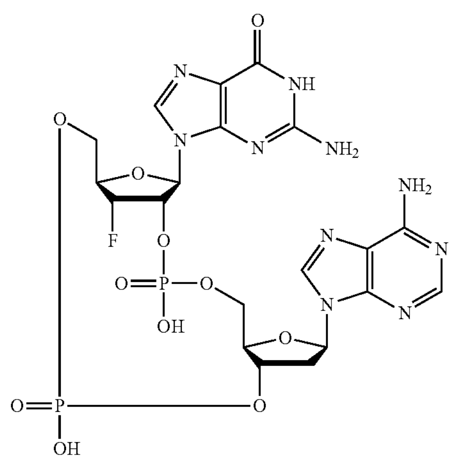 | 2-amino-9-[(5R,7R,8S,12aR,14R,15aS,16R)-14-(6-amino-9H-purin-9-yl)-16-fluoro-2,10-dihydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 659 |
| 23 | 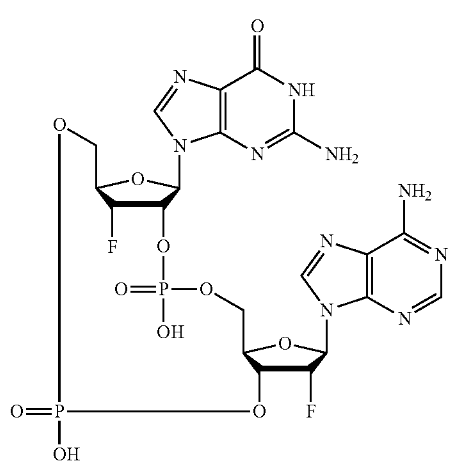 | 2-amino-9-[(5R,7R,8S,12aR,14R,15R,15aR,16R)-14-(6-amino-9H-purin-9-yl)-15,16-difluoro-2,10-dihydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 677 |

TABLE 2-continued

| Ex. | Structure | Name | Mass [M − H] |
|---|---|---|---|
| 24 | 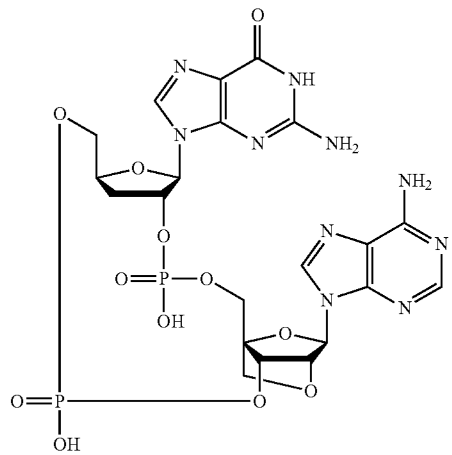 [SMILES: Nc1nc2c(ncn2[C@@H]2O[C@@H]3COP(=O)(O)OC4[C@@H]5OC[C@]4(COP(=O)(O)O[C@H]2C3)O[C@H]5n2cnc3c(N)ncnc32)c(=O)[nH]1] | 2-amino-9-[(5S,7R,8R,12aR,14R,15R,15aS)-14-(6-amino-9H-purin-9-yl)-2,10-dihydroxy-2,10-dioxidohexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one | 669 |
| 25 | 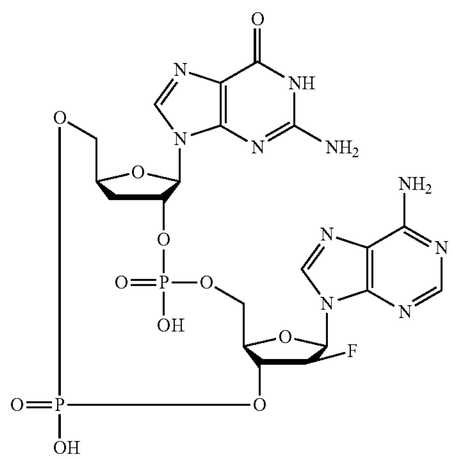 | 2-amino-9-[(5S,7R,8R,12aR,14R,15S,15aR)-14-(6-amino-9H-purin-9-yl)-15-fluoro-2,10-dihydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 659 |
| 26 | 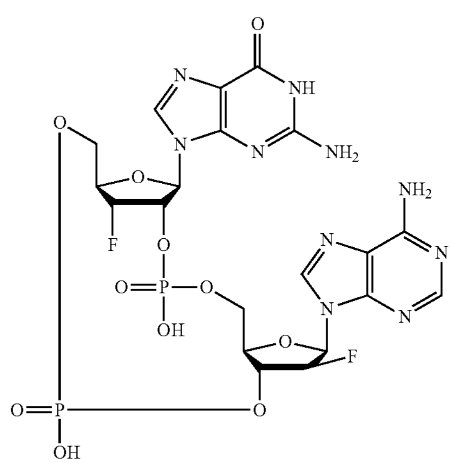 | 2-amino-9-[(2S,5R,7R,8S,10S,12aR,14R,15S,15aR,16R)-14-(6-amino-9H-purin-9-yl)-15,16-difluoro-2,10-dihydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 677 |

TABLE 2-continued

| Ex. | Structure | Name | Mass [M − H] |
|---|---|---|---|
| 27 | 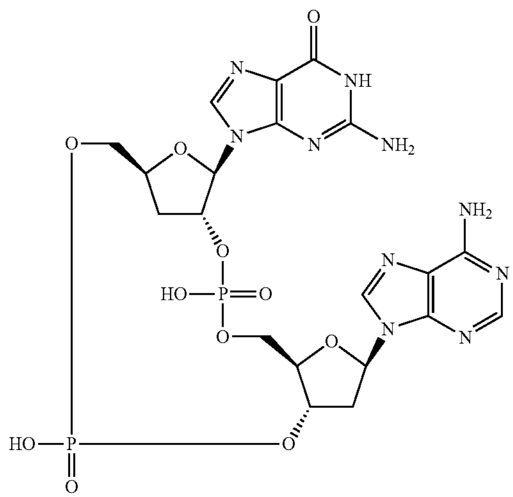 [SMILES: Nc1nc2c(ncn2[C@@H]2O[C@@H]3COP(=O)(O)O[C@H]4C[C@H](n5cnc6c(N)ncnc65)O[C@@H]4COP(=O)(O)O[C@@H]2C3)c(=O)[nH]1] | 2-amino-9-[(5S,7R,8R,12aR,14R,15aS)-14-(6-amino-9H-purin-9-yl)-2,10-dihydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 641 |
| 28 | 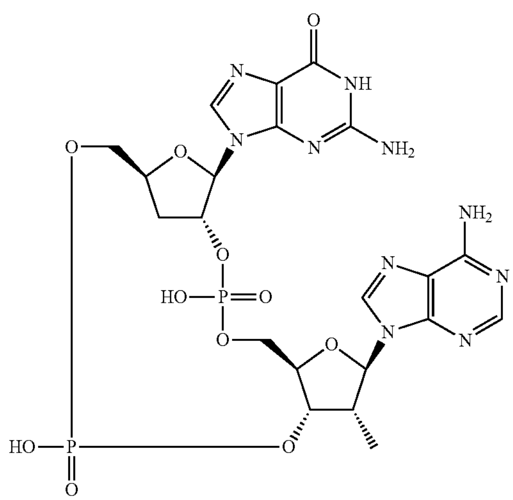 [SMILES: C[C@@H]1[C@@H]2OP(=O)(O)OC[C@@H]3C[C@@H](OP(=O)(O)OC[C@H]2O[C@H]1n1cnc2c(N)ncnc21)[C@H](n1cnc2c(=O)[nH]c(N)nc21)O3] | 2-amino-9-[(5S,7R,8R,12aR,14R,15R,15aS)-14-(6-amino-9H-purin-9-yl)-2,10-dihydroxy-15-methyl-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 655 |
| 29 | 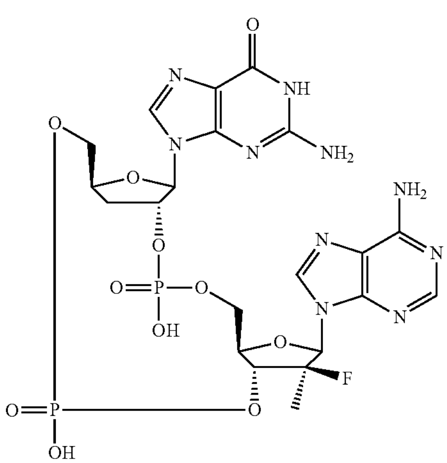 [SMILES: C[C@@]1(F)C(n2cnc3c(N)ncnc32)O[C@@H]2COP(=O)(O)O[C@@H]3C[C@@H](COP(=O)(O)O[C@H]21)OC3n1cnc2c(=O)[nH]c(N)nc21] | 2-amino-9-[(5S,8R,12aR,15S,15aR)-14-(6-amino-9H-purin-9-yl)-15-fluoro-2,10-dihydroxy-15-methyl-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 673 |

Example 30: 2-amino-7-[(5R,7R,8R,12aR,14R,15R,15aS,16R)-14-(6-amino-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-3,7-dihydro-4H-pyrrolo[2,3-d]pyrimidin-4-one

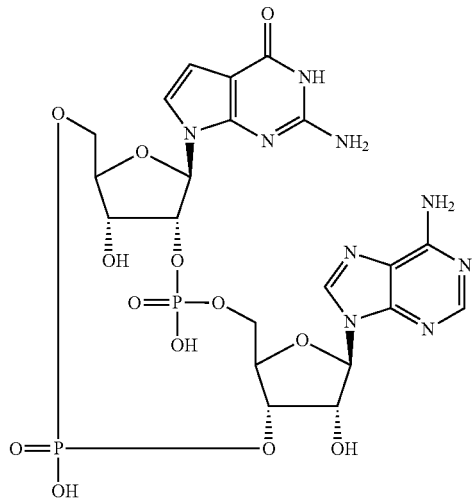 [SMILES: Nc1nc2c(ccn2[C@@H]2OC3COP(=O)(O)O[C@@H]4C(COP(=O)(O)O[C@@H]2[C@@H]3O)O[C@@H](n2cnc3c(N)ncnc32)[C@@H]4O)c(=O)[nH]1]

cGAS buffer consisted of 40 mM Tris-HCL, pH 7.5, 100 uM NaCl, 10 mM MgCl$_2$. cGAS enzyme was purchased from Novoprotein (Novoprotein code: SGCAS), having been expressed in *E. coli* and purified using a HIS tag. The calculated molecular weight was 55.3 kDa, and the sequence was:

(SEQ. ID. NO. 1)
MAHHHHHHGSDSEVNQEAKPEVKPEVKPETHINLKVSDGSSEIFFKIKKT

TPLRRLMEAFAKRQGKEMDSLTFLYDGIEIQADQTPEDLDMEDNDIIEAH

REQIGGENLYFQGGASKLRAVLEKLKLSRDDISTAAGMVKGVVDHLLLRL

KCDSAFRGVGLLNTGSYYEHVKISAPNEFDVMFKLEVPRIQLEEYSNTRA

YYFVKFKRNPKENPLSQFLEGEILSASKMLSKFRKIIKEEINDIKDTDVI

MKRKRGGSPAVTLLISEKISVDITLALESKSSWPASTQEGLRIQNWLSAK

VRKQLRLKPFYLVPKHAKEGNGFQEETWRLSFSHIEKEILNNHGKSKTCC

ENKEEKCCRKDCLKLMKYLLEQLKERFKDKKHLDKFSSYHVKTAFFHVCT

QNPQDSQWDRKDLGLCFDNCVTYFLQCLRTEKLENYFIPEFNLFSSNLID

KRSKEFLTKQIEYERNNEFPVFDEF

To a vial were added Herring DNA (CAS #9007-49-2, 0.3 mg/mL in cGAS buffer; 14.8 mL) and cGAS enzyme (3.1 mg/mL in cGAS buffer; 0.78 mL), and the mixture was incubated at RT for 15 min. 7-Deaza-GTP (TriLink catalog # N-1044; 5 mM in cGAS buffer, 1.95 mL, 9.75 μmol) and ATP (5 mM in cGAS buffer, 1.95 mL, 9.75 μmol) were added, and the mixture was incubated on a Radleys Metz heater shaker set to maintain 37° C. while shaking at 250 rpm for 16 h, after which the mixture was filtered and lyopholyzed. The product was purified using mass-directed reverse phase HPLC with a Waters SunFire C18 OBD Prep Column, 100 Å, 5 μm, 19 mm×150 mm, [Waters Part #186002568] using a gradient solvent system with MeCN and 100 mM aqueous triethylammonium acetate. Lyopholization of the product fractions furnished the title compound. LCMS (ES, m/z): 672 [M−H]$^-$. $^1$H NMR (600 MHz, DMSO-d$_6$) δ 10.33 (s, 1H), 8.37 (s, 1H), 8.10 (s, 1H), 7.56 (s, 1H), 7.24 (s, 2H), 6.94 (d, J=3.4 Hz, 1H), 6.28-6.24 (m, 3H), 6.01 (d, J=8.1 Hz, 1H), 5.86 (d, J=7.9 Hz, 1H), 5.61 (s, 1H), 5.01-4.97 (m, 1H), 4.86-4.83 (m, 1H), 4.70 (s, 1H), 4.25 (s, 1H), 4.21 (dd, J=10.4, 4.8 Hz, 1H), 4.03-3.92 (4, 3H), 3.80-3.75 (m, 1H), 3.69 (d, J=12.1 Hz, 1H), 2.76 (s, 12H), 1.02 (S, 18H).

Examples 31 to 65 in Table 3 below were made using procedures analogous to those described above for Example 30 using the appropriate nucleoside triphosphate monomers. Where necessary, the triphosphates were formed according to methods similar to those described for Preparations 23 to 26 or by submission of the requisite 5'-OH nucleoside monomer to NuBlocks LLC (Oceanside, Calif.). Example 38 was made using ATP and α-thio-GTP (BIOLOG Life Science Institute, catalog # G014/G015).

TABLE 3

| Ex. | Structure | Name | Mass [M − H]$^-$ |
|---|---|---|---|
| 31 | 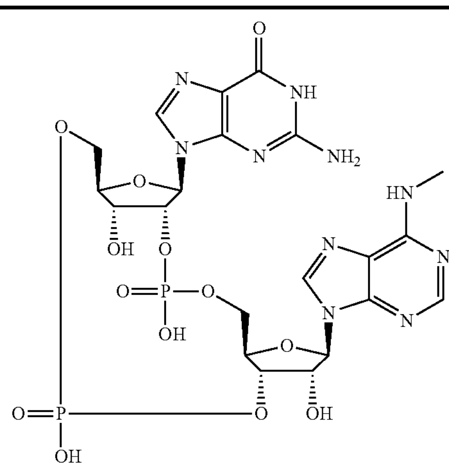 | 2-amino-9-{(5R,7R,8R,12aR,14R,15R,15aS,16R)-2,10,15,16-tetrahydroxy-14-[6-(methylamino)-9H-purin-9-yl]-2,10-dioxidooctahydro-12H-5,8-methanofuro[3,2-l][1,3,6,9,11,2,10]pentaoxadiphosphacyclotetradecin-7-yl}-1,9-dihydro-6H-purin-6-one | 687 |

TABLE 3-continued

| Ex. | Structure | Name | Mass [M − H]⁻ |
|---|---|---|---|
| 32 | 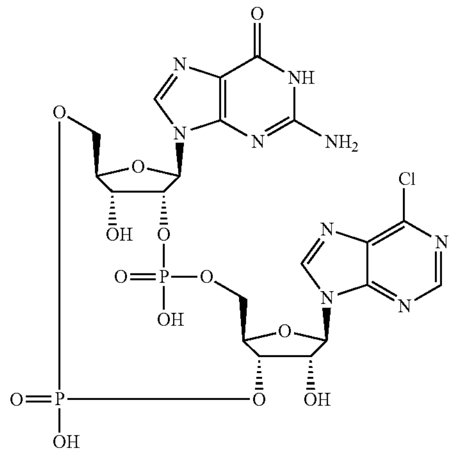 [SMILES: Nc1nc2c(ncn2[C@@H]2O[C@@H]3COP(=O)(O)O[C@H]4[C@@H](O)[C@H](n5cnc6c(Cl)ncnc65)O[C@@H]4COP(=O)(O)O[C@@H]2[C@@H]3O)c(=O)[nH]1] | 2-amino-9-[(5R,7R,8R,12aR,14R,15R,15aS,16R)-14-(6-chloro-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 692 |
| 33 | 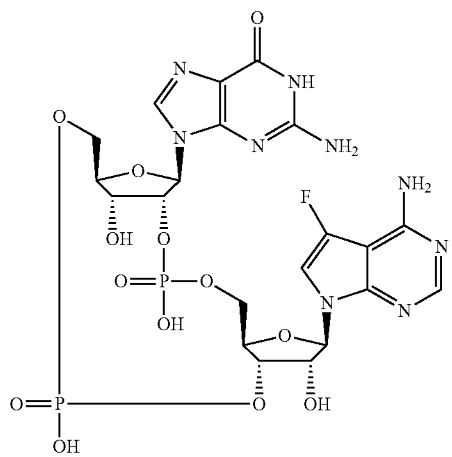 [SMILES: Nc1nc2c(ncn2[C@@H]2O[C@@H]3COP(=O)(O)O[C@H]4[C@@H](O)[C@H](n5cc(F)c6c(N)ncnc65)O[C@@H]4COP(=O)(O)O[C@@H]2[C@@H]3O)c(=O)[nH]1] | 2-amino-9-[(5R,7R,8R,12aR,14R,15R,15aS,16R)-14-(4-amino-5-fluoro-7H-pyrrolo[2,3-d]pyrimidin-7-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 690 |
| 34 | 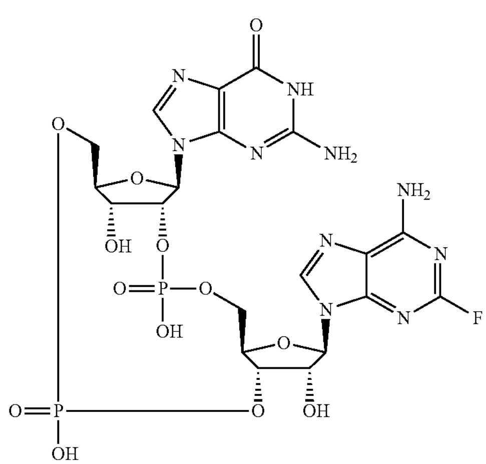 [SMILES: Nc1nc2c(ncn2[C@@H]2O[C@@H]3COP(=O)(O)O[C@H]4[C@@H](O)[C@H](n5cnc6c(N)nc(F)nc65)O[C@@H]4COP(=O)(O)O[C@@H]2[C@@H]3O)c(=O)[nH]1] | 2-amino-9-[(5R,7R,8R,12aR,14R,15R,15aS,16R)-14-(6-amino-2-fluoro-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 691 |

TABLE 3-continued

| Ex. | Structure | Name | Mass [M − H]⁻ |
|---|---|---|---|
| 35 | 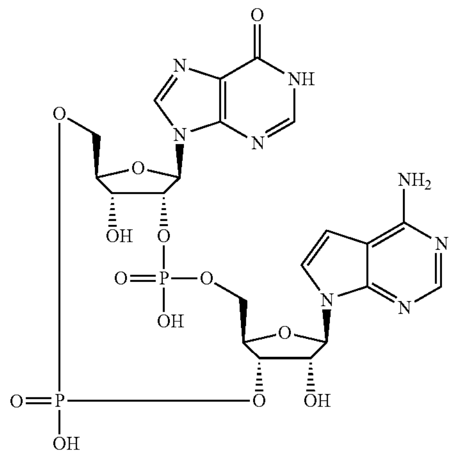 [SMILES: Nc1ncnc2c1ccn2[C@@H]1O[C@@H]2COP(=O)(O)O[C@@H]3[C@H](O)[C@@H](COP(=O)(O)O[C@H]2[C@H]1O)O[C@H]3n1cnc2c(=O)[nH]cnc21] | 9-[(5R,7R,8R,12aR,14R,15R,15aS,16R)-14-(4-amino-7H-pyrrolo[2,3-d]pyrimidin-7-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 657 |
| 36 | 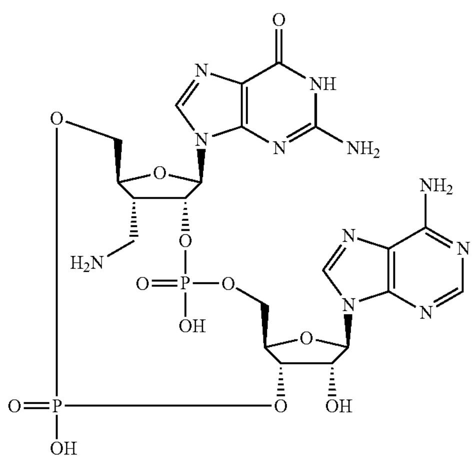 [SMILES: NC[C@H]1[C@H]2OP(=O)(O)OC[C@H]3O[C@@H](n4cnc5c(N)ncnc54)[C@H](O)[C@@H]3OP(=O)(O)OC[C@H]1O[C@H]2n1cnc2c(=O)[nH]c(N)nc21] | 2-amino-9-[(5S,7R,8R,12aR,14R,15R,15aS,16R)-16-(aminomethyl)-14-(6-amino-9H-purin-9-yl)-2,10,15-trihydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 686 |
| 37 | 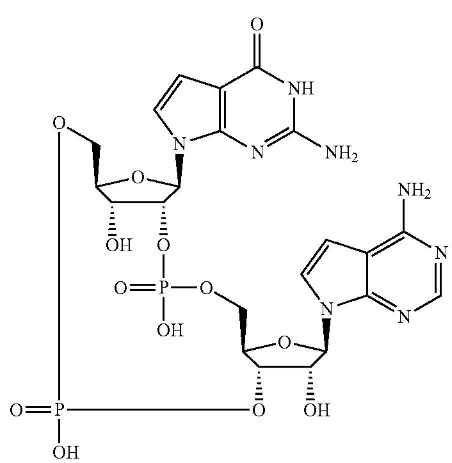 [SMILES: Nc1nc2c(ccn2[C@@H]2O[C@@H]3COP(=O)(O)O[C@H]4[C@@H](O)[C@H](n5ccc6c(N)ncnc65)O[C@@H]4COP(=O)(O)O[C@@H]2[C@@H]3O)c(=O)[nH]1] | 2-amino-7-[(5R,7R,8R,12aR,14R,15R,15aS,16R)-14-(4-amino-7H-pyrrolo[2,3-d]pyrimidin-7-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-3,7-dihydro-4H-pyrrolo[2,3-d]pyrimidin-4-one | 671 |

TABLE 3-continued

| Ex. | Structure | Name | Mass [M − H]⁻ |
|---|---|---|---|
| 38 | 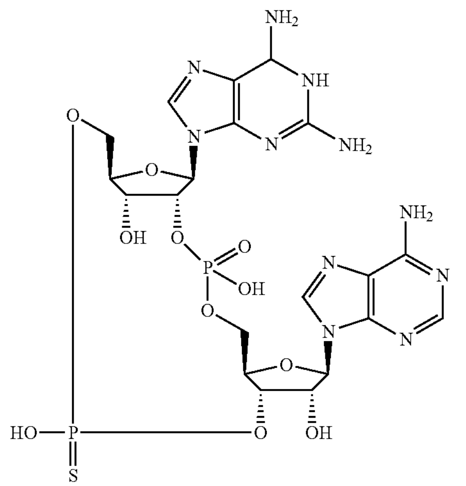 [SMILES: NC1=Nc2c(ncn2[C@@H]2O[C@@H]3COP(O)(=S)O[C@H]4[C@@H](O)[C@H](n5cnc6c(N)ncnc65)O[C@@H]4COP(=O)(O)O[C@@H]2[C@@H]3O)C(N)N1] | 2-amino-9-[(5R,7R,8R,12aR,14R,15R,15aS,16R)-14-(6-amino-9H-purin-9-yl)-2,10,15,16-tetrahydroxy-10-oxido-2-sulfidooctahydro-12H-5,8-methanofuro[3,2-l][1,3,6,9,11,2,10]pentaoxadiphosphacyclotetradecin-7-yl]-1,9-dihydro-6H-purin-6-one | 689 |
| 39 | 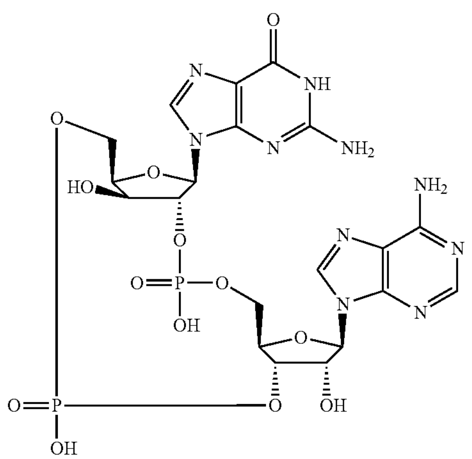 [SMILES: Nc1nc2c(ncn2[C@@H]2O[C@@H]3COP(=O)(O)O[C@H]4[C@@H](O)[C@H](n5cnc6c(N)ncnc65)O[C@@H]4COP(=O)(O)O[C@@H]2[C@H]3O)c(=O)[nH]1] | 2-amino-9-[(5R,7R,8R,12aR,14R,15R,15aS,16S)-14-(6-amino-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 673 |
| 40 | 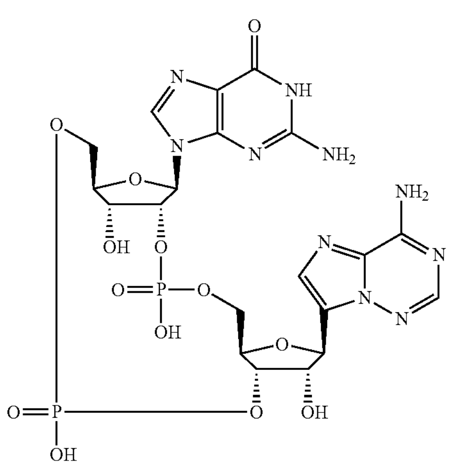 [SMILES: Nc1nc2c(ncn2[C@@H]2O[C@@H]3COP(=O)(O)O[C@H]4[C@@H](O)[C@H](c5cnc6c(N)ncnn56)O[C@@H]4COP(=O)(O)O[C@@H]2[C@@H]3O)c(=O)[nH]1] | 2-amino-9-[(5R,7R,8R,12aR,14S,15S,15aS,16R)-14-(4-aminoimidazo[2,1-f][1,2,4]triazin-7-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 673 |

TABLE 3-continued

| Ex. | Structure | Name | Mass [M − H]⁻ |
|---|---|---|---|
| 41 | 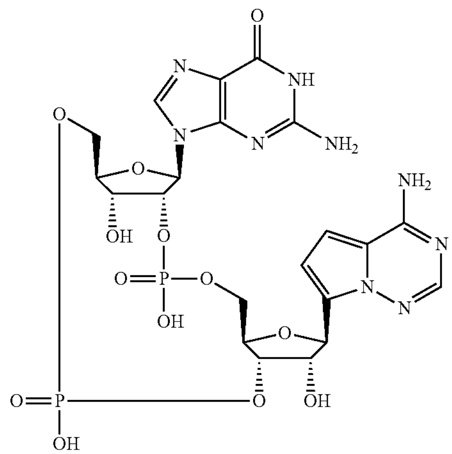 [SMILES: Nc1nc2c(ncn2[C@@H]2O[C@@H]3COP(=O)(O)O[C@H]4[C@@H](O)[C@H](c5ccc6c(N)ncnn56)O[C@@H]4COP(=O)(O)O[C@@H]2[C@@H]3O)c(=O)[nH]1] | 2-amino-9-[(5R,7R,8R,12aR,14S,15S,15aS,16R)-14-(4-aminopyrrolo[2,1-f][1,2,4]triazin-7-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 672 |
| 42 | 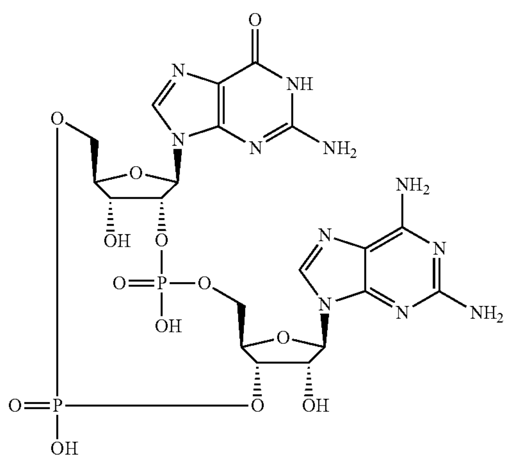 [SMILES: Nc1nc(N)c2ncn([C@@H]3O[C@@H]4COP(=O)(O)O[C@@H]5[C@H](O)[C@@H](COP(=O)(O)O[C@H]4[C@H]3O)O[C@H]5n3cnc4c(=O)[nH]c(N)nc43)c2n1] | 2-amino-9-[(5R,7R,8R,12aR,14R,15R,15aS,16R)-14-(2,6-diamino-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 688 |
| 43 | 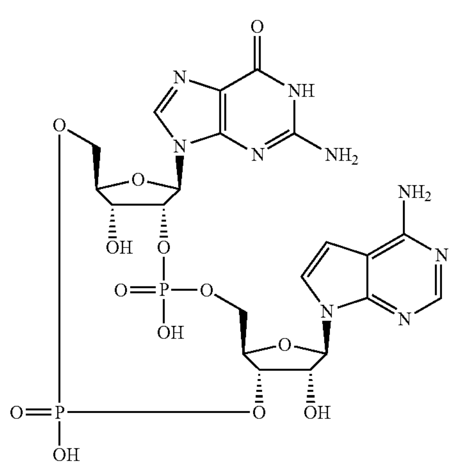 [SMILES: Nc1nc2c(ncn2[C@@H]2O[C@@H]3COP(=O)(O)O[C@H]4[C@@H](O)[C@H](n5ccc6c(N)ncnc65)O[C@@H]4COP(=O)(O)O[C@@H]2[C@@H]3O)c(=O)[nH]1] | 2-amino-9-[(5R,7R,8R,12aR,14R,15R,15aS,16R)-14-(4-amino-7H-pyrrolo[2,3-d]pyrimidin-7-yl)-10,15,16-trihydroxy-2,10-dioxido-2-sulfanyloctahydro-12H-5,8-methanofuro[3,2-l][1,3,6,9,11,2,10]pentaoxadiphosphacyclotetradecin-7-yl]-1,9-dihydro-6H-purin-6-one | 688 |

TABLE 3-continued

| Ex. | Structure | Name | Mass [M − H]⁻ |
|---|---|---|---|
| 44 | 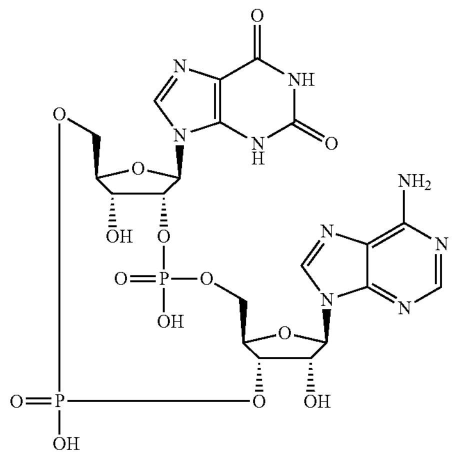 [SMILES: Nc1ncnc2c1ncn2[C@@H]1O[C@@H]2COP(=O)(O)O[C@@H]3[C@H](O)[C@@H](COP(=O)(O)O[C@H]2[C@H]1O)O[C@H]3n1cnc2c(=O)[nH]c(=O)[nH]c21] | 9-[(5R,7R,8R,12aR,14R,15R,15aS,16R)-14-(6-amino-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-3,9-dihydro-1H-purine-2,6-dione | 674 |
| 45 | 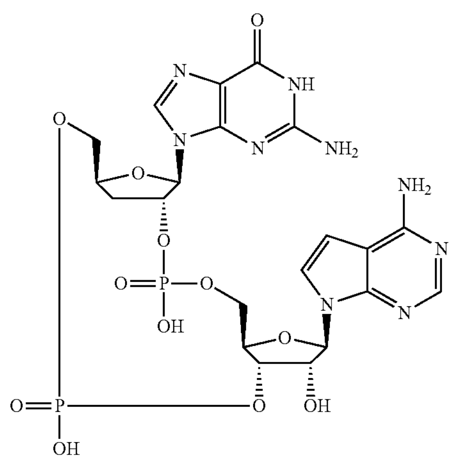 [SMILES: Nc1nc2c(ncn2[C@@H]2O[C@@H]3COP(=O)(O)O[C@H]4[C@@H](O)[C@H](n5ccc6c(N)ncnc65)O[C@@H]4COP(=O)(O)O[C@@H]2C3)c(=O)[nH]1] | 2-amino-9-[(5S,7R,8R,12aR,14R,15R,15aS)-14-(4-amino-7H-pyrrolo[2,3-d]pyrimidin-7-yl)-2,10,15-trihydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 656 |
| 46 | 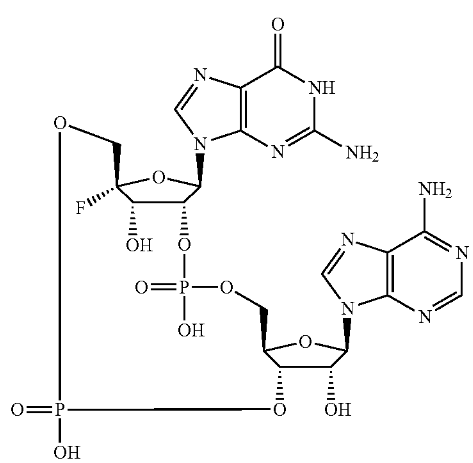 [SMILES: Nc1nc2c(ncn2[C@@H]2O[C@]3(F)COP(=O)(O)O[C@H]4[C@@H](O)[C@H](n5cnc6c(N)ncnc65)O[C@@H]4COP(=O)(O)O[C@@H]2[C@@H]3O)c(=O)[nH]1] | 2-amino-9-[(5S,7R,8R,12aR,14R,15R,15aS,16S)-14-(6-amino-9H-purin-9-yl)-5-fluoro-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 691 |

TABLE 3-continued

| Ex. | Structure | Name | Mass [M − H]⁻ |
|---|---|---|---|
| 47 | 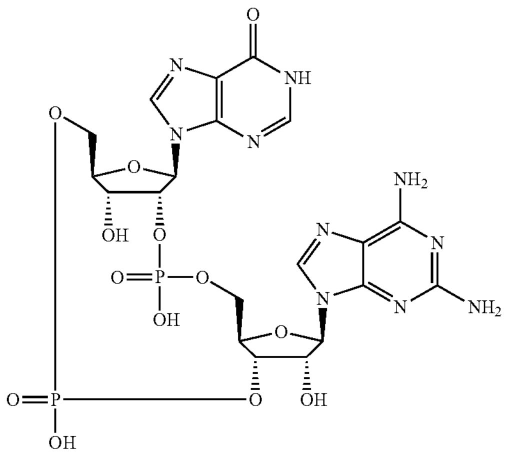 [SMILES: Nc1nc(N)c2ncn([C@@H]3O[C@@H]4COP(=O)(O)O[C@@H]5[C@H](O)[C@@H](COP(=O)(O)O[C@H]4[C@H]3O)O[C@H]5n3cnc4c(=O)[nH]cnc43)c2n1] | 9-[(5R,7R,8R,12aR,14R,15R,15aS,16R)-14-(2,6-diamino-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 673 |
| 48 | 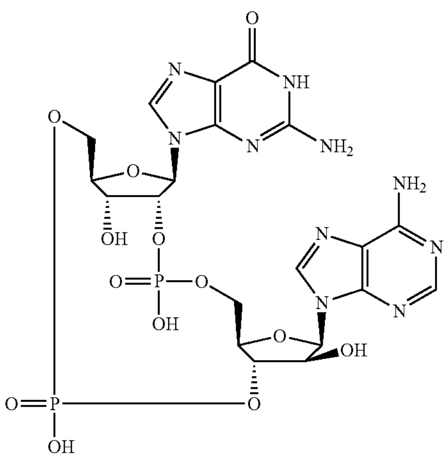 [SMILES: Nc1nc2c(ncn2[C@@H]2O[C@@H]3COP(=O)(O)O[C@H]4[C@H](O)[C@H](n5cnc6c(N)ncnc65)O[C@@H]4COP(=O)(O)O[C@@H]2[C@@H]3O)c(=O)[nH]1] | 2-amino-9-[(5R,7R,8R,12aR,14R,15S,15aS,16R)-14-(6-amino-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 673 |
| 49 | 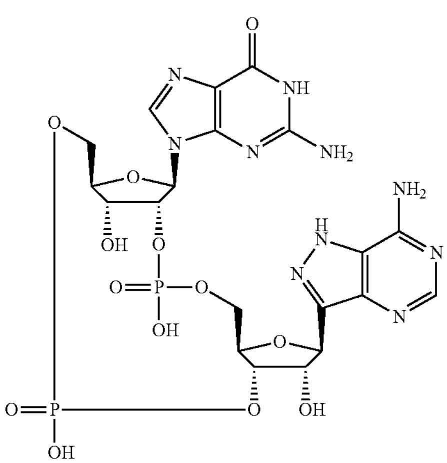 [SMILES: Nc1nc2c(ncn2[C@@H]2O[C@@H]3COP(=O)(O)O[C@H]4[C@@H](O)[C@H](c5n[nH]c6c(N)ncnc56)O[C@@H]4COP(=O)(O)O[C@@H]2[C@@H]3O)c(=O)[nH]1] | 2-amino-9-[(5R,7R,8R,12aR,14S,15S,15aS,16R)-14-(7-amino-1H-pyrazolo[4,3-d]pyrimidin-3-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 673 |

TABLE 3-continued

| Ex. | Structure | Name | Mass [M − H]⁻ |
|---|---|---|---|
| 50 | 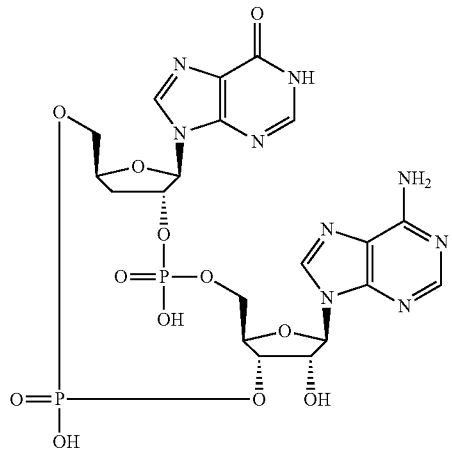 [SMILES: Nc1ncnc2c1ncn2[C@@H]1O[C@@H]2COP(=O)(O)O[C@@H]3C[C@@H](COP(=O)(O)O[C@H]2[C@H]1O)O[C@H]3n1cnc2c(=O)[nH]cnc21] | 9-[(5S,7R,8R,12aR,14R,15R,15aS)-14-(6-amino-9H-purin-9-yl)-2,10,15-trihydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 642 |
| 51 | 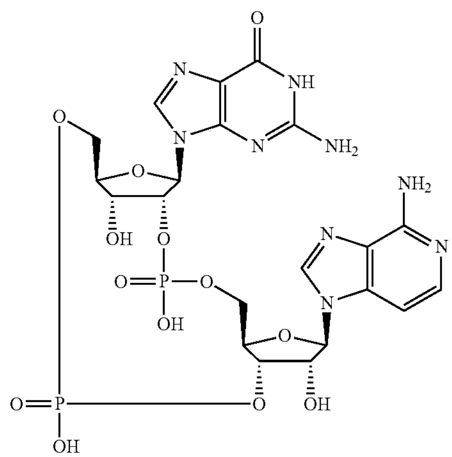 [SMILES: Nc1nc2c(ncn2[C@@H]2O[C@@H]3COP(=O)(O)O[C@H]4[C@@H](O)[C@H](n5cnc6c(N)nccc65)O[C@@H]4COP(=O)(O)O[C@@H]2[C@@H]3O)c(=O)[nH]1] | 2-amino-9-[(5R,7R,8R,12aR,14R,15R,15aS,16R)-14-(4-amino-1H-imidazo[4,5-c]pyridin-1-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 672 |
| 52 | 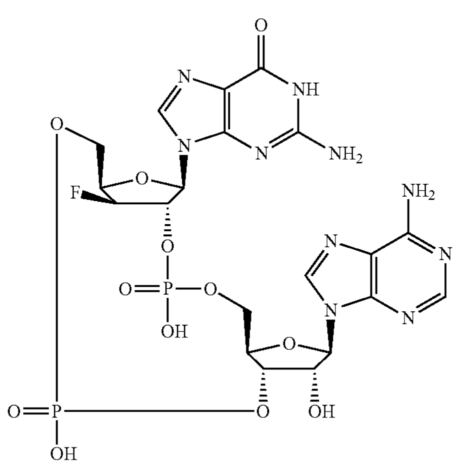 [SMILES: Nc1nc2c(ncn2[C@@H]2O[C@@H]3COP(=O)(O)O[C@H]4[C@@H](O)[C@H](n5cnc6c(N)ncnc65)O[C@@H]4COP(=O)(O)O[C@@H]2[C@H]3F)c(=O)[nH]1] | 2-amino-9-[(5R,7R,8S,12aR,14R,15R,15aS,16S)-14-(6-amino-9H-purin-9-yl)-16-fluoro-2,10,15-trihydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 675 |

TABLE 3-continued

| Ex. | Structure | Name | Mass [M − H]⁻ |
|---|---|---|---|
| 53 | 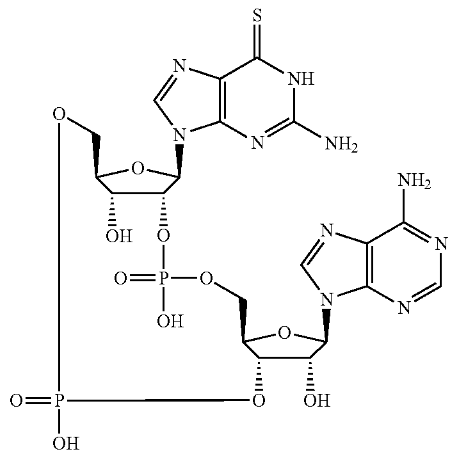 [SMILES: Nc1nc2c(ncn2[C@@H]2O[C@@H]3COP(=O)(O)O[C@H]4[C@@H](O)[C@H](n5cnc6c(N)ncnc65)O[C@@H]4COP(=O)(O)O[C@@H]2[C@@H]3O)c(=S)[nH]1] | 2-amino-9-[(5R,7R,8R,12aR,14R,15R,15aS,16R)-14-(6-amino-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purine-6-thione | 689 |
| 54 | 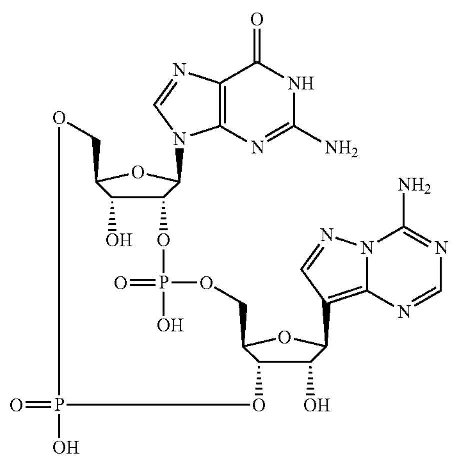 [SMILES: Nc1nc2c(ncn2[C@@H]2O[C@@H]3COP(=O)(O)O[C@H]4[C@@H](O)[C@H](c5cnn6c(N)ncnc56)O[C@@H]4COP(=O)(O)O[C@@H]2[C@@H]3O)c(=O)[nH]1] | 2-amino-9-[(5R,7R,8R,12aR,14S,15S,15aS,16R)-14-(4-aminopyrazolo[1,5-a][1,3,5]triazin-8-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 673 |
| 55 | 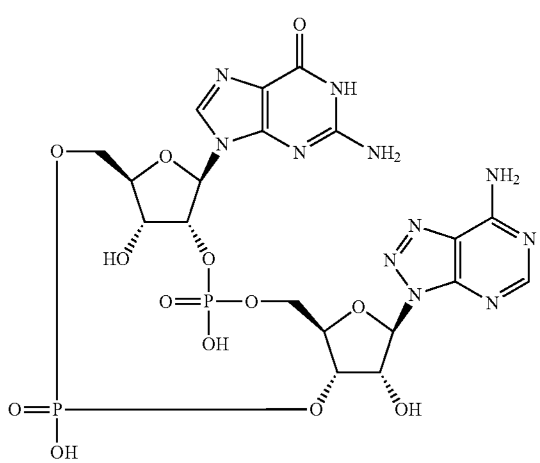 [SMILES: Nc1nc2c(ncn2[C@@H]2O[C@@H]3COP(=O)(O)O[C@H]4[C@@H](O)[C@H](n5nnc6c(N)ncnc65)O[C@@H]4COP(=O)(O)O[C@@H]2[C@@H]3O)c(=O)[nH]1] | 2-amino-9-[(5R,7R,8R,12aR,14R,15R,15aS,16R)-14-(7-amino-3H-[1,2,3]triazolo[4,5-d]pyrimidin-3-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 674 |

TABLE 3-continued

| Ex. | Structure | Name | Mass [M − H]⁻ |
|---|---|---|---|
| 56 | 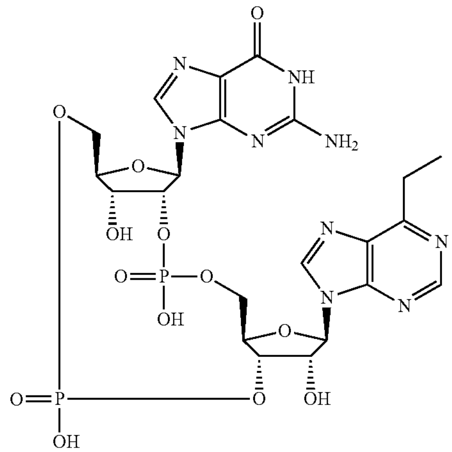 [SMILES: CCc1ncnc2c1ncn2[C@@H]1O[C@@H]2COP(=O)(O)O[C@@H]3[C@H](O)[C@@H](COP(=O)(O)O[C@H]2[C@H]1O)O[C@H]3n1cnc2c(=O)[nH]c(N)nc21] | 2-amino-9-[(5R,7R,8R,12aR,14R,15R,15aS,16R)-14-(6-ethyl-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 686 |
| 57 | 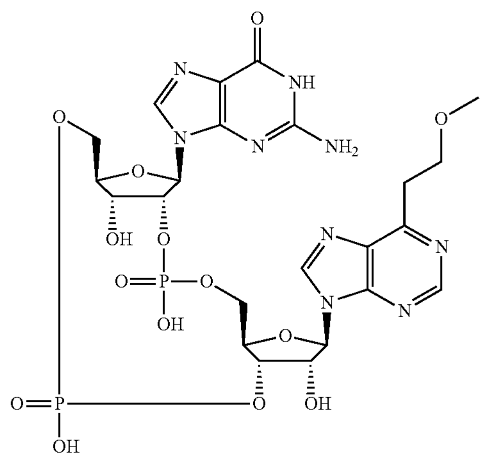 [SMILES: COCCc1ncnc2c1ncn2[C@@H]1O[C@@H]2COP(=O)(O)O[C@@H]3[C@H](O)[C@@H](COP(=O)(O)O[C@H]2[C@H]1O)O[C@H]3n1cnc2c(=O)[nH]c(N)nc21] | 2-amino-9-{(5R,7R,8R,12aR,14R,15R,15aS,16R)-2,10,15,16-tetrahydroxy-14-[6-(2-methoxyethyl)-9H-purin-9-yl]-2,10-dioxidooctahydro-12H-5,8-methanofuro[3,2-l][1,3,6,9,11,2,10]pentaoxadiphosphacyclotetradecin-7-yl}-1,9-dihydro-6H-purin-6-one | 716 |
| 58 | 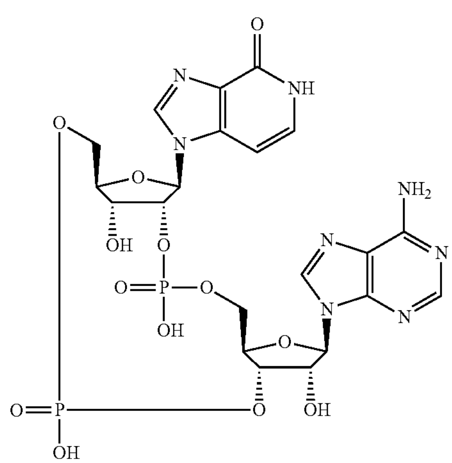 [SMILES: Nc1ncnc2c1ncn2[C@@H]1O[C@@H]2COP(=O)(O)O[C@@H]3[C@H](O)[C@@H](COP(=O)(O)O[C@H]2[C@H]1O)O[C@H]3n1cnc2c(=O)[nH]ccc21] | 1-[(5R,7R,8R,12aR,14R,15R,15aS,16R)-14-(6-amino-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,5-dihydro-4H-imidazo[4,5-c]pyridin-4-one | 657 |

TABLE 3-continued

| Ex. | Structure | Name | Mass [M − H]⁻ |
|---|---|---|---|
| 59 | 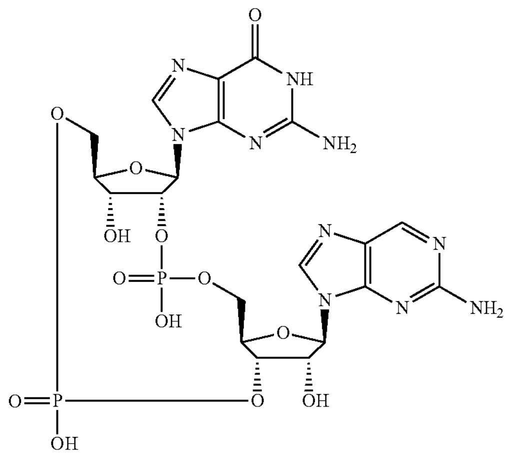 [SMILES: Nc1ncc2ncn([C@@H]3O[C@@H]4COP(=O)(O)O[C@@H]5[C@H](O)[C@@H](COP(=O)(O)O[C@H]4[C@H]3O)O[C@H]5n3cnc4c(=O)[nH]c(N)nc43)c2n1] | 2-amino-9-[(5R,7R,8R,12aR,14R,15R,15aS,16R)-14-(2-amino-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 673 |
| 60 | 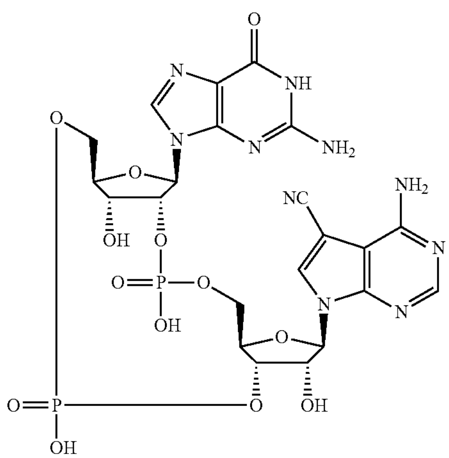 [SMILES: N#Cc1cn([C@@H]2O[C@@H]3COP(=O)(O)O[C@@H]4[C@H](O)[C@@H](COP(=O)(O)O[C@H]3[C@H]2O)O[C@H]4n2cnc3c(=O)[nH]c(N)nc32)c2ncnc(N)c12] | 4-amino-7-[(5R,7R,8R,12aR,14R,15R,15aS,16R)-7-(2-amino-6-oxo-1,6-dihydro-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-14-yl]-7H-pyrrolo[2,3-d]pyrimidine-5-carbonitrile | 697 |
| 61 | 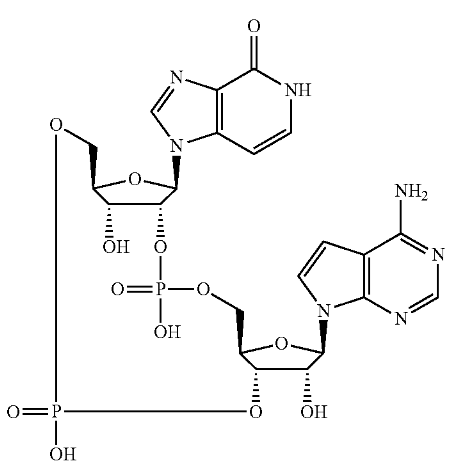 | 1-[(5R,7R,8R,12aR,14R,15R,15aS,16R)-14-(4-amino-7H-pyrrolo[2,3-d]pyrimidin-7-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,5-dihydro-4H-imidazo[4,5-c]pyridin-4-one | 656 |

TABLE 3-continued

| Ex. | Structure | Name | Mass [M − H]⁻ |
|---|---|---|---|
| 62 | 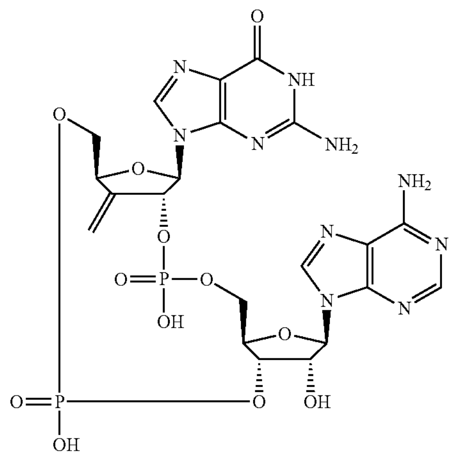 [SMILES: C=C1[C@H]2OP(=O)(O)OC[C@H]3O[C@@H](n4cnc5c(N)ncnc54)[C@H](O)[C@@H]3OP(=O)(O)OC[C@H]1O[C@H]2n1cnc2c(=O)[nH]c(N)nc21] | 2-amino-9-[(5S,7R,8R,12aR,14R,15R,15aS)-14-(6-amino-9H-purin-9-yl)-2,10,15-trihydroxy-16-methylidene-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 669 |
| 63 | 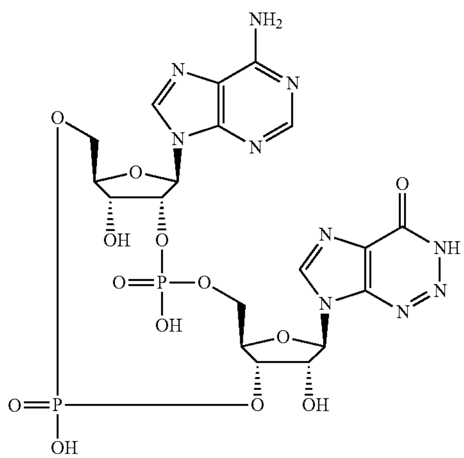 [SMILES: Nc1ncnc2c1ncn2[C@@H]1O[C@@H]2COP(=O)(O)O[C@H]3[C@@H](O)[C@H](n4cnc5c(=O)[nH]nnc54)O[C@@H]3COP(=O)(O)O[C@@H]1[C@@H]2O] | 7-[(5R,7R,8R,12aR,14R,15R,15aS,16R)-7-(6-amino-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-14-yl]-3,7-dihydro-4H-imidazo[4,5-d][1,2,3]triazin-4-one | 659 |
| 64 | 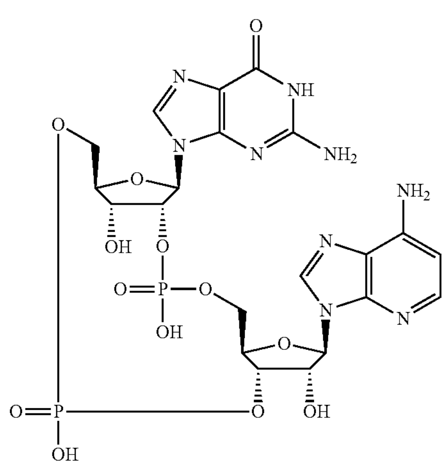 [SMILES: Nc1nc2c(ncn2[C@@H]2O[C@@H]3COP(=O)(O)O[C@H]4[C@@H](O)[C@H](n5cnc6c(N)ccnc65)O[C@@H]4COP(=O)(O)O[C@@H]2[C@@H]3O)c(=O)[nH]1] | 2-amino-9-[(5R,7R,8R,12aR,14R,15R,15aS,16R)-14-(7-amino-3H-imidazo[4,5-b]pyridin-3-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 672 |

TABLE 3-continued

| Ex. | Structure | Name | Mass [M − H]⁻ |
|---|---|---|---|
| 65 | (structure shown) | 1-[(5R,7R,8R,12aR,14R,15R,15aS,16R)-14-(6-amino-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,5-dihydro-4H-imidazo[4,5-d]pyridazin-4-one | 658 |

Example 66: 1-[(5R,7R,8R,12aR,14R,15R,15aS,16R)-14-(6-amino-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,5-dihydro-4H-pyrazolo[3,4-d]pyrimidin-4-one

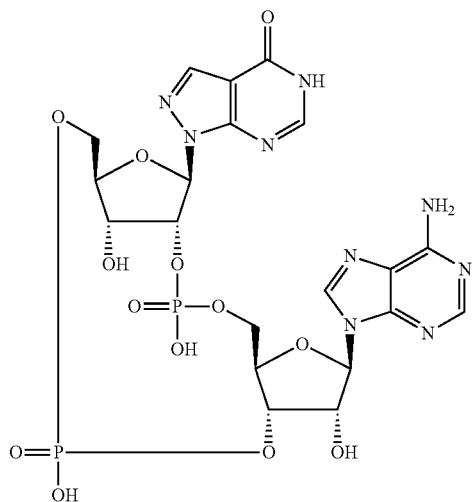 [SMILES: Nc1ncnc2c1ncn2[C@@H]1O[C@@H]2COP(=O)(O)O[C@@H]3[C@H](O)[C@@H](COP(=O)(O)O[C@H]2[C@H]1O)O[C@H]3n1ncc2c(=O)[nH]cnc21]

cGAS buffer consisted of 40 mM Tris-HCL, pH 7.5, 100 uM NaCl, 10 mM MgCl₂. cGAS enzyme was purchased from Novoprotein (Novoprotein code: SGCAS), having been expressed in *E. coli* and purified using a HIS tag. The calculated molecular weight was 55.3 kDa, and the sequence was:

```
                                        (SEQ. ID. NO. 1)
MAHHHHHHGSDSEVNQEAKPEVKPEVKPETHINLKVSDGSSEIFFKIKKT

TPLRRLMEAFAKRQGKEMDSLTFLYDGIEIQADQTPEDLDMEDNDIIEAH

REQIGGENLYFQGGASKLRAVLEKLKLSRDDISTAAGMVKGVVDHLLLRL

KCDSAFRGVGLLNTGSYYEHVKISAPNEFDVMFKLEVPRIQLEEYSNTRA

YYFVKFKRNPKENPLSQFLEGEILSASKMLSKFRKIIKEEINDIKDTDVI

MKRKRGGSPAVTLLISEKISVDITLALESKSSWPASTQEGLRIQNWLSAK

VRKQLRLKPFYLVPKHAKEGNGFQEETWRLSFSHIEKEILNNHGKSKTCC

ENKEEKCCRKDCLKLMKYLLEQLKERFKDKKHLDKFSSYHVKTAFFHVCT

QNPQDSQWDRKDLGLCFDNCVTYFLQCLRTEKLENYFIPEFNLFSSNLID

KRSKEFLTKQIEYERNNEFPVFDEF
```

To a vial were added Herring DNA (CAS #9007-49-2, 0.3 mg/mL in cGAS buffer; 15.2 mL) and cGAS enzyme (3.1 mg/mL in cGAS buffer; 0.8 mL), and the mixture was incubated at RT for 15 min. ATP (5 mM in cGAS buffer, 2.0 mL, 10 μmol), 7-deaza-8-aza-ITP (5 mM in cGAS buffer, 2.0 mL, 10 μmol), and DMSO (5 mL) were added, and the mixture was incubated on a Radleys Metz heater shaker set to maintain 37° C. while shaking at 250 rpm for 3 d. The mixture was filtered, lyopholyzed, and purified by reverse phase HPLC (eluting acetonitrile/water gradient with 100 mM TEAA modifier, linear gradient) to afford the title compound as the TEA salt. LCMS (ES, m/z): 658 [M−H]⁻. $^1$H NMR (600 MHz, D₂O): δ 8.36 (s, 1H), 8.34 (s, 1H), 8.13 (s, 1H), 7.51 (s, 1H), 6.41 (d, J=8.2 Hz, 1H), 6.24 (s, 1H), 5.69 (m, 1H), 5.42 (m, 1H), 4.88 (d, J=4.4 Hz, 1H), 4.66 (d, J=4.1 Hz, 1H), 4.51 (m, 1H), 4.43 (m, 2H), 4.23 (m, 2H), 4.01 (m, 1H).

Examples 67 to 74 in Table 4 below were made using procedures analogous to those described above for Example 66 using the appropriate nucleoside triphosphate monomers. Where necessary, the triphosphates were formed according to methods similar to those described for Preparations 23 to 26 or by submission of the requisite 5'-OH nucleoside monomer to NuBlocks LLC (Oceanside, Calif.).

TABLE 4

| Ex. | Structure | Name | Mass [M − H]⁻ |
|---|---|---|---|
| 67 | 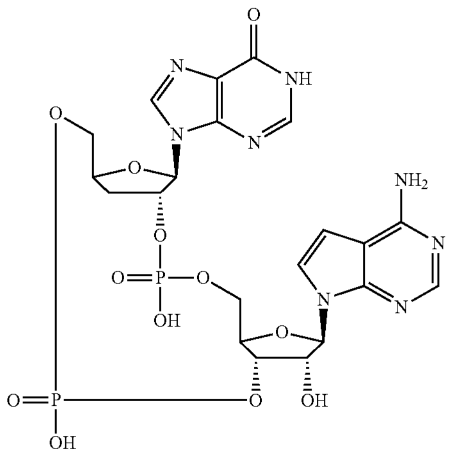 [SMILES: Nc1ncnc2c1ccn2[C@@H]1OC2COP(=O)(O)O[C@@H]3CC(COP(=O)(O)O[C@H]2[C@H]1O)O[C@H]3n1cnc2c(=O)[nH]cnc21] | 9-[(5S,7R,8R,12aR,14R,15R,15aS)-14-(4-amino-7H-pyrrolo[2,3-d]pyrimidin-7-yl)-2,10,15-trihydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 641 |
| 68 | 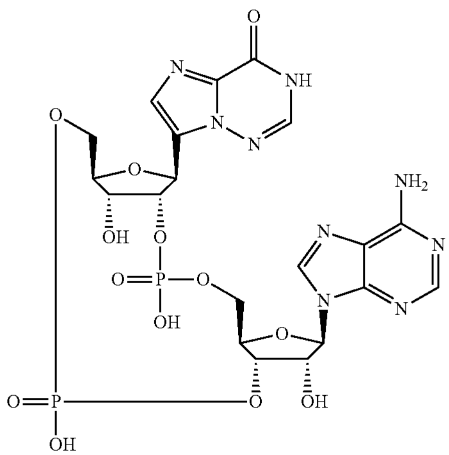 [SMILES: Nc1ncnc2c1ncn2[C@@H]1O[C@@H]2COP(=O)(O)O[C@@H]3[C@H](O)[C@@H](COP(=O)(O)O[C@H]2[C@H]1O)O[C@H]3c1cnc2c(=O)[nH]cnn12] | 7-[(5R,7S,8R,12aR,14R,15R,15aS,16R)-14-(6-amino-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]imidazo[2,1-f][1,2,4]triazin-4(3H)-one | 658 |
| 69 | 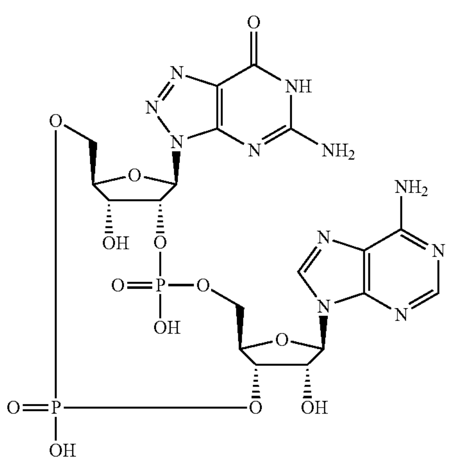 [SMILES: Nc1nc2c(nnn2[C@@H]2O[C@@H]3COP(=O)(O)O[C@H]4[C@@H](O)[C@H](n5cnc6c(N)ncnc65)O[C@@H]4COP(=O)(O)O[C@@H]2[C@@H]3O)c(=O)[nH]1] | 5-amino-3-[(5R,7R,8R,12aR,14R,15R,15aS,16R)-14-(6-amino-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one | 674 |

TABLE 4-continued

| Ex. | Structure | Name | Mass [M − H]⁻ |
|---|---|---|---|
| 70 | 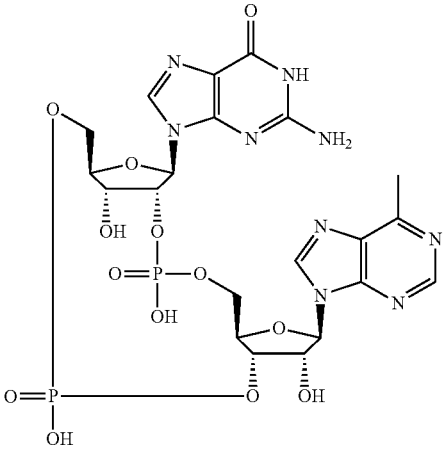 [SMILES: Cc1ncnc2c1ncn2[C@@H]1O[C@@H]2COP(=O)(O)O[C@@H]3[C@H](O)[C@@H](COP(=O)(O)O[C@H]2[C@H]1O)O[C@H]3n1cnc2c(=O)[nH]c(N)nc21] | 2-amino-9-[(5R,7R,8R,12aR,14R,15R,15aS,16R)-2,10,15,16-tetrahydroxy-14-(6-methyl-9H-purin-9-yl)-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 672 |
| 71 | 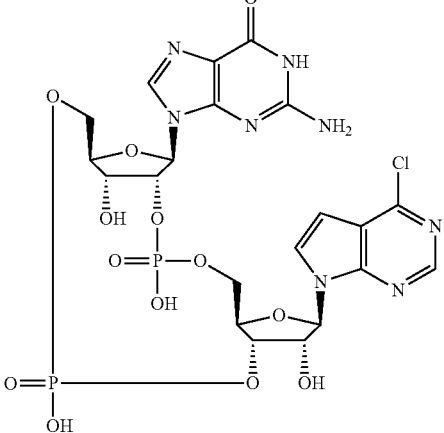 | 2-amino-9-[(5R,7R,8R,12aR,14R,15R,15aS,16R)-14-(4-chloro-7H-pyrrolo[2,3-d]pyrimidin-7-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 691 |
| 72 | 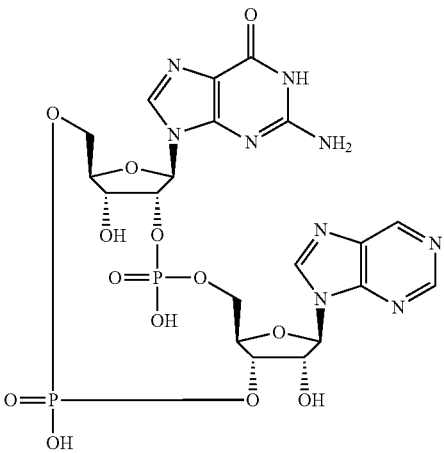 [SMILES: Nc1nc2c(ncn2[C@@H]2O[C@@H]3COP(=O)(O)O[C@H]4[C@@H](O)[C@H](n5cnc6cncnc65)O[C@@H]4COP(=O)(O)O[C@@H]2[C@@H]3O)c(=O)[nH]1] | 2-amino-9-[(5R,7R,8R,12aR,14R,15R,15aS,16R)-2,10,15,16-tetrahydroxy-2,10-dioxido-14-(9H-purin-9-yl)octahydro-12H-5,8-methanofuro[3,2-l][1,3,6,9,11,2,10]pentaoxadiphosphacyclotetradecin-7-yl]-1,9-dihydro-6H-purin-6-one | 658 |

TABLE 4-continued

| Ex. | Structure | Name | Mass [M − H]⁻ |
|---|---|---|---|
| 73 | 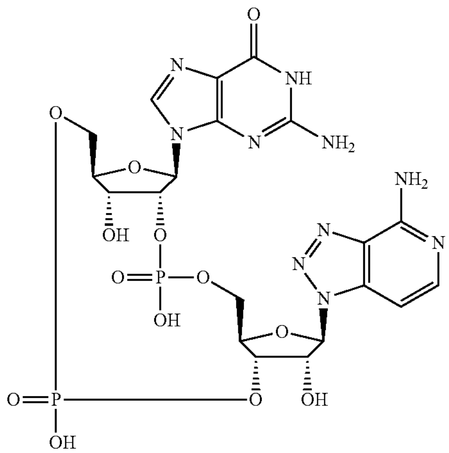 | 2-amino-9-[(5R,7R,8R,12aR,14R,15R,15aS,16R)-14-(4-amino-1H-[1,2,3]triazolo[4,5-c]pyridin-1-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 673 |
| 74 | 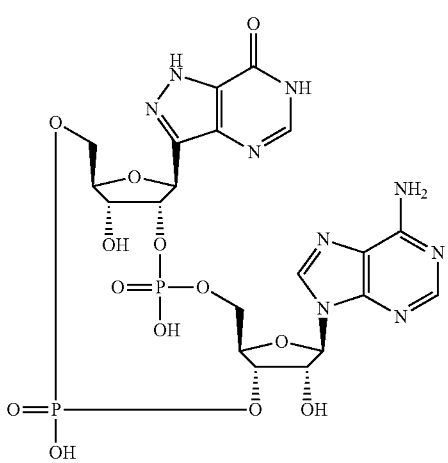 [SMILES: Nc1ncnc2c1ncn2[C@@H]1O[C@@H]2COP(=O)(O)O[C@@H]3[C@H](O)[C@@H](COP(=O)(O)O[C@H]2[C@H]1O)O[C@H]3c1n[nH]c2c(=O)[nH]cnc12] | 3-[(5R,7S,8R,12aR,14R,15R,15aS,16R)-14-(6-amino-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,6-dihydro-7H-pyrazolo[4,3-d]pyrimidin-7-one | 658 |

Example 75: 2-Amino-9-[(5S,7R,8R,12aR,14R,15R, 15aS,16R)-16-amino-14-(6-amino-9H-purin-9-yl)-2, 10,15-trihydroxy-2,10-dioxidooctahydro-12H-5,8-methanofuro[3,2-l][1,3,6,9,11,2,10] pentaoxadiphosphacyclotetradecin-7-yl]-1,9-dihydro-6H-purin-6-one

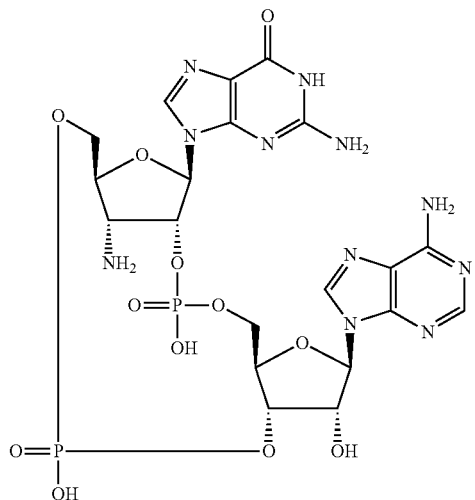 [SMILES: Nc1nc2c(ncn2[C@@H]2O[C@@H]3COP(=O)(O)O[C@H]4[C@@H](O)[C@H](n5cnc6c(N)ncnc65)O[C@@H]4COP(=O)(O)O[C@@H]2[C@@H]3N)c(=O)[nH]1]

Step 1: 2-Amino-9-[(5S,7R,8R,12aR,14R,15R,15aS, 16R)-16-amino-14-(6-amino-9H-purin-9-yl)-2,10, 15-trihydroxy-2,10-dioxidooctahydro-12H-5,8-methanofuro[3,2-l][1,3,6,9,11,2,10] pentaoxadiphosphacyclotetradecin-7-yl]-1,9-dihydro-6H-purin-6-one

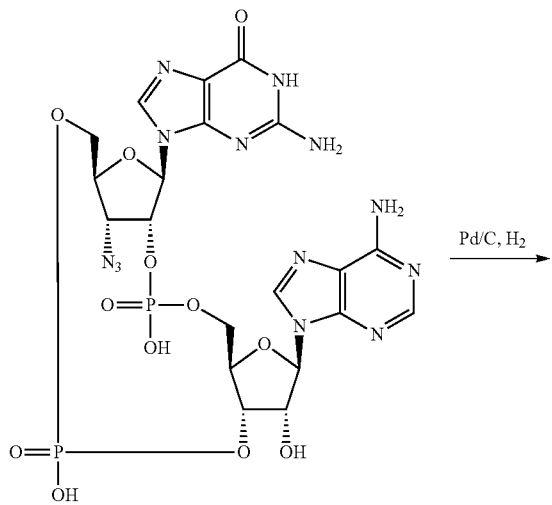

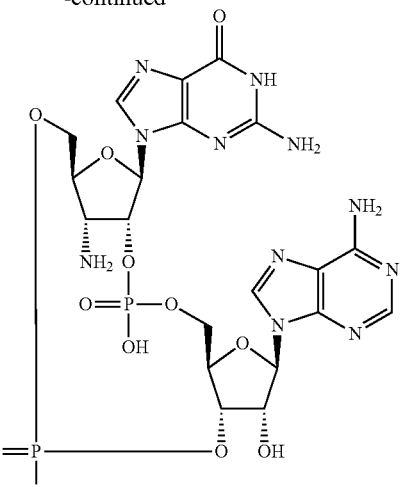

To a stirred solution of 2-amino-9-[(5S,7R,8R,12aR,14R, 15R,15aS,16R)-14-(6-amino-9H-purin-9-yl)-16-azido-2,10, 15-trihydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one (Example 14, 4.0 mg, 0.0055 mmol) in absolute EtOH (1.0 mL) and deionized water (1.0 mL) was added palladium on carbon (1.0 mg, 10 wt. % loading) in one portion under Ar at RT. The reaction vessel was then flushed with hydrogen gas and attached to a hydrogen gas balloon. The reaction mixture was left to stir for 48 h, filtered, and concentrated to afford the title compound. LCMS (ES, m/z): 672 [M–H]⁻. (600 MHz, DMSO-$d_6$) δ 10.70 (s, 1H), 8.42 (s, 1H), 8.12 (s, 1H), 7.96 (s, 1H), 7.70 (s, 1H), 7.29 (br, 2H), 6.56 (br, 2H), 6.00 (d, J=8.3 Hz, 1H), 5.89 (d, J=8.5 Hz, 1H), 5.21 (s, 1H), 5.04 (t, J=6.0 Hz, 1H), 4.16 (s, 1H), 4.05 (dd, J=10.5, 5.0 Hz, 1H), 4.00 (s, 1H), 3.77 (d, J=4.1 Hz, 1H), 3.67 (m, 2H). $^{31}$P NMR: (202 MHz, DMSO-$d_6$): δ −0.4 (s), 2.0 (s).

Alternatively, Example 75 may be prepared from the requisite monomers, according to a method similar to that described above for Example 30.

Example 76: 9-[(5R,7R,8R,12aR,14R,15R,15aS, 16R)-7-(2-amino-6-oxo-1,6-dihydro-9H-purin-9-yl)-2,10,15,16-tetrahydroxy-2,10-dioxidooctahydro-12H-5,8-methanofuro[3,2-l][1,3,6,9,11,2,10] pentaoxadiphosphacyclotetradecin-14-yl]-9H-purine-6-carboxamide

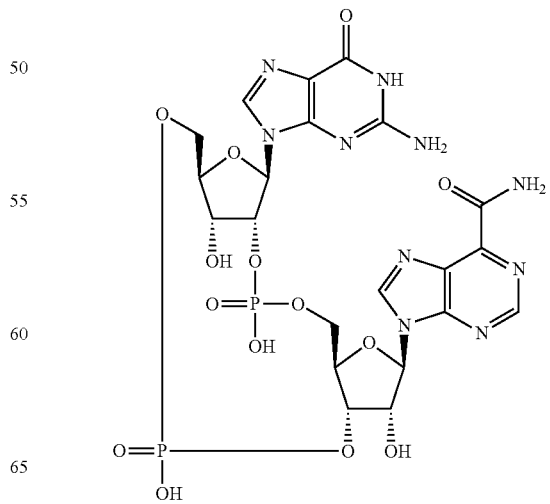

To a stirred solution of 2-amino-9-[(5R,7R,8R,12aR,14R, 15R,15aS,16R)-14-(6-chloro-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one, (Example 32, 16 mg, 0.018 mmol) in DMSO (1.7 mL) was added sodium cyanide (8.0 mg, 0.16 mmol) in one portion under Ar at RT. The reaction mixture was heated to 80° C. and left to stir at the same temperature for 3 h, cooled to ambient temperature, then quenched with cold acetic acid (15 uL). The mixture was filtered and lyophilyzed. The product was purified using mass-directed reverse phase HPLC with a Waters SunFire C18 OBD Prep Column, 100 Å, 5 μm, 19 mm×150 mm, [Waters Part #186002568] using a gradient solvent system with MeCN and 100 mM aqueous triethylammonium acetate. Lyophilization of the product fractions furnished 9-[(5R,7R,8R,12aR,14R,15R,15aS,16R)-7-(2-amino-6-oxo-1,6-dihydro-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-14-yl]-9H-purine-6-carbonitrile. LCMS (ES, m/z): 683 [M–H]⁻.

To a stirred suspension of 9-[(5R,7R,8R,12aR,14R,15R, 15aS,16R)-7-(2-amino-6-oxo-1,6-dihydro-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-14-yl]-9H-purine-6-carbonitrile (3.0 mg, 0.003 mmol) in deionized water (338 uL) was added Hydrido(dimethylphosphinous acid-kP)[hydrogen bis(dimethylphosphinito-kP)]platinum(II) (1.0 mg, 0.002 mmol). The reaction mixture was heated to 85° C. and left to stir at the same temperature for 6 h, cooled to ambient temperature, filtered and lyopholyzed. The product was purified using mass-directed reverse phase HPLC with a Waters SunFire C18 OBD Prep Column, 100 Å, 5 μm, 19 mm×150 mm, [Waters Part #186002568] using a gradient solvent system with MeCN and 100 mM aqueous triethylammonium acetate. Lyopholization of the product fractions furnished 9-[(5R,7R,8R,12aR,14R,15R,15aS,16R)-7-(2-amino-6-oxo-1,6-dihydro-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-14-yl]-9H-purine-6-carboxamide. LCMS (ES, m/z): 701 [M–H]⁻. ¹H NMR (500 MHz, DMSO): δ 10.58 (s, 1H), 9.06 (s, 1H), 8.36 (s, 1H), 8.05 (s, 1H), 7.91 (s, 1H), 7.74 (s, 1H), 6.55 (br, 4H), 6.07 (d, J=7.7 Hz, 1H), 5.81 (d, J=6.0 Hz, 1H), 5.77 (m, 1H), 5.04 (m, 1H), 4.96 (d, J=4.5 Hz, 1H), 4.60 (m, 1H), 4.27 (m, 1H), 4.07-4.04 (m, 2H), 3.99-3.75 (m, 2H). ³¹P NMR: (202 MHz, DMSO): δ 1.9 (s), –0.8 (s).

Examples 77, 78, 79, 80: 2-amino-9-[(5S,7R,8R, 12aR,14R,15R,15aS)-14-(4-amino-7H-pyrrolo[2,3-d]pyrimidin-7-yl)-15-hydroxy-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomers 1-4)

Diastereomer 1

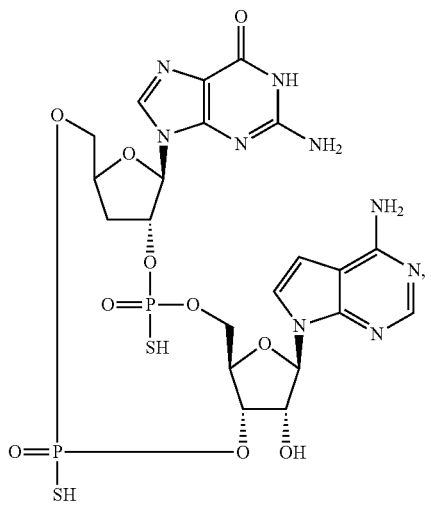

Diastereomer 2

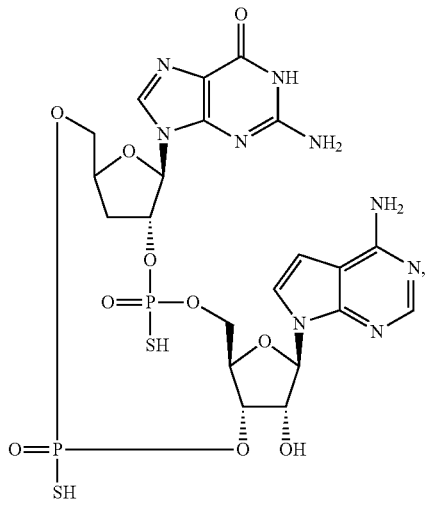

511
-continued
Diastereomer 3
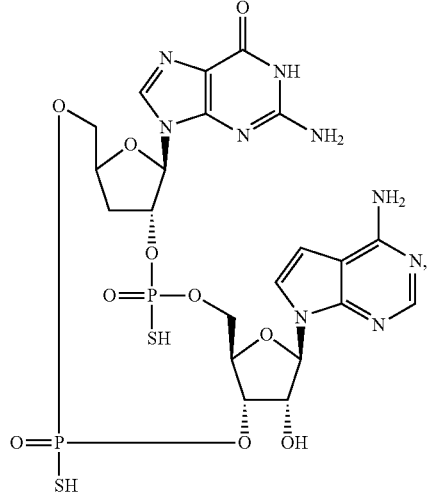
512
-continued
Diastereomer 4
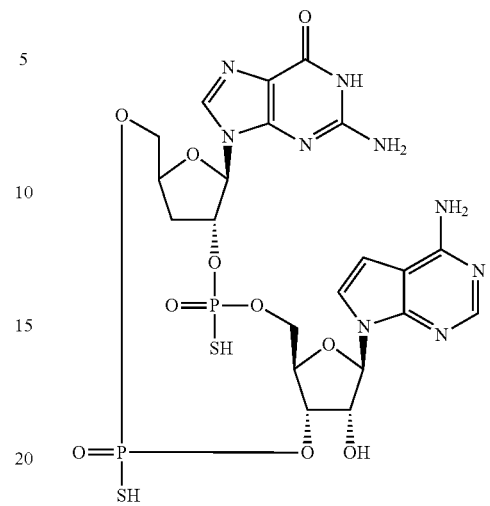
Step 1: (2R,3R)-5-(hydroxymethyl)-2-(2-isobu-tyramido-6-oxo-1,6-dihydro-9H-purin-9-yl)tetrahydrofuran-3-yl hydrogen phosphonate
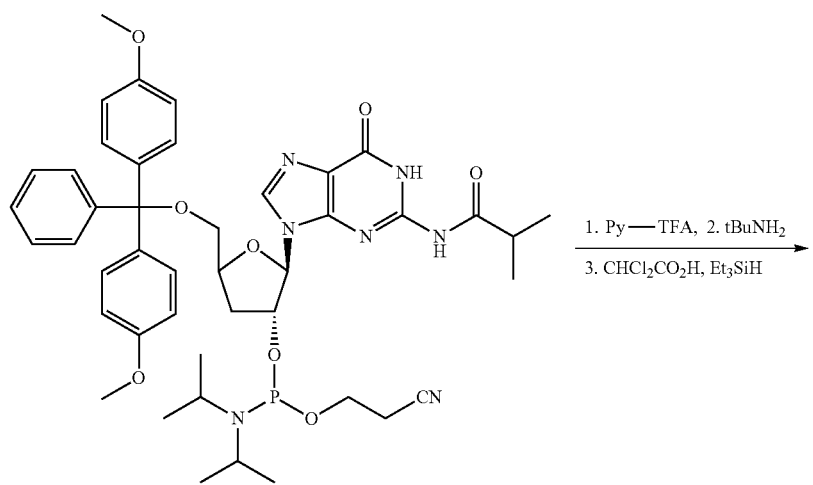
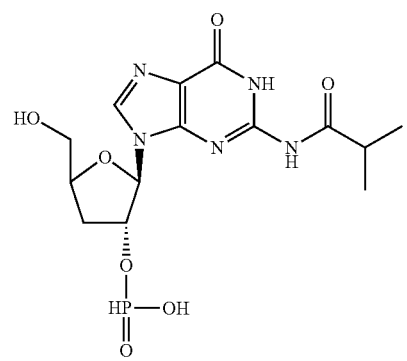

To a flask was added (2R,3R)-5-((bis(4-methoxyphenyl)(phenyl)methoxy)methyl)-2-(2-isobutyramido-6-oxo-1,6-dihydro-9H-purin-9-yl)tetrahydrofuran-3-yl (2-cyanoethyl) diisopropylphosphoramidite (4.00 g, 4.76 mmol), MeCN (23.65 ml), and water (0.158 ml). Pyridine trifluoroacetate (1.104 g, 5.71 mmol) was added, and the reaction was stirred at rt for 1 h. Tert-butylamine (20.02 ml, 190 mmol) was then added, and stirring was continued at rt for 1 h, after which time the reaction was partitioned between hexanes and acetonitrile. The acetonitrile layer was collected and concentrated under vacuum. DCM (39.9 ml) and water (0.798 ml) were added, followed by dichloroacetic acid (55.1 ml, 33.3 mmol), and the solution was stirred for 20 min at rt, after which time triethylsilane (133 ml, 833 mmol) was added, and the reaction was stirred for a further 2 h at rt. The reaction was cooled to 0° C., and pyridine (5.39 mL 66.6 mmol) was added. Then the mixture was concentrated under reduced pressure to give the title compound, which was not purified further. LCMS (ES, m/z): 400 [M−H]⁻.

Step 2: O-((2R,3R,4R,5R)-5-(4-benzamido-7H-pyrrolo[2,3-d]pyrimidin-7-yl)-2-((bis(4-methoxyphenyl)(phenyl)methoxy)methyl)-4-((tert-butyldimethylsilyl)oxy)tetrahydrofuran-3-yl) O-(((2S,4R,5R)-4-((hydroxyhydrophosphoryl)oxy)-5-(2-isobutyramido-6-oxo-1,6-dihydro-9H-purin-9-yl)tetrahydrofuran-2-yl)methyl)O-hydrogen phosphorothioate

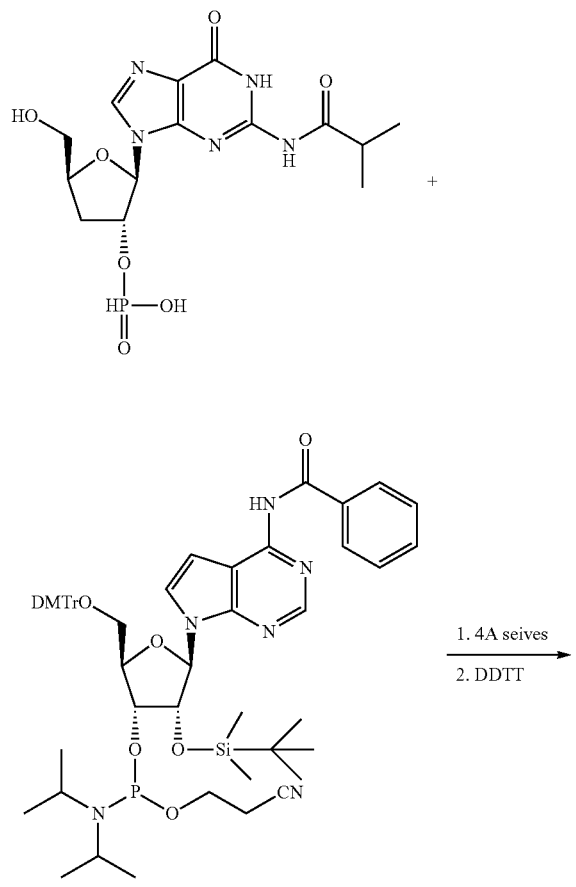

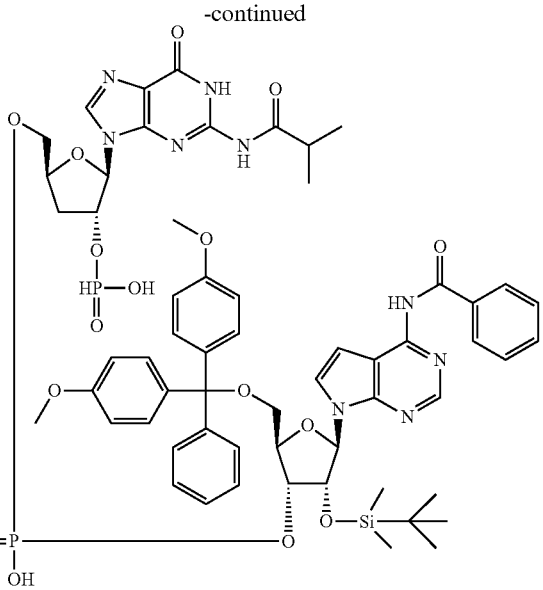

To a flask was added (2R,3R,5S)-5-(hydroxymethyl)-2-(2-isobutyramido-6-oxo-1,6-dihydro-9H-purin-9-yl)tetrahydrofuran-3-yl hydrogen phosphonate (335 mg, 0.836 mmol) and MeCN (20 mL), and then the solution was concentrated under reduced pressure. This process was repeated 2×, and then MeCN (8 mL) was added, followed by activated 4 Å sieves. The mixture was stirred for 20 min at rt. (2R,3R,4R,5R)-5-(4-benzamido-7H-pyrrolo[2,3-d]pyrimidin-7-yl)-2-((bis(4-methoxyphenyl)(phenyl)methoxy)methyl)-4-((tert-butyldimethylsilyl)oxy)tetrahydrofuran-3-yl (2-cyanoethyl) diisopropylphosphoramidite (825 mg, 0.836 mmol) was dissolved in MeCN (5 mL). Molecular sieves (4 Å) were added, and the mixture was stirred for 30 min at rt, after which time this solution was transferred to the hydrogen phosphonate solution and 2×1.5 mL portions of MeCN were used to complete the transfer. After stirring 30 min at rt, ((dimethylamino-methylidine)amino)-3H-1,2,4-dithiazoline-3-thione (189 mg, 0.919 mmol) was added. After stirring 5 min at rt, the mixture was concentrated under reduced pressure and purified using reverse phase HPLC with a 10-100% gradient of MeCN and 100 mM aqueous triethylammonium acetate. The product-containing fractions were collected and lyophilized, during which time the cyanoethyl protecting group was cleaved, to furnish O-((2R,3R,4R,5R)-5-(4-benzamido-7H-pyrrolo[2,3-d]pyrimidin-7-yl)-2-((bis(4-methoxyphenyl)(phenyl)methoxy) methyl)-4-((tert-butyldimethylsilyl)oxy)tetrahydrofuran-3-yl)O-(((2S,4R,5R)-4-((hydroxyhydrophosphoryl)oxy)-5-(2-isobutyramido-6-oxo-1,6-dihydro-9H-purin-9-yl)tetrahydrofuran-2-yl)methyl)O-hydrogen phosphorothioate. LCMS (ES, m/z): 1264 [M−H]⁻.

Step 3: N-{7-[(5S,7R,8R,12aR,14R,15R,15aR)-15-{[tert-butyl(dimethyl)silyl]oxy}-7-{2-[(2-methylpropanoyl)amino]-6-oxo-1,6-dihydro-9H-purin-9-yl}-2,10-dioxido-2,10-disulfanyl}octahydro-12H-5,8-methanofuro[3,2-l][1,3,6,9,11,2,10]pentaoxadiphosphacyclotetradecin-14-yl]-7H-pyrrolo[2,3-d]pyrimidin-4-yl}benzamide (Diastereomers 1-4)

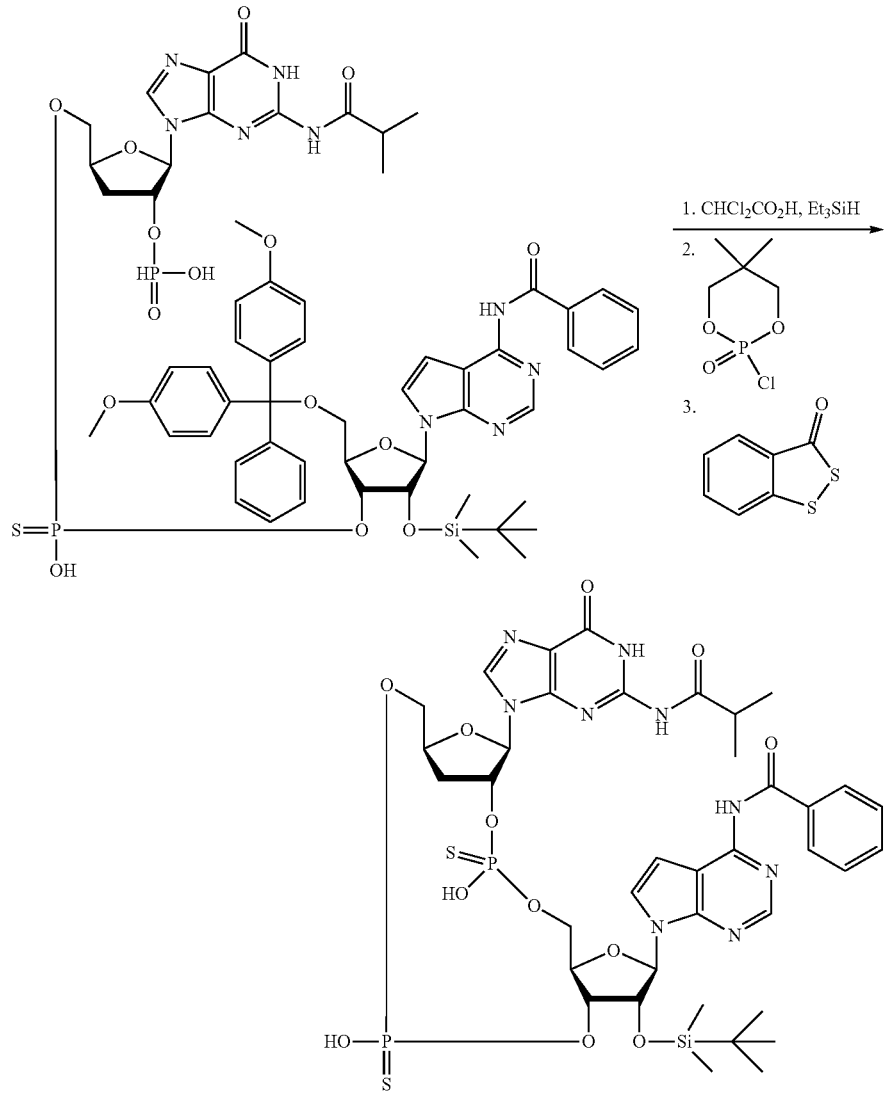

To a flask containing O-((2R,3R,4R,5R)-5-(4-benzamido-7H-pyrrolo[2,3-d]pyrimidin-7-yl)-2-((bis(4-methoxyphenyl)(phenyl)methoxy)methyl)-4-((tert-butyldimethylsilyl)oxy) tetrahydrofuran-3-yl)O-(((2 S,4R,5R)-4-((hydroxyhydrophosphoryl)oxy)-5-(2-isobutyramido-6-oxo-1,6-dihydro-9H-purin-9-yl)tetrahydrofuran-2-yl)methyl)O-hydrogen phosphorothioate (581 mg, 0.440 mmol) was added DCM (8.81 mL), water (0.079 mL, 4.40 mmol) and then dichloroacetic acid (8.74 mL, 5.28 mmol). The mixture was stirred for 15 min at rt, and then triethylsilane (10.97 mL, 68.7 mmol) was added. The mixture was stirred at rt for 1.5 h and then concentrated under reduced pressure. The mixture was dissolved in pyridine (10 mL) and then concentrated under reduced pressure. This process was repeated 2×, and then the resulting sample was dissolved in pyridine (17 ml) and 2-chloro-5,5-dimethyl-1,3,2-dioxaphosphorinan-2-one (81 mg, 0.440 mmol) was added in 1 portion at rt. After stirring for 30 min at rt, additional 2-chloro-5,5-dimethyl-1,3,2-dioxaphosphorinan-2-one (81 mg, 0.440 mmol) was added. This sequence was repeated twice, and then water (238 μl, 13.19 mmol) and 3H-1,2-benzodithiol-3-one (111 mg, 0.660 mmol) were added. The mixture was stirred for 1 h at rt and then partitioned between water (10 mL) and 1:1 EtOAc/ether (10 mL). The layers were separated, and the aqueous phase was extracted with 1:1 EtOAc/ether (3×10 mL). The combined organic phases were dried (MgSO₄), filtered, and concentrated under reduced pressure. Reverse phase HPLC purification (gradient of 30-100% MeCN and 100 mM aqueous triethylammonium acetate) furnished 4 diastereomers of N-{7-[(5S,7R,8R,12aR,14R,15R,15aR)-15-{[tert-butyl(dimethyl) silyl]oxy}-7-{2-[(2-methylpropanoyl)amino]-6-oxo-1,6-dihydro-9H-purin-9-yl}-2,10-dioxido-2,10-disulfanyl}octahydro-12H-5,8-methanofuro[3,2-l][1,3,6,9,11,2,10]pentaoxadiphosphacyclotetradecin-14-yl]-7H-pyrrolo[2,3-d]pyrimidin-4-yl}benzamide, all of which showed LCMS (ES, m/z): 976 [M−H]⁻.

Step 4: 2-amino-9-[(5S,7R,8R,12aR,14R,15R, 15aS)-14-(4-amino-7H-pyrrolo[2,3-d]pyrimidin-7-yl)-15-hydroxy-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomers 1-4)

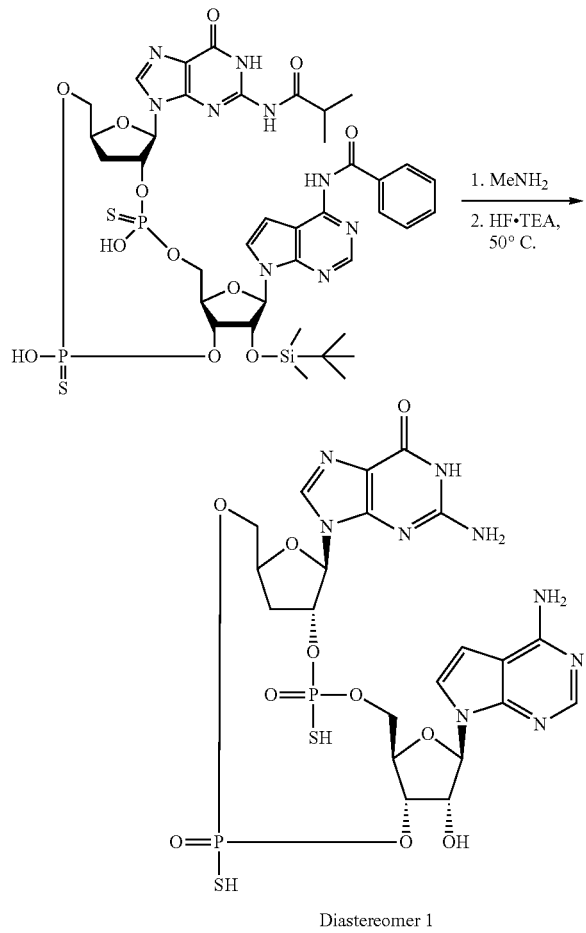

Diastereomer 1

To a flask containing N-{7-[(5 S,7R,8R,12aR,14R,15R, 15aR)-15-{[tert-butyl(dimethyl)silyl]oxy}-7-{2-[(2-methylpropanoyl)amino]-6-oxo-1,6-dihydro-9H-purin-9-yl}-2,10-dioxido-2,10-disulfanyl}octahydro-12H-5,8-methanofuro[3,2-l][1,3,6,9,11,2,10]pentaoxadiphosphacyclotetradecin-14-yl]-7H-pyrrolo[2,3-d]pyrimidin-4-yl}benzamide (fastest eluting peak, 7.4 mg, 7.57 µmol) was added methylamine (33% in EtOH) (1 mL, 8.03 mmol), and the mixture was stirred at rt for 4 h, after which time the mixture was concentrated under reduced pressure. Pyridine (1 mL) was added, and the mixture was concentrated under reduced pressure. Then, pyridine (0.5 ml), triethylamine (0.104 ml, 0.746 mmol) and triethylamine trihydrofluoride (0.030 ml, 0.187 mmol) were added, and the mixture was stirred at 50° C. for 16 h, after which time the mixture was cooled to rt and concentrated under reduced pressure. Purification by reverse phase HPLC (gradient of acetonitrile and 100 mM aqueous triethylammonium acetate) furnished Example 77, 2-amino-9-[(5S,7R,8R,12aR,14R,15R,15aS)-14-(4-amino-7H-pyrrolo[2,3-d]pyrimidin-7-yl)-15-hydroxy-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1). LCMS (ES, m/z): 688 [M−H]⁻. ¹H NMR (600 MHz, Deuterium Oxide) δ 8.06 (s, 1H), 8.03 (s, 1H), 7.41 (d, J=3.8 Hz, 1H), 6.25 (d, J=3.7 Hz, 1H), 6.17 (d, J=2.6 Hz, 1H), 5.68 (d, J=7.5 Hz, 1H), 5.42-5.36 (m, 2H), 5.10-5.06 (m, 1H), 4.83-4.81 (m, 1H), 4.51-4.48 (m, 1H), 4.36-4.33 (m, 1H), 4.28 (dt, J=10.1, 4.9 Hz, 1H), 4.06-3.94 (m, 2H), 3.03 (q, J=7.3 Hz, 12H), 2.44-2.40 (m, 2H), 1.11 (t, J=7.3 Hz, 18H).

The other diastereomers from Step 3 were individually processed in an analogous manner to afford three additional diastereomeric products:

Example 78: 2-Amino-9-[(5 S,7R,8R,12aR,14R,15R, 15aS)-14-(4-amino-7H-pyrrolo[2,3-d]pyrimidin-7-yl)-15-hydroxy-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2). LCMS (ES, m/z): 688 [M−H]⁻. ¹H NMR (600 MHz, Deuterium Oxide) δ 8.04 (s, 1H), 7.75 (s, 1H), 7.50 (d, J=3.6 Hz, 1H), 6.19-6.17 (m, 1H), 6.16 (d, J=3.7 Hz, 1H), 5.65 (d, J=7.4 Hz, 1H), 5.63-5.57 (m, 1H), 5.14 (td, J=7.8, 4.4 Hz, 1H), 4.54 (d, J=4.2 Hz, 1H), 4.52-4.46 (m, 1H), 4.33 (d, J=8.9 Hz, 1H), 4.27 (dd, J=11.9, 3.1 Hz, 1H), 4.18-4.15 (m, 1H), 3.96 (dd, J=11.4, 3.6 Hz, 2H), 3.04 (q, J=7.3 Hz, 12H), 2.44-2.36 (m, 2H), 1.11 (t, J=7.3 Hz, 18H).

Example 79: 2-Amino-9-[(5 S,7R,8R,12aR,14R,15R, 15aS)-14-(4-amino-7H-pyrrolo[2,3-d]pyrimidin-7-yl)-15-hydroxy-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 3). LCMS (ES, m/z): 688 [M−H]⁻. ¹H NMR (600 MHz, Deuterium Oxide) δ 8.00 (s, 1H), 7.97 (s, 1H), 7.19 (d, J=3.8 Hz, 1H), 6.15 (d, J=3.8 Hz, 2H), 5.66 (d, J=7.3 Hz, 1H), 5.32 (dq, J=9.9, 7.2 Hz, 1H), 4.95 (td, J=8.6, 4.6 Hz, 1H), 4.81 (d, J=4.4 Hz, 1H), 4.50 (d, J=8.0 Hz, 1H), 4.32 (d, J=7.8 Hz, 1H), 4.25 (dt, J=12.0, 3.6 Hz, 1H), 4.05-3.97 (m, 3H), 3.03 (q, J=7.3 Hz, 12H), 2.51-2.41 (m, 2H), 1.11 (t, J=7.3 Hz, 18H).

Example 80: 2-Amino-9-[(5 S,7R,8R,12aR,14R,15R, 15aS)-14-(4-amino-7H-pyrrolo[2,3-d]pyrimidin-7-yl)-15-hydroxy-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 4). LCMS (ES, m/z): 688 [M−H]⁻. ¹H NMR (600 MHz, Deuterium Oxide) δ 8.00 (s, 1H), 7.72 (s, 1H), 7.23 (d, J=3.8 Hz, 1H), 6.14 (s, 1H), 6.12 (d, J=3.7 Hz, 1H), 5.64 (d, J=6.9 Hz, 1H), 5.47 (dq, J=14.2, 7.0 Hz, 1H), 5.05 (td, J=8.0, 4.5 Hz, 1H), 4.52 (d, J=4.4 Hz, 1H), 4.49 (dt, J=7.4, 2.7 Hz, 1H), 4.33-4.27 (m, 2H), 4.19 (ddd, J=11.5, 8.5, 3.0 Hz, 1H), 4.00 (dd, J=11.5, 3.9 Hz, 1H), 3.94 (ddd, J=11.6, 5.6, 2.2 Hz, 1H), 3.01 (q, J=7.3 Hz, 12H), 2.49-2.40 (m, 2H), 1.10 (t, J=7.3 Hz, 18H).

Example 81: 2-amino-9-[(5R,7R,8R,12aR,14R,15R, 15aR,16R)-14-(6-amino-9H-purin-9-yl)-15-fluoro-2, 10,16-trihydroxy-2,10-disulfidooctahydro-12H-5,8-methanofuro[3,2-l][1,3,6,9,11,2,10] pentaoxadiphosphacyclotetradecin-7-yl]-1,9-dihydro-6H-purin-6-one (Diastereomer 1)

Diastereomer 1

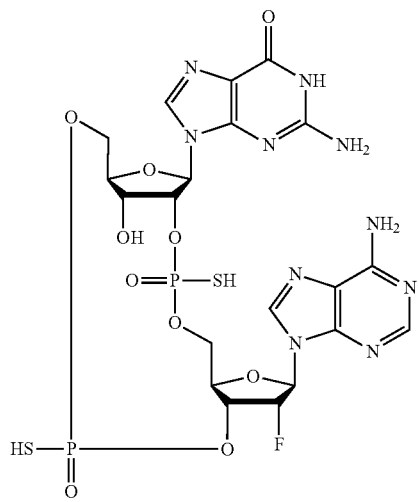

Step 1: (2R,3R,4R,5R)-4-((tert-butyldimethylsilyl) oxy)-5-(hydroxymethyl)-2-(2-isobutyramido-6-oxo-1,6-dihydro-9H-purin-9-yl)tetrahydrofuran-3-yl phosphonate

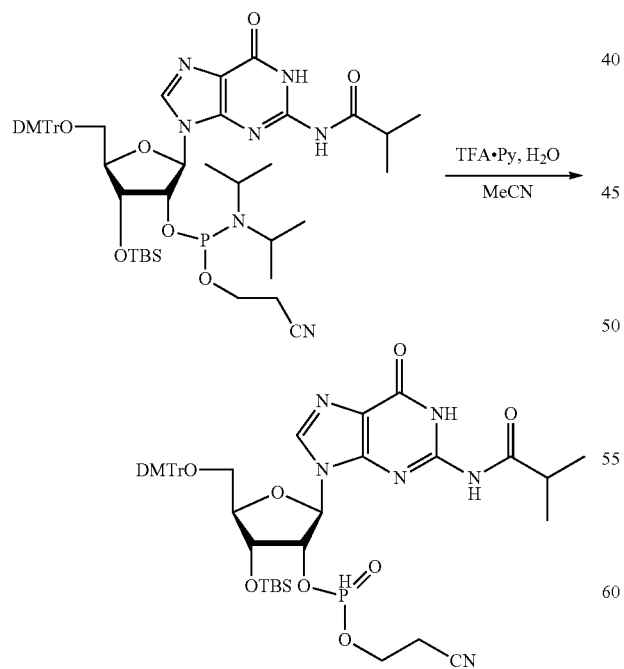

To a stirred solution of (2R,3R,4R,5R)-5-((bis(4-methoxyphenyl)(phenyl) methoxy)methyl)-4-((tert-butyldimethylsilyl)oxy)-2-(2-isobutyramido-6-oxo-1,6-dihydro-9H-purin-9-yl)tetrahydrofuran-3-yl (2-cyanoethyl) diisopropylphosphoramidite (3 g, 3.09 mmol) in MeCN (15 mL) at 25° C. was added $H_2O$ (0.111 mL, 6.18 mmol) and pyridin-1-ium 2,2,2-trifluoroacetate (0.717 g, 3.71 mmol). The resulting mixture was stirred at 25° C. for 20 min. The reaction progress was monitored by LCMS/TLC. After the phosphoramidite starting material was consumed, the reaction mixture that containing the desired product (major) was used for the next step without any after-treatment. LCMS (ES, m/z): 887.4 $[M+H]^+$.

Step 2: (2R,3R,4R,5R)-5-((bis(4-methoxyphenyl) (phenyl)methoxy)methyl)-4-((tert-butyldimethylsilyl)oxy)-2-(2-isobutyramido-6-oxo-1,6-dihydro-9H-purin-9-yl)tetrahydrofuran-3-yl phosphonate

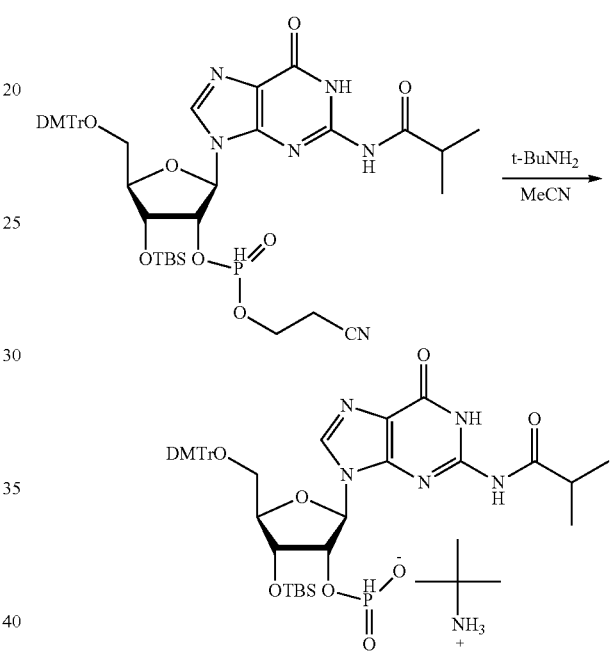

To a stirred solution of the product of Step 1 (15.0 mL, 142 mmol) from the previous reaction was added tert-butylamine in one portion, and it was stirred at 25° C. for 40 min. The resulting solution was concentrated in vacuo. The residue was co-evaporated with dry MeCN (two times, 15 mL each), used for the next step without purification. LCMS (ES, m/z): 832.3 $[M-H]^-$.

Step 3: (2R,3R,4R,5R)-4-((tert-butyldimethylsilyl) oxy)-5-(hydroxymethyl)-2-(2-isobutyramido-6-oxo-1,6-dihydro-9H-purin-9-yl)tetrahydrofuran-3-yl phosphonate

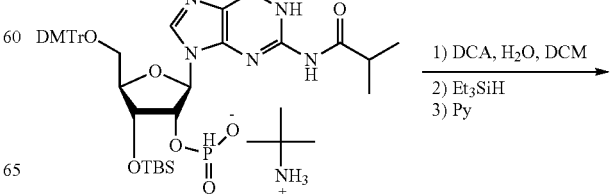

521

-continued

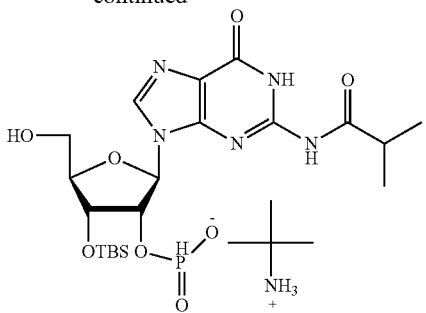

To a stirred solution of the product of Step 2 in CH$_2$Cl$_2$ (37 mL) was added H$_2$O (0.558 mL, 31.0 mmol) and 6% DCA in CH$_2$Cl$_2$ (37 mL, 31.5 mmol) dropwise. The resulting mixture was stirred at 25° C. for 40 min, then Et$_3$SiH (60 mL) was added, and the reaction mixture was stirred for 1.5 h. Pyridine (4.5 mL, 2 eq to DCA) was added to the reaction. The resulting solution was stirred at 25° C. for 5 min and then concentrated in vacuo. The residue was triturated with MTBE/hexane (100 mL, v/v, 1/1), and the supernatant was decanted. This process was repeated two more times. The final residue was concentrated at reduced pressure and was used for the next step without purification. LCMS (ES, m/z): 532.18 [M+H]$^+$.

Step 4. (2R,3R,4R,5R)-5-(((((2R,3R,4R,5R)-5-(6-benzamido-9H-purin-9-yl)-2-((bis(4-methoxyphenyl)(phenyl)methoxy)methyl)-4-fluorotetrahydrofuran-3-yl)oxy)(2-cyanoethoxy)phosphanyl)oxy)methyl)-4-((tert-butyldimethylsilyl)oxy)-2-(2-isobutyramido-6-oxo-1,6-dihydro-9H-purin-9-yl)tetrahydrofuran-3-yl phosphonate

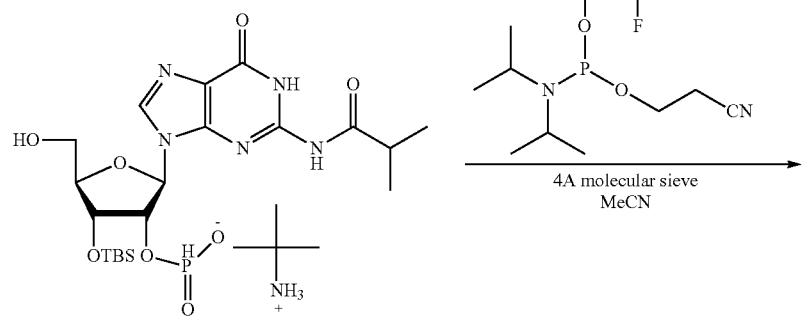

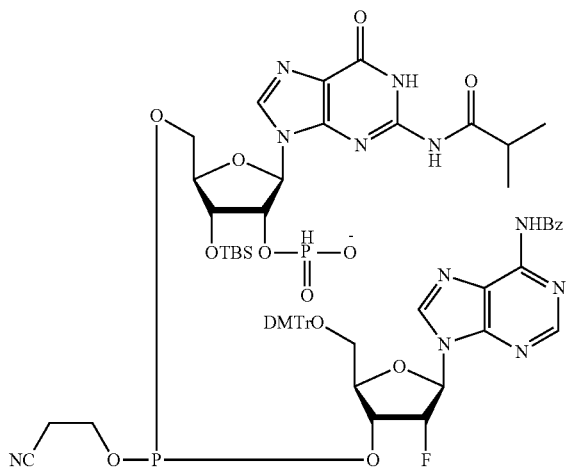

To a stirred solution of the product of Step 3 (0.704 g, 0.722 mmol) in MeCN (5 mL) under Ar was added activated 4 Å molecular sieve (200 mg), and the mixture was stirred at RT over 30 min. (2R,3R,4R,5R)-5-(6-benzamido-9H-purin-9-yl)-2-((bis(4-methoxyphenyl)(phenyl) methoxy) methyl)-4-fluorotetrahydrofuran-3-yl (2-cyanoethyl) diisopropylphosphoramidite (0.822 g, 0.939 mmol) was twice co-evaporated with dry MeCN (3 mL). Activated 4 Å molecular sieve (200 mg) was added. After 30 min, the phosphoramidite solution was transferred into the solution of the product of Step 3 by syringe. The resulting mixture was stirred at RT for 20 min. The desired product was detected by TLC/LCMS, and the reaction solution was used for the next reaction without purification. LCMS (ES, m/z): 1306.7 [M+H]$^+$.

Step 5. (2R,3R,4R,5R)-5-((((((2R,3R,4R,5R)-5-(6-benzamido-9H-purin-9-yl)-2-((bis(4-methoxyphenyl)(phenyl)methoxy)methyl)-4-fluorotetrahydrofuran-3-yl)oxy)(2-cyanoethoxy)phosphorothioyl)oxy)methyl)-4-((tert-butyldimethylsilyl)oxy)-2-(2-isobutyramido-6-oxo-1,6-dihydro-9H-purin-9-yl) tetrahydrofuran-3-yl phosphonate

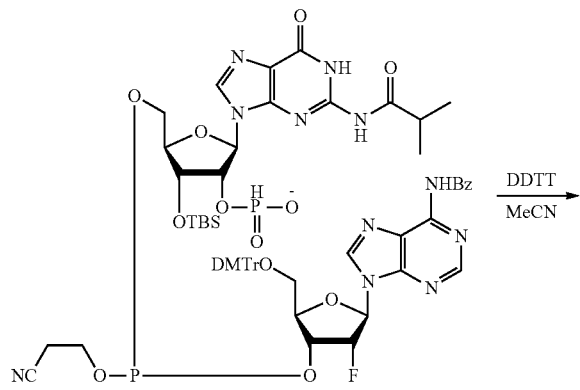

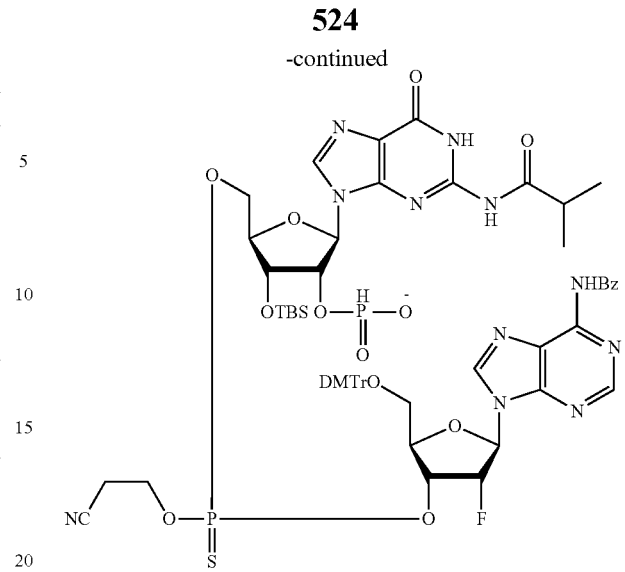

To the reaction mixture containing the product of Step 4 (~0.722 mmol) under Ar was added (E)-N,N-dimethyl-N'-(3-thioxo-3H-1,2,4-dithiazol-5-yl)formimidamide (163 mg, 0.794 mmol) in one portion, and the mixture was stirred at RT for 30 min. The reaction progress was monitored by TLC/LCMS. After the consumption of the starting phosphite, the reaction mixture was concentrated in vacuo, and the residue was purified by reverse phase chromatography (X-Bridge BEH130 Prep C18) eluting with 5 to 95% MeCN in H$_2$O (0.04% NH$_4$HCO$_3$). The product-containing fractions were combined and concentrated under reduced pressure to 2/3 volume. NaCl (10 g) was added, and the aqueous mixture was extracted with EtOAc/Et$_2$O (v/v, 1/1, 3×80 mL). The combined organic layers were dried (Na$_2$SO$_4$) and concentrated. LCMS (ES, m/z): 1339.5 [M+H]$^+$. $^{31}$P-NMR (162 MHz, CD$_3$OD): δ 67.83 (d, J=43.9 Hz), 2.81 (d, J=15.7 Hz).

Step 6. (2R,3R,4R,5R)-5-((((((2R,3R,4R,5R)-5-(6-benzamido-9H-purin-9-yl)-4-fluoro-2-(hydroxymethyl)tetrahydrofuran-3-yl)oxy)(2-cyanoethoxy) phosphorothioyl)oxy)methyl)-4-((tert-butyldimethylsilyl)oxy)-2-(2-isobutyramido-6-oxo-1,6-dihydro-9H-purin-9-yl)tetrahydrofuran-3-yl phosphonate

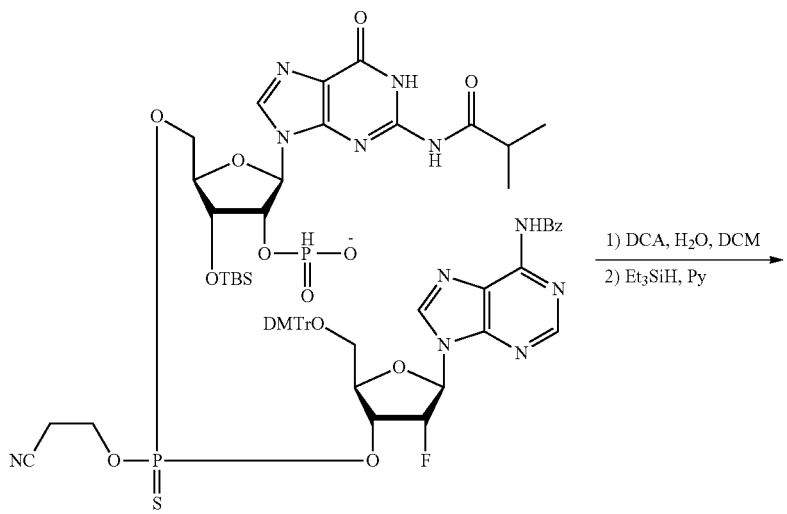

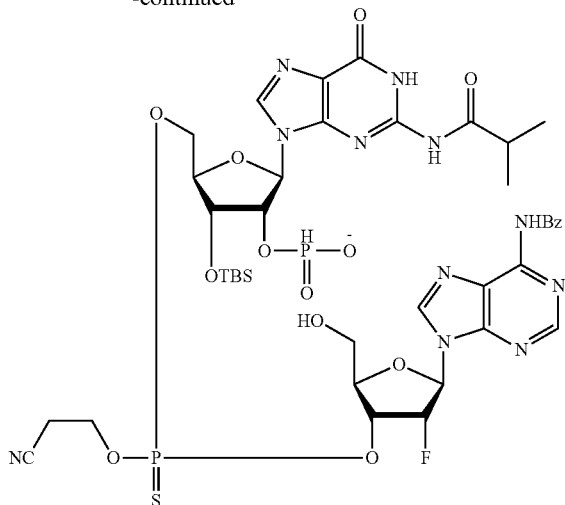

To a stirred solution of the product of Step 5 (180 mg, 0.128 mmol) in CH$_2$Cl$_2$ (7 mL) was added 2,2-dichloroacetic acid in CH$_2$Cl$_2$ (2.47 mg, 1.15 mmol) and H$_2$O (22.97 mg, 1.28 mmol). After stirring at RT for 20 min, Et$_3$SiH (4.5 mL) was added. After 2 h, pyridine (1 mL) was added, and the mixture was stirred for 10 min. After removal of volatiles, the product was used for the next reaction step without purification. LCMS (ES, m/z): 1036.4 [M+H]$^+$.

Step 7: (5R,7R,8R,12aR,14R,15R,15aR,16R)-16-{[tert-butyl(dimethyl)silyl]oxy}-2-(2-cyanoethoxy)-15-fluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10]pentaoxadiphosphacyclotetradecin-10-olate 2-sulfide

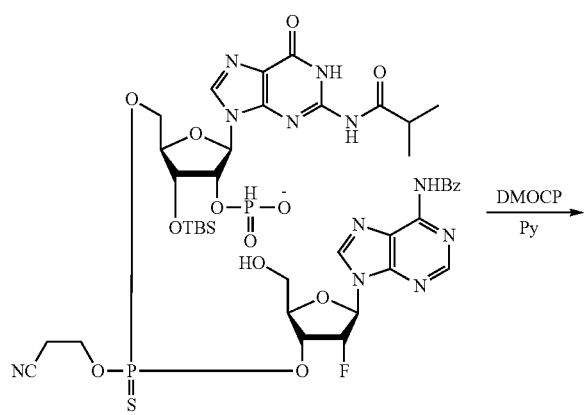

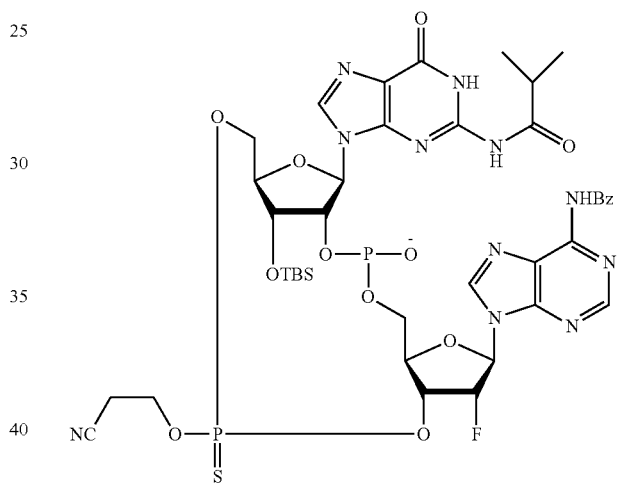

The product of Step 6 (570 mg) was co-evaporated with dry pyridine (1 mL each, three times). To the mixture in dry pyridine (4 mL) at RT under Ar was added 2-chloro-5,5-dimethyl-1,3,2-dioxaphosphinane 2-oxide (71 mg, 0.384 mmol) in one portion. The resulting mixture was stirred for 40 min. The reaction progress was monitored by TLC/LCMS. The desired product as a mixture of diastereomers was observed, and the product was used for the next reaction step directly. LCMS (ES, m/z): 1018.5 [M+H]$^+$.

Step 8: Diastereomeric mixtures (5R,7R,8R,12aR, 14R,15R,15aR,16R)-16-{[tert-butyl(dimethyl)silyl]oxy}-2-(2-cyanoethoxy)-15-fluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10]pentaoxadiphosphacyclotetradecine-O-thiolate 10-oxide 2-sulfide (A1) and (5R,7R,8R,12aR,14R,15R,15aR,16R)-16-{[tert-butyl(dimethyl)silyl]oxy}-2-(2-cyanoethoxy)-15-fluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10]pentaoxadiphosphacyclotetradecine-10-thiolate 10-oxide 2-sulfide (A2)

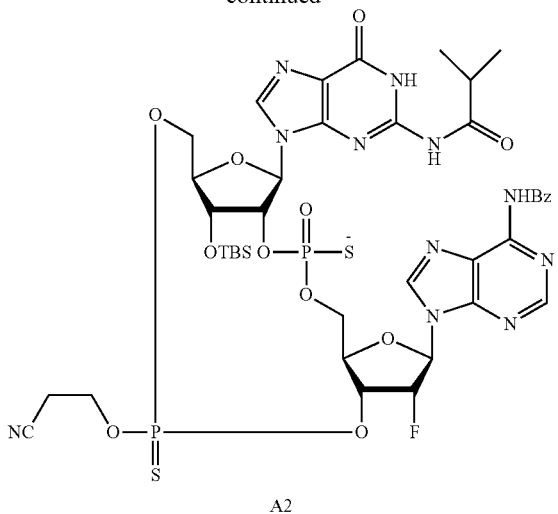

A2

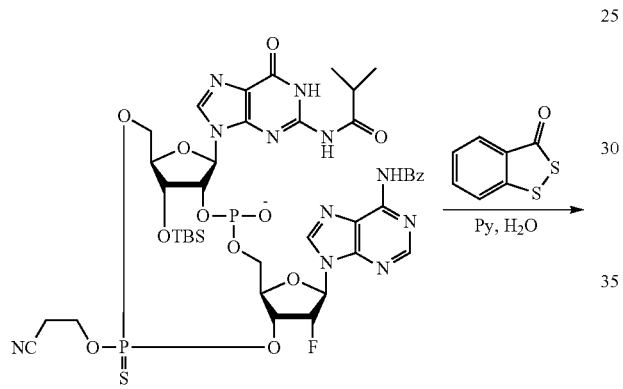

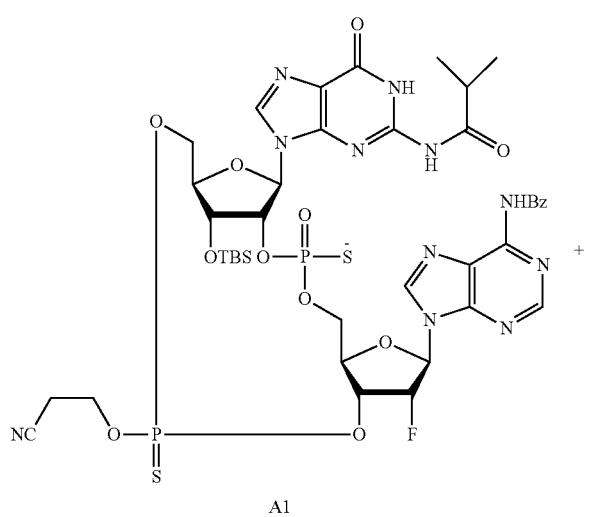

A1

To the stirred mixture of the product of Step 7 was added $H_2O$ (69.2 mg, 3.84 mmol) and 3H-benzo[c][1,2]dithiol-3-one (32.3 mg, 0.192 mmol). The mixture was stirred at RT for 40 min. The reaction progress was monitored by TLC/LCMS. After the reaction completed, the reaction mixture was poured into aq $NaHCO_3$ (0.14 g $NaHCO_3$ in 5 mL $H_2O$) and stirred for 5 min. The resulting mixture was extracted with EtOAc/ether (v/v, 1/1, 3×15 mL). The combined organic layers were dried ($Na_2SO_4$), and purified by silica gel chromatography eluted with 0 to 15% MeOH in $CH_2Cl_2$ to give products: mixture of diastereomers A1 (eluted out at 5.5% MeOH in $CH_2Cl_2$); mixture of diastereomers A2 (eluted out at 9.8% MeOH in $CH_2Cl_2$); (2R,3R,4R,5R)-5-((((((2R,3R,4R,5R)-5-(6-benzamido-9H-purin-9-yl)-4-fluoro-2-(hydroxymethyl)tetrahydrofuran-3-yl)oxy)(2-cyanoethoxy)phosphorothioyl)oxy)methyl)-4-((tert-butyldimethyl silyl)oxy)-2-(2-isobutyramido-6-oxo-1,6-dihydro-9H-purin-9-yl)tetrahydrofuran-3-yl phosphonate (eluted out at 12.6% MeOH in $CH_2Cl_2$). Mixture A1: LCMS (ES, m/z): 1050.30 [M+H]$^+$. $^{31}$P-NMR (162 MHz, $CD_3OD$): δ 66.34 (s), 64.63 (s). Mixture A2: LCMS (ES, m/z): 1050.30 [M+H]$^+$. $^{31}$P-NMR (162 MHz, $CD_3OD$): δ 65.94, 64.17, 62.55, 61.28.

Step 9: Diastereomers (5R,7R,8R,12aR,14R,15R, 15aR,16R)-16-{[tert-butyl(dimethyl)silyl]oxy}-15-fluoro-7-{2-[(2-methylpropanoyl)amino-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10] pentaoxadiphosphacyclotetradecine-2,10-bis(thiolate) 2,10-dioxide (B1) and (5R,7R,8R,12aR, 14R,15R,15aR,16R)-16-{[tert-butyl(dimethyl)silyl]oxy}-15-fluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l]1,3,6,9,11,2,10] pentaoxadiphosphacyclotetradecine-2,10-bis(thiolate) 2,10-dioxide (B2)

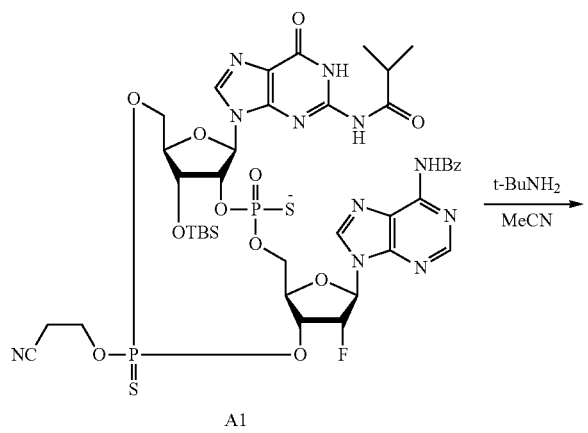

A1

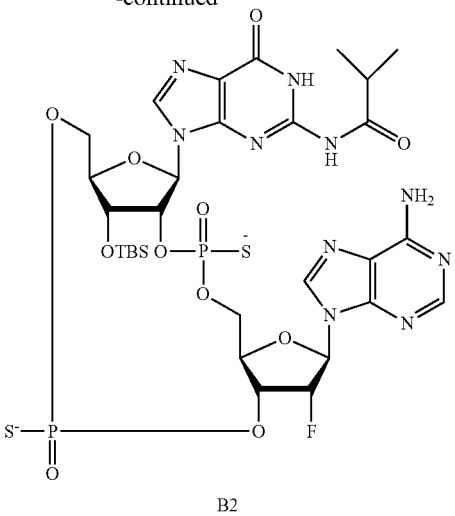

B2

To a stirred suspension of crude A1 (95 mg, ~0.09 mmol) from the previous step in MeCN (1 mL) at RT under Ar was added tert-butylamine (1.5 mL). After 30 min, volatile components were removed in vacuo. The residue was purified by reverse phase prep-HPLC (X-Bridge BEH130 Prep C18) eluted with 25 to 45% MeCN in aq NH$_4$HCO$_3$ (10 mM) over 8 min to give compound B2 as a single diastereomer (T$_R$=5.97 min). LCMS (ES, m/z): 891.4 [M–H]$^-$. H-NMR (300 MHz, CD$_3$OD): δ 8.44 (s, 1H), 8.22 (s, 1H), 8.09 (s, 1H), 6.37 (d, J=14.0 Hz, 1H), 5.95 (d, J=8.0 Hz, 1H), 5.65-5.54 (m, 1H), 5.26-5.10 (m, 2H), 4.57-4.41 (m, 4H), 4.24 (s, 1H), 4.01 (d, J=11.5 Hz, 1H), 3.89 (d, J=11.8 Hz, 1H), 2.75-2.63 (m, 1H), 1.04-0.91 (m, 15H), 0.28-0.24 (m, 6H). $^{31}$P-NMR (121 MHz, CD$_3$OD): δ 57.10 (s), 53.1 (s).

Step 10: (5R,7R,8R,12aR,14R,15R,15aR,16R)-7-(2-amino-6-oxo-1,6-dihydro-9H-purin-9-yl)-14-(6-amino-9H-purin-9-yl)-16-{[tert-butyl(dimethyl)silyl]oxy}-15-fluorooctahydro-12H-5,8-methanofuro[3,2-l][1,3,6,9,11,2,10] pentaoxadiphosphacyclotetradecine-2,10-bis(thiolate) 2,10-dioxide

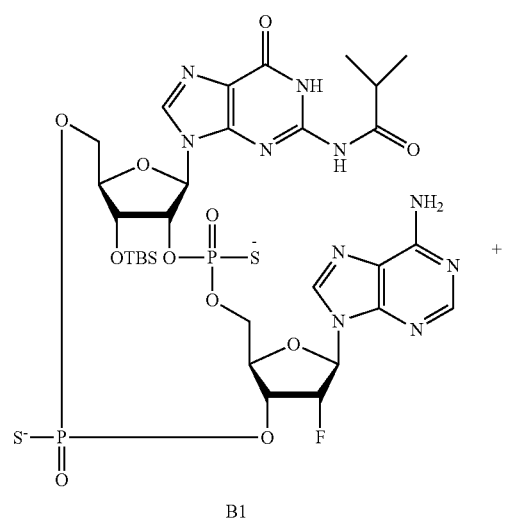

B1

+

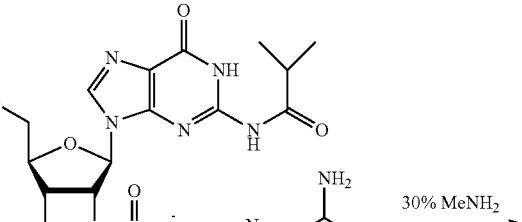

B2

30% MeNH$_2$ / EtOH →

531
-continued

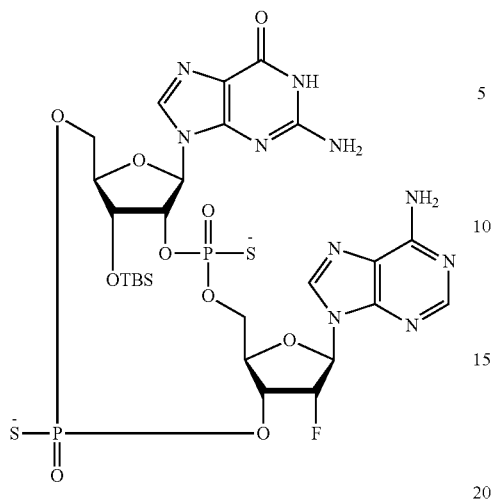

To a stirred solution of compound B2 (13 mg, 0.013 mmol) from the previous step was added a solution of MeNH$_2$ in EtOH (0.6 mL, 30% by weight). The mixture was stirred at RT for 12 h. The volatile components were removed under reduced pressure, and the residue containing product compound was used for the next reaction step without purification. LCMS (ES, m/z): 823.15 [M+H]$^+$.

Step 11: 2-amino-9-[(5R,7R,8R,12aR,14R,15R, 15aR,16R)-14-(6-amino-9H-purin-9-yl)-15-fluoro-2, 10,16-trihydroxy-2,10-disulfidooctahydro-12H-5,8-methanofuro[3,2-l][1,3,6,9,11,2,10] pentaoxadiphosphacyclotetradecin-7-yl]-1,9-dihydro-6H-purin-6-one (Diastereomer 1)

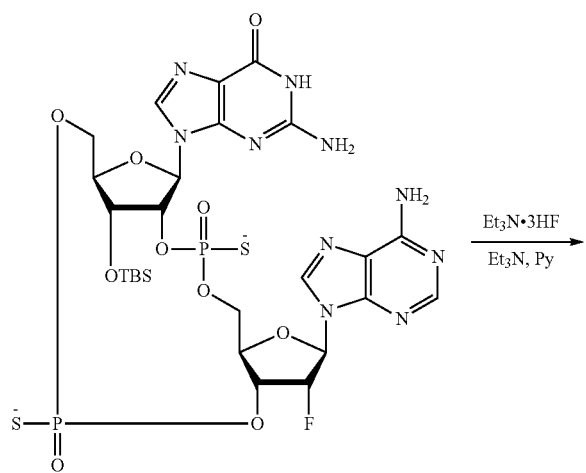

532
-continued

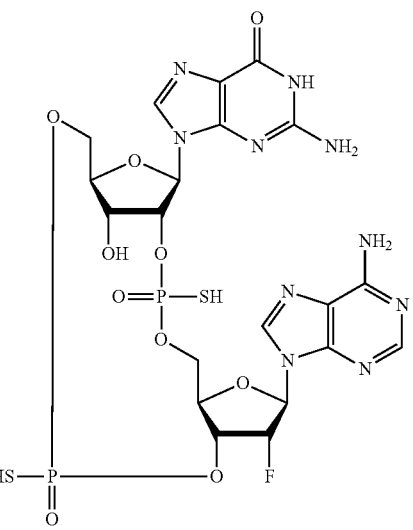

Diastereomer 1

The crude product from Step 10 (25 mg) was co-evaporated with pyridine/Et$_3$N (v/v, 3/1, 1 mL each, three times) and then dissolved in pyridine (0.15 mL). The mixture was charged with Ar and Et$_3$N (0.20 mL) and triethylamine trihydrofluoride (56.4 mg, 0.350 mmol) were added. The resulting solution was warmed at 50° C. for 6 h. The reaction progress was monitored by TLC/LCMS. After completion of the reaction, the mixture was concentrated in vacuo and then, co-evaporated with MeCN (three times, 1 mL each). The residue was purified by reverse phase prep-HPLC (X-Bridge BEH130 Prep C18) eluted with 0 to 22% MeCN in aq NH$_4$HCO$_3$ (50 mM) over 15 min to give the product compound (T$_R$=8.3 min). LCMS (ES, m/z): 708.95 [M+H]$^+$. $^1$H-NMR (400 MHz, D$_2$O): δ 8.18 (s, 1H), 8.16 (s, 1H), 7.77 (s, 1H), 6.37 (d, J=14.3 Hz, 1H), 5.86 (d, J=8.4 Hz, 1H), 5.61-5.54 (m, 1.5H), 5.43 (s, 0.5H), 5.27-5.12 (m, 2H), 4.59 (d, J=3.6 Hz, 1H), 4.47 (t, J=12.9 Hz, 2H), 4.36 (d, J=4.8 Hz, 1H), 4.04 (dd, J=23.2, 12.0 Hz, 2H). $^{31}$P-NMR (162 MHz, D$_2$O): δ 55.63 (s), 51.55 (s).

Example 82: 2-amino-9-[(5R,7R,8R,12aR,14R,15R, 15aR,16R)-14-(6-amino-9H-purin-9-yl)-15-fluoro-2, 10,16-trihydroxy-2,10-disulfidooctahydro-12H-5,8-methanofuro[3,2-l][1,3,6,9,11,2,10] pentaoxadiphosphacyclotetradecin-7-yl]-1,9-dihydro-6H-purin-6-one (Diastereomer 2)

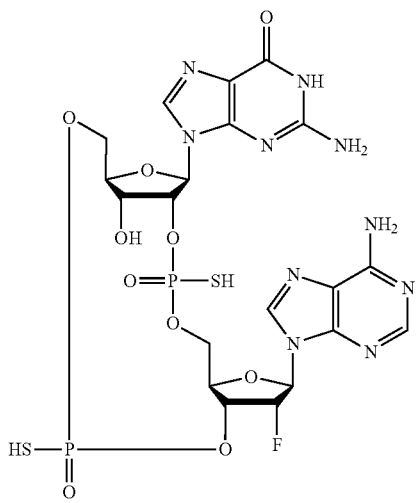

Diastereomer 2

Step 1: Diastereomers (5R,7R,8R,12aR,14R,15R, 15aR,16R)-16-{[tert-butyl(dimethyl)silyl]oxy}-15-fluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10] pentaoxadiphosphacyclotetradecine-2,10-bis(thiolate) 2,10-dioxide (B3) and (5R,7R,8R,12aR, 14R,15R,15aR,16R)-16-{[tert-butyl(dimethyl)silyl]oxy}-15-fluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10] pentaoxadiphosphacyclotetradecine-2,10-bis(thiolate) 2,10-dioxide (B4)

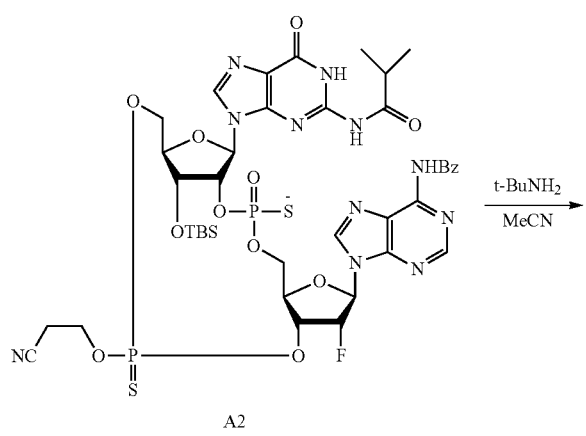

A2

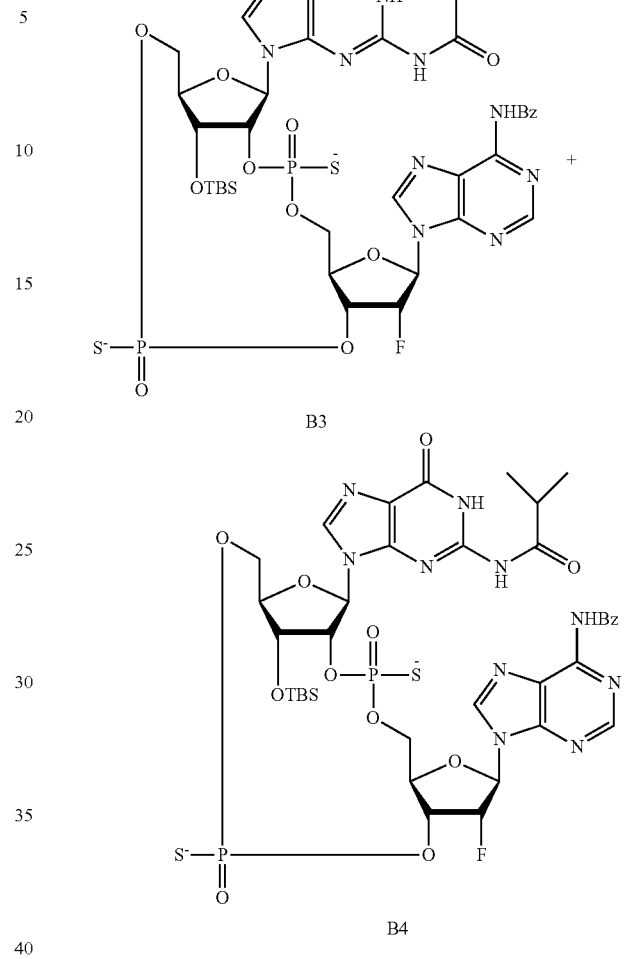

B3

B4

To a stirred suspension of crude A2 (105 mg, ~0.1 mmol) from Example 81, Step 8 in MeCN (1 mL) under Ar was added tert-butylamine (1.5 mL), and the mixture was stirred at RT for 30 min. The volatile components were removed in vacuo. The residue was purified by reverse phase prep-HPLC (X-Bridge BEH130 Prep C18) eluted with 25 to 40% MeCN in aq $NH_4HCO_3$ (10 mM) over 10 min to give two diastereomeric compounds, B3 ($T_R$=6.12 min, 0.025 mmol) and B4 ($T_R$=7.45 min, 0.021 mmol).

Compound B3: LCMS (ES, m/z): 995.3 [M−H]⁻. H-NMR (300 MHz, $CD_3OD$): δ 8.82 (s, 1H), 8.72 (s, 1H), 8.65 (s, 1H), 8.20-8.13 (m, 2H), 7.66-7.54 (m, 3H), 6.47 (d, J=14.0 Hz, 1H), 6.09 (d, J=8.4 Hz, 1H), 5.96-5.95 (m, 0.5H), 5.81-5.78 (m, 0.5H), 5.52-5.36 (m, 2H), 4.64-4.56 (m, 2H), 4.48-4.43 (m, 1H), 4.37-4.30 (m, 1H), 4.25-4.22 (m, 1H), 4.17-4.10 (m, 1H), 3.98 (d, J=11.7 Hz, 1H), 2.65 (p, J=6.8 Hz, 1H), 1.12 (d, J=6.8 Hz, 3H), 0.98-0.95 (m, 12H), 0.22 (d, J=8.0 Hz, 6H). $^{31}$P-NMR (121 MHz, $CD_3OD$): δ 56.96 (s), 55.90 (s).

Compound B4: LCMS (ES, m/z): 995.4 [M−H]⁻. H-NMR (300 MHz, $CD_3OD$): δ 8.97 (s, 1H), 8.68 (s, 1H), 8.24-8.22 (m, 3H), 7.59 (ddd, J=14.5, 7.9, 6.2 Hz, 3H), 6.46 (d, J=13.0 Hz, 1H), 5.99 (d, J=8.3 Hz, 1H), 5.67-5.57 (m, 1H), 5.45-5.33 (m, 2H), 4.56 (dd, J=13.5, 4.9 Hz, 2H), 4.47-4.38 (m, 2H), 4.25 (t, J=3.5 Hz, 1H), 4.07 (d, J=11.3 Hz, 1H), 3.94 (d, J=11.0 Hz, 1H), 2.75 (p, J=6.8 Hz, 1H), 1.04 (d, J=6.8 Hz, 3H), 0.95 (s, 12H), 0.23 (d, J=5.2 Hz, 6H). ³¹P-NMR (121 MHz, CD₃OD): δ 56.81 (s), 54.76 (s).

Step 2. (5R,7R,8R,12aR,14R,15R,15aR,16R)-7-(2-amino-6-oxo-1,6-dihydro-9H-purin-9-yl)-14-(6-amino-9H-purin-9-yl)-16-{[tert-butyl(dimethyl)silyl]oxy}-15-fluorooctahydro-12H-5,8-methanofuro[3,2-l][1,3,6,9,11,2,10]pentaoxadiphosphacyclotetradecine-2,10-bis(thiolate) 2,10-dioxide

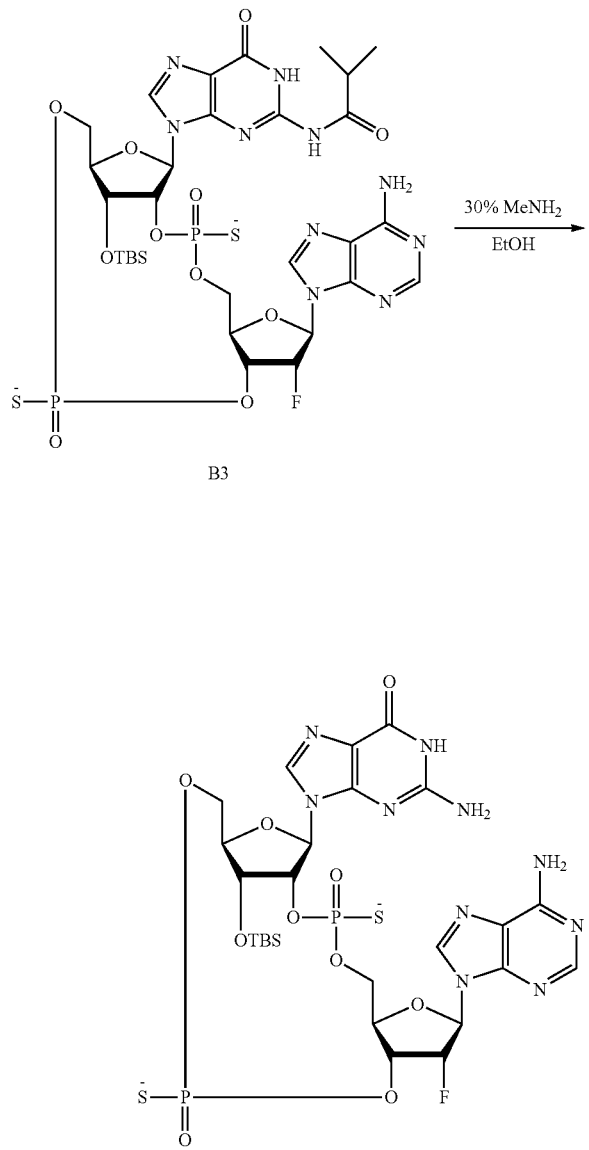

B3

Compound B3 from Step 1 (25 mg, 0.025 mmol) was dissolved in a solution of MeNH₂ in EtOH (1 mL, 30% by weight), and the mixture was stirred at RT for 12 h. The reaction progress was monitored by TLC/LCMS. After the reaction was complete, the volatile components were removed in vacuo, and the residue containing the crude product was used for the next reaction step without purification. LCMS (ES, m/z): 823.25 [M+H]⁺.

Step 3: 2-amino-9-[(5R,7R,8R,12aR,14R,15R,15aR,16R)-14-(6-amino-9H-purin-9-yl)-15-fluoro-2,10,16-trihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2)

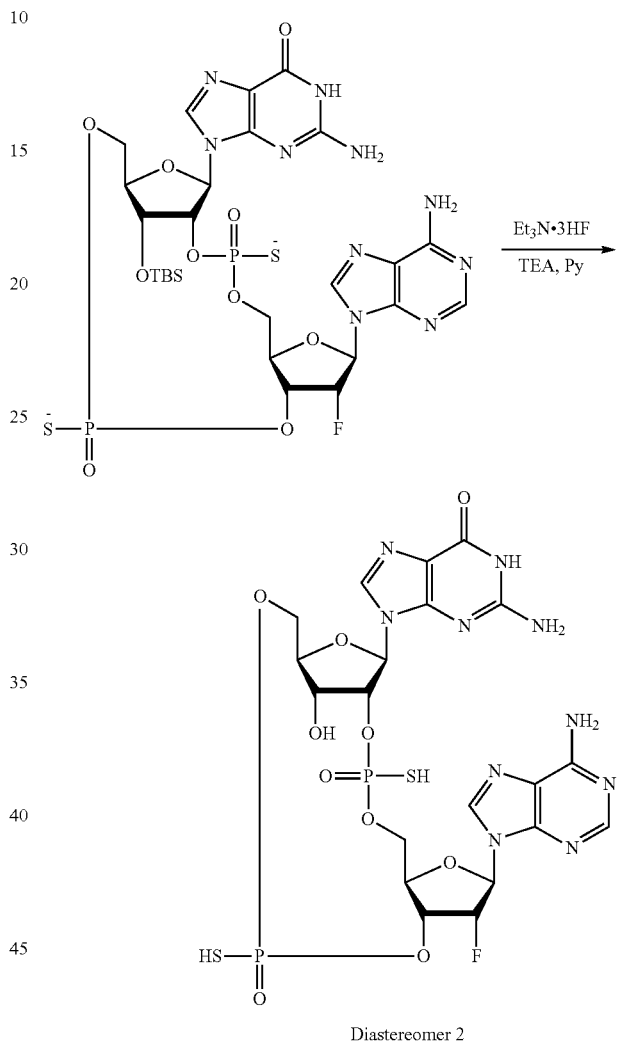

Diastereomer 2

The crude product of Step 2 (35 mg) was co-evaporated with pyridine/Et₃N (v/v, 3/1, 1 mL each, three times) and then re-dissolved in pyridine (0.4 mL). The mixture was charged with Ar and Et₃N (0.34 mL, 2.4 mmol), and triethylamine trihydrofluoride (97 mg, 0.6 mmol) were added. The resulting solution was warmed at 50° C. for 6 h. Then, the mixture was concentrated at reduced pressure and then co-evaporated with MeCN (3×1 mL). The residue was purified by reverse phase prep-HPLC (X-Bridge BEH130 Prep C18) eluted with 0 to 10% MeCN in aq NH₄HCO₃ (50 mM) over 14 min to give the product compound (T_R=9.2 min). LCMS (ES, m/z): 709.00 [M+H]⁺. H-NMR (400 MHz, DMF-d₇+D₂O): δ 8.68 (s, 1H), 8.61 (s, 1H), 8.45 (s, 1H), 6.57 (d, J=14.8 Hz, 1H), 6.27-6.25 (m, 1.5H), 6.15-6.13 (m, 0.5H), 5.72-5.68 (m, 1H), 5.56-5.54 (m, 1H), 4.85-4.83 (m, 1H), 4.71-4.69 (m, 1H), 4.52-4.43 (m, 4H), 4.27-4.24

(m, 1H). $^{31}$P-NMR (162 MHz, DMF-d$_7$+D$_2$O): δ 56.03 (s), 53.37 (s). $^{19}$F-NMR (376 MHz, DMF-d$_7$+D$_2$O): δ −205.44 (s).

Example 83: 2-amino-9-[(5R,7R,8R,12aR,14R,15R, 15aR,16R)-14-(6-amino-9H-purin-9-yl)-15-fluoro-2, 10,16-trihydroxy-2,10-disulfidooctahydro-12H-5,8-methanofuro[3,2-l][1,3,6,9,11,2,10] pentaoxadiphosphacyclotetradecin-7-yl]-1,9-dihydro-6H-purin-6-one (Diastereomer 3)

Diastereomer 3

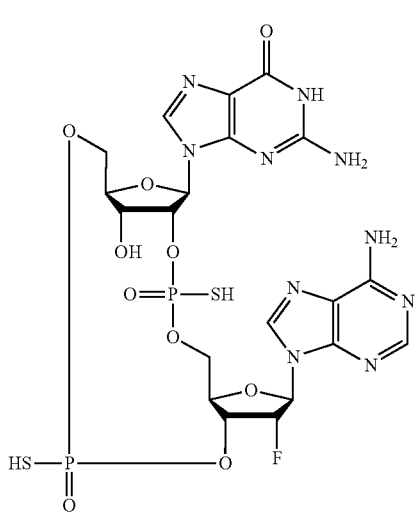

Step 1: (5R,7R,8R,12aR,14R,15R,15aR,16R)-7-(2-amino-6-oxo-1,6-dihydro-9H-purin-9-yl)-14-(6-amino-9H-purin-9-yl)-16-{[tert-butyl(dimethyl)silyl] oxy}-15-fluorooctahydro-12H-5,8-methanofuro[3,2-l][1,3,6,9,11,2,10] pentaoxadiphosphacyclotetradecine-2,10-bis (thiolate) 2,10-dioxide

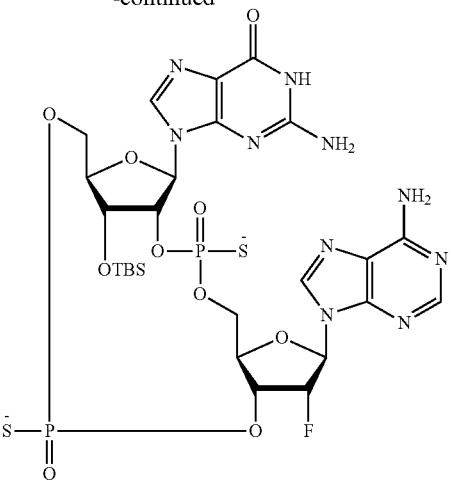

Compound B4 ((5R,7R,8R,12aR,14R,15R,15aR,16R)-7-(2-amino-6-oxo-1,6-dihydro-9H-purin-9-yl)-14-(6-amino-9H-purin-9-yl)-16-{[tert-butyl(dimethyl)silyl]oxy}-15-fluorooctahydro-12H-5,8-methanofuro[3,2-l][1,3,6,9,11,2, 10]pentaoxadiphosphacyclotetradecine-2,10-bis(thiolate) 2,10-dioxide, 21 mg, 0.021 mmol) from Example 82, Step 1 was dissolved in a solution of MeNH$_2$ in EtOH (1 mL, 30% by weight), and the mixture was stirred at RT for 12 h. The reaction progress was monitored by TLC/LCMS. After the reaction was complete, the volatile components were removed in vacuo, and the product was used for the next reaction step without purification. LCMS (ES, m/z): 823.25 [M+H]$^+$.

Step 2: 2-amino-9-[(5R,7R,8R,12aR,14R,15R,15aR, 16R)-14-(6-amino-9H-purin-9-yl)-15-fluoro-2,10, 16-trihydroxy-2,10-disulfidooctahydro-12H-5,8-methanofuro[3,2-l][1,3,6,9,11,2,10] pentaoxadiphosphacyclotetradecin-7-yl]-1,9-dihydro-6H-purin-6-one (Diastereomer 3)

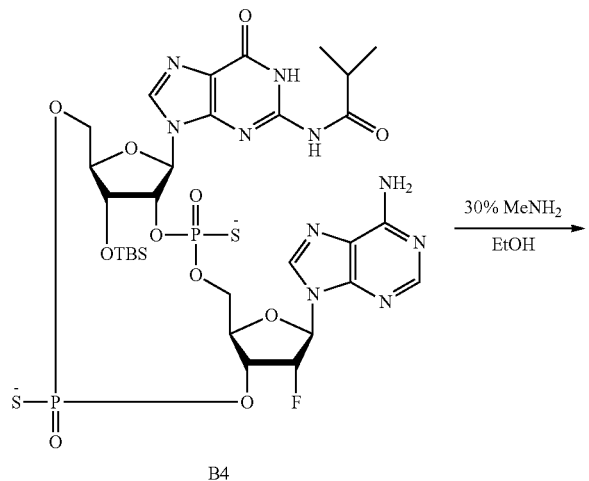

B4

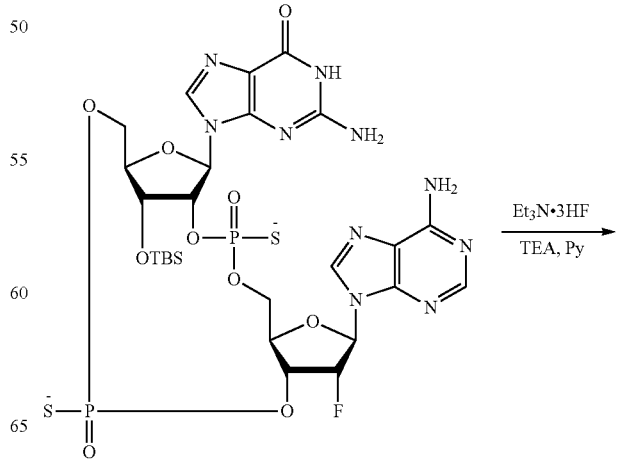

539
-continued

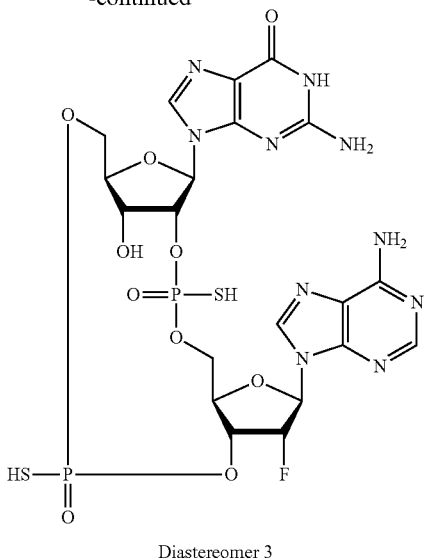

Diastereomer 3

540

The crude product of Step 1 (31 mg) was co-evaporated with pyridine/Et₃N (v/v, 3/1, 3×1 mL) and then, re-dissolved in pyridine (0.4 mL). The mixture was charged with Ar and Et₃N (0.28 mL, 2.0 mmol) and triethylamine trihydrofluoride (81 mg, 0.5 mmol) were added. The resulting solution was warmed at 50° C. for 6 h. The mixture was concentrated at reduced pressure and then co-evaporated with MeCN (3×1 mL). The residue was purified by reverse phase prep-HPLC (X-Bridge BEH130 Prep C18) eluting with 0 to 10% MeCN in aq NH₄HCO₃ (50 mM) over 14 min to give the product compound ($T_R$=10.1 min). LCMS (ES, m/z): 709.00 [M+H]⁺. H-NMR (400 MHz, DMF-$d_7$+$D_2O$): δ 8.73 (s, 1H), 8.28-8.20 (m, 2H), 6.55 (d, J=14.8 Hz, 1H), 6.25-5.85 (m, 3H), 5.62-5.56 (m, 1H), 4.76 (s, 1H), 4.62-4.60 (m, 2H), 4.49-4.41 (m, 3H), 4.18-4.15 (m, 1H). ³¹P-NMR (162 MHz, DMF-$d_7$+$D_2O$): δ 56.09 (s), 54.75 (s). ¹⁹F-NMR (376 MHz, DMF-$d_7$+$D_2O$): δ −203.33 (s).

Examples 84 through 116, shown in Table 5 below, were prepared according to procedures analogous to those outlined in Examples 77 through 83 above using the appropriate monomers, described as Preparations or as obtained from commercial sources, in the coupling step.

TABLE 5

| Ex. | Structure | Name | Mass [M − H]⁻ |
|---|---|---|---|
| 84 | 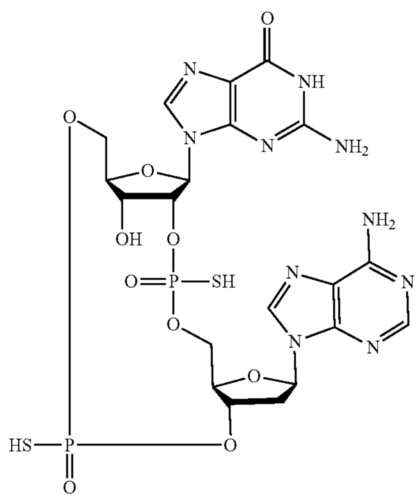 | 2-amino-9-[(5R,7R,8R,12aR,14R,15aS,16R)-14-(6-amino-9H-purin-9-yl)-2,10,16-trihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 691 [M + H]⁺ |
| 85 | 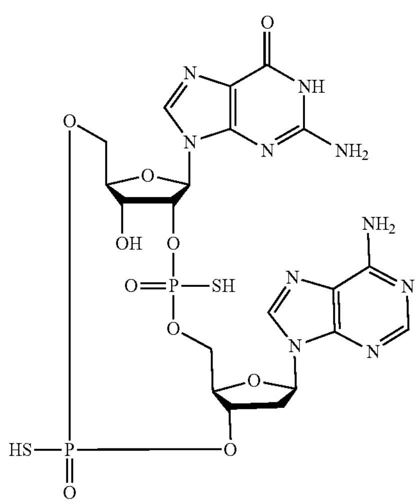 | 2-amino-9-[(5R,7R,8R,12aR,14R,15aS,16R)-14-(6-amino-9H-purin-9-yl)-2,10,16-trihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 691 [M + H]⁺ |

TABLE 5-continued

| Ex. | Structure | Name | Mass [M − H]⁻ |
|---|---|---|---|
| 86 | 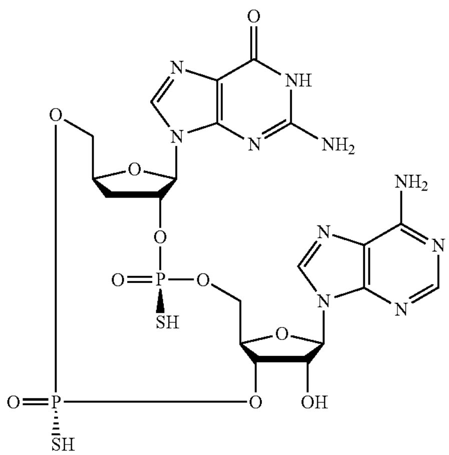 | 2-amino-9-[(2R,5S,7R,8R,10R, 12aR,14R,15R,15aS)-14-(6-amino-9H-purin-9-yl)-2,10,15-trihydroxy-2,10-disulfidooctahydro-12H-5,8-methanofuro[3,2-l][1,3,6,9,11,2,10] pentaoxadiphosphacyclotetradecin-7-yl]-1,9-dihydro-6H-purin-6-one (Diastereomer 1) | 689 |
| 87 | 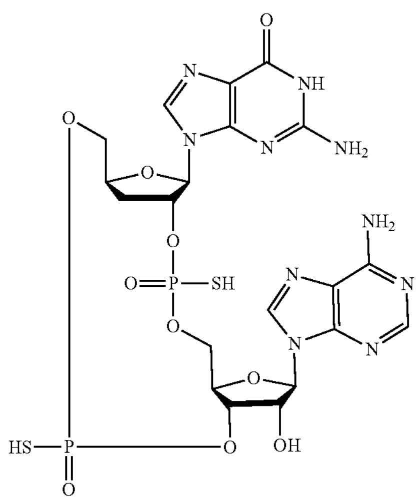 | 2-amino-9-[(5S,7R,8R,12aR,14R,15R,15aS)-14-(6-amino-9H-purin-9-yl)-2,10,15-trihydroxy-2,10-disulfidooctahydro-12H-5,8-methanofuro[3,2-l][1,3,6,9,11,2,10] pentaoxadiphosphacyclotetradecin-7-yl]-1,9-dihydro-6H-purin-6-one (Diastereomer 2) | 689 |
| 88 | 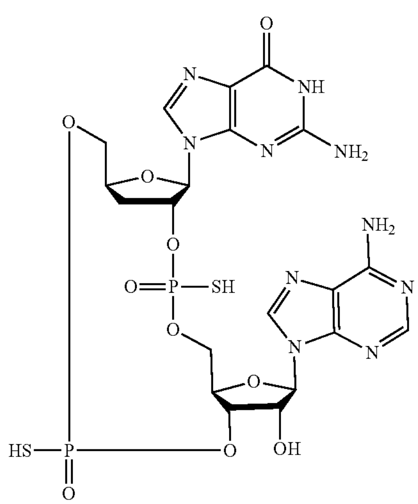 | 2-amino-9-[(5S,7R,8R,12aR,14R,15R,15aS)-14-(6-amino-9H-purin-9-yl)-2,10,15-trihydroxy-2,10-disulfidooctahydro-12H-5,8-methanofuro[3,2-l][1,3,6,9,11,2,10] pentaoxadiphosphacyclotetradecin-7-yl]-1,9-dihydro-6H-purin-6-one (Diastereomer 3) | 689 |

TABLE 5-continued

| Ex. | Structure | Name | Mass [M − H]⁻ |
|---|---|---|---|
| 89 | 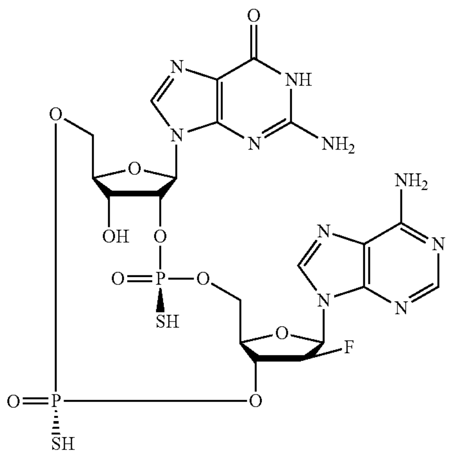 | 2-amino-9-[(2R,5R,7R,8R,10,R, 12aR,14R,15S,15aR,16R)-14-(6-amino-9H-purin-9-yl)-15-fluoro-2,10,16-trihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 707 |
| 90 | 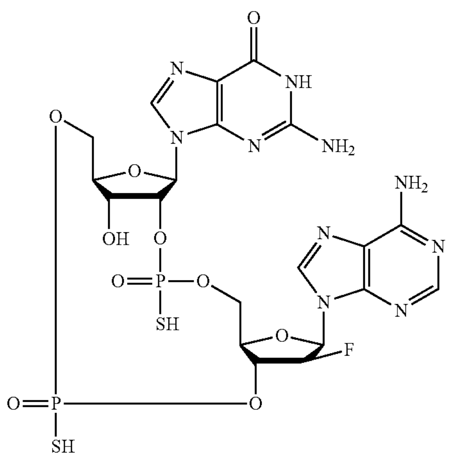 | 2-amino-9-[(5R,7R,8R,12aR,14R,15S,15aR,16R)-14-(6-amino-9H-purin-9-yl)-15-fluoro-2,10,16-trihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 707 |
| 91 | 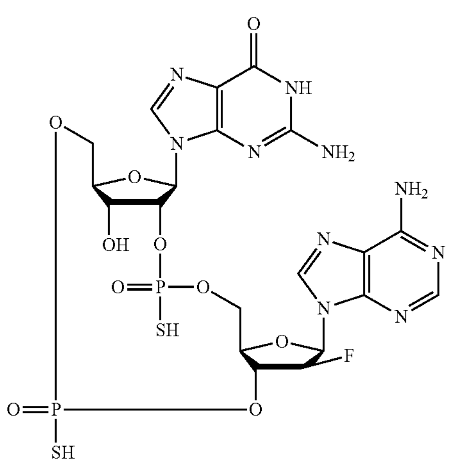 | 2-amino-9-[(5R,7R,8R,12aR,14R,15S,15aR,16R)-14-(6-amino-9H-purin-9-yl)-15-fluoro-2,10,16-trihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 3) | 707 |

TABLE 5-continued

| Ex. | Structure | Name | Mass [M − H]⁻ |
|---|---|---|---|
| 92 | 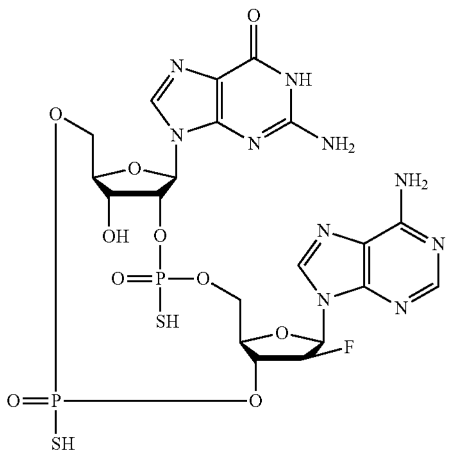 | 2-amino-9-[(5R,7R,8R,12aR,14R,15S,15aR,16R)-14-(6-amino-9H-purin-9-yl)-15-fluoro-2,10,16-trihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 4) | 707 |
| 93 | 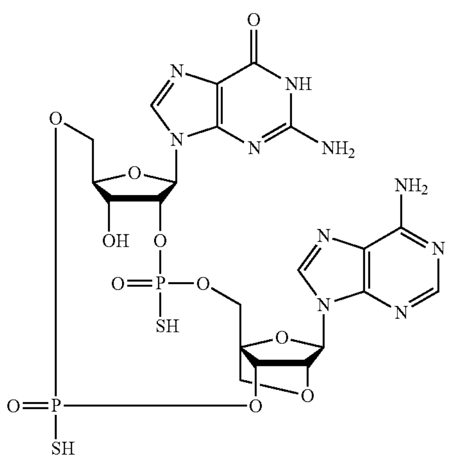 [SMILES: Nc1nc2c(ncn2[C@@H]2O[C@@H]3COP(=O)(S)OC4[C@@H]5OC[C@]4(COP(=O)(S)O[C@H]2C3O)O[C@H]5n2cnc3c(N)ncnc32)c(=O)[nH]1] | 2-amino-9-[(5R,7R,8R,12aR,14R,15R,15aS,18R)-14-(6-amino-9H-purin-9-yl)-2,10,18-trihydroxy-2,10-disulfidohexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one (Diastereomer 1) | 717 |
| 94 | 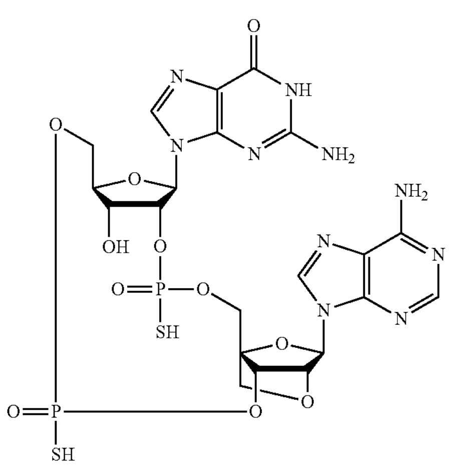 [SMILES: Nc1nc2c(ncn2[C@@H]2O[C@@H]3COP(=O)(S)OC4[C@@H]5OC[C@]4(COP(=O)(S)O[C@H]2C3O)O[C@H]5n2cnc3c(N)ncnc32)c(=O)[nH]1] | 2-amino-9-[(5R,7R,8R,12aR,14R,15R,15aS,18R)-14-(6-amino-9H-purin-9-yl)-2,10,18-trihydroxy-2,10-disulfidohexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one (Diastereomer 2) | 717 |

TABLE 5-continued

| Ex. | Structure | Name | Mass [M − H]⁻ |
|---|---|---|---|
| 95 | 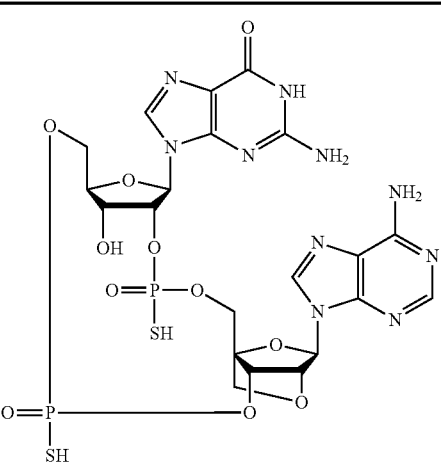 | 2-amino-9-[(5R,7R,8R,12aR,14R,15R,15aS,18R)-14-(6-amino-9H-purin-9-yl)-2,10,18-trihydroxy-2,10-disulfidohexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one (Diastereomer 3) | 719 [M + H]⁺ |
| 96 | 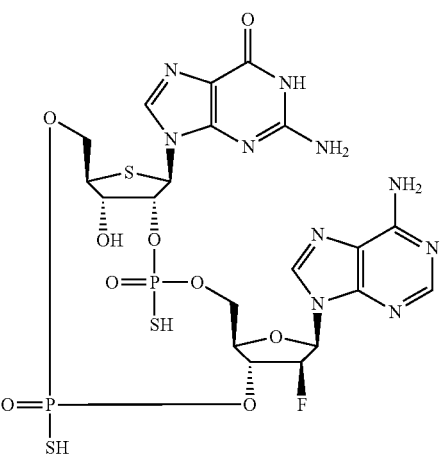 [SMILES: Nc1nc2c(ncn2[C@@H]2S[C@@H]3COP(=O)(S)O[C@H]4[C@H](F)[C@H](n5cnc6c(N)ncnc65)O[C@@H]4COP(=O)(S)O[C@@H]2[C@@H]3O)c(=O)[nH]1] | 2-amino-9-[(5R,7R,8R,12aR,14R,15S,15aR,16S)-14-(6-amino-9H-purin-9-yl)-15-fluoro-16-hydroxy-2,10-dioxido-2,10-disulfanyloctahydro-12H-5,8-methanofuro[3,2-l][1,3,9,11,6,2,10]tetraoxathiadiphosphacyclotetradecin-7-yl]-1,9-dihydro-6H-purin-6-one (Diastereomer 1) | 723 |
| 97 | 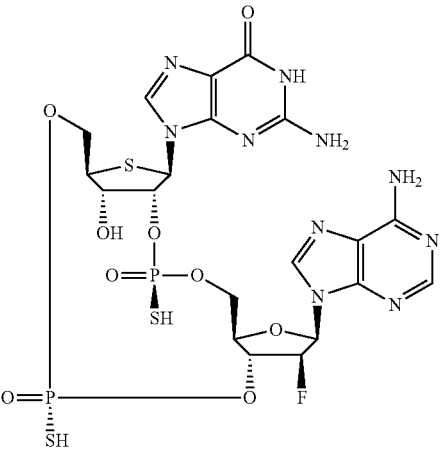 [SMILES: Nc1nc2c(ncn2[C@@H]2S[C@@H]3CO[P@@](=O)(S)O[C@H]4[C@H](F)[C@H](n5cnc6c(N)ncnc65)O[C@@H]4CO[P@@](=O)(S)O[C@@H]2[C@@H]3O)c(=O)[nH]1] | 2-amino-9-[(2R,5R,7R,8R,10R,12aR,14R,15S,15aR,16S)-14-(6-amino-9H-purin-9-yl)-15-fluoro-16-hydroxy-2,10-dioxido-2,10-disulfanyloctahydro-12H-5,8-methanofuro[3,2-l][1,3,9,11,6,2,10]tetraoxathiadiphosphacyclotetradecin-7-yl]-1,9-dihydro-6H-purin-6-one (Diastereomer 2) | 723 |

TABLE 5-continued

| Ex. | Structure | Name | Mass [M − H]⁻ |
|---|---|---|---|
| 98 | 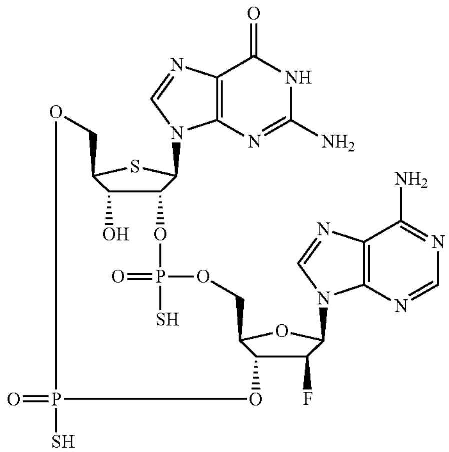 [SMILES: Nc1nc2c(ncn2[C@@H]2S[C@@H]3COP(=O)(S)O[C@H]4[C@H](F)[C@H](n5cnc6c(N)ncnc65)O[C@@H]4COP(=O)(S)O[C@@H]2[C@@H]3O)c(=O)[nH]1] | 2-amino-9-[(5R,7R,8R,12aR,14R,15S,15aR,16S)-14-(6-amino-9H-purin-9-yl)-15-fluoro-16-hydroxy-2,10-dioxido-2,10-disulfanyloctahydro-12H-5,8-methanofuro[3,2-l][1,3,9,11,6,2,10]tetraoxathiadiphosphacyclotetradecin-7-yl]-1,9-dihydro-6H-purin-6-one (Diastereomer 3) | 723 |
| 99 | 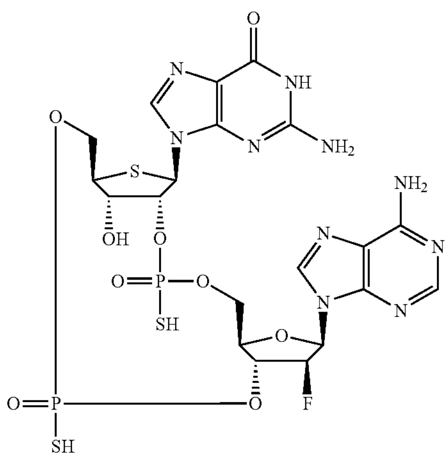 [SMILES: Nc1nc2c(ncn2[C@@H]2S[C@@H]3COP(=O)(S)O[C@H]4[C@H](F)[C@H](n5cnc6c(N)ncnc65)O[C@@H]4COP(=O)(S)O[C@@H]2[C@@H]3O)c(=O)[nH]1] | 2-amino-9-[(5R,7R,8R,12aR,14R,15S,15aR,16S)-14-(6-amino-9H-purin-9-yl)-15-fluoro-16-hydroxy-2,10-dioxido-2,10-disulfanyloctahydro-12H-5,8-methanofuro[3,2-l][1,3,9,11,6,2,10]tetraoxathiadiphosphacyclotetradecin-7-yl]-1,9-dihydro-6H-purin-6-one (Diastereomer 4) | 723 |
| 100 | 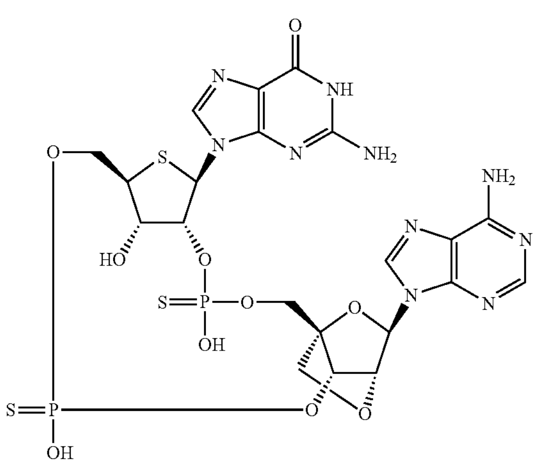 [SMILES: Nc1nc2c(ncn2[C@@H]2S[C@@H]3COP(O)(=S)O[C@H]4[C@H]5OC[C@]4(COP(O)(=S)O[C@@H]2[C@@H]3O)O[C@H]5n2cnc3c(N)ncnc32)c(=O)[nH]1] | 2-amino-9-[(5R,7R,8R,12aR,14R,15R,15aS,18S)-14-(6-amino-9H-purin-9-yl)-2,10,18-trihydroxy-2,10-disulfidohexahydro-14H-15,12a-(epoxymethano)-5,8-methanofuro[3,2-l][1,3,9,11,6,2,10]tetraoxathiadiphosphacyclotetradecin-7(12H)-yl]-1,9-dihydro-6H-purin-6-one (Diastereomer 1) | 733 |

TABLE 5-continued

| Ex. | Structure | Name | Mass [M − H]⁻ |
|---|---|---|---|
| 101 | 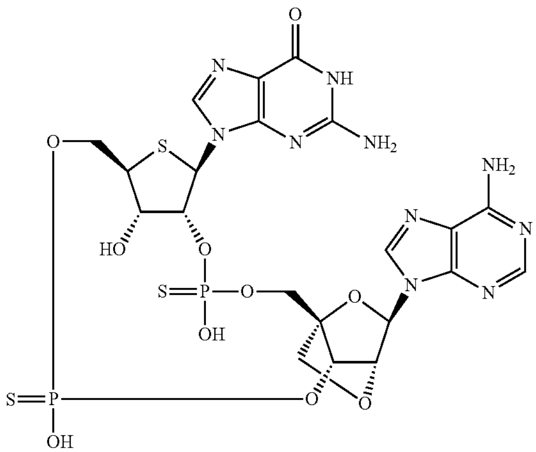 [SMILES: Nc1nc2c(ncn2[C@@H]2S[C@@H]3COP(O)(=S)O[C@H]4[C@H]5OC[C@]4(COP(O)(=S)O[C@@H]2[C@@H]3O)O[C@H]5n2cnc3c(N)ncnc32)c(=O)[nH]1] | 2-amino-9-[(5R,7R,8R,12aR,14R,15R,15aS,18S)-14-(6-amino-9H-purin-9-yl)-2,10,18-trihydroxy-2,10-disulfidohexahydro-14H-15,12a-(epoxymethano)-5,8-methanofuro[3,2-l][1,3,9,11,6,2,10]tetraoxathiadiphosphacyclotetradecin-7(12H)-yl]-1,9-dihydro-6H-purin-6-one (Diastereomer 2) | 733 |
| 102 | 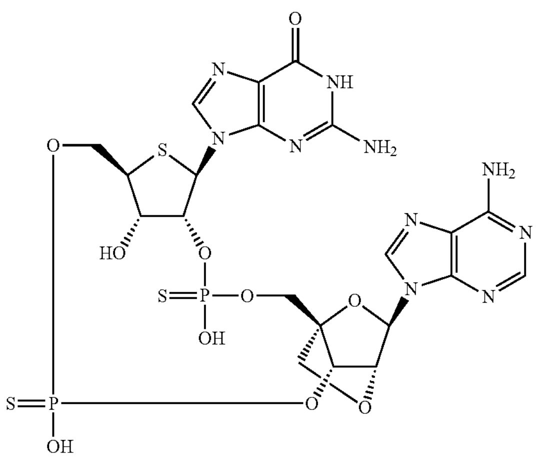 [SMILES: Nc1nc2c(ncn2[C@@H]2S[C@@H]3COP(O)(=S)O[C@H]4[C@H]5OC[C@]4(COP(O)(=S)O[C@@H]2[C@@H]3O)O[C@H]5n2cnc3c(N)ncnc32)c(=O)[nH]1] | 2-amino-9-[(5R,7R,8R,12aR,14R,15R,15aS,18S)-14-(6-amino-9H-purin-9-yl)-2,10,18-trihydroxy-2,10-disulfidohexahydro-14H-15,12a-(epoxymethano)-5,8-methanofuro[3,2-l][1,3,9,11,6,2,10]tetraoxathiadiphosphacyclotetradecin-7(12H)-yl]-1,9-dihydro-6H-purin-6-one (Diastereomer 3) | 733 |
| 103 | 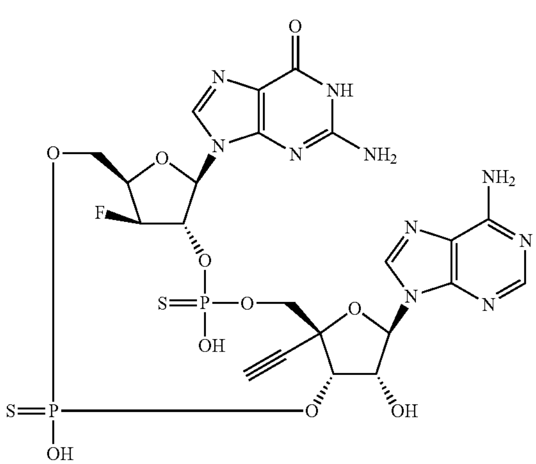 [SMILES: C#C[C@@]12COP(O)(=S)O[C@@H]3[C@@H](F)[C@@H](COP(O)(=S)O[C@H]1[C@@H](O)[C@H](n1cnc4c(N)ncnc41)O2)O[C@H]3n1cnc2c(=O)[nH]c(N)nc21] | 2-amino-9-[(5R,7R,8S,12aR,14R,15R,15aS,16S)-14-(6-amino-9H-purin-9-yl)-12a-ethynyl-16-fluoro-2,10,15-trihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 731 |

TABLE 5-continued

| Ex. | Structure | Name | Mass [M − H]⁻ |
|---|---|---|---|
| 104 | 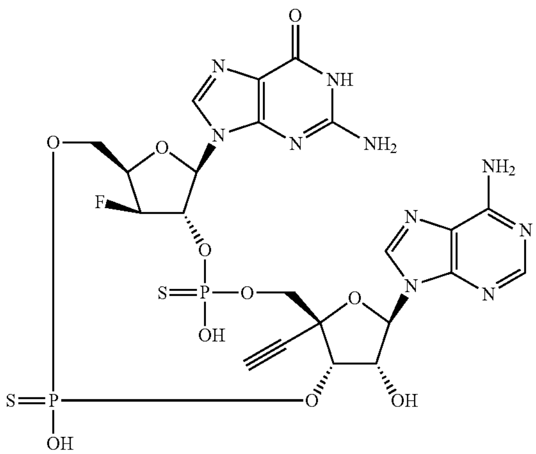 [SMILES: C#C[C@@]12COP(O)(=S)O[C@@H]3[C@@H](F)[C@@H](COP(O)(=S)O[C@H]1[C@@H](O)[C@H](n1cnc4c(N)ncnc41)O2)O[C@H]3n1cnc2c(=O)[nH]c(N)nc21] | 2-amino-9-[(5R,7R,8S,12aR,14R,15R,15aS,16S)-14-(6-amino-9H-purin-9-yl)-12a-ethynyl-16-fluoro-2,10,15-trihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 731 |
| 105 | 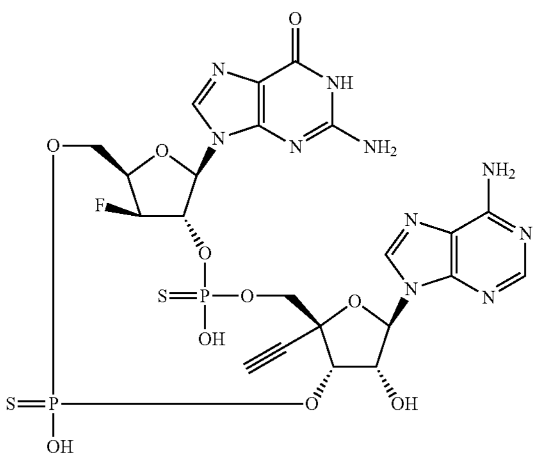 [SMILES: C#C[C@@]12COP(O)(=S)O[C@@H]3[C@@H](F)[C@@H](COP(O)(=S)O[C@H]1[C@@H](O)[C@H](n1cnc4c(N)ncnc41)O2)O[C@H]3n1cnc2c(=O)[nH]c(N)nc21] | 2-amino-9-[(5R,7R,8S,12aR,14R,15R,15aS,16S)-14-(6-amino-9H-purin-9-yl)-12a-ethynyl-16-fluoro-2,10,15-trihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 3) | 731 |
| 106 | 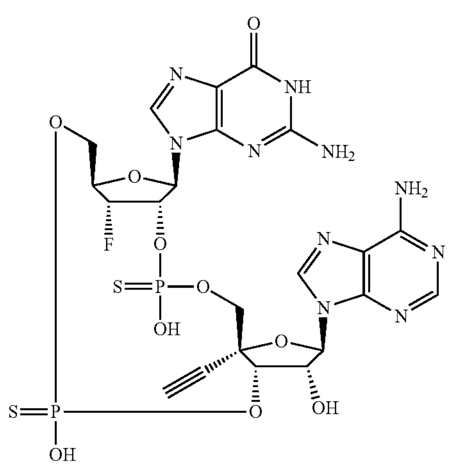 [SMILES: C#C[C@@]12COP(O)(=S)O[C@@H]3[C@H](F)[C@@H](COP(O)(=S)O[C@H]1[C@@H](O)[C@H](n1cnc4c(N)ncnc41)O2)O[C@H]3n1cnc2c(=O)[nH]c(N)nc21] | 2-amino-9-[(5R,7R,8S,12aR,14R,15R,15aS,16R)-14-(6-amino-9H-purin-9-yl)-12a-ethynyl-16-fluoro-2,10,15-trihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 731 |

TABLE 5-continued

| Ex. | Structure | Name | Mass [M − H]⁻ |
|---|---|---|---|
| 107 | 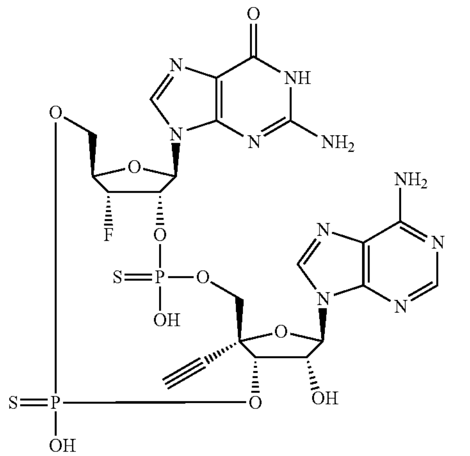 [SMILES: C#C[C@@]12COP(O)(=S)O[C@@H]3[C@H](F)[C@@H](COP(O)(=S)O[C@H]1[C@@H](O)[C@H](n1cnc4c(N)ncnc41)O2)O[C@H]3n1cnc2c(=O)[nH]c(N)nc21] | 2-amino-9-[(5R,7R,8S,12aR,14R,15R,15aS,16R)-14-(6-amino-9H-purin-9-yl)-12a-ethynyl-16-fluoro-2,10,15-trihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 731 |
| 108 | 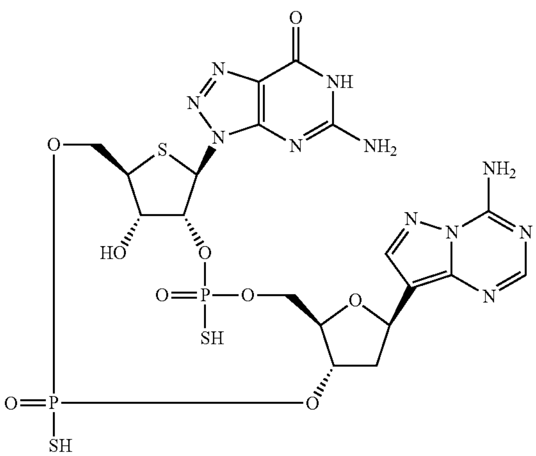 [SMILES: Nc1nc2c(nnn2[C@@H]2S[C@@H]3COP(=O)(S)O[C@H]4C[C@H](c5cnn6c(N)ncnc56)O[C@@H]4COP(=O)(S)O[C@@H]2[C@@H]3O)c(=O)[nH]1] | 5-amino-3-[(5R,7R,8R,12aR,14R,15aS,16S)-14-(4-aminopyrazolo[1,5-a][1,3,5]triazin-8-yl)-16-hydroxy-2,10-dioxido-2,10-disulfanyloctahydro-12H-5,8-methanofuro[3,2-l][1,3,9,11,6,2,10]tetraoxathiadiphosphacyclotetradecin-7-yl]-3,6-dihydro-7H-[1,2,3]triazolo[4,5-d]pyrimidin-7-one (Diastereomer 1) | 706 |
| 109 | 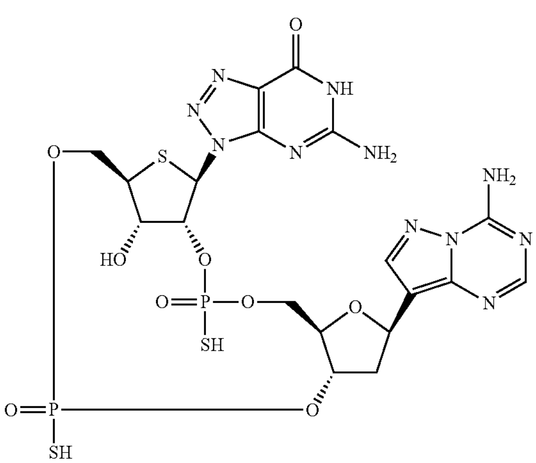 [SMILES: Nc1nc2c(nnn2[C@@H]2S[C@@H]3COP(=O)(S)O[C@H]4C[C@H](c5cnn6c(N)ncnc56)O[C@@H]4COP(=O)(S)O[C@@H]2[C@@H]3O)c(=O)[nH]1] | 5-amino-3-[(5R,7R,8R,12aR,14R,15aS,16S)-14-(4-aminopyrazolo[1,5-a][1,3,5]triazin-8-yl)-16-hydroxy-2,10-dioxido-2,10-disulfanyloctahydro-12H-5,8-methanofuro[3,2-l][1,3,9,11,6,2,10]tetraoxathiadiphosphacyclotetradecin-7-yl]-3,6-dihydro-7H-[1,2,3]triazolo[4,5-d]pyrimidin-7-one (Diastereomer 2) | 706 |

TABLE 5-continued

| Ex. | Structure | Name | Mass [M − H]⁻ |
|---|---|---|---|
| 110 | 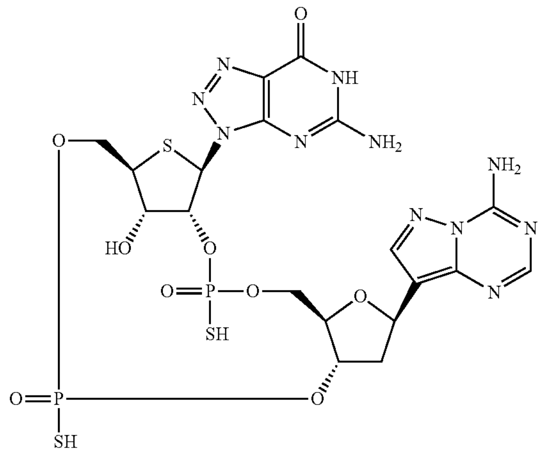 [SMILES: Nc1nc2c(nnn2[C@@H]2S[C@@H]3COP(=O)(S)O[C@H]4C[C@H](c5cnn6c(N)ncnc56)O[C@@H]4COP(=O)(S)O[C@@H]2[C@@H]3O)c(=O)[nH]1] | 5-amino-3-[(5R,7R,8R,12aR,14R,15aS,16S)-14-(4-aminopyrazolo[1,5-a][1,3,5]triazin-8-yl)-16-hydroxy-2,10-dioxido-2,10-disulfanyloctahydro-12H-5,8-methanofuro[3,2-l][1,3,9,11,6,2,10]tetraoxathiadiphosphacyclotetradecin-7-yl]-3,6-dihydro-7H-[1,2,3]triazolo[4,5-d]pyrimidin-7-one (Diastereomer 3) | 706 |
| 111 | 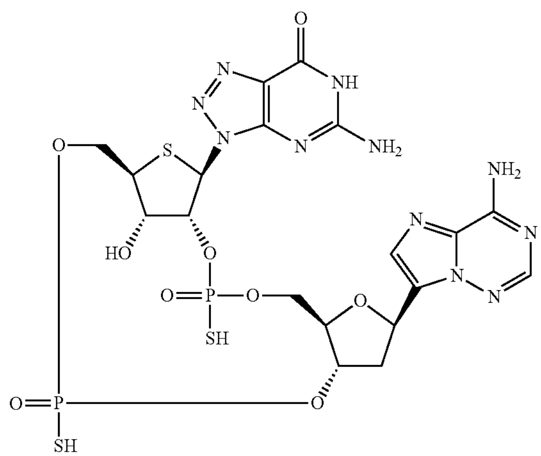 [SMILES: Nc1nc2c(nnn2[C@@H]2S[C@@H]3COP(=O)(S)O[C@H]4C[C@H](c5cnc6c(N)ncnn56)O[C@@H]4COP(=O)(S)O[C@@H]2[C@@H]3O)c(=O)[nH]1] | 5-amino-3-[(5R,7R,8R,12aR,14R,15aS,16S)-14-(4-aminoimidazo[2,1-f][1,2,4]triazin-7-yl)-16-hydroxy-2,10-dioxido-2,10-disulfanyloctahydro-12H-5,8-methanofuro[3,2-l][1,3,9,11,6,2,10]tetraoxathiadiphosphacyclotetradecin-7-yl]-3,6-dihydro-7H-[1,2,3]triazolo[4,5-d]pyrimidin-7-one (Diastereomer 1) | 706 |
| 112 | 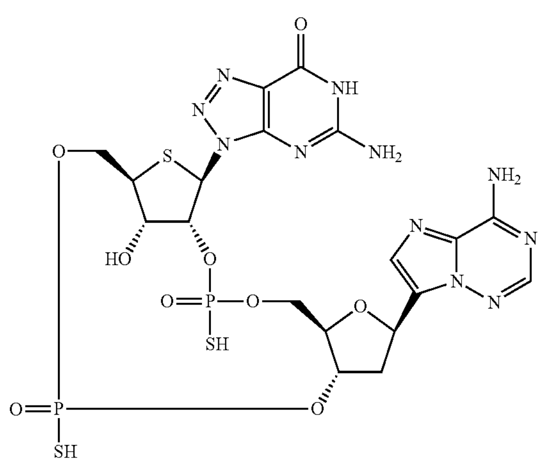 [SMILES: Nc1nc2c(nnn2[C@@H]2S[C@@H]3COP(=O)(S)O[C@H]4C[C@H](c5cnc6c(N)ncnn56)O[C@@H]4COP(=O)(S)O[C@@H]2[C@@H]3O)c(=O)[nH]1] | 5-amino-3-[(5R,7R,8R,12aR,14R,15aS,16S)-14-(4-aminoimidazo[2,1-f][1,2,4]triazin-7-yl)-16-hydroxy-2,10-dioxido-2,10-disulfanyloctahydro-12H-5,8-methanofuro[3,2-l][1,3,9,11,6,2,10]tetraoxathiadiphosphacyclotetradecin-7-yl]-3,6-dihydro-7H-[1,2,3]triazolo[4,5-d]pyrimidin-7-one (Diastereomer 2) | 706 |

| Ex. | Structure | Name | Mass [M − H]⁻ |
|---|---|---|---|
| 113 | 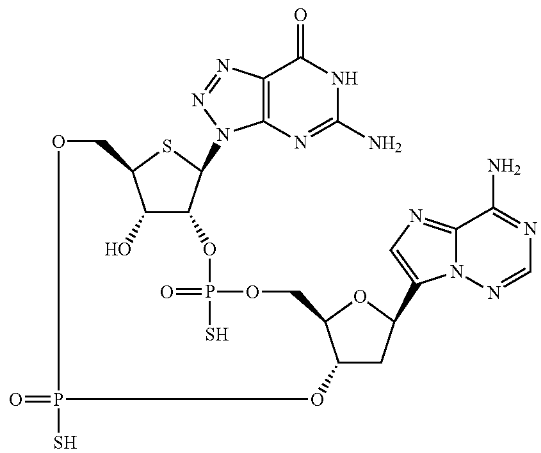 [SMILES: Nc1nc2c(nnn2[C@@H]2S[C@@H]3COP(=O)(S)O[C@H]4C[C@H](c5cnc6c(N)ncnn56)O[C@@H]4COP(=O)(S)O[C@@H]2[C@@H]3O)c(=O)[nH]1] | 5-amino-3-[(5R,7R,8R,12aR,14R,15aS,16S)-14-(4-aminoimidazo[2,1-f][1,2,4]triazin-7-yl)-16-hydroxy-2,10-dioxido-2,10-disulfanyloctahydro-12H-5,8-methanofuro[3,2-l][1,3,9,11,6,2,10]tetraoxathiadiphosphacyclotetradecin-7-yl]-3,6-dihydro-7H-[1,2,3]triazolo[4,5-d]pyrimidin-7-one (Diastereomer 3) | 706 |
| 114 | 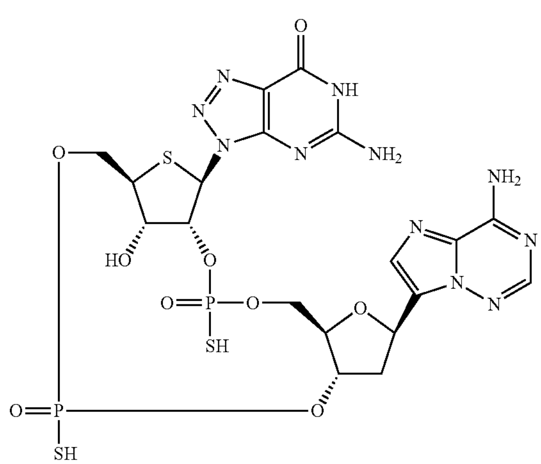 [SMILES: Nc1nc2c(nnn2[C@@H]2S[C@@H]3COP(=O)(S)O[C@H]4C[C@H](c5cnc6c(N)ncnn56)O[C@@H]4COP(=O)(S)O[C@@H]2[C@@H]3O)c(=O)[nH]1] | 5-amino-3-[(5R,7R,8R,12aR,14R,15aS,16S)-14-(4-aminoimidazo[2,1-f][1,2,4]triazin-7-yl)-16-hydroxy-2,10-dioxido-2,10-disulfanyloctahydro-12H-5,8-methanofuro[3,2-l][1,3,9,11,6,2,10]tetraoxathiadiphosphacyclotetradecin-7-yl]-3,6-dihydro-7H-[1,2,3]triazolo[4,5-d]pyrimidin-7-one (Diastereomer 4) | 706 |

TABLE 5-continued

| Ex. | Structure | Name | Mass [M − H]⁻ |
|---|---|---|---|
| 115 | 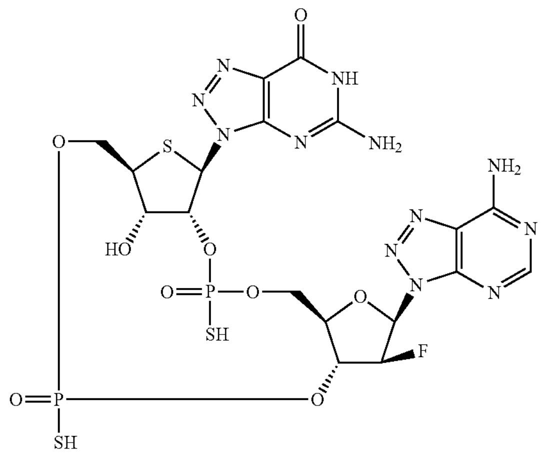 [SMILES: Nc1nc2c(nnn2[C@@H]2S[C@@H]3COP(=O)(S)O[C@H]4[C@H](F)[C@H](n5nnc6c(N)ncnc65)O[C@@H]4COP(=O)(S)O[C@@H]2[C@@H]3O)c(=O)[nH]1] | 5-amino-3-[(5R,7R,8R,12aR,14R,15S,15aR,16S)-14-(7-amino-3H-[1,2,3]triazolo[4,5-d]pyrimidin-3-yl)-15-fluoro-16-hydroxy-2,10-dioxido-2,10-disulfanyloctahydro-12H-5,8-methanofuro[3,2-l][1,3,9,11,6,2,10]tetraoxathiadiphosphacyclotetradecin-7-yl]-3,6-dihydro-7H-[1,2,3]triazolo[4,5-d]pyrimidin-7-one (Diastereomer 1) | 725 |
| 116 | 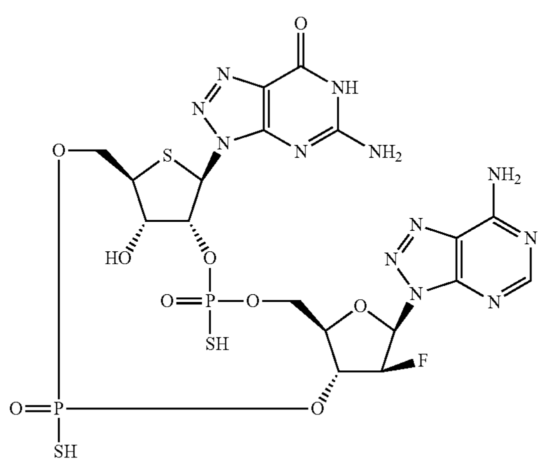 [SMILES: Nc1nc2c(nnn2[C@@H]2S[C@@H]3COP(=O)(S)O[C@H]4[C@H](F)[C@H](n5nnc6c(N)ncnc65)O[C@@H]4COP(=O)(S)O[C@@H]2[C@@H]3O)c(=O)[nH]1] | 5-amino-3-[(5R,7R,8R,12aR,14R,15S,15aR,16S)-14-(7-amino-3H-[1,2,3]triazolo[4,5-d]pyrimidin-3-yl)-15-fluoro-16-hydroxy-2,10-dioxido-2,10-disulfanyloctahydro-12H-5,8-methanofuro[3,2-l][1,3,9,11,6,2,10]tetraoxathiadiphosphacyclotetradecin-7-yl]-3,6-dihydro-7H-[1,2,3]triazolo[4,5-d]pyrimidin-7-one (Diastereomer 2) | 725 |

Examples 117 and 118: 2-amino-9-[(2R,5R,7R,8S,10R,12aR,14R,15aS,16R)-14-(6-amino-9H-purin-9-yl)-16-fluoro-2,10-dihydroxy-2,10-disulfidooctahydro-12H-5,8-methanofuro [3,2-l][1,3,6,9,11,2,10] pentaoxadiphosphacyclotetradecin-7-yl]-1,9-dihydro-6H-purin-6-one (Diastereomer 1) and 2-amino-9-[(5R,7R,8S,12aR,14R,15aS,16R)-14-(6-amino-9H-purin-9-yl)-16-fluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2)

Step 1: 2R,3S,4R,5R)-5-((((((2R,3S,5R)-5-(6-benzamido-9H-purin-9-yl)-2-((bis(4-methoxyphenyl)(phenyl)methoxy)methyl)tetrahydrofuran-3-yl)oxy)(2-cyanoethoxy)phosphanyl)oxy)methyl)-4-fluoro-2-(2-isobutyramido-6-oxo-1,6-dihydro-9H-purin-9-yl)tetrahydrofuran-3-yl phosphonate

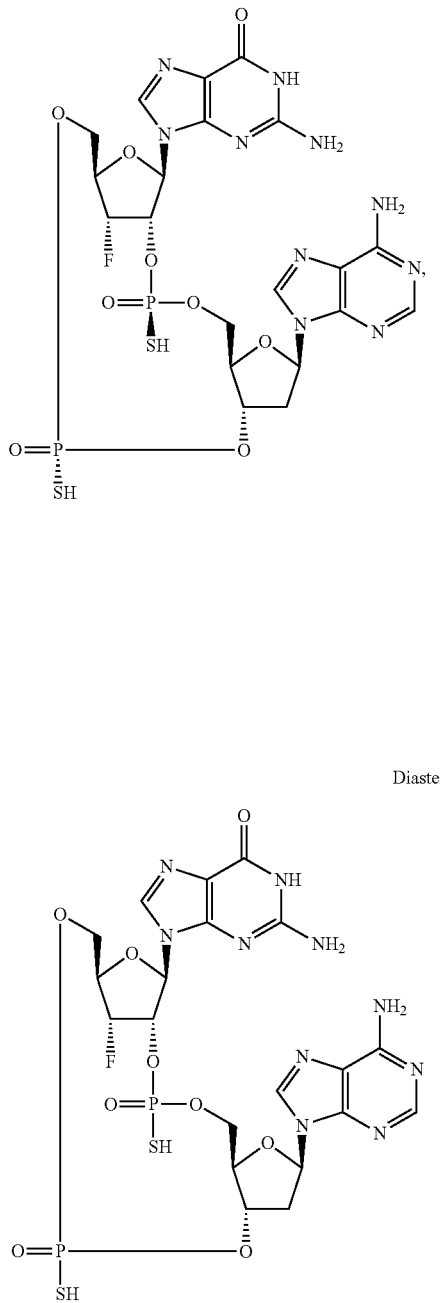

Diastereomer 1

Diastereomer 2

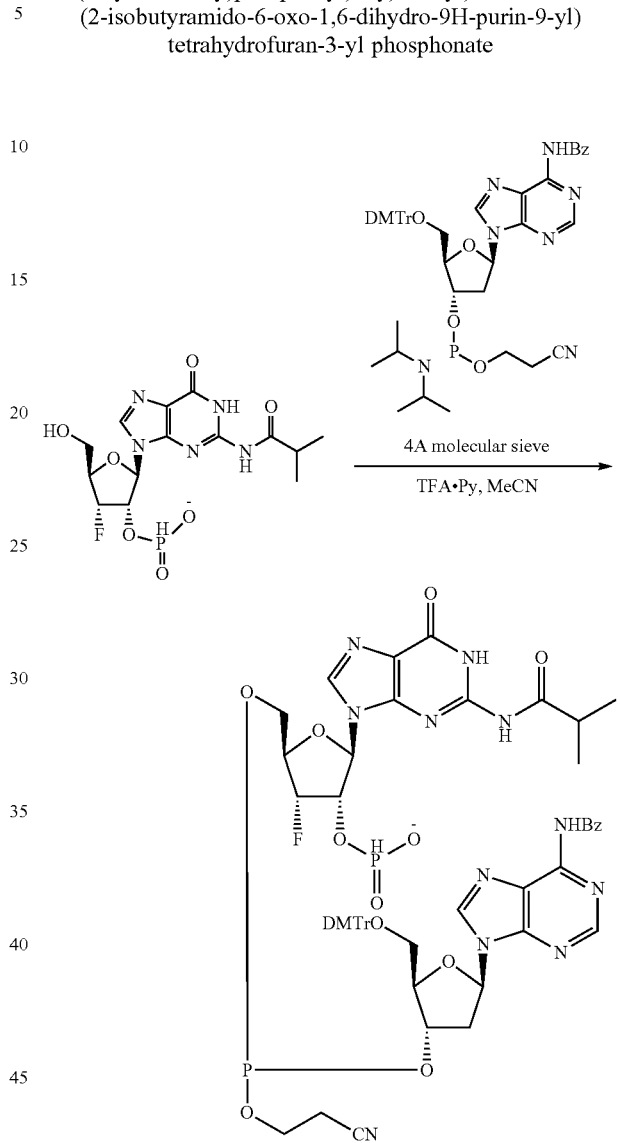

((2R,3 S,5R)-5-(6-benzamido-9H-purin-9-yl)-2-((bis(4-methoxyphenyl)(phenyl)methoxy) methyl)tetrahydrofuran-3-yl (2-cyanoethyl) diisopropylphosphoramidite (1058 mg, 1.234 mmol) was co-evaporated with dry ACN (3×5 mL), re-dissolved in ACN (10 mL) under Ar, and dried by adding activated 4 Å molecular sieve (200 mg). (2R,3S,4R,5R)-4-fluoro-5-(hydroxymethyl)-2-(2-isobutyramido-6-oxo-1,6-dihydro-9H-purin-9-yl)tetrahydrofuran-3-yl phosphonate (430 mg, 1.03 mmol) and pyridinium 2,2,2-trifluoroacetate (298 mg, 1.54 mmol) were co-evaporated with ACN (3×5 mL) and then re-dissolved in ACN (10 mL), and dried by adding activated 4 Å molecular sieve (200 mg). After 30 min, it was added to the previously prepared mixture containing ((2R,3S,5R)-5-(6-benzamido-9H-purin-9-yl)-2-((bis(4-methoxyphenyl)(phenyl) methoxy)methyl)tetrahydrofuran-3-yl (2-cyanoethyl) diisopropylphosphoramidite. It was stirred at rt for 30 min. The reaction mixture was used for the next reaction step without purification. LCMS (ES, m/z): 1173.8 [M−H]⁻.

Step 2. (2R,3S,4R,5R)-5-((((((2R,3S,5R)-5-(6-benzamido-9H-purin-9-yl)-2-((bis(4-methoxyphenyl)(phenyl)methoxy)methyl)tetrahydrofuran-3-yl)oxy)(2-cyanoethoxy)phosphorothioyl)oxy)methyl)-4-fluoro-2-(2-isobutyramido-6-oxo-1,6-dihydro-9H-purin-9-yl)tetrahydrofuran-3-yl phosphonate

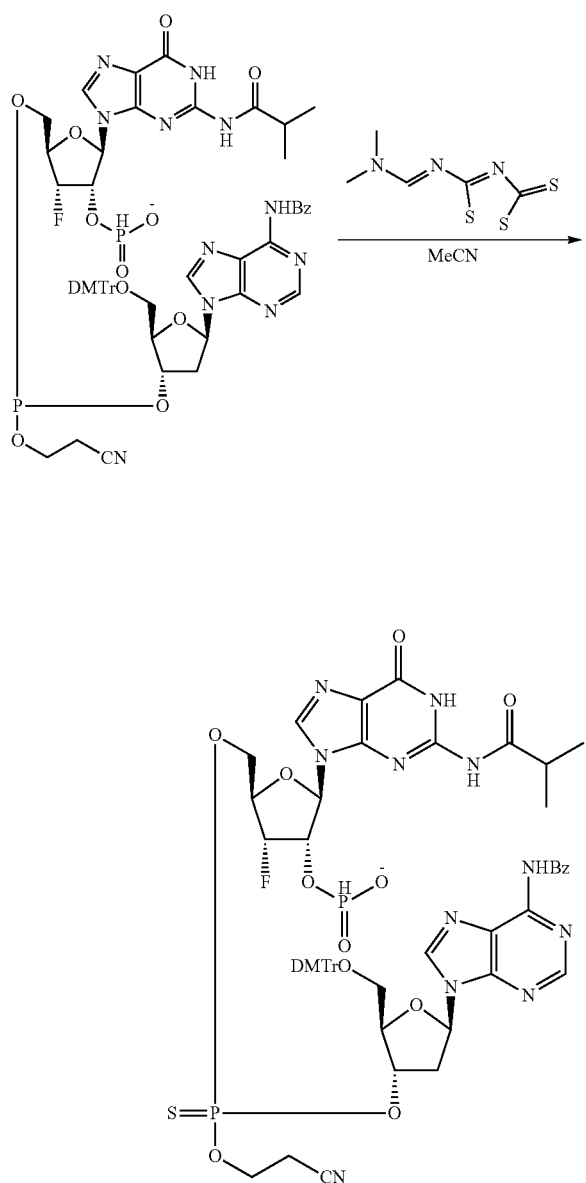

To the reaction mixture from Step 1 was added (E)-N,N-dimethyl-N'-(3-thioxo-3H-1,2,4-dithiazol-5-yl)formimidamide (DDTT, 0.232 g, 1.13 mmol) in one portion. The mixture was stirred at rt for 1 h. It was concentrated to give a crude sample containing the product, which was used for the next reaction step without purification. LCMS (ES, m/z): 1205.8 [M−H]⁻.

Step 3. (2R,3S,4R,5R)-5-((((((2R,3S,5R)-5-(6-benzamido-9H-purin-9-yl)-2-(hydroxymethyl)tetrahydrofuran-3-yl)oxy)(2-cyanoethoxy)phosphorothioyl)oxy)methyl)-4-fluoro-2-(2-isobutyramido-6-oxo-1,6-dihydro-9H-purin-9-yl)tetrahydrofuran-3-yl phosphonate

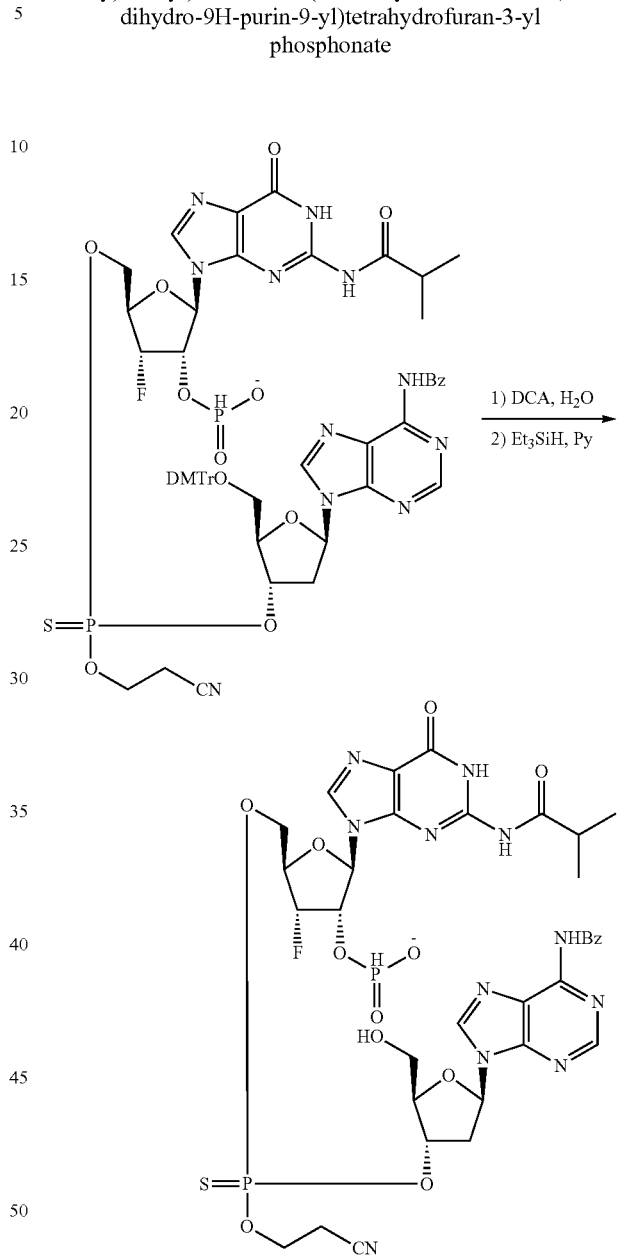

To a solution of the crude from Step 2 in CH₂Cl₂ (15 mL) was added water (0.2 mL, 10 mmol) and 2,2-dichloroacetic acid in CH₂Cl₂ (0.6M, 15 mL, 9 mmol). After 30 min, triethylsilane (28 mL) was added, and it was stirred for 1.5 h. Then, pyridine (1.4 mL) was added. It was concentrated, and the residue was purified by reverse phase (C18) chromatography eluted with 0 to 43% ACN in aq NH₄HCO₃ (5 mM) to give the product. LCMS (ES, m/z): 905.8 [M+H]⁺. ¹H-NMR (300 MHz, CD₃OD): δ 8.71-8.44 (m, 2H), 8.21-8.03 (m, 3H), 7.80 (d, J=10.4 Hz, 0.5H), 7.66-7.61 (m, 1H), 7.54 (t, J=7.6 Hz, 2H), 6.61-6.42 (m, 1H), 6.14 (dd, J=13.2, 6.0 Hz, 1H), 5.68 (d, J=9.9 Hz, 0.5H), 5.60-5.19 (m, 3H), 4.69-4.36 (m, 3H), 4.36-4.17 (m, 3H), 3.92-3.64 (m, 2H), 3.13-2.55 (m, 5H), 1.19 (dd, J=6.9, 2.1 Hz, 6H). ¹⁹F-NMR (282 MHz, CD$_3$OD): δ −202.55, −202.75 (d, 1F). $^{31}$P-NMR (121 MHz, CD$_3$OD): δ 66.91, 66.69 (2s, 1P); 2.66, 2.60 (2s, 1P).

Step 4: (5R,7R,8S,12aR,14R,15aS,16R)-2-(2-cyanoethoxy)-16-fluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10]pentaoxadiphosphacyclotetradecin-10-olate 2-sulfide Step 5: (5R,7R,8S,12aR,14R,15aS,16R)-2-(2-cyanoethoxy)-16-fluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10]pentaoxadiphosphacyclotetradecin-10-olate 2,10-disulfide

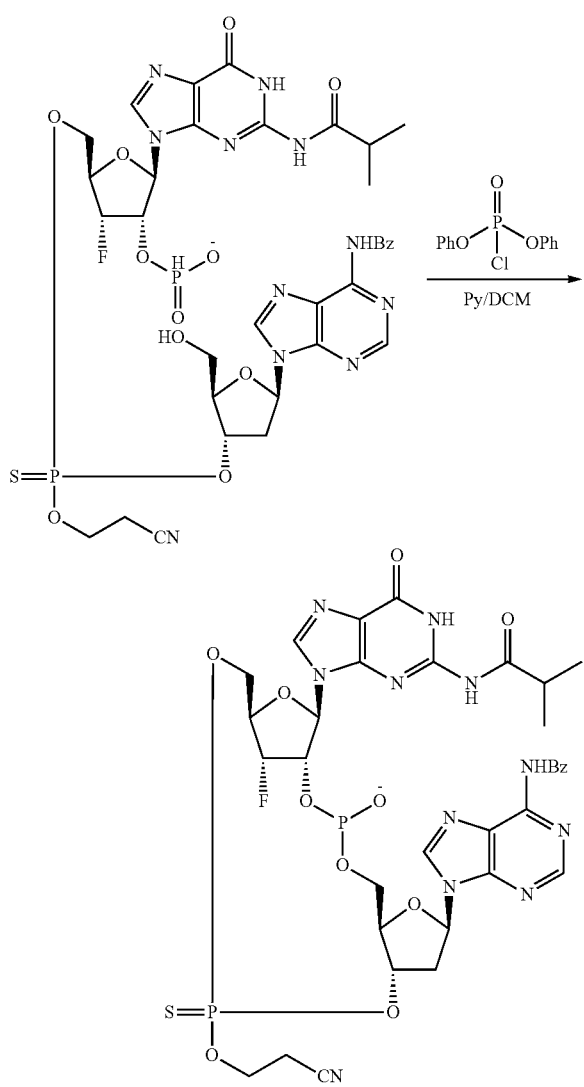

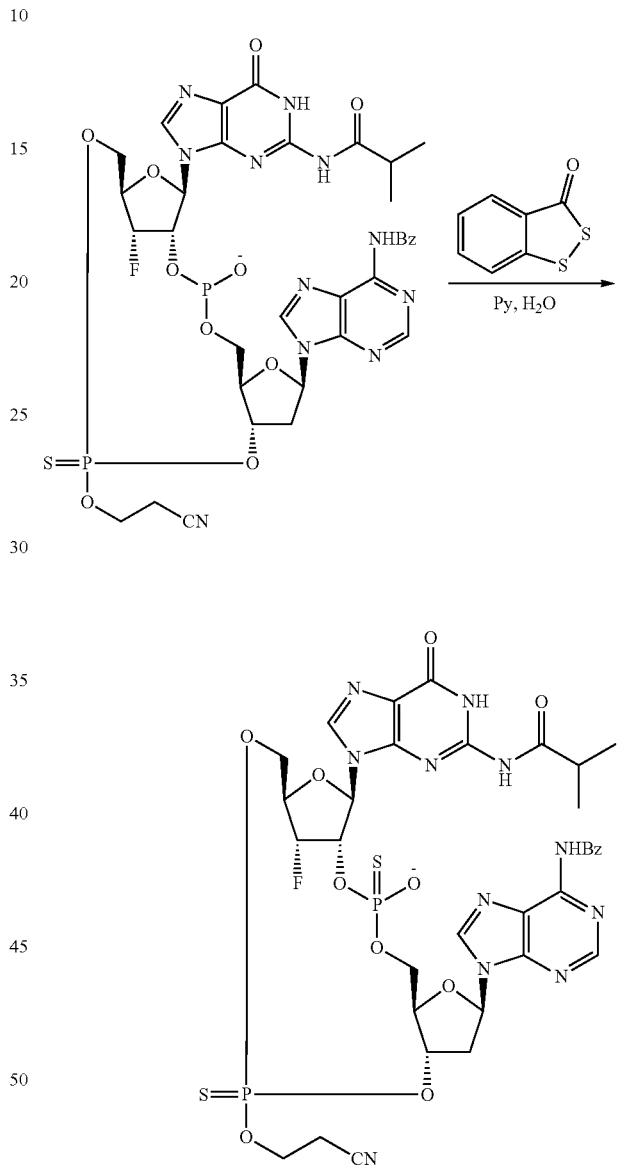

Diphenyl phosphorochloridate (2375 mg, 8.84 mmol) was added to pyridine (45 ml) at −30° C. To the solution at −30° C. was added (2R,3S,4R,5R)-5-(((((2R,3S,5R)-5-(6-benzamido-9H-purin-9-yl)-2-(hydroxymethyl)tetrahydrofuran-3-yl)oxy)(2-cyanoethoxy)phosphorothioyl)oxy)methyl)-4-fluoro-2-(2-isobutyramido-6-oxo-1,6-dihydro-9H-purin-9-yl)tetrahydrofuran-3-yl phosphonate (400 mg, 0.44 mmol) in CH$_2$Cl$_2$ (45 mL) dropwise over 20 min. The resulting mixture was stirred at −30° C. for 40 min. The reaction mixture was used for the next reaction step immediately without purification. LCMS (ES, m/z): 887.8 [M+H]$^+$.

To the mixture from Step 4 at −30° C. was added 3H-benzo[c][1,2]dithiol-3-one (112 mg, 0.663 mmol) and water (279 μL, 15.5 mmol). After stirring at rt for 1 h, the mixture was poured into a solution of Na$_2$S$_2$O$_3$.5H$_2$O (280 mg) in water (10 mL) at 0° C. It was stirred at rt for 5 min, and the mixture was concentrated under reduced pressure. The residue was purified by reverse phase (C18) chromatography eluted with 0 to 28% ACN in aq NH$_4$HCO$_3$ (5 mM) to give the product. LCMS (ES, m/z): 919.8 [M+H]$^+$. $^{19}$F-NMR (376 MHz, CD$_3$OD): δ −198.51, −198.98, −200.16 (3s, 1F).]$^+$. $^{31}$P-NMR (162 MHz, CD$_3$OD): δ 65.90, 65.09, 63.64, 62.95, 57.26, 56.50 (6s, 2P).

Step 6. Diastereomers (5R,7R,8S,12aR,14R,15aS, 16R)-16-fluoro-7-{2-[(2-methylpropanoyl) amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10] pentaoxadiphosphacyclotetradecine-2,10-diolate 2,10-disulfide (28-6-A), (5R,7R,8S,12aR,14R,15aS, 16R)-16-fluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l]1,3,6,9,11,2,10 pentaoxadiphosphacyclotetradecine-2,10-diolate 2,10-disulfide (28-6-B), and (5R,7R,8S,12aR, 15aS,16R)-16-fluoro-7-{2-[(2-methylpropanoyl) amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10] pentaoxadiphosphacyclotetradecine-2,10-diolate 2,10-disulfide (28-6-C)

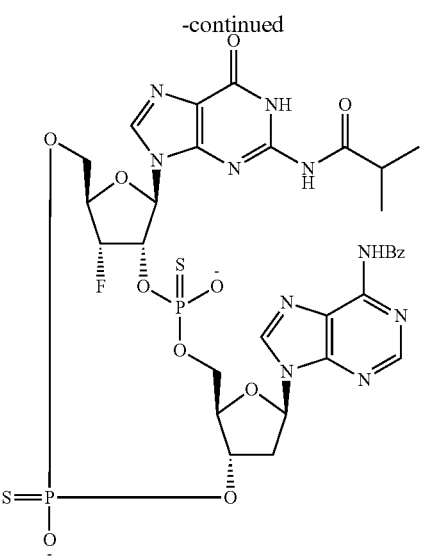

28-6-B

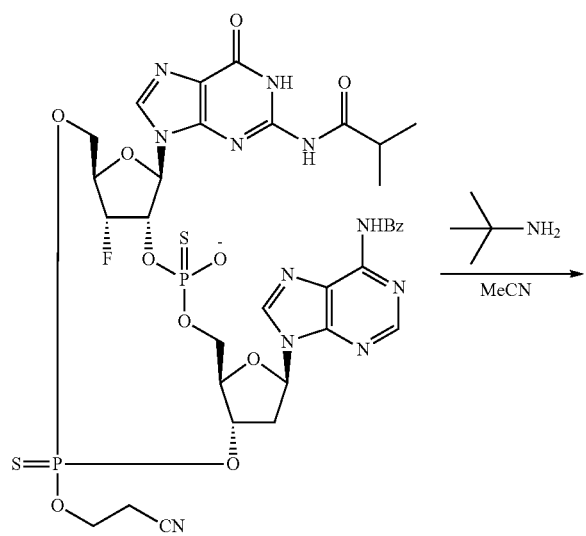

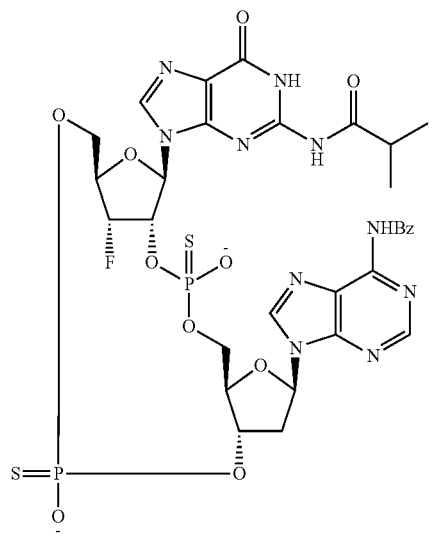

28-6-C

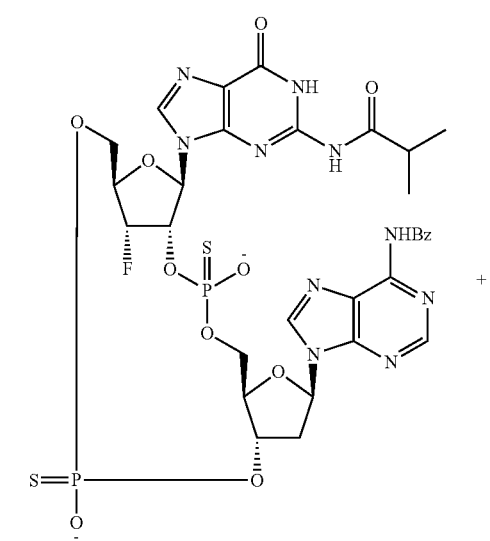

28-6-A

To a solution of (5R,7R,8S,12aR,14R,15aS,16R)-2-(2-cyanoethoxy)-16-fluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10]pentaoxadiphosphacyclotetradecin-10-olate 2,10-disulfide (265 mg, 0.288 mmol) in ACN (5 mL) at rt was added tert-butylamine (5 mL, 0.29 mmol). The reaction mixture was stirred for 10 min. Then, volatile components were removed under reduced pressure. The residue was purified by preparative-HPLC (T3 Prep Column, 19 mm×250 mm) eluted with 5 to 20% ACN in aq NH$_4$HCO$_3$ (50 mM) over 21 min.

The first fractions (T$_R$: 8.95 min) gave (5R,7R,8S,12aR, 14R,15aS,16R)-16-fluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10]pentaoxadiphosphacyclotetradecine-2,10-diolate 2,10-disulfide (28-6-A). LCMS (ES, m/z): 866.7 [M+H]$^+$. $^1$H-NMR (400 MHz, DMSO-d$_6$): δ 8.74 (s, 1H), 8.71 (s, 1H), 8.26 (s, 1H), 8.07 (d, J=7.5 Hz, 1H), 7.65 (d, J=7.7 Hz, 1H), 7.57 (t, J=7.5 Hz, 2H), 6.60-6.34 (m, 1H), 5.94 (d, J=8.6 Hz, 1H), 5.91-5.66 (m, 1H), 5.46-5.16 (m, 2H), 4.50 (d, J=27.0 Hz, 1H), 4.27 (d, J=9.8 Hz, 1H), 4.16 (t, J=10.1 Hz, 1H), 3.98 (q, J=11.0 Hz, 1H), 3.86 (d, J=11.9 Hz, 1H), 3.72-3.69 (m, 1H), 3.10-3.06 (m, 1H), 3.00-2.82 (m, 1H), 2.74-2.70 (m, 1H), 1.06 (dd, J=27.2, 6.8 Hz, 6H). $^{31}$P-NMR (162 MHz, DMSO-d$_6$): δ 53.92 (s, 1P), 52.99 (s, 1P).

The second fractions (T$_R$: 10.00 min) gave (5R,7R,8S,12aR,14R,15aS,16R)-16-fluoro-7-{2-[(2-methylpropanoyl)amino]-6-oxo-1,6-dihydro-9H-purin-9-yl}-14-{6-[(phenylcarbonyl) amino]-9H-purin-9-yl}octahydro-12H-5,8-methanofuro[3,2-l][1,3,6,9,11,2,10]pentaoxadiphosphacyclotetradecine-2,10-diolate 2,10-disulfide (28-6-B). LCMS (ES, m/z): 866.7 [M+H]$^+$.

The third fractions (T$_R$: 11.27-12.16 min) gave (5R,7R,8S,12aR,14R,15aS,16R)-16-fluoro-7-{2-[(2-methylpropanoyl)amino]-6-oxo-1,6-dihydro-9H-purin-9-yl}-14-{6-[(p-henylcarbonyl)amino]-9H-purin-9-yl}octahydro-12H-5,8-methanofuro[3,2-l][1,3,6,9,11,2,10]pentaoxadiphosphacyclotetradecine-2,10-diolate 2,10-disulfide (28-6-C), a mixture of two diastereomers, which was used in next step. LCMS (ES, m/z): 866.7 [M+H]$^+$. $^1$H-NMR (400 MHz, DMSO-d$_6$): δ 8.77 (s, 1H), 8.74 (s, 1H), 8.72 (s, 1H), 8.12-8.02 (m, 2H), 7.66-7.64 (m, 1H), 7.56 (t, J=7.5 Hz, 2H), 6.47-6.44 (m, 1H), 5.99 (d, J=8.6 Hz, 1H), 5.55-5.33 (m, 2H), 5.22 (d, J=11.6 Hz, 1H), 4.47 (d, J=25.7 Hz, 1H), 4.43-4.40 (m, 1H), 4.03-3.98 (m, 2H), 3.84 (d, J=11.8 Hz, 1H), 3.75-3.72 (m, 1H), 3.18-3.15 (m, 1H), 2.82-2.73 (m, 2H), 1.13 (dd, J=6.9, 2.5 Hz, 6H). $^{31}$P-NMR (162 MHz, DMSO): δ 53.42 (s, 1P), 52.16 (s, 1P).

Step 7: 2-amino-9-[(5R,7R,8S,12aR,14R,15aS,16R)-14-(6-amino-9H-purin-9-yl)-16-fluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomers 1 and 2)

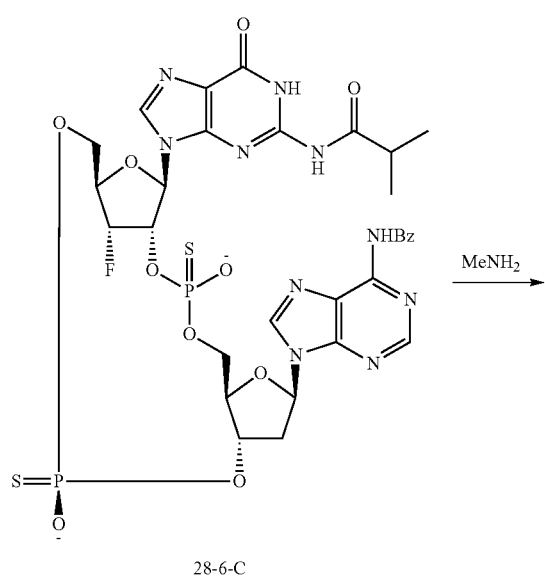

28-6-C

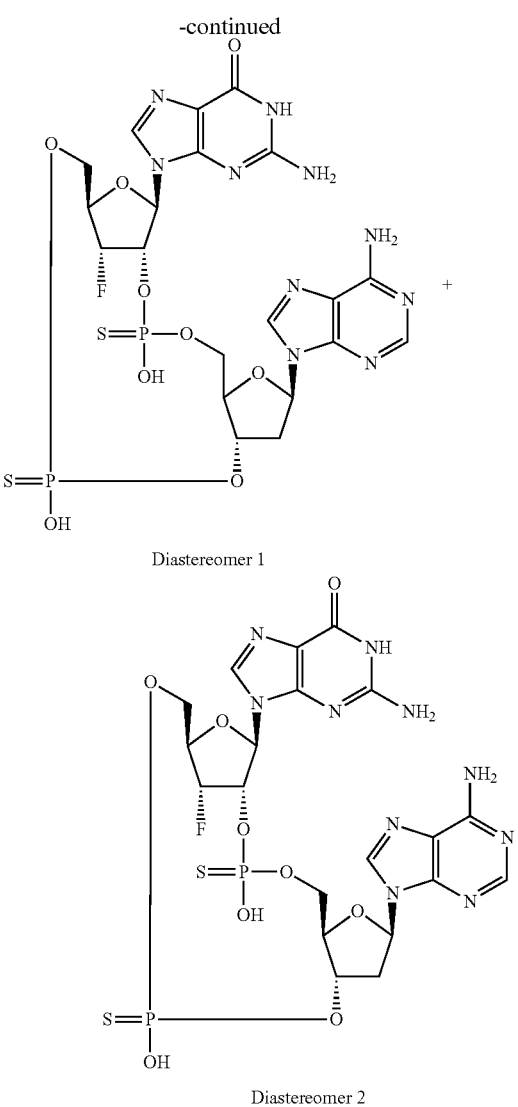

Diastereomer 1

Diastereomer 2

(5R,7R,8S,12aR,14R,15aS,16R)-16-fluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10]pentaoxadiphosphacyclotetradecine-2,10-diolate 2,10-disulfide (28-6-C) (180 mg, 0.208 mmol) was dissolved in a solution of MeNH$_2$ in EtOH (30%, 5.0 mL, 42 mmol), and the resulting solution was stirred at rt for 1 h. The volatile components were removed under reduced pressure to give a crude sample that was purified by Prep-HPLC (Atlantis Prep T3 OBD Column, 19 mm×250 mm) eluted with 5 to 19.5% ACN in aq NH$_4$HCO$_3$ (50 mM) over 19 min to give, after concentration:

Example 117 (T$_R$: 14.82 min): 2-amino-9-[(2R,5R,7R,8S,10R,12aR,14R,15aS,16R)-14-(6-amino-9H-purin-9-yl)-16-fluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1). LCMS (ES, m/z): 690.8 [M−H]$^−$. $^1$H-NMR (400 MHz, D$_2$O): δ 8.14 (s, 1H), 8.13 (s, 1H), 8.11 (s, 1H), 6.37 (t, J=5.5 Hz, 1H), 5.99 (d, J=8.7 Hz, 1H), 5.54 (d, J=3.3 Hz, 0.5H), 5.48-5.30 (m, 1.5H), 5.12 (dd, J=10.2, 5.5 Hz, 1H), 4.66 (d, J=34.1 Hz, 1H), 4.36 (s, 1H), 4.24-4.01 (m, 4H), 3.04 (dt, J=14.1, 5.6 Hz, 1H), 2.79 (dt, J=13.5, 6.4 Hz, 1H).

¹⁹F-NMR (376 MHz, D₂O): δ −198.66 (s, 1F). ³¹P-NMR (162 MHz, D₂O): δ 53.97 (s, 1P), 53.46 (s, 1P).

Example 118 (T$_R$: 15.93 min): 2-amino-9-[(5R,7R,8S,12aR,14R,15aS,16R)-14-(6-amino-9H-purin-9-yl)-16-fluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2). LCMS (ES, m/z): 690.8 [M−H]⁻. ¹H-NMR (400 MHz, D₂O): δ 8.16 (s, 1H), 8.11 (s, 1H), 7.83 (s, 1H), 6.34 (dd, J=6.5, 3.0 Hz, 1H), 5.95 (d, J=8.6 Hz, 1H), 5.69-5.53 (m, 1H), 5.47 (d, J=3.4 Hz, 0.5H), 5.33 (d, J=3.4 Hz, 0.5H), 5.23 (p, J=7.3 Hz, 1H), 4.64 (d, J=26.7 Hz, 1H), 4.35 (ddd, J=10.6, 6.9, 3.2 Hz, 1H), 4.31-4.17 (m, 2H), 4.05-3.95 (m, 2H), 2.94-2.85 (m, 1H), 2.74 (dt, J=14.0, 7.2 Hz, 1H). ¹⁹F-NMR (376 MHz, D₂O): δ −198.74 (s, 1F). ³¹P-NMR (162 MHz, D₂O): δ 55.05 (s, 1P), 52.87 (s, 1P).

Example 119: 2-amino-9-[1(5R,7R,8S,12aR,14R,15aS,16R)-14-(6-amino-9H-purin-9-yl)-16-fluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 3)

Step 1: 2-amino-9-[(5R,7R,8S,12aR,14R,15aS,16R)-14-(6-amino-9H-purin-9-yl)-16-fluoro-2,10-dihydroxy-2,1-disulfidooctahydro-12H-5,8-methanofuro[3,2-l][1,3,6,9,11,2,10]pentaoxadiphosphacyclotetradecin-7-yl]-1,9-dihydro-6H-purin-6-one (5R,7R,8S,12aR,14R,15aS,16R)-16-fluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10]pentaoxadiphosphacyclotetradecine-2,10-diolate 2,10-disulfide (28-6-B) (45 mg, 0.053 mmol) was dissolved in a solution of MeNH$_2$ in EtOH (30%, 1.5 mL, 11 mmol), and the resulting solution was stirred at rt for 1 h. The volatile components were removed under reduced pressure, and the residue was purified by Prep-HPLC (Atlantis Prep T3 OBD Column, 19 mm×250 mm) eluted with 18 to 19.5% ACN in aq NH$_4$HCO$_3$ (50 mM) over 16 min to give the product (T$_R$: 11.22 min). LCMS (ES, m/z): 690.8 [M−H]$^-$. $^1$H-NMR (400 MHz, D$_2$O): δ 8.32 (s, 1H), 8.15 (s, 1H), 7.96 (s, 1H), 6.41 (t, J=5.7 Hz, 1H), 6.00 (d, J=8.6 Hz, 1H), 5.56 (dt, J=22.9, 10.4 Hz, 1H), 5.40-5.30 (m, 1.5H), 5.19 (d, J=3.6 Hz, 0.5H), 4.64 (d, J=28.3 Hz, 1H), 4.40-4.27 (m, 2H), 4.27-4.17 (m, 1H), 4.02 (d, J=11.9 Hz, 1H), 3.95-3.85 (m, 1H), 2.92 (dt, J=14.1, 5.6 Hz, 1H), 2.79 (td, J=13.8, 13.1, 6.1 Hz, 1H). $^{19}$F-NMR (376 MHz, D$_2$O): δ −198.02 (s, 1F). $^{31}$P-NMR (162 MHz, D$_2$O): δ 57.89 (s, 1P), 55.05 (s, 1P).

Example 120: 2-amino-9-[(5R,7R,8S,12aR,14R,15aS,16R)-14-(6-amino-9H-purin-9-yl)-16-fluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 4)

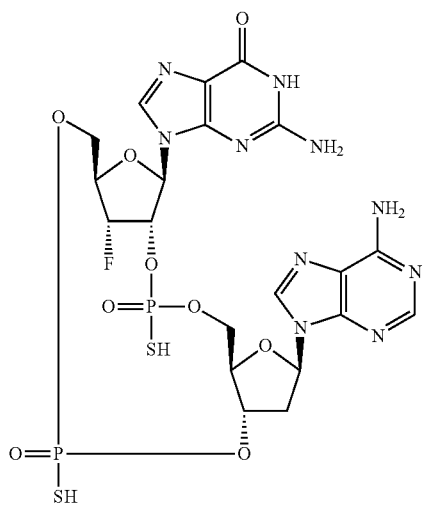

Diastereomer 4

Step 1: 2-amino-9-[(5R,7R,8S,12aR,14R,15aS,16R)-14-(6-amino-9H-purin-9-yl)-16-fluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one

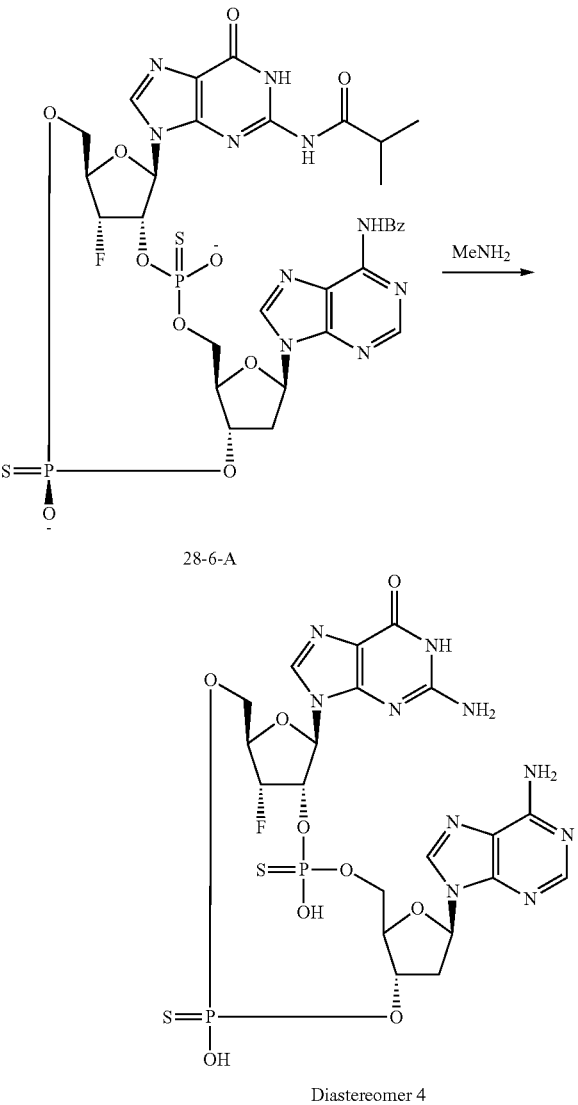

28-6-A

Diastereomer 4

(5R,7R,8S,12aR,14R,15aS,16R)-16-fluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10]pentaoxadiphosphacyclotetradecine-2,10-diolate 2,10-disulfide (28-6-A) (45 mg, 0.053 mmol) was dissolved in a solution of MeNH$_2$ in EtOH (30%, 1.5 mL, 11 mmol), and the resulting solution was stirred at rt for 1 h. The volatile components were removed under reduced pressure, and the residue was purified by Prep-HPLC (Atlantis Prep T3 OBD Column, 19 mm×250 mm) eluted with 4 to 11% ACN in aq NH$_4$HCO$_3$ (50 mM) over 17 min to give the product (T$_R$: 11.72 min). LCMS (ES, m/z): 690.8 [M−H]$^-$. $^1$H-NMR (400 MHz, D$_2$O): δ 8.33 (s, 1H), 8.29 (s, 1H), 8.16 (s, 1H), 6.41 (t, J=6.5 Hz, 1H), 6.05 (d, J=8.6 Hz, 1H), 5.49-5.32 (m, 1.5H), 5.23 (d, J=3.5 Hz, 0.5H), 4.79-4.73 (m, 1H), 4.69-4.59 (m, 1H), 4.40-4.32 (m, 1H), 4.23 (q, J=8.9, 7.5 Hz, 2H), 4.07 (d, J=11.8 Hz, 1H), 3.94-3.84 (m, 1H), 3.00 (dt, J=12.7, 6.2 Hz, 1H), 2.94-2.84 (m, 1H). $^{19}$F-NMR (376 MHz, D$_2$O): δ −197.92 (s, 1F). $^{31}$P-NMR (162 MHz, D$_2$O): δ 59.46 (s, 1P), 54.42 (s, 1P).

Example 121, 122, 123: 2-amino-9-[(2R,5S,7R,8R,10R,12aR,14R,15aS)-14-(4-amino-7H-pyrrolo[2,3-d]pyrimidin-7-yl)-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) and 2-amino-9-[(5S,7R,8R,12aR,14R,15aS)-14-(4-amino-7H-pyrrolo[2,3-d]pyrimidin-7-yl)-2,10-dioxido-2,10-disulfanyloctahydro-12H-5,8-methano-furo[3,2-l][1,3,6,9,11,2,10]pentaoxadiphosphacyclotetradecin-7-yl]-1,9-dihydro-6H-purin-6-one (Diastereomers 2 and 3)

Diastereomer 1

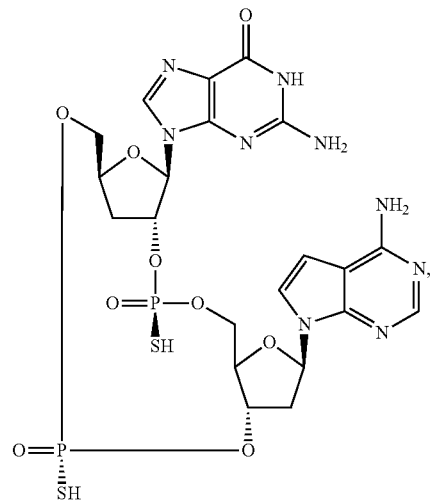

Diastereomer 2

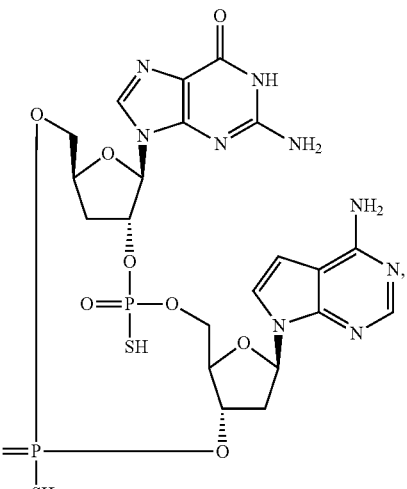

Diastereomer 3

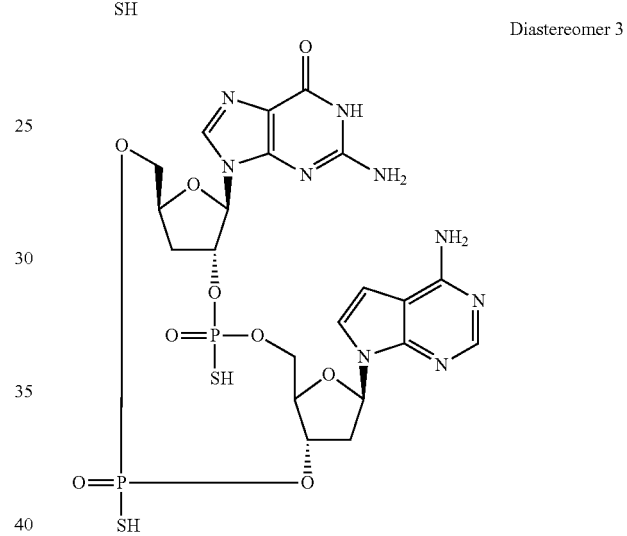

Step 1: (2R,3R,5S)-5-(hydroxymethyl)-2-(2-isobutyramido-6-oxo-1,6-dihydro-9H-purin-9-yl)tetrahydrofuran-3-yl hydrogen phosphonate

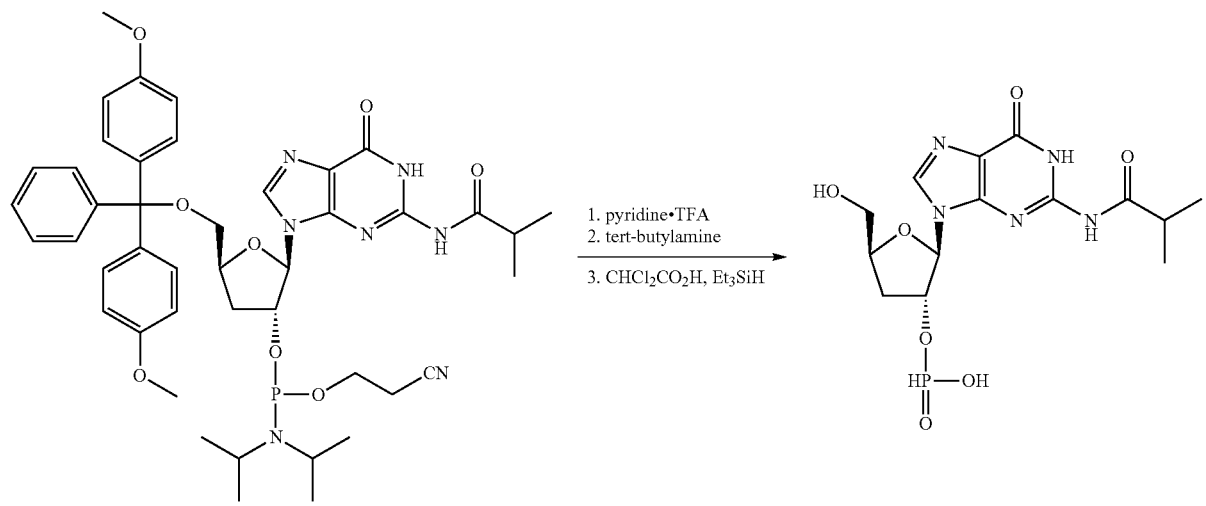

To a flask was added (2R,3R,5 S)-5-((bis(4-methoxyphenyl)(phenyl)methoxy)methyl)-2-(2-isobutyramido-6-oxo-1,6-dihydro-9H-purin-9-yl)tetrahydrofuran-3-yl (2-cyanoethyl) diisopropylphosphoramidite (4 g, 4.76 mmol), MeCN (23.65 ml), and water (0.158 ml). Pyridine trifluoroacetate (1.104 g, 5.71 mmol) was then added, and the mixture was stirred 1 h at rt, after which time tert-butylamine (20.02 ml, 190 mmol) was added. After stirring 1 h at rt, the mixture was concentrated under reduced pressure. The resulting mixture was dissolved in DCM (39.9 ml), and then water (0.798 ml) was added, followed by dichloroacetic acid (2.75 ml, 33.3 mmol). The solution was stirred for 20 min at rt, and then triethylsilane (133 ml, 833 mmol) was added, and the reaction was stirred for a further 2 h at rt. After cooling to 0° C., pyridine was added, and the mixture was concentrated under reduced pressure. The resulting sample was partitioned between hexanes (100 mL) and water (20 mL). The layers were separated, and the aqueous phase was purified by reverse phase HPLC using a gradient solvent system of 0-35% MeCN in 0.04% aq ammonium bicarbonate. The product-containing fractions were collected and lyophilized to give (2R,3R,5S)-5-(hydroxymethyl)-2-(2-isobutyramido-6-oxo-1,6-dihydro-9H-purin-9-yl)tetrahydrofuran-3-yl hydrogen phosphonate. LCMS (ES, m/z): 400 [M−H]⁻.

Step 2: (2R,3S,5R)-5-(4-benzamido-7H-pyrrolo[2,3-d]pyrimidin-7-yl)-2-((bis(4-methoxyphenyl) (phenyl)methoxy)methyl)tetrahydrofuran-3-yl (2-cyanoethyl) diisopropylphosphoramidite

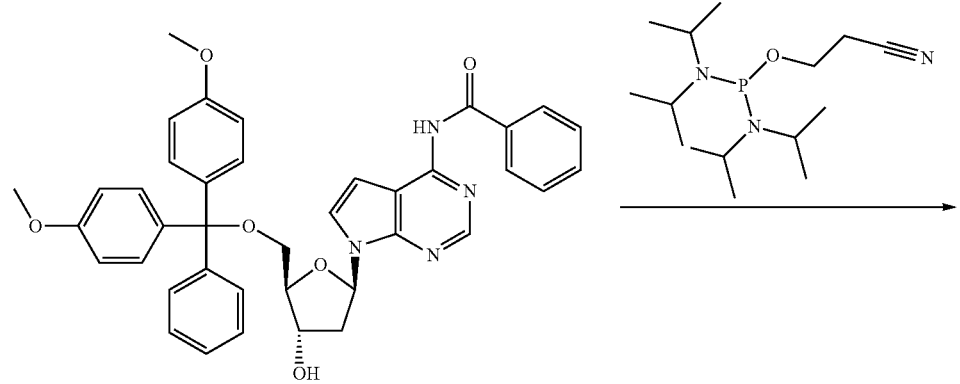

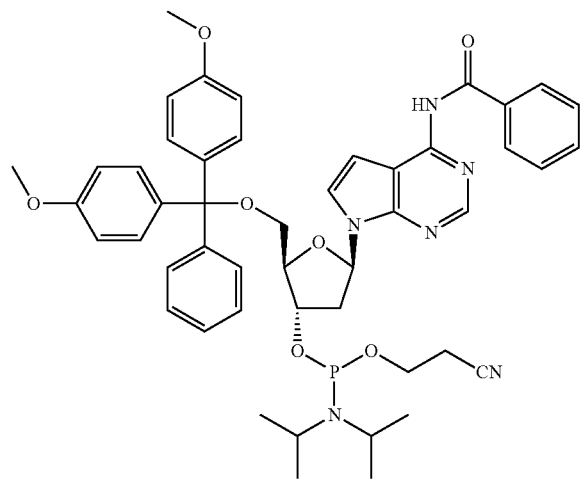

To a flask was added N-(7-((2R,4S,5R)-5-((bis(4-methoxyphenyl)(phenyl)methoxy) methyl)-4-hydroxytetrahydrofuran-2-yl)-7H-pyrrolo[2,3-d]pyrimidin-4-yl)benzamide (4 g, 6.09 mmol), DCM (71.7 ml), and 4,5-dicyanoimidazole (2.158 g, 18.27 mmol), and the solution was cooled to 0° C. 2-Cyanoethyl N,N,N',N'-tetraisopropylphosphorodiamidite (6.77 ml, 21.32 mmol) was added, and the mixture was stirred for 15 min at 0° C., after which time the mixture was concentrated under reduced pressure and purified by silica gel chromatography using a gradient of 30-100% EtOAc in hexanes to yield (2R,3S,5R)-5-(4-benzamido-7H-pyrrolo[2,3-d]pyrimidin-7-yl)-2-((bis(4-methoxyphenyl)(phenyl)methoxy)methyl)tetrahydrofuran-3-yl (2-cyanoethyl) diisopropylphosphoramidite. LCMS (ES, m/z): 857 [M+H]⁻.

Step 3: (2R,3R,5S)-5-((((((2R,3S,5R)-5-(4-benzamido-7H-pyrrolo[2,3-d]pyrimidin-7-yl)-2-((bis(4-methoxyphenyl)(phenyl)methoxy)methyl)tetrahydrofuran-3-yl)oxy) (2-cyanoethoxy)phosphorothioyl) oxy)methyl)-2-(2-isobutyramido-6-oxo-1,6-dihydro-9H-purin-9-yl)tetrahydrofuran-3-yl hydrogen phosphonate

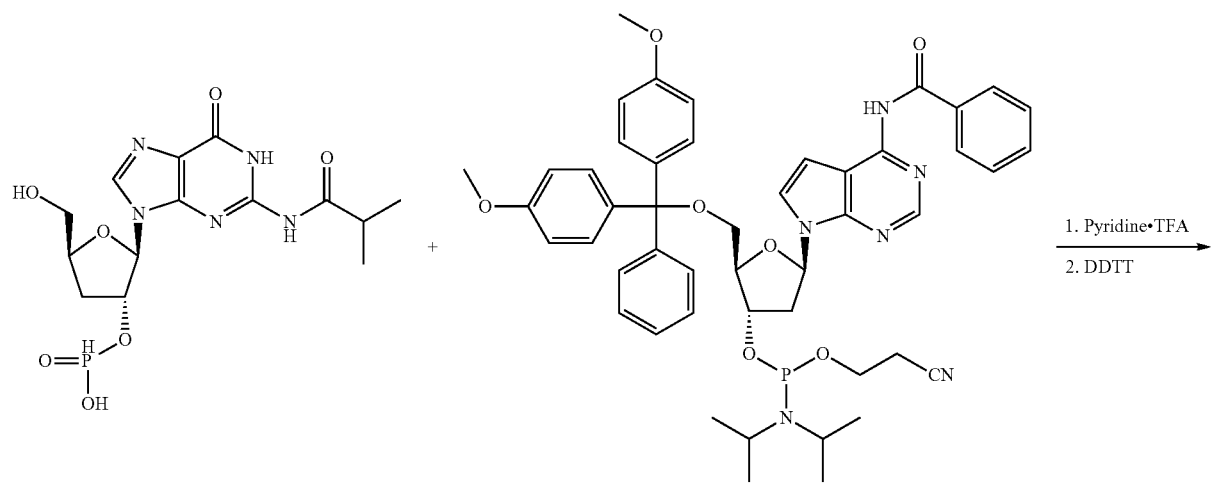

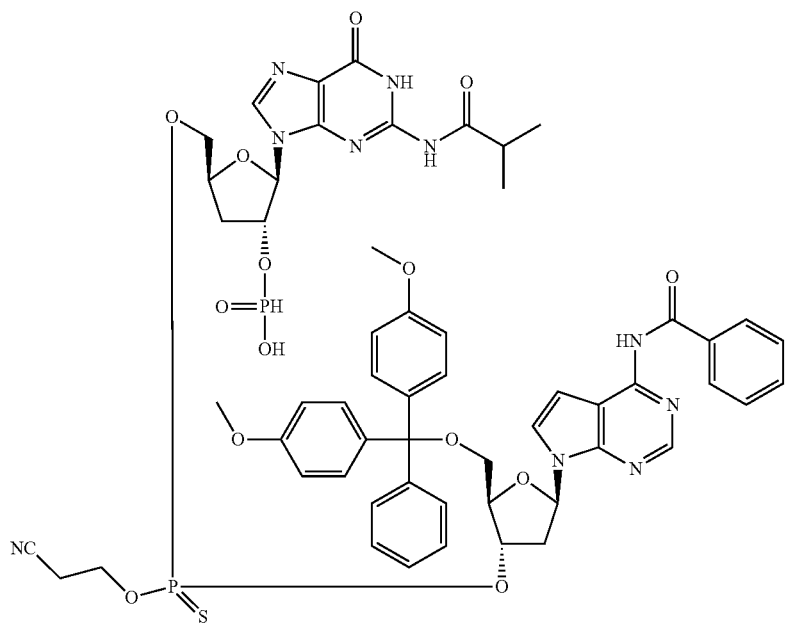

To a flask containing (2R,3R,5S)-5-(hydroxymethyl)-2-(2-isobutyramido-6-oxo-1,6-dihydro-9H-purin-9-yl)tetrahydrofuran-3-yl hydrogen phosphonate (1.62 g, 2.81 mmol) was added pyridine trifluoroacetate (0.543 g, 2.81 mmol), activated 4 Å sieves and MeCN (10 mL), and the mixture was stirred 20 min at rt. To a separate flask containing (2R,3S,5R)-5-(4-benzamido-7H-pyrrolo[2,3-d]pyrimidin-7-yl)-2-((bis(4-methoxyphenyl)(phenyl)methoxy)methyl)tetrahydrofuran-3-yl (2-cyanoethyl) diisopropylphosphoramidite (2.408 g, 2.81 mmol) was added MeCN (10 mL) and activated 4 Å sieves, and the mixture was stirred 20 min at rt, after which time the hydrogen phosphonate solution was added, and MeCN (2×4 mL) was used to complete the transfer. The mixture was stirred 1 h at rt, and then ((dimethylamino-methylidene)amino)-3H-1,2,4-dithiazoline-3-thione (0.634 g, 3.09 mmol) was added. The resulting mixture was stirred 30 min at rt and then concentrated under reduced pressure. Reverse phase HPLC purification using a gradient solvent system of 5-100% MeCN in 0.04% aqueous ammonium bicarbonate yielded (2R,3R,5S)-5-(((((2R,3S,5R)-5-(4-benzamido-7H-pyrrolo[2,3-d]pyrimidin-7-yl)-2-((bis(4-methoxyphenyl)(phenyl)methoxy)methyl)tetrahydrofuran-3-yl)oxy)(2-cyanoethoxy) phosphorothioyl)oxy)methyl)-2-(2-isobutyramido-6-oxo-1,6-dihydro-9H-purin-9-yl)tetrahydrofuran-3-yl hydrogen phosphonate. LCMS (ES, m/z): 1187 [M−H]⁻.

Step 4: N-{7-[(5S,7R,8R,12aR,14R,15aS)-2-(2-cyanoethoxy)-7-{2-[(2-methylpropanoyl)amino]-6-oxo-1,6-dihydro-9H-purin-9-yl}-10-oxido-10-sulfanyl-2-sulfidooctahydro-12H-5,8-methanofuro[3,2-l][1,3,6,9,11,2,10]pentaoxadiphosphacyclotetradecin-14-yl]-7H-pyrrolo[2,3-d]pyrimidin-4-yl}benzamide

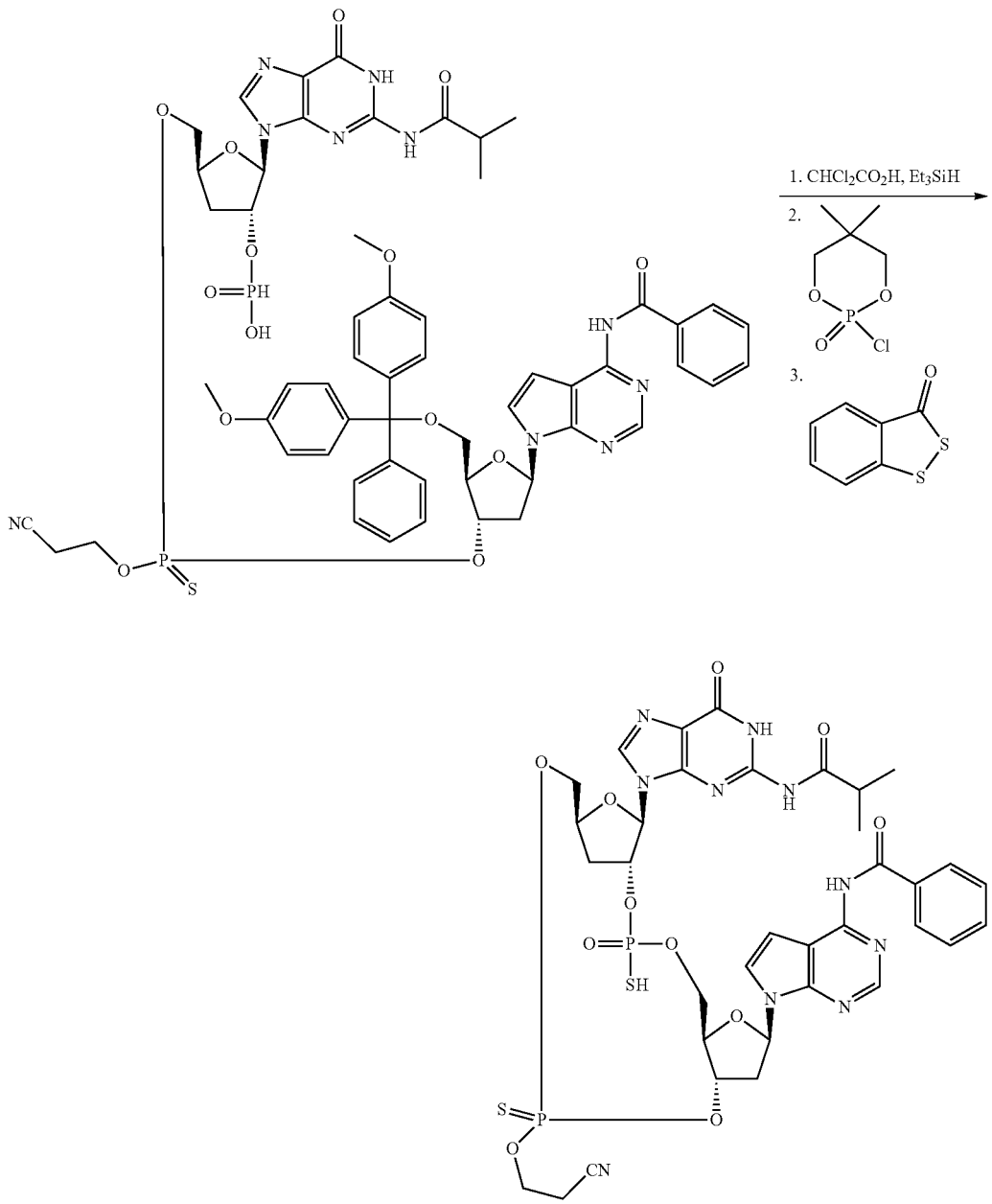

To a flask containing (2R,3R,5S)-5-((((((2R,3 S,5R)-5-(4-benzamido-7H-pyrrolo[2,3-d]pyrimidin-7-yl)-2-((bis(4-methoxyphenyl)(phenyl)methoxy)methyl)tetrahydrofuran-3-yl)oxy)(2-cyanoethoxy)phosphorothioyl)oxy)methyl)-2-(2-isobutyramido-6-oxo-1H-purin-9(6H)-yl)tetrahydrofuran-3-yl hydrogen phosphonate (1.34 g, 1.127 mmol) was added DCM (22.54 ml) and water (0.203 ml, 11.27 mmol), and then dichloroacetic acid (1.116 ml, 13.52 mmol) was added. The solution was stirred for 20 min at rt, and then triethylsilane (28.1 ml, 176 mmol) was added. After stirring 3 h at rt, the mixture was concentrated under reduced pressure. Pyridine (50 mL) was added, and then the mixture was concentrated under reduced pressure. This process was repeated 2x, and then pyridine (37.6 ml) was added, followed by 2-chloro-5,5-dimethyl-1,3,2-dioxaphosphorinane 2-oxide (0.624 g, 3.38 mmol). The resulting mixture was stirred for 1 h at rt, after which time water (610 µl, 33.8 mmol) was added, followed by 3H-1,2-benzodithiol-3-one (285 mg, 1.692 mmol). The resulting mixture was stirred 30 min at rt and then concentrated under reduced pressure. HPLC purification using a gradient solvent system of MeCN in 100 mM aqueous triethylammonium acetate yielded 3 separate diastereomers of N-{7-[(5 S,7R,8R,12aR,14R,15aS)-2-(2-cyanoethoxy)-7-{2-[(2-methylpropanoyl)amino]-6-oxo-1,6-dihydro-9H-purin-9-yl}]-10-oxido-10-sulfanyl-2-sulfidooctahydro-12H-5,8-methanofuro[3,2-l][1,3,6,9,11,2,10]pentaoxadiphosphacyclotetradecin-14-yl]-7H-pyrrolo[2,3-d]pyrimidin-4-yl}benzamide after lyopholization, all of which showed LCMS (ES, m/z): 899 [M–H]⁻.

Step 5: 2-amino-9-[(5S,7R,8R,12aR,14R,15aS)-14-(4-amino-7H-pyrrolo[2,3-d]pyrimidin-7-yl)-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one

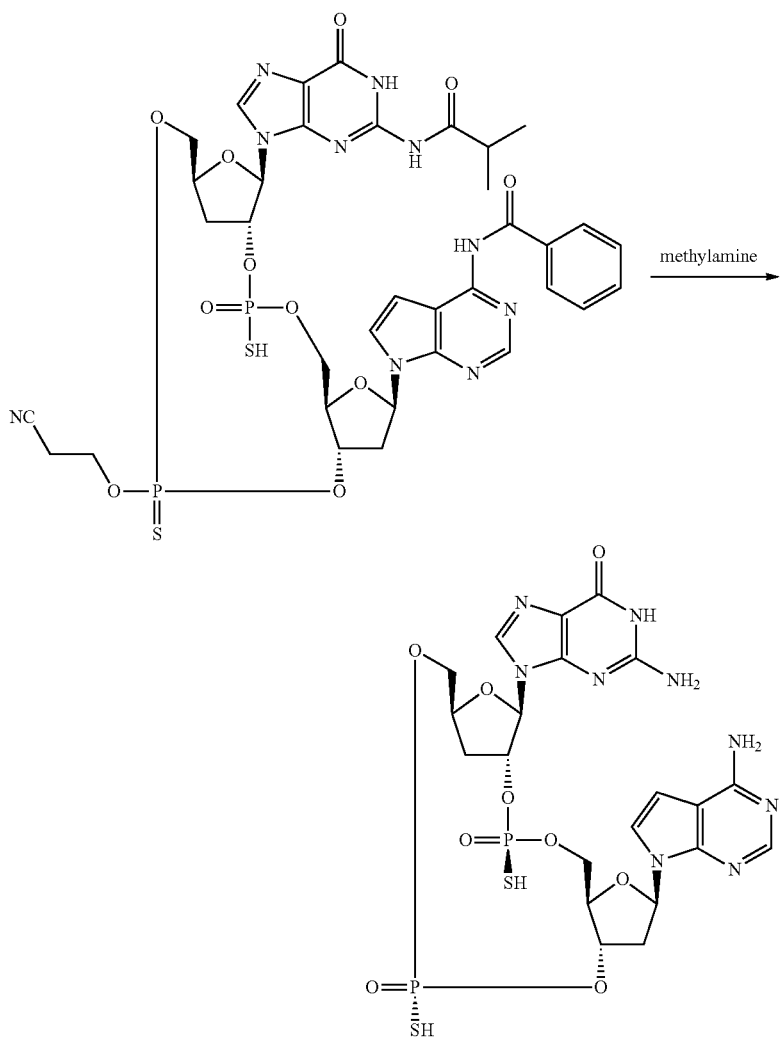

To a vial containing one diastereomer (slowest eluting) of N-{7-[(5 S,7R,8R,12aR,14R,15aS)-2-(2-cyanoethoxy)-7-{2-[(2-methylpropanoyl)amino]-6-oxo-1,6-dihydro-9H-purin-9-yl}-10-oxido-10-sulfanyl-2-sulfidooctahydro-12H-5,8-methanofuro[3,2-l][1,3,6,9,11,2,10]pentaoxadiphosphacyclotetradecin-14-yl]-7H-pyrrolo[2,3-d]pyrimidin-4-yl}benzamide (122 mg, 0.135 mmol) was added methylamine (33% in EtOH) (2 mL, 16.07 mmol) and the resulting solution was stirred for 4 h at rt, after which time it was concentrated under reduced pressure. Purification by reverse phase HPLC using a gradient solvent system of MeCN in 100 mM aqueous triethylammonium acetate yielded Example 121, 2-amino-9-[(2R,5 S,7R,8R,10R,12aR,14R,15aS)-14-(4-amino-7H-pyrrolo[2,3-d]pyrimidin-7-yl)-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1). LCMS (ES, m/z): 672 [M−H]−. $^1$H NMR (600 MHz, DMSO-d$_6$) δ 10.54 (s, 1H), 8.01 (s, 1H), 7.86 (s, 1H), 7.29 (d, J=2.7 Hz, 1H), 6.97 (s, 2H), 6.60-6.53 (m, 3H), 6.44 (t, J=6.9 Hz, 1H), 5.73 (d, J=2.7 Hz, 1H), 4.95 (s, 1H), 4.80 (s, 1H), 4.38-4.27 (m, 2H), 3.97-3.91 (m, 2H), 3.90-3.82 (m, 1H), 3.64 (dt, J=16.1, 9.3 Hz, 1H), 2.69-2.63 (m, 1H), 2.63 (s, 12H), 2.60-2.54 (m, 3H), 2.22-2.13 (m, 1H), 1.01-0.94 (m, 18H).

The other diastereomers from Step 4 were treated in an analogous manner to produce two additional diastereomers of 2-amino-9-[(5 S,7R,8R,12aR,14R,15aS)-14-(4-amino-7H-pyrrolo[2,3-d]pyrimidin-7-yl)-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one:

Example 122 (Diastereomer 2): LCMS (ES, m/z): 672 [M−H]−. $^1$H NMR (600 MHz, DMSO-d$_6$) δ 10.57 (s, 1H), 9.55 (s, 2H), 8.10 (s, 1H), 7.95 (s, 1H), 7.47 (s, 1H), 7.42 (d, J=3.2 Hz, 1H), 6.66 (d, J=3.4 Hz, 1H), 6.51 (s, 2H), 6.49-6.44 (m, 1H), 5.73 (d, J=4.0 Hz, 1H), 5.08-5.00 (m, 2H), 4.31-4.27 (m, 1H), 4.22 (t, J=11.3 Hz, 1H), 4.07 (q, J=10.6 Hz, 1H), 4.00-3.95 (m, 1H), 3.76-3.71 (m, 1H), 3.65 (td, J=11.6, 6.1 Hz, 1H), 3.02 (d, J=4.2 Hz, 12H), 2.67-2.61 (m, 1H), 2.61-2.53 (m, 2H), 2.18 (dt, J=11.7, 5.3 Hz, 1H), 1.12 (t, J=7.3 Hz, 18H).

Example 123 (Diastereomer 3): LCMS (ES, m/z): 672 [M−H]−. $^1$H NMR (600 MHz, DMSO-d$_6$) δ 10.53 (s, 1H), 8.01 (s, 3H), 7.28 (d, J=3.4 Hz, 1H), 6.97 (s, 2H), 6.56 (d, J=3.5 Hz, 1H), 6.49 (s, 2H), 6.44 (dd, J=8.6, 5.8 Hz, 1H), 5.70 (d, J=3.9 Hz, 1H), 5.00-4.92 (m, 1H), 4.90-4.83 (m, 1H), 4.33-4.27 (m, 1H), 4.12-3.96 (m, 4H), 3.81 (q, J=12.8, 11.6 Hz, 1H), 3.69 (dd, J=12.0, 6.0 Hz, 2H), 2.83-2.77 (m, 1H), 2.65 (d, J=37.6 Hz, 12H), 2.23 (dt, J=12.8, 6.7 Hz, 1H), 1.03-0.92 (m, 18H).

Examples 124, 125, and 126: 2-amino-9-[(5R,7R,8S,12aR,14R,15R,15aS,18S)-14-(6-amino-9H-purin-9-yl)-18-fluoro-2,10-dihydroxy-2,10-disulfidohexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one (Diastereomers 1-3)

Diastereomer 1

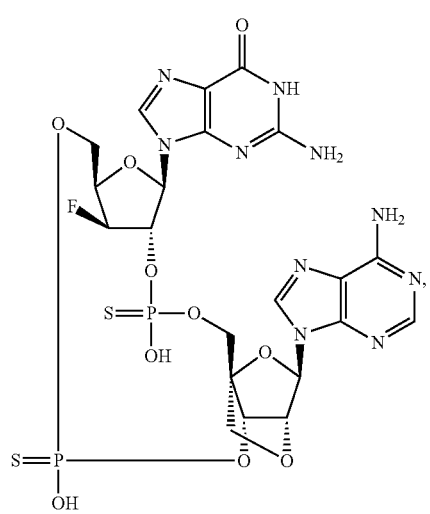

Diastereomer 2

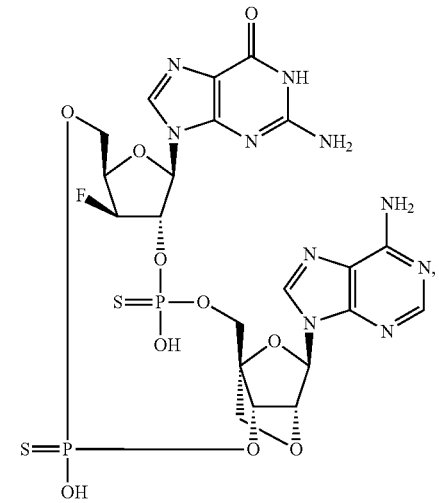

Diastereomer 3

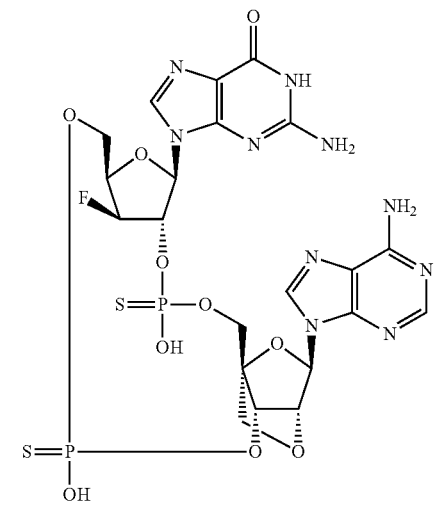

Step 1: (2R,3S,4S,5R)-5-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl phenyl phosphonate

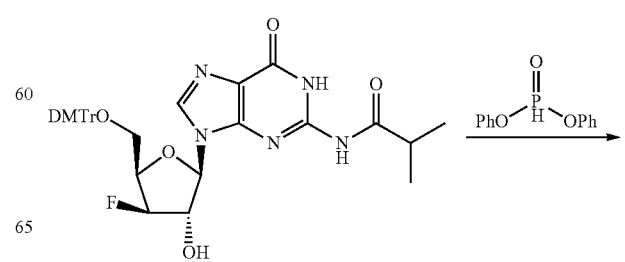

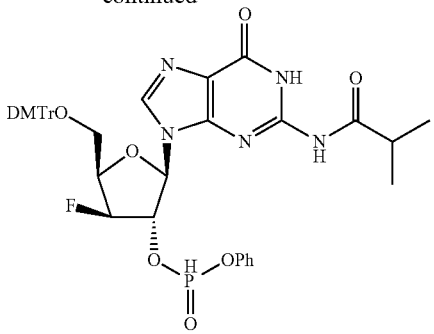

To a solution of N-(9-((2R,3S,4R,5R)-5-((bis(4-methoxyphenyl)(phenyl)methoxy) methyl)-4-fluoro-3-hydroxytetrahydrofuran-2-yl)-6-oxo-6,9-dihydro-1H-purin-2-yl)isobutyramide (630 mg, 0.96 mmol) in pyridine (5 mL) under Ar was added diphenyl phosphonate (1.07 g, 4.56 mmol), and the mixture was stirred at rt for 20 min. It was used for the next reaction step without purification. LCMS (ES, m/z): 798.3 [M+H]$^+$.

Step 2. t (2R,3S,4S,5R)-5-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl phosphonate

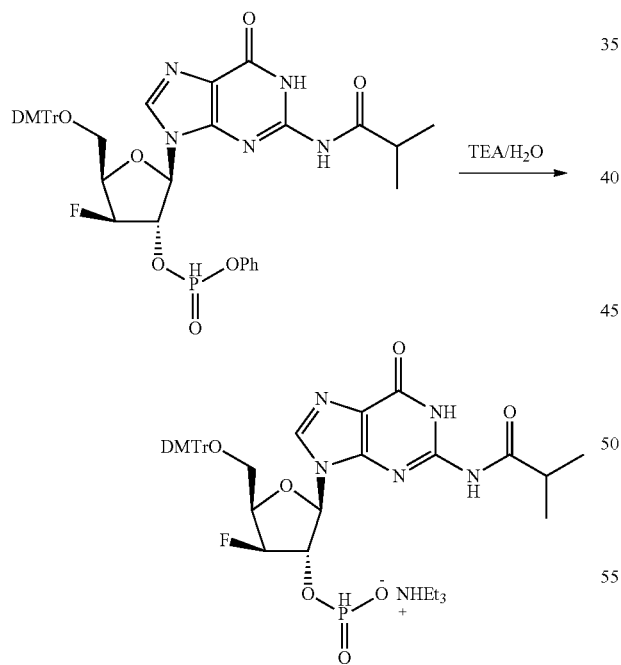

To the reaction mixture from Step 1 at 0° C. was added water (1 mL), triethylamine (1 mL). The resulting mixture was stirred at rt for 20 min. Then, it was concentrated, and the residue was partitioned between CH$_2$Cl$_2$ (50 mL) and aq NaHCO$_3$ (5%, 20 mL). The organic layer was washed with aq NaHCO$_3$ (5%, 20 mL), dried (Na$_2$S$_2$O$_4$), concentrated and purified by silica gel column chromatography using 0-7% MeOH in CH$_2$Cl$_2$ (1% Et$_3$N) to give the product. LCMS (ES, m/z): 722.2 [M+H]$^+$. $^1$H-NMR (400 MHz, CD$_3$OD): δ 7.76 (s, 1H), 7.74 (s, 0.5H), 7.51 (d, J=1.5 Hz, 1H), 7.48 (q, J=2.4, 1.9 Hz, 1H), 7.41-7.34 (m, 4H), 7.34-7.27 (m, 2H), 7.26-7.21 (m, 1H), 6.92-6.85 (m, 4H), 6.22 (s, 1H), 6.15 (s, 0.5H), 5.37 (d, J=2.7 Hz, 0.5H), 5.28-5.19 (m, 1.5H), 4.73-4.69 (m, 0.5H), 4.66-4.62 (m, 1H), 3.80 (s, 6H), 3.65-3.55 (m, 1H), 3.53-3.44 (m, 1H), 3.12 (q, J=7.3 Hz, 8H), 2.75 (p, J=6.8 Hz, 1H), 1.33-1.22 (m, 18H). $^{31}$P-NMR: (162 MHz, CD$_3$OD): δ 2.67 (s, 1P).

Step 3. (2R,3S,4S,5R)-4-fluoro-5-(hydroxymethyl)-2-(2-isobutyramido-6-oxo-1,6-dihydro-9H-purin-9-yl)tetrahydrofuran-3-yl phosphonate

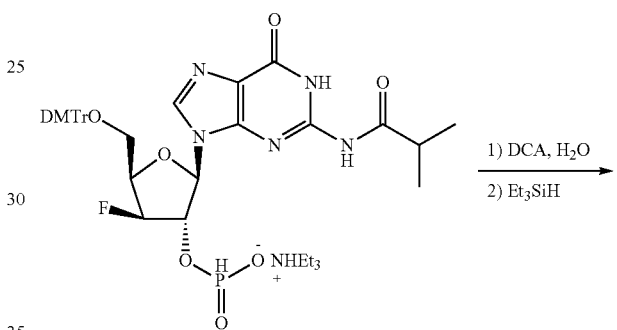

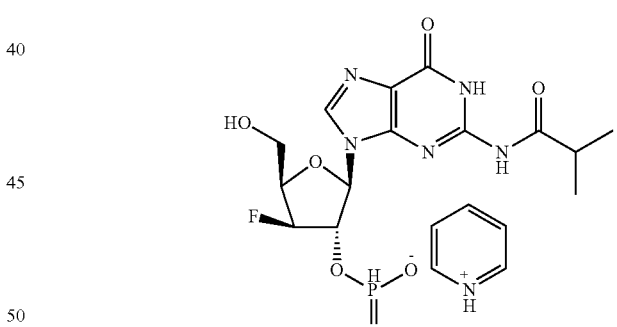

To a stirred solution of (2R,3S,4S,5R)-5-((bis(4-methoxyphenyl)(phenyl)methoxy) methyl)-4-fluoro-2-(2-isobutyramido-6-oxo-1,6-dihydro-9H-purin-9-yl)tetrahydrofuran-3-yl phosphonate (540 mg, 0.64 mmol) in CH$_2$Cl$_2$ (7 mL) at rt was added water (0.115 g, 6.4 mmol) and 2,2-dichloroacetic acid in CH$_2$Cl$_2$ (6%, 7 mL, 5.76 mmol). The mixture was stirred at rt for 15 min, and then Et$_3$SiH (15 mL) was added. After 40 min, pyridine (0.90 mL) was added, and the mixture was stirred for 5 min. It was concentrated, and the residue was used for next reaction step without purification. LCMS (ES, m/z): 419.9 [M+H]$^+$.

Step 4. (2R,3S,4S,5R)-5-((((((1R,3R,4R,7S)-3-(6-benzamido-9H-purin-9-yl)-1-((bis(4-methoxyphenyl)(phenyl)methoxy)methyl)-2,5-dioxabicyclo[2.2.2.1]heptan-7-yl)oxy)(2-cyanoethoxy)phosphanyl)oxy)methyl)-4-fluoro-2-(2-isobutyramido-6-oxo-1,6-dihydro-9H-purin-9-yl)tetrahydrofuran-3-yl phosphonate Step 5. (2R,3S,4S,5R)-5-((((((1R,3R,4R,7S)-3-(6-benzamido-9H-purin-9-yl)-1-((bis(4-methoxyphenyl)(phenyl)methoxy)methyl)-2,5-dioxabicyclo[2.2.1]heptan-7-yl)oxy)(2-cyanoethoxy)phosphorothioyl)oxy)methyl)-4-fluoro-2-(2-isobutyramido-6-oxo-1,6-dihydro-9H-purin-9-yl)tetrahydrofuran-3-yl phosphonate

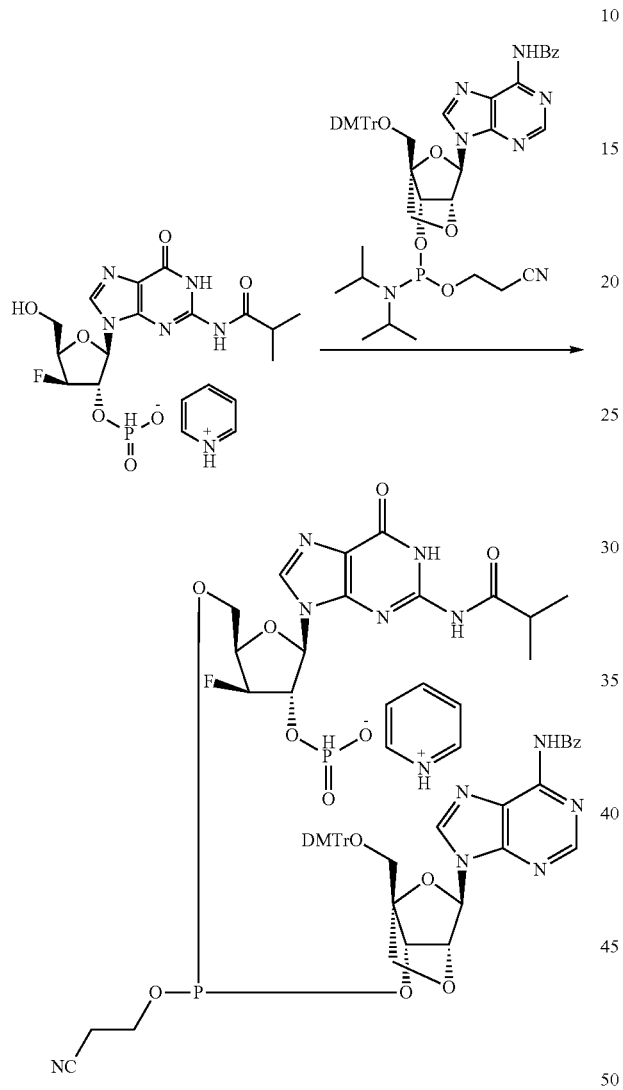

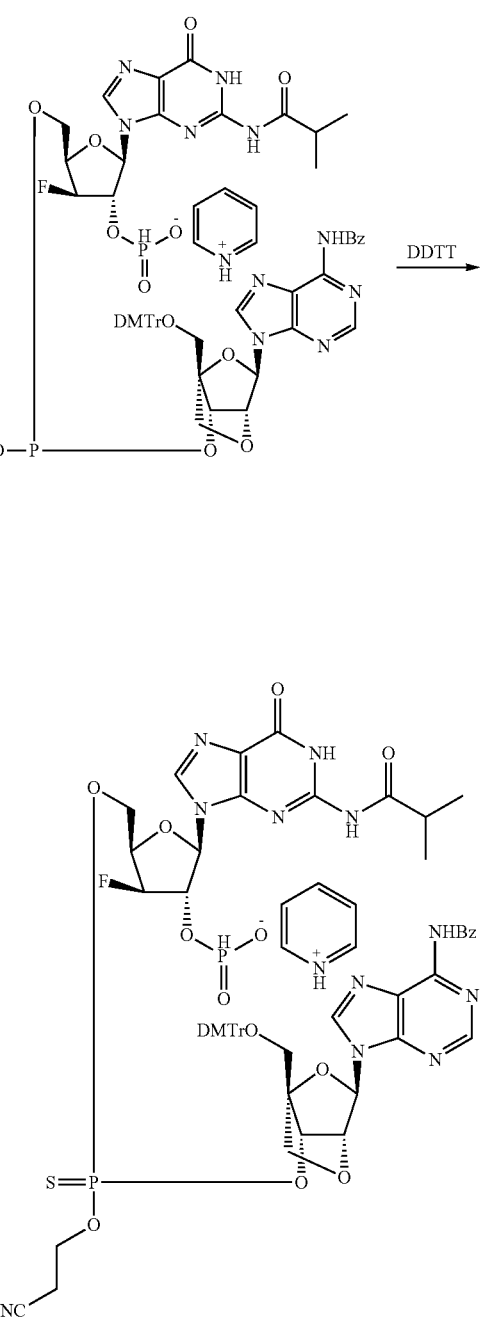

The crude from Step 3 was co-evaporated with ACN (3×5 mL), re-dissolved in ACN (3 mL) under Ar, and dried by adding activated 4 Å molecular sieve (100 mg). (1R,3R,4R,7S)-3-(6-benzamido-9H-purin-9-yl)-1-((bis(4-methoxyphenyl)(phenyl)methoxy)methyl)-2,5-dioxabicyclo[2.2.1]heptan-7-yl (2-cyanoethyl) diisopropylphosphoramidite (684.84 mg, 0.774 mmol) was co-evaporated with ACN (3×5 mL), re-dissolved in ACN (3 mL), and dried by adding activated 4 Å molecular sieve (100 mg). After 30 min, it was added to the previously prepared mixture containing pyridin-1-ium (2R,3 S,4S,5R)-4-fluoro-5-(hydroxymethyl)-2-(2-isobutyramido-6-oxo-1,6-dihydro-9H-purin-9-yl)tetrahydrofuran-3-yl phosphonate. The resulting mixture was stirred at rt for 30 min. Then it was used in the next reaction step without purification. LCMS (ES, m/z): 1202.1 [M+H]⁺.

To the mixture from Step 4 was added (E)-N,N-dimethyl-N'-(3-thioxo-3H-1,2,4-dithiazol-5-yl)formimidamide (144.32 mg, 0.704 mmol), and the mixture was stirred at rt for 30 min. Then, it was concentrated, and the crude was used for the next step without purification. LCMS (ES, m/z): 1234.3 [M+H]⁺.

Step 6. (2R,3S,4S,5R)-5-((((((1S,3R,4R,7S)-3-(6-benzamido-9H-purin-9-yl)-1-(hydroxymethyl)-2,5-dioxabicyclo[2.2.1]heptan-7-yl)oxy)(2-cyanoethoxy)phosphorothioyl)oxy)methyl)-4-fluoro-2-(2-isobutyramido-6-oxo-1,6-dihydro-9H-purin-9-yl)tetrahydrofuran-3-yl phosphonate

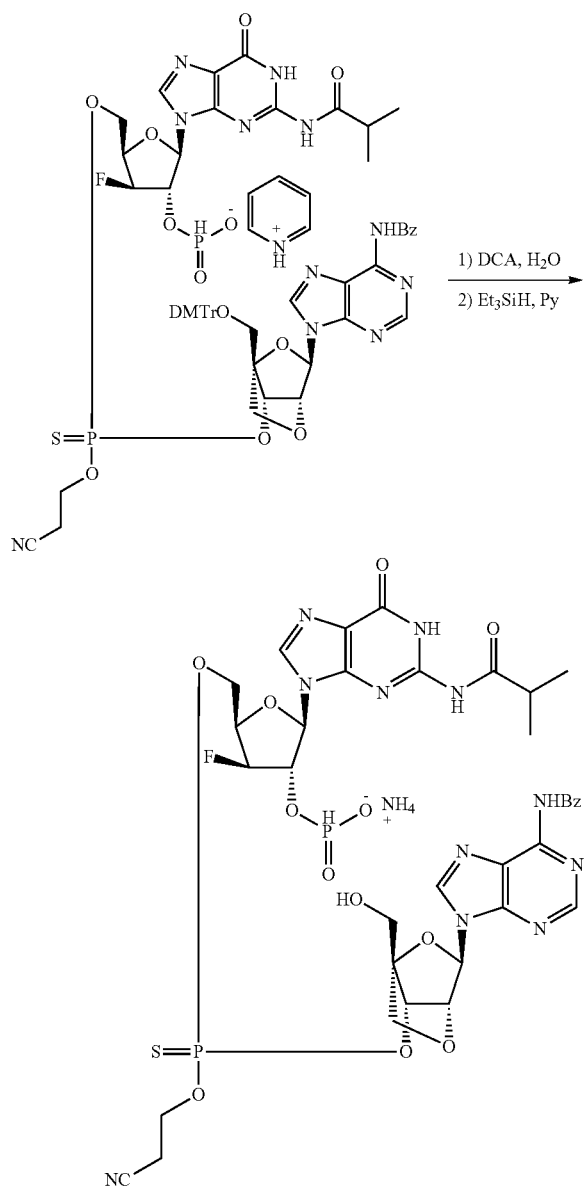

To a solution of the crude from Step 5 in CH$_2$Cl$_2$ (7 mL) at rt was added water (120 mg, 6.4 mmol) and 2,2-dichloroacetic acid in CH$_2$Cl$_2$ (6%, 7 mL, 6 mmol). After 5 min, triethylsilane (15 mL) was added, and it was stirred for additional 2 h. Then, pyridine (0.9 mL) was added, and it was concentrated. The residue was purified by reverse phase (C18) chromatography eluted with 0 to 95% ACN in aq NH$_4$HCO$_3$ (0.04%) to give the product. LCMS (ES, m/z): 933.9 [M+H]$^+$. $^1$H-NMR (400 MHz, CD$_3$OD): δ 8.74-8.64 (m, 1H), 8.58-8.52 (m, 1H), 8.16-8.06 (m, 2H), 7.98-7.88 (m, 1H), 7.75 (d, J=4.6 Hz, 0.5H), 7.67 (t, J=7.3 Hz, 1H), 7.60-7.56 (m, 2H), 6.25-6.22 (m, 1H), 6.19-6.10 (m, 1H), 5.91 (s, 0.5H), 5.46-5.22 (m, 3H), 5.12 (d, J=12.4 Hz, 1H), 4.84-4.49 (m, 3H), 4.35 (tdd, J=13.2, 6.1, 3.0 Hz, 2H), 4.14 (d, J=8.5 Hz, 1H), 4.11-3.96 (m, 3H), 2.91 (dt, J=16.4, 6.0 Hz, 2H), 2.81-2.68 (m, 1H), 1.29-1.21 (m, 6H). $^{31}$P-NMR: (162 MHz, CD$_3$OD): δ 67.84, 66.33 (2 s, 1P); 2.65, 2.52 (2 s, 1P).

Step 7: (5R,7R,8S,12aR,14R,15R,15aS,18S)-2-(2-cyanoethoxy)-18-fluoro-7-{2-[(2-methylpropanoyl)amino]-6-oxo-1,6-dihydro-9H-purin-9-yl}-14-{6-[(phenylcarbonyl)amino]-9H-purin-9-yl}hexahydro-14H-15,12a-(epoxymethano)-5,8-methanofuro[3,2-l][1,3,6,9,11,2,10]pentaoxadiphosphacyclotetradecin-10 (12H)-olate 2-sulfide

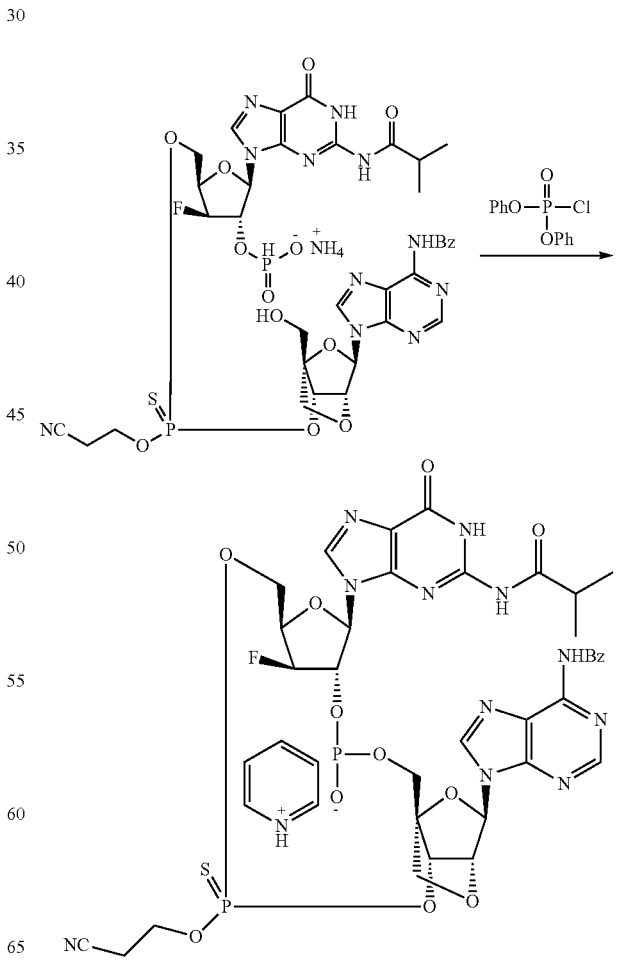

To pyridine (30 mL) at −40° C. under Ar was added diphenyl phosphorochloridate (1783.7 mg, 6.64 mmol) and then, a solution of (2R,3 S,4S,5R)-5-((((((1S,3R,4R,7S)-3-(6-benzamido-9H-purin-9-yl)-1-(hydroxymethyl)-2,5-dioxabicyclo[2.2.1]heptan-7-yl)oxy)(2-cyanoethoxy)phosphorothioyl)oxy)methyl)-4-fluoro-2-(2-isobutyramido-6-oxo-1,6-dihydro-9H-purin-9-yl)tetrahydrofuran-3-yl phosphonate (310 mg, 0.33 mmol, co-evaporated with pyridine 3×5 mL) in CH$_2$Cl$_2$ (30 mL) over 20 min. The resulting mixture was stirred at −40° C. for 20 min. It was used in the next step immediately without purification. LCMS (ES, m/z): 916.1 [M+H]$^+$.

Step 8. (5R,7R,8S,12aR,14R,15R,15aS,18S)-2-(2-cyanoethoxy)-18-fluoro-7-{2-[(2-methylpropanoyl)amino]-6-oxo-1,6-dihydro-9H-purin-9-yl}-14-{6-[(phenylcarbonyl)amino]-9H-purin-9-yl}hexahydro-14H-15,12a-(epoxymethano)-5,8-methanofuro[3,2-l][1,3,6,9,11,2,10]pentaoxadiphosphacyclotetradecin-10(12H)-olate 2,10-disulfide

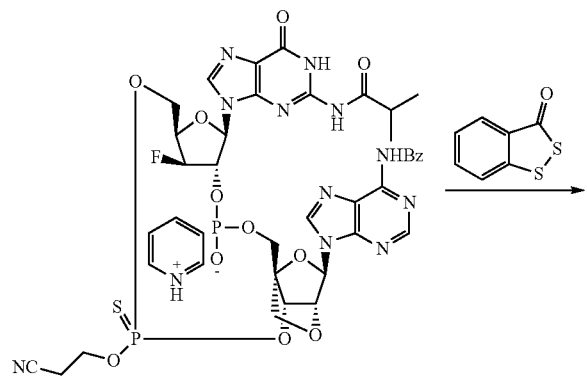

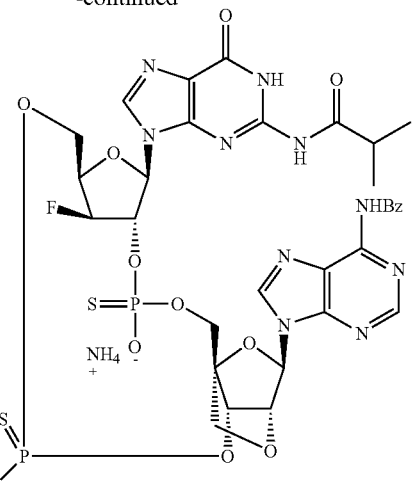

To the solution from Step 7 at −40° C. was added 3H-benzo[c][1,2]dithiol-3-one (83.6 mg, 0.498 mmol) and water (179 mg, 9.92 mmol). The mixture was stirred at rt for 40 min. Then, it was concentrated, and the residue was purified by reverse phase (C18) chromatography eluted with 0 to 95% ACN in aq NH$_4$HCO$_3$ (0.04%) to give the product. LCMS (ES, m/z): 947.8 [M+H]$^+$. $^1$H-NMR (400 MHz, CD$_3$OD): δ 8.79-8.58 (m, 2H), 8.18-8.06 (m, 2H), 7.92 (d, J=13.5 Hz, 1H), 7.69-7.66 (m, 1H), 7.63-7.54 (m, 2H), 6.40-6.14 (m, 2H), 6.03-5.56 (m, 1.5H), 5.39-5.10 (m, 2.5H), 4.93-4.85 (m, 2H), 4.84-4.43 (m, 3H), 4.43-3.98 (m, 3H), 2.95 (t, J=5.9 Hz, 1H), 2.84-2.66 (m, 2H), 1.30-1.19 (m, 6H). $^{31}$P-NMR (162 MHz, CD$_3$OD): δ 66.60-64.98 (m, 1P), 56.95-55.65 (m, 1P).

Step 9: 2-amino-9-[(5R,7R,8S,12aR,14R,15R,15aS,18S)-14-(6-amino-9H-purin-9-yl)-18-fluoro-2,10-dihydroxy-2,10-disulfidohexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one (Diastereomers 13)

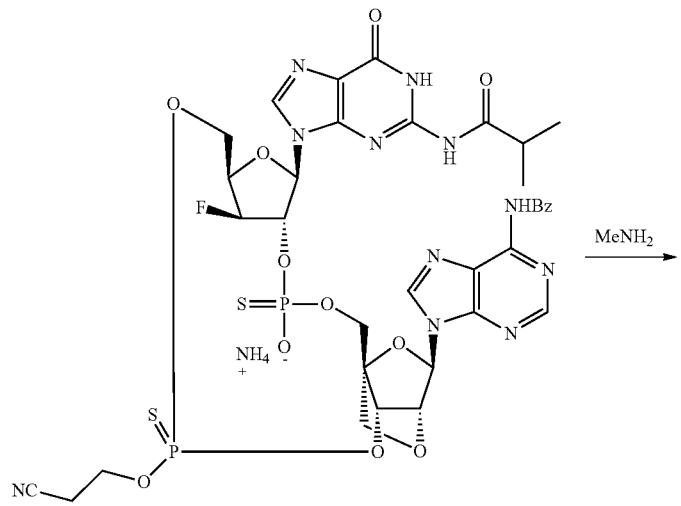

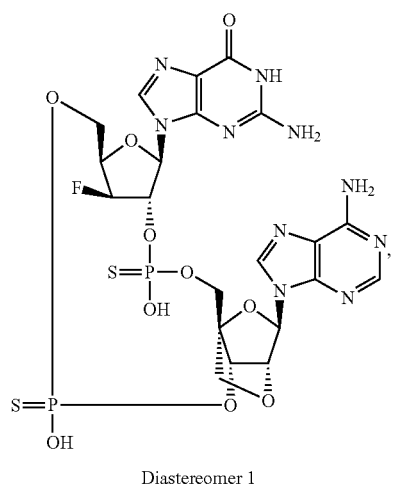
Diastereomer 1

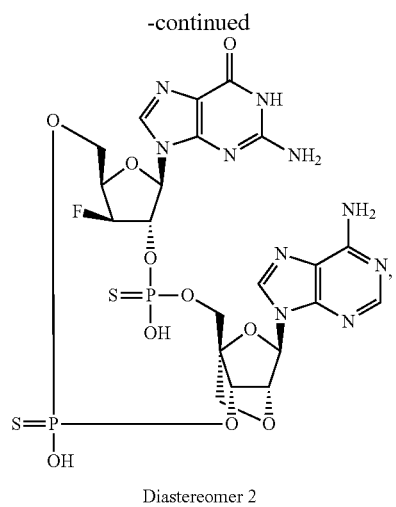
Diastereomer 2

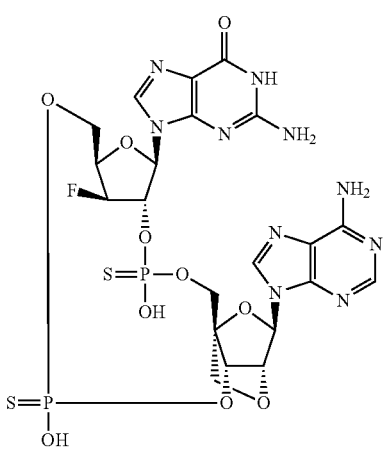
Diastereomer 3

(5R,7R,8S,12aR,14R,15R,15aS,18 S)-2-(2-cyanoethoxy)-18-fluoro-7-{2-[(2-methylpropanoyl)amino]-6-oxo-1,6-dihydro-9H-purin-9-yl}-14-{6-[(phenylcarbonyl)amino]-9H-purin-9-yl}hexahydro-14H-15,12a-(epoxymethano)-5,8-methanofuro[3,2-l][1,3,6,9,11,2,10]pentaoxadiphosphacyclotetradecin-10(12H)-olate 2,10-disulfide (260 mg, 0.27 mmol) was dissolved in a solution of MeNH$_2$ in EtOH (30%, 20 mL), and the resulting solution was stirred at rt for 3 h. Then, it was concentrated, and the residue was purified by Prep-HPLC (Atlantis Prep RP C18 OBD Column, 19 mm×250 mm) eluted with 0 to 14% ACN in aq NH$_4$HCO$_3$ (50 mM) over 25 min to afford the diastereomers of 2-amino-9-[(5R,7R,8S,12aR,14R,15R,15aS,18S)-14-(6-amino-9H-purin-9-yl)-18-fluoro-2,10-dihydroxy-2,10-disulfidohexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one:

Example 124 (T$_R$: 22.52 min): LCMS (ES, m/z): 719.0 [M−H]$^-$. $^1$H-NMR: (400 MHz, D$_2$O+DCl): δ 8.71 (s, 1H), 8.26 (s, 1H), 8.09 (s, 1H), 5.73 (s, 1H), 5.65 (s, 1H), 5.22-5.10 (m, 1H), 4.74-4.72 (m, 2H), 4.45 (d, J=4.1 Hz, 1H), 4.21-4.11 (m, 1H), 4.05-3.94 (m, 2H), 3.83-3.56 (m, 2H), 3.46 (s, 2H). $^{31}$P-NMR: (162 MHz, D$_2$O+DCl): δ 60.35 (s, 1P), 56.87 (s, 1P).

Example 125 (T$_R$: 15.75 min): LCMS (ES, m/z): 719.0 [M−H]$^-$. $^1$H-NMR: (400 MHz, D$_2$O): δ 8.31 (s, 1H), 8.14 (s, 1H), 7.74 (s, 1H), 6.11 (s, 1H), 6.06 (s, 1H), 5.61-5.49 (m, 1H), 5.35 (s, 1H), 5.10 (d, J=9.8 Hz, 1H), 4.71-4.55 (m, 1H), 4.51-4.20 (m, 3H), 4.18-3.95 (m, 4H). $^{31}$P-NMR: (162 MHz, D$_2$O): δ 54.87-51.81 (m, 2P).

Example 126 (T$_R$: 13.17 min): LCMS (ES, m/z): 718.8 [M−H]$^-$. $^1$H-NMR: (300 MHz, D$_2$O+DCl): δ 8.89 (s, 1H), 8.46 (s, 1H), 8.29 (s, 1H), 5.95 (s, 1H), 5.88 (s, 1H), 5.30-5.14 (m, 1H), 4.98 (t, J=5.2 Hz, 1H), 4.89 (s, 1H), 4.60 (s, 1H), 4.35-4.14 (m, 2H), 4.07 (d, J=11.4 Hz, 1H), 4.01-3.85 (m, 2H), 3.68-3.62 (m, 2H). $^{31}$P-NMR: (121 MHz, D$_2$O+DCl): δ 60.15 (s, 1P), 56.60 (s, 1P).

Examples 127 and 128: 2-amino-9-[(5R,7R,8S,12aR,14R,15S,15aR,16R)-14-(7-amino-3H-[1,2,3]triazolo[4,5-d]pyrimidin-3-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer1), and 2-amino-9-[(5R,7R,8S,12aR,14R,15S,15aR,16R)-14-(7-amino-3H-[1,2,3]triazolo[4,5-d]pyrimidin-3-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2)

Diastereomer 1

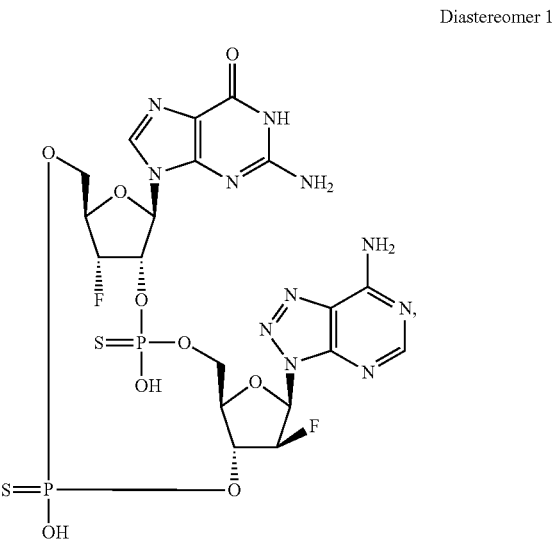

-continued

Diastereomer 2

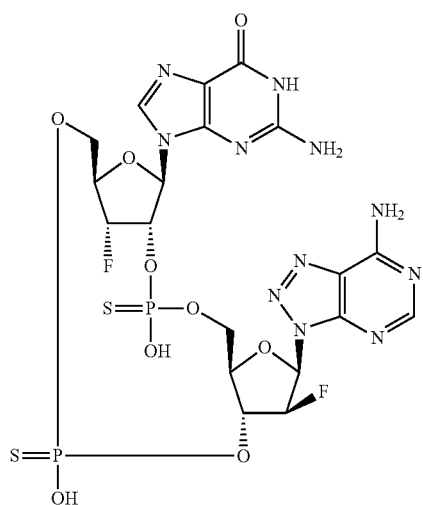

Step 1. (2R,3R,4S,5R)-5-(7-benzamido-3H-[1,2,3]
triazolo[4,5-d]pyrimidin-3-yl)-2-((bis(4-methoxy-
phenyl)(phenyl)methoxy)methyl)-4-fluorotetrahy-
drofuran-3-yl phenyl phosphate

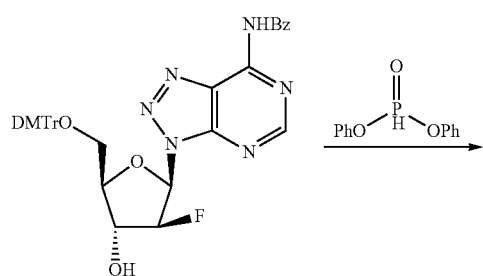

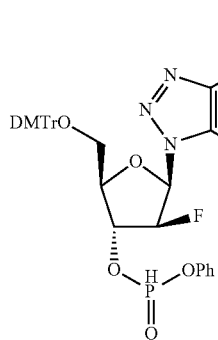

To a stirred solution of N-(3-((2R,3S,4R,5SR)-5-((bis(4-methoxyphenyl)(phenyl)methoxy) methyl)-3-fluoro-4-hydroxytetrahydrofuran-2-yl)-3H-[1,2,3]triazolo[4,5-d]pyrimidin-7-yl)benzamide (770 mg, 1.138 mmol) in pyridine (5 ml) at 0° C. under Ar was added diphenyl phosphonate (1.33 g, 5.69 mmol) over 2 min. The resulting mixture was stirred at rt for 20 min. It was used for the next reaction step directly without purification.

Step 2: (2R,3R,4S,5R)-5-(7-benzamido-3H-[1,2,3]
triazolo[4,5-d]pyrimidin-3-yl)-2-((bis(4-methoxy-
phenyl)(phenyl)methoxy)methyl)-4-fluorotetrahy-
drofuran-3-yl phosphonate

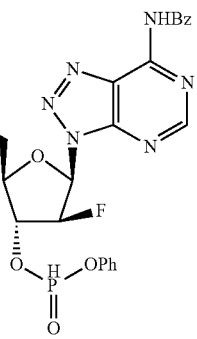

TEA/H₂O →

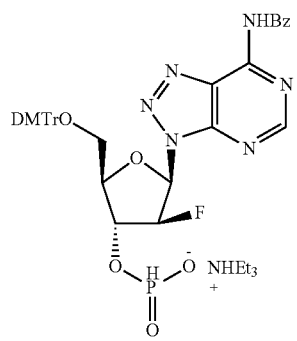

To the reaction mixture from Step 1 at 0° C. was added Et₃N (0.56 mL) in water (0.56 mL) over 5 min. The resulting mixture was stirred at rt for 30 min. It was concentrated, and the residue was partitioned between CH₂Cl₂ (60 mL) and aq NaHCO₃ (5%, 24 mL). The organic layer was washed with aq NaHCO₃ (5%, 2×24 mL), dried (Na₂SO₄), concentrated, and purified by chromatography on silica gel using 0-10% MeOH in CH₂Cl₂ (0.5% Et₃N) to give the product. LCMS (ES, m/z): 741.2 [M+H]⁺. ¹H-NMR (400 MHz, CD₃OD): δ 8.79 (s, 1H), 8.21-8.11 (m, 2H), 7.71 (t, J=7.4 Hz, 1H), 7.67-7.58 (m, 2.5H), 7.46-7.37 (m, 2H), 7.30-7.23 (m, 4H), 7.18-7.13 (m, 2H), 7.03 (dd, J=6.4, 2.8 Hz, 1H), 6.76-6.73 (m, 2H), 6.69-6.65 (m, 2H), 6.04 (s, 0.5H), 5.85 (t, J=6.4 Hz, 0.5H), 5.72 (t, J=6.4 Hz, 0.5H), 5.60 (td, J=16.9, 6.9 Hz, 1H), 4.44-4.40 (m, 1H), 3.77-3.68 (m, 8H), 3.57 (dd, J=10.6, 2.9 Hz, 1H), 2.91 (q, J=7.3 Hz, 18H), 1.20 (t, J=7.3 Hz, 27H). ³¹P-NMR: (162 MHz, CD₃OD): δ 2.48 (s, 1P).

Step 3: (2R,3R,4S,5R)-5-(7-benzamido-3H-[1,2,3]triazolo[4,5-d]pyrimidin-3-yl)-4-fluoro-2-(hydroxymethyl)tetrahydrofuran-3-yl phosphonate

Step 4: (2R,3R,4S,5R)-5-(7-benzamido-3H-[1,2,3]triazolo[4,5-d]pyrimidin-3-yl)-2-((((2-cyanoethoxy)(((2R,3S,4R,5R)-4-fluoro-5-(hydroxymethyl)-2-(2-isobutyramido-6-oxo-1,6-dihydro-9H-purin-9-yl)tetrahydrofuran-3-yl)oxy)phosphanyl)oxy)methyl)-4-fluorotetrahydrofuran-3-yl phosphonate

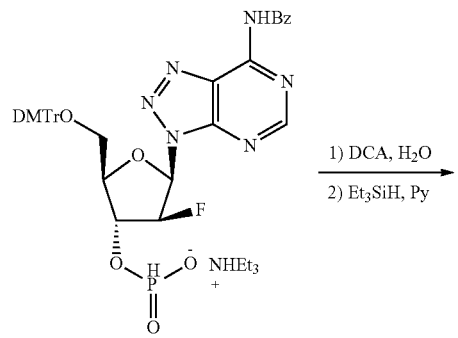

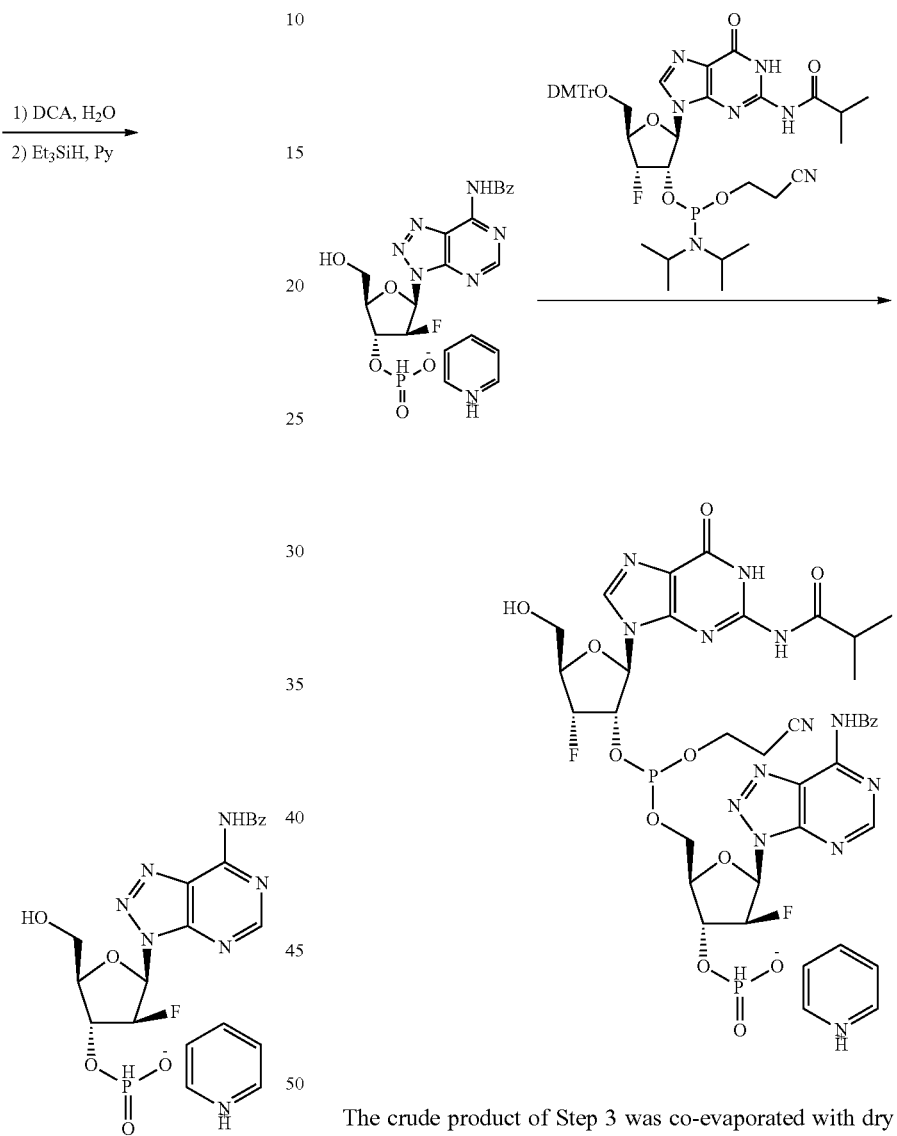

To a solution of (2R,3R,4S,5R)-5-(7-benzamido-3H-[1,2,3]triazolo[4,5-d]pyrimidin-3-yl)-2-((bis(4-methoxyphenyl)(phenyl)methoxy)methyl)-4-fluorotetrahydrofuran-3-yl phosphonate (610 mg, 0.65 mmol) in CH$_2$Cl$_2$ (9.8 mL) was added water (0.12 g, 6.5 mmol) and dichloroacetic acid in CH$_2$Cl$_2$ (0.6M, 9.8 mL, 5.9 mmol). After 30 in, triethylsilane (20 mL) was added and stirring was continued for additional 2 h. Then, pyridine (5 mL) was added, and it was concentrated. The crude was used for the next reaction step without purification. LCMS (ES, m/z): 439.1 [M+H]$^+$.

The crude product of Step 3 was co-evaporated with dry ACN (3×3 mL), re-dissolved in ACN (3 mL), and dried by adding activated 4 Å molecular sieve (200 mg). (2R,3S,4R,5R)-5-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl (2-cyanoethyl) diisopropylphosphoramidite (0.824 g, 0.960 mmol) was co-evaporated with dry ACN (3×3 mL), re-dissolved in ACN (5 mL), and dried by adding activated 4 Å molecular sieve (200 mg). After 30 min, it was added to the previously prepared mixture containing pyridin-1-ium (2R,3R,4S,5R)-5-(7-benzamido-3H-[1,2,3]triazolo [4,5-d]pyrimidin-3-yl)-4-fluoro-2-(hydroxymethyl)tetrahydrofuran-3-yl phosphonate. It was stirred at rt for 30 min, and the reaction mixture was used in the next reaction step directly without purification. LCMS (ES, m/z): 893.2 [M+H]$^+$.

603

Step 5: Diastereomers (2R,3R,4S,5R)-5-(7-benzamido-3H-[1,2,3]triazolo[4,5-d]pyrimidin-3-yl)-2-(((((2-cyanoethoxy) (((2R,3S,4R,5R)-4-fluoro-5-(hydroxymethyl)-2-(2-isobutyramido-6-oxo-1,6-dihydro-9H-purin-9-yl)tetrahydrofuran-3-yl)oxy) phosphorothioyl)oxy)methyl)-4-fluorotetrahydrofuran-3-yl phosphonate (116-5-A) and (2R,3R,4S,5R)-5-(7-benzamido-3H-[1,2,3]triazolo[4,5-d]pyrimidin-3-yl)-2-((((2-cyanoethoxy) (((2R,3S,4R,5R)-4-fluoro-5-(hydroxymethyl)-2-(2-isobutyramido-6-oxo-1,6-dihydro-9H-purin-9-yl) tetrahydrofuran-3-yl)oxy)phosphorothioyl)oxy) methyl)-4-fluorotetrahydrofuran-3-yl phosphonate (116-5-B)

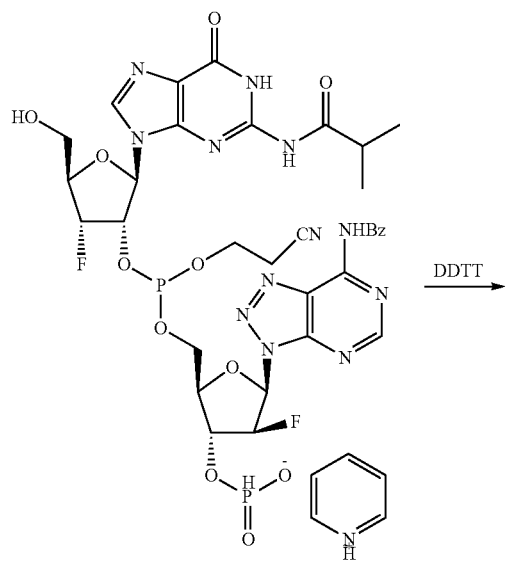

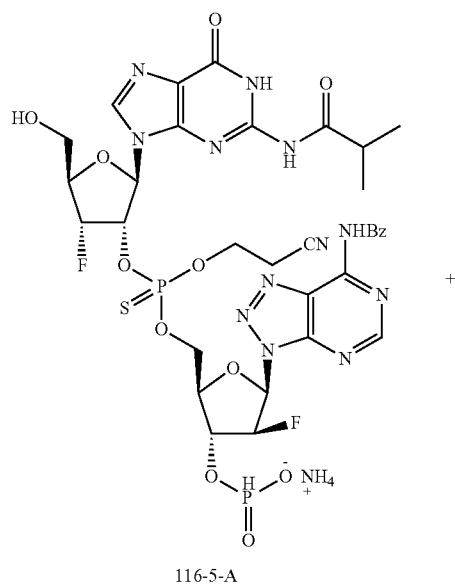

116-5-A

604

-continued

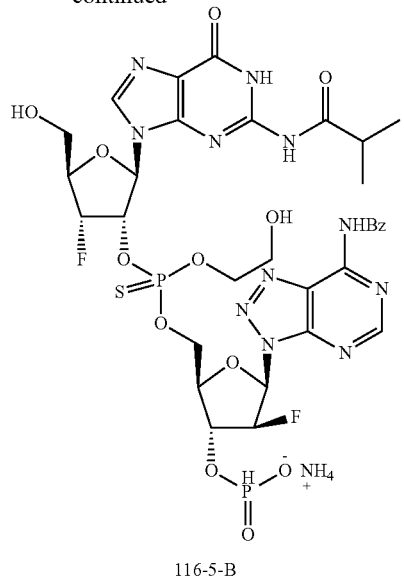

116-5-B

To the reaction mixture from Step 4 at rt, was added (E)-N,N-dimethyl-N-(3-thioxo-3H-1,2,4-dithiazol-5-yl)formimidamide (181 mg, 0.880 mmol), and the mixture was stirred for 1 h. Then, it was concentrated, and the residue was purified by reverse phase (AQ-C18) chromatography eluted with 0 to 28% ACN in aq $NH_4HCO_3$ (5 mM) over 88 min.

The first fractions with desired mass ($T_R$=50 min) gave (2R,3R,4S,5R)-5-(7-benzamido-3H-[1,2,3]triazolo[4,5-d]pyrimidin-3-yl)-2-((((2-cyanoethoxy)(((2R,3 S,4R,5R)-4-fluoro-5-(hydroxymethyl)-2-(2-isobutyramido-6-oxo-1,6-dihydro-9H-purin-9-yl)tetrahydrofuran-3-yl)oxy)phosphorothioyl)oxy)methyl)-4-fluorotetrahydrofuran-3-yl phosphonate (116-5-A). LCMS (ES, m/z): 924.9 [M+H]$^+$. $^1$H-NMR: (400 MHz, $CD_3OD$): δ 8.90 (s, 1H), 8.31 (s, 1H), 8.10 (d, J=7.8 Hz, 2H), 7.75 (s, 0.5H), 7.69 (t, J=7.4 Hz, 1H), 7.57 (t, J=7.7 Hz, 2H), 7.02 (dd, J=6.5, 2.6 Hz, 1H), 6.27-6.13 (m, 1.5H), 5.79-5.51 (m, 3H), 5.47-5.21 (m, 12H), 4.58 (dd, J=15.4, 7.6 Hz, 2H), 4.50-4.25 (m, 3H), 4.05 (ddd, J=24.7, 13.2, 6.1 Hz, 2H), 3.90-3.76 (m, 4H), 2.85-2.56 (m, 3H), 1.34 (d, J=6.5 Hz, 3H), 1.25-1.19 (m, 3H). $^{31}$P-NMR (162 MHz, $CD_3OD$): δ 67.56 (s, 1P), 3.09 (s, 1P).

The second fractions with desired mass ($T_R$=55 min) gave (2R,3R,4S,5R)-5-(7-benzamido-3H-[1,2,3]triazolo[4,5-d]pyrimidin-3-yl)-2-((((2-cyanoethoxy)(((2R,3 S,4R,5R)-4-fluoro-5-(hydroxymethyl)-2-(2-isobutyramido-6-oxo-1,6-dihydro-9H-purin-9-yl)tetrahydrofuran-3-yl)oxy)phosphorothioyl)oxy)methyl)-4-fluorotetrahydrofuran-3-yl phosphonate (116-5-B). LCMS (ES, m/z): 925.1 [M+H]$^+$. $^1$H-NMR: (400 MHz, $CD_3OD$): δ 8.87 (s, 1H), 8.33 (s, 1H), 8.16 (d, J=7.8 Hz, 2H), 7.75 (s, 0.5H), 7.70 (t, J=7.4 Hz, 1H), 7.61 (t, J=7.7 Hz, 2H), 6.91 (dd, J=6.2, 3.4 Hz, 1H), 6.23 (d, J=7.1 Hz, 1H), 6.17 (s, 0.5H), 5.74-5.54 (m, 3H), 5.46 (d, J=4.6 Hz, 0.5H), 5.33 (d, J=4.6 Hz, 0.5H), 4.65-4.24 (m, 4H), 4.15 (dt, J=13.0, 5.8 Hz, 2H), 3.95-3.75 (m, 2H), 2.90-2.67 (m, 3H), 1.36-1.31 (m, 3H), 1.19 (d, J=6.8 Hz, 3H). $^{31}$P-NMR: (162 MHz, $CD_3OD$): δ 67.29 (s, 1P), 3.07 (s, 1P).

Step 6: (5R,7R,8S,12aR,14R,15S,15aR,16R)-10-(2-cyanoethoxy)-15,16-difluoro-7-{2-[(2-methylpropanoyl)amino]-6-oxo-1,6-dihydro-9H-purin-9-yl}-14-{7-[(phenylcarbonyl)amino]-3H-[1,2,3]triazolo[4,5-d]pyrimidin-3-yl}octahydro-12H-5,8-methanofuro[3,2-l][1,3,6,9,11,2,10]pentaoxadiphosphacyclotetradecin-2-olate 10-sulfide Step 7: (5R,7R,8S,12aR,14R,15S,15aR,16R)-10-(2-cyanoethoxy)-15,16-difluoro-7-{2-[(2-methylpropanoyl)amino]-6-oxo-1,6-dihydro-9H-purin-9-yl}-14-{7-[(phenylcarbonyl)amino]-3H-[1,2,3]triazolo[4,5-d]pyrimidin-3-yl}octahydro-12H-5,8-methanofuro[3,2-l][1,3,6,9,11,2,10]pentaoxadiphosphacyclotetradecin-2-olate 2,10-disulfide

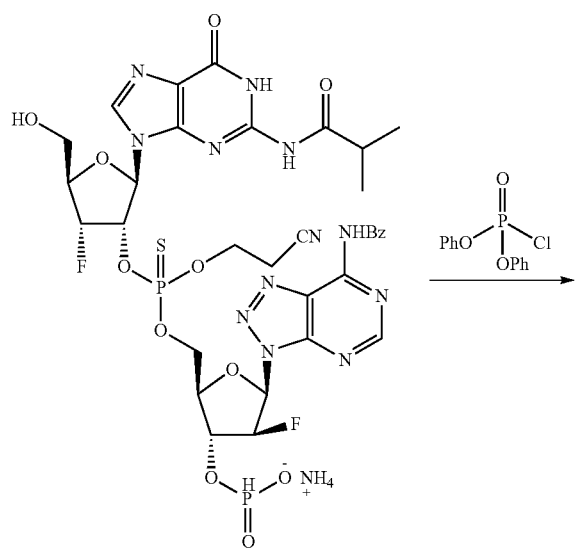

116-5-B

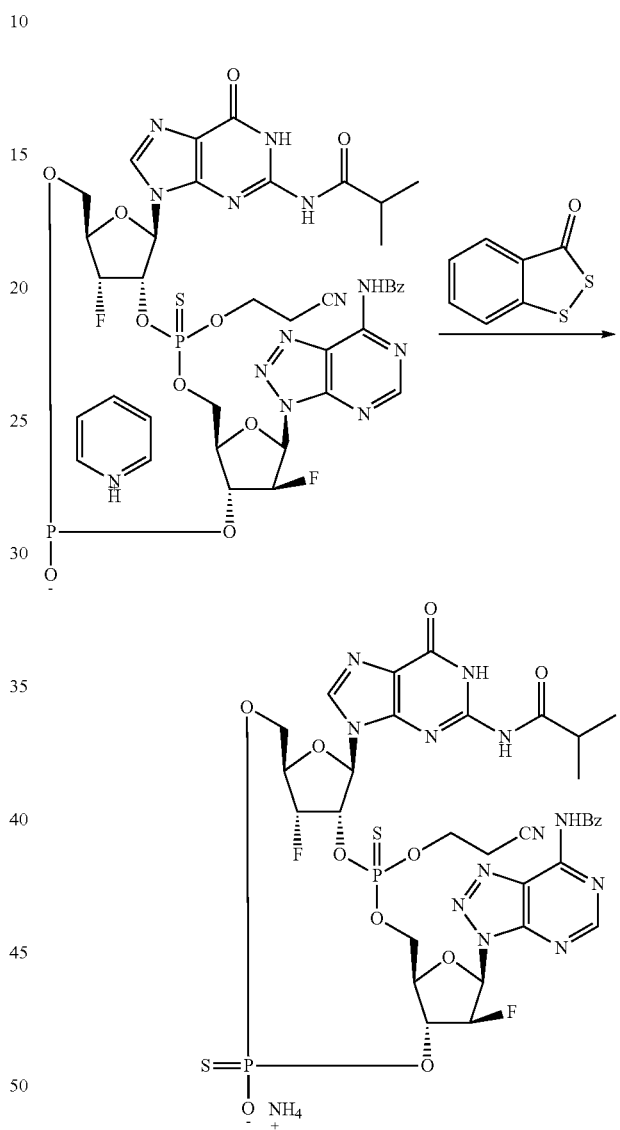

To pyridine (10 mL) at −40° C. under Ar was added diphenyl phosphorochloridate (628 mg, 2.34 mmol), and then, a solution of (2R,3R,4S,5R)-5-(7-benzamido-3H-[1,2,3]triazolo[4,5-d]pyrimidin-3-yl)-2-(((((2-cyanoethoxy)(((2R,3 S,4R,5R)-4-fluoro-5-(hydroxymethyl)-2-(2-isobutyramido-6-oxo-1,6-dihydro-9H-purin-9-yl)tetrahydrofuran-3-yl)oxy)phosphorothioyl)-oxy)methyl)-4-fluorotetrahydrofuran-3-yl phosphonate (116-5-B) (110 mg, 0.105 mmol, co-evaporated with pyridine 3×5 mL) in CH$_2$Cl$_2$ (10 mL) over 20 min. It was stirred at −40° C. for 20 min. The reaction mixture was used in the next step immediately without purification.

To the mixture from Step 6 at −20° C. was added 3H-benzo[c][1,2]dithiol-3-one (27.8 mg, 0.165 mmol) and water (42 mg, 2.3 mmol). The resulting mixture was stirred at rt for 30 min. It was concentrated, and the residue was purified by reverse phase (AQ-C18) chromatography eluted with 0 to 28% ACN in aq NH$_4$HCO$_3$ (5 mM) to give the product. LCMS (ES, m/z): 938.9 [M+H]$^+$. $^1$H-NMR: (400 MHz, CD$_3$OD): δ 8.94-8.71 (m, 2H), 8.23-8.06 (m, 2H), 7.75-7.67 (m, 1H), 7.64 (t, J=7.5 Hz, 2H), 7.11-6.97 (m, 1H), 6.32-6.17 (m, 2H), 6.02-5.73 (m, 2H), 5.68-5.38 (m, 1H), 4.73 (d, J=24.3 Hz, 1H), 4.68-4.42 (m, 4H), 4.39-4.19 (m, 2H), 4.06-3.66 (m, 2H), 2.99-2.62 (m, 2H), 2.61-2.37 (m, 1H), 1.20 (d, J=6.8 Hz, 3H), 1.12 (d, J=6.7 Hz, 3H). $^{31}$P-NMR: (162 MHz, CD$_3$OD): δ 64.05, 63.79 (2 s, 1P); 56.67, 56.27 (2 s, 1P).

Step 8: 2-amino-9-[(5R,7R,8S,12aR,14R,15S,15aR,16R)-14-(7-amino-3H-[1,2,3]triazolo[4,5-d]pyrimidin-3-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-9-dihydro-6H-purin-6-one (Diastereomers 1 and 2)

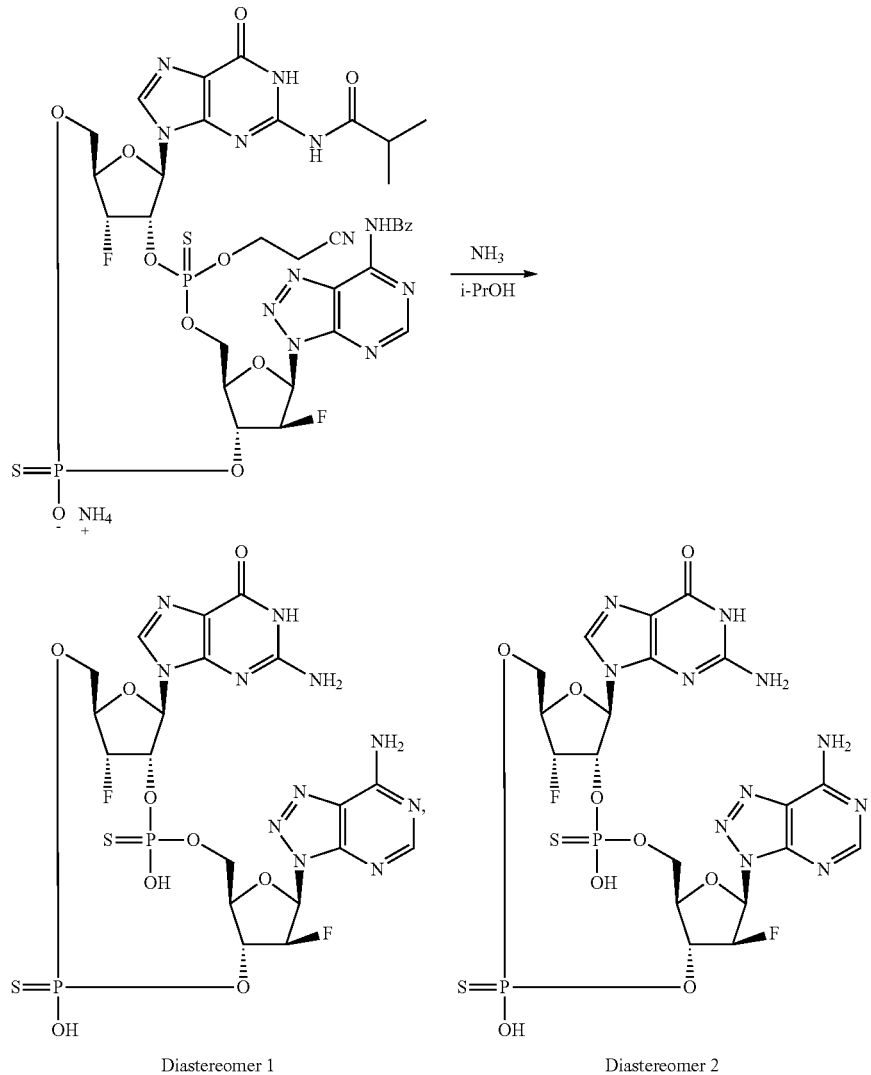

Diastereomer 1   Diastereomer 2

To pyridinium (5R,7R,8S,12aR,14R,15S,15aR,16R)-10-(2-cyanoethoxy)-15,16-difluoro-7-{2-[(2-methylpropanoyl)amino]-6-oxo-1,6-dihydro-9H-purin-9-yl}-14-{7-[(phenylcarbonyl) amino]-3H-[1,2,3]triazolo[4,5-d]pyrimidin-3-yl}octahydro-12H-5,8-methanofuro[3,2-l][1,3,6,9,11,2,10] pentaoxadiphosphacyclotetradecin-2-olate 2,10-disulfide in a steel tank (150 mL) at −60° C. was added ammonia in isopropanol (50 mL) at −60° C. The reactor was tightly sealed and then, heated at 50° C. for 16 h. Then, the volatile components were removed under reduced pressure, and the residue was purified by prep-HPLC (Atlantis Prep T3 OBD Column, 19×250 mm) eluted with 0 to 5% ACN in aq $NH_4HCO_3$ (50 mM) over 25 min.

Example 127 ($T_R$=17.32 min): 2-amino-9-[(5R,7R,8S,12aR,14R,15S,15aR,16R)-14-(7-amino-3H-[1,2,3]triazolo[4,5-d]pyrimidin-3-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1). LCMS (ES, m/z): 709.8 [M−H]−. $^1$H-NMR: (400 MHz, $D_2O$): δ 8.32 (s, 1H), 8.27 (s, 1H), 6.78 (dd, J=11.1, 4.9 Hz, 1H), 6.07 (d, J=8.6 Hz, 1H), 5.81 (t, J=4.6 Hz, 0.5H), 5.68 (t, J=4.7 Hz, 0.5H), 5.63 (dq, J=9.8, 5.0 Hz, 1H), 5.58 (d, J=3.5 Hz, 0.5H), 5.45 (d, J=3.4 Hz, 0.5H), 5.43-5.26 (m, 1H), 4.65-4.63 (m, 1H), 4.56 (q, J=5.6 Hz, 1H), 4.31-4.23 (m, 3H), 4.12-4.05 (m, 1H). $^{31}$P-NMR: (162 MHz, $D_2O$): δ 55.76 (s, 1P), 54.26 (s, 1P).

Example 128 ($T_R$=21.10 min): 2-amino-9-[(5R,7R,8S,12aR,14R,15S,15aR,16R)-14-(7-amino-3H-[1,2,3]triazolo[4,5-d]pyrimidin-3-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2). LCMS (ES, m/z): 709.8 [M−H]−. $^1$H-NMR: (400 MHz, $D_2O$): δ 8.26 (s, 1H), 8.01 (s, 1H), 6.79 (dd, J=9.4, 5.3 Hz, 1H), 6.05 (d, J=8.6 Hz, 1H), 5.85 (t, J=5.0 Hz, 0.5H), 5.72 (t, J=5.0 Hz, 0.5H), 5.65-5.35 (m, 3H), 4.69-4.62 (m, 1H), 4.48 (d, J=5.5 Hz, 1H), 4.42 (t, J=11.1 Hz, 1H), 4.18 (t, J=6.2 Hz, 2H), 4.09-4.06 (m, 1H). $^{31}$P-NMR (162 MHz, D$_2$O): δ 54.74 (s, 1P), 53.84 (s, 1P).

Examples 129 through 243, as shown in Table 6 below, were or may be prepared according to procedures analogous to those outlined in Examples 116 through 128 above using the appropriate monomers, described as Preparations or as obtained from commercial sources, in the coupling step.

TABLE 6

| Ex. | Structure | Name | Mass [M − H]$^-$ |
|---|---|---|---|
| 129 | 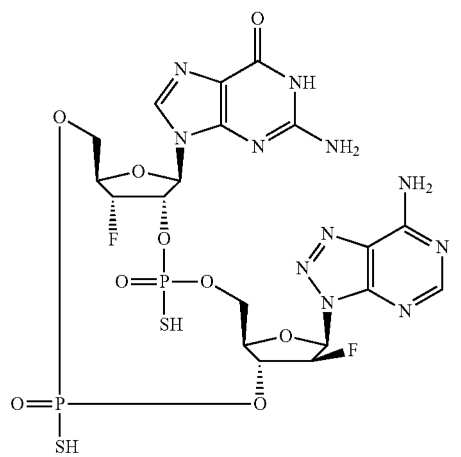 | 2-amino-9-[(5R,7R,8S,12aR,14R,15S,15aR,16R)-14-(7-amino-3H-[1,2,3]triazolo[4,5-d]pyrimidin-3-yl)-15,16-difluoro-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 3) | 710 |
| 130 | 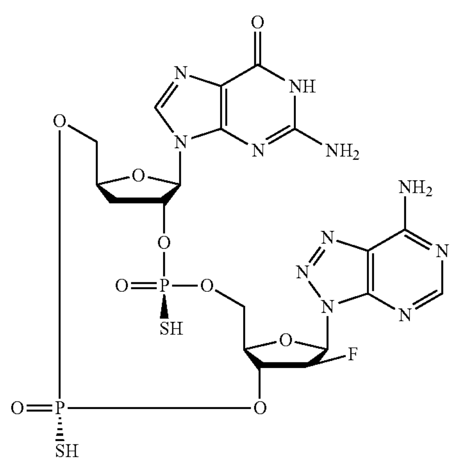 | 2-amino-9-[(2R,5S,7R,8R,10R,12aR,14R,15S,15aR)-14-(6-amino-9H-purin-9-yl)-15-fluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 691 |
| 131 | 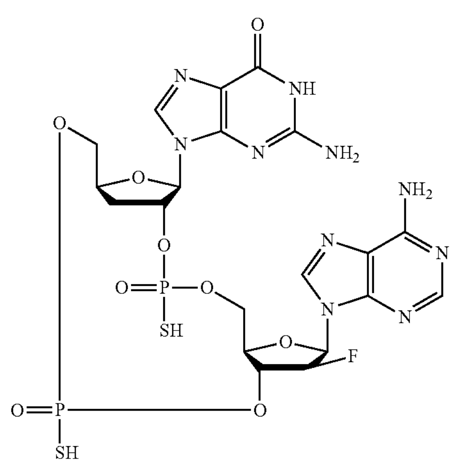 | 2-amino-9-[(5S,7R,8R,12aR,14R,15S,15aR)-14-(6-amino-9H-purin-9-yl)-15-fluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 691 |

TABLE 6-continued

| Ex. | Structure | Name | Mass [M − H]⁻ |
|---|---|---|---|
| 132 | 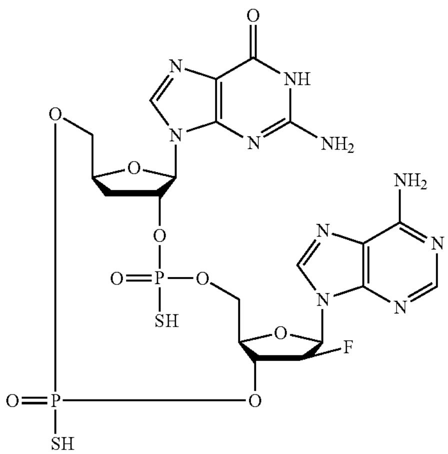 | 2-amino-9-[(5S,7R,8R,12aR,14R,15S,15aR)-14-(6-amino-9H-purin-9-yl)-15-fluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-oe (Diastereomer 3) | 691 |
| 133 | 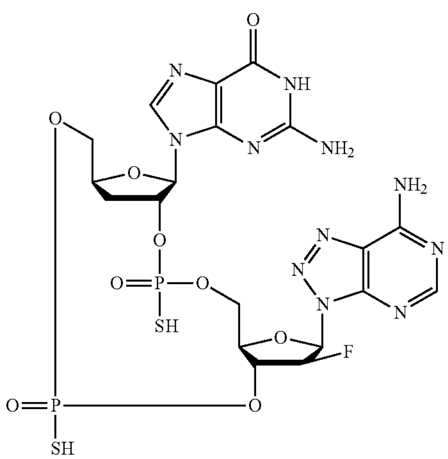 | 2-amino-9-[(5S,7R,8R,12aR,14R,15S,15aR)-14-(7-amino-3H-[1,2,3]triazolo[4,5-d]pyrimidin-3-yl)-15-fluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 694 |
| 134 | 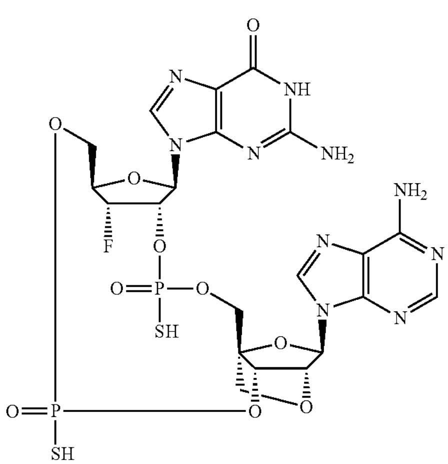 [SMILES: Nc1nc2c(ncn2[C@@H]2O[C@@H]3COP(=O)(S)O[C@H]4[C@H]5OC[C@]4(COP(=O)(S)O[C@@H]2[C@@H]3F)O[C@H]5n2cnc3c(N)ncnc32)c(=O)[nH]1] | 2-amino-9-[(5R,7R,8S,12aR,14R,15R,15aS,18R)-14-(6-amino-9H-purin-9-yl)-18-fluoro-2,10-dioxido-2,10-disulfanylhexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one (Diastereomer 1) | 719 |

TABLE 6-continued

| Ex. | Structure | Name | Mass [M − H]⁻ |
|---|---|---|---|
| 135 | 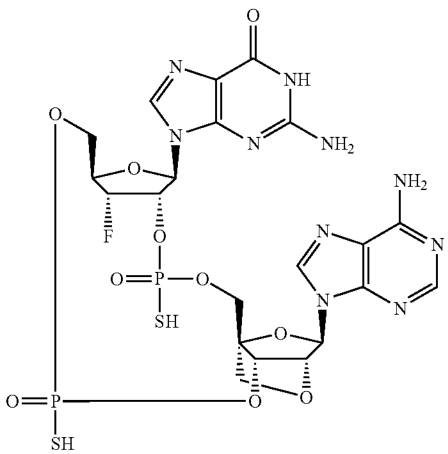 [SMILES: Nc1nc2c(ncn2[C@@H]2O[C@@H]3COP(=O)(S)O[C@H]4[C@H]5OC[C@]4(COP(=O)(S)O[C@@H]2[C@@H]3F)O[C@H]5n2cnc3c(N)ncnc32)c(=O)[nH]1] | 2-amino-9-[(5R,7R,8S,12aR,14R,15R,15aS,18R)-14-(6-amino-9H-purin-9-yl)-18-fluoro-2,10-dioxido-2,10-disulfanylhexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one (Diastereomer 2) | 719 |
| 136 | 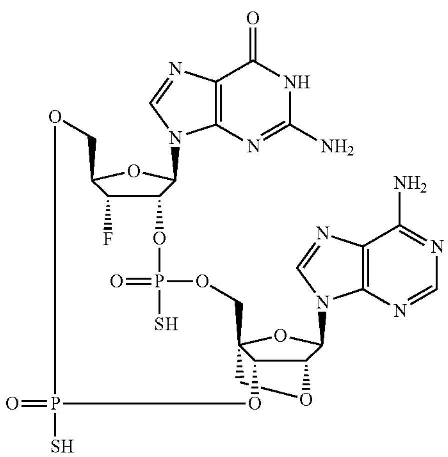 [SMILES: Nc1nc2c(ncn2[C@@H]2O[C@@H]3COP(=O)(S)O[C@H]4[C@H]5OC[C@]4(COP(=O)(S)O[C@@H]2[C@@H]3F)O[C@H]5n2cnc3c(N)ncnc32)c(=O)[nH]1] | 2-amino-9-[(5R,7R,8S,12aR,14R,15R,15aS,18R)-14-(6-amino-9H-purin-9-yl)-18-fluoro-2,10-dioxido-2,10-disulfanylhexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one (Diastereomer 3) | 719 |
| 137 | 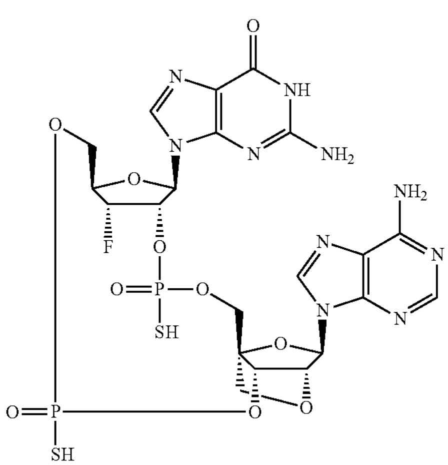 [SMILES: Nc1nc2c(ncn2[C@@H]2O[C@@H]3COP(=O)(S)O[C@H]4[C@H]5OC[C@]4(COP(=O)(S)O[C@@H]2[C@@H]3F)O[C@H]5n2cnc3c(N)ncnc32)c(=O)[nH]1] | 2-amino-9-[(5R,7R,8S,12aR,14R,15R,15aS,18R)-14-(6-amino-9H-purin-9-yl)-18-fluoro-2,10-dioxido-2,10-disulfanylhexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one (Diastereomer 4) | 719 |

TABLE 6-continued

| Ex. | Structure | Name | Mass [M − H]⁻ |
|---|---|---|---|
| 138 | 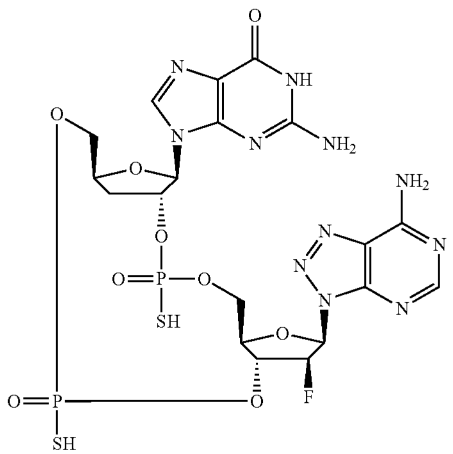 [SMILES: Nc1nc2c(ncn2[C@@H]2O[C@@H]3COP(=O)(S)O[C@H]4[C@H](F)[C@H](n5nnc6c(N)ncnc65)O[C@@H]4COP(=O)(S)O[C@@H]2C3)c(=O)[nH]1] | 2-amino-9-[(5S,7R,8R,12aR,14R,15S,15aR)-14-(7-amino-3H-[1,2,3]triazolo[4,5-d]pyrimidin-3-yl)-15-fluoro-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one | 692 |
| 139 | 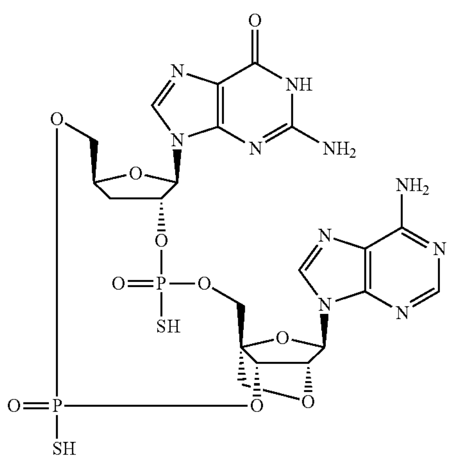 [SMILES: Nc1nc2c(ncn2[C@@H]2O[C@@H]3COP(=O)(S)O[C@H]4[C@H]5OC[C@]4(COP(=O)(S)O[C@@H]2C3)O[C@H]5n2cnc3c(N)ncnc32)c(=O)[nH]1] | 2-amino-9-[(5S,7R,8R,12aR,14R,15R,15aS)-14-(6-amino-9H-purin-9-yl)-2,10-dioxido-2,10-disulfanylhexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one (Diastereomer 1) | 701 |
| 140 | 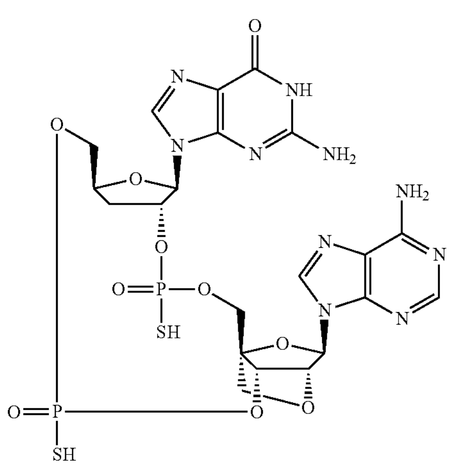 [SMILES: Nc1nc2c(ncn2[C@@H]2O[C@@H]3COP(=O)(S)O[C@H]4[C@H]5OC[C@]4(COP(=O)(S)O[C@@H]2C3)O[C@H]5n2cnc3c(N)ncnc32)c(=O)[nH]1] | 2-amino-9-[(5S,7R,8R,12aR,14R,15R,15aS)-14-(6-amino-9H-purin-9-yl)-2,10-dioxido-2,10-disulfanylhexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one (Diastereomer 2) | 701 |

TABLE 6-continued

| Ex. | Structure | Name | Mass [M − H]⁻ |
|---|---|---|---|
| 141 | 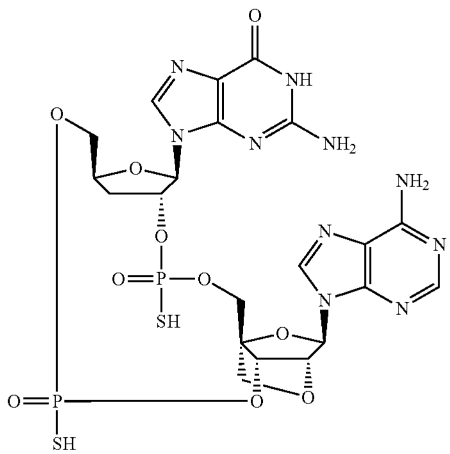 [SMILES: Nc1nc2c(ncn2[C@@H]2O[C@@H]3COP(=O)(S)O[C@H]4[C@H]5OC[C@]4(COP(=O)(S)O[C@@H]2C3)O[C@H]5n2cnc3c(N)ncnc32)c(=O)[nH]1] | 2-amino-9-[(5S,7R,8R,12aR,14R,15R,15aS)-14-(6-amino-9H-purin-9-yl)-2,10-dioxido-2,10-disulfanylhexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one (Diasteroemer 3) | 701 |
| 142 | 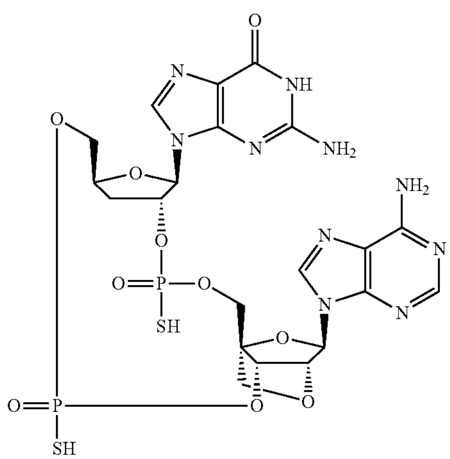 [SMILES: Nc1nc2c(ncn2[C@@H]2O[C@@H]3COP(=O)(S)O[C@H]4[C@H]5OC[C@]4(COP(=O)(S)O[C@@H]2C3)O[C@H]5n2cnc3c(N)ncnc32)c(=O)[nH]1] | 2-amino-9-[(5S,7R,8R,12aR,14R,15R,15aS)-14-(6-amino-9H-purin-9-yl)-2,10-dioxido-2,10-disulfanylhexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one (Diastereomer 4) | 701 |
| 143 | 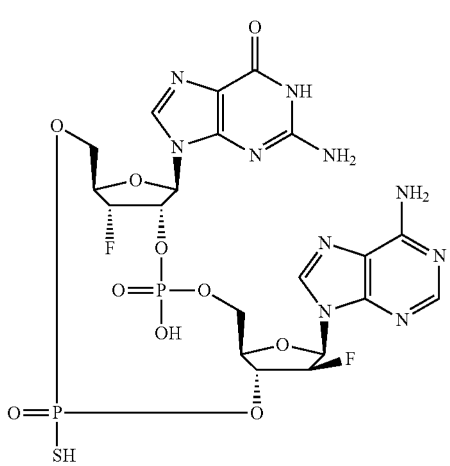 [SMILES: Nc1nc2c(ncn2[C@@H]2O[C@@H]3COP(=O)(S)O[C@H]4[C@H](F)[C@H](n5cnc6c(N)ncnc65)O[C@@H]4COP(=O)(O)O[C@@H]2[C@@H]3F)c(=O)[nH]1] | 2-amino-9-[(5R,7R,8S,12aR,14R,15S,15aR,16R)-14-(6-amino-9H-purin-9-yl)-15,16-difluoro-2,10-dihydroxy-10-oxido-2-sulfidooctahydro-12H-5,8-methanofuro[3,2-l][1,3,6,9,11,2,10]pentaoxadiphosphacyclotetradecin-7-yl]-1,9-dihydro-6H-purin-6-one | 694 |

TABLE 6-continued

| Ex. | Structure | Name | Mass [M − H]⁻ |
|---|---|---|---|
| 144 | 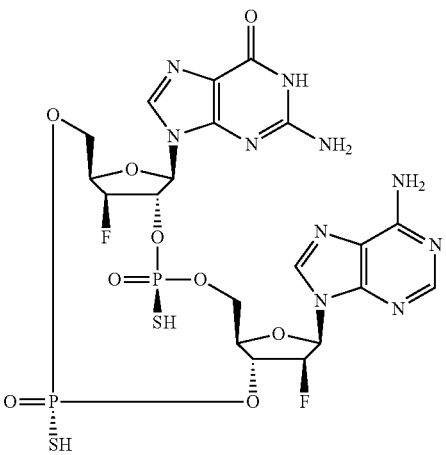 [SMILES: Nc1nc2c(ncn2[C@@H]2O[C@@H]3CO[P@@](=O)(S)O[C@H]4[C@H](F)[C@H](n5cnc6c(N)ncnc65)O[C@@H]4CO[P@@](=O)(S)O[C@@H]2[C@H]3F)c(=O)[nH]1] | 2-amino-9-[(2R,5R,7R,8S,10R,12aR,14R,15S,15aR,16S)-14-(6-amino-9H-purin-9-yl)-15,16-difluoro-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 709 |
| 145 | 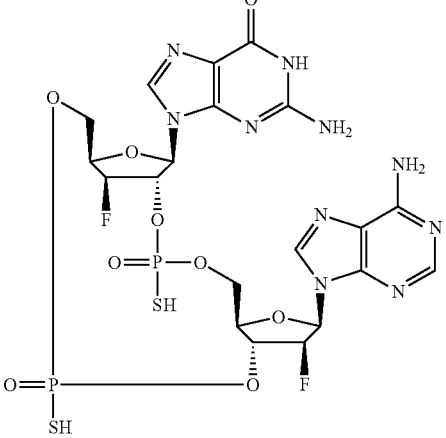 | 2-amino-9-[(5R,7R,8S,12aR,14R,15S,15aR,16S)-14-(6-amino-9H-purin-9-yl)-15,16-difluoro-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 709 |
| 146 | 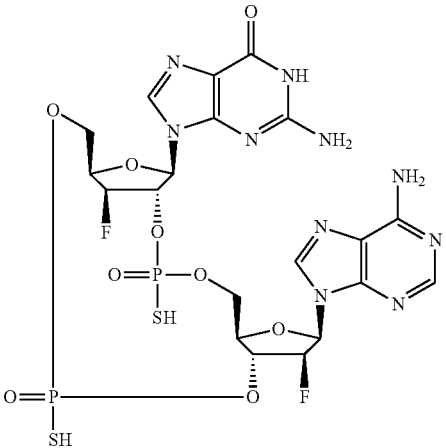 [SMILES: Nc1nc2c(ncn2[C@@H]2O[C@@H]3COP(=O)(S)O[C@H]4[C@H](F)[C@H](n5cnc6c(N)ncnc65)O[C@@H]4COP(=O)(S)O[C@@H]2[C@H]3F)c(=O)[nH]1] | 2-amino-9-[(5R,7R,8S,12aR,14R,15S,15aR,16S)-14-(6-amino-9H-purin-9-yl)-15,16-difluoro-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 3) | 709 |

TABLE 6-continued

| Ex. | Structure | Name | Mass [M − H]⁻ |
|---|---|---|---|
| 147 | 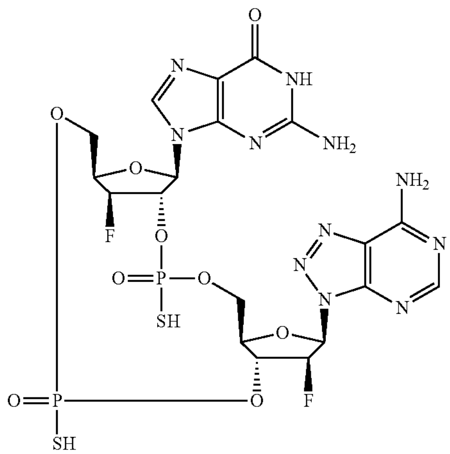 [SMILES: Nc1nc2c(ncn2[C@@H]2O[C@@H]3COP(=O)(S)O[C@H]4[C@H](F)[C@H](n5nnc6c(N)ncnc65)O[C@@H]4COP(=O)(S)O[C@@H]2[C@H]3F)c(=O)[nH]1] | 2-amino-9-[(5R,7R,8S,12aR,14R,15S,15aR,16S)-14-(7-amino-3H-[1,2,3]triazolo[4,5-d]pyrimidin-3-yl)-15,16-difluoro-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 710 |
| 148 | 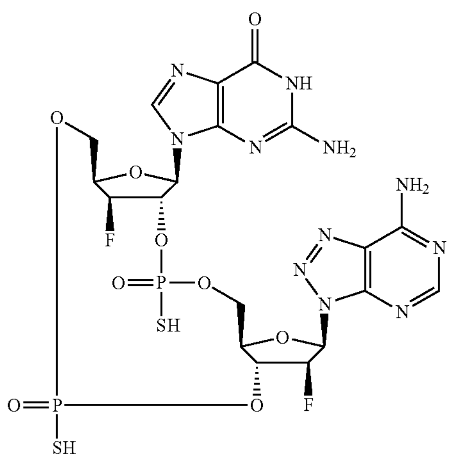 [SMILES: Nc1nc2c(ncn2[C@@H]2O[C@@H]3COP(=O)(S)O[C@H]4[C@H](F)[C@H](n5nnc6c(N)ncnc65)O[C@@H]4COP(=O)(S)O[C@@H]2[C@H]3F)c(=O)[nH]1] | 2-amino-9-[(5R,7R,8S,12aR,14R,15S,15aR,16S)-14-(7-amino-3H-[1,2,3]triazolo[4,5-d]pyrimidin-3-yl)-15,16-difluoro-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 710 |
| 149 | 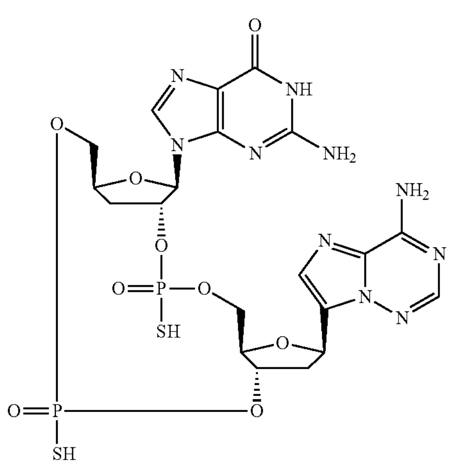 [SMILES: Nc1nc2c(ncn2[C@@H]2O[C@@H]3COP(=O)(S)O[C@H]4C[C@H](c5cnc6c(N)ncnn56)O[C@@H]4COP(=O)(S)O[C@@H]2C3)c(=O)[nH]1] | 2-amino-9-[(5S,7R,8R,12aR,14R,15aS)-14-(4-aminoimidazo[2,1-f][1,2,4]triazin-7-yl)-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 673 |

TABLE 6-continued

| Ex. | Structure | Name | Mass [M − H]⁻ |
|---|---|---|---|
| 150 | 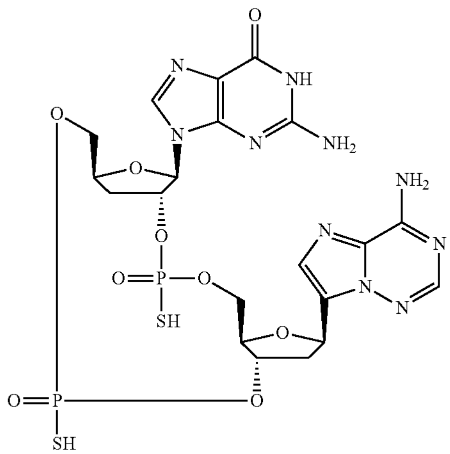 [SMILES: Nc1nc2c(ncn2[C@@H]2O[C@@H]3COP(=O)(S)O[C@H]4C[C@H](c5cnc6c(N)ncnn56)O[C@@H]4COP(=O)(S)O[C@@H]2C3)c(=O)[nH]1] | 2-amino-9-[(5S,7R,8R,12aR,14R,15aS)-14-(4-aminoimidazo[2,1-f][1,2,4]triazin-7-yl)-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 673 |
| 151 | 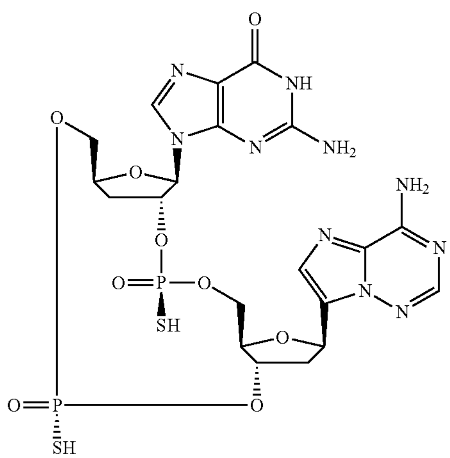 [SMILES: Nc1nc2c(ncn2[C@@H]2O[C@@H]3CO[P@@](=O)(S)O[C@H]4C[C@H](c5cnc6c(N)ncnn56)O[C@@H]4CO[P@@](=O)(S)O[C@@H]2C3)c(=O)[nH]1] | 2-amino-9-[(2R,5S,7R,8R,10R,12aR,14R,15aS)-14-(4-aminoimidazo[2,1-f][1,2,4]triazin-7-yl)-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 3) | 673 |
| 152 | 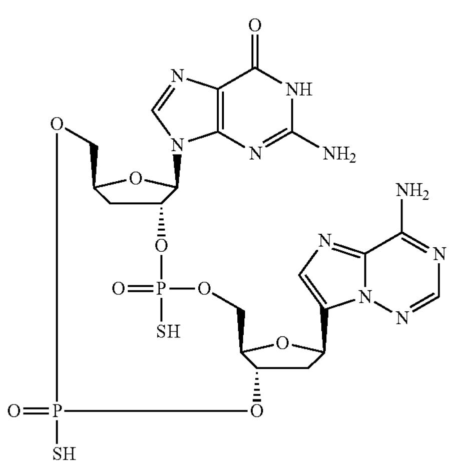 [SMILES: Nc1nc2c(ncn2[C@@H]2O[C@@H]3COP(=O)(S)O[C@H]4C[C@H](c5cnc6c(N)ncnn56)O[C@@H]4COP(=O)(S)O[C@@H]2C3)c(=O)[nH]1] | 2-amino-9-[(5S,7R,8R,12aR,14R,15aS)-14-(4-aminoimidazo[2,1-f][1,2,4]triazin-7-yl)-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 4) | 673 |

TABLE 6-continued

| Ex. | Structure | Name | Mass [M − H]⁻ |
|---|---|---|---|
| 153 | 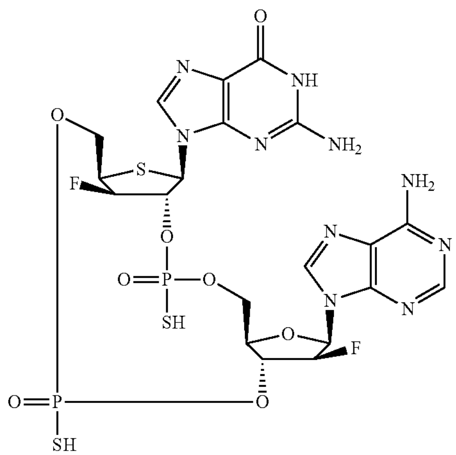 [SMILES: Nc1nc2c(ncn2[C@@H]2S[C@@H]3COP(=O)(S)O[C@H]4[C@H](F)[C@H](n5cnc6c(N)ncnc65)O[C@@H]4COP(=O)(S)O[C@@H]2[C@H]3F)c(=O)[nH]1] | (5R,7R,8R,12aR,14R,15S,15aR,16R)-7-(2-amino-6-oxo-1,6-dihydro-9H-purin-9-yl)-14-(6-amino-9H-purin-9-yl)-15,16-difluorooctahydro-12H-5,8-methanofuro[3,2-l][1,3,9,11,6,2,10]tetraoxathiadiphosphacyclotetradecine-2,10-bis(thiolate) 2,10-dioxide (Diastereomer 1) | 725 |
| 154 | 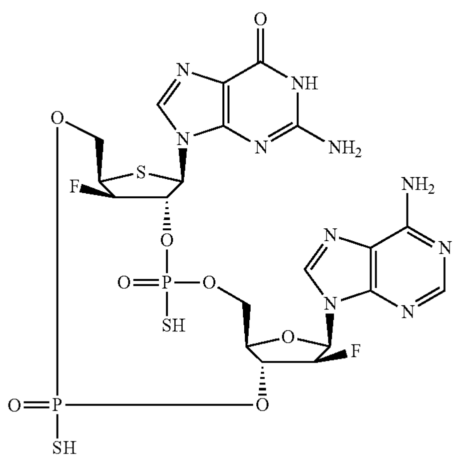 [SMILES: Nc1nc2c(ncn2[C@@H]2S[C@@H]3COP(=O)(S)O[C@H]4[C@H](F)[C@H](n5cnc6c(N)ncnc65)O[C@@H]4COP(=O)(S)O[C@@H]2[C@H]3F)c(=O)[nH]1] | (5R,7R,8R,12aR,14R,15S,15aR,16R)-7-(2-amino-6-oxo-1,6-dihydro-9H-purin-9-yl)-14-(6-amino-9H-purin-9-yl)-15,16-difluorooctahydro-12H-5,8-methanofuro[3,2-l][1,3,9,11,6,2,10]tetraoxathiadiphosphacyclotetradecine-2,10-bis(thiolate) 2,10-dioxide (Diastereomer 2) | 725 |
| 155 | 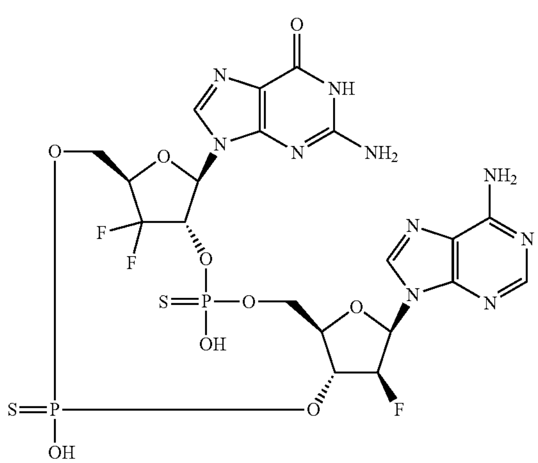 [SMILES: Nc1nc2c(ncn2[C@@H]2O[C@@H]3COP(O)(=S)O[C@H]4[C@H](F)[C@H](n5cnc6c(N)ncnc65)O[C@@H]4COP(O)(=S)O[C@@H]2C3(F)F)c(=O)[nH]1] | 2-amino-9-[(5R,7R,8S,12aR,14R,15S,15aR)-14-(6-amino-9H-purin-9-yl)-15,16,16-trifluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 727 |

TABLE 6-continued

| Ex. | Structure | Name | Mass [M − H]⁻ |
|---|---|---|---|
| 156 | 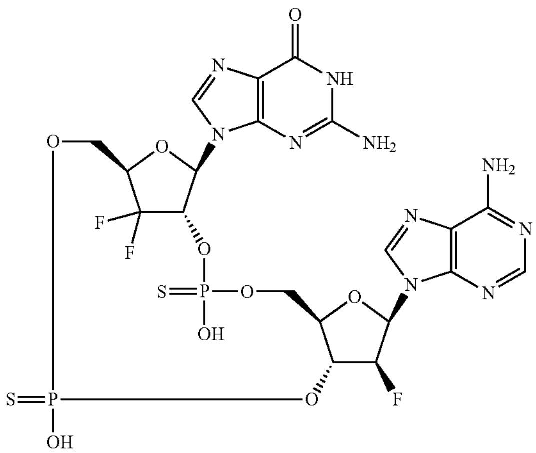 [SMILES: Nc1nc2c(ncn2[C@@H]2O[C@@H]3COP(O)(=S)O[C@H]4[C@H](F)[C@H](n5cnc6c(N)ncnc65)O[C@@H]4COP(O)(=S)O[C@@H]2C3(F)F)c(=O)[nH]1] | 2-amino-9-[(5R,7R,8S,12aR,14R,15S,15aR)-14-(6-amino-9H-purin-9-yl)-15,16,16-trifluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 727 |
| 157 | 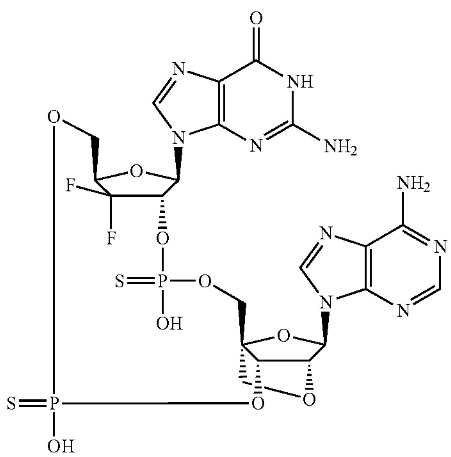 [SMILES: Nc1nc2c(ncn2[C@@H]2O[C@@H]3COP(O)(=S)O[C@H]4[C@H]5OC[C@]4(COP(O)(=S)O[C@@H]2C3(F)F)O[C@H]5n2cnc3c(N)ncnc32)c(=O)[nH]1] | 2-amino-9-[(5R,7R,8S,12aR,14R,15R,15aS)-14-(6-amino-9H-purin-9-yl)-18,18-difluoro-2,10-dihydroxy-2,10-disulfidohexahydro-14H-15,12a-(epoxymethano)-5,8-methanofuro[3,2-l][1,3,6,9,11,2,10] pentaoxadiphosphacyclotetradecin-7(12H)-yl]-1,9-dihydro-6H-purin-6-one (Diastereomer 1) | 737 |
| 158 | 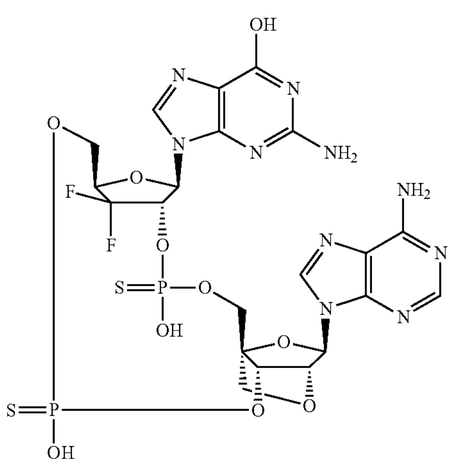 [SMILES: Nc1nc(O)c2ncn([C@@H]3O[C@@H]4COP(O)(=S)O[C@H]5[C@H]6OC[C@]5(COP(O)(=S)O[C@@H]3C4(F)F)O[C@H]6n3cnc4c(N)ncnc43)c2n1] | 2-amino-9-[(5R,7R,8S,12aR,14R,15R,15aS)-14-(6-amino-9H-purin-9-yl)-18,18-difluoro-2,10-dihydroxy-2,10-disulfidohexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one (Diastereomer 2) | 737 |

TABLE 6-continued

| Ex. | Structure | Name | Mass [M − H]⁻ |
|---|---|---|---|
| 159 | 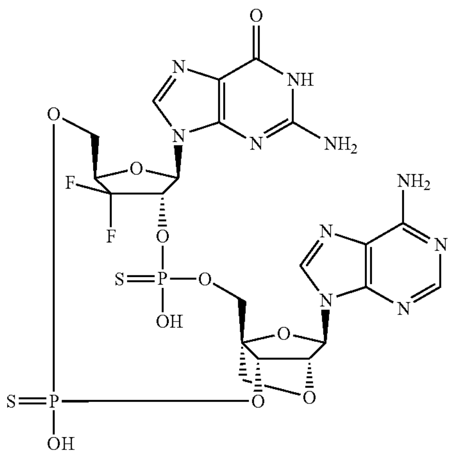 [SMILES: Nc1nc2c(ncn2[C@@H]2O[C@@H]3COP(O)(=S)O[C@H]4[C@H]5OC[C@]4(COP(O)(=S)O[C@@H]2C3(F)F)O[C@H]5n2cnc3c(N)ncnc32)c(=O)[nH]1] | 2-amino-9-[(5R,7R,8S,12aR,14R,15R,15aS)-14-(6-amino-9H-purin-9-yl)-18,18-difluoro-2,10-dihydroxy-2,10-disulfidohexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one (Diastereomer 3) | 737 |
| 160 | 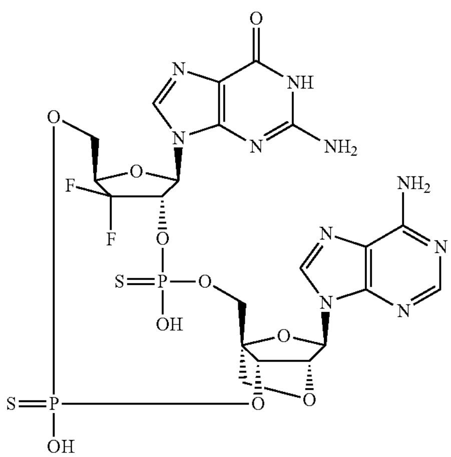 [SMILES: Nc1nc2c(ncn2[C@@H]2O[C@@H]3COP(O)(=S)O[C@H]4[C@H]5OC[C@]4(COP(O)(=S)O[C@@H]2C3(F)F)O[C@H]5n2cnc3c(N)ncnc32)c(=O)[nH]1] | 2-amino-9-[(5R,7R,8S,12aR,14R,15R,15aS)-14-(6-amino-9H-purin-9-yl)-18,18-difluoro-2,10-dihydroxy-2,10-disulfidohexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one (Diastereomer 4) | 737 |
| 161 | 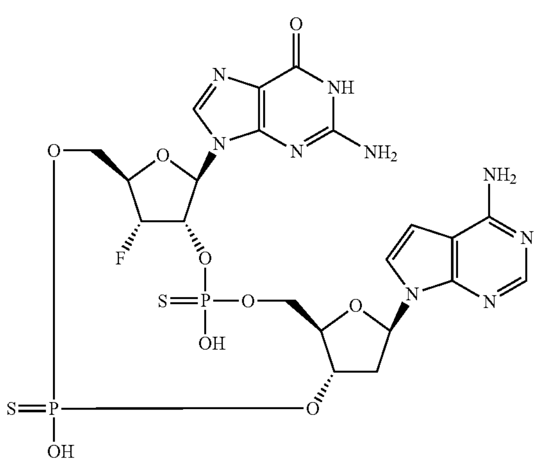 [SMILES: Nc1nc2c(ncn2[C@@H]2O[C@@H]3COP(O)(=S)O[C@H]4C[C@H](n5ccc6c(N)ncnc65)O[C@@H]4COP(O)(=S)O[C@@H]2[C@@H]3F)c(=O)[nH]1] | 2-amino-9-[(5R,7R,8S,12aR,14R,15aS,16R)-14-(4-amino-7H-pyrrolo[2,3-d]pyrimidin-7-yl)-16-fluoro-2,10-dihydroxy-2,10-disulfidooctahydro-12H-5,8-methanofuro[3,2-l][1,3,6, 9,11,2,10]pentaoxadiphosphacyclotetradecin-7-yl]-1,9-dihydro-6H-purin-6-one (Diastereomer 1) | 690 |

TABLE 6-continued

| Ex. | Structure | Name | Mass [M − H]⁻ |
|---|---|---|---|
| 162 | 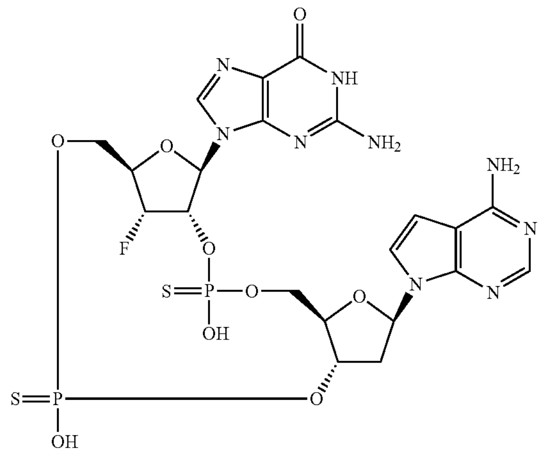 [SMILES: Nc1nc2c(ncn2[C@@H]2O[C@@H]3COP(O)(=S)O[C@H]4C[C@H](n5ccc6c(N)ncnc65)O[C@@H]4COP(O)(=S)O[C@@H]2[C@@H]3F)c(=O)[nH]1] | 2-amino-9-[(5R,7R,8S,12aR,14R,15aS,16R)-14-(4-amino-7H-pyrrolo[2,3-d]pyrimidin-7-yl)-16-fluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 690 |
| 163 | 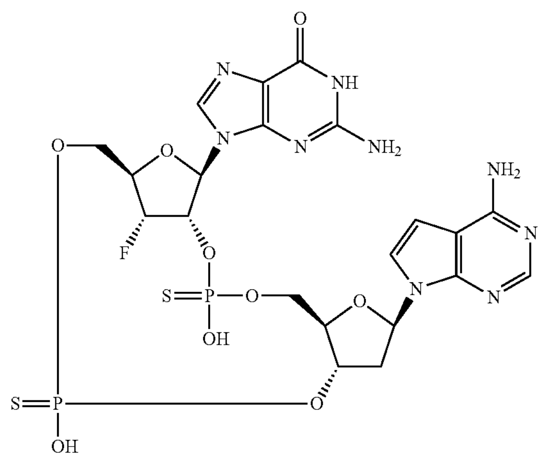 [SMILES: Nc1nc2c(ncn2[C@@H]2O[C@@H]3COP(O)(=S)O[C@H]4C[C@H](n5ccc6c(N)ncnc65)O[C@@H]4COP(O)(=S)O[C@@H]2[C@@H]3F)c(=O)[nH]1] | 2-amino-9-[(5R,7R,8S,12aR,14R,15aS,16R)-14-(4-amino-7H-pyrrolo[2,3-d]pyrimidin-7-yl)-16-fluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 3) | 690 |
| 164 | 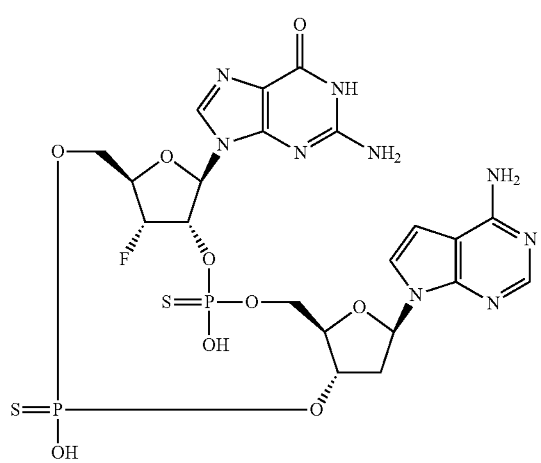 [SMILES: Nc1nc2c(ncn2[C@@H]2O[C@@H]3COP(O)(=S)O[C@H]4C[C@H](n5ccc6c(N)ncnc65)O[C@@H]4COP(O)(=S)O[C@@H]2[C@@H]3F)c(=O)[nH]1] | 2-amino-9-[(5R,7R,8S,12aR,14R,15aS,16R)-14-(4-amino-7H-pyrrolo[2,3-d]pyrimidin-7-yl)-16-fluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 4) | 690 |

TABLE 6-continued

| Ex. | Structure | Name | Mass [M − H]⁻ |
|---|---|---|---|
| 165 | 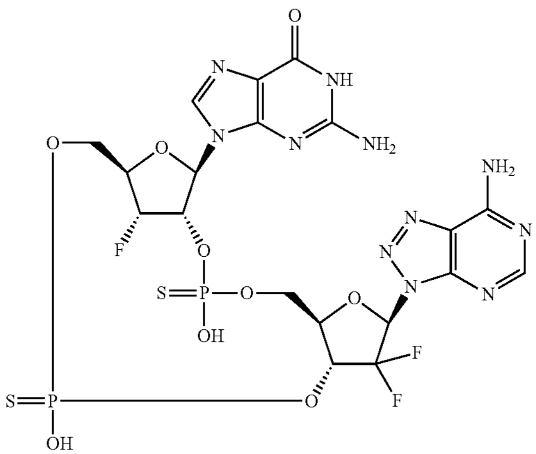 [SMILES: Nc1nc2c(ncn2[C@@H]2O[C@@H]3COP(O)(=S)O[C@@H]4[C@@H](COP(O)(=S)O[C@@H]2[C@@H]3F)O[C@@H](n2nnc3c(N)ncnc32)C4(F)F)c(=O)[nH]1] | 2-amino-9-[(5R,7R,8S,12aR,14R,15aR,16R)-14-(7-amino-3H-[1,2,3]triazolo[4,5-d]pyrimidin-3-yl)-15,15,16-trifluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 728 |
| 166 | 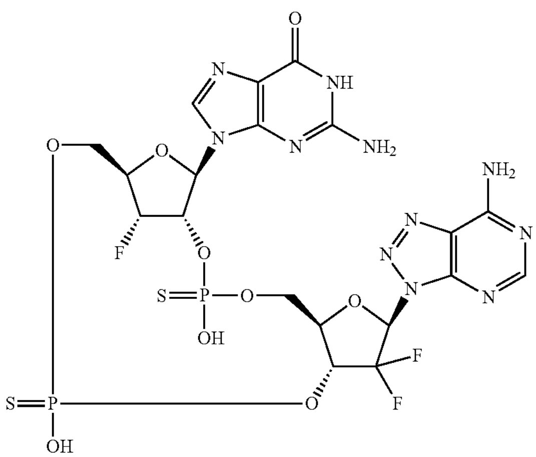 [SMILES: Nc1nc2c(ncn2[C@@H]2O[C@@H]3COP(O)(=S)O[C@@H]4[C@@H](COP(O)(=S)O[C@@H]2[C@@H]3F)O[C@@H](n2nnc3c(N)ncnc32)C4(F)F)c(=O)[nH]1] | 2-amino-9-[(5R,7R,8S,12aR,14R,15aR,16R)-14-(7-amino-3H-[1,2,3]triazolo[4,5-d]pyrimidin-3-yl)-15,15,16-trifluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 728 |
| 167 | 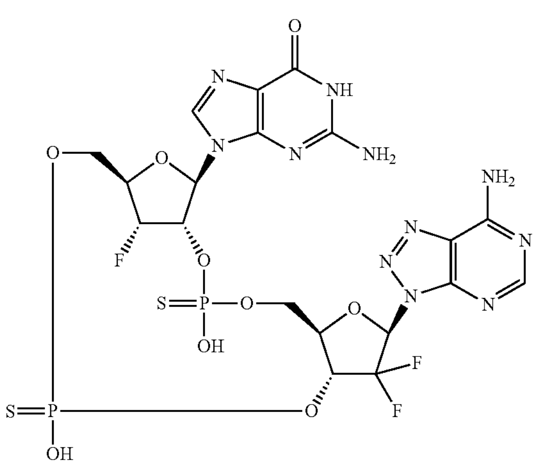 [SMILES: Nc1nc2c(ncn2[C@@H]2O[C@@H]3COP(O)(=S)O[C@@H]4[C@@H](COP(O)(=S)O[C@@H]2[C@@H]3F)O[C@@H](n2nnc3c(N)ncnc32)C4(F)F)c(=O)[nH]1] | 2-amino-9-[(5R,7R,8S,12aR,14R,15aR,16R)-14-(7-amino-3H-[1,2,3]triazolo[4,5-d]pyrimidin-3-yl)-15,15,16-trifluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 3) | 728 |

| Ex. | Structure | Name | Mass [M − H]⁻ |
|---|---|---|---|
| 168 | 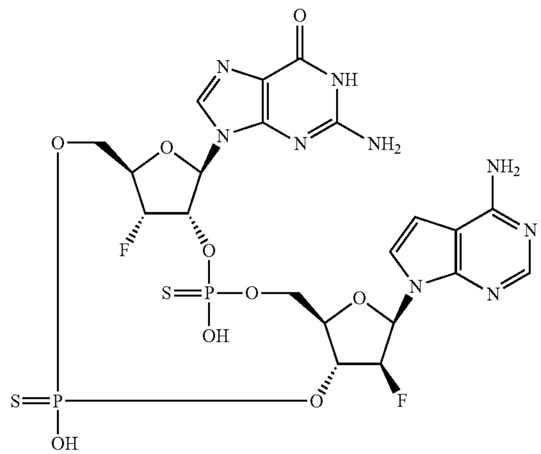 [SMILES: Nc1nc2c(ncn2[C@@H]2O[C@@H]3COP(O)(=S)O[C@H]4[C@H](F)[C@H](n5ccc6c(N)ncnc65)O[C@@H]4COP(O)(=S)O[C@@H]2[C@@H]3F)c(=O)[nH]1] | 2-amino-9-[(5R,7R,8S,12aR,14R,15S,15aR,16R)-14-(4-amino-7H-pyrrolo[2,3-d]pyrimidin-7-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 708 |
| 169 | 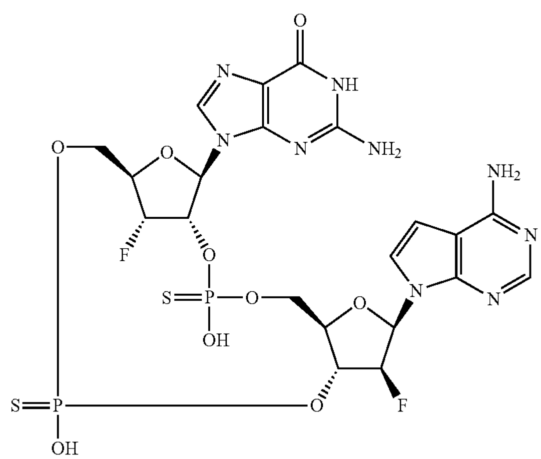 [SMILES: Nc1nc2c(ncn2[C@@H]2O[C@@H]3COP(O)(=S)O[C@H]4[C@H](F)[C@H](n5ccc6c(N)ncnc65)O[C@@H]4COP(O)(=S)O[C@@H]2[C@@H]3F)c(=O)[nH]1] | 2-amino-9-[(5R,7R,8S,12aR,14R,15S,15aR,16R)-14-(4-amino-7H-pyrrolo[2,3-d]pyrimidin-7-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 708 |
| 170 | 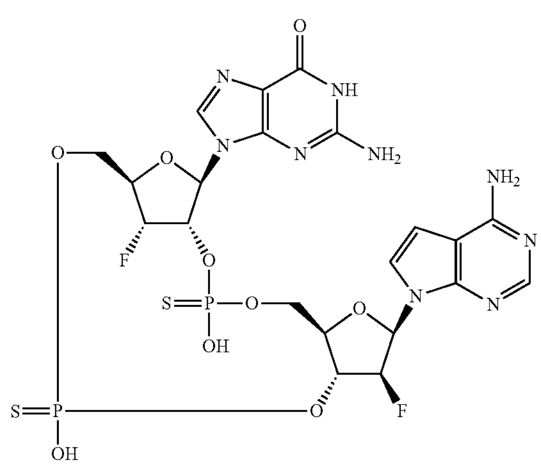 [SMILES: Nc1nc2c(ncn2[C@@H]2O[C@@H]3COP(O)(=S)O[C@H]4[C@H](F)[C@H](n5ccc6c(N)ncnc65)O[C@@H]4COP(O)(=S)O[C@@H]2[C@@H]3F)c(=O)[nH]1] | 2-amino-9-[(5R,7R,8S,12aR,14R,15S,15aR,16R)-14-(4-amino-7H-pyrrolo[2,3-d]pyrimidin-7-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 3) | 708 |

TABLE 6-continued

| Ex. | Structure | Name | Mass [M − H]⁻ |
|---|---|---|---|
| 171 | 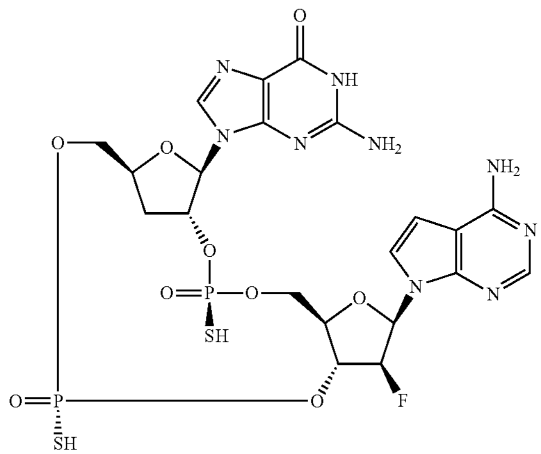 [SMILES: Nc1nc2c(ncn2[C@@H]2O[C@@H]3CO[P@@](=O)(S)O[C@H]4[C@H](F)[C@H](n5ccc6c(N)ncnc65)O[C@@H]4CO[P@@](=O)(S)O[C@@H]2C3)c(=O)[nH]1] | 2-amino-9-[(2R,5S,7R,8R,10R,12aR,14R,15S,15aR)-14-(4-amino-7H-pyrrolo[2,3-d]pyrimidin-7-yl)-15-fluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 690 |
| 172 | 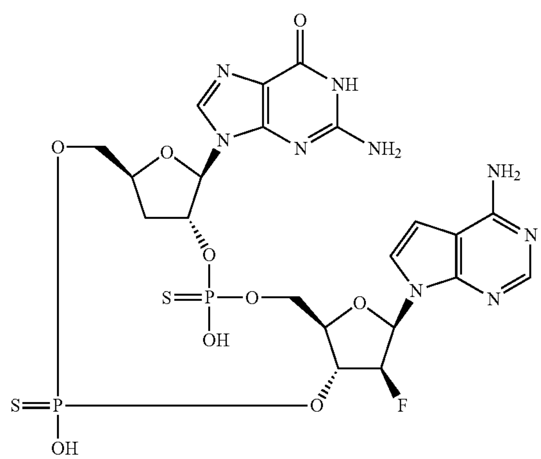 [SMILES: Nc1nc2c(ncn2[C@@H]2O[C@@H]3COP(O)(=S)O[C@H]4[C@H](F)[C@H](n5ccc6c(N)ncnc65)O[C@@H]4COP(O)(=S)O[C@@H]2C3)c(=O)[nH]1] | 2-amino-9-[(5S,7R,8R,12aR,14R,15S,15aR)-14-(4-amino-7H-pyrrolo[2,3-d]pyrimidin-7-yl)-15-fluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 690 |
| 173 | 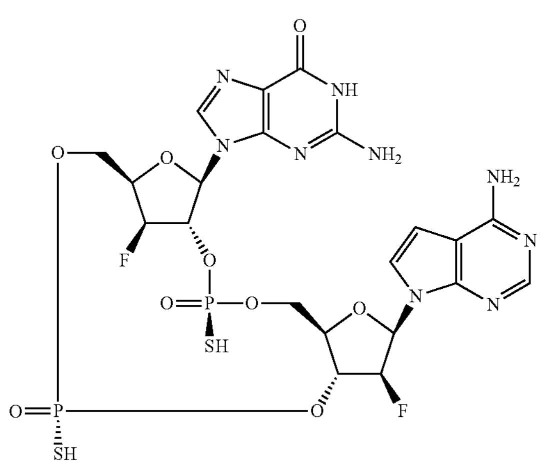 [SMILES: Nc1nc2c(ncn2[C@@H]2O[C@@H]3CO[P@@](=O)(S)O[C@H]4[C@H](F)[C@H](n5ccc6c(N)ncnc65)O[C@@H]4CO[P@@](=O)(S)O[C@@H]2[C@H]3F)c(=O)[nH]1] | 2-amino-9-[(2R,5R,7R,8S,10R,12aR,14R,15S,15aR,16S)-14-(4-amino-7H-pyrrolo[2,3-d]pyrimidin-7-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 708 |

TABLE 6-continued

| Ex. | Structure | Name | Mass [M − H]⁻ |
|---|---|---|---|
| 174 | 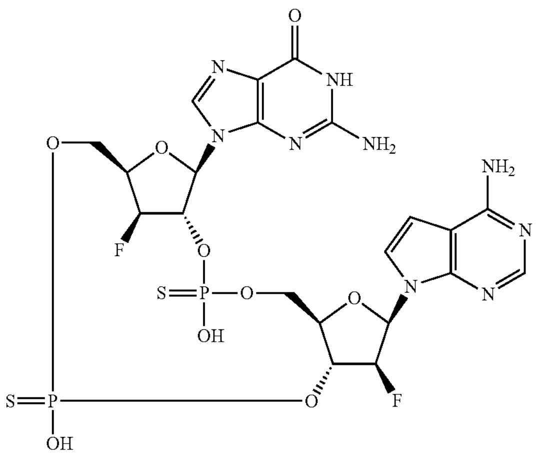 [SMILES: Nc1nc2c(ncn2[C@@H]2O[C@@H]3COP(O)(=S)O[C@H]4[C@H](F)[C@H](n5ccc6c(N)ncnc65)O[C@@H]4COP(O)(=S)O[C@@H]2[C@H]3F)c(=O)[nH]1] | 2-amino-9-[(5R,7R,8S,12aR,14R,15S,15aR,16S)-14-(4-amino-7H-pyrrolo[2,3-d]pyrimidin-7-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 708 |
| 175 | 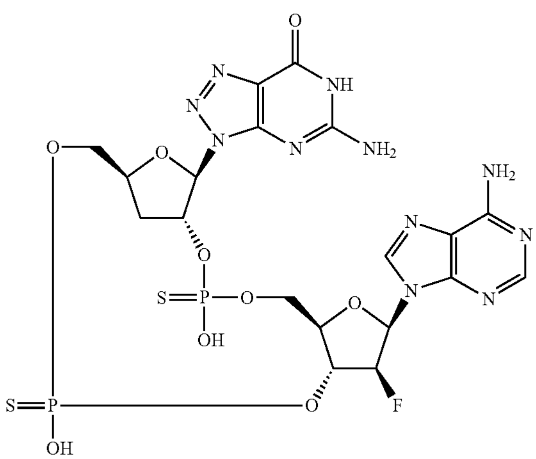 [SMILES: Nc1nc2c(nnn2[C@@H]2O[C@@H]3COP(O)(=S)O[C@H]4[C@H](F)[C@H](n5cnc6c(N)ncnc65)O[C@@H]4COP(O)(=S)O[C@@H]2C3)c(=O)[nH]1] | 5-amino-3-[(5S,7R,8R,12aR,14R,15S,15aR)-14-(6-amino-9H-purin-9-yl)-15-fluoro-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 1) | 692 |
| 176 | 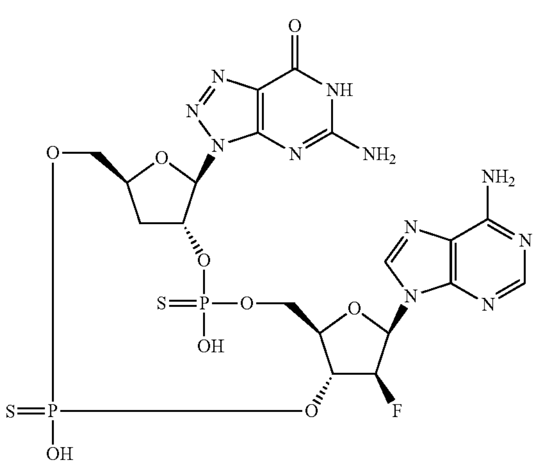 [SMILES: Nc1nc2c(nnn2[C@@H]2O[C@@H]3COP(O)(=S)O[C@H]4[C@H](F)[C@H](n5cnc6c(N)ncnc65)O[C@@H]4COP(O)(=S)O[C@@H]2C3)c(=O)[nH]1] | 5-amino-3-[(5S,7R,8R,12aR,14R,15S,15aR)-14-(6-amino-9H-purin-9-yl)-15-fluoro-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 2) | 692 |

TABLE 6-continued

| Ex. | Structure | Name | Mass [M − H]⁻ |
|---|---|---|---|
| 177 | 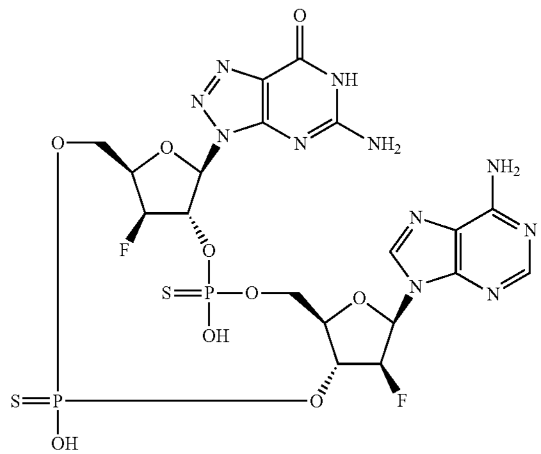 [SMILES: Nc1nc2c(nnn2[C@@H]2O[C@@H]3COP(O)(=S)O[C@H]4[C@H](F)[C@H](n5cnc6c(N)ncnc65)O[C@@H]4COP(O)(=S)O[C@@H]2[C@H]3F)c(=O)[nH]1] | 5-amino-3-[(5R,7R,8S,12aR,14R,15S,15aR,16S)-14-(6-amino-9H-purin-9-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 1) | 710 |
| 178 | 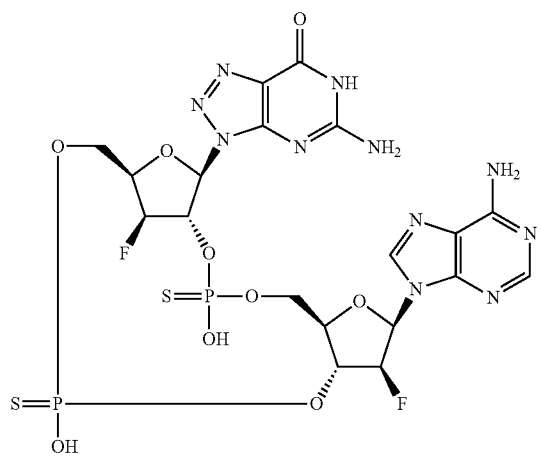 [SMILES: Nc1nc2c(nnn2[C@@H]2O[C@@H]3COP(O)(=S)O[C@H]4[C@H](F)[C@H](n5cnc6c(N)ncnc65)O[C@@H]4COP(O)(=S)O[C@@H]2[C@H]3F)c(=O)[nH]1] | 5-amino-3-[(5R,7R,8S,12aR,14R,15S,15aR,16S)-14-(6-amino-9H-purin-9-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 2) | 710 |
| 179 | 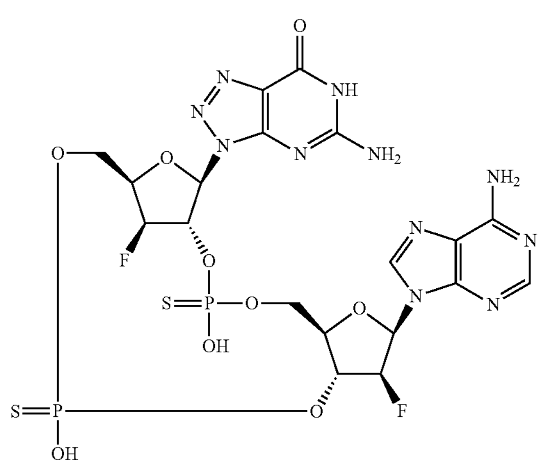 [SMILES: Nc1nc2c(nnn2[C@@H]2O[C@@H]3COP(O)(=S)O[C@H]4[C@H](F)[C@H](n5cnc6c(N)ncnc65)O[C@@H]4COP(O)(=S)O[C@@H]2[C@H]3F)c(=O)[nH]1] | 5-amino-3-[(5R,7R,8S,12aR,14R,15S,15aR,16S)-14-(6-amino-9H-purin-9-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 3) | 710 |

| Ex. | Structure | Name | Mass [M − H]⁻ |
|---|---|---|---|
| 180 | 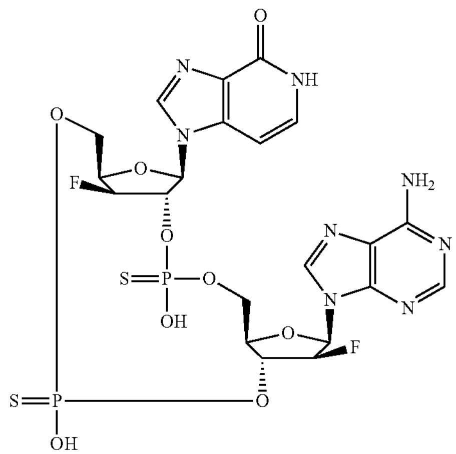 [SMILES: Nc1ncnc2c1ncn2[C@@H]1O[C@@H]2COP(O)(=S)O[C@@H]3[C@@H](F)[C@@H](COP(O)(=S)O[C@H]2[C@@H]1F)O[C@H]3n1cnc2c(=O)[nH]ccc21] | 1-[(5R,7R,8S,12aR,14R,15S,15aR,16S)-14-(6-amino-9H-purin-9-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-1,5-dihydro-4H-imidazo[4,5-c]pyridin-4-one | 693 |
| 181 | 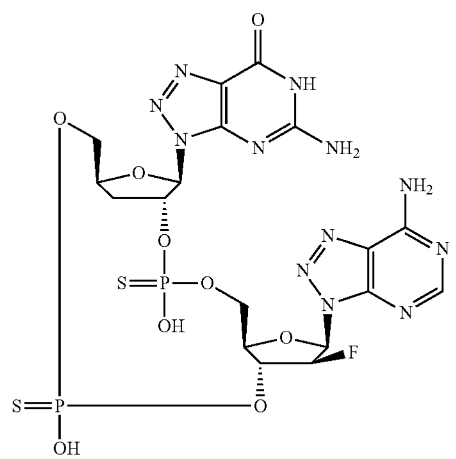 [SMILES: Nc1nc2c(nnn2[C@@H]2O[C@@H]3COP(O)(=S)O[C@H]4[C@H](F)[C@H](n5nnc6c(N)ncnc65)O[C@@H]4COP(O)(=S)O[C@@H]2C3)c(=O)[nH]1] | 5-amino-3-[(5S,7R,8R,12aR,14R,15S,15aR)-14-(7-amino-3H-[1,2,3]triazolo[4,5-d]pyrimidin-3-yl)-15-fluoro-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 1) | 693 |
| 182 | 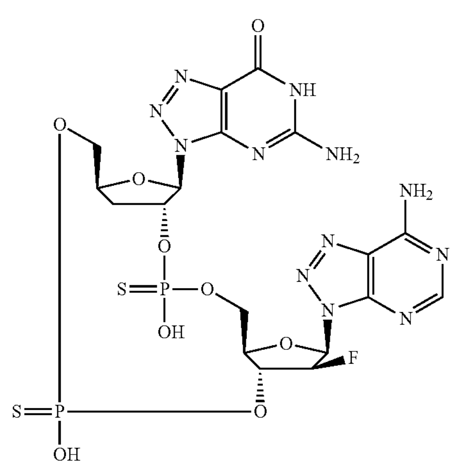 [SMILES: Nc1nc2c(nnn2[C@@H]2O[C@@H]3COP(O)(=S)O[C@H]4[C@H](F)[C@H](n5nnc6c(N)ncnc65)O[C@@H]4COP(O)(=S)O[C@@H]2C3)c(=O)[nH]1] | 5-amino-3-[(5S,7R,8R,12aR,14R,15S,15aR)-14-(7-amino-3H-[1,2,3]triazolo[4,5-d]pyrimidin-3-yl)-15-fluoro-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 2) | 693 |

TABLE 6-continued

| Ex. | Structure | Name | Mass [M − H]⁻ |
|---|---|---|---|
| 183 | 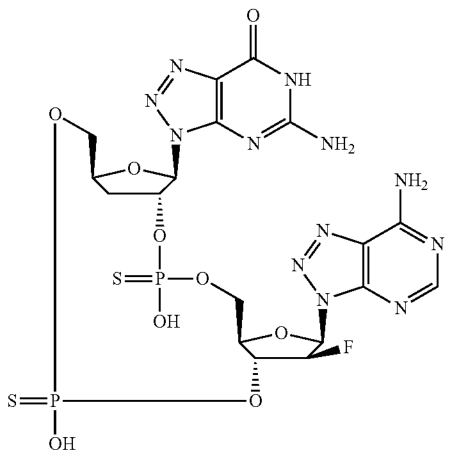 [SMILES: Nc1nc2c(nnn2[C@@H]2O[C@@H]3COP(O)(=S)O[C@H]4[C@H](F)[C@H](n5nnc6c(N)ncnc65)O[C@@H]4COP(O)(=S)O[C@@H]2C3)c(=O)[nH]1] | 5-amino-3-[(5S,7R,8R,12aR,14R,15S,15aR)-14-(7-amino-3H-[1,2,3]triazolo[4,5-d]pyrimidin-3-yl)-15-fluoro-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 3) | 693 |
| 184 | 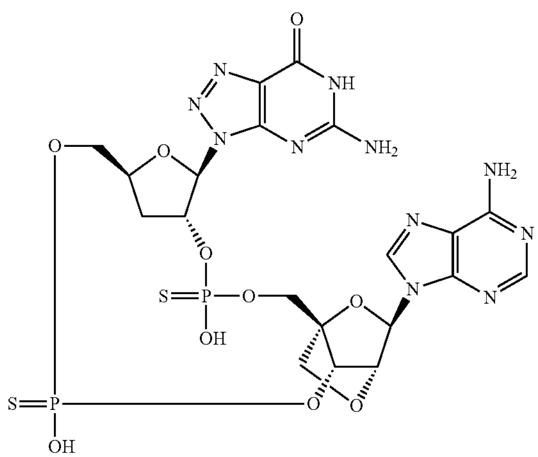 [SMILES: Nc1nc2c(nnn2[C@@H]2O[C@@H]3COP(O)(=S)O[C@H]4[C@H]5OC[C@]4(COP(O)(=S)O[C@@H]2C3)O[C@H]5n2cnc3c(N)ncnc32)c(=O)[nH]1] | 5-amino-3-[(5S,7R,8R,12aR,14R,15R,15aS)-14-(6-amino-9H-purin-9-yl)-2,10-dihydroxy-2,10-disulfidohexahydro-14H-15,12a-(epoxymethano)-5,8-methanofuro[3,2-l][1,3,6,9,11,2,10]pentaoxadiphosphacyclotetradecin-7(12H)-yl]-3,6-dihydro-7H-[1,2,3]triazolo[4,5-d]pyrimidin-7-one (Diastereomer 1) | 702 |
| 185 | 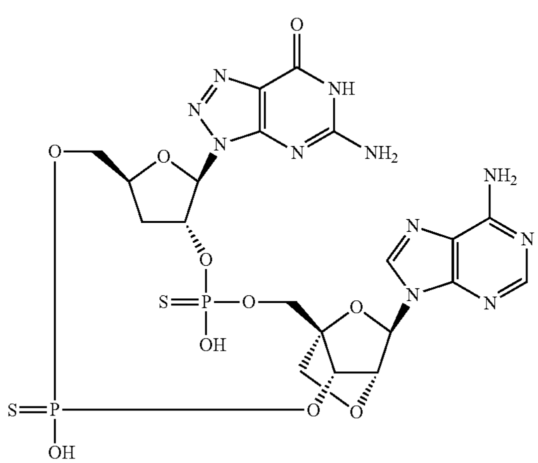 [SMILES: Nc1nc2c(nnn2[C@@H]2O[C@@H]3COP(O)(=S)O[C@H]4[C@H]5OC[C@]4(COP(O)(=S)O[C@@H]2C3)O[C@H]5n2cnc3c(N)ncnc32)c(=O)[nH]1] | 5-amino-3-[(5S,7R,8R,12aR,14R,15R,15aS)-14-(6-amino-9H-purin-9-yl)-2,10-dihydroxy-2,10-disulfidohexahydro-14H-15,12a-(epoxymethano)-5,8-methanofuro[3,2-l][1,3,6,9,11,2,10]pentaoxadiphosphacyclotetradecin-7(12H)-yl]-3,6-dihydro-7H-[1,2,3]triazolo[4,5-d]pyrimidin-7-one (Diastereomer 2) | 702 |

TABLE 6-continued

| Ex. | Structure | Name | Mass [M − H]⁻ |
|---|---|---|---|
| 186 | 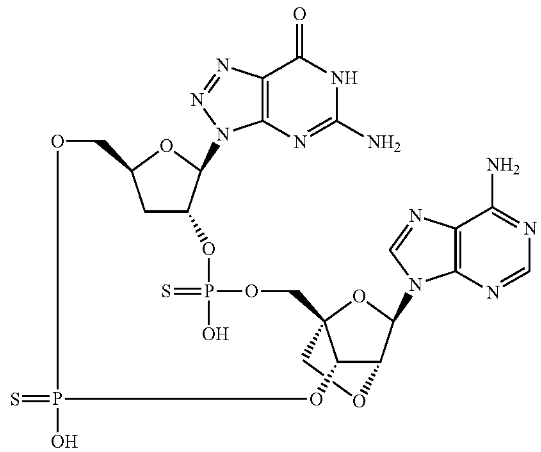 [SMILES: Nc1nc2c(nnn2[C@@H]2O[C@@H]3COP(O)(=S)O[C@H]4[C@H]5OC[C@]4(COP(O)(=S)O[C@@H]2C3)O[C@H]5n2cnc3c(N)ncnc32)c(=O)[nH]1] | 5-amino-3-[(5S,7R,8R,12aR,14R,15R,15aS)-14-(6-amino-9H-purin-9-yl)-2,10-dihydroxy-2,10-disulfidohexahydro-14H-15,12a-(epoxymethano)-5,8-methanofuro[3,2-l][1,3,6,9,11,2,10]pentaoxadiphosphacyclotetradecin-7(12H)-yl]-3,6-dihydro-7H-[1,2,3]triazolo[4,5-d]pyrimidin-7-one (Diastereomer 3) | 702 |
| 187 | 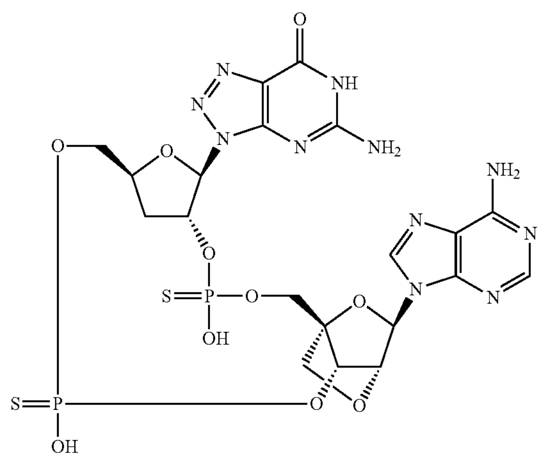 [SMILES: Nc1nc2c(nnn2[C@@H]2O[C@@H]3COP(O)(=S)O[C@H]4[C@H]5OC[C@]4(COP(O)(=S)O[C@@H]2C3)O[C@H]5n2cnc3c(N)ncnc32)c(=O)[nH]1] | 5-amino-3-[(5S,7R,8R,12aR,14R,15R,15aS)-14-(6-amino-9H-purin-9-yl)-2,10-dihydroxy-2,10-disulfidohexahydro-14H-15,12a-(epoxymethano)-5,8-methanofuro[3,2-l][1,3,6,9,11,2,10]pentaoxadiphosphacyclotetradecin-7(12H)-yl]-3,6-dihydro-7H-[1,2,3]triazolo[4,5-d]pyrimidin-7-one (Diastereomer 4) | 702 |
| 188 | 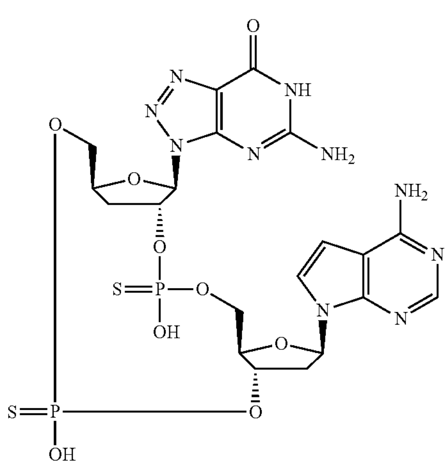 [SMILES: Nc1nc2c(nnn2[C@@H]2O[C@@H]3COP(O)(=S)O[C@H]4C[C@H](n5ccc6c(N)ncnc65)O[C@@H]4COP(O)(=S)O[C@@H]2C3)c(=O)[nH]1] | 5-amino-3-[(5S,7R,8R,12aR,14R,15aS)-14-(4-amino-7H-pyrrolo[2,3-d]pyrimidin-7-yl)-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 1) | 673 |

TABLE 6-continued

| Ex. | Structure | Name | Mass [M − H]⁻ |
|---|---|---|---|
| 189 | 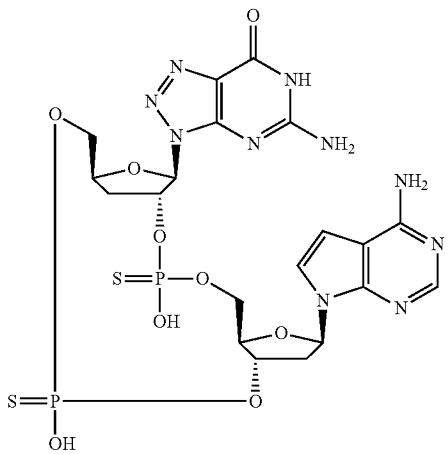 [SMILES: Nc1nc2c(nnn2[C@@H]2O[C@@H]3COP(O)(=S)O[C@H]4C[C@H](n5ccc6c(N)ncnc65)O[C@@H]4COP(O)(=S)O[C@@H]2C3)c(=O)[nH]1] | 5-amino-3-[(5S,7R,8R,12aR,14R,15aS)-14-(4-amino-7H-pyrrolo[2,3-d]pyrimidin-7-yl)-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 2) | 673 |
| 190 | 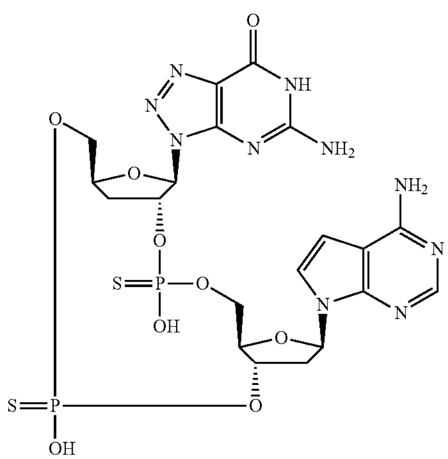 [SMILES: Nc1nc2c(nnn2[C@@H]2O[C@@H]3COP(O)(=S)O[C@H]4C[C@H](n5ccc6c(N)ncnc65)O[C@@H]4COP(O)(=S)O[C@@H]2C3)c(=O)[nH]1] | 5-amino-3-[(5S,7R,8R,12aR,14R,15aS)-14-(4-amino-7H-pyrrolo[2,3-d]pyrimidin-7-yl)-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 3) | 673 |
| 191 | 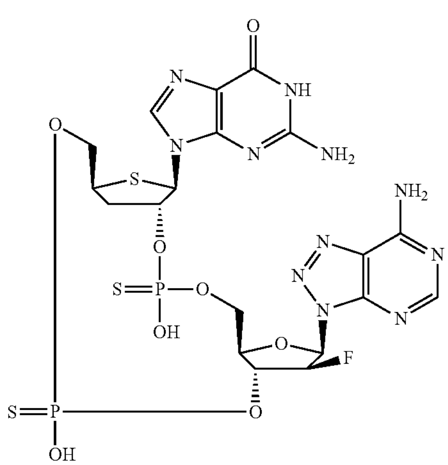 | 2-amino-9-[(5S,7R,8R,12aR,14R,15S,15aR)-14-(7-amino-3H-[1,2,3]triazolo[4,5-d]pyrimidin-3-yl)-15-fluoro-2,10-dihydroxy-2,10-disulfidooctahydro-12H-5,8-methanofuro[3,2-l][1,3,9,11,6,2,10]tetraoxathiadiphosphacyclotetradecin-7-yl]-1,9-dihydro-6H-purin-6-one (Diastereomer 1) | 708 |

TABLE 6-continued

| Ex. | Structure | Name | Mass [M − H]− |
|---|---|---|---|
| 192 | 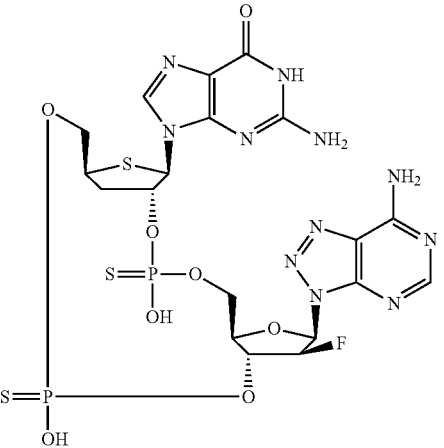 | 2-amino-9-[(5S,7R,8R,12aR,14R,15S,15aR)-14-(7-amino-3H-[1,2,3]triazolo[4,5-d]pyrimidin-3-yl)-15-fluoro-2,10-dihydroxy-2,10-disulfidooctahydro-12H-5,8-methanofuro[3,2-l][1,3,9,11,6,2,10]tetraoxathiadiphosphacyclotetradecin-7-yl]-1,9-dihydro-6H-purin-6-one (Diastereomer 2) | 708 |
| 193 | 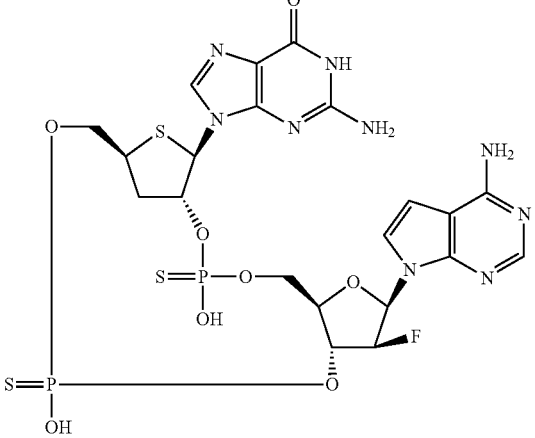 | 2-amino-9-[(5S,7R,8R,12aR,14R,15S,15aR)-14-(4-amino-7H-pyrrolo[2,3-d]pyrimidin-7-yl)-15-fluoro-2,10-dihydroxy-2,10-disulfidooctahydro-12H-5,8-methanofuro[3,2-l][1,3,9,11,6,2,10]tetraoxathiadiphosphacyclotetradecin-7-yl]-1,9-dihydro-6H-purin-6-one | 706 |
| 194 | 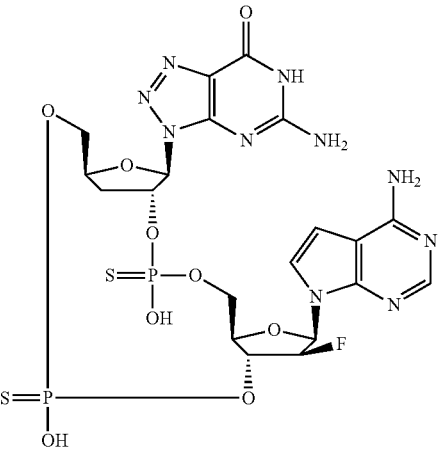 [SMILES: Nc1nc2c(nnn2[C@@H]2O[C@@H]3COP(O)(=S)O[C@H]4[C@H](F)[C@H](n5ccc6c(N)ncnc65)O[C@@H]4COP(O)(=S)O[C@@H]2C3)c(=O)[nH]1] | 5-amino-3-[(5S,7R,8R,12aR,14R,15S,15aR)-14-(4-amino-7H-pyrrolo[2,3-d]pyrimidin-7-yl)-15-fluoro-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 1) | 691 |

TABLE 6-continued

| Ex. | Structure | Name | Mass [M − H]⁻ |
|---|---|---|---|
| 195 | 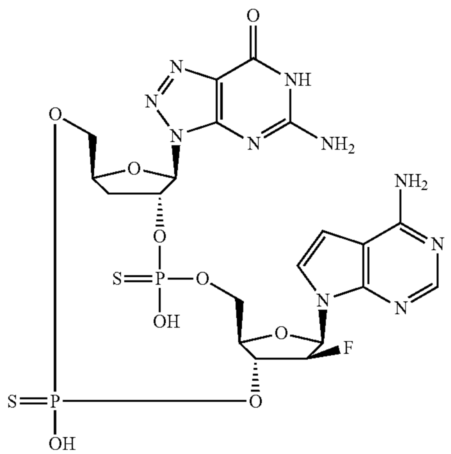 [SMILES: Nc1nc2c(nnn2[C@@H]2O[C@@H]3COP(O)(=S)O[C@H]4[C@H](F)[C@H](n5ccc6c(N)ncnc65)O[C@@H]4COP(O)(=S)O[C@@H]2C3)c(=O)[nH]1] | 5-amino-3-[(5S,7R,8R,12aR,14R,15S,15aR)-14-(4-amino-7H-pyrrolo[2,3-d]pyrimidin-7-yl)-15-fluoro-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 2) | 691 |
| 196 | 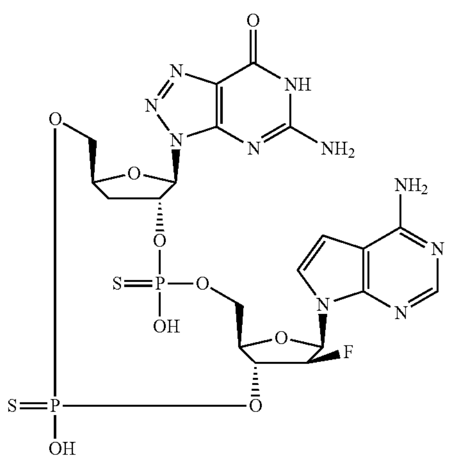 [SMILES: Nc1nc2c(nnn2[C@@H]2O[C@@H]3COP(O)(=S)O[C@H]4[C@H](F)[C@H](n5ccc6c(N)ncnc65)O[C@@H]4COP(O)(=S)O[C@@H]2C3)c(=O)[nH]1] | 5-amino-3-[(5S,7R,8R,12aR,14R,15S,15aR)-14-(4-amino-7H-pyrrolo[2,3-d]pyrimidin-7-yl)-15-fluoro-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 3) | 691 |
| 197 | 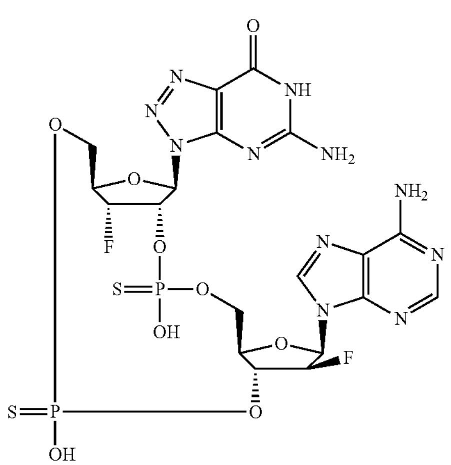 [SMILES: Nc1nc2c(nnn2[C@@H]2O[C@@H]3COP(O)(=S)O[C@H]4[C@H](F)[C@H](n5cnc6c(N)ncnc65)O[C@@H]4COP(O)(=S)O[C@@H]2[C@@H]3F)c(=O)[nH]1] | 5-amino-3-[(5R,7R,8S,12aR,14R,15S,15aR,16R)-14-(6-amino-9H-purin-9-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 1) | 710 |

TABLE 6-continued

| Ex. | Structure | Name | Mass [M − H]⁻ |
|---|---|---|---|
| 198 | 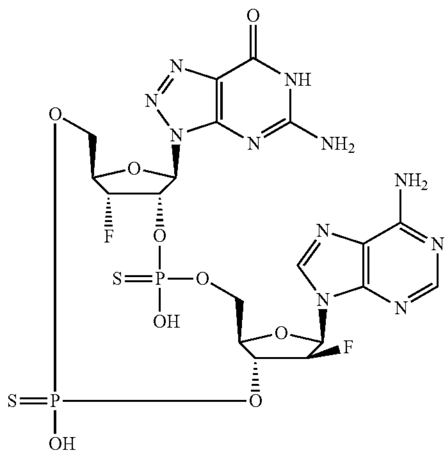 [SMILES: Nc1nc2c(nnn2[C@@H]2O[C@@H]3COP(O)(=S)O[C@H]4[C@H](F)[C@H](n5cnc6c(N)ncnc65)O[C@@H]4COP(O)(=S)O[C@@H]2[C@@H]3F)c(=O)[nH]1] | 5-amino-3-[(5R,7R,8S,12aR,14R,15S,15aR,16R)-14-(6-amino-9H-purin-9-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 2) | 710 |
| 199 | 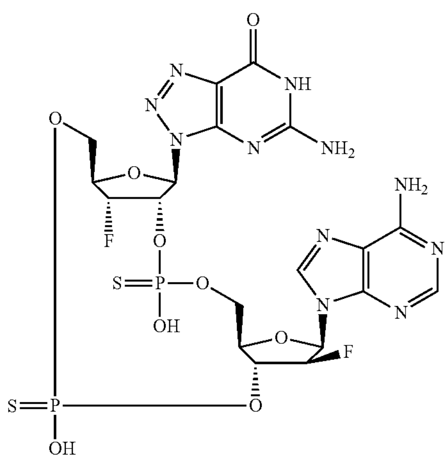 [SMILES: Nc1nc2c(nnn2[C@@H]2O[C@@H]3COP(O)(=S)O[C@H]4[C@H](F)[C@H](n5cnc6c(N)ncnc65)O[C@@H]4COP(O)(=S)O[C@@H]2[C@@H]3F)c(=O)[nH]1] | 5-amino-3-[(5R,7R,8S,12aR,14R,15S,15aR,16R)-14-(6-amino-9H-purin-9-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 3) | 710 |
| 200 | 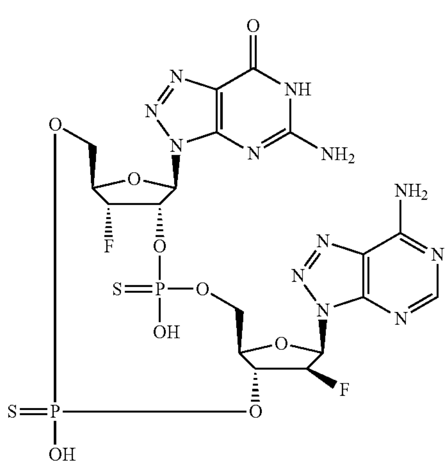 [SMILES: Nc1nc2c(nnn2[C@@H]2O[C@@H]3COP(O)(=S)O[C@H]4[C@H](F)[C@H](n5nnc6c(N)ncnc65)O[C@@H]4COP(O)(=S)O[C@@H]2[C@@H]3F)c(=O)[nH]1] | 5-amino-3-[(5R,7R,8S,12aR,14R,15S,15aR,16R)-14-(7-amino-3H-[1,2,3]triazolo[4,5-d]pyrimidin-3-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 1) | 711 |

TABLE 6-continued

| Ex. | Structure | Name | Mass [M − H]⁻ |
|---|---|---|---|
| 201 | 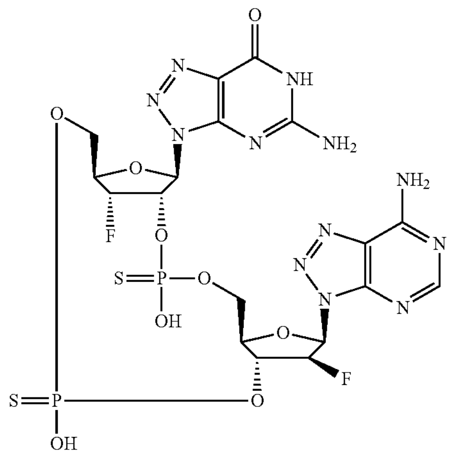 [SMILES: Nc1nc2c(nnn2[C@@H]2O[C@@H]3COP(O)(=S)O[C@H]4[C@H](F)[C@H](n5nnc6c(N)ncnc65)O[C@@H]4COP(O)(=S)O[C@@H]2[C@@H]3F)c(=O)[nH]1] | 5-amino-3-[(5R,7R,8S,12aR,14R,15S,15aR,16R)-14-(7-amino-3H-[1,2,3]triazolo[4,5-d]pyrimidin-3-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 2) | 711 |
| 202 | 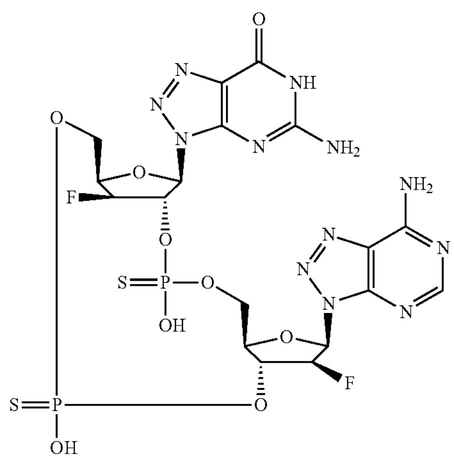 [SMILES: Nc1nc2c(nnn2[C@@H]2O[C@@H]3COP(O)(=S)O[C@H]4[C@H](F)[C@H](n5nnc6c(N)ncnc65)O[C@@H]4COP(O)(=S)O[C@@H]2[C@H]3F)c(=O)[nH]1] | 5-amino-3-[(5R,7R,8S,12aR,14R,15S,15aR,16S)-14-(7-amino-3H-[1,2,3]triazolo[4,5-d]pyrimidin-3-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one | 711 |
| 203 | 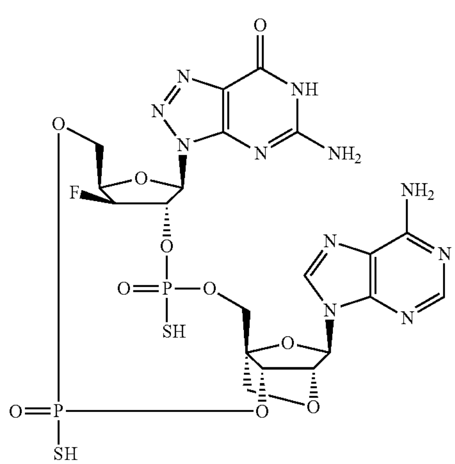 [SMILES: Nc1nc2c(nnn2[C@@H]2O[C@@H]3COP(=O)(S)O[C@H]4[C@H]5OC[C@]4(COP(=O)(S)O[C@@H]2[C@H]3F)O[C@H]5n2cnc3c(N)ncnc32)c(=O)[nH]1] | 5-amino-3-[(5R,7R,8S,12aR,14R,15R,15aS,18S)-14-(6-amino-9H-purin-9-yl)-18-fluoro-2,10-dioxido-2,10-disulfanylhexahydro-14H-15,12a-(epoxymethano)-5,8-methanofuro[3,2-l][1,3,6,9,11,2,10]pentaoxadiphosphacyclotetradecin-7(12H)-yl]-3,6-dihydro-7H-[1,2,3]triazolo[4,5-d]pyrimidin-7-one (Diastereomer 1) | 720 |

TABLE 6-continued

| Ex. | Structure | Name | Mass [M − H]⁻ |
|---|---|---|---|
| 204 | 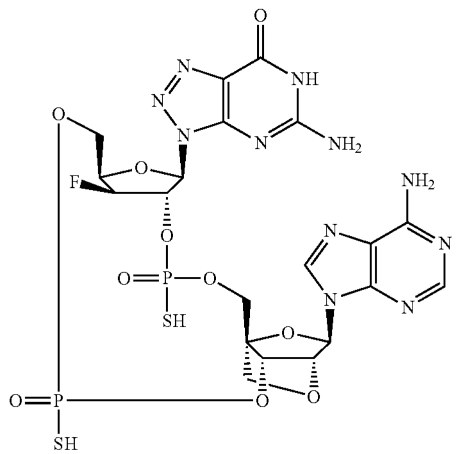 [SMILES: Nc1nc2c(nnn2[C@@H]2O[C@@H]3COP(=O)(S)O[C@H]4[C@H]5OC[C@]4(COP(=O)(S)O[C@@H]2[C@H]3F)O[C@H]5n2cnc3c(N)ncnc32)c(=O)[nH]1] | 5-amino-3-[(5R,7R,8S,12aR,14R,15R,15aS,18S)-14-(6-amino-9H-purin-9-yl)-18-fluoro-2,10-dioxido-2,10-disulfanylhexahydro-14H-15,12a-(epoxymethano)-5,8-methanofuro[3,2-l][1,3,6,9,11,2,10]pentaoxadiphosphacyclotetradecin-7(12H)-yl]-3,6-dihydro-7H-[1,2,3]triazolo[4,5-d]pyrimidin-7-one (Diastereomer 2) | 720 |
| 205 | 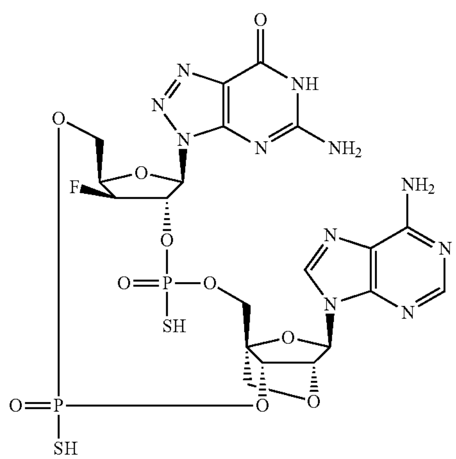 [SMILES: Nc1nc2c(nnn2[C@@H]2O[C@@H]3COP(=O)(S)O[C@H]4[C@H]5OC[C@]4(COP(=O)(S)O[C@@H]2[C@H]3F)O[C@H]5n2cnc3c(N)ncnc32)c(=O)[nH]1] | 5-amino-3-[(5R,7R,8S,12aR,14R,15R,15aS,18S)-14-(6-amino-9H-purin-9-yl)-18-fluoro-2,10-dioxido-2,10-disulfanylhexahydro-14H-15,12a-(epoxymethano)-5,8-methanofuro[3,2-l][1,3,6,9,11,2,10]pentaoxadiphosphacyclotetradecin-7(12H)-yl]-3,6-dihydro-7H-[1,2,3]triazolo[4,5-d]pyrimidin-7-one (Diastereomer 3) | 720 |
| 206 | 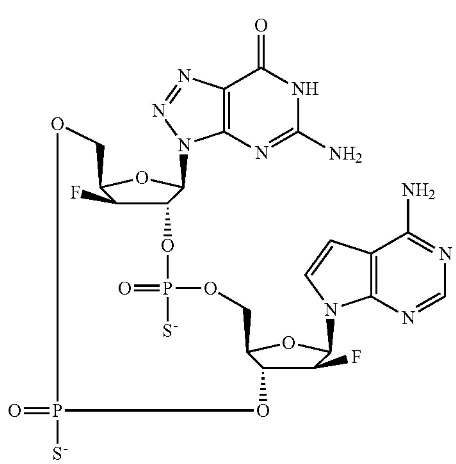 [SMILES: Nc1nc2c(nnn2[C@@H]2O[C@@H]3COP(=O)([S-])O[C@H]4[C@H](F)[C@H](n5ccc6c(N)ncnc65)O[C@@H]4COP(=O)([S-])O[C@@H]2[C@H]3F)c(=O)[nH]1] | 5-amino-3-[(5R,7R,8S,12aR,14R,15S,15aR,16S)-14-(4-amino-7H-pyrrolo[2,3-d]pyrimidin-7-yl)-15,16-difluoro-2,10-dioxido-2,10-disulfanyloctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one | 709 |

TABLE 6-continued

| Ex. | Structure | Name | Mass [M − H]⁻ |
|---|---|---|---|
| 207 | 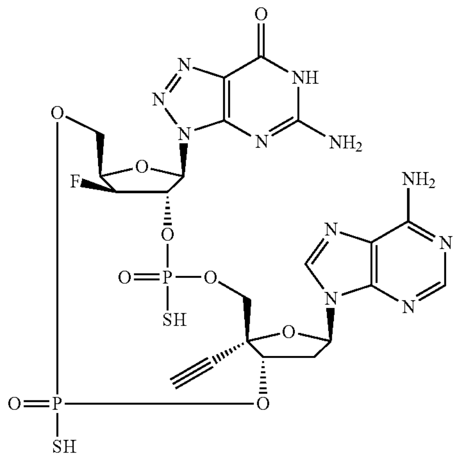 [SMILES: C#C[C@@]12COP(=O)(S)O[C@@H]3[C@@H](F)[C@@H](COP(=O)(S)O[C@H]1C[C@H](n1cnc4c(N)ncnc41)O2)O[C@H]3n1nnc2c(=O)[nH]c(N)nc21] | 5-amino-3-[(5R,7R,8S,112aR,14R,15aS,16S)-14-(6-amino-9H-purin-9-yl)-12a-ethynyl-16-fluoro-2,10-dioxido-2,10-disulfanyloctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 1) | 716 |
| 208 | 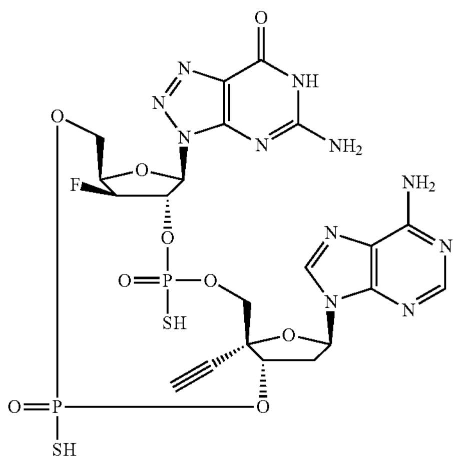 [SMILES: C#C[C@@]12COP(=O)(S)O[C@@H]3[C@@H](F)[C@@H](COP(=O)(S)O[C@H]1C[C@H](n1cnc4c(N)ncnc41)O2)O[C@H]3n1nnc2c(=O)[nH]c(N)nc21] | 5-amino-3-[(5R,7R,8S,112aR,14R,15aS,16S)-14-(6-amino-9H-purin-9-yl)-12a-ethynyl-16-fluoro-2,10-dioxido-2,10-disulfanyloctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 2) | 716 |
| 209 | 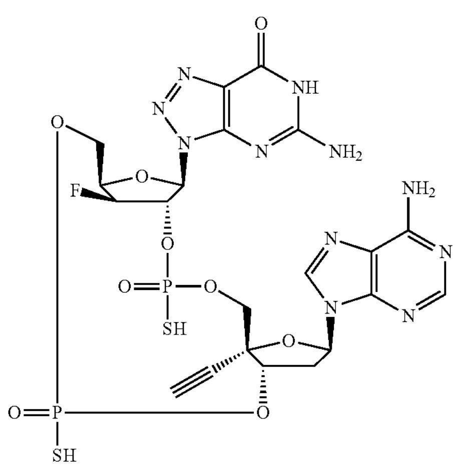 [SMILES: C#C[C@@]12COP(=O)(S)O[C@@H]3[C@@H](F)[C@@H](COP(=O)(S)O[C@H]1C[C@H](n1cnc4c(N)ncnc41)O2)O[C@H]3n1nnc2c(=O)[nH]c(N)nc21] | 5-amino-3-[(5R,7R,8S,112aR,14R,15aS,16S)-14-(6-amino-9H-purin-9-yl)-12a-ethynyl-16-fluoro-2,10-dioxido-2,10-disulfanyloctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 3) | 716 |

TABLE 6-continued

| Ex. | Structure | Name | Mass [M − H]⁻ |
|---|---|---|---|
| 210 | 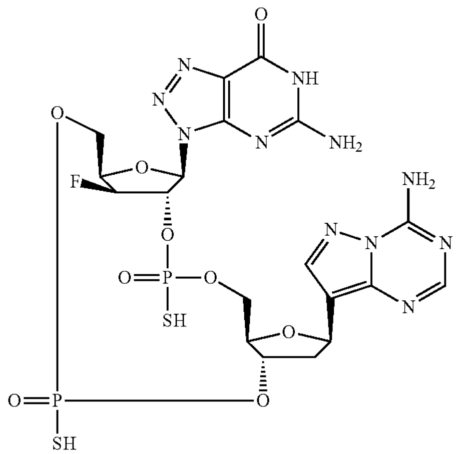 [SMILES: Nc1nc2c(nnn2[C@@H]2O[C@@H]3COP(=O)(S)O[C@H]4C[C@H](c5cnn6c(N)ncnc56)O[C@@H]4COP(=O)(S)O[C@@H]2[C@H]3F)c(=O)[nH]1] | 5-amino-3-[(5R,7R,8S,12aR,14R,15aS,16S)-14-(4-aminopyrazolo[1,5-a][1,3,5]triazin-8-yl)-16-fluoro-2,10-dioxido-2,10-disulfanyloctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 1) | 692 |
| 211 | 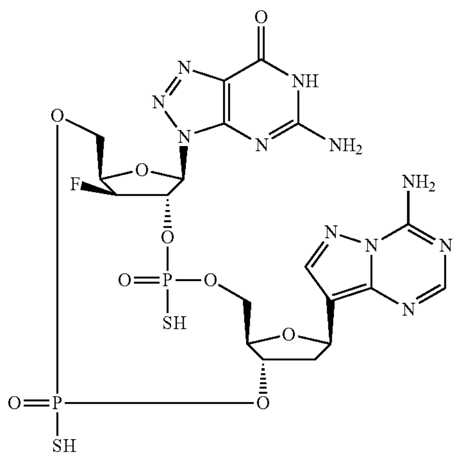 [SMILES: Nc1nc2c(nnn2[C@@H]2O[C@@H]3COP(=O)(S)O[C@H]4C[C@H](c5cnn6c(N)ncnc56)O[C@@H]4COP(=O)(S)O[C@@H]2[C@H]3F)c(=O)[nH]1] | 5-amino-3-[(5R,7R,8S,12aR,14R,15aS,16S)-14-(4-aminopyrazolo[1,5-a][1,3,5]triazin-8-yl)-16-fluoro-2,10-dioxido-2,10-disulfanyloctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 2) | 692 |
| 212 | 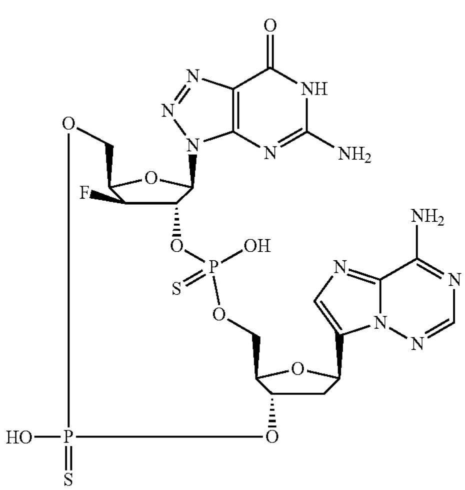 [SMILES: Nc1nc2c(nnn2[C@@H]2O[C@@H]3COP(O)(=S)O[C@H]4C[C@H](c5cnc6c(N)ncnn56)O[C@@H]4COP(O)(=S)O[C@@H]2[C@H]3F)c(=O)[nH]1] | 5-amino-3-[(5R,7R,8S,12aR,14R,15aS,16S)-14-(4-aminoimidazo[2,1-f][1,2,4]triazin-7-yl)-16-fluoro-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 1) | 692 |

TABLE 6-continued

| Ex. | Structure | Name | Mass [M − H]⁻ |
|---|---|---|---|
| 213 | 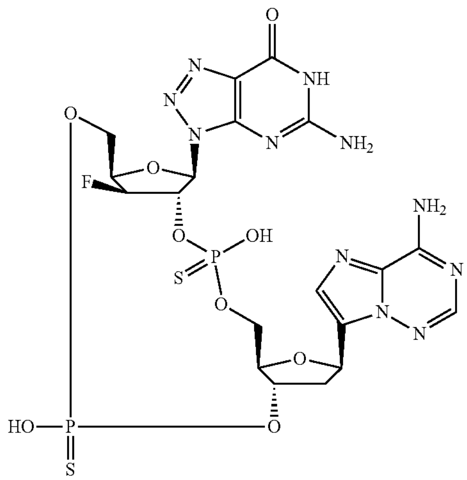 [SMILES: Nc1nc2c(nnn2[C@@H]2O[C@@H]3COP(O)(=S)O[C@H]4C[C@H](c5cnc6c(N)ncnn56)O[C@@H]4COP(O)(=S)O[C@@H]2[C@H]3F)c(=O)[nH]1] | 5-amino-3-[(5R,7R,8S,12aR,14R,15aS,16S)-14-(4-aminoimidazo[2,1-f][1,2,4]triazin-7-yl)-16-fluoro-2,10-dihydroxy-2,10-disulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 2) | 692 |
| 214 | 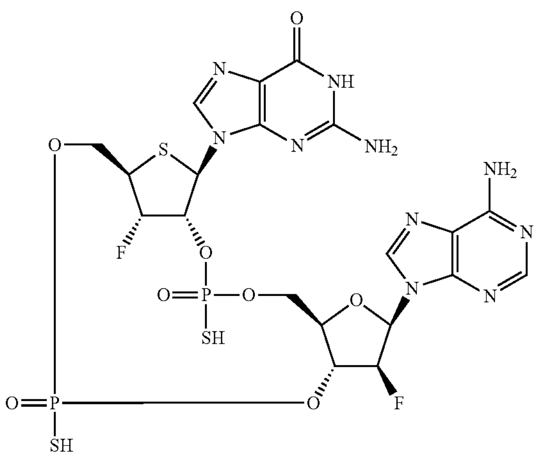 | 2-amino-9-[(5R,7R,8R,12aR,14R,15S,15aR,16S)-14-(6-amino-9H-purin-9-yl)-15,16-difluoro-2,10-dioxido-2,10-disulfanyloctahydro-12H-5,8-methanofuro[3,2-l][1,3,6,9,11,2,10]tetraoxathiadiphosphacyclotetradecin-7-yl]-1,9-dihydro-6H-purin-6-one (Diastereomer 1) | 725 |
| 215 | 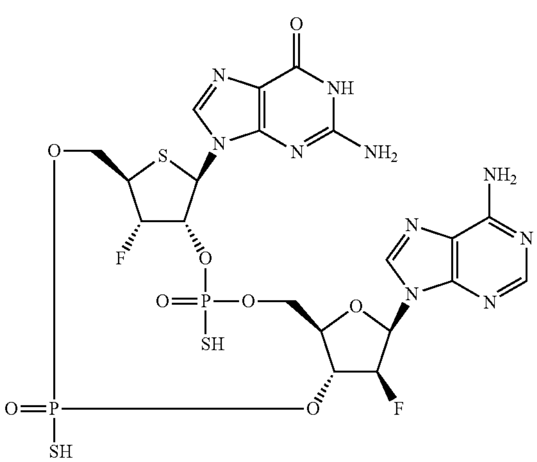 | 2-amino-9-[(5R,7R,8R,12aR,14R,15S,15aR,16S)-14-(6-amino-9H-purin-9-yl)-15,16-difluoro-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 725 |

TABLE 6-continued

| Ex. | Structure | Name | Mass [M − H]⁻ |
|---|---|---|---|
| 216 | 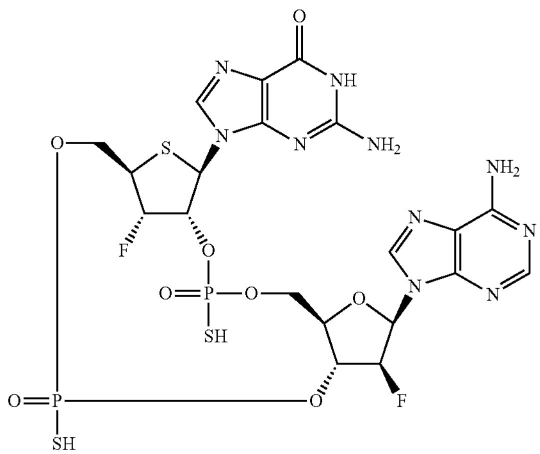 | 2-amino-9-[(5R,7R,8R,12aR,14R,15S,15aR,16S)-14-(6-amino-9H-purin-9-yl)-15,16-difluoro-2,10-dioxido-2,10-disulfanyloctahydro-12H-5,8-methanofuro[3,2-l][1,3,9,11,6,2,10]tetraoxathiadiphosphacyclotetradecin-7-yl]-1,9-dihydro-6H-purin-6-one (Diastereomer 3) | 725 |
| 217 | 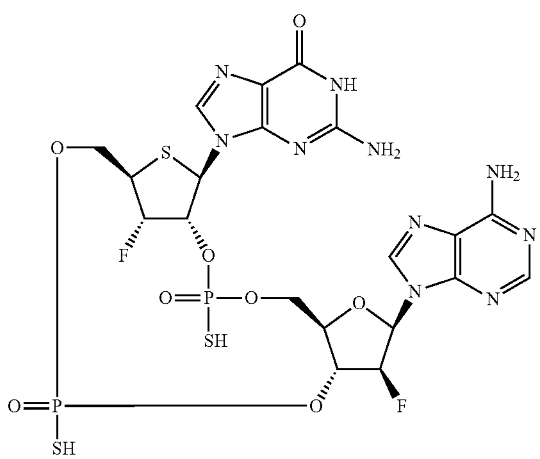 [SMILES: Nc1nc2c(ncn2[C@@H]2S[C@@H]3COP(=O)(S)O[C@H]4[C@H](F)[C@H](n5cnc6c(N)ncnc65)O[C@@H]4COP(=O)(S)O[C@@H]2[C@@H]3F)c(=O)[nH]1] | 2-amino-9-[(2R,5R,7R,8R,10R,12aR,14R,15S,15aR,16S)-14-(6-amino-9H-purin-9-yl)-15,16-difluoro-2,10-dioxido-2,10-disulfanyloctahydro-12H-5,8-methanofuro[3,2-l][1,3,9,11,6,2,10]tetraoxathiadiphosphacyclotetradecin-7-yl]-1,9-dihydro-6H-purin-6-one (Diastereomer 4) | 725 |
| 218 | 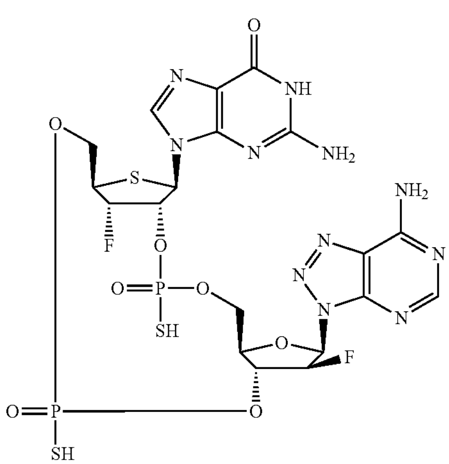 [SMILES: Nc1nc2c(ncn2[C@@H]2S[C@@H]3COP(=O)(S)O[C@H]4[C@H](F)[C@H](n5nnc6c(N)ncnc65)O[C@@H]4COP(=O)(S)O[C@@H]2[C@@H]3F)c(=O)[nH]1] | 2-amino-9-[(5R,7R,8R,12aR,14R,15S,15aR,16S)-14-(7-amino-3H-[1,2,3]triazolo[4,5-d]pyrimidin-3-yl)-15,16-difluoro-2,10-dioxido-2,10-disulfanyloctahydro-12H-5,8-methanofuro[3,2-l][1,3,9,11,6,2,10]tetraoxathiadiphosphacyclotetradecin-7-yl]-1,9-dihydro-6H-purin-6-one (Diastereomer 1) | 726 |

TABLE 6-continued

| Ex. | Structure | Name | Mass [M − H]⁻ |
|---|---|---|---|
| 219 | 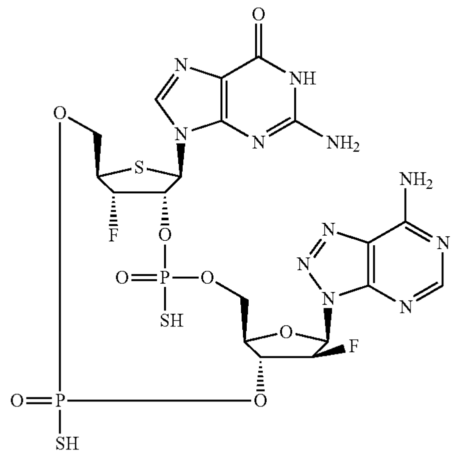 [SMILES: Nc1nc2c(ncn2[C@@H]2S[C@@H]3COP(=O)(S)O[C@H]4[C@H](F)[C@H](n5nnc6c(N)ncnc65)O[C@@H]4COP(=O)(S)O[C@@H]2[C@@H]3F)c(=O)[nH]1] | 2-amino-9-[(5R,7R,8R,12aR,14R,15S,15aR,16S)-14-(7-amino-3H-[1,2,3]triazolo[4,5-d]pyrimidin-3-yl)-15,16-difluoro-2,10-dioxido-2,10-disulfanyloctahydro-12H-5,8-methanofuro[3,2-l][1,3,9,11,6,2,10]tetraoxathiadiphosphacyclotetra-decin-7-yl]-1,9-dihydro-6H-purin-6-one (Diastereomer 2) | 726 |
| 220 | 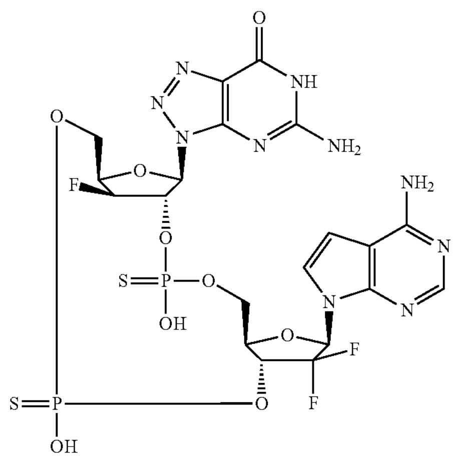 [SMILES: Nc1nc2c(nnn2[C@@H]2O[C@@H]3COP(O)(=S)O[C@@H]4[C@@H](COP(O)(=S)O[C@@H]2[C@H]3F)O[C@@H](n2ccc3c(N)ncnc32)C4(F)F)c(=O)[nH]1] | 5-amino-3-[(5R,7R,8S,12aR,14R,15aR,16S)-14-(4-amino-7H-pyrrolo[2,3-d]pyrimidin-7-yl)-15,15,16-trifluoro-2,10-dihydroxy-2,10-disulfidooctahydro-12H-5,8-methanofuro[3,2-l][1,3,6,9,11,2,10]pentaoxadiphosphacyclotetra-decin-7-yl]-3,6-dihydro-7H-[1,2,3]triazolo[4,5-d]pyrimidin-7-one | 727 |
| 221 | 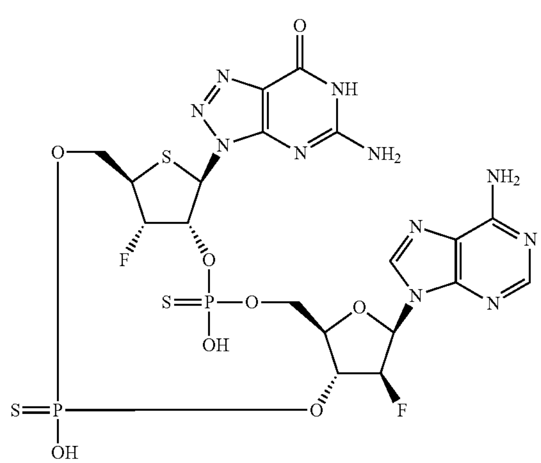 [SMILES: Nc1nc2c(nnn2[C@@H]2S[C@@H]3COP(O)(=S)O[C@H]4[C@H](F)[C@H](n5cnc6c(N)ncnc65)O[C@@H]4COP(O)(=S)O[C@@H]2[C@@H]3F)c(=O)[nH]1] | 5-amino-3-[(5R,7R,8R,12aR,14R,15S,15aR,16S)-14-(6-amino-9H-purin-9-yl)-15,16-difluoro-2,10-dihydroxy-2,10-disulfidooctahydro-12H-5,8-methanofuro[3,2-l][1,3,9,11,6,2,10]tetraoxathiadiphosphacyclotetra-decin-7-yl]-3,6-dihydro-7H41,2,3]triazolo[4,5-d]pyrimidin-7-one (Diastereomer 1) | 726 |

TABLE 6-continued

| Ex. | Structure | Name | Mass [M − H]⁻ |
|---|---|---|---|
| 222 | 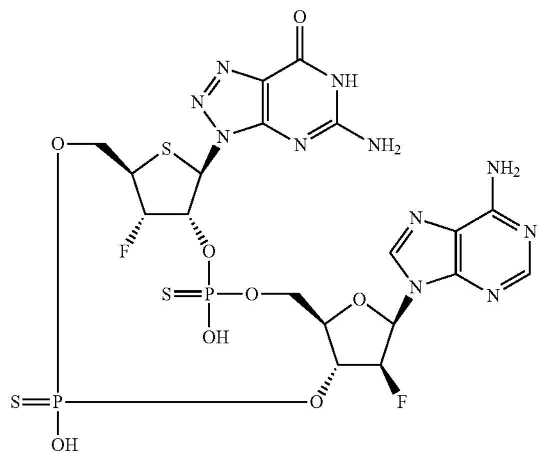 [SMILES: Nc1nc2c(nnn2[C@@H]2S[C@@H]3COP(O)(=S)O[C@H]4[C@H](F)[C@H](n5cnc6c(N)ncnc65)O[C@@H]4COP(O)(=S)O[C@@H]2[C@@H]3F)c(=O)[nH]1] | 5-amino-3-[(5R,7R,8R,12aR,14R,15S,15aR,16S)-14-(6-amino-9H-purin-9-yl)-15,16-difluoro-2,10-dihydroxy-2,10-disulfidooctahydro-12H-5,8-methanofuro[3,2-l][1,3,9,11,6,2,10]tetraoxathiadiphosphacyclotetradecin-7-yl]-3,6-dihydro-7H-[1,2,3]triazolo[4,5-d]pyrimidin-7-one (Diastereomer 2) | 726 |
| 223 | 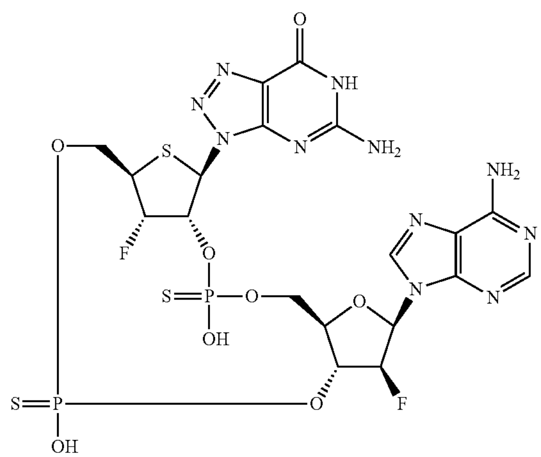 [SMILES: Nc1nc2c(nnn2[C@@H]2S[C@@H]3COP(O)(=S)O[C@H]4[C@H](F)[C@H](n5cnc6c(N)ncnc65)O[C@@H]4COP(O)(=S)O[C@@H]2[C@@H]3F)c(=O)[nH]1] | 5-amino-3-[(5R,7R,8R,12aR,14R,15S,15aR,16S)-14-(6-amino-9H-purin-9-yl)-15,16-difluoro-2,10-dihydroxy-2,10-disulfidooctahydro-12H-5,8-methanofuro[3,2-l][1,3,9,11,6,2,10]tetraoxathiadiphosphacyclotetradecin-7-yl]-3,6-dihydro-7H-[1,2,3]triazolo[4,5-d]pyrimidin-7-one (Diastereomer 3) | 726 |
| 224 | 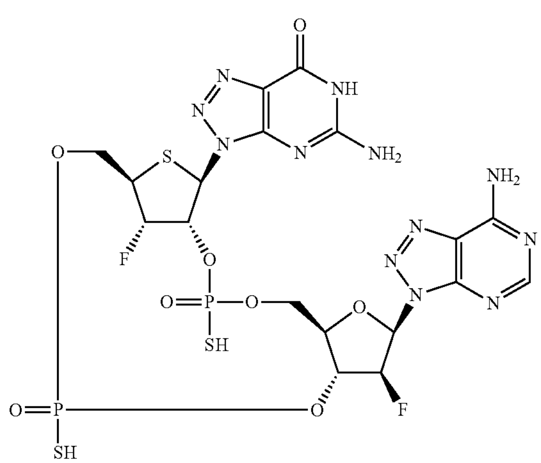 [SMILES: Nc1nc2c(nnn2[C@@H]2S[C@@H]3COP(=O)(S)O[C@H]4[C@H](F)[C@H](n5nnc6c(N)ncnc65)O[C@@H]4COP(=O)(S)O[C@@H]2[C@@H]3F)c(=O)[nH]1] | 5-amino-3-[(5R,7R,8R,12aR,14R,15S,15aR,16S)-14-(7-amino-3H-[1,2,3]triazolo[4,5-d]pyrimidin-3-yl)-15,16-difluoro-2,10-dioxido-2,10-disulfanyloctahydro-12H-5,8-methanofuro[3,2-l][1,3,9,11,6,2,10]tetraoxathi adiphosphacyclotetradecin-7-yl]-3,6-dihydro-7H-[1,2,3]triazolo[4,5-d]pyrimidin-7-one (Diastereomer 1) | 727 |

TABLE 6-continued

| Ex. | Structure | Name | Mass [M − H]⁻ |
|---|---|---|---|
| 225 | 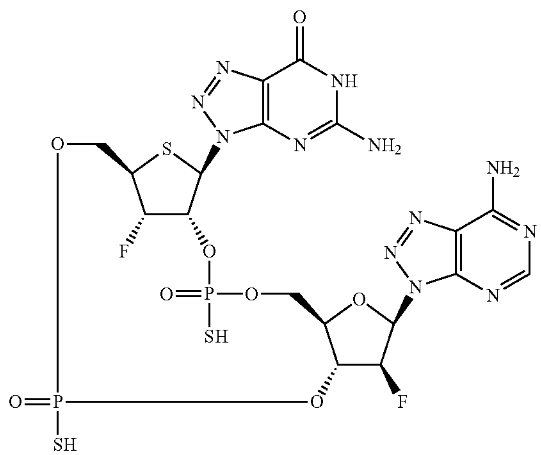 [SMILES: Nc1nc2c(nnn2[C@@H]2S[C@@H]3COP(=O)(S)O[C@H]4[C@H](F)[C@H](n5nnc6c(N)ncnc65)O[C@@H]4COP(=O)(S)O[C@@H]2[C@@H]3F)c(=O)[nH]1] | 5-amino-3-[(5R,7R,8R,12aR,14R,15S,15aR,16S)-14-(7-amino-3H-[1,2,3]triazolo[4,5-d]pyrimidin-3-yl)-15,16-difluoro-2,10-dioxido-2,10-disulfanyloctahydro-12H-5,8-methanofuro[3,2-l][1,3,9,11,6,2,10]tetraoxathiadiphosphacyclotetradecin-7-yl]-3,6-dihydro-7H-[1,2,3]triazolo[4,5-d]pyrimidin-7-one (Diastereomer 2) | 727 |
| 226 | 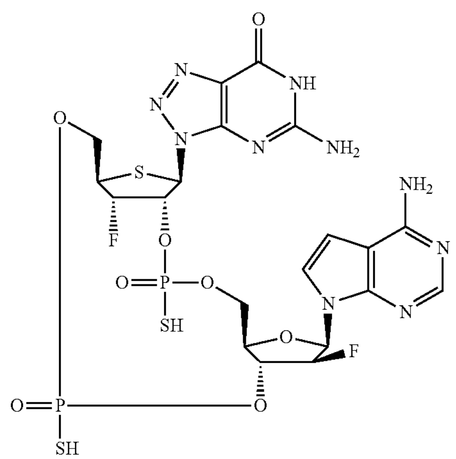 [SMILES: Nc1nc2c(nnn2[C@@H]2S[C@@H]3COP(=O)(S)O[C@H]4[C@H](F)[C@H](n5ccc6c(N)ncnc65)O[C@@H]4COP(=O)(S)O[C@@H]2[C@@H]3F)c(=O)[nH]1] | 5-amino-3-[(5R,7R,8R,12aR,14R,15S,15aR,16S)-14-(4-amino-7H-pyrrolo[2,3-d]pyrimidin-7-yl)-15,16-difluoro-2,10-dioxido-2,10-disulfanyloctahydro-12H-5,8-methanofuro[3,2-l][1,3,9,11,6,2,10]tetraoxathiadiphosphacyclotetradecin-7-yl]-3,6-dihydro-7H-[1,2,3]triazolo[4,5-d]pyrimidin-7-one (Diastereomer 1) | 725 |
| 227 | 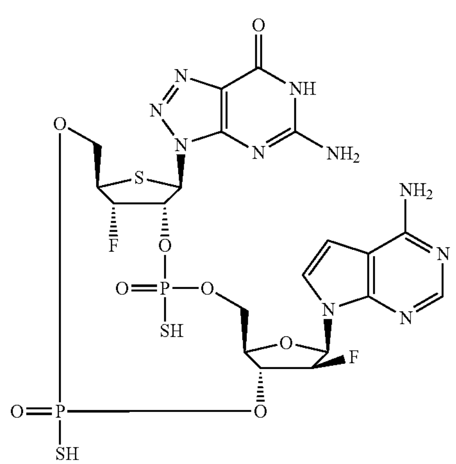 [SMILES: Nc1nc2c(nnn2[C@@H]2S[C@@H]3COP(=O)(S)O[C@H]4[C@H](F)[C@H](n5ccc6c(N)ncnc65)O[C@@H]4COP(=O)(S)O[C@@H]2[C@@H]3F)c(=O)[nH]1] | 5-amino-3-[(5R,7R,8R,12aR,14R,15S,15aR,16S)-14-(4-amino-7H-pyrrolo[2,3-d]pyrimidin-7-yl)-15,16-difluoro-2,10-dioxido-2,10-disulfanyloctahydro-12H-5,8-methanofuro[3,2-l][1,3,9,11,6,2,10]tetraoxathiadiphosphacyclotetradecin-7-yl]-3,6-dihydro-7H-[1,2,3]triazolo[4,5-d]pyrimidin-7-one (Diastereomer 2) | 725 |

TABLE 6-continued

| Ex. | Structure | Name | Mass [M − H]⁻ |
|---|---|---|---|
| 228 | 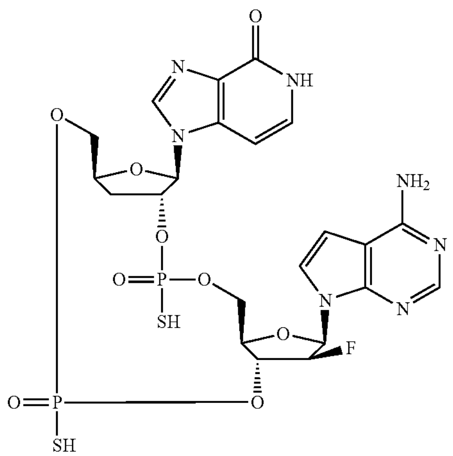 [SMILES: Nc1ncnc2c1ccn2[C@@H]1O[C@@H]2COP(=O)(S)O[C@@H]3C[C@@H](COP(=O)(S)O[C@H]2[C@@H]1F)O[C@H]3n1cnc2c(=O)[nH]ccc21] | 1-[(5S,7R,8R,12aR,14R,15S,15aR)-14-(4-amino-7H-pyrrolo[2,3-d]pyrimidin-7-yl)-15-fluoro-2,10-dioxido-2,10-disulfanyloctahydro-12H-5,8-methanofuro[3,2-l][1,3,6,9,11,2,10]pentaoxadiphosphacyclotetradecin-7-yl]-1,5-dihydro-4H-imidazo[4,5-c]pyridin-4-one | 674 |
| 229 | 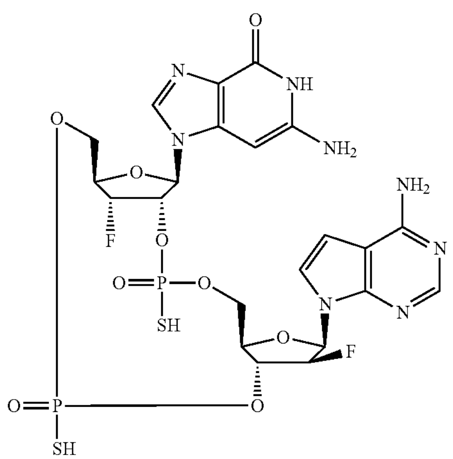 [SMILES: Nc1cc2c(ncn2[C@@H]2O[C@@H]3COP(=O)(S)O[C@H]4[C@H](F)[C@H](n5ccc6c(N)ncnc65)O[C@@H]4COP(=O)(S)O[C@@H]2[C@@H]3F)c(=O)[nH]1] | 6-amino-1-[(5R,7R,8S,12aR,14R,15S,15aR,16R)-14-(4-amino-7H-pyrrolo[2,3-d]pyrimidin-7-yl)-15,16-difluoro-2,10-dioxido-2,10-disulfanyloctahydro-12H-5,8-methanofuro[3,2-l][1,3,6,9,11,2,10]pentaoxadiphosphacyclotetradecin-7-yl]-1,5-dihydro-4H-imidazo[4,5-c]pyridin-4-one (Diastereomer 1) | 707 |
| 230 | 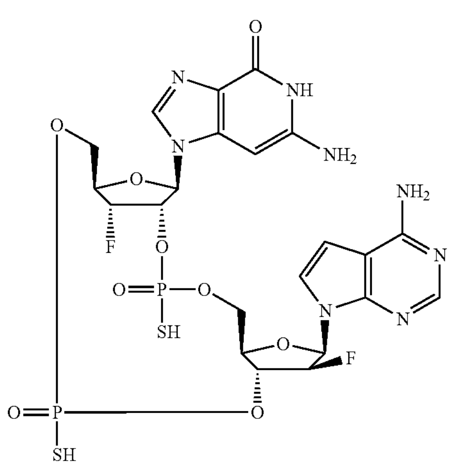 [SMILES: Nc1cc2c(ncn2[C@@H]2O[C@@H]3COP(=O)(S)O[C@H]4[C@H](F)[C@H](n5ccc6c(N)ncnc65)O[C@@H]4COP(=O)(S)O[C@@H]2[C@@H]3F)c(=O)[nH]1] | 6-amino-1-[(5R,7R,8S,12aR,14R,15S,15aR,16R)-14-(4-amino-7H-pyrrolo[2,3-d]pyrimidin-7-yl)-15,16-difluoro-2,10-dioxido-2,10-disulfanyloctahydro-12H-5,8-methanofuro[3,2-l][1,3,6,9,11,2,10]pentaoxadiphosphacyclotetradecin-7-yl]-1,5-dihydro-4H-imidazo[4,5-c]pyridin-4-one (Diastereomer 2) | 707 |

TABLE 6-continued

| Ex. | Structure | Name | Mass [M − H]⁻ |
|---|---|---|---|
| 231 | 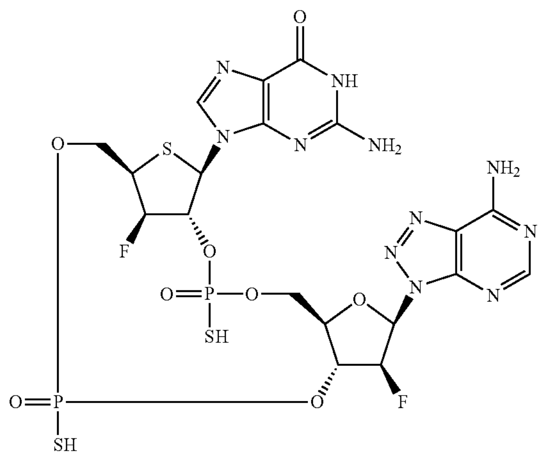 [SMILES: Nc1nc2c(ncn2[C@@H]2S[C@@H]3COP(=O)(S)O[C@H]4[C@H](F)[C@H](n5nnc6c(N)ncnc65)O[C@@H]4COP(=O)(S)O[C@@H]2[C@H]3F)c(=O)[nH]1] | 2-amino-9-[(5R,7R,8R,12aR,14R,15S,15aR,16R)-14-(7-amino-3H-[1,2,3]triazolo[4,5-d]pyrimidin-3-yl)-15,16-difluoro-2,10-dioxido-2,10-disulfanyloctahydro-12H-5,8-methanofuro[3,2-l][1,3,9,11,6,2,10]tetraoxathiadiphosphacyclotetradecin-7-yl]-1,9-dihydro-6H-purin-6-one (Diastereomer 1) | 726 |
| 232 | 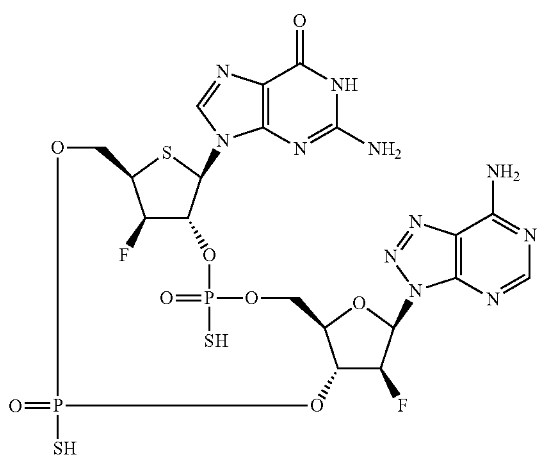 [SMILES: Nc1nc2c(ncn2[C@@H]2S[C@@H]3COP(=O)(S)O[C@H]4[C@H](F)[C@H](n5nnc6c(N)ncnc65)O[C@@H]4COP(=O)(S)O[C@@H]2[C@H]3F)c(=O)[nH]1] | 2-amino-9-[(5R,7R,8R,12aR,14R,15S,15aR,16R)-14-(7-amino-3H-[1,2,3]triazolo[4,5-d]pyrimidin-3-yl)-15,16-difluoro-2,10-dioxido-2,10-disulfanyloctahydro-12H-5,8-methanofuro[3,2-l][1,3,9,11,6,2,10]tetraoxathiadiphosphacyclotetradecin-7-yl]-1,9-dihydro-6H-purin-6-one (Diastereomer 2) | 726 |
| 233 | 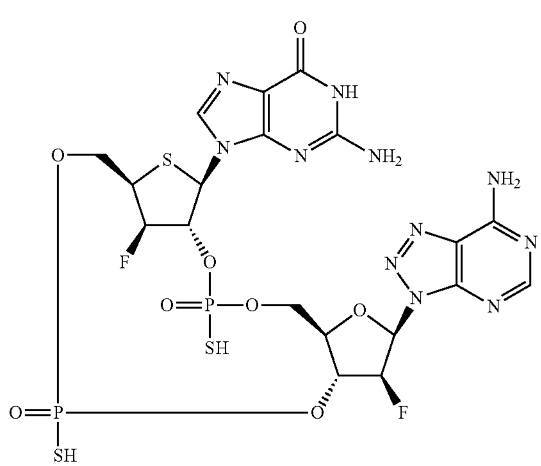 [SMILES: Nc1nc2c(ncn2[C@@H]2S[C@@H]3COP(=O)(S)O[C@H]4[C@H](F)[C@H](n5nnc6c(N)ncnc65)O[C@@H]4COP(=O)(S)O[C@@H]2[C@H]3F)c(=O)[nH]1] | 2-amino-9-[(5R,7R,8R,12aR,14R,15S,15aR,16R)-14-(7-amino-3H-[1,2,3]triazolo[4,5-d]pyrimidin-3-yl)-15,16-difluoro-2,10-dioxido-2,10-disulfanyloctahydro-12H-5,8-methanofuro[3,2-l][1,3,9,11,6,2,10]tetraoxathiadiphosphacyclotetradecin-7-yl]-1,9-dihydro-6H-purin-6-one (Diastereomer 3) | 726 |

TABLE 6-continued

| Ex. | Structure | Name | Mass [M − H]⁻ |
|---|---|---|---|
| 234 | 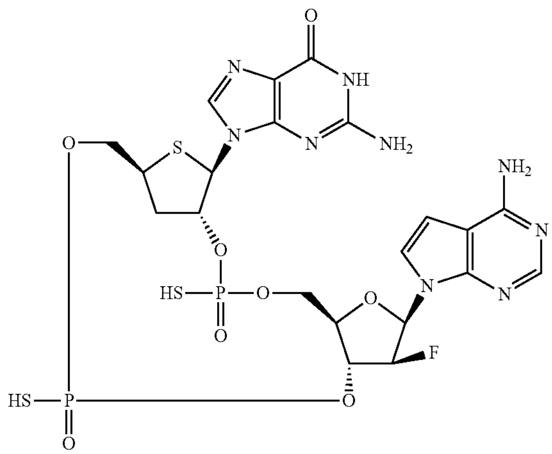 [SMILES: Nc1nc2c(ncn2[C@@H]2S[C@@H]3COP(=O)(S)O[C@H]4[C@H](F)[C@H](n5ccc6c(N)ncnc65)O[C@@H]4COP(=O)(S)O[C@@H]2C3)c(=O)[nH]1] | 2-amino-9-[(5S,7R,8R,12aR,14R,15S,15aR)-14-(4-amino-7H-pyrrolo[2,3-d]pyrimidin-7-yl)-15-fluoro-2,10-dioxido-2,10-disulfanyloctahydro-12H-5,8-methanofuro[3,2-l][1,3,9,11,6,2,10]tetraoxathiadiphosphacyclotetradecin-7-yl]-1,9-dihydro-6H-purin-6-one | 706 |
| 235 | 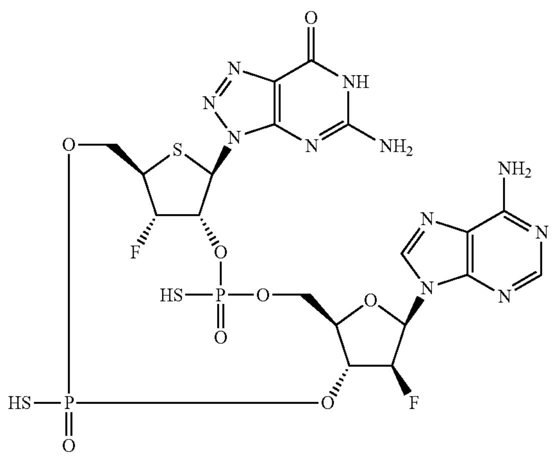 [SMILES: Nc1nc2c(nnn2[C@@H]2S[C@@H]3COP(=O)(S)O[C@H]4[C@H](F)[C@H](n5cnc6c(N)ncnc65)O[C@@H]4COP(=O)(S)O[C@@H]2[C@@H]3F)c(=O)[nH]1] | 5-amino-3-[(5R,7R,8R,12aR,14R,15S,15aR,16S)-14-(6-amino-9H-purin-9-yl)-15,16-difluoro-2,10-dioxido-2,10-disulfanyloctahydro-12H-5,8-methanofuro[3,2-l][1,3,9,11,6,2,10]tetraoxathiadiphosphacyclodecin-7-yl]-3,6-dihydro-7H-[1,2,3]triazolo[4,5-d]pyrimidin-7-one | 726 |
| 236 | 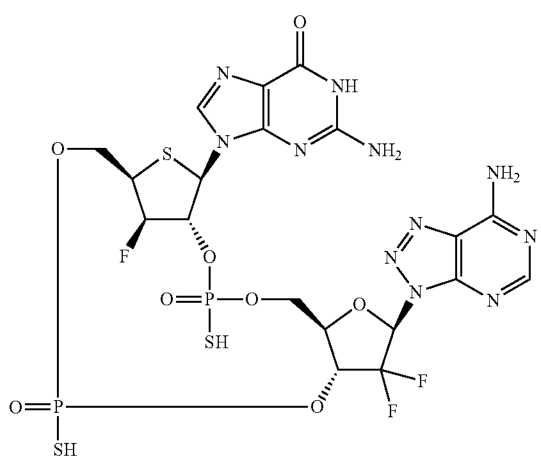 [SMILES: Nc1nc2c(ncn2[C@@H]2S[C@@H]3COP(=O)(S)O[C@@H]4[C@@H](COP(=O)(S)O[C@@H]2[C@H]3F)O[C@@H](n2nnc3c(N)ncnc32)C4(F)F)c(=O)[nH]1] | 2-amino-9-[(5R,7R,8R,12aR,14R,15aR,16R)-14-(7-amino-3H-[1,2,3]triazolo[4,5-d]pyrimidin-3-yl)-15,15,16-trifluoro-2,10-dioxido-2,10-disulfanyloctahydro-12H-5,8-methanofuro[3,2-l][1,3,9,11,6,2,10]tetraoxathiadiphosphacyclotetradecin-7-yl]-1,9-dihydro-6H-purin-6-one (Diastereomer 1) | 744 |

TABLE 6-continued

| Ex. | Structure | Name | Mass [M − H]⁻ |
|---|---|---|---|
| 237 | 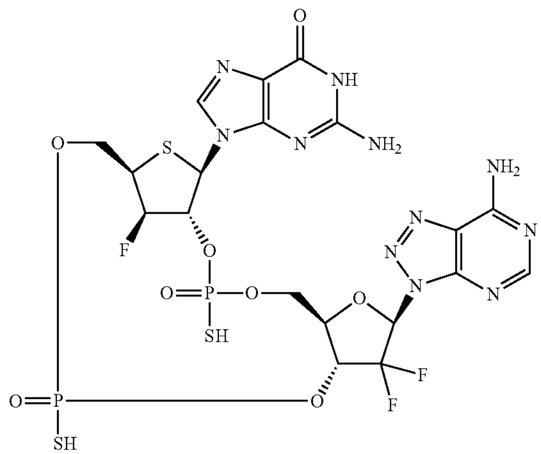 [SMILES: Nc1nc2c(ncn2[C@@H]2S[C@@H]3COP(=O)(S)O[C@@H]4[C@@H](COP(=O)(S)O[C@@H]2[C@H]3F)O[C@@H](n2nnc3c(N)ncnc32)C4(F)F)c(=O)[nH]1] | 2-amino-9-[(5R,7R,8R,12aR,14R,15aR,16R)-14-(7-amino-3H-[1,2,3]triazolo[4,5-d]pyrimidin-3-yl)-15,15,16-trifluoro-2,10-dioxido-2,10-disulfanyloctahydro-12H-5,8-methanofuro[3,2-l][1,3,9,11,6,2,10]tetraoxathiadiphosphacyclotetradecin-7-yl]-1,9-dihydro-6H-purin-6-one (Diastereomer 2) | 744 |
| 238 | 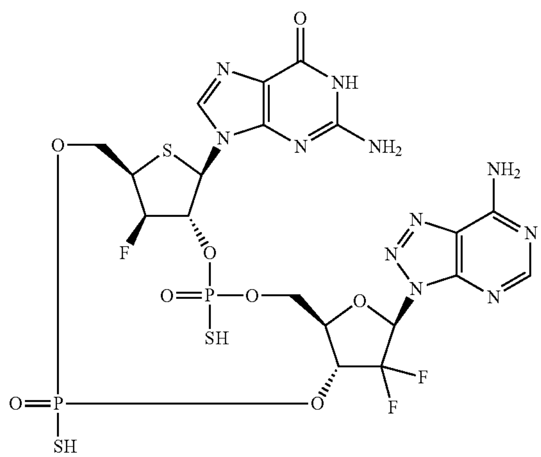 [SMILES: Nc1nc2c(ncn2[C@@H]2S[C@@H]3COP(=O)(S)O[C@@H]4[C@@H](COP(=O)(S)O[C@@H]2[C@H]3F)O[C@@H](n2nnc3c(N)ncnc32)C4(F)F)c(=O)[nH]1] | 2-amino-9-[(5R,7R,8R,12aR,14R,15aR,16R)-14-(7-amino-3H-[1,2,3]triazolo[4,5-d]pyrimidin-3-yl)-15,15,16-trifluoro-2,10-dioxido-2,10-disulfanyloctahydro-12H-5,8-methanofuro[3,2-l][1,3,9,11,6,2,10]tetraoxathiadiphosphacyclotetradecin-7-yl]-1,9-dihydro-6H-purin-6-one (Diastereomer 3) | 744 |
| 239 | 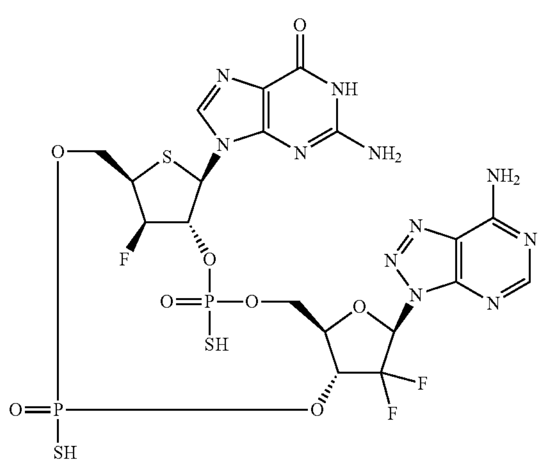 [SMILES: Nc1nc2c(ncn2[C@@H]2S[C@@H]3COP(=O)(S)O[C@@H]4[C@@H](COP(=O)(S)O[C@@H]2[C@H]3F)O[C@@H](n2nnc3c(N)ncnc32)C4(F)F)c(=O)[nH]1] | 2-amino-9-[(5R,7R,8R,12aR,14R,15aR,16R)-14-(7-amino-3H-[1,2,3]triazolo[4,5-d]pyrimidin-3-yl)-15,15,16-trifluoro-2,10-dioxido-2,10-disulfanyloctahydro-12H-5,8-methanofuro[3,2-l][1,3,9,11,6,2,10]tetraoxathiadiphosphacyclotetradecin-7-yl]-1,9-dihydro-6H-purin-6-one (Diastereomer 4) | 744 |

TABLE 6-continued

| Ex. | Structure | Name | Mass [M − H]⁻ |
|---|---|---|---|
| 240 | 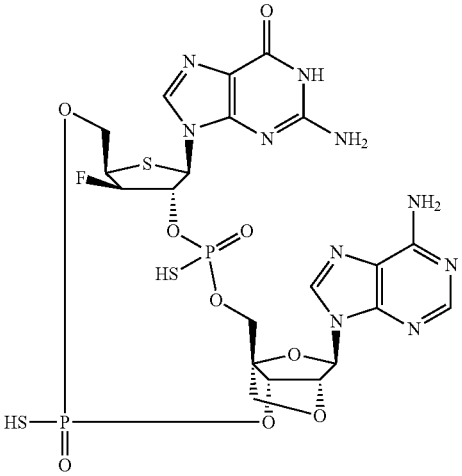 [SMILES: Nc1nc2c(ncn2[C@@H]2S[C@@H]3COP(=O)(S)O[C@H]4[C@H]5OC[C@]4(COP(=O)(S)O[C@@H]2[C@H]3F)O[C@H]5n2cnc3c(N)ncnc32)c(=O)[nH]1] | 2-amino-9-[(5R,7R,8R,12aR,14R,15R,15aS,18R)-14-(6-amino-9H-purin-9-yl)-18-fluoro-2,10-dioxido-2,10-disulfanylhexahydro-14H-15,12a-(epoxymethano)-5,8-methanofuro[3,2-l][1,3,9,11,6,2,10]tetraoxathiadiphosphacyclotetra-decin-7(12H)-yl]-1,9-dihydro-6H-purin-6-one (Diastereomer 1) | 735 |
| 241 | 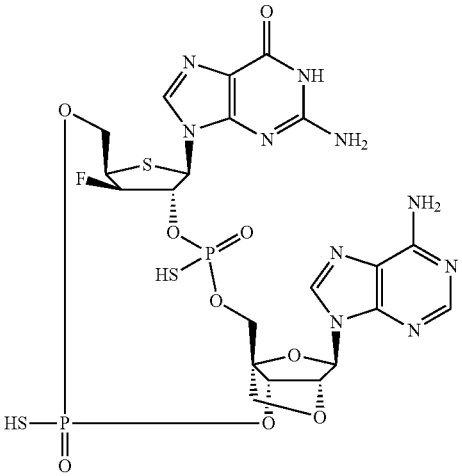 [SMILES: Nc1nc2c(ncn2[C@@H]2S[C@@H]3COP(=O)(S)O[C@H]4[C@H]5OC[C@]4(COP(=O)(S)O[C@@H]2[C@H]3F)O[C@H]5n2cnc3c(N)ncnc32)c(=O)[nH]1] | 2-amino-9-[(5R,7R,8R,12aR,14R,15R,15aS,18R)-14-(6-amino-9H-purin-9-yl)-18-fluoro-2,10-dioxido-2,10-disulfanylhexahydro-14H-15,12a-(epoxymethano)-5,8-methanofuro[3,2-l][1,3,9,11,6,2,10]tetraoxathiadiphosphacyclotetra-decin-7(12H)-yl]-1,9-dihydro-6H-purin-6-one (Diastereomer 2) | 735 |

TABLE 6-continued

| Ex. | Structure | Name | Mass [M − H]⁻ |
|---|---|---|---|
| 242 | 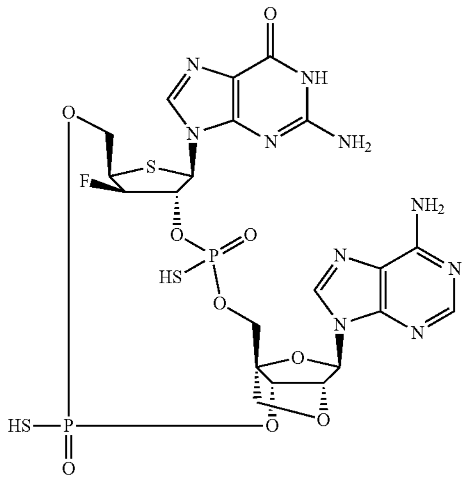 [SMILES: Nc1nc2c(ncn2[C@@H]2S[C@@H]3COP(=O)(S)O[C@H]4[C@H]5OC[C@]4(COP(=O)(S)O[C@@H]2[C@H]3F)O[C@H]5n2cnc3c(N)ncnc32)c(=O)[nH]1] | 2-amino-9-[(5R,7R,8R,12aR,14R,15R,15aS,18R)-14-(6-amino-9H-purin-9-yl)-18-fluoro-2,10-dioxido-2,10-disulfanylhexahydro-14H-15,12a-(epoxymethano)-5,8-methanofuro[3,2-l][1,3,9,11,6,2,10]tetraoxathiadiphosphacyclotetradecin-7(12H)-yl]-1,9-dihydro-6H-purin-6-one (Diastereomer 3) | 735 |
| 243 | 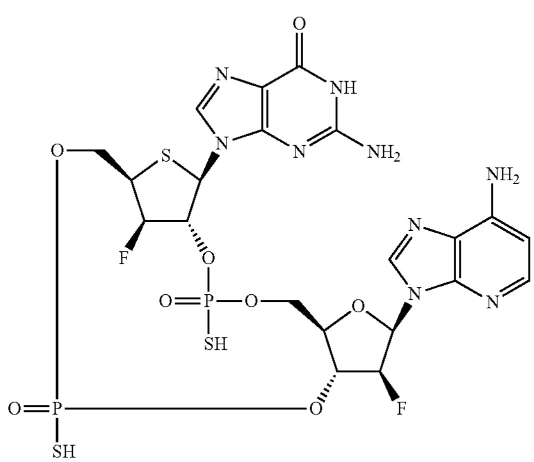 [SMILES: Nc1nc2c(ncn2[C@@H]2S[C@@H]3COP(=O)(S)O[C@H]4[C@H](F)[C@H](n5cnc6c(N)ccnc65)O[C@@H]4COP(=O)(S)O[C@@H]2[C@H]3F)c(=O)[nH]1] | 2-amino-9-[(5R,7R,8R,12aR,14R,15S,15aR,16R)-14-(7-amino-3H-imidazo[4,5-b]pyridin-3-yl)-15,16-difluoro-2,10-dioxido-2,10-disulfanyloctahydro-12H-5,8-methanofuro[3,2-l][1,3,9,11,6,2,10]tetraoxathiadiphosphacyclotetradecin-7-yl]-1,9-dihydro-6H-purin-6-one | 724 |

Examples 244, 245, 246, and 247: 2-amino-9-[(5R,7R,8S,12aR,14R,15S,15aR,16R)-14-(6-amino-9H-purin-9-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomers 1-3) and 2-amino-9-[(2R,5R,7R,8S,10R,12aR,14R,15S,15aR,16R)-14-(6-amino-9H-purin-9-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 4)

Diastereomer 1

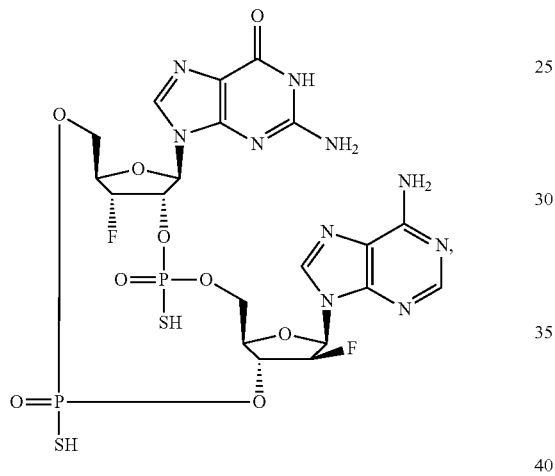

Diastereomer 2

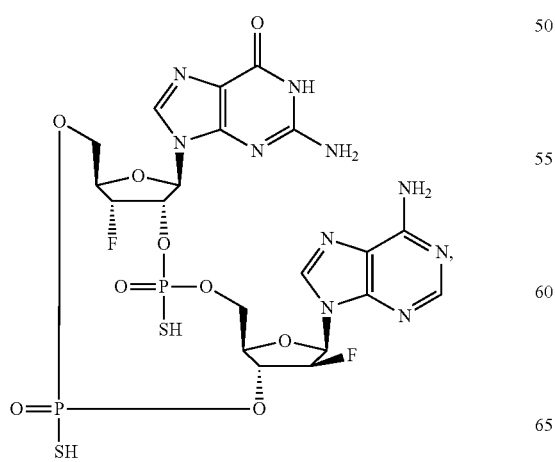

-continued

Diastereomer 3

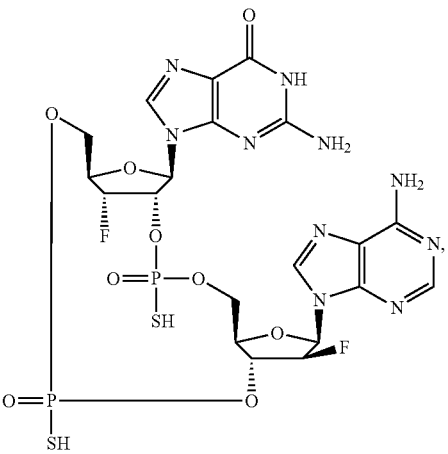

Diastereomer 4

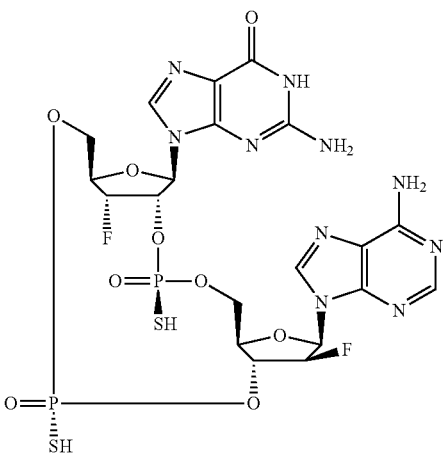

Step 1. (2R,3S,4R,5R)-5-(((((2R,3R,4S,5R)-5-(6-benzamido-9H-purin-9-yl)-2-((bis(4-methoxyphenyl)(phenyl)methoxy)methyl)-4-fluorotetrahydrofuran-3-yl)oxy)(2-cyanoethoxy)phosphanyl)oxy)methyl)-4-fluoro-2-(2-isobutyramido-6-oxo-1,6-dihydro-9H-purin-9-yl)tetrahydrofuran-3-yl hydrogen phosphonate

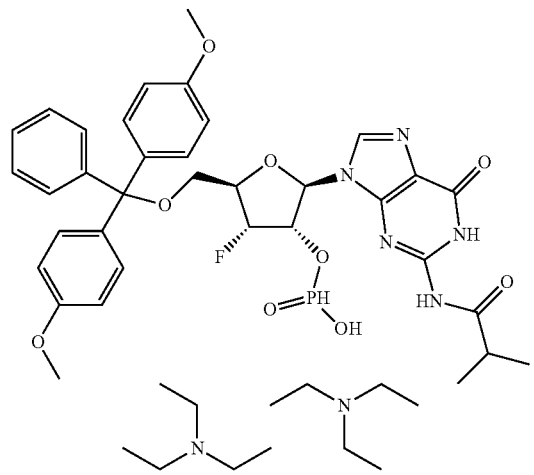
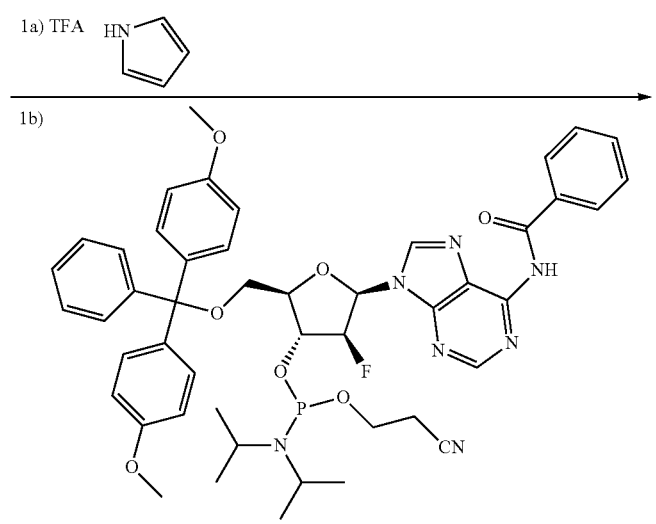
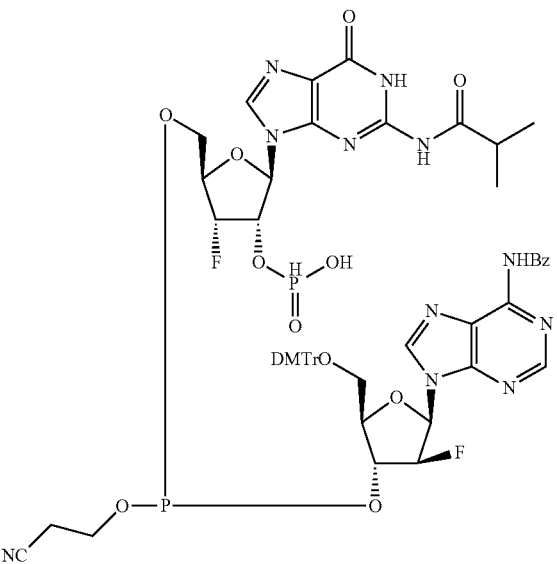

Pyrrole (0.087 mL, 1.2 mmol) was added to a solution of (2R,3S,4R,5R)-5-((bis(4-methoxyphenyl)(phenyl)methoxy)methyl)-4-fluoro-2-(2-isobutyramido-6-oxo-1,6-dihydro-9H-purin-9-yl)tetrahydrofuran-3-yl hydrogen phosphonate triethylamine salt (1:2) (0.34 g, 0.41 mmol) in acetonitrile (3.0 mL) under an argon atmosphere at 0° C. After 5 min, TFA (0.096 mL, 0.14 mmol) was added, and the reaction mixture was stirred at 0° C. for 30 min. Pyridine (0.13 mL, 1.7 mmol) was added drop wise at 0° C. The reaction mixture was then stirred for 10 min at 0° C. At that time, a mixture of (2R,3R,4S,5R)-5-(6-benzamido-9H-purin-9-yl)-2-((bis(4-methoxyphenyl)(phenyl)methoxy)methyl)-4-fluorotetrahydrofuran-3-yl (2-cyanoethyl) diisopropylphosphoramidite (0.48 g, 0.55 mmol) in acetonitrile (3.0 mL) was added drop wise over 5 min to the reaction mixture under an argon atmosphere at 0° C. The reaction mixture was stirred at 0° C. for 20 min and immediately used in the next step without further manipulation.

Step 2. (2R,3S,4R,5R)-5-((((((2R,3R,4S,5R)-5-(6-benzamido-9H-purin-9-yl)-4-fluoro-2-(hydroxymethyl)tetrahydrofuran-3-yl)oxy)(2-cyanoethoxy)phosphorothioyl)oxy)methyl)-4-fluoro-2-(2-isobutyramido-6-oxo-1,6-dihydro-9H-purin-9-yl)tetrahydrofuran-3-yl hydrogen phosphonate

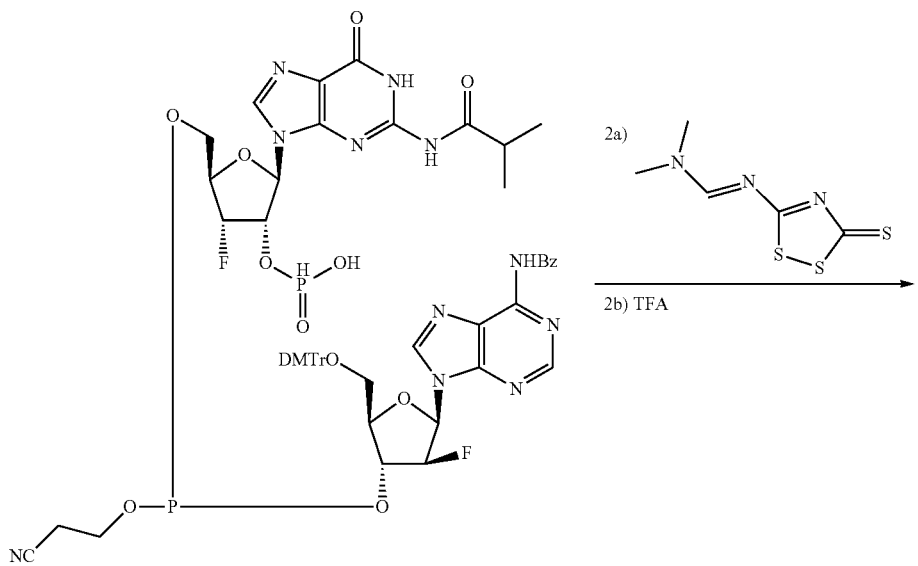

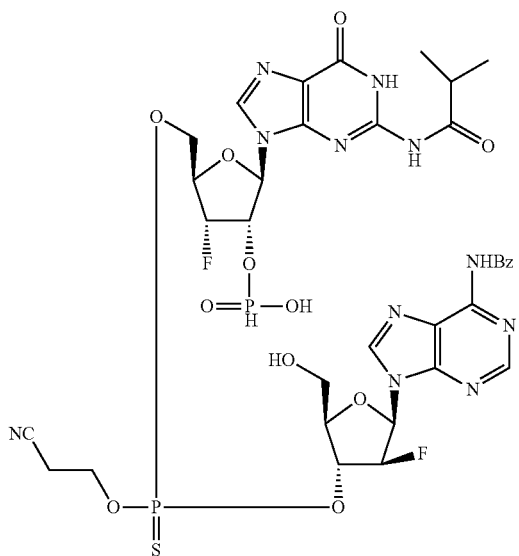

To the crude reaction mixture from Step 1 was added (E)-N,N-dimethyl-N'-(3-thioxo-3H-1,2,4-dithiazol-5-yl)formimidamide (0.10 g, 0.50 mmol) under an argon atmosphere at 0° C. The reaction mixture was stirred for 45 minutes at 0° C. At that time, 1-propanol (0.31 mL, 4.13 mmol) was added to the reaction mixture under an argon atmosphere at 0° C. The reaction mixture was then allowed to warm to ambient temperature and stirred for 10 min. TFA (0.32 mL, 4.1 mmol) was added to the reaction mixture, and the reaction mixture was stirred for 30 min at ambient temperature. Pyridine (0.37 mL, 4.6 mmol) was added at ambient temperature, and the reaction mixture was stirred for 10 min. The reaction mixture was concentrated under reduced pressure to approximately one-half volume. The mixture was then diluted with isopropyl acetate (20 mL) and stirred for 30 min at ambient temperature. The resulting suspension was filtered. The collected solids were dried overnight under high vacuum to afford (2R,3 S,4R,5R)-5-((((((2R,3R,4S,5R)-5-(6-benzamido-9H-purin-9-yl)-4-fluoro-2-(hydroxymethyl)tetrahydrofuran-3-yl)oxy)(2-cyanoethoxy)phosphorothioyl)oxy)methyl)-4-fluoro-2-(2-isobutyramido-6-oxo-1,6-dihydro-9H-purin-9-yl)tetrahydrofuran-3-yl hydrogen phosphonate. LCMS (ES, m/z): 922 [M−H]⁻.

Step 3: 2-amino-9-[(5R,7R,8S,12aR,14R,15S,15aR, 16R)-14-(6-amino-9H-purin-9-yl)-15,16-difluoro-2, 10-dihydroxy-2,10-disulfidooctahydro-12H-5,8-methanofuro[3,2-l][1,3,6,9,11,2,10] pentaoxadiphosphacyclotetradecin-7-yl]-1,9-dihydro-6H-purin-6-one

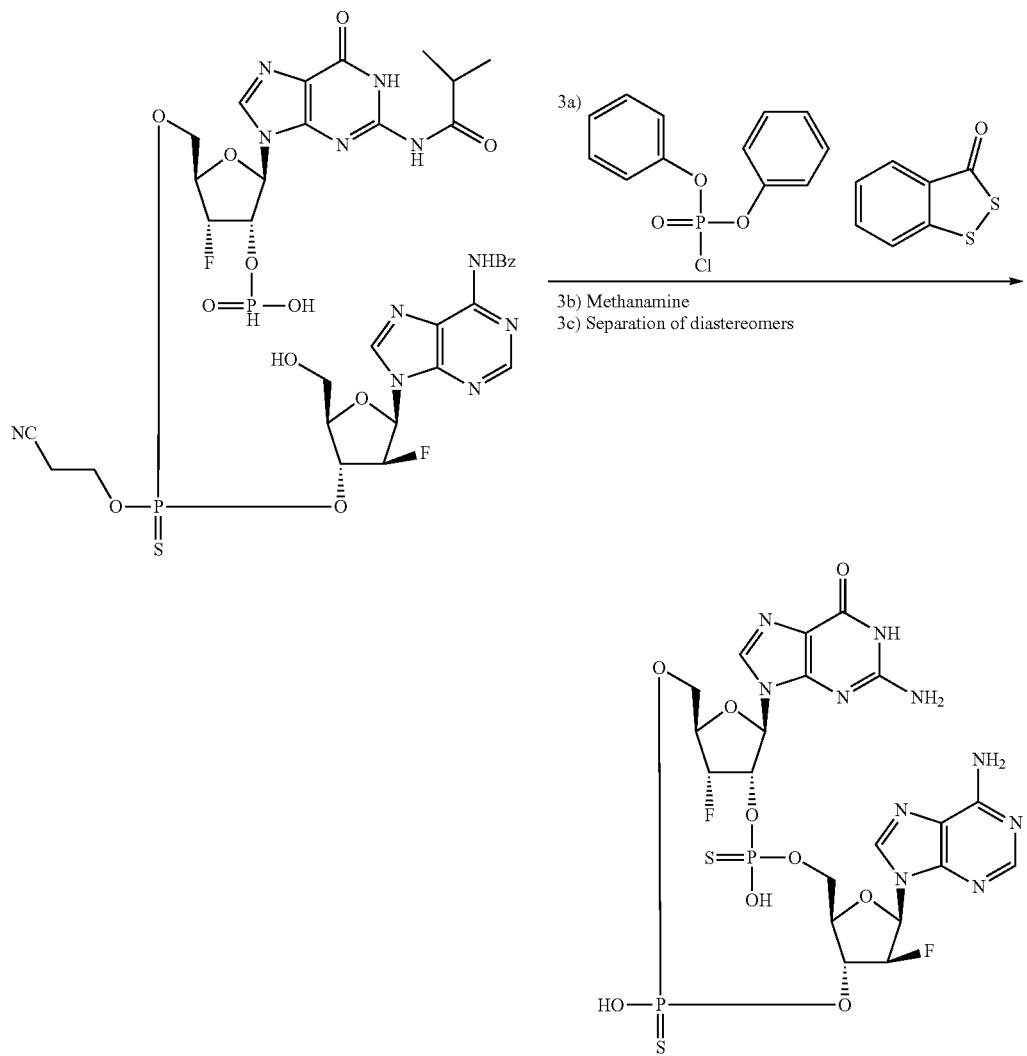

Diastereomers 1-4

(2R,3 S,4R,5R)-5-((((((2R,3R,4S,5R)-5-(6-benzamido-9H-purin-9-yl)-4-fluoro-2-(hydroxymethyl)tetrahydrofuran-3-yl)oxy)(2-cyanoethoxy)phosphorothioyl)oxy)methyl)-4-fluoro-2-(2-isobutyramido-6-oxo-1,6-dihydro-9H-purin-9-yl)tetrahydrofuran-3-yl hydrogen phosphonate (0.30 g, 0.33 mmol) was azeotroped with dry pyridine (2×10 mL) and then dried under high vacuum for 1 h. In a separate flask, diphenyl phosphorochloridate (0.34 mL, 1.6 mmol) was added to a mixture of acetonitrile (15 mL) and pyridine (1.0 mL). The resulting solution was then cooled to −20° C. To this mixture was added drop wise over a period of 5 min a mixture of (2R,3 S,4R,5R)-5-((((((2R,3R,4S,5R)-5-(6-benzamido-9H-purin-9-yl)-4-fluoro-2-(hydroxymethyl)tetrahydrofuran-3-yl)oxy)(2-cyanoethoxy)phosphorothioyl)oxy)methyl)-4-fluoro-2-(2-isobutyramido-6-oxo-1,6-dihydro-9H-purin-9-yl)tetrahydrofuran-3-yl hydrogen phosphonate (0.30 g, 0.33 mmol) in pyridine (4.0 mL) at −20° C. The reaction mixture was then stirred at −20° C. for 15 min post-addition. 3H-benzo[c][1,2]dithiol-3-one (0.066 g, 0.39 mmol) and water (0.12 mL, 6.5 mmol) were then added to the reaction mixture at −20° C. The reaction mixture was allowed to gradually warm to ambient temperature. The reaction mixture was stirred for 30 min at ambient temperature. The reaction mixture was then concentrated under reduced pressure to approximately one quarter volume. The reaction mixture was cooled to 0° C., and methanamine (33% in ethanol) (2.63 mL, 24 mmol) was added drop wise. After the addition was complete, the reaction mixture was allowed to warm to ambient temperature. The reaction mixture was stirred at ambient temperature for 18 h. The reaction mixture was concentrated under reduced pressure to afford the crude product residue. The crude product residue was azeotroped (3×30 mL ethanol) to afford the crude product. This material was dissolved in water (5 mL) and acetonitrile (1 mL). The resulting mixture was purified by mass-directed reverse phase HPLC (Waters Sunfire 19×250 mm, UV 215/254 nm, fraction trigger by SIM negative MS monitoring mass 709; mobile phase=100 mM triethylammonium acetate in water/acetonitrile gradient, 2-30% acetonitrile over 40 min) to afford the 4 diastereomers of 2-amino-9-[(5R,7R,8S,12aR,14R,15S,15aR,16R)-14-(6-amino-9H-purin-9-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one.

Example 244: 2-amino-9-[(5R,7R,8S,12aR,14R,15S,15aR,16R)-14-(6-amino-9H-purin-9-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1): $T_R$=17.7 min. LCMS (ES, m/z): 709 [M−H]⁻.

Example 245: 2-amino-9-[(5R,7R,8S,12aR,14R,15S,15aR,16R)-14-(6-amino-9H-purin-9-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2): $T_R$=21.9 min. LCMS (ES, m/z): 709 [M−H]⁻. 1H NMR (500 MHz, DMSO-$d_6$) δ 8.32 (s, 1H), 8.21-8.09 (m, 2H), 7.46-7.29 (m, 2H), 6.59-6.43 (m, 2H), 6.40-6.29 (m, 1H), 5.88 (d, J=8.8 Hz, 1H), 5.49-5.19 (m, 4H), 4.45-4.32 (m, 2H), 4.10-3.93 (m, 2H), 3.94-3.82 (m, 1H), 3.80-3.68 (m, 1H).

Example 246: 2-amino-9-[(5R,7R,8S,12aR,14R,15S,15aR,16R)-14-(6-amino-9H-purin-9-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 3): $T_R$=23.8 min. LCMS (ES, m/z): 709 [M−H]⁻. 1H NMR (500 MHz, DMSO-$d_6$) δ 8.18-8.08 (m, 3H), 7.41-7.33 (m, 2H), 6.59-6.47 (m, 2H), 6.37-6.27 (m, 1H), 5.84 (d, J=8.7 Hz, 1H), 5.52-5.26 (m, 2H), 5.21-5.11 (m, 1H), 4.46-4.35 (m, 2H), 4.19-4.02 (m, 2H), 3.83-3.65 (m, 2H).

Example 247: 2-amino-9-[(2R,5R,7R,8S,10R,12aR,14R,15S,15aR,16R)-14-(6-amino-9H-purin-9-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 4): $T_R$=26.4 min. LCMS (ES, m/z): 709 [M−H]⁻. 1H NMR (500 MHz, DMSO-$d_6$) δ 8.19-8.07 (m, 3H), 7.41-7.32 (m, 2H), 6.70-6.50 (m, 2H), 6.40-6.29 (m, 1H), 5.85 (d, J=8.7 Hz, 1H), 5.33-5.25 (m, 2H), 5.23-5.12 (m, 1H), 4.48-4.35 (m, 1H), 4.33-4.24 (m, 1H), 4.09-3.93 (m, 2H), 3.92-3.81 (m, 1H), 3.83-3.70 (m, 1H).

Examples 248 through 256, as shown in Table 7 below, were prepared according to procedures analogous to those outlined in Examples 244 through 247 above using the appropriate monomers, described as Preparations or as obtained from commercial sources, in the coupling step.

TABLE 7

| Ex. | Structure | Name | Mass [M − H]⁻ |
|---|---|---|---|
| 248 | 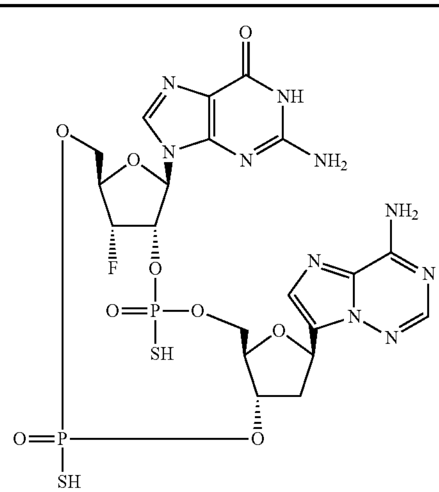 | 2-amino-9-[(5R,7R,8S,12aR,14R,15aS,16R)-14-(4-aminoimidazo[2,1-f][1,2,4]triazin-7-yl)-16-fluoro-2,10-dioxido-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 691 |

| Ex. | Structure | Name | Mass [M − H]⁻ |
|---|---|---|---|
| 249 | 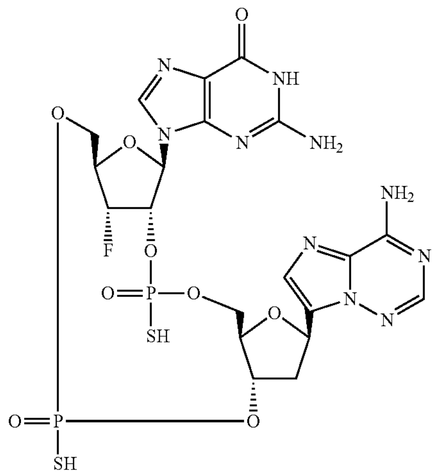 [SMILES: Nc1nc2c(ncn2[C@@H]2O[C@@H]3COP(=O)(S)O[C@H]4C[C@H](c5cnc6c(N)ncnn56)O[C@@H]4COP(=O)(S)O[C@@H]2[C@@H]3F)c(=O)[nH]1] | 2-amino-9-[(5R,7R,8S,12aR,14R,15aS,16R)-14-(4-aminoimidazo[2,1-f][1,2,4]triazin-7-yl)-16-fluoro-2,10-dioxido-2,10-disulfanyloctahydro-12H-5,8-methanofuro[3,2-1][1,3,6,9,11,2,10]pentaoxadiphosphacyclotetra-decin-7-yl]-1,9-dihydro-6H-purin-6-one (Diastereomer 2) | 691 |
| 250 | 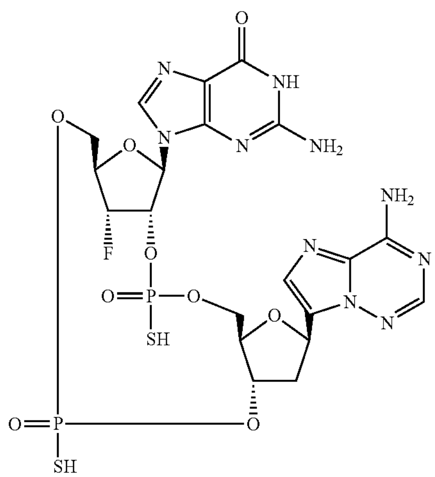 [SMILES: Nc1nc2c(ncn2[C@@H]2O[C@@H]3COP(=O)(S)O[C@H]4C[C@H](c5cnc6c(N)ncnn56)O[C@@H]4COP(=O)(S)O[C@@H]2[C@@H]3F)c(=O)[nH]1] | 2-amino-9-[(5R,7R,8S,12aR,14R,15aS,16R)-14-(4-aminoimidazo[2,1-f][1,2,4]triazin-7-yl)-16-fluoro-2,10-dioxido-2,10-disulfanyloctahydro-12H-5,8-methanofuro[3,2-1][1,3,6,9,11,2,10]pentaoxadiphosphacyclotetra-decin-7-yl]-1,9-dihydro-6H-purin-6-one (Diastereomer 3) | 691 |
| 251 | 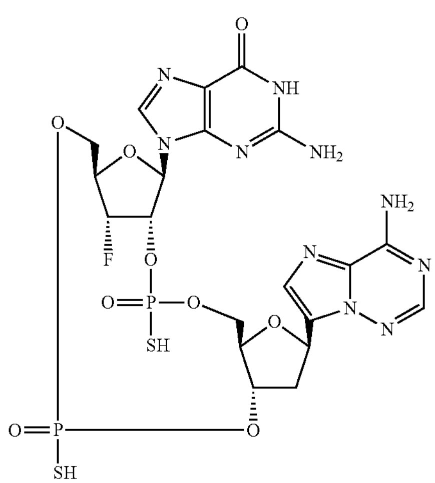 [SMILES: Nc1nc2c(ncn2[C@@H]2O[C@@H]3COP(=O)(S)O[C@H]4C[C@H](c5cnc6c(N)ncnn56)O[C@@H]4COP(=O)(S)O[C@@H]2[C@@H]3F)c(=O)[nH]1] | 2-amino-9-[(5R,7R,8S,12aR,14R,15aS,16R)-14-(4-aminoimidazo[2,1-f][1,2,4]triazin-7-yl)-16-fluoro-2,10-dioxido-2,10-disulfanyloctahydro-12H-5,8-methanofuro[3,2-1][1,3,6,9,11,2,10]pentaoxadiphosphacyclotetra-decin-7-yl]-1,9-dihydro-6H-purin-6-one (Diastereomer 4) | 691 |

TABLE 7-continued

| Ex. | Structure | Name | Mass [M − H]⁻ |
|---|---|---|---|
| 252 | 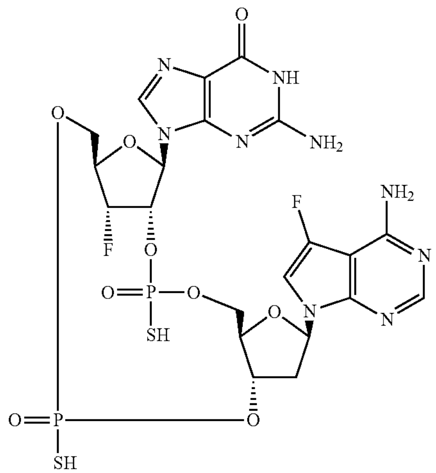 [SMILES: Nc1nc2c(ncn2[C@@H]2O[C@@H]3COP(=O)(S)O[C@H]4C[C@H](n5cc(F)c6c(N)ncnc65)O[C@@H]4COP(=O)(S)O[C@@H]2[C@@H]3F)c(=O)[nH]1] | 2-amino-9-[(5R,7R,8S,12aR,14R,15aS,16R)-14-(4-amino-5-fluoro-7H-pyrrolo[2,3-d]pyrimidin-7-yl)-16-fluoro-2,10-dioxido-2,10-disulfanyloctahydro-12H-5,8-methanofuro[3,2-1][1,3,6,9,11,2,10]pentaoxadiphosphacyclotetradecin-7-yl]-1,9-dihydro-6H-purin-6-one (Diastereomer 1) | 708 |
| 253 | 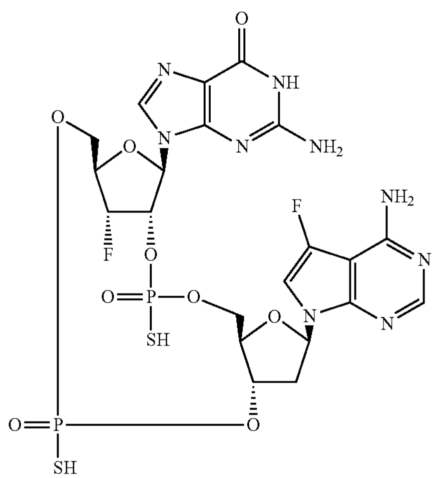 [SMILES: Nc1nc2c(ncn2[C@@H]2O[C@@H]3COP(=O)(S)O[C@H]4C[C@H](n5cc(F)c6c(N)ncnc65)O[C@@H]4COP(=O)(S)O[C@@H]2[C@@H]3F)c(=O)[nH]1] | 2-amino-9-[(5R,7R,8S,12aR,14R,15aS,16R)-14-(4-amino-5-fluoro-7H-pyrrolo[2,3-d]pyrimidin-7-yl)-16-fluoro-2,10-dioxido-2,10-disulfanyloctahydro-12H-5,8-methanofuro[3,2-1][1,3,6,9,11,2,10]pentaoxadiphosphacyclotetradecin-7-yl]-1,9-dihydro-6H-purin-6-one (Diastereomer 2) | 708 |
| 254 | 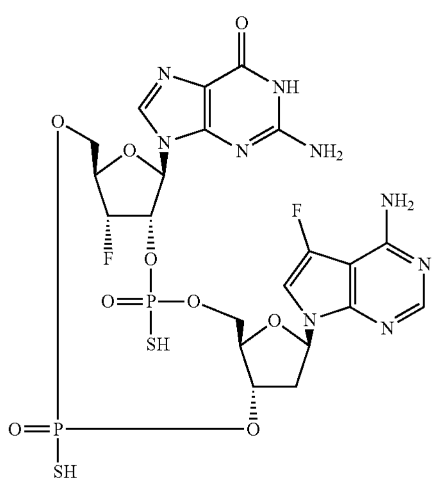 [SMILES: Nc1nc2c(ncn2[C@@H]2O[C@@H]3COP(=O)(S)O[C@H]4C[C@H](n5cc(F)c6c(N)ncnc65)O[C@@H]4COP(=O)(S)O[C@@H]2[C@@H]3F)c(=O)[nH]1] | 2-amino-9-[(5R,7R,8S,12aR,14R,15aS,16R)-14-(4-amino-5-fluoro-7H-pyrrolo[2,3-d]pyrimidin-7-yl)-16-fluoro-2,10-dioxido-2,10-disulfanyloctahydro-12H-5,8-methanofuro[3,2-1][1,3,6,9,11,2,10]pentaoxadiphosphacyclotetradecin-7-yl]-1,9-dihydro-6H-purin-6-one (Diastereomer 3) | 708 |

TABLE 7-continued

| Ex. | Structure | Name | Mass [M − H]⁻ |
|---|---|---|---|
| 255 | 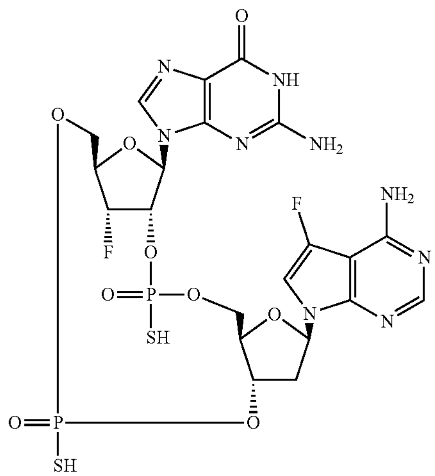 [SMILES: Nc1nc2c(ncn2[C@@H]2O[C@@H]3COP(=O)(S)O[C@H]4C[C@H](n5cc(F)c6c(N)ncnc65)O[C@@H]4COP(=O)(S)O[C@@H]2[C@@H]3F)c(=O)[nH]1] | 2-amino-9-[(5R,7R,8S,12aR,14R,15aS,16R)-14-(4-amino-5-fluoro-7H-pyrrolo[2,3-d]pyrimidin-7-yl)-16-fluoro-10-hydroxy-2,10-dioxido-2-sulfanyloctahydro-12H-5,8-methanofuro[3,2-l][1,3,6,9,11,2,10]pentaoxadiphosphacyclo-tetradecin-7-yl]-1,9-dihydro-6H-purin-6-one (Diastereomer 1) | 692 |
| 256 | 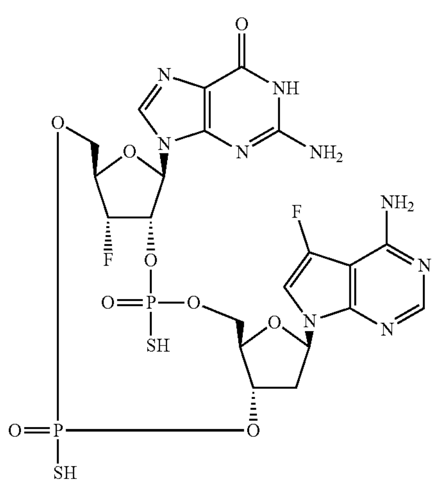 [SMILES: Nc1nc2c(ncn2[C@@H]2O[C@@H]3COP(=O)(S)O[C@H]4C[C@H](n5cc(F)c6c(N)ncnc65)O[C@@H]4COP(=O)(S)O[C@@H]2[C@@H]3F)c(=O)[nH]1] | 2-amino-9-[(5R,7R,8S,12aR,14R,15aS,16R)-14-(4-amino-5-fluoro-7H-pyrrolo[2,3-d]pyrimidin-7-yl)-16-fluoro-10-hydroxy-2,10-dioxido-2-sulfanyloctahydro-12H-5,8-methanofuro[3,2-l][1,3,6,9,11,2,10]pentaoxadiphosphacyclo-tetradecin-7-yl]-1,9-dihydro-6H-purin-6-one (Diastereomer 2) | 692 |

Examples 257 through 259 in Table 8 were made according to procedures analogous to those described above for Examples 244 through 247 using the appropriate monomeric nucleosides, described as Preparations or as obtained from commercial sources, with the following additional representative treatment as a final step: A sample (0.12 mmol) was dissolved in water (6 mL), and the resulting mixture was applied to ion exchange resin in a column (DOWEX 50WX2 hydrogen form, 100-200 mesh, 1.5 g, pre-washed with 10 mL water, and then packed in column before compound loading occurred). After loading mixture had completely absorbed to column, the column was then washed with additional water (10 mL). The eluent was lyophilized to afford product.

TABLE 8

| Ex. | Structure | Name | Mass [M − H]− |
|---|---|---|---|
| 257 | 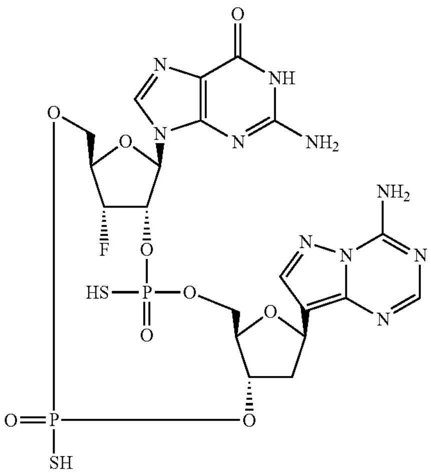 [SMILES: Nc1nc2c(ncn2[C@@H]2O[C@@H]3COP(=O)(S)O[C@H]4C[C@H](c5cnn6c(N)ncnc56)O[C@@H]4COP(=O)(S)O[C@@H]2[C@@H]3F)c(=O)[nH]1] | 2-amino-9-[(5R,7R,8S,12aR,14R,15aS,16R)-14-(4-aminopyrazolo[1,5-a][1,3,5]triazin-8-yl)-16-fluoro-2,10-dihydroxy-2,10-disulfidooctahydro-12H-5,8-methanofuro[3,2-1][1,3,6,9,11,2,10]pentaoxadiphosphacyclotetradecin-7-yl]-1,9-dihydro-6H-purin-6-one (Diastereomer 1) | 691 |
| 258 | 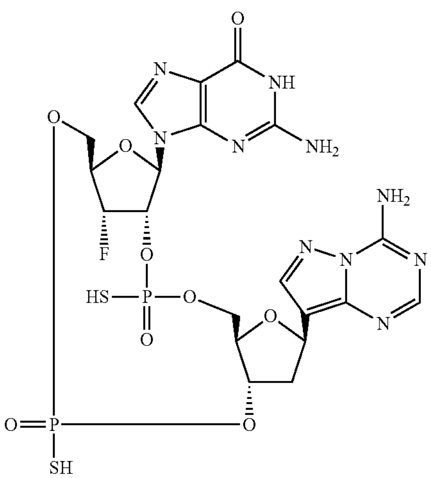 [SMILES: Nc1nc2c(ncn2[C@@H]2O[C@@H]3COP(=O)(S)O[C@H]4C[C@H](c5cnn6c(N)ncnc56)O[C@@H]4COP(=O)(S)O[C@@H]2[C@@H]3F)c(=O)[nH]1] | 2-amino-9-[(5R,7R,8S,12aR,14R,15aS,16R)-14-(4-aminopyrazolo[1,5-a][1,3,5]triazin-8-yl)-16-fluoro-2,10-dihydroxy-2,10-disulfidooctahydro-12H-5,8-methanofuro[3,2-1][1,3,6,9,11,2,10]pentaoxadiphosphacyclotetradecin-7-yl]-1,9-dihydro-6H-purin-6-one (Diastereomer 2) | 691 |
| 259 | 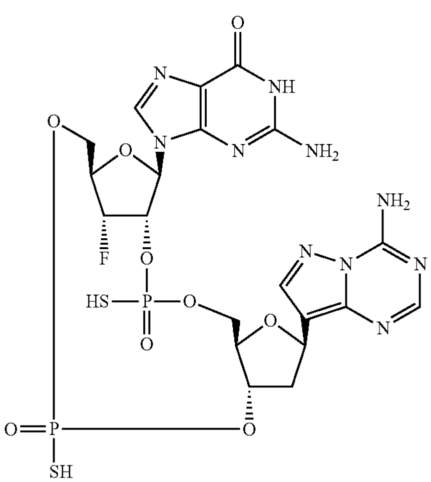 [SMILES: Nc1nc2c(ncn2[C@@H]2O[C@@H]3COP(=O)(S)O[C@H]4C[C@H](c5cnn6c(N)ncnc56)O[C@@H]4COP(=O)(S)O[C@@H]2[C@@H]3F)c(=O)[nH]1] | 2-amino-9-[(5R,7R,8S,12aR,14R,15aS,16R)-14-(4-aminopyrazolo[1,5-a][1,3,5]triazin-8-yl)-16-fluoro-2,10-dihydroxy-2,10-disulfidooctahydro-12H-5,8-methanofuro[3,2-1][1,3,6,9,11,2,10]pentaoxadiphosphacyclotetradecin-7-yl]-1,9-dihydro-6H-purin-6-one (Diastereomer 3) | 691 |

Alternatively, Examples 117-142, 144-152, 172, 174, and 244-247, above were made using procedures similar to those described for Examples 81 through 83 above.

Example 260: 2-amino-9-[(5R,7R,8S,12aR,14R,15R,15aR,16R)-14-(6-amino-9H-purin-9-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one
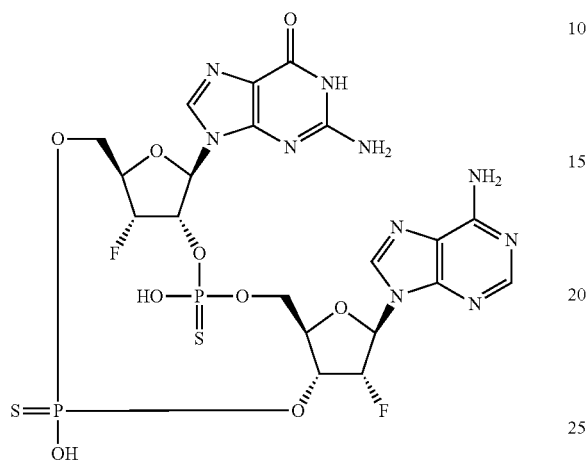
Step 1. ((2R,3R,4R,5R)-5-(6-benzamido-9H-purin-9-yl)-4-fluoro-3-((triethylsilyl)oxy)tetrahydrofuran-2-yl)methyl (2-cyanoethyl) diisopropylphosphoramidite
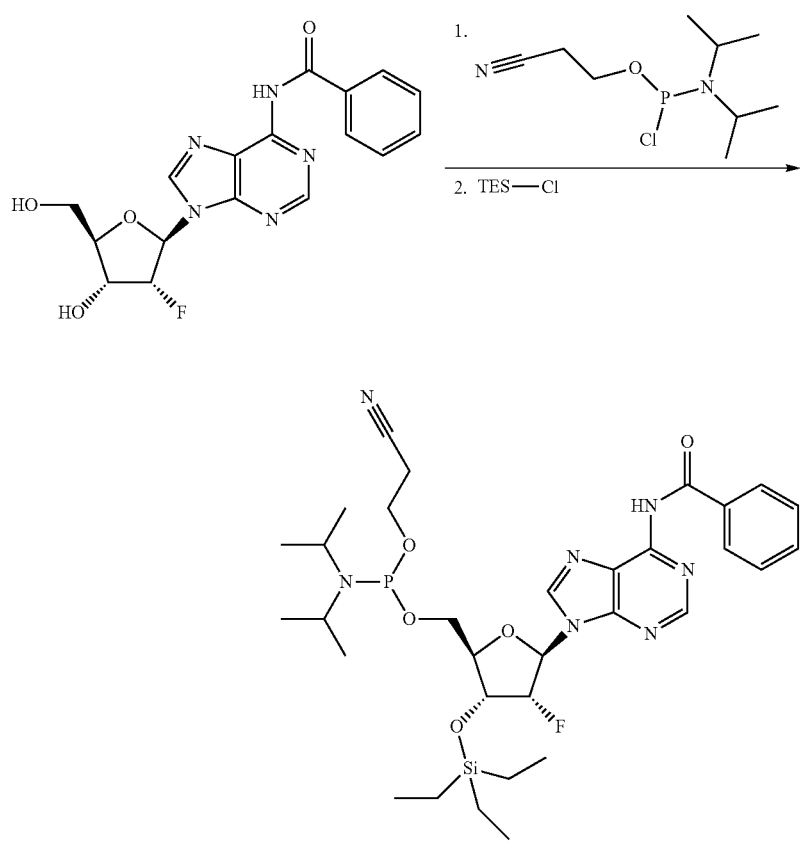

To a solution of N-(9-((2R,3R,4R,5R)-3-fluoro-4-hydroxy-5-(hydroxymethyl)tetrahydrofuran-2-yl)-9H-purin-6-yl)benzamide (780 mg, 2.089 mmol) in DMF (8 mL) and DIPEA (1.116 mL, 6.39 mmol) at 0° C. was added 200 mg activated molecular sieve 4 Å and 2-cyanoethyl N,N-diisopropylchlorophosphoramidite (572 mg, 2.343 mmol) in 1 ml dry CH$_3$CN. The resulting mixture was stirred at 0° C. for 5 h; chlorotriethylsilane (401 mg, 2.66 mmol) was added dropwise. The resulting mixture was stirred at rt overnight. The reaction carried directly to next step. LCMS (ES, m/z): 686 [M−H]$^−$.

Step 2: O-(((2R,3R,4R,5R)-5-(6-benzamido-9H-purin-9-yl)-4-fluoro-3-((triethylsilyl)oxy) tetrahydrofuran-2-yl)methyl)O-((2R,3S,4R,5R)-5-(((tert-butyldimethylsilyl)oxy)methyl)-4-fluoro-2-(2-isobutyramido-6-oxo-1,6-dihydro-9H-purin-9-yl)tetrahydrofuran-3-yl)O-(2-cyanoethyl) phosphorothioate To a solution of the product of step 1 was added N-(9-((2R,3S,4S,5R)-5-(((tert-butyldimethylsilyl)oxy)methyl)-4-fluoro-3-hydroxytetrahydrofuran-2-yl)-6-oxo-6,9-dihydro-1H-purin-2-yl)isobutyramide (500 mg, 1.065 mmol) and 1H-tetrazole (895 mg, 12.78 mmol). The mixture was stirred at RT for 2 h, and DDTT (568 g, 2.77 mmol) was added. The mixture was stirred for 1 h, then partitioned between ethyl acetate and H$_2$O, dried over Na$_2$SO$_4$, filtered and concentrated in vacuo. The residue was purified by column chromatography on silica gel, eluting with 0-6% MeOH/DCM to give O-(((2R,3R,4R,5R)-5-(6-benzamido-9H-purin-9-yl)-4-fluoro-3-((triethyl silyl)oxy)tetrahydrofuran-2-yl)methyl)O-((2R,3S,4R,5R)-5-(((tert-butyldimethylsilyl)oxy)methyl)-4-fluoro-2-(2-isobutyramido-6-oxo-1,6-dihydro-9H-purin-9-yl)tetrahydrofuran-3-yl)O-(2-cyanoethyl) phosphorothioate. LCMS (ES, m/z): 1088 [M+H]$^+$

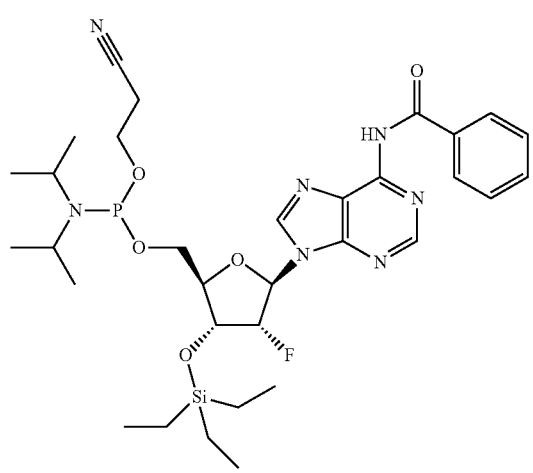

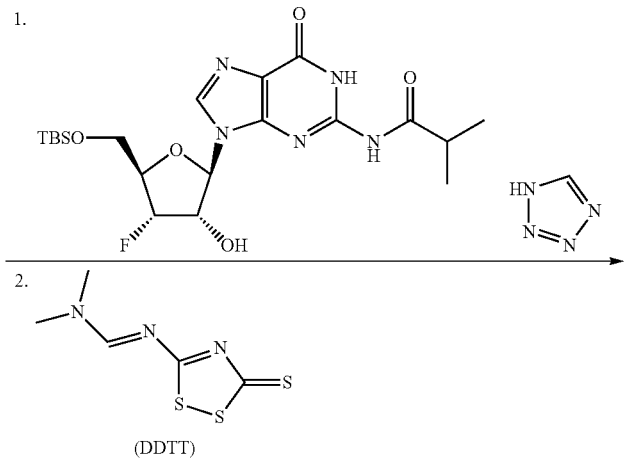

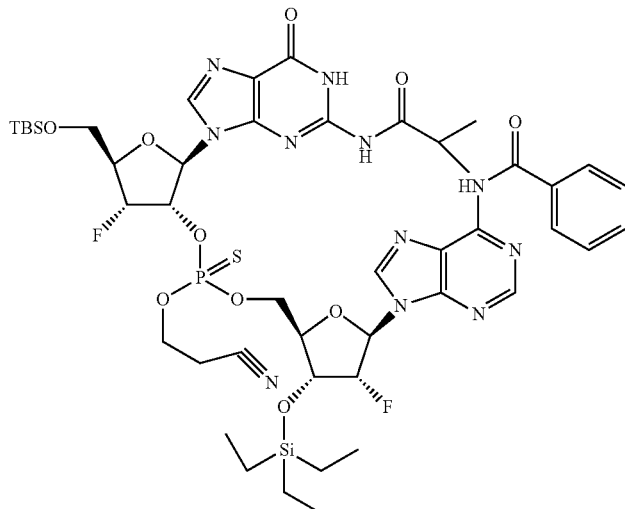

Step 3: O-(((2R,3R,4R,5R)-5-(6-benzamido-9H-purin-9-yl)-4-fluoro-3-hydroxytetrahydrofuran-2-yl)methyl)O-((2R,3S,4R,5R)-4-fluoro-5-(hydroxymethyl)-2-(2-isobutyramido-6-oxo-1,6-dihydro-9H-purin-9-yl)tetrahydrofuran-3-yl)O-hydrogen phosphorothioate

Step 4. N-{9-[(5R,7R,8S,12aR,14R,15R,15aR,16R)-15,16-difluoro-2,10-dihydroxy-7-{2-[(2-methylpropanoyl)amino]-6-oxo-1,6-dihydro-9H-purin-9-yl}-2,10-disulfidooctahydro-12H-5,8-methanofuro[3,2-l][1,3,6,9,11,2,10]pentaoxadiphosphacyclotetradecin-14-yl]-9H-purin-6-yl}benzamide

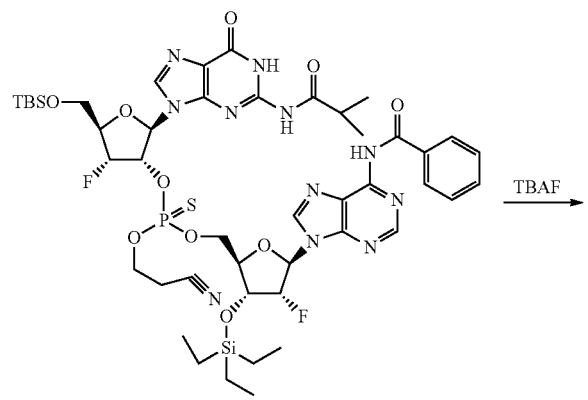

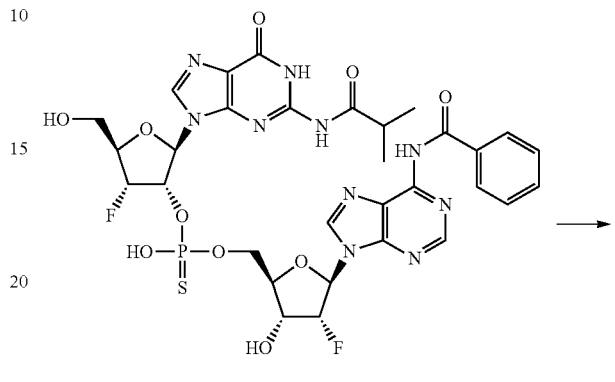

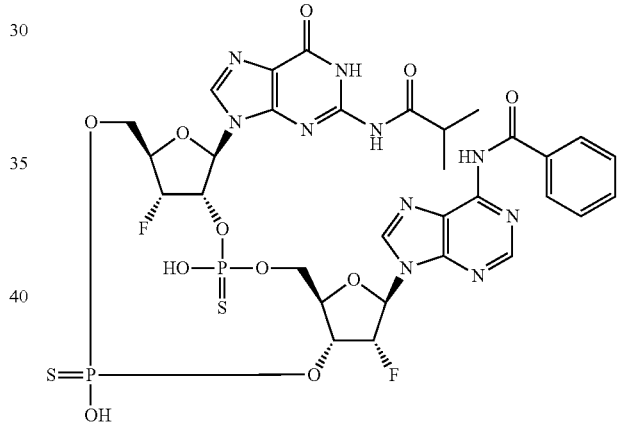

To a solution of the mixture (520 mg) from step 3 in THF (5 mL) was added TBAF (1.0M in THF) (1.140 mL, 1.140 mmol). The resulting mixture was stirred at RT for 2 h and concentrated in vacuo. The residue was purified by column chromatography on silica gel, eluting with 0-8% MeOH/DCM to give O-(((2R,3R,4R,5R)-5-(6-benzamido-9H-purin-9-yl)-4-fluoro-3-hydroxytetrahydrofuran-2-yl)methyl) O-((2R,3 S,4R,5R)-4-fluoro-5-(hydroxymethyl)-2-(2-isobutyramido-6-oxo-1H-purin-9(6H)-yl)tetrahydrofuran-3-yl) O-hydrogen phosphorothioate. LCMS (ES, m/z): 807 [M+H]+

O-(((2R,3R,4R,5R)-5-(6-benzamido-9H-purin-9-yl)-4-fluoro-3-hydroxytetrahydrofuran-2-yl)methyl)O-((2R,3S,4R,5R)-4-fluoro-5-(hydroxymethyl)-2-(2-isobutyramido-6-oxo-1H-purin-9(6H)-yl)tetrahydrofuran-3-yl)O-hydrogen phosphorothioate (250 mg, 0.310 mmol) and diisopropylammonium tetrazolide (80 mg, 0.465 mmol) were azeotrope with dry $CH_3CN$ (3×10 ml) and dried under high vacuum for 30 min.

The above mixture was dissolved in DMF (1 mL) and acetonitrile (7 mL) and added 200 mg active molecular sieve 4 Å and a solution of 2-cyanoethyl N,N,N',N'-tetraisopropylphosphorodiamidite (128 mg, 0.403 mmol) in 1 ml dry $CH_3CN$. The resulting mixture was stirred at rt for 30 min, followed by addition of 1H-tetrazole (109 mg, 1.550 mmol). The reaction stayed at rt for 1 h and added DDTT (95 mg, 0.465 mmol). The stirring continued for 1 h and concentrated in vacuo. The residue was purified by column chromatography on silica gel, eluting with 0-10% MeOH/DCM with 1% ET3N to give the desired product. LCMS (ES, m/z): 883 [M−H]−.

Step 5: 2-amino-9-[(5R,7R,8S,12aR,14R,15R,15aR,16R)-14-(6-amino-9H-purin-9-yl)-15,16-difluoro-2,10-dihydroxy-2,10-disulfidooctahydro-12H-5,8-methanofuro[3,2-l]1,3,6,9,11,2,10]pentaoxadiphosphacyclotetradecin-7-yl-1,9-dihydro-6H-purin-6-one Examples 261, 262, 263: 2-amino-9-[(5R,7R,8S,12aR,14R,15aS,16R)-14-(4-amino-5-fluoro-7H-pyrrolo[2,3-d]pyrimidin-7-yl)-12a-ethynyl-16-fluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomers 1-3)

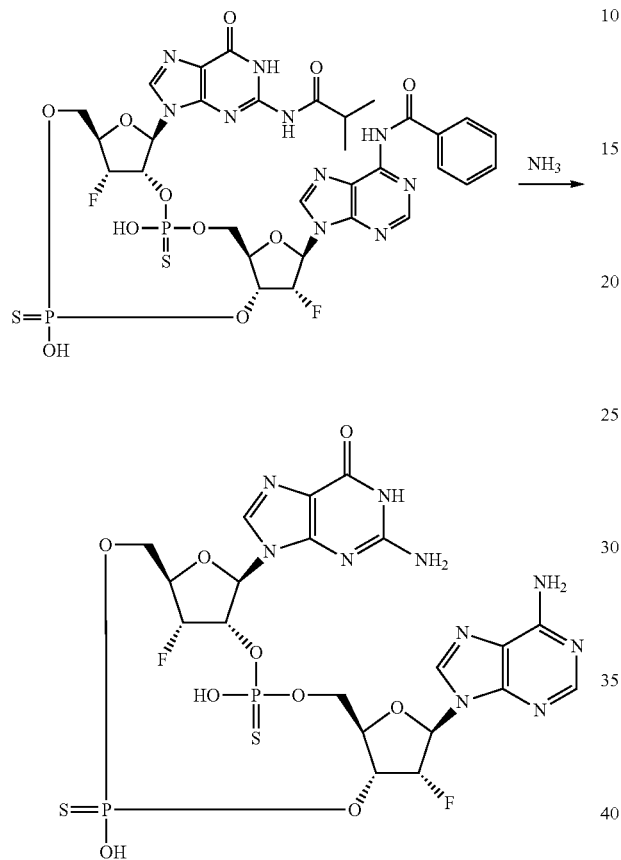

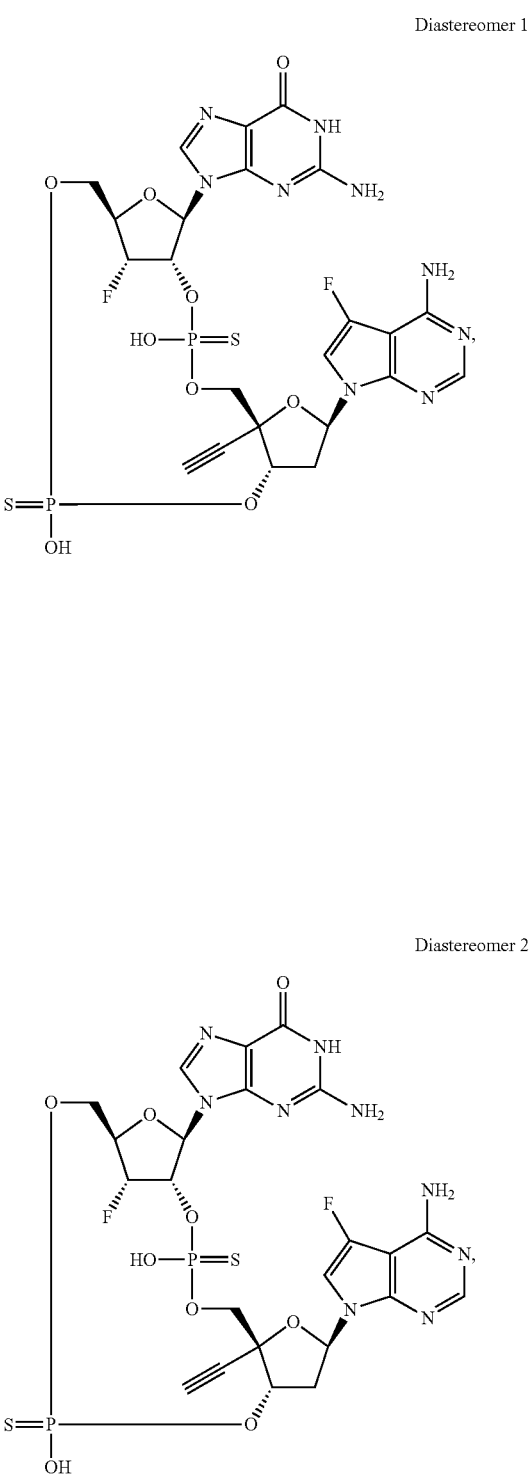

N-{9-[(5R,7R,8S,12aR,14R,15R,15aR,16R)-15,16-difluoro-2,10-dihydroxy-7-{2-[(2-methylpropanoyl)amino]-6-oxo-1,6-dihydro-9H-purin-9-yl}-2,10-disulfidooctahydro-12H-5,8-methanofuro[3,2-l][1,3,6,9,11,2,10]pentaoxadiphosphacyclotetradecin-14-yl]-9H-purin-6-yl}benzamide (120 mg, 0.136 mmol) and ammonia (7.0M in MeOH) (2 ml, 14.00 mmol) were sealed in a microwave tube. The reaction mixture was heated to 50° C. and stirred for 4 h. The reaction mixture was concentrated, and purified using mass-directed reverse phase HPLC (X-Bridge BEH 150 Prep C18) using a gradient solvent system with MeCN and 100 mM aqueous triethylammonium acetate to give desired product. Lyopholization of the product fractions furnished 2-amino-9-[(5R,7R,8S,12aR,14R,15R,15aR,16R)-14-(6-amino-9H-purin-9-yl)-15,16-difluoro-2,10-dihydroxy-2,10-disulfidooctahydro-12H-5,8-methanofuro[3,2-l][1,3,6,9,11,2,10]-pentaoxadiphosphacyclotetradecin-7-yl]-1,9-dihydro-6H-purin-6-one. LCMS (ES, m/z): 709 [M−H]⁻. $^1$H NMR (H$_2$O-d2,500 MHz): $\delta_H$ 8.23 (1H, s), 8.17 (1H, s), 7.93 (1H, s), 6.43 (1H, d, J=15.0 Hz), 6.00 (1H, d, J=8.7 Hz), 5.75 (1H, m), 5.58 (2H, m), 5.15 (1H, m), 4.65 (2H, m), 4.54 (1H, m), 4.15-4.30 (3H, m). $^{31}$P NMR: (H$_2$O-d$_2$, 202 MHz): δ 52.1, 52.2.

-continued

Diastereomer 3

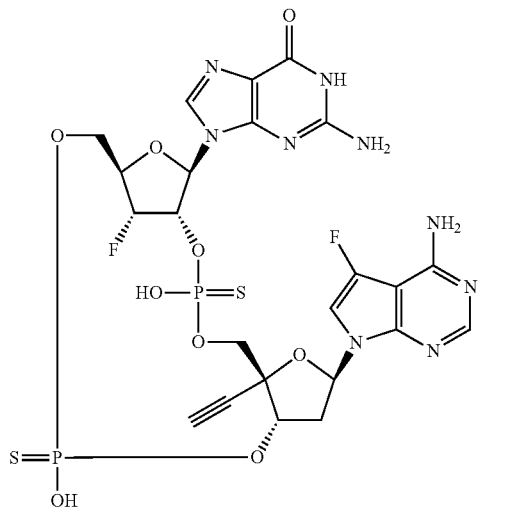

Step 1: ((2R,3R,4S,5R)-4-(((2-cyanoethoxy) (diisopropylamino)phosphanyl)oxy)-3-fluoro-5-(2-isobutyramido-6-oxo-1,6-dihydro-9H-purin-9-yl)tetrahydrofuran-2-yl)methyl (2-cyanoethyl) diisopropylphosphoramidite

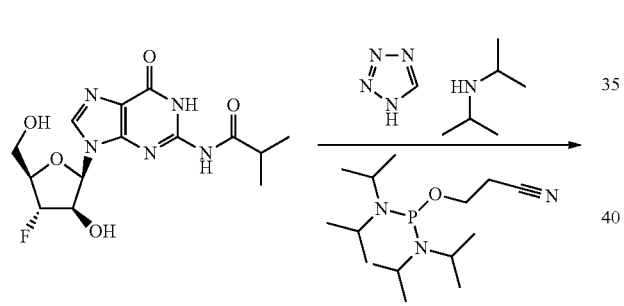

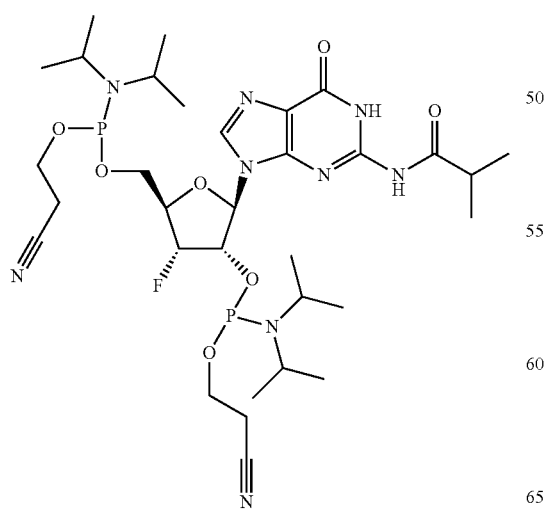

To a solution of N-(9-((2R,3R,4S,5R)-4-fluoro-3-hydroxy-5-(hydroxymethyl)tetrahydrofuran-2-yl)-6-oxo-6,9-dihydro-1H-purin-2-yl)isobutyramide (190 mg, 0.535 mmol) and 3-((bis(diisopropylamino)phosphino)oxy)propanenitrile (95%) (373 mg, 1.176 mmol) in DMF (5 ml) was added diisopropylammonium tetrazolide (137 mg, 0.802 mmol). The mixture was stirred at RT for 2 h, then added 1H-tetrazole (15.77 mg, 0.225 mmol) and continued for 2 h. 300 mg activated molecular sieve 4A was added and continued stirring at RT for 2 h. The reaction carried directly to next step. LCMS (ES, m/z): 754 [M−H]⁻.

Step 2: N-{7-[(5R,7R,8S,12aR,14R,15aS,16R)-2,10-bis(2-cyanoethoxy)-12a-ethynyl-16-fluoro-7-{2-[(2-methylpropanoyl)amino]-6-oxo-1,6-dihydro-9H-purin-9-yl}-2,10-disulfidooctahydro-12H-5,8-methanofuro[3,2-l][1,3,6,9,11,2,10]pentaoxadiphosphacyclotetradecin-14-yl]-5-fluoro-7H-pyrrolo[2,3-d]pyrimidin-4-yl}benzamide

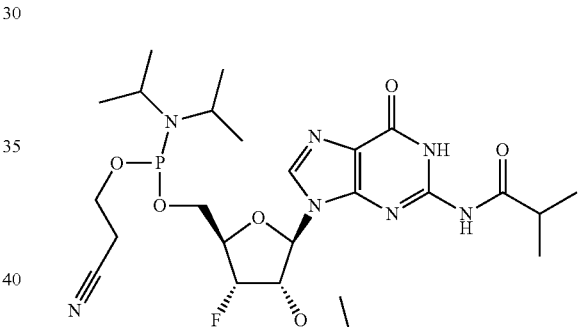

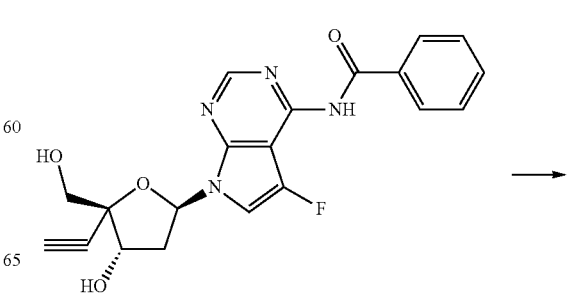

715
-continued

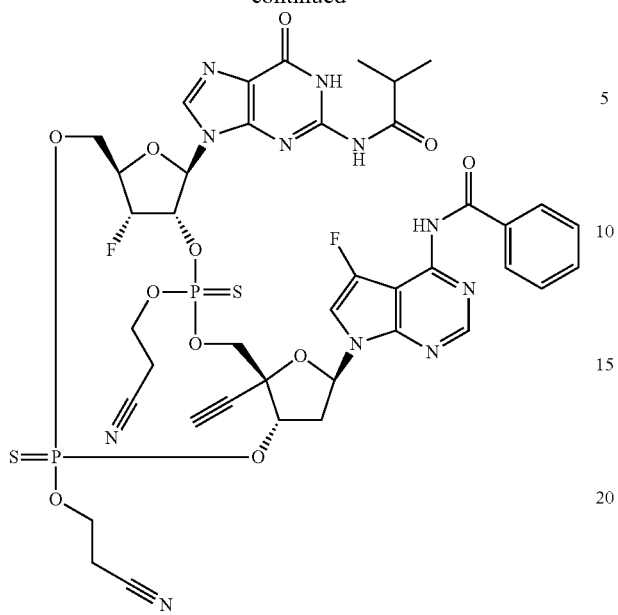

To a solution of N-(7-((2R,4S,5R)-5-ethynyl-4-hydroxy-5-(hydroxymethyl)tetrahydrofuran-2-yl)-5-fluoro-7H-pyrrolo[2,3-d]pyrimidin-4-yl)benzamide (180 mg, 0.454 mmol) and Et$_3$N (0.114 mL, 0.817 mmol) in DMF (4 mL) at −78° C. was added a solution of TMS-C$_1$ (0.070 mL, 0.545 mmol) in CH$_2$Cl$_2$ (1 mL) dropwise. The mixture was stirred at −78° C. for 20 min and warmed to 0° C. within 1 h, then added 200 mg activated molecular sieve 4 Å and continued stirring at RT for 2 h. The mixture was cooled to 0° C. and transferred to a stirred solution of the product of Step 1 (394 mg, 0.454 mmol) (precooled to −0° C.), followed by addition of 1H-tetrazole (191 mg, 2.72 mmol). The mixture was gradually warmed to RT and stirred at RT for 2 h. The filtration removed the solids. After washed with 3 ml DMF, the combined filtrate was added additional 1H-tetrazole (191 mg, 2.72 mmol) and stirred at RT overnight.

After completion of reaction, the reaction mixture was diluted with ethyl acetate and washed successively with H$_2$O and brine. The organic layer was dried over anhydrous Na$_2$SO$_4$ and purified by a silica gel chromatography, eluting with 0-8% MeOH/DCM to give two desired fractions with the same molecular weight. LCMS (ES, m/z): 1014 [M+H]$^+$ 716
Step 3: 2-amino-9-[(5R,7R,8S,12aR,14R,15aS,16R)-14-(4-amino-5-fluoro-7H-pyrrolo[2,3-d]pyrimidin-7-yl)-12a-ethynyl-16-fluoro-2,10-dihydroxy-2,10-disulfidooctahydro-12H-5,8-methanofuro[3,2-l][1,3,6,9,11,2,10]pentaoxadiphosphacyclotetradecin-7-yl-]1,9-dihydro-6H-purin-6-one

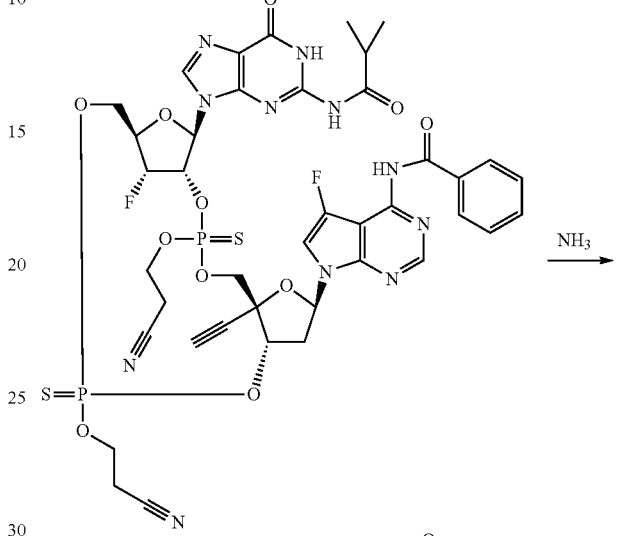

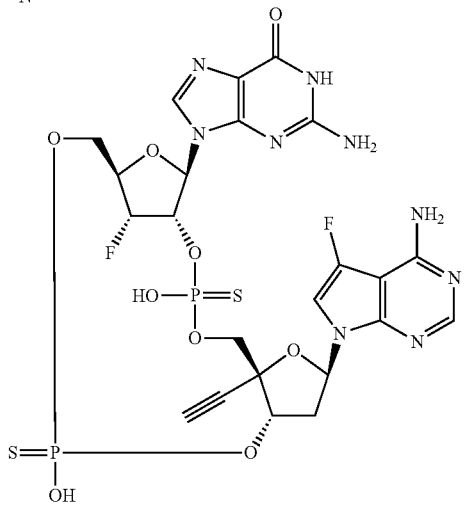

Diastereomer 1

N-{7-[(5R,7R,8S,12aR,14R,15aS,16R)-2,10-bis(2-cyanoethoxy)-12a-ethynyl-16-fluoro-7-{2-[(2-methylpropanoyl)amino]-6-oxo-1,6-dihydro-9H-purin-9-yl}-2,10-disulfidooctahydro-12H-5,8-methanofuro[3,2-l][1,3,6,9,11,2,10]pentaoxadiphosphacyclotetradecin-14-yl]-5-fluoro-7H-pyrrolo[2,3-d]pyrimidin-4-yl}benzamide (faster fraction from step 2) (30 mg, 0.030 mmol) and 7.0M ammonia in MeOH (2 ml, 14.00 mmol) were sealed in a microwave tube. The mixture was heated to 50° C. and stirred for 8 h. The reaction mixture was concentrated, and the product was purified using mass-directed reverse phase HPLC (X-Bridge BEH 150 Prep C18) using a gradient solvent system with MeCN and 100 mM aqueous triethylammonium acetate. Lyopholization of the product fractions furnished 2-amino-9-[(5R,7R,8S,12aR,14R,15aS,16R)-14-(4-amino-5-fluoro- 7H-pyrrolo[2,3-d]pyrimidin-7-yl)-12a-ethynyl-16-fluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one as the bis-triethylamine salt.

Example 261 (Diastereomer 1): LCMS (ES, m/z): 732 [M−H]⁻. ¹H NMR (H₂O-d₂, 500 MHz): $\delta_H$ 8.32 (1H, s), 8.08 (1H, s), 7.05 (1H, s), 6.70 (1H, t, J=6.1 Hz), 6.08 (1H, d, J=8.7 Hz), 5.71 (1H, d, J=53.2 Hz), 5.47-5.40 (1H, m), 5.14-5.10 (1H, m), 4.65 (2H, m), 4.28 (1H, t, J=8.7 Hz), 4.14-4.02 (3H, m), 2.85 (2H, d, J=6.4 Hz). ³¹P NMR: (H₂O-d₂, 202 MHz): δ 53.7, 54.0.

Step 4: 2-amino-9-[(5R,7R,8S,12aR,14R,15aS,16R)-14-(4-amino-5-fluoro-7H-pyrrolo[2,3-d]pyrimidin-7-yl)-12a-ethynyl-16-fluoro-2,1-dihydroxy-2,10-disulfidooctahydro-12H-5,8-methanofuro[3,2-l][1,3,6,9,11,2,10]pentaoxadiphosphacyclotetradecin-7-yl-], 9-dihydro-6H-purin-6-one

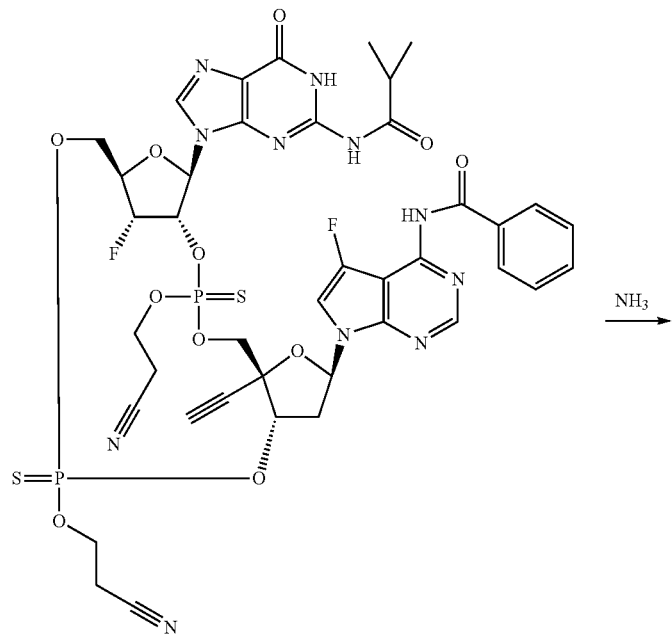

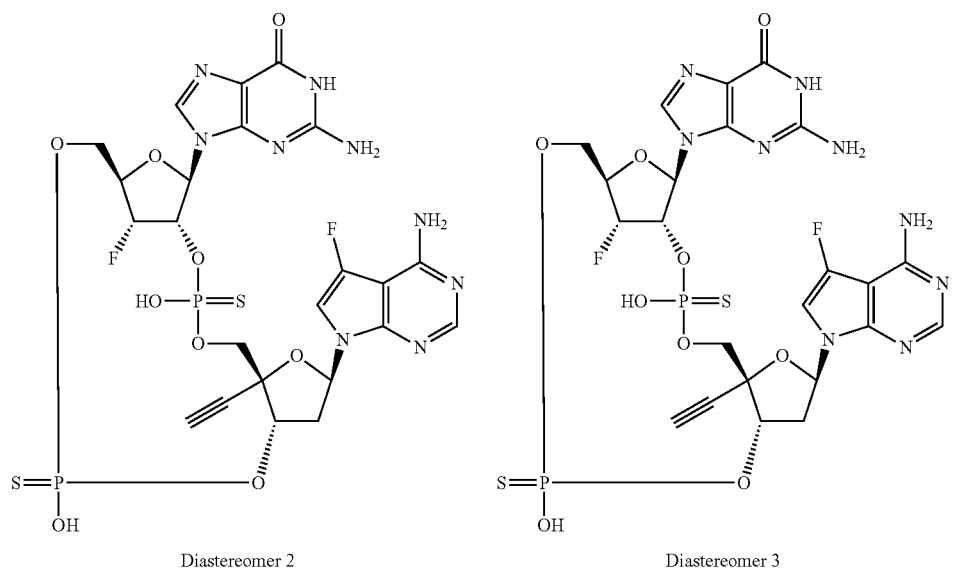

Diastereomer 2          Diastereomer 3

N-{7-[(5R,7R,8S,12aR,14R,15aS,16R)-2,10-bis(2-cyanoethoxy)-12a-ethynyl-16-fluoro-7-{2-[(2-methylpropanoyl)amino]-6-oxo-1,6-dihydro-9H-purin-9-yl}-2,10-disulfidooctahydro-12H-5,8-methanofuro[3,2-l][1,3,6,9,11,2,10]pentaoxadiphosphacyclotetradecin-14-yl]-5-fluoro-7H-pyrrolo[2,3-d]pyrimidin-4-yl}benzamide (slow fraction from Step 2, 65 mg, 0.064 mmol) and 7.0M ammonia in MeOH (2 ml, 14.00 mmol) were sealed in a microwave tube and heated to 50° C. and stirred for 8 h. The reaction mixture was concentrated and purified using mass-directed reverse phase HPLC (X-Bridge BEH 150 Prep C18) using a gradient solvent system with MeCN and 100 mM aqueous triethylammonium acetate to give two additional diastereomers after lyopholization of the product fractions.

Example 262 (Diastereomer 2): LCMS (ES, m/z): 732 [M–H]⁻. ¹H NMR (H₂O-d₂, 500 MHz): $\delta_H$ 8.09 (2H, d, J=3.0 Hz), 7.19 (1H, s), 6.74 (1H, s), 6.08 (1H, d, J=8.3 Hz), 5.63 (1H, s), 5.53 (1H, s), 5.35-5.33 (1H, m), 4.65 (2H, m), 4.34 (1H, d, J=8.8 Hz), 4.28 (1H, t, J=10.3 Hz), 4.11 (1H, d, J=12.1 Hz), 3.89 (1H, dd, J=10.6, 4.0 Hz), 2.85 (2H, d, J=6.4 Hz). ³¹P NMR: (H₂O-d₂, 202 MHz): δ 54.7, 59.8.

Example 263 (Diastereomer 3): LCMS (ES, m/z): 732 [M–H]⁻. ¹H NMR (H₂O-d₂, 500 MHz): $\delta_H$ 8.08 (1H, s), 7.94 (1H, s), 7.04 (1H, s), 6.68 (1H, s), 6.04 (1H, d, J=8.6 Hz), 5.64 (1H, s), 5.54 (1H, d, J=3.3 Hz), 5.24 (1H, d, J=7.7 Hz), 4.65 (2H, m), 4.40 (1H, d, J=8.2 Hz), 4.18 (1H, dd, J=11.0, 5.5 Hz), 4.09-4.00 (2H, m), 2.93-2.89 (1H, m), 2.82 (1H, d, J=7.1 Hz). ³¹P NMR: (H₂O-d₂, 202 MHz): δ 53.1, 54.9.

Examples 264 and 265: 2-amino-9-[(5R,7R,8R,12aR,14R,15R,15aS,18S)-14-(6-amino-9H-purin-9-yl)-2,10,18-trihydroxy-2-oxido-10-sulfidohexahydro-14H-15,12a-(epoxymethano)-5,8-methanofuro[3,2-l][1,3,9,11,6,2,10]tetraoxathiadiphosphacyclotetradecin-7(12H)-yl]-1,9-dihydro-6H-purin-6-one (Diastereomer 1) and 2-amino-9-[(5R,7R,8R,12aR,14R,15R,15aS,18S)-14-(6-amino-9H-purin-9-yl)-2,10,18-trihydroxy-2-oxido-10-sulfidohexahydro-14H-15,12a-(epoxymethano)-5,8-methanofuro[3,2-l][1,3,9,11,6,2,10]tetraoxathiadiphosphacyclotetradecin-7(12H)-yl]-1,9-dihydro-6H-purin-6-one (Diastereomer 2)

Diastereomer 1

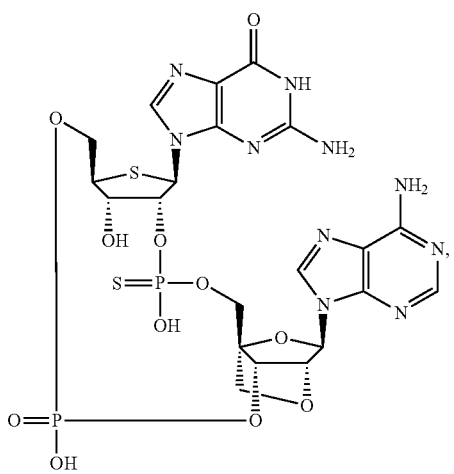

Diastereomer 2

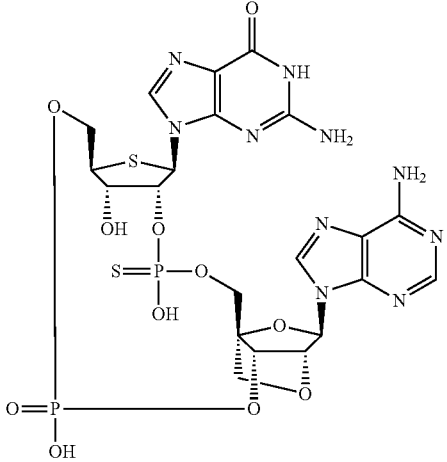

Step 1: (2R,3R,4S,5R)-4-((tert-butyldimethylsilyl)oxy)-5-(hydroxymethyl)-2-(2-isobutyramido-6-oxo-1,6-dihydro-9H-purin-9-yl)tetrahydrothiophen-3-yl phosphonate

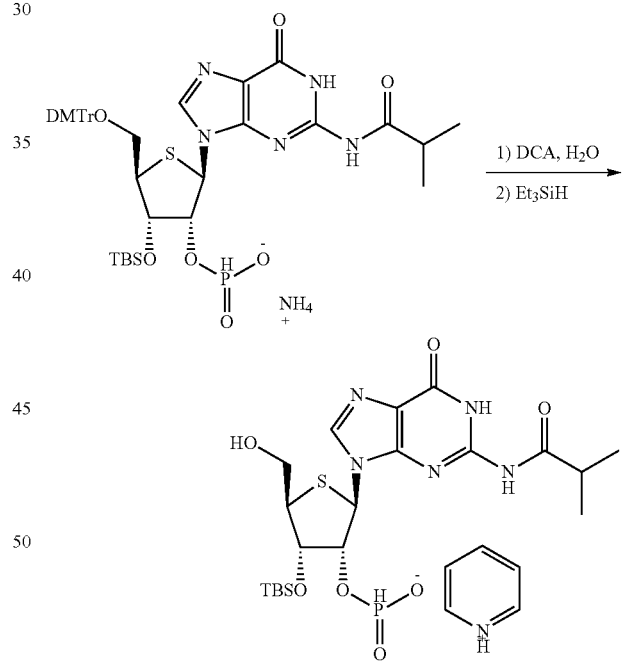

To a solution of (2R,3R,4S,5R)-5-((bis(4-methoxyphenyl)(phenyl)methoxy)methyl)-4-((tert-butyldimethylsilyl)oxy)-2-(2-isobutyramido-6-oxo-1,6-dihydro-9H-purin-9-yl)tetrahydrothiophen-3-yl phosphonate (750 mg, 0.865 mmol) in CH₂Cl₂ (9 mL) was added water (156 mg, 8.65 mmol) and 2,2-dichloroacetic acid in CH₂Cl₂ (0.6M, 11 mL, 6.6 mmol). The mixture was stirred at rt for 15 min, and then, Et₃SiH (4.00 mL) was added. After 1 h, pyridine (1232 mg, 15.57 mmol) was added, and it was concentrated to give a crude sample that was used for next reaction step without purification. LCMS (ES, m/z): 548.1 [M+H]⁺.

721

Step 2. (2R,3R,4S,5R)-5-((((((R,3R,4R,7S)-3-(6-benzamido-9H-purin-9-yl)-1-((bis(4-methoxyphenyl)(phenyl)methoxy)methyl)-2,5-dioxabicyclo[2.2.1]heptan-7-yl)oxy)(2-cyanoethoxy)phosphanyl)oxy)methyl)-4-((tert-butyldimethylsilyl)oxy)-2-(2-isobutyramido-6-oxo-1,6-dihydro-9H-purin-9-yl)tetrahydrothiophen-3-yl phosphonate

722

Step 3. (2R,3R,4S,5R)-5-((((((R,3R,4R,7S)-3-(6-benzamido-9H-purin-9-yl)-1-((bis(4-methoxyphenyl)(phenyl)methoxy)methyl)-2,5-dioxabicyclo[2.2.1]heptan-7-yl)oxy)(2-cyanoethoxy)phosphoryl)oxy)methyl)-4-((tert-butyldimethylsilyl)oxy)-2-(2-isobutyramido-6-oxo-1,6-dihydro-9H-purin-9-yl)tetrahydrothiophen-3-yl phosphonate

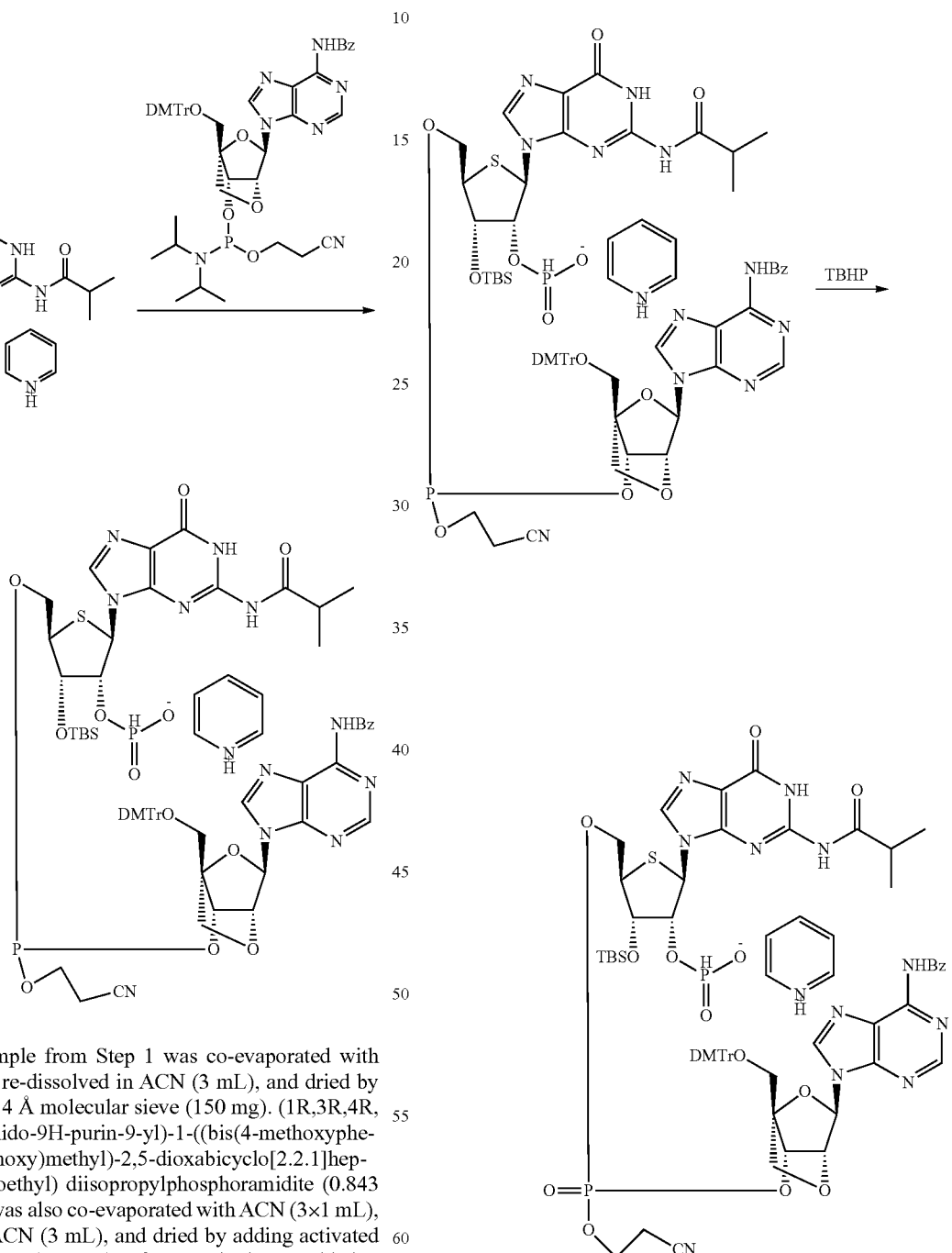

The crude sample from Step 1 was co-evaporated with ACN (3×2 mL), re-dissolved in ACN (3 mL), and dried by adding activated 4 Å molecular sieve (150 mg). (1R,3R,4R,7S)-3-(6-benzamido-9H-purin-9-yl)-1-((bis(4-methoxyphenyl)(phenyl)methoxy)methyl)-2,5-dioxabicyclo[2.2.1]heptan-7-yl (2-cyanoethyl) diisopropylphosphoramidite (0.843 g, 0.952 mmol) was also co-evaporated with ACN (3×1 mL), re-dissolved in ACN (3 mL), and dried by adding activated 4 Å molecular sieve (150 mg). After 30 min, it was added to the previously prepared mixture containing pyridin-1-ium (2R,3R,4S,5R)-4-((tert-butyldimethylsilyl)oxy)-5-(hydroxymethyl)-2-(2-isobutyramido-6-oxo-1,6-dihydro-9H-purin-9-yl)tetrahydrothiophen-3-yl phosphonate. The reaction mixture was used in the next reaction step without purification. LCMS (ES, m/z): 1332.1 [M+H]⁺.

To a reaction mixture from Step 2 at rt was added 2-hydroperoxy-2-methylpropane (0.234 g, 2.60 mmol), and it was stirred for 40 min. It was concentrated to give a crude product, which was used for the next step without purification. LCMS (ES, m/z): 1347.1 [M+H]⁺.

723

Step 4: (2R,3R,4S,5R)-5-((((((1S,3R,4R,7S)-3-(6-benzamido-9H-purin-9-yl)-1-(hydroxymethyl)-2,5-dioxabicyclo[2.2.1]heptan-7-yl)oxy)(2-cyanoethoxy)phosphoryl)oxy)methyl)-4-((tert-butyldimethylsilyl)oxy)-2-(2-isobutyramido-6-oxo-1,6-dihydro-9H-purin-9-yl)tetrahydrothiophen-3-yl phosphonate

724

Step 5. (5R,7R,8R,12aR,14R,15R,15aS,18S)-18-{[tert-butyl(dimethyl)silyl]oxy}-2-(2-cyanoethoxy)-7-{2-[(2-methylpropanoyl)amino]-6-oxo-1,6-dihydro-9H-purin-9-yl}-14-{6-[(phenylcarbonyl)amino]-9H-purin-9-yl}hexahydro-14H-15,12a-(epoxymethano)-5,8-methanofuro[3,2-l][1,3,9,11,6,2,10]tetraoxathiadiphosphacyclotetradecin-10(12H)-olate 2-oxide

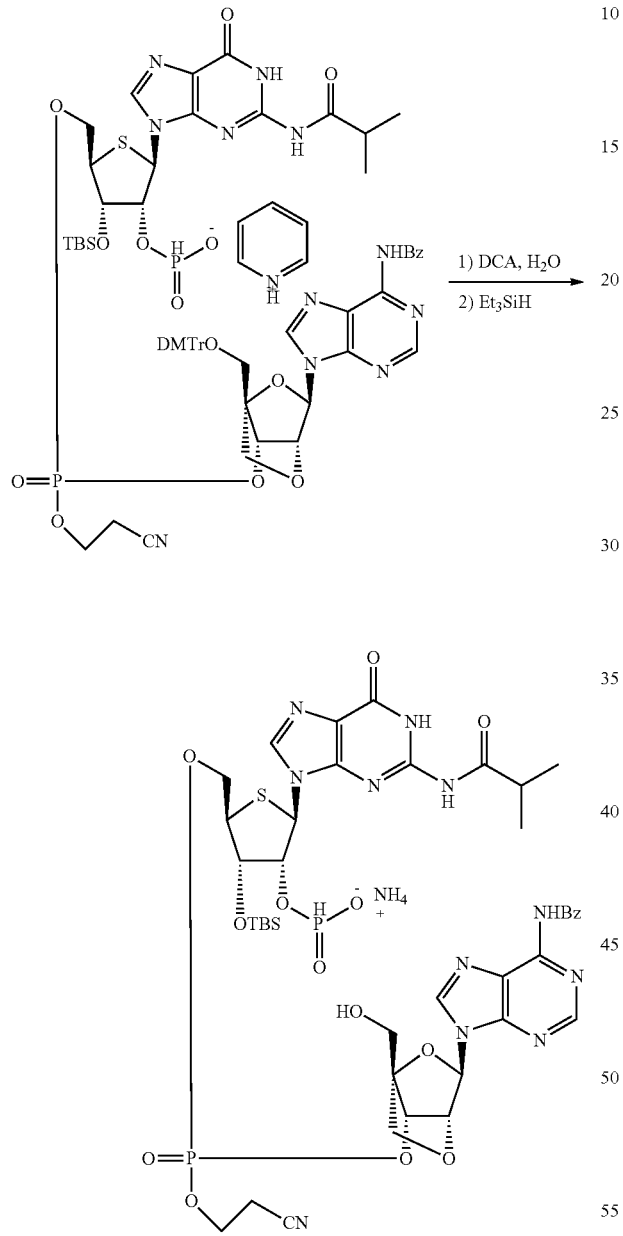

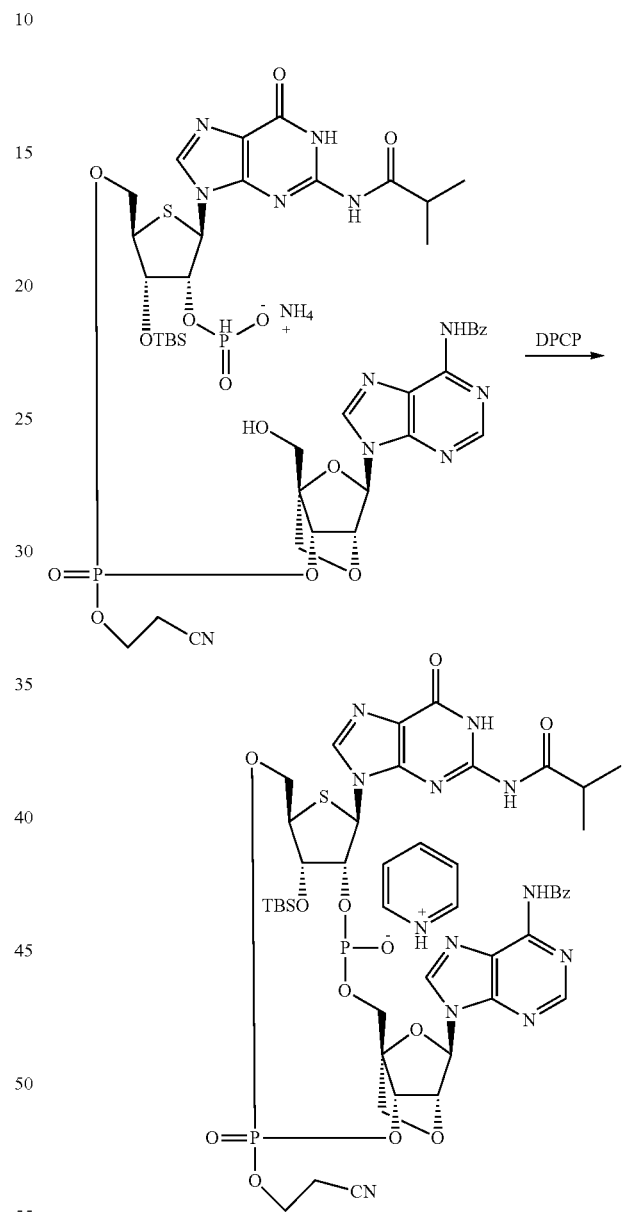

To the crude from Step 3 in CH$_2$Cl$_2$ (9 mL) was added water (156 mg, 8.65 mmol) and 2,2-dichloroacetic acid in CH$_2$Cl$_2$ (0.6N, 10 mL, 6 mmol). The resulting mixture was stirred at rt for 15 min. Then, triethylsilane (4 mL, 0.21 mmol) was added, and the stirring was continued for 40 min. Pyridine (1232 mg, 15.57 mmol) was added. The mixture was concentrated, and the residue was purified by reverse phase (C18) chromatography eluted with 0 to 95% ACN in aq NH$_4$HCO$_3$ (5 mM) to give the product. LCMS (ES, m/z): 1046.3 [M+H]$^+$.

To pyridine (20 mL) at −40° C. under Ar was added diphenyl phosphorochloridate (1.28 g, 4.78 mmol) over 5 min. To the solution at −40° C. was added a solution of (2R,3R,4S,5R)-5-((((((1 S,3R,4R,7S)-3-(6-benzamido-9H-purin-9-yl)-1-(hydroxymethyl)-2,5-dioxabicyclo [2.2.1] heptan-7-yl)oxy)(2-cyanoethoxy)phosphoryl)oxy)methyl)-4-((tert-butyldimethylsilyl)oxy)-2-(2-isobutyramido-6-oxo-1,6-dihydro-9H-purin-9-yl)tetrahydrothiophen-3-yl phosphonate (250 mg, 0.239 mmol, co-evaporated with pyridine, 3×10 mL) in CH$_2$Cl$_2$ (20 mL) dropwise. The resulting mixture was stirred at −40° C. for 30 min. The reaction mixture was used for the next reaction step immediately without purification. LCMS (ES, m/z): 1028.4 [M+H]+.

Step 6: (5R,7R,8R,12aR,14R,15R,15aS,18S)-18-{[tert-butyl(dimethyl)silyl]oxy}-2-(2-cyanoethoxy)-7-{2-[(2-methylpropanoyl)amino]-6-oxo-1,6-dihydro-9H-purin-9-yl}-14-{6-[(phenylcarbonyl)amino]-9H-purin-9-yl}hexahydro-14H-15,12a-(epoxymethano)-5,8-methanofuro[3,2-l][1,3,9,11,6,2,10]tetraoxathiadiphosphacyclotetradecin-10(12H)-olate 2-oxide 10-sulfide

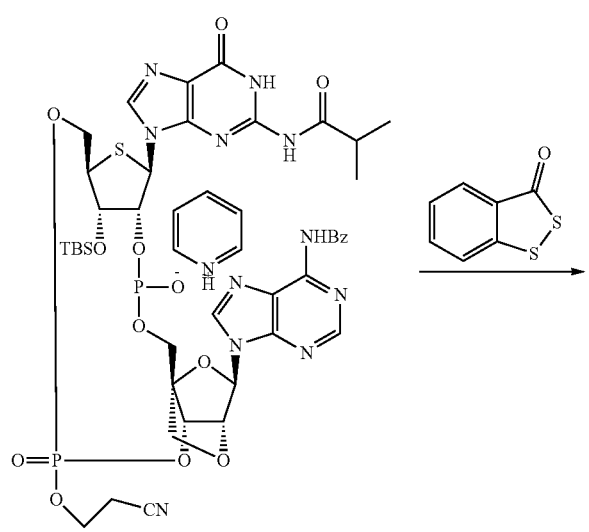

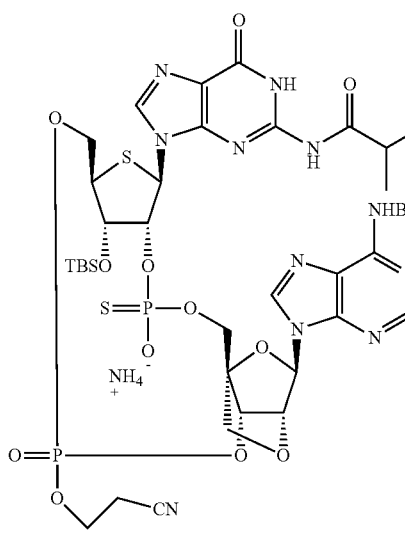

To the reaction mixture at rt from Step 5 was added 3H-benzo[c][1,2]dithiol-3-one (121 mg, 0.717 mmol). After stirring at 25° C. for 40 min, water (431 mg, 23.9 mmol) was added. The reaction mixture was concentrated under reduced pressure, and the residue was purified by reverse phase (C18) chromatography eluted with 0 to 95% ACN in aq NH4HCO3 (5 mM) to give the product. LCMS (ES, m/z): 1060.3 [M+H]+. 31P-NMR: (121 MHz, D2O) δ 54.91, 54.61 (m, 1P), 6-6.08, −6.48 (m, 1P).

Step 7: (5R,7R,8R,12aR,14R,15R,15aS,18S)-7-(2-amino-6-oxo-1,6-dihydro-9H-purin-9-yl)-14-(6-amino-9H-purin-9-yl)-18-{[tert-butyl(dimethyl)silyl]oxy}hexahydro-14H-15,12a-(epoxymethano)-5,8-methanofuro[3,2-l][1,3,9,11,6,2,10]tetraoxathiadiphosphacyclotetradecine-2,10(12H)-diolate 2-oxide 10-sulfide

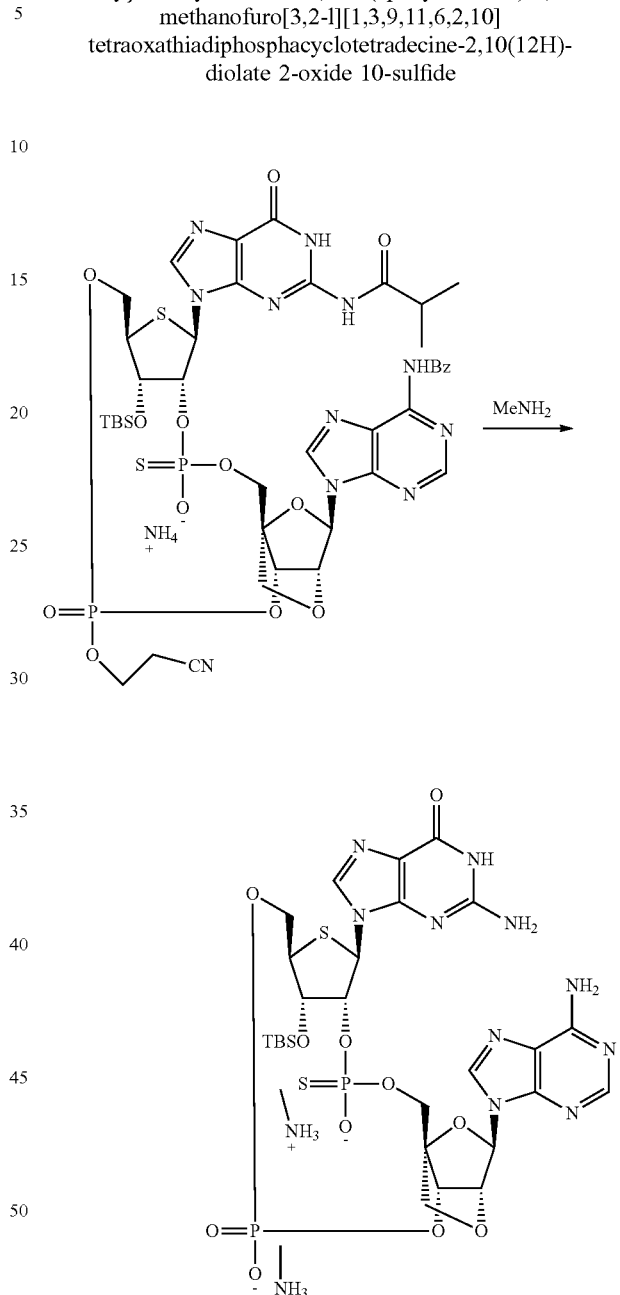

(5R,7R,8R,12aR,14R,15R,15aS,18S)-18-{[tert-butyl(dimethyl)silyl]oxy}-2-(2-cyanoethoxy)-7-{2-[(2-methylpropanoyl)amino]-6-oxo-1,6-dihydro-9H-purin-9-yl}-14-{6-[(phenylcarbonyl)amino]-9H-purin-9-yl}hexahydro-14H-15,12a-(epoxymethano)-5,8-methanofuro[3,2-l][1,3,9,11,6,2,10]tetraoxathiadiphosphacyclotetradecin-10(12H)-olate 2-oxide 10-sulfide (190 mg, 0.178 mmol) was dissolved in a solution of methylamine in EtOH (30%, 1 mL), and the resulting solution was stirred at rt for 2 h. Then, it was concentrated to give a crude sample containing the product. LCMS (ES, m/z): 833.2 [M+H]+.

Step 8: 2-amino-9-[(5R,7R,8R,12aR,14R,15R,15aS,18S)-14-(6-amino-9H-purin-9-yl)-2,10,18-trihydroxy-2-oxido-10-sulfidohexahydro-14H-15,2a-(epoxymethano)-5,8-methanofuro[3,2-l][1,3,9,11,6,2,10]tetraoxathiadiphosphacyclotetradecin-7(12H)-yl]-1,9-dihydro-6H-purin-6-one

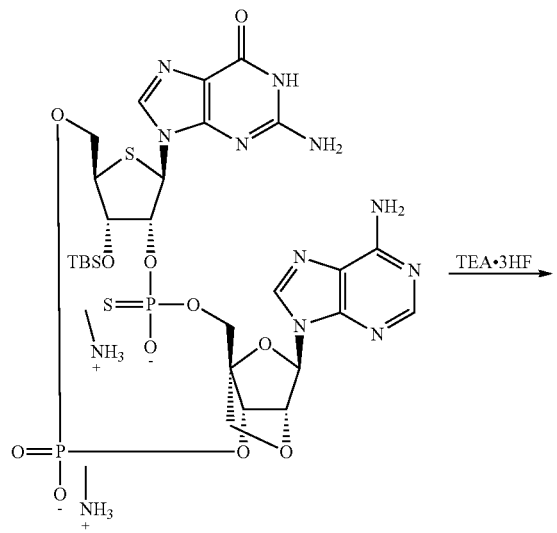

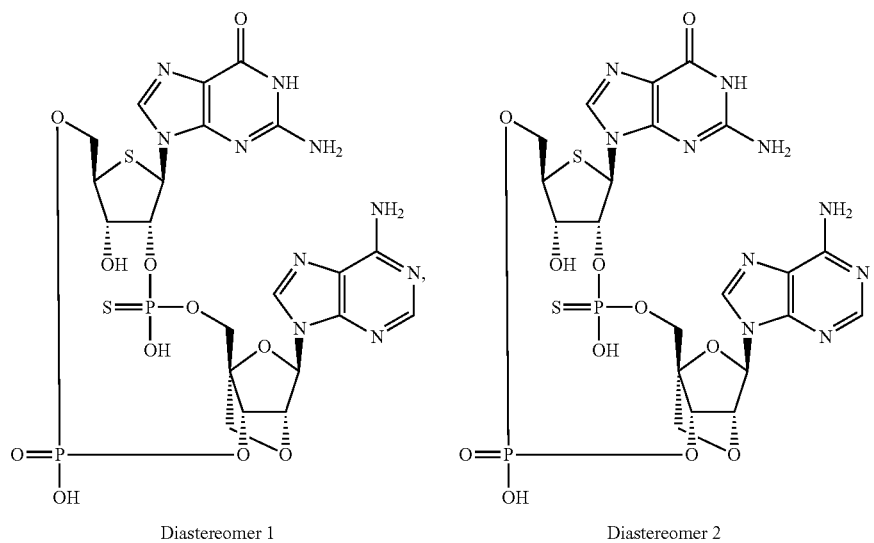

Diastereomer 1                    Diastereomer 2

The crude from Step 7 was suspended in pyridine (5 mL) under Ar. To the mixture was added Et$_3$N (1864 mg, 18.42 mmol) and triethylamine trihydrofluoride (742 mg, 4.60 mmol) dropwise. The mixture was heated to 50° C. for 16 h. Then, it was concentrated, and the residue was purified by preparative-HPLC (XBridge Shield RP18 OBD Column, 19×150 mm) eluted with 0 to 14% ACN in aq NH$_4$HCO$_3$ (10 mM) over 16 min to give two products after concentration.

Example 264: 2-amino-9-[(5R,7R,8R,12aR,14R,15R,15aS,18S)-14-(6-amino-9H-purin-9-yl)-2,10,18-trihydroxy-2-oxido-10-sulfidohexahydro-14H-15,12a-(epoxymethano)-5,8-methanofuro[3,2-l][1,3,9,11,6,2,10]tetraoxathiadiphosphacyclotetradecin-7(12H)-yl]-1,9-dihydro-6H-purin-6-one (Diastereomer 1): T$_R$: 11.00 min. LCMS (ES, m/z): 719.0 [M+H]$^+$. $^1$H-NMR: (300 MHz, D$_2$O): δ 8.13 (s, 1H), 7.94 (s, 1H), 7.64 (s, 1H), 6.11-5.97 (m, 2H), 5.92-5.85 (m, 1H), 5.25-5.05 (m, 1H), 4.87 (s, 1H), 4.75 (s, 2H), 4.30-4.21 (m, 1H), 4.12-3.78 (m, 4H), 3.50-3.45 (m, 1H). $^{31}$P-NMR: (121 MHz, D$_2$O) δ 52.06 (s, 1P), 6-0.86 (s, 1P)

Example 265: 2-amino-9-[(5R,7R,8R,12aR,14R,15R,15aS,18S)-14-(6-amino-9H-purin-9-yl)-2,10,18-trihydroxy-2-oxido-10-sulfidohexahydro-14H-15,12a-(epoxymethano)-5,8-methanofuro[3,2-l][1,3,9,11,6,2,10]tetraoxathiadiphosphacyclotetradecin-7(12H)-yl]-1,9-dihydro-6H-purin-6-one (Diastereomer 2): T$_R$: 12.32 min. LCMS (ES, m/z): 719.0 [M+H]$^+$. $^1$H-NMR: (300 MHz, D$_2$O): δ 8.13-8.03 (m, 2H), 7.64 (s, 1H), 6.11-5.97 (m, 2H), 5.92-5.90 (m, 1H), 5.20-5.15 (m, 1H), 4.87-4.75 (m, 3H), 4.33-4.20 (m, 1H), 4.12-4.00 (m, 2H), 3.90-3.78 (m, 2H), 3.45-3.40 (m, 1H). $^{31}$P-NMR: (121 MHz, D$_2$O) δ 54.88 (s, 1P), 6-0.97 (s, 1P).

Examples 266 through 272, as shown in Table 9 below, were prepared according to procedures analogous to those outlined for Examples 264 and 265 above using the appropriate monomeric nucleosides, described as Preparations or as obtained from commercial sources.

TABLE 9

| Ex. | Structure | Name | Mass [M − H]⁻ |
|---|---|---|---|
| 266 | 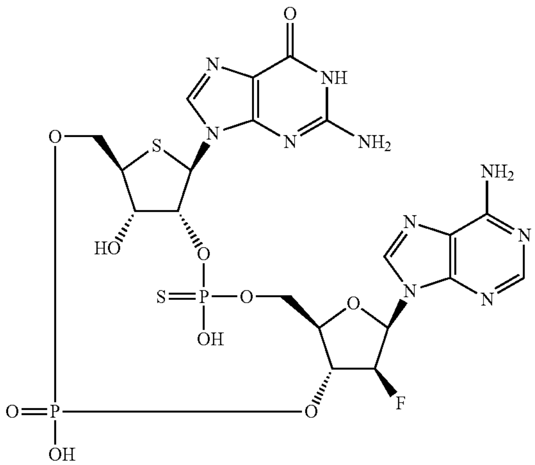 [SMILES: Nc1nc2c(ncn2[C@@H]2S[C@@H]3COP(=O)(O)O[C@H]4[C@H](F)[C@H](n5cnc6c(N)ncnc65)O[C@@H]4COP(O)(=S)O[C@@H]2[C@@H]3O)c(=O)[nH]1] | 2-amino-9-[(5R,7R,8R,12aR,14R,15S,15aR,16S)-14-(6-amino-9H-purin-9-yl)-15-fluoro-2,10,16-trihydroxy-2-oxido-10-sulfidooctahydro-12H-5,8-methanofuro[3,2-1][1,3,9,11,6,2,10]tetraoxathiadiphosphacyclotetradecin-7-yl]-1,9-dihydro-6H-purin-6-one | 707 |
| 267 | 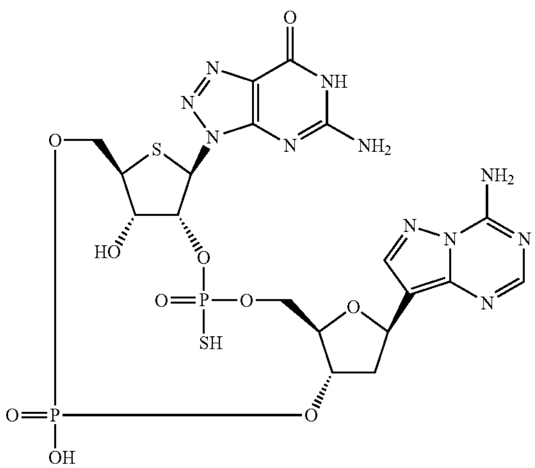 [SMILES: Nc1nc2c(nnn2[C@@H]2S[C@@H]3COP(=O)(O)O[C@H]4C[C@H](c5cnn6c(N)ncnc56)O[C@@H]4COP(=O)(S)O[C@@H]2[C@@H]3O)c(=O)[nH]1] | 5-amino-3-[(5R,7R,8R,12aR,14R,15aS,16S)-14-(4-aminopyrazolo[1,5-a][1,3,5]triazin-8-yl)-2,16-dihydroxy-2,10-dioxido-10-sulfanyloctahydro-12H-5,8-methanofuro[3,2-1][1,3,9,11,6,2,10]tetraoxathiadiphosphacyclotetradecin-7-yl]-3,6-dihydro-7H-[1,2,3]triazolo[4,5-d]pyrimidin-7-one (Diastereomer 1) | 690 |
| 268 | 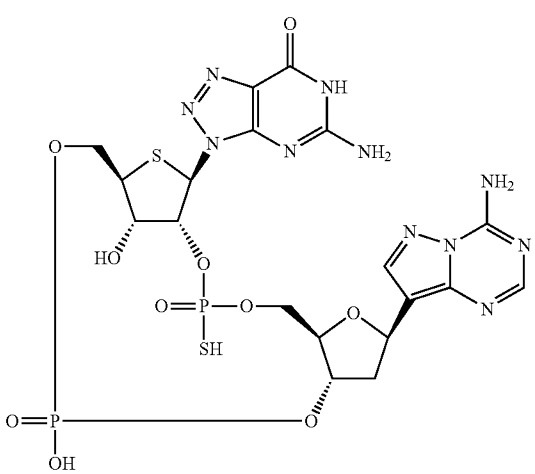 [SMILES: Nc1nc2c(nnn2[C@@H]2S[C@@H]3COP(=O)(O)O[C@H]4C[C@H](c5cnn6c(N)ncnc56)O[C@@H]4COP(=O)(S)O[C@@H]2[C@@H]3O)c(=O)[nH]1] | 5-amino-3-[(5R,7R,8R,12aR,14R,15aS,16S)-14-(4-aminopyrazolo[1,5-a][1,3,5]triazin-8-yl)-2,16-dihydroxy-2,10-dioxido-10-sulfanyloctahydro-12H-5,8-methanofuro[3,2-1][1,3,9,11,6,2,10]tetraoxathiadiphosphacyclotetradecin-7-yl]-3,6-dihydro-7H-[1,2,3]triazolo[4,5-d]pyrimidin-7-one (Diastereomer 2) | 690 |

TABLE 9-continued

| Ex. | Structure | Name | Mass [M − H]⁻ |
|---|---|---|---|
| 269 | 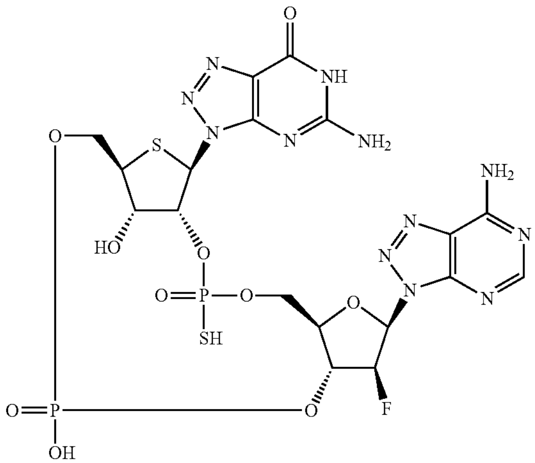 [SMILES: Nc1nc2c(nnn2[C@@H]2S[C@@H]3COP(=O)(O)O[C@H]4[C@H](F)[C@H](n5nnc6c(N)ncnc65)O[C@@H]4COP(=O)(S)O[C@@H]2[C@@H]3O)c(=O)[nH]1] | 5-amino-3-[(5R,7R,8R,12aR,14R,15S,15aR,16S)-14-(7-amino-3H-[1,2,3]triazolo[4,5-d]pyrimidin-3-yl)-15-fluoro-2,16-dihydroxy-2,10-dioxido-10-sulfanyloctahydro-12H-5,8-methanofuro[3,2-1][1,3,9,11,6,2,10]tetraoxathiadiphosphacyclotetradecin-7-yl]-3,6-dihydro-7H-[1,2,3]triazolo[4,5-d]pyrimidin-7-one (Diastereomer 1) | 709 |
| 270 | 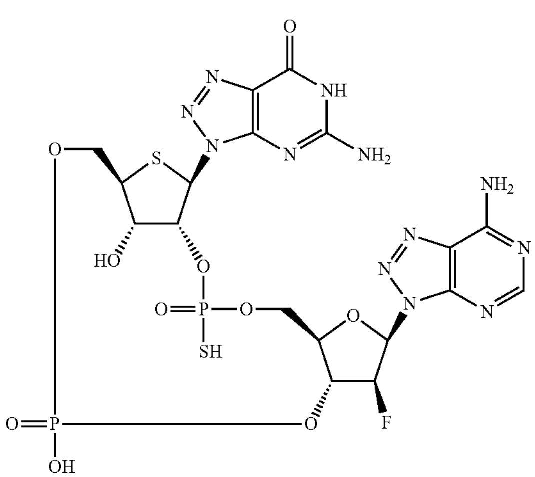 [SMILES: Nc1nc2c(nnn2[C@@H]2S[C@@H]3COP(=O)(O)O[C@H]4[C@H](F)[C@H](n5nnc6c(N)ncnc65)O[C@@H]4COP(=O)(S)O[C@@H]2[C@@H]3O)c(=O)[nH]1] | 5-amino-3-[(5R,7R,8R,12aR,14R,15S,15aR,16S)-14-(7-amino-3H-[1,2,3]triazolo[4,5-d]pyrimidin-3-yl)-15-fluoro-2,16-dihydroxy-2,10-dioxido-10-sulfanyloctahydro-12H-5,8-methanofuro[3,2-1][1,3,9,11,6,2,10]tetraoxathiadiphosphacyclotetradecin-7-yl]-3,6-dihydro-7H-[1,2,3]triazolo[4,5-d]pyrimidin-7-one (Diastereomer 2) | 709 |

TABLE 9-continued

| Ex. | Structure | Name | Mass [M − H]⁻ |
|---|---|---|---|
| 271 | 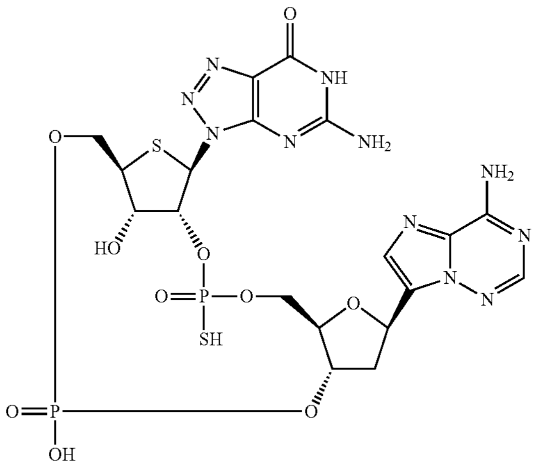 [SMILES: Nc1nc2c(nnn2[C@@H]2S[C@@H]3COP(=O)(O)O[C@H]4C[C@H](c5cnc6c(N)ncnn56)O[C@@H]4COP(=O)(S)O[C@@H]2[C@@H]3O)c(=O)[nH]1] | 5-amino-3-[(5R,7R,8R,12aR,14R,15aS,16S)-14-(4-aminoimidazo[2,1-f][1,2,4]triazin-7-yl)-2,16-dihydroxy-2,10-dioxido-10-sulfanyloctahydro-12H-5,8-methanofuro[3,2-1][1,3,9,11,6,2,10]tetraoxathiadiphosphacyclo-tetradecin-7-yl]-3,6-dihydro-7H-[1,2,3]triazolo[4,5-d]pyrimidin-7-one (Diastereomer 1) | 690 |
| 272 | 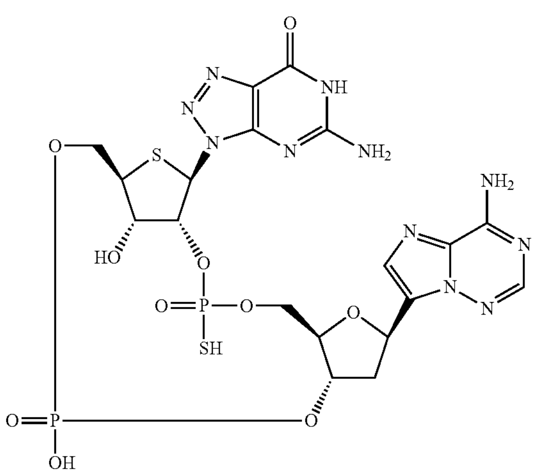 [SMILES: Nc1nc2c(nnn2[C@@H]2S[C@@H]3COP(=O)(O)O[C@H]4C[C@H](c5cnc6c(N)ncnn56)O[C@@H]4COP(=O)(S)O[C@@H]2[C@@H]3O)c(=O)[nH]1] | 5-amino-3-[(5R,7R,8R,12aR,14R,15aS,16S)-14-(4-aminoimidazo[2,1-f][1,2,4]triazin-7-yl)-2,16-dihydroxy-2,10-dioxido-10-sulfanyloctahydro-12H-5,8-methanofuro[3,2-1][1,3,9,11,6,2,10]tetraoxathiadiphosphacyclo-tetradecin-7-yl]-3,6-dihydro-7H-[1,2,3]triazolo[4,5-d]pyrimidin-7-one (Diastereomer 2) | 690 |

Examples 273 and 274: 2-amino-9-[(5R,7R,8S,12aR,14R,15S,15aR,16R)-14-(6-amino-9H-purin-9-yl)-15,16-difluoro-2,10-dihydroxy-2-oxido-10-sulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) and 2-amino-9-[(5R,7R,8S,12aR,14R,15S,15aR,16R)-14-(6-amino-911-purin-9-yl)-15,16-difluoro-2,10-dihydroxy-2-oxido-10-sulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2)

Step 1. (2R,3S,4R,5R)-5-((((((2R,3R,4S,5R)-5-(6-benzamido-9H-purin-9-yl)-2-(bis(4-methoxyphenyl)(phenyl)methoxy)methyl)-4-fluorotetrahydrofuran-3-yl)oxy)(2-cyanoethoxy)phosphoryl)oxy)methyl)-4-fluoro-2-(2-isobutyramido-6-oxo-, 6-dihydro-9H-purin-9-yl)tetrahydrofuran-3-yl phosphonate

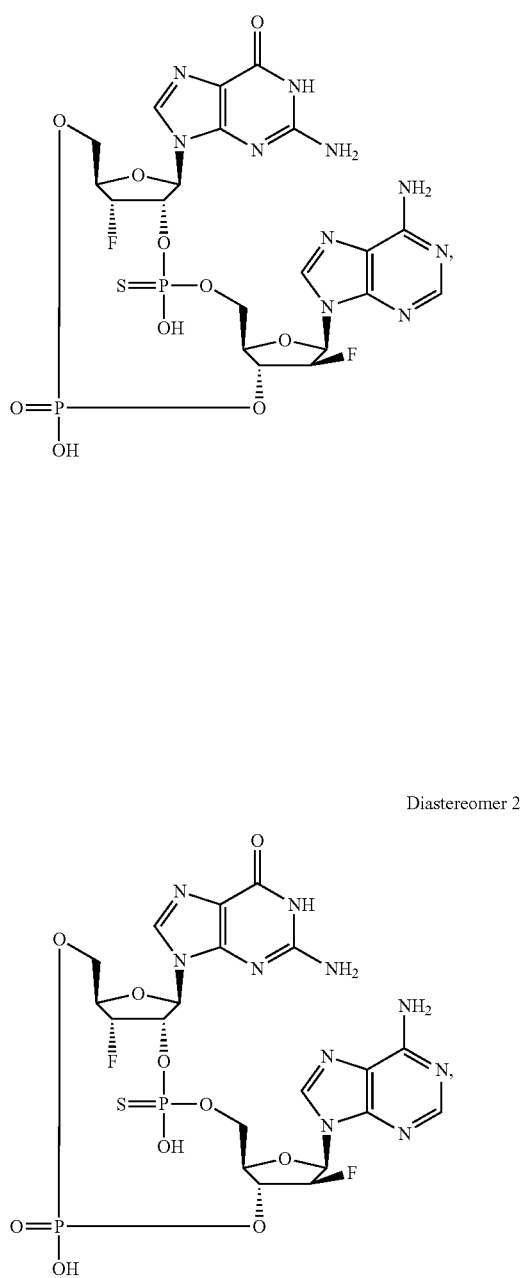

Diastereomer 1

Diastereomer 2

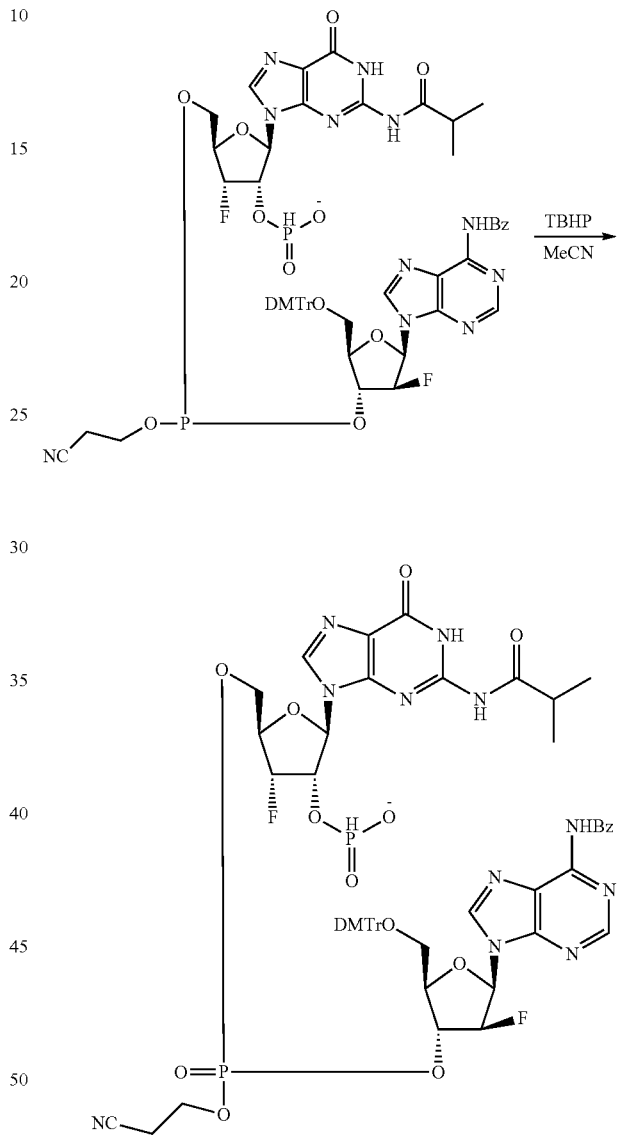

To a mixture containing the crude (2R,3S,4R,5R)-5-((((((2R,3R,4S,5R)-5-(6-benzamido-9H-purin-9-yl)-2-((bis(4-methoxyphenyl)(phenyl)methoxy)methyl)-4-fluorotetrahydrofuran-3-yl)oxy)(2-cyanoethoxy)phosphanyl)oxy)methyl)-4-fluoro-2-(2-isobutyramido-6-oxo-1,6-dihydro-9H-purin-9-yl)tetrahydrofuran-3-yl phosphonate (product of Step 1, Examples 244-247, crude, assumed 0.75 mmol) was added tert-butyl hydroperoxide in decane (5.5M, 0.48 mL, 2.6 mmol) dropwise, and the mixture was stirred at rt for 1 h. Then, it was cooled to 0° C., and a solution of $Na_2S_2O_3$ (553 mg) in water (2 mL) was added slowly. The mixture was stirred at rt for 5 min and then, concentrated to give the product. LCMS (ES, m/z): 1208.5 [M−H]⁻.

737

Step 2. (2R,3S,4R,5R)-5-((((((2R,3R,4S,5R)-5-(6-benzamido-9H-purin-9-yl)-4-fluoro-2-(hydroxymethyl)tetrahydrofuran-3-yl)oxy)(2-cyanoethoxy)phosphoryl)oxy)methyl)-4-fluoro-2-(2-isobutyramido-6-oxo-1,6-dihydro-9H-purin-9-yl)tetrahydrofuran-3-yl phosphonate

738

Step 3. (5R,7R,8S,12aR,14R,15S,15aR,16R)-2-(2-cyanoethoxy)-15,16-difluoro-7-{2-[(2-methylpropanoyl)amino]-6-oxo-1,6-dihydro-9H-purin-9-yl}-14-{6-[(phenylcarbonyl)amino]-9H-purin-9-yl}octahydro-12H-5,8-methanofuro[3,2-l][1,3,6,9,11,2,10]pentaoxadiphosphacyclotetradecin-10-olate 2-oxide

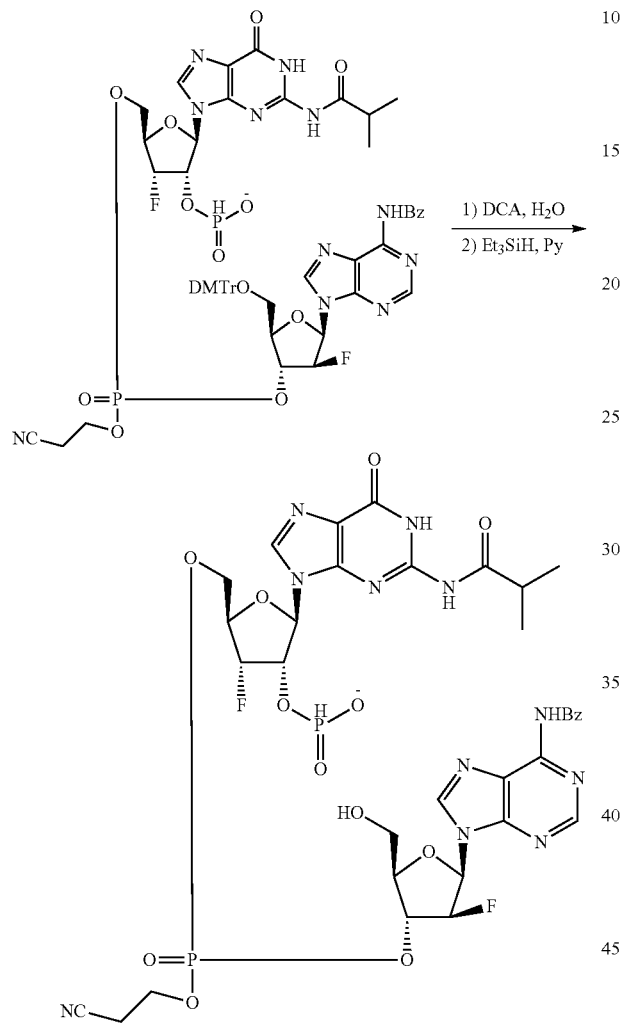

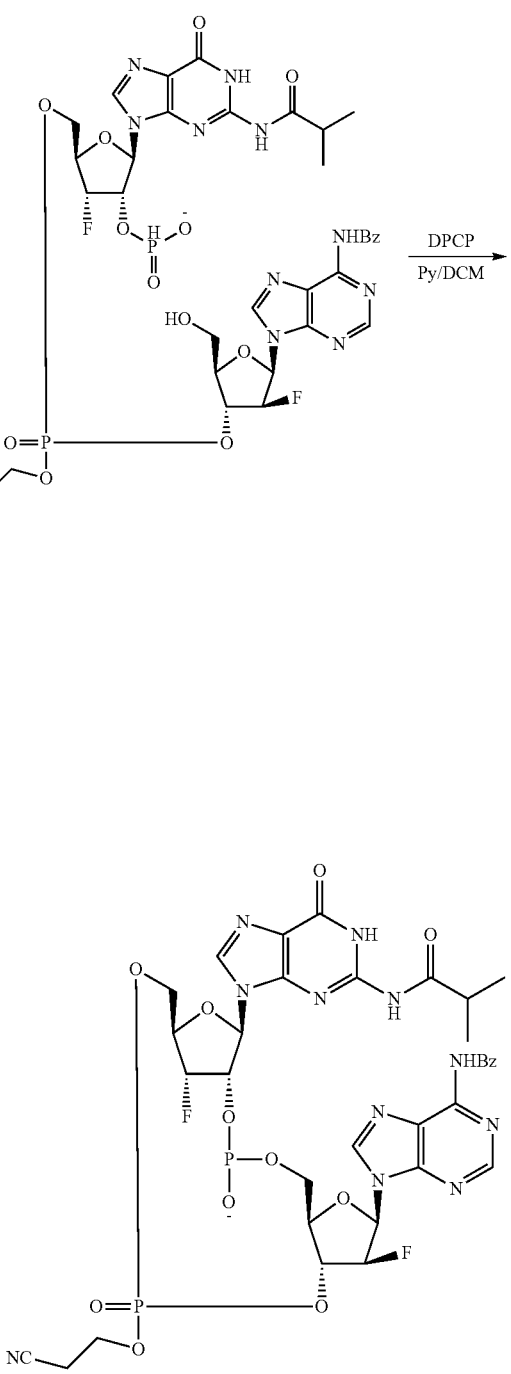

To a solution of the crude from Step 1 in CH$_2$Cl$_2$ (10 mL) was added water (130 mg, 7.5 mmol) and 2,2-dichloroacetic acid (0.77 g, 6 mmol) in CH$_2$Cl$_2$ (10 mL). After 20 min, triethylsilane (20 mL) was added, and stirring was continued for 2 h. Pyridine (1 mL) was added, and the reaction mixture was concentrated. The residue was purified by reverse phase (C18) chromatography eluted with 0 to 95% ACN in aq NH$_4$HCO$_3$ (0.04%) to give the product. LCMS (ES, m/z): 908.2 [M+H]$^+$. $^1$H-NMR: (400 MHz, CD$_3$OD) δ 8.76 (d, J=7.7 Hz, 2H), 8.65 (s, 1H), 8.56 (s, 1H), 8.21-8.08 (m, 6H), 7.69 (t, J=7.4 Hz, 2H), 7.64-7.50 (m, 5H), 6.67 (ddd, J=32.7, 14.9, 4.4 Hz, 2H), 6.21-6.10 (m, 2H), 5.99-5.91 (m, 1H), 5.64-5.57 (m, 1H), 5.56-5.45 (m, 3H), 5.38 (s, 3H), 4.71-4.54 (m, 6H), 4.47-4.23 (m, 5H), 3.92 (d, J=3.8 Hz, 1H), 3.89-3.80 (m, 2H), 2.94 (dt, J=31.1, 5.9 Hz, 4H), 2.83-2.74 (m, 2H), 1.36-1.19 (m, 13H), 1.12 (s, 2H). $^{31}$P-NMR: (162 MHz, CD$_3$OD) δ 2.55, −1.33, −3.09, −3.11, −155.89.

To pyridine (50 mL) under Ar was added diphenyl chlorophosphate (2.66 g, 9.92 mmol). It was cooled at −40° C., and then, a solution of (2R,3 S,4R,5R)-5-(((((2R,3R,4S, 5R)-5-(6-benzamido-9H-purin-9-yl)-4-fluoro-2-(hydroxymethyl)tetrahydrofuran-3-yl)oxy)(2-cyanoethoxy)phosphoryl)oxy)methyl)-4-fluoro-2-(2-isobutyramido-6-oxo-1, 6-dihydro-9H-purin-9-yl)tetrahydrofuran-3-yl phosphonate (450 mg, 496 mmol, co-evaporated with pyridine 3×5 mL) in $CH_2Cl_2$ (50 mL) was added dropwise over 20 min. The resulting mixture was stirred at −40° C. for 20 min. The reaction mixture was immediately used in the next step without purification. LCMS (ES, m/z): 891.1 [M+H]$^+$.

Step 4: (5R,7R,8S,12aR,14R,15S,15aR,16R)-2-(2-cyanoethoxy)-15,16-difluoro-7-{2-[(2-methylpropanoyl)amino-6-oxo-1,6-dihydro-9H-purin-9-yl}-14-{6-[(phenylcarbonyl)amino]-9H-purin-9-yl}octahydro-12H-5,8-methanofuro[3,2-l]1,3,6,9,11,2,10]pentaoxadiphosphacyclotetradecin-10-olate 2-oxide 10-sulfide

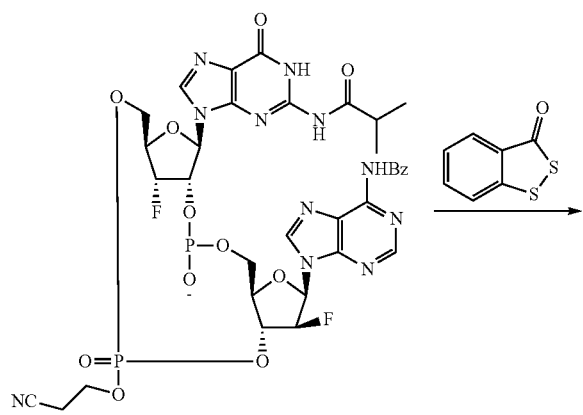

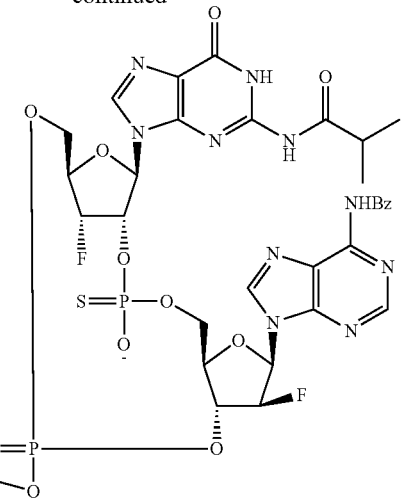

To the reaction mixture of Step 3 at −40° C. was added 3H-benzo[c][1,2]dithiol-3-one (32.76 mg, 0.195 mmol) and water (125 mg, 0.744 mmol). After stirring at rt for 40 min, the reaction mixture was concentrated under reduced pressure. The residue was purified by reverse phase (C18) chromatography eluted with 0 to 95% ACN in aq $NH_4HCO_3$ (0.04%) to give the product. LCMS (ES, m/z): 922.1 [M+H]$^+$. $^1$H-NMR: (400 MHz, $CD_3OD$) δ 8.81-8.73 (m, 2H), 8.63-8.48 (m, 2H), 8.24 (s, 1H), 8.21-8.10 (m, 5H), 7.73-7.56 (m, 7H), 6.83-6.72 (m, 2H), 6.28 (d, J=8.6 Hz, 1H), 6.14 (d, J=8.5 Hz, 1H), 5.83-5.56 (m, 4H), 5.49 (d, J=11.1 Hz, 1H), 4.76-4.46 (m, 11H), 4.37 (s, 1H), 4.29 (d, J=6.8 Hz, 1H), 4.18 (d, J=10.2 Hz, 1H), 3.04 (dd, J=6.5, 5.1 Hz, 4H), 2.83-2.68 (m, 1H), 2.06 (s, 2H), 1.23 (dd, J=22.5, 6.9 Hz, 9H), 1.14-1.05 (m, 3H). $^{31}$P-NMR: (162 MHz, $CD_3OD$) δ62.41, 56.84, 56.29, −3.14, −3.35, −4.77, −5.06, −60.84.

Step 5: 2-amino-9-[(5R,7R,8S,12aR,14R,15S,15aR, 16R)-14-(6-amino-9H-purin-9-yl)-15,16-difluoro-2, 10-dihydroxy-2-oxido-10-sulfidooctahydro-12H-5,8-methanofuro[3,2-l][1,3,6,9,11,2,10] pentaoxadiphosphacyclotetradecin-7-yl]-1,9-dihydro-6H-purin-6-one (Diastereomers 1 and 2)

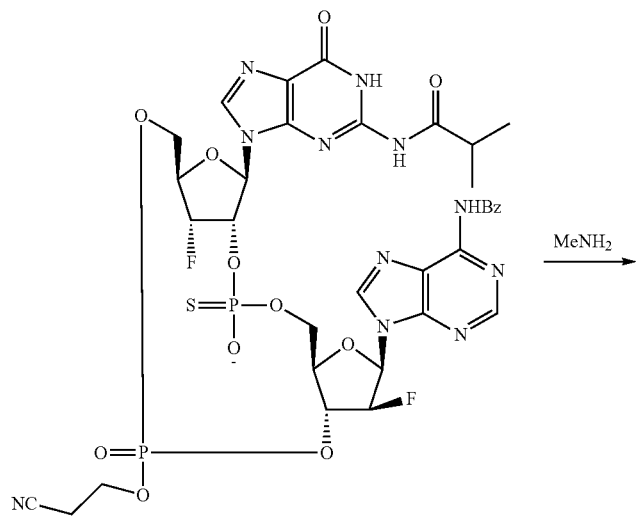

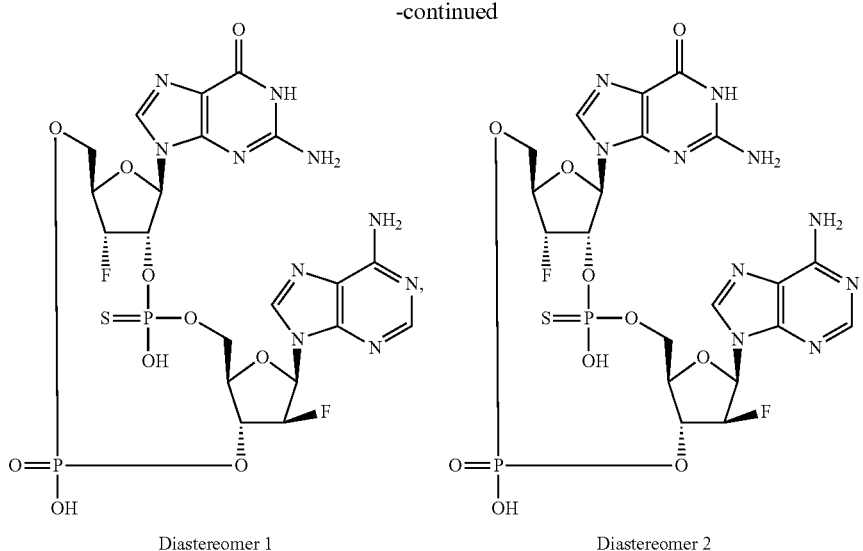

Diastereomer 1                    Diastereomer 2

The (5R,7R,8S,12aR,14R,15S,15aR,16R)-2-(2-cyanoethoxy)-15,16-difluoro-7-{2-[(2-methylpropanoyl)amino]-6-oxo-1,6-dihydro-9H-purin-9-yl}-4-{6-[(phenylcarbonyl)amino]-9H-purin-9-yl}octahydro-12H-5,8-methanofuro[3,2-l][1,3,6,9,11,2,10]pentaoxadiphosphacyclotetradecin-10-olate 2-oxide 10-sulfide (380 mg, 0.377 mmol) was dissolved in a solution of MeNH$_2$ in EtOH (30%, 30 mL), and the resulting solution was stirred at rt for 2 h. Then, it was concentrated, and the residue was purified by Prep-HPLC (XBridge Shield RP18 OBD Column, 19×150 mm) eluted with 4 to 10% ACN in aq NH$_4$HCO$_3$ (10 mM) over 20 min.

Example 273: 2-amino-9-[(5R,7R,8 S,12aR,14R,15S,15aR,16R)-14-(6-amino-9H-purin-9-yl)-15,16-difluoro-2,10-dihydroxy-2-oxido-10-sulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1): T$_R$=10.10 min. LCMS (ES, m/z): 693.0 [M−H]$^-$. $^1$H-NMR: (400 MHz, CDCl$_3$) δ 10.84 (d, J=2.4 Hz, 1H), 10.72 (s, 1H), 10.59 (d, J=3.9 Hz, 1H), 9.01 (dd, J=19.4, 3.0 Hz, 1H), 8.56 (d, J=8.5 Hz, 1H), 8.14-7.96 (m, 2H), 7.93-7.82 (m, 1H), 7.73 (dd, J=12.0, 6.5 Hz, 2H), 7.31-7.19 (m, 2H), 7.15 (d, J=2.8 Hz, 1H), 6.94-6.74 (m, 3H), 6.71-6.53 (m, 2H). $^{31}$P-NMR: (162 MHz, D$_2$O): δ 62.301 (s, 1P), 0.976 (s, 1P).

Example 274: 2-amino-9-[(5R,7R,8 S,12aR,14R,15S,15aR,16R)-14-(6-amino-9H-purin-9-yl)-15,16-difluoro-2,10-dihydroxy-2-oxido-10-sulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2): T$_R$: 14.27 min. LCMS (ES, m/z): 692.9 [M−H]$^-$. $^1$H-NMR: (400 MHz, DMSO-d6) δ 8.31 (d, J=11.0 Hz, 2H), 8.18 (s, 1H), 6.40 (dd, J=22.6, 2.6 Hz, 1H), 5.88 (d, J=8.8 Hz, 1H), 5.44 (d, J=33.7 Hz, 2H), 5.35-5.23 (m, 1H), 5.24-5.05 (m, 2H), 4.48-4.34 (m, 1H), 4.31 (dd, J=10.6, 4.5 Hz, 1H), 4.16-3.87 (m, 3H). $^{31}$P-NMR: (162 MHz, DMSO-d6): δ 55.096 (s, 1P), −2.731 (s, 1P).

Examples 275 through 288, as shown in Table 10 below, were prepared according to procedures analogous to those outlined in Examples 274 and 275 above using the appropriate monomeric nucleosides, described as Preparations or as obtained from commercial sources.

TABLE 10

| Ex. | Structure | Name | Mass [M − H] |
|---|---|---|---|
| 275 | (structure shown) | 2-amino-9-[(5S,7R,8R,12aR,14R,15aS)-14-(4-amino-7H-pyrrolo[2,3-d]pyrimidin-7-yl)-2,10-dihydroxy-2-oxido-10-sulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 656 |

TABLE 10-continued

| Ex. | Structure | Name | Mass [M − H] |
|---|---|---|---|
| 276 | 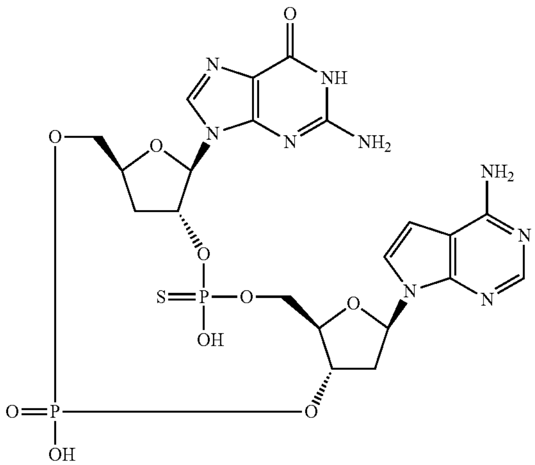 [SMILES: Nc1nc2c(ncn2[C@@H]2O[C@@H]3COP(=O)(O)O[C@H]4C[C@H](n5ccc6c(N)ncnc65)O[C@@H]4COP(O)(=S)O[C@@H]2C3)c(=O)[nH]1] | 2-amino-9-[(5S,7R,8R,12aR,14R,15aS)-14-(4-amino-7H-pyrrolo[2,3-d]pyrimidin-7-yl)-2,10-dihydroxy-2-oxido-10-sulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 656 |
| 277 | 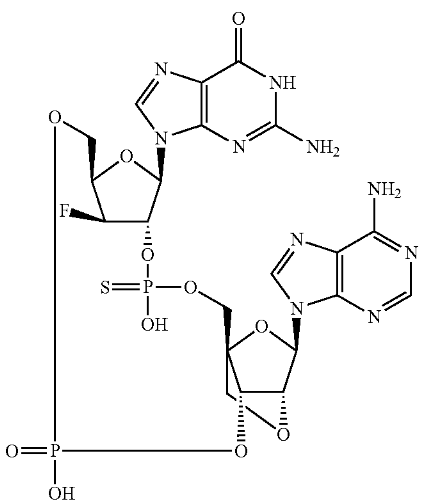 [SMILES: Nc1nc2c(ncn2[C@@H]2O[C@@H]3COP(=O)(O)O[C@H]4[C@H]5OC[C@]4(COP(O)(=S)O[C@@H]2[C@H]3F)O[C@H]5n2cnc3c(N)ncnc32)c(=O)[nH]1] | 2-amino-9-[(5R,7R,8S,12aR,14R,15R,15aS,18S)-14-(6-amino-9H-purin-9-yl)-18-fluoro-2,10-dihydroxy-2-oxido-10-sulfindohexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one (Diastereomer 1) | 703 |
| 278 | 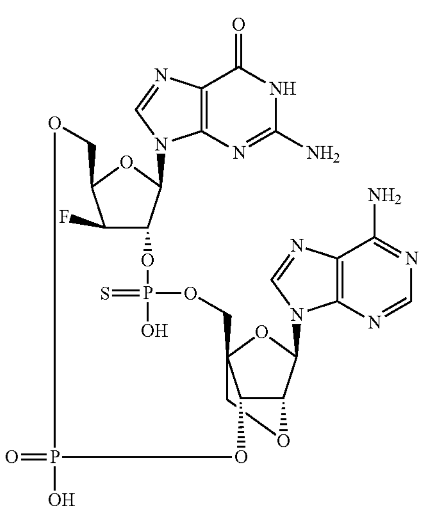 [SMILES: Nc1nc2c(ncn2[C@@H]2O[C@@H]3COP(=O)(O)O[C@H]4[C@H]5OC[C@]4(COP(O)(=S)O[C@@H]2[C@H]3F)O[C@H]5n2cnc3c(N)ncnc32)c(=O)[nH]1] | 2-amino-9-[(5R,7R,8S,12aR,14R,15R,15aS,18S)-14-(6-amino-9H-purin-9-yl)-18-fluoro-2,10-dihydroxy-2-oxido-10-sulfidohexahydro-14H-15,12a-(epoxymethano)-5,8-methanofuro[3,2-l][1,3,6,9,11,2,10]pentaoxadiphosphacyclotetradecin-7(12H)-yl]-1,9-dihydro-6H-purin-6-one (Diastereomer 2) | 703 |

TABLE 10-continued

| Ex. | Structure | Name | Mass [M − H] |
|---|---|---|---|
| 279 | 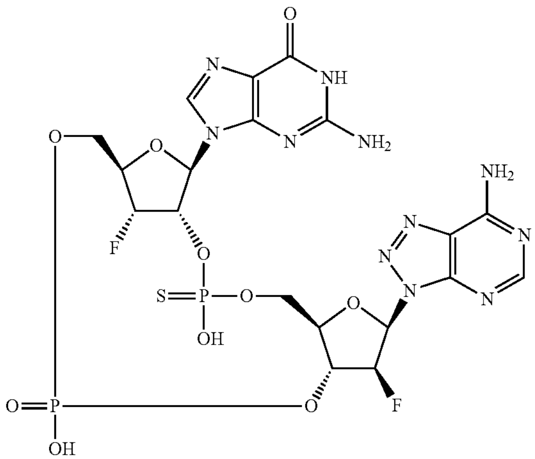 [SMILES: Nc1nc2c(ncn2[C@@H]2O[C@@H]3COP(=O)(O)O[C@H]4[C@H](F)[C@H](n5nnc6c(N)ncnc65)O[C@@H]4COP(O)(=S)O[C@@H]2[C@@H]3F)c(=O)[nH]1] | 2-amino-9-[(5R,7R,8S,12aR,14R,15S,15aR,16R)-14-(7-amino-3H-[1,2,3]triazolo[4,5-d]pyrimidin-3-yl)-15,16-difluoro-2,10-dihydroxy-2-oxido-10-sulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 694 |
| 280 | 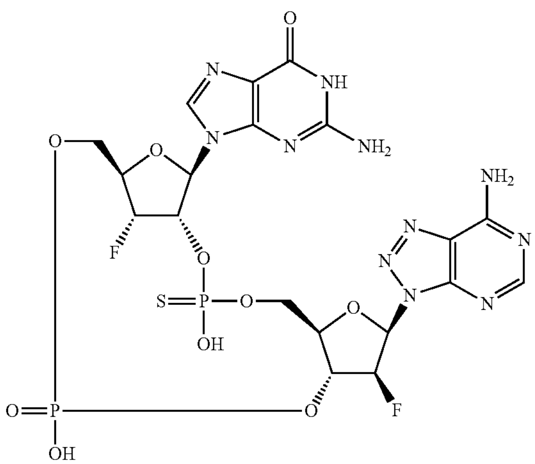 [SMILES: Nc1nc2c(ncn2[C@@H]2O[C@@H]3COP(=O)(O)O[C@H]4[C@H](F)[C@H](n5nnc6c(N)ncnc65)O[C@@H]4COP(O)(=S)O[C@@H]2[C@@H]3F)c(=O)[nH]1] | 2-amino-9-[(5R,7R,8S,12aR,14R,15S,15aR,16R)-14-(7-amino-3H-[1,2,3]triazolo[4,5-d]pyrimidin-3-yl)-15,16-difluoro-2,10-dihydroxy-2-oxido-10-sulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 694 |
| 281 | 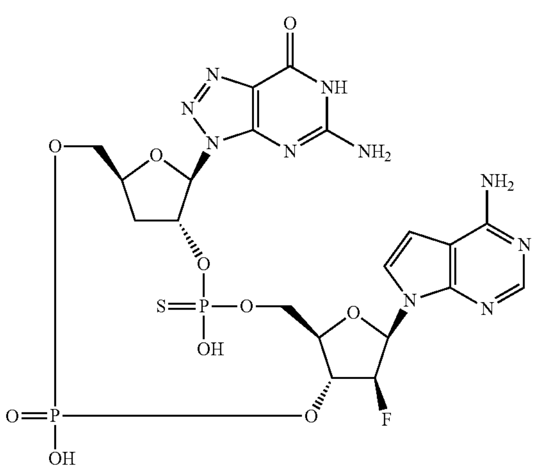 [SMILES: Nc1nc2c(nnn2[C@@H]2O[C@@H]3COP(=O)(O)O[C@H]4[C@H](F)[C@H](n5ccc6c(N)ncnc65)O[C@@H]4COP(O)(=S)O[C@@H]2C3)c(=O)[nH]1] | 5-amino-3-[(5S,7R,8R,12aR,14R,15S,15aR)-14-(4-amino-7H-pyrrolo[2,3-d]pyrimidin-7-yl)-15-fluoro-2,10-dihydroxy-2-oxido-10-sulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one | 675 |

TABLE 10-continued

| Ex. | Structure | Name | Mass [M − H] |
|---|---|---|---|
| 282 | 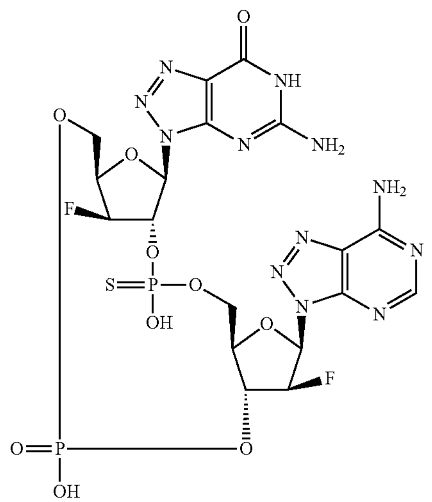 [SMILES: Nc1nc2c(nnn2[C@@H]2O[C@@H]3COP(=O)(O)O[C@H]4[C@H](F)[C@H](n5nnc6c(N)ncnc65)O[C@@H]4COP(O)(=S)O[C@@H]2[C@H]3F)c(=O)[nH]1] | 5-amino-3-[(5R,7R,8S,12aR,14R,15S,15aR,16S)-14-(7-amino-3H-[1,2,3]triazolo[4,5-d]pyrimidin-3-yl)-15,16-difluoro-2,10-dihydroxy-2-oxido-10-sulfidooctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one | 695 |
| 283 | 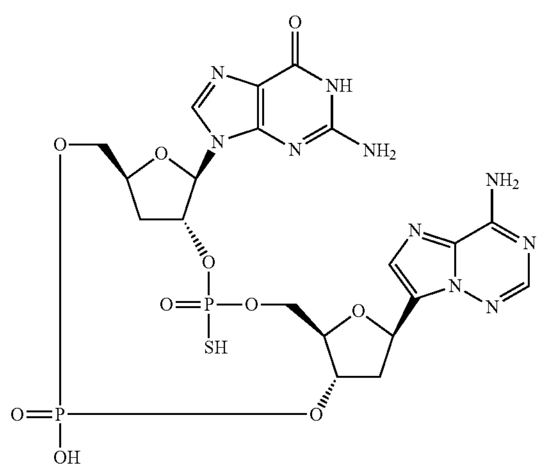 [SMILES: Nc1nc2c(ncn2[C@@H]2O[C@@H]3COP(=O)(O)O[C@H]4C[C@H](c5cnc6c(N)ncnn56)O[C@@H]4COP(=O)(S)O[C@@H]2C3)c(=O)[nH]1] | 2-amino-9-[(5S,7R,8R,12aR,14R,15aS)-14-(4-aminoimidazo[2,1-f][1,2,4]triazin-7-yl)-2-hydroxy-2,10-dioxido-10-sulfanyloctahydro-12H-5,8-methanofuro[3,2-1][1,3,6,9,11,2,10]pentaoxadiphosphacyclotetradecin-7-yl]-1,9-dihydro-6H-purin-6-one | 657 |
| 284 | 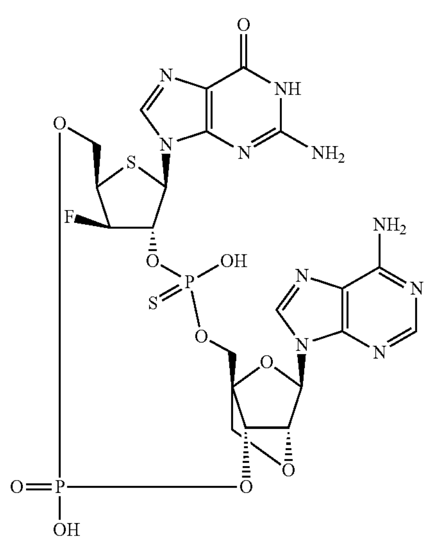 [SMILES: Nc1nc2c(ncn2[C@@H]2S[C@@H]3COP(=O)(O)O[C@H]4[C@H]5OC[C@]4(COP(O)(=S)O[C@@H]2[C@H]3F)O[C@H]5n2cnc3c(N)ncnc32)c(=O)[nH]1] | 2-amino-9-[(5R,7R,8R,12aR,14R,15R,15aS,18R)-14-(6-amino-9H-purin-9-yl)-18-fluoro-2,10-dihydroxy-2-oxido-10-sulfidohexahydro-14H-15,12a-(epoxymethano)-5,8-methanofuro[3,2-l][1,3,9,11,6,2,10]tetraoxathiadiphosphacyclotetradecin-7(12H)-yl]-1,9-dihydro-6H-purin-6-one | 719 |

TABLE 10-continued

| Ex. | Structure | Name | Mass [M − H] |
|---|---|---|---|
| 285 | 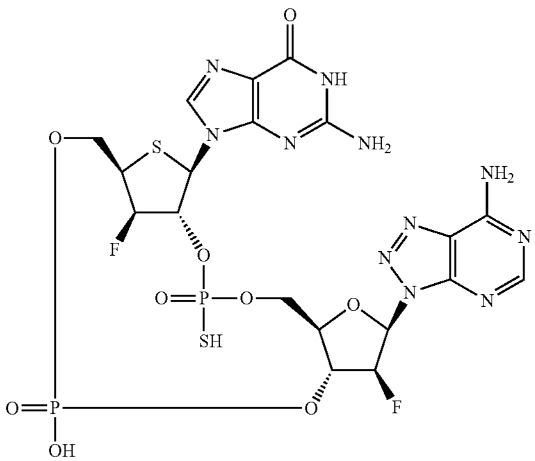 [SMILES: Nc1nc2c(ncn2[C@@H]2S[C@@H]3COP(=O)(O)O[C@H]4[C@H](F)[C@H](n5nnc6c(N)ncnc65)O[C@@H]4COP(=O)(S)O[C@@H]2[C@H]3F)c(=O)[nH]1] | 2-amino-9-[(5R,7R,8R,12aR,14R,15S,15aR,16R)-14-(7-amino-3H-[1,2,3]triazolo[4,5-d]pyrimidin-3-yl)-15,16-difluoro-2-hydroxy-2,10-dioxido-10-sulfanyloctahydro-12H-5,8-methanofuro[3,2-l][1,3,9,11,6,2,10]tetraoxathiadiphosphacyclo-tetradecin-7-yl]-1,9-dihydro-6H-purin-6-one | 710 |
| 286 | 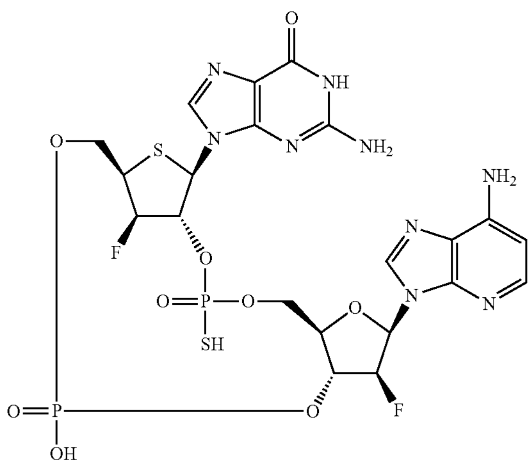 [SMILES: Nc1nc2c(ncn2[C@@H]2S[C@@H]3COP(=O)(O)O[C@H]4[C@H](F)[C@H](n5cnc6c(N)ccnc65)O[C@@H]4COP(=O)(S)O[C@@H]2[C@H]3F)c(=O)[nH]1] | 2-amino-9-[(5R,7R,8R,12aR,14R,15S,15aR,16R)-14-(7-amino-3H-imidazo[4,5-b]pyridin-3-yl)-15,16-difluoro-2-hydroxy-2,10-dioxido-10-sulfanyloctahydro-12H-5,8-methanofuro[3,2-l][1,3,9,11,6,2,10]tetraoxathiadiphosphacyclo-tetradecin-7-yl]-1,9-dihydro-6H-purin-6-one (Diastereomer 1) | 708 |
| 287 | 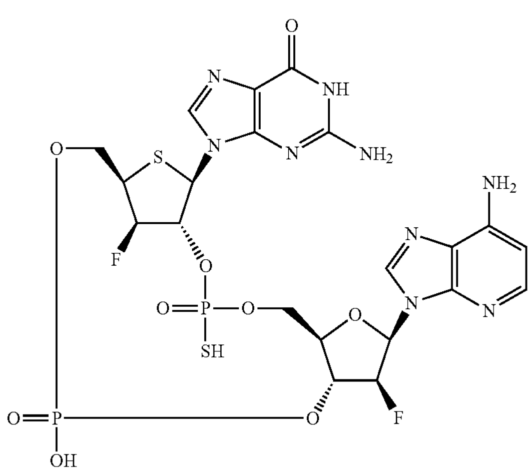 [SMILES: Nc1nc2c(ncn2[C@@H]2S[C@@H]3COP(=O)(O)O[C@H]4[C@H](F)[C@H](n5cnc6c(N)ccnc65)O[C@@H]4COP(=O)(S)O[C@@H]2[C@H]3F)c(=O)[nH]1] | 2-amino-9-[(5R,7R,8R,12aR,14R,15S,15aR,16R)-14-(7-amino-3H-imidazo[4,5-b]pyridin-3-yl)-15,16-difluoro-2-hydroxy-2,10-dioxido-10-sulfanyloctahydro-12H-5,8-methanofuro[3,2-l][1,3,9,11,6,2,10]tetraoxathiadiphosphacyclo-tetradecin-7-yl]-1,9-dihydro-6H-purin-6-one (Diastereomer 2) | 708 |

TABLE 10-continued

| Ex. | Structure | Name | Mass [M − H] |
|---|---|---|---|
| 288 | 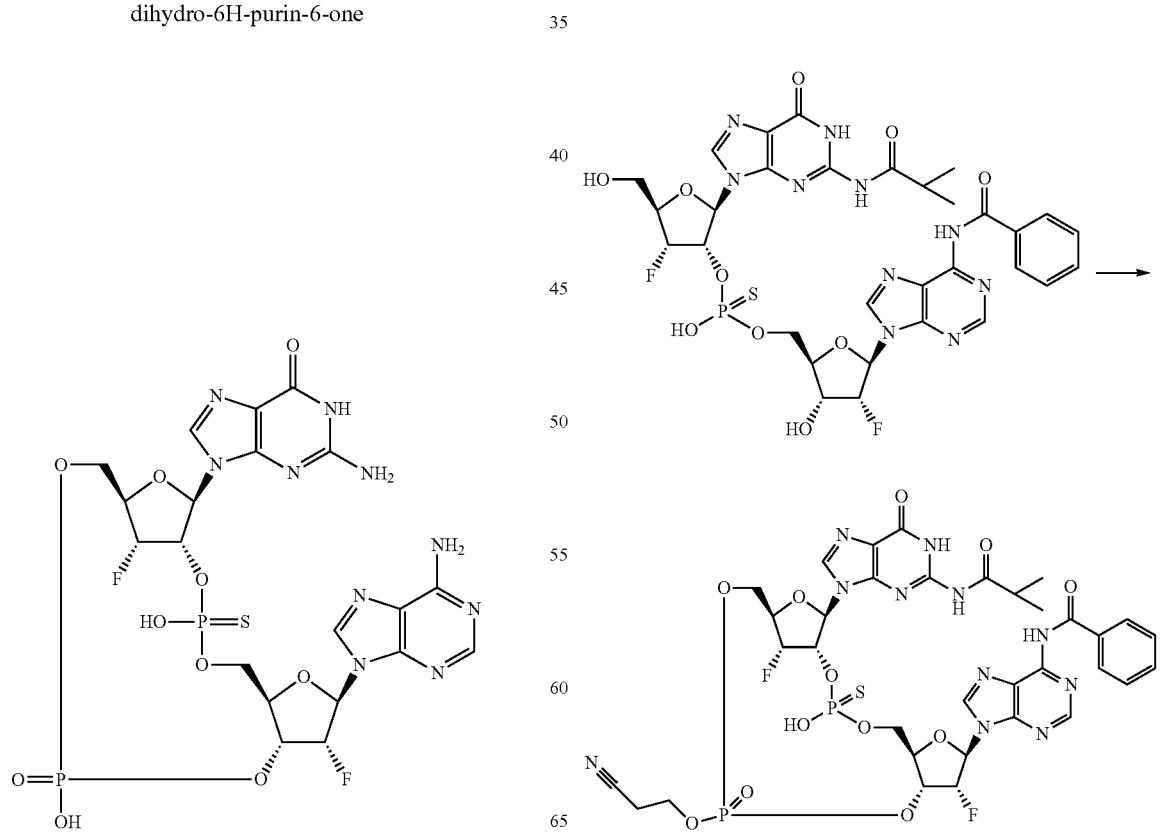 | 2-amino-9-[(5R,7R,8R,12aR,14R,15aR,16R)-14-(7-amino-3H-[1,2,3]triazolo[4,5-d]pyrimidin-3-yl)-15,15,16-trifluoro-2-hydroxy-2,10-dioxido-10-sulfanyloctahydro-12H-5,8-methanofuro[3,2-l][1,3,9,11,6,2,10]tetraoxathiadiphosphacyclo-tetradecin-7-yl]-1,9-dihydro-6H-purin-6-one | 728 |

Example 289: 2-amino-9-[(5R,7R,8S,12aR,14R,15R,15aR,16R)-14-(6-amino-9H-purin-9-yl)-15,16-difluoro-2,10-dihydroxy-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one Step 1: N-{9-[(5R,7R,8S,12aR,14R,15R,15aR,16R)-2-(2-cyanoethoxy)-15,16-difluoro-10-hydroxy-7-{2-[(2-methylpropanoyl)amino]-6-oxo-1,6-dihydro-9H-purin-9-yl}-2-oxido-10-sulfidooctahydro-12H-5,8-methanofuro[3,2-l][1,3,6,9,11,2,10]pentaoxadiphosphacyclotetradecin-14-yl]-9H-purin-6-yl}benzamide O-(((2R,3R,4R,5R)-5-(6-benzamido-9H-purin-9-yl)-4-fluoro-3-hydroxytetrahydrofuran-2-yl)methyl)O-((2R,3S,4R,5R)-4-fluoro-5-(hydroxymethyl)-2-(2-isobutyramido-6-oxo-1H-purin-9(6H)-yl)tetrahydrofuran-3-yl)O-hydrogen phosphorothioate (product of Step 3, Example 261, 100 mg, 0.124 mmol) and diisopropylammonium tetrazolide (31.8 mg, 0.186 mmol) were azeotrope with dry CH₃CN (3×10 ml) and dried under high vacuum for 30 min.

The above mixture was dissolved in DMF (1 mL) and acetonitrile (7 mL) and added 200 mg active MS 4 Å and a solution of 2-cyanoethyl N,N,N',N'-tetraisopropylphosphorodiamidite (51.1 mg, 0.161 mmol) in 1 ml dry CH₃CN. The resulting mixture was stirred at rt for 30 min, followed by addition of 1H-tetrazole (43.4 mg, 0.620 mmol). The reaction stayed at rt for 1 h and added tert-butyl hydroperoxide (5.0M in Decane)(0.074 mL, 0.372 mmol). The stirring continued for 1 h and concentrated in vacuo. The residue was purified by column chromatography on silica gel, eluting with 0-8% MeOH/DCM to give the desired product. LCMS (ES, m/z): 922 [M+H]⁺

Step 2: 2-amino-9-[(5R,7R,8S,12aR,14R,15R,15aR,16R)-14-(6-amino-9H-purin-9-yl)-15,16-difluoro-2,10-dihydroxy-2-oxido-10-sulfidooctahydro-12H-5,8-methanofuro[3,2-l][1,3,6,9,11,2,10]pentaoxadiphosphacyclotetradecin-7-yl]-1,9-dihydro-6H-purin-6-one

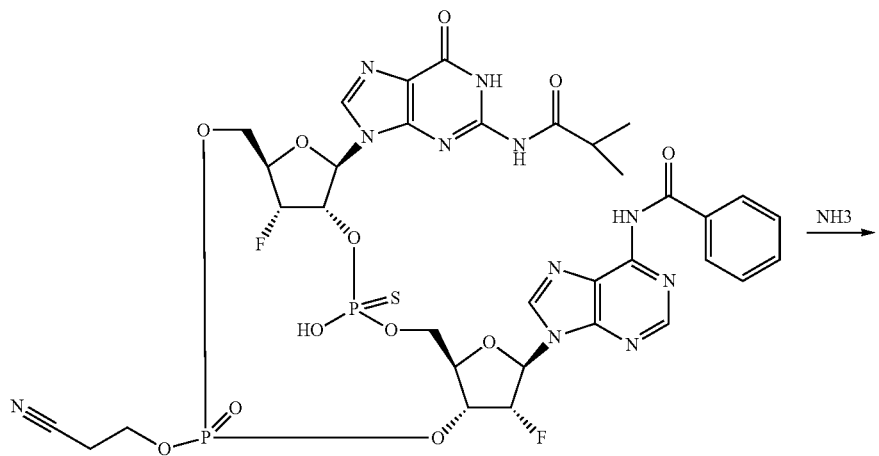

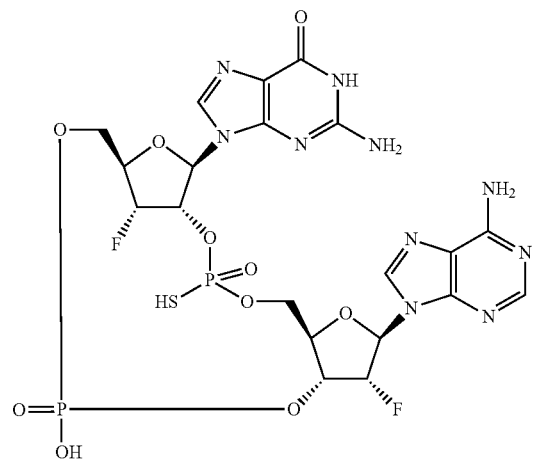

N-{9-[(5R,7R,8S,12aR,14R,15R,15aR,16R)-2-(2-cyan-oethoxy)-15,16-difluoro-10-hydroxy-7-{2-[(2-methylpropanoyl)amino]-6-oxo-1,6-dihydro-9H-purin-9-yl}-2-oxido-10-sulfidooctahydro-12H-5,8-methanofuro[3,2-l][1,3,6,9,11,2,10]pentaoxadiphosphacyclotetradecin-14-yl]-9H-purin-6-yl}benzamide (90 mg, 0.098 mmol) and ammonia (7.0M in MeOH) (2 ml, 14.00 mmol) were sealed in a microwave tube. The mixture was heated to 50° C. and stirred for 4 h. The reaction mixture was concentrated, and purified using mass-directed reverse phase HPLC (X-Bridge BEH 150 Prep C18) using a gradient solvent system with MeCN and 100 mM aqueous triethylammonium acetate to give three desired diastereomers. Lyophilization of the product fractions furnished 2-amino-9-[(5R,7R,8S,12aR,14R,15R,15aR,16R)-14-(6-amino-9H-purin-9-yl)-15,16-difluoro-2,10-dihydroxy-2-oxido-10-sulfidooctahydro-12H-5,8-methanofuro[3,2-l][1,3,6,9,11,2,10]pentaoxadiphosphacyclotetradecin-7-yl]-1,9-dihydro-6H-purin-6-one. LCMS (ES, m/z): 693 [M−H]$^-$. $^1$H NMR (H2O-d2, 500 MHz): $\delta_H$ 8.23 (2H, d, J=5.2 Hz), 7.81 (1H, s), 6.42 (1H, d, J=14.2 Hz), 5.99 (1H, d, J=8.6 Hz), 5.70 (1H, m), 5.40 (2H, m), 5.20 (1H, m), 4.62 (2H, m), 4.54 (1H, s), 4.15-4.30 (3H, m). $^{31}$P NMR: (H$_2$O-d$_2$, 202 MHz): $\delta$ −1.6, 52.1.

Example 290: 2-amino-9-[(2R,5S,7R,8R,10R,12aR,14R,15R,15aS)-15-hydroxy-2,10-dioxido-14-(6-oxo-1,6-dihydro-9H-purin-9-yl)-2,10-disulfanyloctahydro-12H-5,8-methanofuro[3,2-l][1,3,6,9,11,2,10] pentaoxadiphosphacyclotetradecin-7-yl]-1,9-dihydro-6H-purin-6-one

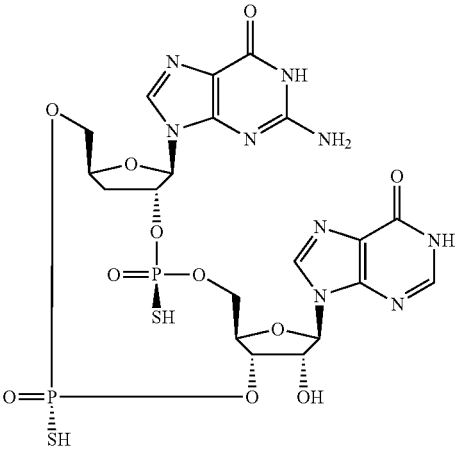 [SMILES: Nc1nc2c(ncn2[C@@H]2O[C@@H]3CO[P@@](=O)(S)O[C@H]4[C@@H](O)[C@H](n5cnc6c(=O)[nH]cnc65)O[C@@H]4CO[P@@](=O)(S)O[C@@H]2C3)c(=O)[nH]1]

To (2R,5S,7R,8R,10R,12aR,14R,15R,15aS)-7-(2-amino-6-oxo-1,6-dihydro-9H-purin-9-yl)-14-(6-amino-9H-purin-9-yl)-15-hydroxyoctahydro-12H-5,8-methanofuro[3,2-l][1,3,6,9,11,2,10]pentaoxadiphosphacyclotetradecine-2,10-bis(thiolate) 2,10-dioxide (Example 86, 5.0 mg, 0.0071 mmol) were added sodium phosphate buffer (pH 6.8, 50 mM, 0.5 mL) and adenosine monophosphate deaminase (3 mg). The reaction mixture was left to stir overnight, filtered, and purified by reverse phase HPLC (1-10% MeCN in aq NH$_4$HCO$_3$ (100 mM)) to afford the title compound as a diammonium salt. LCMS (ES, m/z): 690 [M−H]$^-$. $^1$H NMR (500 MHz, D$_2$O): $\delta$ 8.30 (s, 1H), 8.20 (s, 1H), 7.95 (s, 1H), 6.19 (s, 1H), 5.82 (d, J=6.0 Hz, 1H), 5.64 (m, 1H), 5.15 (m, 1H), 4.86 (d, J=4.5 Hz, 1H), 4.60 (m, 1H), 4.48-4.53 (m, 2H), 4.38 (m, 1H), 4.11 (dd, J=11.5, 4.0 Hz, 1H), 4.05 (m, 1H), 2.63 (m, 1H), 2.52 (m, 1H). $^{31}$P NMR: (202 MHz, D$_2$O): $\delta$ 55.78 (s), 52.44 (s).

Examples 291 through 348 as shown in Table 11 below, were prepared according to procedures analogous to those outlined in Example 290 above, from the starting compound ("St. Cmpd.") indicated.

TABLE 11

| Ex. | Structure | Name | Mass [M − H]$^-$ | St. Cmpd. |
|---|---|---|---|---|
| 291 | ![structure] | 9-[(5R,7R,8R,12aR,14R,15aS,16R)-7-(6-amino-9H-purin-9-yl)-2,10,16-trihydroxy-2,10-dioxidooctahydro-12H-5,8-methanofuro[3,2-l][1,3,6,9,11,2,10]pentaoxadiphosphacyclotetradecin-14-yl]-1,9-dihydro-6H-purin-6-one | 642 | 3 |

TABLE 11-continued

| Ex. | Structure | Name | Mass [M − H]⁻ | St. Cmpd. |
|---|---|---|---|---|
| 292 | 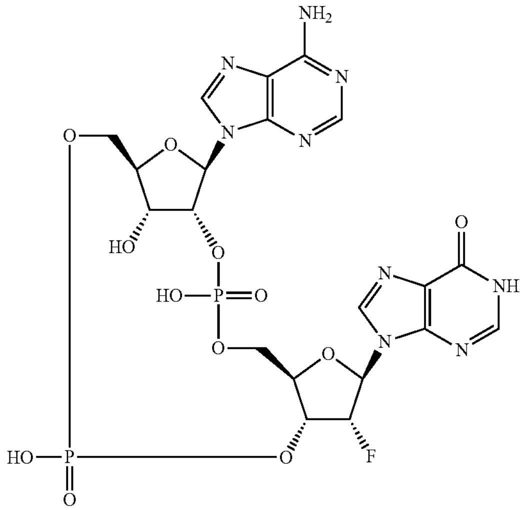 [SMILES: Nc1ncnc2c1ncn2[C@@H]1O[C@@H]2COP(=O)(O)O[C@H]3[C@@H](F)[C@H](n4cnc5c(=O)[nH]cnc54)O[C@@H]3COP(=O)(O)O[C@@H]1[C@@H]2O] | 9-[(5R,7R,8R,12aR,14R,15R,15aR,16R)-7-(6-amino-9H-purin-9-yl)-15-fluoro-2,10,16-trihydroxy-2,10-dioxidooctahydro-12H-5,8-methanofuro[3,2-l][1,3,6,9,11,2,10]pentaoxadiphosphacyclotetradecin-14-yl]-1,9-dihydro-6H-purin-6-one | 660 | 4 |
| 293 | 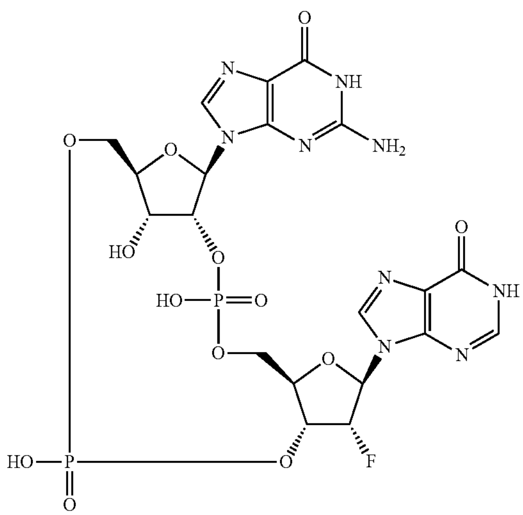 [SMILES: Nc1nc2c(ncn2[C@@H]2O[C@@H]3COP(=O)(O)O[C@H]4[C@@H](F)[C@H](n5cnc6c(=O)[nH]cnc65)O[C@@H]4COP(=O)(O)O[C@@H]2[C@@H]3O)c(=O)[nH]1] | 2-amino-9-[(5R,7R,8R,12aR,14R,15R,15aR,16R)-15-fluoro-2,10,16-trihydroxy-2,10-dioxido-14-(6-oxo-1,6-dihydro-9H-purin-9-yl)octahydro-12H-5,8-methanofuro[3,2-l][1,3,6,9,11,2,10]pentaoxadiphosphacyclo-tetradecin-7-yl]-1,9-dihydro-6H-purin-6-one | 676 | 2 |
| 294 | 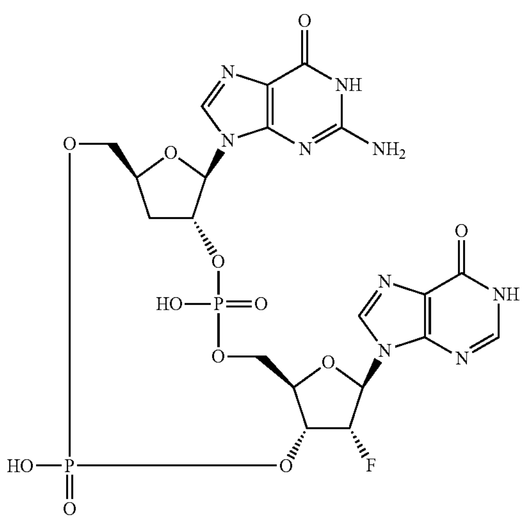 [SMILES: Nc1nc2c(ncn2[C@@H]2O[C@@H]3COP(=O)(O)O[C@H]4[C@@H](F)[C@H](n5cnc6c(=O)[nH]cnc65)O[C@@H]4COP(=O)(O)O[C@@H]2C3)c(=O)[nH]1] | 2-amino-9-[(5S,7R,8R,12aR,14R,15R,15aR)-15-fluoro-2,10-dihydroxy-2,10-dioxido-14-(6-oxo-1,6-dihydro-9H-purin-9-yl)octahydro-12H-5,8-methanofuro[3,2-l][1,3,6,9,11,2,10]pentaoxadiphosphacyclo-tetradecin-7-yl]-1,9-dihydro-6H-purin-6-one | 660 | 21 |

TABLE 11-continued

| Ex. | Structure | Name | Mass [M − H]⁻ | St. Cmpd. |
|---|---|---|---|---|
| 295 | 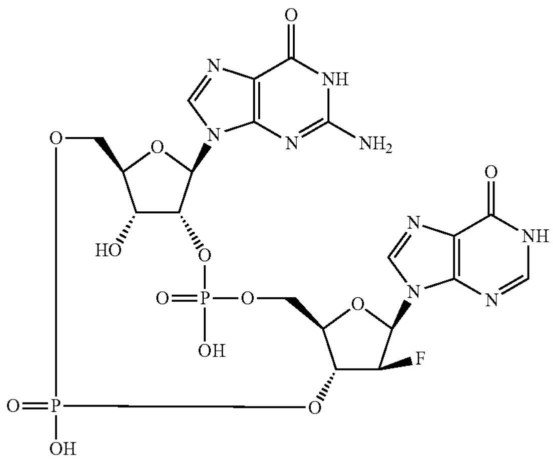 | 2-amino-9-[(5R,7R,8R,12aR,14R,15S,15aR,16R)-15-fluoro-2,10,16-trihydroxy-2,10-dioxido-14-(6-oxo-1,6-dihydro-9H-purin-9-yl)octahydro-12H-5,8-methanofuro[3,2-l][1,3,6,9,11,2,10]pentaoxadiphosphacyclotetradecin-7-yl]-1,9-dihydro-6H-purin-6-one | 676 | 7 |
| 296 | 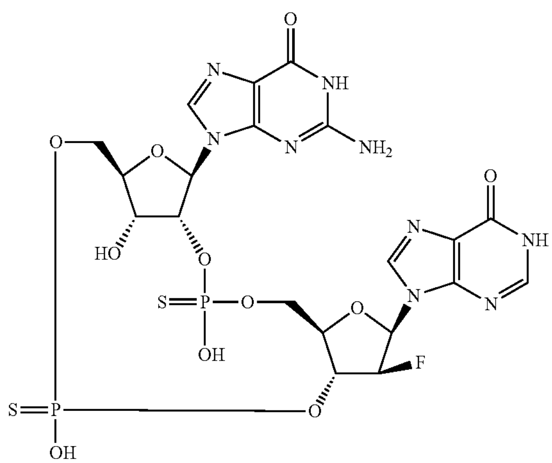 [SMILES: Nc1nc2c(ncn2[C@@H]2O[C@@H]3COP(O)(=S)O[C@H]4[C@H](F)[C@H](n5cnc6c(=O)[nH]cnc65)O[C@@H]4COP(O)(=S)O[C@@H]2[C@@H]3O)c(=O)[nH]1] | 2-amino-9-[(5R,7R,8R,12aR,14R,15S,15aR,16R)-15-fluoro-2,10,16-trihydroxy-14-(6-oxo-1,6-dihydro-9H-purin-9-yl)-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 708 | 90 |
| 297 | 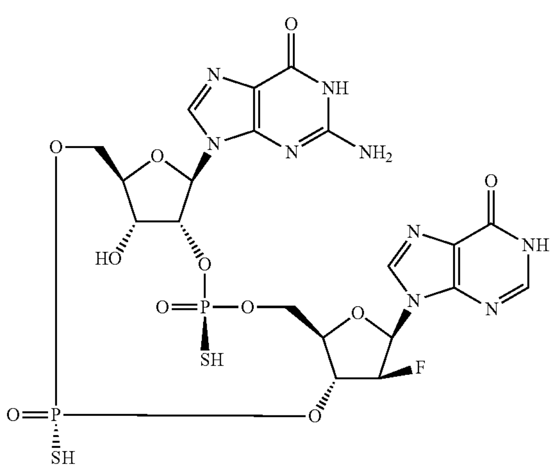 [SMILES: Nc1nc2c(ncn2[C@@H]2O[C@@H]3CO[P@@](=O)(S)O[C@H]4[C@H](F)[C@H](n5cnc6c(=O)[nH]cnc65)O[C@@H]4CO[P@@](=O)(S)O[C@@H]2[C@@H]3O)c(=O)[nH]1] | 2-amino-9-[(2R,5R,7R,8R,10R,12aR,14R,15S,15aR,16R)-15-fluoro-2,10,16-trihydroxy-14-(6-oxo-1,6-dihydro-9H-purin-9-yl)-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 708 | 89 |

TABLE 11-continued

| Ex. | Structure | Name | Mass [M − H]⁻ | St. Cmpd. |
|---|---|---|---|---|
| 298 | 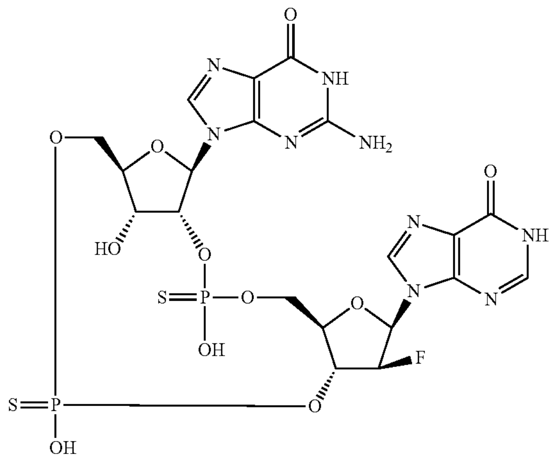 [SMILES: Nc1nc2c(ncn2[C@@H]2O[C@@H]3COP(O)(=S)O[C@H]4[C@H](F)[C@H](n5cnc6c(=O)[nH]cnc65)O[C@@H]4COP(O)(=S)O[C@@H]2[C@@H]3O)c(=O)[nH]1] | 2-amino-9-[(5R,7R,8R,12aR,14R,15S,15aR,16R)-15-fluoro-2,10,16-trihydroxy-14-(6-oxo-1,6-dihydro-9H-purin-9-yl)-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 3) | 708 | 91 |
| 299 | 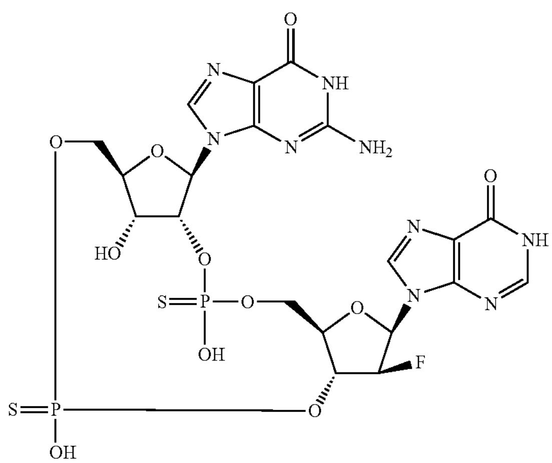 [SMILES: Nc1nc2c(ncn2[C@@H]2O[C@@H]3COP(O)(=S)O[C@H]4[C@H](F)[C@H](n5cnc6c(=O)[nH]cnc65)O[C@@H]4COP(O)(=S)O[C@@H]2[C@@H]3O)c(=O)[nH]1] | 2-amino-9-[(5R,7R,8R,12aR,14R,15S,15aR,16R)-15-fluoro-2,10,16-trihydroxy-14-(6-oxo-1,6-dihydro-9H-purin-9-yl)-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 4) | 708 | 92 |
| 300 | 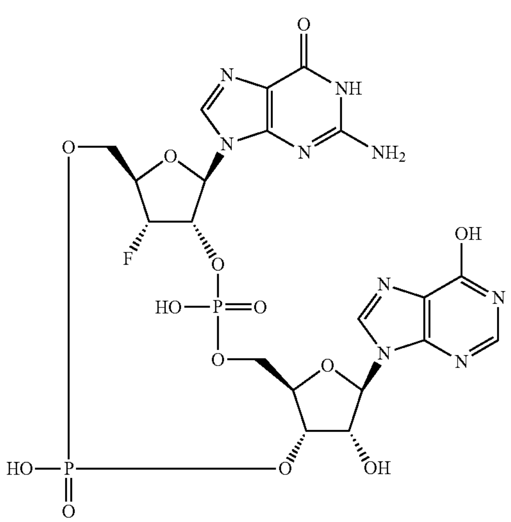 [SMILES: Nc1nc2c(ncn2[C@@H]2O[C@@H]3COP(=O)(O)O[C@H]4[C@@H](O)[C@H](n5cnc6c(O)ncnc65)O[C@@H]4COP(=O)(O)O[C@@H]2[C@@H]3F)c(=O)[nH]1] | 2-amino-9-[(5R,7R,8S,12aR,14R,15R,15aS,16R)-16-fluoro-2,10,15-trihydroxy-14-(6-hydroxy-9H-purin-9-yl)-2,10-dioxidooctahydro-12H-5,8-methanofuro[3,2-l][1,3,6,9,11,2,10]pentaoxadiphosphacyclo-tetradecin-7-yl]-1,9-dihydro-6H-purin-6-one | 676 | 5 |

TABLE 11-continued

| Ex. | Structure | Name | Mass [M − H]⁻ | St. Cmpd. |
|---|---|---|---|---|
| 301 | 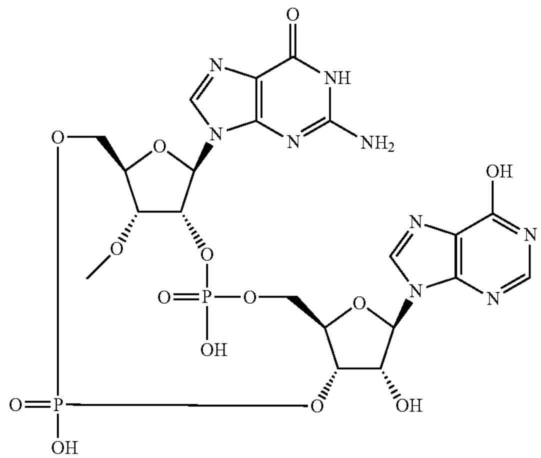 [SMILES: CO[C@H]1[C@H]2OP(=O)(O)OC[C@H]3O[C@@H](n4cnc5c(O)ncnc54)[C@H](O)[C@@H]3OP(=O)(O)OC[C@H]1O[C@H]2n1cnc2c(=O)[nH]c(N)nc21] | 2-amino-9-[(5R,7R,8R,12aR,14R,15R,15aS,16R)-2,10,15-trihydroxy-14-(6-hydroxy-9H-purin-9-yl)-16-methoxy-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 688 | 13 |
| 302 | 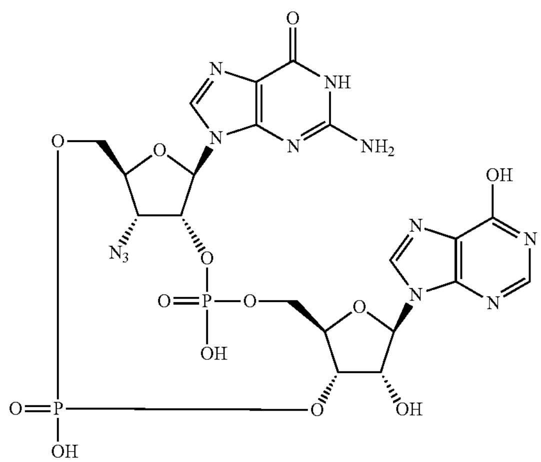 [SMILES: [N-]=[N+]=N[C@H]1[C@H]2OP(=O)(O)OC[C@H]3O[C@@H](n4cnc5c(O)ncnc54)[C@H](O)[C@@H]3OP(=O)(O)OC[C@H]1O[C@H]2n1cnc2c(=O)[nH]c(N)nc21] | 2-amino-9-[(5S,7R,8R,12aR,14R,15R,15aS,16R)-16-azido-2,10,15-trihydroxy-14-(6-hydroxy-9H-purin-9-yl)-2,10-dioxidooctahydro-12H-5,8-methanofuro[3,2-l][1,3,6,9,11,2,10]pentaoxadiphosphacyclotetradecin-7-yl]-1,9-dihydro-6H-purin-6-one | 699 | 14 |
| 303 | 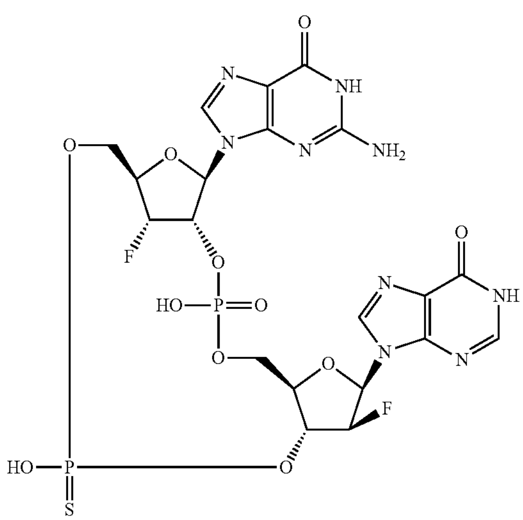 [SMILES: Nc1nc2c(ncn2[C@@H]2O[C@@H]3COP(O)(=S)O[C@H]4[C@H](F)[C@H](n5cnc6c(=O)[nH]cnc65)O[C@@H]4COP(=O)(O)O[C@@H]2[C@@H]3F)c(=O)[nH]1] | 2-amino-9-[(5R,7R,8S,12aR,14R,15S,15aR,16R)-15,16-difluoro-2,10-dihydroxy-10-oxido-14-(6-oxo-1,6-dihydro-9H-purin-9-yl)-2-sulfidooctahydro-12H-5,8-methanofuro[3,2-l][1,3,6,9,11,2,10]pentaoxadiphosphacyclotetradecin-7-yl]-1,9-dihydro-6H-purin-6-one | 694 | 143 |

TABLE 11-continued

| Ex. | Structure | Name | Mass [M − H]⁻ | St. Cmpd. |
|---|---|---|---|---|
| 304 | 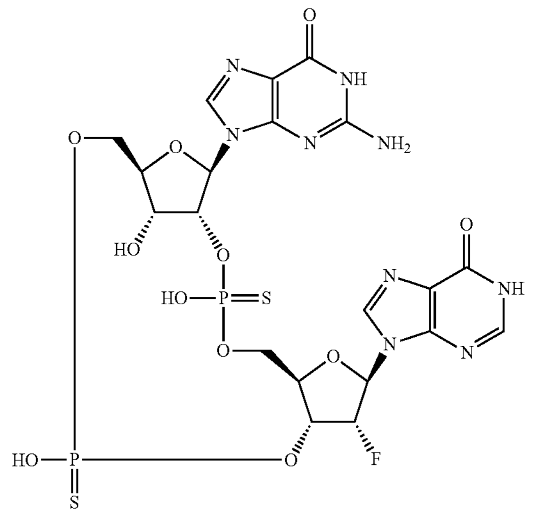 | 2-amino-9-[(5R,7R,8R,12aR,14R,15R,15aR,16R)-15-fluoro-2,10,16-trihydroxy-14-(6-oxo-1,6-dihydro-9H-purin-9-yl)-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one | 708 | 81 |
| 305 | 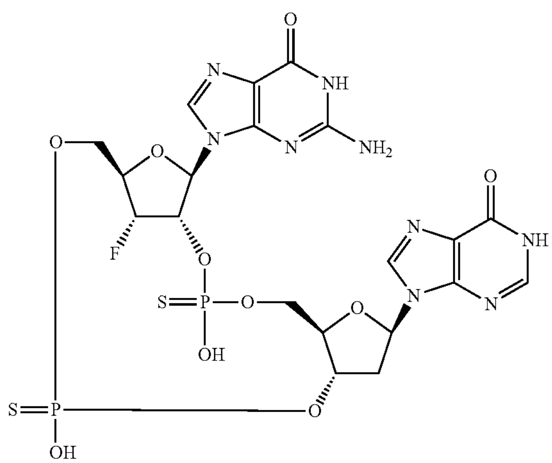 [SMILES: Nc1nc2c(ncn2[C@@H]2O[C@@H]3COP(O)(=S)O[C@H]4C[C@H](n5cnc6c(=O)[nH]cnc65)O[C@@H]4COP(O)(=S)O[C@@H]2[C@@H]3F)c(=O)[nH]1] | 2-amino-9-[(5R,7R,8S,12aR,14R,15aS,16R)-16-fluoro-2,10-dihydroxy-14-(6-oxo-1,6-dihydro-9H-purin-9-yl)-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 692 | 120 |
| 306 | 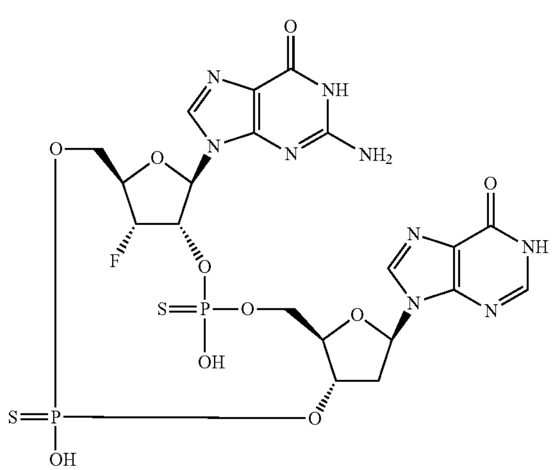 [SMILES: Nc1nc2c(ncn2[C@@H]2O[C@@H]3COP(O)(=S)O[C@H]4C[C@H](n5cnc6c(=O)[nH]cnc65)O[C@@H]4COP(O)(=S)O[C@@H]2[C@@H]3F)c(=O)[nH]1] | 2-amino-9-[(5R,7R,8S,12aR,14R,15aS,16R)-16-fluoro-2,10-dihydroxy-14-(6-oxo-1,6-dihydro-9H-purin-9-yl)-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 692 | 118 |

TABLE 11-continued

| Ex. | Structure | Name | Mass [M − H]⁻ | St. Cmpd. |
|---|---|---|---|---|
| 307 | 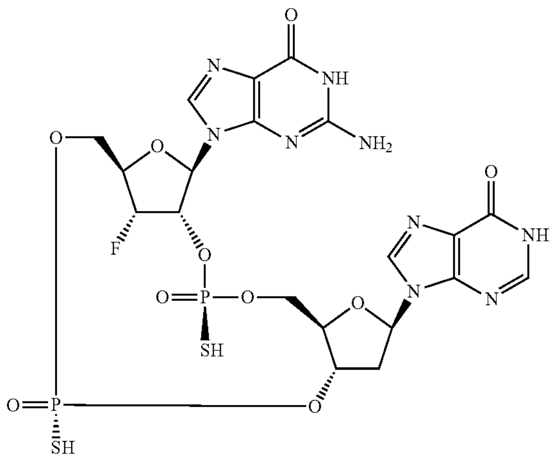 [SMILES: Nc1nc2c(ncn2[C@@H]2O[C@@H]3CO[P@@](=O)(S)O[C@H]4C[C@H](n5cnc6c(=O)[nH]cnc65)O[C@@H]4CO[P@@](=O)(S)O[C@@H]2[C@@H]3F)c(=O)[nH]1] | 2-amino-9-[(2R,5R,7R,8S,10R,12aR,14R,15aS,16R)-16-fluoro-2,10-dihydroxy-14-(6-oxo-1,6-dihydro-9H-purin-9-yl)-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 3) | 692 | 117 |
| 308 | 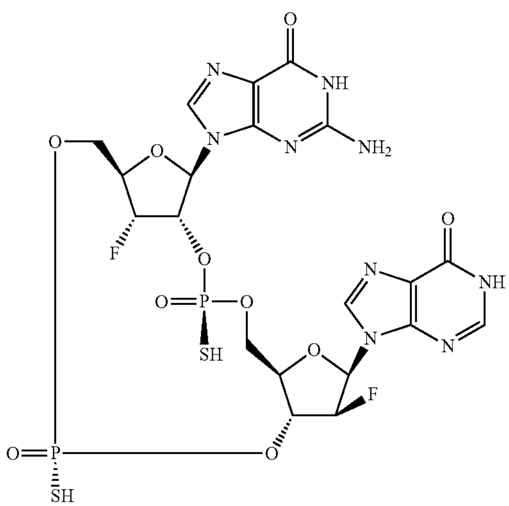 [SMILES: Nc1nc2c(ncn2[C@@H]2O[C@@H]3CO[P@@](=O)(S)O[C@H]4[C@H](F)[C@H](n5cnc6c(=O)[nH]cnc65)O[C@@H]4CO[P@@](=O)(S)O[C@@H]2[C@@H]3F)c(=O)[nH]1] | 2-amino-9-[(2R,5R,7R,8S,10R,12aR,14R,15S,15aR,16R)-15,16-difluoro-2,10-dihydroxy-14-(6-oxo-1,6-dihydro-9H-purin-9-yl)-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 710 | 247 |
| 309 | 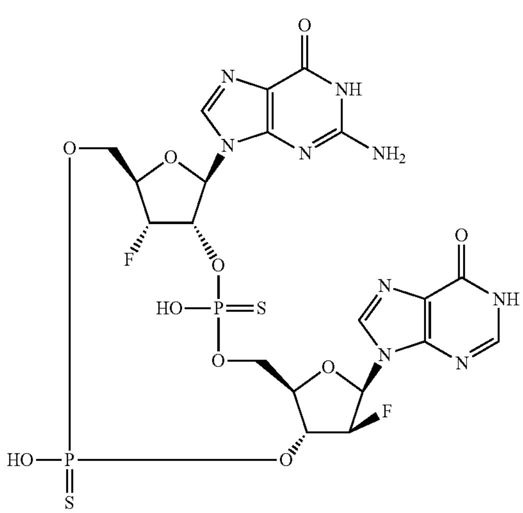 | 2-amino-9-[(5R,7R,8S,12aR,14R,15S,15aR,16R)-15,16-difluoro-2,10-dihydroxy-14-(6-oxo-1,6-dihydro-9H-purin-9-yl)-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 710 | 245 |

TABLE 11-continued

| Ex. | Structure | Name | Mass [M − H]⁻ | St. Cmpd. |
|---|---|---|---|---|
| 310 | 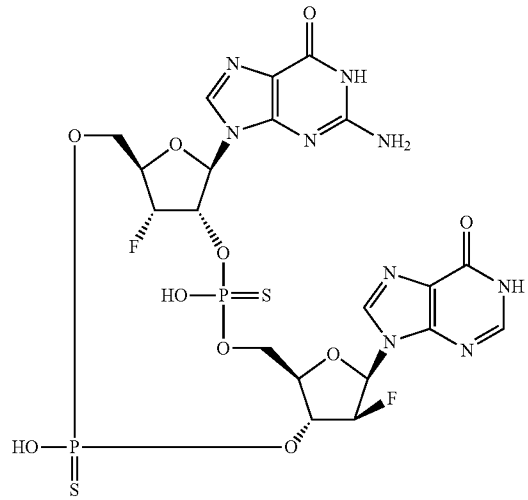 | 2-amino-9-[(5R,7R,8S,12aR,14R,15S,15aR,16R)-15,16-difluoro-2,10-dihydroxy-14-(6-oxo-1,6-dihydro-9H-purin-9-yl)-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 3) | 710 | 246 |
| 311 | 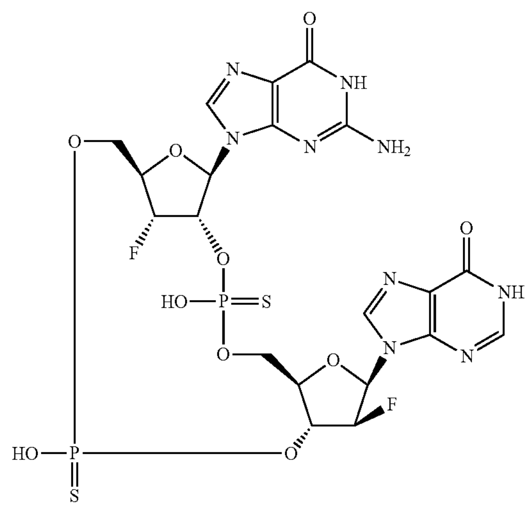 | 2-amino-9-[(5R,7R,8S,12aR,15S,15aR,16R)-15,16-difluoro-2,10-dihydroxy-14-(6-oxo-1,6-dihydro-9H-purin-9-yl)-2,10-disulfidooctahydro-12H-5,8-methanofuro[3,2-l][1,3,6,9,11,2,10]pentaoxadiphosphacyclotetradecin-7-yl]-1,9-dihydro-6H-purin-6-one (Diastereomer 4) | 710 | 244 |
| 312 | 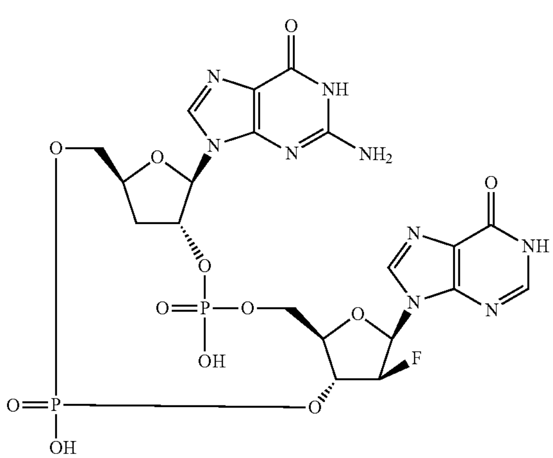 [SMILES: Nc1nc2c(ncn2[C@@H]2O[C@@H]3COP(=O)(O)O[C@H]4[C@H](F)[C@H](n5cnc6c(=O)[nH]cnc65)O[C@@H]4COP(=O)(O)O[C@@H]2C3)c(=O)[nH]1] | 2-amino-9-[(5S,7R,8R,12aR,14R,15S,15aR)-15-fluoro-2,10-dihydroxy-2,10-dioxido-14-(6-oxo-1,6-dihydro-9H-purin-9-yl)octahydro-12H-5,8-methanofuro[3,2-l][1,3,6,9,11,2,10]pentaoxadiphosphacyclotetradecin-7-yl]-1,9-dihydro-6H-purin-6-one | 660 | 25 |

TABLE 11-continued

| Ex. | Structure | Name | Mass [M − H]⁻ | St. Cmpd. |
|---|---|---|---|---|
| 313 | 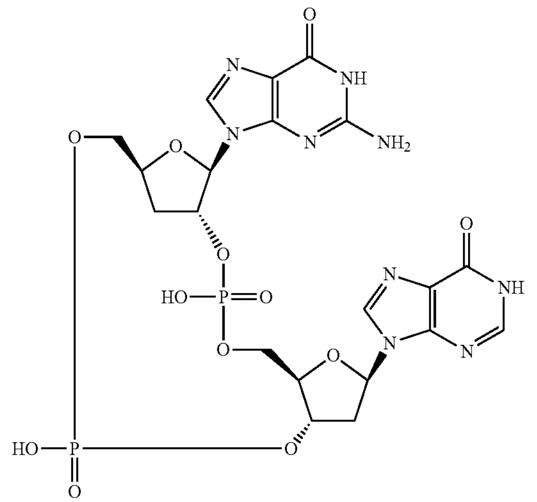 [SMILES: Nc1nc2c(ncn2[C@@H]2O[C@@H]3COP(=O)(O)O[C@H]4C[C@H](n5cnc6c(=O)[nH]cnc65)O[C@@H]4COP(=O)(O)O[C@@H]2C3)c(=O)[nH]1] | 2-amino-9-[(5S,7R,8R,12aR,14R,15aS)-2,10-dihydroxy-2,10-dioxido-14-(6-oxo-1,6-dihydro-9H-purin-9-yl)octahydro-12H-5,8-methanofuro[3,2-l][1,3,6,9,11,2,10]pentaoxadiphosphacyclotetradecin-7-yl]-1,9-dihydro-6H-purin-6-one | 642 | 27 |
| 314 | 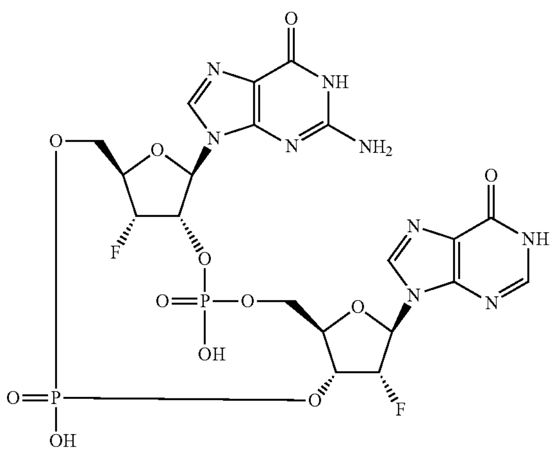 [SMILES: Nc1nc2c(ncn2[C@@H]2O[C@@H]3COP(=O)(O)O[C@H]4[C@@H](F)[C@H](n5cnc6c(=O)[nH]cnc65)O[C@@H]4COP(=O)(O)O[C@@H]2[C@@H]3F)c(=O)[nH]1] | 2-amino-9-[(5R,7R,8S,12aR,14R,15R,15aR,16R)-15,16-difluoro-2,10-dihydroxy-2,10-dioxido-14-(6-oxo-1,6-dihydro-9H-purin-9-yl)octahydro-12H-5,8-methanofuro[3,2-l][1,3,6,9,11,2,10]pentaoxadiphosphacyclotetradecin-7-yl]-1,9-dihydro-6H-purin-6-one | 678 | 23 |
| 315 | 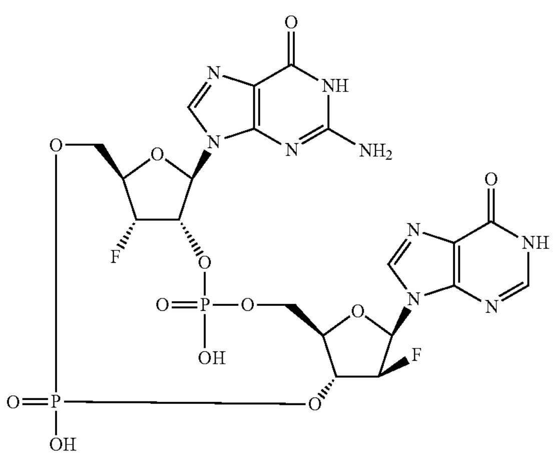 [SMILES: Nc1nc2c(ncn2[C@@H]2O[C@@H]3COP(=O)(O)O[C@H]4[C@H](F)[C@H](n5cnc6c(=O)[nH]cnc65)O[C@@H]4COP(=O)(O)O[C@@H]2[C@@H]3F)c(=O)[nH]1] | 2-amino-9-[(5R,7R,8S,12aR,14R,15S,15aR,16R)-15,16-difluoro-2,10-dihydroxy-2,10-dioxido-14-(6-oxo-1,6-dihydro-9H-purin-9-yl)octahydro-12H-5,8-methanofuro[3,2-l][1,3,6,9,11,2,10]pentaoxadiphosphacyclotetradecin-7-yl]-1,9-dihydro-6H-purin-6-one | 678 | 26 |

TABLE 11-continued

| Ex. | Structure | Name | Mass [M − H]⁻ | St. Cmpd. |
|---|---|---|---|---|
| 316 | 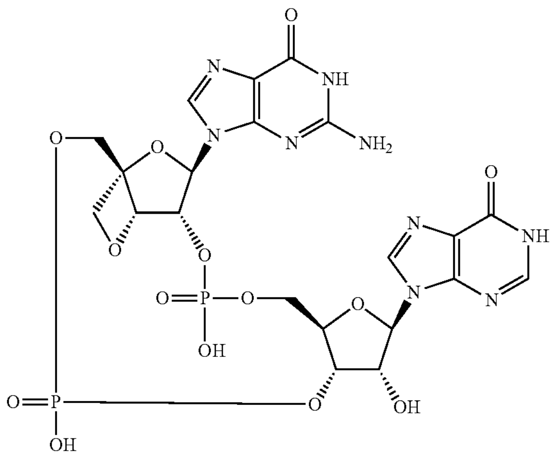 [SMILES: Nc1nc2c(ncn2[C@@H]2O[C@@]34CO[C@H]3[C@H]2OP(=O)(O)OC[C@H]2O[C@@H](n3cnc5c(=O)[nH]cnc53)[C@H](O)[C@@H]2OP(=O)(O)OC4)c(=O)[nH]1] | 2-amino-9-[(2aR,6aS,7R,8R,9aR,14R,14aS,15R)-5,7,12-trihydroxy-5,12-dioxido-8-(6-oxo-1,6-dihydro-9H-purin-9-yl)hexahydro-6aH,2a,14-(epoxymethano)furo[3,2-d]oxeto[2,3-k][1,3,7,9,2,8]tetraoxadiphosphacyclotridecin-15(2H,3H)-yl]-1,9-dihydro-6H-purin-6-one | 686 | 17 |
| 317 | 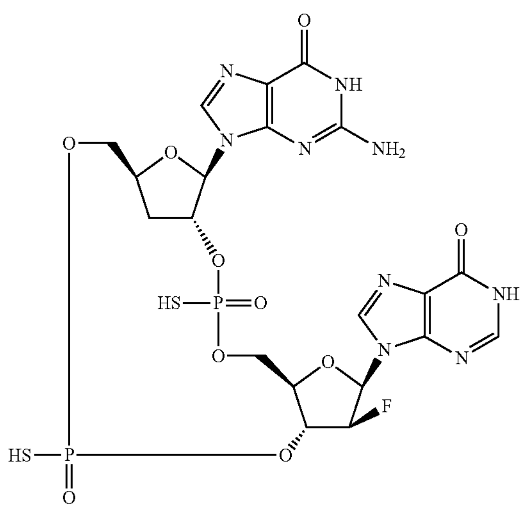 [SMILES: Nc1nc2c(ncn2[C@@H]2O[C@@H]3COP(=O)(S)O[C@H]4[C@H](F)[C@H](n5cnc6c(=O)[nH]cnc65)O[C@@H]4COP(=O)(S)O[C@@H]2C3)c(=O)[nH]1] | 2-amino-9-[(2R,5S,7R,8R,10R,12aR,14R,15S,15aR)-15-fluoro-2,10-dioxido-14-(6-oxo-1,6-dihydro-9H-purin-9-yl)-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 692 | 130 |
| 318 | 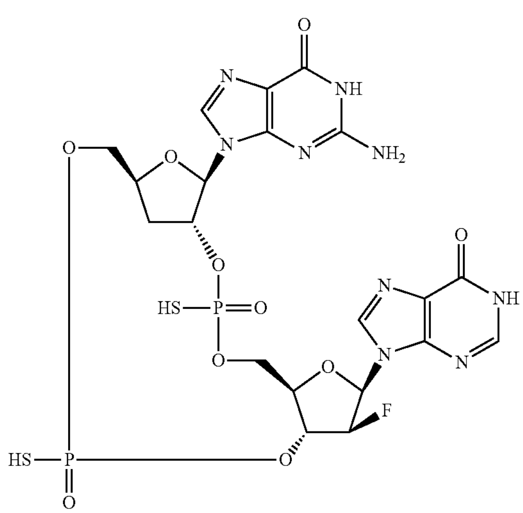 [SMILES: Nc1nc2c(ncn2[C@@H]2O[C@@H]3COP(=O)(S)O[C@H]4[C@H](F)[C@H](n5cnc6c(=O)[nH]cnc65)O[C@@H]4COP(=O)(S)O[C@@H]2C3)c(=O)[nH]1] | 2-amino-9-[(5S,7R,8R,12aR,14R,15S,15aR)-15-fluoro-2,10-dioxido-14-(6-oxo-1,6-dihydro-9H-purin-9-yl)-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 692 | 131 |

TABLE 11-continued

| Ex. | Structure | Name | Mass [M − H]⁻ | St. Cmpd. |
|---|---|---|---|---|
| 319 | 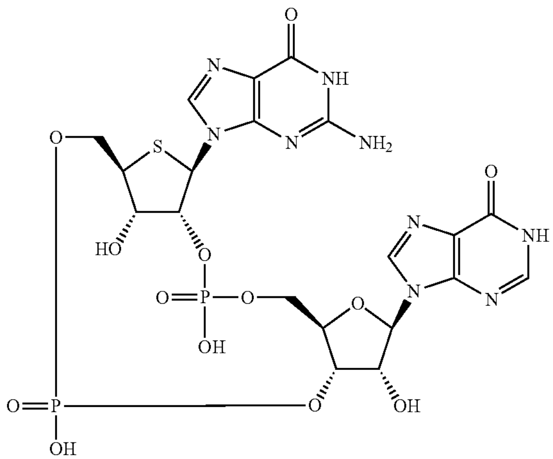 [SMILES: Nc1nc2c(ncn2[C@@H]2S[C@@H]3COP(=O)(O)O[C@H]4[C@@H](O)[C@H](n5cnc6c(=O)[nH]cnc65)O[C@@H]4COP(=O)(O)O[C@@H]2[C@@H]3O)c(=O)[nH]1] | 2-amino-9-[(5R,7R,8R,12aR,14R,15R,15aS,16S)-2,10,15,16-tetrahydroxy-2,10-dioxido-14-(6-oxo-1,6-dihydro-9H-purin-9-yl)octahydro-12H-5,8-methanofuro[3,2-l][1,3,6,9,11,6,2,10]tetraoxathiadiphosphacyclotetradecin-7-yl]-1,9-dihydro-6H-purin-6-one | 690 | 11 |
| 320 | 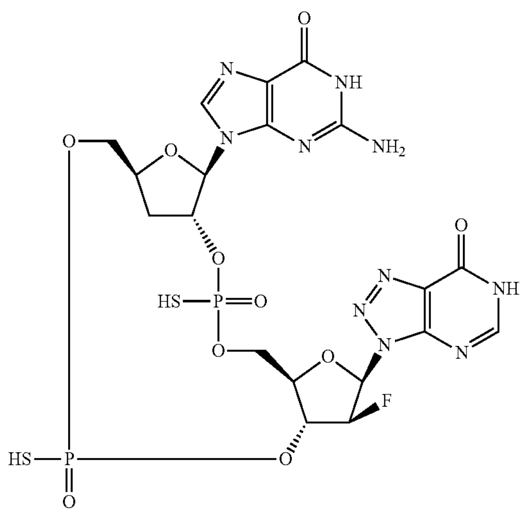 [SMILES: Nc1nc2c(ncn2[C@@H]2O[C@@H]3COP(=O)(S)O[C@H]4[C@H](F)[C@H](n5nnc6c(=O)[nH]cnc65)O[C@@H]4COP(=O)(S)O[C@@H]2C3)c(=O)[nH]1] | 3-[(5S,7R,8R,12aR,14R,15S,15aR)-7-(2-amino-6-oxo-1,6-dihydro-9H-purin-9-yl)-15-fluoro-2,10-dioxido-2,10-disulfanyloctahydro-12H-5,8-methanofuro[3,2-l][1,3,6,9,11,2,10]pentaoxadiphosphacyclotetradecin-14-yl]-3,6-dihydro-7H-[1,2,3]triazolo[4,5-d]pyrimidin-7-one | 693 | 133 |
| 321 | 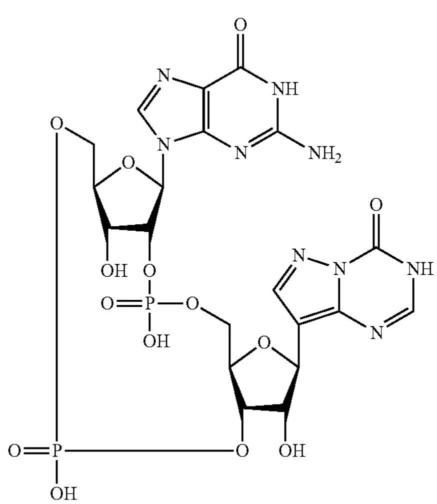 | 8-[(5R,7R,8R,12aR,14S,15S,15aS,16R)-7-(2-amino-6-oxo-1,6-dihydro-9H-purin-9-yl)-2,10,15,16-tetrahydroxy-2,10-dioxidooctahydro-12H-5,8-methanofuro[3,2-l][1,3,6,9,11,2,10]pentaoxadiphosphacyclotetradecin-14-yl]pyrazolo[1,5-a][1,3,5]triazin-4(3H)-one | 674 | 54 |

TABLE 11-continued

| Ex. | Structure | Name | Mass [M − H]⁻ | St. Cmpd. |
|---|---|---|---|---|
| 322 | 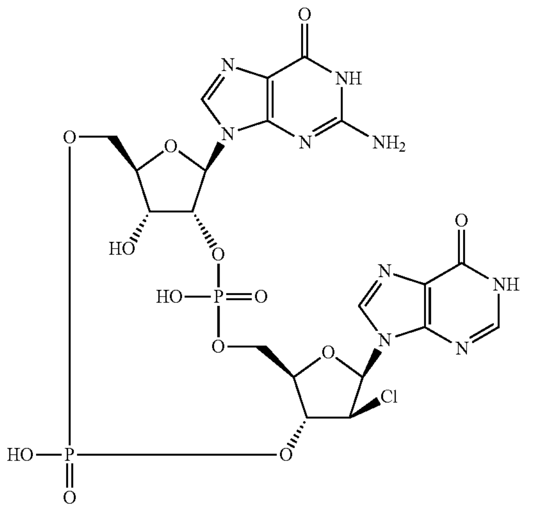 [SMILES: Nc1nc2c(ncn2[C@@H]2O[C@@H]3COP(=O)(O)O[C@H]4[C@H](Cl)[C@H](n5cnc6c(=O)[nH]cnc65)O[C@@H]4COP(=O)(O)O[C@@H]2[C@@H]3O)c(=O)[nH]1] | 2-amino-9-[(5R,7R,8R,12aR,14R, 15S,15aR,16R)-15-chloro-2,10,16-trihydroxy-2,10-dioxido-14-(6-oxo-1,6-dihydro-9H-purin-9-yl)octahydro-12H-5,8-methanofuro[3,2-l][1,3,6,9,11,2,10] pentaoxadiphosphacyclotetradecin-7-yl]-1,9-dihydro-6H-purin-6-one | 692 | 15 |
| 323 | 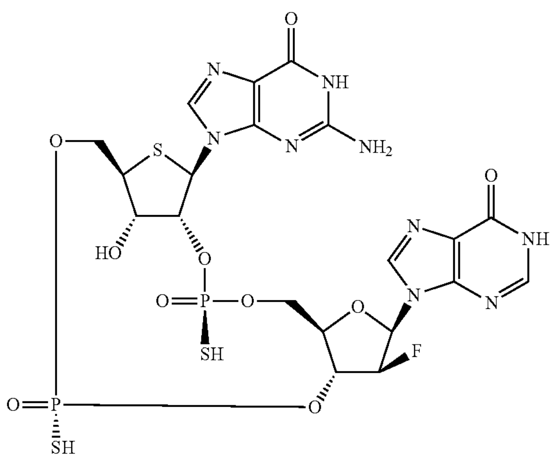 [SMILES: Nc1nc2c(ncn2[C@@H]2S[C@@H]3CO[P@@](=O)(S)O[C@H]4[C@H](F)[C@H](n5cnc6c(=O)[nH]cnc65)O[C@@H]4CO[P@@](=O)(S)O[C@@H]2[C@@H]3O)c(=O)[nH]1] | 2-amino-9-[(2R,5R,7R,8R,10R, 12aR,14R,15S,15aR,16S)-15-fluoro-16-hydroxy-2,10-dioxido-14-(6-oxo-1,6-dihydro-9H-purin-9-yl)-2,10-disulfanyloctahydro-12H-5,8-methanofuro[3,2-l][1,3,9,11,6,2,10] tetraoxathiadiphosphacyclotetradecin-7-yl]-1,9-dihydro-6H-purin-6-one (Diastereomer 1) | 724 | 97 |
| 324 | 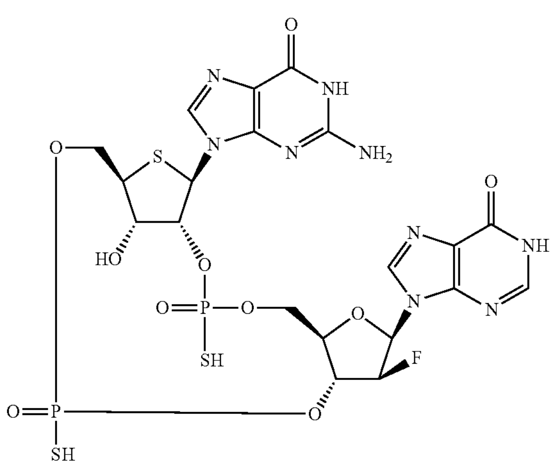 [SMILES: Nc1nc2c(ncn2[C@@H]2S[C@@H]3COP(=O)(S)O[C@H]4[C@H](F)[C@H](n5cnc6c(=O)[nH]cnc65)O[C@@H]4COP(=O)(S)O[C@@H]2[C@@H]3O)c(=O)[nH]1] | 2-amino-9-[(5R,7R,8R,12aR,14R,15S, 15aR,16S)-15-fluoro-16-hydroxy-2,10-dioxido-14-(6-oxo-1,6-dihydro-9H-purin-9-yl)-2,10-disulfanyloctahydro-12H-5,8-methanofuro[3,2-l][1,3,9,11,6,2,10] tetraoxathiadiphosphacyclotetradecin-7-yl]-1,9-dihydro-6H-purin-6-one (Diastereomer 2) | 724 | 99 |

TABLE 11-continued

| Ex. | Structure | Name | Mass [M − H]⁻ | St. Cmpd. |
|---|---|---|---|---|
| 325 | 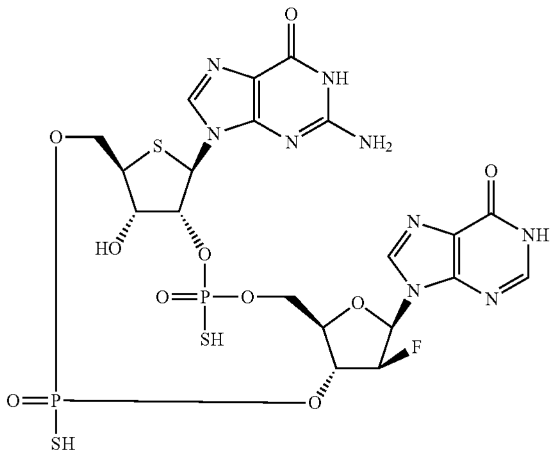 | 2-amino-9-[(5R,7R,8R,12aR,14R,15S,15aR,16S)-15-fluoro-16-hydroxy-2,10-dioxido-14-(6-oxo-1,6-dihydro-9H-purin-9-yl)-2,10-disulfanyloctahydro-12H-5,8-methanofuro[3,2-l][1,3,9,11,6,2,10]tetraoxathiadiphosphacyclotetradecin-7-yl]-1,9-dihydro-6H-purin-6-one (Diastereomer 3) | 724 | 96 |
| 326 | 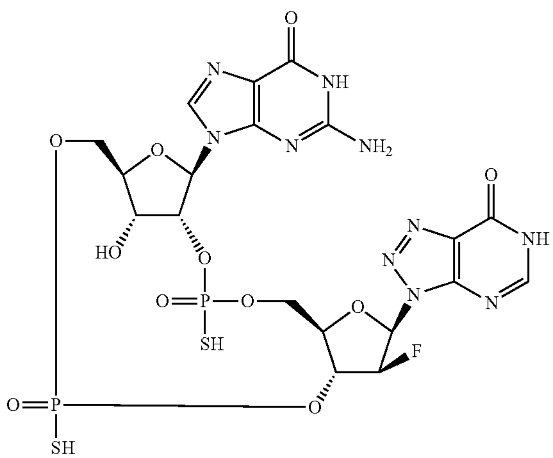 [SMILES: Nc1nc2c(ncn2[C@@H]2S[C@@H]3COP(=O)(S)O[C@H]4[C@H](F)[C@H](n5cnc6c(=O)[nH]cnc65)O[C@@H]4COP(=O)(S)O[C@@H]2[C@@H]3O)c(=O)[nH]1] | 3-[(5R,7R,8S,12aR,14R,15S,15aR,16R)-7-(2-amino-6-oxo-1,6-dihydro-9H-purin-9-yl)-15,16-difluoro-2,10-dioxido-2,10-disulfanyloctahydro-12H-5,8-methanofuro[3,2-l][1,3,6,9,11,2,10]pentaoxadiphosphacyclotetradecin-14-yl]-3,6-dihydro-7H-[1,2,3]triazolo[4,5-d]pyrimidin-7-one (Diastereomer 1) | 711 | 130 |
| 327 | 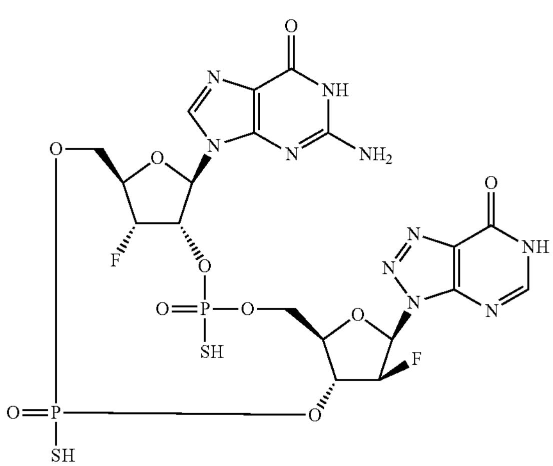 [SMILES: Nc1nc2c(ncn2[C@@H]2O[C@@H]3COP(=O)(S)O[C@H]4[C@H](F)[C@H](n5nnc6c(=O)[nH]cnc65)O[C@@H]4COP(=O)(S)O[C@@H]2[C@@H]3F)c(=O)[nH]1] | 3-[(5R,7R,8S,12aR,14R,15S,15aR,16R)-7-(2-amino-6-oxo-1,6-dihydro-9H-purin-9-yl)-15,16-difluoro-2,10-dioxido-2,10-disulfanyloctahydro-12H-5,8-methanofuro[3,2-l][1,3,6,9,11,2,10]pentaoxadiphosphacyclotetradecin-14-yl]-3,6-dihydro-7H-[1,2,3]triazolo[4,5-d]pyrimidin-7-one (Diastereomer 2) | 711 | 128 |

TABLE 11-continued

| Ex. | Structure | Name | Mass [M − H]⁻ | St. Cmpd. |
|---|---|---|---|---|
| 328 | 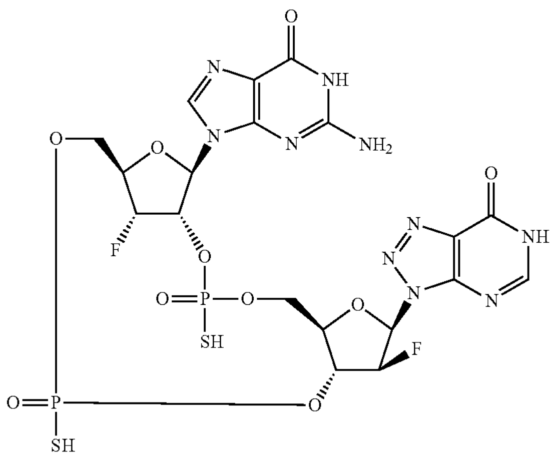 [SMILES: Nc1nc2c(ncn2[C@@H]2O[C@@H]3COP(=O)(S)O[C@H]4[C@H](F)[C@H](n5nnc6c(=O)[nH]cnc65)O[C@@H]4COP(=O)(S)O[C@@H]2[C@@H]3F)c(=O)[nH]1] | 3-[(5R,7R,8S,12aR,14R,15S,15aR,16R)-7-(2-amino-6-oxo-1,6-dihydro-9H-purin-9-yl)-15,16-difluoro-2,10-dioxido-2,10-disulfanyloctahydro-12H-5,8-methanofuro[3,2-l][1,3,6,9,11,2,10]pentaoxadiphosphacyclotetradecin-14-yl]-3,6-dihydro-7H-[1,2,3]triazolo[4,5-d]pyrimidin-7-one (Diastereomer 3) | 711 | 127 |
| 329 | 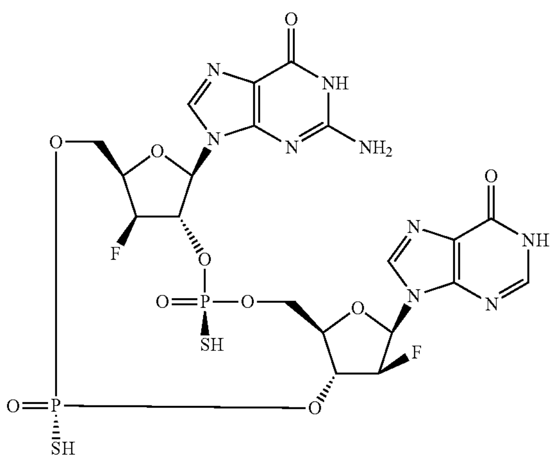 [SMILES: Nc1nc2c(ncn2[C@@H]2O[C@@H]3CO[P@@](=O)(S)O[C@H]4[C@H](F)[C@H](n5cnc6c(=O)[nH]cnc65)O[C@@H]4CO[P@@](=O)(S)O[C@@H]2[C@H]3F)c(=O)[nH]1] | 2-amino-9-[(2R,5R,7R,8S,10R,12aR,14R,15S,15aR,16S)-15,16-difluoro-2,10-dioxido-14-(6-oxo-1,6-dihydro-9H-purin-9-yl)-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 1) | 710 | 144 |
| 330 | 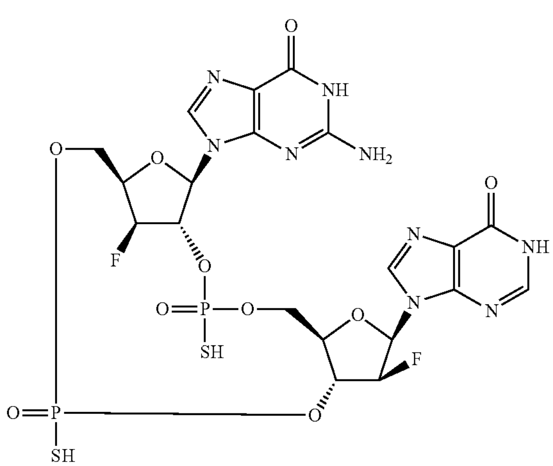 | 2-amino-9-[(5R,7R,8S,12aR,14R,15S,15aR,16S)-15,16-difluoro-2,10-dioxido-14-(6-oxo-1,6-dihydro-9H-purin-9-yl)-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one (Diastereomer 2) | 710 | 145 |

TABLE 11-continued

| Ex. | Structure | Name | Mass [M − H]⁻ | St. Cmpd. |
|---|---|---|---|---|
| 331 | 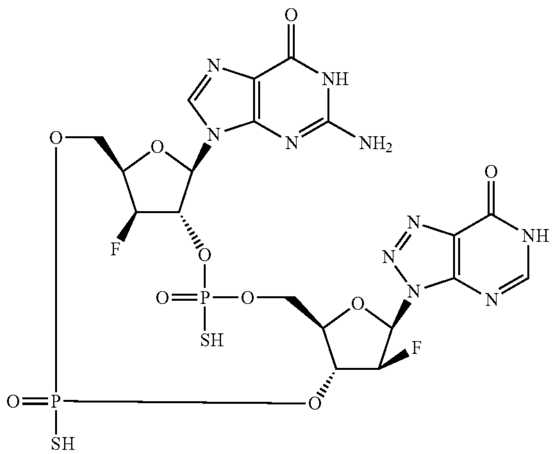 [SMILES: Nc1nc2c(ncn2[C@@H]2O[C@@H]3COP(=O)(S)O[C@H]4[C@H](F)[C@H](n5nnc6c(=O)[nH]cnc65)O[C@@H]4COP(=O)(S)O[C@@H]2[C@H]3F)c(=O)[nH]1] | 3-[(5R,7R,8S,12aR,14R,15S,15aR,16S)-7-(2-amino-6-oxo-1,6-dihydro-9H-purin-9-yl)-15,16-difluoro-2,10-dioxido-2,10-disulfanyloctahydro-12H-5,8-methanofuro[3,2-l][1,3,6,9,11,2,10]pentaoxadiphosphacyclotetradecin-14-yl]-3,6-dihydro-7H-[1,2,3]triazolo[4,5-d]pyrimidin-7-one | 711 | 147 |
| 332 | 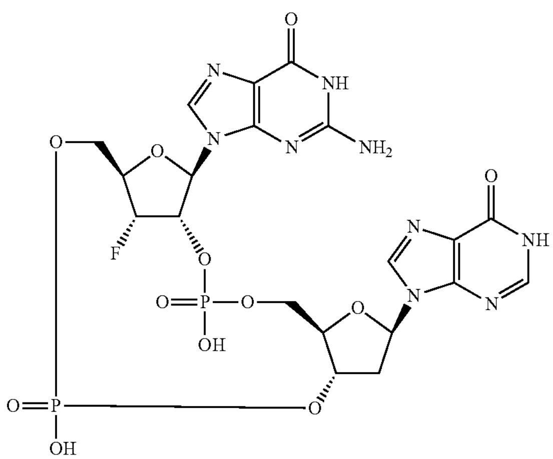 [SMILES: Nc1nc2c(ncn2[C@@H]2O[C@@H]3COP(=O)(O)O[C@H]4C[C@H](n5cnc6c(=O)[nH]cnc65)O[C@@H]4COP(=O)(O)O[C@@H]2[C@@H]3F)c(=O)[nH]1] | 2-amino-9-[(5R,7R,8S,12aR,14R,15aS,16R)-16-fluoro-2,10-dihydroxy-2,10-dioxido-14-(6-oxo-1,6-dihydro-9H-purin-9-yl)octahydro-12H-5,8-methanofuro[3,2-l][1,3,6,9,11,2,10]pentaoxadiphosphacyclotetradecin-7-yl]-1,9-dihydro-6H-purin-6-one | 660 | 22 |
| 333 | 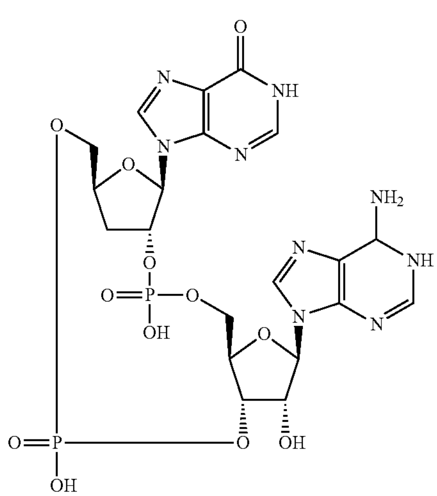 [SMILES: NC1NC=Nc2c1ncn2[C@@H]1O[C@@H]2COP(=O)(O)O[C@@H]3C[C@@H](COP(=O)(O)O[C@H]2[C@H]1O)O[C@H]3n1cnc2c(=O)[nH]cnc21] | 9,9'-[(5S,7R,8R,12aR,14R,15R,15aS)-2,10,15-trihydroxy-2,10-dioxidooctahydro-12H-5,8-methanofuro[3,2-l][1,3,6,9,11,2,10]pentaoxaciphosphacyclotetradecine-7,14-diyl]bis(1,9-dihydro-6H-purin-6-one | 643 | 50 |

TABLE 11-continued

| Ex. | Structure | Name | Mass [M − H]⁻ | St. Cmpd. |
|---|---|---|---|---|
| 334 | 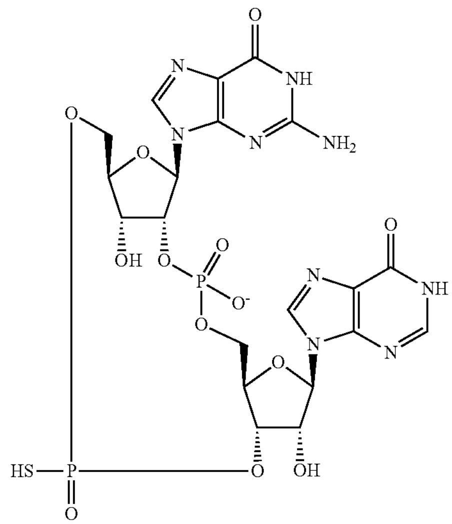 [SMILES: Nc1nc2c(ncn2[C@@H]2O[C@@H]3COP(=O)(S)O[C@H]4[C@@H](O)[C@H](n5cnc6c(=O)[nH]cnc65)O[C@@H]4COP(=O)([O-])O[C@@H]2[C@@H]3O)c(=O)[nH]1] | 2-amino-9-[(5R,7R,8R,12ar,14R,15R,15aS,16R)-10,15,16-trihydroxy-2,10-dioxido-14-(6-oxo-1,6-dihydro-9H-purin-9-yl)-2-sulfanyloctahydro-12H-5,8-methanofuro[3,2-l][1,3,6,9,11,2,10]pentaoxadiphosphacyclotetradecin-7-yl]-1,9-dihydro-6H-purin-6-one | 690 | 38 |
| 335 | 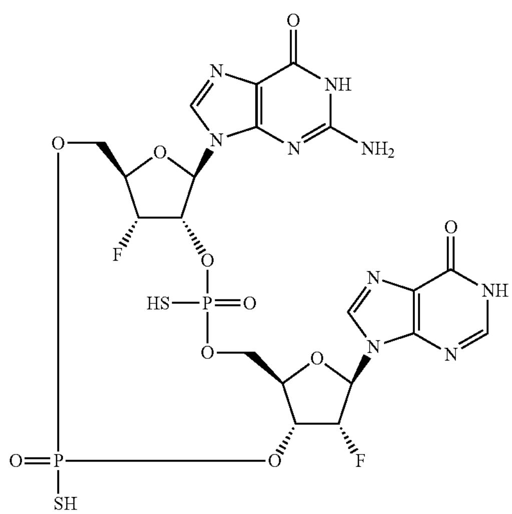 [SMILES: Nc1nc2c(ncn2[C@@H]2O[C@@H]3COP(=O)(S)O[C@H]4[C@@H](F)[C@H](n5cnc6c(=O)[nH]cnc65)O[C@@H]4COP(=O)(S)O[C@@H]2[C@@H]3F)c(=O)[nH]1] | 2-amino-9-[(5R,7R,8S,12aR,14R,15R,15aR,16R)-15,16-difluoro-2,10-dioxido-14-(6-oxo-1,6-dihydro-9H-purin-9-yl)-2,10-disulfanyloctahydro-12H-5,8-methanofuro[3,2-l][1,3,6,9,11,2,10]pentaoxadiphosphacyclotetradecin-7-yl]-1,9-dihydro-6H-purin-6-one | 710 | 260 |
| 336 | 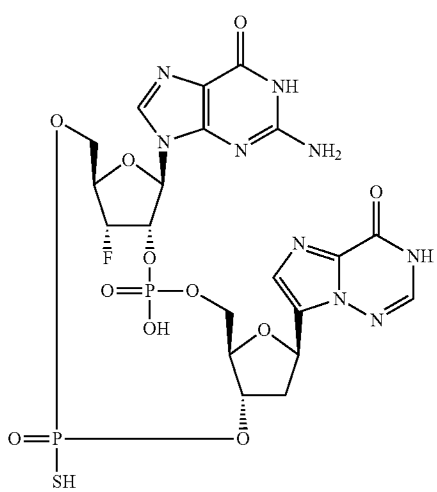 [SMILES: Nc1nc2c(ncn2[C@@H]2O[C@@H]3COP(=O)(S)O[C@H]4C[C@H](c5cnc6c(=O)[nH]cnn56)O[C@@H]4COP(=O)(O)O[C@@H]2[C@@H]3F)c(=O)[nH]1] | 7-[(5R,7R,8S,12aR,14R,15aS,16R)-7-(2-amino-6-oxo-1,6-dihydro-9H-purin-9-yl)-16-fluoro-2,10-dioxido-2,10-disulfanyloctahydro-12H-5,8-methanofuro[3,2-l][1,3,6,9,11,2,10]pentaoxadiphosphacyclotetradecin-14-yl]imidazo[2,1-f][1,2,4]triazin-4(3H)-one (Diastereomer 1) | 692 | 249 |

TABLE 11-continued

| Ex. | Structure | Name | Mass [M − H]⁻ | St. Cmpd. |
|---|---|---|---|---|
| 337 | 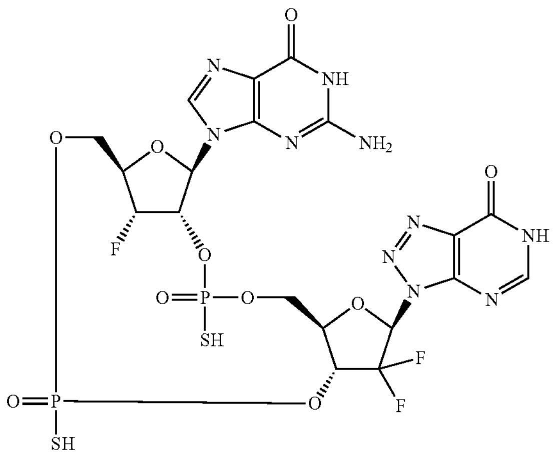 [SMILES: Nc1nc2c(ncn2[C@@H]2O[C@@H]3COP(=O)(S)O[C@@H]4[C@@H](COP(=O)(S)O[C@@H]2[C@@H]3F)O[C@@H](n2nnc3c(=O)[nH]cnc32)C4(F)F)c(=O)[nH]1] | 3-[5R,7R,8S,12aR,14R,15aR,16R)-7-(2-amino-6-oxo-1,6-dihydro-9H-purin-9-yl)-15,15,16-trifluoro-2,10-dioxido-2,10-disulfanyloctahydro-12H-5,8-methanofuro[3,2-l][1,3,6,9,11,2,10]pentaoxadiphosphacyclotetradecin-14-yl]-3,6-dihydro-7H-[1,2,3]triazolo[4,5-d]pyrimidin-7-one (Diastereomer 1) | 729 | 165 |
| 338 | 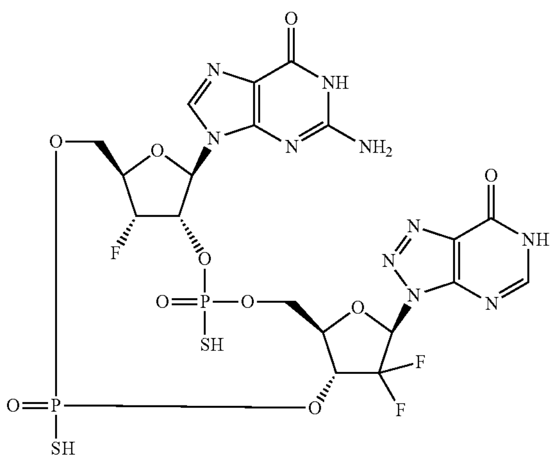 [SMILES: Nc1nc2c(ncn2[C@@H]2O[C@@H]3COP(=O)(S)O[C@@H]4[C@@H](COP(=O)(S)O[C@@H]2[C@@H]3F)O[C@@H](n2nnc3c(=O)[nH]cnc32)C4(F)F)c(=O)[nH]1] | 3-[(5R,7R,8S,12aR,14R,15aR,16R)-7-(2-amino-6-oxo-1,6-dihydro-9H-purin-9-yl)-15,15,16-trifluoro-2,10-dioxido-2,10-disulfanyloctahydro-12H-5,8-methanofuro[3,2-l][1,3,6,9,11,2,10]pentaoxadiphosphacyclotetradecin-14-yl]-3,6-dihydro-7H-[1,2,3]triazolo[4,5-d]pyrimidin-7-one (Diastereomer 2) | 729 | 167 |
| 339 | 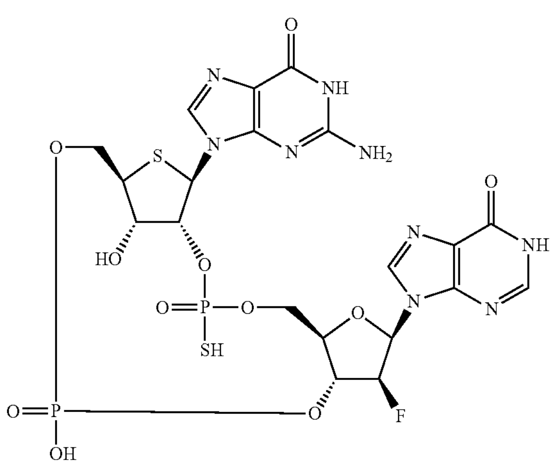 [SMILES: Nc1nc2c(ncn2[C@@H]2S[C@@H]3COP(=O)(O)O[C@H]4[C@H](F)[C@H](n5cnc6c(=O)[nH]cnc65)O[C@@H]4COP(=O)(S)O[C@@H]2[C@@H]3O)c(=O)[nH]1] | 2-amino-9-[(5R,7R,8R,12aR,14R,15S,15aR,16S)-15-fluoro-2,16-dihydroxy-2,10-dioxido-14-(6-oxo-1,6-dihydro-9H-purin-9-yl)-10-sulfanyloctahydro-12H-5,8-methanofuro[3,2-l][1,3,9,11,6,2,10]tetraoxathiadiphosphacyclotetradecin-7-yl]-1,9-dihydro-6H-purin-6-one | 708 | 266 |

TABLE 11-continued

| Ex. | Structure | Name | Mass [M − H]⁻ | St. Cmpd. |
|---|---|---|---|---|
| 340 | 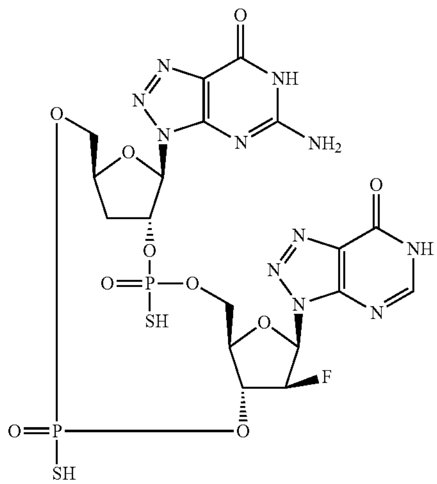 [SMILES: Nc1nc2c(nnn2[C@@H]2O[C@@H]3COP(=O)(S)O[C@H]4[C@H](F)[C@H](n5nnc6c(=O)[nH]cnc65)O[C@@H]4COP(=O)(S)O[C@@H]2C3)c(=O)[nH]1] | 5-amino-3-[(5S,7R,8R,12aR,14R,15S,15aR)-15-fluoro-2,10-dioxido-14-(7-oxo-6,7-dihydro-3H-[1,2,3]triazolo[4,5-c]pyrimidin-3-yl)-2,10-disulfanyloctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 1) | 694 | 181 |
| 341 | 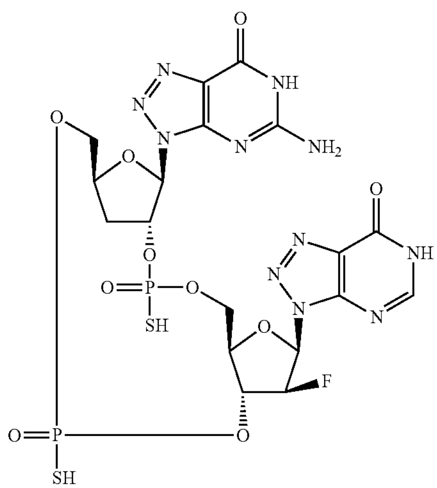 [SMILES: Nc1nc2c(nnn2[C@@H]2O[C@@H]3COP(=O)(S)O[C@H]4[C@H](F)[C@H](n5nnc6c(=O)[nH]cnc65)O[C@@H]4COP(=O)(S)O[C@@H]2C3)c(=O)[nH]1] | 5-amino-3-[(5S,7R,8R,12aR,14R,15S,15aR)-15-fluoro-2,10-dioxido-14-(7-oxo-6,7-dihydro-3H-[1,2,3]triazolo[4,5-c][pyrimidin-3-yl)-2,10-disulfanyloctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 2) | 694 | 182 |
| 342 | 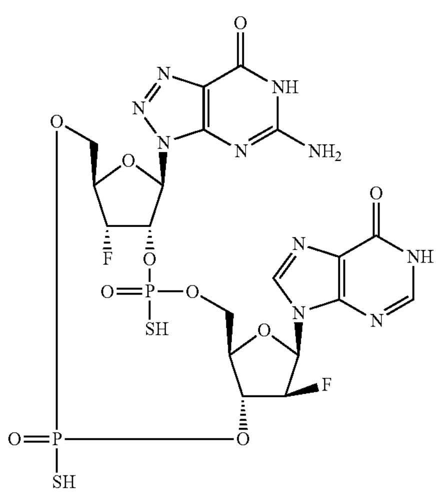 [SMILES: Nc1nc2c(nnn2[C@@H]2O[C@@H]3COP(=O)(S)O[C@H]4[C@H](F)[C@H](n5cnc6c(=O)[nH]cnc65)O[C@@H]4COP(=O)(S)O[C@@H]2[C@@H]3F)c(=O)[nH]1] | 5-amino-3-[(5R,7R,8S,12aR,14R,15S,15aR,16R)-15,16-difluoro-2,10-dioxido-14-(6-oxo-1,6-dihydro-9H-purin-9-yl)-2,10-disulfanyloctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 1) | 711 | 199 |

TABLE 11-continued

| Ex. | Structure | Name | Mass [M − H]⁻ | St. Cmpd. |
|---|---|---|---|---|
| 343 | 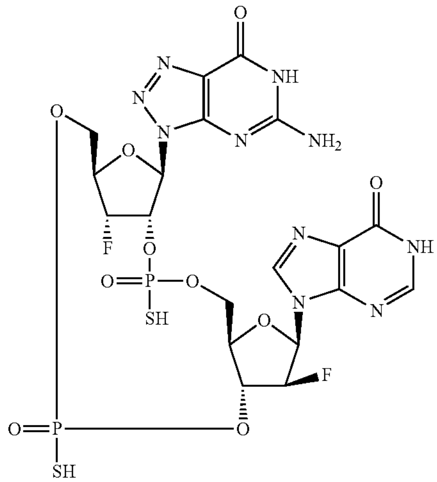 [SMILES: Nc1nc2c(nnn2[C@@H]2O[C@@H]3COP(=O)(S)O[C@H]4[C@H](F)[C@H](n5cnc6c(=O)[nH]cnc65)O[C@@H]4COP(=O)(S)O[C@@H]2[C@@H]3F)c(=O)[nH]1] | 5-amino-3-[(5R,7R,8S,12aR,14R,15S,15aR,16R)-15,16-difluoro-2,10-dioxido-14-(6-oxo-1,6-dihydro-9H-purin-9-yl)-2,10-disulfanyloctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 2) | 711 | 197 |
| 344 | 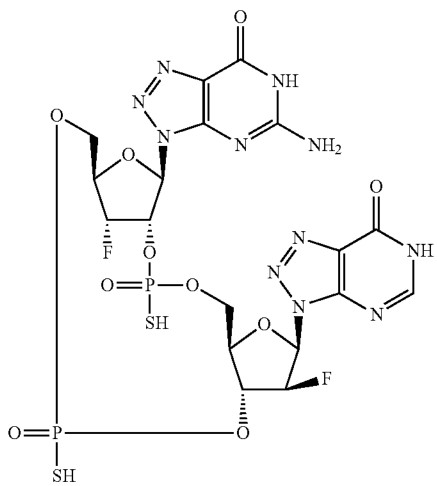 [SMILES: Nc1nc2c(nnn2[C@@H]2O[C@@H]3COP(=O)(S)O[C@H]4[C@H](F)[C@H](n5nnc6c(=O)[nH]cnc65)O[C@@H]4COP(=O)(S)O[C@@H]2[C@@H]3F)c(=O)[nH]1] | 5-amino-3-[(5R,7R,8S,12aR,14R,15S,15aR,16R)-15,16-difluoro-2,10-dioxido-14-(7-oxo-6,7-dihydro-3H-[1,2,3]triazolo[4,5-c]pyrimidin-3-yl)-2,10-disulfanyloctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 1) | 712 | 200 |
| 345 | 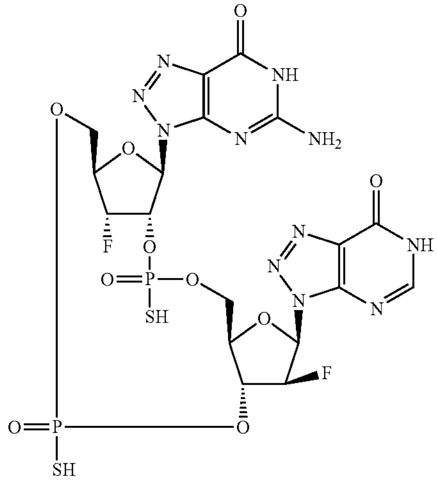 [SMILES: Nc1nc2c(nnn2[C@@H]2O[C@@H]3COP(=O)(S)O[C@H]4[C@H](F)[C@H](n5nnc6c(=O)[nH]cnc65)O[C@@H]4COP(=O)(S)O[C@@H]2[C@@H]3F)c(=O)[nH]1] | 5-amino-3-[(5R,7R,8S,12aR,14R,15S,15aR,16R)-15,16-difluoro-2,10-dioxido-14-(7-oxo-6,7-dihydro-3H-[1,2,3]triazolo[4,5-d]pyrimidin-3-yl)-2,10-disulfanyloctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one (Diastereomer 2) | 712 | 201 |

TABLE 11-continued

| Ex. | Structure | Name | Mass [M − H]⁻ | St. Cmpd. |
|---|---|---|---|---|
| 346 | 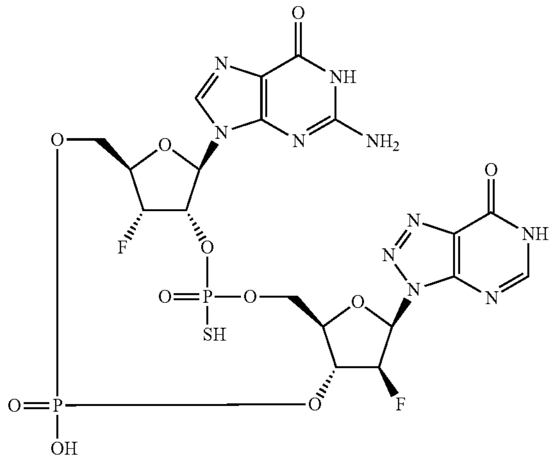 [SMILES: Nc1nc2c(ncn2[C@@H]2O[C@@H]3COP(=O)(O)O[C@H]4[C@H](F)[C@H](n5nnc6c(=O)[nH]cnc65)O[C@@H]4COP(=O)(S)O[C@@H]2[C@@H]3F)c(=O)[nH]1] | 3-[(5R,7R,8S,12aR,14R,15S,15aR,16R)-7-(2-amino-6-oxo-1,6-dihydro-9H-purin-9-yl)-15,16-difluoro-2-hydroxy-2,10-dioxido-10-sulfanyloctahydro-12H-5,8-methanofuro[3,2-l][1,3,6,9,11,2,10]pentaoxadiphosphacyclotetradecin-14-yl]-3,6-dihydro-7H-[1,2,3]triazolo[4,5-d]pyrimidin-7-one (Diastereomer 1) | 695 | 279 |
| 347 | 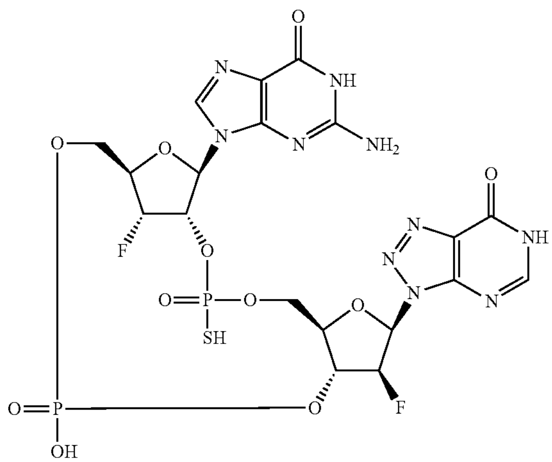 [SMILES: Nc1nc2c(ncn2[C@@H]2O[C@@H]3COP(=O)(O)O[C@H]4[C@H](F)[C@H](n5nnc6c(=O)[nH]cnc65)O[C@@H]4COP(=O)(S)O[C@@H]2[C@@H]3F)c(=O)[nH]1] | 3-[(5R,7R,8S,12aR,14R,15S,15aR,16R)-7-(2-amino-6-oxo-1,6-dihydro-9H-purin-9-yl)-15,16-difluoro-2-hydroxy-2,10-dioxido-10-sulfanyloctahydro-12H-5,8-methanofuro[3,2-l][1,3,6,9,11,2,10]pentaoxadiphosphacyclotetradecin-14-yl]-3,6-dihydro-7H-[1,2,3]triazolo[4,5-d]pyrimidin-7-one (Diastereomer 2) | 695 | 280 |
| 348 | 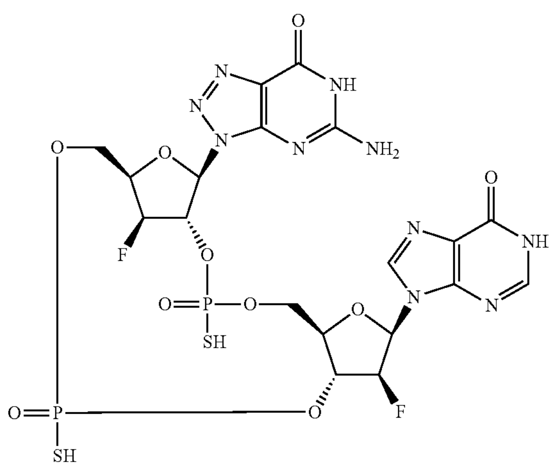 [SMILES: Nc1nc2c(nnn2[C@@H]2O[C@@H]3COP(=O)(S)O[C@H]4[C@H](F)[C@H](n5cnc6c(=O)[nH]cnc65)O[C@@H]4COP(=O)(S)O[C@@H]2[C@H]3F)c(=O)[nH]1] | 5-amino-3-[(5R,7R,8S,12aR,14R,15S,15aR,16S)-15,16-difluoro-2,10-dioxido-14-(6-oxo-1,6-dihydro-9H-purin-9-yl)-2,10-disulfanyloctahydro-12H-5,8-methanofuro[3,2-l][1,3,6,9,11,2,10]pentaoxadiphosphacyclotetradecin-7-yl]-3,6-dihydro-7H-[1,2,3]triazolo[4,5-d]pyrimidin-7-one | 711 | 179 |

Biological Evaluation

The individual compounds described in the Examples are defined as STING agonists by demonstrating binding to the STING protein with an $EC_{50}$ of 20 uM or less in the STING Biochemical [³H]cGAMP Competition Assay (using either HAQ or wild type (WT) STING) and demonstrating interferon production with a 5% or greater luminescence induction at 30 uM in the INF-β secretion in the THP1 cell assay. The methods below describe each of these assays.

[³H]-cGAMP Synthesis 2.3 mL of buffer solution containing 80 mM tris Cl, 200 mM $MgCl_2$ and 20 mM NaCl followed by 0.32 mL of a 10 mM aq solution of GTP was added to a plastic 50 mL AMICON tube. A solution of [³H]ATP (21 Ci/mmol, 45 mCi) in 0.5 mL H$_2$O was then added followed by 1 mL of a 1 mg/mL solution of DNA (Herring testes activator DNA, Sigma, # D6898) and 53 uL of a 47 mM solution of cGAS enzyme. Additional H$_2$O was added to bring the total volume to 10 mL.

The reaction was stirred for 2 h at 37° C. and then added directly to an Amicon Ultra-15 10K centrifuge tube and spun for 1 h at 4,000 g. The collected solution was then purified on a semi-prep Mono Q column using the following mobile phases:

A: 0.05M TrisCl pH 8.5 adjusted with 1M NaOH
B: 0.05M TrisCl, 0.5M NaCl pH 8.5 adjusted with 1M NaOH Gradient: 100% A for 5 min followed by a linear gradient to 50:50 (A:B) over 25 min, 3 mL/min, 254 nm.

The collected product fractions were pooled and adjusted to a total volume of 30 mL with buffer A. A total yield of 15.5 mCi of [$^3$H]cGAMP was isolated at a radiochemical purity of 98.0% at a specific activity of 21.5 Ci/mmol.

cGAS Enzyme

A recombinant DNA vector was chemically synthesized to express the truncated human cGAS enzyme (residues 161-522). To aid in expression and purification, the amino terminus contains a hexahistidine tag, SUMO tag and TEV cleavage site. The recombinant enzyme was overexpressed in Rosetta™ 2(DE3) Single Competent Cells (Novagen). Affinity purification was carried out using HIS-Select HF Nickel Affinity Gel (Sigma) followed by size exclusion chromatography using a Hi-Load 26/60 Superdex200 prep grade column (GE Healthcare).

Fractions were pooled, concentrated, flash frozen in liquid nitrogen and stored at −80° C. until needed for research applications.

Example 349: $^3$H-cGAMP Filtration Binding Assay (HAQ STING)

The ability of compounds to bind STING is quantified by their ability to compete with tritiated cGAMP ligand for human STING receptor membrane using a radioactive filter-binding assay. The binding assay employs STING receptor obtained from *Trichoplusia ni* cell membranes (*T. ni*; Expression Systems, cat #94-002F, wwwv.expressionsystems.com) overexpressing full-length HAQ STING prepared in-house and tritiated cGAMP ligand also purified in-house.

The basic HAQ STING filtration assay protocol is as follows:

The compounds were serially titrated by the Hamilton STARPlus CORE in a 96-well plate (Greiner, #651201) using a 1:3 ten-point dose response format. After compound preparation, a 2.2 ug/ml working concentration of STING membrane (SEQ. ID. No. 2) was prepared by diluting concentrated membrane into assay buffer (1×PBS; Invitrogen # SH30028.02) and douncing 7× using a manual tissue homogenizer (Wheaton, #357546). 148 uL of prepared membrane was then manually added to each well of a 96-well deep-well polypropylene plate (Fisher Scientific, #12-566-121). Following membrane addition, 2 uL of either titrated test compound, DMSO control (Sigma #276855), or cold cGAMP control (prepared in-house) was added to the appropriate wells using a Biomek FX. Compound and membrane then preincubated for 60 min at RT to allow compound binding to equilibrate. Following equilibration, 8 nM of [$^3$H] c-GAMP ligand was prepared by diluting into assay buffer, and 50 uL of this working stock was then manually added to each well of the assay plate. Plates were then incubated at RT for 60 min, and the contents of each assay plate were then filtered through a 96-well GF/B filter plate (PerkinElmer, #6005250) using a TomTec MachIII Cell Harvester equipped with 20 mM HEPES buffer (Fisher Scientific, # BP299500). The filter plates were then dried at 55° C. for 30 min using a pressurized VWR oven before 30 uL of Ultima GoldF scintillate was added to each well. Tritium levels for each reaction well were then measured using a PerkinElmer TopCount plate reader.

After normalization to controls, the percent activity for each compound concentration was calculated by measuring the amount of remaining radioactivity. The plot of percent activity versus the log of compound concentration was fit with a 4-parameter dose response equation to calculate EC$_{50}$ values.

The final reaction conditions were:

| Component | Volume (uL) | Final Concentration |
|---|---|---|
| STING membrane | 148 | 1.5 ug/ml |
| $^3$H-cGAMP | 50 | 2.0 nM |
| Low Control (cold cGAMP) | 2 | 10 uM |
| Test compound/DMSO | 2 | 10 uM |

Compound concentrations tested were 20.000, 637.00, 2.200, 0.740, 0.247, 0.082, 0.027, 0.009, 0.003, and 0.001M with 1.0% residual DMSO.

Full-Length STING (HAQ) Virus Generation

STING virus was generated using an insect cell baculovirus system. *Spodoptera frugiperda* Sf21 cells (Kempbio, Inc.) were diluted to 5e5 cells/ml in Sf-900II SFM media (LifeTechnologies #10902088) without antibiotics. The cell suspension was added to each well of a treated 6-well plate (2 mL per well, 1e6 cells total), and the cells were allowed to adhere for at least 30 min. Meanwhile, a 1 mL co-transfection mix was assembled by combining 500 ng of HAQ STING [STING(1-379)R71H,G230A,H232R,R293Q-GG-AviTag-GS-HRV3C-HIS8/pBAC1] DNA (Genewiz custom synthesis) with 1 mL Sf-900II SFM media containing 10 µL Cellfectin® II Reagent (Invitrogen #10362100) and 100 ng viral backbone BestBac 2.0, v-cath/chiA Deleted Linearized Baculovirus DNA (Expression Systems #91-002). The transfection mixtures were allowed to incubate for 30 min. After incubation, media was gently removed from the adhered cells in the 6-well plate, the 1 mL transfection mixtures were added (1 mL per well), and the plate was placed in a humidified incubator at 27° C. The following day, 1 mL Sf-900II SFM media (no antibiotics) was added to each well of the 6-well plate. After media addition, the cells were allowed to incubate with DNA (SEQ. ID. No. 3) at 27° C. for 5-7 days to generate the P0 viral stock. To generate P1 viral stocks, 0.5 mL of P0 viral supernatant was added to 50 mL uninfected Sf21 cells (seeded the day prior to infection at a density of 5×10$^5$ cells/mL to allow for one overnight doubling) in Sf-900II SFM media containing 5 g/mL gentamicin (Invitrogen #15710072). The infected cells were then incubated at 27° C. for 3 d while shaking at 110 rpm (ATR Biotech Multitron Infors HT # AJ118). On day 3, P1 cultures were counted using a ViCell XR (Beckman Coulter Life Sciences #383556) to confirm infection had occurred (cell size ≥3 µm larger than uninfected cells and viability approximately 85-95%). Cultures were harvested in 50 mL conical tubes and centrifuged at 2000×g for 10 min at 4° C. The P1 viral supernatants were poured off into clean 50 ml centrifuge tubes, and the remaining P1 cell pellets were used to generate Baculovirus Infected Insect Cells (BIICs) according to in-house validated SOP. Cryopreservation media containing Sf-900II SFM media with 10% heat inactivated FBS, 10% DMSO (Sigma # D2650), and 5 µg/ml gentamicin was prepared in-house and sterilized through 0.22 µM filter immediately prior to use. P1 cell pellets were resuspended to a density of 2e7 cells/ml and aliquoted into cryovials (1 mL per vial). Cryovials were placed in Mr. Frosty cell freezers O/N at −80° C. and transferred to liquid nitrogen for long term storage the following day. To generate P2 viral stock, 0.5 mL of the P1 viral supernatant was added to 50 mL uninfected Sf21 cells (seeded the day prior to infection at a density of $5 \times 10^5$ cells/mL to allow for one overnight doubling) in Sf-900II SFM media containing 5 µg/mL gentamicin. These cells were incubated at 27° C. for 3 d while shaking at 110 rpm before harvesting P2 stock with centrifugation at 2000×g for 10 min at 4° C. The P2 viral supernatants were poured off and discarded, while the P2 cell pellets were used to generate P2 BIICs following the same protocol described above. The baculovirus generation protocol has been validated to consistently produce P1/P2 BIICs with titers of 2e9 pfu/mL (2e7 cells/mLx 100 pfu/cell).

Full-Length STING (HAQ) Expression

To generate STING membranes, P1/P2 BIICs were amplified overnight by adding thawed BIICs to Sf21 cells seeded at a density of $1.0 \times 10^6$ cells/mL. The volume of BIIC used to infect the culture was calculated using an assumed BIIC titer of 2e9 pfu/ml to achieve an MOI of 10 in the overnight amplification. After culturing overnight, the cells were counted on a ViCell XR to confirm infection had occurred (cell size ≥3 µm larger than uninfected cells and viability approximately 80-90%). The volume of infected Sf21 cells from the overnight amplification used to infect the large-scale expression of *Trichoplusia ni* (*T. ni*; Expression Systems, cat #94-002F, www.expressionsystems.com) seeded at a density of $1.0 \times 10^6$ in cell media (ESF921 SFM containing 5 µg/mL gentamicin) at MOI=2.0 was calculated based on (100 pfu/infected Sf21 cell). The cells were allowed to express for 48 h at 27° C. before harvesting the cell pellet, by centrifugation at 3,400×g for 10 min at 4° C. *T. ni* cells were counted on a ViCell XR to confirm infection had occurred (cell size ≥3 µm larger than uninfected cells and viability approximately 80-90%) prior to harvest.

Full-Length STING (HAQ) Membrane Generation

Buffer stock reagents:
1) 1 M HEPES pH 7.5, Teknova, Cat # H1035
2) 5 M NaCl, Sigma Aldrich, Cat # S5150-1L
3) KCl, Sigma Aldrich, Cat #319309-500ML
4) Complete EDTA-free protease inhibitor tablets, Roche Diagnostics, Cat #11873580001
5) Benzonase, Universal Nuclease, Pierce, Cat #88702

Lysis buffer [25 mM HEPES pH 7.5, 10 mM $MgCl_2$, 20 mM KCl, (Benzonase 1:5000, Complete Protease Inhibitor tab/50 mL)] was added to the pellet of cells expressing full-length STING (HAQ) prepared above at 5 mL Lysis buffer/g of cell pellet. The pellet was resuspended and dounced twenty times using a Wheaton Dounce Homogenizer to disrupt the cell membrane. Homogenized lysate was then passed through the emulsiflex-$C_5$ microfluidizer at a pressure close to 5000 PSI. The resuspended pellet was centrifuged at 36,000 rpm (100,000×g) in a 45Ti rotor in the ultra-high speed centrifuge for 45 min, 4° C. The supernatant was removed. The pellet then was resuspended in wash buffer [(25 mM HEPES pH7.5, 1 mM $MgCl_2$, 20 mM KCl, 1M NaCl (Complete Protease Inhibitor tab/50 mL)] at a volume of 50 mL pellet/centrifuge tube. The pellet/wash buffer mixture was then homogenized, using a glass homogenizer on ice (20 strokes), followed by centrifugation at 36,000 rpm for 45 min at 4° C. The supernatant was removed. The wash step was repeated once more. The resulting membrane was resuspended in 20 mM HEPES pH 7.5, 500 mM NaCl, 10% glycerol, EDTA-free Protease Inhibitors (1 tablet/50 mL). The protein concentration was measured by Bradford assay (Bio-Rad Protein Assay, Cat #500-0006), and protein enrichment was determined by SDS-PAGE and confirmed by Western blot. The resuspended membranes were stored at −80° C.

Full-Length HAQ STING [STING(1-379)R71H, G230A, H232R,R293Q-GG-AviTag-GS-HRV3C-HIS8]Amino Acid Sequence.

(SEQ. ID. No. 2)
MPHSSLHPSIPCPRGHGAQKAALVLLSACLVTLWGLGEPPEHTLRYLVLH

LASLQLGLLLNGVCSLAEELHHIHSRYRGSYWRTVRACLGCPLRRGALLL

LSIYFYYSLPNAVGPPFTWMLALLGLSQALNILLGLKGLAPAEISAVCEK

GNFNVAHGLAWSYYIGYLRLILPELQARIRTYNQHYNNLLRGAVSQRLYI

LLPLDCGVPDNLSMADPNIRFLDKLPQQTADRAGIKDRVYSNSIYELLEN

GQRAGTCVLEYATPLQTLFAMSQYSQAGFSREDRLEQAKLFCQTLEDILA

DAPESQNNCRLIAYQEPADDSSFSLSQEVLRHLRQEEKEEVTVGSLKTSA

VPSTSTMSQEPELLISGMEKPLPLRTDFSGGGLNDIFEAQKIEWHEGSLE

VLFQGPHHHHHHHH

Full-length HAQ [STING(1-379)R71H, G230A,H232R, R293Q-GG-AviTag-GS-HRV3C-HIS8/pBAC1] Plasmid DNA Sequence.

(SEQ. ID. No. 3)
GGAACGGCTCCGCCCACTATTAATGAAATTAAAAATTCCAATTTTAAAAA

ACGCAGCAAGAGAAACATTTGTATGAAAGAATGCGTAGAAGGAAAGAAAA

ATGTCGTCGACATGCTGAACAACAAGATTAATATGCCTCCGTGTATAAAA

AAAATATTGAACGATTTGAAAGAAAACAATGTACCGCGCGGCGGTATGTA

CAGGAAGAGGTTTATACTAAACTGTTACATTGCAAACGTGGTTTCGTGTG

CCAAGTGTGAAAACCGATGTTTAATCAAGGCTCTGACGCATTTCTACAAC

CACGACTCCAAGTGTGTGGGTGAAGTCATGCATCTTTTAATCAAATCCCA

AGATGTGTATAAACCACCAAACTGCCAAAAAATGAAAACTGTCGACAAGC

TCTGTCCGTTTGCTGGCAACTGCAAGGGTCTCAATCCTATTTGTAATTAT

TGAATAATAAAACAATTATAAATGCTAAATTTGTTTTTTATTAACGATAC

AAACCAAACGCAACAAGAACATTTGTAGTATTATCTATAATTGAAAACGC

GTAGTTATAATCGCTGAGGTAATATTTAAAATCATTTTCAAATGATTCAC

AGTTAATTTGCGACAATATAATTTTATTTTCACATAAACTAGACGCCTTG

TCGTCTTCTTCTTCGTATTCCTTCTCTTTTTCATTTTTCTCTTCATAAAA

ATTAACATAGTTATTATCGTATCCATATATGTATCTATCGTATAGAGTAA

ATTTTTTGTTGTCATAAATATATATGTCTTTTTTAATGGGGTGTATAGTA

CCGCTGCGCATAGTTTTTCTGTAATTTACAACAGTGCTATTTTCTGGTAG

TTCTTCGGAGTGTGTTGCTTTAATTATTAAATTTATATAATCAATGAATT

TGGGATCGTCGGTTTTGTACAATATGTTGCCGGCATAGTACGCAGCTTCT

-continued

TCTAGTTCAATTACACCATTTTTTAGCAGCACCGGATTAACATAACTTTC

CAAAATGTTGTACGAACCGTTAAACAAAAACAGTTCACCTCCCTTTTCTA

TACTATTGTCTGCGAGCAGTTGTTTGTTGTTAAAAATAACAGCCATTGTA

ATGAGACGCACAAACTAATATCACAAACTGGAAATGTCTATCAATATATA

GTTGCTGATCAGATCTGATCATGGAGATAATTAAAATGATAACCATCTCG

CAAATAAATAAGTATTTTACTGTTTTCGTAACAGTTTTGTAATAAAAAAA

CCTATAAATATAGGATCCATGCCCCACTCCAGCCTGCATCCATCCATCCC

GTGTCCCAGGGGTCACGGGGCCCAGAAGGCAGCCTTGGTTCTGCTGAGTG

CCTGCCTGGTGACCCTTTGGGGGCTAGGAGAGCCACCAGAGCACACTCTC

CGGTACCTGGTGCTCCACCTAGCCTCCCTGCAGCTGGGACTGCTGTTAAA

CGGGGTCTGCAGCCTGGCTGAGGAGCTGCACCACATCCACTCCAGGTACC

GGGGCAGCTACTGGAGGACTGTGCGGGCCTGCCTGGGCTGCCCCCTCCGC

CGTGGGGCCCTGTTGCTGCTGTCCATCTATTTCTACTACTCCCTCCCAAA

TGCGGTCGGCCCGCCCTTCACTTGGATGCTTGCCCTCCTGGGCCTCTCGC

AGGCACTGAACATCCTCCTGGGCCTCAAGGGCCTGGCCCCAGCTGAGATC

TCTGCAGTGTGTGAAAAAGGGAATTTCAACGTGGCCCATGGGCTGGCATG

GTCATATTACATCGGATATCTGCGGCTGATCCTGCCAGAGCTCCAGGCCC

GGATTCGAACTTACAATCAGCATTACAACAACCTGCTACGGGGTGCAGTG

AGCCAGCGGCTGTATATTCTCCTCCCATTGGACTGTGGGGTGCCTGATAA

CCTGAGTATGGCTGACCCCAACATTCGCTTCCTGGATAAACTGCCCCAGC

AGACCGCTGACCGTGCTGGCATCAAGGATCGGGTTTACAGCAACAGCATC

TATGAGCTTCTGGAGAACGGGCAGCGGGCGGGCACCTGTGTCCTGGAGTA

CGCCACCCCCTTGCAGACTTTGTTTGCCATGTCACAATACAGTCAAGCTG

GCTTTAGCCGGGAGGATAGGCTTGAGCAGGCCAAACTCTTCTGCCAGACA

CTTGAGGACATCCTGGCAGATGCCCCTGAGTCTCAGAACAACTGCCGCCT

CATTGCCTACCAGGAACCTGCAGATGACAGCAGCTTCTCGCTGTCCCAGG

AGGTTCTCCGGCACCTGCGGCAGGAGGAAAAGGAAGAGGTTACTGTGGGC

AGCTTGAAGACCTCAGCGGTGCCCAGTACCTCCACGATGTCCCAAGAGCC

TGAGCTCCTCATCAGTGGAATGGAAAAGCCCCTCCCTCTCCGCACGGATT

TCTCTGGCGGTGGCCTGAACGACATCTTCGAAGCCCAGAAAATCGAATGG

CATGAAGGCAGCCTGGAAGTGCTGTTCCAGGGCCCACACCACCATCATCA

CCATCACCATTAATGAGCGGCCGCACTCGAGCACCACCACCACCACCACT

AACCTAGGTAGCTGAGCGCATGCAAGCTGATCCGGGTTATTAGTACATTT

ATTAAGCGCTAGATTCTGTGCGTTGTTGATTTACAGACAATTGTTGTACG

TATTTTAATAATTCATTAAATTTATAATCTTTAGGGTGGTATGTTAGAGC

GAAAATCAAATGATTTTCAGCGTCTTTATATCTGAATTTAAATATTAAAT

CCTCAATAGATTTGTAAAATAGGTTTCGATTAGTTTCAAACAAGGGTTGT

TTTTCCGAACCGATGGCTGGACTATCTAATGGATTTTCGCTCAACGCCAC

AAAACTTGCCAAATCTTGTAGCAGCAATCTAGCTTTGTCGATATTCGTTT

GTGTTTTGTTTTGTAATAAAGGTTCGACGTCGTTCAAAATATTATGCGCT

-continued

TTTGTATTTCTTTCATCACTGTCGTTAGTGTACAATTGACTCGACGTAAA

CACGTTAAATAGAGCTTGGACATATTTAACATCGGGCGTGTTAGCTTTAT

TAGGCCGATTATCGTCGTCGTCCCAACCCTCGTCGTTAGAAGTTGCTTCC

GAAGACGATTTTGCCATAGCCACACGACGCCTATTAATTGTGTCGGCTAA

CACGTCCGCGATCAAATTTGTAGTTGAGCTTTTTGGAATTATTTCTGATT

GCGGGCGTTTTTGGGCGGGTTTCAATCTAACTGTGCCCGATTTTAATTCA

GACAACACGTTAGAAAGCGATGGTGCAGGCGGTGGTAACATTTCAGACGG

CAAATCTACTAATGGCGGCGGTGGTGGAGCTGATGATAAATCTACCATCG

GTGGAGGCGCAGGCGGGGCTGGCGGCGGAGGCGGAGGCGGAGGTGGTGGC

GGTGATGCAGACGGCGGTTTAGGCTCAAATGTCTCTTTAGGCAACACAGT

CGGCACCTCAACTATTGTACTGGTTTCGGGCGCCGTTTTTGGTTTGACCG

GTCTGAGACGAGTGCGATTTTTTTCGTTTCTAATAGCTTCCAACAATTGT

TGTCTGTCGTCTAAAGGTGCAGCGGGTTGAGGTTCCGTCGGCATTGGTGG

AGCGGGCGGCAATTCAGACATCGATGGTGGTGGTGGTGGAGGCGCTG

GAATGTTAGGCACGGGAGAAGGTGGTGGCGGCGGTGCCGCCGGTATAATT

TGTTCTGGTTTAGTTTGTTCGCGCACGATTGTGGGCACCGGCGCAGGCGC

CGCTGGCTGCACAACGGAAGGTCGTCTGCTTCGAGGCAGCGCTTGGGGTG

GTGGCAATTCAATATTATAATTGGAATACAAATCGTAAAAATCTGCTATA

AGCATTGTAATTTCGCTATCGTTTACCGTGCCGATATTTAACAACCGCTC

AATGTAAGCAATTGTATTGTAAAGAGATTGTCTCAAGCTCGGATCGATCC

CGCACGCCGATAACAAGCCTTTTCATTTTTACTACAGCATTGTAGTGGCG

AGACACTTCGCTGTCGTCGAGGTTTAAACGCTTCCTCGCTCACTGACTCG

CTGCGCTCGGTCGTTCGGCTGCGGCGAGCGGTATCAGCTCACTCAAAGGC

GGTAATACGGTTATCCACAGAATCAGGGGATAACGCAGGAAAGAACATGT

GAGCAAAAGGCCAGCAAAAGGCCAGGAACCGTAAAAAGGCCGCGTTGCTG

GCGTTTTTCCATAGGCTCCGCCCCCCTGACGAGCATCACAAAAATCGACG

CTCAAGTCAGAGGTGGCGAAACCCGACAGGACTATAAAGATACCAGGCGT

TTCCCCCTGGAAGCTCCCTCGTGCGCTCTCCTGTTCCGACCCTGCCGCTT

ACCGGATACCTGTCCGCCTTTCTCCCTTCGGGAAGCGTGGCGCTTTCTCA

TAGCTCACGCTGTAGGTATCTCAGTTCGGTGTAGGTCGTTCGCTCCAAGC

TGGGCTGTGTGCACGAACCCCCCGTTCAGCCCGACCGCTGCGCCTTATCC

GGTAACTATCGTCTTGAGTCCAACCCGGTAAGACACGACTTATCGCCACT

GGCAGCAGCCACTGGTAACAGGATTAGCAGAGCGAGGTATGTAGGCGGTG

CTACAGAGTTCTTGAAGTGGTGGCCTAACTACGGCTACACTAGAAGGACA

GTATTTGGTATCTGCGCTCTGCTGAAGCCAGTTACCTTCGGAAAAAGAGT

TGGTAGCTCTTGATCCGGCAAACAAACCACCGCTGGTAGCGGTGGTTTTT

TTGTTTGCAAGCAGCAGATTACGCGCAGAAAAAAAGGATCTCAAGAAGAT

CCTTTGATCTTTTCTACGGGGTCTGACGCTCAGTGGAACGAAAACTCACG

TTAAGGGATTTTGGTCATGAGATTATCAAAAAGGATCTTCACCTAGATCC

TTTTAAATTAAAAATGAAGTTTTAAATCAATCTAAAGTATATATGAGTAA

ACTTGGTCTGACAGTTACCAATGCTTAATCAGTGAGGCACCTATCTCAGC

-continued

```
GATCTGTCTATTTCGTTCATCCATAGTTGCCTGACTCCCCGTCGTGTAGA
TAACTACGATACGGGAGGGCTTACCATCTGGCCCCAGTGCTGCAATGATA
CCGCGAGACCCACGCTCACCGGCTCCAGATTTATCAGCAATAAACCAGCC
AGCCGGAAGGGCCGAGCGCAGAAGTGGTCCTGCAACTTTATCCGCCTCCA
TCCAGTCTATTAATTGTTGCCGGGAAGCTAGAGTAAGTAGTTCGCCAGTT
AATAGTTTGCGCAACGTTGTTGCCATTGCTACAGGCATCGTGGTGTCACG
CTCGTCGTTTGGTATGGCTTCATTCAGCTCCGGTTCCCAACGATCAAGGC
GAGTTACATGATCCCCCATGTTGTGCAAAAAAGCGGTTAGCTCCTTCGGT
CCTCCGATCGTTGTCAGAAGTAAGTTGGCCGCAGTGTTATCACTCATGGT
TATGGCAGCACTGCATAATTCTCTTACTGTCATGCCATCCGTAAGATGCT
TTTCTGTGACTGGTGAGTACTCAACCAAGTCATTCTGAGAATAGTGTATG
CGGCGACCGAGTTGCTCTTGCCCGGCGTCAATACGGGATAATACCGCGCC
ACATAGCAGAACTTTAAAAGTGCTCATCATTGGAAAACGTTCTTCGGGGC
GAAAACTCTCAAGGATCTTACCGCTGTTGAGATCCAGTTCGATGTAACCC
ACTCGTGCACCCAACTGATCTTCAGCATCTTTTACTTTCACCAGCGTTTC
TGGGTGAGCAAAAACAGGAAGGCAAAATGCCGCAAAAAAGGGAATAAGGG
CGACACGGAAATGTTGAATACTCATACTCTTCCTTTTTCAATATTATTGA
AGCATTTATCAGGGTTATTGTCTCATGAGCGGATACATATTTGAATGTAT
TTAGAAAAATAAACAAATAGGGGTTCCGCGCACATTTCCCCGAAAAGTGC
CACCTGACGCGCCCTGTAGCGGCGCATTAAGCGCGGCGGGTGTGGTGGTT
ACGCGCAGCGTGACCGCTACACTTGCCAGCGCCCTAGCGCCCGCTCCTTT
CGCTTTCTTCCCTTCCTTTCTCGCCACGTTCGCCGGCTTTCCCCGTCAAG
CTCTAAATCGGGGGCTCCCTTTAGGGTTCCGATTTAGTGCTTTACGGCAC
CTCGACCCCAAAAAACTTGATTAGGGTGATGGTTCACGTAGTGGGCCATC
GCCCTGATAGACGGTTTTTCGCCCTTTGACGTTGGAGTCCACGTTCTTTA
ATAGTGGACTCTTGTTCCAAACTGGAACAACACTCAACCCTATCTCGGTC
TATTCTTTTGATTTATAAGGGATTTTGCCGATTTCGGCCTATTGGTTAAA
AAATGAGCTGATTTAACAAAAATTTAACGCGAATTTTAACAAAATATTAA
CGTTTACAATTTCCCATTCGCCATTCAGGCTGCGCAACTGTTGGGAAGGG
CGATCGGTGCGGGCCTCTTCGCTATTACGCCA
```

Certain compounds of the disclosure were evaluated in HAQ STING in vitro binding assay as described above. The following table tabulates the biological data for these compounds as $EC_{50}$ values.

TABLE 12

$^3$H-cGAMP filtration binding assay for HAQ STING

| Compound | $EC_{50}$ (nM) |
| --- | --- |
| Example 1 | <1 |
| Example 2 | 1.3 |
| Example 3 | 257.1 |
| Example 4 | 22 |
| Example 5 | 1.1 |
| Example 6 | <1 |
| Example 7 | 1.2 |
| Example 8 | 13.6 |
| Example 9 | 7.2 |
| Example 10 | 4.9 |
| Example 11 | 1.2 |
| Example 12 | <1 |
| Example 13 | 1.5 |
| Example 14 | <1 |
| Example 15 | 378.1 |
| Example 16 | 12.4 |
| Example 17 | 121 |
| Example 18 | 53.9 |
| Example 19 | 173 |
| Example 20 | <1 |
| Example 21 | 1.3 |
| Example 22 | 4822 |
| Example 23 | <1 |
| Example 24 | 2.4 |
| Example 25 | 3.4 |
| Example 26 | <1 |
| Example 27 | 1.3 |
| Example 28 | 18.7 |
| Example 30 | 91 |
| Example 31 | 94 |
| Example 32 | 11.1 |
| Example 33 | 11.9 |
| Example 34 | 24.6 |
| Example 35 | 7.9 |
| Example 36 | 21.5 |
| Example 37 | 619.6 |
| Example 38 | 3 |
| Example 69 | <1 |
| Example 70 | 2 |
| Example 71 | <1 |
| Example 72 | <1 |
| Example 73 | 834 |
| Example 74 | 5.8 |
| Example 39 | 24.4 |
| Example 40 | 3.2 |
| Example 41 | 11.8 |
| Example 42 | 15.2 |
| Example 43 | 162.2 |
| Example 44 | 17.1 |
| Example 45 | 24.8 |
| Example 46 | 11.7 |
| Example 47 | 39.2 |
| Example 48 | 1.2 |
| Example 49 | 30 |
| Example 50 | 2.7 |
| Example 51 | 287.1 |
| Example 52 | 1.5 |
| Example 53 | 1.7 |
| Example 54 | <1 |
| Example 55 | 55.3 |
| Example 56 | 89.4 |
| Example 57 | 437.9 |
| Example 58 | 3.1 |
| Example 59 | 11.8 |
| Example 60 | 42.5 |
| Example 61 | 18.2 |
| Example 66 | 117.1 |
| Example 67 | 6.4 |
| Example 68 | 63.8 |
| Example 69 | <1 |
| Example 70 | 2 |
| Example 71 | <1 |
| Example 72 | <1 |
| Example 73 | 834 |
| Example 74 | 5.8 |
| Example 75 | 2.6 |
| Example 76 | 75.4 |
| Example 77 | 160.5 |
| Example 78 | 14.6 |
| Example 79 | 103.2 |
| Example 80 | 1.3 |
| Example 81 | <1 |
| Example 82 | 21.5 |
| Example 83 | 3.7 |

TABLE 12-continued

³H-cGAMP filtration binding assay for HAQ STING

| Compound | EC$_{50}$ (nM) |
|---|---|
| Example 85 | <1 |
| Example 86 | <1 |
| Example 87 | <1 |
| Example 88 | <1 |
| Example 89 | 8272 |
| Example 90 | 1.7 |
| Example 91 | 15.8 |
| Example 92 | 114 |
| Example 93 | <1 |
| Example 94 | 24.6 |
| Example 95 | 13.9 |
| Example 96 | 5.3 |
| Example 97 | <1 |
| Example 98 | 1.8 |
| Example 99 | <1 |
| Example 100 | 16.7 |
| Example 101 | 8 |
| Example 102 | <1 |
| Example 117 | 1 |
| Example 118 | 1.4 |
| Example 119 | 17.8 |
| Example 120 | 45.1 |
| Example 121 | <1 |
| Example 123 | 5.1 |
| Example 124 | <1 |
| Example 125 | 21.7 |
| Example 126 | 9.7 |
| Example 127 | 24.4 |
| Example 128 | <1 |
| Example 129 | 88.6 |
| Example 130 | <1 |
| Example 131 | 2.4 |
| Example 132 | 25.9 |
| Example 133 | 61.4 |
| Example 134 | <1 |
| Example 135 | 253.4 |
| Example 136 | 3.7 |
| Example 137 | 11.4 |
| Example 138 | 738.8 |
| Example 139 | <1 |
| Example 140 | 12.9 |
| Example 141 | <1 |
| Example 142 | 6.2 |
| Example 143 | 1.05 |
| Example 144 | <1 |
| Example 145 | <1 |
| Example 146 | 5.6 |
| Example 147 | 1.4 |
| Example 148 | 33.3 |
| Example 149 | 8.4 |
| Example 150 | <1 |
| Example 151 | <1 |
| Example 152 | <1 |
| Example 244 | 156.6 |
| Example 245 | 2.7 |
| Example 246 | 21.3 |
| Example 247 | <1 |
| Example 290 | 2.5 |
| Example 291 | 64.7 |
| Example 292 | 2.6 |
| Example 293 | 1.9 |
| Example 294 | 6.6 |
| Example 295 | 29.6 |
| Example 296 | 4.1 |
| Example 297 | <1 |
| Example 298 | 52.9 |
| Example 299 | 1325 |
| Example 300 | 5.1 |
| Example 301 | 4.8 |
| Example 302 | 2.3 |
| Example 303 | <1 |
| Example 304 | 3.3 |
| Example 305 | 326.2 |
| Example 306 | 3.6 |
| Example 307 | <1 |
| Example 308 | 1.6 |
| Example 309 | 4 |
| Example 310 | 27.6 |
| Example 311 | 1595 |
| Example 312 | 122.5 |
| Example 313 | 210.6 |
| Example 314 | <1 |
| Example 315 | 49.9 |
| Example 316 | 2324 |
| Example 317 | <1 |
| Example 318 | 6.2 |
| Example 319 | 7.3 |
| Example 320 | 6.3 |
| Example 321 | 112.2 |
| Example 322 | 68.8 |
| Example 332 | 8.2 |
| Example 333 | 45.9 |

Example 350: ³H-cGAMP Filtration Binding Assay (WT STING)

The ability of compounds to bind STING is quantified by their ability to compete with tritiated cGAMP ligand for human STING receptor membrane using a radioactive filter-binding assay. The binding assay employs STING receptor obtained from *Trichoplusia ni* cell membranes (*T. ni*; Expression Systems, cat #94-002F, www.expressionsystems.com) overexpressing full-length WT STING prepared in-house and tritiated cGAMP ligand also purified in-house.

The basic WT STING filtration assay protocol is as follows:

16 nM of [³H] c-GAMP ligand was prepared by diluting into assay buffer, and 50 uL of this working stock was manually added to each well of the assay plate. After ligand addition, 2 uL of either titrated test compound, DMSO control (Sigma #276855), or cold cGAMP control (prepared in-house) was added to the appropriate wells using a Biomek FX. The serially titrated compound was prepared on a Hamilton STARPlus CORE in a 96-well plate (Greiner, #651201) using a 1:3 ten-point dose response format. Following compound addition, a 2.2 ug/ml working concentration of STING membrane (SEQ. ID. No. 4) was prepared by diluting concentrated membrane into assay buffer (1×PBS; Invitrogen # SH30028.02) and douncing 7× using a manual tissue homogenizer (Wheaton, #357546). 148 uL of this prepared membrane was then manually added to each well of a 96-well deep-well polypropylene plate (Fisher Scientific, #12-566-121). Compound, ligand, and membrane then incubated for 60 min at RT before the contents of each assay plate were filtered through a 96-well GF/B filter plate (PerkinElmer, #6005250) using a TomTec MachIII Cell Harvester equipped with 20 mM HEPES buffer (Fisher Scientific, # BP299500). The filter plates were then dried at 55° C. for 30 min using a pressurized VWR oven before 30 uL of Ultima GoldF scintillate was added to each well. Tritium levels for each reaction well were then measured using a PerkinElmer TopCount plate reader.

After normalization to controls, the percent activity for each compound concentration was calculated by measuring the amount of remaining radioactivity. The plot of percent activity versus the log of compound concentration was fit with a 4-parameter dose response equation to calculate EC$_{50}$ values.

The final reaction conditions were:

| Component | Volume (uL) | Final Concentration |
| --- | --- | --- |
| STING membrane | 148 | 1.5 ug/ml |
| $^3$H-cGAMP | 50 | 4.0 nM |
| Low Control (cold cGAMP) | 2 | 10 uM |
| Test compound/DMSO | 2 | 10 uM |

Compound concentrations tested were 20.000, 637.00, 2.200, 0.740, 0.247, 0.082, 0.027, 0.009, 0.003, and 0.001 μM with 1.0% residual DMSO.

Full-Length STING (WT) Virus Generation

STING virus was generated using an insect cell baculovirus system. *Spodoptera frugiperda* Sf21 cells (Kempbio, Inc.) were diluted to 5e5 cells/ml in Sf-900II SFM media (LifeTechnologies #10902088) without antibiotics. The cell suspension was added to each well of a treated 6-well plate (2 mL per well, 1e6 cells total), and the cells were allowed to adhere for at least 30 min. Meanwhile, a 1 mL co-transfection mix was assembled by combining 500 ng of WT STING[STING(1-379)H232R-gg-AviTag-gs-HRV3C-HIS8/pBAC1] (Genewiz custom synthesis) with 1 mL Sf-900II SFM media containing 10 μL Cellfectin® II Reagent (Invitrogen #10362100) and 100 ng viral backbone BestBac 2.0, v-cath/chiA Deleted Linearized Baculovirus DNA (Expression Systems #91-002). The transfection mixtures were allowed to incubate for 30 min. After incubation, media was gently removed from the adhered cells in the 6-well plate, the 1 mL transfection mixtures were added (1 mL per well), and the plate was placed in a humidified incubator at 27° C. The following day, 1 mL Sf-900II SFM media (no antibiotics) was added to each well of the 6-well plate. After media addition, the cells were allowed to incubate with DNA [(SEQ. ID. No. 5) and linearized viral backbone BestBac 2.0] at 27° C. for 5-7 days to generate the P0 viral stock. To generate P1 viral stocks, 0.5 mL of P0 viral supernatant was added to 50 mL uninfected Sf21 cells (seeded the day prior to infection at a density of 5×10$^5$ cells/mL to allow for one overnight doubling) in Sf-900II SFM media containing 5 g/mL gentamicin (Invitrogen #15710072). The infected cells were then incubated at 27° C. for 3 d while shaking at 110 rpm (ATR Biotech Multitron Infors HT # AJ118). On day 3, P1 cultures were counted using a ViCell XR (Beckman Coulter Life Sciences #383556) to confirm infection had occurred (cell size ≥3 μm larger than uninfected cells and viability approximately 85-95%). Cultures were harvested in 50 mL conical tubes and centrifuged at 2000×g for 10 min at 4° C. The P1 viral supernatants were poured off into clean 50 ml centrifuge tubes, and the remaining P1 cell pellets were used to generate Baculovirus Infected Insect Cells (BIICs) according to in-house validated SOP. Cryopreservation media containing Sf-900II SFM media with 10% heat inactivated FBS, 10% DMSO (Sigma # D2650), and 5 μg/ml gentamicin was prepared in-house and sterilized through 0.22 μM filter immediately prior to use. P1 cell pellets were resuspended to a density of 2e7 cells/ml and aliquoted into cryovials (1 mL per vial). Cryovials were placed in Mr. Frosty cell freezers O/N at −80° C. and transferred to liquid nitrogen for long term storage the following day. To generate P2 viral stock, 0.5 mL of the P1 viral supernatant was added to 50 mL uninfected Sf21 cells (seeded the day prior to infection at a density of 5×10$^5$ cells/mL to allow for one overnight doubling) in Sf-900II SFM media containing 5 μg/mL gentamicin. These cells were incubated at 27° C. for 3 d while shaking at 110 rpm before harvesting P2 stock with centrifugation at 2000×g for 10 min at 4° C. The P2 viral supernatants were poured off and discarded, while the P2 cell pellets were used to generate P2 BIICs following the same protocol described above. The baculovirus generation protocol has been validated to consistently produce P1/P2 BIICs with titers of 2e9 pfu/mL (2e7 cells/mLx 100 pfu/cell).

Full-Length STING (WT) Expression

To generate STING membranes, P1/P2 BIICs were amplified overnight by adding thawed BIICs to Sf21 cells seeded at a density of 1.0×10$^6$ cells/mL. The volume of BIIC used to infect the culture was calculated using an assumed BIIC titer of 2e9 pfu/ml to achieve an MOI of 10 in the overnight amplification. After culturing overnight, the cells were counted on a ViCell XR to confirm infection had occurred (cell size ≥3 μm larger than uninfected cells and viability approximately 80-90%). The volume of infected Sf21 cells from the overnight amplification used to infect the large-scale expression of *Trichoplusia ni* (*T. ni*; Expression Systems, cat #94-002F, www.expressionsystems.com) seeded at a density of 1.0×10$^6$ in cell media (ESF921 SFM containing 5 μg/mL gentamicin) at MOI=2.0 was calculated based on (100 pfu/infected Sf21 cell). The cells were allowed to express for 48 h at 27° C. before harvesting the cell pellet, by centrifugation at 3,400×g for 10 min at 4° C. *T. ni* cells were counted on a ViCell XR to confirm infection had occurred (cell size ≥3 μm larger than uninfected cells and viability approximately 80-90%) prior to harvest.

Full-Length STING (WT) Membrane Generation

Buffer stock reagents:

1) 1 M HEPES pH 7.5, Teknova, Cat # H1035

2) 5 M NaCl, Sigma Aldrich, Cat # S5150-1L

3) KCl, Sigma Aldrich, Cat #319309-500ML

4) Complete EDTA-free protease inhibitor tablets, Roche Diagnostics, Cat #11873580001

5) Benzonase, Universal Nuclease, Pierce, Cat #88702

Lysis buffer [25 mM HEPES pH 7.5, 10 mM MgCl$_2$, 20 mM KCl, (Benzonase 1:5000, Complete Protease Inhibitor tab/50 mL)] was added to the pellet of cells expressing full-length STING (WT) prepared above at 5 mL Lysis buffer/g of cell pellet. The pellet was resuspended and dounced twenty times using a Wheaton Dounce Homogenizer to disrupt the cell membrane. Homogenized lysate was then passed through the emulsiflex-C$_5$ microfluidizer at a pressure close to 5000 PSI. The resuspended pellet was centrifuged at 36,000 rpm (100,000×g) in a 45Ti rotor in the ultra-high speed centrifuge for 45 min, 4° C. The supernatant was removed. The pellet then was resuspended in wash buffer [(25 mM HEPES pH 7.5, 1 mM MgCl$_2$, 20 mM KCl, 1M NaCl (Complete Protease Inhibitor tab/50 mL)] at a volume of 50 mL/pellet/centrifuge tube. The pellet/Wash buffer mixture was then homogenized, using a glass homogenizer on ice (20 strokes), followed by centrifugation at 36,000 rpm for 45 min at 4° C. The supernatant was removed. The wash step was repeated once more. The resulting membrane was resuspended in 20 mM HEPES pH 7.5, 500 mM NaCl, 10% glycerol, EDTA-free Protease Inhibitors (1 tablet/50 mL). The protein concentration was measured by Bradford assay (Bio-Rad Protein Assay, Cat #500-0006), and protein enrichment was determined by SDS-PAGE and confirmed by Western blot. The resuspended membranes were stored at −80° C.

Full-Length STING WT [STING(1-379)H232R-gg-AviTag-gs-HRV3C-HIS8] Amino Acid Sequence:

(SEQ. ID. No. 4)
MPHSSLHPSIPCPRGHGAQKAALVLLSACLVTLWGLGEPPEHTLRYLVLH
LASLQLGLLLNGVCSLAEELRHIHSRYRGSYWRTVRACLGCPLRRGALLL
LSIYFYYSLPNAVGPPFTWMLALLGLSQALNILLGLKGLAPAEISAVCEK
GNFNVAHGLAWSYYIGYLRLILPELQARIRTYNQHYNNLLRGAVSQRLYI
LLPLDCGVPDNLSMADPNIRFLDKLPQQTGDRAGIKDRVYSNSIYELLEN
GQRAGTCVLEYATPLQTLFAMSQYSQAGFSREDRLEQAKLFCRTLEDILA
DAPESQNNCRLIAYQEPADDSSFSLSQEVLRHLRQEEKEEVTVGSLKTSA
VPSTSTMSQEPELLISGMEKPLPLRTDFSGGGLNDIFEAQKIEWHEGSLE
VLFQGPHHHHHHHH

Full-length WT STING [STING(1-379)H232R-gg-AviTag-gs-HRV3C-HIS8/pBAC$_1$] plasmid sequence:

(SEQ. ID. No. 5)
GGAACGGCTCCGCCCACTATTAATGAAATTAAAAATTCCAATTTTAAAA
ACGCAGCAAGAGAAACATTTGTATGAAAGAATGCGTAGAAGGAAAGAAAA
ATGTCGTCGACATGCTGAACAACAAGATTAATATGCCTCCGTGTATAAAA
AAAATATTGAACGATTTGAAAGAAAACAATGTACCGCGCGGCGGTATGTA
CAGGAAGAGGTTTATACTAAACTGTTACATTGCAAACGTGGTTTCGTGTG
CCAAGTGTGAAAACCGATGTTTAATCAAGGCTCTGACGCATTTCTACAAC
CACGACTCCAAGTGTGTGGGTGAAGTCATGCATCTTTTAATCAAATCCCA
AGATGTGTATAAACCACCAAACTGCCAAAAAATGAAAACTGTCGACAAGC
TCTGTCCGTTTGCTGGCAACTGCAAGGGTCTCAATCCTATTTGTAATTAT
TGAATAATAAAACAATTATAAATGTCAAATTTGTTTTTTATTAACGATAC
AAACCAAACGCAACAAGAACATTTGTAGTATTATCTATAATTGAAAACGC
GTAGTTATAATCGCTGAGGTAATATTTAAAATCATTTTCAAATGATTCAC
AGTTAATTTGCGACAATATAATTTTATTTTCACATAAACTAGACGCCTTG
TCGTCTTCTTCTTCGTATTCCTTCTCTTTTTCATTTTTCTCTTCATAAAA
ATTAACATAGTTATTATCGTATCCATATATGTATCTATCGTATAGAGTAA
ATTTTTTGTTGTCATAAATATATATGTCTTTTTTAATGGGGTGTATAGTA
CCGCTGCGCATAGTTTTTCTGTAATTTACAACAGTGCTATTTTCTGGTAG
TTCTTCGGAGTGTGTTGCTTTAATTATTAAATTTATATAATCAATGAATT
TGGGATCGTCGGTTTTGTACAATATGTTGCCGGCATAGTACGCAGCTTCT
TCTAGTTCAATTACACCATTTTTTAGCAGCACCGGATTAACATAACTTTC
CAAAATGTTGTACGAACCGTTAAACAAAAACAGTTCACCTCCCTTTTCTA
TACTATTGTCTGCGAGCAGTTGTTTGTTGTTAAAAATAACAGCCATTGTA
ATGAGACGCACAAACTAATATCACAAACTGGAAATGTCTATCAATATATA
GTTGCTGATCAGATCTGATCATGGAGATAATTAAAATGATAACCATCTCG
CAAATAAATAAGTATTTTACTGTTTTCGTAACAGTTTTGTAATAAAAAAAA
CCTATAAATATAGGATCCATGCCCCACTCCAGCCTGCATCCATCCATCCC

-continued
GTGTCCCAGGGGTCACGGGGCCCAGAAGGCAGCCTTGGTTCTGCTGAGTG
CCTGCCTGGTGACCCTTTGGGGGCTAGGAGAGCCACCAGAGCACACTCTC
CGGTACCTGGTGCTCCACCTAGCCTCCCTGCAGCTGGGACTGCTGTTAAA
CGGGGTCTGCAGCCTGGCTGAGGAGCTGCGCCACATCCACTCCAGGTACC
GGGGCAGCTACTGGAGGACTGTGCGGGCCTGCCTGGGCTGCCCCCTCCGC
CGTGGGGCCCTGTTGCTGCTGTCCATCTATTTCTACTACTCCCTCCCAAA
TGCGGTCGGCCCGCCCTTCACTTGGATGCTTGCCCTCCTGGGCCTCTCGC
AGGCACTGAACATCCTCCTGGGCCTCAAGGGCCTGGCCCCAGCTGAGATC
TCTGCAGTGTGTGAAAAAGGGAATTTCAACGTGGCCCATGGGCTGGCATG
GTCATATTACATCGGATATCTGCGGCTGATCCTGCCAGAGCTCCAGGCCC
GGATTCGAACTTACAATCAGCATTACAACAACCTGCTACGGGGTGCAGTG
AGCCAGCGGCTGTATATTCTCCTCCCATTGGACTGTGGGGTGCCTGATAA
CCTGAGTATGGCTGACCCCAACATTCGCTTCCTGGATAAACTGCCCCAGC
AGACCGGTGACCGTGCTGGCATCAAGGATCGGGTTTACAGCAACAGCATC
TATGAGCTTCTGGAGAACGGGCAGCGGGCGGGCACCTGTGTCCTGGAGTA
CGCCACCCCCTTGCAGACTTTGTTTGCCATGTCACAATACAGTCAAGCTG
GCTTTAGCCGGGAGGATAGGCTTGAGCAGGCCAAACTCTTCTGCCGGACA
CTTGAGGACATCCTGGCAGATGCCCCTGAGTCTCAGAACAACTGCCGCCT
CATTGCCTACCAGGAACCTGCAGATGACAGCAGCTTCTCGCTGTCCCAGG
AGGTTCTCCGGCACCTGCGGCAGGAGGAAAAGGAAGAGGTTACTGTGGGC
AGCTTGAAGACCTCAGCGGTGCCCAGTACCTCCACGATGTCCCAAGAGCC
TGAGCTCCTCATCAGTGGAATGGAAAAGCCCCTCCCTCTCCGCACGGATT
TCTCTGGCGGTGGCCTGAACGACATCTTCGAAGCCCAGAAAATCGAATGG
CATGAAGGCAGCCTGGAAGTGCTGTTCCAGGGCCCACACCACCATCATCA
CCATCACCATTAATGAGCGGCCGCACTCGAGCACCACCACCACCACCACT
AACCTAGGTAGCTGAGCGCATGCAAGCTGATCCGGGTTATTAGTACATTT
ATTAAGCGCTAGATTCTGTGCGTTGTTGATTTACAGACAATTGTTGTACG
TATTTTAATAATTCATTAAATTTATAATCTTTAGGGTGGTATGTTAGAGC
GAAAATCAAATGATTTTCAGCGTCTTTATATCTGAATTTAAATATTAAAT
CCTCAATAGATTTGTAAAATAGGTTTCGATTAGTTTCAAACAAGGGTTGT
TTTTCCGAACCGATGGCTGGACTATCTAATGGATTTTCGCTCAACGCCAC
AAAACTTGCCAAATCTTGTAGCAGCAATCTAGCTTTGTCGATATTCGTTT
GTGTTTTGTTTTGTAATAAAGGTTCGACGTCGTTCAAAATATTATGCGCT
TTTGTATTTCTTTCATCACTGTCGTTAGTGTACAATTGACTCGACGTAAA
CACGTTAAATAGAGCTTGGACATATTTAACATCGGGCGTGTTAGCTTTAT
TAGGCCGATTATCGTCGTCGTCCCAACCCTCGTCGTTAGAAGTTGCTTCC
GAAGACGATTTTGCCATAGCCACACGACGCCTATTAATTGTGTCGGCTAA
CACGTCCGCGATCAAATTTGTAGTTGAGCTTTTTGGAATTATTTCTGATT
GCGGGCGTTTTTGGGCGGGTTTCAATCTAACTGTGCCCGATTTTAATTCA
GACAACACGTTAGAAAGCGATGGTGCAGGCGGTGGTAACATTTCAGACGG
CAAATCTACTAATGGCGGCGGTGGTGGAGCTGATGATAAATCTACCATCG -continued

```
GTGGAGGCGCAGGCGGGGCTGGCGGCGGAGGCGGAGGCGGAGGTGGTGGC
GGTGATGCAGACGGCGGTTTAGGCTCAAATGTCTCTTTAGGCAACACAGT
CGGCACCTCAACTATTGTACTGGTTTCGGGCGCCGTTTTTGGTTTGACCG
GTCTGAGACGAGTGCGATTTTTTTCGTTTCTAATAGCTTCCAACAATTGT
TGTCTGTCGTCTAAAGGTGCAGCGGGTTGAGGTTCCGTCGGCATTGGTGG
AGCGGGCGGCAATTCAGACATCGATGGTGGTGGTGGTGGTGGAGGCGCTG
GAATGTTAGGCACGGGAGAAGGTGGTGGCGGCGGTGCCGCCGGTATATTT
GTTCTGGTTTAGTTTGTTCGCGCACGATTGTGGGCACCGGCGCAGGCGCC
GCTGGCTGCACAACGGAAGGTCGTCTGCTTCGAGGCAGCGCTTGGGGTGG
TGGCAATTCAATATTATAATTGGAATACAAATCGTAAAAATCTGCTATAA
GCATTGTAATTTCGCTATCGTTTACCGTGCCGATATTTAACAACCGCTCA
ATGTAAGCAATTGTATTGTAAAGAGATTGTCTCAAGCTCGGATCGATCCC
GCACGCCGATAACAAGCCTTTTCATTTTTACTACAGCATTGTAGTGGCGA
GACACTTCGCTGTCGTCGAGGTTTAAACGCTTCCTCGCCACTGACTCGCT
GCGCTCGGTCGTTCGGCTGCGGCGAGCGGTATCAGCTCACTCAAAGGCGG
TAATACGGTTATCCACAGAATCAGGGGATAACGCAGGAAAGAACATGTGA
GCAAAAGGCCAGCAAAAGGCCAGGAACCGTAAAAAGGCCGCGTTGCTGGC
GTTTTTCATAGGCTCCGCCCCCTGACGAGCATCACAAAAATCGACGCTC
AAGTCAGAGGTGGCGAAACCCGACAGGACTATAAAGATACCAGGCGTTTC
CCCCTGGAAGCTCCCTCGTGCGCTCTCCTGTTCCGACCCTGCCGCTTACC
GGATACCTGTCCGCCTTTCTCCCTTGGGAAGCGTGGCGCTTTCTCATAGC
TCACGCTGTAGGTATCTCAGTTCGGTGTAGGTCGTTCGCTCCAAGCTGGG
CTGTGTGCACGAACCCCCCGTTCAGCCCGACCGCTGCGCCTTATCCGGTA
ACTATCGTCTTGAGTCCAACCCGGTAAGACACGACTTATCGCCACTGGCA
GCAGCCACTGGTAACAGGATTAGCAGAGCGAGGTATGTAGGCGGTGCTAC
AGAGTTCTTGAAGTGGTGGCCTAACTACGGCTACACTAGAAGGACAGTAT
TTGGTATCTGCGCTCTGCTGAAGCCAGTTACCTTCGGAAAAAGAGTTGGT
AGCTCTTGATCCGGCAAACAAACCACCGCTGGTAGCGGTGGTTTTTTTGT
TTGCAAGCAGCAGATTACGCGCAGAAAAAAAGGATCTCAAGAAGATCCTT
TGATCTTTTCTACGGGGTCTGACGCTCAGTGGAACGAAAACTCACGTTAA
GGGATTTTGGTCATGAGATTATCAAAAAGGATCTTCACCTAGATCCTTTT
AAATTAAAAATGAAGTTTTAAATCAATCTAAAGTATATATGAGTAAACTT
GGTCTGACAGTTACCAATGCTTAATCAGTGAGGCACCTATCTCAGCGATC
TGTCTATTTCGTTCATCCATAGTTGCCTGACTCCCCGTCGTGTAGATAAC
TACGATACGGGAGGGCTTACCATCTGGCCCCAGTGCTGCAATGATACCGC
GAGACCCACGCTCACCGGCTCCAGATTTATCAGCAATAAACCAGCCAGCC
GGAAGGGCCGAGCGCAGAAGTGGTCCTGCAACTTTATCCGCCTCCATCCA
GTCTATTAATTGTTGCCGGGAAGCTAGAGTAAGTAGTTCGCCAGTTAATA
GTTTGCGCAACGTTGTTGCCATTGCTACAGGCATCGTGGTGTCACGCTCG
TCGTTTGGTATGGCTTCATTCAGCTCCGGTTCCCAACGATCAAGGCGAGT
TACATGATCCCCCATGTTGTGCAAAAAAGCGGTTAGCTCCTTCGGTCCTC
CGATCGTTGTCAGAAGTAAGTTGGCCGCAGTGTTATCACTCATGGTTATG
GCAGCACTGCATAATTCTCTTACTGTCATGCCATCCGTAAGATGCTTTTC
TGTGACTGGTGAGTACTCAACCAAGTCATTCTGAGAATAGTGTATGCGGC
GACCGAGTTGCTCTTGCCCGGCGTCAATACGGGATAATACCGCGCCACAT
AGCAGAACTTTAAAAGTGCTCATCATTGGAAAACGTTCTTCGGGGCGAAA
ACTCTCAAGGATCTTACCGCTGTTGAGATCCAGTTCGATGTAACCCACTC
GTGCACCCAACTGATCTTCAGCATCTTTTACTTTCACCAGCGTTTCTGGG
TGAGCAAAAACAGGAAGGCAAAATGCCGCAAAAAAGGGAATAAGGGCGAC
ACGGAAATGTTGAATACTCATACTCTTCCTTTTTCAATATTATTGAAGCA
TTTATCAGGGTTATTGTCTCATGAGCGGATACATATTTGAATGTATTTAG
AAAAATAAACAAATAGGGGTTCCGCGCACATTTCCCCGAAAAGTGCCACC
TGACGCGCCCTGTAGCGGCGCATTAAGCGCGGCGGGTGTGGTGGTTACGC
GCAGCGTGACCGCTACACTTGCCAGCGCCCTAGCGCCCGCTCCTTTCGCT
TTCTTCCCTTCCTTTCTCGCCACGTTCGCCGGCTTTCCCCGTCAAGCTCT
AAATCGGGGGCTCCCTTTAGGGTTCCGATTTAGTGCTTTACGGCACCTCG
ACCCCAAAAAACTTGATTAGGGTGATGGTTCACGTAGTGGGCCATCGCCC
TGATAGACGGTTTTTCGCCCTTTGACGTTGGAGTCCACGTTCTTTAATAG
TGGACTCTTGTTCCAAACTGGAACAACACTCAACCCTATCTCGGTCTATT
CTTTTGATTTATAAGGGATTTTGCCGATTTCGGCCTATTGGTTAAAAAAT
GAGCTGATTTAACAAAAATTTAACGCGAATTTTAACAAAATATTAACGTT
TACAATTTCCCATTCGCCATTCAGGCTGCGCAACTGTTGGGAAGGGCGAT
CGGTGCGGGCCTCTTCGCTATTACGCCA
```

Certain compounds of the disclosure were evaluated in WT STING in vitro binding assay as described above. The following table tabulates the biological data for these compounds as $EC_{50}$ values.

TABLE 13

$^3$H-cGAMP filtration binding assay for WT STING

| Compound | $EC_{50}$ (nM) |
| --- | --- |
| Example 1 | 3.5 |
| Example 2 | 0.7 |
| Example 3 | 574.3 |
| Example 4 | 43.5 |
| Example 5 | 1.5 |
| Example 6 | 2.9 |
| Example 7 | <1 |
| Example 8 | 81.4 |
| Example 9 | 12.4 |
| Example 10 | 23.2 |
| Example 13 | 0.7 |
| Example 14 | 1.4 |
| Example 20 | 1.4 |
| Example 21 | 1.4 |
| Example 25 | 16.1 |
| Example 26 | 3.7 |
| Example 27 | 10 |
| Example 28 | 264.9 |
| Example 29 | 5835 |
| Example 32 | 25 |
| Example 38 | 24.9 |
| Example 41 | 505.9 |
| Example 42 | 219 |

TABLE 13-continued $^3$H-cGAMP filtration binding assay for WT STING

| Compound | EC$_{50}$ (nM) |
|---|---|
| Example 43 | 1015 |
| Example 44 | 1363 |
| Example 45 | 104.8 |
| Example 46 | 337 |
| Example 47 | 444.1 |
| Example 51 | 995.8 |
| Example 61 | 378.7 |
| Example 62 | 2.6 |
| Example 63 | 68.8 |
| Example 64 | 61.6 |
| Example 65 | 249.6 |
| Example 70 | 19.4 |
| Example 71 | 4.4 |
| Example 72 | <1 |
| Example 81 | 3.1 |
| Example 82 | 14.6 |
| Example 84 | 6.3 |
| Example 86 | 2 |
| Example 89 | <1 |
| Example 90 | 4.4 |
| Example 93 | 1.9 |
| Example 94 | 523.8 |
| Example 95 | 64 |
| Example 96 | 57.8 |
| Example 97 | 0.4 |
| Example 98 | 151.7 |
| Example 99 | 1.8 |
| Example 100 | 552 |
| Example 101 | 74.4 |
| Example 84 | 6.3 |
| Example 86 | 2 |
| Example 102 | 1 |
| Example 103 | <1 |
| Example 104 | 11.6 |
| Example 105 | 3.9 |
| Example 106 | <1 |
| Example 107 | 17.9 |
| Example 108 | 1784 |
| Example 109 | 1393 |
| Example 110 | 141.4 |
| Example 111 | 155.1 |
| Example 112 | 1279 |
| Example 113 | 44.2 |
| Example 114 | 3.3 |
| Example 115 | 67.9 |
| Example 116 | 1624 |
| Example 117 | 1.7 |
| Example 118 | 1.6 |
| Example 119 | 40 |
| Example 120 | 393.7 |
| Example 122 | 179.2 |
| Example 124 | 4 |
| Example 126 | 447.4 |
| Example 128 | 19.5 |
| Example 129 | 973.3 |
| Example 139 | 1.2 |
| Example 141 | <1 |
| Example 142 | 174.8 |
| Example 144 | 4.6 |
| Example 145 | 14 |
| Example 148 | 1932 |
| Example 149 | 110.8 |
| Example 152 | 5.7 |
| Example 153 | 6.5 |
| Example 154 | 60 |
| Example 155 | <1 |
| Example 156 | <1 |
| Example 157 | <1 |
| Example 158 | 40 |
| Example 159 | 7.1 |
| Example 160 | 10.3 |
| Example 161 | 6.2 |
| Example 162 | 100.7 |
| Example 163 | 14.3 |
| Example 164 | 312.4 |
| Example 165 | 2.9 |
| Example 166 | 463.2 |
| Example 167 | 87.7 |
| Example 168 | 8.6 |
| Example 169 | 186.6 |
| Example 170 | 25.5 |
| Example 171 | 18.7 |
| Example 172 | 105.9 |
| Example 176 | 16.2 |
| Example 177 | 7.9 |
| Example 178 | 37.4 |
| Example 179 | 111.7 |
| Example 180 | 832.1 |
| Example 181 | 459.2 |
| Example 182 | 3276 |
| Example 183 | 3180 |
| Example 184 | <1 |
| Example 185 | 201.1 |
| Example 186 | 30.2 |
| Example 187 | 6.5 |
| Example 188 | 47.6 |
| Example 189 | 423.9 |
| Example 190 | 408.7 |
| Example 191 | 281.2 |
| Example 192 | 3867 |
| Example 193 | 190.5 |
| Example 194 | 159.2 |
| Example 195 | 1855 |
| Example 196 | 1033 |
| Example 197 | 1.2 |
| Example 198 | 19.1 |
| Example 199 | 72 |
| Example 200 | 15 |
| Example 201 | 649.5 |
| Example 202 | 813.5 |
| Example 203 | 7.3 |
| Example 204 | 1233 |
| Example 205 | 42.7 |
| Example 206 | 259.7 |
| Example 207 | 1.4 |
| Example 208 | 23.3 |
| Example 209 | 9.5 |
| Example 210 | 28.5 |
| Example 211 | 1045 |
| Example 212 | 11.8 |
| Example 213 | 135 |
| Example 214 | 2.1 |
| Example 215 | 33.1 |
| Example 216 | 3.4 |
| Example 217 | 66.2 |
| Example 218 | 13.8 |
| Example 219 | 530.5 |
| Example 220 | 29% Inh @ 20 uM |
| Example 221 | <1 |
| Example 222 | 60 |
| Example 223 | 302.5 |
| Example 224 | 37.4 |
| Example 225 | 779.3 |
| Example 226 | 27.8 |
| Example 227 | 260.6 |
| Example 228 | 1005 |
| Example 229 | 31% Inh @ 20 uM |
| Example 230 | 382.4 |
| Example 231 | 540.4 |
| Example 232 | 3283 |
| Example 233 | 33.8 |
| Example 234 | 275.2 |
| Example 235 | 14.9 |
| Example 236 | 6963 |
| Example 237 | 307.2 |
| Example 238 | 66.3 |
| Example 239 | 3.2 |
| Example 240 | 73.6 |
| Example 241 | 471.8 |
| Example 242 | 1.1 |
| Example 243 | 26.3 |

TABLE 13-continued $^3$H-cGAMP filtration binding assay for WT STING

| Compound | EC$_{50}$ (nM) |
|---|---|
| Example 247 | 1.1 |
| Example 248 | 31.7 |
| Example 249 | <1 |
| Example 250 | 17.3 |
| Example 251 | <1 |
| Example 252 | 768.4 |
| Example 253 | 54.5 |
| Example 254 | 39.7 |
| Example 255 | 301.9 |
| Example 256 | 93.5 |
| Example 257 | 135.9 |
| Example 258 | 5 |
| Example 259 | 1.5 |
| Example 260 | 7.2 |
| Example 261 | 21.8 |
| Example 262 | 57.3 |
| Example 263 | 4.8 |
| Example 264 | 177.5 |
| Example 265 | 5473 |
| Example 266 | 1.9 |
| Example 267 | 6267 |
| Example 268 | 77 |
| Example 269 | 4837 |
| Example 270 | 4383 |
| Example 271 | 12.8 |
| Example 272 | 749.6 |
| Example 273 | 216.4 |
| Example 274 | 2.3 |
| Example 275 | 21.8 |
| Example 276 | 321.5 |
| Example 277 | 28.7 |
| Example 278 | 477.9 |
| Example 279 | 1235 |
| Example 280 | 1186 |
| Example 281 | 2485 |
| Example 282 | 12190 |
| Example 283 | 17.2 |
| Example 284 | 128.3 |
| Example 285 | 277.1 |
| Example 286 | 4010 |
| Example 287 | 80.2 |
| Example 288 | 24.9 |
| Example 289 | 5.3 |
| Example 308 | 3.3 |
| Example 323 | 3.7 |
| Example 324 | 10.7 |
| Example 325 | 866.1 |
| Example 326 | 89.7 |
| Example 327 | 14 |
| Example 328 | 74.4 |
| Example 329 | 31.7 |
| Example 330 | 204 |
| Example 331 | 182.9 |
| Example 334 | 110.5 |
| Example 335 | 5.2 |
| Example 336 | 422.2 |
| Example 337 | 29.2 |
| Example 338 | 441.7 |

Example 351: IFN-β Secretion in THP1 Cell Culture (5 h)

The ability of compounds to stimulate the secretion of interferon-beta from THP1 cells was measured using a human IFN-β AlphaLISA kit (Perkin Elmer, Cat. No. AL265F). The basic protocol is as follows:

A Labcyte Echo 550 acoustic dispenser was used to transfer 120 nL of compound dissolved in DMSO into the wells of an empty, sterile 384-well microplate, (Corning, Cat. No. 3712). THP1 cells (American Type Culture Collection, Cat. No. TIB202) previously frozen in Recovery Medium (Life Technologies, Cat. No. 12648-010) were thawed and immediately diluted 10-fold into 37° C. assay medium (RPMI 1640+L-Glutamine & phenol red, Life Technologies, Cat. No. 11875-085; 0.5% heat inactivated fetal bovine serum, Sigma Aldrich, Cat. No. F4135; 1 mM Sodium Pyruvate, Life Technologies, Cat. No. 11360-070; 1× non-essential amino acids; Life Technologies, Cat. No. 11140-050). The cell viability and count was ascertained using a Beckman Coulter V-Cell XR cell counter. The cells suspension was centrifuged at 200×g for 5 min at RT. Cells were resuspended to a density of 0.8×10$^6$/mL in 37° C. assay medium. Subsequent liquid transfers were performed using either a Matrix electronic multichannel pipette or an Agilent Bravo Automated Liquid Handling Platform.

The assay was started by dispensing 40 μL of the previously prepared cell suspension into the wells of the plate containing compounds. After 5 h incubation at 37° C., 5% CO$_2$ in a humidified atmosphere, the plate of cells and compounds was centrifuged at 200×g for 5 min at RT. From each well, 5 μL of supernatant was transferred into corresponding wells of a white 384-well plate (Perkin Elmer, Cat. No. 6005620). To these supernatant-containing wells was added 10 μL of 5× Anti-Analyte Acceptor beads (50 μg/mL of AlphaLISA HiBlock Buffer) and incubated for 30 min at RT while shaking on an orbital plate shaker. To each well was added 10 μL of 5× Biotinylated Antibody Anti-analyte (5 nM in AlphaLISA HiBlock Buffer) and incubated on an orbital plate shaker for 60 min at RT or overnight at 4° C. To each well was added 25 μL of 2× SA-Donor beads (80 μg/mL in AlphaLISA HiBlock Buffer) and incubated for 30-45 min at RT in the dark while shaking on an orbital plate shaker. The plate was then read on a Perkin Elmer Envision ($\lambda_{ex}$=680 nm, $\lambda_{em}$=570 nm). The percent effect of the AlphaLISA signal at each compound concentration was calculated based on 30 uM cGAMP positive controls and 0.3% DMSO negative controls. The plot of percent effect versus the log of compound concentration was fit with a 4-parameter concentration response equation to calculate EC$_{50}$ values. The test compounds were tested at concentrations 30000, 10000, 3333, 1111, 370.4, 123.4, 41.2, 13.7, 4.6, and 1.5 nM with 0.3% residual DMSO. The control compound, cGAMP was tested at concentrations 100000, 33333, 11111, 3704, 1235, 412, 137, 46, and 15 nM with 0.3% residual DMSO.

Compounds of the disclosure were evaluated for IFN-β secretion in THP1 cell culture as described above. The following table tabulates the biological data for these compounds as percent activation relative to 2'3'-cGAMP at the 30 μM concentration.

TABLE 14

IFN-β secretion in THP1 cell culture (5 h)

| Compound | % Effect at 30 μM relative to 2'3'-cGAMP |
|---|---|
| Example 1 | 154 |
| Example 2 | 148 |
| Example 3 | 149 |
| Example 4 | 171 |
| Example 5 | 152 |
| Example 6 | 114 |
| Example 7 | 112 |
| Example 8 | 98 |
| Example 9 | 143 |
| Example 10 | 126 |
| Example 11 | 169 |
| Example 12 | 89 |

TABLE 14-continued

IFN-β secretion in THP1 cell culture (5 h)

| Compound | % Effect at 30 μM relative to 2'3'-cGAMP |
|---|---|
| Example 13 | 39 |
| Example 14 | 139 |
| Example 15 | 39 |
| Example 16 | 57 |
| Example 17 | 81 |
| Example 18 | 74 |
| Example 19 | 49 |
| Example 20 | 159 |
| Example 21 | 142 |
| Example 22 | 109 |
| Example 23 | 125 |
| Example 24 | 90 |
| Example 25 | 145 |
| Example 26 | 150 |
| Example 27 | 164 |
| Example 28 | 60 |
| Example 29 | 25 |
| Example 30 | 131 |
| Example 31 | 100 |
| Example 32 | 125 |
| Example 33 | 200 |
| Example 34 | 125 |
| Example 35 | 51 |
| Example 36 | 120 |
| Example 37 | 57 |
| Example 38 | 123 |
| Example 39 | 74 |
| Example 40 | 77 |
| Example 41 | 8 |
| Example 42 | 101 |
| Example 43 | 130 |
| Example 44 | 135 |
| Example 45 | 161 |
| Example 46 | 143 |
| Example 47 | 141 |
| Example 48 | 104 |
| Example 49 | 74 |
| Example 50 | 85 |
| Example 51 | 36 |
| Example 52 | 143 |
| Example 53 | 127 |
| Example 54 | 83 |
| Example 55 | 83 |
| Example 56 | 64 |
| Example 57 | 7 |
| Example 58 | 92 |
| Example 59 | 76 |
| Example 60 | 12 |
| Example 61 | 34 |
| Example 62 | 68 |
| Example 63 | 83 |
| Example 64 | 93 |
| Example 65 | 87 |
| Example 66 | 54 |
| Example 67 | 111 |
| Example 68 | 72 |
| Example 69 | 31 |
| Example 70 | 100 |
| Example 71 | 113 |
| Example 72 | 102 |
| Example 73 | 5 |
| Example 74 | 57 |
| Example 75 | 96 |
| Example 76 | 39 |
| Example 77 | 39 |
| Example 78 | 162 |
| Example 79 | 145 |
| Example 80 | 234 |
| Example 81 | 138 |
| Example 82 | 111 |
| Example 83 | 133 |
| Example 84 | 128 |
| Example 85 | 154 |
| Example 86 | 137 |
| Example 87 | 99 |
| Example 88 | 54 |
| Example 89 | 119 |
| Example 90 | 117 |
| Example 91 | 106 |
| Example 92 | 62 |
| Example 93 | 155 |
| Example 94 | 138 |
| Example 95 | 118 |
| Example 96 | 67 |
| Example 97 | 113 |
| Example 98 | 54 |
| Example 99 | 135 |
| Example 100 | 35 |
| Example 101 | 129 |
| Example 102 | 132 |
| Example 103 | 114 |
| Example 104 | 154 |
| Example 105 | 137 |
| Example 106 | 208 |
| Example 107 | 171 |
| Example 108 | 15 |
| Example 109 | 151 |
| Example 110 | 181 |
| Example 111 | 200 |
| Example 112 | 33 |
| Example 113 | 154 |
| Example 114 | 163 |
| Example 115 | 177 |
| Example 116 | 149 |
| Example 117 | 211 |
| Example 118 | 174 |
| Example 119 | 151 |
| Example 120 | 72 |
| Example 121 | 108 |
| Example 122 | 75 |
| Example 123 | 128 |
| Example 124 | 128 |
| Example 125 | 138 |
| Example 126 | 167 |
| Example 127 | 145 |
| Example 128 | 146 |
| Example 129 | 33 |
| Example 130 | 215 |
| Example 131 | 238 |
| Example 132 | 150 |
| Example 133 | 117 |
| Example 134 | 138 |
| Example 135 | 43 |
| Example 136 | 131 |
| Example 137 | 124 |
| Example 138 | 51 |
| Example 139 | 110 |
| Example 140 | 96 |
| Example 141 | 111 |
| Example 142 | 111 |
| Example 143 | 157 |
| Example 144 | 114 |
| Example 145 | 141 |
| Example 146 | 59 |
| Example 147 | 146 |
| Example 148 | 13 |
| Example 149 | 8 |
| Example 150 | 89 |
| Example 151 | 57 |
| Example 152 | 16 |
| Example 153 | 234 |
| Example 154 | 198 |
| Example 155 | 139 |
| Example 156 | 119 |
| Example 157 | 151 |
| Example 158 | 123 |

TABLE 14-continued

IFN-β secretion in THP1 cell culture (5 h)

| Compound | % Effect at 30 μM relative to 2'3'-cGAMP |
|---|---|
| Example 159 | 140 |
| Example 160 | 12 |
| Example 161 | 130 |
| Example 162 | 116 |
| Example 163 | 127 |
| Example 164 | 41 |
| Example 165 | 245 |
| Example 166 | 143 |
| Example 167 | 278 |
| Example 168 | 164 |
| Example 169 | 117 |
| Example 170 | 134 |
| Example 171 | 142 |
| Example 172 | 26 |
| Example 173 | 142 |
| Example 174 | 5 |
| Example 175 | 120 |
| Example 176 | 114 |
| Example 177 | 180 |
| Example 178 | 111 |
| Example 179 | 66 |
| Example 180 | 143 |
| Example 181 | 178 |
| Example 182 | 47 |
| Example 183 | 23 |
| Example 184 | 108 |
| Example 185 | 61 |
| Example 186 | 179 |
| Example 187 | 134 |
| Example 188 | 251 |
| Example 189 | 93 |
| Example 190 | 200 |
| Example 191 | 516 |
| Example 192 | 50 |
| Example 193 | 399 |
| Example 194 | 258 |
| Example 195 | 61 |
| Example 196 | 14 |
| Example 197 | 237 |
| Example 198 | 205 |
| Example 199 | 139 |
| Example 200 | 219 |
| Example 201 | 222 |
| Example 202 | 171 |
| Example 203 | 194 |
| Example 204 | 101 |
| Example 205 | 132 |
| Example 206 | 166 |
| Example 207 | 189 |
| Example 208 | 163 |
| Example 209 | 170 |
| Example 210 | 178 |
| Example 211 | 114 |
| Example 212 | 285 |
| Example 213 | 255 |
| Example 214 | 224 |
| Example 215 | 277 |
| Example 216 | 170 |
| Example 217 | 70 |
| Example 218 | 152 |
| Example 219 | 142 |
| Example 220 | 6 |
| Example 221 | 405 |
| Example 222 | 171 |
| Example 223 | 11 |
| Example 224 | 288 |
| Example 225 | 467 |
| Example 226 | 439 |
| Example 227 | 290 |
| Example 228 | 6 |
| Example 229 | 6 |
| Example 230 | 116 |
| Example 231 | 189 |
| Example 232 | 21 |
| Example 233 | 254 |
| Example 234 | 75 |
| Example 235 | 262 |
| Example 236 | 5 |
| Example 237 | 222 |
| Example 238 | 183 |
| Example 239 | 164 |
| Example 240 | 141 |
| Example 241 | 300 |
| Example 242 | 156 |
| Example 243 | 165 |
| Example 244 | 96 |
| Example 245 | 234 |
| Example 246 | 217 |
| Example 247 | 166 |
| Example 248 | 42 |
| Example 249 | 106 |
| Example 250 | 6 |
| Example 251 | 175 |
| Example 252 | 23 |
| Example 253 | 73 |
| Example 254 | 131 |
| Example 255 | 49 |
| Example 256 | 149 |
| Example 257 | 8 |
| Example 258 | 120 |
| Example 259 | 91 |
| Example 260 | 113 |
| Example 261 | 90 |
| Example 262 | 108 |
| Example 263 | 114 |
| Example 264 | 123 |
| Example 265 | 25 |
| Example 266 | 168 |
| Example 267 | 5 |
| Example 268 | 181 |
| Example 269 | 109 |
| Example 270 | 235 |
| Example 271 | 229 |
| Example 272 | 44 |
| Example 273 | 85 |
| Example 274 | 124 |
| Example 275 | 157 |
| Example 276 | 45 |
| Example 277 | 174 |
| Example 278 | 68 |
| Example 279 | 160 |
| Example 280 | 191 |
| Example 281 | 8 |
| Example 282 | 39 |
| Example 283 | 288 |
| Example 284 | 260 |
| Example 285 | 195 |
| Example 286 | 16 |
| Example 287 | 202 |
| Example 288 | 153 |
| Example 289 | 58 |
| Example 290 | 90 |
| Example 291 | 98 |
| Example 292 | 114 |
| Example 293 | 86 |
| Example 294 | 84 |
| Example 295 | 70 |
| Example 296 | 92 |
| Example 297 | 176 |
| Example 298 | 121 |
| Example 299 | 5 |
| Example 300 | 86 |
| Example 301 | 107 |
| Example 302 | 103 |
| Example 303 | 106 |
| Example 304 | 104 |

TABLE 14-continued

IFN-β secretion in THP1 cell culture (5 h)

| Compound | % Effect at 30 µM relative to 2'3'-cGAMP |
|---|---|
| Example 305 | 50 |
| Example 306 | 153 |
| Example 307 | 174 |
| Example 308 | 132 |
| Example 309 | 232 |
| Example 310 | 117 |
| Example 311 | 9 |
| Example 312 | 90 |
| Example 313 | 117 |
| Example 314 | 143 |
| Example 315 | 92 |
| Example 316 | 12 |
| Example 317 | 107 |
| Example 318 | 150 |
| Example 319 | 143 |
| Example 320 | 115 |
| Example 321 | 36 |
| Example 322 | 41 |
| Example 323 | 92 |
| Example 324 | 99 |
| Example 325 | 10 |
| Example 326 | 34 |
| Example 327 | 126 |
| Example 328 | 99 |
| Example 329 | 105 |
| Example 330 | 67 |
| Example 331 | 116 |
| Example 332 | 113 |
| Example 333 | 10 |
| Example 334 | 66 |
| Example 335 | 60 |
| Example 336 | 85 |
| Example 337 | 204 |
| Example 338 | 219 |
| Example 339 | 175 |
| Example 340 | 306 |
| Example 341 | 7 |
| Example 342 | 23 |
| Example 343 | 255 |
| Example 344 | 337 |
| Example 345 | 144 |
| Example 346 | 182 |
| Example 347 | 225 |
| Example 348 | 8 |

It will be appreciated that various of the above-discussed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:
1. A method of inducing STING-dependent type I interferon production in a subject, said method comprising administering a therapeutically effective amount of a compound selected from the group consisting of:
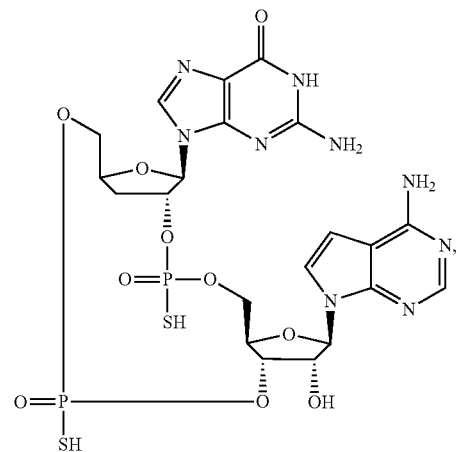
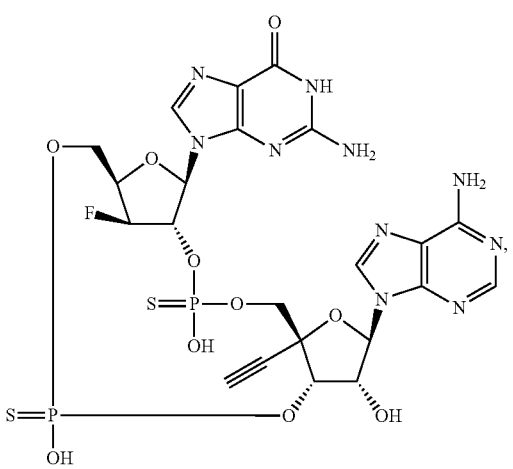
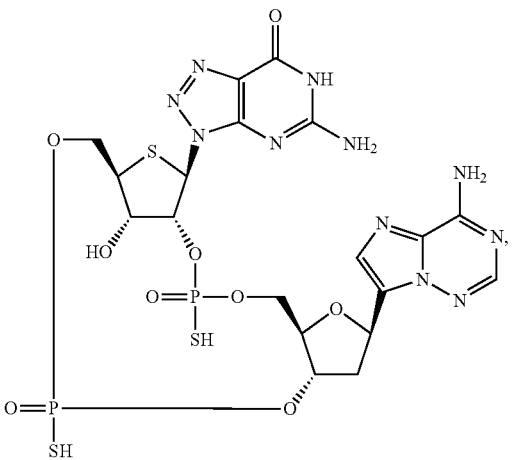
-continued
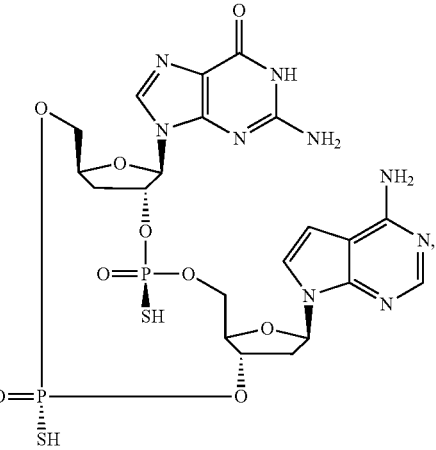
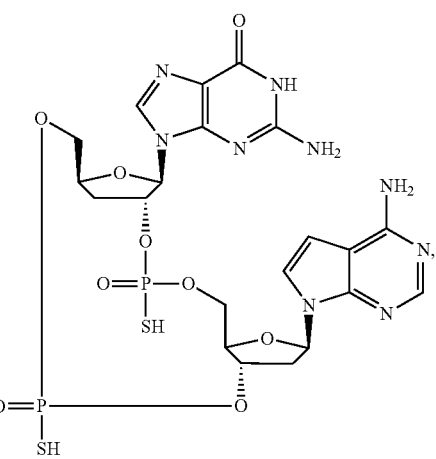
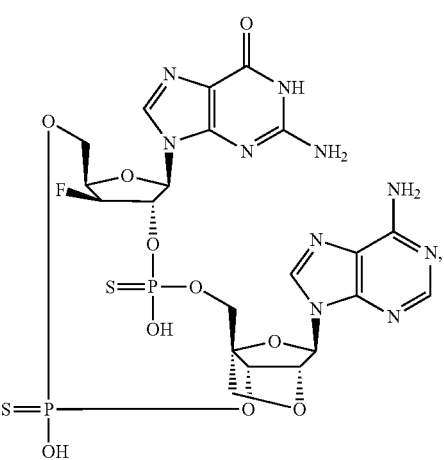

-continued

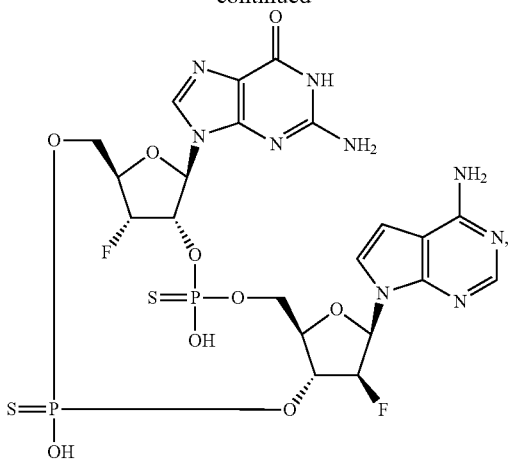

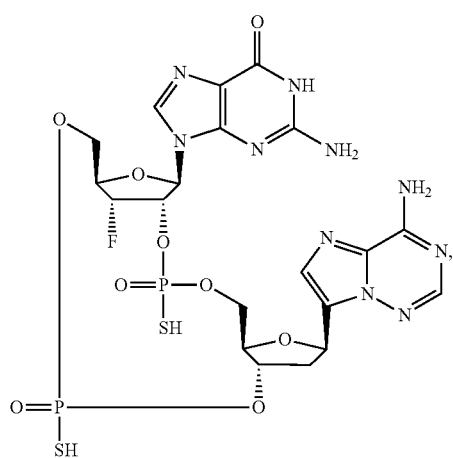

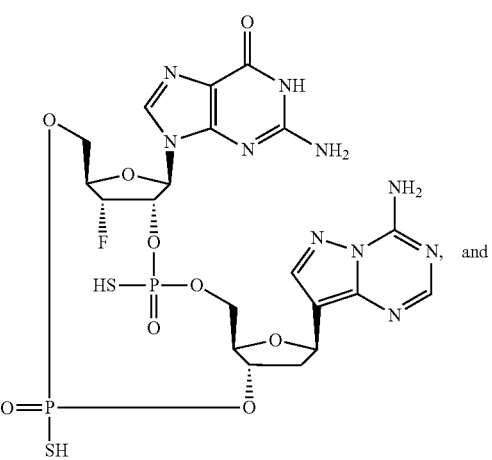

-continued

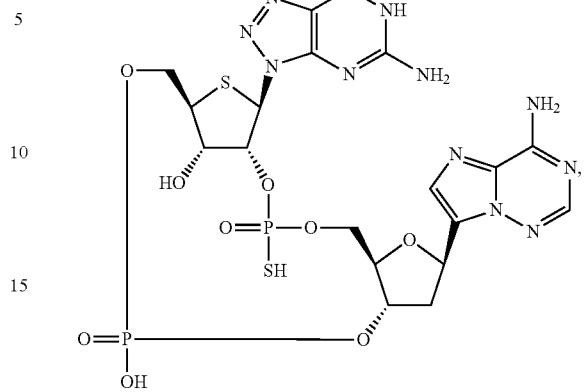

or a pharmaceutically acceptable salt thereof to the subject.

2. A method of inducing a-STING-dependent type I interferon production in a subject, said method comprising administering a therapeutically effective amount of a pharmaceutical composition to the subject, said pharmaceutical composition comprising:

(a) a compound selected from the group consisting of a compound selected from the group consisting of:

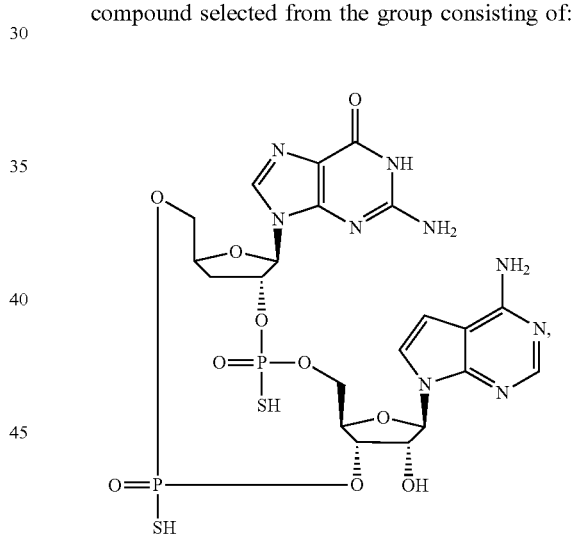

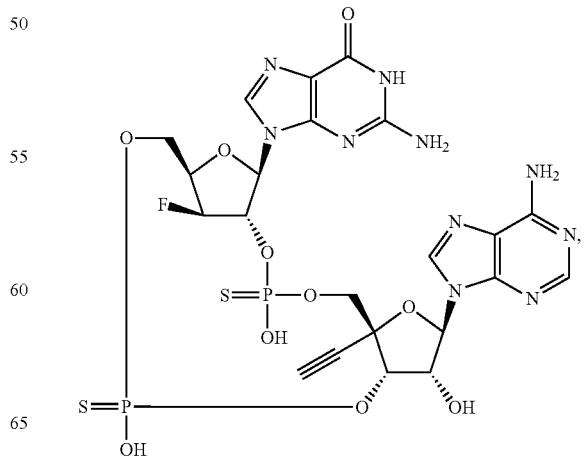

843
-continued
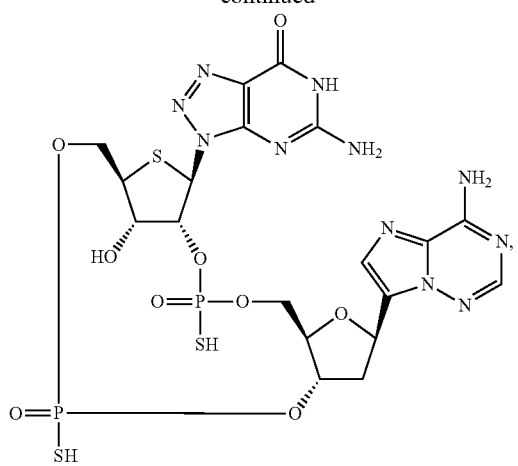
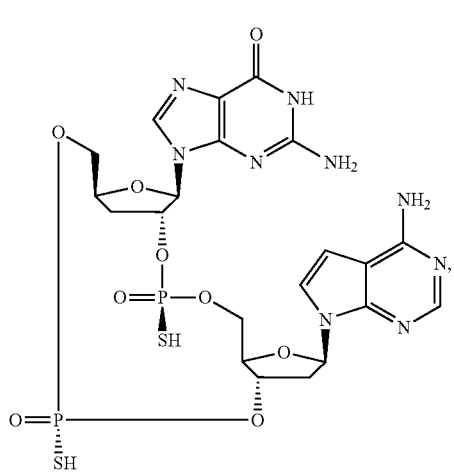
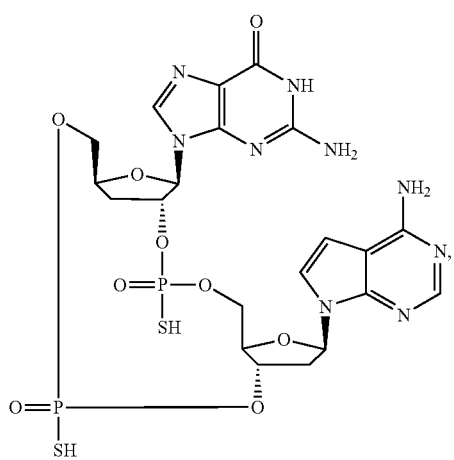
844
-continued
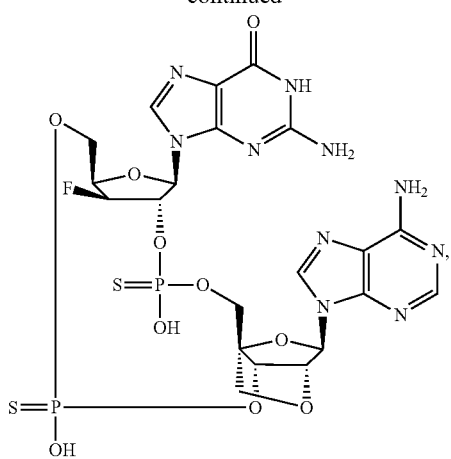
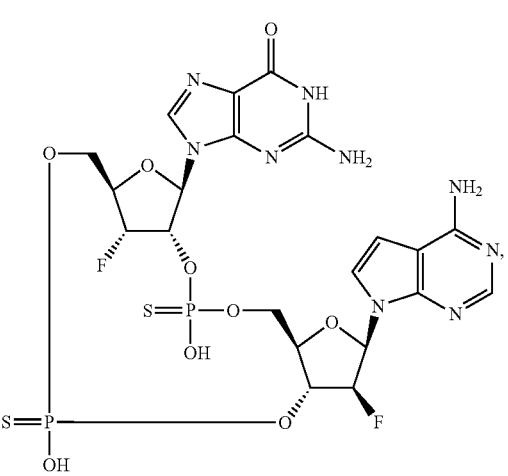
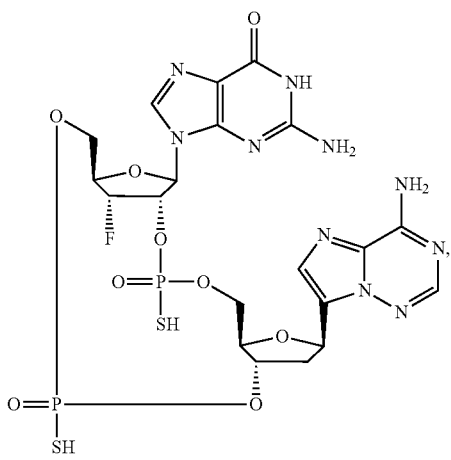

-continued

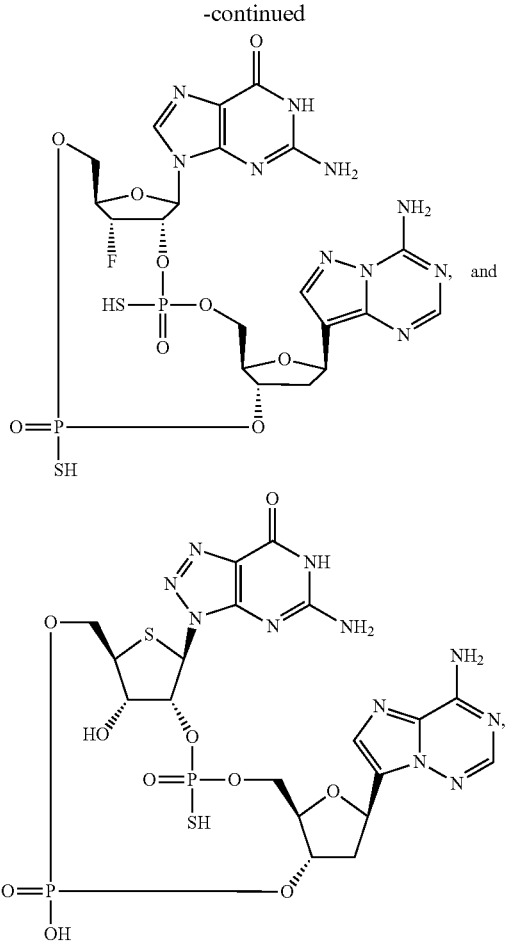

or a pharmaceutically acceptable salt thereof; and (b) a pharmaceutically acceptable carrier.

3. A method of inducing STING-dependent type I interferon production in a subject, said method comprising administering a therapeutically effective amount of a compound to the subject, wherein the compound is selected from the group consisting of

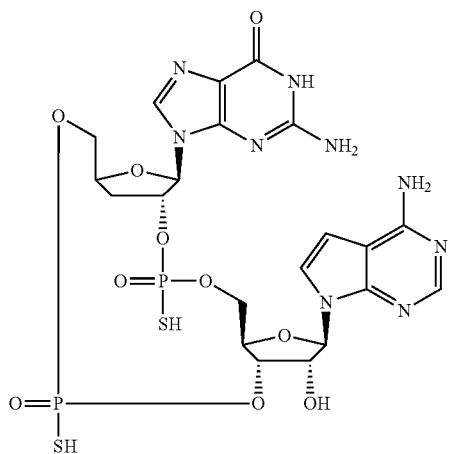 [SMILES: Nc1nc2c(ncn2[C@@H]2OC3COP(=O)(S)O[C@H]4[C@@H](O)[C@H](n5ccc6c(N)ncnc65)O[C@@H]4COP(=O)(S)O[C@@H]2C3)c(=O)[nH]1]

or a pharmaceutically acceptable salt thereof.

4. The method according to claim 3, wherein the compound is a pharmaceutically acceptable salt of

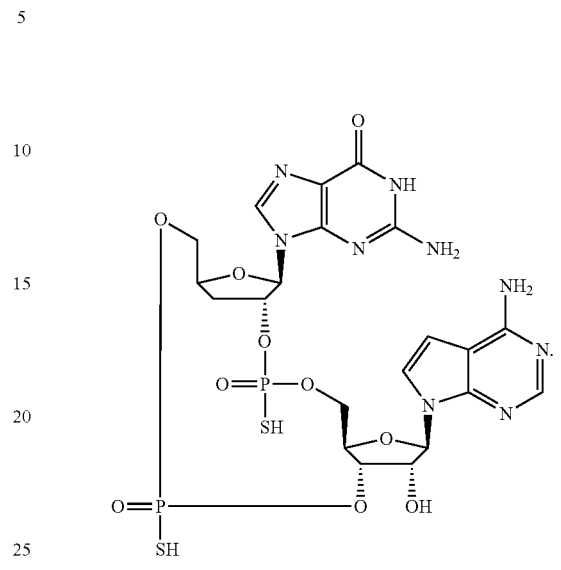

5. A method of inducing STING-dependent type I interferon production in a subject, said method comprising administering a therapeutically effective amount of a compound to the subject, wherein the compound is selected from the group consisting of

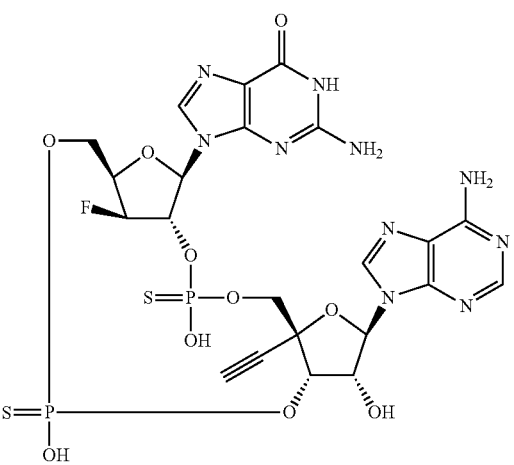 [SMILES: C#C[C@@]12COP(O)(=S)O[C@@H]3[C@@H](F)[C@@H](COP(O)(=S)O[C@H]1[C@@H](O)[C@H](n1cnc4c(N)ncnc41)O2)O[C@H]3n1cnc2c(=O)[nH]c(N)nc21]

or a pharmaceutically acceptable salt thereof.

6. The method according to claim 5, wherein the compound is a pharmaceutically acceptable salt of

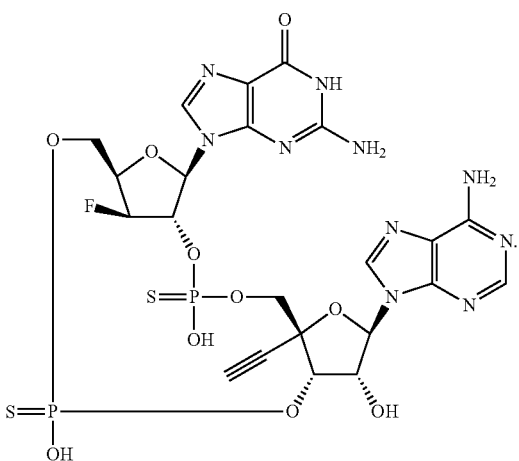 [SMILES: C#C[C@@]12COP(O)(=S)O[C@@H]3[C@@H](F)[C@@H](COP(O)(=S)O[C@H]1[C@@H](O)[C@H](n1cnc4c(N)ncnc41)O2)O[C@H]3n1cnc2c(=O)[nH]c(N)nc21]

7. A method of inducing STING-dependent type I interferon production in a subject, said method comprising administering a therapeutically effective amount of a compound to the subject, wherein the compound is selected from the group consisting of

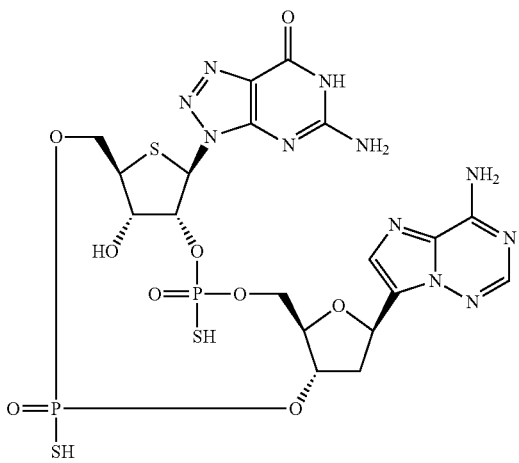 [SMILES: Nc1nc2c(nnn2[C@@H]2S[C@@H]3COP(=O)(S)O[C@H]4C[C@H](c5cnc6c(N)ncnn56)O[C@@H]4COP(=O)(S)O[C@@H]2[C@@H]3O)c(=O)[nH]1]

or a pharmaceutically acceptable salt thereof.

8. The method according to claim 7, wherein the compound is a pharmaceutically acceptable salt of

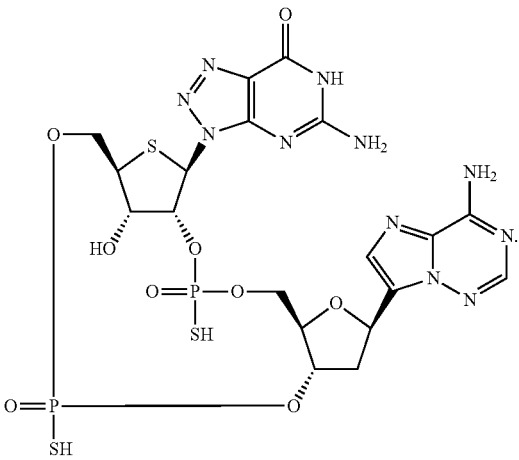 [SMILES: Nc1nc2c(nnn2[C@@H]2S[C@@H]3COP(=O)(S)O[C@H]4C[C@H](c5cnc6c(N)ncnn56)O[C@@H]4COP(=O)(S)O[C@@H]2[C@@H]3O)c(=O)[nH]1]

9. A method of inducing STING-dependent type I interferon production in a subject, said method comprising administering a therapeutically effective amount of a compound to the subject, wherein the compound is selected from the group consisting of

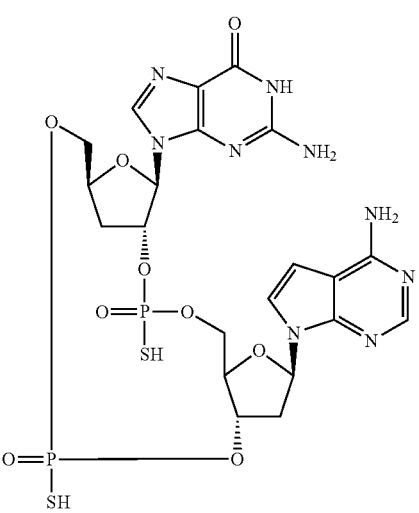 [SMILES: Nc1nc2c(ncn2[C@@H]2O[C@@H]3COP(=O)(S)O[C@H]4C[C@H](n5ccc6c(N)ncnc65)OC4COP(=O)(S)O[C@@H]2C3)c(=O)[nH]1]

or a pharmaceutically acceptable salt thereof.

10. The method according to claim 9, wherein the compound is a pharmaceutically acceptable salt of

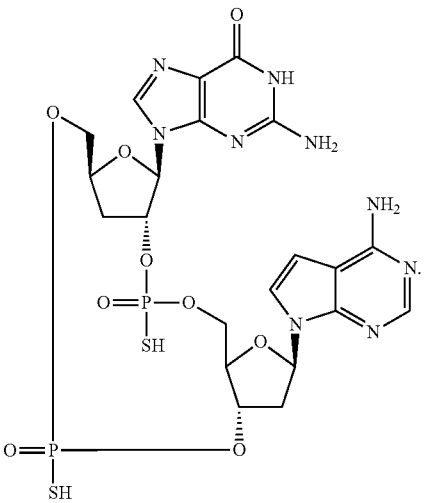 [SMILES: Nc1nc2c(ncn2[C@@H]2O[C@@H]3COP(=O)(S)O[C@H]4C[C@H](n5ccc6c(N)ncnc65)OC4COP(=O)(S)O[C@@H]2C3)c(=O)[nH]1]

11. The method according to claim 9, wherein the compound is selected from the group consisting of

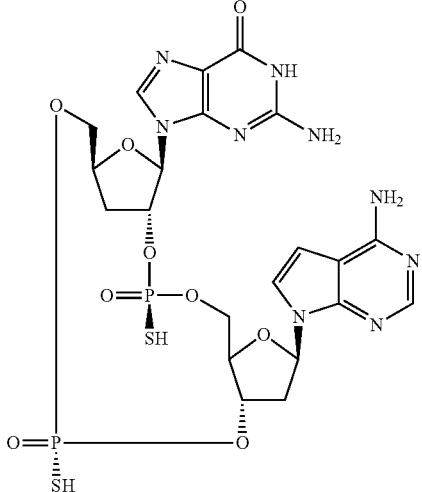 [SMILES: Nc1nc2c(ncn2[C@@H]2O[C@@H]3CO[P@@](=O)(S)O[C@H]4C[C@H](n5ccc6c(N)ncnc65)OC4CO[P@@](=O)(S)O[C@@H]2C3)c(=O)[nH]1]

or a pharmaceutically acceptable salt thereof.

12. The method according to claim 11, wherein the compound is a pharmaceutically acceptable salt of

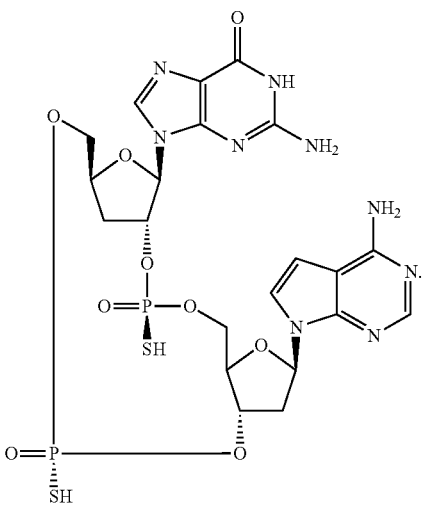 [SMILES: Nc1nc2c(ncn2[C@@H]2O[C@@H]3CO[P@@](=O)(S)O[C@H]4C[C@H](n5ccc6c(N)ncnc65)OC4CO[P@@](=O)(S)O[C@@H]2C3)c(=O)[nH]1]

13. A method of inducing STING-dependent type I interferon production in a subject, said method comprising administering a therapeutically effective amount of a compound to the subject, wherein the compound is selected from the group consisting of

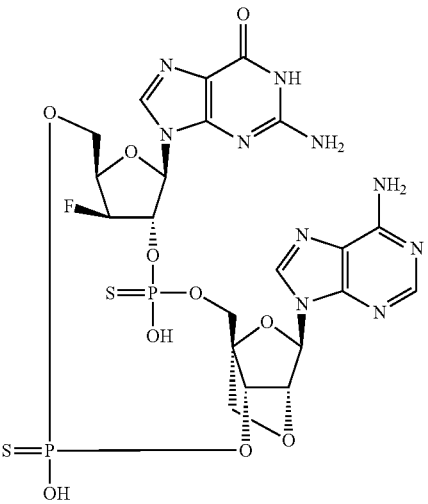

or a pharmaceutically acceptable salt thereof.

14. The method according to claim 13, wherein the compound is a pharmaceutically acceptable salt of

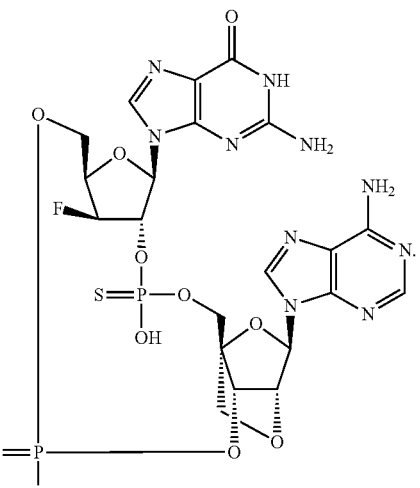

15. A method of inducing STING-dependent type I interferon production in a subject, said method comprising administering a therapeutically effective amount of a compound to the subject, wherein the compound is selected from the group consisting of

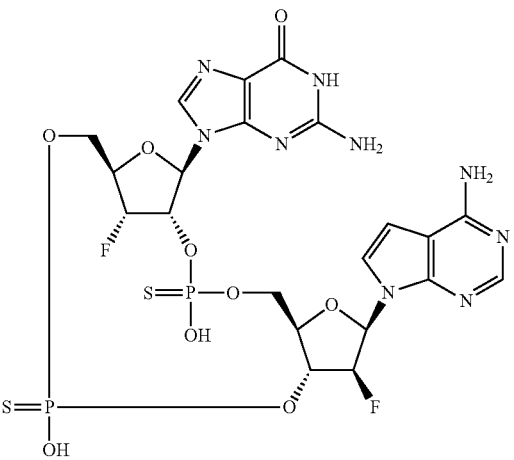 [SMILES: Nc1nc2c(ncn2[C@@H]2O[C@@H]3COP(O)(=S)O[C@H]4[C@H](F)[C@H](n5ccc6c(N)ncnc65)O[C@@H]4COP(O)(=S)O[C@@H]2[C@@H]3F)c(=O)[nH]1]

or a pharmaceutically acceptable salt thereof.

16. The method according to claim 15, wherein the compound is a pharmaceutically acceptable salt of

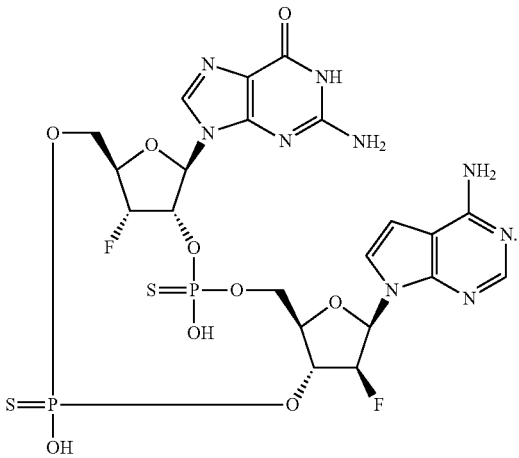 [SMILES: Nc1nc2c(ncn2[C@@H]2O[C@@H]3COP(O)(=S)O[C@H]4[C@H](F)[C@H](n5ccc6c(N)ncnc65)O[C@@H]4COP(O)(=S)O[C@@H]2[C@@H]3F)c(=O)[nH]1]

17. A method of inducing STING-dependent type I interferon production in a subject, said method comprising administering a therapeutically effective amount of a compound to the subject, wherein the compound is selected from the group consisting of

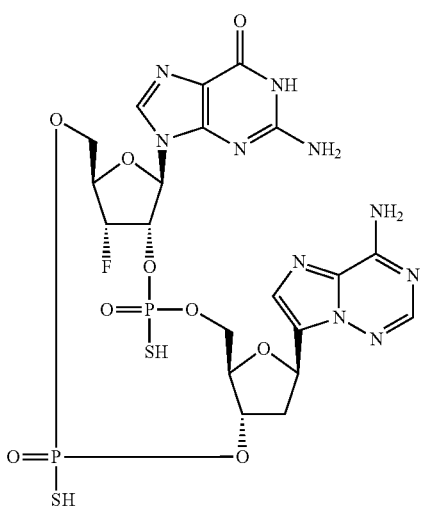 [SMILES: Nc1nc2c(ncn2[C@@H]2O[C@@H]3COP(=O)(S)O[C@H]4C[C@H](c5cnc6c(N)ncnn56)O[C@@H]4COP(=O)(S)O[C@@H]2[C@@H]3F)c(=O)[nH]1]

or a pharmaceutically acceptable salt thereof.

18. The method according to claim 17, wherein the compound is a pharmaceutically acceptable salt of

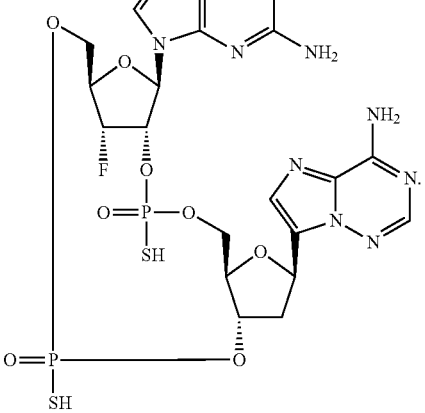

19. A method of inducing STING-dependent type I interferon production in a subject, said method comprising administering a therapeutically effective amount of a compound to the subject, wherein the compound is selected from the group consisting of

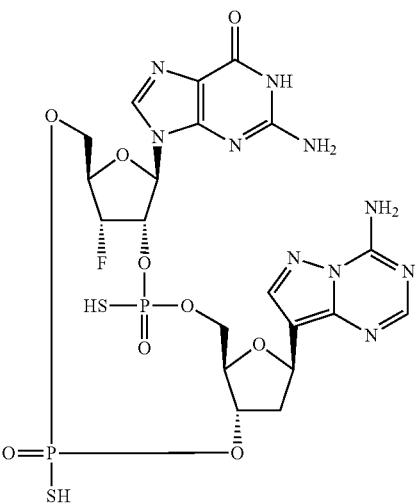 [SMILES: Nc1nc2c(ncn2[C@@H]2O[C@@H]3COP(=O)(S)O[C@H]4C[C@H](c5cnn6c(N)ncnc56)O[C@@H]4COP(=O)(S)O[C@@H]2[C@@H]3F)c(=O)[nH]1]

or a pharmaceutically acceptable salt thereof.

20. The method according to claim 19, wherein the compound is a pharmaceutically acceptable salt of

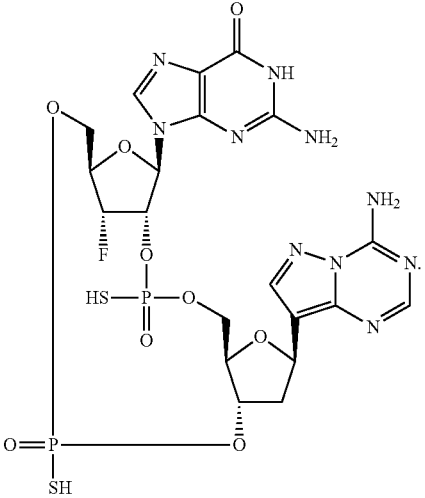 [SMILES: Nc1nc2c(ncn2[C@@H]2O[C@@H]3COP(=O)(S)O[C@H]4C[C@H](c5cnn6c(N)ncnc56)O[C@@H]4COP(=O)(S)O[C@@H]2[C@@H]3F)c(=O)[nH]1]

21. A method of inducing STING-dependent type I interferon production in a subject, said method comprising administering a therapeutically effective amount of a compound to the subject, wherein the compound is selected from the group consisting of

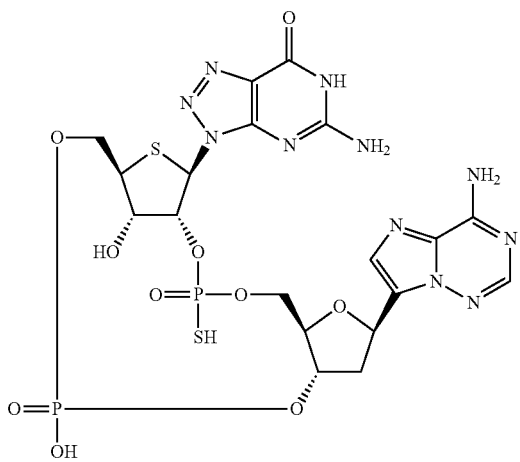

or a pharmaceutically acceptable salt thereof.

22. The method according to claim 21, wherein the compound is a pharmaceutically acceptable salt of

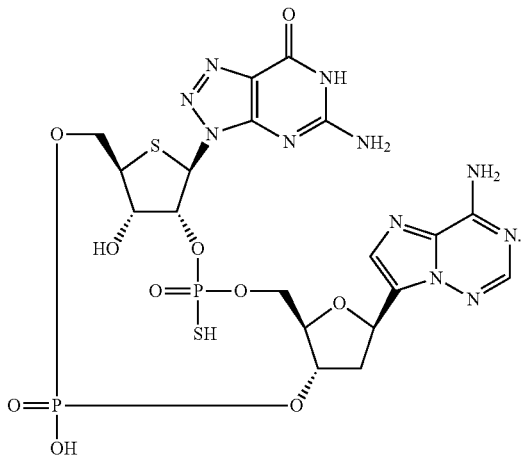

* * * * *

SEQUENCE LISTING

```
<160> NUMBER OF SEQ ID NOS: 5

<210> SEQ ID NO 1
<211> LENGTH: 475
<212> TYPE: PRT
<213> ORGANISM: Unknown
<220> FEATURE:
<223> OTHER INFORMATION: cGAS enzyme

<400> SEQUENCE: 1

Met Ala His His His His His His Gly Ser Asp Ser Glu Val Asn Gln
1               5                   10                  15

Glu Ala Lys Pro Glu Val Lys Pro Glu Val Lys Pro Glu Thr His Ile
            20                  25                  30

Asn Leu Lys Val Ser Asp Gly Ser Ser Glu Ile Phe Phe Lys Ile Lys
        35                  40                  45

Lys Thr Thr Pro Leu Arg Arg Leu Met Glu Ala Phe Ala Lys Arg Gln
    50                  55                  60

Gly Lys Glu Met Asp Ser Leu Thr Phe Leu Tyr Asp Gly Ile Glu Ile
65                  70                  75                  80

Gln Ala Asp Gln Thr Pro Glu Asp Leu Asp Met Glu Asp Asn Asp Ile
                85                  90                  95

Ile Glu Ala His Arg Glu Gln Ile Gly Gly Glu Asn Leu Tyr Phe Gln
            100                 105                 110

Gly Gly Ala Ser Lys Leu Arg Ala Val Leu Glu Lys Leu Lys Leu Ser
        115                 120                 125

Arg Asp Asp Ile Ser Thr Ala Ala Gly Met Val Lys Gly Val Val Asp
    130                 135                 140

His Leu Leu Leu Arg Leu Lys Cys Asp Ser Ala Phe Arg Gly Val Gly
```

|   |   |   | 145 |   |   |   | 150 |   |   |   | 155 |   |   |   | 160 |
|---|---|---|---|---|---|---|---|---|---|---|---|---|---|---|---|

Leu Leu Asn Thr Gly Ser Tyr Tyr Glu His Val Lys Ile Ser Ala Pro
                    165                   170               175

Asn Glu Phe Asp Val Met Phe Lys Leu Glu Val Pro Arg Ile Gln Leu
         180                   185                   190

Glu Glu Tyr Ser Asn Thr Arg Ala Tyr Tyr Phe Val Lys Phe Lys Arg
            195                 200              205

Asn Pro Lys Glu Asn Pro Leu Ser Gln Phe Leu Glu Gly Glu Ile Leu
210                  215                   220

Ser Ala Ser Lys Met Leu Ser Lys Phe Arg Lys Ile Lys Glu Glu
225            230              235            240

Ile Asn Asp Ile Lys Asp Thr Asp Val Ile Met Lys Arg Lys Arg Gly
            245               250              255

Gly Ser Pro Ala Val Thr Leu Leu Ile Ser Glu Lys Ile Ser Val Asp
         260                   265             270

Ile Thr Leu Ala Leu Glu Ser Lys Ser Ser Trp Pro Ala Ser Thr Gln
     275               280               285

Glu Gly Leu Arg Ile Gln Asn Trp Leu Ser Ala Lys Val Arg Lys Gln
    290               295              300

Leu Arg Leu Lys Pro Phe Tyr Leu Val Pro Lys His Ala Lys Glu Gly
305            310              315           320

Asn Gly Phe Gln Glu Glu Thr Trp Arg Leu Ser Phe Ser His Ile Glu
            325               330             335

Lys Glu Ile Leu Asn Asn His Gly Lys Ser Lys Thr Cys Cys Glu Asn
         340                   345             350

Lys Glu Glu Lys Cys Cys Arg Lys Asp Cys Leu Lys Leu Met Lys Tyr
       355               360             365

Leu Leu Glu Gln Leu Lys Glu Arg Phe Lys Asp Lys Lys His Leu Asp
    370               375             380

Lys Phe Ser Ser Tyr His Val Lys Thr Ala Phe Phe His Val Cys Thr
385            390              395          400

Gln Asn Pro Gln Asp Ser Gln Trp Asp Arg Lys Asp Leu Gly Leu Cys
            405               410          415

Phe Asp Asn Cys Val Thr Tyr Phe Leu Gln Cys Leu Arg Thr Glu Lys
         420                   425             430

Leu Glu Asn Tyr Phe Ile Pro Glu Phe Asn Leu Phe Ser Ser Asn Leu
       435              440              445

Ile Asp Lys Arg Ser Lys Glu Phe Leu Thr Lys Gln Ile Glu Tyr Glu
    450               455              460

Arg Asn Asn Glu Phe Pro Val Phe Asp Glu Phe
465            470              475

```
<210> SEQ ID NO 2
<211> LENGTH: 414
<212> TYPE: PRT
<213> ORGANISM: Homo Sapien

<400> SEQUENCE: 2
```

Met Pro His Ser Ser Leu His Pro Ser Ile Pro Cys Pro Arg Gly His
1              5                 10              15

Gly Ala Gln Lys Ala Ala Leu Val Leu Leu Ser Ala Cys Leu Val Thr
          20                  25              30

Leu Trp Gly Leu Gly Glu Pro Pro Glu His Thr Leu Arg Tyr Leu Val
       35               40              45

```
Leu His Leu Ala Ser Leu Gln Leu Gly Leu Leu Asn Gly Val Cys
     50                  55                  60
Ser Leu Ala Glu Glu Leu His His Ile His Ser Arg Tyr Arg Gly Ser
 65                  70                  75                  80
Tyr Trp Arg Thr Val Arg Ala Cys Leu Gly Cys Pro Leu Arg Arg Gly
                 85                  90                  95
Ala Leu Leu Leu Leu Ser Ile Tyr Phe Tyr Tyr Ser Leu Pro Asn Ala
                100                 105                 110
Val Gly Pro Pro Phe Thr Trp Met Leu Ala Leu Leu Gly Leu Ser Gln
            115                 120                 125
Ala Leu Asn Ile Leu Leu Gly Leu Lys Gly Leu Ala Pro Ala Glu Ile
        130                 135                 140
Ser Ala Val Cys Glu Lys Gly Asn Phe Asn Val Ala His Gly Leu Ala
145                 150                 155                 160
Trp Ser Tyr Tyr Ile Gly Tyr Leu Arg Leu Ile Leu Pro Glu Leu Gln
                165                 170                 175
Ala Arg Ile Arg Thr Tyr Asn Gln His Tyr Asn Asn Leu Leu Arg Gly
            180                 185                 190
Ala Val Ser Gln Arg Leu Tyr Ile Leu Leu Pro Leu Asp Cys Gly Val
        195                 200                 205
Pro Asp Asn Leu Ser Met Ala Asp Pro Asn Ile Arg Phe Leu Asp Lys
210                 215                 220
Leu Pro Gln Gln Thr Ala Asp Arg Ala Gly Ile Lys Asp Arg Val Tyr
225                 230                 235                 240
Ser Asn Ser Ile Tyr Glu Leu Leu Glu Asn Gly Gln Arg Ala Gly Thr
                245                 250                 255
Cys Val Leu Glu Tyr Ala Thr Pro Leu Gln Thr Leu Phe Ala Met Ser
            260                 265                 270
Gln Tyr Ser Gln Ala Gly Phe Ser Arg Glu Asp Arg Leu Glu Gln Ala
        275                 280                 285
Lys Leu Phe Cys Gln Thr Leu Glu Asp Ile Leu Ala Asp Ala Pro Glu
290                 295                 300
Ser Gln Asn Asn Cys Arg Leu Ile Ala Tyr Gln Glu Pro Ala Asp Asp
305                 310                 315                 320
Ser Ser Phe Ser Leu Ser Gln Glu Val Leu Arg His Leu Arg Gln Glu
                325                 330                 335
Glu Lys Glu Glu Val Thr Val Gly Ser Leu Lys Thr Ser Ala Val Pro
            340                 345                 350
Ser Thr Ser Thr Met Ser Gln Glu Pro Glu Leu Leu Ile Ser Gly Met
        355                 360                 365
Glu Lys Pro Leu Pro Leu Arg Thr Asp Phe Ser Gly Gly Leu Asn
370                 375                 380
Asp Ile Phe Glu Ala Gln Lys Ile Glu Trp His Glu Gly Ser Leu Glu
385                 390                 395                 400
Val Leu Phe Gln Gly Pro His His His His His His
                405                 410

<210> SEQ ID NO 3
<211> LENGTH: 6482
<212> TYPE: DNA
<213> ORGANISM: Homo Sapien

<400> SEQUENCE: 3
ggaacggctc cgcccactat taatgaaatt aaaaattcca attttaaaaa acgcagcaag     60
```

-continued

```
agaaacattt gtatgaaaga atgcgtagaa ggaaagaaaa atgtcgtcga catgctgaac    120
aacaagatta atatgcctcc gtgtataaaa aaatattga acgatttgaa agaaaacaat    180
gtaccgcgcg gcggtatgta caggaagagg tttatactaa actgttacat tgcaaacgtg    240
gtttcgtgtg ccaagtgtga aaaccgatgt ttaatcaagg ctctgacgca tttctacaac    300
cacgactcca agtgtgtggg tgaagtcatg catcttttaa tcaaatccca agatgtgtat    360
aaaccaccaa actgccaaaa aatgaaaact gtcgacaagc tctgtccgtt tgctggcaac    420
tgcaagggtc tcaatcctat ttgtaattat tgaataataa aacaattata aatgctaaat    480
ttgtttttta ttaacgatac aaaccaaacg caacaagaac atttgtagta ttatctataa    540
ttgaaaacgc gtagttataa tcgctgaggt aatatttaaa atcattttca aatgattcac    600
agttaatttg cgacaatata atttatttt cacataaact agacgccttg tcgtcttctt    660
cttcgtattc cttctctttt tcattttct cttcataaaa attaacatag ttattatcgt    720
atccatatat gtatctatcg tatagagtaa attttttgtt gtcataaata tatatgtctt    780
ttttaatggg gtgtatagta ccgctgcgca tagttttttct gtaatttaca acagtgctat    840
tttctggtag ttcttcggag tgtgttgctt taattattaa atttatataa tcaatgaatt    900
tgggatcgtc ggttttgtac aatatgttgc cggcatagta cgcagcttct tctagttcaa    960
ttacaccatt ttttagcagc accggattaa cataactttc caaaatgttg tacgaaccgt    1020
taaacaaaaa cagttcacct ccctttttcta tactattgtc tgcgagcagt tgtttgttgt    1080
taaaaataac agccattgta atgagacgca caaactaata tcacaaactg gaaatgtcta    1140
tcaatatata gttgctgatc agatctgatc atggagataa ttaaaatgat aaccatctcg    1200
caaataaata agtattttac tgttttcgta acagttttgt aataaaaaaa cctataaata    1260
taggatccat gccccactcc agcctgcatc catccatccc gtgtcccagg ggtcacgggg    1320
cccagaaggc agccttggtt ctgctgagtg cctgcctggt gacccttttgg gggctaggag    1380 agccaccaga gcacactctc cggtacctgg tgctccacct agcctccctg cagctgggac    1440
tgctgttaaa cggggtctgc agcctggctg aggagctgca ccacatccac tccaggtacc    1500
ggggcagcta ctggaggact gtgcgggcct gcctgggctg cccccctccgc cgtgggggccc    1560 tgttgctgct gtccatctat ttctactact ccctcccaaa tgcggtcggc ccgcccttca    1620
cttggatgct tgccctcctg ggcctctcgc aggcactgaa catcctcctg ggcctcaagg    1680
gcctggcccc agctgagatc tctgcagtgt gtgaaaaagg gaatttcaac gtggcccatg    1740
ggctggcatg gtcatattac atcggatatc tgccgctgat cctgccagag ctccaggccc    1800
ggattcgaac ttacaatcag cattacaaca acctgctacg gggtgcagtg agccagcggc    1860
tgtatattct cctcccattg gactgtgggg tgcctgataa cctgagtatg gctgacccca    1920
acattcgctt cctggataaa ctgccccagc agaccgctga ccgtgctggc atcaaggatc    1980
gggtttacag caacagcatc tatgagcttc tggagaacgg gcagcgggcg ggcacctgtg    2040
tcctggagta cgccaccccc ttgcagactt tgtttgccat gtcacaatac agtcaagctg    2100
gctttagccg ggaggatagg cttgagcagg ccaaactctt ctgccagaca cttgaggaca    2160
tcctggcaga tgcccctgag tctcagaaca actgccgcct cattgcctac caggaacctg    2220
cagatgacag cagcttctcg ctgtcccagg aggttctccg gcacctgcgg caggaggaaa    2280
aggaagaggt tactgtgggc agcttgaaga cctcagcggt gcccagtacc tccacgatgt    2340
cccaagagcc tgagctcctc atcagtggaa tggaaaagcc cctccctctc cgcacggatt    2400
tctctggcgg tggcctgaac gacatcttcg aagcccagaa aatcgaatgg catgaaggca    2460
```

```
gcctggaagt gctgttccag ggcccacacc accatcatca ccatcaccat taatgagcgg   2520
ccgcactcga gcaccaccac caccaccact aacctaggta gctgagcgca tgcaagctga   2580
tccgggttat tagtacattt attaagcgct agattctgtg cgttgttgat ttacagacaa   2640
ttgttgtacg tattttaata attcattaaa tttataatct ttagggtggt atgttagagc   2700
gaaaatcaaa tgattttcag cgtctttata tctgaattta aatattaaat cctcaataga   2760
tttgtaaaat aggtttcgat tagtttcaaa caagggttgt ttttccgaac cgatggctgg   2820
actatctaat ggattttcgc tcaacgccac aaaacttgcc aaatcttgta gcagcaatct   2880
agctttgtcg atattcgttt gtgttttgtt ttgtaataaa ggttcgacgt cgttcaaaat   2940
attatgcgct tttgtatttc tttcatcact gtcgttagtg tacaattgac tcgacgtaaa   3000
cacgttaaat agagcttgga catatttaac atcgggcgtg ttagctttat taggccgatt   3060
atcgtcgtcg tcccaaccct cgtcgttaga agttgcttcc gaagacgatt ttgccatagc   3120
cacacgacgc ctattaattg tgtcggctaa cacgtccgcg atcaaatttg tagttgagct   3180
ttttggaatt atttctgatt gcgggcgttt ttgggcgggt ttcaatctaa ctgtgcccga   3240
ttttaattca gacaacacgt tagaaagcga tggtgcaggc ggtggtaaca tttcagacgg   3300
caaatctact aatggcggcg gtggtggagc tgatgataaa tctaccatcg gtggaggcgc   3360
aggcggggct ggcggcggag gcggaggcgg aggtggtggc ggtgatgcag acggcggttt   3420
aggctcaaat gtctctttag gcaacacagt cggcacctca actattgtac tggtttcggg   3480
cgccgttttt ggtttgaccg gtctgagacg agtgcgattt ttttcgtttc taatagcttc   3540
caacaattgt tgtctgtcgt ctaaaggtgc agcgggttga ggttccgtcg gcattggtgg   3600
agcgggcggc aattcagaca tcgatggtgg tggtggtggt ggaggcgctg gaatgttagg   3660
cacgggagaa ggtggtggcg gcggtgccgc cggtataatt tgttctggtt tagtttgttc   3720
gcgcacgatt gtgggcaccg cgcaggcgc cgctggctgc acaacggaag gtcgtctgct   3780
tcgaggcagc gcttggggtg gtggcaattc aatattataa ttggaataca aatcgtaaaa   3840
atctgctata agcattgtaa tttcgctatc gtttaccgtg ccgatattta acaaccgctc   3900
aatgtaagca attgtattgt aaagagattg tctcaagctc ggatcgatcc cgcacgccga   3960
taacaagcct tttcattttt actacagcat tgtagtggcg agacacttcg ctgtcgtcga   4020
ggtttaaacg cttcctcgct cactgactcg ctgcgctcgg tcgttcggct gcggcgagcg   4080
gtatcagctc actcaaaggc ggtaatacgg ttatccacag aatcagggga taacgcagga   4140
aagaacatgt gagcaaaagg ccagcaaaag gccaggaacc gtaaaaaggc cgcgttgctg   4200 gcgttttttcc ataggctccg cccccctgac gagcatcaca aaaatcgacg ctcaagtcag   4260
aggtggcgaa acccgacagg actataaaga taccaggcgt ttccccctgg aagctccctc   4320
gtgcgctctc ctgttccgac cctgccgctt accggatacc tgtccgcctt tctcccttcg   4380
ggaagcgtgg cgctttctca tagctcacgc tgtaggtatc tcagttcggt gtaggtcgtt   4440
cgctccaagc tgggctgtgt gcacgaaccc cccgttcagc ccgaccgctg cgccttatcc   4500
ggtaactatc gtcttgagtc aacccggta agacacgact tatcgccact ggcagcagcc   4560
actggtaaca ggattagcag agcgaggtat gtaggcggtg ctacagagtt cttgaagtgg   4620
tggcctaact acggctacac tagaaggaca gtatttggta tctgcgctct gctgaagcca   4680
gttaccttcg gaaaaagagt tggtagctct tgatccggca acaaaccac cgctggtagc   4740 ggtggttttt ttgtttgcaa gcagcagatt acgcgcagaa aaaaaggatc tcaagaagat   4800
```

```
ccctttgatct tttctacggg gtctgacgct cagtggaacg aaaactcacg ttaagggatt    4860
ttggtcatga gattatcaaa aaggatcttc acctagatcc ttttaaatta aaaatgaagt    4920
tttaaatcaa tctaaagtat atatgagtaa acttggtctg acagttacca atgcttaatc    4980
agtgaggcac ctatctcagc gatctgtcta tttcgttcat ccatagttgc ctgactcccc    5040
gtcgtgtaga taactacgat acgggagggc ttaccatctg gccccagtgc tgcaatgata    5100
ccgcgagacc cacgctcacc ggctccagat ttatcagcaa taaaccagcc agccggaagg    5160
gccgagcgca gaagtggtcc tgcaacttta tccgcctcca tccagtctat taattgttgc    5220
cgggaagcta gagtaagtag ttcgccagtt aatagtttgc gcaacgttgt tgccattgct    5280
acaggcatcg tggtgtcacg ctcgtcgttt ggtatggctt cattcagctc cggttcccaa    5340
cgatcaaggc gagttacatg atcccccatg ttgtgcaaaa aagcggttag ctccttcggt    5400
cctccgatcg ttgtcagaag taagttggcc gcagtgttat cactcatggt tatggcagca    5460
ctgcataatt ctcttactgt catgccatcc gtaagatgct tttctgtgac tggtgagtac    5520
tcaaccaagt cattctgaga atagtgtatg cggcgaccga gttgctcttg cccggcgtca    5580
atacgggata taccgcgcc acatagcaga actttaaaag tgctcatcat tggaaaacgt    5640
tcttcggggc gaaaactctc aaggatctta ccgctgttga gatccagttc gatgtaaccc    5700
actcgtgcac ccaactgatc ttcagcatct tttactttca ccagcgtttc tgggtgagca    5760
aaaacaggaa ggcaaaatgc cgcaaaaaag gaataagggc gacacggaaa tgttgaata    5820
ctcatactct tcctttttca atattattga agcatttatc agggttattg tctcatgagc    5880
ggatacatat ttgaatgtat ttagaaaaat aaacaaatag gggttccgcg cacatttccc    5940
cgaaaagtgc cacctgacgc gccctgtagc ggcgcattaa gcgcggcggg tgtggtggtt    6000
acgcgcagcg tgaccgctac acttgccagc gccctagcgc ccgctccttt cgctttcttc    6060
ccttcctttc tcgccacgtt cgccggcttt ccccgtcaag ctctaaatcg ggggctccct    6120
ttagggttcc gatttagtgc tttacggcac ctcgacccca aaaaacttga ttagggtgat    6180
ggttcacgta gtgggccatc gccctgatag acggtttttc gccctttgac gttggagtcc    6240
acgttcttta atagtggact cttgttccaa actggaacaa cactcaaccc tatctcggtc    6300
tattcttttg atttataagg gattttgccg atttcggcct attggttaaa aaatgagctg    6360
atttaacaaa aatttaacgc gaattttaac aaaatattaa cgtttacaat ttcccattcg    6420
ccattcaggc tgcgcaactg ttgggaaggg cgatcggtgc gggcctcttc gctattacgc    6480
ca                                                                   6482
```

<210> SEQ ID NO 4
<211> LENGTH: 414
<212> TYPE: PRT
<213> ORGANISM: Homo Sapien

<400> SEQUENCE: 4

Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Asn Gly Val Cys
    50                  55                  60

Ser Leu Ala Glu Glu Leu Arg His Ile His Ser Arg Tyr Arg Gly Ser

```
                65                  70                  75                  80
Tyr Trp Arg Thr Val Arg Ala Cys Leu Gly Cys Pro Leu Arg Arg Gly
                    85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
            115                 120                 125

Ala Leu Asn Ile Leu Leu Gly Leu Lys Gly Leu Ala Pro Ala Glu Ile
            130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
                180                 185                 190

Ala Val Ser Gln Arg Leu Tyr Ile Leu Leu Pro Leu Asp Cys Gly Val
                195                 200                 205

Pro Asp Asn Leu Ser Met Ala Asp Pro Asn Ile Arg Phe Leu Asp Lys
            210                 215                 220

Leu Pro Gln Gln Thr Gly Asp Arg Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
                260                 265                 270

Gln Tyr Ser Gln Ala Gly Phe Ser Arg Glu Asp Arg Leu Glu Gln Ala
                275                 280                 285

Lys Leu Phe Cys Arg Thr Leu Glu Asp Ile Leu Ala Asp Ala Pro Glu
            290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
            355                 360                 365

Glu Lys Pro Leu Pro Leu Arg Thr Asp Phe Ser Gly Gly Gly Leu Asn
            370                 375                 380

Asp Ile Phe Glu Ala Gln Lys Ile Glu Trp His Glu Gly Ser Leu Glu
385                 390                 395                 400

Val Leu Phe Gln Gly Pro His His His His His His
                405                 410

<210> SEQ ID NO 5
<211> LENGTH: 6482
<212> TYPE: DNA
<213> ORGANISM: Homo Sapien

<400> SEQUENCE: 5
ggaacggctc cgcccactat taatgaaatt aaaaattcca attttaaaaa acgcagcaag    60
agaaacattt gtatgaaaga atgcgtagaa ggaaagaaaa atgtcgtcga catgctgaac   120
aacaagatta atatgcctcc gtgtataaaa aaatattga acgatttgaa agaaaacaat    180
```

-continued

```
gtaccgcgcg gcggtatgta caggaagagg tttatactaa actgttacat tgcaaacgtg      240
gtttcgtgtg ccaagtgtga aaaccgatgt ttaatcaagg ctctgacgca tttctacaac      300
cacgactcca agtgtgtggg tgaagtcatg catcttttaa tcaaatccca agatgtgtat      360
aaaccaccaa actgccaaaa aatgaaaact gtcgacaagc tctgtccgtt tgctggcaac      420
tgcaagggtc tcaatcctat ttgtaattat tgaataataa aacaattata aatgtcaaat      480
ttgtttttta ttaacgatac aaaccaaacg caacaagaac atttgtagta ttatctataa      540
ttgaaaacgc gtagttataa tcgctgaggt aatatttaaa atcattttca aatgattcac      600
agttaatttg cgacaatata atttttatttt cacataaact agacgccttg tcgtcttctt      660
cttcgtattc cttctctttt tcattttttct cttcataaaa attaacatag ttattatcgt      720
atccatatat gtatctatcg tatagagtaa attttttgtt gtcataaata tatatgtctt      780
ttttaatggg gtgtatagta ccgctgcgca tagttttttct gtaatttaca acagtgctat      840
tttctggtag ttcttcggag tgtgttgctt taattattaa atttatataa tcaatgaatt      900
tgggatcgtc ggttttgtac aatatgttgc cggcatagta cgcagcttct tctagttcaa      960
ttacaccatt ttttagcagc accggattaa cataactttc caaaatgttg tacgaaccgt     1020
taaacaaaaa cagttcacct ccctttttcta tactattgtc tgcgagcagt tgtttgttgt     1080
taaaaataac agccattgta atgagacgca caaactaata tcacaaactg gaaatgtcta     1140
tcaatatata gttgctgatc agatctgatc atggagataa ttaaaatgat aaccatctcg     1200
caaataaata agtattttac tgttttcgta acagttttgt aataaaaaaa cctataaata     1260
taggatccat gccccactcc agcctgcatc catccatccc gtgtcccagg ggtcacgggg     1320
cccagaaggc agccttggtt ctgctgagtg cctgcctggt gacccctttgg gggctaggag     1380 agccaccaga gcacactctc cggtacctgg tgctccacct agcctccctg cagctgggac     1440
tgctgttaaa cggggtctgc agcctggctg aggagctgcg ccacatccac tccaggtacc     1500
ggggcagcta ctgagggact gtgcgggcct gcctgggctg ccccctccgc cgtgggggcc     1560
tgttgctgct gtccatctat ttctactact ccctcccaaa tgcggtcggc ccgcccttca     1620
cttggatgct tgccctcctg ggcctctcgc aggcactgaa catcctcctg ggcctcaagg     1680
gcctggcccc agctgagatc tctgcagtgt gtgaaaaagg gaatttcaac gtggcccatg     1740
ggctggcatg gtcatattac atcggatatc tgccggctgat cctgccagag ctccaggccc     1800
ggattcgaac ttacaatcag cattacaaca acctgctacg gggtgcagtg agccagcggc     1860
tgtatattct cctcccattg gactgtgggg tgcctgataa cctgagtatg ctgaccccca     1920
acattcgctt cctggataaa ctgccccagc agaccggtga ccgtgctggc atcaaggatc     1980
gggtttacag caacagcatc tatgagcttc tggagaacgg gcagcgggcg ggcacctgtg     2040
tcctggagta cgccacccccc ttgcagactt tgtttgccat gtcacaatac agtcaagctg     2100
gctttagccg ggaggatagg cttgagcagg ccaaactctt ctgccggaca cttgaggaca     2160
tcctggcaga tgcccctgag tctcagaaca actgccgcct cattgcctac caggaacctg     2220
cagatgacag cagcttctcg ctgtcccagg aggttctccg gcacctgcgg caggaggaaa     2280
aggaagaggt tactgtgggc agcttgaaga cctcagcggt gcccagtacc tccacgatgt     2340
cccaagagcc tgagctcctc atcagtggaa tggaaaagcc cctccctctc cgcacggatt     2400
tctctggcgg tggcctgaac gacatcttcg aagcccagaa aatcgaatgg catgaaggca     2460
gcctggaagt gctgttccag ggcccacacc accatcatca ccatcaccat taatgagcgg     2520
ccgcactcga gcaccaccac caccaccact aacctaggta gctgagcgca tgcaagctga     2580
```

-continued

```
tccgggttat tagtacattt attaagcgct agattctgtg cgttgttgat ttacagacaa    2640
ttgttgtacg tattttaata attcattaaa tttataatct ttagggtggt atgttagagc    2700
gaaaatcaaa tgattttcag cgtctttata tctgaattta aatattaaat cctcaataga    2760
tttgtaaaat aggtttcgat tagtttcaaa caagggttgt ttttccgaac cgatggctgg    2820
actatctaat ggattttcgc tcaacgccac aaaacttgcc aaatcttgta gcagcaatct    2880
agctttgtcg atattcgttt gtgttttgtt ttgtaataaa ggttcgacgt cgttcaaaat    2940
attatgcgct tttgtatttc tttcatcact gtcgttagtg tacaattgac tcgacgtaaa    3000
cacgttaaat agagcttgga catatttaac atcgggcgtg ttagctttat taggccgatt    3060
atcgtcgtcg tcccaaccct cgtcgttaga agttgcttcc gaagacgatt ttgccatagc    3120
cacacgacgc ctattaattg tgtcggctaa cacgtccgcg atcaaatttg tagttgagct    3180
ttttggaatt atttctgatt gcgggcgttt ttgggcgggt ttcaatctaa ctgtgcccga    3240
ttttaattca gacaacacgt tagaaagcga tggtgcaggc ggtggtaaca tttcagacgg    3300
caaatctact aatggcggcg gtggtggagc tgatgataaa tctaccatcg gtggaggcgc    3360
aggcggggct ggcggcggag gcggaggcgg aggtggtggc ggtgatgcag acggcggttt    3420
aggctcaaat gtctctttag gcaacacagt cggcacctca actattgtac tggtttcggg    3480
cgccgttttt ggtttgaccg gtctgagacg agtgcgattt ttttcgtttc taatagcttc    3540
caacaattgt tgtctgtcgt ctaaaggtgc agcgggttga ggttccgtcg gcattggtgg    3600
agcgggcggc aattcagaca tcgatggtgg tggtggtggt ggaggcgctg gaatgttagg    3660
cacgggagaa ggtggtggcg gcggtgccgc cggtataatt tgttctggtt tagtttgttc    3720
gcgcacgatt gtgggcaccg cgcaggcgc cgctggctgc acaacggaag gtcgtctgct    3780
tcgaggcagc gcttggggtg gtggcaattc aatattataa ttggaataca aatcgtaaaa    3840
atctgctata agcattgtaa tttcgctatc gtttaccgtg ccgatattta acaaccgctc    3900
aatgtaagca attgtattgt aaagagattg tctcaagctc ggatcgatcc cgcacgccga    3960
taacaagcct tttcattttt actacagcat tgtagtggcg agacacttcg ctgtcgtcga    4020
ggtttaaacg cttcctcgct cactgactcg ctgcgctcgg tcgttcggct gcggcgagcg    4080
gtatcagctc actcaaaggc ggtaatacgg ttatccacag aatcagggga taacgcagga    4140
aagaacatgt gagcaaaagg ccagcaaaag gccaggaacc gtaaaaaggc cgcgttgctg    4200
gcgttttccc ataggctccg cccccctgac gagcatcaca aaaatcgacg ctcaagtcag    4260
aggtggcgaa acccgacagg actataaaga taccaggcgt ttccccctgg aagctccctc    4320
gtgcgctctc ctgttccgac cctgccgctt accggatacc tgtccgcctt tctcccttcg    4380
ggaagcgtgg cgctttctca tagctcacgc tgtaggtatc tcagttcggt gtaggtcgtt    4440
cgctccaagc tgggctgtgt gcacgaaccc cccgttcagc ccgaccgctg cgccttatcc    4500
ggtaactatc gtcttgagtc aacccggta  agacacgact tatcgccact ggcagcagcc    4560
actggtaaca ggattagcag agcgaggtat gtaggcggtg ctacagagtt cttgaagtgg    4620
tggcctaact acggctacac tagaaggaca gtatttggta tctgcgctct gctgaagcca    4680
gttaccttcg gaaaagagt tggtagctct tgatccggca acaaaccac cgctggtagc    4740 ggtggttttt tgtttgcaa gcagcagatt acgcgcagaa aaaaggatc tcaagaagat    4800 cctttgatct tttctacggg gtctgacgct cagtggaacg aaaactcacg ttaagggatt    4860
ttggtcatga gattatcaaa aaggatcttc acctagatcc ttttaaatta aaatgaagt    4920
```

```
tttaaatcaa tctaaagtat atatgagtaa acttggtctg acagttacca atgcttaatc    4980
agtgaggcac ctatctcagc gatctgtcta tttcgttcat ccatagttgc ctgactcccc    5040
gtcgtgtaga taactacgat acgggagggc ttaccatctg gccccagtgc tgcaatgata    5100
ccgcgagacc cacgctcacc ggctccagat ttatcagcaa taaaccagcc agccggaagg    5160
gccgagcgca gaagtggtcc tgcaacttta tccgcctcca tccagtctat taattgttgc    5220
cgggaagcta gagtaagtag ttcgccagtt aatagtttgc gcaacgttgt tgccattgct    5280
acaggcatcg tggtgtcacg ctcgtcgttt ggtatggctt cattcagctc cggttcccaa    5340
cgatcaaggc gagttacatg atcccccatg ttgtgcaaaa aagcggttag ctccttcggt    5400
cctccgatcg ttgtcagaag taagttggcc gcagtgttat cactcatggt tatggcagca    5460
ctgcataatt ctcttactgt catgccatcc gtaagatgct tttctgtgac tggtgagtac    5520
tcaaccaagt cattctgaga atagtgtatg cggcgaccga gttgctcttg cccggcgtca    5580
atacgggata taccgcgcc acatagcaga actttaaaag tgctcatcat tggaaaacgt    5640
tcttcggggc gaaaactctc aaggatctta ccgctgttga gatccagttc gatgtaaccc    5700
actcgtgcac ccaactgatc ttcagcatct tttactttca ccagcgtttc tgggtgagca    5760
aaaacaggaa ggcaaaatgc cgcaaaaaag ggaataaggg cgacacggaa atgttgaata    5820
ctcatactct tcctttttca atattattga agcatttatc agggttattg tctcatgagc    5880
ggatacatat ttgaatgtat ttagaaaaat aaacaaatag gggttccgcg cacatttccc    5940
cgaaaagtgc cacctgacgc gccctgtagc ggcgcattaa gcgcggcggg tgtggtggtt    6000
acgcgcagcg tgaccgctac acttgccagc gccctagcgc ccgctccttt cgctttcttc    6060
ccttcctttc tcgccacgtt cgccggcttt ccccgtcaag ctctaaatcg ggggctccct    6120
ttagggttcc gatttagtgc tttacggcac ctcgacccca aaaaacttga ttagggtgat    6180
ggttcacgta gtgggccatc gccctgatag acggtttttc gccctttgac gttggagtcc    6240
acgttcttta atagtggact cttgttccaa actggaacaa cactcaaccc tatctcggtc    6300 tattctttg atttataagg gattttgccg atttcggcct attggttaaa aaatgagctg    6360
atttaacaaa aatttaacgc gaattttaac aaaatattaa cgtttacaat ttcccattcg    6420
ccattcaggc tgcgcaactg ttgggaaggg cgatcggtgc gggcctcttc gctattacgc    6480
ca                                                                  6482
```